United States Patent
Siddiqui et al.

(10) Patent No.: US 9,227,971 B2
(45) Date of Patent: Jan. 5, 2016

(54) PYRAZOLO[1,5-A]PYRIMIDINE COMPOUNDS AS MTOR INHIBITORS

(75) Inventors: M. Arshad Siddiqui, Newton, MA (US); Yang Nan, Malden, MA (US); Mehul F. Patel, Blue Bell, PA (US); Panduranga Adulla P. Reddy, Walpole, MA (US); Umar Faruk Mansoor, Framingham, MA (US); Zhaoyang Meng, Lansdale, PA (US); Lalanthi Dilrukshi Vitharana, Somerville, MA (US); Lianyun Zhao, Blue Bell, PA (US); Amit K. Mandal, Shrewsbury, MA (US); Duan Liu, Arlington, MA (US); Shuyi Tang, Belmont, MA (US); Andrew McRiner, Melrose, MA (US); David B. Belanger, Cambridge, MA (US); Patrick J. Curran, Saugus, MA (US); Chaoyang Dai, Acton, MA (US); Angie R. Angeles, Boston, MA (US); Liping Yang, Arlington, MA (US); Matthew Hersh Daniels, Cambridge, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 320 days.

(21) Appl. No.: 13/520,274

(22) PCT Filed: Jan. 18, 2011

(86) PCT No.: PCT/US2011/021534
§ 371 (c)(1),
(2), (4) Date: Jul. 2, 2012

(87) PCT Pub. No.: WO2011/090935
PCT Pub. Date: Jul. 28, 2011

(65) Prior Publication Data
US 2012/0322791 A1   Dec. 20, 2012

Related U.S. Application Data

(60) Provisional application No. 61/296,252, filed on Jan. 19, 2010, provisional application No. 61/393,162, filed on Oct. 14, 2010.

(51) Int. Cl.
C07D 487/04 (2006.01)
A61K 31/519 (2006.01)
C07D 471/08 (2006.01)
C07D 498/08 (2006.01)
C07D 491/147 (2006.01)
C07D 487/08 (2006.01)
C07D 513/08 (2006.01)
C07D 519/00 (2006.01)
A61P 35/00 (2006.01)

(52) U.S. Cl.
CPC ............ *C07D 471/08* (2013.01); *C07D 487/04* (2013.01); *C07D 487/08* (2013.01); *C07D 491/147* (2013.01); *C07D 498/08* (2013.01); *C07D 513/08* (2013.01)

(58) Field of Classification Search
CPC ... A61K 31/519; C07D 487/04; C07D 519/00
See application file for complete search history.

(56) References Cited

U.S. PATENT DOCUMENTS

| 7,605,155 B2 | 10/2009 | Guzi et al. |
| 8,591,943 B2 | 11/2013 | Deng et al. |
| 2007/0082900 A1 | 4/2007 | Guzi |
| 2013/0150362 A1 | 6/2013 | Zhao et al. |

FOREIGN PATENT DOCUMENTS

| WO | WO2004022561 | 3/2004 |
| WO | WO2004087707 | 10/2004 |
| WO | WO2008058126 | 5/2008 |
| WO | WO2008130569 | 10/2008 |
| WO | WO2009052145 | 4/2009 |

(Continued)

OTHER PUBLICATIONS

Zaytseva et al. (Cancer Letters, 2012, (319), pp. 1-7.*

(Continued)

*Primary Examiner* — Susanna Moore
(74) *Attorney, Agent, or Firm* — Richard S. Parr; Laura M. Ginkel

(57) ABSTRACT

The present invention provides Pyrazolopyrimidine Compounds of Formula (I):

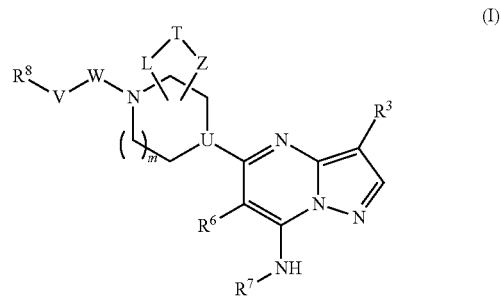

wherein L, T, Z, U, V, W, $R^3$, $R^6$, $R^7$, $R^8$, and m are as defined herein, and pharmaceutically acceptable salts of such Pyrazolopyrimidine Compounds. The Pyrazolopyrimidine Compounds are useful in the treatment of cancer and other diseases or disorders wherein mTOR is deregulated.

13 Claims, No Drawings

(56) References Cited

FOREIGN PATENT DOCUMENTS

| | | | |
|---|---|---|---|
| WO | WO2009061781 | | 5/2009 |
| WO | WO 2009061781 | * | 5/2009 |

OTHER PUBLICATIONS

Cancer Drug Design and Discovery Neidle, Stephen, ed. (Elsevier/Academic Press, 2008) pp. 427-431.*

* cited by examiner

PYRAZOLO[1,5-A]PYRIMIDINE COMPOUNDS AS MTOR INHIBITORS

FIELD OF THE INVENTION

This invention is directed to certain pyrazolo[1,5-a]pyrimidine compounds of Formula (I) as inhibitors of mammalian Target Of Rapamycin (mTOR) kinase, which is also known as FRAP, RAFT, RAPT or SEP. The compounds are useful in the treatment of cancer and other disorders where mTOR is deregulated.

BACKGROUND OF THE INVENTION

The mammalian target of rapamycin (mTOR) is a central regulator of cell growth and proliferation and plays a gatekeeper role in the control of cell cycle progression. The mTOR signaling pathway, which integrates both extracellular and intracellular signals, is activated in certain cellular processes such as tumor formation, angiogenesis, insulin resistance, adipogenesis, and T-lymphocyte activation. In addition, the mTOR signaling pathway is deregulated in diseases such as cancer and type 2 diabetes. See Laplante et al., *J. Cell Science* 122, pp 3589-3593 (2009).

mTOR mediates mitogenic signals from PI3K/AKT through to the downstream targets S6K1 (ribosomal S6 kinase 1), 4E-BP1 (eukaryotic translation initiation factor 4E-binding protein) and AKT. Recently, it has been shown that mTOR exists in two complexes. Raptor-mTOR complex (mTORC1) is a rapamycin-sensitive complex that phosphorylates S6K1 and 4E-BP1. Rictor-mTOR complex (mTORC2) is a rapamycin-insensitive complex that phosphorylates AKT at Ser473. Although the precise mechanism by which rapamycin inhibits mTOR function is not well understood, rapamycin partially inhibits mTOR function through mTORC1. Since mTORC2 is involved in the regulation of cell survival, metabolism, proliferation, and cytoskeletal organization in a rapamycin-independent manner, complete inhibition of mTOR function through inhibition of both mTORC1 and mTORC2 may lead to a broader spectrum antitumor activity in the treatment of cancer or better efficacy. In addition, inhibition of both mTORC1 and mTORC2 may lead to better efficacy in treating other diseases than through inhibition of mTORC1 alone.

There exists a need in the art for small-molecule compounds having desirable physicochemical properties that are useful for treating cancer and other disorders associated with deregulated mTOR activity. Specifically, there exists a need for small molecule inhibitors of mTOR kinase that block signaling through mTORC1 and mTORC2 for treating cancer and other disorders.

SUMMARY OF THE INVENTION

In one aspect, the present invention provides compounds of Formula (I) (herein referred to as the "Pyrazolopyrimidine Compounds" or "compounds of Formula (I)"):

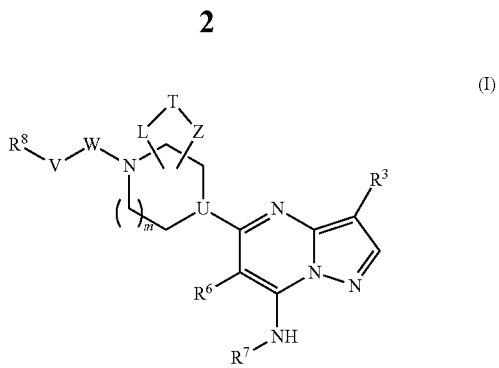

and pharmaceutically acceptable salts thereof.

In another aspect, the invention provides a pharmaceutical composition comprising a Pyrazolopyrimidine Compound, or a pharmaceutically acceptable salt thereof, and at least one pharmaceutically acceptable carrier.

In yet another aspect, the invention provides a method of treating a cancer, comprising administering a therapeutically effective amount of a Pyrazolopyrimidine Compound or a pharmaceutically acceptable salt thereof to a patient, e.g., a human patient, in need thereof.

In yet another aspect, the invention provides a method of treating a cancer, comprising administering an amount of a Pyrazolopyrimidine Compound or a pharmaceutically acceptable salt thereof, and an amount of one or more of additional anticancer drugs to a patient in need thereof.

In another aspect, the invention provides a method of treating a disease or disorder associated with deregulated mTOR activity, comprising administering a therapeutically effective amount of a Pyrazolopyrimidine Compound or a pharmaceutically acceptable salt thereof to a patient, e.g., a human patient, in need thereof.

DETAILED DESCRIPTION OF THE INVENTION

The present invention provides Pyrazolopyrimidine Compounds, pharmaceutical compositions comprising a Pyrazolopyrimidine Compound, and methods of using the Pyrazolopyrimidine Compounds for treating cancer in a patient. In addition, the present invention provides methods of using the Pyrazolopyrimidine Compounds for treating a disease or disorder associated with deregulated mTOR activity in a patient.

DEFINITIONS AND ABBREVIATIONS

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., $=$N—OH), —NH (alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl. The term "C$_1$-C$_6$ alkyl" refers to an alkyl group having from 1 to 6 carbon atoms.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. In one embodiment, an alkylene group has from 1 to 6 carbon atoms. In one embodiment, an alkylene is branched. In another embodiment, the alkylene is linear.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The "alkynyl" may be unsubstituted or optionally substituted by one or more substituents which may be the same or different, each substituent being independently selected from the group consisting of aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide (indicated herein as "N(O)"). "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In describing the heteroatoms contained in the heteroaryl group the expressions, "having one to x heteroatoms selected from the group of N, O, and S" or "having one to x heteroatoms selected from the group of N, N(O), O, and S" (wherein x is an a specified integer), for example, mean that each heteroatom in the specified heteroaryl is independently selected from the specified selection of heteroatoms.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which ring system contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. A non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred halogens are fluorine, chlorine and bromine.

"Haloalkyl" means an alkyl as defined above wherein one or more hydrogen atoms on the alkyl is replaced by a halogen group as defined above. Non-limiting examples of haloalkyl include trifluoromethyl, 2,2,2-trifluoroethyl, and 2-chloropropyl.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$^1$Y$^2$, -alkyl-NY$^1$Y$^2$, —C(O)NY$^1$Y$^2$, —SO$_2$NY$^1$Y$^2$ and —S(O)NY$_1$Y$_2$, wherein Y$^1$ and Y$^2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such a moiety are methylene dioxy, ethylenedioxy, —C(CH$_3$)$_2$— and the like which form moieties such as for example:

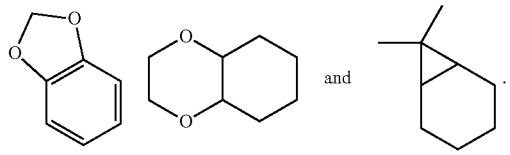

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example, nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom. Respectively, is present as a ring atom. Any —NH in a heterocyclyl ring may exist in protected form such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

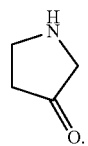

In describing the heteroatoms contained in a specified heterocyclyl group, the expression, "having one to x heteroatoms selected from the group of N, O, and S" (wherein x is an a specified integer), for example, means that each heteroatom in the specified heterocyclyl is independently selected from the specified selection of heteroatoms.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of

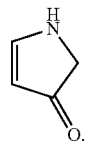

In describing the heteroatoms contained in a specified heterocyclenyl group, the expression, "having one to x heteroatoms selected from the group of N, O, and S" (wherein x is an a specified integer), for example, means that each heteroatom in the specified heterocyclenyl is independently selected from the specified selection of heteroatoms.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

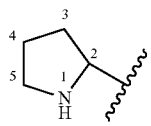

there is no —OH attached directly to carbons marked 2 and 5.

It should also be noted that tautomeric forms such as, for example, the moieties:

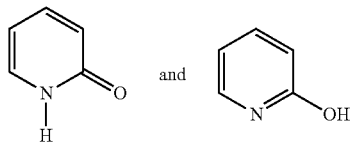 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkanoyl" refers to an alkyl —C(O)— group in which the alkyl group is as previously described. Non limiting examples of alkanoyl groups include methylcarbonyl and ethylcarbonyl. The bond to the parent moiety is through the carbonyl group.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. A non-limiting example of a suitable aralkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. A reference to a "stable compound' or "stable structure" means that the compound is sufficiently robust to survive isolation to a useful degree of purity from a reaction mixture, and to survive formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterized by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. In addition, any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) or a Pyrazolopyrimidine Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The compounds of Formula (I), and salts thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention. Various stereoisomers are discussed in J. Org. Chem. 35, 2849 (1970).

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. For instance those compounds labeled with positron-emitting isotopes like $^{11}C$ or $^{18}F$ can be useful for application in Positron Emission Tomography (PET) and those labeled with gamma ray emitting isotopes like $^{123}$I can be useful for application in Single Photon Emission Computed Tomography (SPECT). Further, substitution of compounds with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Additionally, isotopic substitution of a compound at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula (I), and of the salts, of the compounds of Formula (I), are intended to be included in the present invention.

The present invention further includes the compounds of Formula (I) in all their isolated forms. For example, the above-identified compounds are intended to encompass all forms of the compounds such as, any solvates, hydrates, stereoisomers, and tautomers thereof.

The following abbreviations are used below and have the following meanings: BINAP is racemic-2,2'-bis(diphenylphosphino)-1,1'-binaphthyl; CDI is carbonyl diimidazole; CSA is camphorsulfonic acid; DBU is 1,8-diazabicyclo[5.4.0]undec-7-ene; DBN is 1,5-diazabicyclo[4.3.0]non-5-ene; DCC is dicyclohexylcarbodiimide; DCM is dichloromethane; Dibal-H is diisobutylaluminum hydride; DIPEA is N,N-Diisopropylethylamine; DMAP is dimethylaminopyridine; DME is dimethoxyethane; DMF is dimethylformamide; DMPU is N,N'-Dimethylpropyleneurea; dppf is diphenylphosphinoferrocene; EDCI is 1-(3-dimethylaminopropyl)-3-ethylcarbodiimide; EtOAc is ethyl acetate; FABMS is fast atom bombardment mass spectrometry; HATU is O-(7-azabenzotriazol-1-yl)-N,N,N',N'-tetramethyluronium hexafluorophosphate; HOBT is 1-hydroxybenzotriazole; HOOBt is 3-hydroxy-1,2,3-benzotriazin-4(3H)-one; HPLC is high performance liquid chromatography; HRMS is high resolution mass spectrometry; Hunig's base is N,N-diisopropylethylamine;

LAH is lithium aluminum hydride; LDA is lithium diisopropylamide; LRMS is low resolution mass spectrometry; m-CPBA is m-chloroperbenzoic acid; MeOH is methanol; NaBH(OAc)$_3$ is sodium triacetoxyborohydride; NaHMDS is sodium hexamethyldisilazane; NH$_4$OAc is ammonium acetate; p-TsOH is p-toluenesulfonic acid; p-TsCl is p-toluenesulfonyl chloride; PPTS is pyridinium p-toluenesulfonate; PYBROP is bromotripyrrolidinophosphonium hexafluorophosphate; RT is room temperature; SEM is β-(trimethylsilyl)ethoxy]methyl; SEMCl is β-(trimethylsilyl)ethoxy]methyl chloride; THF is tetrahydrofuran; TLC is thin-layer chromatography; TMAD is N,N,N',N'-tetramethylazodicarboxamide; Tr is triphenylmethyl; and Tris is tris(hydroxymethyl)aminomethane.

Compounds of Formula (I)

In one aspect, the present invention provides compounds of Formula (I)

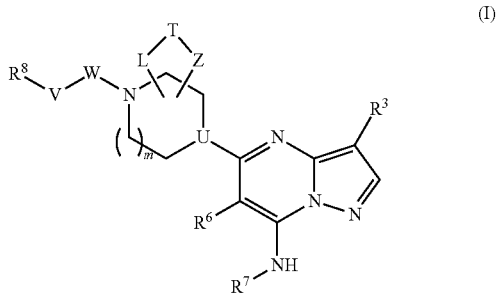

or a pharmaceutically acceptable salt thereof, wherein
U is N, CH, or C($R^{13}$);
$R^{13}$ is selected from the group consisting of
  $C_1$-$C_6$ alkyl, hydroxy, —$OR^{16}$, —$N(R^{14})(R^{15})$, —$N(R^{14})$—C(O)—$R^{16}$, —$N(R^{14})$—S(O)—$R^{16}$, —$N(R^{14})$—S(O)$_2R^{16}$, —$N(R^{14})$—C(O)—$N(R^{14})(R^{15})$, $C_3$-$C_8$ cycloalkyl, $C_6$-$C_{10}$ mono or bicyclic aryl, —C(O)$R^{16}$, —C(O)O$R^{16}$, —C(O)N($R^{14}$)($R^{15}$), —S(O)$R^{16}$, —S(O)$_2R^{16}$, —S(O)—N($R^{14}$)($R^{15}$), —S(O)$_2$—N($R^{14}$)($R^{15}$), —O—C(O)O$R^{17}$, —O—C(O)N($R^{17}$)($R^{18}$),
  3- to 8-membered monocyclic heterocyclyl and having one to three heteroatoms selected from the group consisting of N, O, and S; and
  $C_5$-$C_{10}$ mono or bicyclic heteroaryl and having one to three heteroatoms selected from the group consisting of N, O, and S;
  $R^{14}$ and $R^{15}$ are independently selected from the group consisting of H, $C_1$-$C_6$ alkyl, $C_3$-$C_8$ cycloalkyl, and phenyl;
  $R^{16}$ is independently selected from the group consisting of $C_1$-$C_6$ alkyl, $C_3$-$C_8$ cycloalkyl, and phenyl;
  $R^{17}$ and $R^{18}$ are independently selected from the group consisting of $C_1$-$C_6$ alkyl, $C_3$-$C_8$ cycloalkyl, $C_6$-$C_{10}$ mono or bicyclic aryl, 3- to 8-membered monocyclic heterocyclyl, and $C_5$-$C_{10}$ mono or bicyclic heteroaryl;
L and Z are bonded to any two carbon atoms of the ring comprising U and are independently selected from the group consisting of $CH_2$, $C(H)(R^1)$, $C(R^1)(R^2)$, $N(R^1)$, C(O), O, S, S(O), and S(O)$_2$,
T is absent such that L is bonded directly to Z, or T is selected from the group consisting of C(O), O, S, N($R^1$), S(O), S(O)$_2$, and $C_1$-$C_4$ alkylene, wherein said alkylene of T is unsubstituted or substituted with 1 to 2 moieties, which moieties are independently selected from the group consisting of $C_1$-$C_3$ alkyl, halo, hydroxy, $C_1$-$C_3$ alkoxy, amino, $C_1$-$C_3$ alkylamino and $C_1$-$C_3$ dialkylamino;
m is 0 or 1;
n is independently 0, 1, 2, 3 or 4;
$R^1$ and $R^2$ are independently selected from the group consisting of H, $C_1$-$C_3$ alkyl, halo, hydroxy, $C_1$-$C_3$ alkoxy, amino, $C_1$-$C_3$ alkylamino and $C_1$-$C_3$ dialkylamino;
W is absent, or W is selected from the group consisting of C(O), C(N), S(O), S(O)$_2$, $C_1$-$C_4$ alkylene, $C_3$-$C_8$ cycloalkyl, phenyl, 5- to 6-membered heteroaryl, and 3- to 8-membered heterocyclyl;
V is absent, or V is selected from the group consisting of C(O), O, S, N(H), N($C_1$-$C_3$ alkyl), N($C_1$-$C_3$ alkyl), N($C_3$-$C_8$ cycloalkyl), S(O), S(O)$_2$, and $C_1$-$C_4$ alkylene;
or W and V together form a $C_3$-$C_8$ cycloalkyl, phenyl, 5- to 6-membered heteroaryl, or 3 to 8-membered heterocyclyl ring;

$R^8$ is selected from the group consisting of
(i) CN, $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, halo, $C_1$-$C_6$ haloalkyl, O—$C_1$-$C_6$ haloalkyl, —$NR^aR^b$, —$OR^a$, carboxy, 5- to 6-membered heteroaryl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;
(ii) 3- to 8-membered heterocyclyl wherein said heterocyclyl of $R^8$ is unsubstituted or substituted with one to three moieties independently selected from the group consisting of halo, $C_1$-$C_6$ alkyl, $C_1$-$C_6$ haloalkyl, O—$C_1$-$C_6$ haloalkyl, $C_1$-$C_6$ alkoxy, cyano, hydroxy, —$(CR^aR^b)_nOR^a$, —$(CR^aR^b)_nNR^aR^b$, —$(CR^aR^b)_nNR^aC(O)R^b$, —$(CR^aR^b)_nC(O)NR^aR^b$, amino, $C_1$-$C_6$ alkylamino, and $C_1$-$C_6$ dialkylamino;
(iii) $C_6$-$C_{10}$ aryl or 5- to 10-membered heteroaryl, wherein said aryl or heteroaryl of $R^8$ is unsubstituted or is substituted with one to three moieties independently selected from the group consisting of 5- to 10-membered heterocyclyl, halo, $C_1$-$C_6$ haloalkyl, haloalkyl, $C_1$-$C_6$ alkyl, $C_1$-$C_6$ alkoxy, cyano, hydroxy, —$(CR^aR^b)_nOR^a$, —$(CR^aR^b)_nNR^aR^b$, —$(CR^aR^b)_nNR^aC(O)R^b$, —$(CR^aR^b)_nC(O)NR^aR^b$, amino, $C_1$-$C_6$ alkylamino, and $C_1$-$C_6$ dialkylamino,
wherein said heterocyclyl is optionally substituted with one to three moieties independently selected from the group consisting of OH, $NH_2$ and $C_1$-$C_6$ alkyl; and
(iv) —OH, —$OR^a$, —$OR^aOR^b$, —$NR^aOR^b$, —$NR^aR^b$, —$C(O)NR^aR^b$, —$NR^aC(O)R^b$, $C(=N-R^a)NR^aR^b$;

$R^a$ and $R^b$ are independently selected from H, halogen, OH, CN, $C_1$-$C_6$ alkoxy, $C_1$-$C_6$ haloalkyl and $C_1$-$C_6$ alkyl, wherein the alkyl is optionally substituted with one to three moieties selected from OH, $NH_2$, $C_1$-$C_3$ alkylamino, and $C_1$-$C_3$ dialkylamino and $C_1$-$C_3$ alkoxy;

$R^3$ is selected from the group consisting of H, $C_1$-$C_6$ alkyl, $C_1$-$C_6$ alkenyl, $C_1$-$C_6$ alkynyl, halo-$C_1$-$C_6$alkyl, —$CF_3$, —$C(O)R^9$, $C_6$-$C_{12}$aryl, $C_3$-$C_8$cycloalkyl, $C_3$-$C_3$cycloalkenyl, 5- to 10-membered heteroaryl, 5- to 10-membered heterocyclyl, 5- to 10-membered heterocyclenyl, $C_6$-$C_{12}$aryl$C_1$-$C_6$alkyl, $C_3$-$C_8$cycloalkyl$C_1$-$C_6$alkyl, $C_3$-$C_8$cycloalkenyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenylalkyl,
wherein each of said alkyl, alkenyl, alkynyl, aryl, cycloalkyl, cycloalkenyl, heteroaryl, heterocyclyl, heterocyclenyl, arylalkyl, cycloalkylalkyl, cycloalkenylalkyl, heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_1$-$C_6$alkenyl, $C_1$-$C_6$alkynyl, $C_3$-$C_{10}$cycloalkyl, —$CF_3$, —CN, —CN—$R^{25}$, —C(O)OH, —$(CR^aR^b)_nC(O)OH$, —$OCF_3$, —$(CR^aR^b)_nOR^9$, —$(CR^aR^b)_nC(O)R^9$, —$(CR^aR^b)_nNR^{10}R^9$, —$(CR^aR^b)_nNR^{10}$—$NR^{10}R^9$, —$(CR^aR^b)_nNR^{10}$—$NR^{10}C(O)R^9$, —$(CR^aR^b)_nC(O)O$—$C_1$-$C_6$alkyl, —O- halo$C_1$-$C_6$alkyl, —$(CR^aR^b)_nC(O)NR^{10}R^9$, —$(CR^aR^b)_nC(=N)NR^{10}R^9$, —$(CR^aR^b)_nC(O)NR^{10}S(O)_2R^9$, —$(CR^aR^b)_nNR^{10}C(O)R^9$, —$(CR^aR^b)_nNR^{10}C(O)OR^9$, —$(CR^aR^b)_nNR^{10}C(O)NR^{10}R^9$, —$(CR^aR^b)_nS(O)_2NR^{10}R^9$, —$(CR^aR^b)_nS(O)_2NR^{10}C(O)R^9$, —$(CR^aR^b)_nNR^{10}S(O)_2R^9$, —$(CR^aR^b)_nSR^9$, —$(CR^aR^b)_nS(O_2)R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl, wherein each of said alkyl, alkenyl, alkynyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, $C_1$-$C_6$hydroxyalkyl, —$(CR^aR^b)_{nOR}{}^9$, —$(CR^aR^b)_nC(O)R^9$, —$(CR^aR^b)_nNR^{10}R^9$, —$(CR^aR^b)_nC(O)O$—$C_1$-$C_6$alkyl, —$(CR^aR^b)_nC(O)NR^{10}R^9$, —$(CR^aR^b)_nNR^{10}C(O)R^9$, —$(CR^aR^b)_nS(O_2)NR^{10}R^9$, —$(CR^aR^b)_nNR^{10}S(O_2)R^9$, —$(CR^aR^b)_nSR^9$, and —$(CR^aR^b)_nS(O_2)R^9$, $R^6$ is selected from the group consisting of H, —$CHR^{10}R^9$, —$(CR^aR^b)_nOR^{10}$, —$(CR^aR^b)_nNR^{10}R^9$, —$(CR^aR^b)_nSR^{10}$, —$(CR^aR^b)_nS(O)R^{10}$, —$(CR^aR^b)_nS(O_2)R^{10}$, —$(CR^b)_nC(O)C_1$-$C_6$alkyl, —$(CR^aR^b)_nC(O)NR^{10}R^9$, —$(CR^aR^b)_nC(O)OR^{10}$, —$(CR^aR^b)_nS(O_2)NR^{10}R^9$, —$(CR^aR^b)_nNR^{10}C(O)R^9$, —$(CR^aR^b)_nNR^{10}S(O_2)R^9$, $C_1$-$C_6$alkyl, halo-$C_1$-$C_6$alkyl, $C_1$-$C_6$alkoxy, halogen, hydroxyl, amino, —$(CR^aR^b)_nCN$, 5- to 10-membered heteroaryl, 5- to 10 membered heterocyclyl, $C_3$-$C_8$cycloalkyl and $C_6$-$C_{10}$aryl, wherein each of said heteroaryl, heterocyclyl, cycloalkyl and aryl can be unsubstituted or substituted with one to three moieties selected from the group consisting of $C_1$-$C_3$alkyl, $C_1$-$C_3$alkenyl, $C_1$-$C_3$alkynyl, $C_1$-$C_3$alkoxy, $C_1$-$C_3$alkylamino, $C_1$-$C_3$dialkylamino, amino, halo or OH;

$R^7$ is selected from the group consisting of H, OH, $OR^{10}$, $C_1$-$C_6$alkyl, $C_6$-$C_{10}$aryl, $C_6$-$C_{10}$aryl$C_1$-$C_6$alkyl, 5- to 10-membered heteroaryl, 5- to 10-membered heteroaryl$C_1$-$C_6$alkyl, $C_3$-$C_8$cycloalkyl, $C_3$-$C_8$cycloalkyl$C_1$-$C_6$alkyl, 5- to 10-membered heterocyclyl, 5- to 10-membered heterocyclyl$C_1$-$C_6$alkyl, 5- to 10-membered heterocyclenyl, 5- to 10-membered heterocyclenyl$C_1$-$C_6$alkyl, $C_1$-$C_6$alkenyl, $C_1$-$C_6$alkynyl, $C_6$-$C_{10}$aryl-S(O)$C_1$-$C_6$alkyl, —$S(O_2)C_1$-$C_6$alkyl, —$C(O)C_1$-$C_6$alkyl, —$C(O)NR^{10}R^9$, —$C(O)OR^{10}$ and —$S(O_2)NR^{10}R^9$, wherein each of said alkyl, aryl, arylalkyl, heteroaryl, heteroarylalkyl, cycloalkyl, cycloalkylalkyl, heterocyclyl, heterocyclylalkyl, heterocyclenyl, heterocyclenylalkyl, alkenyl and alkynyl can be unsubstituted or substituted with one to three moieties, which can be the same or different, each moiety being selected from the group consisting of halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^{10}R^9$, —$C(O)O$—$C_1$-$C_6$alkyl, —$C(O)NR^{10}R^9$, —$SR^9$, and —$S(O_2)R^9$;

$R^{10}$ and $R^9$ are independently selected from the group consisting of H, OH, $C_1$-$C_6$alkyl, $C_1$-$C_6$alkenyl, $C_1$-$C_6$alkynyl $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, alkenyl, alkynyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —$C(O)O$—$C_1$-$C_6$alkyl, —$C(O)NR^aR^b$, —$SR^a$, and —$S(O_2)R^a$; or $R^{10}$ and $R^9$ together with the nitrogen atom to which they are attached form a 3- to 6-membered heterocyclyl ring;

$R^{25}$ is independently selected from the group consisting of H, $C_3$-$C_8$cycloalkyl, $C_1$-$C_6$alkyl, wherein the alkyl or cycloalkyl is optionally substituted with $OR^a$, $OR^b$—$OR^a$.

The invention also provides compounds of formula I

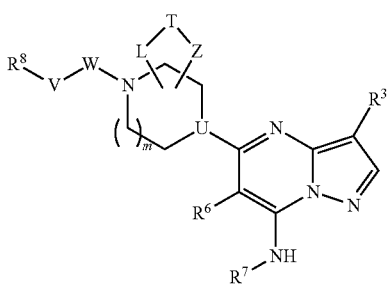

(I)

and pharmaceutically acceptable salts thereof, wherein

U is N, CH, or $C(R^{13})$;

$R^{13}$ is selected from the group consisting of
$C_1$-$C_6$ alkyl, hydroxy, —$OR^{16}$, —$N(R^{14})(R^{15})$, —$N(R^{14})$—C(O)—$R^{16}$, —$N(R^{14})$—S(O)—$R^{16}$, —$N(R^{14})$—S(O)$_2R^{16}$, —$N(R^{14})$—C(O)—$N(R^{14})$ $(R^{15})$, $C_3$-$C_8$ cycloalkyl, $C_8$-$C_{10}$ mono or bicyclic aryl, —$C(O)R^{16}$, —$C(O)OR^{16}$, —$C(O)N(R^{14})(R^{15})$, —$S(O)R^{16}$, —$S(O)_2R^{16}$, —$S(O)$—$N(R^{14})(R^{15})$, —$S(O)_2$—$N(R^{14})(R^{15})$, —O—$C(O)OR^{17}$, —O—C(O)$N(R^{17})(R^{18})$, 3- to 8-membered monocyclic heterocyclyl and having one to three heteroatoms selected from the group consisting of N, O, and S; and $C_5$-$C_{10}$ mono or bicyclic heteroaryl and having one to three heteroatoms selected from the group consisting of N, O, and S;

$R^{14}$ and $R^{15}$ are independently selected from the group consisting of H, $C_1$-$C_8$ alkyl, $C_3$-$C_8$ cycloalkyl, and phenyl;

$R^{16}$ is independently selected from the group consisting of $C_1$-$C_6$ alkyl, $C_3$-$C_8$ cycloalkyl, and phenyl;

$R^{17}$ and $R^{18}$ are independently selected from the group consisting of $C_1$-$C_6$ alkyl, $C_3$-$C_8$ cycloalkyl, $C_8$-$C_{10}$ mono or bicyclic aryl, 3- to 8-membered monocyclic heterocyclyl, and $C_5$-$C_{10}$ mono or bicyclic heteroaryl;

L and Z are bonded to any two carbon atoms of the ring comprising U and are independently selected from the group consisting of $CH_2$, $C(H)(R^1)$, $C(R^1)(R^2)$, $N(R^1)$, C(O), O, S, S(O), and $S(O)_2$;

T is absent such that L is bonded directly to Z, or T is selected from the group consisting of C(O), O, S, $N(R^1)$, S(O), $S(O)_2$, and $C_1$-$C_4$ alkylene, wherein said alkylene of T is unsubstituted or substituted with 1 to 2 moieties, which moieties are independently selected from the group consisting of $C_1$-$C_3$ alkyl, halo, hydroxy, $C_1$-$C_3$ alkoxy, amino, $C_1$-$C_3$ alkylamino and $C_1$-$C_3$ dialkylamino;

m is 0 or 1;

$R^1$ and $R^2$ are independently selected from the group consisting of H, $C_1$-$C_3$ alkyl, halo, hydroxy, $C_1$-$C_3$ alkoxy, amino, $C_1$-$C_3$ alkylamino and $C_1$-$C_3$ dialkylamino;

W is absent, or W is selected from the group consisting of C(O), S(O), $S(O)_2$, $C_1$-$C_4$ alkylene, $C_3$-$C_8$ cycloalkyl, phenyl, 5- to 6-membered heteroaryl, and 3- to 8-membered heterocyclyl;

V is absent, or V is selected from the group consisting of C(O), O, S, N(H), $N(C_1$-$C_3$ alkyl), $N(C_1$-$C_3$ alkyl), $N(C_3$-$C_8$ cycloalkyl), S(O), $S(O)_2$, and $C_1$-$C_4$ alkylene;

or W and V together form a $C_3$-$C_8$ cycloalkyl, phenyl, 5- to 6-membered heteroaryl, or 3 to 8-membered heterocyclyl ring;

$R^8$ is selected from the group consisting of (i) $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, halo, trifluoromethyl, carboxy, 5- to 6-membered heteroaryl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;

(ii) 3- to 8-membered heterocyclyl wherein said heterocyclyl of $R^8$ is unsubstituted or substituted with one to three moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino;

(iii) $C_6$-$C_{10}$ aryl or 5- to 10-membered heteroaryl, wherein said aryl or heteroaryl of $R^8$ is unsubstituted or is substituted with one to three moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and (iv) —N(H)OH or —N(H)—$C_1$-$C_3$ alkoxy;

$R^3$ is H, $C_1$-$C_6$ alkyl, $C_1$-$C_6$ alkenyl, $C_1$-$C_6$ alkynyl, —C(O)$R^{10}$, $C_6$-$C_{12}$ aryl, $C_3$-$C_8$ cycloalkyl, $C_3$-$C_8$ cycloalkenyl, 5- to 10-membered heteroaryl, 3- to 8-membered heterocyclyl, 3- to 8-membered heterocyclenyl, $(C_6$-$C_{12})$aryl$(C_1$-$C_6)$alkyl, $(C_3$-$C_8)$cycloalkyl$(C_1$-$C_6)$alkyl, $(C_3$-$C_8)$cycloalkenyl$(C_1$-$C_6)$alkyl, (5- to 10-membered) heteroaryl$(C_1$-$C_6)$alkyl, (3- to 8-membered)heterocyclyl$(C_1$-$C_6)$alkyl, (3- to 8-membered) heterocyclenyl$(C_1$-$C_6)$alkyl, wherein said aryl, cycloalkyl, cycloalkenyl, heteroaryl, heterocyclyl, heterocyclenyl, arylalkyl, cycloalkylalkyl, cycloalkenylalkyl, heteroarylalkyl, heterocyclylalkyl, and heterocyclenylalkyl of $R^3$ is unsubstituted or substituted with one to three moieties independently selected from the group consisting of Y, halogen, $C_1$-$C_6$ alkyl, $C_3$-$C_{10}$ cycloalkyl, trifluoromethyl, cyano, —C(O)OH, —$(CH_2)_x$—C(O)OH, trifluoromethoxy, —$OR^{11}$, —C(O)$R^{10}$, —$NR^9R^{10}$, —$C(O)_2$-alkyl, —$C(O)NR^9R^{10}$, —$SR^{11}$, and —$S(O)_2R^{12}$;

Y is $C_6$-$C_{10}$ aryl or 5- to 10-membered heteroaryl, wherein said aryl or heteroaryl of Y is unsubstituted or substituted with one to five moieties independently selected from the group consisting of $^2$H, halo, cyano, hydroxy, amino, $C_1$-$C_6$ alkylamino, $C_1$-$C_6$ dialkylamino, trifluoromethyl, trifluoromethoxy, $C_1$-$C_6$ alkyl, $C_1$-$C_6$ hydroxyalkyl, and $C_1$-$C_6$ alkoxy; and each occurrence of $R^9$ is independently H, $C_1$-$C_6$ alkyl, $C_3$-$C_{10}$ cycloalkyl, phenyl, 5- to 6-membered heteroaryl or 3- to 8-membered heterocyclyl;

each occurrence of $R^{10}$ is independently H, $C_1$-$C_6$ alkyl, $C_3$-$C_{10}$ cycloalkyl, phenyl, 5- to 6-membered heteroaryl, or 3- to 8-membered heterocyclyl, or $R^9$ and $R^{10}$ together with the nitrogen atom to which they are attached form a 3- to 6-membered heterocyclyl ring;

each occurrence of $R^{11}$ is independently H, $C_1$-$C_6$ alkyl, $C_3$-$C_{10}$ cycloalkyl, phenyl, 5- to 6-membered heteroaryl, or 3- to 8-membered heterocyclyl;

each occurrence of $R^{12}$ is independently $C_1$-$C_6$ alkyl, $C_3$-$C_{10}$ cycloalkyl, phenyl, 5- to 6-membered heteroaryl, or 3- to 8-membered heterocyclyl; and x is an integer from 1 to 4;

$R^7$ is selected from the group consisting of H, $C_1$-$C_6$ alkyl, and $C_3$-$C_8$ cycloalkyl, wherein said alkyl or cycloalkyl of $R^7$ is unsubstituted or substituted with one to two moieties selected from the group consisting of halo, $C_1$-$C_3$ alkyl, $C_1$-$C_3$ alkoxy, amino, $C_1$-$C_3$ alkylamino, and $C_1$-$C_3$ dialkylamino; and $R^6$ is selected from the group consisting of H, halo, hydroxyl, cyano, $C_1$-$C_6$ alkyl, $C_1$-$C_6$ alkanoyl, $C_1$-$C_6$ alkylsulfonyl, alkylsulfinyl, alkoxy, $C_1$-$C_6$ haloalkyl, amino, $C_1$-$C_6$ alkylamino, $C_1$-$C_6$ dialkylamino, $C_3$-$C_8$ cycloalkyl, $C_6$-$C_{10}$ aryl, 5- to 10-membered heteroaryl, and 5- to 10-membered heterocyclyl, wherein each of said aryl, heteroaryl, and heterocyclyl of $R^6$ is unsubstituted or substituted with one to two moieties selected from the group consisting of halo, $C_1$-$C_3$ alkyl, $C_1$-$C_3$ alkoxy, amino, $C_1$-$C_3$ alkylamino, and $C_1$-$C_3$ dialkylamino.

The present invention provides Pyrazolopyrimidine Compounds having the Formula (I), or pharmaceutically acceptable salts thereof:

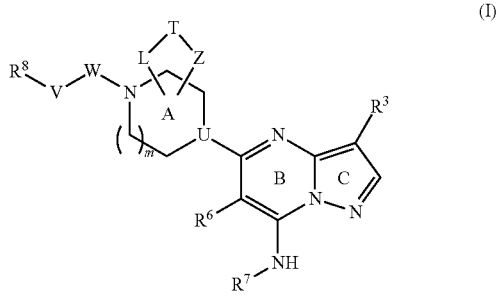

(I)

wherein L, T, Z, U, V, W, $R^3$, $R^6$, $R^7$, $R^8$, and m are as defined above for the compound of Formula (I). The compounds of Formulas (IA) and (IB) as are described in detail below are embodiments of the compound of Formula (I).

In the illustration of the compound of Formula (I) above, ring A is the ring comprising U, ring B is the pyrimidine ring of the pyrazolo[1,5-a]pyrimidine moiety, and ring C is the pyrazole ring of the pyrazolo[1,5-a]pyrimidine moiety.

In some embodiments of the compound of Formula (I), m is 1.

In certain embodiments of the compound of Formula (I), L and Z are bonded to any two non-vicinal carbon atoms of the ring comprising U, i.e., ring A. In specific embodiments, the carbon atoms of ring A to which L and Z are bonded have a single ring atom between them.

In some embodiments of the compound of Formula (I), U is N or CH.

In certain embodiments of the compound of Formula (I), U is N.

In other embodiments of the compound of Formula (I), U is CH.

In other embodiments of the compound of Formula (I), U is $C(R^{13})$. In some embodiments, $R^{13}$ is OH, —OC(O)OR$^{17}$, or —OC(O)N(R$^{17}$)(R$^{18}$). In specific embodiments, $R^{13}$ is OH.

In certain embodiments of the compound of Formula (I), T is unsubstituted $C_1$-$C_2$ alkylene.

In some embodiments of the compound of Formula (I), the group -L-T-Z— is selected from the group consisting of —CH$_2$OCH$_2$—, —CH$_2$CH$_2$OCH$_2$—, and $C_2$-$C_4$ alkylene, wherein said alkylene is unsubstituted or substituted with one to two moieties selected from the group consisting of $C_1$-$C_3$ alkyl, fluoro, and hydroxy.

In specific embodiments of the compound of Formula (I), m is 1; and
the group -L-T-Z— is selected from the group consisting of —CH$_2$OCH$_2$—, —CH$_2$CH$_2$OCH$_2$—, and $C_2$-$C_4$ alkylene, wherein said alkylene is unsubstituted or substituted with one to two moieties selected from the group consisting of $C_1$-$C_3$ alkyl, fluoro, and hydroxy.

In certain embodiments of the compound of Formula (I), W is C(O).

In some embodiments of the compound of Formula (I), V is absent.

In other embodiments of the compound of Formula (I), both W and V are absent such that $R^8$ is bonded directly to the nitrogen atom of ring A.

In specific embodiments of the compound of Formula (I), both W and V are absent, and $R^8$ is a 5- to 10-membered mono or bicyclic heteroaryl, wherein said heteroaryl of $R^8$ is unsubstituted or is substituted with one to three moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and wherein said heteroaryl of $R^8$ has from one to five heteroatoms selected from the group consisting N, O, and S.

In certain embodiments of the compound of Formula (IA), W is C(O), V is absent, and $R^8$ is —N(H)OH or —N(H)—$C_1$-$C_3$ alkoxy.

In specific embodiments of the compound of Formula (I), m is 1;
the group -L-T-Z— is selected from the group consisting of —CH$_2$OCH$_2$—, —CH$_2$CH$_2$OCH$_2$—, and $C_2$-$C_4$ alkylene, wherein said alkylene is unsubstituted or substituted with one to two moieties selected from the group consisting of $C_1$-$C_3$ alkyl, fluoro, and hydroxy;
W is C(O); and
V is absent.

In some embodiments of the compound of Formula (I), $R^8$ is selected from the group consisting of
(i) CN, $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, halo, $C_1$-$C_6$ haloalkyl, O—$C_1$-$C_6$ haloalkyl, —NR$^a$R$^b$, —OR$^a$, carboxy, 5- to 6-membered heteroaryl, —SO$_2$H, $C_1$-$C_6$ alkyl-C(O)—NH—, $C_1$-$C_6$ alkyl-SO$_2$—NH—, and $C_1$-$C_6$ alkyl-SO—NH—;
(ii) 3- to 8-membered heterocyclyl wherein said heterocyclyl of $R^8$ is unsubstituted or substituted with one to three moieties independently selected from the group consisting of halo, $C_1$-$C_6$ alkyl, $C_1$-$C_6$ haloalkyl, O—$C_1$-$C_6$ haloalkyl, $C_1$-$C_6$ alkoxy, cyano, hydroxy, —(CR$^a$R$^b$)$_n$OR$^a$, —(CR$^a$R$^b$)$_n$NR$^a$R$^b$, —(CR$^a$R$^b$)$_n$NR$^a$C(O)R$^b$, —(CR$^a$R$^b$)$_n$C(O)NR$^a$R$^b$, amino, $C_1$-$C_6$ alkylamino, and $C_1$-$C_6$ dialkylamino;
(iii) $C_6$-$C_{10}$ aryl or 5- to 10-membered heteroaryl, wherein said aryl or heteroaryl of $R^8$ is unsubstituted or is substituted with one to three moieties independently selected from the group consisting of 5- to 10-membered heterocyclyl, halo, $C_1$-$C_6$ haloalkyl, haloalkyl, $C_1$-$C_6$ alkyl, $C_1$-$C_6$ alkoxy, cyano, hydroxy, —(CR$^a$R$^b$)$_n$OR$^a$, —(CR$^a$R$^b$)$_n$NR$^a$R$^b$, —(CR$^a$R$^b$)$_n$NR$^a$C(O)R$^b$, —(CR$^a$R$^b$)$_n$C(O)NR$^a$R$^b$, amino, $C_1$-$C_6$ alkylamino, and $C_1$-$C_6$ dialkylamino,
wherein said heterocyclyl is optionally substituted with one to three moieties independently selected from the group consisting of OH, NH$_2$ and $C_1$-$C_6$ alkyl; and
(iv) —OH, —OR$^a$, —OR$^a$OR$^b$, —NR$^a$OR$^b$, —NR$^a$R$^b$, —C(O)NR$^a$R$^b$, —NR$^a$C(O)R$^b$, C(=N—R$^a$)NR$^a$R$^b$,
$R^a$ and $R^b$ are independently selected from H, halogen, OH, CN, $C_1$-$C_6$ alkoxy, $C_1$-$C_6$ haloalkyl and $C_1$-$C_6$ alkyl, wherein the alkyl is optionally substituted with one to three moieties selected from OH, NH$_2$, $C_1$-$C_3$ alkylamino, and $C_1$-$C_3$ dialkylamino and $C_1$-$C_3$ alkoxy;

In some embodiments of the compound of Formula (I), $R^8$ is selected from the group consisting of (i) $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, fluoro, trifluoromethyl, carboxy, tetrazolyl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;

(ii) 5- to 6-membered heterocyclyl containing 1 to 3 heteroatoms selected from the group consisting of N, O, S, and $S(O)_2$ wherein said heterocyclyl of $R^8$ is unsubstituted or substituted with one to two moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino; and (iii) phenyl or 5- to 6-membered heteroaryl containing 1 to 3 heteroatoms selected from the group consisting of N, O, and S, wherein said phenyl or heteroaryl of $R^8$ is unsubstituted or is substituted with one to two moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino;

In some embodiments of the compound of Formula (I), $R^6$ is selected from the group consisting of H, —$CHR^{10}R^9$, —$(CR^aR^b)_nOR^{10}$, —$(CR^aR^b)$, $NR^{10}R^9$, —$(CR^aR^b)_nSR^{10}$, —$(CR^aR^b)_nS(O)R^{10}$, —$(CR^aR^b)_nS(O_2)R^{10}$, —$(CR^aR^b)_nC(O)C_1$-$C_6$alkyl, —$(CR^aR^b)_nC(O)NR^{10}R^9$, —$(CR^aR^b)_nC(O)OR^{10}$, —$(CR^aR^b)_nS(O_2)NR^{10}R^9$, —$(CR^aR^b)_nNR^{10}C(O)R^9$, —$(CR^aR^b)_nNR^{10}S(O_2)R^9$, $C_1$-$C_6$alkyl, halo-$C_1$-$C_6$alkyl, $C_1$-$C_6$alkoxy, halogen, hydroxyl, amino, —$(CR^aR^b)_nCN$, 5- to 10-membered heteroaryl, 5- to 10 membered heterocyclyl, $C_3$-$C_8$cycloalkyl and $C_6$-$C_{10}$aryl, wherein each of said heteroaryl, heterocyclyl, cycloalkyl and aryl can be unsubstituted or substituted with one to three moieties selected from the group consisting of $C_1$-$C_3$alkyl, $C_1$-$C_3$alkenyl, $C_1$-$C_3$alkynyl, $C_1$-$C_3$alkoxy, $C_1$-$C_3$alkylamino, $C_1$-$C_3$dialkylamino, amino, halo or OH; wherein all other substituents are as defined above.

In certain embodiments of the compound of Formula (I), $R^6$ is selected from the group consisting of H, $C_1$-$C_6$ alkyl, $C_1$-$C_6$ alkanoyl, cyano, $C_1$-$C_6$ alkylsulfonyl, cyano, halo, hydroxy, amino, $C_1$-$C_6$ alkylamino, and $C_1$-$C_6$ dialkylamino.

In certain embodiments of the compound of Formula (I), $R^6$ is selected from the group consisting of H, $C_1$-$C_6$ alkyl, $C_1$-$C_6$ alkanoyl, cyano, $C_1$-$C_6$ alkylsulfonyl, $C_3$-$C_8$ cycloalkylsulfonyl, $C_3$-$C_8$ cycloalkyl, cyano, halo, hydroxy, amino, $C_1$-$C_6$ alkylamino, and $C_1$-$C_6$ dialkylamino.

In certain embodiments of the compound of Formula (I), $R^6$ is selected from the group consisting of H, halo, $C_1$-$C_3$ alkyl, $C_1$-$C_3$ alkanoyl, cyano, $C_1$-$C_3$ alkylsulfonyl, $C_3$-$C_4$ cycloalkylsulfonyl, $C_3$-$C_4$ cycloalkyl, wherein the $C_1$-$C_3$ alkyl or $C_3$-$C_4$ cycloalkyl is optionally substituted with $C_1$-$C_3$alkenyl, $C_1$-$C_3$alkynyl, cyano, halo, hydroxy or amino.

In certain embodiments of the compound of Formula (I), $R^6$ is selected from the group consisting of H, halo, $C_1$-$C_3$ alkyl, —C(O)Me, —$S(O_2)$Me, —$S(O_2)$cyclopropyl, cyano, cyclopropyl, wherein the $C_1$-$C_3$ alkyl or cyclopropyl is optionally substituted with =$CH_2$ or hydroxy.

In specific embodiments of the compound of Formula (I), $R^6$ is selected from the group consisting of halo, $C_1$-$C_3$ alkanoyl, $C_1$-$C_3$ alkylsulfonyl, and cyano.

In specific embodiments of the compound of Formula (I), $R^6$ is selected from the group consisting of $C_1$-$C_3$ alkanoyl, $C_1$-$C_3$ alkylsulfonyl, and cyclopropyl.

In specific embodiments of the compound of Formula (I), $R^7$ is selected from the group consisting of H, OH, $OR^{10}$, $C_1$-$C_6$alkyl, $C_6$-$C_{10}$aryl, $C_6$-$C_{10}$aryl$C_1$-$C_6$alkyl, 5- to 10-membered heteroaryl, 5- to 10-membered heteroaryl$C_1$-$C_6$alkyl, $C_3$-$C_8$cycloalkyl, $C_3$-$C_8$cycloalkyl$C_1$-$C_6$alkyl, 5- to 10-membered heterocyclyl, 5- to 10-membered heterocyclenyl, 5- to 10-membered heterocyclyl$C_1$-$C_6$alkyl, 5- to 10-membered heterocyclenyl$C_1$-$C_6$alkyl, $C_1$-$C_6$alkenyl, $C_1$-$C_6$alkynyl, $C_6$-$C_{10}$aryl-$S(O)C_1$-$C_6$alkyl, —$S(O_2)C_1$-$C_6$alkyl, —$C(O)C_1$-$C_6$alkyl, —$C(O)NR^{10}R^9$, —$C(O)OR^{10}$ and —$S(O_2)NR^{10}R^9$, wherein each of said alkyl, aryl, arylalkyl, heteroaryl, heteroarylalkyl, cycloalkyl, cycloalkylalkyl, heterocyclyl, heterocyclylalkyl, heterocyclenyl, heterocyclenylalkyl, alkenyl and alkynyl can be unsubstituted or substituted with one to three moieties, which can be the same or different, each moiety being selected from the group consisting of halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^{10}R^9$, —$C(O)O$—$C_1$-$C_6$alkyl, —$C(O)NR^{10}R^9$, —$SR^9$, and —$S(O_2)R^9$; wherein all other substituents are as defined above.

In some embodiments of the compound of Formula (I), $R^7$ is H.

In certain embodiments of the compound of Formula (I), $R^3$ is selected from the group consisting of $C_1$-$C_6$ alkyl, $C_1$-$C_6$alkenyl, $C_1$-$C_6$alkynyl, halo-$C_1$-$C_6$alkyl, —$CF_3$, —$C(O)R^9$, $C_6$-$C_{12}$aryl, $C_3$-$C_8$cycloalkyl, $C_3$-$C_8$cycloalkenyl, 5- to 10-membered heteroaryl, 5- to 10-membered heterocyclyl, 5- to 10-membered heterocyclenyl, $C_6$-$C_{12}$aryl$C_1$-$C_6$alkyl, $C_3$-$C_8$cycloalkyl$C_1$-$C_6$alkyl, $C_3$-$C_8$cycloalkenyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenylalkyl, wherein each of said alkyl, alkenyl, alkynyl, aryl, cycloalkyl, cycloalkenyl, heteroaryl, heterocyclyl, heterocyclenyl, arylalkyl, cycloalkylalkyl, cycloalkenylalkyl heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_1$-$C_6$alkenyl, $C_1$-$C_6$alkynyl, $C_3$-$C_{10}$cycloalkyl, —$CF_3$, —CN, —CN—$R^{25}$, —$C(O)OH$, —$(CR^aR^b)_nC(O)OH$, —$OCF_3$, —$(CR^aR^b)_nOR^9$, —$(CR^aR^b)_nC(O)R^9$, —$(CR^aR^b)_nNR^{10}R^9$, —$(CR^aR^{13})_nNR^{10}$—$NR^{10}R^9$, —$(CR^aR^b)_nNR^{10}$—$NR^{10}C(O)R^9$, —$(CR^aR^b)_nC(O)O$—$C_1$-$C_6$alkyl, —O- halo$C_1$-$C_6$alkyl, —$(CR^aR^b)_nC(O)NR^{10}R^9$, —$(CR^aR^b)_nC(=N)NR^{10}R^9$, —$(CR^aR^b)_nC(O)NR^{10}S(O)_2R^9$, —$(CR^aR^b)_nNR^{10}C(O)R^9$, —$(CR^aR^b)_nNR^{10}C(O)OR^9$, —$(CR^aR^b)_nNR^{19}C(O)NR^{19}R^9$, —$(CR^aR^b)_nS(O_2)NR^{19}R^9$, —$(CR^aR^b)_nS(O_2)NR^{10}C(O)R^9$, —$(CR^aR^b)_nNR^{10}S(O_2)R^9$, —$(CR^aR^b)_nSR^9$, —$(CR^aR^b)_nS(O_2)R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl, wherein each of said alkyl, alkenyl, alkynyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, $C_1$-$C_6$hydroxyalkyl, —$(CR^aR^b)_nOR^9$, —$(CR^aR^b)_nC(O)R^9$, —$(CR^aR^b)_nNR^{10}R^9$, —$(CR^aR^b)_nC(O)O$—$C_1$-$C_6$alkyl, —$(CR^aR^b)_nC(O)NR^{10}R^9$, —$(CR^aR^b)_nNR^{10}C(O)R^9$, —$(CR^aR^b)_nS(O_2)NR^{10}R^9$, —$(CR^aR^b)_nNR^{10}S(O_2)R^9$, —$(CR^aR^b)_nSR^9$, and —$(CR^aR^b)_nS(O_2)R^9$;

$R^a$ and $R^b$ are independently selected from H, halogen, OH, $C_1$-$C_6$ alkoxy, $C_1$-$C_6$ haloalkyl and $C_1$-$C_6$ alkyl, wherein the alkyl is optionally substituted with one to three moieties selected from OH, $NH_2$, $C_1$-$C_3$ alkylamino, and $C_1$-$C_3$ dialkylamino and $C_1$-$C_3$ alkoxy;

$R^{10}$ and $R^9$ are independently selected from the group consisting of H, OH, $C_1$-$C_6$alkyl, $C_1$-$C_6$alkenyl, $C_1$-$C_6$alkynyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, alkenyl, alkynyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —C(O)O—$C_1$-$C_6$alkyl, —C(O)$NR^aR^b$, —$SR^a$, and —$S(O_2)R^a$; or $R^{10}$ and $R^9$ together with the nitrogen atom to which they are attached form a 3- to 6-membered heterocyclyl ring;

$R^{25}$ is independently selected from the group consisting of H, $C_3$-$C_8$cycloalkyl, $C_1$-$C_6$alkyl, wherein the alkyl or cycloalkyl is optionally substituted with $OR^E$, $OR^b$—$OR^a$.

In one embodiment, $R^3$ is selected from $C_6$-$C_{12}$aryl and 5- to 6-membered heteroaryl, optionally substituted as defined above.

In certain embodiments of the compound of Formula (I), $R^3$ is 5- to 10-membered mono- or bicyclic aryl or heteroaryl, wherein said heteroaryl of $R^3$ contains from one to three heteroatoms selected from the group consisting of N, N(O), O, and S, and wherein said aryl or heteroaryl of $R^3$ is unsubstituted or substituted with one to three moieties independently selected from the group consisting of Y, halogen, $C_1$-$C_6$ alkyl, cyano, —C(O)OH, —C(O)$NH_2$, $C_1$-$C_6$ alkanoyl, trifluoromethyl, trifluoromethoxy, hydroxy, $C_1$-$C_6$ alkoxy, amino, $C_1$-$C_6$ alkylamino, and $C_1$-$C_6$ dialkylamino; and Y is phenyl or 5 to 6-membered heteroaryl, wherein said heteroaryl of Y contains 1 to 2 heteroatoms selected from the group consisting of N, N(O), O, and S; wherein Y is unsubstituted or substituted with one to two moieties independently selected from the group consisting of halogen, $C_1$-$C_6$ alkyl, —CN, —C(O)OH, —C(O)$NH_2$, —C(O)—$C_1$-$C_6$ alkyl, trifluoromethyl, trifluoromethoxy, hydroxy, $C_1$-$C_6$ alkoxy, amino, $C_1$-$C_6$ alkylamino, and $C_1$-$C_6$ dialkylamino;

with the proviso that when $R^3$ is bicyclic aryl or heteroaryl, said bicyclic aryl or heteroaryl is not substituted by Y.

In specific embodiments of the compound of Formula (I), $R^3$ is 5- to 10-membered mono- or bicyclic heteroaryl, wherein said heteroaryl of $R^3$ contains from 1 to 2 heteroatoms selected from the group consisting of N and N(O);

Y is phenyl or 5-membered heteroaryl, wherein said heteroaryl of Y contains 1 to 2 heteroatoms selected from the group consisting of N and S; wherein Y is unsubstituted or substituted with one to two moieties independently selected from the group consisting of halo, $C_1$-$C_3$ alkyl, $C_1$-$C_3$ hydroxyalkyl, and $C_1$-$C_3$ alkoxy.

In some embodiments of the compound of Formula (I), $R^9$ and $R^{10}$ are independently H or $C_1$-$C_3$ alkyl.

In certain embodiments of the compound of Formula (I), $R^{11}$ is H or $C_1$-$C_3$ alkyl.

In some embodiments of the compound of Formula (I), $R^{12}$ is $C_1$-$C_3$ alkyl.

In another aspect, the invention provides a compound of the Formula (IA)

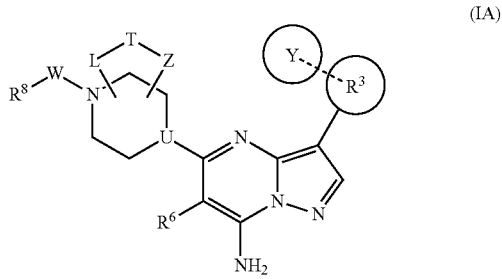

(IA)

wherein
U is N, CH, or $C(R^{13})$;
$R^{13}$ is selected from the group consisting of
$C_1$-$C_6$ alkyl, hydroxy, —$OR^{16}$, —$N(R^{14})(R^{15})$, —$N(R^{14})$—C(O)—$R^{16}$, —$N(R^{14})$—S(O)—$R^{16}$, —$N(R^{14})$—$S(O)_2R^{16}$, —$N(R^{14})$—C(O)—$N(R^{14})(R^{15})$, $C_3$-$C_8$ cycloalkyl, $C_6$-$C_{10}$ mono or bicyclic aryl, —C(O)$R^{16}$, —C(O)$OR^{16}$, —C(O)$N(R^{14})(R^{15})$, —S(O)$R^{16}$, —$S(O)_2R^{16}$, —S(O)—$N(R^{14})(R^{15})$, —$S(O)_2$—$N(R^{14})(R^{15})$, —O—C(O)$OR^{17}$, —O—C(O)$N(R^{17})(R^{18})$,
3- to 8-membered monocyclic heterocyclyl and having one to three heteroatoms selected from the group consisting of N, O, and S; and
$C_5$-$C_{10}$ mono or bicyclic heteroaryl and having one to three heteroatoms selected from the group consisting of N, O, and S;
$R^{14}$ and $R^{15}$ are independently selected from the group consisting of H, $C_1$-$C_6$ alkyl, $C_3$-$C_8$ cycloalkyl, and phenyl;
$R^{16}$ is independently selected from the group consisting of $C_1$-$C_6$ alkyl, $C_3$-$C_8$ cycloalkyl, and phenyl;
$R^{17}$ and $R^{18}$ are independently selected from the group consisting of $C_1$-$C_6$ alkyl, $C_3$-$C_8$ cycloalkyl, $C_6$-$C_{10}$ mono or bicyclic aryl, 3- to 8-membered monocyclic heterocyclyl, and $C_5$-$C_{10}$ mono or bicyclic heteroaryl;
L and Z are bonded to any two carbon atoms of the ring comprising U;
T is absent or present;
-L-T-Z— is selected from the group consisting of —$CH_2OCH_2$—, —$CH_2CH_2OCH_2$—, and $C_2$-$C_4$ alkylene, wherein said alkylene is unsubstituted or substituted with one to two moieties selected from the group consisting of $C_1$-$C_3$ alkyl, fluoro, and hydroxy;
W is C(O), S(O), $S(O)_2$, and $C_1$-$C_4$ alkylene;
$R^8$ is selected from the group consisting of
(i) $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, fluoro, trifluoromethyl, carboxy, tetrazolyl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;
(ii) 5- to 6-membered heterocyclyl containing 1 to 3 heteroatoms selected from the group consisting of N, O, S, and $S(O)_2$ wherein said heterocyclyl of $R^8$ is unsubstituted or substituted with one to two moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino;
(iii) phenyl or 5- to 6-membered heteroaryl containing 1 to 3 heteroatoms selected from the group consisting of N, O, and S, wherein said phenyl or heteroaryl of $R^8$ is unsubstituted or is substituted with one to two moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and (iv) —N(H)OH or —N(H)—$C_1$-$C_3$ alkoxy;

$R^3$ is 5- to 10-membered mono or bicyclic aryl or heteroaryl, wherein said heteroaryl of $R^3$ contains from one to three heteroatoms selected from the group consisting of N, N(O), O, and S, and wherein said aryl or heteroaryl of $R^3$ is unsubstituted or substituted with one to three moieties independently selected from the group consisting of halogen, $C_1$-$C_6$ alkyl, cyano, —C(O)OH, —C(O)NH$_2$, $C_1$-$C_6$ alkanoyl, trifluoromethyl, trifluoromethoxy, hydroxy, $C_1$-$C_6$ alkoxy, amino, $C_1$-$C_6$ alkylamino, and $C_1$-$C_6$ dialkylamino;

Y is phenyl or 5 to 6-membered heteroaryl, wherein said heteroaryl of Y contains 1 to 2 heteroatoms selected from the group consisting of N, N(O), O, and S; wherein Y is unsubstituted or substituted with one to two moieties independently selected from the group consisting of halogen, $C_1$-$C_6$ alkyl, —CN, —C(O)OH, —C(O)NH$_2$, —C(O)—$C_1$-$C_6$ alkyl, trifluoromethyl, trifluoromethoxy, hydroxy, $C_1$-$C_6$ alkoxy, amino, $C_1$-$C_6$ alkylamino, and $C_1$-$C_6$ dialkylamino;

or Y is absent when $R^3$ is bicyclic aryl or heteroaryl; and $R^6$ is selected from the group consisting of H, $C_1$-$C_6$ alkyl, $C_1$-$C_6$ alkanoyl, cyano, $C_1$-$C_6$ alkylsulfonyl, cyano, halo, hydroxy, amino, $C_1$-$C_6$ alkylamino, and $C_1$-$C_6$ dialkylamino;

or a pharmaceutically acceptable salt thereof.

In some embodiments of the compound of Formula (IA), L and Z are bonded to any two non-vicinal carbon atoms.

In certain embodiments of the compound of Formula (IA), -L-T-Z— is selected from the group consisting of —CH$_2$CH$_2$— and —CH$_2$OCH$_2$—;

In some embodiments of the compound of Formula (IA), U is N or CH.

In certain embodiments of the compound of Formula (IA), U is CH.

In other embodiments of the compound of Formula (IA), U is N.

In other embodiments of the compound of Formula (IA), U is C($R^{13}$). In some embodiments, $R^{13}$ is OH, —OC(O)O$R^{17}$, or —OC(O)N($R^{17}$)($R^{18}$) In specific embodiments, $R^{13}$ is OH.

In certain embodiments of the compound of Formula (IA), the group

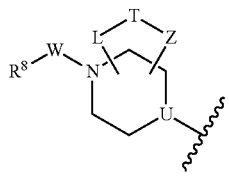

is selected from one of the following moieties:

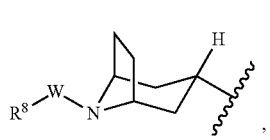

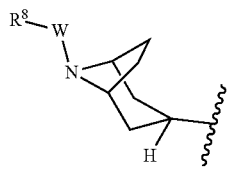

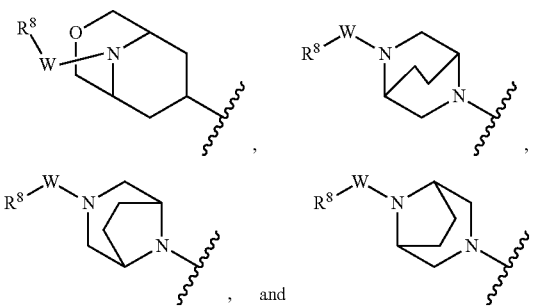

, and

In some embodiments of the compound of Formula (IA), W is C(O).

In specific embodiments of the compound of Formula (IA), $R^8$ is selected from the group consisting of

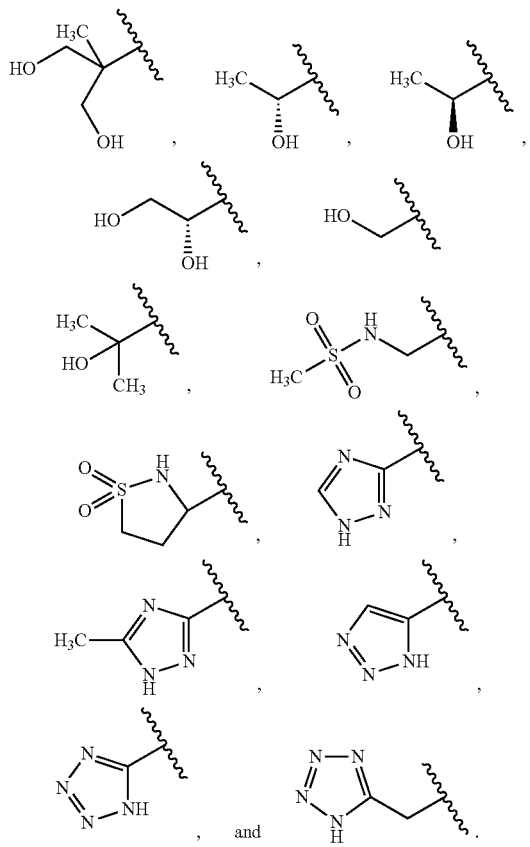

, and

In some embodiments of the compound of Formula (IA), the group

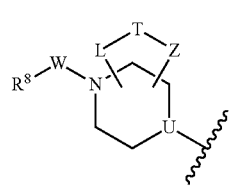

is selected from one of the following moieties:

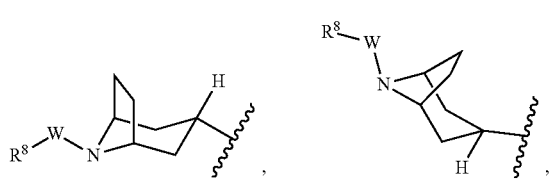
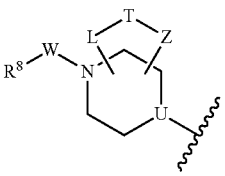
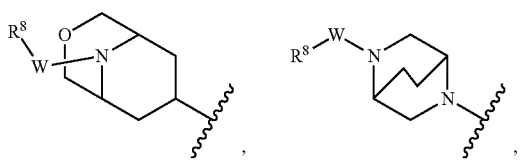
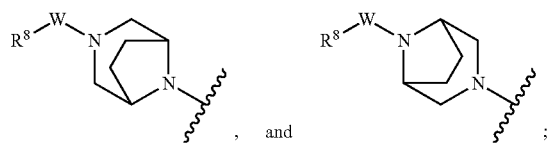
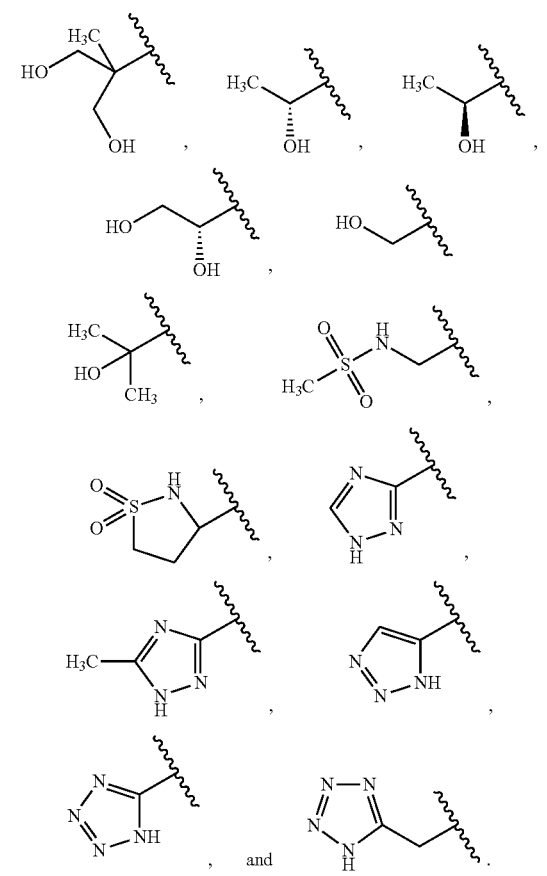

W is C(O); and
R⁸ is selected from the group consisting of

In some embodiments of the compound of Formula (IA), the group

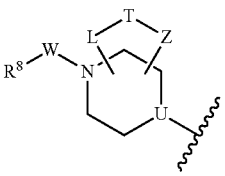
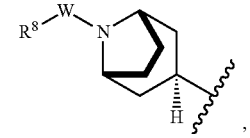

is

W is C(O). In another embodiment,

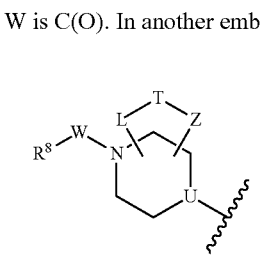
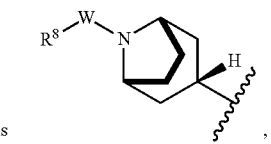

is

W is C(O).

In other embodiments of the compound of Formula (IA), W is C(O) and $R^8$ is —N(H)OH or —N(H)—$C_1$-$C_3$ alkoxy.

In certain embodiments of the compound of Formula (IA), $R^6$ is selected from the group consisting of halo, $C_1$-$C_3$ alkanoyl, $C_1$-$C_3$ alkylsulfonyl, and cyano.

In certain embodiments of the compound of Formula (IA), $R^6$ is selected from the group consisting of halo, $C_1$-$C_3$ alkanoyl, $C_1$-$C_3$ alkylsulfonyl, cyclopropyl, and cyano.

In specific embodiments of the compound of Formula (IA), $R^6$ is selected from the group consisting of $C_1$-$C_3$ alkanoyl, $C_1$-$C_3$ alkylsulfonyl, and cyclopropyl.

In some embodiments of the compound of Formula (IA), $R^3$ is 5- to 6-membered monocyclic heteroaryl, wherein said heteroaryl of $R^3$ contains from 1 to 2 heteroatoms selected from the group consisting of N and N(O), and is substituted by Y;

wherein Y is phenyl or 5-membered heteroaryl, wherein said heteroaryl of Y contains 1 to 2 heteroatoms selected from the group consisting of N and S; wherein Y is unsubstituted or substituted with one to two moieties independently selected from the group consisting of halo, $C_1$-$C_3$ alkyl, $C_1$-$C_3$ hydroxyalkyl, and $C_1$-$C_3$ alkoxy.

In some embodiments of the compound of Formula (I), (IA), (IB) or (IC), $R^3$ is pyrazolyl, pyrimidinyl, phenyl or pyridyl, unsubstituted or substituted with one to three moieties as defined above. In another embodiment, $R^3$ is phenyl or pyridyl, unsubstituted or substituted with one to three moieties as defined above.

In other embodiments of the compound of Formula (IA), $R^3$ is 9- to 10-membered bicyclic heteroaryl, wherein said heteroaryl of $R^3$ is unsubstituted or substituted with one to two moieties independently selected from the group consisting of halogen, $C_1$-$C_6$ alkyl, cyano, —C(O)OH, —C(O)NH_2, $C_1$-$C_6$ alkanoyl, trifluoromethyl, trifluoromethoxy, hydroxy, $C_1$-$C_6$ alkoxy, amino, $C_1$-$C_6$ alkylamino, and $C_1$-$C_6$ dialkylamino. In one embodiment, $R^3$ is isoquinolinyl optionally substituted.

In another aspect, the invention provides a compound of the Formula (IB)

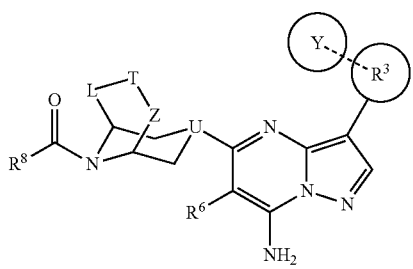
(IB)

wherein
U is N or CH;
-L-T-Z— is selected from the group consisting of —CH$_2$CH$_2$— and —CH$_2$OCH$_2$—;
R$^8$ is selected from the group consisting of

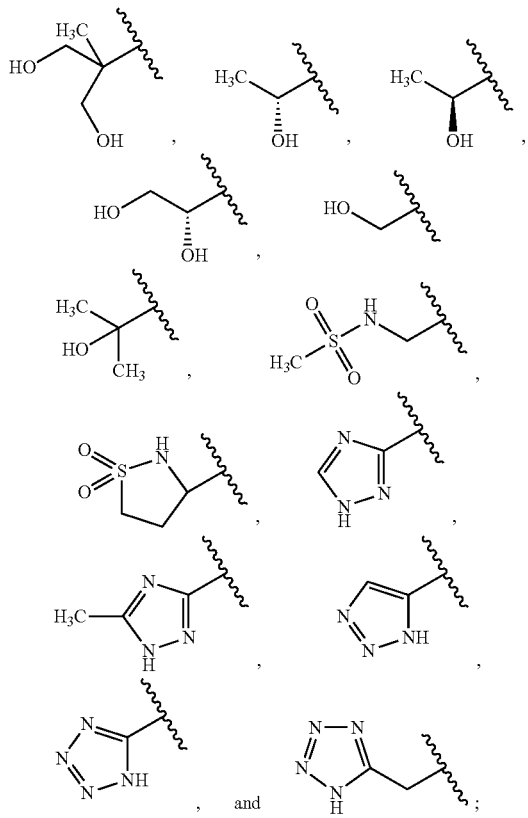

and

R$^3$ is 5- to 10-membered mono- or bicyclic heteroaryl, wherein said heteroaryl of R$^3$ contains from 1 to 2 heteroatoms selected from the group consisting of N and N(O);
Y is phenyl or 5-membered heteroaryl, wherein said heteroaryl of Y contains 1 to 2 heteroatoms selected from the group consisting of N and S; wherein Y is unsubstituted or substituted with one to two moieties independently selected from the group consisting of halo, C$_1$-C$_3$ alkyl, C$_1$-C$_3$ hydroxyalkyl, and C$_1$-C$_3$ alkoxy;
or Y is absent when R$^3$ is bicyclic heteroaryl; and
R$^6$ is selected from the group consisting of halo, C$_1$-C$_3$ alkanoyl, C$_1$-C$_3$ alkylsulfonyl, and cyano; or
a pharmaceutically acceptable salt thereof.

In certain embodiments of the compound of Formula (IB), U is N.
In other embodiments of the compound of Formula (IB), U is CH.
In specific embodiments of the compound of Formula (IB), the moiety

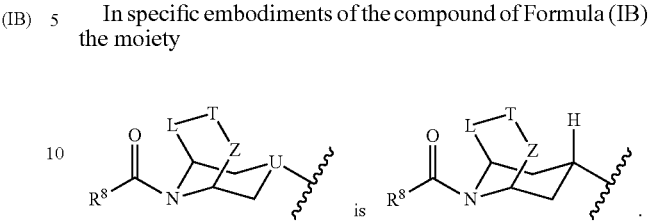

is

In other specific embodiments of the compound of Formula (IB), the moiety

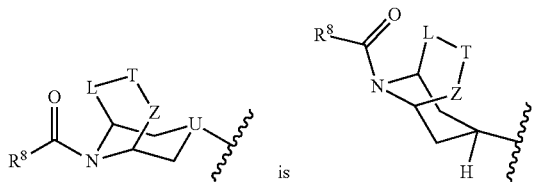

is

In certain embodiments of the compound of Formula (IB), R$^3$ is a 5- to 6-membered monocyclic heteroaryl containing from 1 to 2 heteroatoms selected from the group consisting of N and N(O).
In other embodiments of the compound of Formula (IB), R$^3$ is a 9- to 10-membered bicyclic heteroaryl containing from 1 to 2 nitrogen atoms wherein Y is absent.
The present invention also provides compounds under Formula (IC):

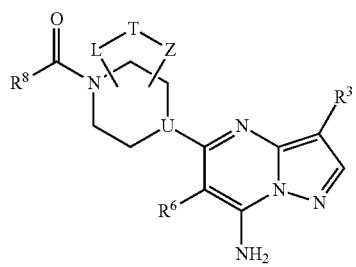
IC

Wherein U is N or CH;
wherein the group -L-T-Z— is selected from the group consisting of —CH$_2$OCH$_2$—, —CH$_2$CH$_2$OCH$_2$—, and C$_2$-C$_4$ alkylene, wherein said alkylene is unsubstituted or substituted with one to two moieties selected from the group consisting of C$_1$-C$_3$ alkyl, fluoro, and hydroxy;
R$^8$ is selected from the group consisting of
(i) CN, C$_1$-C$_6$ alkyl or C$_3$-C$_{10}$ cycloalkyl, wherein said alkyl or cycloalkyl of R$^8$ is unsubstituted or substituted with one to three moieties independently selected from the group consisting of hydroxy, C$_1$-C$_6$ alkoxy, halo, C$_1$-C$_6$ haloalkyl, O—C$_1$-C$_6$ haloalkyl, —NR$^a$R$^b$, —OR$^a$, carboxy, 5- to 6-membered heteroaryl, —SO$_2$H, C$_1$-C$_6$ alkyl-C(O)—NH—, C$_1$-C$_6$ alkyl-SO$_2$—NH—, and C$_1$-C$_6$ alkyl-SO—NH—;
(ii) 3- to 8-membered heterocyclyl wherein said heterocyclyl of R$^8$ is unsubstituted or substituted with one to three moieties independently selected from the group consisting of halo, C$_1$-C$_6$ alkyl, C$_1$-C$_6$ haloalkyl, O—$C_1$-$C_6$ haloalkyl, $C_1$-$C_6$ alkoxy, cyano, hydroxy, —$(CR^aR^b)_nOR^a$, —$(CR^aR^b)_nNR^aR^b$, —$(CR^aR^b)_n NR^aC(O)R^b$, —$(CR^aR^b)_nC(O)NR^aR^b$, amino, $C_1$-$C_6$ alkylamino, and $C_1$-$C_6$ dialkylamino;

(iii) $C_6$-$C_{10}$ aryl or 5- to 10-membered heteroaryl, wherein said aryl or heteroaryl of $R^8$ is unsubstituted or is substituted with one to three moieties independently selected from the group consisting of 5- to 10-membered heterocyclyl, halo, $C_1$-$C_6$ haloalkyl, haloalkyl, $C_1$-$C_6$ alkyl, $C_1$-$C_6$ alkoxy, cyano, hydroxy, —$(CR^aR^b)_nOR^a$, —$(CR^aR^b)_nNR^aR^b$, —$(CR^aR^b)_nNR^aC(O)R^b$, —$(CR^aR^b)_nC(O)NR^aR^b$, amino, $C_1$-$C_6$ alkylamino, and $C_1$-$C_6$ dialkylamino, wherein said heterocyclyl is optionally substituted with one to three moieties independently selected from the group consisting of OH, $NH_2$ and $C_1$-$C_6$ alkyl; and (iv) —OH, —$OR^a$, —$OR^aOR^b$, —$NR^aOR^b$, —$NR^aR^b$, —$C(O)NR^aR^b$, —$NR^aC(O)R^b$, $C(=N-R^a)NR^aR^b$;

$R^3$ is selected from the group consisting of:

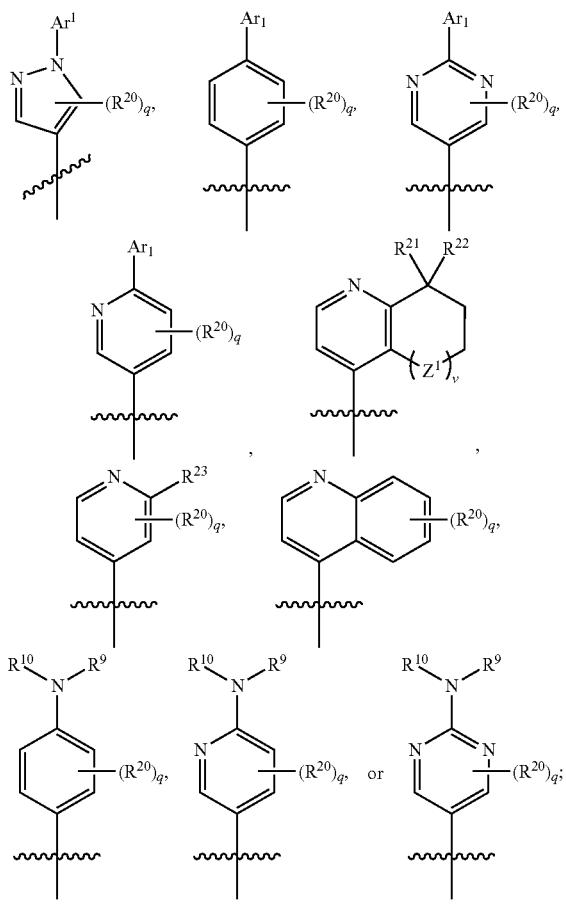

$Ar^1$ is $C_6$-$C_{10}$aryl or a 5- to 6-membered heteroaryl optionally substituted with one to three of $R^{19}$, which can be the same or different, each $R^{19}$ being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —$C(O)O$—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$;

$R^{20}$ is independently selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —$C(O)O$—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$;

$R^{21}$ and $R^{22}$ are independently selected from $C_1$-$C_3$ alkyl and OH;

$R^{23}$ is selected from $C_1$-$C_3$ hydroxyalkyl, $C_3$-$C_6$ hydroxycycloalkyl, —$NHC(O)C_1$-$C_3$ alkyl, —$NHC(O)OC_1$-$C_3$ alkyl, and —$NHC(O)NHC_1$-$C_3$ alkyl;

$R^a$ and $R^b$ are independently selected from H, halogen, OH, $C_1$-$C_6$ alkoxy, $C_1$-$C_6$ haloalkyl and $C_1$-$C_6$ alkyl, wherein the alkyl is optionally substituted with one to three moieties selected from OH, $NH_2$, $C_1$-$C_3$ alkylamino, and $C_1$-$C_3$ dialkylamino and $C_1$-$C_3$ alkoxy;

$Z^1$ is $CH_2$, NH, S or O;

q is 0, 1 or 2;

v is 0, or 1.

$R^6$ is selected from the group consisting of H, halo, $C_1$-$C_3$ alkyl, $C_1$-$C_3$ alkanoyl, cyano, $C_1$-$C_3$ alkylsulfonyl, $C_3$-$C_4$ cycloalkylsulfonyl, $C_3$-$C_4$ cycloalkyl, wherein the $C_1$-$C_3$ alkyl or $C_3$-$C_4$ cycloalkyl is optionally substituted with $C_1$-$C_3$alkenyl, $C_1$-$C_3$alkynyl, cyano, halo, hydroxy or amino. All other substituents are as defined above.

In one embodiment, $R^8$ is selected from the group consisting of amino, $NR^aR^b$, $C_1$-$C_3$ alkyl, $C_3$-$C_4$ hydroxycycloalkyl, $C_1$-$C_3$ hydroxyalkyl, 5-10 membered heteroaryl containing one or two N atoms, wherein said heteroaryl is optionally substituted with one or two $R^{24}$, which can be the same or different, selected from H, methyl, amino, OH and methylamino;

$R^a$ and $R^b$ are independently selected from H and $C_1$-$C_3$ alkyl;

$Z^1$ is $CH_2$ or O.

In the foregoing embodiments of the compound of Formula (I), (IA) or (IB), $R^3$ is selected from the group consisting of $C_6$-$C_{12}$aryl or 5- to 10-membered heteroaryl, wherein each of said aryl or heteroaryl, is unsubstituted or substituted with one to three moieties which can be the same or different, each moiety being selected from the group consisting of halogen, $C_1$-$C_6$alkyl, $C_1$-$C_6$alkenyl, $C_1$-$C_6$alkynyl, $C_3$-$C_{10}$cycloalkyl, —$CF_3$, —CN, —CN—$R^{25}$, —C(O)OH, —$(CR^aR^b)_nC(O)OH$, —$OCF_3$, —$(CR^aR^b)_nOR^9$, —$(CR^aR^b)_nC(O)R^9$, —$(CR^aR^b)_nNR^{19}R^9$, —$(CR^aR^b)_n NR^{19}$—$NR^{10}R^9$, —$(CR^aR^b)_nNR^{19}$—$NR^{10}C(O)R^9$, —$(CR^aR^b)_nC(O)O$—$C_1$-$C_6$alkyl, —$(CR^aR^b)_nC(O)NR^{10}R^9$, —$(CR^aR^b)_nC(=N)NR^{10}R^9$, —$(CR^aR^b)_nC(O)NR^{10}S(O)_2R^9$, —$(CR^aR^b)_nNR^{19}C(O)R^9$, —$(CR^aR^b)_nNR^{10}C(O)OR^9$, —$(CR^aR^b)_nNR^{10}C(O)NR^{10}R^9$, —$(CR^aR^b)_nS(O_2)NR^{10}R^9$, —$(CR^aR^b)_nS(O_2)NR^{19}C(O)R^9$, —$(CR^aR^b)_nNR^{10}S(O_2)R^9$, —$(CR^aR^b)_nSR^9$, —$(CR^aR^b)_nS(O_2)R^9$, wherein Y is selected from $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl, wherein each of said alkyl, alkenyl, alkynyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, $C_1$-$C_6$hydroxyalkyl, —$(CR^aR^b)_{nOR}^9$, —$(CR^aR^b)_nC(O)R^9$, —$(CR^aR^b)_nNR^{10}R^9$, —$(CR^aR^b)_nC(O)O$—$C_1$-$C_6$alkyl, —$(CR^aR^b)_nC(O)NR^{10}R^9$, —(CR$^a$R$^b$)$_n$NR$^{10}$C(O)R$^9$, —(CR$^a$R$^b$)$_n$S(O)$_2$NR$^{10}$R$^9$,
—(CR$^a$R$^b$)$_n$NR$^{10}$S(O)$_2$R$^9$, —(CR$^a$R$^b$)$_n$SR$^9$, and
—(CR$^a$R$^b$)$_n$S(O)$_2$R$^9$.

In some embodiments of the compound of Formula (I), (IA) or (IB), —R$^3$—Y is

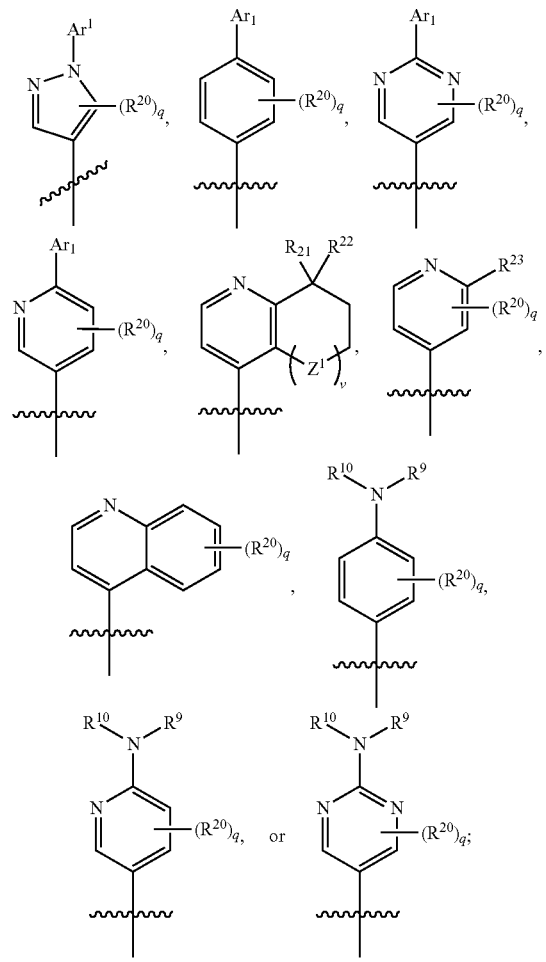

Ar$^1$ is C$_6$-C$_{10}$aryl or a 5- to 6-membered heteroaryl optionally substituted with one to three of R$^{19}$, which can be the same or different, each R$^{19}$ being selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$;
R$^{20}$ is independently selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$;
R$^9$ and R$^{10}$ are as defined above;
R$^{21}$ and R$^{22}$ are independently selected from C$_1$-C$_3$ alkyl and OH;
R$^{23}$ is selected from C$_1$-C$_3$ hydroxyalkyl, C$_3$-C$_5$ hydroxycycloalkyl, —NHC(O)C$_1$-C$_3$ alkyl, —NHC(O)OC$_1$-C$_3$ alkyl, and —NHC(O)NHC$_1$-C$_3$ alkyl;
R$^a$ and R$^b$ are independently selected from H, halogen, OH, C$_1$-C$_6$ alkoxy, C$_1$-C$_6$ haloalkyl and C$_1$-C$_6$ alkyl, wherein the alkyl is optionally substituted with one to three moieties selected from OH, NH$_2$, C$_1$-C$_3$ alkylamino, and C$_1$-C$_3$ dialkylamino and C$_1$-C$_3$ alkoxy;
Z$^1$ is CH$_2$, NH, S or O;
q is 0, 1 or 2;
v is 0, or 1.

In one embodiment, Ar$^1$ is phenyl or a 5- to 6-membered heteroaryl optionally substituted. In a further embodiment, Ar$^1$ is phenyl, pyrazolyl, pyrimidinyl, pyridyl, triazolyl, pyrolyl, thienyl, imidazolyl, pyrazinyl or thiazolyl optionally substituted with one to three of R$^{19}$. In a another embodiment, Ar$^1$ is phenyl, pyridyl or imidazolyl optionally substituted with one to three of R$^{19}$. In another embodiment, Ar$^1$ is phenyl or imidazolyl optionally substituted.

In one embodiment, in the foregoing embodiments, R$^{19}$ and R$^{20}$ are independently selected from the group consisting of halogen, CN, C$_1$-C$_2$alkyl, haloC$_1$-C$_2$alkyl, C$_1$-C$_2$alkoxy, O-haloC$_1$-C$_2$alkyl. In one embodiment, in the foregoing embodiments, R$^{19}$ and R$^{20}$ are independently selected from the group consisting of F, CN, C$_1$-C$_2$alkyl, fluoroC$_1$-C$_2$alkyl, O-fluoroC$_1$-C$_2$alkyl. In one embodiment, R$^{19}$ is F or methyl. In another embodiment, R$^{20}$ is F or methyl.

In one embodiment, R$^{23}$ is

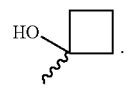

In one embodiment, R$^9$ is H and R$^{10}$ is cyclopropyl, cyclobutyl or cyclopentyl.

In another embodiment, R$^a$ and R$^b$ are independently selected from H and C$_1$-C$_3$ alkyl.

In some embodiments of the compound of Formula (I), (IA), (IB) or (IC), —R$^3$—Y (I, IA, IB), or —R$^3$ (IC) is selected from the group consisting of,

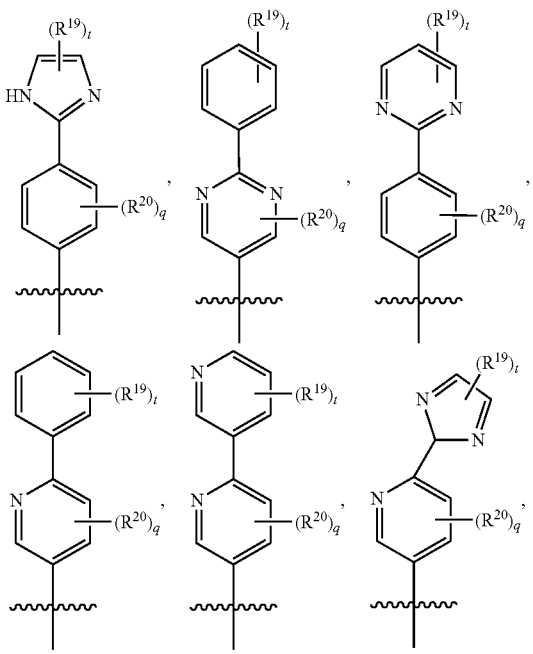

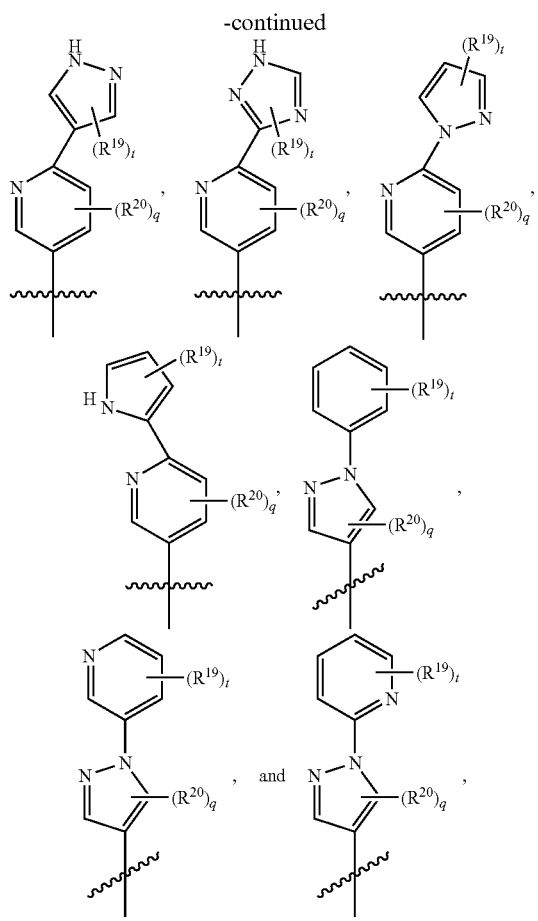

and $R^{19}$, $R^{20}$ q are defined above; t is 0, 1 or 2.

In another embodiment, —$R^3$—Y is selected from the group consisting of,

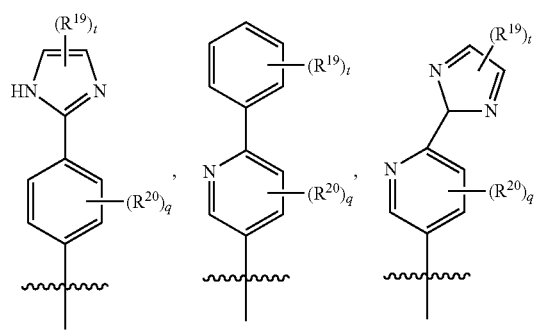

and t, q, $R^{19}$ and $R^{20}$ are defined above.

In specific embodiments of the compound of Formula (I), (IA), (IB) or (IC), $R^6$ is selected from the group consisting of H, —CHR$^a$R$^b$, —(CR$^a$R$^b$)$_n$OR$^a$, —(CR$^a$R$^b$)$_n$NR$^a$R$^b$, —(CR$^a$R$^b$)$_n$SR$^a$, —(CR$^a$R$^b$)$_n$S(O)R$^a$, —(CR$^a$R$^b$)$_n$S(O$_2$)R$^a$, —(CR$^a$R$^b$)$_n$C(O)C$_1$-C$_6$alkyl, —(CR$^a$R$^b$)$_n$C(O)NR$^a$R$^b$, —(CR$^a$R$^b$)$_n$C(O)OR$^a$, —(CR$^a$R$^b$)$_n$S(O$_2$)NR$^a$R$^b$, —(CR$^a$R$^b$)$_n$NR$^a$C(O)R$^b$, —(CR$^a$R$^b$)$_n$NR$^a$S(O$_2$)R$^b$, $C_1$-$C_6$alkyl, halo-$C_1$-$C_6$alkyl, $C_1$-$C_6$alkoxy, halogen, hydroxyl, amino, —(CR$^a$R$^b$)$_n$CN. In another embodiment, $R^6$ is selected from the group consisting of halo, CN, $C_1$-$C_3$ alkanoyl, $C_1$-$C_3$ alkylsulfonyl, and cyclopropyl.

In certain embodiments of the compound of Formula (I), (IA), (IB) or (IC), $R^6$ is selected from the group consisting of H, $C_1$-$C_6$ alkyl, $C_1$-$C_6$ alkanoyl, cyano, $C_1$-$C_6$ alkylsulfonyl, cyano, halo, hydroxy, amino, $C_1$-$C_6$ alkylamino, and $C_1$-$C_6$ dialkylamino.

In certain embodiments of the compound of Formula (I), (IA), (IB) or (IC), $R^6$ is selected from the group consisting of H, $C_1$-$C_6$ alkyl, $C_1$-$C_6$ alkanoyl, cyano, $C_1$-$C_6$ alkylsulfonyl, $C_3$-$C_8$ cycloalkylsulfonyl, $C_3$-$C_8$ cycloalkyl, cyano, halo, hydroxy, amino, $C_1$-$C_6$ alkylamino, and $C_1$-$C_6$ dialkylamino.

In certain embodiments of the compound of Formula (I), (IA), (IB) or (IC), $R^6$ is selected from the group consisting of H, halo, $C_1$-$C_3$ alkyl, $C_1$-$C_3$ alkanoyl, cyano, $C_1$-$C_3$ alkylsulfonyl, $C_3$-$C_4$ cycloalkylsulfonyl, $C_3$-$C_4$ cycloalkyl, wherein the $C_1$-$C_3$ alkyl or $C_3$-$C_4$ cycloalkyl is optionally substituted with $C_1$-$C_3$alkenyl, $C_1$-$C_3$alkynyl, cyano, halo, hydroxy or amino.

In certain embodiments of the compound of Formula (I), (IA), (IB) or (IC), $R^6$ is selected from the group consisting of H, halo, $C_1$-$C_3$ alkyl, —C(O)Me, —S(O$_2$)Me, —S(O$_2$)cyclopropyl, cyano, cyclopropyl, wherein the $C_1$-$C_3$ alkyl or cyclopropyl is optionally substituted with =CH$_2$ or hydroxy.

In specific embodiments of the compound of Formula (I), (IA), (IB) or (IC), $R^6$ is selected from the group consisting of halo, $C_1$-$C_3$ alkanoyl, $C_1$-$C_3$ alkylsulfonyl, and cyano.

In specific embodiments of the compound of Formula (I), (IA), (IB) or (IC), $R^6$ is selected from the group consisting of $C_1$-$C_3$ alkanoyl, $C_1$-$C_3$ alkylsulfonyl, and cyclopropyl.

In specific embodiments of the compound of Formula (I), (IA), (IB) or (IC), W is C(O), $R^8$ is selected from the group consisting of amino, NR$^a$R$^b$, $C_1$-$C_3$ alkyl, $C_3$-$C_4$ hydroxycycloalkyl, $C_1$-$C_3$ hydroxyalkyl, 5-10 membered heteroaryl containing one or two N atoms, wherein said heteroaryl is optionally substituted with one or two $R^{24}$, which can be the same or different, selected from H, methyl, amino, OH and methylamino. In one embodiment, the 5-10 membered heteroaryl is pyrazolyl, pyrolyl, or triazolyl.

In specific embodiments of the compound of Formula (I), (IA), (IB) or (IC), $R^8$ is selected from the group consisting of amino, NR$^a$R$^b$, $C_1$-$C_3$ alkyl, $C_3$-$C_4$ hydroxycycloalkyl,

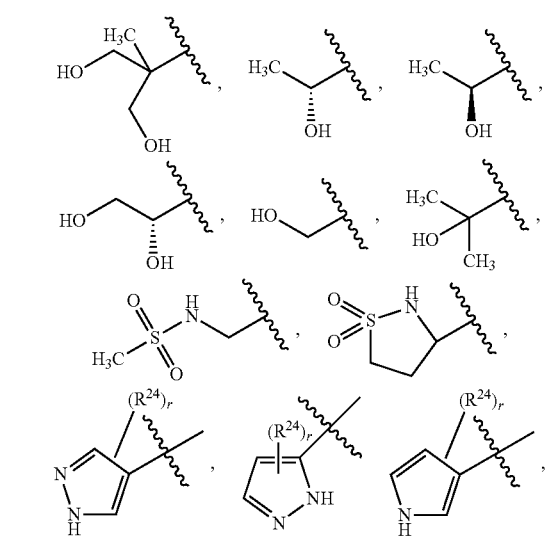

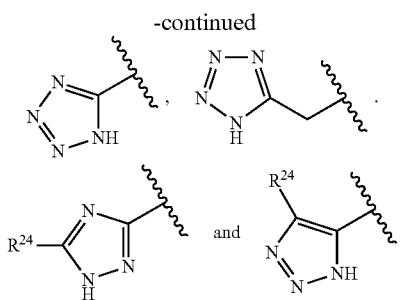

wherein $R^{24}$ is independently selected from the group consisting of H, methyl, amino, OH and methylamino; r is 1 or 2.

In specific embodiments of the compound of Formula (I), (IA), (IB) or (IC), $R^8$ is selected from the group consisting of amino,

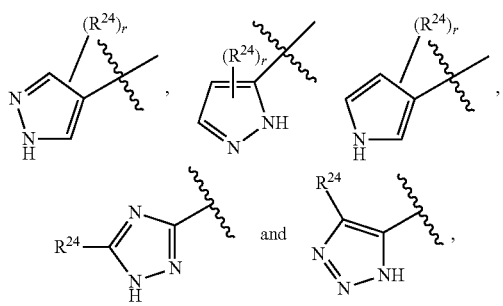

wherein $R^{24}$ is independently selected from the group consisting of H, methyl, amino, OH and methylamino; r is 1 or 2. In one embodiment, $R^{24}$ is independently selected from the group consisting of H, methyl, and amino.

In specific embodiments of the compound of Formula (I), (IA), (IB) or (IC), $R^8$ is selected from the group consisting of

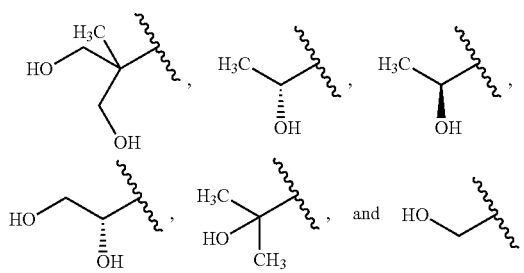

In specific embodiments of the compound of Formula (I), (IA), (IB) or (IC), $R^8$ is selected from

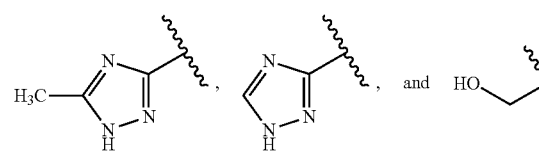

In specific embodiments of the compound of Formula (I), (IA), (IB) or (IC), $R^7$ is selected from the group consisting of H, OH, $OR^a$, $C_1$-$C_6$alkyl, —C(O)$NR^aR^b$, —C(O)$OR^a$ and —S($O_2$)$NR^aR^b$, wherein said alkyl can be unsubstituted or substituted with one to three moieties, which can be the same or different, each moiety being selected from the group consisting of halogen, —$CF_3$, —CN, —$(CR^aR^b)_nC(O)OH$, —$OCF_3$, —$OR^a$, —C(O)$R^a$, —$NR^aR^b$, —C(O)O—$C_1$-$C_6$alkyl, —C(O)$NR^aR^b$, —$SR^a$, and —S($O_2$)$R^a$;

In specific embodiments of the compound of Formula (I), (IA), (IB) or (IC), $R^{10}$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —C(O)O—$C_1$-$C_6$alkyl, —C(O)$NR^aR^b$, —$SR^a$, and —S($O_2$)$R^a$.

Non-limiting examples of the compounds of Formula (I) include compounds 1-54 as set forth below, and pharmaceutically acceptable salts thereof:

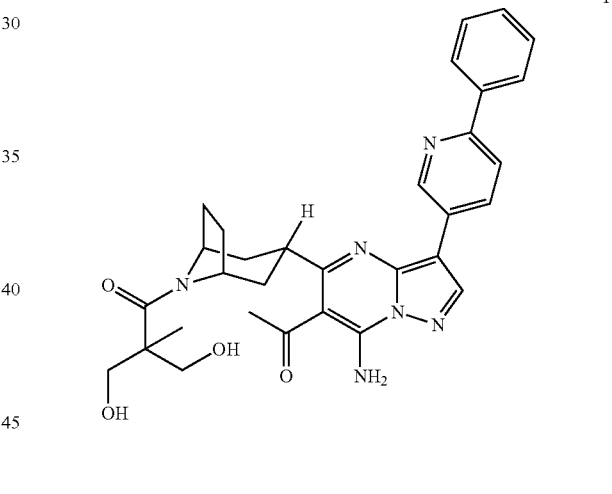

1

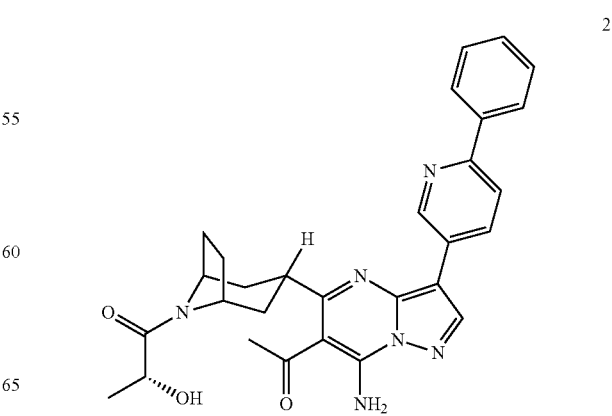

2

3
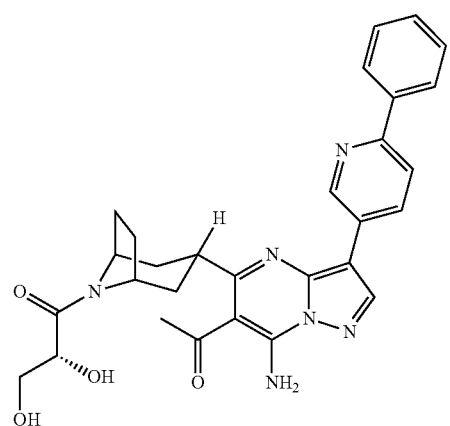
4
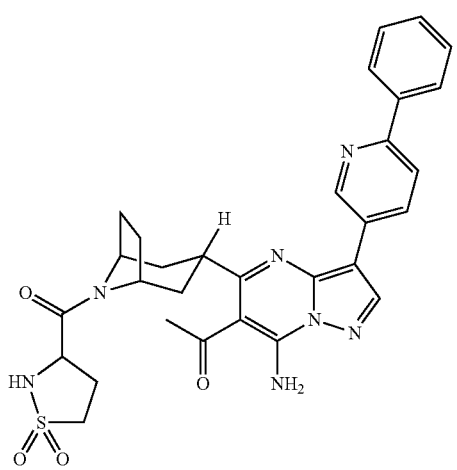
5
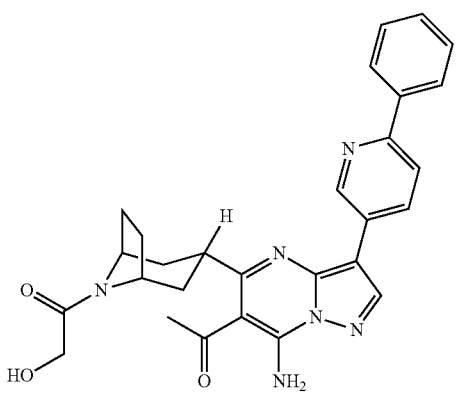
6
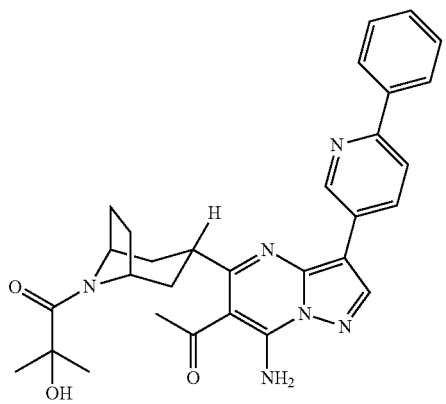
7
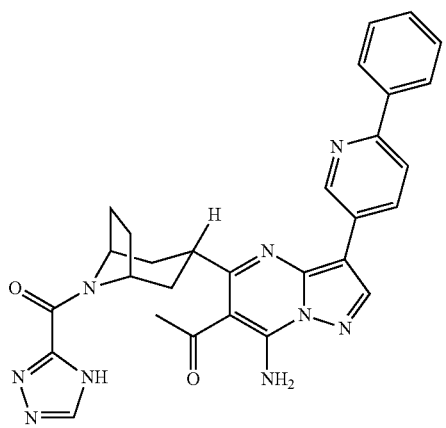
8
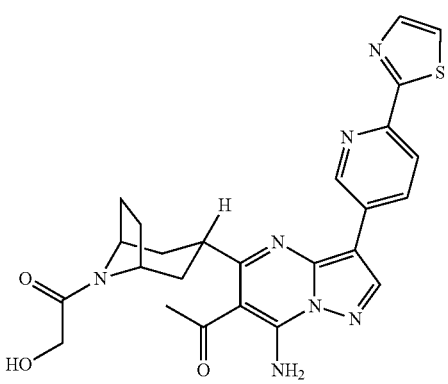
9
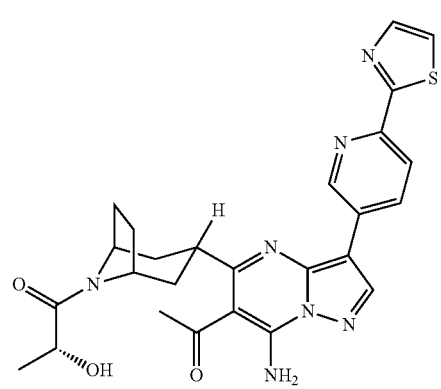

10
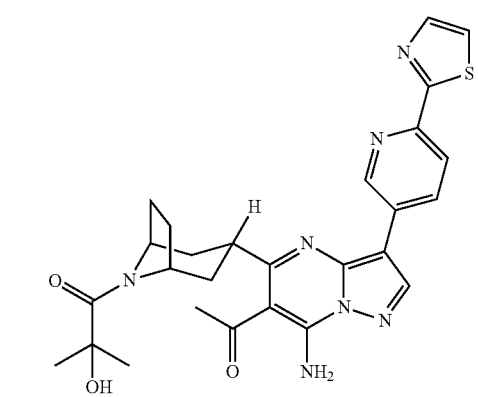
11
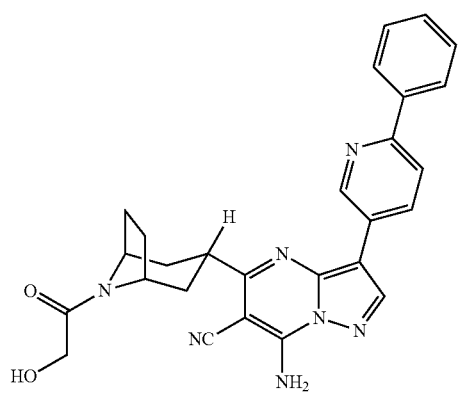
12
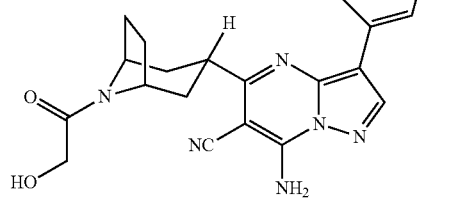
13
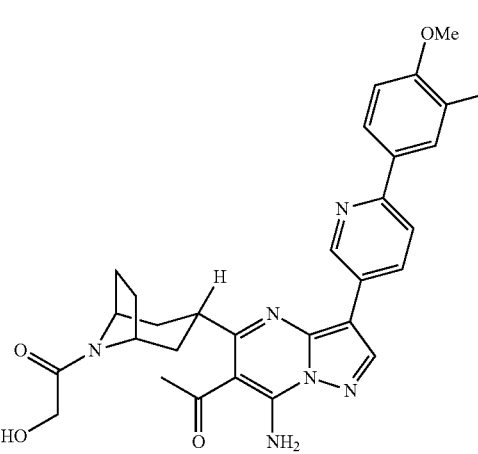
14
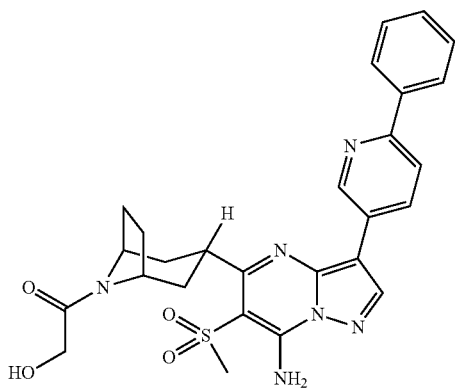
15
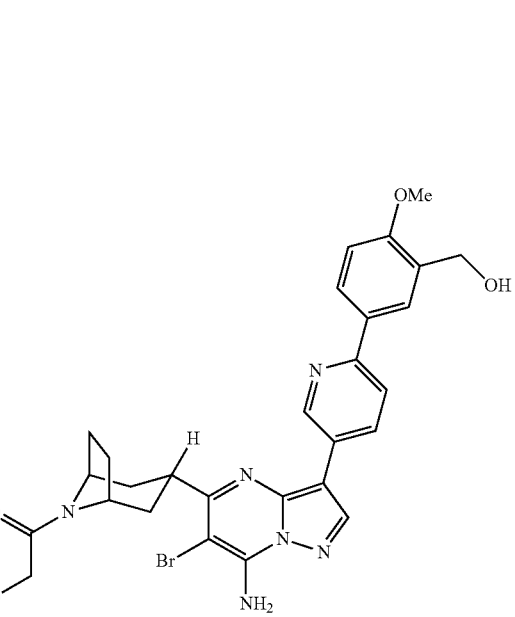
16
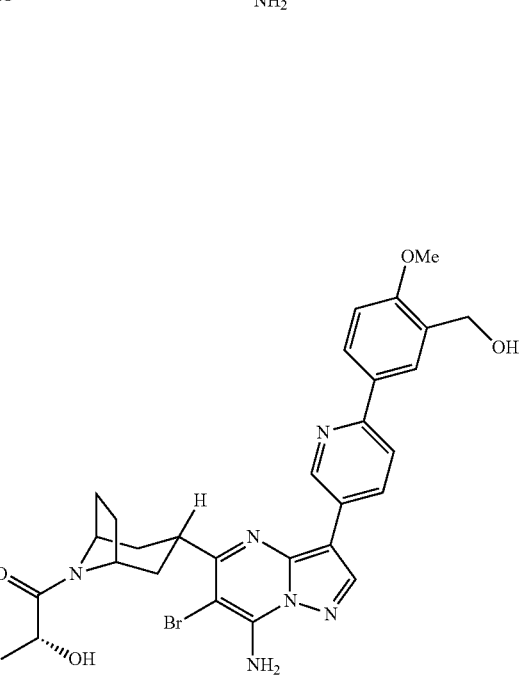

17
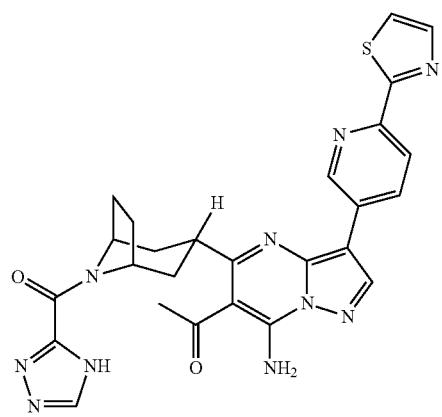
18
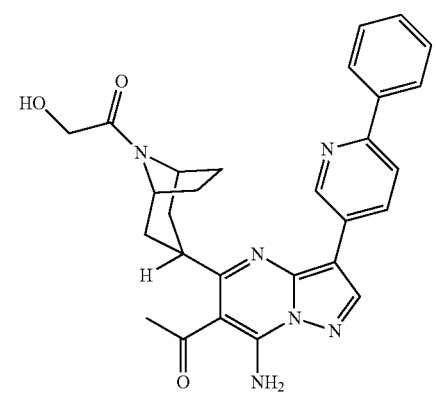
19
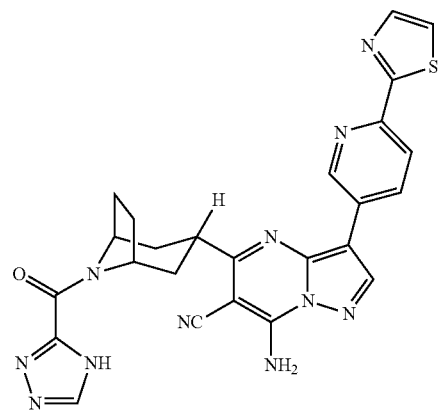
20
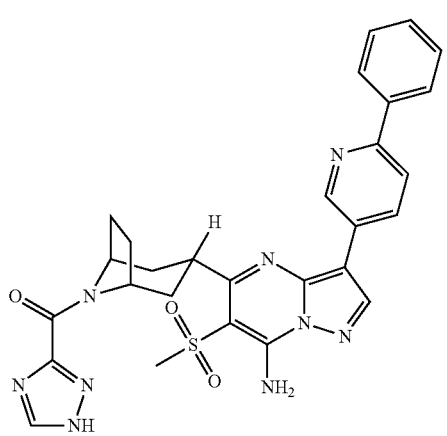
21
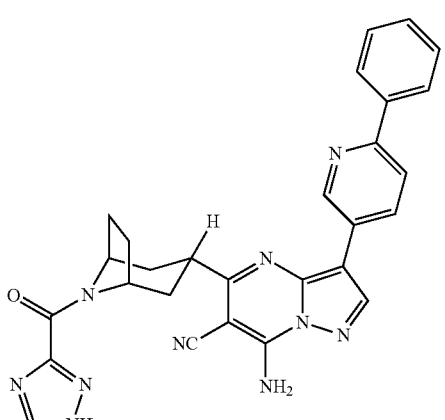
22
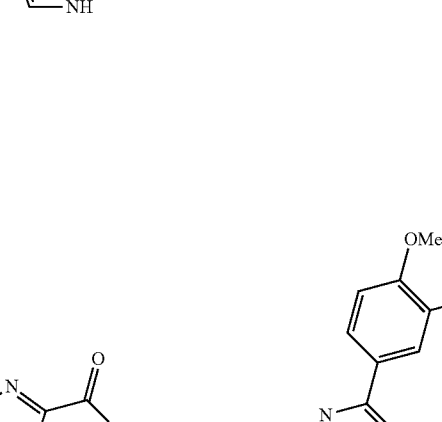
23
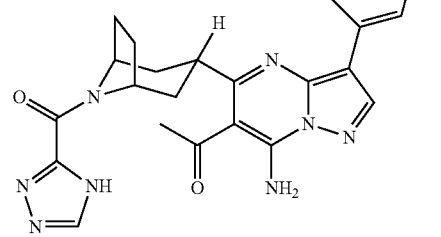

24
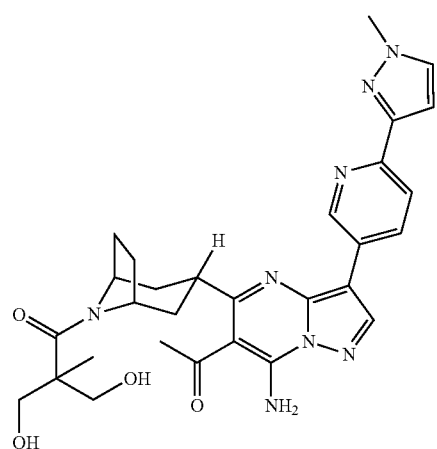
25
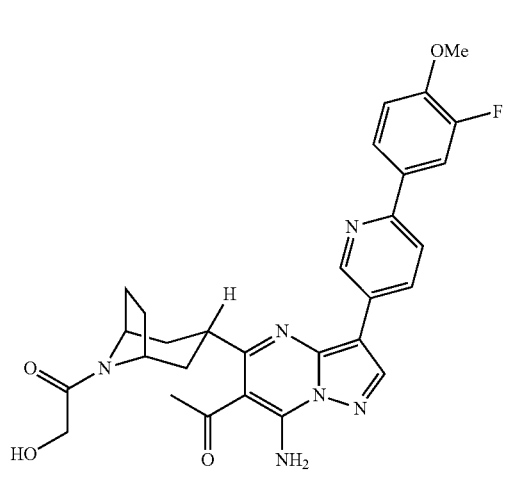
26
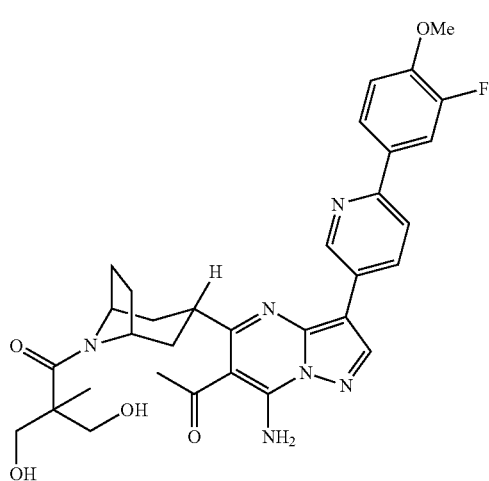
27
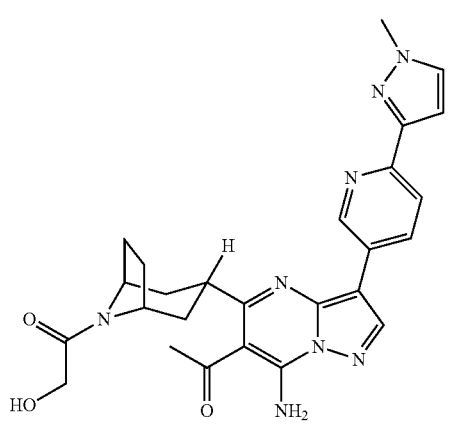
28
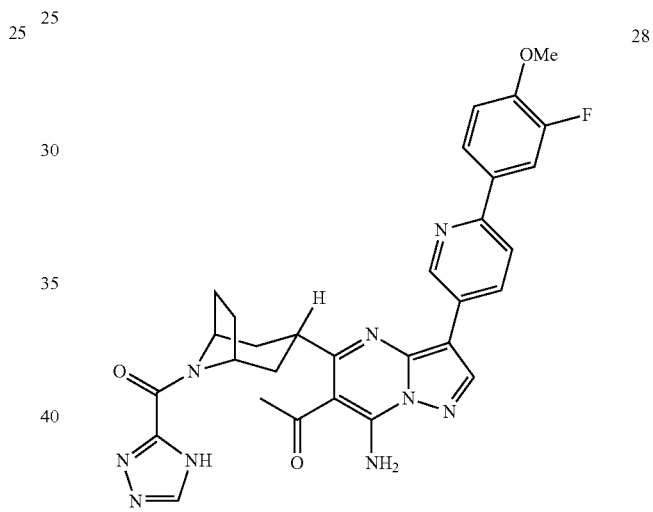
29
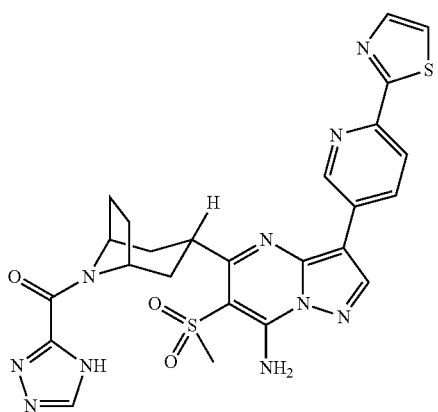

-continued
30
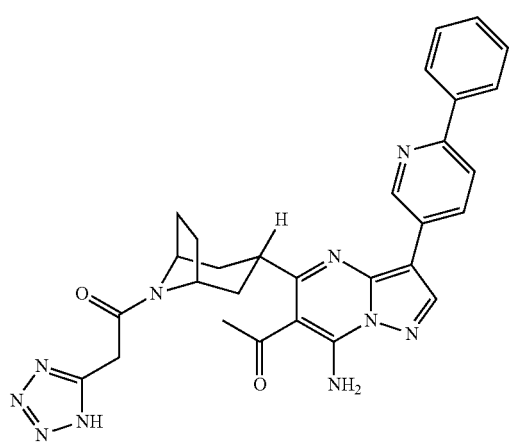
31
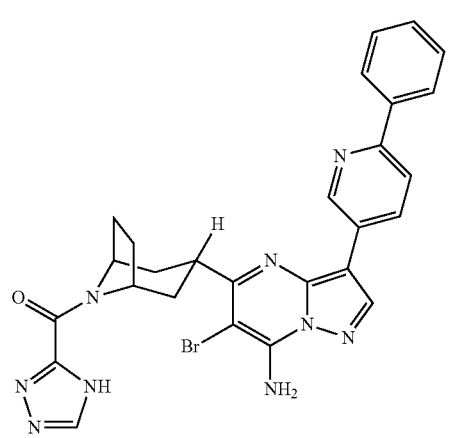
32
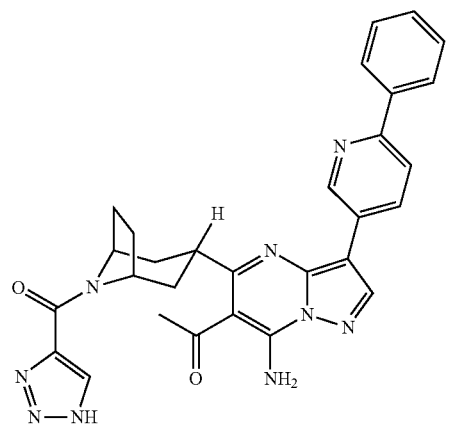
-continued
33
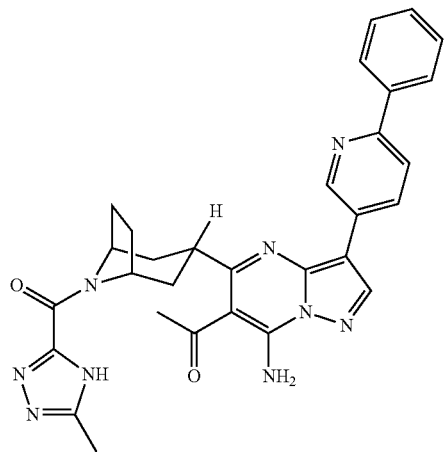
34
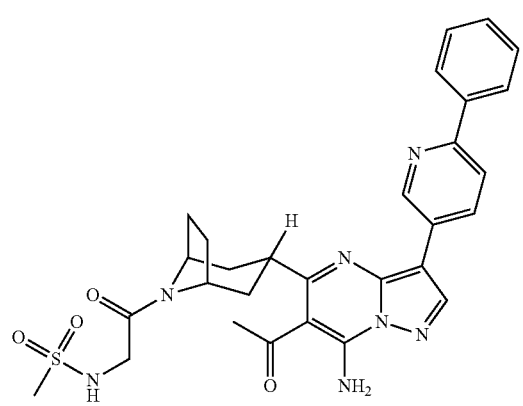
35
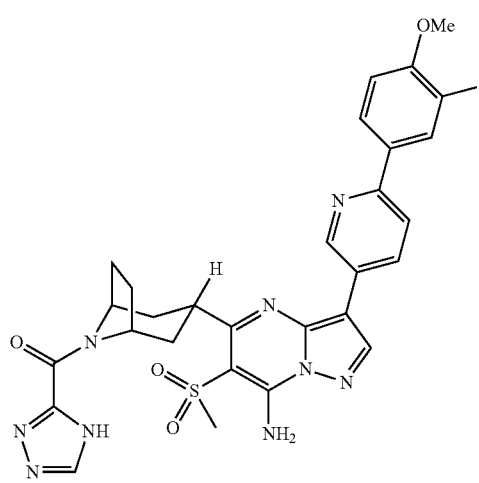

36
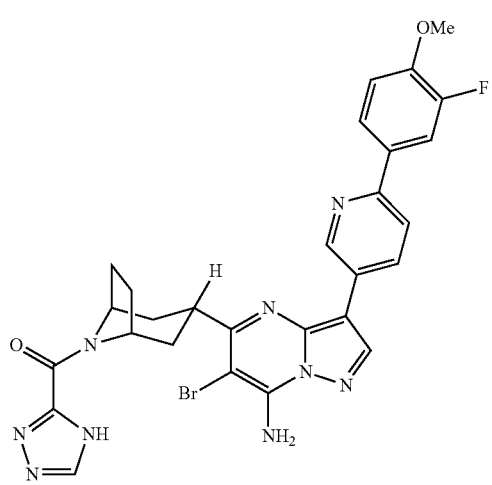
37
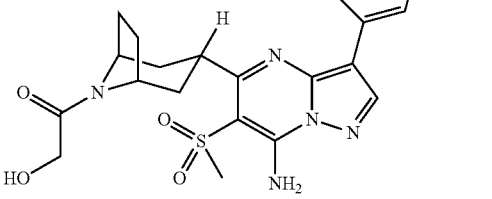
38
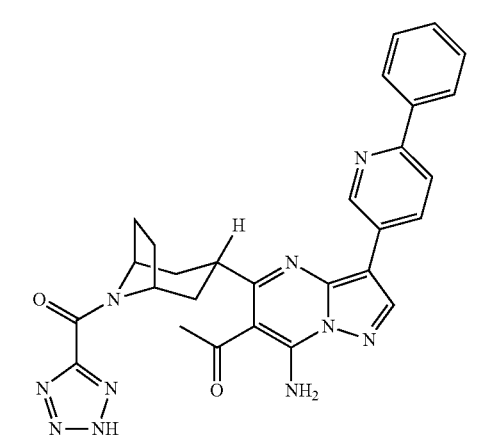
39
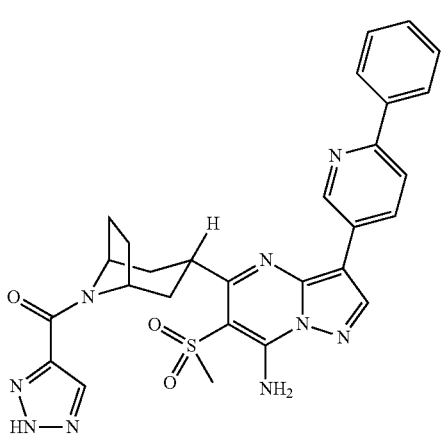
40
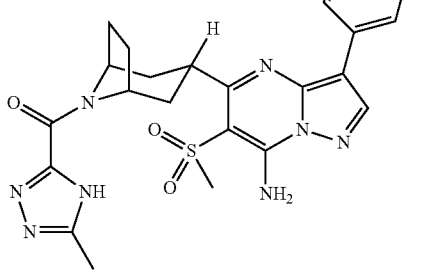
41
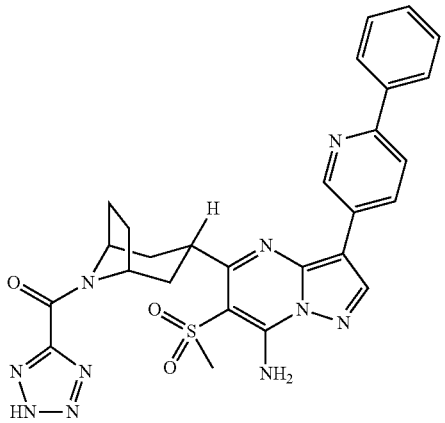
42
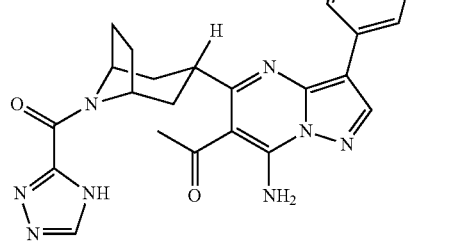

-continued
43
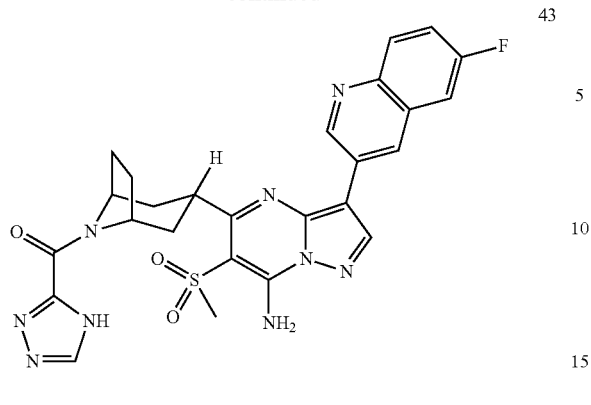
44
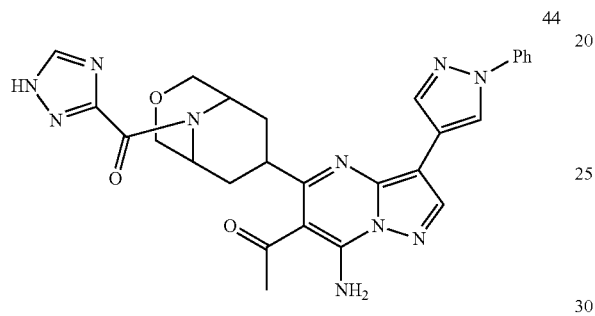
45
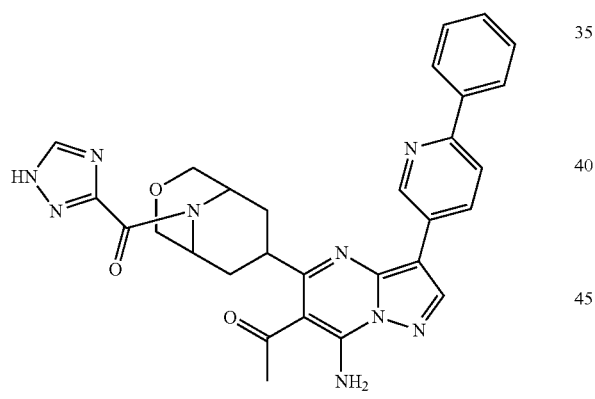
46
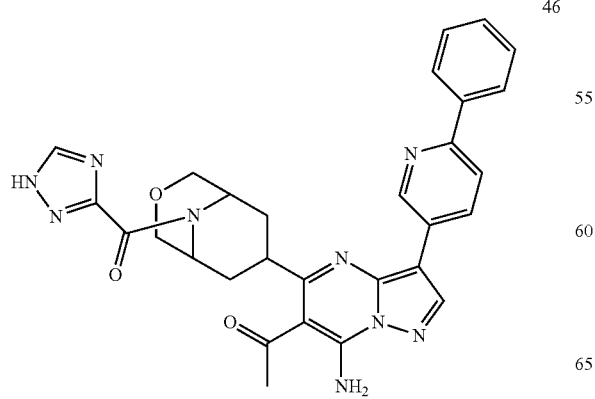
-continued
47
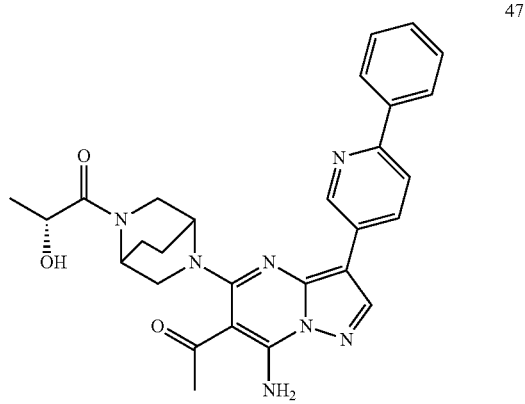
48
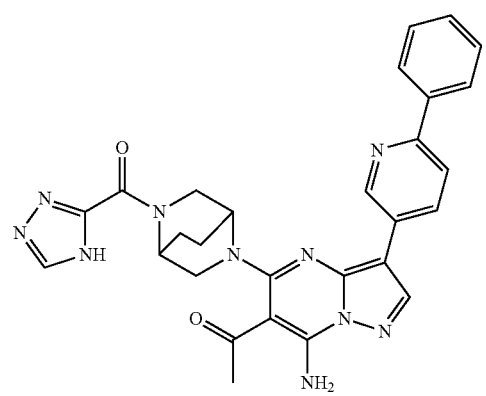
49
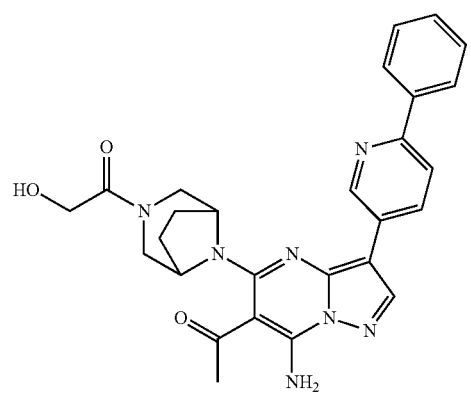
50
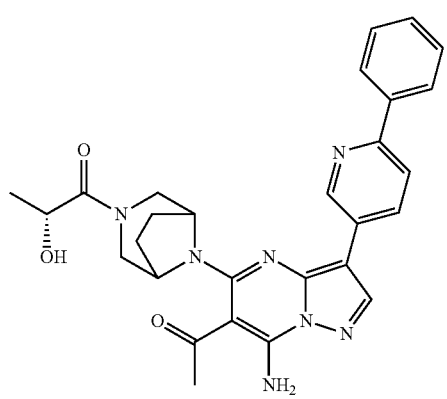

51

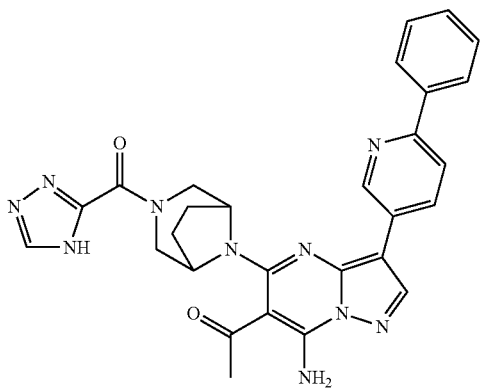

52

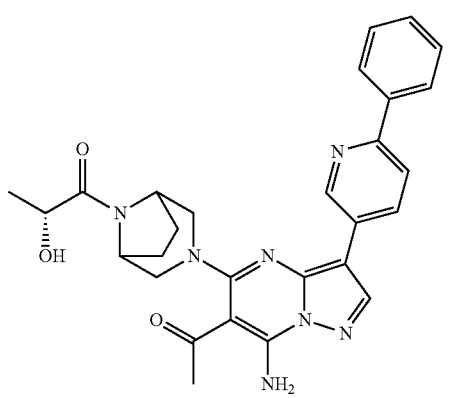

53

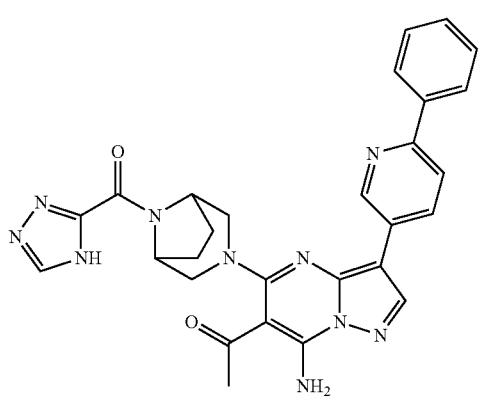

54

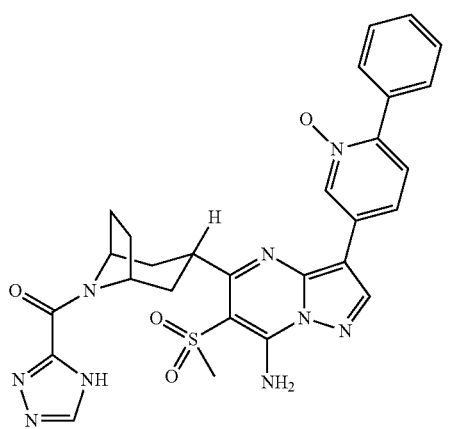

and pharmaceutically acceptable salts thereof.

The present invention also provides a compound selected from the group consisting of:

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one;

((R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one;

(R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2,3-dihydroxypropan-1-one;

(exo)-3-[6-acetyl-7-amino-3-(6-phenyl-3-pyridinyl)pyrazolo[1,5-a][pyrimidin-5-yl]-8-[(1,1-dioxido-3-isothiazolidinyl)carbonyl]-8-azabicyclo[3.2.1]octane;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxy-2-methylpropan-1-one;

1-(5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)ethanone;

(S)-1-((1R,3R,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one;

1-((1R,3r,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-(1H-tetrazol-5-yl)ethanone;

1-(5-((1R,3s,5S)-8-(1H-1,2,3-triazole-5-carbonyl)-8-azabicyclo[3.2.1]octan-3-yl)-7-amino-3-(6-phenylpyridin-3-yl)pyrazolo[1,5-a]pyrimidin-6-yl)ethanone;

1-(7-amino-5-((1R,3s,5S)-8-(3-methyl-1H-1,2,4-triazole-5-carbonyl)-8-azabicyclo[3.2.1]octan-3-yl)-3-(6-phenylpyridin-3-yl)pyrazolo[1,5-a]pyrimidin-6-yl)ethanone;

N-(2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoethyl)methanesulfonamide;

1-(5-((1R,3s,5S)-8-(1H-tetrazole-5-carbonyl)-8-azabicyclo[3.2.1]octan-3-yl)-7-amino-3-(6-phenylpyridin-3-yl)pyrazolo[1,5-a]pyrimidin-6-yl)ethanone;

5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carboxamide;

1-(5-((1R,3s,5S)-8-(1H-1,2,4-triazole-3-carbonyl)-8-azabicyclo[3.2.1]octan-3-yl)-7-amino-3-(6-(5-(difluoromethyl)thiazol-2-yl)pyridin-3-yl)pyrazolo[1,5-a]pyrimidin-6-yl)ethanone;

1-(5-((1R,3s,5S)-8-(1H-1,2,4-triazole-3-carbonyl)-8-azabicyclo[3.2.1]octan-3-yl)-7-amino-3-(4-(pyrimidin-2-yl)phenyl)pyrazolo[1,5-a]pyrimidin-6-yl)ethanone;

5-(5-((1R,3s,5S)-8-(1H-1,2,4-triazole-3-carbonyl)-8-azabicyclo[3.2.1]octan-3-yl)-6-acetyl-7-aminopyrazolo[1,5-a]pyrimidin-3-yl)-N-methylpicolinamide;

5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)-N-methylpicolinamide;

1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(5-hydroxy-6-phenylpyridin-3-yl)pyrazolo[1,5-a]pyrimidin-6-yl)ethanone;

1-((1R,3s,5S)-3-(6-acetyl-7-amino-3-(5-hydroxy-6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxyethanone;

(R)-1-((1R,3S,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxypropan-1-one;

1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxy-2-methylpropan-1-one;

1-((1R,3s,5S)-3-(6-acetyl-7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(7-fluoronaphthalen-2-yl)pyrazolo[1,5-a]pyrimidin-6-yl)ethanone;

(1R,3s,5S)-3-(6-acetyl-7-amino-3-(6-phenylpyridin-3-yl)pyrazolo[1,5-a]pyrimidin-5-yl)-N-methyl-8-azabicyclo[3.2.1]octane-8-carboxamide;

1-(7-amino-5-((1R,3s,5S)-8-(5-hydroxy-4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-(5-((1R,3s,5S)-8-(1H-pyrrole-3-carbonyl)-8-azabicyclo[3.2.1]octan-3-yl)-7-amino-3-(6-phenylpyridin-3-yl)pyrazolo[1,5-a]pyrimidin-6-yl)ethanone;

1-(5-((1R,3s, 5S)-8-(4H-1,2,4-triazol-3-ylsulfonyl)-8-azabicyclo[3.2.1]octan-3-yl)-7-amino-3-(6-phenylpyridin-3-yl)pyrazolo[1,5-a]pyrimidin-6-yl)ethanone;

1-(5-((1R,3s,5S)-8-(1H-pyrrole-2-carbonyl)-8-azabicyclo[3.2.1]octan-3-yl)-7-amino-3-(6-phenylpyridin-3-yl)pyrazolo[1,5-a]pyrimidin-6-yl)ethanone;

1-((1R,3s,5S)-3-(6-acetyl-7-amino-3-(6-(4-methoxy-3-(methoxymethyl)phenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-methoxy-3-(methoxymethyl)phenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-fluoro-4-methoxyphenyl)pyridin-3-yl)pyrazolo[1,5-a]pyrimidin-6-yl)ethanone;

1-(7-amino-5-((1R,3s,5S)-8-(1-hydroxycyclopropanecarbonyl)-8-azabicyclo[3.2.1]octan-3-yl)-3-(6-phenylpyridin-3-yl)pyrazolo[1,5-a]pyrimidin-6-yl)ethanone;

(1R,3s,5S)-3-(6-acetyl-7-amino-3-(6-phenylpyridin-3-yl)pyrazolo[1,5-a]pyrimidin-5-yl)-8-azabicyclo[3.2.1]octane-8-sulfonic acid;

1-(7-amino-5-((1R,3s,5S)-8-(5-hydroxynicotinoyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s,5S)-8-(4-hydroxynicotinoyl)-8-azabicyclo[3.2.1]octan-3-yl)-3-(6-phenylpyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(5-(methoxymethyl)thiazol-2-yl)pyridin-3-yl)pyrazolo[1,5-a]pyrimidin-6-yl)ethanone;

1-(5-((1R,3s,5S)-8-(1H-imidazole-4-carbonyl)-8-azabicyclo[3.2.1]octan-3-yl)-7-amino-3-(6-phenylpyridin-3-yl)pyrazolo[1,5-a]pyrimidin-6-yl)ethanone;

1-(5-((1R,3r,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one;

1-(5-((1R,3s,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone;

1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one;

1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(2,3-difluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2'-fluoro-2,3'-bipyridin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-methyl-2H-tetrazol-5-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3,5-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,3-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-methoxy-3-methylphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-chloro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(benzo[d][1,3]dioxol-5-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-(difluoromethoxy)phenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-fluoro-3-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-(2-methoxyethoxy)phenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-methyl-2H-indazol-5-yl)pyridin-3-yl)pyrazolo[1,5-a]pyrimidin-6-yl)ethanone;

1-(3-(6-(1H-benzo[d]imidazol-6-yl)pyridin-3-yl)-5-(1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,5-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-ethoxyphenyl)pyridin-3-yl)pyrazolo[1,5-a]pyrimidin-6-yl)ethanone;

1-(3-(6-(1H-pyrazol-3-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-pyrazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(3-(2,4'-bipyridin-5-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-methoxy-(D$_3$)-phenyl)pyridin-3-yl)pyrazolo[1,5-a]pyrimidin-6-yl)ethanone;

1-((1R,3s,5S)-3-(6-acetyl-7-amino-3-(6-(4-methoxy-(D$_3$)-phenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-methylpyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(pyridin-3-yl)pyrazolo[1,5-a]pyrimidin-6-yl)ethanone;

5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinic acid;

1-(5-((1R,3s,5S)-8-(4H-1,2,4-triazole-3-carbonyl)-8-azabicyclo[3.2.1]octan-3-yl)-7-amino-3-(6-(1-methyl-(D$_3$)-1H-pyrazol-3-yl)pyridin-3-yl)pyrazolo[1,5-a]pyrimidin-6-yl)ethanone;

1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)propan-1-one, 1-((1R,3s,5S)-3-(6-acetyl-7-amino-3-(6-(1-methyl-(D$_3$)-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(3-hydroxypentan-3-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-(fluoromethyl)-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(1-(fluoromethyl)-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-1,2,4-triazol-3-yl)pyridin-3-yl)pyrazolo[1,5-a]pyrimidin-6-yl)ethanone;

1-((1R,3s,5S)-3-(6-acetyl-7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-methylpyridin-3-yl)pyrazolo[1,5-a]pyrimidin-5-yl)-8-azabicyclo[3.2.1]octan-8-yl)-2-hydroxyethanone;

1-(3-(6-(1H-1,2,4-triazol-3-yl)pyridin-3-yl)-5-(1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(6-acetyl-7-amino-3-(6-(fluoromethyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(4-fluoro-1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(5-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(3-(6-(1H-imidazol-4-yl)pyridin-3-yl)-5-(1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-imidazol-4-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-ethylpyridin-3-yl)pyrazolo[1,5-a]pyrimidin-6-yl)ethanone;

1-(5-((1R,3r,5S)-8-(4H-1,2,4-triazole-3-carbonyl)-8-azabicyclo[3.2.1]octan-3-yl)-7-amino-3-(6-(3,5-difluorophenyl)pyridin-3-yl)pyrazolo[1,5-a]pyrimidin-6-yl)ethanone;

1-((1R,3r,5S)-3-(6-acetyl-7-amino-3-(6-(3,5-difluorophenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-1,2,4-triazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3r,5S)-8-(4H-1,2,4-triazole-3-carbonyl)-8-azabicyclo[3.2.1]octan-3-yl)-7-amino-3-(6-(3-fluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(trifluoromethyl)pyridin-3-yl)pyrazolo[1,5-a]pyrimidin-6-yl)ethanone;

1-((1R,3r,5S)-3-(6-acetyl-7-amino-3-(6-(3-fluorophenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-imidazol-4-yl)pyridin-3-yl)pyrazolo[1,5-a]pyrimidin-6-yl)ethanone;

(1R,3s,5S)-2-methoxyethyl 3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octane-8-carboxylate;

1-(5-((1R,3s,5S)-8-(4H-1,2,4-triazole-3-carbonyl)-8-azabicyclo[3.2.1]octan-3-yl)-7-amino-3-(5-fluoro-6-(1H-pyrazol-3-yl)pyridin-3-yl)pyrazolo[1,5-a]pyrimidin-6-yl)ethanone;

1-((1R,3s,5S)-3-(6-acetyl-7-amino-3-(5-fluoro-6-(1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(5-fluoro-6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(5-fluoro-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(5-methyl-6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(5-methyl-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyridin-2(1H)-one;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)propane-1,2-dione;

2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoacetamide;

1-(5-((1R,3s,5S)-8-(4H-1,2,4-triazole-3-carbonyl)-8-azabicyclo[3.2.1]octan-3-yl)-7-amino-3-(5-fluoropyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-methyl-2H-indazol-6-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone;

1-(7-amino-5-((1R,3s,5S)-8-(morpholine-4-carbonyl)-8-azabicyclo[3.2.1]octan-3-yl)-3-(6-phenylpyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(1-(4-fluorophenyl)-1H-pyrazol-4-yl)pyrazolo[1,5-a]pyrimidin-6-yl)ethanone;

5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-2-methoxybenzonitrile;

1-(5-((1R,3s,5S)-8-(4H-1,2,4-triazole-3-carbonyl)-8-azabicyclo[3.2.1]octan-3-yl)-7-amino-3-(6-methoxyquinolin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(hydroxymethyl)quinolin-3-yl)pyrazolo[1,5-a]pyrimidin-6-yl)ethanone;

1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-methyl-1H-imidazol-1-yl)pyridin-3-yl)pyrazolo[1,5-a]pyrimidin-6-yl)ethanone;

1-(3-(6-(1H-imidazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(7-amino-5-((1R,3s,5S)-8-(5-amino-4H-1,2,4-triazole-3-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone;

1-((1R,3s,5S)-3-(6-acetyl-7-amino-3-(6-(3-methyl-1H-pyrazol-1-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(4-methyl-1H-pyrazol-1-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-methyl-1H-pyrazol-1-yl)pyridin-3-yl)pyrazolo[1,5-a]pyrimidin-6-yl)ethanone;

1-((1R,3s,5S)-3-(6-acetyl-7-amino-3-(6-(1-ethyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-ethyl-1H-pyrazol-3-yl)pyridin-3-yl)pyrazolo[1,5-a]pyrimidin-6-yl)ethanone;

1-(7-amino-5-((1R,3s,5S)-8-(5-(dimethylamino)-1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s, 5S)-8-(5-amino-1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s,5S)-8-(5-amino-1H-pyrazole-4-carbonyl)-8-azabicyclo[3.2.1]octan-3-yl)-3-(6-phenylpyridin-3-yl)pyrazolo[1,5-a]pyrimidin-6-yl)ethanone;

N-(3-((1R,3s,5S)-3-(6-acetyl-7-amino-3-(6-phenylpyridin-3-yl)pyrazolo[1,5-a]pyrimidin-5-yl)-8-azabicyclo[3.2.1]octane-8-carbonyl)-1H-1,2,4-triazol-5-yl)acetamide;

1-(5-((1R,3s,5S)-8-(4H-1,2,4-triazole-3-carbonyl)-8-azabicyclo[3.2.1]octan-3-yl)-7-amino-3-(1-phenyl-1H-pyrazol-4-yl)pyrazolo[1,5-a]pyrimidin-6-yl)ethanone;

1-(7-amino-5-((1R,3s,5S)-8-(5-amino-4H-1,2,4-triazole-3-carbonyl)-8-azabicyclo[3.2.1]octan-3-yl)-3-(6-(3-fluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-fluorophenyl)pyridin-3-yl)pyrazolo[1,5-a]pyrimidin-6-yl)ethanone;

1-(3-(2,2'-bipyridin-5-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,6-difluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-4-yl)pyridin-3-yl)pyrazolo[1,5-a]pyrimidin-6-yl)ethanone;

1-((1R,3s,5S)-3-(6-acetyl-7-amino-3-(1-methyl-1H-pyrazol-4-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(1-methyl-1H-pyrazol-4-yl)pyrazolo[1,5-a]pyrimidin-6-yl)ethanone;

1-((1R,3s,5S)-3-(6-acetyl-7-amino-3-(1-(2-hydroxy-2-methylpropyl)-1H-pyrazol-4-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(1-(2-hydroxy-2-methylpropyl)-1H-pyrazol-4-yl)pyrazolo[1,5-a]pyrimidin-6-yl)ethanone;

1-((1R,3s,5S)-3-(6-acetyl-7-amino-3-(1-(2-hydroxyethyl)-1H-pyrazol-4-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(1-(2-hydroxyethyl)-1H-pyrazol-4-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(4-fluorophenyl)pyridin-3-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone;

(R)-1-((1R,3S,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxypropan-1-one;

1-((1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(4-fluorophenyl)pyridin-3-yl)-5-(1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(1-(pyridin-2-yl)-1H-pyrazol-4-yl)pyrazolo[1,5-a]pyrimidin-6-yl)ethanone;

1-((1R,3s,5S)-3-(6-acetyl-7-amino-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone;

1-((1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(2,4-difluorophenyl)pyridin-3-yl)-5-(1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(2,4-difluorophenyl)pyridin-3-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone;

(R)-1-((1R,3S,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxypropan-1-one;

(1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octane-8-carboxamide;

(1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octane-8-carboxamide;

1-((1R,3s,5S)-3-(6-acetyl-7-amino-3-(6-(2,6-difluorophenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-fluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

(1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octane-8-carboxamide;

(1R,3s,5S)-3-(6-acetyl-7-amino-3-(6-(1-methyl-1H-pyrazol-4-yl)pyridin-3-yl)pyrazolo[1,5-a]pyrimidin-5-yl)-8-azabicyclo[3.2.1]octane-8-carboxamide;

1-(7-amino-5-((1R,3s,5S)-8-(3-amino-1H-pyrazole-5-carbonyl)-8-azabicyclo[3.2.1]octan-3-yl)-3-(6-(1-methyl-1H-pyrazol-4-yl)pyridin-3-yl)pyrazolo[1,5-a]pyrimidin-6-yl)ethanone;

1-(3-(6-(1H-pyrazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-pyrazol-1-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(2-phenylpyrimidin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-(2-hydroxypropan-2-yl)pyrimidin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(5-chloro-6-(2-hydroxypropan-2-yl)pyridin-3-yl)pyrazolo[1,5-a]pyrimidin-6-yl)ethanone;

1-(5-((1R,3r,5S)-8-(4H-1,2,4-triazole-3-carbonyl)-8-azabicyclo[3.2.1]octan-3-yl)-7-amino-3-(6-fluoro-8-methoxyquinolin-3-yl)pyrazolo[1,5-a]pyrimidin-6-yl)ethanone;
1-((1R,3r,5S)-3-(6-acetyl-7-amino-3-(6-fluoro-8-methoxyquinolin-3-yl)pyrazolo[1,5-a]pyrimidin-5-yl)-8-azabicyclo[3.2.1]octan-8-yl)-2-hydroxyethanone;
1-(5-((1R,3s,5S)-8-(4H-1,2,4-triazole-3-carbonyl)-8-azabicyclo[3.2.1]octan-3-yl)-7-amino-3-(5-(hydroxymethyl)pyridin-3-yl)pyrazolo[1,5-a]pyrimidin-6-yl)ethanone;
1-((1R,3s,5S)-3-(6-acetyl-7-amino-3-(1H-benzo[d]imidazol-5-yl)pyrazolo[1,5-a]pyrimidin-5-yl)-8-azabicyclo[3.2.1]octan-8-yl)-2-hydroxyethanone;
((1R,3s,5S)-3-(7-amino-6-bromo-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone;
1-((1R,3s,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;
(R)-1-(1R,3S,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxypropan-1-one;
((1R,3s, 5S)-3-(7-amino-6-bromo-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;
1-((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;
1-((1R,3s,5S)-3-(7-amino-3-(6-phenylpyridin-3-yl)pyrazolo[1,5-a]pyrimidin-5-yl)-8-azabicyclo[3.2.1]octan-8-yl)-2-hydroxyethanone;
1-((1R,3s,5S)-3-(7-1-((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone;
((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(1H-indazol-5-yl)pyrazolo[1,5-a]pyrimidin-5-yl)-8-azabicyclo[3.2.1]octan-8-yl)(1H-1,2,4-triazol-5-yl)methanone;
((1R,3s,5S)-3-(7-amino-3-(1H-pyrrolo[2,3-b]pyridin-5-yl)pyrazolo[1,5-a]pyrimidin-5-yl)-8-azabicyclo[3.2.1]octan-8-yl)(1H-1,2,4-triazol-5-yl)methanone;
((1R,3s,5S)-3-(7-amino-3-(1H-indazol-6-yl)pyrazolo[1,5-a]pyrimidin-5-yl)-8-azabicyclo[3.2.1]octan-8-yl)(1H-1,2,4-triazol-5-yl)methanone;
((1R,3s,5S)-3-(7-amino-3-(1H-indazol-4-yl)pyrazolo[1,5-a]pyrimidin-5-yl)-8-azabicyclo[3.2.1]octan-8-yl)(1H-1,2,4-triazol-5-yl)methanone;
((1R,3s,5S)-3-(7-amino-3-(6-(2-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(6-(2-fluoro-4-(trifluoromethyl)phenyl)pyridin-3-yl)pyrazolo[1,5-a]pyrimidin-5-yl)-8-azabicyclo[3.2.1]octan-8-yl)(4H-1,2,4-triazol-3-yl)methanone;
((1R,3s,5S)-3-(7-amino-3-(1-methyl-1H-pyrazol-4-yl)pyrazolo[1,5-a]pyrimidin-5-yl)-8-azabicyclo[3.2.1]octan-8-yl)(4H-1,2,4-triazol-3-yl)methanone;
((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-pyrrolidin-2-yl)methanone;
((1R,3R,5S)-3-(7-amino-3-(6-phenylpyridin-3-yl)pyrazolo[1,5-a]pyrimidin-5-yl)-8-azabicyclo[3.2.1]octan-8-yl)((S)-pyrrolidin-2-yl)methanone;
((1R,3s,5S)-3-(7-amino-3-(6-phenylpyridin-3-yl)pyrazolo[1,5-a]pyrimidin-5-yl)-8-azabicyclo[3.2.1]octan-8-yl)(morpholin-3-yl)methanone;
((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-piperidin-2-yl)methanone;
5-((1R,3s,5S)-8-azabicyclo[3.2.1]octan-3-yl)-3-(6-phenylpyridin-3-yl)pyrazolo[1,5-a]pyrimidin-7-amine;
1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxyethanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,3-triazol-5-yl)methanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-tetrazol-5-yl)methanone;
5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-phenylpyridine 1-oxide;
(R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,3-dihydroxypropan-1-one;
(1R,3s,5S)-3-(7-amino-6-(methylsulfonyl)-3-(6-phenylpyridin-3-yl)pyrazolo[1,5-a]pyrimidin-5-yl)-N-ethyl-8-azabicyclo[3.2.1]octane-8-carboxamide;
(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboxamide;
(1R,3s,5S)-3-(7-amino-6-(methylsulfonyl)-3-(6-phenylpyridin-3-yl)pyrazolo[1,5-a]pyrimidin-5-yl)-N-cyclopropyl-8-azabicyclo[3.2.1]octane-8-carboxamide;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1-hydroxycyclopropyl)methanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-hydroxypyridin-2-yl)methanone;
((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-hydroxypyridin-2-yl)methanone;
1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-3,3,3-trifluoro-2-hydroxypropan-1-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxypyridin-2-yl)methanone;

5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-N-methylpicolinamide;

5-((1R,3s,5S)-8-(1H-tetrazol-5-yl)-8-azabicyclo[3.2.1]octan-3-yl)-6-(methylsulfonyl)-3-(6-phenylpyridin-3-yl)pyrazolo[1,5-a]pyrimidin-7-amine;

(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbaldehyde;

5-((1R,3s,5S)-8-(5-methyl-4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine;

5-((1R,3s,5S)-8-(4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine;

((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(thiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(7-fluoronaphthalen-2-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

5-((1R,3s,5S)-8-(4H-1,2,4-triazol-3-ylsulfonyl)-8-azabicyclo[3.2.1]octan-3-yl)-6-(methylsulfonyl)-3-(6-phenylpyridin-3-yl)pyrazolo[1,5-a]pyrimidin-7-amine;

(S)-1-((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one;

(R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone;

(1R,3s,5S)-3-(7-amino-6-(methylsulfonyl)-3-(6-phenylpyridin-3-yl)pyrazolo[1,5-a]pyrimidin-5-yl)-N-methyl-8-azabicyclo[3.2.1]octane-8-carboxamide;

((1R,3s,5S)-3-(7-amino-6-(methylsulfonyl)-3-(4-(pyridin-2-yl)phenyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(5-methoxythiophen-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3,4-dimethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-(1-methyl-1H-pyrazol-3-yl)pyridine 1-oxide;

((1R,3s,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluoro-4-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,3-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(3'-fluoro-2,2'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxy-3-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-chloro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(benzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,2-difluorobenzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,3-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(difluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(2-methoxyethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-methyl-2H-indazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-methoxypyrimidin-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-ethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-cyclopropoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxy-(D$_3$)-phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(fluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-butylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(4-methoxy-(D$_3$)-phenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-(D$_3$)-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(1-methyl-(D$_3$)-1H-pyrazol-3-yl)pyridin-3-yl)-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(2-methoxyethoxy)ethanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-pyrazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-5-yl)methanone;

(3-amino-1H-pyrazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[3,2-c]pyridin-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[2,3-b]pyridin-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-imidazol-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-benzo[d]imidazol-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-5-yl)methanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(3-methyl-1H-1,2,4-triazol-5-yl)ethanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(hydroxymethyl)-1H-pyrazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(aminomethyl)-1H-pyrazol-5-yl)methanone;

((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-morpholin-3-yl)methanone;

((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-morpholin-3-yl)methanone;

((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

N-(5-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide;

(5-amino-1H-pyrazol-4-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,2,2-trifluoroethanone;

5-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)-2-methoxybenzonitrile;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-(dimethylamino)-4H-1,2,4-triazol-3-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-1H-pyrazol-4-yl)methanone;

((1R,3s,5S)-3-(7-amino-3-(7-(hydroxymethyl)quinolin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2-methyl-2H-indazol-5-yl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone;

(3-amino-1H-1,2,4-triazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-1,2,4-triazol-5-yl)methanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(5-amino-4H-1,2,4-triazol-3-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(3-(2,2'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

2-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)pyridine 1-oxide;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-1H-pyrazol-4-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(3-(6-(1H-pyrazol-4-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-fluoro-4-(trifluoromethyl)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(1H-pyrazol-5-yl)methanone;

1-((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)methanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone;

(R)-1-((1R,3S,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxypropan-1-one;

((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone;

(1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octane-8-carboxamide;

(1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octane-8-carboxamide;

((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

1-((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

(3-amino-1H-pyrazol-5-yl)((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)methanone;

(1R,3s,5S)-3-(7-amino-3-(6-(2-fluorophenyl)pyridin-3-yl)-6-(methylsulfonyl)pyrazolo[1,5-a]pyrimidin-5-yl)-N-ethyl-8-azabicyclo[3.2.1]octane-8-carboxamide;

(1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carboxamide;

1-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)methanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(4H-1,2,4-triazol-3-yl)methanone;

(2-amino-4-methylpyrimidin-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazol-2(3H)-one;

4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-1H-imidazol-2(3H)-one;

6-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)pyridin-2(1H)-one;

(S)-4-((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one;

(R)-4-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyrimidin-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyridin-3-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-aminopyrimidin-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-aminopyrazin-2-yl)methanone;

((1R,3s,5S)-3-(7-amino-3-(2-(3-fluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(imidazo[1,2-a]pyrimidin-6-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2-hydroxypropan-2-yl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(7-amino-6-(methylsulfonyl)-3-(tetrahydro-2H-pyran-4-yl)pyrazolo[1,5-a]pyrimidin-5-yl)-8-azabicyclo[3.2.1]octan-8-yl)-2-hydroxyethanone;

4-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-fluorobenzamide;

4-(7-amino-5-((1R,3s,5S)-8-(2-hydroxyacetyl)-8-azabicyclo[3.2.1]octan-3-yl)-6-(methylsulfonyl)pyrazolo[1,5-a]pyrimidin-3-yl)-2-fluorobenzamide;

((1R,3s,5S)-3-(7-amino-3-(6-(2-hydroxypropan-2-yl)-5-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(5-chloro-6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(cyclopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(ethylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-phenylpyridin-3-yl)-6-(propylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(isopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6'-methoxy-2,3'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclohexylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclopentylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone;

1-((1R,3s,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

(1R,3s,5S)-3-(7-amino-6-(methylsulfonyl)-3-(6-phenylpyridin-3-yl)pyrazolo[1,5-a]pyrimidin-5-yl)-N-methoxy-8-azabicyclo[3.2.1]octane-8-carboxamide;

(1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboxamide;

((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(6-fluoroquinolin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)ethanone;

(3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-1H-1,2,4-triazol-3-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(1-hydroxycyclopropyl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoro-2-hydroxypropan-1-one;

2-amino-1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoropropan-1-one;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone;

1-((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)ethanone;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

(3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(5-methyl-1H-1,2,4-triazol-3-yl)methanone;

((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

(3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(5-methyl-1H-1,2,4-triazol-3-yl)methanone;

1-((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)ethanone;

((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(2H-1,2,3-triazol-4-yl)methanone;

5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-oxoethyl)acetamide;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-oxoethyl)-2,2,2-trifluoroacetamide;

((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-pyrrolidin-2-yl)methanone;

((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-pyrrolidin-2-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methyl-4H-1,2,4-triazol-3-yl)methanone;

5-((1R,3s,5S)-8-(4H-1,2,4-triazol-3-ylsulfonyl)-8-azabicyclo[3.2.1]octan-3-yl)-6-cyclopropyl-3-(6-phenylpyridin-3-yl)pyrazolo[1,5-a]pyrimidin-7-amine;

(1R,3s,5S)-3-(7-amino-6-cyclopropyl-3-(6-phenylpyridin-3-yl)pyrazolo[1,5-a]pyrimidin-5-yl)-N-methyl-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-ethyl-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-(2-methoxyethyl)-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-(2-hydroxyethyl)-8-azabicyclo[3.2.1]octane-8-carboxamide;

((1R,3s,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(2,3-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-fluoro-3-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(2,5-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-ethoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-(2-methoxyethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-(difluoromethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-methylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(1-methyl-1H-imidazol-4-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-methoxyquinolin-3-yl)pyrazolo[1,5-a]pyrimidin-5-yl)-8-azabicyclo[3.2.1]octan-8-yl)(4H-1,2,4-triazol-3-yl)methanone, ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(3-chlorophenyl)methanone;

((1R,3s,5S)-3-(7-amino-6-cyclopropyl-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone;

(5-amino-4H-1,2,4-triazol-3-yl)((1R,3s,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)methanone;

N-(5-(((1R,3s,5S)-3-(7-amino-6-cyclopropyl-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(dimethylamino)-4H-1,2,4-triazol-3-yl)methanone;

(3-amino-1H-pyrazol-4-yl)((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(2-methoxyethylamino)-4H-1,2,4-triazol-3-yl)methanone;

(1R,3s,5S)-3-(7-amino-6-cyclopropyl-3-(6-phenylpyridin-3-yl)pyrazolo[1,5-a]pyrimidin-5-yl)-N-hydroxy-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-hydroxy-8-azabicyclo[3.2.1]octane-8-carboxamide;

7-amino-5-((1R,3s,5S)-8-(2-hydroxyacetyl)-8-azabicyclo[3.2.1]octan-3-yl)-3-(6-phenylpyridin-3-yl)pyrazolo[1,5-a]pyrimidine-6-carbonitrile;

5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carbonitrile;

5-((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidine-6-carbonitrile;

((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

(3-amino-1H-pyrazol-5-yl)((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methoxymethyl)-3-(6-(4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(hydroxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone;

1-((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)-2-hydroxyethanone;

((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(3-(6-(1H-imidazol-2-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-imidazol-2-yl)pyridin-3-yl)-7-amino-6-ethylpyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-7-amino-6-(prop-1-en-2-yl)pyrazolo[1,5-a]pyrimidin-5-yl)-8-azabicyclo[3.2.1]octan-8-yl)-2-hydroxyethanone;

(S)-1-((1R,3R,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one;

2-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-oxoethyl acetate;

1-(3-(6-(1H-imidazol-2-yl)pyridin-3-yl)-7-amino-5-((1R,3s,5S)-8-(methylsulfonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-5-((1R,3s,5S)-8-(1H-pyrrole-3-carbonyl)-8-azabicyclo[3.2.1]octan-3-yl)-7-aminopyrazolo[1,5-a]pyrimidin-6-yl)ethanone;

(R)-1-((1R,3S,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-(2-methoxyethoxy)ethanone;

((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(1H-pyrrol-3-yl)methanone;

(1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carbaldehyde;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-methoxyethanone;

1-(3-(6-(1H-imidazol-2-yl)pyridin-3-yl)-7-amino-5-((1R,3s,5S)-8-(3-amino-1H-pyrazole-5-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-5-((1R,3s,5S)-8-acetyl-8-azabicyclo[3.2.1]octan-3-yl)-7-aminopyrazolo[1,5-a]pyrimidin-6-yl)ethanone;

1-(3-(6-(1H-imidazol-2-yl)pyridin-3-yl)-7-amino-5-((1R,3s,5S)-8-(tetrahydrofuran-2-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-7-amino-5-((1R,3s,5S)-8-(5-amino-4H-1,2,4-triazole-3-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-7-amino-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoroethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoropropan-1-one;

(1R,3s,5S)-3-(3-(6-(1H-imidazol-2-yl)pyridin-3-yl)-6-acetyl-7-aminopyrazolo[1,5-a]pyrimidin-5-yl)-N-methyl-8-azabicyclo[3.2.1]octane-8-carboxamide;

(1R,3s,5S)-methyl 3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxylate;

1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(7-amino-6-cyclopropyl-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(7-amino-6-cyclopropyl-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone;

(1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxamide;

(1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octane-8-carboxamide;

1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)-5-methylpyridin-3-yl)-6-acetyl-7-aminopyrazolo[1,5-a]pyrimidin-5-yl)-8-azabicyclo[3.2.1]octan-8-yl)-2-hydroxyethanone;

1-(3-(6-(1H-imidazol-2-yl)-5-methylpyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(4-(1H-imidazol-2-yl)phenyl)-7-amino-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(3-fluoro-4-(5-methyl-1H-imidazol-2-yl)phenyl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(3-fluoro-4-(5-methyl-1H-imidazol-2-yl)phenyl)pyrazolo[1,5-a]pyrimidin-6-yl)ethanone;

1-((1R,3s,5S)-3-(6-acetyl-7-amino-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(3-fluoro-4-(1H-imidazol-2-yl)phenyl)pyrazolo[1,5-a]pyrimidin-6-yl)ethanone;

1-((1R,3s,5S)-3-(3-(4-(1H-imidazol-2-yl)phenyl)-6-acetyl-7-aminopyrazolo[1,5-a]pyrimidin-5-yl)-8-azabicyclo[3.2.1]octan-8-yl)-2-hydroxyethanone;

1-(3-(4-(1H-imidazol-2-yl)phenyl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2,2-dimethylpropan-1-one;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2-(hydroxymethyl)-2-methylpropan-1-one;

1-(5-((1R,3s,5S)-8-(4H-1,2,4-triazole-3-carbonyl)-8-azabicyclo[3.2.1]octan-3-yl)-7-amino-3-(6-(hydroxymethyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxybutyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxypropyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxyethyl)pyridin-3-yl)pyrazolo[1,5-a]pyrimidin-6-yl)ethanone;

1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxy-3-methylbutyl)pyridin-3-yl)pyrazolo[1,5-a]pyrimidin-6-yl)ethanone;

1-(7-amino-5-((1R,3s,5S)-8-(1-hydroxycyclopropanecarbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-((1R,3s,5S)-3-(6-acetyl-7-amino-3-(6-(2-hydroxypropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-hydroxypropan-2-yl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(5-((1R,3s,5S)-8-(1H-1,2,3-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(1H-pyrazole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(1H-pyrazole-4-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(7-amino-5-((1R,3s,5S)-8-(5-amino-4H-1,2,4-triazole-3-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone;

1-(7-amino-5-((1R,3s,5S)-8-(5-amino-1H-pyrazole-4-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-(5-((1R,3s,5S)-8-(1H-pyrrole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(7-amino-3-(6-(1-hydroxycyclobutyl)pyridin-3-yl)-5-((1R,3s,5S)-8-(3-methyl-1H-1,2,4-triazole-5-carbonyl)-8-azabicyclo[3.2.1]octan-3-yl)pyrazolo[1,5-a]pyrimidin-6-yl)ethanone;

1-((1R,3s,5S)-3-(6-acetyl-7-amino-3-(6-(1-hydroxycyclobutyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(1H-1,2,3-triazole-5-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

1-(5-((1R,3s,5S)-8-(1H-1,2,4-triazole-3-carbonyl)-8-azabicyclo[3.2.1]octan-3-yl)-7-amino-3-(4-(1-hydroxyethyl)phenyl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(4-((R)-1-hydroxyethyl)phenyl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(4-((S)-1-hydroxyethyl)phenyl)pyrazolo[1,5-a]pyrimidin-6-yl)ethanone;

1-((1R,3s,5S)-3-(6-acetyl-7-amino-3-(6-(2-hydroxypropan-2-yl)-5-methylpyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(2-hydroxypropan-2-yl)-5-methylpyridin-3-yl)pyrazolo[1,5-a]pyrimidin-6-yl)ethanone;

((1R,3s,5S)-3-(7-amino-3-(6-(1-hydroxybutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-hydroxypropyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone;

1-((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(3-methyl-1H-1,2,4-triazol-5-yl)methanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

1-(5-((1R,3s,5S)-8-(4H-1,2,4-triazole-3-carbonyl)-8-azabicyclo[3.2.1]octan-3-yl)-7-amino-3-(6-((2-methoxyethoxy)methyl)pyridin-3-yl)pyrazolo[1,5-a]pyrimidin-6-yl)ethanone;

((1R,3s,5S)-3-(7-amino-3-(6-((2-methoxyethoxy)methyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-((S)-1-hydroxyethyl)pyridin-3-yl)pyrazolo[1,5-a]pyrimidin-6-yl)ethanone;

((1R,3s,5S)-3-(7-amino-3-(6-(hydroxymethyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(2-(1-hydroxyethyl)thiazol-5-yl)pyrazolo[1,5-a]pyrimidin-6-yl)ethanone;

((1R,3s,5S)-3-(7-amino-3-(2-(1-hydroxyethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

((1R,3s,5S)-3-(7-amino-6-cyclopropyl-3-(6-(2-hydroxypropan-2-yl)pyridin-3-yl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-bromo-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(3-hydroxyoxetan-3-yl)pyridin-3-yl)pyrazolo[1,5-a]pyrimidin-6-yl)ethanone;

((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-hydroxyoxetan-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(3-hydroxyoxetan-3-yl)pyridin-3-yl)-6-(methylsulfonyl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-hydroxycyclopentyl)pyridin-3-yl)pyrazolo[1,5-a]pyrimidin-6-yl)ethanone;

((1R,3s,5S)-3-(7-amino-3-(4-(1-hydroxyethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(1,2-dihydroxyethyl)pyridin-3-yl)pyrazolo[1,5-a]pyrimidin-6-yl)ethanone;

((1R,3s,5S)-3-(7-amino-3-(8-hydroxy-5,6,7,8-tetrahydroquinolin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(8-hydroxy-5,6,7,8-tetrahydroquinolin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(8-hydroxy-8-methyl-5,6,7,8-tetrahydroquinolin-3-yl)pyrazolo[1,5-a]pyrimidin-5-yl)-8-azabicyclo[3.2.1]octan-8-yl)(4H-1,2,4-triazol-3-yl)methanone;

Deuterated-(3-exo)-3-[7-amino-6-cyclopropy-3-(5,6,7,8-tetrahydro-8-hydroxy-3-quinolinyl-(D))pyrazolo[1,5-a]pyrimidin-5-yl]-8-(4H-1,2,4-triazol-3-ylcarbonyl)-8-azabicyclo[3.2.1]octane;

Deuterated-(3-exo)-3-[6-acetyl-7-amino-3-(5,6,7,8-tetrahydro-8-hydroxy-3-quinolinyl-(D))pyrazolo[1,5-a]pyrimidin-5-yl]-8-(4H-1,2,4-triazol-3-ylcarbonyl)-8-azabicyclo[3.2.1]octane;

1-(5-((1R,3s,5S)-8-(4H-1,2,4-triazole-3-carbonyl)-8-azabicyclo[3.2.1]octan-3-yl)-7-amino-3-(8-hydroxy-5,6,7,8-tetrahydroquinolin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(8-hydroxy-5,6,7,8-tetrahydroquinolin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(7-hydroxy-6,7-dihydro-5H-cyclopenta[b]pyridin-3-yl)pyrazolo[1,5-a]pyrimidin-6-yl)ethanone;

((1R,3s,5S)-3-(7-amino-6-cyclopropyl-3-(7-hydroxy-6,7-dihydro-5H-cyclopenta[b]pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(7-hydroxy-6,7-dihydro-5H-cyclopenta[b]pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-(((1R,3s,5S)-8-(4H-1,2,4-triazole-3-carbonyl)-8-azabicyclo[3.2.1]octan-3-yl)-7-amino-3-(4-hydroxy-3,4-dihydro-2H-pyrano[3,2-b]pyridin-7-yl)pyrazolo[1,5-a]pyrimidin-6-yl)ethanone;

((1R,3s,5S)-3-(7-amino-6-cyclopropyl-3-(4-hydroxy-3,4-dihydro-2H-pyrano[3,2-b]pyridin-7-yl)pyrazolo[1,5-a]pyrimidin-5-yl)-8-azabicyclo[3.2.1]octan-8-yl)(4H-1,2,4-triazol-3-yl)methanone;

1-(5-(((1R,3s,5S)-8-(4H-1,2,4-triazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone;

1-(5-(((1R,3s,5S)-8-(1H-pyrazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone;

1-((1R,3s,5S)-3-(6-acetyl-7-amino-3-(6-(2,2,2-trifluoro-1-hydroxyethyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s, 5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)(1H-pyrazol-3-yl)methanone;

1-((1R,3s,5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)(5-methyl-4H-1,2,4-triazol-3-yl)methanone;

1-((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(6-((R)-2,2,2-trifluoro-1-hydroxyethyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-((S)-2,2,2-trifluoro-1-hydroxyethyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(1,1,1,3,3,3-hexafluoro-2-hydroxypropan-2-yl)pyridin-3-yl)pyrazolo[1,5-a]pyrimidin-6-yl)ethanone;

1-((1R,3s,5S)-3-(6-acetyl-7-amino-3-(6-(1,1,1,3,3,3-hexafluoro-2-hydroxypropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(1,1,1,3,3,3-hexafluoro-2-hydroxypropan-2-yl)pyridin-3-yl)-5-(((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(7-amino-5-(((1R,3s,5S)-8-(5-amino-4H-1,2,4-triazole-3-carbonyl)-8-azabicyclo[3.2.1]octan-3-yl)-3-(6-(1,1,1,3,3,3-hexafluoro-2-hydroxypropan-2-yl)pyridin-3-yl)pyrazolo[1,5-a]pyrimidin-6-yl)ethanone;

1-(7-amino-5-(((1R,3s,5S)-8-(3-amino-1H-pyrazole-5-carbonyl)-8-azabicyclo[3.2.1]octan-3-yl)-3-(6-(1,1,1,3,3,3-hexafluoro-2-hydroxypropan-2-yl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(2-amino-1,1,1,3,3,3-hexafluoropropan-2-yl)pyridin-3-yl)pyrazolo[1,5-a]pyrimidin-6-yl)ethanone;

1-((1R,3s,5S)-3-(6-acetyl-7-amino-3-(6-(2-amino-1,1,1,3,3,3-hexafluoropropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-amino-1,1,1,3,3,3-hexafluoropropan-2-yl)pyridin-3-yl)-5-(((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-((1R,3s,5S)-3-(6-acetyl-7-amino-3-(6-(1,1,1,3,3,3-hexafluoro-2-hydroxypropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-amino-1,1,1,3,3,3-hexafluoropropan-2-yl)pyridin-3-yl)-5-(((1R,3s,5S)-8-(3-amino-1H-pyrazole-5-carbonyl)-8-azabicyclo[3.2.1]octan-3-yl)pyrazolo[1,5-a]pyrimidin-6-yl)ethanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)-2-hydroxyethanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-amino-4H-1,2,4-triazol-3-yl)methanone;

(3-amino-1H-pyrazol-5-yl)((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)methanone;

1-(5-(((1R,3s,5S)-8-(4H-1,2,4-triazole-3-carbonyl)-8-azabicyclo[3.2.1]octan-3-yl)-7-amino-3-(2-(hydroxymethyl)thiazol-5-yl)pyrazolo[1,5-a]pyrimidin-6-yl)ethanone;

((1R,3s,5S)-3-(7-amino-3-(2-(hydroxymethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

(5-(5-(((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl 4H-1,2,4-triazole-3-carboxylate;

((1R,3s,5S)-3-(7-amino-3-(2-(aminomethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

N-((5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl)-4H-1,2,4-triazole-3-carboxamide;

((1R,3s,5S)-3-(7-amino-3-(2-(aminomethyl)thiazol-5-yl)-6-cyclopropylpyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(aminomethyl)-4-cyclopropylthiazol-5-yl)-6-cyclopropylpyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(1H-1,2,4-triazole-5-carbonyl)-8-azabicyclo[3.2.1]octan-3-yl)-7-amino-3-(5-fluoro-6-(2-hydroxypropan-2-yl)pyridin-3-yl)pyrazolo[1,5-a]pyrimidin-6-yl)ethanone;

1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone;

(2R)-1-(3-(6-acetyl-7-amino-3-(6-phenylpyridin-3-yl)pyrazolo[1,5-a]pyrimidin-5-yl)-3,8-diazabicyclo[3.2.1]octan-8-yl)-2-hydroxypropan-1-one;

1-(5-(5-(4H-1,2,4-triazole-3-carbonyl)-2,5-diazabicyclo[2.2.2]octan-2-yl)-7-amino-3-(6-phenylpyridin-3-yl)pyrazolo[1,5-a]pyrimidin-6-yl)ethanone;

(2R)-1-(5-(6-acetyl-7-amino-3-(6-phenylpyridin-3-yl)pyrazolo[1,5-a]pyrimidin-5-yl)-2,5-diazabicyclo[2.2.2]octan-2-yl)-2-hydroxypropan-1-one;

1-(5-(3-(4H-1,2,4-triazole-3-carbonyl)-3,8-diazabicyclo[3.2.1]octan-8-yl)-7-amino-3-(6-phenylpyridin-3-yl)pyrazolo[1,5-a]pyrimidin-6-yl)ethanone;

(2R)-1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxypropan-1-one;

1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxyethanone;

N-(5-((1R,3s,5S)-8-(4H-1,2,4-triazole-3-carbonyl)-8-azabicyclo[3.2.1]octan-3-yl)-6-cyclopropyl-3-(6-phenylpyridin-3-yl)pyrazolo[1,5-a]pyrimidin-7-yl)acetamide;

N-(5-((1R,3s,5S)-8-(4H-1,2,4-triazole-3-carbonyl)-8-azabicyclo[3.2.1]octan-3-yl)-6-acetyl-3-(6-phenylpyridin-3-yl)pyrazolo[1,5-a]pyrimidin-7-yl)acetamide;

N-(5-((1R,3s,5S)-8-(4H-1,2,4-triazole-3-carbonyl)-8-azabicyclo[3.2.1]octan-3-yl)-3-(6-phenylpyridin-3-yl)pyrazolo[1,5-a]pyrimidin-7-yl)acetamide;

1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone;

1-((1R,3s,5S)-3-(6-acetyl-7-amino-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

(R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one;

(S)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one;

(S)-4-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)oxazolidin-2-one;

2-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrazolidin-3-one;

2-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)pyrazolidin-3-one;

1-(7-amino-5-((1R,3r,5S)-3-hydroxy-8-(4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

((1R,3r,5S)-3-(7-amino-6-(methylsulfonyl)-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3r,5S)-3-(7-amino-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3r,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

1-(5-(9-(1H-1,2,4-triazole-3-carbonyl)-3-oxa-9-azabicyclo[3.3.1]nonan-7-yl)-7-amino-3-(1-phenyl-1H-pyrazol-4-yl)pyrazolo[1,5-a]pyrimidin-6-yl)ethanone;

1-(5-(9-(1H-1,2,4-triazole-3-carbonyl)-3-oxa-9-azabicyclo[3.3.1]nonan-7-yl)-7-amino-3-(6-phenylpyridin-3-yl)pyrazolo[1,5-a]pyrimidin-6-yl)ethanone;

1-(7-(6-acetyl-7-amino-3-(6-phenylpyridin-3-yl)pyrazolo[1,5-a]pyrimidin-5-yl)-3-oxa-9-azabicyclo[3.3.1]nonan-9-yl)-2-hydroxyethanone;

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (mixture of stereoisomer);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (isomer 1);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (isomer II);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1-hydroxycyclopropyl)methanone; (isomer II);

1-(5-(9-(1H-1,2,4-triazole-3-carbonyl)-9-azabicyclo[3.3.1]nonan-3-yl)-7-amino-3-(6-phenylpyridin-3-yl)pyrazolo[1,5-a]pyrimidin-6-yl)ethanone;

1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-((1S,3R,5R)-3-(6-acetyl-7-amino-3-(6-phenylpyridin-3-yl)pyrazolo[1,5-a]pyrimidin-5-yl)-6-hydroxy-8-azabicyclo[3.2.1]octan-8-yl)-2-hydroxyethanone;

1-(5-(7-(1H-1,2,4-triazole-3-carbonyl)-7-azabicyclo[2.2.1]heptan-2-yl)-7-amino-3-(6-phenylpyridin-3-yl)pyrazolo[1,5-a]pyrimidin-6-yl)ethanone;

((1R,3s,5S)-7-(7-amino-3-(6-phenylpyridin-3-yl)pyrazolo[1,5-a]pyrimidin-5-yl)-3,9-diazabicyclo[3.3.1]nonan-9-yl)(1H-1,2,4-triazol-3-yl)methanone;

endo/exo-7-[6-acetyl-7-amino-3-(6-phenyl-3-pyridinyl) pyrazolo[1,5-a]pyrimidin-5-yl]-9-(4h-1,2,4-triazol-3-yl-carbonyl)-3-thia-9-azabicyclo[3.3.1]nonane, 3,3-dioxide;

((1R,3s,5S)-3-(7-amino-6-(1-hydroxycyclopropyl)-3-(6-phenylpyridin-3-yl)pyrazolo[1,5-a]pyrimidin-5-yl)-8-azabicyclo[3.2.1]octan-8-yl)(1H-1,2,4-triazol-3-yl) methanone;

5-((1R,3s,5S)-8-(1H-1,2,4-triazole-3-carbonyl)-8-azabicyclo[3.2.1]octan-3-yl)-7-amino-3-(6-phenylpyridin-3-yl) pyrazolo[1,5-a]pyrimidine-6-carboxamide;

((1R,3s,5S)-3-(7-(methylamino)-6-(methylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl) methanone;

((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl) methanone;

1-((1R,3s,5S)-3-(7-amino-3-(3-fluoro-4-(hydroxymethyl) phenyl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(4-(1-aminocyclopropyl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(4-(2-aminopropan-2-yl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

(E)-4-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carbonyl)-N'-(3-(dimethylamino)propyl)-N-ethyl-2H-1,2,3-triazole-2-carboximidamide;

1-(5-((1R,3s,5S)-8-(4H-1,2,4-triazole-3-carbonyl)-8-azabicyclo[3.2.1]octan-3-yl)-7-amino-3-(6-(cyclopropylamino)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-aminopyridin-3-yl) pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-(cyclopropylamino)pyrimidin-3-yl)pyrazolo[1,5-a]pyrimidin-6-yl) ethanone;

1-((1R,3s,5S)-3-(6-acetyl-7-amino-3-(6-(cyclopropylamino)pyridin-3-yl)pyrazolo[1,5-a]pyrimidin-5-yl)-8-azabicyclo[3.2.1]octan-8-yl)-2-hydroxyethanone;

N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)acetohydrazide;

N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)propionohydrazide;

((1R,3s,5S)-3-(7-amino-3-(6-cyclobutoxypyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(cyclopropylmethoxy)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl) methanone;

((1R,3r,5S)-3-(7-amino-6-cyclopropyl-3-(2H-pyrazolo[4,3-h]pyrano[3,2-b]pyridin-7-yl)pyrazolo[1,5-a]pyrimidin-5-yl)-8-azabicyclo[3.2.1]octan-8-yl)(4H-1,2,4-triazol-3-yl) methanone;

1-(5-((1R,3s,5S)-8-(4H-1,2,4-triazole-3-carbonyl)-8-azabicyclo[3.2.1]octan-3-yl)-7-amino-3-(6-(3-hydroxyprop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-methoxyprop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-(2-hydroxyethoxy)prop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-(2-methoxyethoxy)prop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(cyclopropylethynyl)pyridin-3-yl)pyrazolo[1,5-a]pyrimidin-6-yl)ethanone;

1-((1R,3s,5S)-3-(6-acetyl-7-amino-3-(6-(cyclopropylethynyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(pyridin-3-ylethynyl)pyrazolo[1,5-a]pyrimidin-5-yl)-8-azabicyclo[3.2.1] octan-8-yl)(4H-1,2,4-triazol-3-yl)methanone;

5-((1R,3s,5S)-8-(4-aminopyrimidin-2-yl)-8-azabicyclo [3.2.1]octan-3-yl)-6-(methylsulfonyl)-3-(6-phenylpyridin-3-yl)pyrazolo[1,5-a]pyrimidin-7-amine;

5-((1R,3s,5S)-8-(5-aminopyrimidin-4-yl)-8-azabicyclo [3.2.1]octan-3-yl)-6-(methylsulfonyl)-3-(6-phenylpyridin-3-yl)pyrazolo[1,5-a]pyrimidin-7-amine;

5-((1R,3s,5S)-8-(3-aminopyridin-2-yl)-8-azabicyclo[3.2.1] octan-3-yl)-6-(methylsulfonyl)-3-(6-phenylpyridin-3-yl) pyrazolo[1,5-a]pyrimidin-7-amine;

N-(4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyrimidin-5-yl)acetamide;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyridin-3-yl)acetamide;

5-(5-(5-((1R,3s,5S)-8-(4H-1,2,4-triazole-3-carbonyl)-8-azabicyclo[3.2.1]octan-3-yl)-6-acetyl-7-aminopyrazolo [1,5-a]pyrimidin-3-yl)pyridin-2-yl)-5-methylimidazolidine-2,4-dione;

5-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)-5-methylimidazolidine-2,4-dione;

(1R,3s,5S)-3-(7-amino-6-(methylsulfonyl)-3-(6-phenylpyridin-3-yl)pyrazolo[1,5-a]pyrimidin-5-yl)-8-azabicyclo [3.2.1]octane-8-carbonitrile;

(1R,3s,5S)-3-(6-acetyl-7-amino-3-(6-phenylpyridin-3-yl) pyrazolo[1,5-a]pyrimidin-5-yl)-8-azabicyclo[3.2.1]octane-8-carbonitrile;

(1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboximidamide;

(1R,3s,5S)-3-(7-amino-6-(methylsulfonyl)-3-(6-phenylpyridin-3-yl)pyrazolo[1,5-a]pyrimidin-5-yl)-8-azabicyclo [3.2.1]octane-8-carboximidamide;

3-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one;

1-(5-(5-((1R,3s,5S)-8-(1H-1,2,4-triazole-5-carbonyl)-8-azabicyclo[3.2.1]octan-3-yl)-6-acetyl-7-aminopyrazolo [1,5-a]pyrimidin-3-yl)pyridin-2-yl)-3-methylurea;

N-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)acetamide;
ethyl 5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-ylcarbamate;
ethyl 5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-ylcarbamate;
1-(4-(7-amino-5-((1R,3s,5S)-8-azabicyclo[3.2.1]octan-3-yl)pyrazolo[1,5-a]pyrimidin-3-yl)phenyl)-3-methylurea;
1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)phenyl)-3-methylurea;
1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)-2-methoxyphenyl)-3-ethylurea;
1-(4-(7-amino-5-((1R,3s,5S)-8-(2-hydroxyacetyl)-8-azabicyclo[3.2.1]octan-3-yl)pyrazolo[1,5-a]pyrimidin-3-yl)phenyl)-3-methylurea;
1-(4-(7-amino-5-((1R,3s,5S)-8-(morpholine-3-carbonyl)-8-azabicyclo[3.2.1]octan-3-yl)pyrazolo[1,5-a]pyrimidin-3-yl)phenyl)-3-methylurea;
1-(5-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyridin-2-yl)-3-ethylurea;
1-(4-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)phenyl)-3-methylurea;
(1R,3s,5S,E)-3-(7-amino-3-(6-phenylpyridin-3-yl)pyrazolo[1,5-a]pyrimidin-5-yl)-N'-cyano-8-azabicyclo[3.2.1]octane-8-carboximidamide;
(1R,3s, 5S, E)-3-(7-amino-6-(methylsulfonyl)-3-(6-phenylpyridin-3-yl)pyrazolo[1,5-a]pyrimidin-5-yl)-N'-cyano-8-azabicyclo[3.2.1]octane-8-carboximidamide;
((1R,3s,5S)-3-(7-amino-3-(2-aminopyrimidin-5-yl)pyrazolo[1,5-a]pyrimidin-5-yl)-8-azabicyclo[3.2.1]octan-8-yl)(4H-1,2,4-triazol-3-yl)methanone;
6-(methylsulfonyl)-3-(6-phenylpyridin-3-yl)-5-(1R,3s,5S)-8-(2,2,2-trifluoroethyl)-8-azabicyclo[3.2.1]octan-3-yl)pyrazolo[1,5-a]pyrimidin-7-amine;
1-(4-(7-amino-5-((1R,3s,5S)-8-(2,2,2-trifluoroethyl)-8-azabicyclo[3.2.1]octan-3-yl)pyrazolo[1,5-a]pyrimidin-3-yl)phenyl)-3-methylurea;
5-((1R,3s,5S)-8-(4H-1,2,4-triazol-3-yl)methyl)-8-azabicyclo[3.2.1]octan-3-yl)-6-(methylsulfonyl)-3-(6-phenylpyridin-3-yl)pyrazolo[1,5-a]pyrimidin-7-amine;
2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)acetamide;
1-(5-((1R,3s,5S)-8-(4H-1,2,4-triazole-3-carbonyl)-8-azabicyclo[3.2.1]octan-3-yl)-7-amino-3-(6-(1-amino-2,2,2-trifluoroethyl)pyridin-3-yl)pyrazolo[1,5-a]pyrimidin-6-yl)ethanone;
((1R,3s,5S)-3-(7-amino-3-(2-(aminomethyl)pyrimidin-5-yl)-6-bromopyrazolo[1,5-a]pyrimidin-5-yl)-8-azabicyclo[3.2.1]octan-8-yl)(4H-1,2,4-triazol-3-yl)methanone;
5-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyrimidine-2-carbonitrile;
5-(5-((1R,3s,5S)-8-(4H-1,2,4-triazole-3-carbonyl)-8-azabicyclo[3.2.1]octan-3-yl)-7-amino-6-cyclopropylpyrazolo[1,5-a]pyrimidin-3-yl)pyrimidine-2-carbonitrile;
5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyrimidine-2-carboxamide;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(piperazin-1-yl)-4H-1,2,4-triazol-3-yl)methanone;
((1R,3S,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-((R)-3-hydroxypyrrolidin-1-yl)-4H-1,2,4-triazol-3-yl)methanone;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(2-methoxyethoxy)-4H-1,2,4-triazol-3-yl)methanone;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4-methyl-4H-1,2,4-triazol-3-yl)methanone;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(4-methylpiperazin-1-yl)-4H-1,2,4-triazol-3-yl)methanone;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4H-1,2,4-triazol-3-yl)methanone;
(5-amino-4H-1,2,4-triazol-3-yl)((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)methanone;
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-morpholino-4H-1,2,4-triazol-3-yl)methanone; and
((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone; and
1-[(3-Exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone;
Or a stereoisomer thereof;
Or a pharmaceutically acceptable salt thereof;
Or a pharmaceutically acceptable salt of the stereoisomer thereof.

The compounds according to the invention have pharmacological properties; in particular, the compounds of the present invention can be inhibitors, regulators or modulators of protein kinases, such as mTOR protein kinases. As inhibitors of mTOR, preferred compounds of the present invention can exhibit $IC_{50}$ values of less than about 5 μm, preferably about 0.001 to about 1.0 μm, and more preferably about 0.001 to about 0.1 μm. The assay methods are described in the Examples set forth below.

Methods for Making the Compounds of Formula (I)

The compounds of Formula (I) can be prepared from known or readily prepared starting materials, following methods known to one skilled in the art of organic synthesis. Methods useful for making the compounds of Formula (I) are set forth in the Examples below. Alternative synthetic pathways and analogous structures will be apparent to those skilled in the art of organic synthesis. All stereoisomers and tautomeric forms of the compounds are contemplated.

EXAMPLES

Solvents, reagents, and intermediates that are commercially available were used as received. Reagents and intermediates that are not commercially available were prepared in the manner as described below. ¹H NMR spectra were obtained on a Varian spectrometer (400 MHz and 500 MHz) are reported as ppm down field from Me₄Si with number of protons, multiplicities, and coupling constants, in Hertz indicated parenthetically. Where LC/MS data are presented, analyses was performed using an Agilent 1100 Series LC w/ MicroMass Quattro MS Varian Pursuit XRs C18, 5 micron, 150 mm×4.6 mm ID gradient flow (0.1% TFA or 0.2% FA): 0 min—5% ACN, 7.5 min—100% ACN, 8.5 min—100 ACN, 8.51 min—5% ACN, 10 min—stop 3 ml/min. The retention time and observed parent ion are given. Where the description indicates the reaction mixture was purified by HPLC, the description refers to using a preparative Agilent 1100 Series LC/MSD SL system: Column Reverse Phase-Varian Pursuit XRs 100-18 250×21.2 mm; elution with gradient Acetonitrile/water with 0.1% TFA or 0.2% formic acid. The desired product was detected and collected by a mass-triggered automatic sample collector. Flash column chromatography was performed using pre-packed normal phase silica from Biotage, Inc.

The following solvents, reagents and reaction conditions may be referred to by their abbreviations:
Aq: aqueous
g or gm: grams
psi: pounds per square inch
pH: concentration of hydronium ions in a solution
° C.: degrees Celsius
h: hours
THF: Tetrahydrofuran
Et₂O: diethyl ether
SEM: 2-(trimethylsilyl)ethoxymethyl
LC-MS: Liquid chromatography mass spectrometry
DCM: dichloromethane
N: Normal
ml: milliliter
NBS: N-Bromosuccinimide
NCS: N-Chlorosuccinimide
NIS: N-iodosuccinimide
r.t.: room temperature
MeOH: methanol
DIEA: diisopropylethylamine
EtOAc: ethyl acetate
EtOH: ethanol
DMF: dimethylformamide
wt %: weight percent
m/z: mass per charge
LiOH: lithium hydroxide
DMSO: dimethylsulfoxide
HPLC: high performance liquid chromatography
IPA: isopropanol
Ret: retention
R$_t$: retention time
RP: reverse phase
ACN: acetonitrile
CH₃CN: acetonitrile
MeCN: acetonitrile
MeI: iodomethane
r.t.: room temperature
pTSA: para-toluene sulfonic acid
CDI: N,N'-carbonyldiimidazole
mg: milligram
PMA: phosphomolybdic acid
LiHMDS: Lithium bis(trimethylsilyl)amide
HMDS: hexamethyldisilazane
Pd/C: palladium on carbon
H₂: hydrogen gas
PdCl₂(dppf): [1,1'-bis(diphenylphosphino)ferrocene]dichloropalladium(II)
μmol: micromole
TFA: trifluoroacetic acid
NMP: N-methyl-2-pyrrolidone
min: minute
DME: dimethylethane
AcOH: acetic acid
BBN: 9-borabicyclo[3.3.1]nonane
BOC: tertiary-butyloxycarbonyl
M: Molar
mmol: millimolar
DIEA: diisopropylethylamine
Bu₃SnCN: tributyltin cyanide
Pd[P(t-Bu)₃]₂: bis(tributyl)Phosphine) palladium
Pd(PPh₃)₄: tetrakis(triphenylphosphine) palladium
EDCI: 1-ethyl-3-(3-dimethylaminopropyl)-carbodiimide
UV: ultraviolet
LDA: lithium diisopropylamide
Tf: trifluoromethanesulfonyl In certain instances, where the piperidine moiety attached to the pyrazolo[1,5-a]pyrimidine core is drawn in the chair conformation (i.e.

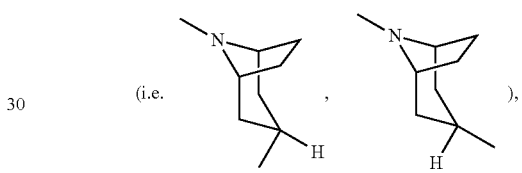

the chair conformation is interchangeable with the flat structure (i.e.

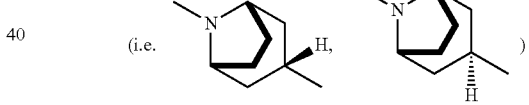

and other conformational isomers including but not limited to the half chair, twist-boat or boat conformation, which can interconvert with each other thermodynamically.

Example 1-1

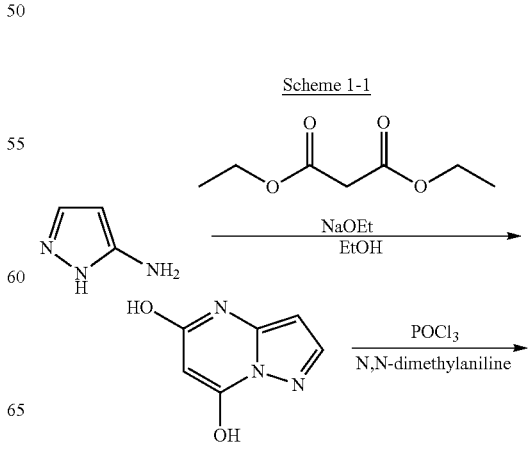

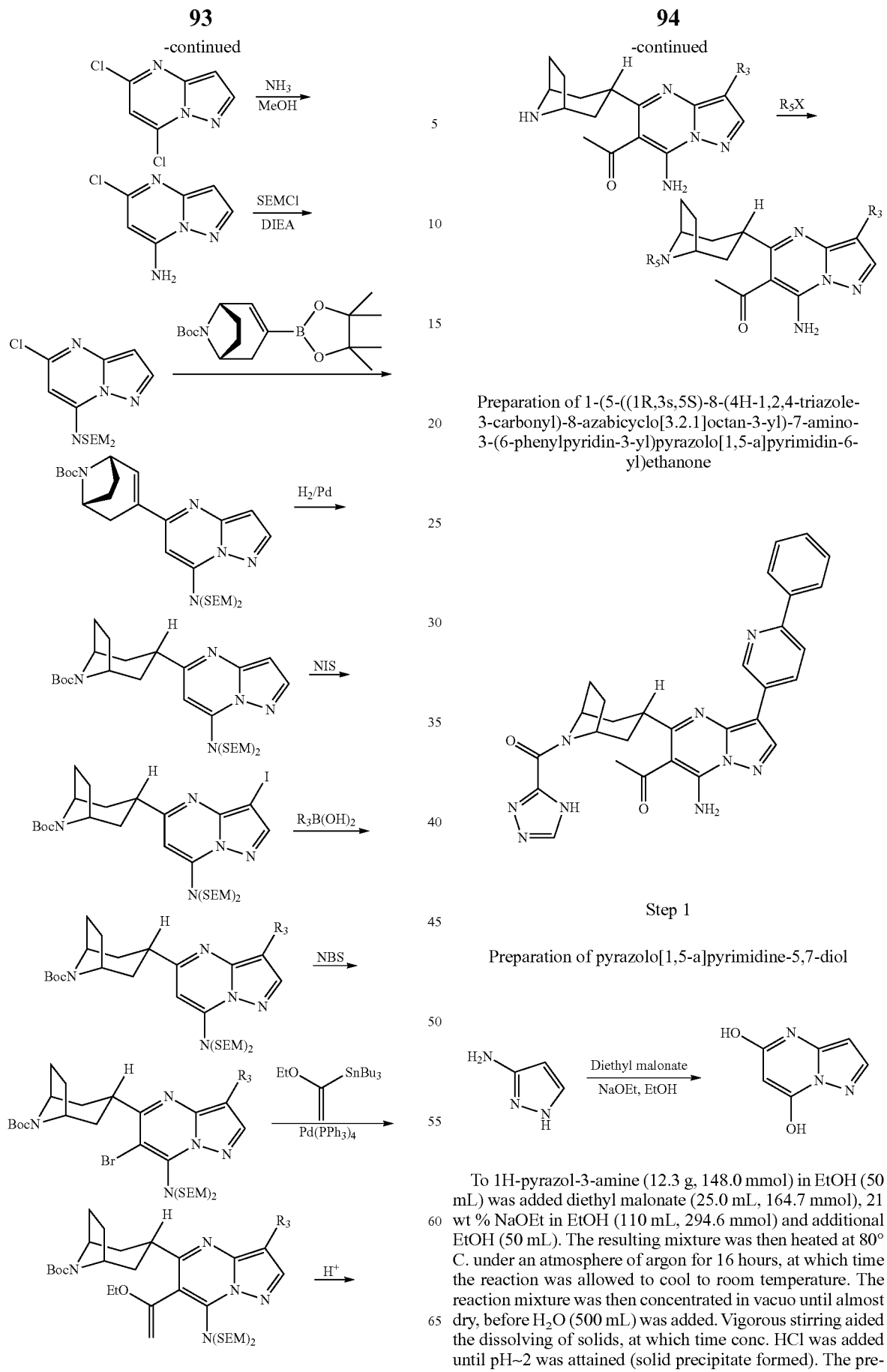

Preparation of 1-(5-(((1R,3s,5S)-8-(4H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)ethanone Step 1

Preparation of pyrazolo[1,5-a]pyrimidine-5,7-diol

To 1H-pyrazol-3-amine (12.3 g, 148.0 mmol) in EtOH (50 mL) was added diethyl malonate (25.0 mL, 164.7 mmol), 21 wt % NaOEt in EtOH (110 mL, 294.6 mmol) and additional EtOH (50 mL). The resulting mixture was then heated at 80° C. under an atmosphere of argon for 16 hours, at which time the reaction was allowed to cool to room temperature. The reaction mixture was then concentrated in vacuo until almost dry, before H₂O (500 mL) was added. Vigorous stirring aided the dissolving of solids, at which time conc. HCl was added until pH~2 was attained (solid precipitate formed). The precipitate was collected and dried by vacuum filtration giving pyrazolo[1,5-a]pyrimidine-5,7-diol as a tan solid (17.13 g).

Step 2

Synthesis of 5,7-dichloropyrazolo[1,5-a]pyrimidine

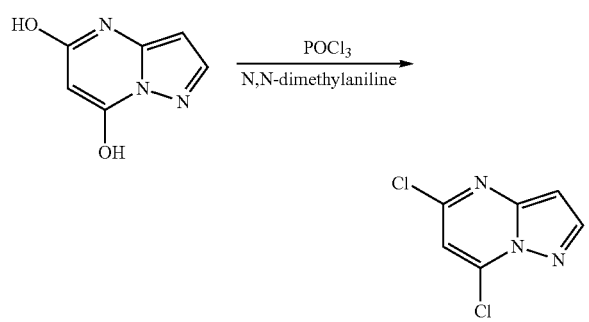

To pyrazolo[1,5-a]pyrimidine-5,7-diol (9.6 g, 63.5 mmol) in a 500 mL flask was added POCl$_3$ (125 mL, 1341.1 mmol). The flask was then cooled to 0° C. and N,N-dimethylaniline (22 mL, 173.6 mmol) was carefully added. On warming to room temperature, the reaction was then heated at 60° C. under an atmosphere of argon for 16 hours. On cooling, the reaction mixture was concentrated in vacuo to give a brown viscous liquid. This brown viscous liquid was carefully poured onto ice and allowed to warm to room temperature overnight. To the brown solution was carefully added saturated NaHCO$_3$ solution until no further effervescence was observed and pH~8 was attained. Organics were then extracted with CH$_2$Cl$_2$ (4×50 mL), dried (Na$_2$SO$_4$) and concentrated in vacuo to give a brown liquid (29.8 g). Gradient column chromatography on silica eluting with 50% CH$_2$Cl$_2$/hexanes (to elute aniline) followed by 75% CH$_2$Cl$_2$/hexanes (to elute product) gave 5,7-dichloropyrazolo[1,5-a]pyrimidine as a white solid (7.7 g).

Step 3

Synthesis of 5-chloropyrazolo[1,5-a]pyrimidin-7-amine

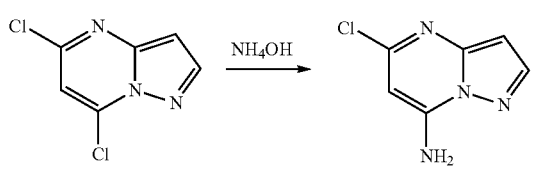

To 5,7-dichloropyrazolo[1,5-a]pyrimidine (7.6 g, 40.4 mmol) in a sealed vessel was added NH$_4$OH (100 mL). The vessel was then sealed and heated at 85° C. for 2.5 hours, at which time the consistency of the white solid had changed (from foamy white solid to free-flowing white solid). The vessel was removed from the heat source and allowed to cool to room temperature overnight. On cooling, the contents of the vessel were collected and dried by vacuum filtration giving 5-chloropyrazolo[1,5-a]pyrimidin-7-amine as a yellow-tinged white solid (6.8 g).

Step 4

Synthesis of 5-chloro-N,N-bis((2-(trimethylsilyl)ethoxy)methyl)pyrazolo[1,5-a]pyrimidin-7-amine

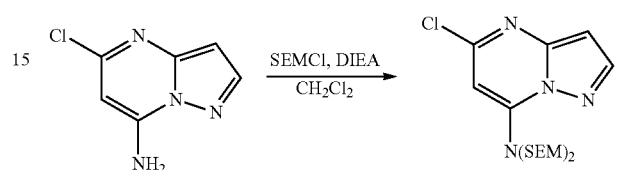

To 5-chloropyrazolo[1,5-a]pyrimidin-7-amine (6.7 g, 39.7 mmol) in CH$_2$Cl$_2$ (30 mL) was added N,N-diisopropylethylamine (48.0 mL, 275.6 mmol) followed by 2-(Trimethylsilyl)ethoxymethyl chloride (25.0 mL, 141.7 mmol). The reaction was heated at 45° C. for 3 hours before being allowed to cool to room temperature. The reaction mixture was then poured into a separatory funnel containing ~100 mL saturated NaHCO$_3$ solution and CH$_2$Cl$_2$ (50 mL). Organics were then extracted with CH$_2$Cl$_2$ (4×50 mL), dried (Na$_2$SO$_4$) and concentrated in vacuo to give a thick orange liquid (33.8 g). Gradient column chromatography on silica eluting with 5% to 15% EtOAc/hexanes gave crude 5-chloro-N,N-bis((2-(trimethylsilyl)ethoxy)methyl)pyrazolo[1,5-a]pyrimidin-7-amine as a colorless liquid (18.7 g).

Step 5

Synthesis of tert-butyl 3-(trifluoromethylsulfonyloxy)-8-azabicyclo[3.2.1]oct-3-ene-8-carboxylate

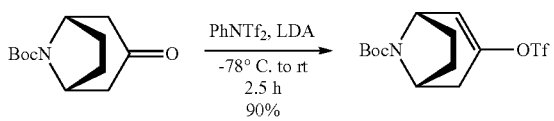

To a solution of N-Boc-nortropinone (6 g, 26.6 mmol) in THF (70 ml) at −78° C. was added LDA (2 M in heptane/THF/ethyl benzene, 20 ml, 40 mmol) slowly and the reaction mixture was stirred for 10 min. A solution of N-phenylbis(trifluoromethanesulfonimide) (10.5 g, 29.3 mmol) in THF (48 ml) was added. The reaction mixture was stirred at −78° C. for 30 min and the cooling bath was removed to warm it up to room temperature for 1.5 h until all N-Boc-nortropinone was utilized. Saturated NH$_4$Cl solution (~10 mL) was added and stirring continued for 5 minutes before the reaction mixture was transferred to a separatory funnel using EtOAc (150 mL). Organics were then extracted with EtOAc (2×125 ml), and washed with water (2×30 ml), brine (1×30 ml), and dried over MgSO$_4$. Solvent was removed in vacuo and the residue was purified by column chromatography on silica gel. Elution with EtOAc/Hexanes (0-35%) gave desired product, tert-butyl 3-(trifluoromethylsulfonyloxy)-8-azabicyclo[3.2.1]oct-3-ene-8-carboxylate (8.5 g).

Step 6

Synthesis of tert-butyl 3-(4,4,5,5-tetramethyl-1,3,2-dioxaborolan-2-yl)-8-azabicyclo[3.2.1]oct-3-ene-8-carboxylate

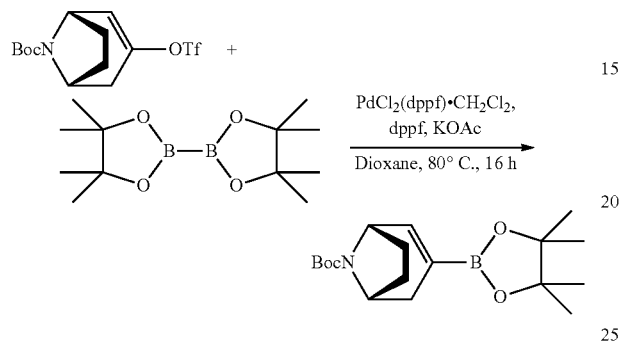

A mixture of tert-butyl 3-(trifluoromethylsulfonyloxy)-8-azabicyclo[3.2.1]oct-3-ene-8-carboxylate (10.1 g, 28.4 mmol), bis(pinacolato)diboron (8.7 g, 34.1 mmol), KOAc (8.4 g, 85.3 mmol), PdCl$_2$(dppf).CH$_2$Cl$_2$ (1.4 g, 1.7 mmol), and dppf (1 g, 1.8 mmol) in dioxane (170 ml) was flushed with Argon and stirred at 80° C. for 16 h. On cooling, the solvent was rotoevaporated, and the crude was redissolved in EtOAc (500 ml), washed with water (1×125 ml), brine (1×125 ml), and dried over MgSO$_4$. Solvent was removed in vacuo and the residue was purified by column chromatography on silica gel. Elution with EtOAc/Hexanes (0-40%) gave desired product, tert-butyl 3-(4,4,5,5-tetramethyl-1,3,2-dioxaborolan-2-yl)-8-azabicyclo[3.2.1]oct-2-ene-8-carboxylate (8.6 g).

Step 7

Synthesis of tert-butyl 3-(7-(bis((2-(trimethylsilyl)ethoxy)methyl)amino)pyrazolo[1,5-a]pyrimidin-5-yl)-8-azabicyclo[3.2.1]oct-3-ene-8-carboxylate

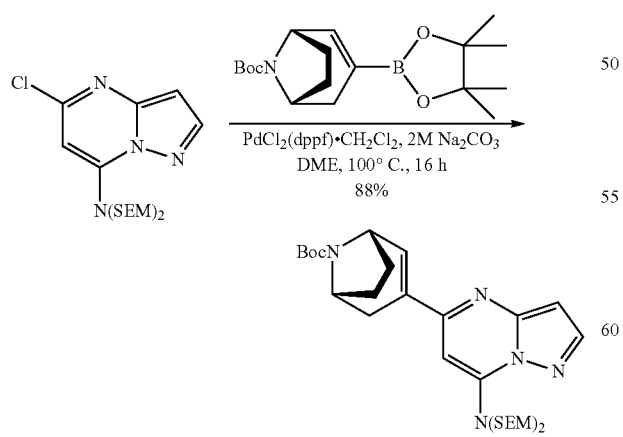

To 5-chloro-N,N-bis((2-(trimethylsilyl)ethoxy)methyl)pyrazolo[1,5-a]pyrimidin-7-amine (11.1 g, 25.8 mmol) in DME (200 mL) was added tert-butyl 3-(4,4,5,5-tetramethyl-1,3,2-dioxaborolan-2-yl)-8-azabicyclo[3.2.1]oct-2-ene-8-carboxylate (9.5 g, 28.4 mmol), PdCl$_2$(dppf).CH$_2$Cl$_2$ (2.1 g, 2.6 mmol) and 2M Na$_2$CO$_3$ (100 ml). The reaction was heated at 100° C. for 16 hours, at which time LC/MS analysis confirmed full consumption of starting material. On cooling, H$_2$O (80 ml) and EtOAc (200 ml) were added and organics were extracted with EtOAc (2×250 ml), dried (Na$_2$SO$_4$) and concentrated in vacuo to give a crude product. Gradient column chromatography on silica eluting with 10% to 60% EtOAc/hexanes (0-50%) gave tert-butyl 3-(7-(bis((2-(trimethylsilyl)ethoxy)methyl)amino)pyrazolo[1,5-a]pyrimidin-5-yl)-8-azabicyclo[3.2.1]oct-2-ene-8-carboxylate (13.7 g).

Step 8

Synthesis of tert-butyl 3-(7-(bis((2-(trimethylsilyl)ethoxy)methyl)amino)pyrazolo[1,5-a]pyrimidin-5-yl)-8-azabicyclo[3.2.1]octane-8-carboxylate

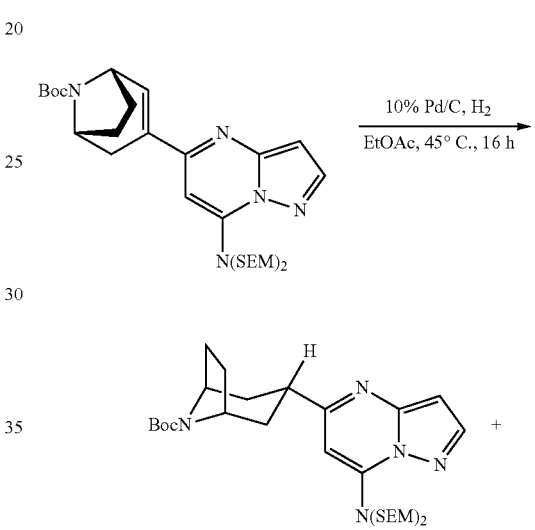

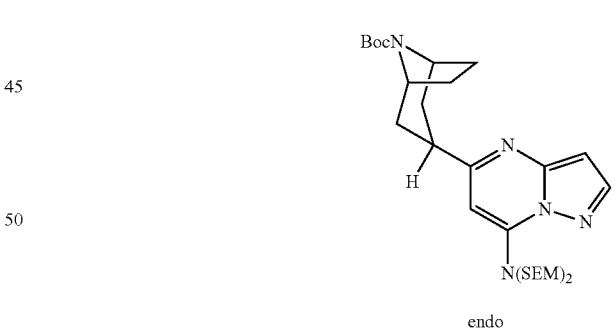

A mixture of tert-butyl 3-(7-(bis((2-(trimethylsilyl)ethoxy)methyl)amino)pyrazolo[1,5-a]pyrimidin-5-yl)-8-azabicyclo[3.2.1]oct-3-ene-8-carboxylate (12.2 g, 20.3 mmol) and 10% Pd/C (2.1 g) in EtOAc (175 ml) was stirred at 45° C. under hydrogen (balloon pressure) for 16 hours. After filtration and concentration, the crude mixture of two isomers was purified by gradient column chromatography on silica eluting with EtOAc/Hexanes (0-35%) to give the slightly impure "endo" product (6.24 g, R$_f$=0.6 in 25% EtOAc/Hexanes) and the "exo" product (5.44 g, R$_f$=0.5 in 25% EtOAc/Hexanes) which was used in the following reaction sequences.

Step 9

Synthesis of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate

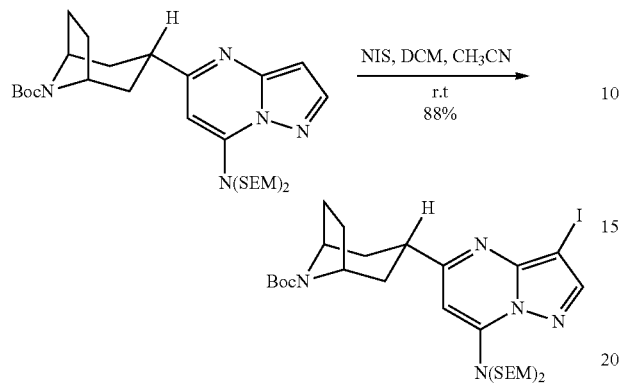

To the "exo" tert-butyl 3-(7-(bis((2-(trimethylsilyl)ethoxy)methyl)amino)pyrazolo[1,5-a]pyrimidin-5-yl)-8-azabicyclo[3.2.1]octane-8-carboxylate (6.04 g, 10 mmol) in CH$_3$CN (40 mL) and DCM (40 mL) was added N-iodosuccinimide (2.5 g, 11 mmol) portionwise and the resulting mixture was stirred at room temperature for 1.5 h, at which time LC/MS confirmed full conversion of starting material to product. Solvent was removed in vacuo and the residue was purified by column chromatography on silica gel. Elution with EtOAc/Hexanes (0-50%) gave desired title product (6.4 g).

Step 10

Synthesis of (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate

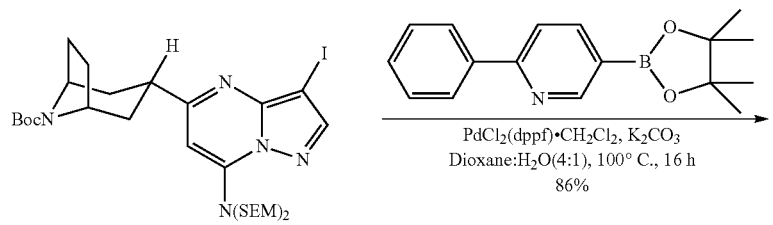

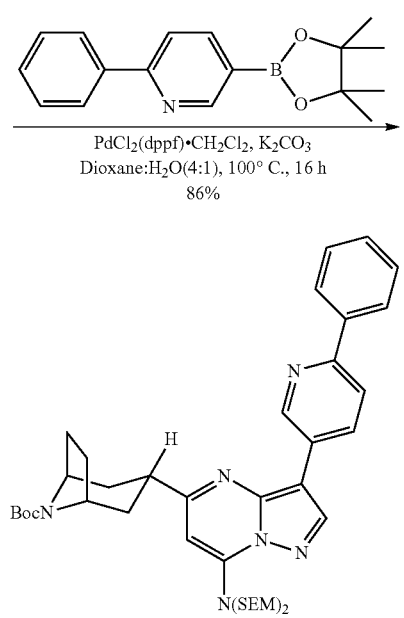

To tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (2 g, 2.7 mmol) in dioxane (22 mL) and H$_2$O (5.5 mL) was added the 2-phenyl-5-(4,4,5,5-tetramethyl-1,3,2-dioxaborolan-2-yl)pyridine (1.2 g, 4.1 mmol), PdCl$_2$(dppf).CH$_2$Cl$_2$ (0.3 g, 0.3 mmol) and K$_2$CO$_3$ (1.2 g, 8.2 mmol). The reaction was heated at 100° C. for 15 hours, at which time LC/MS analysis confirmed full consumption of starting material. On cooling, H$_2$O (40 ml) and EtOAc (100 mL) were added and organics were extracted with EtOAc (2×75 ml), dried (Na$_2$SO$_4$) and concentrated in vacuo to crude. Gradient column chromatography on silica eluting with 0 to 50% EtOAc/hexanes gave the desired product (1.8 g).

Step 11

Synthesis of (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate

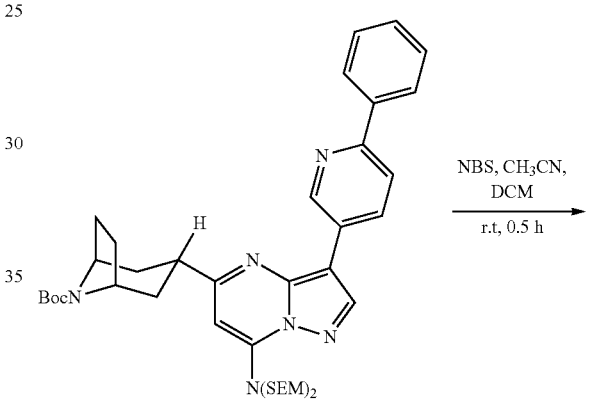

-continued

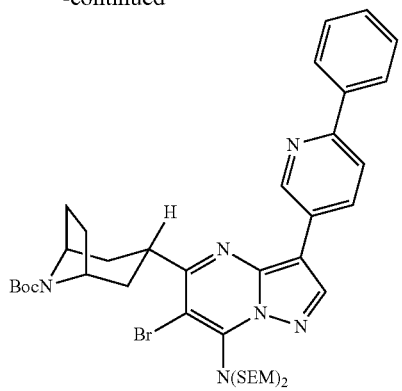

To a mixture of (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate in CH$_3$CN (10 mL) and dichloromethane (10 mL) was added N-bromosuccinimide (0.45 g, 2.5 mmol) portionwise and the resulting mixture was stirred at room temperature for 0.5 h, at which time LC/MS confirmed full conversion of starting material to product. Solvent was removed in vacuo and the residue was purified by column chromatography on silica gel. Elution with EtOAc/Hexanes (0-50%) gave the title product (1.7 g).

Step 12

Synthesis of (1R,3s,5S)-tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-8-azabicyclo[3.2.1]octane-8-carboxylate

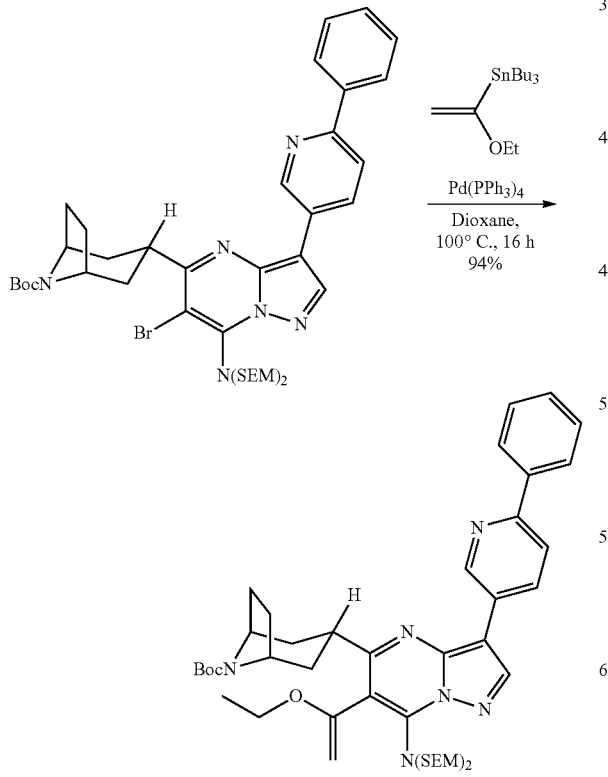

A mixture of (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (1.2 g, 1.5 mmol), tributyl(1-ethoxyvinyl)tin (1 mL, 2.9 mmol), tetrakis(triphenylphosphine)palladium (0.17 g, 0.15 mmol) in dioxane (12 mL) was degassed with argon for five minutes. It was then heated at 100° C. in a sealed tube for 16 h, at which time LC/MS analysis confirmed full consumption of starting material. On cooling, the solvent was rotoevaporated, and the crude was redissolved in EtOAc (125 mL), washed with 0.5 M KF solution (1×12 mL), water (1×25 mL), brine (1×25 mL), and dried over MgSO$_4$. Solvent was removed in vacuo and the residue was purified by column chromatography on silica gel. Elution with EtOAc/Hexanes (0-50%) gave the title product (1.2 g).

Step 13

Synthesis of 1-(7-amino-5-((1R,3s,5S)-8-azabicyclo[3.2.1]octan-3-yl)-3-(6-phenylpyridin-3-yl)pyrazolo[1,5-a]pyrimidin-6-yl)ethanone

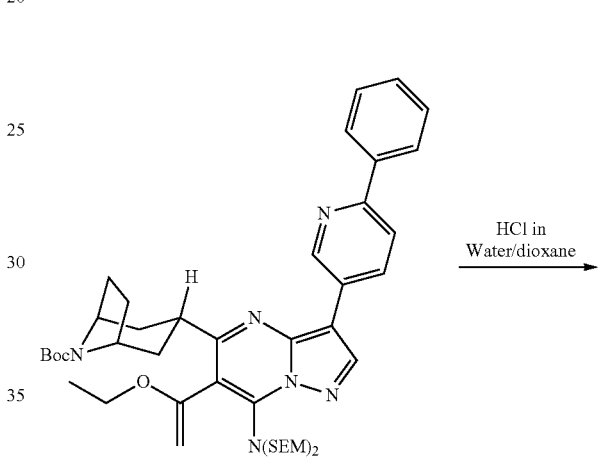

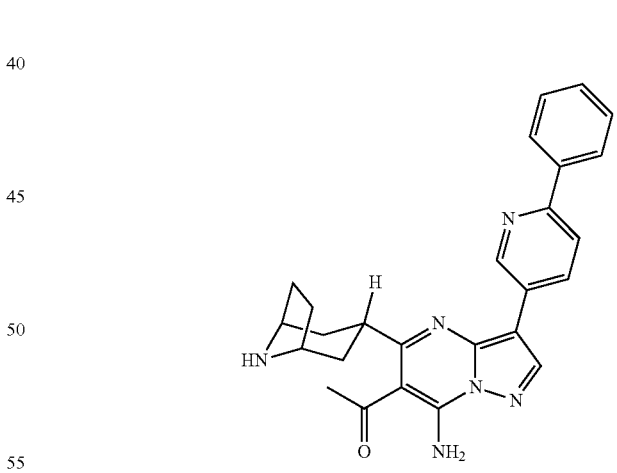

To a mixture of (1R,3s,5S)-tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-8-azabicyclo[3.2.1]octane-8-carboxylate (1.1 g, 1.3 mmol) in dioxane (7 mL) was added 4M HCl in water (2.6 ml) at 0° C. After stirring for 10 min at 0° C., 4 M HCl in dioxane (2.6 mL) was added. The reaction mixture was stirred at 0° C. for 30 min. It was then heated at 45° C. for 4 h at which time LC/MS analysis confirmed full consumption of starting material. Solvent was removed in vacuo to get the desired product as an HCl salt.

Step 14

Synthesis of 1-(5-((1R,3s,5S)-8-(4H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)ethanone

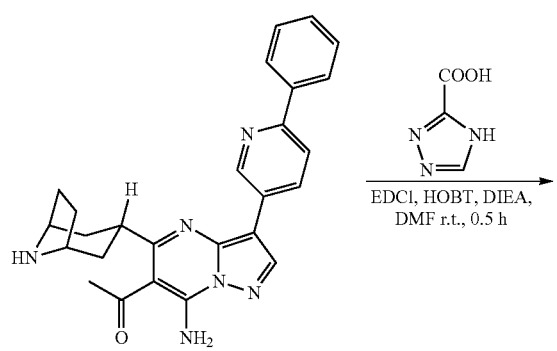

A mixture of 1H-1,2,4-triazole-3-carboxylic acid (29.4 mg, 0.26 mmol), EDCI (76.7 mg, 0.4 mmol), and 1-hydroxybenzotriazole (27 mg, 0.2 mmol) in DMF (2 ml) was stirred at room temperature for 10 min. Compound 1-(7-amino-5-((1R,3s,5S)-8-azabicyclo[3.2.1]octan-3-yl)-3-(6-phenylpyridin-3-yl)pyrazolo[1,5-a]pyrimidin-6-yl)ethanone hydrochloride (0.2 mmol) was added followed by N,N-diisopropylethylamine (0.17 ml, 1 mmol). It was stirred further for 20 min at room temperature at which time LC/MS analysis confirmed full consumption of starting material. This crude compound was submitted to the analytical group for purification to afford the desired product. LC/MS RT=2.42 min. Mass calculated for M+H 534.2, observed 534.2.

Example 1-2

Synthesis of (1R,3s,5S)-tert-butyl 3-(7-(bis((2-(trimethylsilyl)ethoxy)methyl)amino)-3-(6-(3-fluoro-4-methoxyphenyl)pyridin-3-yl)pyrazolo[1,5-a]pyrimidin-5-yl)-8-azabicyclo[3.2.1]octane-8-carboxylate

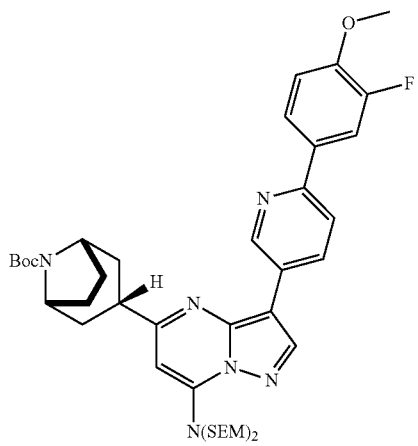

Step 1

Preparation of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate

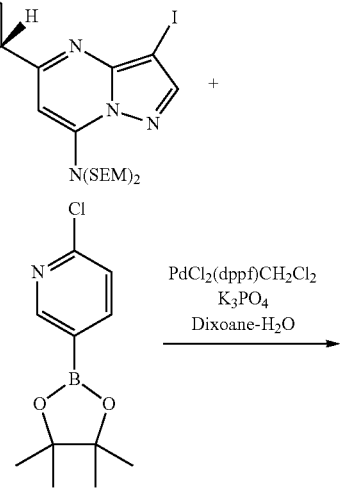

105

-continued

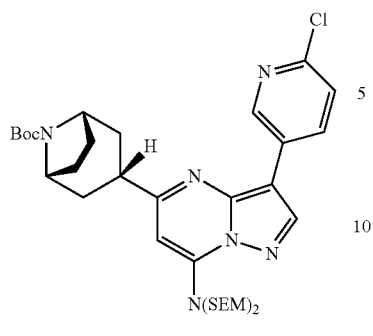

2-Chloro-5-(4,4,5,5-tetramethyl-1,3,2-dioxaborolan-2-yl)pyridine (5.55 mmol, 1327 mg), K₃PO₄ (14.48 mmol, 3070 mg), and PdCl₂(dppf).CH₂Cl₂ (0.48 mmol, 394 mg) were added to a solution of tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (1.98 mmol, 1101 mg) in dioxane (40 mL) and H₂O (4 mL). The resulting solution was stirred at 70° C. under argon overnight. The mixture was diluted with H₂O and then extracted with ethyl acetate (×2). The combined organic layers were washed with brine and dried with Na₂SO₄. Evaporation and purification by column chromatography afforded tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate, LCMS t$_R$=3.29 Min (5 min run, UV$_{254nm}$). Mass calculated for M+H 715.35, observed LC/MS m/z 715.02 (M+H).

Step 2

Preparation of (1R,3s,5S)-tert-butyl 3-(7-(bis((2-(trimethylsilyl)ethoxy)methyl)amino)-3-(6-(3-fluoro-4-methoxyphenyl)pyridin-3-yl)pyrazolo[1,5-a]pyrimidin-5-yl)-8-azabicyclo[3.2.1]octane-8-carboxylate

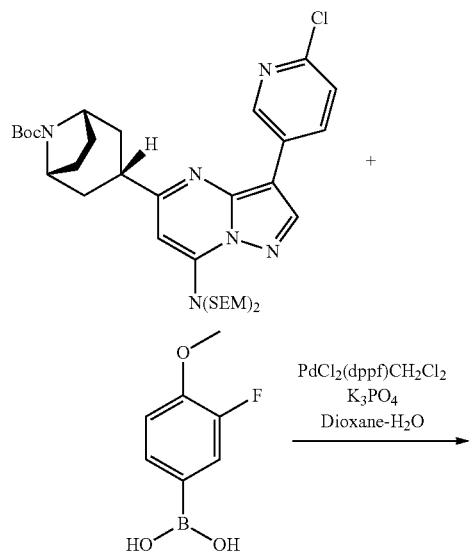

106

-continued

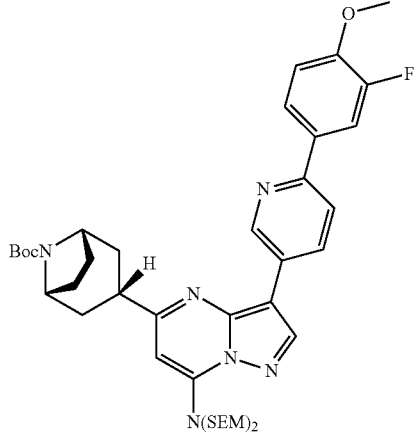

3-Fluoro-4-methoxyphenylboronic acid (2.79 mmol, 475.7 mg), K₃PO₄ (4.20 mmol, 890.4 mg), and PdCl₂(dppf).CH₂Cl₂ (0.14 mmol, 114.3 mg) were added to a solution of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.40 mmol, 1000 mg) in dioxane (12 mL) and H₂O (1.5 mL). The resulting solution was stirred at 150° C. under microwave condition for 1 h. The mixture was diluted with H₂O and then extracted with ethyl acetate (×2). The combined organic layers were washed with brine and dried with Na₂SO₄. Evaporation and purification by column chromatography afforded the title product, LCMS t$_R$=3.31 Min (5 min run, UV$_{254nm}$). Mass calculated for, M+H 805.42, observed LC/MS m/z 805.17 (M+H).

Example 1-3

Preparation of (1R,3s,5S)-tert-butyl 3-(7-(bis((2-(trimethylsilyl)ethoxy)methyl)amino)-3-(6-(thiazol-2-yl)pyridin-3-yl)pyrazolo[1,5-a]pyrimidin-5-yl)-8-azabicyclo[3.2.1]octane-8-carboxylate

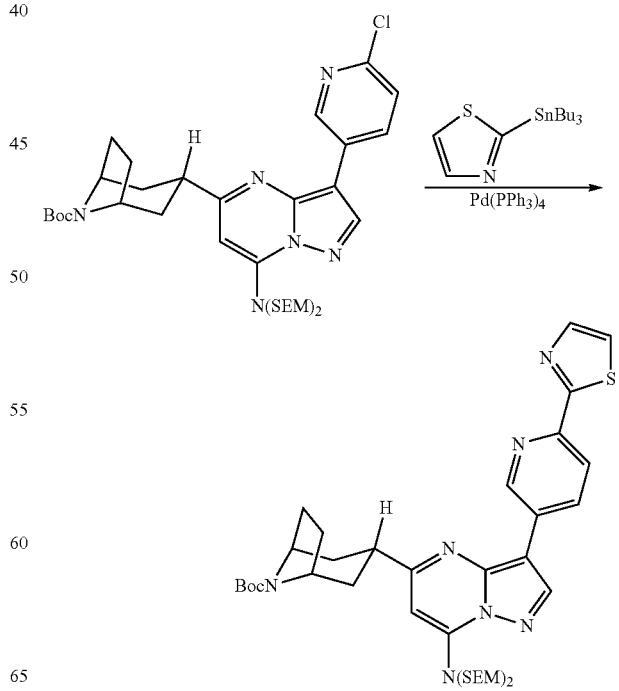

To a pressure tube were charged (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (4.17 g, 5.83 mmol), Pd(PPh₃)₄ (350 mg, 0.3 mmol), dioxane (30 mL) and 2-(tri-n-butylstannyl)thiazole (3.8 ml, 12 mmol). The resulting mixture was briefly degassed with Argon; the tube was capped, and heated with stirring under 100° C. overnight. After cooling, solvent was removed. The residue was diluted with EtOAc (30 mL), washed with 0.5 M KF (10 mL) once, brine and dried (MgSO₄). The solution was passed through a short KF pad filled with Celite and concentrated. The residue was purified on silica gel eluting with EtOAc/Hexanes (0-40%) to provide the title compound (3.97 g).

Example 1-4

Preparation of (1R,3s,5S)-tert-butyl 3-(7-(bis((2-(trimethylsilyl)ethoxy)methyl)amino)-6-bromo-3-(6-(3-(hydroxymethyl)-4-methoxyphenyl)pyridin-3-yl)pyrazolo[1,5-a]pyrimidin-5-yl)-8-azabicyclo[3.2.1]octane-8-carboxylate

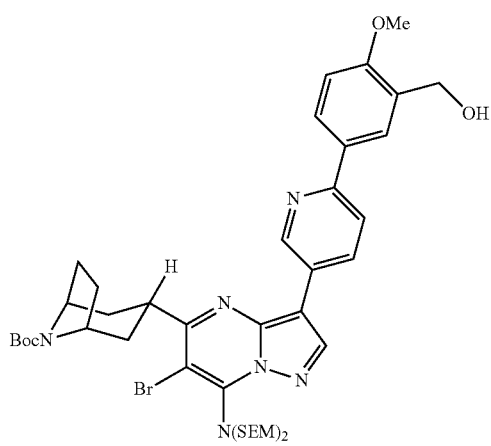

Step 1

Preparation of (1R,3s,5S)-tert-butyl 3-(7-(bis((2-(trimethylsilyl)ethoxy)methyl)amino)-3-(6-(3-formyl-4-methoxyphenyl)pyridin-3-yl)pyrazolo[1,5-a]pyrimidin-5-yl)-8-azabicyclo[3.2.1]octane-8-carboxylate

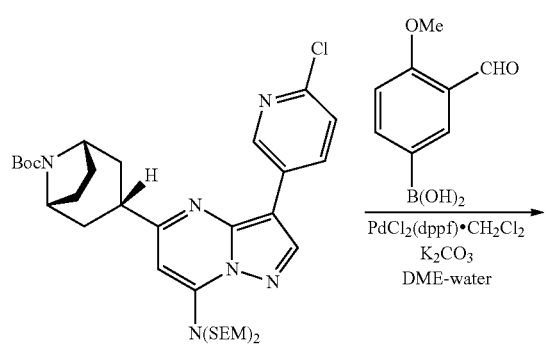

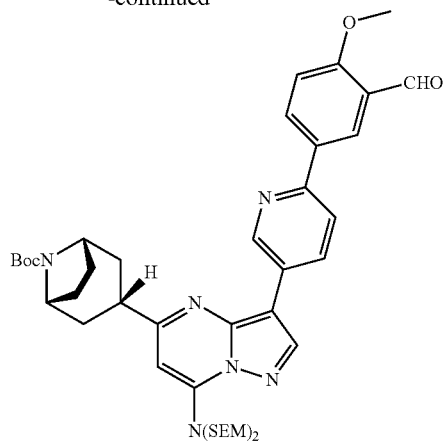

To a pressure tube were charged tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (416 mg, 0.58 mmol), 3-formyl-4-methoxyphenylboronic acid (147 mg, 0.82 mmol), PdCl₂(dppf).CH₂Cl₂ (40 mg, 0.05 mmol), DME (5 mL) and water (2 mL). The resulting mixture was briefly degassed with Argon; the tube was capped, and heated with stirring under 100° C. overnight. After cooling, solvent was removed. The residue was diluted with water (10 mL) and EtOAc (20 mL). Organic layer was separated, and aqueous layer was extracted with EtOAc (3×). Combined organic layers were dried over (MgSO₄). After concentration, the residue was purified on silica gel eluting with EtOAc/Hexanes (0-40%) to provide the title compound (412 mg).

Step 2

Preparation of (1R,3s,5S)-tert-butyl 3-(7-(bis((2-(trimethylsilyl)ethoxy)methyl)amino)-6-bromo-3-(6-(3-formyl-4-methoxyphenyl)pyridin-3-yl)pyrazolo[1,5-a]pyrimidin-5-yl)-8-azabicyclo[3.2.1]octane-8-carboxylate

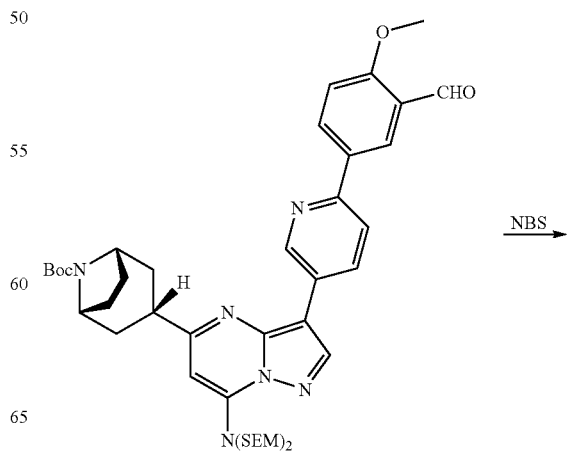

109
-continued

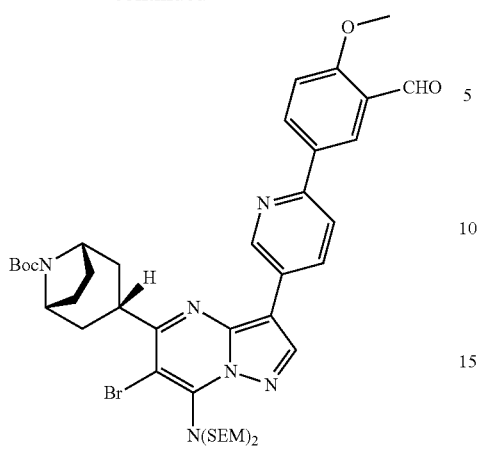

To a mixture of (1R,3s,5S)-tert-butyl 3-(7-(bis((2-(trimethylsilyl)ethoxy)methyl)amino)-3-(6-(3-formyl-4-methoxyphenyl)pyridin-3-yl)pyrazolo[1,5-a]pyrimidin-5-yl)-8-azabicyclo[3.2.1]octane-8-carboxylate (412 mg, 0.51 mmol) in CH₃CN (3 mL) and dichloromethane (3 ml) was added N-bromosuccinimide (90 mg, 2.5 mmol) and the resulting mixture was stirred at room temperature for 20 minutes, at which time LC/MS confirmed full conversion of starting material to product. Solvent was removed in vacuo and the residue was purified by column chromatography on silica gel. Elution with EtOAc/Hexanes (0-40%) gave the title product (371 mg).

Step 3

Preparation of (1R,3s,5S)-tert-butyl 3-(7-(bis((2-(trimethylsilyl)ethoxy)methyl)amino)-6-bromo-3-(6-(3-(hydroxymethyl)-4-methoxyphenyl)pyridin-3-yl)pyrazolo[1,5-a]pyrimidin-5-yl)-8-azabicyclo[3.2.1]octane-8-carboxylate

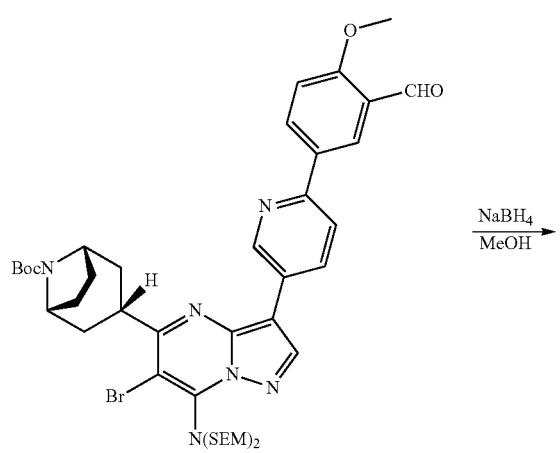

110
-continued

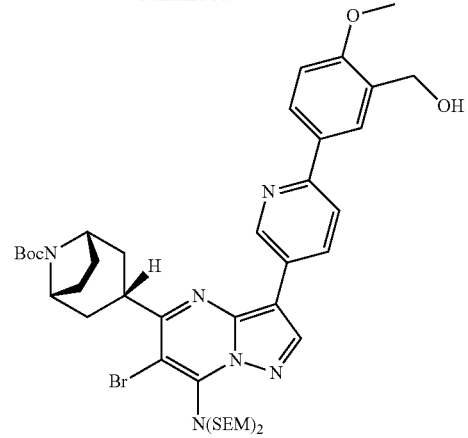

To a solution of (1R,3s,5S)-tert-butyl 3-(7-(bis((2-(trimethylsilyl)ethoxy)methyl)amino)-6-bromo-3-(6-(3-formyl-4-methoxyphenyl)pyridin-3-yl)pyrazolo[1,5-a]pyrimidin-5-yl)-8-azabicyclo[3.2.1]octane-8-carboxylate (370 mg, 0.41 mmol) in MeOH (4 ml) was added NaBH₄ (8 mg, 0.21 mmol) and resulting mixture was allowed to stir for 15 minutes. Solvent was removed in vacuo and the residue was purified by column chromatography on silica gel. Elution with EtOAc/Hexanes (0-40%) gave the title product (370 mg).

Example 1-5

Preparation of (1R,3s,5S)-tert-butyl 3-(7-(bis((2-(trimethylsilyl)ethoxy)methyl)amino)-3-(6-(5-(difluoromethyl)thiazol-2-yl)pyridin-3-yl)pyrazolo[1,5-a]pyrimidin-5-yl)-8-azabicyclo[3.2.1]octane-8-carboxylate

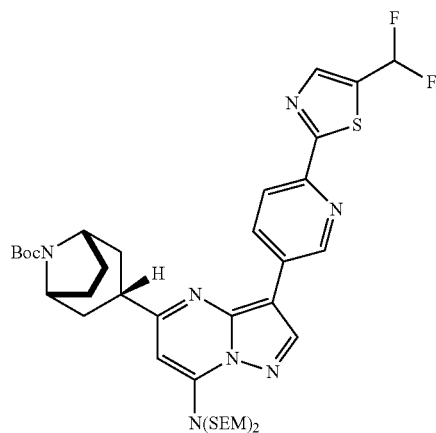

Step A. Synthesis of
2-bromo-5-(difluoromethyl)thiazole

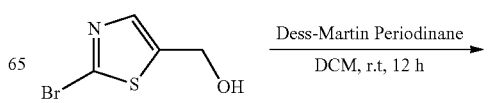

-continued

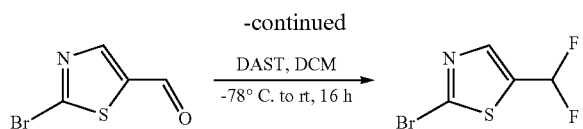

To 2-bromo-5-hydroxymethylthiazole (1.6 g, 8.1 mmol) in DCM (65 mL) was added dess-martinperiodinane (3.8 g, 8.9 mmol). It was stirred for 12 hour at room temperature, at which time LC/MS analysis confirmed full consumption of starting material. Reaction mixture was diluted with DCM (200 mL), washed with water (1×50 mL), brine (1×50 mL), and dried over MgSO$_4$. Gradient column chromatography on silica gel eluting with 0 to 65% EtOAc/hexanes gave the desired 2-bromothiazole-5-carbaldehyde (1.3 g).

To 2-bromothiazole-5-carbaldehyde (1.1 g, 6 mmol) in dry DCM (80 mL) at −78° C. was added DAST (2.4 mL, 18 mmol). The resulting mixture was warmed to room temperature over 16 hour time period, at which time LC/MS analysis confirmed full consumption of starting material. Saturated NaHCO$_3$ (50 mL) was added slowly and stirring continued for 10 minutes before the reaction mixture was transferred to a separatory funnel using DCM (100 mL). Organics were then extracted with DCM (2×50 mL), and washed with water (2×50 mL), brine (1×50 mL), and dried over MgSO$_4$. Gradient column chromatography on silica gel eluting with 0 to 40% EtOAc/hexanes gave the desired 2-bromo-5-(difluoromethyl)thiazole (0.8 g).

Step B. Synthesis of (1R,3s,5S)-tert-butyl 3-(7-(bis((2-(trimethylsilyl)ethoxy)methyl)amino)-3-(6-(trimethylstannyl)pyridin-3-yl)pyrazolo[1,5-a]pyrimidin-5-yl)-8-azabicyclo[3.2.1]octane-8-carboxylate

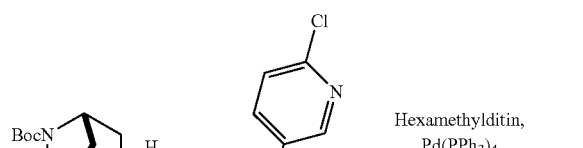

A mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.3 g, 1.8 mmol), hexamethylditin (0.75 mL, 3.6 mmol) and Pd(PPh$_3$)$_4$ in dioxane (15 mL) was degassed with argon and heated at 100° C. for 16 hour, at which time LC/MS analysis confirmed full consumption of starting material. On cooling, EtOAc (250 mL) was added and washed with brine (1×50 mL), and dried over MgSO$_4$. Solvent was removed in vacuo and the crude product (1R,3s,5S)-tert-butyl 3-(7-(bis((2-(trimethyl silyl)ethoxy)methyl)amino)-3-(6-(trimethylstannyl)pyridin-3-yl)pyrazolo[1,5-a]pyrimidin-5-yl)-8-azabicyclo[3.2.1]octane-8-carboxylate was used for the next step without any further purification.

Step C. Synthesis of (1R,3s,5S)-tert-butyl 3-(7-(bis((2-(trimethylsilyl)ethoxy)methyl)amino)-3-(6-(5-(difluoromethyl)thiazol-2-yl)pyridin-3-yl)pyrazolo[1,5-a]pyrimidin-5-yl)-8-azabicyclo[3.2.1]octane-8-carboxylate

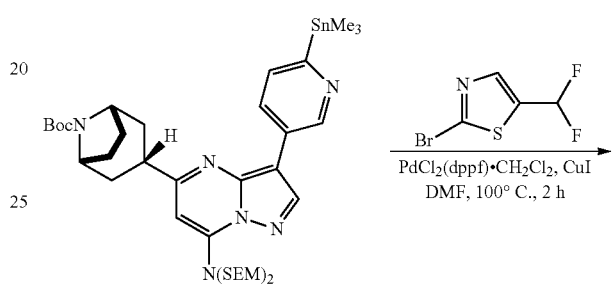

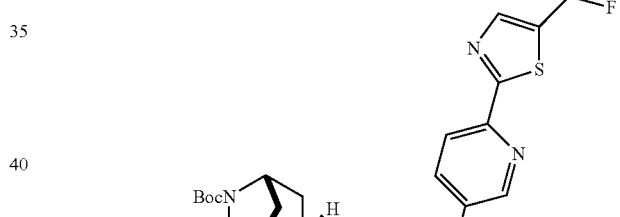

A mixture of (1R,3s,5S)-tert-butyl 3-(7-(bis((2-(trimethylsilyl)ethoxy)methyl)amino)-3-(6-(trimethylstannyl)pyridin-3-yl)pyrazolo[1,5-a]pyrimidin-5-yl-8-azabicyclo[3.2.1]octane-8-carboxylate (1 g, 0.8 mmol), 2-bromo-5-(difluoromethyl)thiazole (0.2 g, 0.8 mmol), PdCl$_2$(dppf).CH$_2$Cl$_2$ (0.07 g, 0.08 mmol), CuI (0.015 g, 0.08 mmol) in DMF (6.4 mL) was degassed with argon and heated at 100° C. for 2 hour, at which time LC/MS analysis confirmed full consumption of starting material. On cooling, EtOAc (250 mL) was added and washed with water (2×25 mL), brine (1×25 mL), and dried over MgSO$_4$. Solvent was removed in vacuo and the residue was purified by column chromatography on silica gel. Elution with EtOAc/Hexanes (0-50%) gave desired product, (1R,3s,5S)-tert-butyl 3-(7-(bis((2-(trimethylsilyl)ethoxy)methyl)amino)-3-(6-(5-(difluoromethyl)thiazol-2-yl)pyridin-3-yl)pyrazolo[1,5-a]pyrimidin-5-yl)-8-azabicyclo[3.2.1]octane-8-carboxylate (0.38 g).

Example 1-6

Preparation of (1R,3s,5S)-tert-butyl 3-(7-(bis((2-(trimethylsilyl)ethoxy)methyl)amino)-3-(4-(pyrimidin-2-yl)phenyl)pyrazolo[1,5-a]pyrimidin-5-yl)-8-azabicyclo[3.2.1]octane-8-carboxylate

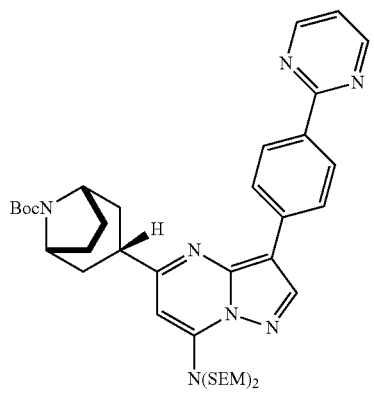

Step A. Synthesis of (1R,3s,5S)-tert-butyl 3-(7-(bis((2-(trimethylsilyl)ethoxy)methyl)amino)-3-(4-(pyrimidin-2-yl)phenyl)pyrazolo[1,5-a]pyrimidin-5-yl-8-azabicyclo[3.2.1]octane-8-carboxylate

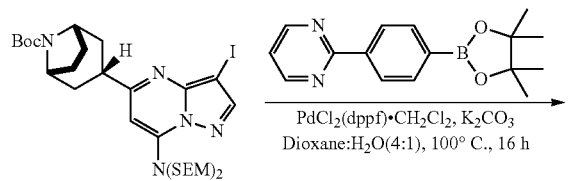

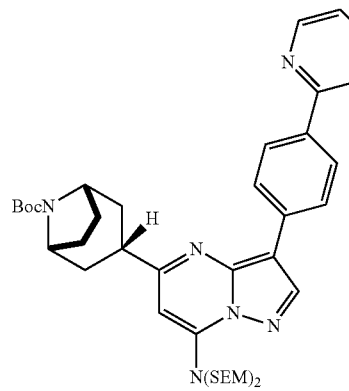

To (1R,3s,5S)-tert-butyl 3-(7-(bis((2-(trimethylsilyl)ethoxy)methyl)amino)-3-iodo pyrazolo[1,5-a]pyrimidin-5-yl)-8-azabicyclo[3.2.1]octane-8-carboxylate (4.4 g, 6 mmol) in dioxane (48 mL) and water (12 mL) was added 2-(4-(4,4,5,5-tetramethyl-1,3,2-dioxaborolan-2-yl)phenyl)pyrimidine (3 g, 7.9 mmol), $PdCl_2(dppf) \cdot CH_2Cl_2$ (0.5 g, 0.6 mmol) and $K_2CO_3$ (2.5 g, 18.1 mmol). The reaction mixture was heated at 100° C. for 16 hour, at which time LC/MS analysis confirmed full consumption of starting material. On cooling, the solvent was removed in vacuo, and the crude was redissolved in DCM (500 mL), washed with water (1×125 mL), brine (1×125 mL), and dried over $MgSO_4$. Gradient column chromatography on silica gel eluting with 0 to 40% EtOAc/hexanes gave the desired (1R,3s,5S)-tert-butyl 3-(7-(bis((2-(trimethylsilyl)ethoxy)methyl)amino)-3-(4-(pyrimidin-2-yl)phenyl)pyrazolo[1,5-a]pyrimidin-5-yl)-8-azabicyclo[3.2.1]octane-8-carboxylate (1.7 g).

Example 1-7

Preparation of 5-bromo-2-(1-methyl-1H-1,2,4-triazol-3-yl)pyridine

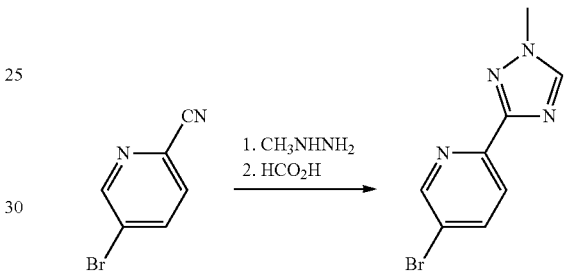

5-bromo-2-(1-methyl-1H-1,2,4-triazol-3-yl)pyridine was synthesized from 5-bromopicolinonitrile according to reference procedure (Polyhedron (2004), 23(13), 2141-2151). LCMS $t_R$=0.62 Min (5 min run, $UV_{254nm}$). Mass calculated for, M+ 237.9, observed LC/MS m/z 239.0 (M+H).

Example 1-8

Preparation of 5-bromo-2-(1-methyl-($D_3$)-1H-pyrazol-3-yl)pyridine

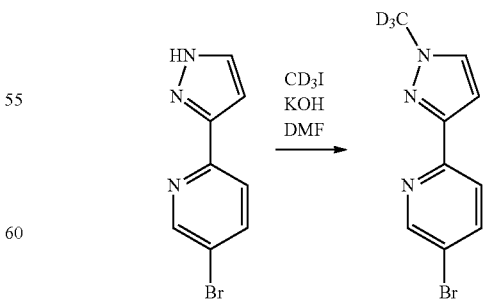

5-bromo-2-(1-methyl-($D_3$)-1H-pyrazol-3-yl)pyridine was prepared from 5-bromo-2-(1H-pyrazol-3-yl)pyridine according to reference procedure (Bioorganic & Medicinal Chemistry (2004), 12(22), 5909-5915). LCMS $t_R$=0.92 Min (5 min run, $UV_{254nm}$). Mass calculated for, M+ 240.0, observed LC/MS m/z 241.1 (M+H).

Example 1-9

Preparation of 2-(4-methoxy-($D_3$)-phenyl)-4,4,5,5-tetramethyl-1,3,2-dioxaborolane

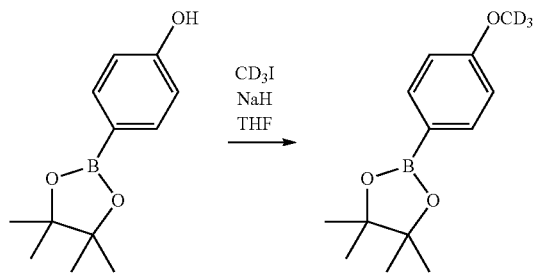

At 0° C., 4-(4,4,5,5-tetramethyl-1,3,2-dioxaborolan-2-yl)phenol (189.5 mg, 0.86 mmol) was added to a mixture of NaH (60%, 68.9 mg, 1.72 mmol) in THF (5 ml). After stirring at room temperature for 10 min, the mixture was cooled to 0° C. and $CD_3I$ (624 mg, 4.30 mmol) was added dropwise. The mixture was stirred at room temperature overnight and then diluted with $H_2O$ and then extracted with ethyl acetate (×2). The combined organic layers were washed with brine and dried with $Na_2SO_4$. Evaporation and purification by column chromatography afforded 2-(4-methoxy-($D_3$)-phenyl)-4,4,5,5-tetramethyl-1,3,2-dioxaborolane: LCMS $t_R$=1.39 Min (5 min run, $UV_{254nm}$). Mass calculated for, M+ 237.1, observed LC/MS m/z 238.2 (M+H).

Example 1-10

Preparation of 2-(4-(fluoromethoxy)phenyl)-4,4,5,5-tetramethyl-1,3,2-dioxaborolane

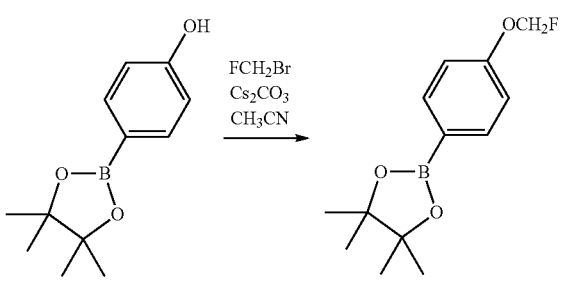

$Cs_2CO_3$ (651.6 mg, 2.0 mmol) and then $FCH_2Br$ (446.6 mg, 4.0 mmol) were added to a mixture of 4-(4,4,5,5-tetramethyl-1,3,2-dioxaborolan-2-yl)phenol (220 mg, 1.0 mmol)) in $CH_3CN$ (10 ml). After stirring at room temperature overnight, the mixture was filtered and concentrated. Purification by column chromatography afforded 2-(4-(fluoromethoxy)phenyl)-4,4,5,5-tetramethyl-1,3,2-dioxaborolane: LCMS $t_R$=1.39 Min (5 min run, $UV_{254nm}$). Mass calculated for, M+ 252.1, observed LC/MS m/z 253.1 (M+H).

Example 1-11

Preparation of 3-(4,4,5,5-tetramethyl-1,3,2-dioxaborolan-2-yl)-1-((2-(trimethylsilyl)ethoxy)methyl)-1H-pyrazole

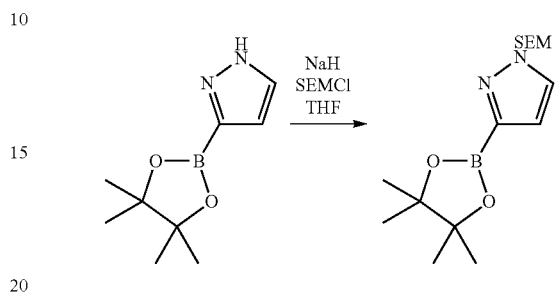

At 0° C., NaH (60%, 160 mg, 4.0 mmol) was added to a mixture of 3-(4,4,5,5-tetramethyl-1,3,2-dioxaborolan-2-yl)-1H-pyrazole (388.0 mg, 2 mmol) in THF (12 ml). After stirring at room temperature for 30 min, the mixture was cooled to 0° C. and SEMCl (705.7 ul, 4.0 mmol) was added dropwise. The mixture was stirred at room temperature overnight and then diluted with $H_2O$ and then extracted with ethyl acetate (×2). The combined organic layers were washed with brine and dried with $Na_2SO_4$. Evaporation and purification by column chromatography afforded 3-(4,4,5,5-tetramethyl-1,3,2-dioxaborolan-2-yl)-1-((2-(trimethylsilyl)ethoxy)methyl)-1H-pyrazole: LCMS $t_R$=1.47 Min (5 min run, $UV_{254nm}$). Mass calculated for, M+ 324.2, observed LC/MS m/z 325.0 (M+H).

Example 1-12

Preparation of 3-bromo-4-((2-(trimethylsilyl)ethoxy)methyl)-4H-1,2,4-triazole

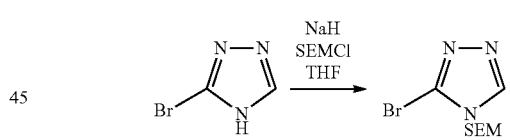

By applying the chemistry described in Example 1-11, 3-bromo-4-((2-(trimethylsilyl)ethoxy)methyl)-4H-1,2,4-triazole was prepared from 3-bromo-4H-1,2,4-triazole. LCMS $t_R$=1.22 Min (5 min run, $UV_{254nm}$). Mass calculated for, M+ 277.0, observed LC/MS m/z 278.0 (M+H).

Example 1-13

Preparation of 4-bromo-1-((2-(trimethylsilyl)ethoxy)methyl)-1H-imidazole

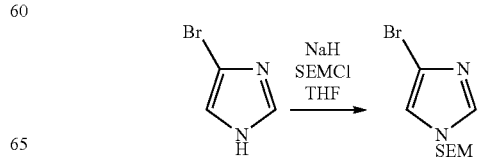

By applying the chemistry described in Example 1-11, 4-bromo-1-((2-(trimethylsilyl)ethoxy)methyl)-1H-imidazole was prepared from 4-bromo-1H-imidazole. LCMS $t_R$=1.16 Min (5 min run, $UV_{254nm}$). Mass calculated for, M+ 276.0, observed LC/MS m/z 277.1 (M+H).

Example 1-14

Preparation of 5-bromo-2-(4-fluoro-1-methyl-1H-pyrazol-3-yl)pyridine

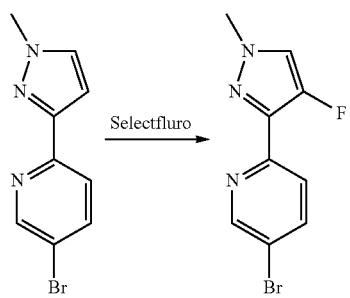

At 0° C., Selectfluoro (1223.3 mg, 3.45 mmol) was added to 5-bromo-2-(1-methyl-1H-pyrazol-3-yl)pyridine (817.4 mg, 3.45 mmol) in $CH_3CN$ (20 ml). The mixture was slowly warmed up to room temperature. Selectfluoro (2446 mg) was added after stirring at room temperature overnight and more Selectfluoro (1223 mg) was added after 2 days stirring. The mixture was diluted with sat. $NaHCO_3$ and then extracted with ethyl acetate (×2). The combined organic layers were washed with brine and dried with $Na_2SO_4$. Evaporation and purification by column chromatography afforded 5-bromo-2-(4-fluoro-1-methyl-1H-pyrazol-3-yl)pyridine: LCMS $t_R$=1.00 Min (5 min run, $UV_{254nm}$). Mass calculated for, M+ 254.98 observed LC/MS m/z 256.0 (M+H).

Example 1-15

Preparation of 5-bromo-2-(5-methyl-1H-pyrazol-3-yl)pyridine

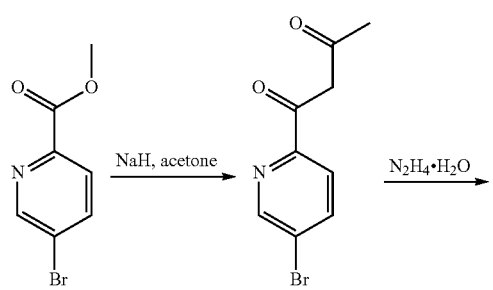

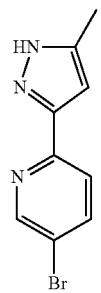

5-bromo-2-(5-methyl-1H-pyrazol-3-yl)pyridine was prepared according to reference procedure (Journal of the American Chemical Society (2003), 125(36), 10800-10801) from methyl 5-bromopicolinate. LCMS $t_R$=0.86 Min (5 min run, $UV_{254nm}$). Mass calculated for, M+ 236.9, observed LC/MS m/z 238.0 (M+H).

Example 1-16

Preparation of 5-bromo-2-(5-methyl-1((2-(trimethylsilyl)ethoxy)methyl)-1H-pyrazol-3-yl)pyridine

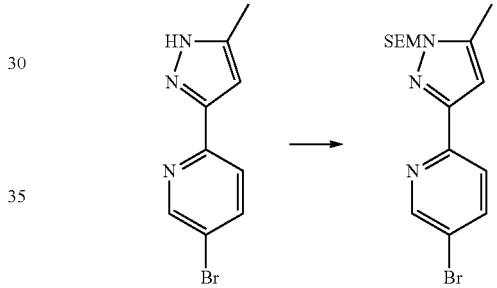

By applying the chemistry described in Example 1-11, 5-bromo-2-(5-methyl-1-((2-(trimethylsilyl)ethoxy)methyl)-1H-pyrazol-3-yl)pyridine was prepared from 5-bromo-2-(5-methyl-1H-pyrazol-3-yl)pyridine. LCMS $t_R$=1.56 Min (5 min run, $UV_{254nm}$). Mass calculated for, M+ 367.0, observed LC/MS m/z 368.0 (M+H).

Example 1-17

Preparation of 5-bromo-2-(4-fluoro-5-methyl-1-((2-(trimethylsilyl)ethoxy)methyl)-1H-pyrazol-3-yl)pyridine

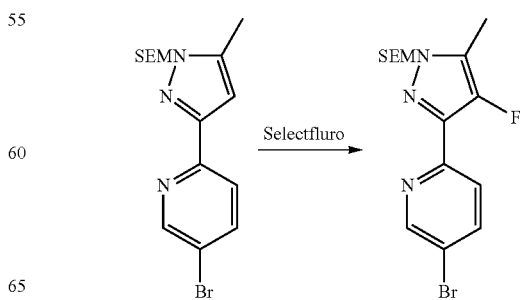

By applying the chemistry described in Example 1-14, 5-bromo-2-(4-fluoro-5-methyl-1-((2-(trimethylsilyl)ethoxy)methyl)-1H-pyrazol-3-yl)pyridine was synthesized from 5-bromo-2-(5-methyl-1((2-(trimethylsilyl)ethoxy)methyl)-1H-pyrazol-3-yl)pyridine. LCMS $t_R$=1.59 Min (5 min run, $UV_{254nm}$). Mass calculated for, M+ 385.0, observed LC/MS m/z 386.2 (M+H).

Example 1-18

Preparation of 2-(2-methyl-2H-tetrazol-5-yl)-5-(4,4,5,5-tetramethyl-1,3,2-dioxaborolan-2-yl)pyridine

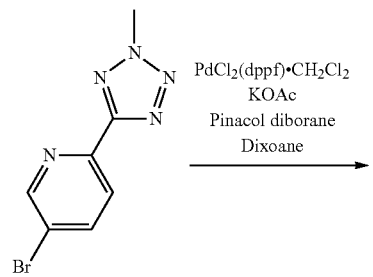

Pinacol diborane (3047 mg, 12 mmol), KOAc (2944 mg, 30 mmol), and PdCl$_2$(dppf).CH$_2$Cl$_2$ (816 mg, 1 mmol) were added to a mixture of 5-bromo-2-(2-methyl-2H-tetrazol-5-yl)pyridine (2400 mg, 10 mmol) in dioxane (70 mL). The resulting solution was stirred at 80° C. under argon overnight. The mixture was filtered through celite and concentrated to afford crude 2-(2-methyl-2H-tetrazol-5-yl)-5-(4,4,5,5-tetramethyl-1,3,2-dioxaborolan-2-yl)pyridine: LCMS $t_R$=0.45 Min (5 min run, $UV_{254nm}$). Mass calculated for, M+ 287.1, observed LC/MS m/z 282.2 (M+H).

By applying the chemistry above, the following compounds were synthesized.

| Example No. | Structures | FW | M + H | Retention Time, 5 min method |
|---|---|---|---|---|
| 1-19 | 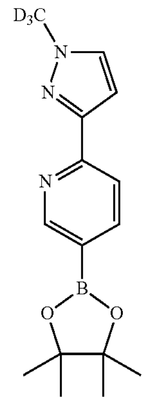 | 288.1 (boronic ester) 206.1 (boronic acid) | 207.1 (observed) | 0.38 |
| 1-20 | 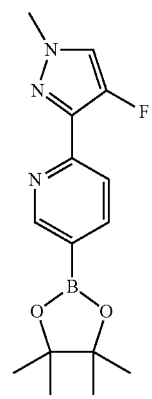 [SMILES: Cn1cc(F)c(-c2ccc(B3OC(C)(C)C(C)(C)O3)cn2)n1] | 303.1 (boronic ester) 221.0 (boronic acid) | 222.1 (observed) | 0.51 |
| 1-21 | 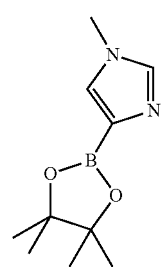 | 208.1 (boronic ester) 126.0 (boronic acid) | 127.0 (observed) | 0.12 |
| 1-22 | 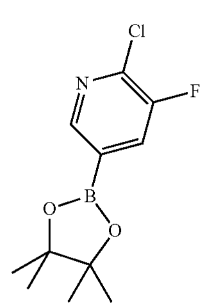 [SMILES: CC1(C)OB(c2cnc(Cl)c(F)c2)OC1(C)C] | 257.0 (boronic ester) 175.0 (boronic acid) | 176.1 (observed) | 0.73 |

-continued

| Example No. | Structures | FW | M + H | Retention Time, 5 min method |
|---|---|---|---|---|
| 1-23 | 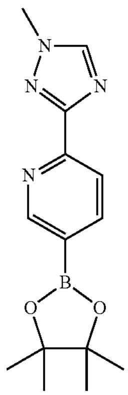 | 286.1 (boronic ester) 204.0 (boronic acid) | 205.1 (observed) | 0.21 |
| 1-24 | 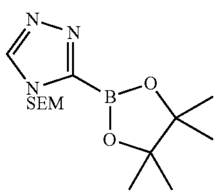 [SMILES: CC1(C)OB(c2nncn2COCC[Si](C)(C)C)OC1(C)C] | 325.2 (boronic ester) 243.1 (boronic acid) | 244.2 (observed) | 0.86 |
| 1-25 | 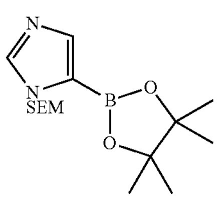 [SMILES: CC1(C)OB(c2cncn2COCC[Si](C)(C)C)OC1(C)C] | 324.2 (boronic ester) 242.1 (boronic acid) | 243.2 (observed) | 0.86 |
| 1-26 | 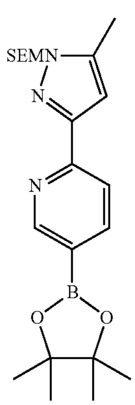 | 415.2 (boronic ester) 333.1 (boronic acid) | 334.1 (observed) | 0.99 |

-continued

| Example No. | Structures | FW | M + H | Retention Time, 5 min method |
|---|---|---|---|---|
| 1-27 | 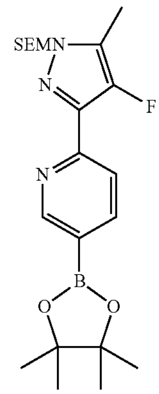 [SMILES: Cc1c(F)c(-c2ccc(B3OC(C)(C)C(C)(C)O3)cn2)nn1COCC[Si](C)(C)C] | 433.2 (boronic ester) 351.1 (boronic acid) | 352.1 (observed) | 1.04 |

Example 1-28

Preparation of (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate

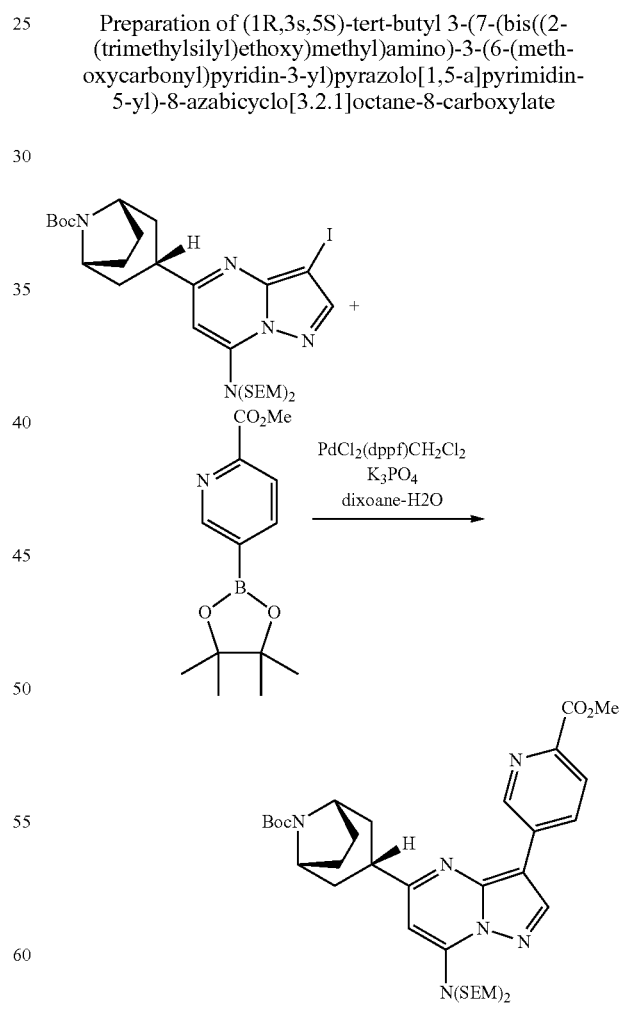

Methyl 5-(4,4,5,5-tetramethyl-1,3,2-dioxaborolan-2-yl)picolinate (2100 mg, 7.98 mmol), $K_3PO_4$ (4230 mg, 19.95 mmol), and $PdCl_2(dppf) \cdot CH_2Cl_2$ (542.7 mg, 0.66 mmol) were added to a mixture of (1R,3s,5S)-tert-butyl 3-(7-(bis((2-

(trimethylsilyl)ethoxy)methyl)amino)-3-iodopyrazolo[1,5-a]pyrimidin-5-yl)-8-azabicyclo[3.2.1]octane-8-carboxylate (4848.9 mg, 6.65 mmol) in dioxane (100 mL) and H₂O (10 mL). The resulting solution was stirred at 90° C. under argon overnight. The mixture was diluted with H₂O and then extracted with ethyl acetate (×2). The combined organic layers were washed with brine and dried with Na₂SO₄. Evaporation and purification by column chromatography afforded (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate: LCMS $t_R$=1.88 Min (5 min run, $UV_{254nm}$). Mass calculated for, M+ 738.4, observed LC/MS m/z 739.3 (M+H).

Example 1-29

Preparation of methyl 5-(6-acetyl-7-amino-5((1R,3s,5S)-8-azabicyclo[3.2.1]octan-3-yl)pyrazolo[1,5-a]pyrimidin-3-yl)picolinate By applying the chemistry in example 1-1, methyl 5-(6-acetyl-7-amino-5-((1R,3s,5S)-8-azabicyclo[3.2.1]octan-3-yl)pyrazolo[1,5-a]pyrimidin-3-yl)picolinate was prepared: LCMS $t_R$=0.75 Min (5 min run, $UV_{254nm}$). Mass calculated for, M+ 420.2, observed LC/MS m/z 421.1 (M+H).

Example 1-30

Preparation of provided 5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinic acid

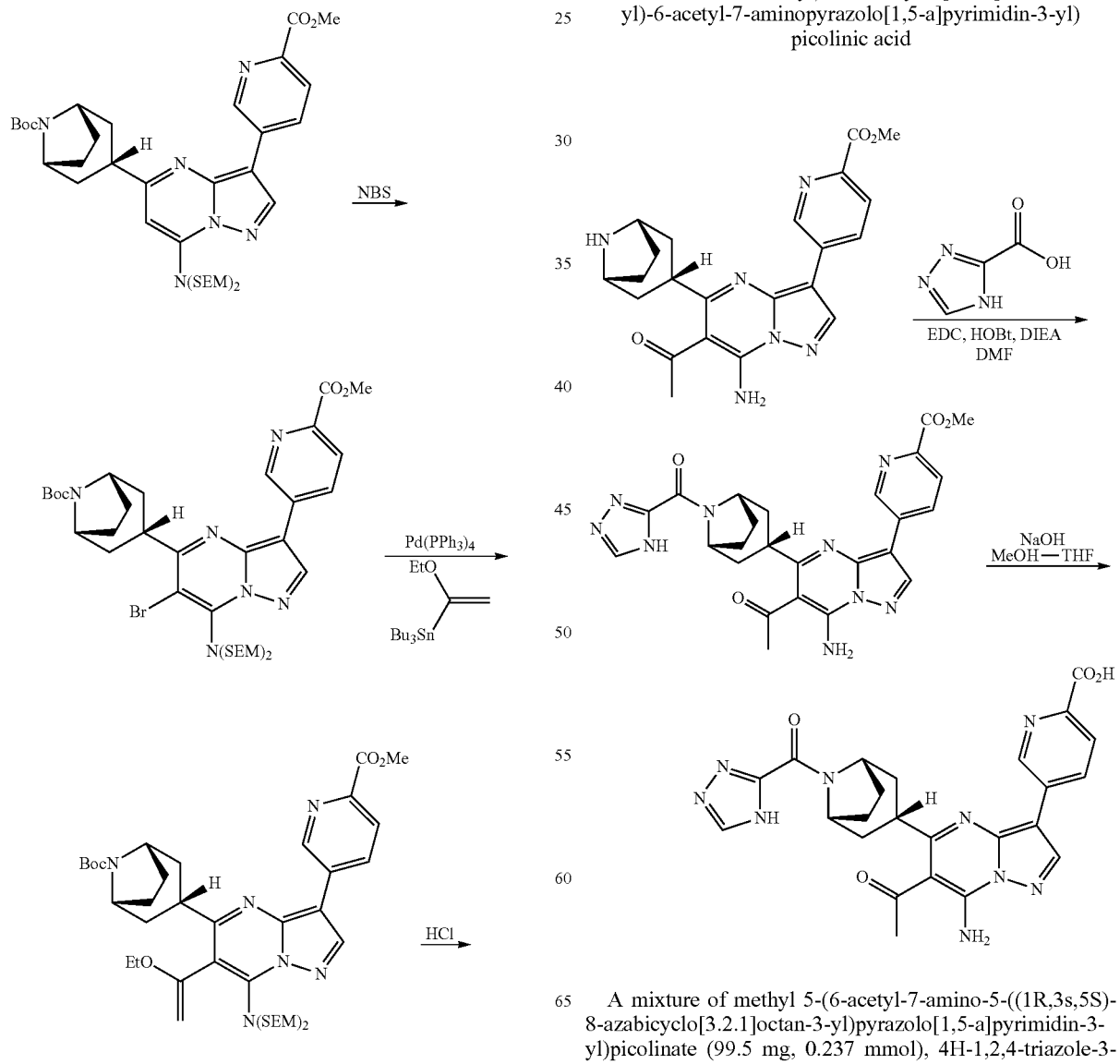

A mixture of methyl 5-(6-acetyl-7-amino-5-((1R,3s,5S)-8-azabicyclo[3.2.1]octan-3-yl)pyrazolo[1,5-a]pyrimidin-3-yl)picolinate (99.5 mg, 0.237 mmol), 4H-1,2,4-triazole-3- carboxylic acid (32.2 mg, 0.285 mmoL), EDC (90.7 mg, 0.475 mmol), HOBt (64.1 mg, 0.475 mmol) and DIEA (247.6 ul, 1.42 mmol) in DMF (5 mL) was stirred at room temperature for 1 h. Concentration provided crude methyl 5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinate. MeOH (2 ml), THF (1 ml) and 1N NaOH (2 ml) were added and the mixture was stirred at 50° C. until LCMS indicated complete conversion. Concentration and Purification with prep-LC provided 5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinic acid, LCMS $t_R$=1.85 Min (10 min run, $UV_{254nm}$). Mass calculated for, M+ 501.1, observed LC/MS m/z 501.96 (M+H).

Example 1-31

Preparation of (1R,3s,5S)-tert-butyl 3-(7-(bis((2-(trimethylsilyl)ethoxy)methyl)amino)-6-(1-ethoxyvinyl)-3-(6-(1-hydroxycyclopropyl)pyridin-3-yl)pyrazolo[1,5-a]pyrimidin-5-yl)-8-azabicyclo[3.2.1]octane-8-carboxylate

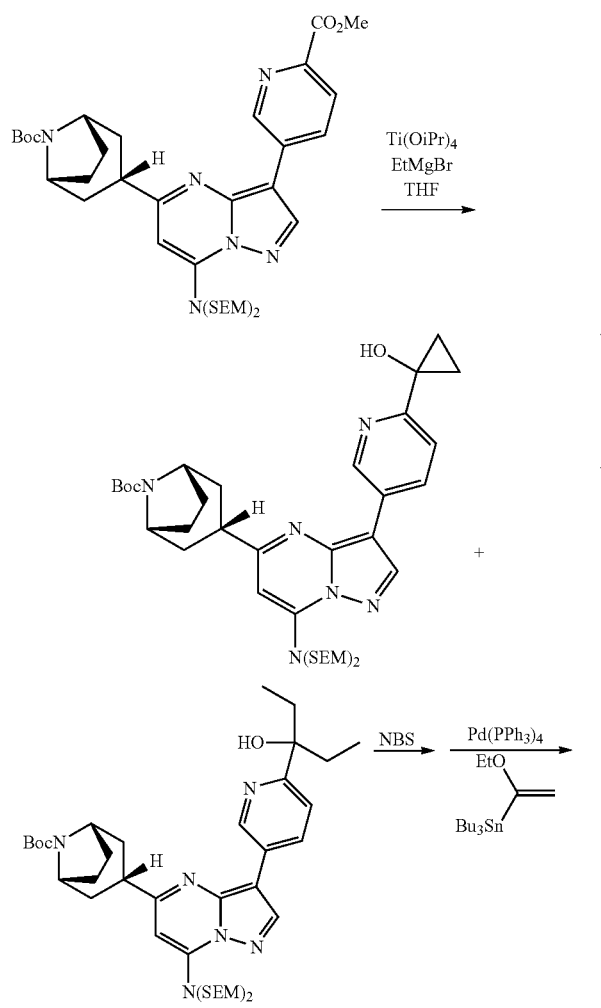

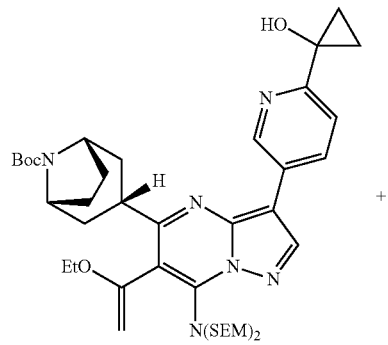

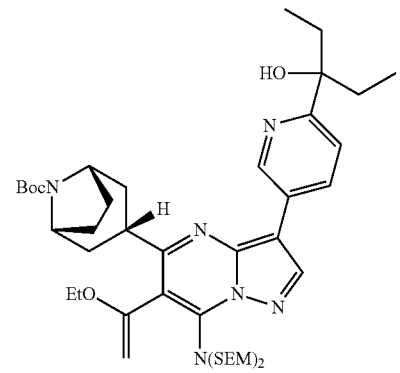

EtMgBr (1.0 M in THF, 1.4 ml, 1.4 mmol) was added dropwise to a mixture of (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate (369.2 mg, 0.5 mmol) and Ti(OiPr)$_4$ (205.1 ul, 0.7 mmol) in THF (5 ml) at room temperature. After stirring overnight, the mixture was diluted with H$_2$O and then extracted with EtOAc (×2). The combined organic layers were washed with brine and dried with Na$_2$SO$_4$. Concentration and purification by column chromatography afforded an inseparable mixture: (1R,3s,5S)-tert-butyl 3-(7-(bis((2-(trimethylsilyl)ethoxy)methyl)amino)-3-(6-(1-hydroxycyclopropyl)pyridin-3-yl)pyrazolo[1,5-a]pyrimidin-5-yl)-8-azabicyclo[3.2.1]octane-8-carboxylate and (1R,3s,5S)-tert-butyl 3-(7-(bis((2-(trimethylsilyl)ethoxy)methyl)amino)-3-(6-(3-hydroxypentan-3-yl)pyridin-3-yl)pyrazolo[1,5-a]pyrimidin-5-yl)-8-azabicyclo[3.2.1]octane-8-carboxylate, which by applying chemistry in example 1-1 was converted to a mixture of (1R,3s,5S)-tert-butyl 3-(7-(bis((2-(trimethylsilyl)ethoxy)methyl)amino)-6-(1-ethoxyvinyl)-3-(6-(1-hydroxycyclopropyl)pyridin-3-yl)pyrazolo[1,5-a]pyrimidin-5-yl)-8-azabicyclo[3.2.1]octane-8-carboxylate and (1R,3s,5S)-tert-butyl 3-(7-(bis((2-(trimethylsilyl)ethoxy)methyl)amino)-6-(1-ethoxyvinyl)-3-(6-(3-hydroxypentan-3-yl)pyridin-3-yl)pyrazolo[1,5-a]pyrimidin-5-yl)-8-azabicyclo[3.2.1]octane-8-carboxylate.

Example 1-32

Preparation of 1-(5-(6-acetyl-7-amino-5-((1R,3s,5S)-8-azabicyclo[3.2.1]octan-3-yl)pyrazolo[1,5-a]pyrimidin-3-yl)pyridin-2-yl)propan-1-one

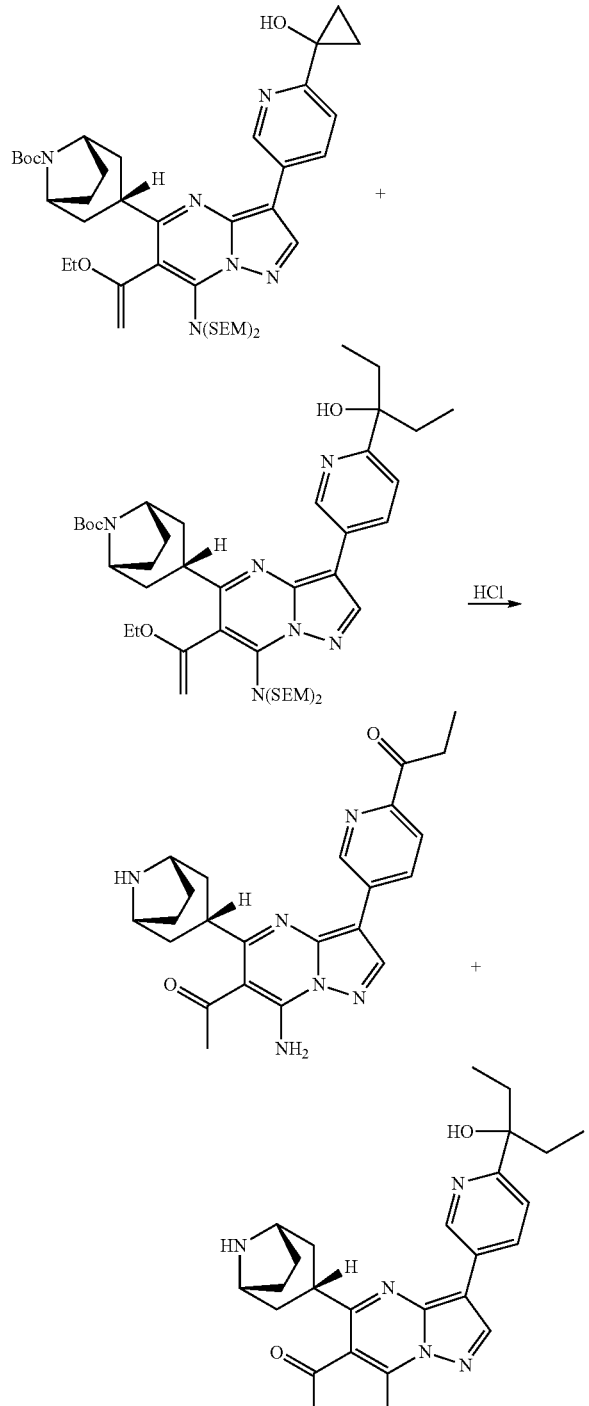

Example 1-33

A mixture of (1R,3s,5S)-tert-butyl 3-(7-(bis((2-(trimethylsilyl)ethoxy)methyl)amino)-6-(1-ethoxyvinyl)-3-(6-(1-hydroxycyclopropyl)pyridin-3-yl)pyrazolo[1,5-a]pyrimidin-5-yl)-8-azabicyclo[3.2.1]octane-8-carboxylate and (1R,3s,5S)-tert-butyl 3-(7-(bis((2-(trimethylsilyl)ethoxy)methyl)amino)-6-(1-ethoxyvinyl)-3-(6-(3-hydroxypentan-3-yl)pyridin-3-yl)pyrazolo[1,5-a]pyrimidin-5-yl)-8-azabicyclo[3.2.1]octane-8-carboxylate (180.1 mg) was treated 4N HCl in H₂O (6 ml) and Dioxane (3 ml) at 50° C. for 0.5 h. Concentration afforded crude mixture of 1-(5-(6-acetyl-7-amino-5-((1R,3s,5S)-8-azabicyclo[3.2.1]octan-3-yl)pyrazolo[1,5-a]pyrimidin-3-yl)pyridin-2-yl)propan-1-one and 1-(7-amino-5-((1R,3s,5S)-8-azabicyclo[3.2.1]octan-3-yl)-3-(6-(3-hydroxypentan-3-yl)pyridin-3-yl)pyrazolo[1,5-a]pyrimidin-6-yl)ethanone.

Example 1-34

Preparation of 1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)propan-1-one

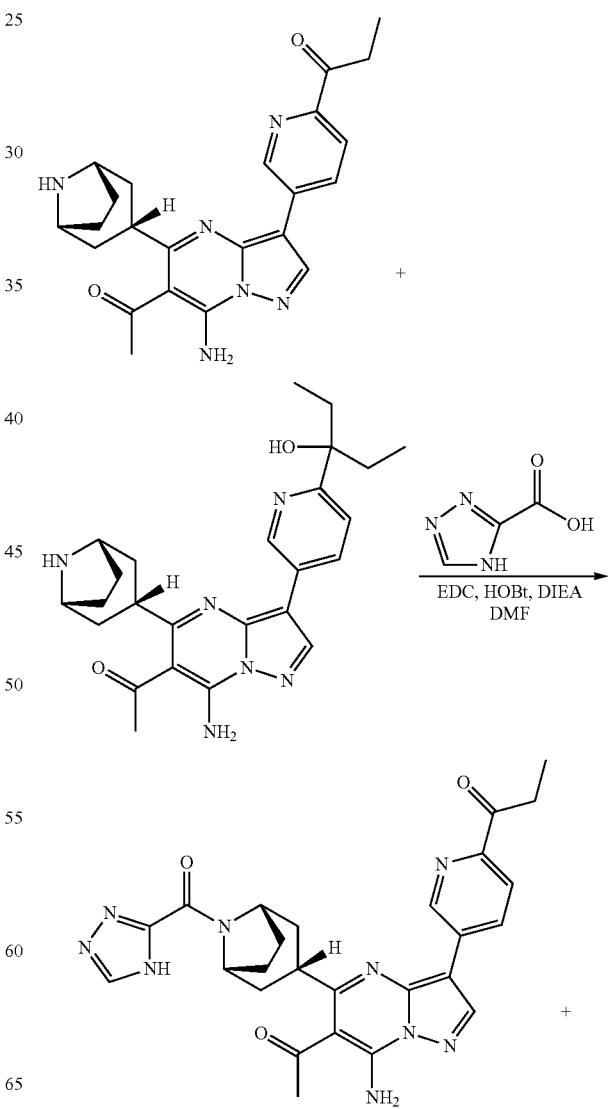

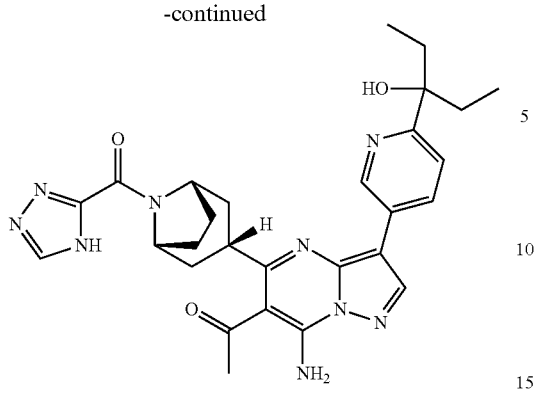

By applying the chemistry in previous examples, the mixture of 1-(5-(6-acetyl-7-amino-5-((1R,3s,5S)-8-azabicyclo[3.2.1]octan-3-yl)pyrazolo[1,5-a]pyrimidin-3-yl)pyridin-2-yl)propan-1-one and 1-(7-amino-5-((1R,3s,5S)-8-azabicyclo[3.2.1]octan-3-yl)-3-(6-(3-hydroxypentan-3-yl)pyridin-3-yl)pyrazolo[1,5-a]pyrimidin-6-yl)ethanone was submitted for EDC-mediated amide coupling reaction. Purification by prep-LC afforded pure 1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)propan-1-one, LCMS $t_R$=2.47 Min (10 min run, $UV_{254nm}$), Mass calculated for, M+ 513.2, observed LC/MS m/z 514.08 (M+H) and pure 1-(5-((1R,3s,5S)-8-(4H-1,2,4-triazole-3-carbonyl)-8-azabicyclo[3.2.1]octan-3-yl)-7-amino-3-(6-(3-hydroxypentan-3-yl)pyridin-3-yl)pyrazolo[1,5-a]pyrimidin-6-yl)ethanone, LCMS $t_R$=2.10 Min (10 min run, $UV_{254nm}$), Mass calculated for, M+ 543.2, observed LC/MS m/z 544.03.

Example 1-35

Preparation of (1R,3s,5S)-tert-butyl 3-(7-(bis((2-(trimethylsilyl)ethoxy)methyl)amino)-3-(6-(hydroxymethyl)pyridin-3-yl)pyrazolo[1,5-a]pyrimidin-5-yl)-8-azabicyclo[3.2.1]octane-8-carboxylate

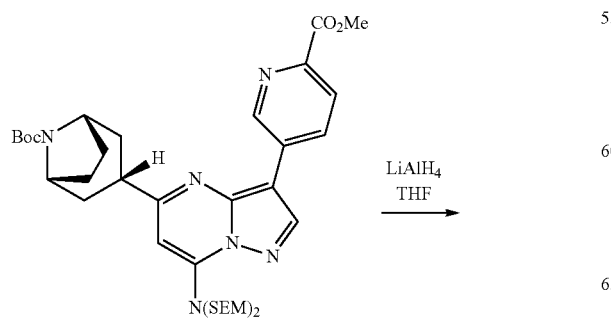

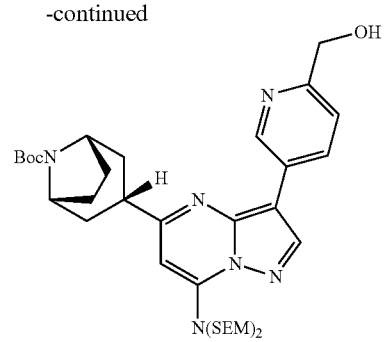

At 0° C., LiAlH₄ (55.3 mg, 1.46 mmol) was added to (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate (537.9 mg, 0.73 mmol) in THF (10 ml). The mixture was slowly warmed up to room temperature. and stirred for 1 h. EtOAc (10 ml), followed by H₂O (80 ul), 15% NaOH (80 ul) and H₂O (240 ul) were added to reaction mixture and the mixture was further stirred for 2 h. Filtration, concentration and purification by column chromatography afforded (1R,3s,5S)-tert-butyl 3-(7-(bis((2-(trimethylsilyl)ethoxy)methyl)amino)-3-(6-(hydroxymethyl)pyridin-3-yl)pyrazolo[1,5-a]pyrimidin-5-yl)-8-azabicyclo[3.2.1]octane-8-carboxylate: LCMS $t_R$=1.50 Min (5 min run, $UV_{254nm}$). Mass calculated for, M+ 710.4, observed LC/MS m/z 711.2 (M+H).

Example 1-36

Preparation of (1R,3s,5S)-tert-butyl 3-(7-(bis((2-(trimethylsilyl)ethoxy)methyl)amino)-3-(5-(fluoromethyl)pyridin-3-yl)pyrazolo[1,5-a]pyrimidin-5-yl-8-azabicyclo[3.2.1]octane-8-carboxylate

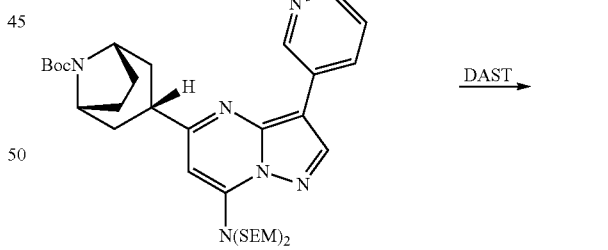

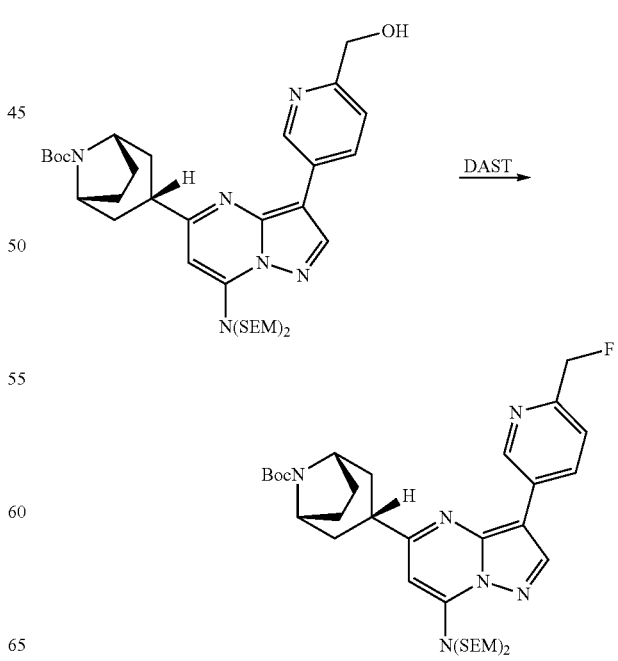

At 0° C., DAST (112.5 mg, 0.69 mmol) was added to (1R,3s,5S)-tert-butyl 3-(7-(bis((2-(trimethylsilyl)ethoxy)methyl)amino)-3-(6-(hydroxymethyl)pyridin-3-yl)pyrazolo[1,5-a]pyrimidin-5-yl)-8-azabicyclo[3.2.1]octane-8-carboxylate (309.9 mg, 0.43 mmol) in DCM (10 ml). The mixture was slowly warmed up to room temperature and stirred for 2 h. More DAST (309.9 mg, 0.43 mmol) was added. Once LCMS indicated complete conversion, the mixture was diluted with sat. NaHCO$_3$ and then extracted with DCM (×2). The combined organic layers were washed with brine and dried with Na$_2$SO$_4$. Concentration and purification by column chromatography afforded (1R,3s,5S)-tert-butyl 3-(7-(bis((2-(trimethylsilyl)ethoxy)methyl)amino)-3-(6-(fluoromethyl)pyridin-3-yl)pyrazolo[1,5-a]pyrimidin-5-yl)-8-azabicyclo[3.2.1]octane-8-carboxylate: LCMS t$_R$=1.79 Min (5 min run, UV$_{254nm}$). Mass calculated for, M+ 712.4, observed LC/MS m/z 713.3 (M+H).

Example 1-37

Preparation of (1R,3s,5S)-tert-butyl 3-(7-(bis((2-(trimethylsilyl)ethoxy)methyl)amino)-3-(6-(2-oxopyridin-1(2H)-yl)pyridin-3-yl)pyrazolo[1,5-a]pyrimidin-5-yl)-8-azabicyclo[3.2.1]octane-8-carboxylate

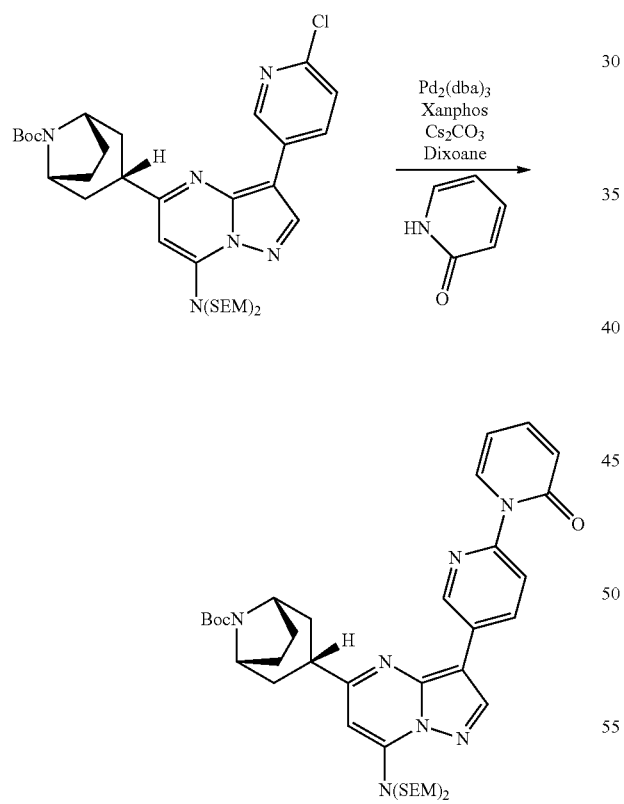

A degassed mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (357 mg, 0.50 mmol), Cs$_2$CO$_3$ (244.4 mg, 0.75 mmol), pyridin-2(1H)-one (95 mg, 1.0 mmol), Xanphos (43.4 mg, 0.075 mmol), Pd$_2$(dba)$_3$ (22.9 mg, 0.025 mmol) in Dioxane (6 ml) was heated at 110° C. overnight. The mixture was cooled to room temperature, filtered and evaporated. Purification by column chromatography afforded (1R,3s,5S)-tert-butyl 3-(7-(bis((2-(trimethylsilyl)ethoxy)methyl)amino)-3-(6-(2-oxopyridin-1(2H)-yl)pyridin-3-yl)pyrazolo[1,5-a]pyrimidin-5-yl)-8-azabicyclo[3.2.1]octane-8-carboxylate: LCMS t$_R$=1.88 Min (5 min run UV$_{254nm}$). Mass calculated for, M+ 773.4, observed LC/MS m/z 774.3 (M+H).

Example 1-38

Preparation of (1R,3s,5S)-tert-butyl 3-(7-(bis((2-(trimethylsilyl)ethoxy)methyl)amino)-3-(6-chloro-5-methylpyridin-3-yl)pyrazolo[1,5-a]pyrimidin-5-yl)-8-azabicyclo[3.2.1]octane-8-carboxylate

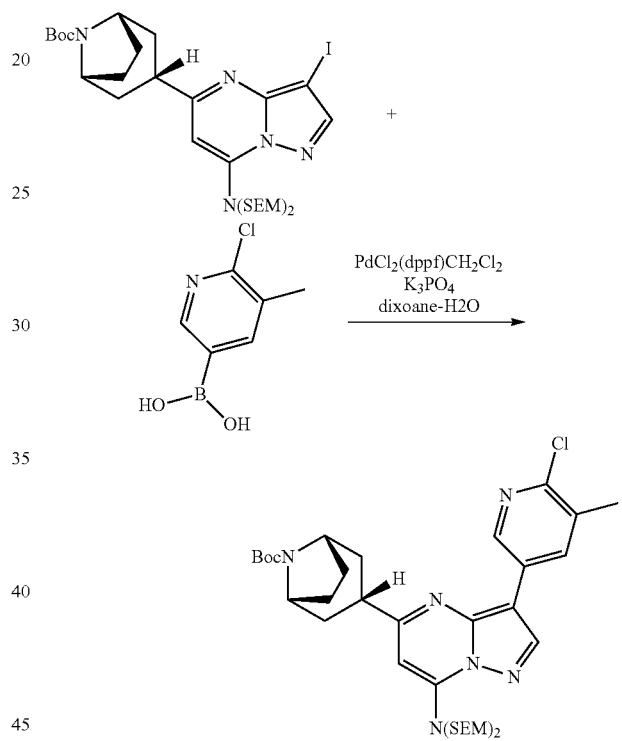

6-chloro-5-methylpyridin-3-ylboronic acid (347.2 mg, 2.02 mmol), K$_3$PO$_4$ (1171.5 mg, 5.52 mmol), and PdCl$_2$(dppf).CH$_2$Cl$_2$ (150.3 mg, 0.18 mmol) were added to a mixture of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (1342.8 mg, 1.84 mmol) in dioxane (20 mL) and H$_2$O (2 mL). The resulting solution was stirred at 65° C. under argon overnight. The mixture was diluted with H$_2$O and then extracted with ethyl acetate (×2). The combined organic layers were washed with brine and dried with Na$_2$SO$_4$. Evaporation and purification by column chromatography afforded (1R,3s,5S)-tert-butyl 3-(7-(bis((2-(trimethylsilyl)ethoxy)methyl)amino)-3-(6-chloro-5-methylpyridin-3-yl)pyrazolo[1,5-a]pyrimidin-5-yl)-8-azabicyclo[3.2.1]octane-8-carboxylate: LCMS t$_R$=1.56 Min (5 min run UV$_{254nm}$). Mass calculated for, M+ 774.4, observed LC/MS m/z 775.3 (M+H).

Example 1-39

Preparation of (1R,3s,5S)-tert-butyl 3-(7-(bis((2-(trimethylsilyl)ethoxy)methyl)amino)-3-(6-chloro-5-fluoropyridin-3-yl)pyrazolo[1,5-a]pyrimidin-5-yl)-8-azabicyclo[3.2.1]octane-8-carboxylate

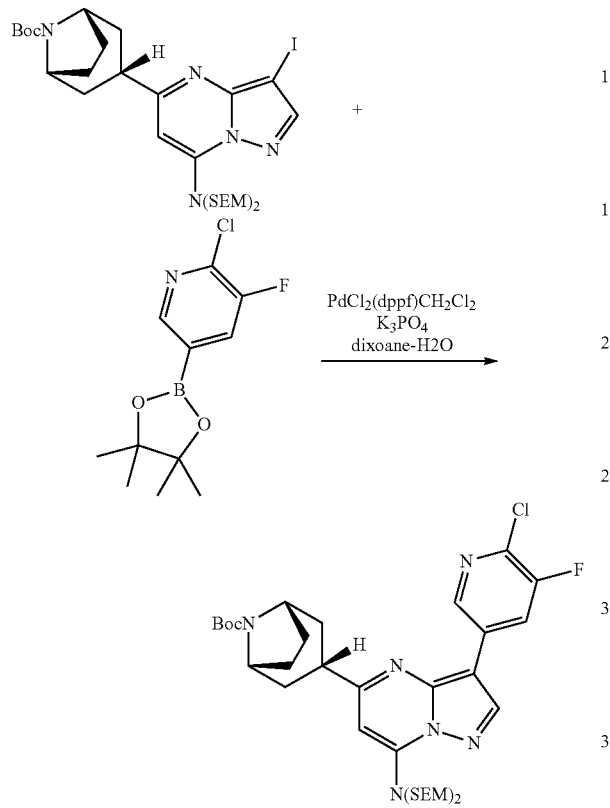

By applying the chemistry described in Example 36, (1R,3s,5S)-tert-butyl 3-(7-(bis((2-(trimethylsilyl)ethoxy)methyl)amino)-3-(6-chloro-5-fluoropyridin-3-yl)pyrazolo[1,5-a]pyrimidin-5-yl)-8-azabicyclo[3.2.1]octane-8-carboxylate was prepared from (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate: LCMS $t_R$=2.02 Min (5 min run $UV_{254nm}$). Mass calculated for, M+ 732.3, observed LC/MS m/z 733.3 (M+H).

Example 1-40

Preparation of (1R,3s,5S)-tert-butyl 3-(7-(bis((2-(trimethylsilyl)ethoxy)methyl)amino)-3-(3'-fluoro-2,2'-bipyridin-5-yl)pyrazolo[1,5-a]pyrimidin-5-yl)-8-azabicyclo[3.2.1]octane-8-carboxylate

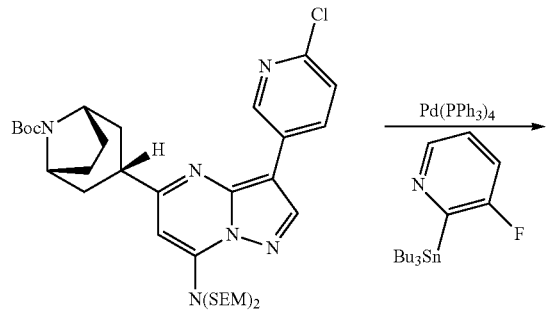

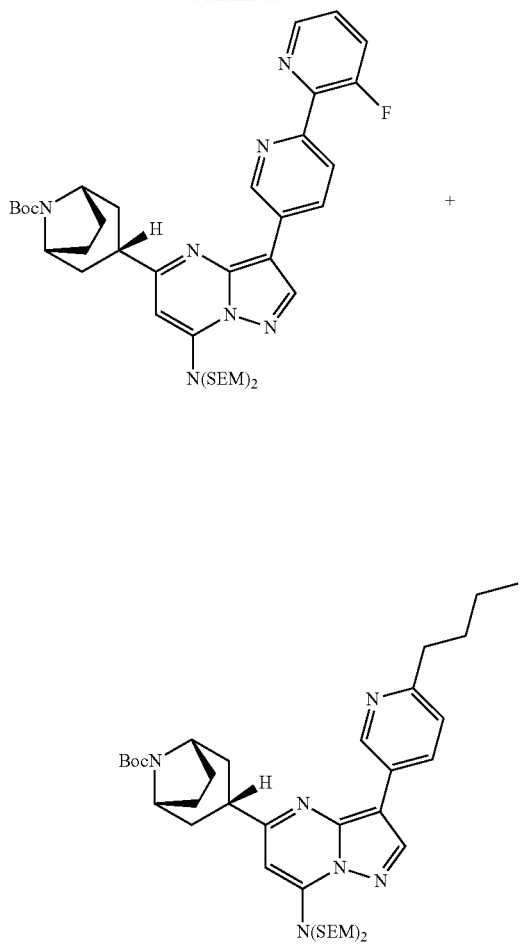

A degassed mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1000 mg, 1.40 mmol), Pd(PPh₃)₄ (161.9 mg, 0.14 mmol), 3-fluoro-2-(tributylstannyl)pyridine (1080 mg, 2.80 mmol) in Dioxane (6 mL) and CH₃CN (6 mL) was heated at 180° C. for 60 min under microwave condition. The reaction mixture was cooled to room temperature, filtered through 9:1 SiO₂:KF plug and concentrated in vacuo. Purification by column chromatography afforded (1R,3s,5S)-tert-butyl 3-(7-(bis((2-(trimethylsilyl)ethoxy)methyl)amino)-3-(3'-fluoro-2,2'-bipyridin-5-yl)pyrazolo[1,5-a]pyrimidin-5-yl)-8-azabicyclo[3.2.1]octane-8-carboxylate, LCMS $t_R$=1.62 Min (5 min run, $UV_{254nm}$). Mass calculated for, M+ 775.4, observed LC/MS m/z 776.3 (M+H) and (1R,3s,5S)-tert-butyl 3-(7-(bis((2-(trimethylsilyl)ethoxy)methyl)amino)-3-(6-butylpyridin-3-yl)pyrazolo[1,5-a]pyrimidin-5-yl)-8-azabicyclo[3.2.1]octane-8-carboxylate: LCMS $t_R$=1.57 Min (5 min run, $UV_{254nm}$). Mass calculated for, M+ 736.4, observed LC/MS m/z 737.3 (M+H).

Example 1-41

Preparation of 1-(5-(((1R,3s,5S)-8-(4H-1,2,4-triazole-3-carbonyl)-8-azabicyclo[3.2.1]octan-3-yl)-7-amino-3-(6-(hydroxymethyl)quinolin-3-yl)pyrazolo[1,5-a]pyrimidin-6-yl)ethanone

Step 1: Preparation of 3-bromoquinoline-6-carboxylic acid

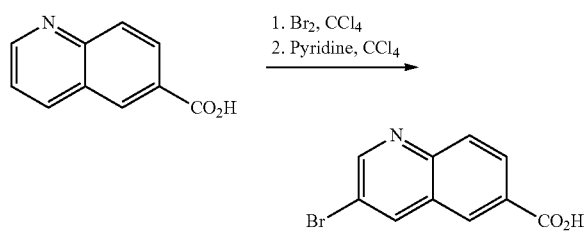

To a suspension of quinoline-6-carboxylic acid (2.77 g, 16.0 mmol) in $CCl_4$ (20 ml) in a flask wrapped with Al foil was added bromine (987 uL, 19.2 mmol) dropwise. The resulting mixture was stirred at rt for 30 min, then heated under reflux for 30 min. A solution of pyridine (1.55 mL, 19.2 mmol) in $CCl_4$ (4 mL) was added dropwise at refluxing temperature. Then the reaction mixture was heated under reflux for 4 h. The reaction mixture was treated with 3 N NaOH until all the precipitates were dissolved. The aqueous layer was separated and washed with DCM once more, then acidified with 3 N HCl. The resulting orange precipitates were filtered, and washed with $H_2O$, and a small amount of MeOH to afford the titled compound as an off-white solid (3.36 g).

Step 2: Preparation of (3-bromoquinolin-6-yl)methanol

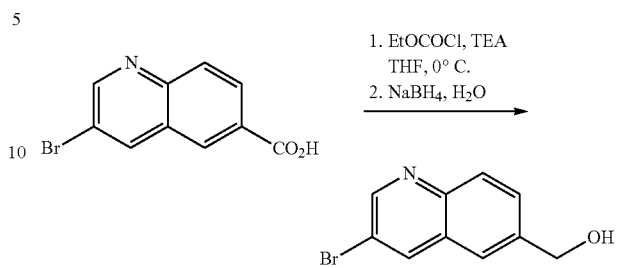

To a mixture of 3-bromoquinoline-6-carboxylic acid (1.32 g, 5.24 mmol) and TEA (876 uL, 6.29 mmol) in THF (30 mL) was added EtOCOCl (599 uL, 6.29 mmol) at 0° C. and stirred for 30 min. Then, a solution of $NaBH_4$ (793 mg, 21.0 mmol) in $H_2O$ (6 mL) was added at the same temperature. The resulting reaction mixture was stirred at 0° C. for 30 min before being warmed to it and stirred overnight. THF was removed. The residue was diluted with $H_2O$, acidified with 4 N HCl, then neutralized with $NaHCO_3$, extracted with EtOAc, and purified by a $SiO_2$ column (0-50% EtOAc/Hexanes, $R_f$=0.35 in 50% EtOAc) to afford the titled compound as a colorless oil (220 mg).

Step 3: Preparation of 1-(5-(((1R,3s,5S)-8-(4H-1,2,4-triazole-3-carbonyl)-8-azabicyclo[3.2.1]octan-3-yl)-7-amino-3-(6-(hydroxymethyl)quinolin-3-yl)pyrazolo[1,5-a]pyrimidin-6-yl)ethanone This compound was prepared from (3-bromoquinolin-6-yl)methanol, following essentially the same procedures given previously.

Following Scheme 1-1 and using procedures similar to the preparation of above examples, the following compounds listed in Table 1-1 were prepared.

TABLE 1-1

| Compound ID | Structures | Compound Name | M + H (calculated)/ M + H (observed) | pAKT S473 IC50 | p4E-1 Thr37/ 46 IC50 |
|---|---|---|---|---|---|
| 1.1.1 | 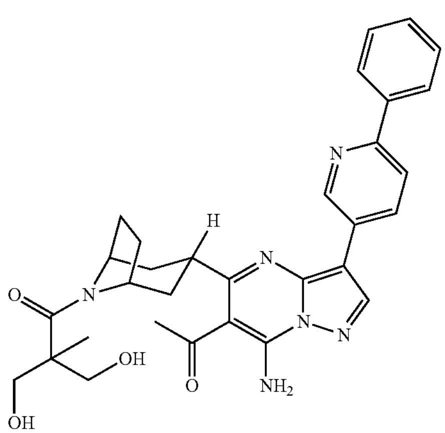 [SMILES: CC(=O)c1c(C2CC3CCC(C2)N3C(=O)C(C)(CO)CO)nc2c(-c3ccc(-c4ccccc4)nc3)cnn2c1N] | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one | 555.2/555.2 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| | | | | | |
| 1.1.2 | 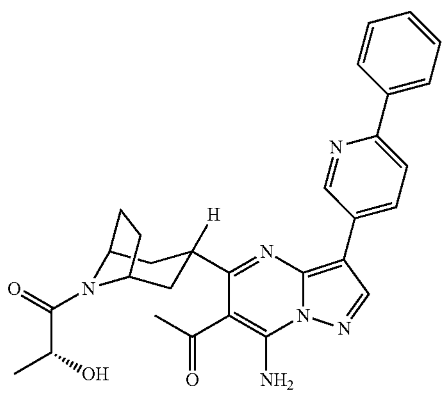 [SMILES: CC(=O)c1c(C2CC3CCC(C2)N3C(=O)[C@@H](C)O)nc2c(-c3ccc(-c4ccccc4)nc3)cnn2c1N] | ((R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one | 511.2/511.7 | A | B |

TABLE 1-1-continued
| Compound ID | Structures | Compound Name | M + H (calculated)/ M + H (observed) | pAKT S473 IC50 | p4E-1 Thr37/ 46 IC50 |
| --- | --- | --- | --- | --- | --- |
| 1.1.3 | 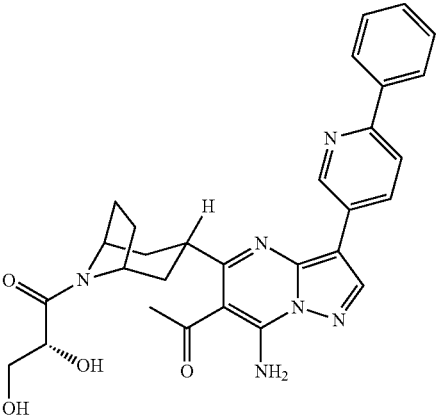 [SMILES: CC(=O)c1c(C2CC3CCC(C2)N3C(=O)[C@H](O)CO)nc2c(-c3ccc(-c4ccccc4)nc3)cnn2c1N] | (R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2,3-dihydroxypropan-1-one | 527.2/527.6 | B | ND |
| 1.1.4 | 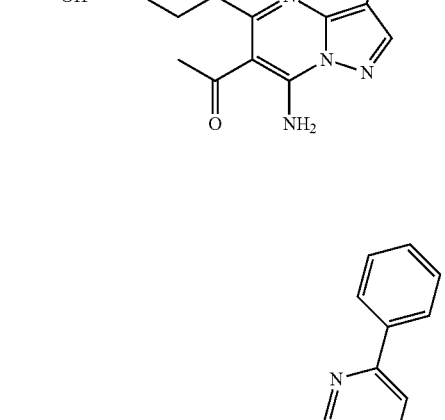 | (EXO)-3-[6-ACETYL-7-AMINO-3-(6-PHENYL-3-PYRIDINYL)PYRAZOLO[1,5-a]PYRIMIDIN-5-YL]-8-[(1,1-DIOXIDO-3-ISOTHIAZOLIDINYL)CARBONYL]-8-AZABICYCLO[3.2.1]OCTANE (MIX. OF 2 DIASTEREOMERS) | 586.2/586.0 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.5 | 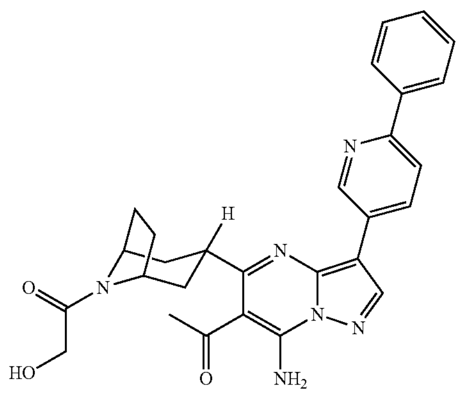 [SMILES: CC(=O)c1c(C2CC3CCC(C2)N3C(=O)CO)nc2c(-c3ccc(-c4ccccc4)nc3)cnn2c1N] | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone | 497.2/497.1 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.6 | 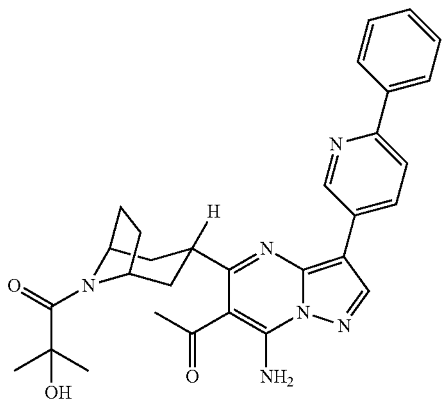 [SMILES: CC(=O)c1c(C2CC3CCC(C2)N3C(=O)C(C)(C)O)nc2c(-c3ccc(-c4ccccc4)nc3)cnn2c1N] | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxy-2-methylpropan-1-one | 525.2/525.2 | B | ND |
| 1.1.7 | 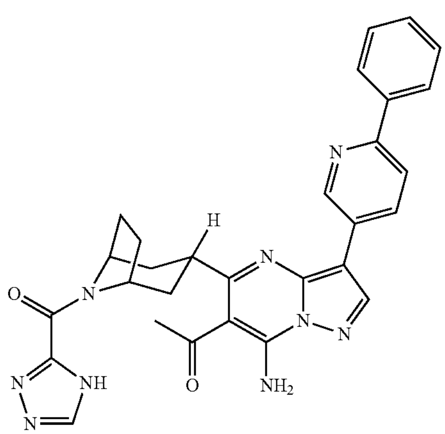 [SMILES: CC(=O)c1c(C2CC3CCC(C2)N3C(=O)c2nnc[nH]2)nc2c(-c3ccc(-c4ccccc4)nc3)cnn2c1N] | 1-(5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)ethanone | 534.2/534.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.8 | 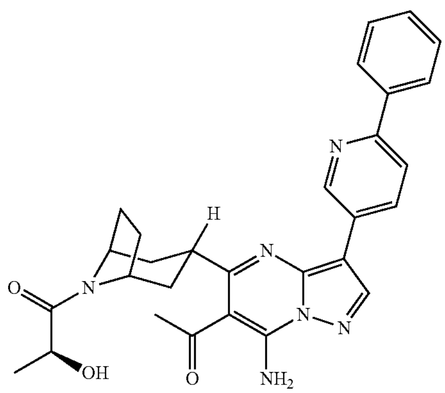 | (S)-1-((1R,3R,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one | 511.2/510.9 | A | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.9 | 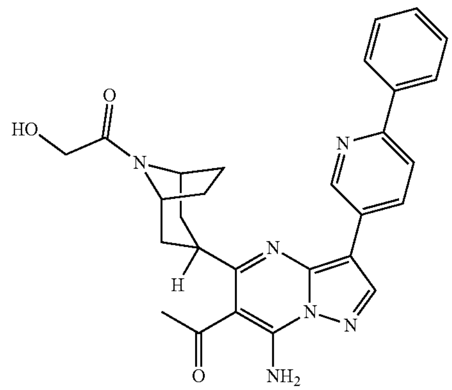 [SMILES: CC(=O)c1c(C2CC3CCC(C2)N3C(=O)CO)nc2c(-c3ccc(-c4ccccc4)nc3)cnn2c1N] | 1-((1R,3r,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone | 497.2/496.9 | B | B |
|  | | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone |  |  |  |
| 1.1.20 | 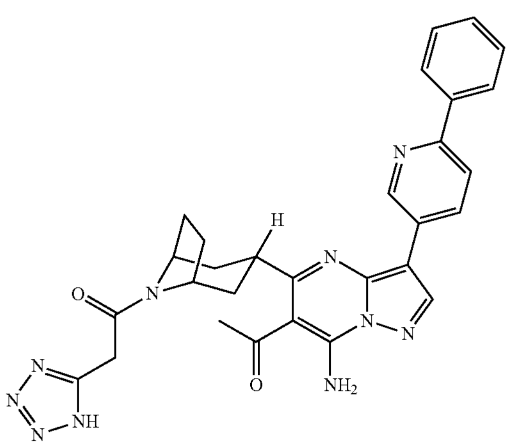 [SMILES: CC(=O)c1c(C2CC3CCC(C2)N3C(=O)Cc2nnn[nH]2)nc2c(-c3ccc(-c4ccccc4)nc3)cnn2c1N] | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-(1H-tetrazol-5-yl)ethanone | 549.2/549.1 | B | C |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.21 | 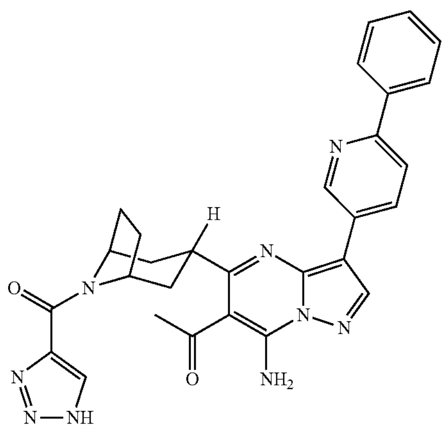 [SMILES: CC(=O)c1c(C2CC3CCC(C2)N3C(=O)c2c[nH]nn2)nc2c(-c3ccc(-c4ccccc4)nc3)cnn2c1N] | 1-(5-(((1R,3s,5S)-8-(1H-1,2,3-triazole-5-carbonyl)-8-azabicyclo[3.2.1]octan-3-yl)-7-amino-3-(6-phenylpyridin-3-yl)pyrazolo[1,5-a]pyrimidin-6-yl)ethanone | 534.2/534.0 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.22 | 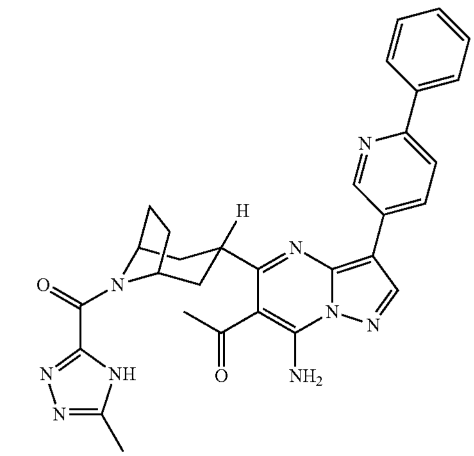 [SMILES: CC(=O)c1c(C2CC3CCC(C2)N3C(=O)c2nnc(C)[nH]2)nc2c(-c3ccc(-c4ccccc4)nc3)cnn2c1N] | 1-(7-amino-5-((1R,3s,5S)-8-(3-methyl-1H-1,2,4-triazole-5-carbonyl)-8-azabicyclo[3.2.1]octan-3-yl)-3-(6-phenylpyridin-3-yl)pyrazolo[1,5-a]pyrimidin-6-yl)ethanone | 548.2/547.9 | A | A |
| 1.1.23 | 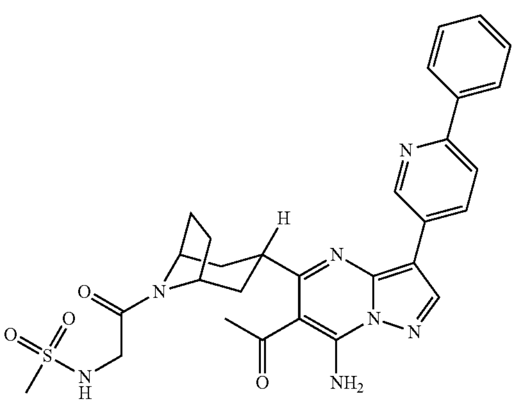 [SMILES: CC(=O)c1c(C2CC3CCC(C2)N3C(=O)CNS(C)(=O)=O)nc2c(-c3ccc(-c4ccccc4)nc3)cnn2c1N] | N-(2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoethyl)methanesulfonamide | 574.2/573.9 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.24 | 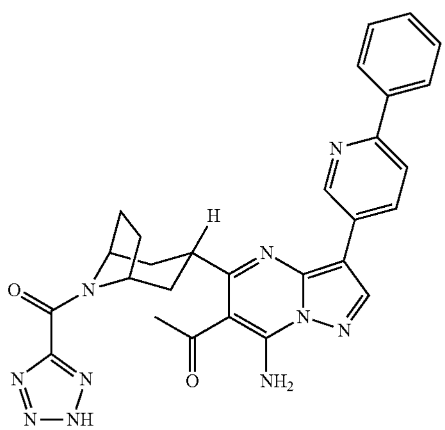 [SMILES: CC(=O)c1c(C2CC3CCC(C2)N3C(=O)c2nn[nH]n2)nc2c(-c3ccc(-c4ccccc4)nc3)cnn2c1N] | 1-(5-((1R,3s,5S)-8-(1H-tetrazole-5-carbonyl)-8-azabicyclo[3.2.1]octan-3-yl)-7-amino-3-(6-phenylpyridin-3-yl)pyrazolo[1,5-a]pyrimidin-6-yl)ethanone | 535.2/535.2 | C | C |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.25 | 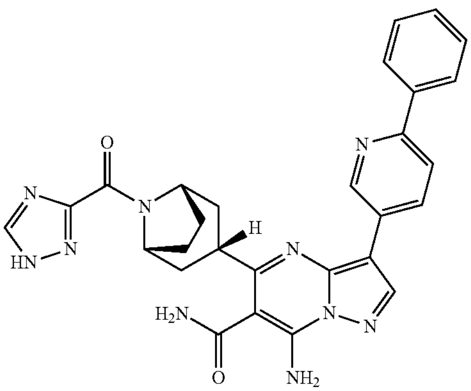 [SMILES: NC(=O)c1c([C@@H]2C[C@H]3CC[C@@H](C2)N3C(=O)c2nc[nH]n2)nc2c(-c3ccc(-c4ccccc4)nc3)cnn2c1N] | 5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carboxamide | 535.2/534.9 | A | A |
| 1.1.26 | 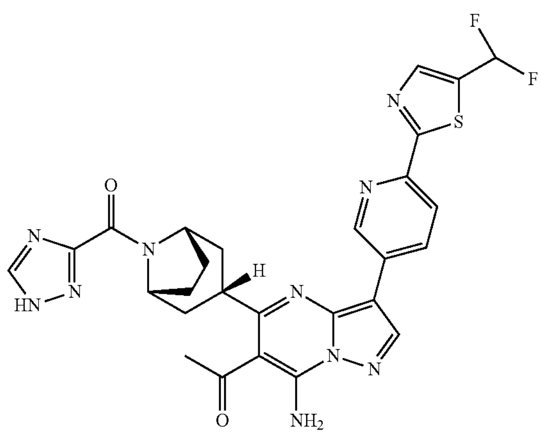 [SMILES: CC(=O)c1c([C@@H]2C[C@H]3CC[C@@H](C2)N3C(=O)c2nc[nH]n2)nc2c(-c3ccc(-c4ncc(C(F)F)s4)nc3)cnn2c1N] | 1-(5-((1R,3s,5S)-8-(1H-1,2,4-triazole-3-carbonyl)-8-azabicyclo[3.2.1]octan-3-yl)-7-amino-3-(6-(5-(difluoromethyl)thiazol-2-yl)pyridin-3-yl)pyrazolo[1,5-a]pyrimidin-6-yl)ethanone | 591.1/590.9 | B | B |
| 1.1.27 | 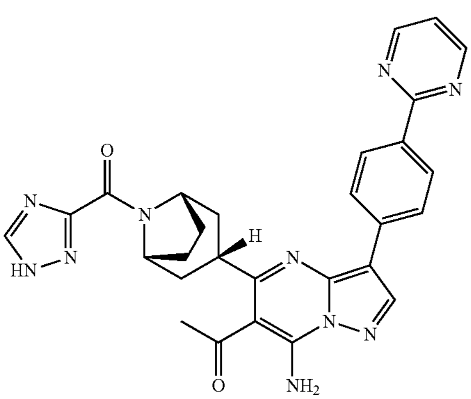 [SMILES: CC(=O)c1c([C@@H]2C[C@H]3CC[C@@H](C2)N3C(=O)c2nc[nH]n2)nc2c(-c3ccc(-c4ncccn4)cc3)cnn2c1N] | 1-(5-((1R,3s,5S)-8-(1H-1,2,4-triazole-3-carbonyl)-8-azabicyclo[3.2.1]octan-3-yl)-7-amino-3-(4-(pyrimidin-2-yl)phenyl)pyrazolo[1,5-a]pyrimidin-6-yl)ethanone | 535.2/534.9 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.28 | 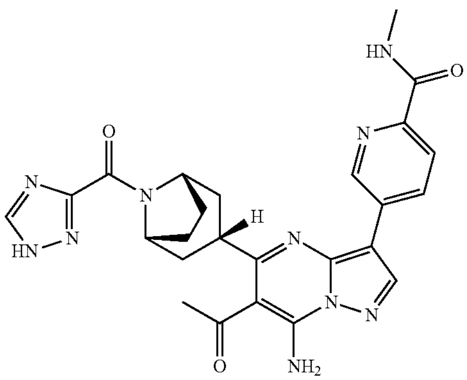 [SMILES: CNC(=O)c1ccc(-c2cnn3c(N)c(C(C)=O)c([C@@H]4C[C@H]5CC[C@@H](C4)N5C(=O)c4nc[nH]n4)nc23)cn1] | 5-(5-((1R,3s,5S)-8-(1H-1,2,4-triazole-3-carbonyl)-8-azabicyclo[3.2.1]octan-3-yl)-6-acetyl-7-aminopyrazolo[1,5-a]pyrimidin-3-yl)-N-methylpicolinamide | 515.2/515.0 | C | C |
| 1.1.29 | 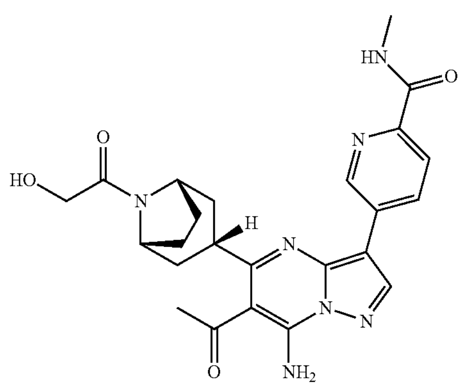 [SMILES: CNC(=O)c1ccc(-c2cnn3c(N)c(C(C)=O)c([C@@H]4C[C@H]5CC[C@@H](C4)N5C(=O)CO)nc23)cn1] | 5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)-N-methylpicolinamide | 478.2/477.9 | ND | ND |
| 1.1.30 | 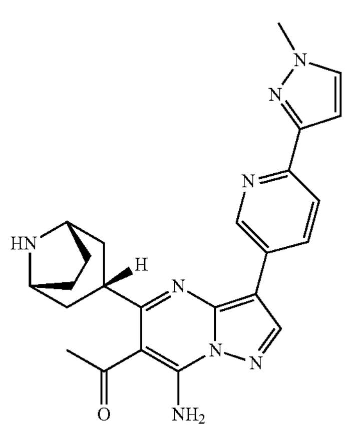 [SMILES: CC(=O)c1c([C@@H]2C[C@H]3CC[C@@H](C2)N3)nc2c(-c3ccc(-c4ccn(C)n4)nc3)cnn2c1N] | 1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone | 443.2/443.0 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.31 | 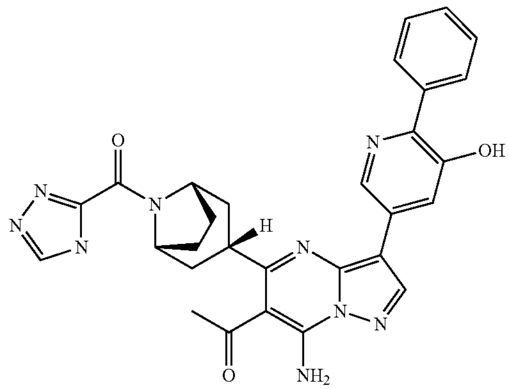 [SMILES: CC(=O)c1c([C@@H]2C[C@H]3CC[C@@H](C2)N3C(=O)c2nnc[nH]2)nc2c(-c3cnc(-c4ccccc4)c(O)c3)cnn2c1N] | 1-(5-((1R,3s,5S)-8-(4H-1,2,4-triazole-3-carbonyl)-8-azabicyclo[3.2.1]octan-3-yl)-7-amino-3-(5-hydroxy-6-phenylpyridin-3-yl)pyrazolo[1,5-a]pyrimidin-6-yl)ethanone | 550.2/549.9 | C | C |
| 1.1.32 | 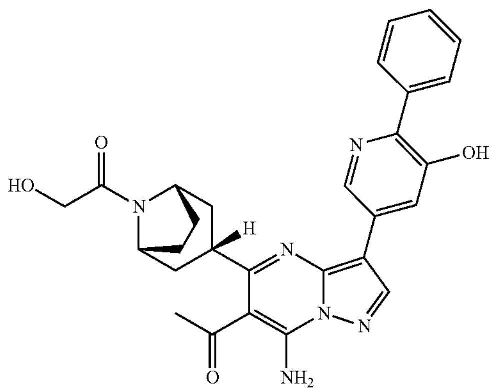 [SMILES: CC(=O)c1c([C@@H]2C[C@H]3CC[C@@H](C2)N3C(=O)CO)nc2c(-c3cnc(-c4ccccc4)c(O)c3)cnn2c1N] | 1-((1R,3s,5S)-3-(6-acetyl-7-amino-3-(5-hydroxy-6-phenylpyridin-3-yl)pyrazolo[1,5-a]pyrimidin-5-yl)-8-azabicyclo[3.2.1]octan-8-yl)-2-hydroxyethanone | 513.2/512.9 | C | C |
| 1.1.33 | | 1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxyethanone | 504.2/503.9 | A | B |

TABLE 1-1-continued
| Compound ID | Structures | Compound Name | M + H (calculated)/ M + H (observed) | pAKT S473 IC50 | p4E-1 Thr37/ 46 IC50 |
|---|---|---|---|---|---|
| 1.1.34 | 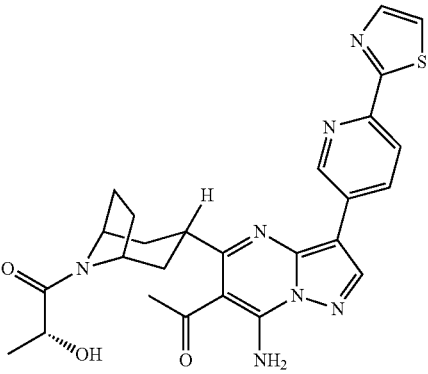 [SMILES: CC(=O)c1c(C2CC3CCC(C2)N3C(=O)[C@@H](C)O)nc2c(-c3ccc(-c4nccs4)nc3)cnn2c1N] 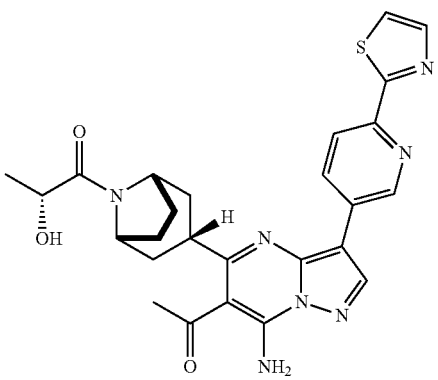 | (R)-1-((1R,3S,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxypropan-1-one | 518.2/517.9 | B | ND |
| 1.1.35 | 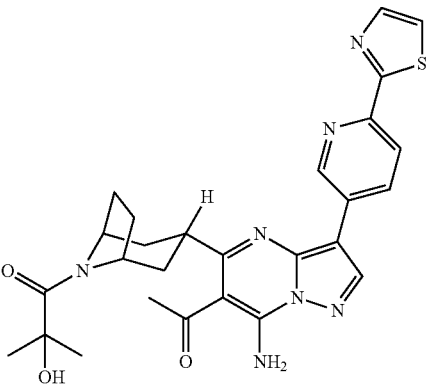 [SMILES: CC(=O)c1c(C2CC3CCC(C2)N3C(=O)C(C)(C)O)nc2c(-c3ccc(-c4nccs4)nc3)cnn2c1N] 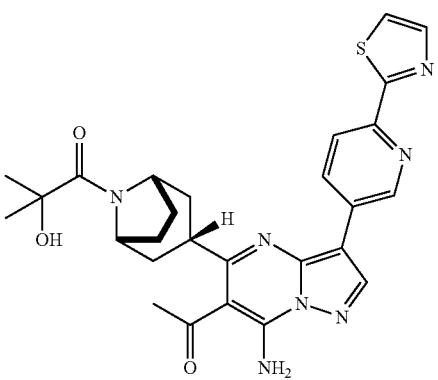 | 1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxy-2-methylpropan-1-one | 532.2/532.0 | B | ND |

TABLE 1-1-continued
| Compound ID | Structures | Compound Name | M + H (calculated)/ M + H (observed) | pAKT S473 IC50 | p4E-1 Thr37/ 46 IC50 |
|---|---|---|---|---|---|
| 1.1.36 | 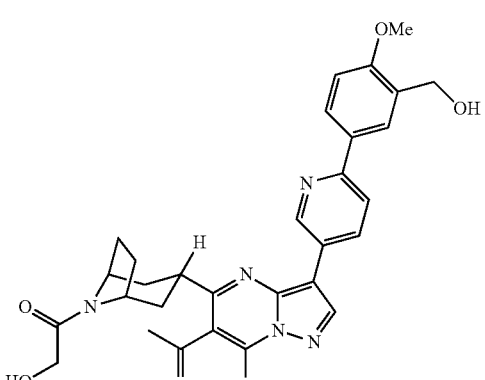 | 1-((1R,3s,5S)-3-(6-acetyl-7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone | 557.2/557.0 | A | A |
| 1.1.37 | 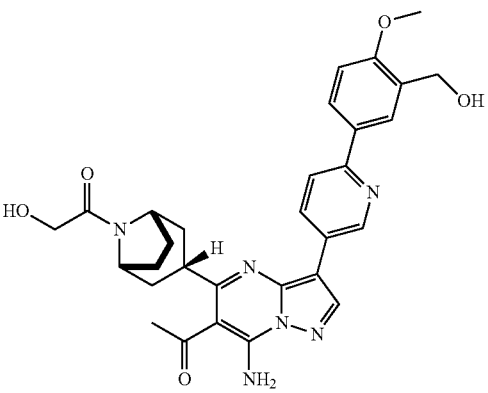 | 1-(5-((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidin-6-yl)ethanone | 541.2/540.8 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.38 | 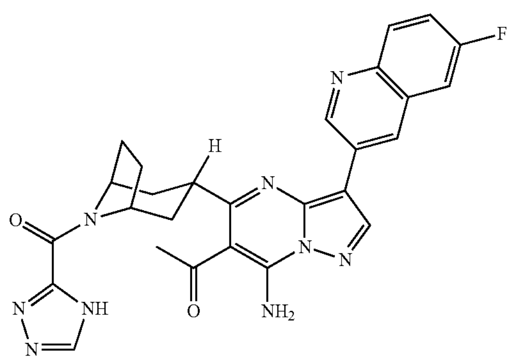 [SMILES: CC(=O)c1c(C2CC3CCC(C2)N3C(=O)c2nnc[nH]2)nc2c(-c3cnc4ccc(F)cc4c3)cnn2c1N] | 1-(5-((1R,3s,5S)-8-(4H-1,2,4-triazole-3-carbonyl)-8-azabicyclo[3.2.1]octan-3-yl)-7-amino-3-(7-fluoronaphthalen-2-yl)pyrazolo[1,5-a]pyrimidin-6-yl)ethanone | 525.2/526.0 | B | A |
| 1.1.39 | 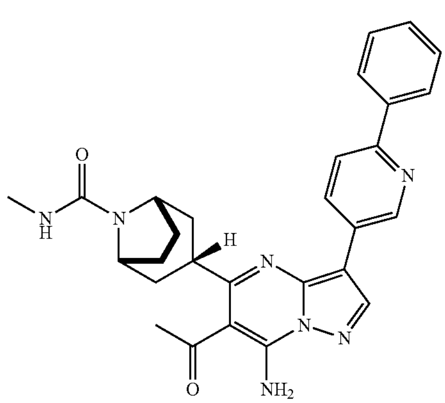 | (1R,3s,5S)-3-(6-acetyl-7-amino-3-(6-phenylpyridin-3-yl)pyrazolo[1,5-a]pyrimidin-5-yl)-N-methyl-8-azabicyclo[3.2.1]octane-8-carboxamide | 496.2/496.0 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.40 | 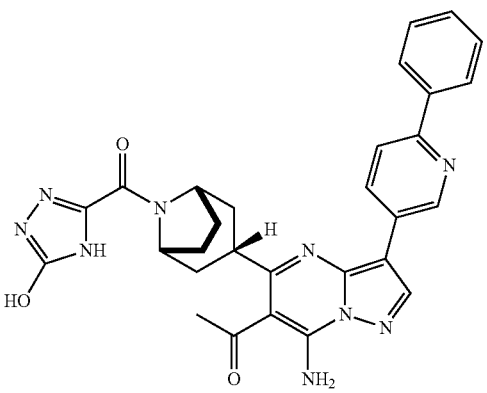 | 1-(7-amino-5-((1R,3s,5S)-8-(5-hydroxy-4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone | 550.2/550.0 | B | B |
| 1.1.41 | 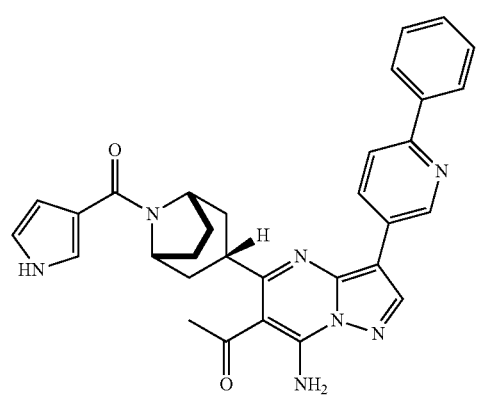 | 1-(5-((1R,3s,5S)-8-(1H-pyrrole-3-carbonyl)-8-azabicyclo[3.2.1]octan-3-yl)-7-amino-3-(6-phenylpyridin-3-yl)pyrazolo[1,5-a]pyrimidin-6-yl)ethanone | 532.2/532.0 | A | A |
| 1.1.42 | 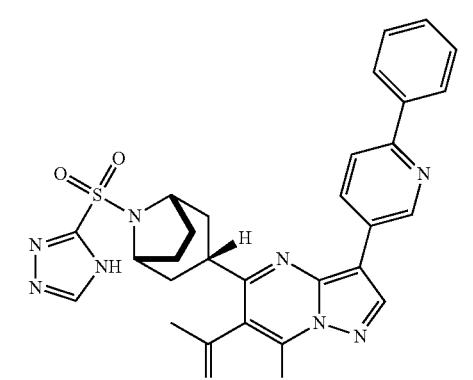 | 1-(5-((1R,3s,5S)-8-(4H-1,2,4-triazol-3-ylsulfonyl)-8-azabicyclo[3.2.1]octan-3-yl)-7-amino-3-(6-phenylpyridin-3-yl)pyrazolo[1,5-a]pyrimidin-6-yl)ethanone | 570.2/569.9 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.43 | 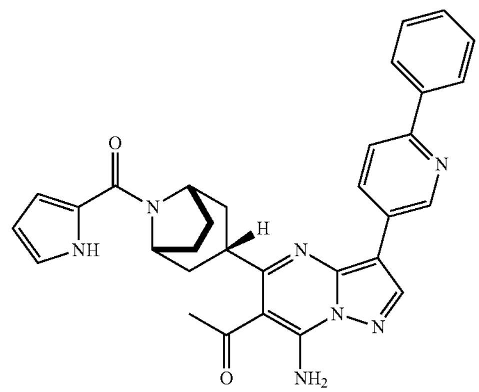 | 1-(5-((1R,3s,5S)-8-(1H-pyrrole-2-carbonyl)-8-azabicyclo[3.2.1]octan-3-yl)-7-amino-3-(6-phenylpyridin-3-yl)pyrazolo[1,5-a]pyrimidin-6-yl)ethanone | 532.2/532.0 | B | B |
| 1.1.44 | 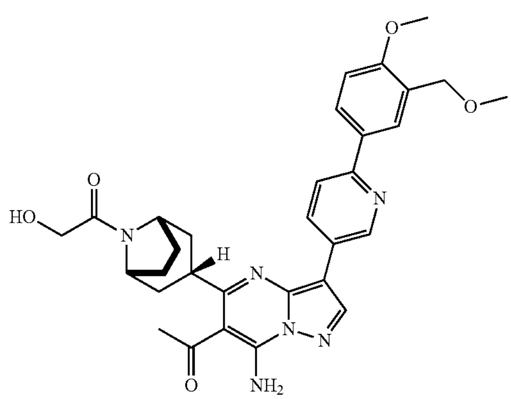 | 1-((1R,3s,5S)-3-(6-acetyl-7-amino-3-(6-(4-methoxy-3-(methoxymethyl)phenyl)pyridin-3-yl)pyrazolo[1,5-a]pyrimidin-5-yl)-8-azabicyclo[3.2.1]octan-8-yl)-2-hydroxyethanone | 571.3/571.0 | A | B |
| 1.1.45 | 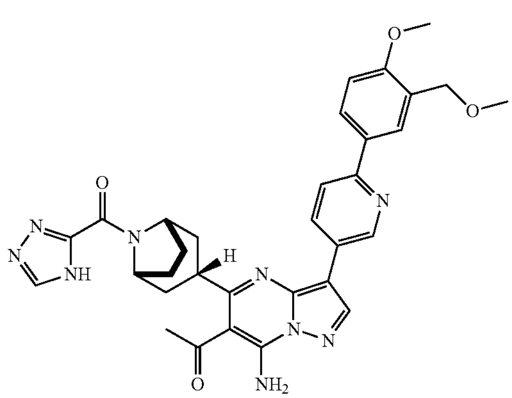 | 1-(5-((1R,3s,5S)-8-(4H-1,2,4-triazole-3-carbonyl)-8-azabicyclo[3.2.1]octan-3-yl)-7-amino-3-(6-(4-methoxy-3-(methoxymethyl)phenyl)pyridin-3-yl)pyrazolo[1,5-a]pyrimidin-6-yl)ethanone | 608.3/608.0 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.46 | 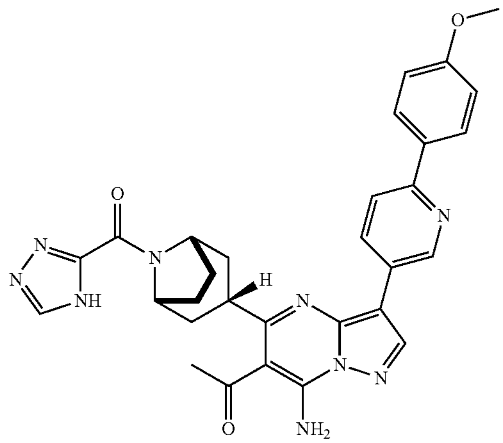 | 1-(5-((1R,3s,5S)-8-(4H-1,2,4-triazole-3-carbonyl)-8-azabicyclo[3.2.1]octan-3-yl)-7-amino-3-(6-(4-methoxyphenyl)pyridin-3-yl)pyrazolo[1,5-a]pyrimidin-6-yl)ethanone | 564.2/564.0 | A | A |
| 1.1.47 | 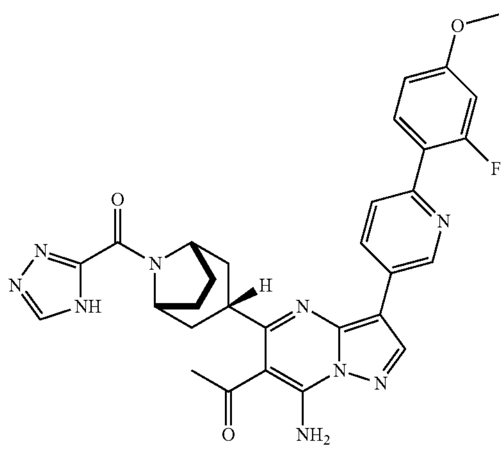 | 1-(5-((1R,3s,5S)-8-(4H-1,2,4-triazole-3-carbonyl)-8-azabicyclo[3.2.1]octan-3-yl)-7-amino-3-(6-(2-fluoro-4-methoxy-phenyl)pyridin-3-yl)pyrazolo[1,5-a]pyrimidin-6-yl)ethanone | 582.2/582.0 | A | A |
| 1.1.48 | 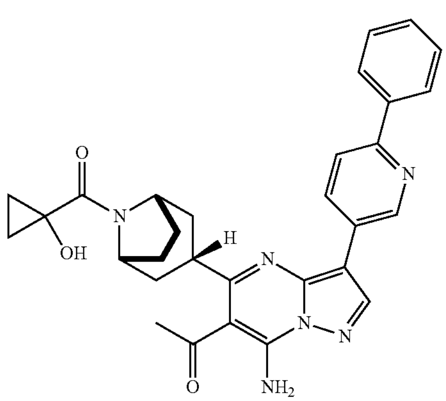 | 1-(7-amino-5-((1R,3s,5S)-8-(1-hydroxy-cyclopropanecarbonyl)-8-azabicyclo[3.2.1]octan-3-yl)-3-(6-phenylpyridin-3-yl)pyrazolo[1,5-a]pyrimidin-6-yl)ethanone | 523.2/523.0 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.49 | 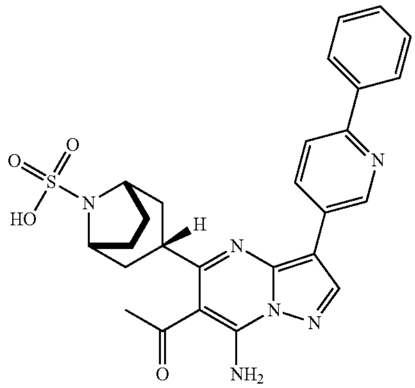 | (1R,3s,5S)-3-(6-acetyl-7-amino-3-(6-phenylpyridin-3-yl)pyrazolo[1,5-a]pyrimidin-5-yl)-8-azabicyclo[3.2.1]octane-8-sulfonic acid | 519.2/518.9 | C | D |
| 1.1.50 | 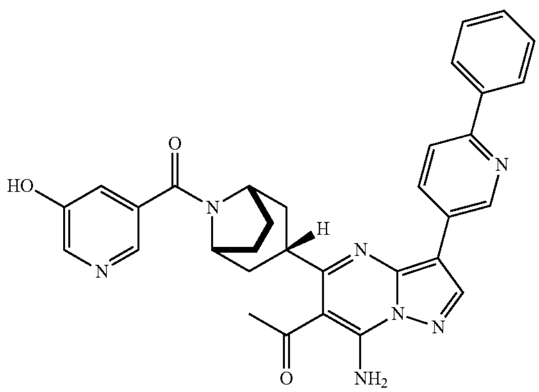 | 1-(7-amino-5-((1R,3s,5S)-8-(5-hydroxynicotinoyl)-8-azabicyclo[3.2.1]octan-3-yl)-3-(6-phenylpyridin-3-yl)pyrazolo[1,5-a]pyrimidin-6-yl)ethanone | 560.2/560.0 | B | B |
| 1.1.51 | 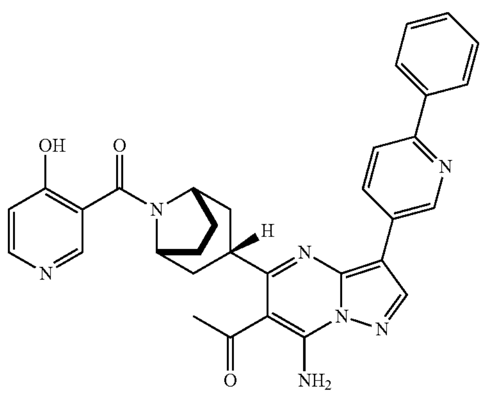 | 1-(7-amino-5-((1R,3s,5S)-8-(4-hydroxynicotinoyl)-8-azabicyclo[3.2.1]octan-3-yl)-3-(6-phenylpyridin-3-yl)pyrazolo[1,5-a]pyrimidin-6-yl)ethanone | 560.2/560.0 | B | B |
| 1.1.52 | 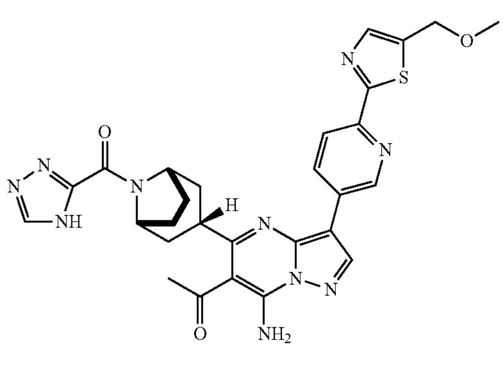 | 1-(5-((1R,3s,5S)-8-(4H-1,2,4-triazole-3-carbonyl)-8-azabicyclo[3.2.1]octan-3-yl)-7-amino-3-(6-(5-(methoxymethyl)thiazol-2-yl)pyridin-3-yl)pyrazolo[1,5-a]pyrimidin-6-yl)ethanone | 585.2/585.0 | B | B |

| Compound ID | Structures | Compound Name | M + H (calculated)/ M + H (observed) | pAKT S473 IC50 | p4E-1 Thr37/ 46 IC50 |
|---|---|---|---|---|---|
| 1.1.53 | 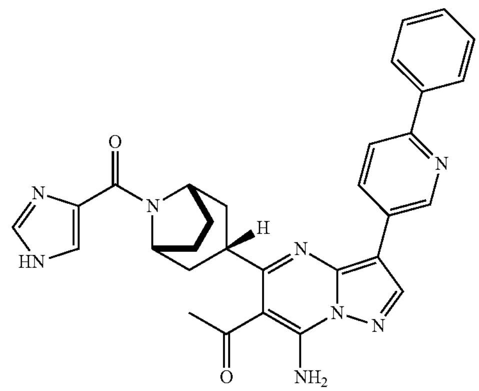 | 1-(5-((1R,3s,5S)-8-(1H-imidazole-4-carbonyl)-8-azabicyclo[3.2.1]octan-3-yl)-7-amino-3-(6-phenylpyridin-3-yl)pyrazolo[1,5-a]pyrimidin-6-yl)ethanone | 533.2/533.0 | ND | ND |
| 1.1.54 | 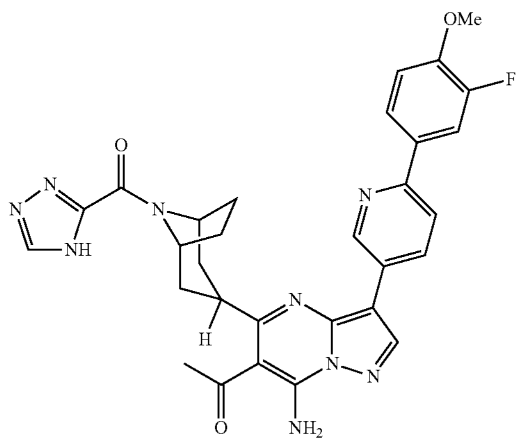 [SMILES: COc1ccc(-c2ccc(-c3cnn4c(N)c(C(C)=O)c(C5CC6CCC(C5)N6C(=O)c5nnc[nH]5)nc34)cn2)cc1F] | 1-(5-((1R,3r,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone | 582.23/581.92 | B | B |

TABLE 1-1-continued
| Compound ID | Structures | Compound Name | M + H (calculated)/ M + H (observed) | pAKT S473 IC50 | p4E-1 Thr37/ 46 IC50 |
|---|---|---|---|---|---|
| 1.1.55 | 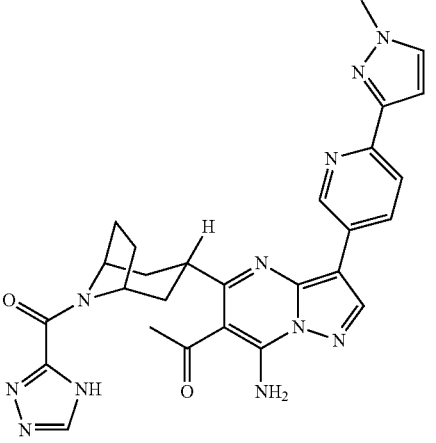 [SMILES: CC(=O)c1c(C2CC3CCC(C2)N3C(=O)c2nnc[nH]2)nc2c(-c3ccc(-c4ccn(C)n4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone | 538.23/538.01 | A | A |
| 1.1.56 | 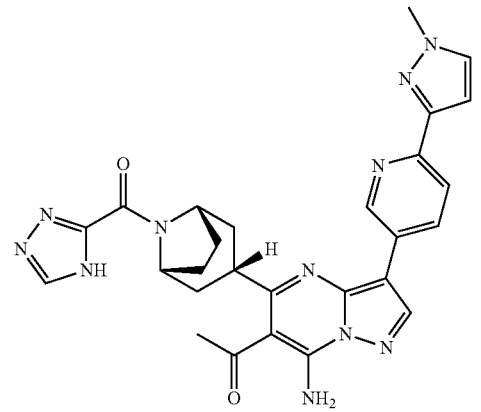 [SMILES: CC(=O)c1c([C@@H]2C[C@H]3CC[C@@H](C2)N3C(=O)c2nnc[nH]2)nc2c(-c3ccc(-c4ccn(C)n4)nc3)cnn2c1N] | 1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one | 559.3/558.88 | B | B |

| Compound ID | Structures | Compound Name | M + H (calculated)/ M + H (observed) | pAKT S473 IC50 | p4E-1 Thr37/ 46 IC50 |
|---|---|---|---|---|---|
| 1.1.57 | 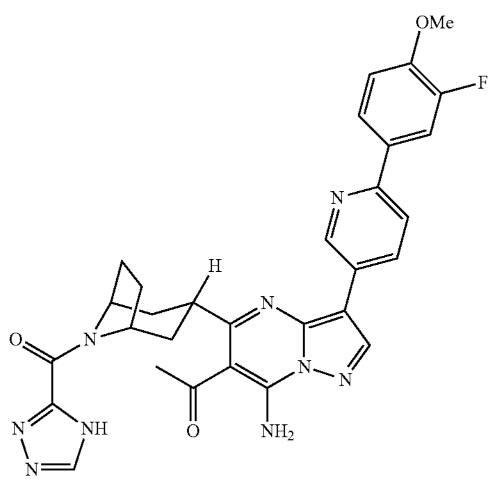 [SMILES: COc1ccc(-c2ccc(-c3cnn4c(N)c(C(C)=O)c(C5CC6CCC(C5)N6C(=O)c5nnc[nH]5)nc34)cn2)cc1F] | 1-(5-((1R,3s,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone | 582.23/581.90 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.58 | 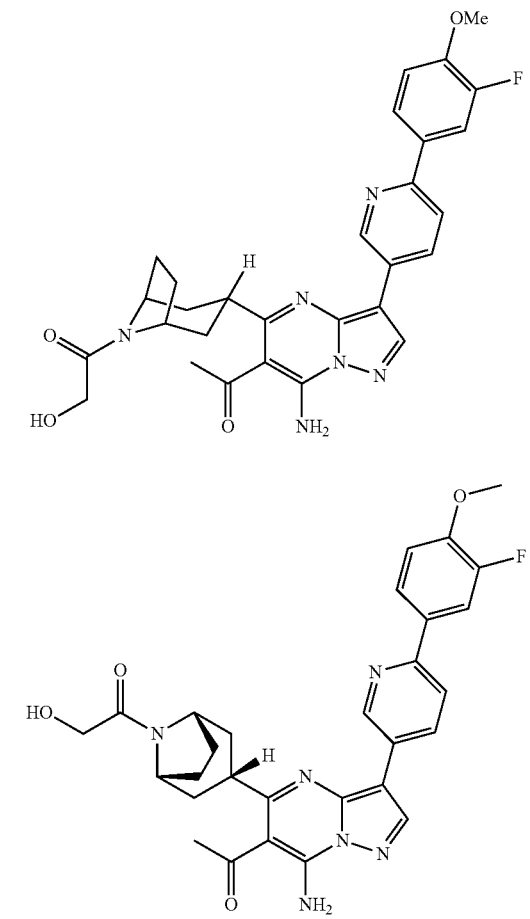 | 1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-2-hydroxyethanone | 545.22/545.20 | B | B |
| 1.1.59 | 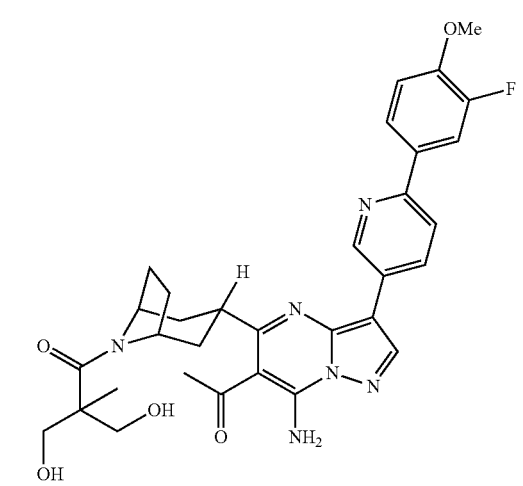 [SMILES: COc1ccc(-c2ccc(-c3cnn4c(N)c(C(C)=O)c(C5CC6CCC(C5)N6C(=O)C(C)(CO)CO)nc34)cn2)cc1F] | 1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one | 603.26/602.95 | A | A |

| Compound ID | Structures | Compound Name | M + H (calculated)/ M + H (observed) | pAKT S473 IC50 | p4E-1 Thr37/46 IC50 |
|---|---|---|---|---|---|
| 1.1.60 | 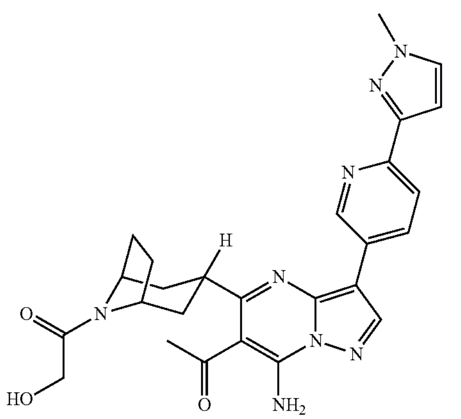 [SMILES: CC(=O)c1c(C2CC3CCC(C2)N3C(=O)CO)nc2c(-c3ccc(-c4ccn(C)n4)nc3)cnn2c1N] | 1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 501.22/500.97 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.61 | 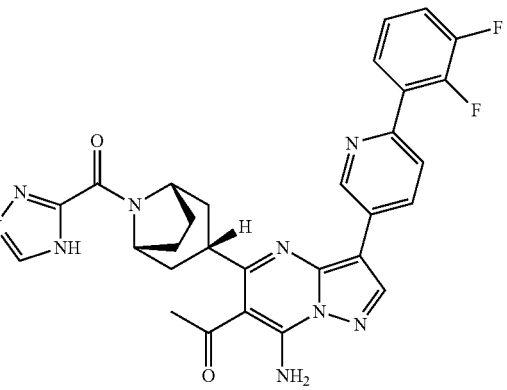 | 1-(5-((1R,3s,5S)-8-(4H-1,2,4-triazole-3-carbonyl)-8-azabicyclo[3.2.1]octan-3-yl)-7-amino-3-(6-(2,3-difluorophenyl)pyridin-3-yl)pyrazolo[1,5-a]pyrimidin-6-yl)ethanone | 570.21/569.92 | A | A |
| 1.1.62 | 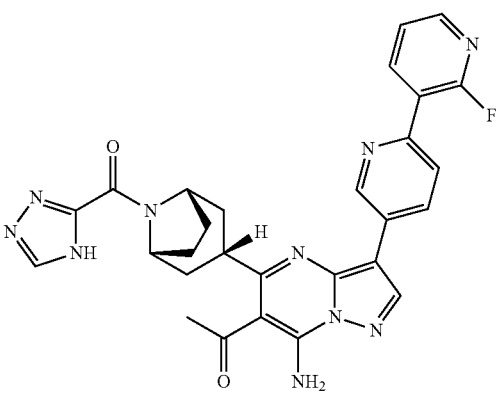 [SMILES: CC(=O)c1c([C@@H]2C[C@H]3CC[C@@H](C2)N3C(=O)c2nnc[nH]2)nc2c(-c3ccc(-c4cccnc4F)nc3)cnn2c1N] | 1-(5-((1R,3s,5S)-8-(4H-1,2,4-triazole-3-carbonyl)-8-azabicyclo[3.2.1]octan-3-yl)-7-amino-3-(2'-fluoro-2,3'-bipyridin-5-yl)pyrazolo[1,5-a]pyrimidin-6-yl)ethanone | 553.21/553.0 | A | A |
| 1.1.63 | 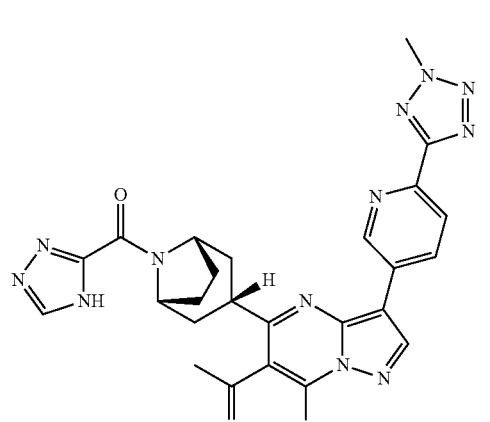 | 1-(5-((1R,3s,5S)-8-(4H-1,2,4-triazole-3-carbonyl)-8-azabicyclo[3.2.1]octan-3-yl)-7-amino-3-(6-(2-methyl-2H-tetrazol-5-yl)pyridin-3-yl)pyrazolo[1,5-a]pyrimidin-6-yl)ethanone | 540.22/539.94 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.64 | 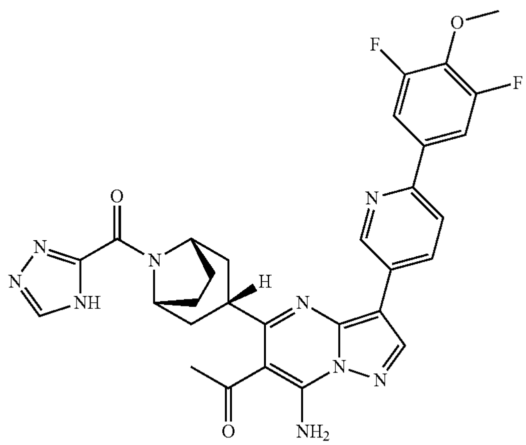 [SMILES: COc1c(F)cc(-c2ccc(-c3cnn4c(N)c(C(C)=O)c([C@@H]5C[C@H]6CC[C@@H](C5)N6C(=O)c5nnc[nH]5)nc34)cn2)cc1F] | 1-(5-((1R,3s,5S)-8-(4H-1,2,4-triazole-3-carbonyl)-8-azabicyclo[3.2.1]octan-3-yl)-7-amino-3-(6-(3,5-difluoro-4-methoxyphenyl)pyridin-3-yl)pyrazolo[1,5-a]pyrimidin-6-yl)ethanone | 600.22/599.97 | B | B |
| 1.1.65 | 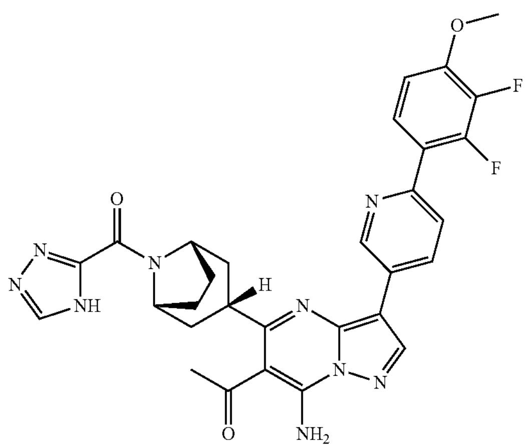 [SMILES: COc1ccc(-c2ccc(-c3cnn4c(N)c(C(C)=O)c([C@@H]5C[C@H]6CC[C@@H](C5)N6C(=O)c5nnc[nH]5)nc34)cn2)c(F)c1F] | 1-(5-((1R,3s,5S)-8-(4H-1,2,4-triazole-3-carbonyl)-8-azabicyclo[3.2.1]octan-3-yl)-7-amino-3-(6-(2,3-difluoro-4-methoxyphenyl)pyridin-3-yl)pyrazolo[1,5-a]pyrimidin-6-yl)ethanone | 600.22/599.99 | A | A |
| 1.1.66 | 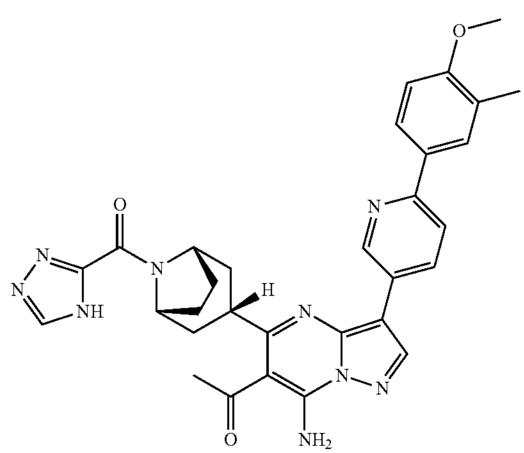 [SMILES: COc1ccc(-c2ccc(-c3cnn4c(N)c(C(C)=O)c([C@@H]5C[C@H]6CC[C@@H](C5)N6C(=O)c5nnc[nH]5)nc34)cn2)cc1C] | 1-(5-((1R,3s,5S)-8-(4H-1,2,4-triazole-3-carbonyl)-8-azabicyclo[3.2.1]octan-3-yl)-7-amino-3-(6-(4-methoxy-3-methylphenyl)pyridin-3-yl)pyrazolo[1,5-a]pyrimidin-6-yl)ethanone | 578.25/577.88 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.67 | | 1-(5-((1R,3s,5S)-8-(4H-1,2,4-triazole-3-carbonyl)-8-azabicyclo[3.2.1]octan-3-yl)-7-amino-3-(6-(3-chloro-4-methoxyphenyl)pyridin-3-yl)pyrazolo[1,5-a]pyrimidin-6-yl)ethanone | 598.20/597.88 | B | B |
| 1.1.66 | 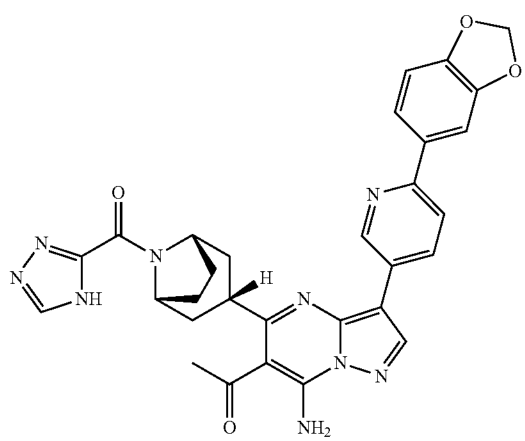 [SMILES: CC(=O)c1c([C@@H]2C[C@H]3CC[C@@H](C2)N3C(=O)c2nnc[nH]2)nc2c(-c3ccc(-c4ccc5c(c4)OCO5)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(benzo[d][1,3]dioxol-5-yl)pyridin-3-yl)pyrazolo[1,5-a]pyrimidin-6-yl)ethanone | 578.21/577.90 | A | A |
| 1.1.67 | | 1-(5-((1R,3s,5S)-8-(4H-1,2,4-triazole-3-carbonyl)-8-azabicyclo[3.2.1]octan-3-yl)-7-amino-3-(6-(4-(difluoromethoxy)phenyl)pyridin-3-yl)pyrazolo[1,5-a]pyrimidin-6-yl)ethanone | 600.22/600.04 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.68 | 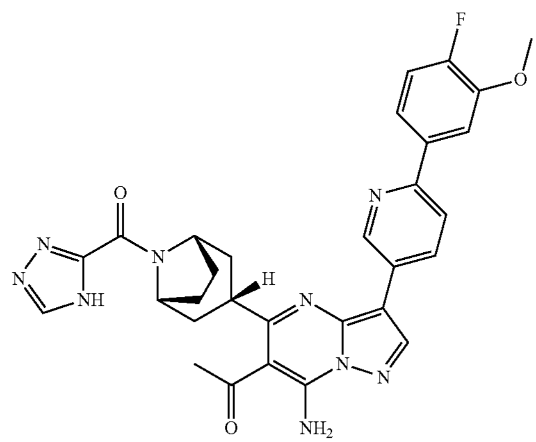 [SMILES: COc1cc(-c2ccc(-c3cnn4c(N)c(C(C)=O)c([C@@H]5C[C@H]6CC[C@@H](C5)N6C(=O)c5nnc[nH]5)nc34)cn2)ccc1F] | 1-(5-((1R,3s,5S)-8-(4H-1,2,4-triazole-3-carbonyl)-8-azabicyclo[3.2.1]octan-3-yl)-7-amino-3-(6-(4-fluoro-3-methoxyphenyl)pyridin-3-yl)pyrazolo[1,5-a]pyrimidin-6-yl)ethanone | 582.23/582.00 | ND | ND |
| 1.1.69 | 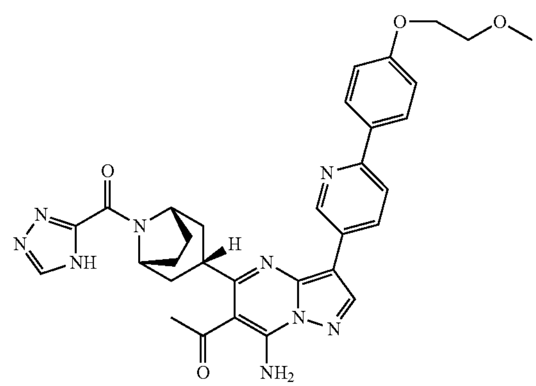 [SMILES: COCCOc1ccc(-c2ccc(-c3cnn4c(N)c(C(C)=O)c([C@@H]5C[C@H]6CC[C@@H](C5)N6C(=O)c5nnc[nH]5)nc34)cn2)cc1] | 1-(5-((1R,3s,5S)-8-(4H-1,2,4-triazole-3-carbonyl)-8-azabicyclo[3.2.1]octan-3-yl)-7-amino-3-(6-(4-(2-methoxyethoxy)phenyl)pyridin-3-yl)pyrazolo[1,5-a]pyrimidin-6-yl)ethanone | 608.26/608.04 | B | B |
| 1.1.70 | 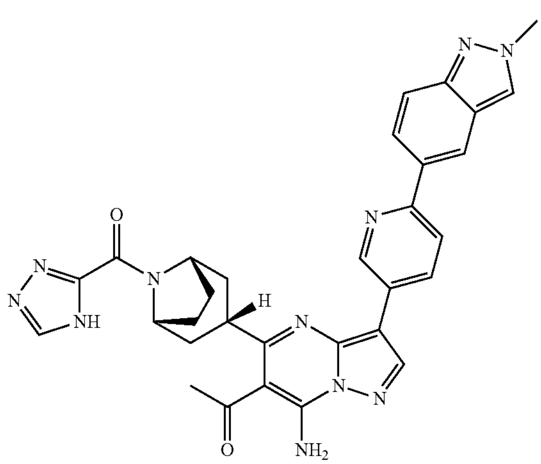 [SMILES: CC(=O)c1c([C@@H]2C[C@H]3CC[C@@H](C2)N3C(=O)c2nnc[nH]2)nc2c(-c3ccc(-c4ccc5nn(C)cc5c4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(2-methyl-2H-indazol-5-yl)pyridin-3-yl)pyrazolo[1,5-a]pyrimidin-6-yl)ethanone | 588.25/588.04 | A | A |

TABLE 1-1-continued

| Compound ID | Structures | Compound Name | M + H (calculated)/ M + H (observed) | pAKT S473 IC50 | p4E-1 Thr37/ 46 IC50 |
| --- | --- | --- | --- | --- | --- |
| 1.1.71 | 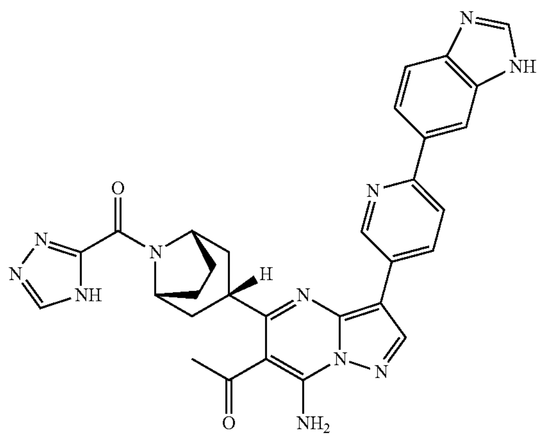 [SMILES: CC(=O)c1c([C@@H]2C[C@H]3CC[C@@H](C2)N3C(=O)c2nnc[nH]2)nc2c(-c3ccc(-c4ccc5nc[nH]c5c4)nc3)cnn2c1N] | 1-(3-(6-(1H-benzo[d]imidazol-6-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 574.23/574.00 | B | B |
| 1.1.72 | 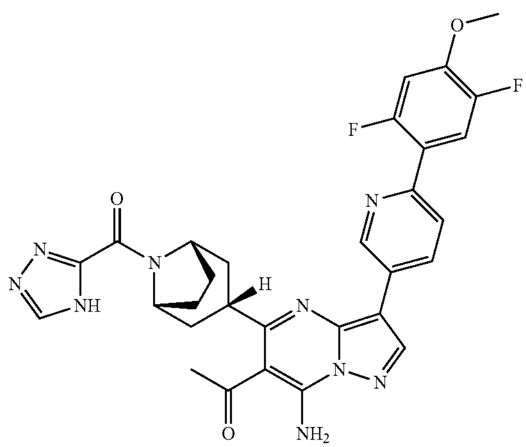 [SMILES: COc1cc(F)c(-c2ccc(-c3cnn4c(N)c(C(C)=O)c([C@@H]5C[C@H]6CC[C@@H](C5)N6C(=O)c5nnc[nH]5)nc34)cn2)cc1F] | 1-(5-((1R,3s,5S)-8-(4H-1,2,4-triazole-3-carbonyl)-8-azabicyclo[3.2.1]octan-3-yl)-7-amino-3-(6-(2,5-difluoro-4-methoxyphenyl)pyridin-3-yl)pyrazolo[1,5-a]pyrimidin-6-yl)ethanone | 600.22/600.00 | A | A |
| 1.1.73 | 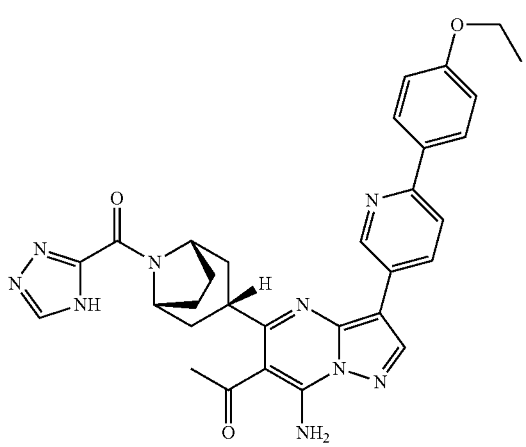 [SMILES: CCOc1ccc(-c2ccc(-c3cnn4c(N)c(C(C)=O)c([C@@H]5C[C@H]6CC[C@@H](C5)N6C(=O)c5nnc[nH]5)nc34)cn2)cc1] | 1-(5-((1R,3s,5S)-8-(4H-1,2,4-triazole-3-carbonyl)-8-azabicyclo[3.2.1]octan-3-yl)-7-amino-3-(6-(4-ethoxyphenyl)pyridin-3-yl)pyrazolo[1,5-a]pyrimidin-6-yl)ethanone | 578.25/578.01 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.74 | 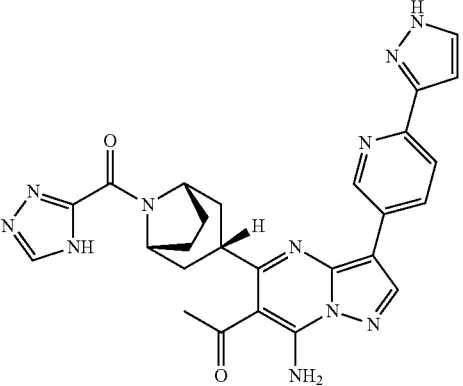 [SMILES: CC(=O)c1c([C@@H]2C[C@H]3CC[C@@H](C2)N3C(=O)c2nnc[nH]2)nc2c(-c3ccc(-c4cc[nH]n4)nc3)cnn2c1N] | 1-(3-(6-(1H-pyrazol-3-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 524.21/523.97 | A | A |
| 1.1.75 | 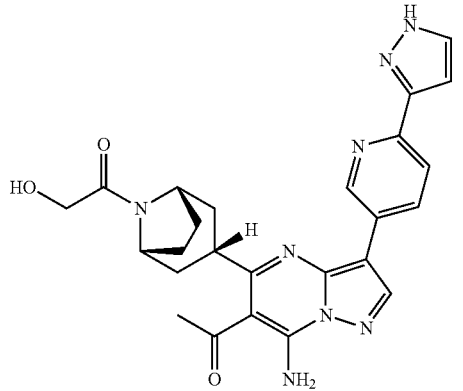 [SMILES: CC(=O)c1c([C@@H]2C[C@H]3CC[C@@H](C2)N3C(=O)CO)nc2c(-c3ccc(-c4cc[nH]n4)nc3)cnn2c1N] | 1-((1R,3s,5S)-3-(3-(6-(1H-pyrazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone | 487.21/487.03 | A | A |
| 1.1.76 | 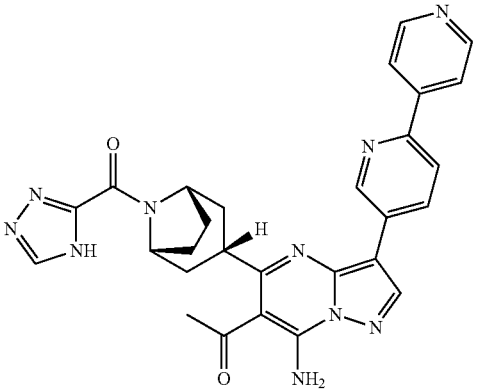 [SMILES: CC(=O)c1c([C@@H]2C[C@H]3CC[C@@H](C2)N3C(=O)c2nnc[nH]2)nc2c(-c3ccc(-c4ccncc4)nc3)cnn2c1N] | 1-(3-(2,4'-bipyridin-5-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 535.22/535.04 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.77 | 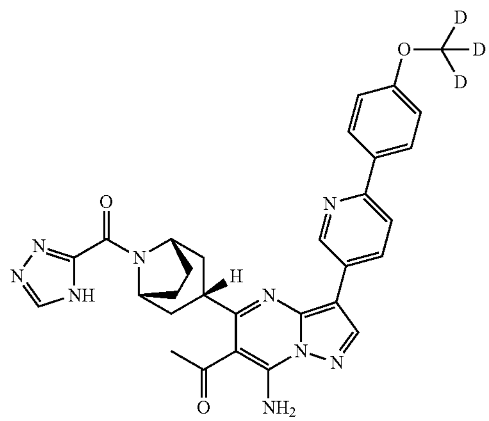 [SMILES: [2H]C([2H])([2H])Oc1ccc(-c2ccc(-c3cnn4c(N)c(C(C)=O)c([C@@H]5C[C@H]6CC[C@@H](C5)N6C(=O)c5nnc[nH]5)nc34)cn2)cc1] | 1-(5-((1R,3s,5S)-8-(4H-1,2,4-triazole-3-carbonyl)-8-azabicyclo[3.2.1]octan-3-yl)-7-amino-3-(6-(4-methoxy-(D₃)-phenyl)pyridin-3-yl)pyrazolo[1,5-a]pyrimidin-6-yl)ethanone | 567.25/567.02 | A | A |
| 1.1.78 | 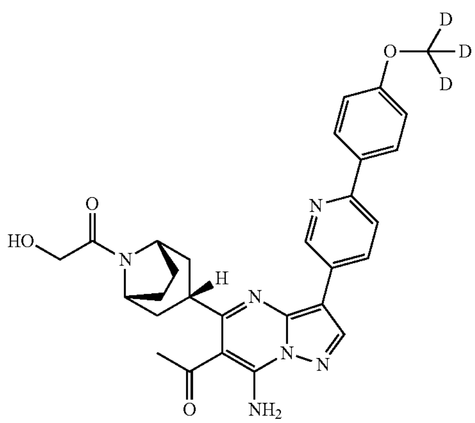 [SMILES: [2H]C([2H])([2H])Oc1ccc(-c2ccc(-c3cnn4c(N)c(C(C)=O)c([C@@H]5C[C@H]6CC[C@@H](C5)N6C(=O)CO)nc34)cn2)cc1] | 1-((1R,3s,5S)-3-(6-acetyl-7-amino-3-(6-(4-methoxy-(D₃)-phenyl)pyridin-3-yl)pyrazolo[1,5-a]pyrimidin-5-yl)-8-azabicyclo[3.2.1]octan-8-yl)-2-hydroxyethanone | 530.25/530.01 | A | A |
| 1.1.79 | 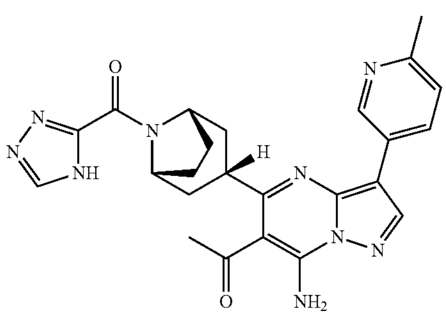 [SMILES: CC(=O)c1c([C@@H]2C[C@H]3CC[C@@H](C2)N3C(=O)c2nnc[nH]2)nc2c(-c3ccc(C)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-methylpyridin-3-yl)pyrazolo[1,5-a]pyrimidin-6-yl)ethanone | 472.21/471.98 | A | A |
| 1.1.80 | 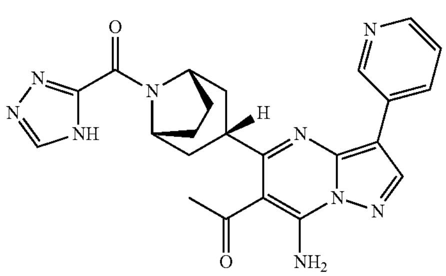 [SMILES: CC(=O)c1c([C@@H]2C[C@H]3CC[C@@H](C2)N3C(=O)c2nnc[nH]2)nc2c(-c3cccnc3)cnn2c1N] | 1-(5-((1R,3s,5S)-8-(4H-1,2,4-triazole-3-carbonyl)-8-azabicyclo[3.2.1]octan-3-yl)-7-amino-3-(pyridin-3-yl)pyrazolo[1,5-a]pyrimidin-6-yl)ethanone | 458.19/457.98 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.81 | 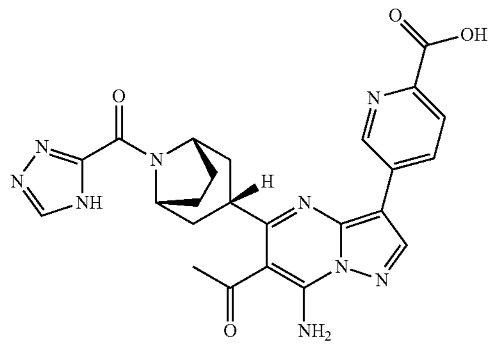 [SMILES: CC(=O)c1c([C@@H]2C[C@H]3CC[C@@H](C2)N3C(=O)c2nnc[nH]2)nc2c(-c3ccc(C(=O)O)nc3)cnn2c1N] | 5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinic acid | 502.18/501.96 | ND | ND |
| 1.1.82 | 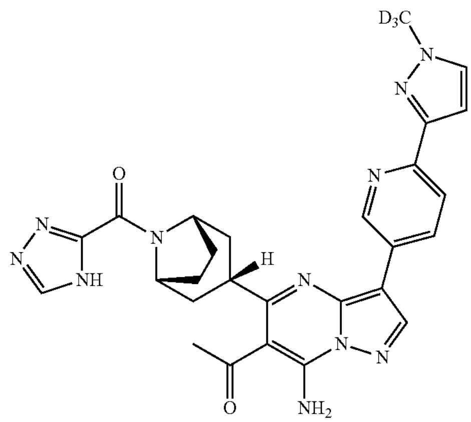 [SMILES: [2H]C([2H])([2H])n1ccc(-c2ccc(-c3cnn4c(N)c(C(C)=O)c([C@@H]5C[C@H]6CC[C@@H](C5)N6C(=O)c5nnc[nH]5)nc34)cn2)n1] | 1-(5-((1R,3s,5S)-8-(4H-1,2,4-triazole-3-carbonyl)-8-azabicyclo[3.2.1]octan-3-yl)-7-amino-3-(6-(1-methyl-(D$_3$)-1H-pyrazol-3-yl)pyridin-3-yl)pyrazolo[1,5-a]pyrimidin-6-yl)ethanone | 541.25/541.05 | B | B |
| 1.1.83 | 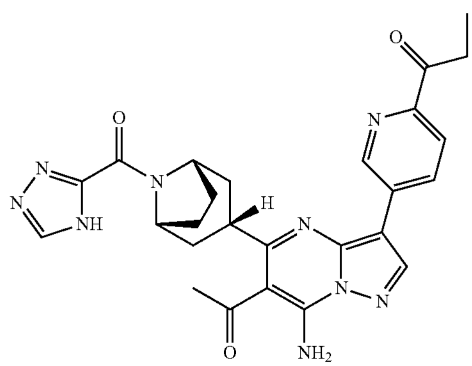 [SMILES: CCC(=O)c1ccc(-c2cnn3c(N)c(C(C)=O)c([C@@H]4C[C@H]5CC[C@@H](C4)N5C(=O)c4nnc[nH]4)nc23)cn1] | 1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)propan-1-one | 514.22/514.08 | B | B |
| 1.1.84 | 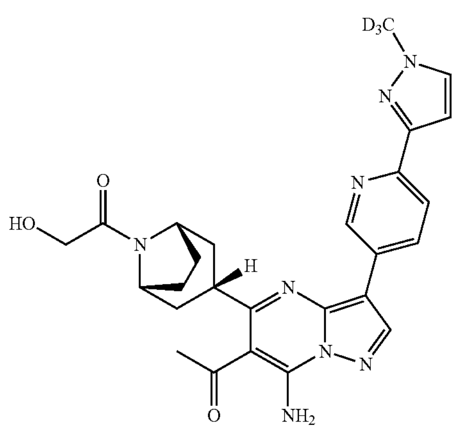 [SMILES: [2H]C([2H])([2H])n1ccc(-c2ccc(-c3cnn4c(N)c(C(C)=O)c([C@@H]5C[C@H]6CC[C@@H](C5)N6C(=O)CO)nc34)cn2)n1] | 1-((1R,3s,5S)-3-(6-acetyl-7-amino-3-(6-(1-methyl-(D$_3$)-1H-pyrazol-3-yl)pyridin-3-yl)pyrazolo[1,5-a]pyrimidin-5-yl)-8-azabicyclo[3.2.1]octan-8-yl)-2-hydroxyethanone | 504.24/504.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.85 | 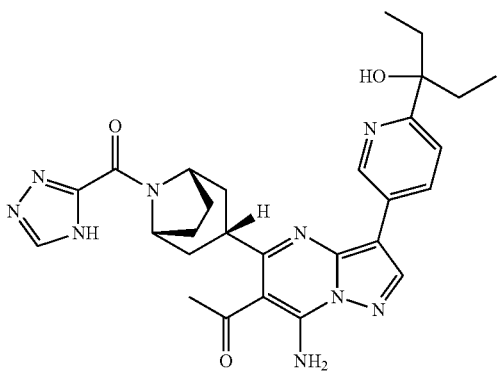 [SMILES: CCC(O)(CC)c1ccc(-c2cnn3c(N)c(C(C)=O)c([C@@H]4C[C@H]5CC[C@@H](C4)N5C(=O)c4nnc[nH]4)nc23)cn1] | 1-(5-((1R,3s,5S)-8-(4H-1,2,4-triazole-3-carbonyl)-8-azabicyclo[3.2.1]octan-3-yl)-7-amino-3-(6-(3-hydroxypentan-3-yl)pyridin-3-yl)pyrazolo[1,5-a]pyrimidin-6-yl)ethanone | 544.27/544.03 | C | C |
| 1.1.86 | 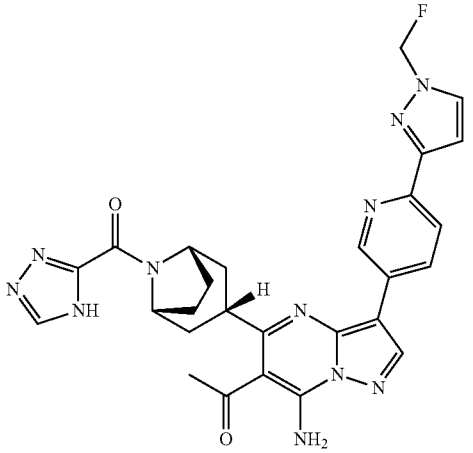 [SMILES: CC(=O)c1c([C@@H]2C[C@H]3CC[C@@H](C2)N3C(=O)c2nnc[nH]2)nc2c(-c3ccc(-c4ccn(CF)n4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-(fluoromethyl)-1H-pyrazol-3-yl)pyridin-3-yl)pyrazolo[1,5-a]pyrimidin-6-yl)ethanone | 556.22/556.09 | A | A |
| 1.1.87 | 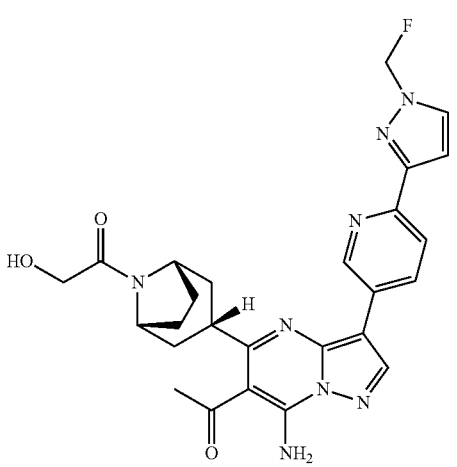 [SMILES: CC(=O)c1c([C@@H]2C[C@H]3CC[C@@H](C2)N3C(=O)CO)nc2c(-c3ccc(-c4ccn(CF)n4)nc3)cnn2c1N] | 1-((1R,3s,5S)-3-(6-acetyl-7-amino-3-(6-(1-(fluoromethyl)-1H-pyrazol-3-yl)pyridin-3-yl)pyrazolo[1,5-a]pyrimidin-5-yl)-8-azabicyclo[3.2.1]octan-8-yl)-2-hydroxyethanone | 519.21/519.04 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.88 | 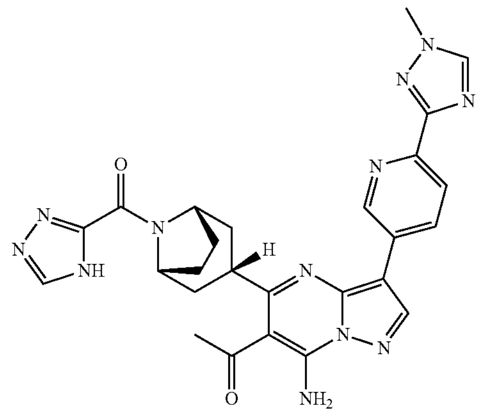 [SMILES: CC(=O)c1c([C@@H]2C[C@H]3CC[C@@H](C2)N3C(=O)c2nnc[nH]2)nc2c(-c3ccc(-c4ncn(C)n4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-methyl-1H-1,2,4-triazol-3-yl)pyridin-3-yl)pyrazolo[1,5-a]pyrimidin-6-yl)ethanone | 539.23/539.03 | A | A |
| 1.1.89 | 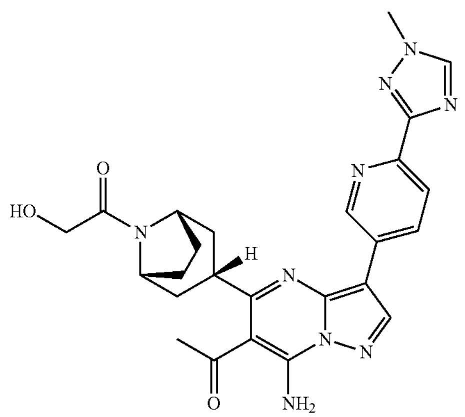 [SMILES: CC(=O)c1c([C@@H]2C[C@H]3CC[C@@H](C2)N3C(=O)CO)nc2c(-c3ccc(-c4ncn(C)n4)nc3)cnn2c1N] | 1-((1R,3s,5S)-3-(6-acetyl-7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone | 502.22/502.04 | B | B |
| 1.1.90 | 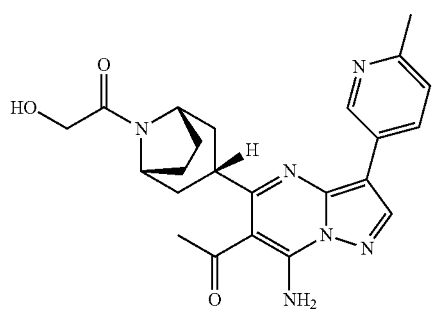 [SMILES: CC(=O)c1c([C@@H]2C[C@H]3CC[C@@H](C2)N3C(=O)CO)nc2c(-c3ccc(C)nc3)cnn2c1N] | 1-((1R,3s,5S)-3-(6-acetyl-7-amino-3-(6-methylpyridin-3-yl)pyrazolo[1,5-a]pyrimidin-5-yl)-8-azabicyclo[3.2.1]octan-8-yl)-2-hydroxyethanone | 435.20/435.03 | C | C |
| 1.1.91 | 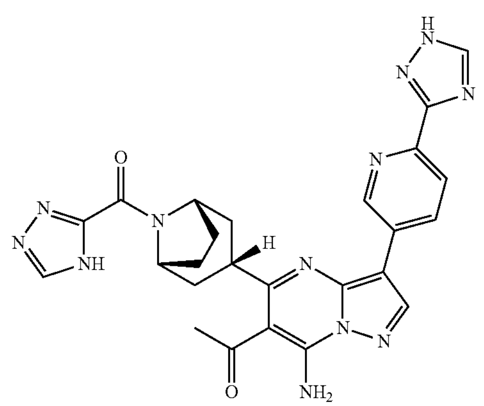 [SMILES: CC(=O)c1c([C@@H]2C[C@H]3CC[C@@H](C2)N3C(=O)c2nnc[nH]2)nc2c(-c3ccc(-c4nc[nH]n4)nc3)cnn2c1N] | 1-(3-(6-(1H-1,2,4-triazol-3-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 525.21/525.1 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.92 | 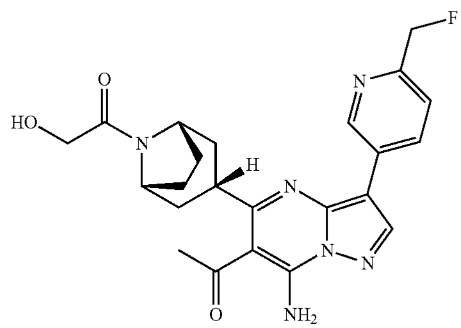 [SMILES: CC(=O)c1c([C@@H]2C[C@H]3CC[C@@H](C2)N3C(=O)CO)nc2c(-c3ccc(CF)nc3)cnn2c1N] | 1-((1R,3s,5S)-3-(6-acetyl-7-amino-3-(6-(fluoromethyl)pyridin-3-yl)pyrazolo[1,5-a]pyrimidin-5-yl)-8-azabicyclo[3.2.1]octan-8-yl)-2-hydroxyethanone | 490.20/490.1 | A | A |
| 1.1.93 | 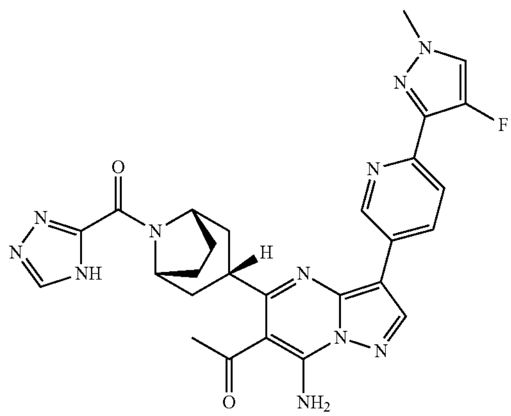 [SMILES: CC(=O)c1c([C@@H]2C[C@H]3CC[C@@H](C2)N3C(=O)c2nnc[nH]2)nc2c(-c3ccc(-c4nn(C)cc4F)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone | 556.22/556.2 | 4066.4 | 3883.2 |
| 1.1.94 | 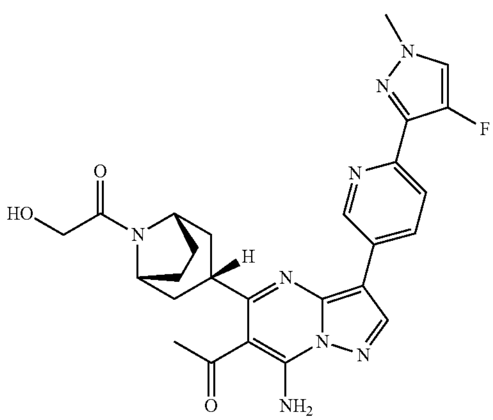 [SMILES: CC(=O)c1c([C@@H]2C[C@H]3CC[C@@H](C2)N3C(=O)CO)nc2c(-c3ccc(-c4nn(C)cc4F)nc3)cnn2c1N] | 1-((1R,3s,5S)-3-(6-acetyl-7-amino-3-(6-(4-fluoro-1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 519.21/519.1 | B | B |
| 1.1.95 | 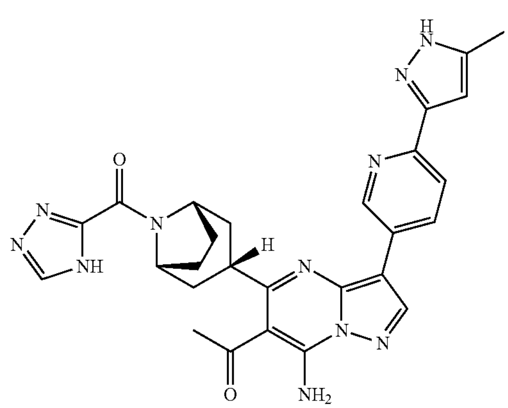 [SMILES: CC(=O)c1c([C@@H]2C[C@H]3CC[C@@H](C2)N3C(=O)c2nnc[nH]2)nc2c(-c3ccc(-c4cc(C)[nH]n4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(5-methyl-1H-pyrazol-3-yl)pyridin-3-yl)pyrazolo[1,5-a]pyrimidin-6-yl)ethanone | 538.23/538.0 | C | C |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.96 | 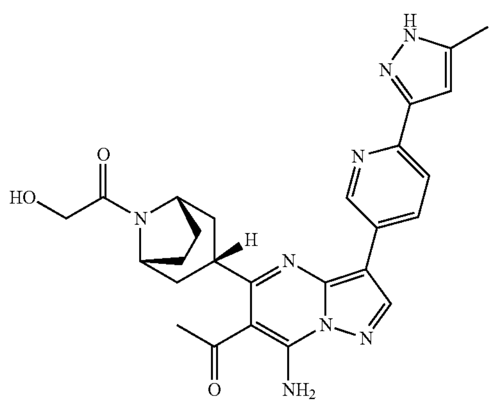 [SMILES: CC(=O)c1c([C@@H]2C[C@H]3CC[C@@H](C2)N3C(=O)CO)nc2c(-c3ccc(-c4cc(C)[nH]n4)nc3)cnn2c1N] | 1-((1R,3s,5S)-3-(6-acetyl-7-amino-3-(6-(5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 501.22/501.0 | D | D |
| 1.1.97 | 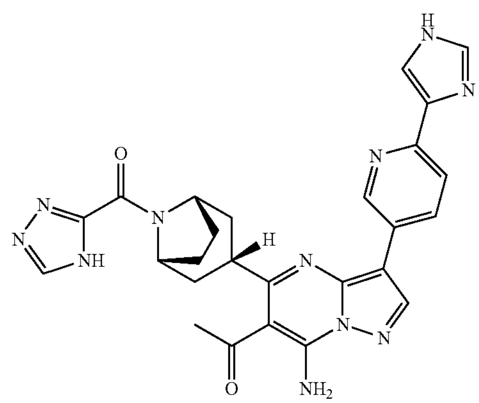 [SMILES: CC(=O)c1c([C@@H]2C[C@H]3CC[C@@H](C2)N3C(=O)c2nnc[nH]2)nc2c(-c3ccc(-c4c[nH]cn4)nc3)cnn2c1N] | 1-(3-(6-(1H-imidazol-4-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 524.21/523.9 | ND | ND |
| 1.1.98 | 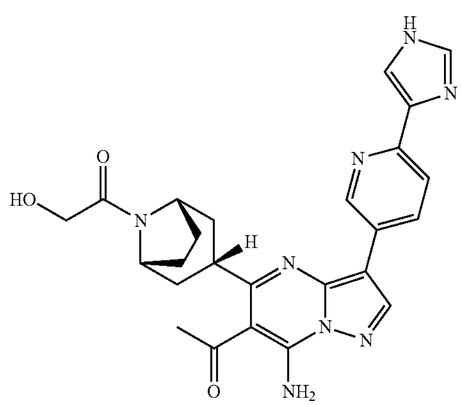 | 1-((1R,3s,5S)-3-(3-(6-(1H-imidazol-4-yl)pyridin-3-yl)-6-acetyl-7-aminopyrazolo[1,5-a]pyrimidin-5-yl)-8-azabicyclo[3.2.1]octan-8-yl)-2-hydroxyethanone | 487.21/487.0 | ND | ND |
| 1.1.99 | 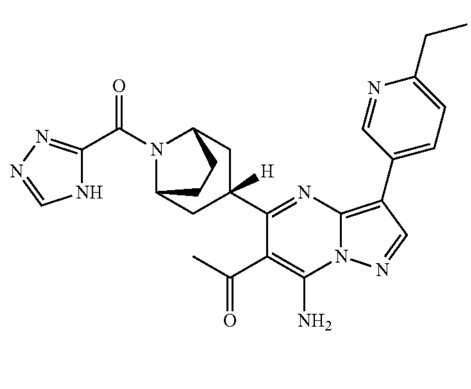 [SMILES: CCc1ccc(-c2cnn3c(N)c(C(C)=O)c([C@@H]4C[C@H]5CC[C@@H](C4)N5C(=O)c4nnc[nH]4)nc23)cn1] | 1-(5-((1R,3s,5S)-8-(4H-1,2,4-triazole-3-carbonyl)-8-azabicyclo[3.2.1]octan-3-yl)-7-amino-3-(6-ethylpyridin-3-yl)pyrazolo[1,5-a]pyrimidin-6-yl)ethanone | 486.22/486.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.100 | 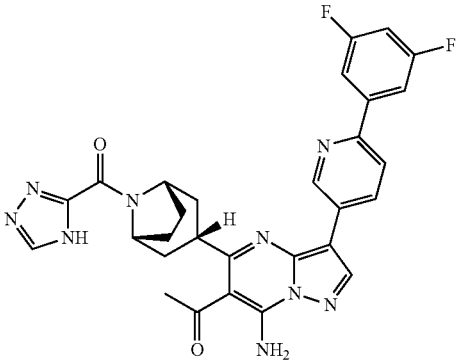 [SMILES: CC(=O)c1c([C@@H]2C[C@H]3CC[C@@H](C2)N3C(=O)c2nnc[nH]2)nc2c(-c3ccc(-c4cc(F)cc(F)c4)nc3)cnn2c1N] | 1-(5-((1R,3r,5S)-8-(4H-1,2,4-triazole-3-carbonyl)-8-azabicyclo[3.2.1]octan-3-yl)-7-amino-3-(6-(3,5-difluorophenyl)pyridin-3-yl)pyrazolo[1,5-a]pyrimidin-6-yl)ethanone | 570.21/570.2 | B | B |
| 1.1.101 | 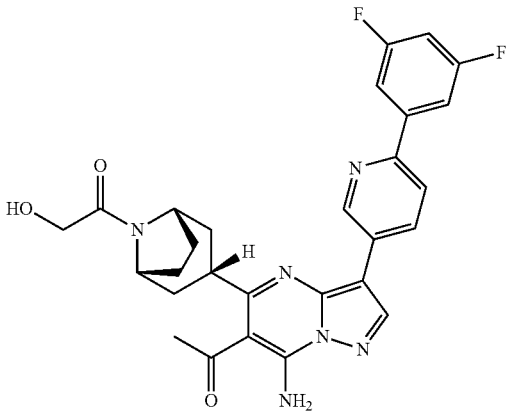 [SMILES: CC(=O)c1c([C@@H]2C[C@H]3CC[C@@H](C2)N3C(=O)CO)nc2c(-c3ccc(-c4cc(F)cc(F)c4)nc3)cnn2c1N] | 1-((1R,3r,5S)-3-(6-acetyl-7-amino-3-(6-(3,5-difluorophenyl)pyridin-3-yl)pyrazolo[1,5-a]pyrimidin-5-yl)-8-azabicyclo[3.2.1]octan-8-yl)-2-hydroxyethanone | 533.20/533.1 | B | B |
| 1.1.102 | 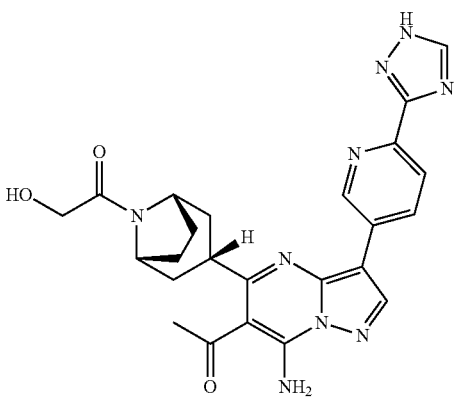 [SMILES: CC(=O)c1c([C@@H]2C[C@H]3CC[C@@H](C2)N3C(=O)CO)nc2c(-c3ccc(-c4nc[nH]n4)nc3)cnn2c1N] | 1-((1R,3s,5S)-3-(3-(6-(1H-1,2,4-triazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone | 488.20/488.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.103 | 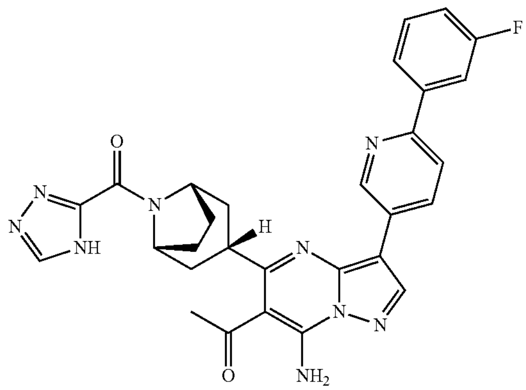 [SMILES: CC(=O)c1c([C@@H]2C[C@H]3CC[C@@H](C2)N3C(=O)c2nnc[nH]2)nc2c(-c3ccc(-c4cccc(F)c4)nc3)cnn2c1N] | 1-(5-((1R,3r,5S)-8-(4H-1,2,4-triazole-3-carbonyl)-8-azabicyclo[3.2.1]octan-3-yl)-7-amino-3-(6-(3-fluorophenyl)pyridin-3-yl)pyrazolo[1,5-a]pyrimidin-6-yl)ethanone | 552.21/552.1 | A | A |
| 1.1.104 | 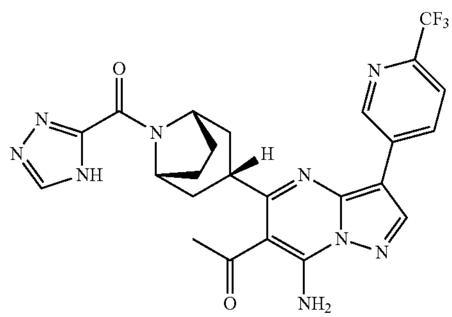 [SMILES: CC(=O)c1c([C@@H]2C[C@H]3CC[C@@H](C2)N3C(=O)c2nnc[nH]2)nc2c(-c3ccc(C(F)(F)F)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(trifluoromethyl)pyridin-3-yl)pyrazolo[1,5-a]pyrimidin-6-yl)ethanone | 526.18/526.03 | B | B |
| 1.1.105 | 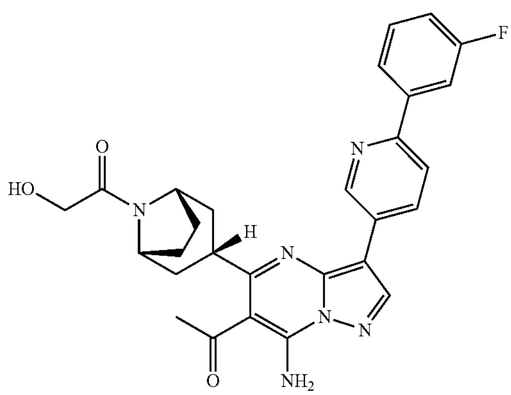 [SMILES: CC(=O)c1c([C@@H]2C[C@H]3CC[C@@H](C2)N3C(=O)CO)nc2c(-c3ccc(-c4cccc(F)c4)nc3)cnn2c1N] | 1-((1R,3r,5S)-3-(6-acetyl-7-amino-3-(6-(3-fluorophenyl)pyridin-3-yl)pyrazolo[1,5-a]pyrimidin-5-yl)-8-azabicyclo[3.2.1]octan-8-yl)-2-hydroxyethanone | 515.21/514.99 | B | B |
| 1.1.106 | 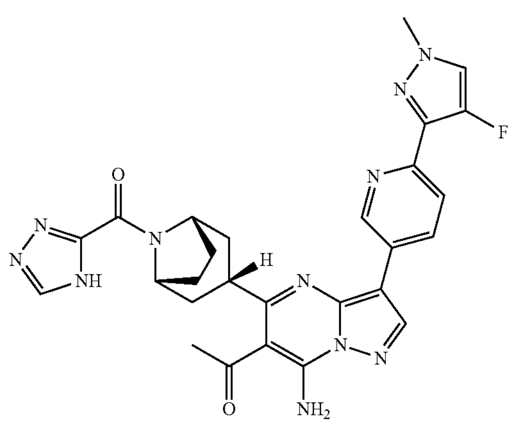 [SMILES: CC(=O)c1c([C@@H]2C[C@H]3CC[C@@H](C2)N3C(=O)c2nnc[nH]2)nc2c(-c3ccc(-c4nn(C)cc4F)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone | 556.22/555.98 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.1.107 | | 1-((1R,3s,5S)-3-(6-acetyl-7-amino-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 519.21/518.99 | B | B |
| 1.1.108 | 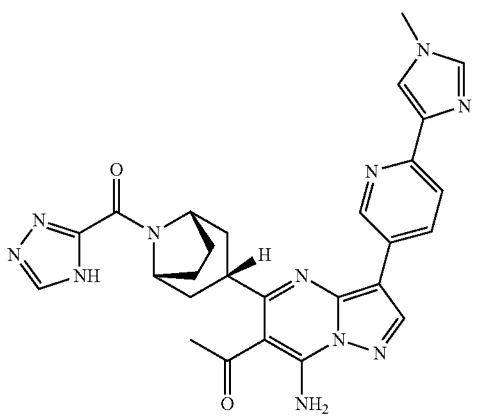 | 1-(5-((1R,3s,5S)-8-(4H-1,2,4-triazole-3-carbonyl)-8-azabicyclo[3.2.1]octan-3-yl)-7-amino-3-(6-(1-methyl-1H-imidazol-4-yl)pyridin-3-yl)pyrazolo[1,5-a]pyrimidin-6-yl)ethanone | 538.23/538.05 | C | C |
| 1.1.109 | 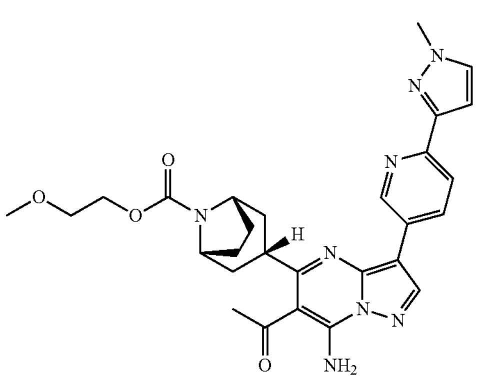 [SMILES: COCCOC(=O)N1[C@@H]2CC[C@H]1C[C@H](c1nc3c(-c4ccc(-c5ccn(C)n5)nc4)cnn3c(N)c1C(C)=O)C2] | (1R,3s,5S)-2-methoxyethyl 3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octane-8-carboxylate | 559.27/558.99 | C | C |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.110 | 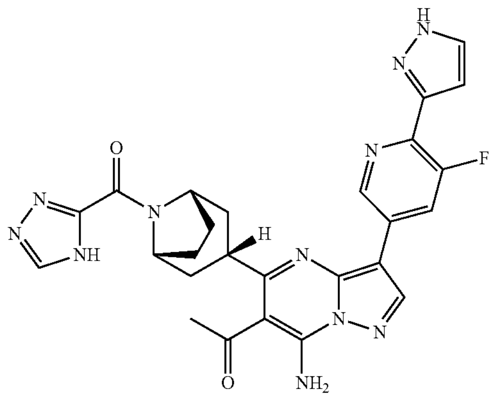 [SMILES: CC(=O)c1c([C@@H]2C[C@H]3CC[C@@H](C2)N3C(=O)c2nnc[nH]2)nc2c(-c3cnc(-c4cc[nH]n4)c(F)c3)cnn2c1N] | 1-(5-((1R,3s,5S)-8-(4H-1,2,4-triazole-3-carbonyl)-8-azabicyclo[3.2.1]octan-3-yl)-7-amino-3-(5-fluoro-6-(1H-pyrazol-3-yl)pyridin-3-yl)pyrazolo[1,5-a]pyrimidin-6-yl)ethanone | 542.21/541.98 | B | B |
| 1.1.111 | 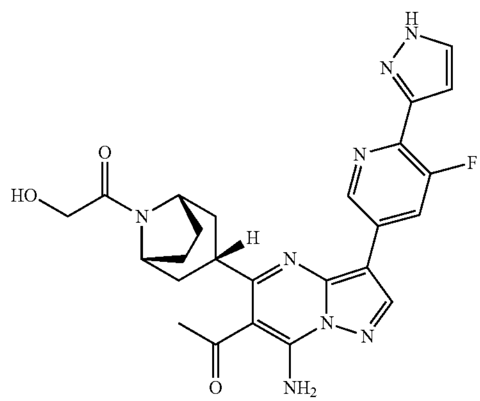 [SMILES: CC(=O)c1c([C@@H]2C[C@H]3CC[C@@H](C2)N3C(=O)CO)nc2c(-c3cnc(-c4cc[nH]n4)c(F)c3)cnn2c1N] | 1-((1R,3s,5S)-3-(6-acetyl-7-amino-3-(5-fluoro-6-(1H-pyrazol-3-yl)pyridin-3-yl)pyrazolo[1,5-a]pyrimidin-5-yl)-8-azabicyclo[3.2.1]octan-8-yl)-2-hydroxyethanone | 505.20/504.96 | C | C |
| 1.1.112 | 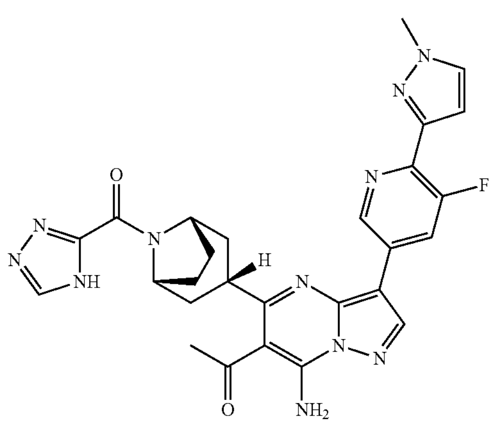 [SMILES: CC(=O)c1c([C@@H]2C[C@H]3CC[C@@H](C2)N3C(=O)c2nnc[nH]2)nc2c(-c3cnc(-c4ccn(C)n4)c(F)c3)cnn2c1N] | 1-(5-((1R,3s,5S)-8-(4H-1,2,4-triazole-3-carbonyl)-8-azabicyclo[3.2.1]octan-3-yl)-7-amino-3-(5-fluoro-6-(1-methyl-1H-pyrazol-3-yl)pyridin-3-yl)pyrazolo[1,5-a]pyrimidin-6-yl)ethanone | 556.22/555.95 | C | C |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.113 | 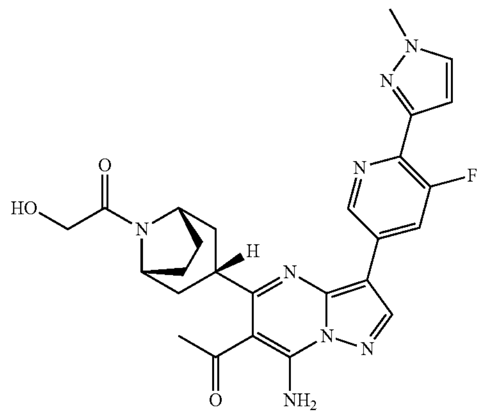 [SMILES: CC(=O)c1c([C@@H]2C[C@H]3CC[C@@H](C2)N3C(=O)CO)nc2c(-c3cnc(-c4ccn(C)n4)c(F)c3)cnn2c1N] | 1-((1R,3s,5S)-3-(6-acetyl-7-amino-3-(5-fluoro-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 519.21/518.95 | ND | ND |
| 1.1.114 | 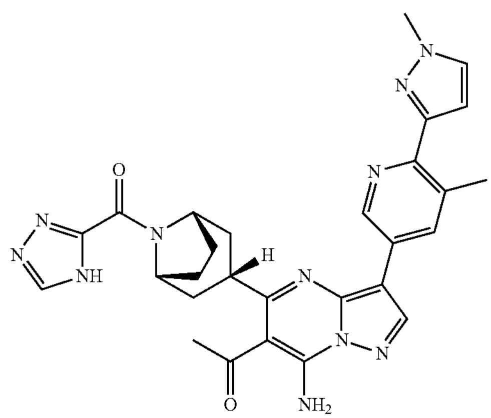 [SMILES: CC(=O)c1c([C@@H]2C[C@H]3CC[C@@H](C2)N3C(=O)c2nnc[nH]2)nc2c(-c3cnc(-c4ccn(C)n4)c(C)c3)cnn2c1N] | 1-(5-((1R,3s,5S)-8-(4H-1,2,4-triazole-3-carbonyl)-8-azabicyclo[3.2.1]octan-3-yl)-7-amino-3-(5-methyl-6-(1-methyl-1H-pyrazol-3-yl)pyridin-3-yl)pyrazolo[1,5-a]pyrimidin-6-yl)ethanone | 552.25/551.97 | C | C |
| 1.1.115 | 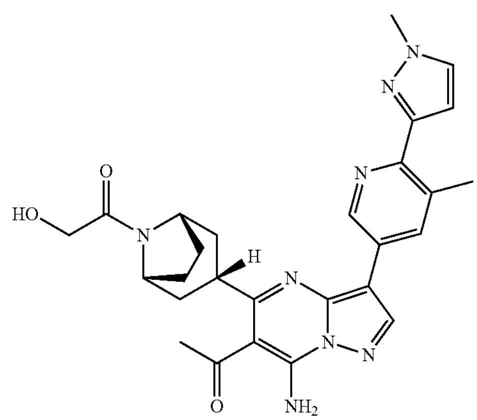 [SMILES: CC(=O)c1c([C@@H]2C[C@H]3CC[C@@H](C2)N3C(=O)CO)nc2c(-c3cnc(-c4ccn(C)n4)c(C)c3)cnn2c1N] | 1-((1R,3s,5S)-3-(6-acetyl-7-amino-3-(5-methyl-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 515.24/514.96 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.116 | 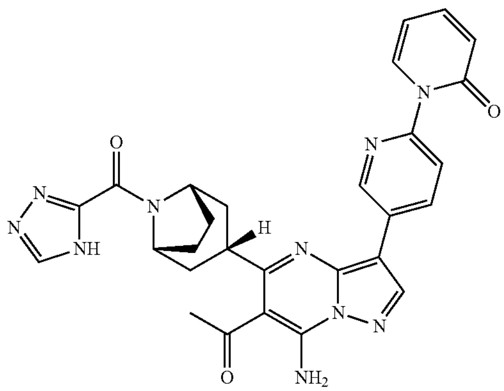 [SMILES: CC(=O)c1c([C@@H]2C[C@H]3CC[C@@H](C2)N3C(=O)c2nnc[nH]2)nc2c(-c3ccc(-n4ccccc4=O)nc3)cnn2c1N] | 1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyridin-2(1H)-one | 551.21/550.96 | ND | ND |
| 1.1.117 | 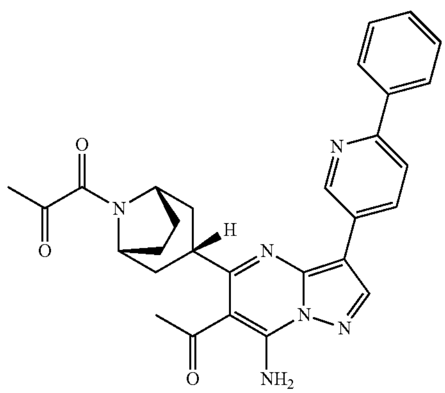 [SMILES: CC(=O)C(=O)N1[C@@H]2CC[C@H]1C[C@H](c1nc3c(-c4ccc(-c5ccccc5)nc4)cnn3c(N)c1C(C)=O)C2] | 1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)propane-1,2-dione | 509.22/509.1 | B | B |
| 1.1.118 | 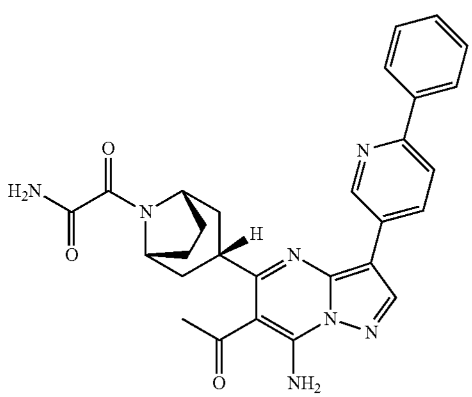 [SMILES: CC(=O)c1c([C@@H]2C[C@H]3CC[C@@H](C2)N3C(=O)C(N)=O)nc2c(-c3ccc(-c4ccccc4)nc3)cnn2c1N] | 2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoacetamide | 510.21/510.1 | B | B |
| 1.1.119 | 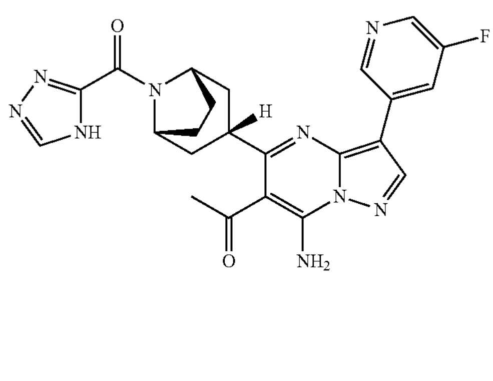 [SMILES: CC(=O)c1c([C@@H]2C[C@H]3CC[C@@H](C2)N3C(=O)c2nnc[nH]2)nc2c(-c3cncc(F)c3)cnn2c1N] | 1-(5-((1R,3s,5S)-8-(4H-1,2,4-triazole-3-carbonyl)-8-azabicyclo[3.2.1]octan-3-yl)-7-amino-3-(5-fluoropyridin-3-yl)pyrazolo[1,5-a]pyrimidin-6-yl)ethanone | 476.18/475.86 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.120 | 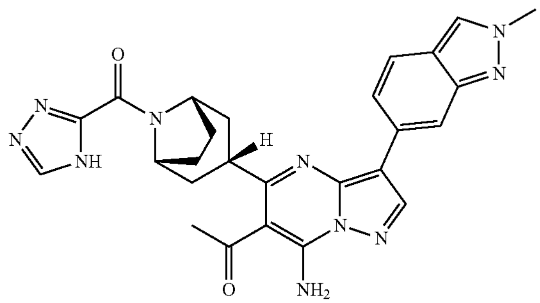 [SMILES: CC(=O)c1c([C@@H]2C[C@H]3CC[C@@H](C2)N3C(=O)c2nnc[nH]2)nc2c(-c3ccc4cn(C)nc4c3)cnn2c1N] | 1-(5-((1R,3s,5S)-8-(4H-1,2,4-triazole-3-carbonyl)-8-azabicyclo[3.2.1]octan-3-yl)-7-amino-3-(2-methyl-2H-indazol-6-yl)pyrazolo[1,5-a]pyrimidin-6-yl)ethanone | 511.22/511.0 | ND | ND |
| 1.1.121 | 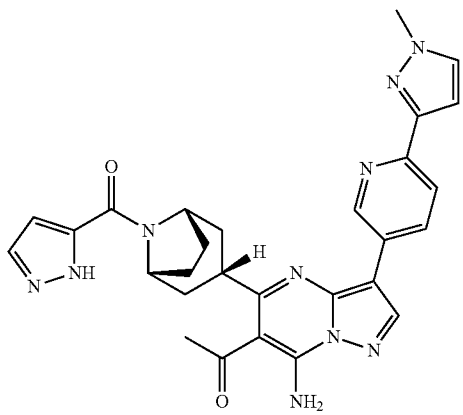 [SMILES: CC(=O)c1c([C@@H]2C[C@H]3CC[C@@H](C2)N3C(=O)c2ccn[nH]2)nc2c(-c3ccc(-c4ccn(C)n4)nc3)cnn2c1N] | 1-(5-((1R,3s,5S)-8-(1H-pyrazole-5-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone | 537.2/537.3 | A | B |
| 1.1.122 | 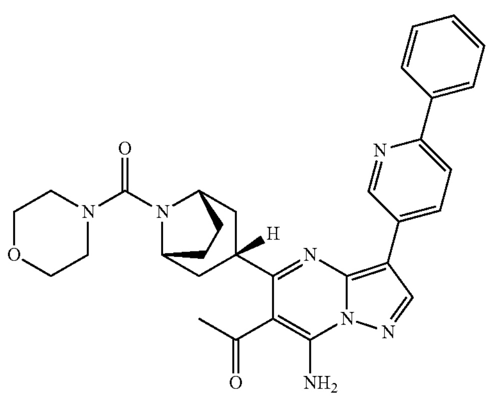 [SMILES: CC(=O)c1c([C@@H]2C[C@H]3CC[C@@H](C2)N3C(=O)N2CCOCC2)nc2c(-c3ccc(-c4ccccc4)nc3)cnn2c1N] | 1-(7-amino-5-((1R,3s,5S)-8-(morpholine-4-carbonyl)-8-azabicyclo[3.2.1]octan-3-yl)-3-(6-phenylpyridin-3-yl)pyrazolo[1,5-a]pyrimidin-6-yl)ethanone | 552.2/552.0 | C | C |
| 1.1.123 | 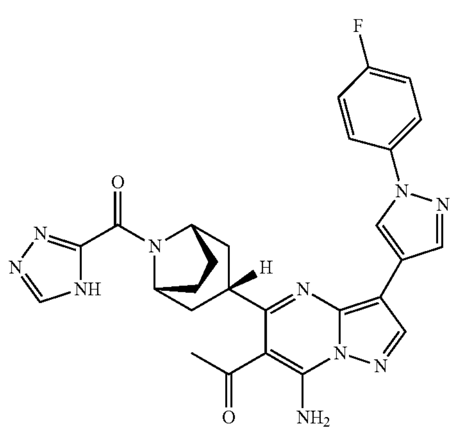 | 1-(5-((1R,3s,5S)-8-(4H-1,2,4-triazole-3-carbonyl)-8-azabicyclo[3.2.1]octan-3-yl)-7-amino-3-(1-(4-fluorophenyl)-1H-pyrazol-4-yl)pyrazolo[1,5-a]pyrimidin-6-yl)ethanone | 541.2/541.2 | B | C |

| Compound ID | Structures | Compound Name | M + H (calculated)/ M + H (observed) | pAKT S473 IC50 | p4E-1 Thr37/ 46 IC50 |
|---|---|---|---|---|---|
| 1.1.124 | 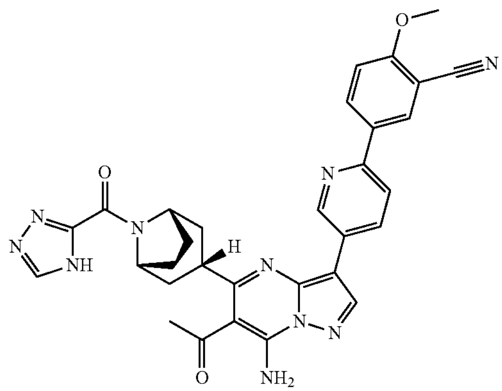 | 5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-2-methoxybenzonitrile | 589.2/589.2 | B | B |
| 1.1.125 | 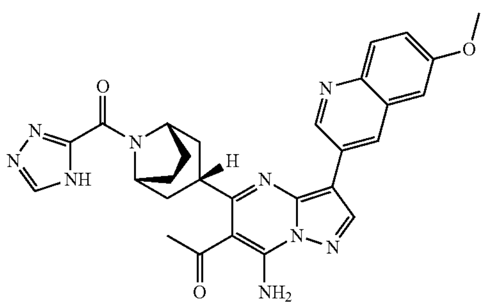 | 1-(5-((1R,3s,5S)-8-(4H-1,2,4-triazole-3-carbonyl)-8-azabicyclo[3.2.1]octan-3-yl)-7-amino-3-(6-methoxyquinolin-3-yl)pyrazolo[1,5-a]pyrimidin-6-yl)ethanone | 538.2/538.2 | C | B |
| 1.1.126 | 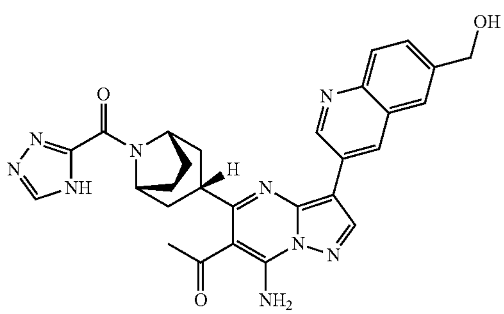 | 1-(5-((1R,3s,5S)-8-(4H-1,2,4-triazole-3-carbonyl)-8-azabicyclo[3.2.1]octan-3-yl)-7-amino-3-(6-(hydroxymethyl)quinolin-3-yl)pyrazolo[1,5-a]pyrimidin-6-yl)ethanone | 538.2/538.2 | C | C |
| 1.1.127 | 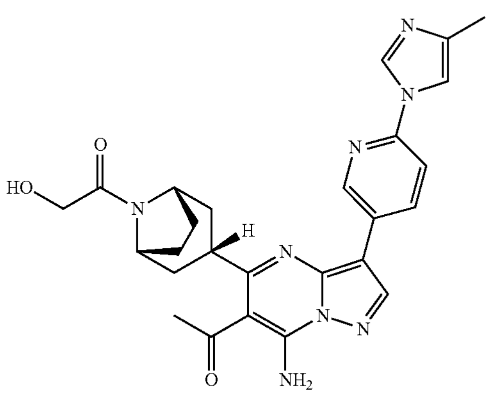 [SMILES: CC(=O)c1c([C@@H]2C[C@H]3CC[C@@H](C2)N3C(=O)CO)nc2c(-c3ccc(-n4cnc(C)c4)nc3)cnn2c1N] | 1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone | 501.23/500.89 | D | D |

TABLE 1-1-continued

| Compound ID | Structures | Compound Name | M + H (calculated)/ M + H (observed) | pAKT S473 IC50 | p4E-1 Thr37/46 IC50 |
|---|---|---|---|---|---|
| 1.1.128 | 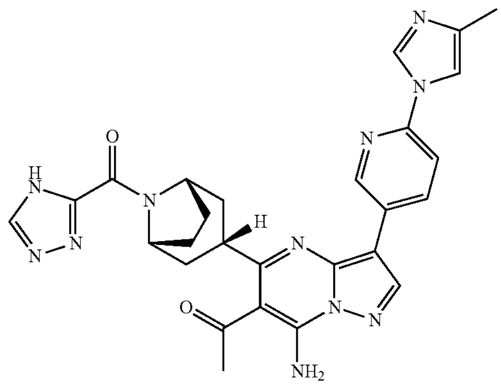 [SMILES: CC(=O)c1c([C@@H]2C[C@H]3CC[C@@H](C2)N3C(=O)c2nnc[nH]2)nc2c(-c3ccc(-n4cnc(C)c4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(4-methyl-1H-imidazol-1-yl)pyridin-3-yl)pyrazolo[1,5-a]pyrimidin-6-yl)ethanone | 538.23/538.00 | D | D |
| 1.1.129 | 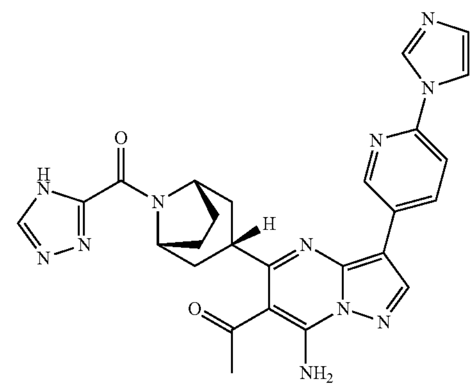 [SMILES: CC(=O)c1c([C@@H]2C[C@H]3CC[C@@H](C2)N3C(=O)c2nnc[nH]2)nc2c(-c3ccc(-n4ccnc4)nc3)cnn2c1N] | 1-(3-(6-(1H-imidazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 524.22/523.90 | D | D |
| 1.1.130 | 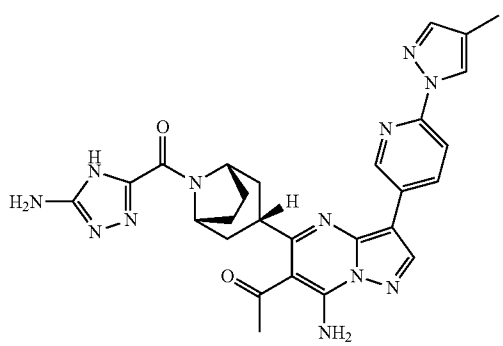 [SMILES: CC(=O)c1c([C@@H]2C[C@H]3CC[C@@H](C2)N3C(=O)c2nnc(N)[nH]2)nc2c(-c3ccc(-n4cc(C)cn4)nc3)cnn2c1N] | 1-(7-amino-5-((1R,3s,5S)-8-(5-amino-4H-1,2,4-triazole-3-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone | 553.25/552.96 | A | A |
| 1.1.131 | 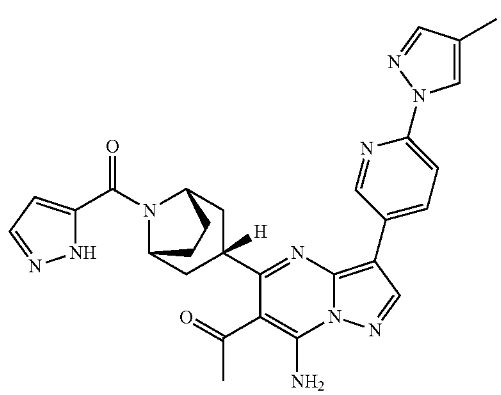 [SMILES: CC(=O)c1c([C@@H]2C[C@H]3CC[C@@H](C2)N3C(=O)c2ccn[nH]2)nc2c(-c3ccc(-n4cc(C)cn4)nc3)cnn2c1N] | 1-(5-((1R,3s,5S)-8-(1H-pyrazole-5-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone | 537.24/536.93 | B | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.132 | 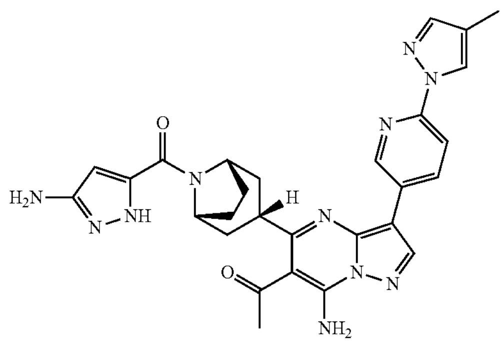 [SMILES: CC(=O)c1c([C@@H]2C[C@H]3CC[C@@H](C2)N3C(=O)c2cc(N)n[nH]2)nc2c(-c3ccc(-n4cc(C)cn4)nc3)cnn2c1N] | 1-(7-amino-5-((1R,3s,5S)-8-(3-amino-1H-pyrazole-5-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone | 552.25/552.00 | A | A |
| 1.1.133 | 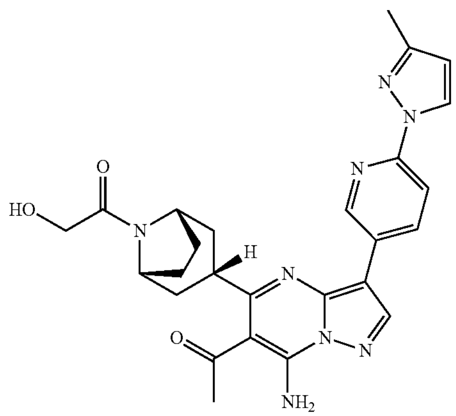 [SMILES: CC(=O)c1c([C@@H]2C[C@H]3CC[C@@H](C2)N3C(=O)CO)nc2c(-c3ccc(-n4ccc(C)n4)nc3)cnn2c1N] | 1-((1R,3s,5S)-3-(6-acetyl-7-amino-3-(6-(3-methyl-1H-pyrazol-1-yl)pyridin-3-yl)pyrazolo[1,5-a]pyrimidin-5-yl)-8-azabicyclo[3.2.1]octan-8-yl)-2-hydroxyethanone | 501.23/501.00 | B | C |
| 1.1.134 | 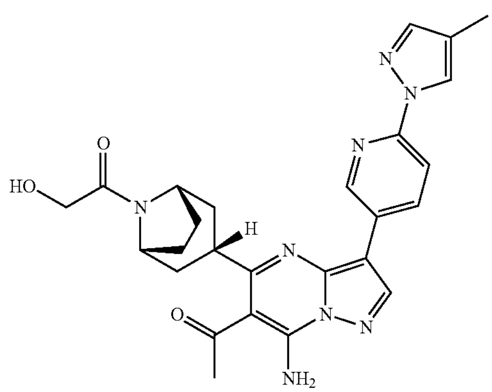 [SMILES: CC(=O)c1c([C@@H]2C[C@H]3CC[C@@H](C2)N3C(=O)CO)nc2c(-c3ccc(-n4cc(C)cn4)nc3)cnn2c1N] | 1-((1R,3s,5S)-3-(6-acetyl-7-amino-3-(6-(4-methyl-1H-pyrazol-1-yl)pyridin-3-yl)pyrazolo[1,5-a]pyrimidin-5-yl)-8-azabicyclo[3.2.1]octan-8-yl)-2-hydroxyethanone | 501.23/501.00 | A | B |
| 1.1.135 | 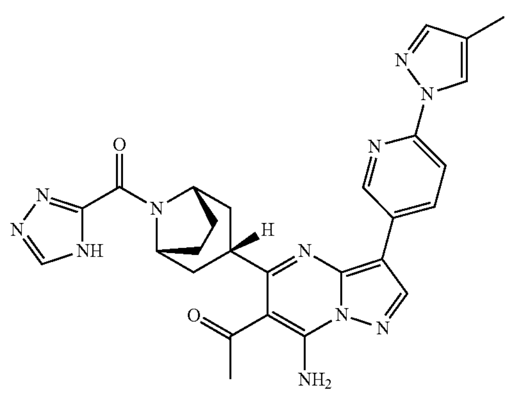 [SMILES: CC(=O)c1c([C@@H]2C[C@H]3CC[C@@H](C2)N3C(=O)c2nnc[nH]2)nc2c(-c3ccc(-n4cc(C)cn4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone | 538.23/538.20 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.136 | 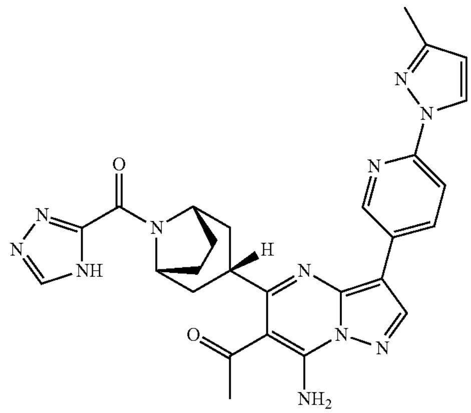 [SMILES: CC(=O)c1c([C@@H]2C[C@H]3CC[C@@H](C2)N3C(=O)c2nnc[nH]2)nc2c(-c3ccc(-n4ccc(C)n4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(3-methyl-1H-pyrazol-1-yl)pyridin-3-yl)pyrazolo[1,5-a]pyrimidin-6-yl)ethanone | 538.23/538.00 | A | B |
| 1.1.137 | 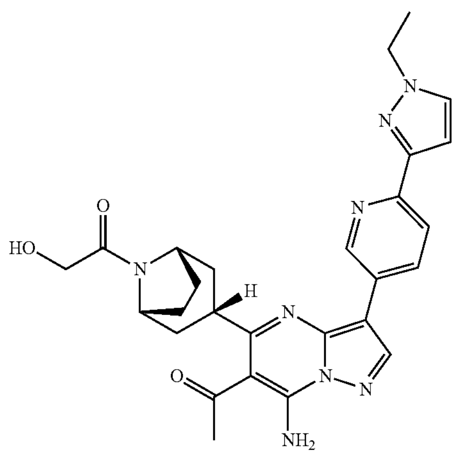 [SMILES: CCn1ccc(-c2ccc(-c3cnn4c(N)c(C(C)=O)c([C@@H]5C[C@H]6CC[C@@H](C5)N6C(=O)CO)nc34)cn2)n1] | 1-((1R,3s,5S)-3-(6-acetyl-7-amino-3-(6-(1-ethyl-1H-pyrazol-3-yl)pyridin-3-yl)pyrazolo[1,5-a]pyrimidin-5-yl)-8-azabicyclo[3.2.1]octan-8-yl)-2-hydroxyethanone | 515.24/515.06 | A | B |
| 1.1.138 | 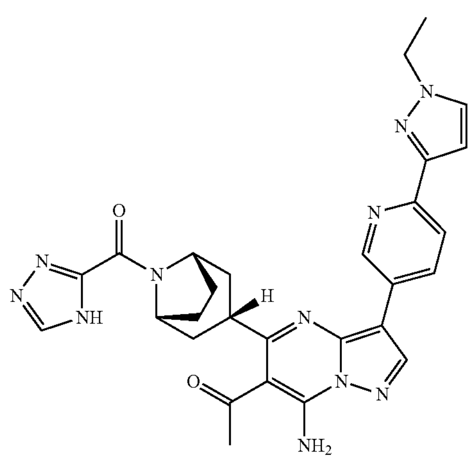 [SMILES: CCn1ccc(-c2ccc(-c3cnn4c(N)c(C(C)=O)c([C@@H]5C[C@H]6CC[C@@H](C5)N6C(=O)c5nnc[nH]5)nc34)cn2)n1] | 1-(5-((1R,3s,5S)-8-(4H-1,2,4-triazole-3-carbonyl)-8-azabicyclo[3.2.1]octan-3-yl)-7-amino-3-(6-(1-ethyl-1H-pyrazol-3-yl)pyridin-3-yl)pyrazolo[1,5-a]pyrimidin-6-yl)ethanone | 552.25/552.07 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.139 | 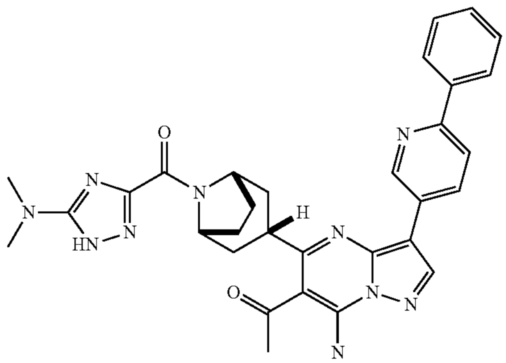 [SMILES: CC(=O)c1c([C@@H]2C[C@H]3CC[C@@H](C2)N3C(=O)c2n[nH]c(N(C)C)n2)nc2c(-c3ccc(-c4ccccc4)nc3)cnn2c1N] | 1-(7-amino-5-((1R,3s,5S)-8-(5-(dimethylamino)-1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone | 577.2/577.2 | C | C |
| 1.1.140 | 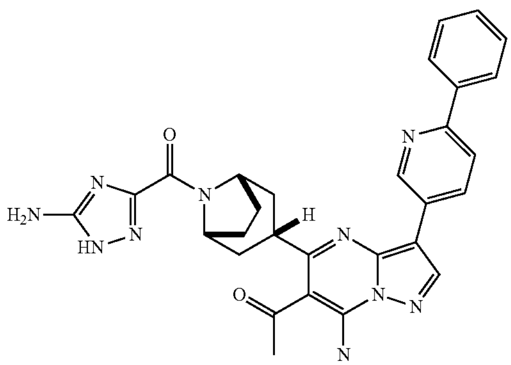 [SMILES: CC(=O)c1c([C@@H]2C[C@H]3CC[C@@H](C2)N3C(=O)c2n[nH]c(N)n2)nc2c(-c3ccc(-c4ccccc4)nc3)cnn2c1N] | 1-(7-amino-5-((1R,3s,5S)-8-(5-amino-1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone | 549.2/549.3 | A | A |
| 1.1.141 | 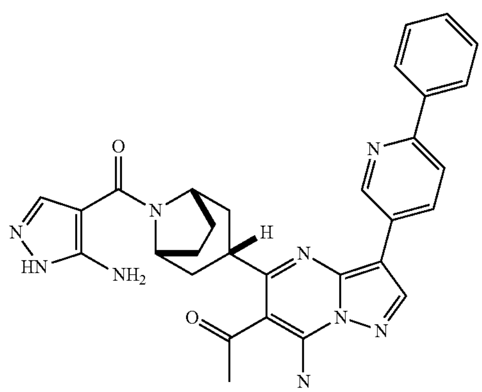 [SMILES: CC(=O)c1c([C@@H]2C[C@H]3CC[C@@H](C2)N3C(=O)c2cn[nH]c2N)nc2c(-c3ccc(-c4ccccc4)nc3)cnn2c1N] | 1-(7-amino-5-((1R,3s,5S)-8-(5-amino-1H-pyrazole-4-carbonyl)-8-azabicyclo[3.2.1]octan-3-yl)-3-(6-phenylpyridin-3-yl)pyrazolo[1,5-a]pyrimidin-6-yl)ethanone | 548.2/548.2 | A | A |
| 1.1.142 | 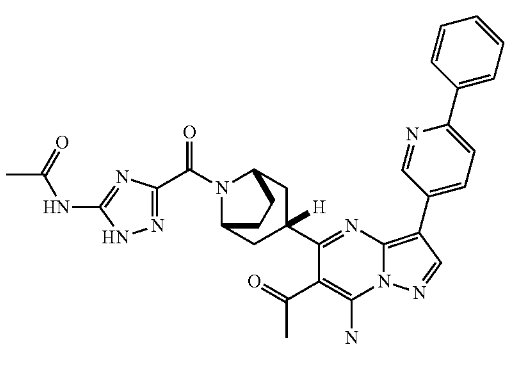 [SMILES: CC(=O)Nc1nc(C(=O)N2[C@@H]3CC[C@H]2C[C@H](c2nc4c(-c5ccc(-c6ccccc6)nc5)cnn4c(N)c2C(C)=O)C3)n[nH]1] | N-(3-((1R,3s,5S)-3-(6-acetyl-7-amino-3-(6-phenylpyridin-3-yl)pyrazolo[1,5-a]pyrimidin-5-yl)-8-azabicyclo[3.2.1]octane-8-carbonyl)-1H-1,2,4-triazol-5-yl)acetamide | 591.2/591.2 | B | B |

TABLE 1-1-continued

| Compound ID | Structures | Compound Name | M + H (calculated)/ M + H (observed) | pAKT S473 IC50 | p4E-1 Thr37/46 IC50 |
|---|---|---|---|---|---|
| 1.1.143 | 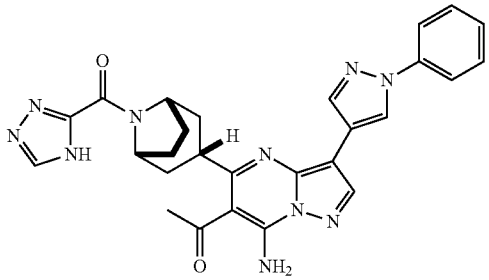 | 1-(5-((1R,3s,5S)-8-(4H-1,2,4-triazole-3-carbonyl)-8-azabicyclo[3.2.1]octan-3-yl)-7-amino-3-(1-phenyl-1H-pyrazol-4-yl)pyrazolo[1,5-a]pyrimidin-6-yl)ethanone | 523.2/523.2 | A | A |
| 1.1.144 | 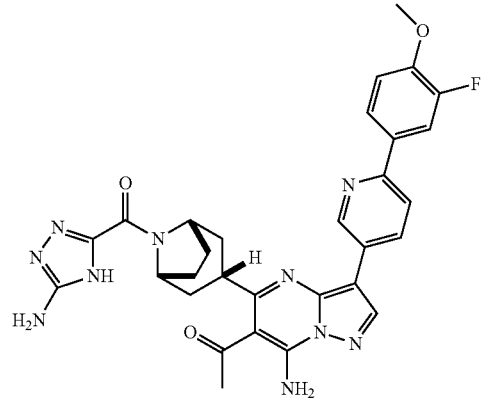 [SMILES: COc1ccc(-c2ccc(-c3cnn4c(N)c(C(C)=O)c([C@@H]5C[C@H]6CC[C@@H](C5)N6C(=O)c5nnc(N)[nH]5)nc34)cn2)cc1F] | 1-(7-amino-5-((1R,3s,5S)-8-(5-amino-4H-1,2,4-triazole-3-carbonyl)-8-azabicyclo[3.2.1]octan-3-yl)-3-(6-(3-fluoro-4-methoxyphenyl)pyridin-3-yl)pyrazolo[1,5-a]pyrimidin-6-yl)ethanone | 597.2/597.2 | A | A |
| 1.1.145 | 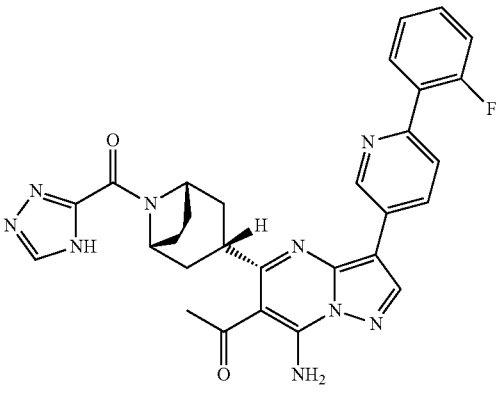 | 1-(5-((1R,3s,5S)-8-(4H-1,2,4-triazole-3-carbonyl)-8-azabicyclo[3.2.1]octan-3-yl)-7-amino-3-(6-(2-fluorophenyl)pyridin-3-yl)pyrazolo[1,5-a]pyrimidin-6-yl)ethanone | 552.2/552.1 | A | A |
| 1.1.146 | 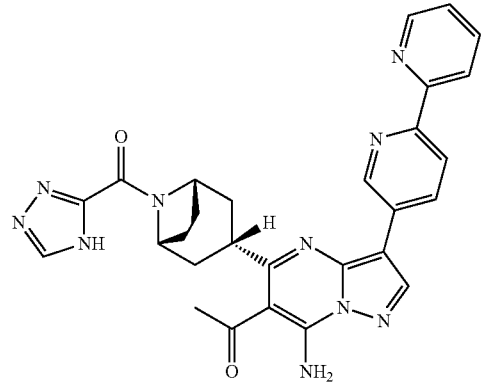 [SMILES: CC(=O)c1c([C@@H]2C[C@H]3CC[C@@H](C2)N3C(=O)c2nnc[nH]2)nc2c(-c3ccc(-c4ccccn4)nc3)cnn2c1N] | 1-(3-(2,2'-bipyridin-5-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 535.2/535.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.147 | 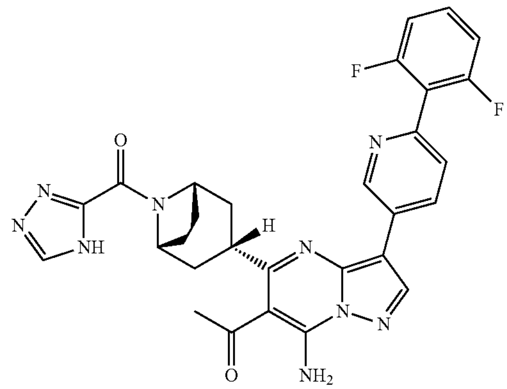 [SMILES: CC(=O)c1c([C@@H]2C[C@H]3CC[C@@H](C2)N3C(=O)c2nnc[nH]2)nc2c(-c3ccc(-c4c(F)cccc4F)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(2,6-difluorophenyl)pyridin-3-yl)pyrazolo[1,5-a]pyrimidin-6-yl)ethanone | 570.2/570.2 | A | A |
| 1.1.148 | 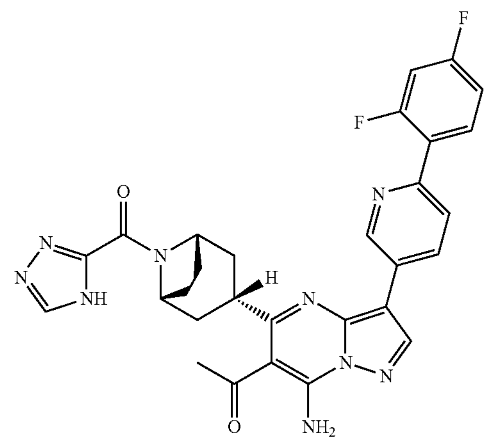 [SMILES: CC(=O)c1c([C@@H]2C[C@H]3CC[C@@H](C2)N3C(=O)c2nnc[nH]2)nc2c(-c3ccc(-c4ccc(F)cc4F)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone | 570.2/570.2 | A | A |
| 1.1.149 | 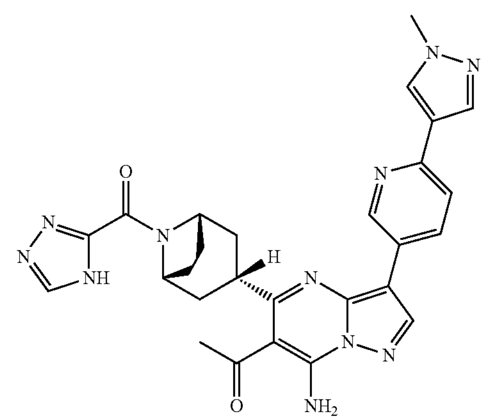 [SMILES: CC(=O)c1c([C@@H]2C[C@H]3CC[C@@H](C2)N3C(=O)c2nnc[nH]2)nc2c(-c3ccc(-c4cnn(C)c4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-4-yl)pyridin-3-yl)pyrazolo[1,5-a]pyrimidin-6-yl)ethanone | 538.2/538.2 | A | A |
| 1.1.150 | 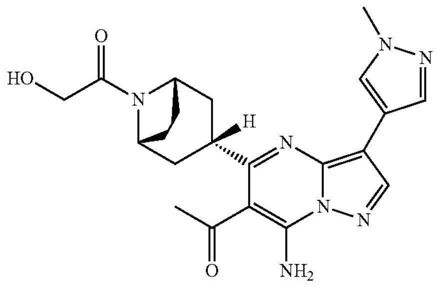 [SMILES: CC(=O)c1c([C@@H]2C[C@H]3CC[C@@H](C2)N3C(=O)CO)nc2c(-c3cnn(C)c3)cnn2c1N] | 1-((1R,3s,5S)-3-(6-acetyl-7-amino-3-(1-methyl-1H-pyrazol-4-yl)pyrazolo[1,5-a]pyrimidin-5-yl)-8-azabicyclo[3.2.1]octan-8-yl)-2-hydroxyethanone | 424.2/424.0 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.151 | 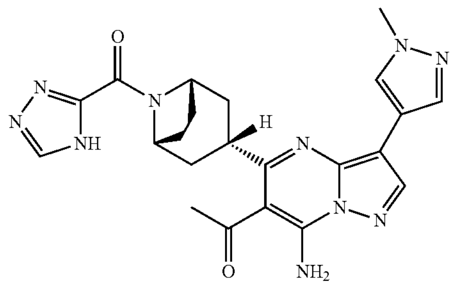 [SMILES: CC(=O)c1c([C@@H]2C[C@H]3CC[C@@H](C2)N3C(=O)c2nnc[nH]2)nc2c(-c3cnn(C)c3)cnn2c1N] | 1-(5-((1R,3s,5S)-8-(4H-1,2,4-triazole-3-carbonyl)-8-azabicyclo[3.2.1]octan-3-yl)-7-amino-3-(1-methyl-1H-pyrazol-4-yl)pyrazolo[1,5-a]pyrimidin-6-yl)ethanone | 461.2/460.9 | B | B |
| 1.1.152 | 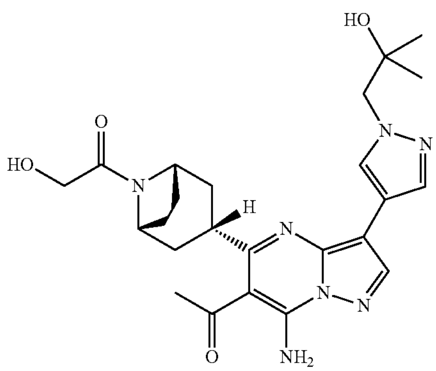 [SMILES: CC(=O)c1c([C@@H]2C[C@H]3CC[C@@H](C2)N3C(=O)CO)nc2c(-c3cnn(CC(C)(C)O)c3)cnn2c1N] | 1-((1R,3s,5S)-3-(6-acetyl-7-amino-3-(1-(2-hydroxy-2-methylpropyl)-1H-pyrazol-4-yl)pyrazolo[1,5-a]pyrimidin-5-yl)-8-azabicyclo[3.2.1]octan-8-yl)-2-hydroxyethanone | 482.2/482.2 | ND | ND |
| 1.1.153 | 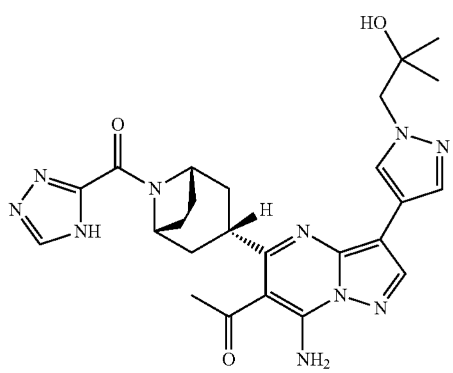 [SMILES: CC(=O)c1c([C@@H]2C[C@H]3CC[C@@H](C2)N3C(=O)c2nnc[nH]2)nc2c(-c3cnn(CC(C)(C)O)c3)cnn2c1N] | 1-(5-((1R,3s,5S)-8-(4H-1,2,4-triazole-3-carbonyl)-8-azabicyclo[3.2.1]octan-3-yl)-7-amino-3-(1-(2-hydroxy-2-methylpropyl)-1H-pyrazol-4-yl)pyrazolo[1,5-a]pyrimidin-6-yl)ethanone | 519.3/519.2 | ND | ND |
| 1.1.154 | 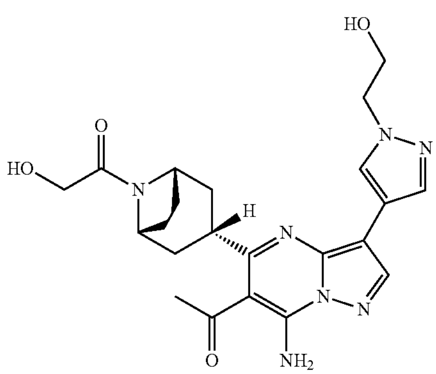 [SMILES: CC(=O)c1c([C@@H]2C[C@H]3CC[C@@H](C2)N3C(=O)CO)nc2c(-c3cnn(CCO)c3)cnn2c1N] | 1-((1R,3s,5S)-3-(6-acetyl-7-amino-3-(1-(2-hydroxyethyl)-1H-pyrazol-4-yl)pyrazolo[1,5-a]pyrimidin-5-yl)-8-azabicyclo[3.2.1]octan-8-yl)-2-hydroxyethanone | 454.2/454.1 | ND | ND |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.155 | 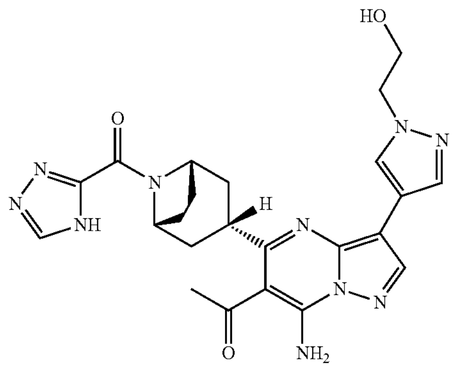 [SMILES: CC(=O)c1c([C@@H]2C[C@H]3CC[C@@H](C2)N3C(=O)c2nnc[nH]2)nc2c(-c3cnn(CCO)c3)cnn2c1N] | 1-(5-((1R,3s,5S)-8-(4H-1,2,4-triazole-3-carbonyl)-8-azabicyclo[3.2.1]octan-3-yl)-7-amino-3-(1-(2-hydroxyethyl)-1H-pyrazol-4-yl)pyrazolo[1,5-a]pyrimidin-6-yl)ethanone | 491.2/491.2 | C | C |
| 1.1.156 | 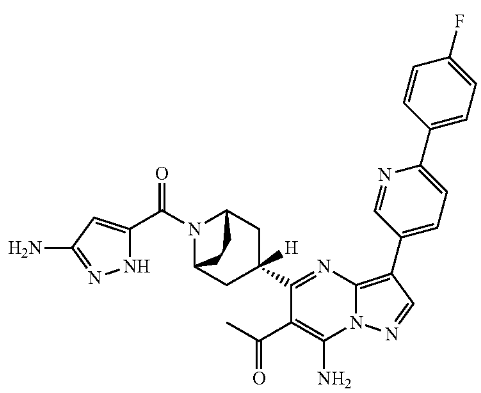 [SMILES: CC(=O)c1c([C@@H]2C[C@H]3CC[C@@H](C2)N3C(=O)c2cc(N)n[nH]2)nc2c(-c3ccc(-c4ccc(F)cc4)nc3)cnn2c1N] | 1-(7-amino-5-((1R,3s,5S)-8-(3-amino-1H-pyrazole-5-carbonyl)-8-azabicyclo[3.2.1]octan-3-yl)-3-(6-(4-fluorophenyl)pyridin-3-yl)pyrazolo[1,5-a]pyrimidin-6-yl)ethanone | 566.2/566.2 | A | A |
| 1.1.157 | 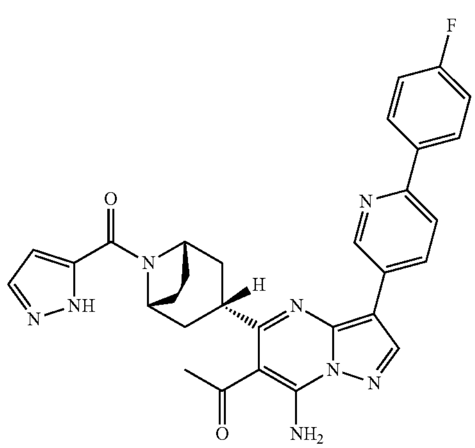 [SMILES: CC(=O)c1c([C@@H]2C[C@H]3CC[C@@H](C2)N3C(=O)c2ccn[nH]2)nc2c(-c3ccc(-c4ccc(F)cc4)nc3)cnn2c1N] | 1-(5-((1R,3s,5S)-8-(1H-pyrazole-5-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone | 551.2/551.2 | A | ND |

TABLE 1-1-continued

| Compound ID | Structures | Compound Name | M + H (calculated)/ M + H (observed) | pAKT S473 IC50 | p4E-1 Thr37/46 IC50 |
|---|---|---|---|---|---|
| 1.1.158 | 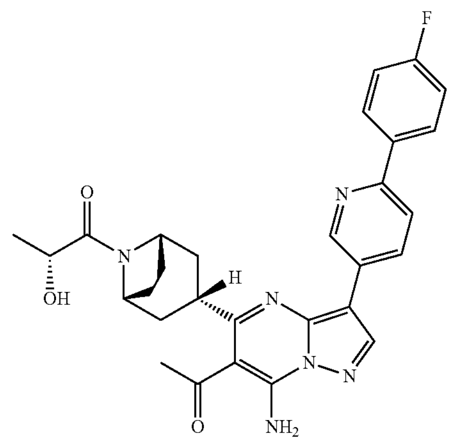 [SMILES: CC(=O)c1c([C@@H]2C[C@H]3CC[C@@H](C2)N3C(=O)[C@@H](C)O)nc2c(-c3ccc(-c4ccc(F)cc4)nc3)cnn2c1N] | (R)-1-((1R,3S,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxypropan-1-one | 529.2/529.2 | B | ND |
| 1.1.159 | 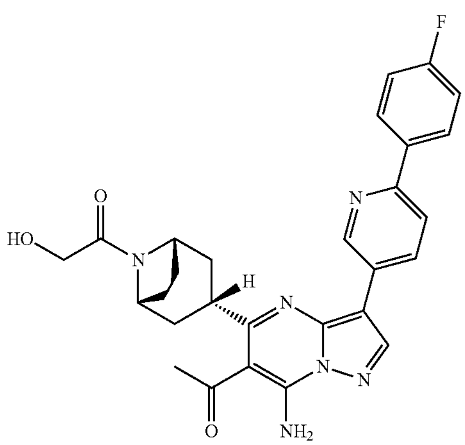 [SMILES: CC(=O)c1c([C@@H]2C[C@H]3CC[C@@H](C2)N3C(=O)CO)nc2c(-c3ccc(-c4ccc(F)cc4)nc3)cnn2c1N] | 1-((1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxyethanone | 515.2/515.2 | B | B |
| 1.1.160 | 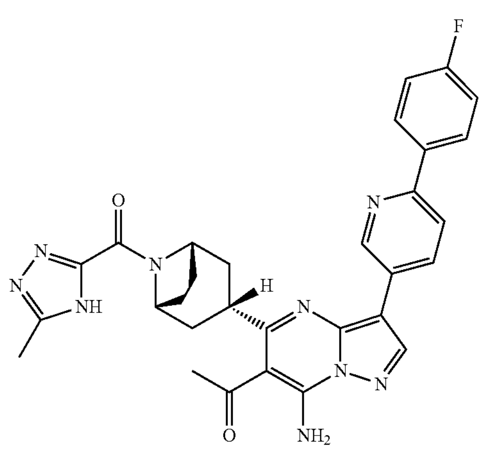 [SMILES: CC(=O)c1c([C@@H]2C[C@H]3CC[C@@H](C2)N3C(=O)c2nnc(C)[nH]2)nc2c(-c3ccc(-c4ccc(F)cc4)nc3)cnn2c1N] | 1-(7-amino-3-(6-(4-fluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 566.2/566.2 | A | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.161 | 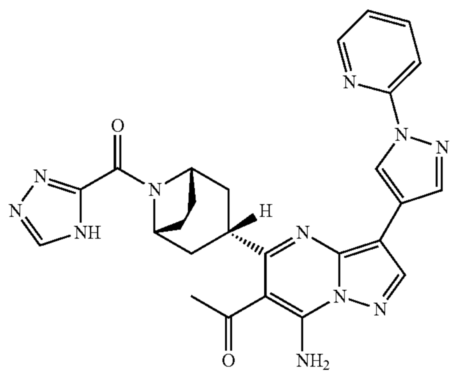 [SMILES: CC(=O)c1c([C@@H]2C[C@H]3CC[C@@H](C2)N3C(=O)c2nnc[nH]2)nc2c(-c3cnn(-c4ccccn4)c3)cnn2c1N] | 1-(5-((1R,3s,5S)-8-(4H-1,2,4-triazole-3-carbonyl)-8-azabicyclo[3.2.1]octan-3-yl)-7-amino-3-(1-(pyridin-2-yl)-1H-pyrazol-4-yl)pyrazolo[1,5-a]pyrimidin-6-yl)ethanone | 524.2/524.2 | B | B |
| 1.1.162 | 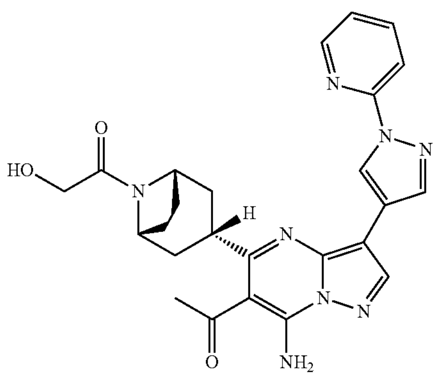 [SMILES: CC(=O)c1c([C@@H]2C[C@H]3CC[C@@H](C2)N3C(=O)CO)nc2c(-c3cnn(-c4ccccn4)c3)cnn2c1N] | 1-((1R,3s,5S)-3-(6-acetyl-7-amino-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone | 487.2/487.1 | B | B |
| 1.1.163 | 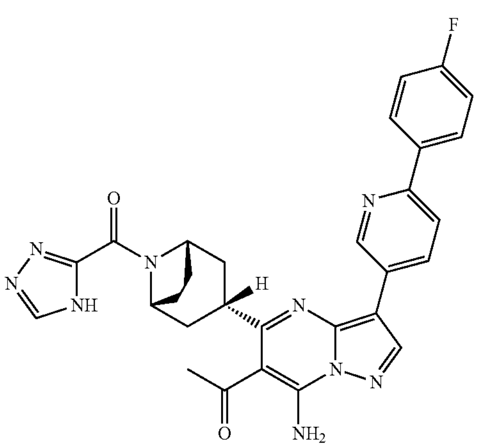 [SMILES: CC(=O)c1c([C@@H]2C[C@H]3CC[C@@H](C2)N3C(=O)c2nnc[nH]2)nc2c(-c3ccc(-c4ccc(F)cc4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone | 552.2/552.1 | A | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.164 | 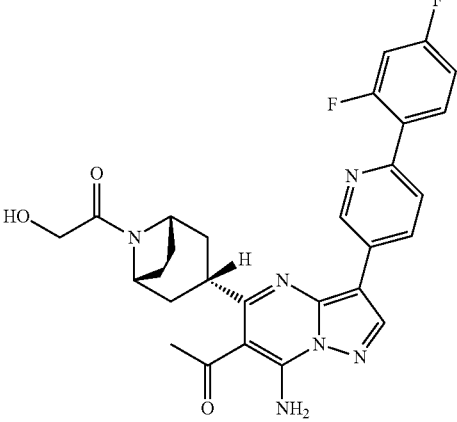 | 1-((1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxyethanone | 533.2/533.2 | A | B |
| 1.1.165 | 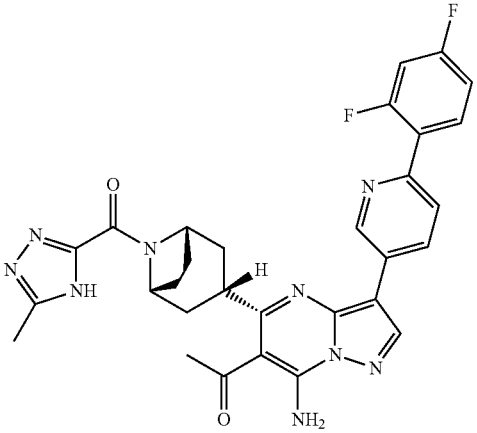 | 1-(7-amino-3-(6-(2,4-difluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 584.2/584.2 | A | A |
| 1.1.166 | 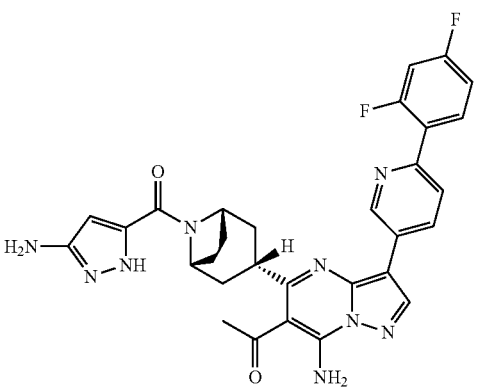 [SMILES: CC(=O)c1c([C@@H]2C[C@H]3CC[C@@H](C2)N3C(=O)c2cc(N)n[nH]2)nc2c(-c3ccc(-c4ccc(F)cc4F)nc3)cnn2c1N] | 1-(7-amino-5-((1R,3s,5S)-8-(3-amino-1H-pyrazole-5-carbonyl)-8-azabicyclo[3.2.1]octan-3-yl)-3-(6-(2,4-difluorophenyl)pyridin-3-yl)pyrazolo[1,5-a]pyrimidin-6-yl)ethanone | 584.2/584.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.167 | 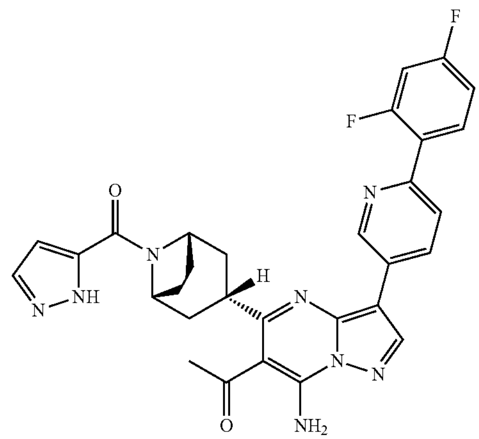 [SMILES: CC(=O)c1c([C@@H]2C[C@H]3CC[C@@H](C2)N3C(=O)c2ccn[nH]2)nc2c(-c3ccc(-c4ccc(F)cc4F)nc3)cnn2c1N] | 1-(5-((1R,3s,5S)-8-(1H-pyrazole-5-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone | 569.2/569.2 | A | B |
| 1.1.168 | 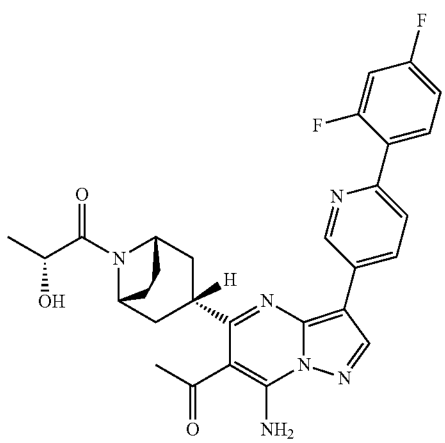 [SMILES: CC(=O)c1c([C@@H]2C[C@H]3CC[C@@H](C2)N3C(=O)[C@@H](C)O)nc2c(-c3ccc(-c4ccc(F)cc4F)nc3)cnn2c1N] | (R)-1-((1R,3S,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxypropan-1-one | 547.2/547.2 | B | B |
| 1.1.169 | 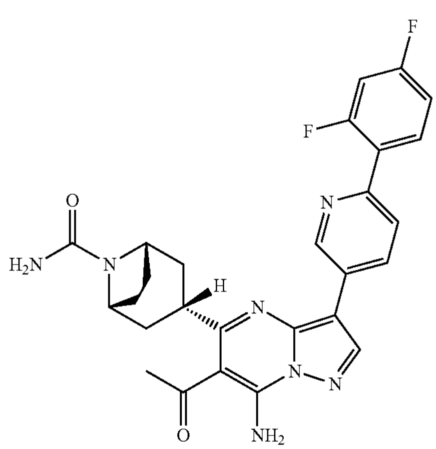 | (1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octane-8-carboxamide | 518.2/518.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.11..170 | 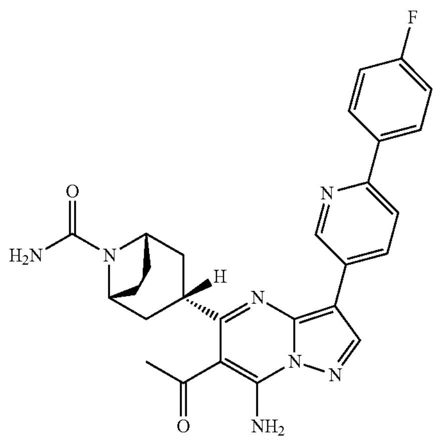 [SMILES: CC(=O)c1c([C@@H]2C[C@H]3CC[C@@H](C2)N3C(N)=O)nc2c(-c3ccc(-c4ccc(F)cc4)nc3)cnn2c1N] | (1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octane-8-carboxamide | 500.2/500.2 | A | A |
| 1.1.171 | 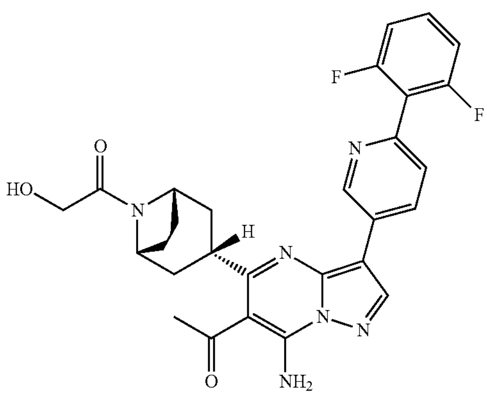 [SMILES: CC(=O)c1c([C@@H]2C[C@H]3CC[C@@H](C2)N3C(=O)CO)nc2c(-c3ccc(-c4c(F)cccc4F)nc3)cnn2c1N] | 1-((1R,3s,5S)-3-(6-acetyl-7-amino-3-(6-(2,6-difluorophenyl)pyridin-3-yl)pyrazolo[1,5-a]pyrimidin-5-yl)-8-azabicyclo[3.2.1]octan-8-yl)-2-hydroxyethanone | 533.2/533.3 | A | A |
| 1.1.172 | 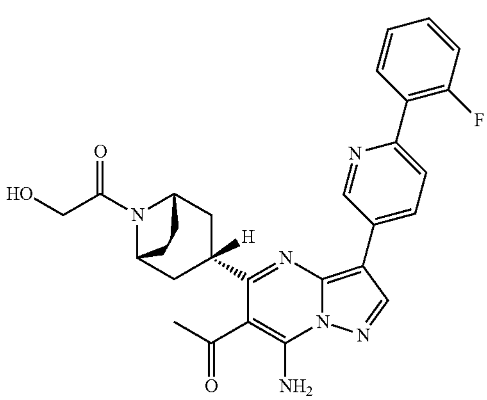 [SMILES: CC(=O)c1c([C@@H]2C[C@H]3CC[C@@H](C2)N3C(=O)CO)nc2c(-c3ccc(-c4ccccc4F)nc3)cnn2c1N] | 1-((1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octan-8-yl)-2-hydroxyethanone | 515.2/515.2 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.173 | 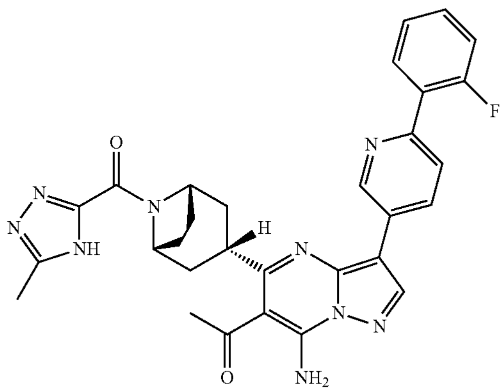 [SMILES: CC(=O)c1c([C@@H]2C[C@H]3CC[C@@H](C2)N3C(=O)c2nnc(C)[nH]2)nc2c(-c3ccc(-c4ccccc4F)nc3)cnn2c1N] | 1-(7-amino-3-(6-(2-fluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 566.2/566.2 | A | A |
| 1.1.174 | 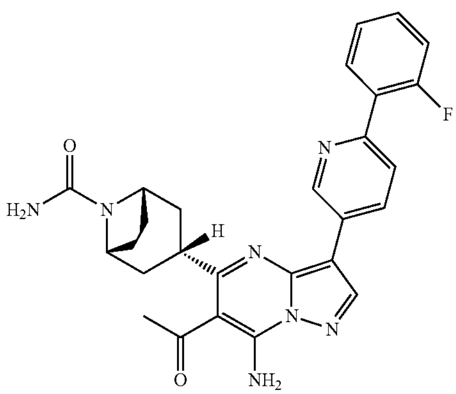 [SMILES: CC(=O)c1c([C@@H]2C[C@H]3CC[C@@H](C2)N3C(N)=O)nc2c(-c3ccc(-c4ccccc4F)nc3)cnn2c1N] | (1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octane-8-carboxamide | 500.2/500.2 | A | A |
| 1.1.175 | 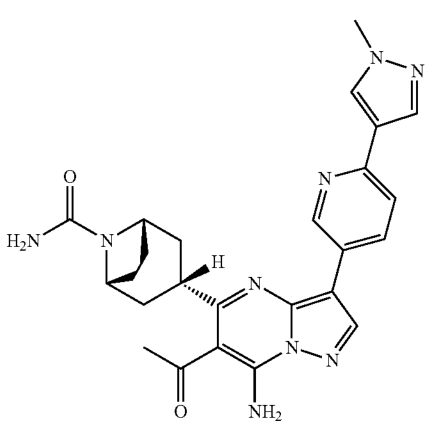 [SMILES: CC(=O)c1c([C@@H]2C[C@H]3CC[C@@H](C2)N3C(N)=O)nc2c(-c3ccc(-c4cnn(C)c4)nc3)cnn2c1N] | (1R,3s,5S)-3-(6-acetyl-7-amino-3-(6-(1-methyl-1H-pyrazolo-4-yl)pyridin-3-yl)pyrazolo[1,5-a]pyrimidin-5-yl)-8-azabicyclo[3.2.1]octane-8-carboxamide | 486.2/486.2 | A | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.176 | 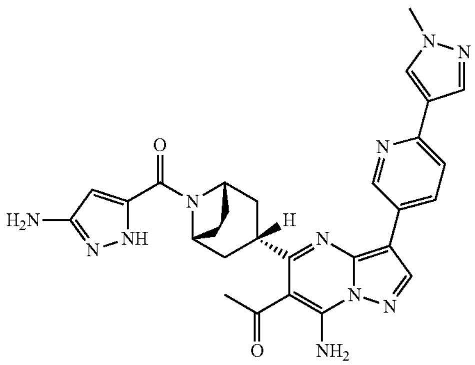 [SMILES: CC(=O)c1c([C@@H]2C[C@H]3CC[C@@H](C2)N3C(=O)c2cc(N)n[nH]2)nc2c(-c3ccc(-c4cnn(C)c4)nc3)cnn2c1N] | 1-(7-amino-5-((1R,3s,5S)-8-(3-amino-1H-pyrazole-5-carbonyl)-8-azabicyclo[3.2.1]octan-3-yl)-3-(6-(1-methyl-1H-pyrazol-4-yl)pyridin-3-yl)pyrazolo[1,5-a]pyrimidin-6-yl)ethanone | 552.3/552.2 | B | B |
| 1.1.177 | 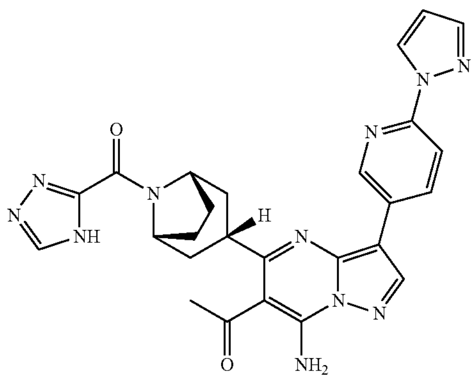 [SMILES: CC(=O)c1c([C@@H]2C[C@H]3CC[C@@H](C2)N3C(=O)c2nnc[nH]2)nc2c(-c3ccc(-n4cccn4)nc3)cnn2c1N] | 1-(3-(6-(1H-pyrazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 524.22/524.3 | A | A |
| 1.1.178 | 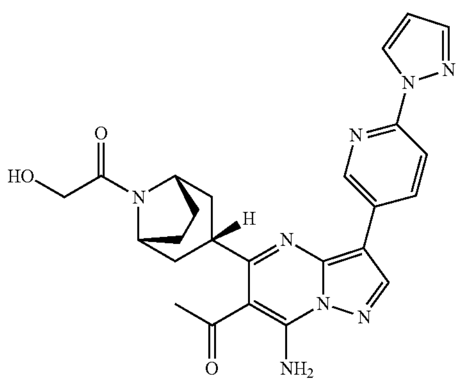 [SMILES: CC(=O)c1c([C@@H]2C[C@H]3CC[C@@H](C2)N3C(=O)CO)nc2c(-c3ccc(-n4cccn4)nc3)cnn2c1N] | 1-((1R,3s,5S)-3-(3-(6-(1H-pyrazol-1-yl)pyridin-3-yl)-6-acetyl-7-aminopyrazolo[1,5-a]pyrimidin-5-yl)-8-azabicyclo[3.2.1]octan-8-yl)-2-hydroxyethanone | 487.21/487.1 | A | B |
| 1.1.179 | 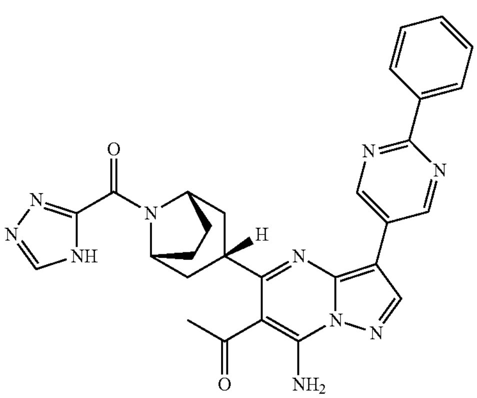 [SMILES: CC(=O)c1c([C@@H]2C[C@H]3CC[C@@H](C2)N3C(=O)c2nnc[nH]2)nc2c(-c3cnc(-c4ccccc4)nc3)cnn2c1N] | 1-(5-((1R,3s,5S)-8-(4H-1,2,4-triazole-3-carbonyl)-8-azabicyclo[3.2.1]octan-3-yl)-7-amino-3-(2-phenylpyrimidin-5-yl)pyrazolo[1,5-a]pyrimidin-6-yl)ethanone | 535.22/535.3 | A | A |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.180 | 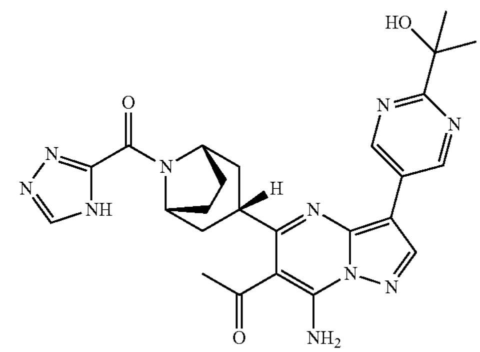 [SMILES: CC(=O)c1c([C@@H]2C[C@H]3CC[C@@H](C2)N3C(=O)c2nnc[nH]2)nc2c(-c3cnc(C(C)(C)O)nc3)cnn2c1N] | 1-(5-((1R,3s,5S)-8-(4H-1,2,4-triazole-3-carbonyl)-8-azabicyclo[3.2.1]octan-3-yl)-7-amino-3-(2-(2-hydroxypropan-2-yl)pyrimidin-5-yl)pyrazolo[1,5-a]pyrimidin-6-yl)ethanone | 517.23/517.3 | B | B |
| 1.1.181 | 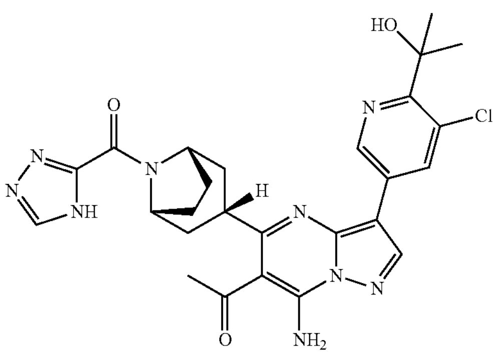 [SMILES: CC(=O)c1c([C@@H]2C[C@H]3CC[C@@H](C2)N3C(=O)c2nnc[nH]2)nc2c(-c3cnc(C(C)(C)O)c(Cl)c3)cnn2c1N] | 1-(5-((1R,3s,5S)-8-(4H-1,2,4-triazole-3-carbonyl)-8-azabicyclo[3.2.1]octan-3-yl)-7-amino-3-(5-chloro-6-(2-hydroxypropan-2-yl)pyridin-3-yl)pyrazolo[1,5-a]pyrimidin-6-yl)ethanone | 550.2/550.4 | A | A |
| 1.1.182 | 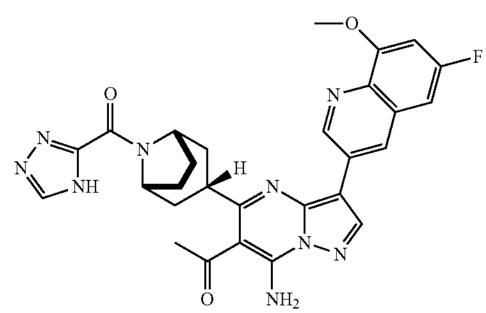 | 1-(5-((1R,3r,5S)-8-(4H-1,2,4-triazole-3-carbonyl)-8-azabicyclo[3.2.1]octan-3-yl)-7-amino-3-(6-fluoro-8-methoxyquinolin-3-yl)pyrazolo[1,5-a]pyrimidin-6-yl)ethanone | 555.2/556.2 | A | A |
| 1.1.183 | 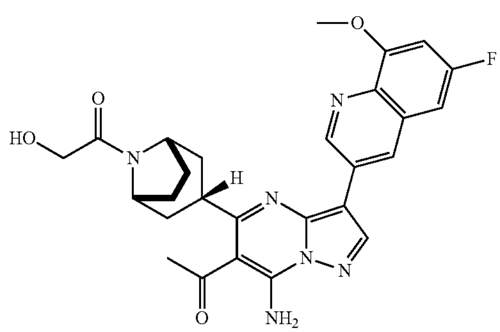 | 1-((1R,3r,5S)-3-(6-acetyl-7-amino-3-(6-fluoro-8-methoxyquinolin-3-yl)pyrazolo[1,5-a]pyrimidin-5-yl)-8-azabicyclo[3.2.1]octan-8-yl)-2-hydroxyethanone | 518.2/519.2 | A | B |

TABLE 1-1-continued

| Compound ID | Structures | Compound Name | M + H (calculated)/ M + H (observed) | pAKT S473 IC50 | p4E-1 Thr37/ 46 IC50 |
|---|---|---|---|---|---|
| 1.1.184 | 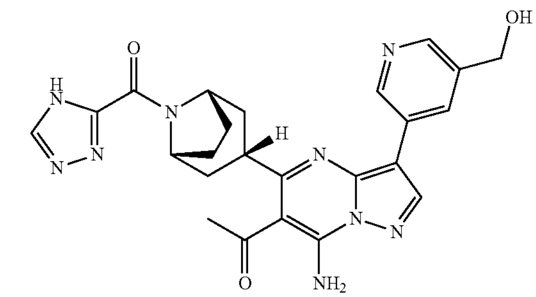 [SMILES: CC(=O)c1c([C@@H]2C[C@H]3CC[C@@H](C2)N3C(=O)c2nnc[nH]2)nc2c(-c3cncc(CO)c3)cnn2c1N] | 1-(5-((1R,3s,5S)-8-(4H-1,2,4-triazole-3-carbonyl)-8-azabicyclo[3.2.1]octan-3-yl)-7-amino-3-(5-(hydroxymethyl)pyridin-3-yl)pyrazolo[1,5-a]pyrimidin-6-yl)ethanone | 487.21/488.2 | B | B |
| 1.1.185 | 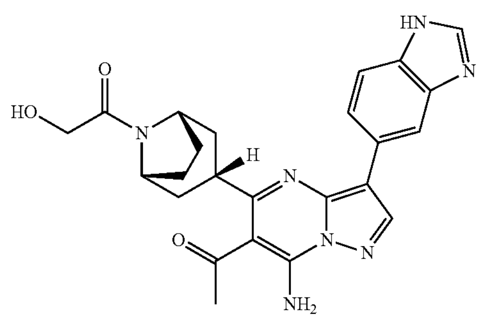 [SMILES: CC(=O)c1c([C@@H]2C[C@H]3CC[C@@H](C2)N3C(=O)CO)nc2c(-c3ccc4[nH]cnc4c3)cnn2c1N] | 1-((1R,3s,5S)-3-(6-acetyl-7-amino-3-(1H-benzo[d]imidazol-5-yl)pyrazolo[1,5-a]pyrimidin-5-yl)-8-azabicyclo[3.2.1]octan-8-yl)-2-hydroxyethanone | 459.20/460.1 | ND | ND |

Example 1-42

Preparation of 1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone

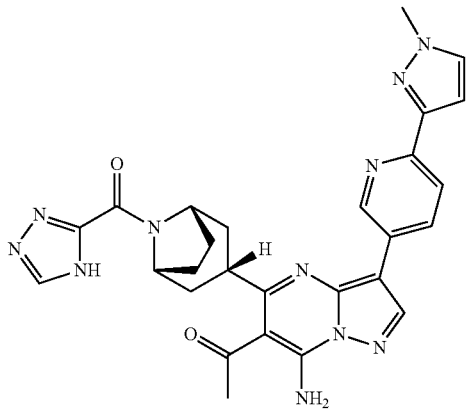 [SMILES: CC(=O)c1c([C@@H]2C[C@H]3CC[C@@H](C2)N3C(=O)c2nnc[nH]2)nc2c(-c3ccc(-c4ccn(C)n4)nc3)cnn2c1N]

Step 1: Preparation of (1R,3s,5S)-tert-butyl 3-(7-(bis((2-(trimethylsilyl)ethoxy)methyl)amino)-3-(6-(1-methyl-1H-pyrazol-3-yl)pyridin-3-yl)pyrazolo[1,5-a]pyrimidin-5-yl)-8-azabicyclo[3.2.1]octane-8-carboxylate

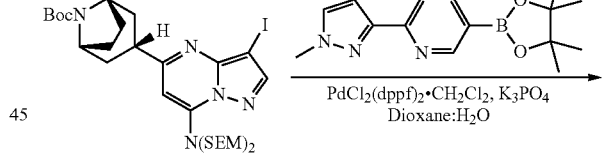

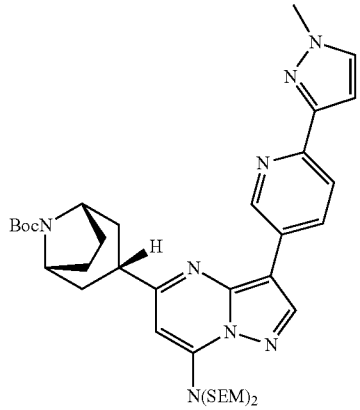

To tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (9.96 g, 13.67 mmol) in dioxane (100 mL) and H₂O (10 mL) was added 2-(1-methyl-1H- pyrazol-3-yl)-5-(4,4,5,5-tetramethyl-1,3,2-dioxaborolan-2-yl)pyridine (5.84 g, 20.50 mmol), PdCl$_2$(dppf).CH$_2$Cl$_2$ (1.15 g, 1.36 mmol) and K$_3$PO$_4$ (8.69 g, 40.9 mmol). The reaction was heated at 80° C. over night. On cooling, filtration and concentration afforded crude product. Gradient column chromatography on silica gave (1R,3s,5S)-tert-butyl 3-(7-(bis((2-(trimethylsilyl)ethoxy)methyl)amino)-3-(6-(1-methyl-1H-pyrazol-3-yl)pyridin-3-yl)pyrazolo[1,5-a]pyrimidin-5-yl)-8-azabicyclo[3.2.1]octane-8-carboxylate.

Step 2: Preparation of (1R,3s,5S)-tert-butyl 3-(7-(bis((2-(trimethylsilyl)ethoxy)methyl)amino)-6-bromo-3-(6-(1-methyl-1H-pyrazol-3-yl)pyridin-3-yl)pyrazolo[1,5-a]pyrimidin-5-yl-8-azabicyclo[3.2.1]octane-8-carboxylate

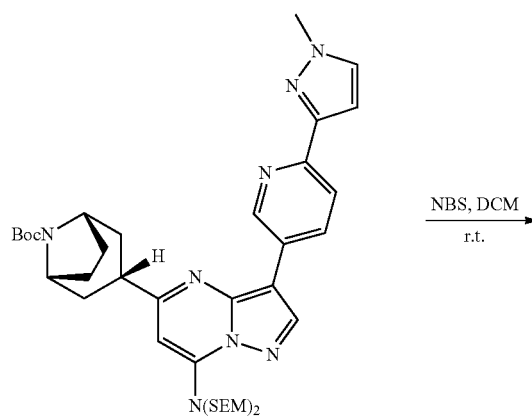

At 0° C., to a mixture of (1R,3s,5S)-tert-butyl 3-(7-(bis((2-(trimethylsilyl)ethoxy)methyl)amino)-3-(6-(1-methyl-1H-pyrazol-3-yl)pyridin-3-yl)pyrazolo[1,5-a]pyrimidin-5-yl)-8-azabicyclo[3.2.1]octane-8-carboxylate (10.92 g, 14.4 mmol) in dichloromethane (40 mL) was added N-bromosuccinimide (2.33 g, 13.07 mmol) portionwise and the resulting mixture was warmed up to room temperature slowly. The mixture was purified by column chromatography on silica gel to give (1R,3s,5S)-tert-butyl 3-(7-(bis((2-(trimethylsilyl)ethoxy)methyl)amino)-6-bromo-3-(6-(1-methyl-1H-pyrazol-3-yl)pyridin-3-yl)pyrazolo[1,5-a]pyrimidin-5-yl)-8-azabicyclo[3.2.1]octane-8-carboxylate.

Step 3: Preparation of (1R,3s,5S)-tert-butyl 3-(7-(bis((2-(trimethylsilyl)ethoxy)methyl)amino)-6-(1-ethoxyvinyl)-3-(6-(1H-pyrazol-3-yl)pyridin-3-yl)pyrazolo[1,5-a]pyrimidin-5-yl)-8-azabicyclo[3.2.1]octane-8-carboxylate

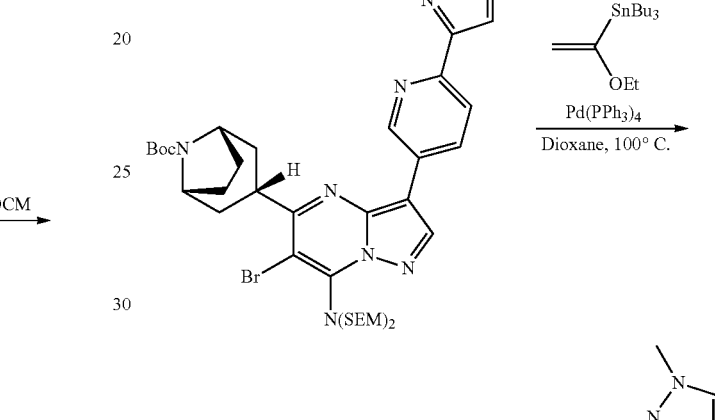

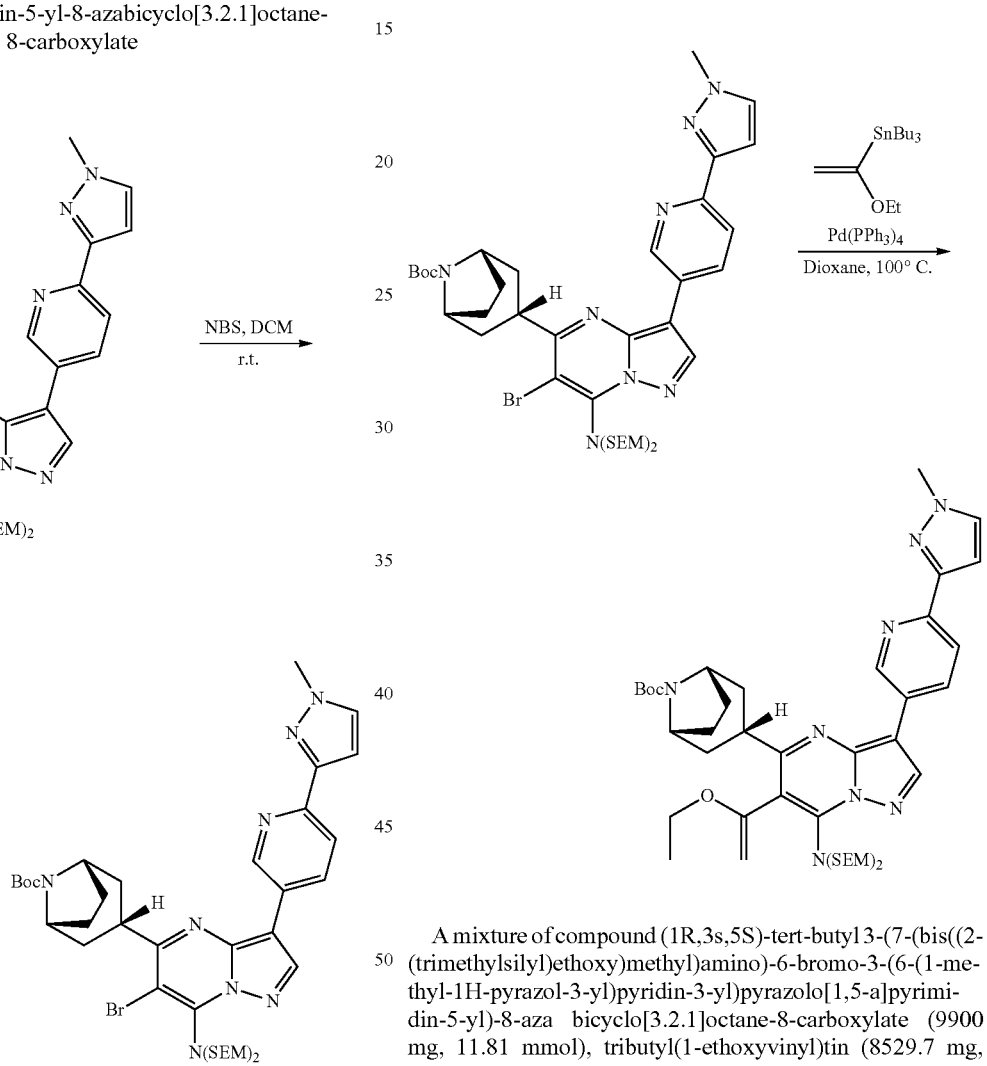

A mixture of compound (1R,3s,5S)-tert-butyl 3-(7-(bis((2-(trimethylsilyl)ethoxy)methyl)amino)-6-bromo-3-(6-(1-methyl-1H-pyrazol-3-yl)pyridin-3-yl)pyrazolo[1,5-a]pyrimidin-5-yl)-8-aza bicyclo[3.2.1]octane-8-carboxylate (9900 mg, 11.81 mmol), tributyl(1-ethoxyvinyl)tin (8529.7 mg, 23.63 mmol), tetrakis(triphenylphosphine)palladium (1365.6 mg, 1.18 mmol) in dioxane (100 mL) was degassed with argon for five minutes. It was then heated at 100° C. in a sealed tube for 16 h, at which time LC/MS analysis confirmed full consumption of starting material. On cooling, the solvent was rotoevaporated, and the crude residue was redissolved in EtOAc, washed with 0.5 M KF solution, brine (1×25 mL), and dried over MgSO$_4$. The solvent was removed in vacuo and the residue was purified by column chromatography on silica gel to give (1R,3s,5S)-tert-butyl 3-(7-(bis((2-(trimethylsilyl)ethoxy)methyl)amino)-6-(1-ethoxyvinyl)-3-(6-(1-methyl-1H-pyrazol-3-yl)pyridin-3-yl)pyrazolo[1,5-a]pyrimidin-5-yl)-8-azabicyclo[3.2.1]octane-8-carboxylate.

Step 4: Preparation of 1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone

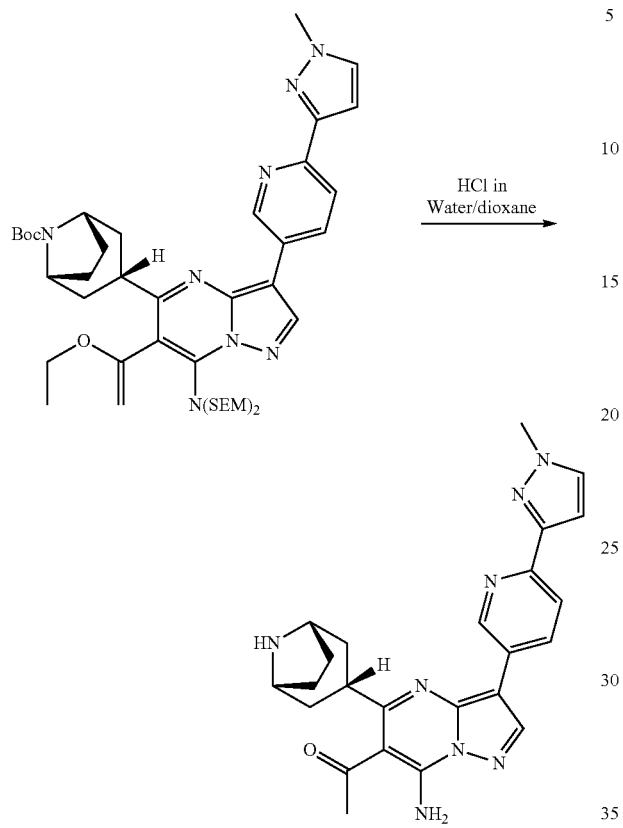

To a mixture of (1R,3s,5S)-tert-butyl 3-(7-(bis((2-(trimethylsilyl)ethoxy)methyl)amino)-6-(1-ethoxyvinyl)-3-(6-(1-methyl-1H-pyrazol-3-yl)pyridin-3-yl)pyrazolo[1,5-a]pyrimidin-5-yl)-8-azabicyclo[3.2.1]octane-8-carboxylate (6058.3 mg, 7.30 mmol) in dioxane (50 mL) was added 4 M HCl in water (60 ml) slowly. After stirring for 30 min at 50° C., the solvent was removed in vacuo to get 1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone as a HCl salt.

Step 5: Preparation of 1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone

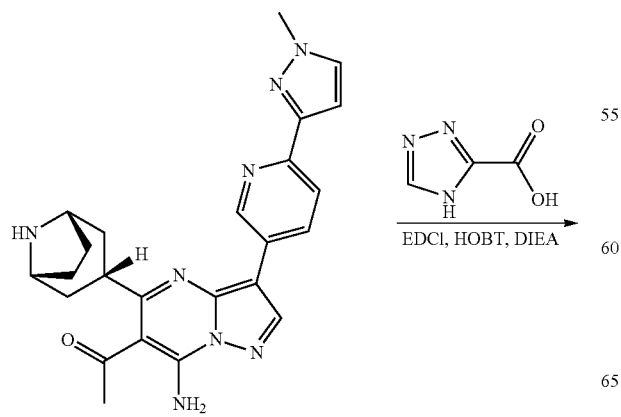

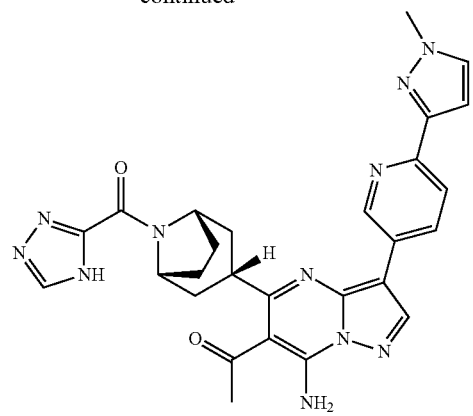

1H-1,2,4-triazole-3-carboxylic acid (58.0 mg, 0.51 mmol), EDC (133.7 mg, 0.70 mmol), HOBt (94.5 mg, 0.70 mmol) and DIEA (730 uL, 4.20 mmol) were added to a mixture of 1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone (207.7 mg, 0.47 mmol) in DMF (5 mL) and the mixture was stirred at room temperature for 1 h. Purification with prep-LC provided 1-(5-((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone.

Example 2-1

Preparation of ((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone

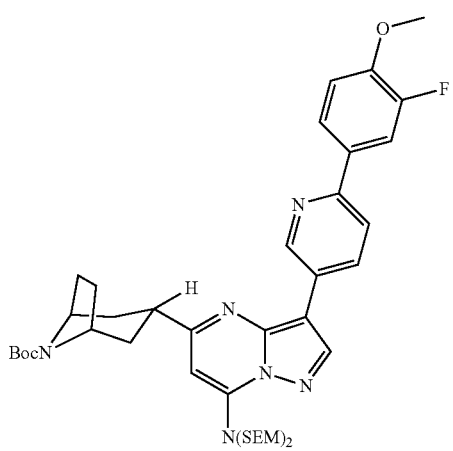

Step A—Synthesis of Tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate

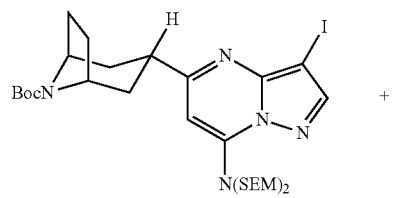

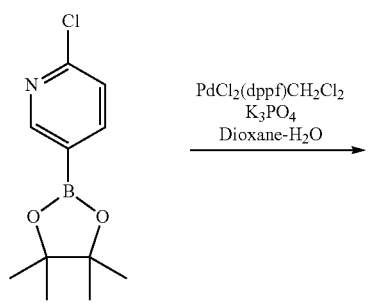

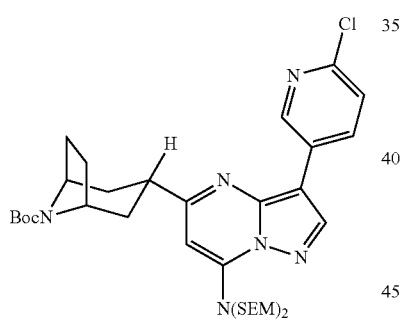

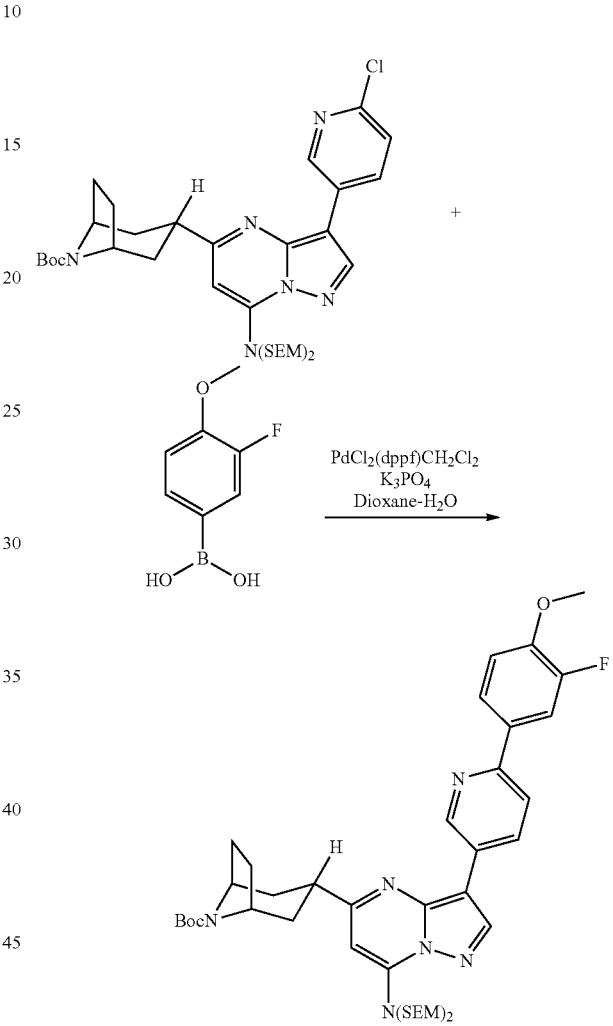

2-Chloro-5-(4,4,5,5-tetramethyl-1,3,2-dioxaborolan-2-yl)pyridine (5.55 mmol, 1327 mg), K$_3$PO$_4$ (14.48 mmol, 3070 mg), and PdCl$_2$(dppf).CH$_2$Cl$_2$ (0.48 mmol, 394 mg) were added to a solution of tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (1.98 mmol, 1101 mg) in dioxane (40 mL) and H$_2$O (4 mL). The resulting solution was stirred at 70° C. under argon overnight. The mixture was diluted with H$_2$O and then extracted with ethyl acetate (×2). The combined organic layers were washed with brine and dried with Na$_2$SO$_4$. Evaporation and purification by column chromatography afforded tert-butyl 3-(7-(bis((2-(trimethylsilyl)ethoxy)methyl)amino)-3-(6-chloropyridin-3-yl)pyrazolo[1,5-a]pyrimidin-5-yl)-8- azabicyclo[3.2.1]octane-8-carboxylate, LCMS t$_R$=3.29 Min (5 min run, UV$_{254nm}$, Mass calculated for M+H 715.35, observed LC/MS m/z 715.02 (M+H).

Step B—Synthesis of Tert-butyl 3-(7-(bis((2-(trimethylsilyl)ethoxy)methyl)amino)-3-(6-(3-fluoro-4-methoxyphenyl)pyridin-3-yl)pyrazolo[1,5-a]pyrimidin-5-yl)-8-azabicyclo[3.2.1]octane-8-carboxylate 3-Fluoro-4-methoxyphenylboronic acid (2.79 mmol, 475.7 mg), K$_3$PO$_4$ (4.20 mmol, 890.4 mg), and PdCl$_2$(dppf).CH$_2$Cl$_2$ (0.14 mmol, 114.3 mg) were added to a solution of tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.40 mmol, 1000 mg) in dioxane (12 mL) and H$_2$O (1.5 mL). The resulting solution was stirred at 150° C. under microwave condition for 1 h. The mixture was diluted with H$_2$O and then extracted with ethyl acetate (×2). The combined organic layers were washed with brine and dried with Na$_2$SO$_4$. Evaporation and purification by column chromatography afforded tert-butyl 3-(7-(bis((2-(trimethylsilyl)ethoxy)methyl)amino)-3-(6-(3-fluoro-4-methoxyphenyl)pyridin-3-yl)pyrazolo[1,5-a]pyrimidin-5-yl)-8-azabicyclo[3.2.1]octane-8-carboxylate, LCMS t$_R$=3.31 Min (5 min run, UV$_{254nm}$) Mass calculated for, M+H 805.42, observed LC/MS m/z 805.17 (M+H).

Example 2-2

Scheme 2-1

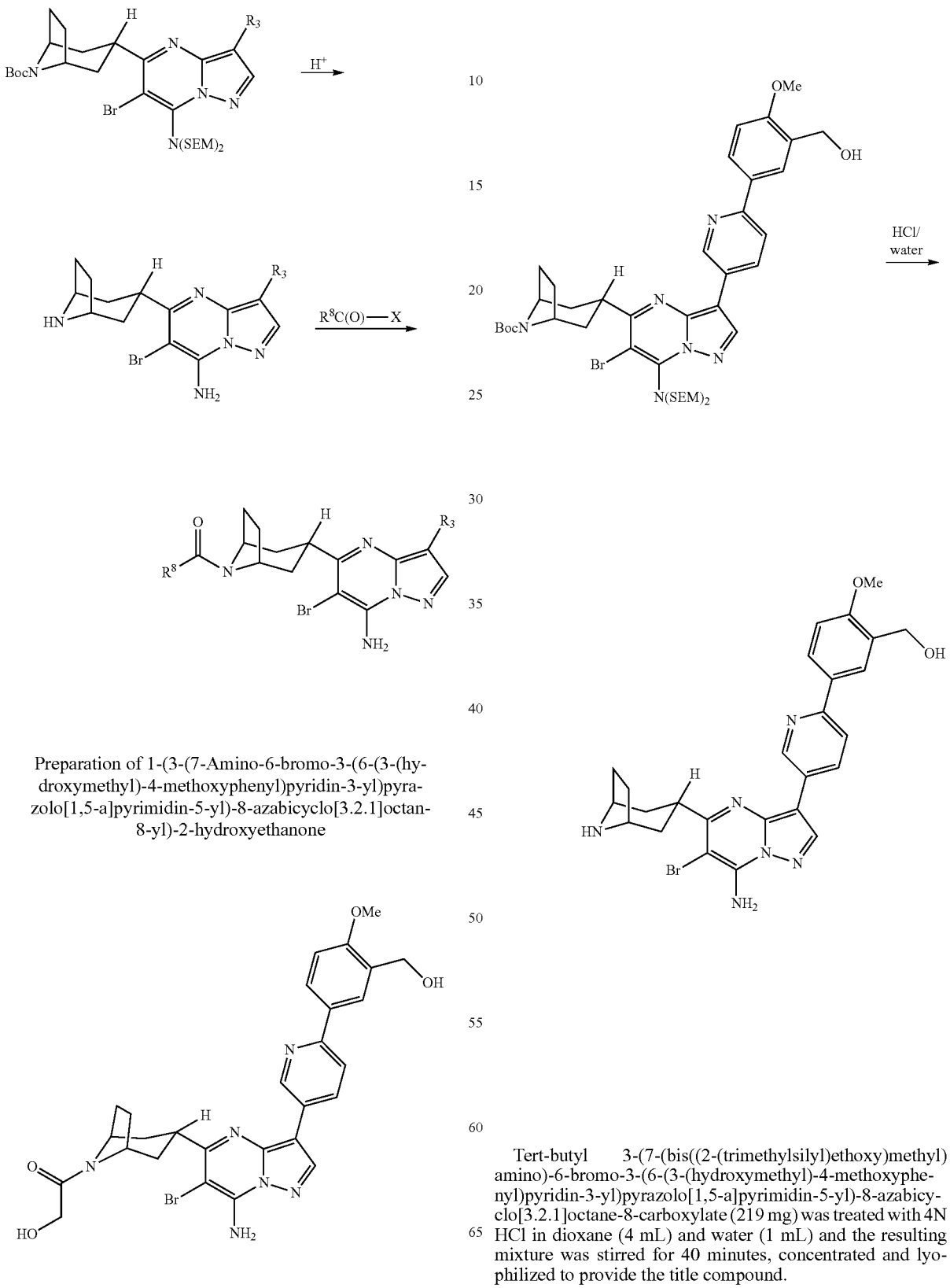

Preparation of 1-(3-(7-Amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone Step A—Synthesis of (5-(5-(7-Amino-5-(--8-azabicyclo[3.2.1]octan-3-yl)-6-bromopyrazolo[1,5-a]pyrimidin-3-yl)pyridin-2-yl-2-methoxyphenyl)methanol Tert-butyl 3-(7-(bis((2-(trimethylsilyl)ethoxy)methyl)amino)-6-bromo-3-(6-(3-(hydroxymethyl)-4-methoxyphenyl)pyridin-3-yl)pyrazolo[1,5-a]pyrimidin-5-yl)-8-azabicyclo[3.2.1]octane-8-carboxylate (219 mg) was treated with 4N HCl in dioxane (4 mL) and water (1 mL) and the resulting mixture was stirred for 40 minutes, concentrated and lyophilized to provide the title compound.

Step B—Synthesis of 1-(–3-(7-Amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone

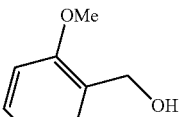

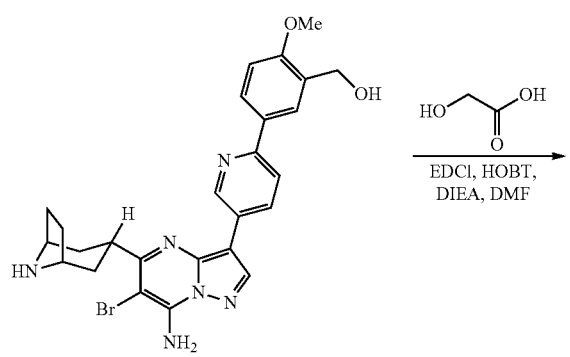

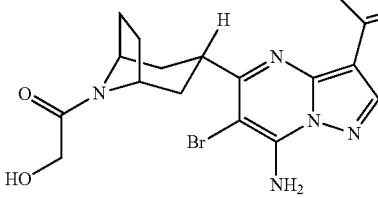

The preparation is similar to that described in Example 1-1 except using glycolic acid to replace 1H-1,2,4-triazole-3-carboxylic acid. LC/MS Retention time=3.34 min. Mass calculated for M+H 593.1, observed 592.9.

Following the procedures similar to preparation of ((1R, 3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone, the following compounds (Table 2-1) can be prepared:

TABLE 2-1

| Compound ID | Structures | Compound Name | M + H (calculated)/ M + H (observed) | pAKT S473 IC50 | p4E-BP1 Thr37/46 IC50 |
|---|---|---|---|---|---|
| 2.1 | 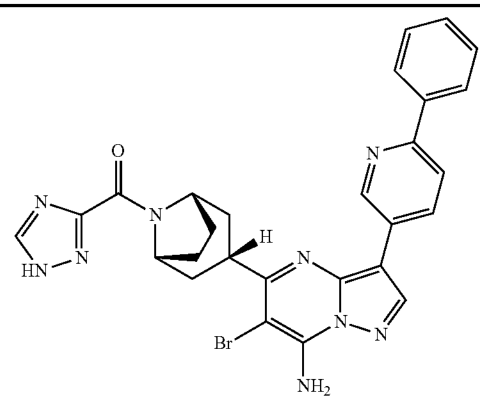 | ((1R,3s,5S)-3-(7-amino-6-bromo-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone | 570.1/569.7 | B | A |

TABLE 2-1-continued
| Compound ID | Structures | Compound Name | M + H (calculated)/ M + H (observed) | pAKT S473 IC50 | p4E-BP1 Thr37/46 IC50 |
|---|---|---|---|---|---|
| 2.2 | 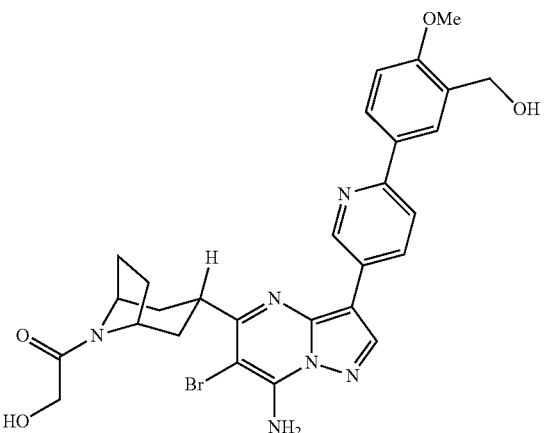 | 1-((1R,3s,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone | 593.2/593.0 | A | B |
| 2.3 | 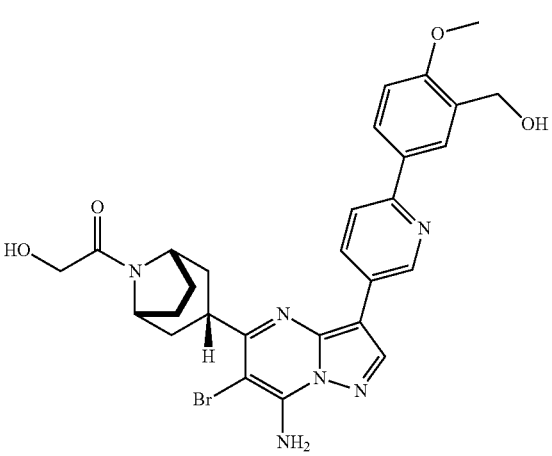 | (R)-1-((1R,3S,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxypropan-1-one | 607.2/606.9 | A | A |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.4 | 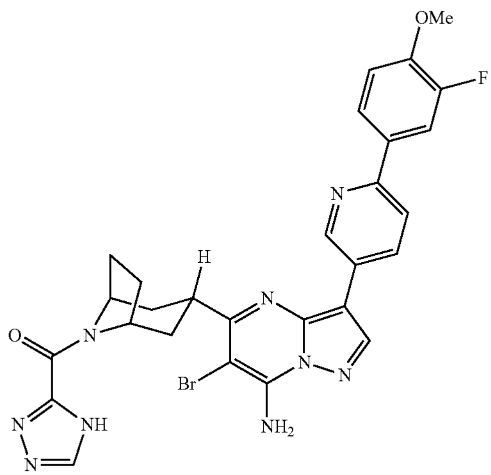 [SMILES: COc1ccc(-c2ccc(-c3cnn4c(N)c(Br)c(C5CC6CCC(C5)N6C(=O)c5nnc[nH]5)nc34)cn2)cc1F] | ((1R,3s,5S)-3-(7-amino-6-bromo-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 618.1/617.9 | B | B |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.5 | 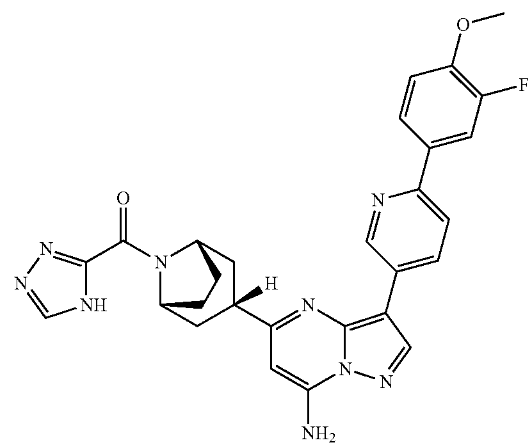 [SMILES: COc1ccc(-c2ccc(-c3cnn4c(N)cc([C@@H]5C[C@H]6CC[C@@H](C5)N6C(=O)c5nnc[nH]5)nc34)cn2)cc1F] | ((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 540.2/539.9 | B | C |
| 2.6 | 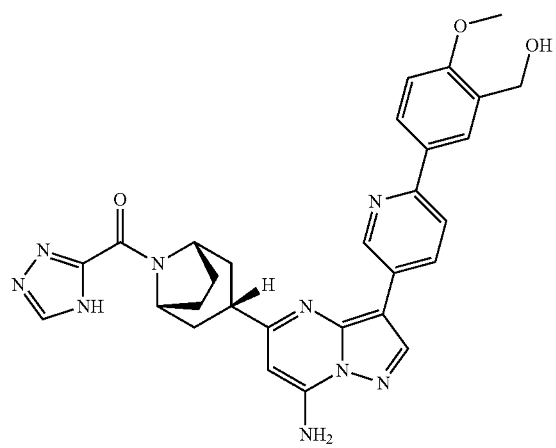 [SMILES: COc1ccc(-c2ccc(-c3cnn4c(N)cc([C@@H]5C[C@H]6CC[C@@H](C5)N6C(=O)c5nnc[nH]5)nc34)cn2)cc1CO] | ((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 552.2/552.2 | B | B |
| 2.7 | 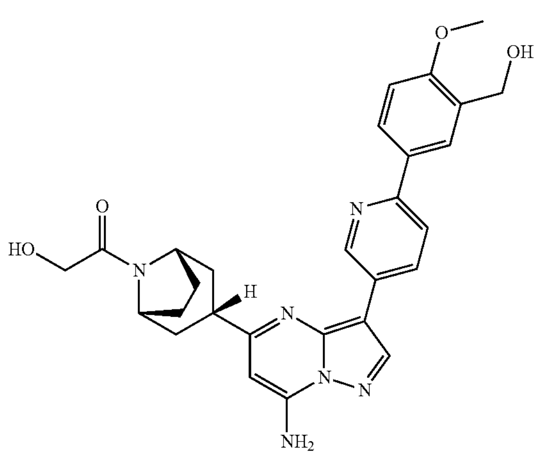 [SMILES: COc1ccc(-c2ccc(-c3cnn4c(N)cc([C@@H]5C[C@H]6CC[C@@H](C5)N6C(=O)CO)nc34)cn2)cc1CO] | 1-((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone | 515.2/515.2 | B | B |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.8 | 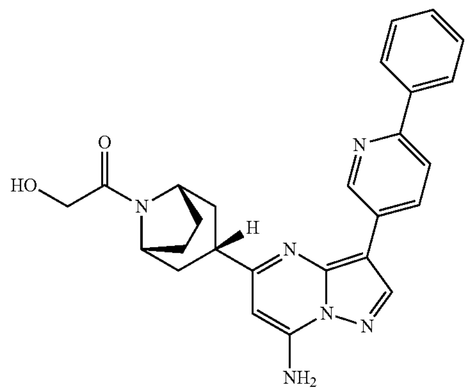 [SMILES: Nc1cc([C@@H]2C[C@H]3CC[C@@H](C2)N3C(=O)CO)nc2c(-c3ccc(-c4ccccc4)nc3)cnn12] | 1-((1R,3s,5S)-3-(7-amino-3-(6-phenylpyridin-3-yl)pyrazolo[1,5-a]pyrimidin-5-yl)-8-azabicyclo[3.2.1]octan-8-yl)-2-hydroxyethanone | 455.2/454.9 | B | C |
| 2.9 | 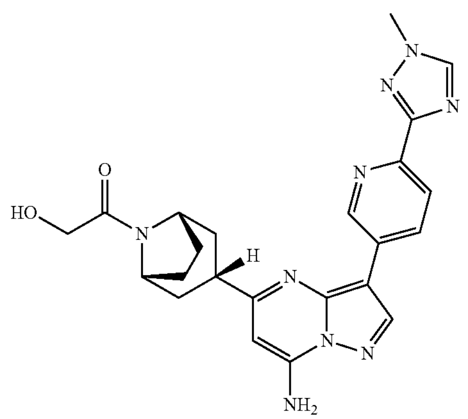 [SMILES: Cn1cnc(-c2ccc(-c3cnn4c(N)cc([C@@H]5C[C@H]6CC[C@@H](C5)N6C(=O)CO)nc34)cn2)n1] | 1-((1R,3s,5S)-3-(7-1-((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone | 460.2/460.0 | ND | ND |
| 2.10 | 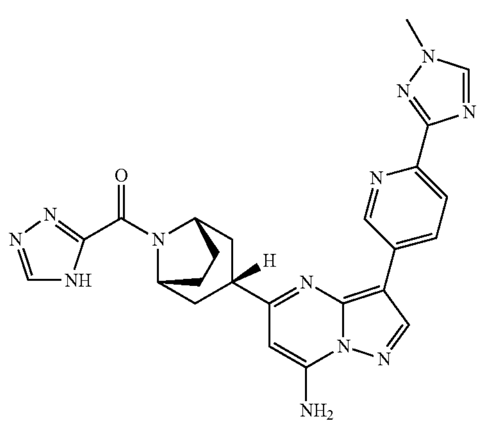 [SMILES: Cn1cnc(-c2ccc(-c3cnn4c(N)cc([C@@H]5C[C@H]6CC[C@@H](C5)N6C(=O)c5nnc[nH]5)nc34)cn2)n1] | ((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)(4H-1,2,4-triazol-3-yl)methanone | 497.2/497.0 | D | D |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.11 | 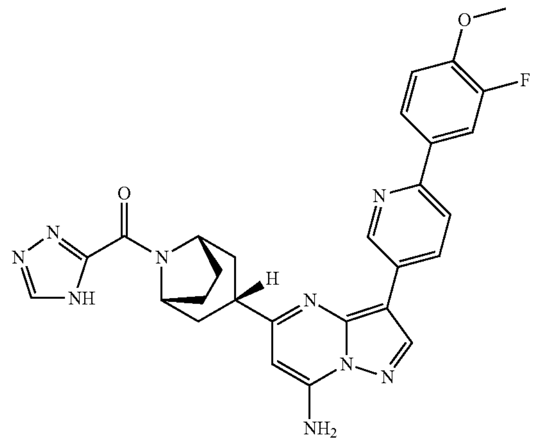 [SMILES: COc1ccc(-c2ccc(-c3cnn4c(N)cc([C@@H]5C[C@H]6CC[C@@H](C5)N6C(=O)c5nnc[nH]5)nc34)cn2)cc1F] | ((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 540.2/539.9 | B | C |
| 2.12 | 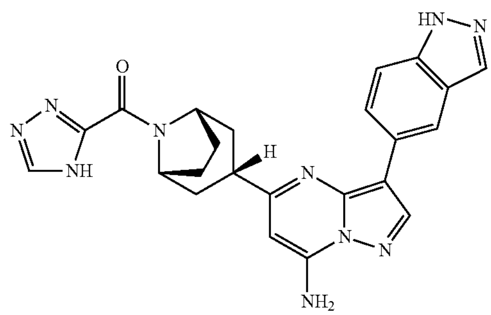 [SMILES: Nc1cc([C@@H]2C[C@H]3CC[C@@H](C2)N3C(=O)c2nnc[nH]2)nc2c(-c3ccc4[nH]ncc4c3)cnn12] | ((1R,3s,5S)-3-(7-amino-3-(1H-indazol-5-yl)pyrazolo[1,5-a]pyrimidin-5-yl)-8-azabicyclo[3.2.1]octan-8-yl)(1H-1,2,4-triazol-5-yl)methanone | 455.2/454.9 | D | D |
| 2.13 | 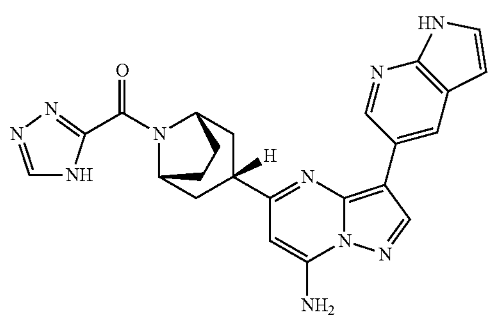 [SMILES: Nc1cc([C@@H]2C[C@H]3CC[C@@H](C2)N3C(=O)c2nnc[nH]2)nc2c(-c3cnc4[nH]ccc4c3)cnn12] | ((1R,3s,5S)-3-(7-amino-3-(1H-pyrrolo[2,3-b]pyridin-5-yl)pyrazolo[1,5-a]pyrimidin-5-yl)-8-azabicyclo[3.2.1]octan-8-yl)(1H-1,2,4-triazol-5-yl)methanone | 455.2/454.9 | C | C |
| 2.14 | 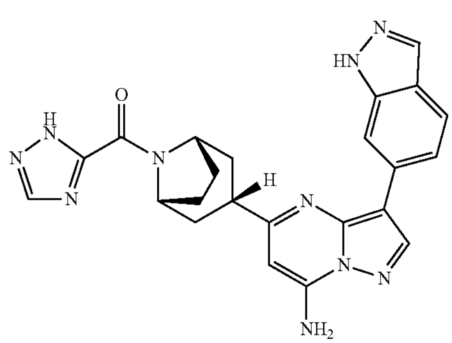 [SMILES: Nc1cc([C@@H]2C[C@H]3CC[C@@H](C2)N3C(=O)c2ncn[nH]2)nc2c(-c3ccc4cn[nH]c4c3)cnn12] | ((1R,3s,5S)-3-(7-amino-3-(1H-indazol-6-yl)pyrazolo[1,5-a]pyrimidin-5-yl)-8-azabicyclo[3.2.1]octan-8-yl)(1H-1,2,4-triazol-5-yl)methanone | 454.2/455.0 | ND | ND |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.15 | 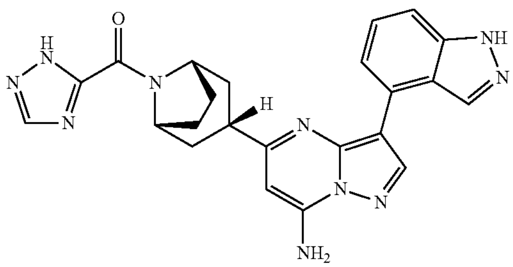 [SMILES: Nc1cc([C@@H]2C[C@H]3CC[C@@H](C2)N3C(=O)c2ncn[nH]2)nc2c(-c3cccc4[nH]ncc34)cnn12] | ((1R,3s,5S)-3-(7-amino-3-(1H-indazol-4-yl)pyrazolo[1,5-a]pyrimidin-5-yl)-8-azabicyclo[3.2.1]octan-8-yl)(1H-1,2,4-triazol-5-yl)methanone | 454.2/455.0 | ND | ND |
| 2.16 | 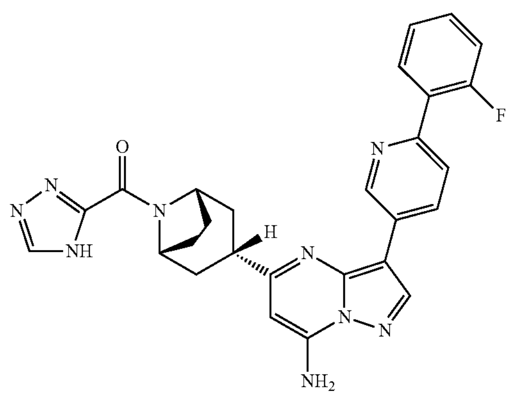 [SMILES: Nc1cc([C@@H]2C[C@H]3CC[C@@H](C2)N3C(=O)c2nnc[nH]2)nc2c(-c3ccc(-c4ccccc4F)nc3)cnn12] | ((1R,3s,5S)-3-(7-amino-3-(6-(2-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone | 510.2/510.2 | B | B |
| 2.17 | 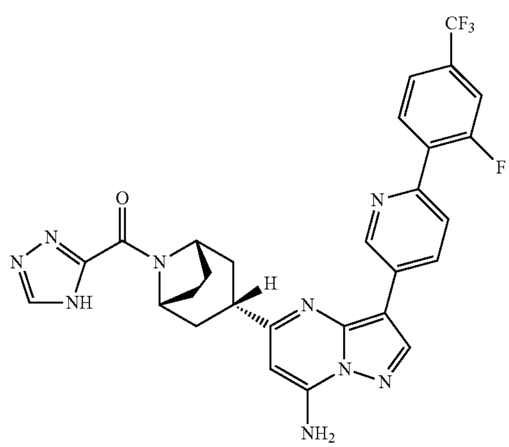 [SMILES: Nc1cc([C@@H]2C[C@H]3CC[C@@H](C2)N3C(=O)c2nnc[nH]2)nc2c(-c3ccc(-c4ccc(C(F)(F)F)cc4F)nc3)cnn12] | ((1R,3s,5S)-3-(7-amino-3-(6-(2-fluoro-4-(trifluoromethyl)phenyl)pyridin-3-yl)pyrazolo[1,5-a]pyrimidin-5-yl)-8-azabicyclo[3.2.1]octan-8-yl)(4H-1,2,4-triazol-3-yl)methanone | 578.2/578.2 | C | C |
| 2.18 | 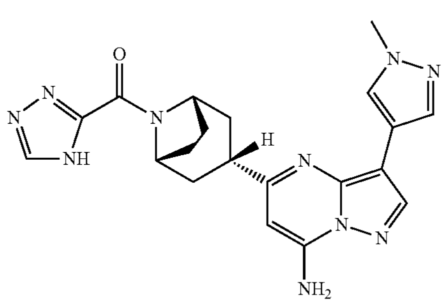 [SMILES: Cn1cc(-c2cnn3c(N)cc([C@@H]4C[C@H]5CC[C@@H](C4)N5C(=O)c4nnc[nH]4)nc23)cn1] | ((1R,3s,5S)-3-(7-amino-3-(1-methyl-1H-pyrazol-4-yl)pyrazolo[1,5-a]pyrimidin-5-yl)-8-azabicyclo[3.2.1]octan-8-yl)(4H-1,2,4-triazol-3-yl)methanone | 419.2/419.2 | ND | ND |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.19 | 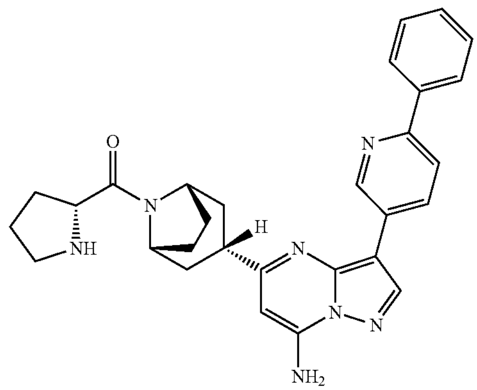 [SMILES: Nc1cc([C@@H]2C[C@H]3CC[C@@H](C2)N3C(=O)[C@H]2CCCN2)nc2c(-c3ccc(-c4ccccc4)nc3)cnn12] | ((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-pyrrolidin-2-yl)methanone | 493.3/494.2 | B | C |
| 2.20 | 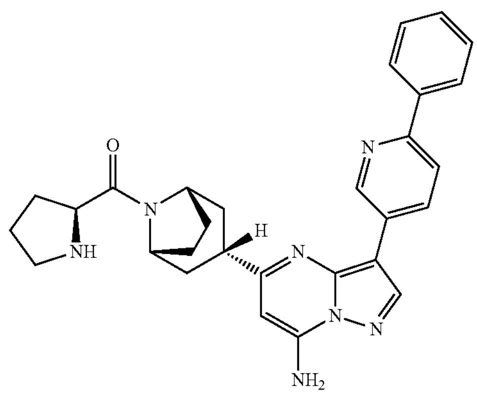 [SMILES: Nc1cc([C@@H]2C[C@H]3CC[C@@H](C2)N3C(=O)[C@@H]2CCCN2)nc2c(-c3ccc(-c4ccccc4)nc3)cnn12] | ((1R,3R,5S)-3-(7-amino-3-(6-phenylpyridin-3-yl)pyrazolo[1,5-a]pyrimidin-5-yl)-8-azabicyclo[3.2.1]octan-8-yl((S)-pyrrolidin-2-yl)methanone | 493.3/494.2 | C | C |
| 2.21 | 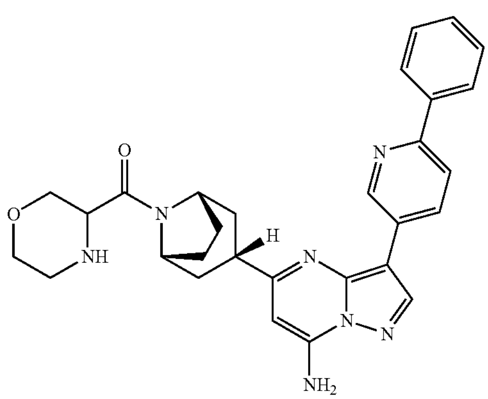 [SMILES: Nc1cc([C@@H]2C[C@H]3CC[C@@H](C2)N3C(=O)C2COCCN2)nc2c(-c3ccc(-c4ccccc4)nc3)cnn12] | ((1R,3s,5S)-3-(7-amino-3-(6-phenylpyridin-3-yl)pyrazolo[1,5-a]pyrimidin-5-yl)-8-azabicyclo[3.2.1]octan-8-yl)(morpholin-3-yl)methanone | 509.3/510.2 | ND | ND |

TABLE 2-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 2.22 | 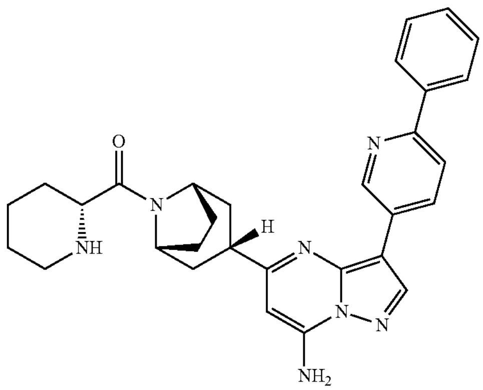 [SMILES: Nc1cc([C@@H]2C[C@H]3CC[C@@H](C2)N3C(=O)[C@H]2CCCCN2)nc2c(-c3ccc(-c4ccccc4)nc3)cnn12] | ((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-piperidin-2-yl)methanone | 507.3/508.0 | ND | ND |
| 2.23 | 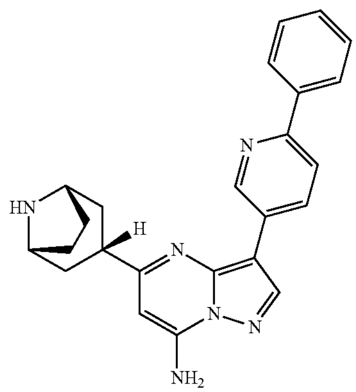 [SMILES: Nc1cc([C@@H]2C[C@H]3CC[C@@H](C2)N3)nc2c(-c3ccc(-c4ccccc4)nc3)cnn12] | 5-((1R,3s,5S)-8-azabicyclo[3.2.1]octan-3-yl)-3-(6-phenylpyridin-3-yl)pyrazolo[1,5-a]pyrimidin-7-amine | 396.2/397.0 | C | C |

Example 3-1

Preparation of (((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone

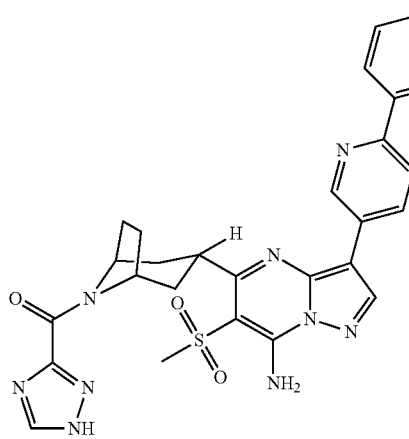

Method A:

Scheme 3-1

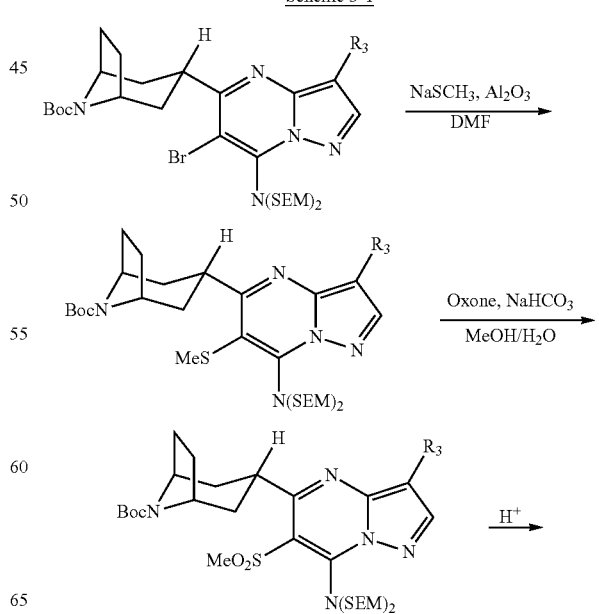

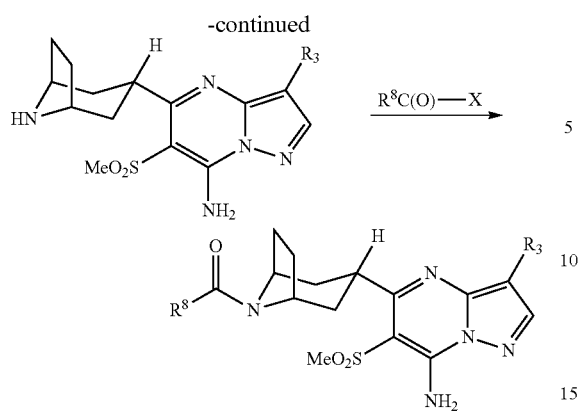

Step A—Synthesis of Tert-butyl 3-(7-(bis((2-(trimethylsilyl)ethoxy)methyl)amino)-6-(methylthio)-3-(6-phenylpyridin-3-yl)pyrazolo[1,5-a]pyrimidin-5-yl)-8-azabicyclo[3.2.1]octane-8-carboxylate

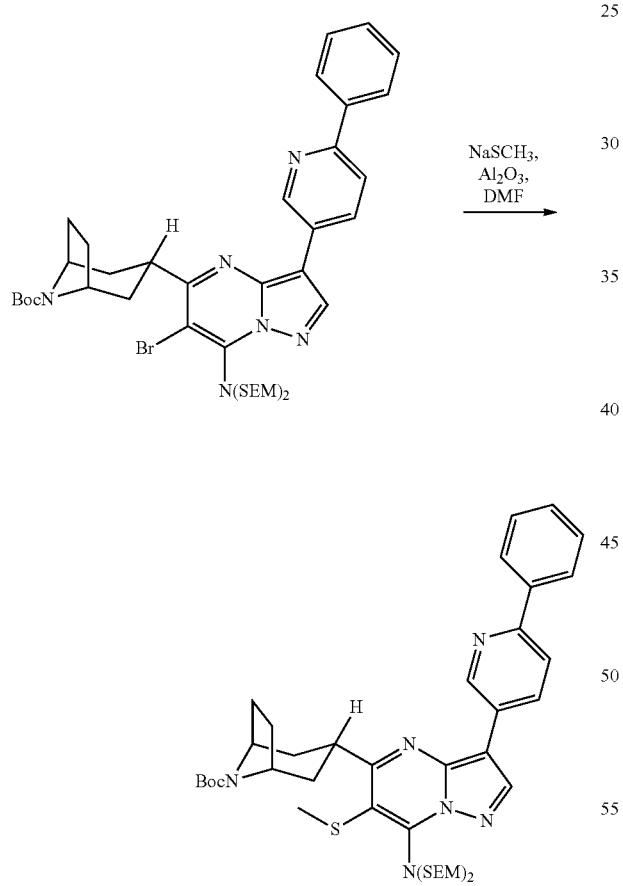

A mixture of tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (417 mg, 0.5 mmol), Al$_2$O$_3$ (510 mg, 5 mmol) and NaSCH$_3$ (70 mg, 1 mmol) in DMF (4 mL) was heated at 80° C. for 15 h, at which time LC/MS confirmed full conversion of starting material to product (i.e., no starting material was present). The reaction mixture was cooled to room temperature and diluted with EtOAc (25 mL). It was then filtered and the filtrate was washed with water (2×3 mL), brine (1×3 mL) and dried over MgSO$_4$. The solvent was removed to give the crude product which was purified by column chromatography on silica gel eluting with 25% EtOAc/Hexanes to give the desired product (301 mg).

Step B—Synthesis of Tert-butyl 3-(7-amino-6-(methylsulfonyl)-3-(6-phenylpyridin-3-yl)pyrazolo[1,5-a]pyrimidin-5-yl)-8-azabicyclo[3.2.1]octane-8-carboxylate

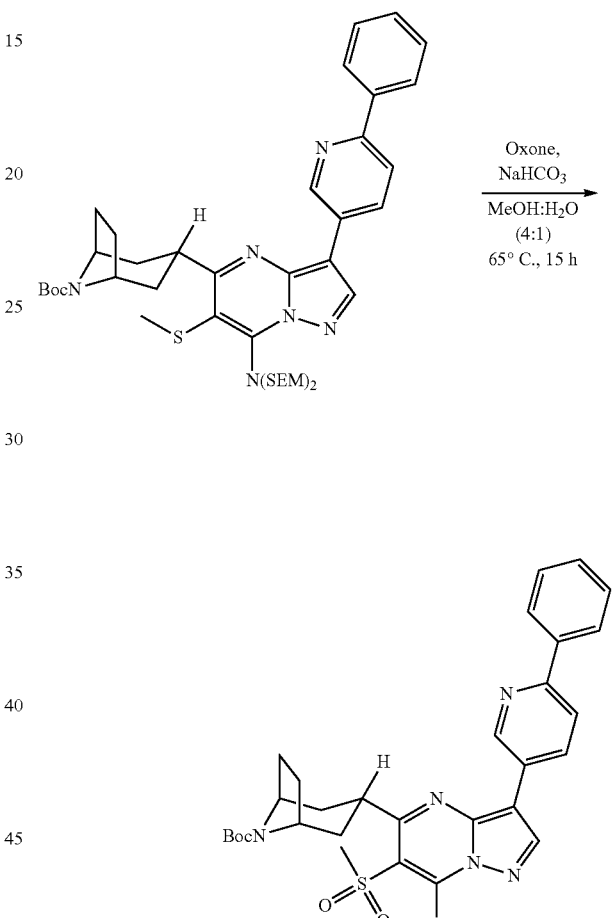

A mixture of compound tert-butyl 3-(7-(bis((2-(trimethylsilyl)ethoxy)methyl)amino)-6-(methylthio)-3-(6-phenylpyridin-3-yl)pyrazolo[1,5-a]pyrimidin-5-yl)-8-azabicyclo[3.2.1]octane-8-carboxylate (319 mg, 0.4 mmol), Oxone (1.2 g, 2 mmol) and NaHCO$_3$ (336 mg, 4 mmol) in MeOH (12 mL) and Water (3 mL) was heated at 65° C. for 15 h, at which time LC/MS analysis confirmed full consumption of starting material. After cooling, it was diluted with DCM: MeOH (1:1, 100 mL) and filtered. The filtrate was concentrated to afford the crude title product which was used for the next step without further purification.

Step C—Preparation of 5-(8-Azabicyclo[3.2.1]octan-3-yl-6-(methylsulfonyl)-3-(6-phenylpyridin-3-yl)pyrazolo[1,5-a]pyrimidin-7-amine

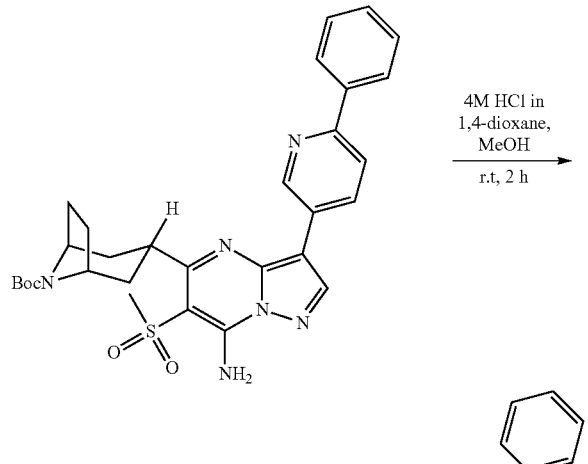

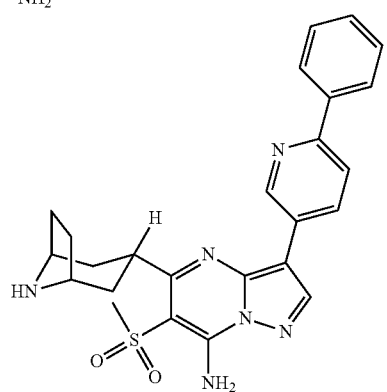

To the crude tert-butyl 3-(7-amino-6-(methylsulfonyl)-3-(6-phenylpyridin-3-yl)pyrazolo[1,5-a]pyrimidin-5-yl)-8-azabicyclo[3.2.1]octane-8-carboxylate in MeOH (5 mL) was added 4M HCl in 1,4-dioxane at r.t. It was stirred further at room temperature for 2 h, at which time LC/MS analysis confirmed full consumption of the starting material. The solvent was removed in vacuo to afford the desired product as an HCl salt.

Step D—Synthesis ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone

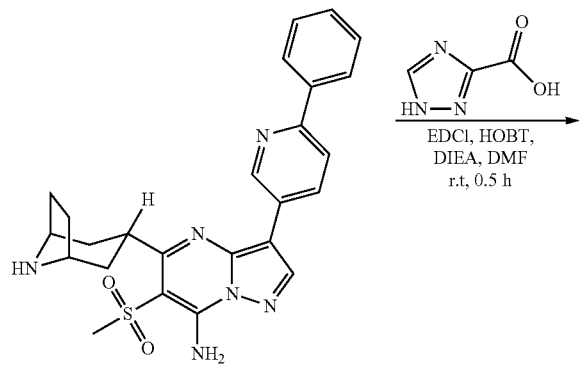

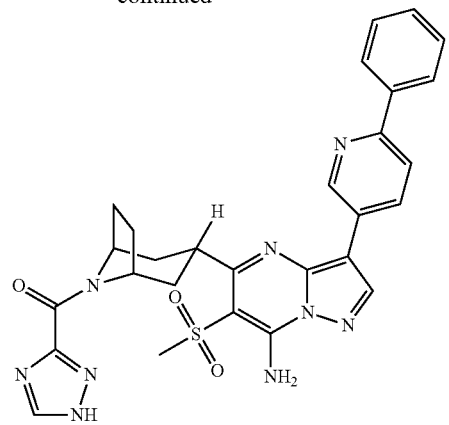

A mixture of 1H-1,2,4-triazole-3-carboxylic acid (29.4 mg, 0.26 mmol), EDCI (76.7 mg, 0.4 mmol), and 1-hydroxybenzotriazole (27 mg, 0.2 mmol) in DMF (2 mL) was stirred at room temperature for 10 min. The 5-(8-azabicyclo[3.2.1]octan-3-yl)-6-(methylsulfonyl)-3-(6-phenylpyridin-3-yl)pyrazolo[1,5-a]pyrimidin-7-amine HCl (0.2 mmol) was added, followed by N,N-diisopropylethylamine (0.17 mL, 1 mmol). It was stirred further for 20 min at room temperature at which time LC/MS analysis confirmed full consumption of starting material. This crude compound was purification by HPLC to afford the desired title product.

Method 2:

Scheme 3-2

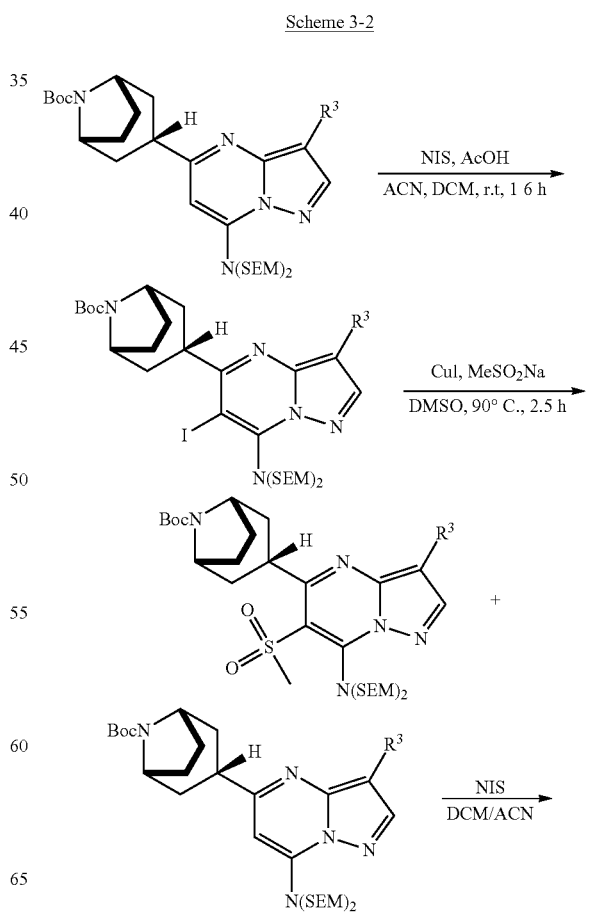

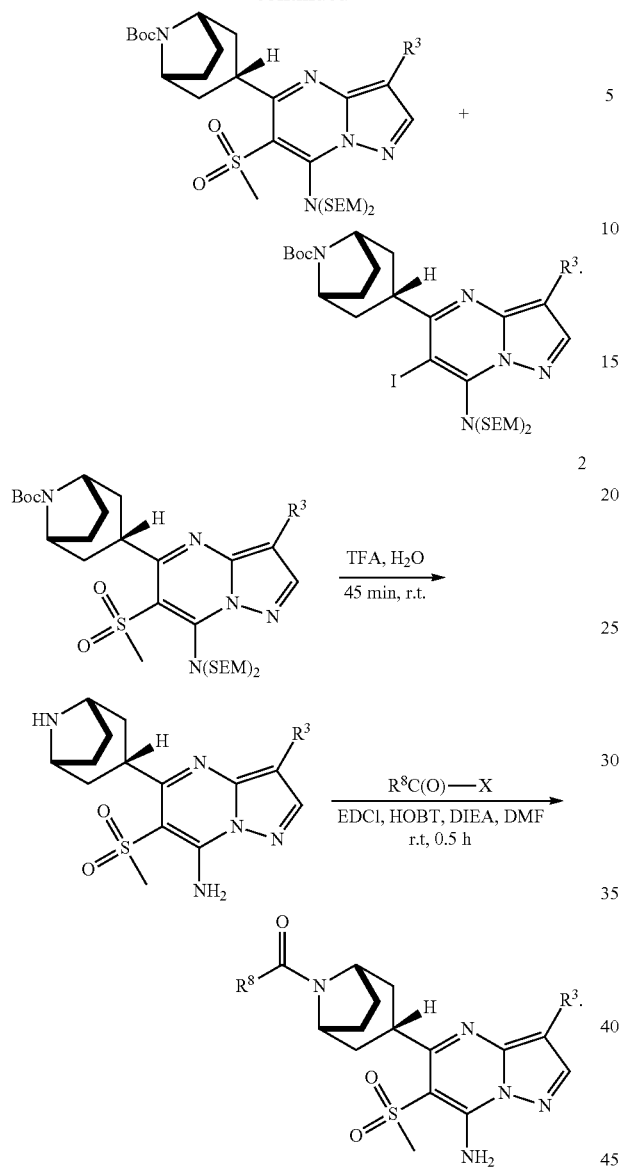

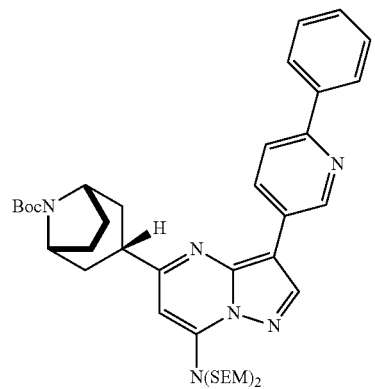

To (1R,3s,5S)-tert-butyl 3-(7-(bis((2-(trimethylsilyl)ethoxy)methyl)amino)-3-iodo pyrazolo[1,5-a]pyrimidin-5-yl)-8-azabicyclo[3.2.1]octane-8-carboxylate (10.1 g, 13.9 mmol) in dioxane (100 mL) and water (25 mL) was added 2-phenyl-5-(4,4,5,5-tetra methyl-1,3,2-dioxaborolan-2-yl)pyridine (5.9 g, 20.8 mmol), PdCl$_2$(dppf)·CH$_2$Cl$_2$ (1.4 g, 1.7 mmol) and K$_2$CO$_3$ (5.8 g, 41.6 mmol). The reaction mixture was heated at 100° C. for 16 hour, at which time LC/MS analysis confirmed full consumption of starting material. On cooling, the solvent was removed in vacuo, and the crude was redissolved in EtOAc (500 mL), washed with water (1×125 mL), brine (1×125 mL), and dried over MgSO$_4$. Gradient column chromatography on silica gel eluting with 0 to 50% EtOAc/hexanes gave the desired (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl-8-azabicyclo[3.2.1]octane-8-carboxylate (8.6 g).

Step 2. Synthesis of (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate Step 1. Synthesis of (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate

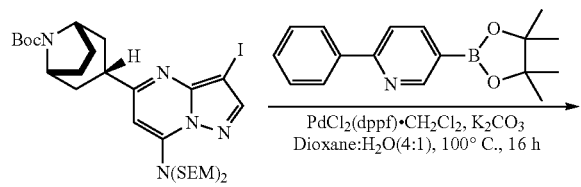

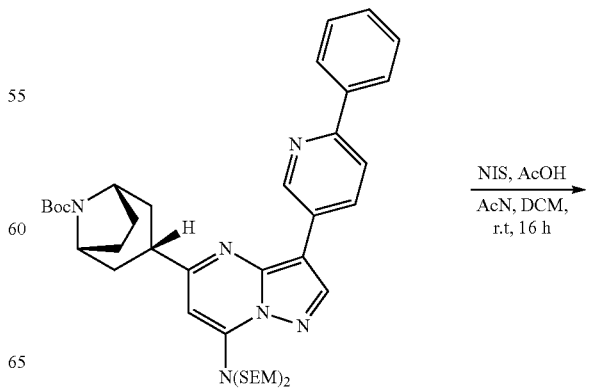

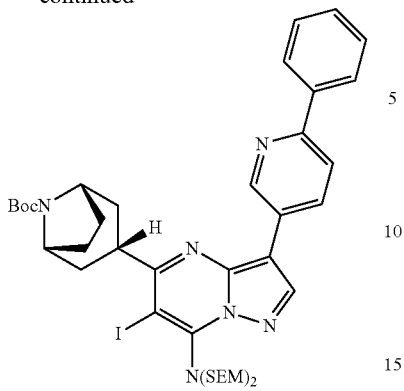

To (1R,3s,5S)-tert-butyl 3-(7-(bis((2-(trimethylsilyl)ethoxy)methyl)amino)-3-(6-phenyl pyridin-3-yl)pyrazolo[1,5-a]pyrimidin-5-yl)-8-azabicyclo[3.2.1]octane-8-carboxylate (16.9 g, 22.4 mmol) in CH$_3$CN (75 mL) and DCM (75 mL) was added AcOH (15.4 mL, 268.6 mmol) followed by N-iodosuccinimide (10.1 g, 44.8 mmol) portionwise and the resulting mixture was stirred at room temperature for 16 hour, at which time LC/MS confirmed full conversion of starting material to product. Solvent was removed in vacuo and the residue was dissolved in EtOAc (500 mL). To this solution was added 28 g of NaHCO$_3$ in 200 mL of water. It was then stirred at room temperature for 20 min. Organics were extracted and washed with water (1×200 mL), brine (1×200 mL), and dried over MgSO$_4$. Solvent was removed in vacuo and the residue was purified by column chromatography on silica gel. Elution with EtOAc/Hexanes (0-40%) gave desired product, (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate (18.2 g).

Step 3. Synthesis of (1R,3s,5S)-tert-butyl 3-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-8-azabicyclo[3.2.1]octane-8-carboxylate

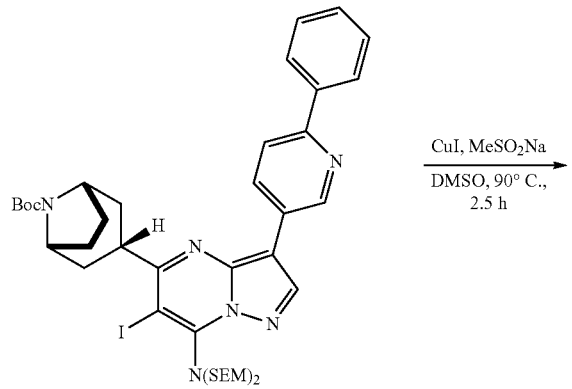

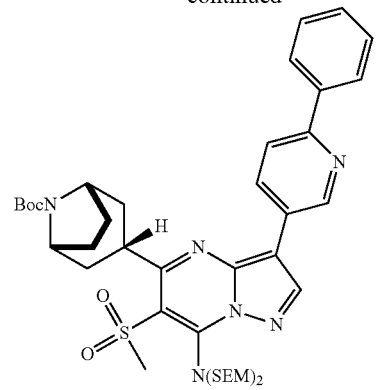

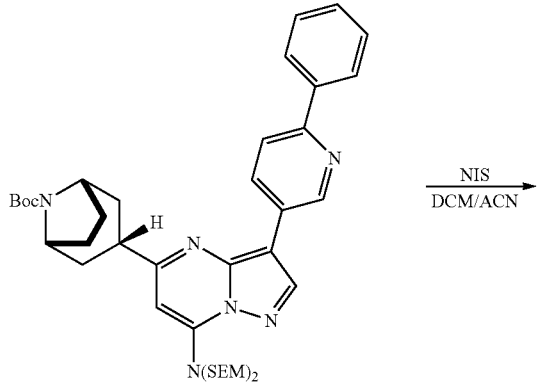

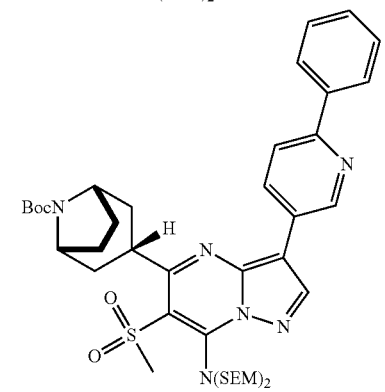

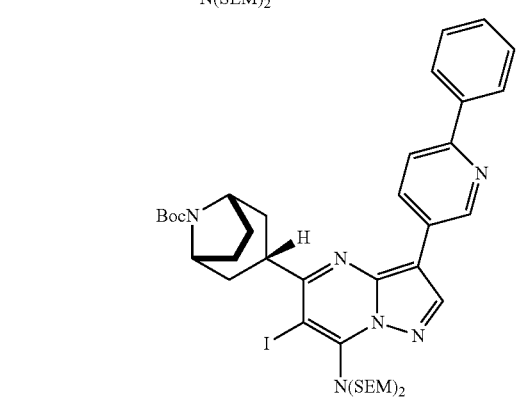

A mixture of (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl-8-azabicyclo[3.2.1]octane-8-carboxylate (21.5 g, 24.4 mmol), CuI (27.9 g, 146.3 mmol) and sodiummethane sulfinate (7.5 g, 73.2 mmol) in DMSO (195 mL) was degassed with argon for five minutes. It was then heated at 90° C. in a sealed tube for 2.5 hour, at which time LC/MS analysis confirmed full consumption of starting material to product. On cooling, EtOAc (1000 mL) were added and solids were filtered off on a celite pad. Filtrate was washed with sat. NH$_4$Cl (1×200 mL), water (3×200 mL), brine (1×200 mL), and dried over MgSO$_4$. Solvent was removed in vacuo and the crude was subjected to iodination condition one more time in order to purify it by column chromatography on silica gel.

To the above crude mixture in CH$_3$CN (90 mL) and DCM (90 mL) was added AcOH (16.8 mL, 292.7 mmol) followed by N-iodosuccinimide (2.7 g, 12.2 mmol) portionwise and the resulting mixture was stirred at room temperature for 16 hour, at which time LC/MS confirmed full conversion of starting material to product. Solvent was removed in vacuo and the residue was dissolved in EtOAc (500 mL). To this solution was added 28 g of NaHCO$_3$ in 200 mL of water. It was then stirred at room temperature for 20 minutes. Organics were extracted and washed with water (1×200 mL), brine (1×200 mL), and dried over MgSO4. Solvent was removed in vacuo and the residue was purified by column chromatography on silica gel. Elution with EtOAc/Hexanes (0-40%) gave desired product, (1R,3s,5S)-tert-butyl 3-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-8-aza bicyclo[3.2.1]octane-8-carboxylate (12.6 g, 62%) and starting material (1R,3s,5S)-tert-butyl 3-(7-(bis((2-(trimethylsilyl)ethoxy)methyl)amino)-6-iodo-3-(6-phenyl pyridin-3-yl)pyrazolo[1,5-a]pyrimidin-5-yl-8-azabicyclo[3.2.1]octane-8-carboxylate (5.8 g).

Step 4. Synthesis of 5-((1R,3s,5S)-8-azabicyclo[3.2.1]octan-3-yl)-6-(methyl sulfonyl)-3-(6-phenylpyridin-3-yl)pyrazolo[1,5-a]pyrimidin-7-amine (1R,3s,5S)-tert-butyl 3-(7-(bis((2-(trimethylsilyl)ethoxy)methyl)amino)-6-(methyl sulfonyl)-3-(6-phenylpyridin-3-yl)pyrazolo[1,5-a]pyrimidin-5-yl)-8-azabicyclo[3.2.1]octane-8-carboxylate (12.3 g, 14.8 mmol) was dissolved in a mixture of TFA (60 mL) and water (6 mL) at room temperature. Stirring continued for 45 min at room temperature. LC/MS analysis confirmed full consumption of starting material to product. TFA along with water was rotoevaporated, and the crude product 5-((1R,3s,5S)-8-aza bicyclo[3.2.1]octan-3-yl)-6-(methylsulfonyl)-3-(6-phenylpyridin-3-yl)pyrazolo[1,5-a]pyrimidin-7-amine was dried under the high vacuum for 24 hour, which was used without further purification for the next step.

Step 5. Synthesis of ((1R,3s,5S)-3-(7-amino-6-(methylsulfonyl)-3-(6-phenyl pyridin-3-yl)pyrazolo[1,5-a]pyrimidin-5-yl-8-azabicyclo[3.2.1]octan-8-yl)(1H-1,2,4-triazol-3-yl)methanone

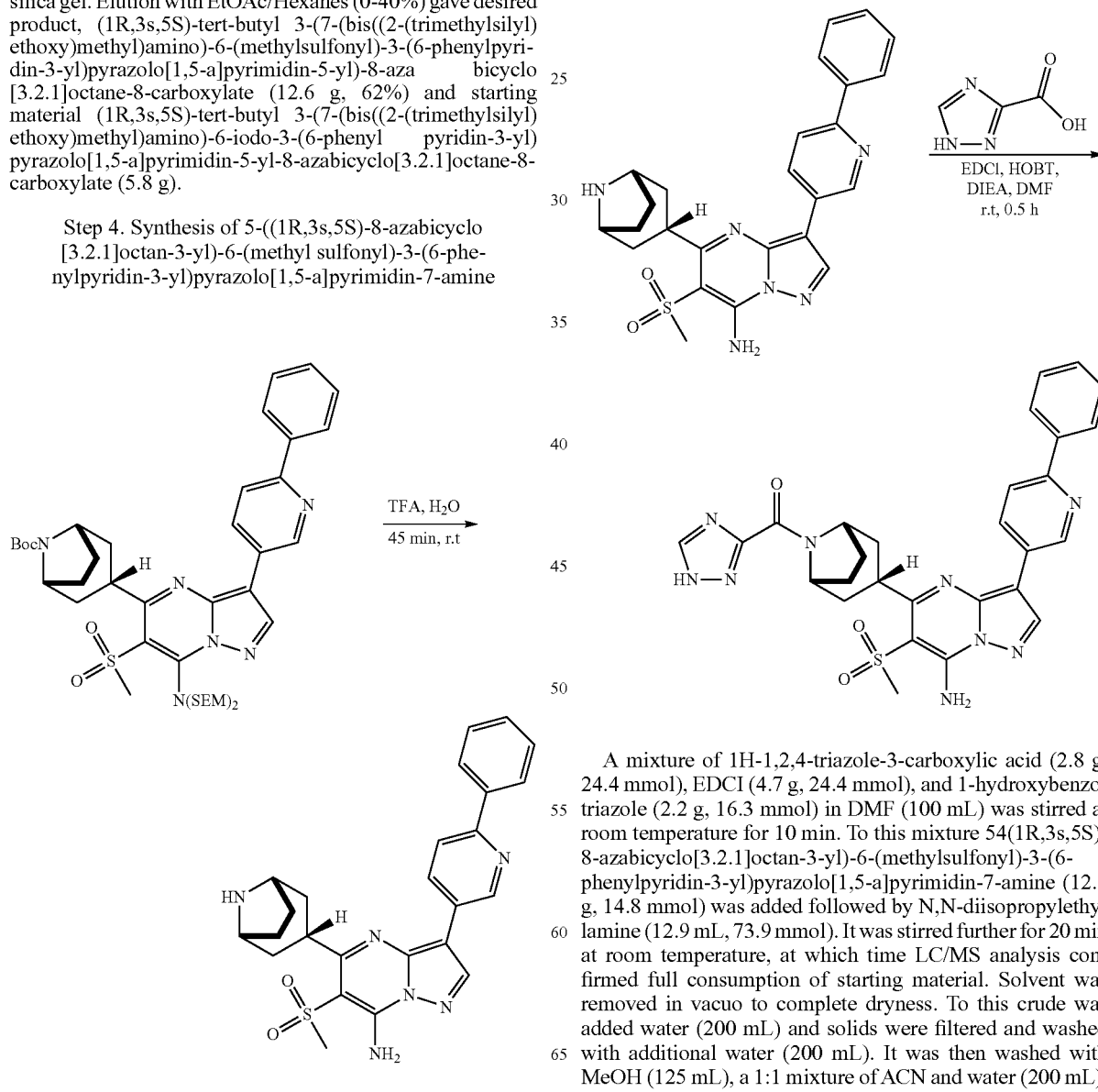

A mixture of 1H-1,2,4-triazole-3-carboxylic acid (2.8 g, 24.4 mmol), EDCI (4.7 g, 24.4 mmol), and 1-hydroxybenzotriazole (2.2 g, 16.3 mmol) in DMF (100 mL) was stirred at room temperature for 10 min. To this mixture 54(1R,3s,5S)-8-azabicyclo[3.2.1]octan-3-yl)-6-(methylsulfonyl)-3-(6-phenylpyridin-3-yl)pyrazolo[1,5-a]pyrimidin-7-amine (12.2 g, 14.8 mmol) was added followed by N,N-diisopropylethylamine (12.9 mL, 73.9 mmol). It was stirred further for 20 min at room temperature, at which time LC/MS analysis confirmed full consumption of starting material. Solvent was removed in vacuo to complete dryness. To this crude was added water (200 mL) and solids were filtered and washed with additional water (200 mL). It was then washed with MeOH (125 mL), a 1:1 mixture of ACN and water (200 mL), ACN (100 mL) and diethyl ether (100 mL) successively to afford ((1R,3s,5S)-3-(7-amino-6-(methylsulfonyl)-3-(6-phenyl pyridin-3-yl)pyrazolo[1,5-a]pyrimidin-5-yl)-8-azabicyclo[3.2.1]octan-8-yl)(1H-1,2,4-triazol-3-yl)methanone (7.5 g).

Step 6. Synthesis of ((1R,3s,5S)-3-(7-amino-6-(methylsulfonyl)-3-(6-phenyl pyridin-3-yl)pyrazolo[1,5-a]pyrimidin-5-yl)-8-azabicyclo[3.2.1]octan-8-yl)(1H-1,2,4-triazol-3-yl)methanone hydrochloride pyrimidin-5-yl)-8-azabicyclo[3.2.1]octan-8-yl)(1H-1,2,4-triazol-3-yl)methanone as an HCl salt (8.5 g).

Example 3-2

Synthesis of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboxamide

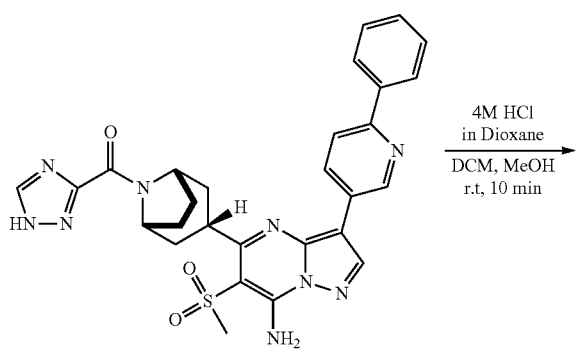

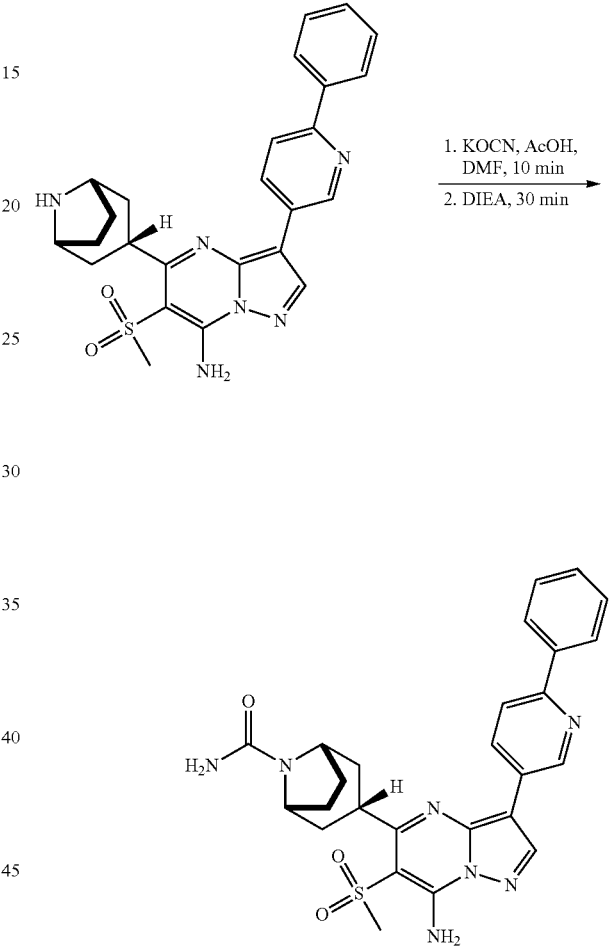

To a suspension of ((1R,3s,5S)-3-(7-amino-6-(methylsulfonyl)-3-(6-phenyl pyridin-3-yl)pyrazolo[1,5-a]pyrimidin-5-yl)-8-azabicyclo[3.2.1]octan-8-yl)(1H-1,2,4-triazol-3-yl)methanone (8 g, 14.1 mmol) in DCM (350 mL) and MeOH (100 mL) was added 4M HCl in 1,4-dioxane (14.1 mL, 56.2 mmol). It was stirred further for 10 min at room temperature during which time solution became clear. Solvent was removed in vacuo until solids were precipitate out. To this crude was added diethyl ether (200 mL) and solids were filtered and washed with additional diethyl ether (800 mL). Solids were redissolved in a 1:1 mixture of ACN and water and lyophilized to get the desired ((1R,3s,5S)-3-(7-amino-6-(methyl sulfonyl)-3-(6-phenylpyridin-3-yl)pyrazolo[1,5-a]

A mixture of potassium cyanate (0.24 g, 3 mmol) and AcOH (0.17 mL, 3 mmol) in DMF (2 mL) was stirred at room temperature for 10 minutes. To this solution was added 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine (0.17 g, 0.2 mmol) followed by N,N-diisopropyl ethylamine (0.5 mL, 3 mmol). It was stirred further for 30 min at room temperature, at which time LC/MS analysis confirmed full consumption of starting material. Pure compound (1R, 3s,5S)-3-(7-amino-6- (methylsulfonyl)-3-(6-phenylpyridin- 3-yl)pyrazolo[1,5-a]pyrimidin-5-yl)-8-azabicyclo[3.2.1]octane-8-carboxamide was isolated by preparative HPLC.

Example 3-3

Synthesis of (1R,3s,5S)-3-(7-amino-6-(methylsulfonyl)-3-(6-phenylpyridin-3-yl)pyrazolo[1,5-a]pyrimidin-5-yl)-N-ethyl-8-azabicyclo[3.2.1]octane-8-carboxamide

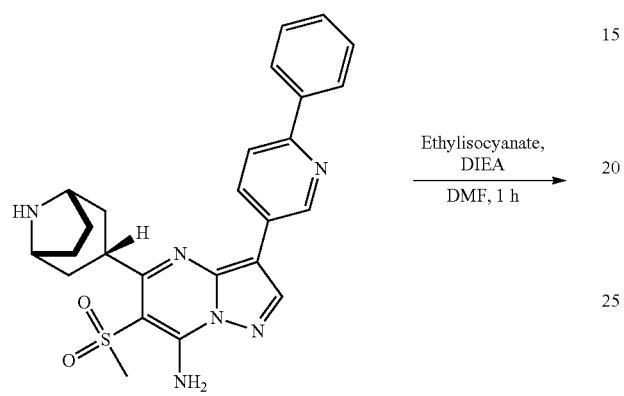

To 5-((1R,3s,5S)-8-azabicyclo[3.2.1]octan-3-yl)-6-(methylsulfonyl)-3-(6-phenyl pyridin-3-yl)pyrazolo[1,5-a]pyrimidin-7-amine (0.17 g, 0.2 mmol) in DMF (2 mL) was added N,N-diisopropylethylamine (0.18 mL, 1 mmol) followed by ethyl isocyanate (16 μL, 0.2 mmol). The reaction mixture was stirred at room temperature for 1 hour, at which time LC/MS analysis confirmed full consumption of starting material. Pure compound (1R,3s,5S)-3-(7-amino-6-(methylsulfonyl)-3-(6-phenylpyridin-3-yl)pyrazolo[1,5-a]pyrimidin-5-yl)-N-ethyl-8-azabicyclo[3.2.1]octane-8-carboxamide was isolated by preparative HPLC.

Example 3-4

Preparation of (1R,3s,5S)-tert-butyl 3-(7-(bis((2-(trimethylsilyl)ethoxy)methyl)amino)-3-(6-(methylcarbamoyl)pyridin-3-yl)pyrazolo[1,5-a]pyrimidin-5-yl)-8-azabicyclo[3.2.1]octane-8-carboxylate

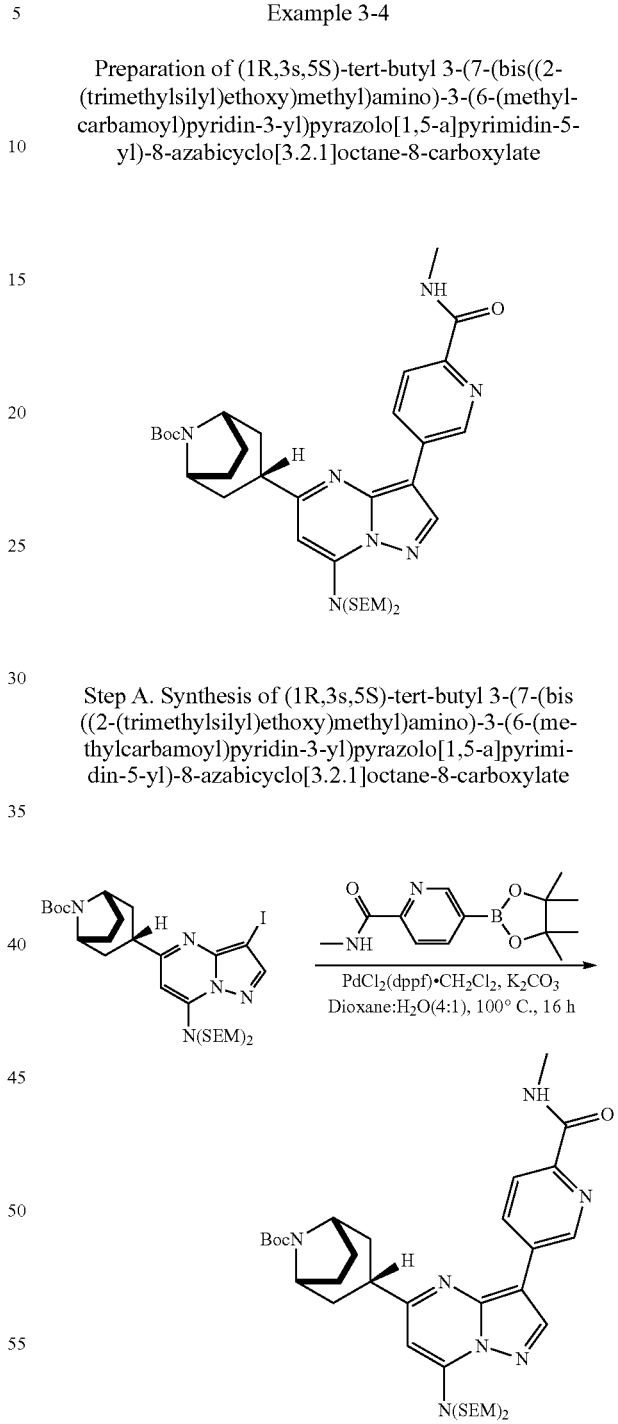

Step A. Synthesis of (1R,3s,5S)-tert-butyl 3-(7-(bis((2-(trimethylsilyl)ethoxy)methyl)amino)-3-(6-(methylcarbamoyl)pyridin-3-yl)pyrazolo[1,5-a]pyrimidin-5-yl)-8-azabicyclo[3.2.1]octane-8-carboxylate To (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (3.5 g, 4.8 mmol) in dioxane (40 mL) and water (10 mL) was added N-methyl-5-(4,4,5,5-tetramethyl-1,3,2-dioxaborolan-2-yl) picolinamide (2.5 g, 9.5 mmol), PdCl₂(dppf).CH₂Cl₂ (0.5 g, 0.6 mmol) and K₂CO₃ (2 g, 14.3 mmol). The reaction mixture was heated at 100° C. for 16 hour, at which time LC/MS analysis confirmed full consumption of starting material. On cooling, the solvent was removed in vacuo, and the crude was redissolved in DCM (500 mL), washed with water (1×125 mL), brine (1×125 mL), and dried over MgSO₄. Gradient column chromatography on silica gel eluting with 0 to 100% EtOAc/hexanes gave the desired (1R,3s,5S)-tert-butyl 3-(7-(bis((2-(trimethylsilyl)ethoxy)methyl)amino)-3-(6-(methylcarbamoyl)pyridin-3-yl)pyrazolo[1,5-a]pyrimidin-5-yl)-8-azabicyclo[3.2.1]octane-8-carboxylate (3.2 g).

Example 3-5

Preparation of (1R,3s,5S)-tert-butyl 3-(7-(bis((2-(trimethylsilyl)ethoxy)methyl)amino)-3-(5-(methoxymethoxy)-6-phenylpyridin-3-yl)pyrazolo[1,5-a]pyrimidin-5-yl)-8-azabicyclo[3.2.1]octane-8-carboxylate

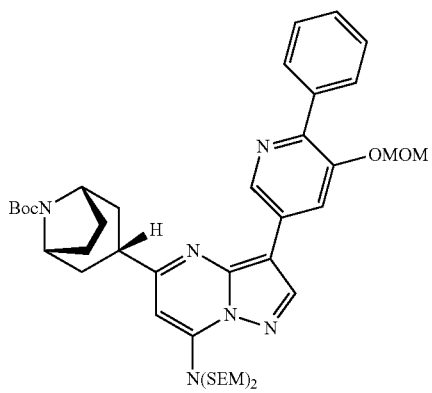

Step A. Synthesis of 5-bromo-2-chloro-3-(methoxymethoxy)pyridine

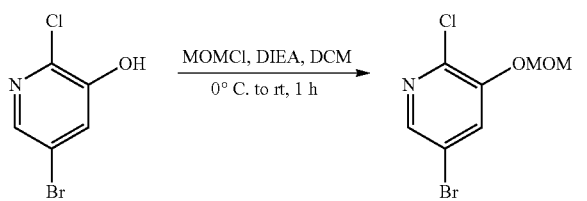

To 5-bromo-2-chloropyridin-3-ol (2.3 g, 11 mmol) in DCM (88 mL) was added N,N-diisopropylethylamine (9.6 mL, 55 mmol) at 0° C. followed by MOMCl (4.2 mL, 55 mmol). Reaction mixture was warmed up to room temperature and stirred further for one hour at which time LC/MS analysis confirmed full consumption of starting material. Organics were then extracted with DCM (1×500 mL), and washed with water (1×125), brine (1×125 mL), and dried over MgSO₄. Solvent was removed in vacuo and the residue was purified by column chromatography on silica gel. Elution with EtOAc/hexanes (0-30%) gave desired product, 5-bromo-2-chloro-3-(methoxymethoxy)pyridine (2.5 g).

Step B. Synthesis of 2-chloro-3-(methoxymethoxy)-5-(4,4,5,5-tetramethyl-1,3,2-dioxaborolan-2-yl)pyridine

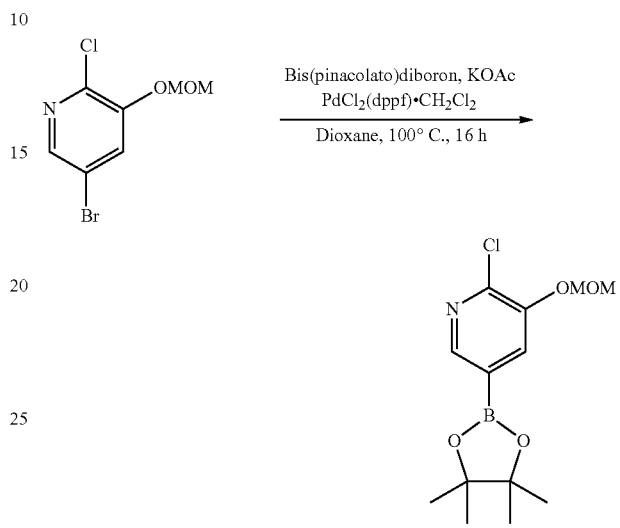

To 5-bromo-2-chloro-3-(methoxymethoxy)pyridine (2.5 g, 10.1 mmol) in dioxane (80 mL) was added bis(pinacolato)diboron (3.3 g, 13.1 mmol), PdCl₂(dppf).CH₂Cl₂ (0.8 g, 1 mmol) and KOAc (3 g, 30.1 mmol). It was then degassed with Argon for five minute before heating at 100° C. for 16 hours, at which time LC/MS analysis confirmed full consumption of starting material. On cooling, the solvent was rotoevaporated, and the crude was redissolved in DCM (500 mL), washed with water (1×125 mL), brine (1×125 mL), and dried over MgSO₄. Solvent was removed in vacuo to get the crude compound 2-chloro-3-(methoxymethoxy)-5-(4,4,5,5-tetramethyl-1,3,2-dioxaborolan-2-yl)pyridine, which was used for the next step without any further purification.

Step C. Synthesis of (1R,3s,5S)-tert-butyl 3-(7-(bis((2-(trimethylsilyl)ethoxy)methyl)amino)-3-(6-chloro-5-(methoxymethoxy)pyridine-3-yl)pyrazolo[1,5-a]pyrimidin-5-yl)-8-azabicyclo[3.2.1]octane-8-carboxylate

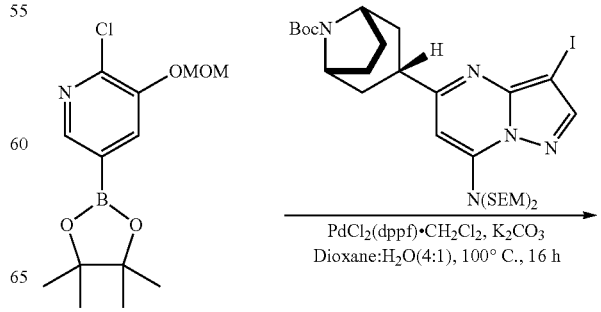

-continued

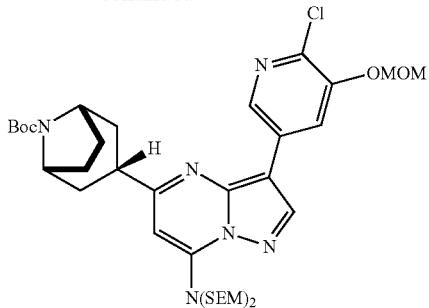

To 2-chloro-3-(methoxymethoxy)-5-(4,4,5,5-tetramethyl-1,3,2-dioxaborolan-2-yl)pyridine (6.5 g, 10.52 mmol) in dioxane (28 mL) and water (7 mL) was added (1R,3s,5S)-tert-butyl 3-(7-(bis((2-(trimethylsilyl)ethoxy)methyl)amino)-3-iodo pyrazolo[1,5-a]pyrimidin-5-yl)-8-azabicyclo[3.2.1]octane-8-carboxylate (2.4 g, 3.3 mmol), PdCl$_2$(dppf)·CH$_2$Cl$_2$ (0.3 g, 0.4 mmol) and K$_2$CO$_3$ (1.4 g, 10 mmol). The reaction was heated at 100° C. for 16 hours, at which time LC/MS analysis confirmed full consumption of starting material. On cooling, the solvent was rotoevaporated, and the crude was redissolved in DCM (500 mL), washed with water (1×125 mL), brine (1×125 mL), dried (MgSO$_4$) and concentrated in vacuo to crude. Gradient column chromatography on silica gel eluting with 0 to 45% EtOAc/hexanes gave the desired (1R,3s,5S)-tert-butyl 3-(7-(bis((2-(trimethylsilyl)ethoxy)methyl)amino)-3-(6-chloro-5-(methoxymethoxy)pyridine-3-yl)pyrazolo[1,5-a]pyrimidin-5-yl)-8-azabicyclo[3.2.1]octane-8-carboxylate (2.4 g).

Step D. Synthesis of (1R,3s,5S)-tert-butyl 3-(7-(bis((2-(trimethylsilyl)ethoxy)methyl)amino)-3-(5-(methoxymethoxy)-6-phenylpyridin-3-yl)pyrazolo[1,5-a]pyrimidin-5-yl)-8-azabicyclo[3.2.1]octane-8-carboxylate

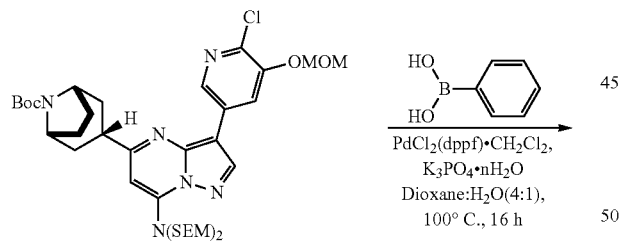

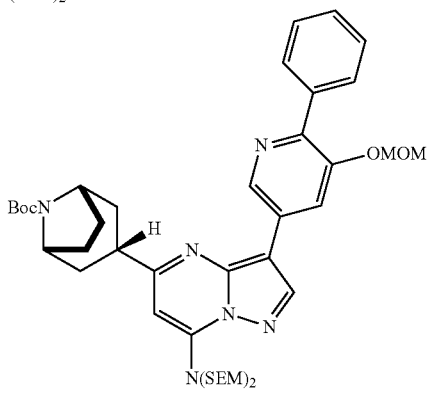

To (1R,3s,5S)-tert-butyl 3-(7-(bis((2-(trimethylsilyl)ethoxy)methyl)amino)-3-(6-chloro-5-(methoxymethoxy)pyridine-3-yl)pyrazolo[1,5-a]pyrimidin-5-yl)-8-azabicyclo[3.2.1]octane-8-carboxylate (2.1 g, 2.6 mmol) in dioxane (21 mL) and water (5.2 mL) was added phenylboronic acid (0.6 g, 5.2 mmol), PdCl$_2$(dppf)·CH$_2$Cl$_2$ (0.26 g, 0.3 mmol) and K$_3$PO$_4$·nH$_2$o (1.4 g, 6.5 mmol). The reaction was heated at 100° C. for 16 hours, at which time LC/MS analysis confirmed full consumption of starting material. On cooling, the solvent was rotoevaporated, and the crude was redissolved in DCM (250 mL), washed with water (1×50 mL), brine (1×50 mL), dried (MgSO$_4$) and concentrated in vacuo to crude. Gradient column chromatography on silica gel eluting with 0 to 50% EtOAc/hexanes gave the desired (1R,3s,5S)-tert-butyl 3-(7-(bis((2-(trimethylsilyl)ethoxy)methyl)amino)-3-(5-(methoxymethoxy)-6-phenylpyridin-3-yl)pyrazolo[1,5-a]pyrimidin-5-yl)-8-azabicyclo[3.2.1]octane-8-carboxylate (1.7 g).

Example 3-6

Preparation of 5-((1R,3s,5S)-8-(1H-tetrazol-5-yl)-8-azabicyclo[3.2.1]octan-3-yl)-6-(methylsulfonyl)-3-(6-phenylpyridin-3-yl)pyrazolo[1,5-a]pyrimidin-7-amine

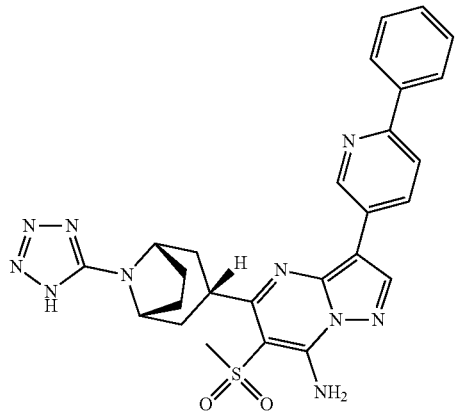 [SMILES: CS(=O)(=O)c1c([C@@H]2C[C@H]3CC[C@@H](C2)N3c2nnn[nH]2)nc2c(-c3ccc(-c4ccccc4)nc3)cnn2c1N]

Step A. Synthesis of (1R,3s,5S)-3-(7-amino-6-(methylsulfonyl)-3-(6-phenyl pyridin-3-yl)pyrazolo[1,5-a]pyrimidin-5-yl)-8-azabicyclo[3.2.1]octane-8-carbonitrile

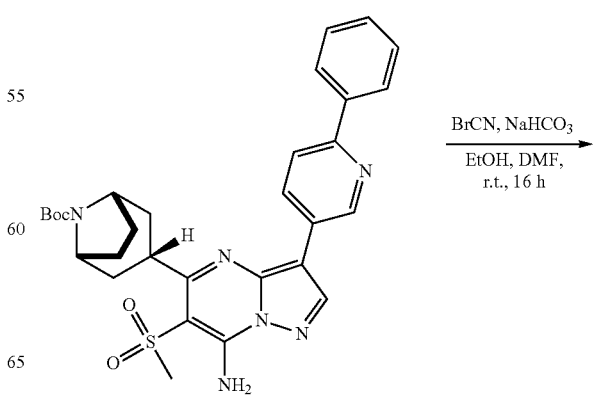

303

-continued

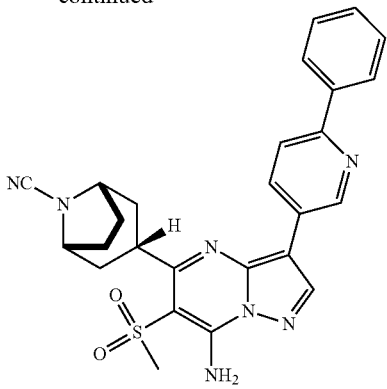

5-((1R,3s,5S)-8-azabicyclo[3.2.1]octan-3-yl)-6-(methylsulfonyl)-3-(6-phenyl pyridin-3-yl)pyrazolo[1,5-a]pyrimidin-7-amine (0.8 g, 0.97 mmol) in EtOH (18 mL) and DMF (4 mL) was treated with NaHCO$_3$ (0.5 g, 5.9 mmol) for 10 minutes at room temperature. Cyanic bromide (3M in DCM, 1 mL, 2.9 mmol) was added and the resulting mixture was stirred at room temperature for 16 hours, at which time LC/MS confirmed full conversion of starting material to product. Solvent was removed in vacuo to complete dryness. To this crude was added water (30 mL) and solids were filtered and washed with additional water (30 mL) to afford (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile (0.4 g).

Step B. Synthesis of 5-((1R,3s,5S)-8-(1H-tetrazol-5-yl)-8-azabicyclo[3.2.1]octan-3-yl)-6-(methylsulfonyl)-3-(6-phenylpyridin-3-yl)pyrazolo[1,5-a]pyrimidin-7-amine

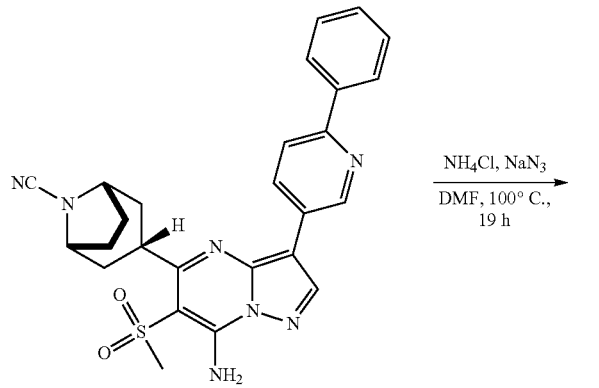

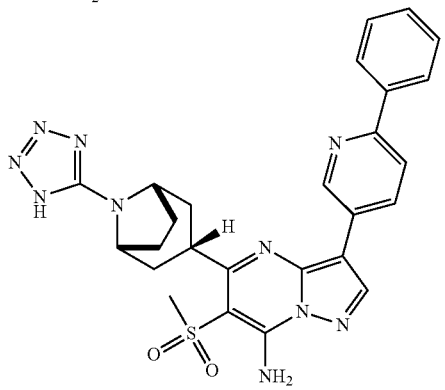

304

A mixture of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile (29.4 mg, 0.05 mmol), NH$_4$Cl (4 mg, 0.08 mmol) and sodium azide (4.9 mg, 0.08 mmol) in DMF (0.5 mL) was heated at 100° C. for 19 hours, at which time LC/MS analysis confirmed full consumption of starting material. Pure compound 5-((1R,3s,5S)-8-(1H-tetrazol-5-yl)-8-azabicyclo[3.2.1]octan-3-yl)-6-(methylsulfonyl)-3-(6-phenyl pyridin-3-yl)pyrazolo[1,5-a]pyrimidin-7-amine was isolated by preparative HPLC.

Example 3-7

Preparation of 5-((1R,3s,5S)-8-(5-methyl-4H-1,2,4-triazol-3-yl)-8-aza bicyclo[3.2.1]octan-3-yl)-6-(methylsulfonyl)-3-(6-phenylpyridin-3-yl)pyrazolo[1,5-a]pyrimidin-7-amine

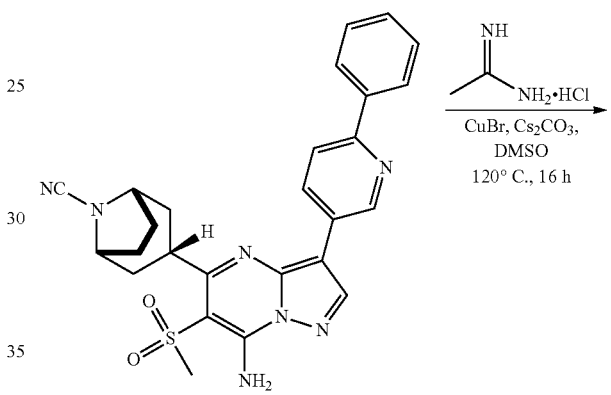

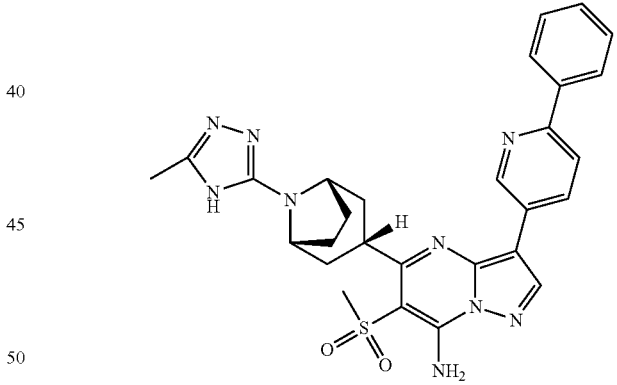

A mixture of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile (0.12 g, 0.21 mmol), acetamidine hydrochloride (49.6 mg, 0.53 mmol), Cs$_2$CO$_3$ (0.34 g, 1.1 mmol) and CuBr (1.5 mg, 0.01 mmol) in DMSO (1.5 mL) was degassed with argon and heated at 120° C. for 16 hours, at which time LC/MS analysis confirmed full consumption of starting material. Pure compound 5-((1R,3s,5S)-8-(5-methyl-4H-1,2,4-triazol-3-yl)-8-aza bicyclo[3.2.1]octan-3-yl)-6-(methylsulfonyl)-3-(6-phenylpyridin-3-yl)pyrazolo[1,5-a]pyrimidin-7-amine was isolated by preparative HPLC.

Example 3-8

Preparation of 5-((1R,3s,5S)-8-(4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine

Example 3-9

Preparation of (1R,3s,5S)-3-(7-amino-6-(methylsulfonyl)-3-(6-phenyl pyridin-3-yl)pyrazolo[1,5-a]pyrimidin-5-yl)-8-azabicyclo[3.2.1]octane-8-carbaldehyde

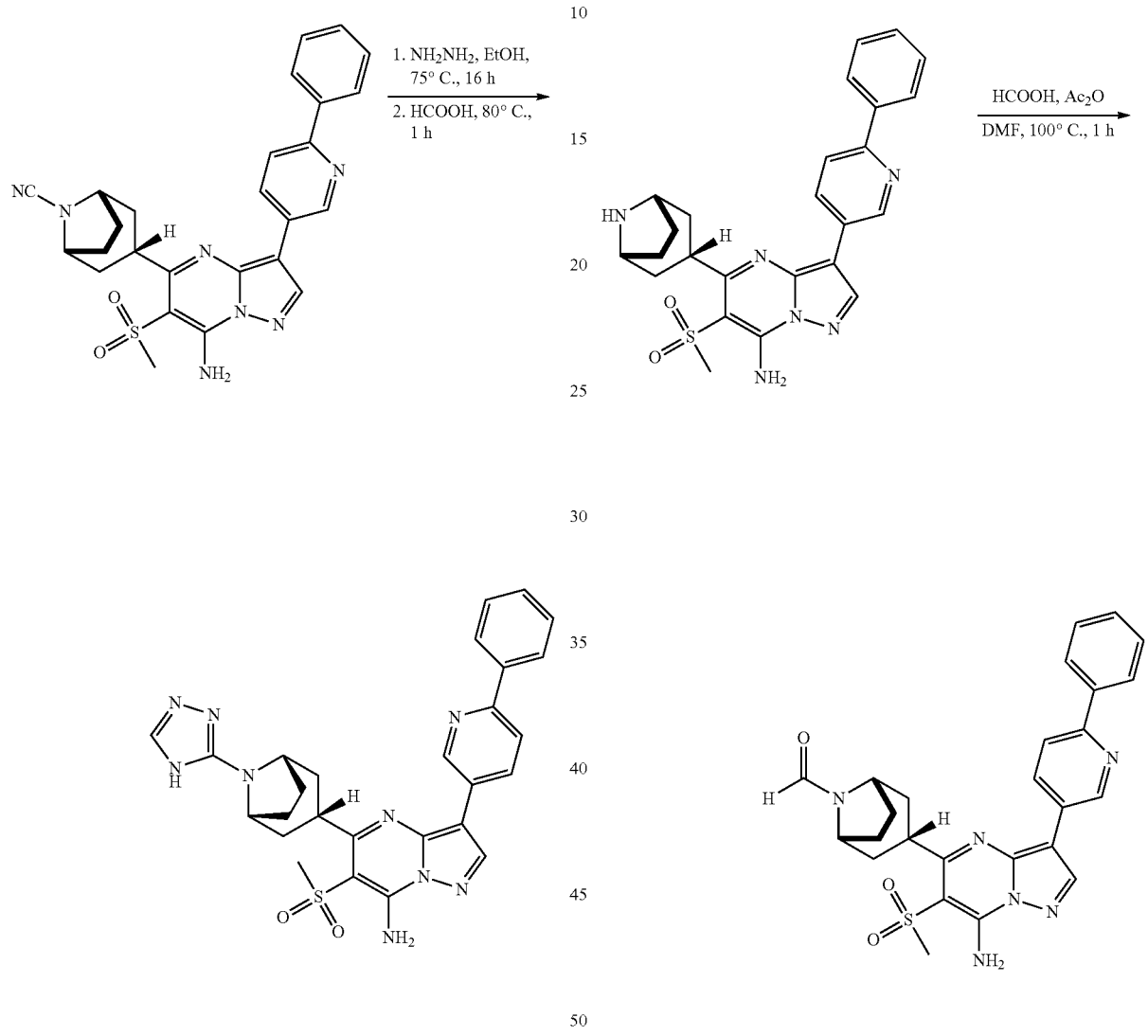

A mixture of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile (23.5 mg, 0.04 mmol) and hydrazine (0.01 mL) in EtOH (0.3 mL) was heated at 75° C. for 16 hours, at which time LC/MS analysis confirmed full consumption of starting material. After cooling, formic acid (0.32 mL) was added and it was heated further at 80° C. for 1 hour. Pure compound 5-((1R,3s,5S)-8-(4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine was isolated by preparative HPLC.

A mixture of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine (0.3 g, 0.35 mmol), formic acid (0.71 mL) and acetic anhydride (0.71 mL) in DMF (3 mL) was degassed with argon and heated at 100° C. for one hour, at which time LC/MS analysis confirmed full consumption of starting material. Pure compound (1R,3s,5S)-3-(7-amino-6-(methylsulfonyl)-3-(6-phenylpyridin-3- yl)pyrazolo[1,5-a]

pyrimidin-5-yl)-8-azabicyclo[3.2.1]octane-8-carbaldehyde was isolated by preparative HPLC.

Example 3-10

Preparation of N-(5-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide

Step 1: Preparation of methyl 5-acetamido-4H-1,2,4-triazole-3-carboxylate

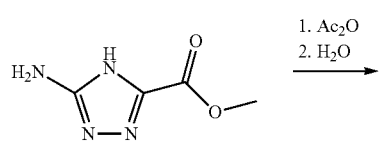

A suspension of methyl 5-amino-4H-1,2,4-triazole-3-carboxylate (1.42 g, 10.0 mmol) in acetic anhydride (30 mL) was refluxed for 30 min until a clear solution was formed. The solution was evaporated to dryness and $H_2O$ (40 mL) was added. The resulting suspension was stirred at rt overnight. $H_2O$ was evaporated to afford the titled compound as a white powder (1.85 g), which was used without further purification.

Step 2: Preparation of 5-acetamido-4H-1,2,4-triazole-3-carboxylic acid

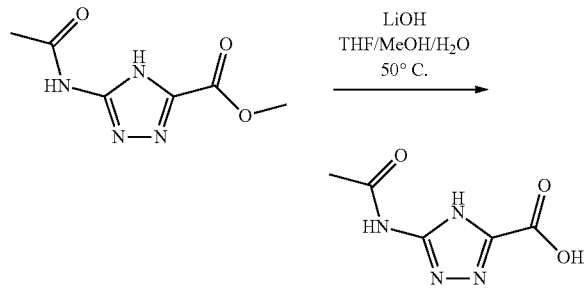

A mixture of methyl 5-acetamido-4H-1,2,4-triazole-3-carboxylate (500 mg, 2.72 mmol) and LiOH (2.1 eq) in THF/MeOH/$H_2O$ (8/4/2 mL) was stirred at 50° C. for 1 h (precipitates formed). All the volatiles were removed and the white solid residue was acidified with 7 mL of HCl (1 N), filtered and washed with $H_2O$ to afford the titled compound as a white solid (413 mg), which was used without further purification.

Step 3: Preparation of N-(5-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide

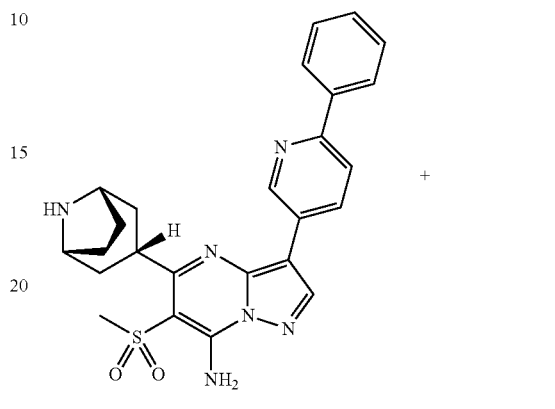

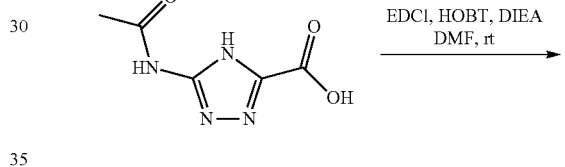

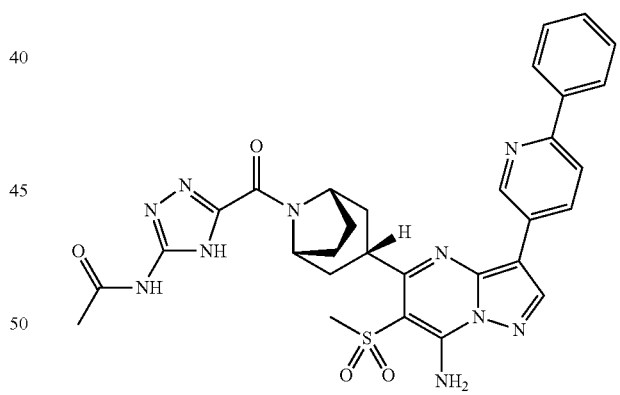

A mixture of 5-acetamido-4H-1,2,4-triazole-3-carboxylic acid (31.3 mg, 0.184 mmol), HOBT (16.5 mg, 0.122 mmol), EDCI.HCl (30.5 mg, 0.159 mmol) in DMF (2 mL) was stirred at rt for 10 min. Then a slurry of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine TFA salt (100 mg, 0.122 mmol, preparation described previously) in DMF (2 mL) was added, followed by DIEA (6 eq). The resulting solution was stirred at rt for 1 h. The reaction mixture was concentrated to half volume, diluted with DMSO and purified by a reverse phase HPLC to afford the titled compound as a pale yellow solid (57 mg).

Example 3-11

Preparation of ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-1H-pyrazol-4-yl)methanone

Step 1: Preparation of ethyl 3-hydroxy-1H-pyrazole-4-carboxylate

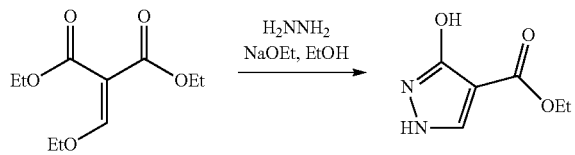 [SMILES: CCOC=C(C(=O)OCC)C(=O)OCC ; CCOC(=O)c1c[nH]nc1O]

To a solution of NaOEt in EtOH (60 mL, 21 w %) were added diethyl 2-(ethoxymethylene)malonate (10.4 mL, 52.0 mmol) and hydrazine monohydrate (5.04 mL, 104 mmol) with cooling in an ice-water bath. The resulting mixture was then heated at 80° C. for 4 h. After cooling to rt, HCl (1 N, 180 mL) was added to the reaction mixture and then extracted with EtOAc three time. The combined organic layers were washed with brine and dried over Na$_2$SO$_4$. A solid obtained after evaporation was washed with ether and dried under high vacuum to afford the titled compound as an off-white solid (4.42 g), which was used without further purification.

Step 2: Preparation of 3-hydroxy-1H-pyrazole-4-carboxylic acid

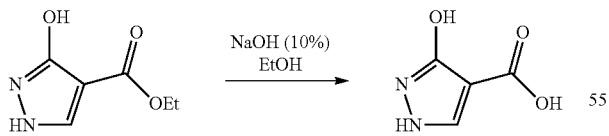

A solution of ethyl 3-hydroxy-1H-pyrazole-4-carboxylate (625 mg, 4.00 mmol) in 10% NaOH (aq) (20 mL) and EtOH (10 mL) was heated under reflux for 20 h. EtOH was removed under reduced pressure. The residue was diluted with 10 mL of H$_2$O and acidified with 4 N HCl. The precipitates were filtered to afford the titled compound as a white solid (460 mg), which was used without further purification.

Step 3: Preparation of ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-1H-pyrazol-4-yl)methanone

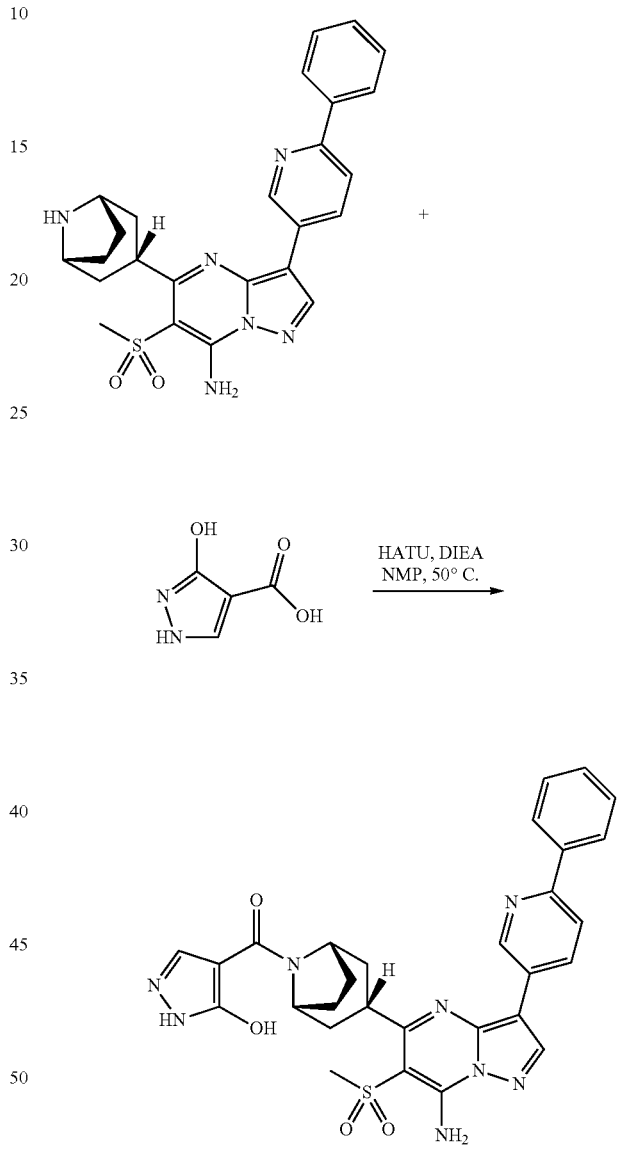

A mixture of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine HCl salt (58.4 mg, 0.100 mmol, preparation described previously), 3-hydroxy-1H-pyrazole-4-carboxylic acid (16.7 mg, 0.130 mmol), and DIEA (5 eq) was stirred in NMP (2 mL) until completely dissolved. Then HATU (49.4 mg, 0.130 mmol) was added. The resulting mixture was stirred at 50° C. for 4 h. The reaction mixture was concentrated to half volume, diluted with DMSO and purified by a reverse phase HPLC to afford the titled compound as a pale yellow solid (8.4 mg).

Example 3-12

Preparation of 2-phenyl-5-(4,4,5,5-tetramethyl-1,3,2-dioxaborolan-2-yl)pyrimidine

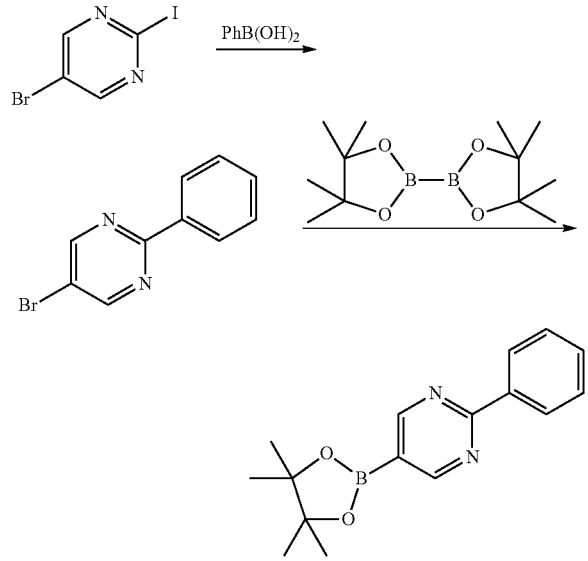

Step A—Synthesis of 5-bromo-2-phenylpyrimidine

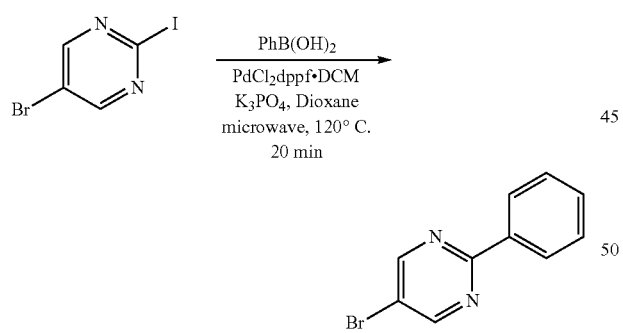

A mixture of 5-bromo-2-iodopyrimidine (285 mg, 1.0 mmol), potassium phosphate (637 mg, 3.0 mmol), phenylboronic acid (134 mg, 1.1 mmol) and dichloro[1,1'-bis(diphenylphosphino)ferrocene]palladium (II) dichloromethane adduct (73 mg, 0.1 mmol) in dioxane (5 mL) was heated to 120° C. for 20 minutes in a microwave. LC/MS analysis of the reaction indicated that the reaction was complete. DCM (10 mL) was added, and the precipitates removed by passing through a plug of celite. The filtrate was concentrated, and the crude residue purified by flash column chromatography, gradient elution (0 to 100%) hexane/ethyl acetate, to afford compound Int-1a as a white solid (201 mg, 86% yield). HPLC-MS tR=1.39 min (UV254 nm); mass calculated for formula C10H7BrN4 233.98, observed LCMS m/z 235.0 (M+H).

Step B—Synthesis of 2-phenyl-5-(4,4,5,5-tetramethyl-1,3,2-dioxaborolan-2-yl)pyrimidine

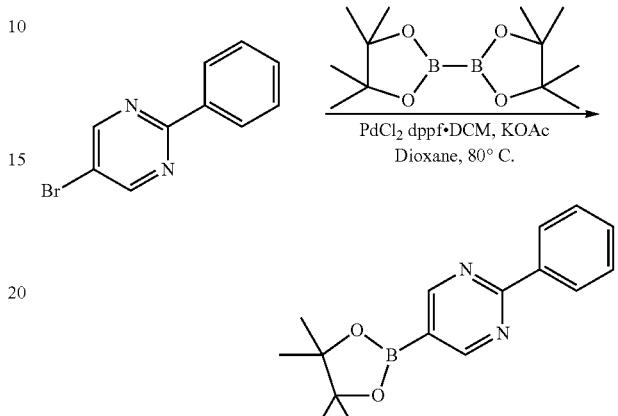

A mixture of 5-bromo-2-phenylpyrimidine (1.17 g, 5.0 mmol), bis(pinacolato)diboron (2.54 g, 10.0 mmol), potassium acetate (1.47 g, 15.0 mmol), dichloro[1,1'-bis(diphenylphosphino)ferrocene]palladium (II) dichloromethane adduct (408 mg, 0.5 mmol) in dioxane (20 mL) was flushed with argon and stirred at 80° C. for 16 h. On cooling, the solvent was evaporated in vacuo, the crude residue redissolved in EtOAc (50 ml), washed with water (1×50 mL), brine (1×50 mL), and dried over MgSO4. The solvent was concentrated to yield crude residue (Int-1b) which was taken forward as is in the next step. HPLC-MS tR=0.72 min (UV254 nm); mass calculated for formula C16H19BN2O2 282.15, observed LCMS m/z 201.0 (M+H).

Example 3-13

Preparation of 2-(5-(4,4,5,5-tetramethyl-1,3,2-dioxaborolan-2-yl)pyrimidin-2-yl)propan-2-ol

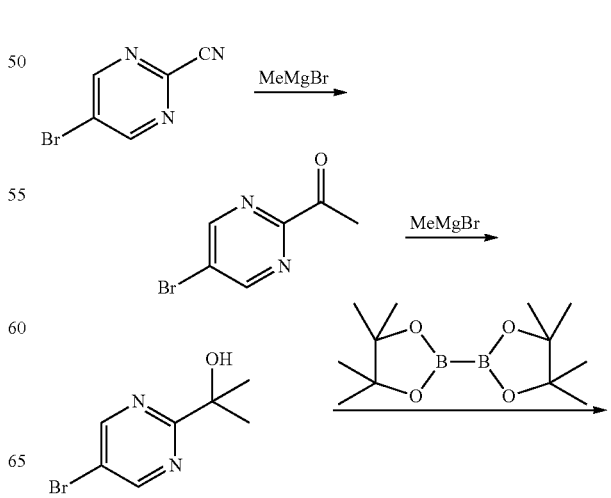

Step A—Synthesis of 1-(5-bromopyrimidin-2-yl)ethanone

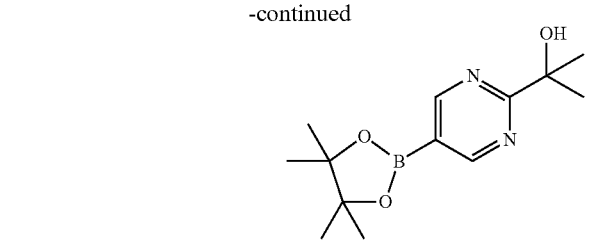

To a stirred solution of 5-bromo-2-cyanopyrimidine (600 mg, 3.26 mmol) in THF (40 mL) at −78° C. was added methylmagnesium bromide (1.4M solution, 7 mL, 9.78 mmol). The reaction mixture was stirred for an additional 20 minutes until LC/MS analysis indicated that the reaction was complete. Quenching with saturated NH$_4$Cl, extraction with EtOAc and drying over MgSO$_4$, afforded the crude residue which was purified by flash column chromatography, gradient elution (0 to 50%) hexane/ethyl acetate, to afford compound Int-2a as a white solid (170 mg, 26% yield). HPLC-MS tR=0.54 min (UV254 nm); mass calculated for formula C6H5BrN2O 199.96, observed LCMS m/z 201.0 (M+H).

Step B—Synthesis of 2-(5-bromopyrimidin-2-yl)propan-2-ol

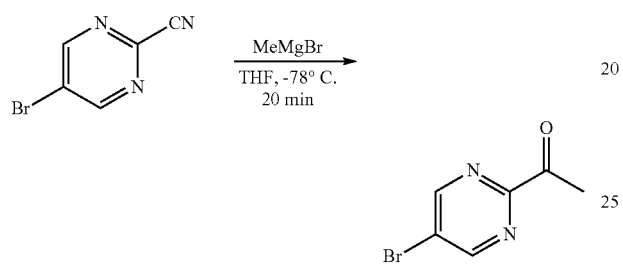

To a stirred solution of 1-(5-bromopyrimidin-2-yl)ethanone (100 mg, 0.5 mmol) in THF (10 mL) at −78° C. was added methylmagnesium bromide (1.4M solution, 3.6 mL, 5 mmol). The reaction mixture was stirred for an additional 20 minutes until LC/MS analysis indicated that the reaction was complete. Quenching with saturated NH$_4$Cl, extraction with EtOAc and drying over MgSO$_4$, afforded the crude residue which was taken forward as is in the next step.

Step C—Synthesis of 2-(5-(4,4,5,5-tetramethyl-1,3,2-dioxaborolan-2-yl)pyrimidin-2-yl)propan-2-ol

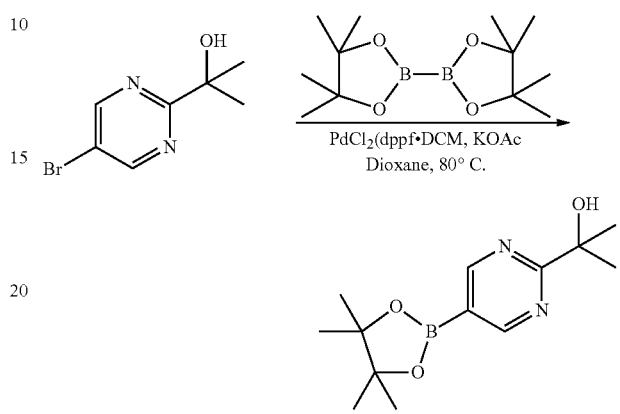

A mixture of 2-(5-bromopyrimidin-2-yl)propan-2-ol (0.5 mmol), bis(pinacolato)diboron (254 mg, 1.0 mmol), potassium acetate (150 mg, 1.5 mmol), dichloro[1,1'-bis(diphenylphosphino)ferrocene]palladium (II) dichloromethane adduct (41 mg, 0.05 mmol) in dioxane (3 mL) was flushed with argon and stirred at 80° C. for 16 h. On cooling, the solvent was evaporated in vacuo, the crude residue redissolved in EtOAc (10 mL), washed with water (1×10 mL), brine (1×10 mL), and dried over MgSO$_4$. The solvent was concentrated to yield crude residue which was taken forward as is in the next step. HPLC-MS tR=0.33 min (UV254 nm); mass calculated for formula C13H21BN2O3 2642.135, observed LCMS m/z 183.0 (M+H).

Example 3-14

Preparation of 5-((1R,3s,5S)-8-azabicyclo[3.2.1]octan-3-yl)-6-(cyclopropylsulfonyl)-3-(6-phenylpyridin-3-yl)pyrazolo[1,5-a]pyrimidin-7-amine

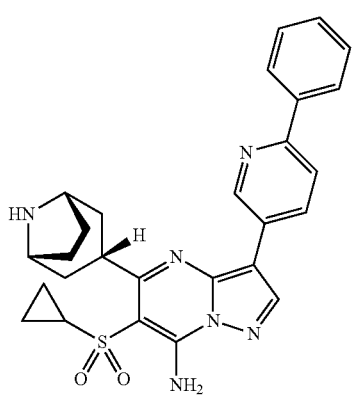

Step A—Preparation of 5-((1R,3s,5S)-8-azabicyclo[3.2.1]octan-3-yl)-6-iodo-3-(6-phenylpyridin-3-yl)pyrazolo[1,5-a]pyrimidin-7-amine

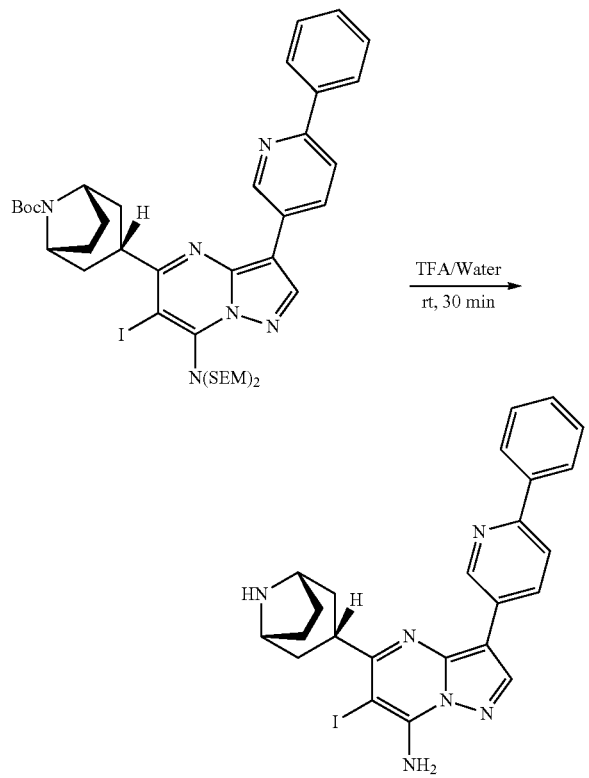

To (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate (2.6 g, 2.95 mmol) was added TFA/water (15:1, 16 mL) at r.t. It was stirred further at room temperature for 30 min at which time LC/MS analysis confirmed full consumption of the starting material. The solvent was removed in vacuo, the resulting residue re-dissolved in MeCN/water (2 mL) and lyophilized overnight to afford the desired product as a TFA salt. HPLC-MS tR=0.82 min (UV254 nm); mass calculated for formula C24H23IN6 522.10, observed LCMS m/z 523.0 (M+H).

Step B—Synthesis of 5-((1R,3s,5S)-8-azabicyclo[3.2.1]octan-3-yl)-6-(cyclopropylsulfonyl)-3-(6-phenylpyridin-3-yl)pyrazolo[1,5-a]pyrimidin-7-amine

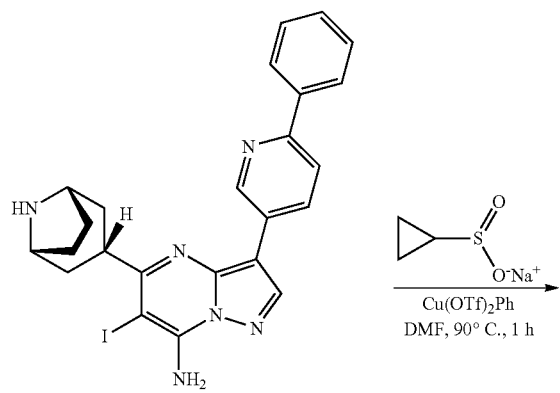

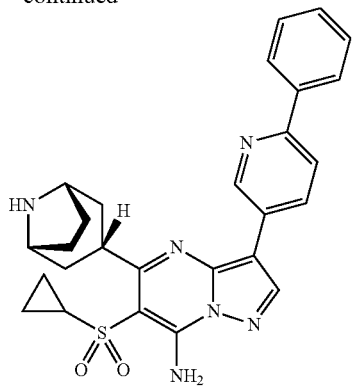

A mixture of compound 5-((1R,3s,5S)-8-azabicyclo[3.2.1]octan-3-yl)-6-iodo-3-(6-phenylpyridin-3-yl)pyrazolo[1,5-a]pyrimidin-7-amine (200 mg, 0.38 mmol), bis[copper(I)trifluoromethanesulfonate]benzene complex (96 mg, 0.38 mmol) and sodium cyclopropanesulfinate (197 mg, 1.15 mmol) in DMF (3 mL) was heated at 90° C. for 1 h, at which time LC/MS analysis confirmed full consumption of starting material. After cooling, the volatiles were removed in vacuo. The residue was redissolved in DCM/iPrOH (9:1, 20 mL), washed with a mixture of $NH_4Cl_{(aq)}$/$NH_4OH$ (7:3, 20 mL) and dried with $Na_2SO_4$. The organics were removed in vacuo, the resulting residue re-dissolved in MeCN/water (2 mL) and lyophilized overnight to afford the desired product. HPLC-MS tR=0.68 min (UV254 nm); mass calculated for formula C25H26N6O2S 474.20, observed LCMS m/z 475.1 (M+H).

Example 3-15

Preparation of (1R,3s,5S)-3-(7-amino-6-(methylsulfonyl)-3-(6-phenylpyridin-3-yl)pyrazolo[1,5-a]pyrimidin-5-yl)-N-methoxy-8-azabicyclo[3.2.1]octane-8-carboxamide

Step 1: Preparation of 4-nitrophenyl methoxycarbamate

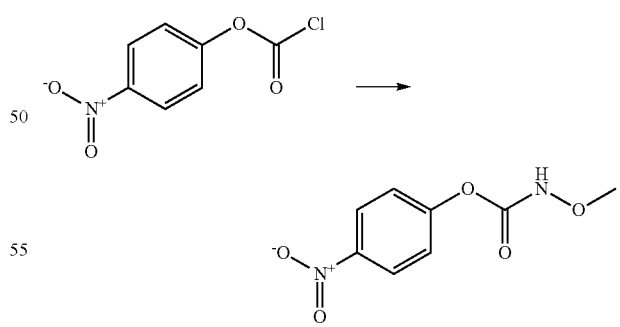

Methoxylamine hydrochloride (1.00 g, 12.0 mmol) was suspended in a mixture of dry pyridine (0.97 mL, 12.0 mmol) and dichloromethane (24 mL), and a solution of 4-nitrophenyl chlorocarbonate (2.41 g, 12.0 mmol) in dichloromethane (12 mL) was added over 30 min with stirring. The resulting heavy white suspension was warmed to reflux, refluxed for 6 h, and cooled to room temperature. The suspension was diluted with dichloromethane and washed with 1M HCl, keeping the emulsion with the aqueous layer, and the aqueous layer was re-extracted with dichloromethane. The combined organic phase was washed with water, saturated aqueous sodium bicarbonate and brine, keeping any emulsions with the aqueous layer, and then dried over magnesium sulfate and concentrated under reduced pressure. The crude product was purified by chromatography (90 g silica gel, 20-40% EtOAc/hexanes) to give the title compound (0.92 g) as a white crystalline solid. A second set of less pure product fractions was isolated to give additional product (0.21 g) as a white solid.

Step 2: Preparation of (1R,3s,5S)-3-(7-amino-6-(methylsulfonyl)-3-(6-phenylpyridin-3-yl)pyrazolo[1,5-a]pyrimidin-5-yl)-N-methoxy-8-azabicyclo[3.2.1]octane-8-carboxamide

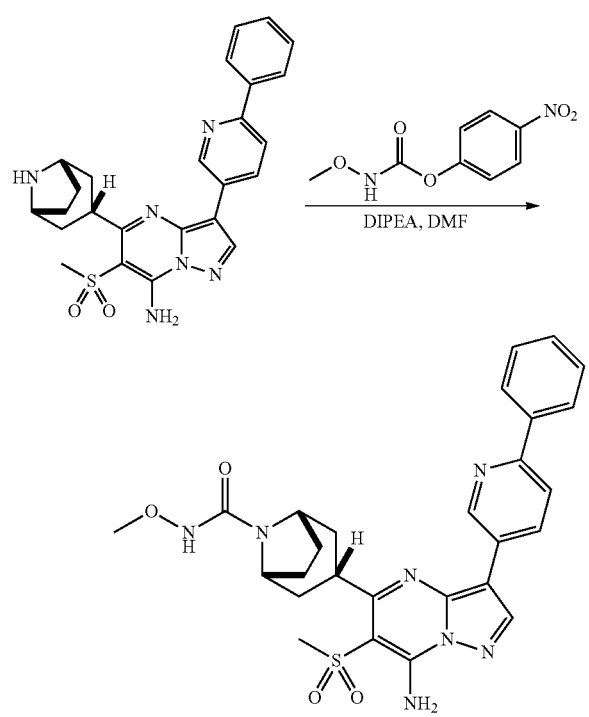

5-[(3-exo)-8-azabicyclo[3.2.1]oct-3-yl]-6-(methylsulfonyl)-3-(6-phenylpyridin-3-yl)pyrazolo[1,5-a]pyrimidin-7-amine (56.5 mg, 0.119 mmol) was dissolved in a solution of N,N-Diisopropylethylamine (108 mg, 0.833 mmol) and dry DMF (1.5 mL). To the reaction was added a solution of 4-nitrophenyl methoxycarbamate (30.3 mg, 0.143 mmol) and dry DMF (1.5 mL). The yellow reaction appeared to become a little darker yellow. After stirring for 40 min at room temperature additional 4-nitrophenyl methoxycarbamate (approx. 5 mg, 0.023 mmol) was added to the reaction. After another 20 min of stirring the reaction was complete. The homogeneous reaction was filtered through a syringe filter and purified by preparative chromatography. Like fractions of pure product were combined and lyophilized to give 59.3 mg of free base as a flocculent yellow powder. The free base was dissolved in a minimum amount of methanol, and 1M HCl (1 mL) was added, and the resultant solution was concentrated in vacuo. The wet residue was suspended in methanol, again treated with 1M HCl (1 mL), and concentrated in vacuo. The residue was suspended in methanol and concentrated in vacuo, and dried under vacuum. The title compound (49 mg, 66%) was obtained as a tan solid as its dihydrochloride salt.

Example 3-16

Preparation of (1R,3s,5S)-tert-butyl 3-(7-(bis((2-(trimethylsilyl)ethoxy)methyl)amino)-3-(6-(2,6-difluorophenyl)pyridin-3-yl)pyrazolo[1,5-a]pyrimidin-5-yl)-8-azabicyclo[3.2.1]octane-8-carboxylate Step 1: Preparation of 5-bromo-2-(2,6-difluorophenyl)pyridine

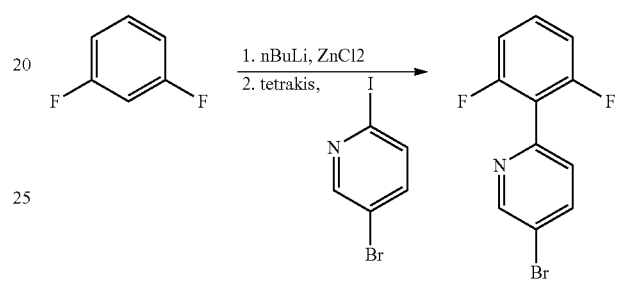

n-Butyllithium in hexane(2.50 M, 9.02 mL, 22.5 mmol) was added dropwise to a solution of 1,3-difluorobenzene (2.03 mL, 20.6 mmol) in anhydrous tetrahydrofuran (30 mL) at −78° C. and the resulting solution was stirred at the same temperature for 30 min, then warmed to −50° C. and zinc dichloride in tetrahydrofuran 0.50 M, 45.1 mL, 22.5 mmol) was added slowly. After 20 min, 5-bromo-2-iodopyridine (7.0 g, 25 mmol) in tetrahydrofuran (20 mL) and tetrakis(triphenylphosphine)palladium(0) (1.19 g, 1.03 mmol) were added sequentially. The vessel was partially evacuated and back filled with nitrogen three times, sparged with a gentle stream of nitrogen for 5 minutes, and warmed to ambient temperature. The bright yellow, translucent reaction solution was stirred for 15 minutes at ambient temperature, then heated at 40° C. for 16 hr. The reaction mixture as then cooled to ambient temperature, concentrated, and purified by flash chromatography (90 g silica gel, 0 to 10% ethyl acetate in hexanes) to afford the title compound (14 g) as a tan solid.

Step 2: Preparation of 2-(2,6-difluorophenyl)-5-(4,4,5,5-tetramethyl-1,3,2-dioxaborolan-2-yl)pyridine

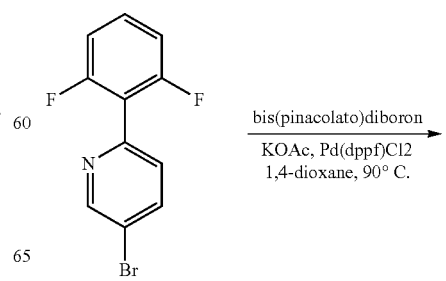

-continued

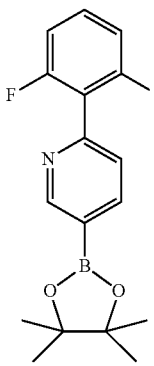

5-bromo-2-(2,6-difluorophenyl)pyridine (0.89 g, 3.3), potassium acetate (0.970 g, 9.89 mmol), bs(pinacolato)diboron (1.26 g, 4.94 mmol), and [1,1'-bis(diphenylphosphino)ferrocene]dichloropalladium(II), complex with dichloromethane (1:1) (0.269 g, 0.330 mmol) were placed in a 3-neck 50 mL round bottom flask equipped with a reflux condenser and rubber septum. The vessel was evacuated and filled with nitrogen (×3) and 1,4-dioxane (11.3 mL) was added. The mixture was sparged with nitrogen for 5-10 minutes and then maintained under nitrogen with a balloon at 95° C. for 3 h. The reaction was then cooled to ambient temperature then filtered through a short plug of magnesol (about 50 mL), and the filtrate was concentrated. The reside was taken up in 250 mL of 1:1 ether:hexanes and filtered through a short plug of magnesol (about 50 mL), and the clear filtrate was concentrated to dryness to afford 1.1 g of product that was ~56% (by weight) the desired product. This material was used without further purification.

Step 3: Preparation of tert-butyl 3-{7-(bis{[2-(trimethylsilyl)ethoxy]methyl}amino)-3-[6-(2,6-difluorophenyl)pyridin-3-yl]pyrazolo[1,5-a]pyrimidin-5-yl}-8-azabicyclo[3.2.1]octane-8-carboxylate

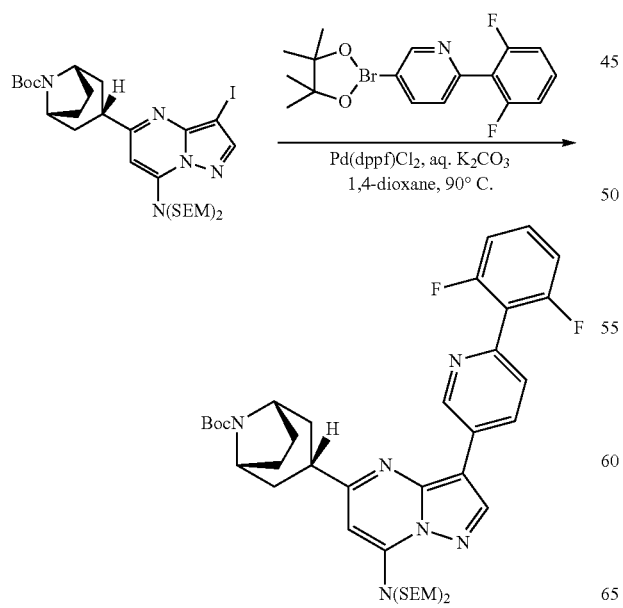

tert-Butyl 3-[7-(bis{[2-(trimethylsilyl)ethoxy]methyl}amino)-3-iodopyrazolo[1,5-a]pyrimidin-5-yl]-8-azabicyclo[3.2.1]octane-8-carboxylate (1.26 g, 1.73 mmol), 2-(2,6-difluorophenyl)-5-(4,4,5,5-tetramethyl-1,3,2-dioxaborolan-2-yl)pyridine (0.88 g, 2.1 mmol), [1,1'-Bis(diphenylphosphino)ferrocene]dichloropalladium(II)complex with dichloromethane (1:1) (141 mg, 0.173 mmol), and potassium carbonate (0.716 g, 5.18 mmol) were placed in a 100-mL round bottom flask equipped with a reflux condenser and rubber septa. Then, the reaction vessel was evacuated and back filled with nitrogen 3 times before adding 1,4-dioxane (3.50 mL) and water (0.933 mL). Then, the reaction was sparged with nitrogen for 8 minutes, then maintained under nitrogen with a balloon and heated at 95° C. for 6 hr. The reaction mixture was then cooled to ambient temperature, diluted with dichloromethane (100 mL), filtered through a plug of Magnesol (ca. 60 mL). and the filtrate was concentrated. The crude product was purified by flash chromatography, (0 to 10% ethylacetate/dichloromethane) to afford the title compound (690 mg, 50%) as an ivory foam.

Example 3-17

Preparation of ((1R,3s,5S)-3-(7-amino-6-(methylsulfonyl)-3-(6-(5-methylthiazol-2-yl)pyridin-3-yl)pyrazolo[1,5-a]pyrimidin-5-yl-8-azabicyclo[3.2.1]octan-8-yl)(2H-1,2,3-triazol-4-yl)methanone Step 1: Preparation of 2-(5-bromopyridin-2-yl)-5-methylthizaole

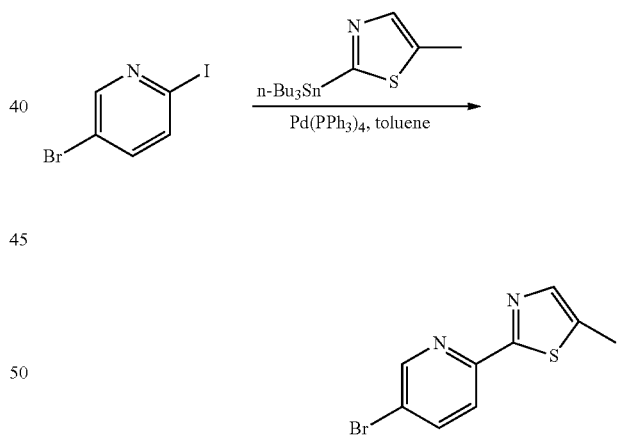

A solution of 5-methyl-2-(tributylstannyl)thiazole (2.87 g, 6.65 mmol), 5-bromo-2-iodopyridine (1.97 g, 6.73 mmol), and Pd(PPh$_3$)$_4$ (0.38 g, 0.33 mmol) in toluene (35 mL) was degassed and heated to 100° C. for 12 hours. Solvent was removed under vacuum and the residue was partitioned between diethyl ether and 0.5 M aqueous potassium fluoride. The ether layer was washed with brine, dried with Na$_2$SO$_4$, and the solvent was removed under vacuum. The resulting residue was purified by flash chromatography (1-10%, EtOAc/Hexanes) to afford the title compound as an orange solid (1.39 g).

Step 2: Preparation of 5-methyl-2-(5-(4,4,5,5-tetramethyl-1,3,2-dioxaborolan-2-yl)pyridine-2-yl)thiazole

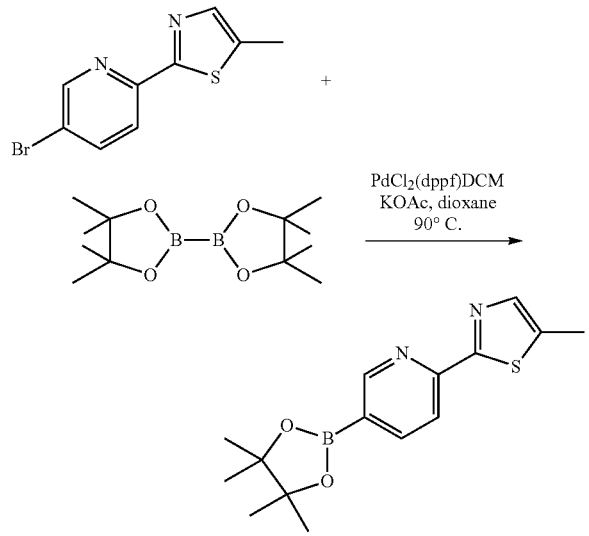

A mixture of 2-(5-bromopyridin-2-yl)-5-methylthizaole (2.00 g, 7.84 mmol), bis(pinacolato)diboron (2.08 g, 8.18 mmol), PdCl₂(dppf).DCM (320 mg, 0.390 mmol), and KOAc (2.30 g, 24.0 mmol) in dioxane (20 mL) and DMSO (2.0 mL) was degassed and then heated at 90° C. for 16 hours. It was then partitioned between ethyl acetate and water and the organic layer was washed twice with water, and then 0.5 M aqueous NaOH. The combined aqueous layers were neutralized with 2 M aqueous HCl, and extracted twice with ethyl acetate. The resulting organic layers were washed with brine and the solvent was removed under vacuum to afford the title compound (1.72 g) as a yellow solid which was used without further purification.

Step 3: Preparation of (1R,3s,5S)-tert-butyl 3-(7-(bis((2-(trimethylsilyl)ethoxy)methyl)amino)-3-(6-(5-methylthiazol-2-yl)pyridin-3-yl)pyrazolo[1,5-a]pyrimidin-5-yl)-8-azabicyclo[3.2.1]octane-8-carboxylate

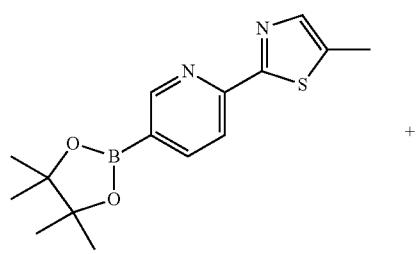

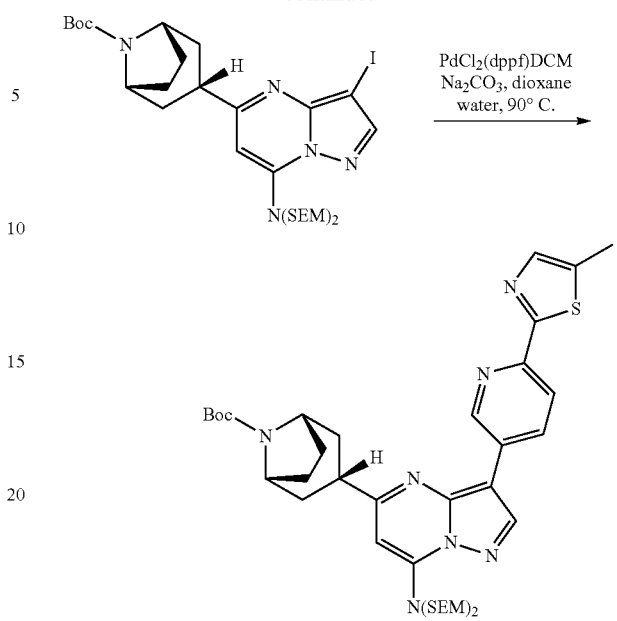

A mixture of 5-methyl-2-(5-(4,4,5,5-tetramethyl-1,3,2-dioxaborolan-2-yl)pyridine-2-yl)thiazole (338 mg, 1.12 mmol), (1R,3s,5S)-tert-butyl 3-(7-(bis((2-(trimethylsilyl)ethoxy)methyl)amino)-3-(6-iodopyridin-3-yl)pyrazolo[1,5-a]pyrimidin-5-yl)-8-azabicyclo[3.2.1]octane-8-carboxylate (627 mg, 0.859 mmol), PdCl₂(dppf).DCM (70.2 mg, 0.086 mmol), and K₂CO₃ (356 mg, 2.58 mmol) in dioxane (6.3 mL) and water (1.6 mL) was degassed and then heated at 90° C. for 5 hours. It was then partitioned between EtOAc and water and the organic layer was washed with brine, dried with Na₂SO₄, and the solvent was removed under vacuum. The resulting residue was purified by flash chromatography (10-25%, EtOAc/Hexanes) to afford the title compound as a yellow solid (579 mg).

Step 4: Preparation of (1R,3s,5S)-tert-butyl 3-(7-(bis((2-(trimethylsilyl)ethoxy)methyl)amino)-6-bromo-3-(6-(5-methylthiazol-2-yl)pyridin-3-yl)pyrazolo[1,5-a]pyrimidin-5-yl)-8-azabicyclo[3.2.1]octane-8-carboxylate

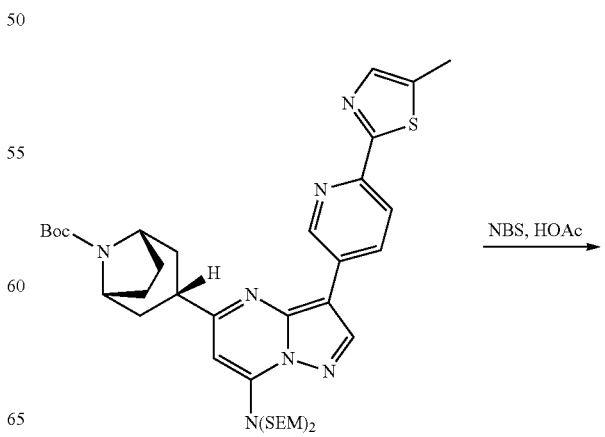

-continued

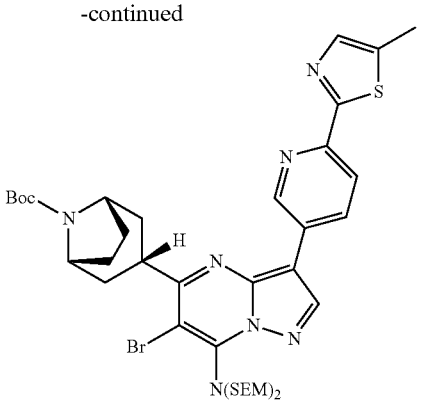

NBS (108 mg, 0.606 mmol) was added to a solution of (1R,3s,5S)-tert-butyl 3-(7-(bis((2-(trimethylsilyl)ethoxy)methyl)amino)-3-(6-(5-methylthiazol-2-yl)pyridin-3-yl)pyrazolo[1,5-a]pyrimidin-5-yl)-8-azabicyclo[3.2.1]octane-8-carboxylate (472 mg, 0.606 mmol) in HOAc (5.0 mL). After 20 minutes it was quenched with 20% aqueous $Na_2S_2O_3$ and saturated aqueous sodium bicarbonate was added. The mixture was partitioned between EtOAc and water and the organic layer was washed with saturated aqueous bicarbonate and brine, dried with $Na_2SO_4$, and the solvent was removed under vacuum. The resulting residue was purified by flash chromatography (25%, EtOAc/Hexanes) to afford the title compound as a yellow solid (548 mg).

Step 5: Preparation of (1R,3s,5S)-tert-butyl 3-(7-(bis((2-(trimethylsilyl)ethoxy)methyl)amino)-3-(6-(5-methylthiazol-2-yl)pyridin-3-yl)-6-(methylthio)pyrazolo[1,5-a]pyrimidin-5-yl)-8-azabicyclo[3.2.1]octane-8-carboxylate

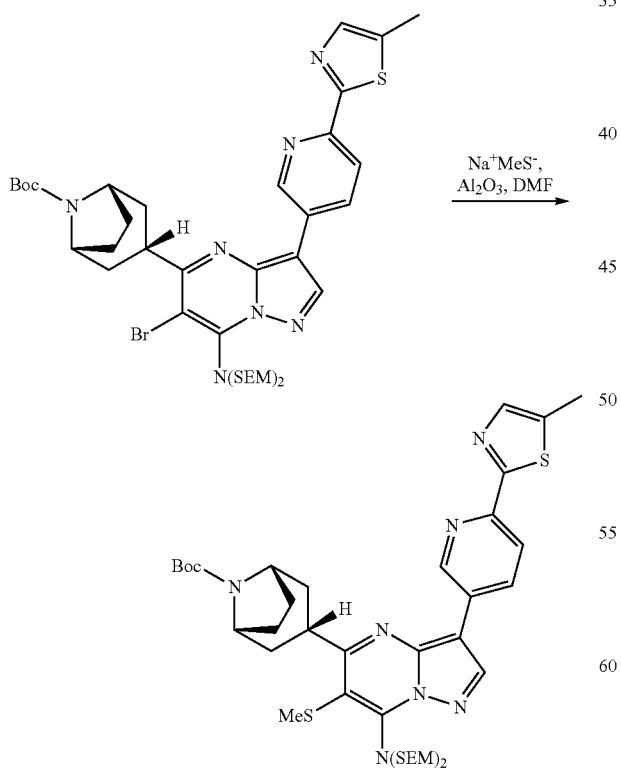

Degassed DMF (8 mL) was used to dissolve (1R,3s,5S)-tert-butyl 3-(7-(bis((2-(trimethylsilyl)ethoxy)methyl)amino)-6-bromo-3-(6-(5-methylthiazol-2-yl)pyridin-3-yl)pyrazolo[1,5-a]pyrimidin-5-yl)-8-azabicyclo[3.2.1]octane-8-carboxylate (425 mg, 0.496 mmol), and $Al_2O_3$ (505.6 mg) and sodium methyl mercaptide (115.8 mg, 1.49 mmol) were added. The mixture was heated at 80° C. for 16 hours and then cooled to room temperature. EtOAc (42 mL) was added and after stirring, the mixture was filtered and the solid was washed with EtOAc. The filtrate was washed with water and brine, dried with $Na_2SO_4$, and the solvent was removed under vacuum. The resulting residue was purified by flash chromatography (20-25%, EtOAc/Hexanes) to afford the title compound as a yellow solid (130 mg).

Step 6: Preparation of (1R,3s,5S)-tert-butyl 3-(7-(bis((2-(trimethylsilyl)ethoxy)methyl)amino)-6-(methylsulfonyl)-3-(6-(5-methylthiazol-2-yl)pyridin-3-yl)pyrazolo[1,5-a]pyrimidin-5-yl)-8-azabicyclo[3.2.1]octane-8-carboxylate

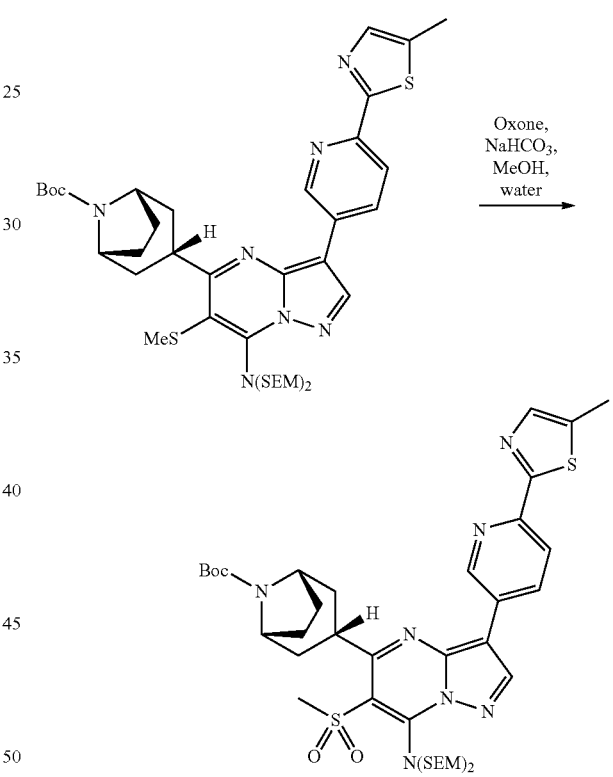

A mixture of (1R,3s,5S)-tert-butyl 3-(7-(bis((2-(trimethylsilyl)ethoxy)methyl)amino)-3-(6-(5-methylthiazol-2-yl)pyridin-3-yl)-6-(methylthio)pyrazolo[1,5-a]pyrimidin-5-yl-8-azabicyclo[3.2.1]octane-8-carboxylate (82.4 mg, 0.100 mmol), $NaHCO_3$ (84.0 mg, 1.00 mmol), Oxone® (307.4 mg, 0.500 mmol), methanol (3.0 mL), and water (0.80 mL) was rapidly stirred while heated at 65° C. for 15 hours and then cooled to room temperature. DCM/MeOH (1:1, 30 mL) was added and the mixture was filtered and solvent was removed from the filtrate under vacuum to afford the title compound as an orange solid (97.2 mg) that was used as is in the next reaction.

Step 7: Preparation of 5-((1R,3s,5S)-8-azabicyclo[3.2.1]octan-3-yl)-6-(methylsulfonyl)-3-(6-(5-methylthiazol-2-yl)pyridin-3-yl)pyrazolo[1,5-a]pyrimidin-7-amine hydrochloride

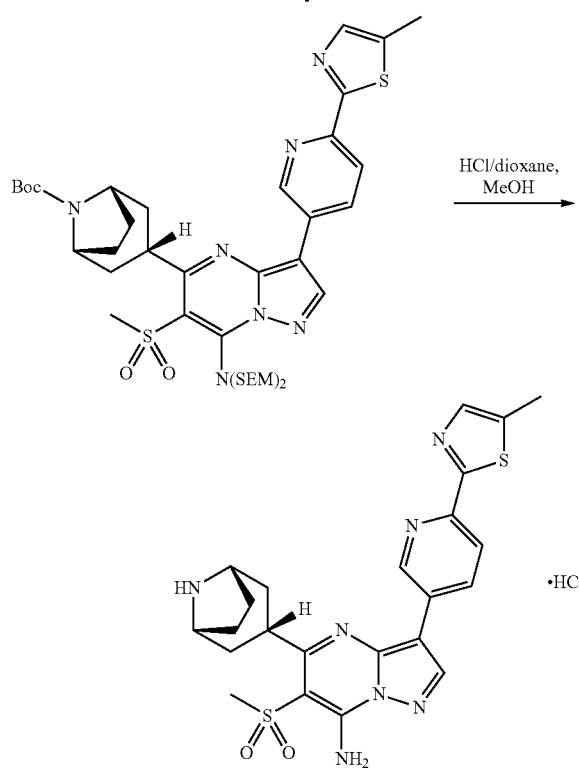

A mixture of (1R,3s,5S)-tert-butyl 3-(7-(bis((2-(trimethylsilyl)ethoxy)methyl)amino)-6-(methylsulfonyl)-3-(6-(5-methylthiazol-2-yl)pyridin-3-yl)pyrazolo[1,5-a]pyrimidin-5-yl)-8-azabicyclo[3.2.1]octane-8-carboxylate from the previous step was partially dissolved in methanol (2.0 mL), 4M HCl in 1,4-dioxane (2.0 mL) was added, and the solution was stirred for 2 hours. Solvent was removed under vacuum to afford the title compound as an orange solid (95.0 mg) that was used as is in the next reaction.

Step 8: Preparation of 5-((1R,3s,5S)-8-azabicyclo[3.2.1]octan-3-yl)-6-(methylsulfonyl)-3-(6-(5-methylthiazol-2-yl)pyridin-3-yl)pyrazolo[1,5-a]pyrimidin-7-amine

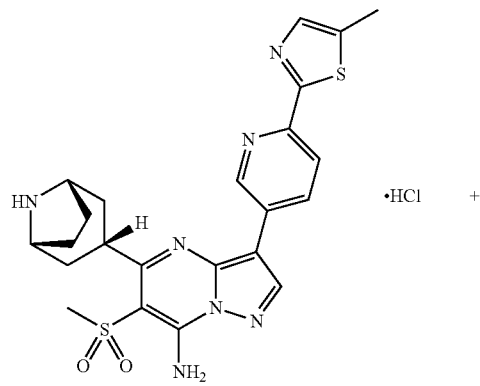

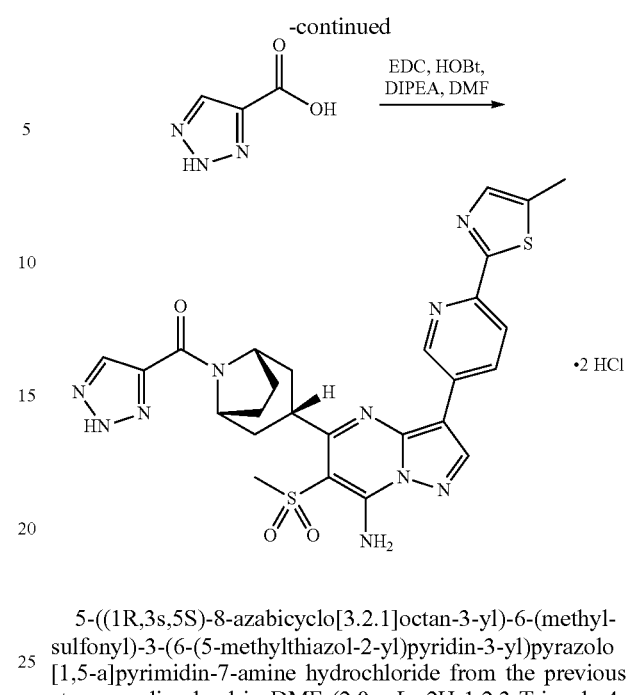

5-((1R,3s,5S)-8-azabicyclo[3.2.1]octan-3-yl)-6-(methylsulfonyl)-3-(6-(5-methylthiazol-2-yl)pyridin-3-yl)pyrazolo[1,5-a]pyrimidin-7-amine hydrochloride from the previous step was dissolved in DMF (2.0 mL). 2H-1,2,3-Triazole-4-carboxylic acid (15.0 mg, 0.132 mmol), EDC (48.8 mg, 0.254 mmol), HOBt (35.1 mg, 0.229 mmol), and DIPEA (88.7 uL, 0.509 mmol) were added and stirred for 22 hours. The solution was purified by preparative reversed-phase liquid chromatography and converted to the dihydrochloride salt to afford the desired compound as a yellow solid (9.3 mg).

Example 3-18

Preparation of 5-((1R,3s,5S)-8-azabicyclo[3.2.1]octan-3-yl)-3-(6-(5,6-dihydro-4H-cyclopenta[d]thiazol-2-yl)pyridin-3-yl)-6-(methylsulfonyl)pyrazolo[1,5-a]pyrimidin-7-amine

Step 1: Preparation of 5,6-dihydro-4H-cyclopenta[d]thiazol-2-amine

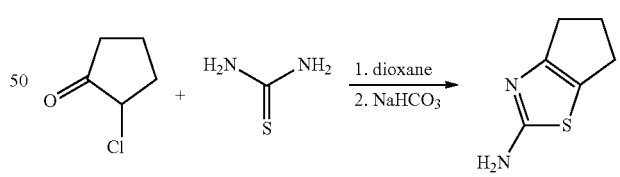

2-Chlorocyclopentanone (9.01 g, 74.4 mmol) was added slowly to a 95° C. stirred mixture of thiourea (5.77 g, 75.0 mmol) in 1,4-dioxane (150 mL). After full addition, the temperature was maintained for an hour then the mixture was cooled to room temperature. It was then filtered and washed with 1,4-dioxane and diethyl ether, and dried under air suction to afford 11.15 g white solid. This was partitioned between diethyl ether and saturated aqueous sodium carbonate. The ether layer was washed with brine, dried with Na$_2$SO$_4$, and solvent removed by rotoevaporation to afford 9.8 g beige solid. (Modified procedure from US Patent application 64 699, 2008, Florjancic, A. S.; et al).

Step 2: Preparation of 2-bromo-5,6-dihydro-4H-cyclopenta[d]thiazole

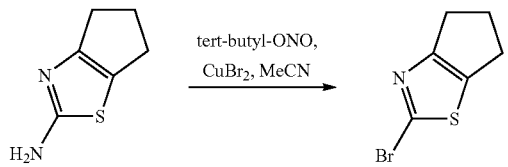 [SMILES: Nc1nc2c(s1)CCC2 ; "tert-butyl-ONO," ; Brc1nc2c(s1)CCC2]

Step 3: Preparation of (1R,3s,5S)-tert-butyl 3-(7-(bis((2-(trimethylsilyl)ethoxy)methyl)amino)-3-(6-(5,6-dihydro-4H-cyclopenta[d]thiazol-2-yl)pyridin-3-yl)pyrazolo[1,5-a]pyrimidin-5-yl)-8-azabicyclo[3.2.1]octane-8-carboxylate

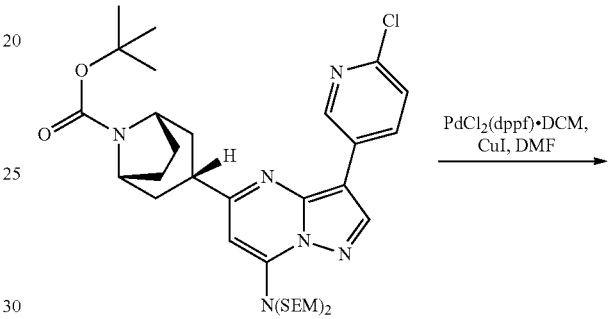

Copper (II) bromide (13.5 g, 60.0 mmol) was added to a mixture of 5,6-dihydro-4H-cyclopental[d]thiazol-2-amine (7.01 g, 50.0 mmol) and tert-butyl nitrite (9.91 mL, 75.0 mmol) in anhydrous acetonitrile (50 mL) creating an exotherm. After an hour, it was poured into a solution of saturated aqueous NH$_4$Cl (140 mL) and concentrated NH$_4$OH (60 mL) diluted with water (to 800 mL) and stirred for 30 minutes. It was extracted with 20% dichloromethane in diethyl ether and the ether layer was washed with water, 20% aqueous NaO$_3$S$_2$, and brine. It was dried with Na$_2$SO$_4$ and solvent removed by rotoevaporation. The brown residue was purified by flash chromatography (25-50%, DCM/Hexanes) to afford the title compound as a white solid (3.53 g). (Modified procedure from Caleta, I.; et. al. *J. Med. Chem.* 2009, 52, 1744.).

Step 2: Preparation of 2-(tributylstannyl)-5,6-dihydro-4H-cyclopental[d]thiazole

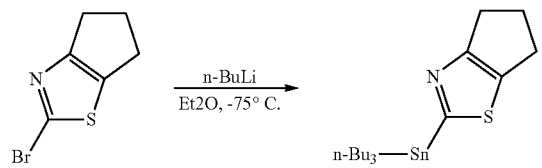

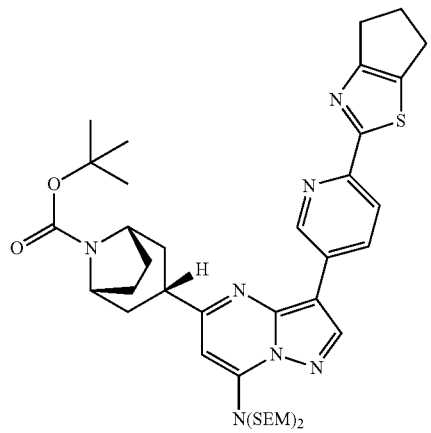

n-Butyllithium (2.5M, 8.2 mL, 21 mmol) was added dropwise to a slurry of 2-bromo-5,6-dihydro-4H-cyclopenta[d]thiazole (3.5 g, 17 mmol) in diethyl ether (34 mL) at −75° C. After stirring an hour, tributylchlorostannane (5.3 mL, 19 mmol) was added in bolus and the cold bath was removed. After 2 hours, it was quenched with saturated aqueous sodium bicarbonate and extracted with more diethyl ether. The ether layer was washed with brine and dried with Na$_2$SO$_4$, and solvent was removed by rotoevaporation to afford red oil (8.3 g) that was used as is.

A mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.97 g, 2.75 mmol), copper(I) iodide (0.11 g, 0.55 mmol), PdCl$_2$(dppf)DCM (0.45 g, 0.55 mmol), and DMF (30 mL) was degassed and heated at 95° C. with rapid stirring for 30 minutes. It was cooled to room temperature and poured into a rapidly stirring mixture of concentrated NH$_4$OH and saturated aqueous NH$_4$Cl (3:7, 200 mL) and diethyl ether with enough DCM to dissolve the suspended solids. After 10 minutes the layers were partitioned, the organic layer was washed with water and brine, dried with Na$_2$SO$_4$, and solvent was removed by rotoevaporation. The brown residue was purified by flash chromatography (10-20%, DCM/Hexanes) to afford the title compound as a beige solid (2.09 g). (Modified procedure from Nyffenegger, C.; et al. *Tetrahedron* 2008, 64, 9567.).

Step 4: Preparation of (1R,3s,5S)-tert-butyl 3-(7-(bis((2-(trimethylsilyl)ethoxy)methyl)amino)-3-(6-(5,6-dihydro-4H-cyclopenta[d]thiazol-2-yl)pyridin-3-yl-6-iodopyrazolo[1,5-a]pyrimidin-5-yl)-8-azabicyclo[3.2.1]octane-8-carboxylate Step 5: Preparation of 5-((1R,3s,5S)-8-azabicyclo[3.2.1]octan-3-yl)-3-(6-(5,6-dihydro-4H-cyclopenta[d]thiazol-2-yl)pyridin-3-yl)-6-iodopyrazolo[1,5-a]pyrimidin-7-amine tris(2,2,2-trifluoroacetate)

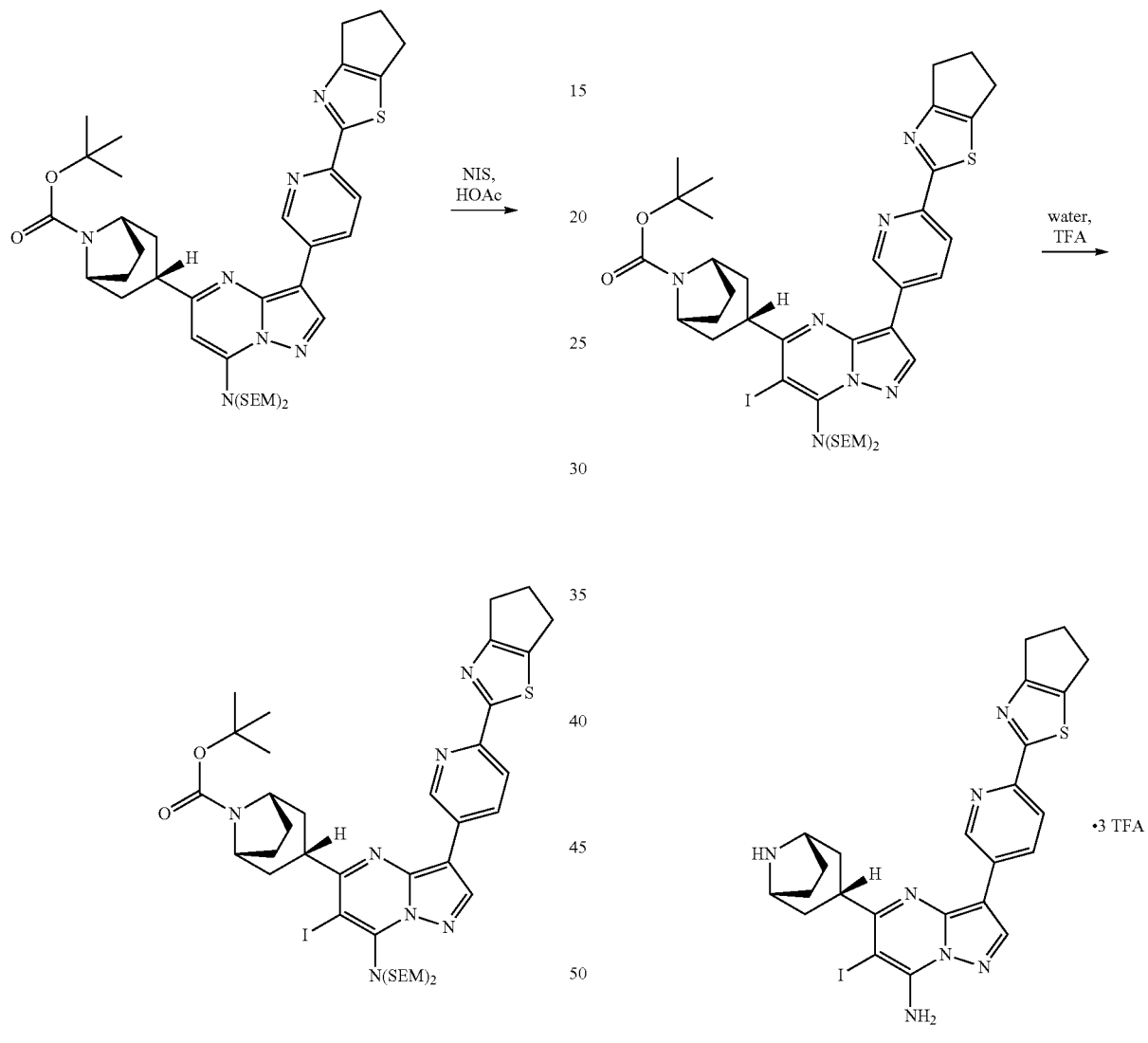

DCM (5 mL) was added to a mixture of (1R,3s,5S)-tert-butyl 3-(7-(bis((2-(trimethylsilyl)ethoxy)methyl)amino)-3-(6-(5,6-dihydro-4H-cyclopenta[d]thiazol-2-yl)pyridin-3-yl)pyrazolo[1,5-a]pyrimidin-5-yl)-8-azabicyclo[3.2.1]octane-8-carboxylate (0.42 g, 0.53 mmol) in HOAc (4 mL) to make a solution and N-iodosuccinimide (0.13 g, 0.55 mmol) was added at room temperature. After 45 minutes 20% aqueous $Na_2S_2O_3$ was added and the mixture was basified with $NaHCO_3$. The mixture was then partitioned between water and EtOAc. The organic layer was washed with water and brine, dried with $Na_2SO_4$, and solvent was removed by rotoevaporation to afford the title compound as a yellow solid (0.57 g) that was used as is in the next reaction.

Water (4 mL) and TFA (8 mL) were premixed then added to (1R,3s,5S)-tert-butyl 3-(7-(bis((2-(trimethylsilyl)ethoxy)methyl)amino)-3-(6-(5,6-dihydro-4H-cyclopenta[d]thiazol-2-yl)pyridin-3-yl)-6-iodopyrazolo[1,5-a]pyrimidin-5-yl)-8-azabicyclo[3.2.1]octane-8-carboxylate (0.49 g, 0.53 mmol) to form a solution. After 15 minutes, solvent was removed by rotoevaporation to afford the title compound as a red solid (0.54 g) that was used as is in the next reaction.

Step 6: Preparation of 5-((1R,3s,5S)-8-azabicyclo[3.2.1]octan-3-yl)-3-(6-(5,6-dihydro-4H-cyclopenta[d]thiazol-2-yl)pyridin-3-yl)-6-(methylsulfonyl)pyrazolo[1,5-a]pyrimidin-7-amine

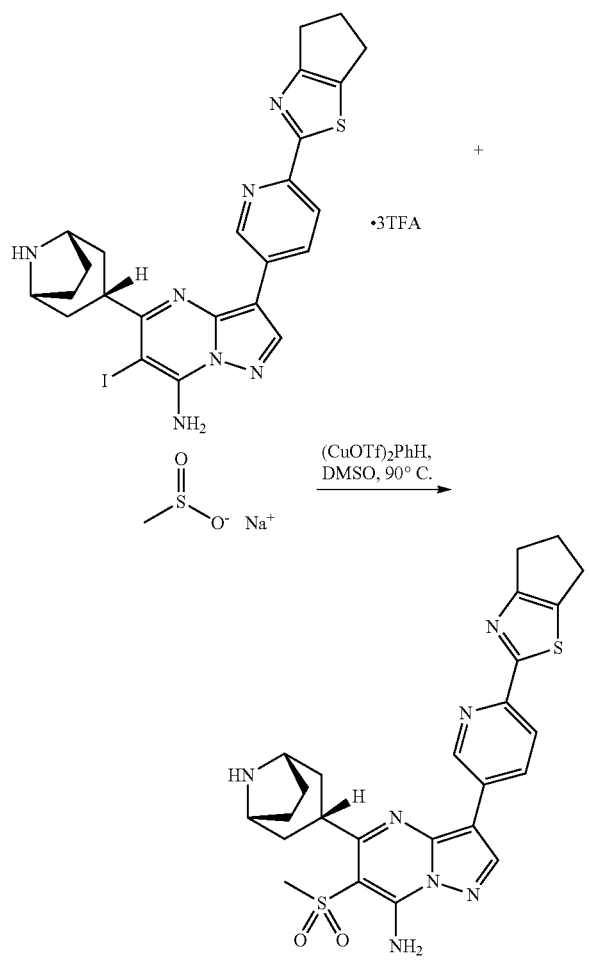

A mixture of sodium methanesulfonate (0.42 g, 3.49 mmol), copper (I) trifluoromethanesulfonate benzene complex (0.65 g, 1.16 mmol), and DMSO (4 mL) were degassed and then heated at 90° C. for 5 minutes. A solution of 5-((1R, 3s,5S)-8-azabicyclo[3.2.1]octan-3-yl)-3-(6-(5,6-dihydro-4H-cyclopenta[d]thiazol-2-yl)pyridin-3-yl)-6-iodopyrazolo[1,5-a]pyrimidin-7-amine tris(2,2,2-trifluoroacetate) (0.53 g, 0.58 mmol) in DMSO (7.2 mL) was added and after 30 minutes, solvent was removed under vacuum. The residue was partitioned between 10% isopropyl alcohol/DCM and (7:3) saturated aqueous NH$_4$Cl/concentrated aqueous NH$_4$OH. The organic layer was washed with water and brine, dried with sodium sulfate, and solvent was removed by rotoevaporation. The orange residue was purified by flash chromatography [5-10%, (10% NH$_4$OH/Methanol)/DCM] to afford the title compound as a yellow solid (0.12 g).

Example 3-19

Preparation of 4-(5-bromopyridin-2-yl)-2-methylthiazole

Step 1: Preparation of 2-bromo-1-(5-bromopyridin-2-yl)ethanone

This compound was prepared by the method of Reck, F.; Zhou, F.; Eyermann, C. J.; Kern, G.; Carcanague, D.; Ioannidis, G.; Illingworth, R.; Poon, G.; Gravestock, M. B. *J. Med. Chem.* 2007, 50, 4868-4881.

1-(5-bromopyridin-2-yl)ethanone (200 mg, 1.0 mmol) was dissolved in Acetic acid (50 mL) and HBr in Acetic acid (48% solution, 280 uL) was added along with water (100 uL). Warmed to 70 C and added Bromine (51.5 uL, 1.0 mmol) and stirred for 1 hour. The reaction was concentrated to give the desired product (280 mg) containing a small amount of dibrominated product. This material was used as is.

Step 2: Preparation of: 5-bromo-2-(2-methyl-1,3-thiazol-4-yl)pyridine

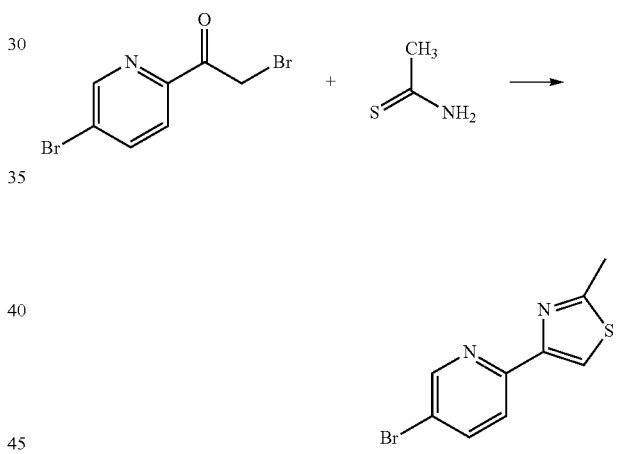

2-bromo-1-(5-bromopyridin-2-yl)ethanone (3.77 g, 13.5 mmol) was dissolved in ethanol (32 mL) and ethanethioamide (1.12 g, 14.8 mmol) was added and the reaction stirred for 18 h at 75° C. The mixture was concentrated; the residual solid was dispersed in ethyl acetate (100 mL), and treated with saturated sodium bicarbonate solution (100 mL) until no further gas evolution was noted. The combined organics were washed with water (50 mL) and brine (50 mL). The aqueous washes were back-extracted with ethyl acetate (100 mL) and the combined organic layers were dried over magnesium sulfate, treated with Darco, filtered through a paper filter, and concentrated to give a yellow solid. The crude product was purified by flash chromatography (90 g silica gel, 1-5% methanol in ethyl acetate). The major product was further purified by flash chromatography (40 g silica gel, 10% ethyl acetate in hexane) to give the title compound (1.94 g) as a colorless crystalline solid.

Following the Scheme 3-1 and Scheme 3-2 and the examples listed above, the following compounds (Table 3-1) can be prepared:

TABLE 3-1

| Compound ID | Structures | Compound Name | M + H (calculated)/ M + H (observed) | pAKT S473 IC50 | p4E-BP1 Thr37/46 IC50 |
|---|---|---|---|---|---|
| 3.1 | 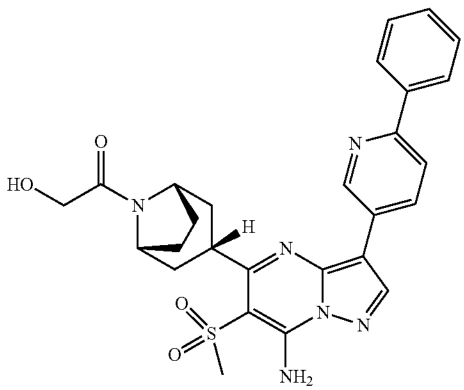 [SMILES: CS(=O)(=O)c1c([C@@H]2C[C@H]3CC[C@@H](C2)N3C(=O)CO)nc2c(-c3ccc(-c4ccccc4)nc3)cnn2c1N] | 1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxyethanone | 533.1/532.9 | A | B |
| 3.2 | 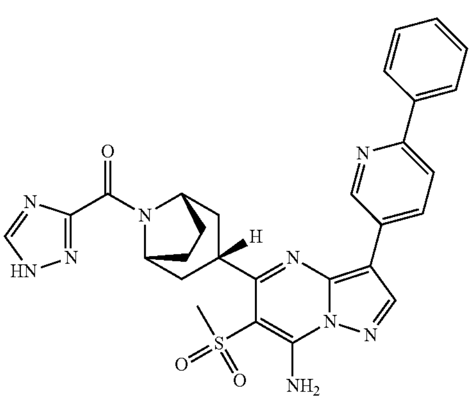 [SMILES: CS(=O)(=O)c1c([C@@H]2C[C@H]3CC[C@@H](C2)N3C(=O)c2nc[nH]n2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone | 570.1/569.8 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.3 | 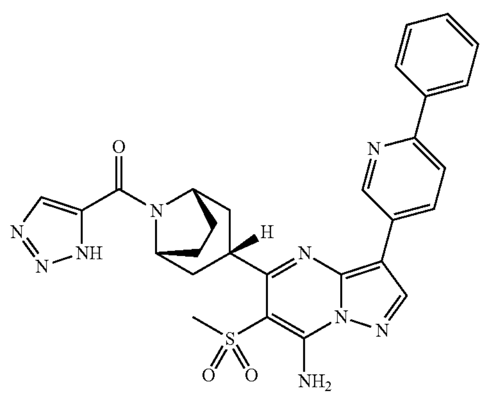 [SMILES: CS(=O)(=O)c1c([C@@H]2C[C@H]3CC[C@@H](C2)N3C(=O)c2cnn[nH]2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,3,-triazol-5-yl)methanone | 570.1/570.1 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.4 | | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone | 584.2/584.0 | A | A |
| 3.5 | 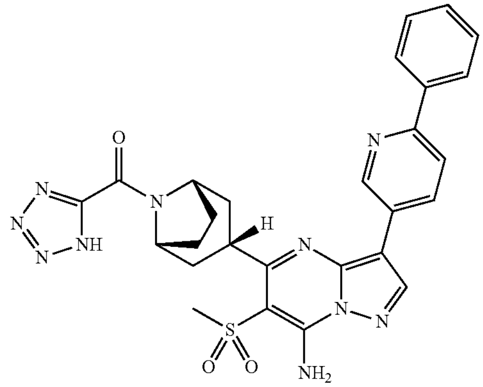 [SMILES: CS(=O)(=O)c1c([C@@H]2C[C@H]3CC[C@@H](C2)N3C(=O)c2nnn[nH]2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-tetrazol-5-yl)methanone | 571.1/570.9 | C | D |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.6 | 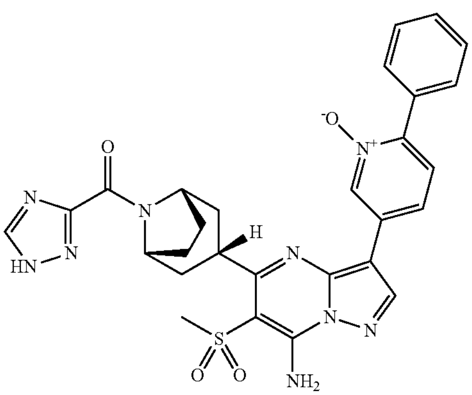 | 5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-phenylpyridine 1-oxide | 586.1/586.2 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.7 | 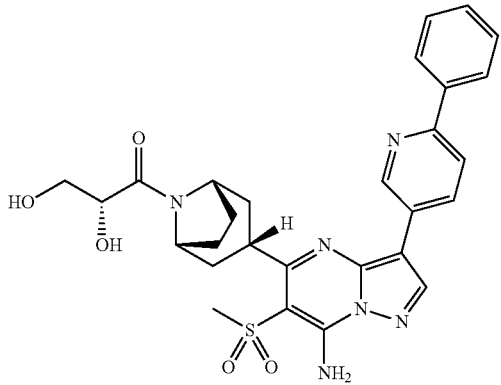 [SMILES: CS(=O)(=O)c1c([C@@H]2C[C@H]3CC[C@@H](C2)N3C(=O)[C@H](O)CO)nc2c(-c3ccc(-c4ccccc4)nc3)cnn2c1N] | (R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,3-dihydroxypropan-1-one | 563.2/562.8 | B | C |
| 3.8 | 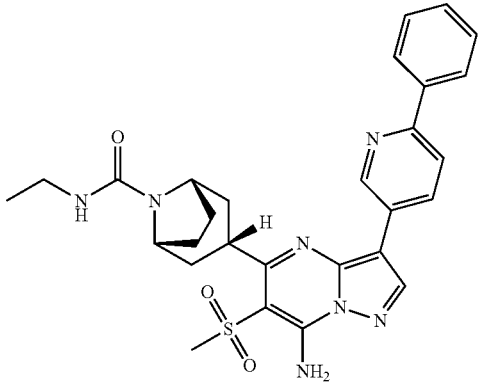 [SMILES: CCNC(=O)N1[C@@H]2CC[C@H]1C[C@H](c1nc3c(-c4ccc(-c5ccccc5)nc4)cnn3c(N)c1S(C)(=O)=O)C2] | (1R,3s,5S)-3-(7-amino-6-(methylsulfonyl)-3-(6-phenylpyridin-3-yl)pyrazolo[1,5-a]pyrimidin-5-yl)-N-ethyl-8-azabicyclo[3.2.1]octane-8-carboxamide | 546.2/546.0 | B | B |
| 3.10 | 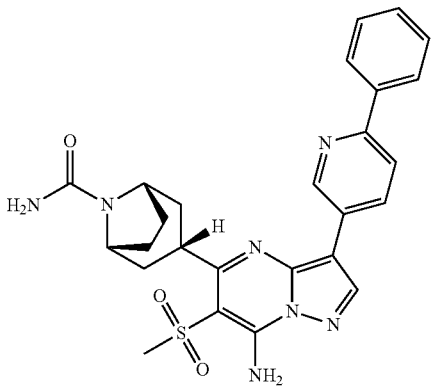 [SMILES: CS(=O)(=O)c1c([C@@H]2C[C@H]3CC[C@@H](C2)N3C(N)=O)nc2c(-c3ccc(-c4ccccc4)nc3)cnn2c1N] | (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboxamide | 518.1/517.9 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.11 | 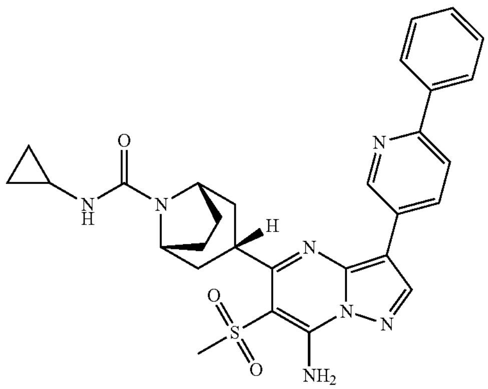 [SMILES: CS(=O)(=O)c1c([C@@H]2C[C@H]3CC[C@@H](C2)N3C(=O)NC2CC2)nc2c(-c3ccc(-c4ccccc4)nc3)cnn2c1N] | (1R,3s,5S)-3-(7-amino-6-(methylsulfonyl)-3-(6-phenylpyridin-3-yl)pyrazolo[1,5-a]pyrimidin-5-yl)-N-cyclopropyl-8-azabicyclo[3.2.1]octane-8-carboxamide | 558.2/557.9 | B | C |
| 3.12 | 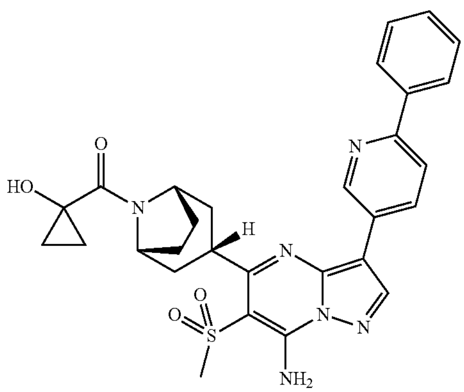 [SMILES: CS(=O)(=O)c1c([C@@H]2C[C@H]3CC[C@@H](C2)N3C(=O)C2(O)CC2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1-hydroxycyclopropyl)methanone | 559.2/558.9 | B | C |
| 3.13 | 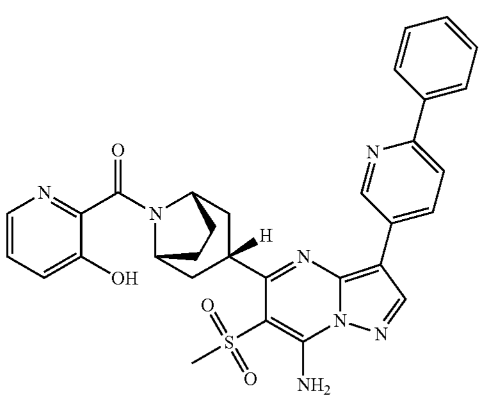 [SMILES: CS(=O)(=O)c1c([C@@H]2C[C@H]3CC[C@@H](C2)N3C(=O)c2ncccc2O)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-hydroxypyridin-3-yl)methanone | 596.2/596.0 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.14 | 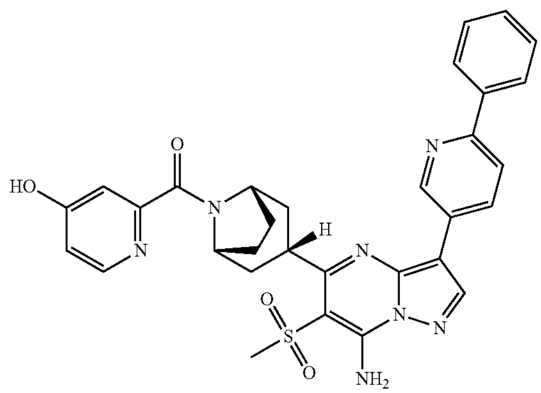 [SMILES: CS(=O)(=O)c1c([C@@H]2C[C@H]3CC[C@@H](C2)N3C(=O)c2cc(O)ccn2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-hydroxypyridin-2-yl)methanone | 596.2/595.9 | B | C |
| 3.15 | 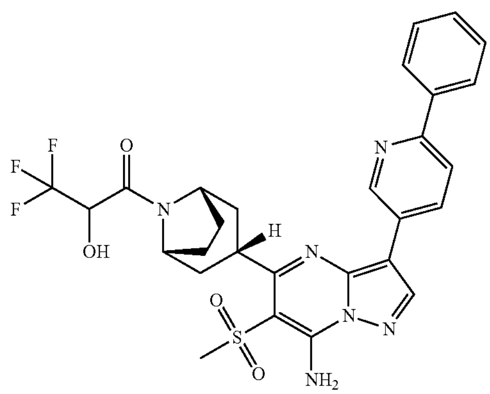 [SMILES: CS(=O)(=O)c1c([C@@H]2C[C@H]3CC[C@@H](C2)N3C(=O)C(O)C(F)(F)F)nc2c(-c3ccc(-c4ccccc4)nc3)cnn2c1N] | 1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-3,3,3-trifluoro-2-hydroxypropan-1-one | 601.1/601.2 | C | C |
| 3.16 | 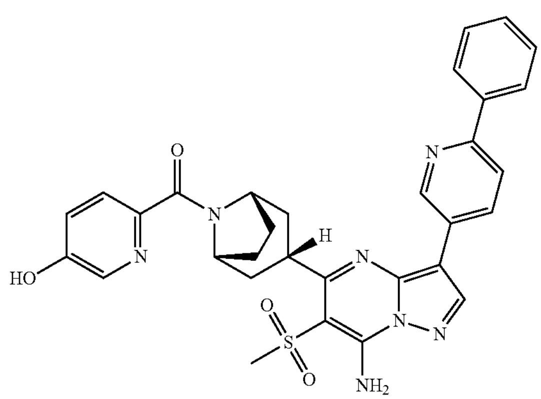 [SMILES: CS(=O)(=O)c1c([C@@H]2C[C@H]3CC[C@@H](C2)N3C(=O)c2ccc(O)cn2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxypyridin-2-yl)methanone | 596.2/595.9 | A | B |
| 3.17 | 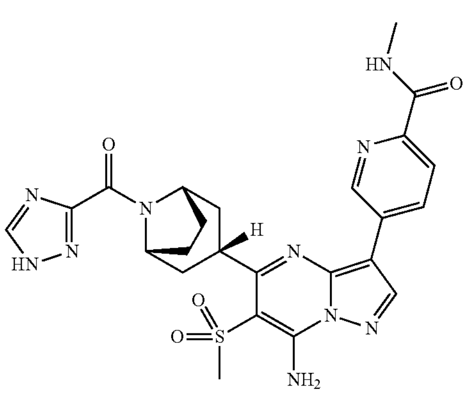 [SMILES: CNC(=O)c1ccc(-c2cnn3c(N)c(S(C)(=O)=O)c([C@@H]4C[C@H]5CC[C@@H](C4)N5C(=O)c4nc[nH]n4)nc23)cn1] | 5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-N-methylpicolinamide | 551.1/550.9 | D | C |

TABLE 3-1-continued

| Compound ID | Structures | Compound Name | M + H (calculated)/ M + H (observed) | pAKT S473 IC50 | p4E-BP1 Thr37/46 IC50 |
| --- | --- | --- | --- | --- | --- |
| 3.18 | 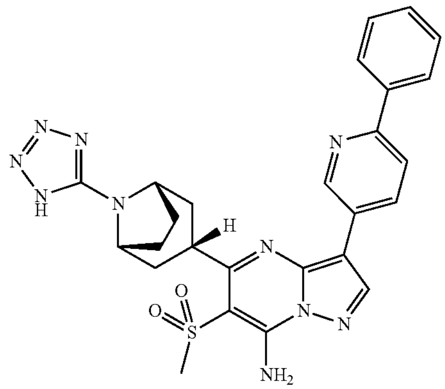 [SMILES: CS(=O)(=O)c1c([C@@H]2C[C@H]3CC[C@@H](C2)N3c2nnn[nH]2)nc2c(-c3ccc(-c4ccccc4)nc3)cnn2c1N] | 5-((1R,3s,5S)-8-(1H-tetrazol-5-yl)-8-azabicyclo[3.2.1]octan-3-yl)-6-(methylsulfonyl)-3-(6-phenylpyridin-3-yl)pyrazolo[1,5-a]pyrimidin-7-amine | 543.1/542.9 | D | D |
| 3.19 | 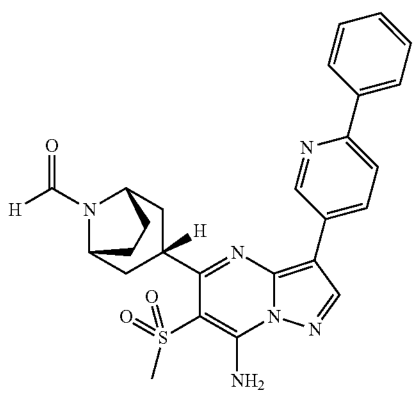 [SMILES: CS(=O)(=O)c1c([C@@H]2C[C@H]3CC[C@@H](C2)N3C=O)nc2c(-c3ccc(-c4ccccc4)nc3)cnn2c1N] | (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbaldehyde | 503.1/502.8 | B | B |
| 3.20 | 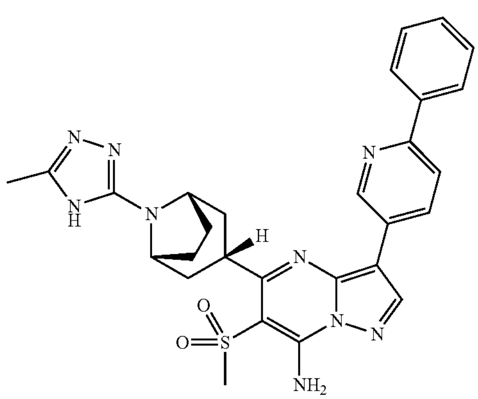 [SMILES: Cc1nnc(N2[C@@H]3CC[C@H]2C[C@H](c2nc4c(-c5ccc(-c6ccccc6)nc5)cnn4c(N)c2S(C)(=O)=O)C3)[nH]1] | 5-((1R,3s,5S)-8-(5-methyl-4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine | 556.2/555.9 | ND | ND |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.21 | 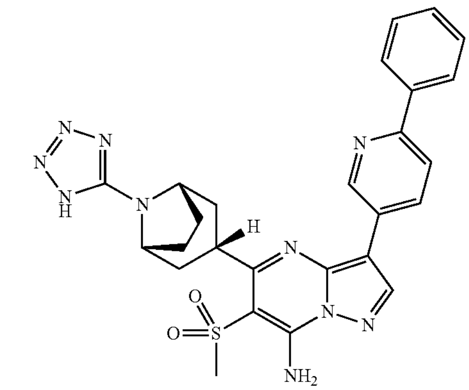 [SMILES: CS(=O)(=O)c1c([C@@H]2C[C@H]3CC[C@@H](C2)N3c2nnn[nH]2)nc2c(-c3ccc(-c4ccccc4)nc3)cnn2c1N] | 5-((1R,3s,5S)-8-(4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine | 542.2/541.9 | C | C |
| 3.22 | 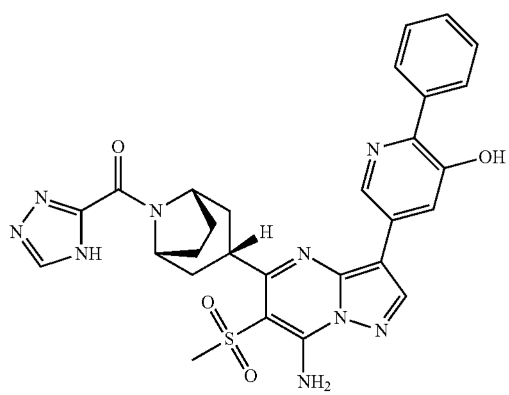 [SMILES: CS(=O)(=O)c1c([C@@H]2C[C@H]3CC[C@@H](C2)N3C(=O)c2nnc[nH]2)nc2c(-c3cnc(-c4ccccc4)c(O)c3)cnn2c1N] | ((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 586.1/585.8 | B | C |
| 3.23 | 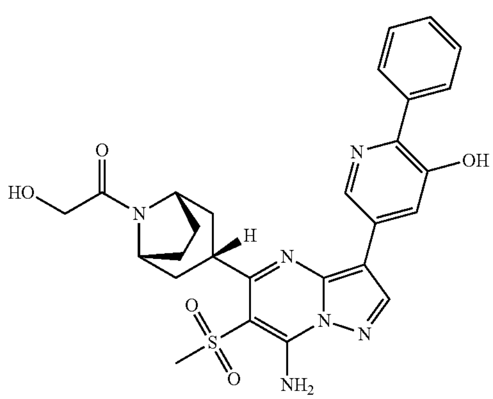 [SMILES: CS(=O)(=O)c1c([C@@H]2C[C@H]3CC[C@@H](C2)N3C(=O)CO)nc2c(-c3cnc(-c4ccccc4)c(O)c3)cnn2c1N] | 1-((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)-2-hydroxyethanone | 549.1/548.9 | C | C |

TABLE 3-1-continued
| Compound ID | Structures | Compound Name | M + H (calculated)/ M + H (observed) | pAKT S473 IC50 | p4E-BP1 Thr37/46 IC50 |
|---|---|---|---|---|---|
| 3.24 | 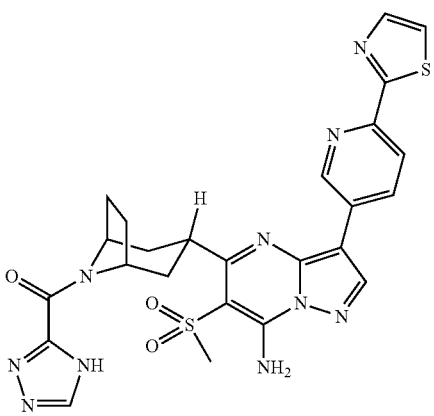 [SMILES: CS(=O)(=O)c1c(C2CC3CCC(C2)N3C(=O)c2nnc[nH]2)nc2c(-c3ccc(-c4nccs4)nc3)cnn2c1N] | ((1R,3s,5S)-3-(7-amino-6-(methylsulfonyl)-3-(6-(thiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone | 576.2/576.8 | A | A |
| 3.25 | 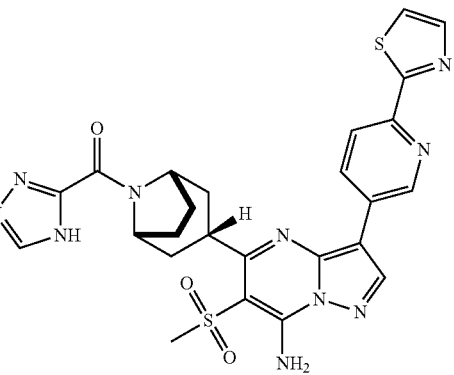 | ((1R,3s,5S)-3-(7-amino-3-(7-fluoronaphthalen-2-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 561.2/562.0 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.26 | 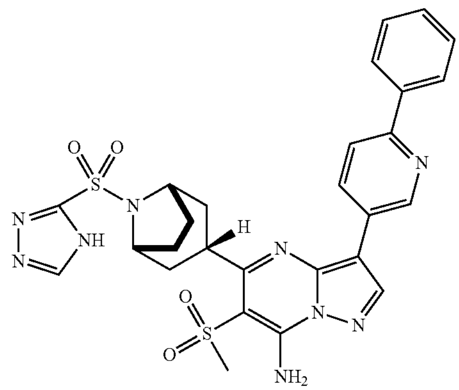 | 5-((1R,3s,5S)-8-(4H-1,2,4-triazol-3-ylsulfonyl)-8-azabicyclo[3.2.1]octan-3-yl)-6-(methylsulfonyl)-3-(6-phenylpyridin-3-yl)pyrazolo[1,5-a]pyrimidin-7-amine | 606.2/606.1 | B | C |
| 3.27 | 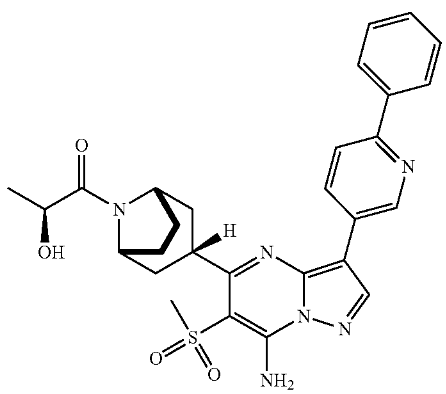 | (S)-1-((1R,3R,5S)-3-(7-amino-6-methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one | 547.2/547.0 | B | B |
| 3.28 | 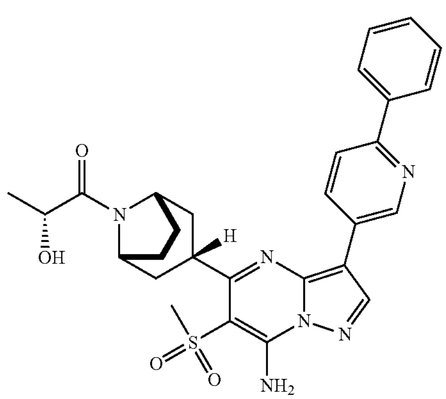 | (R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one | 547.2/547.0 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.29 | 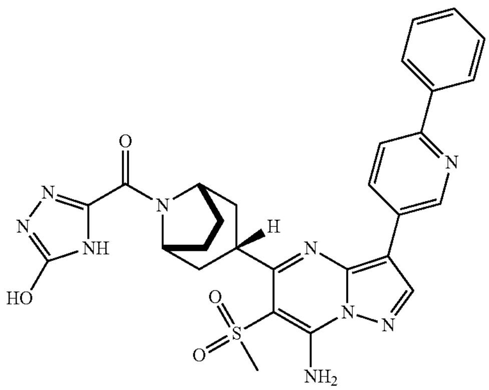 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone | 586.2/586.0 | B | B |
| 3.30 | 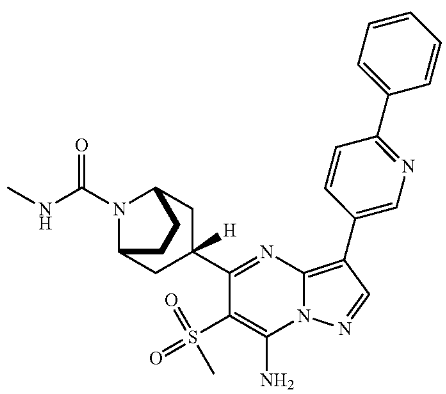 | (1R,3s,5S)-3-(7-amino-6-(methylsulfonyl)-3-(6-phenylpyridin-3-yl)pyrazolo[1,5-a]pyrimidin-5-yl)-N-methyl-8-azabicyclo[3.2.1]octane-8-carboxamide | 532.2/532.0 | B | B |
| 3.31 | 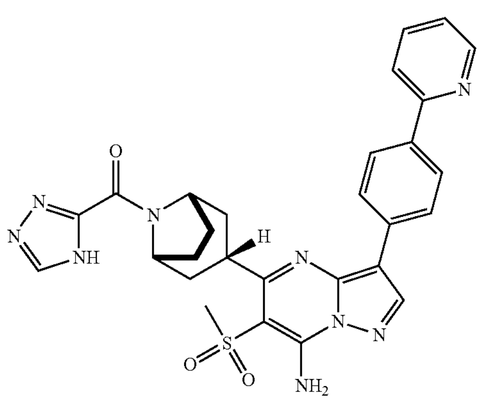 | ((1R,3s,5S)-3-(7-amino-6-(methylsulfonyl)-3-(4-(pyridin-2-yl)phenyl)pyrazolo[1,5-a]pyrimidin-5-yl)-8-azabicyclo[3.2.1]octan-8-yl)(4H-1,2,4-triazol-3-yl)methanone | 570.2/570.0 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.32 | 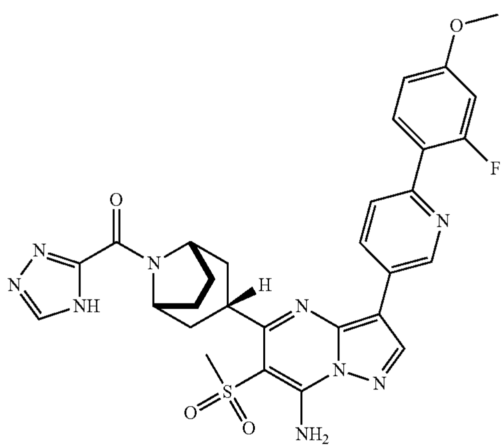 | ((1R,3s,5S)-3-(7-amino-3-(6-(2-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 618.2/618.0 | A | A |
| 3.33 | 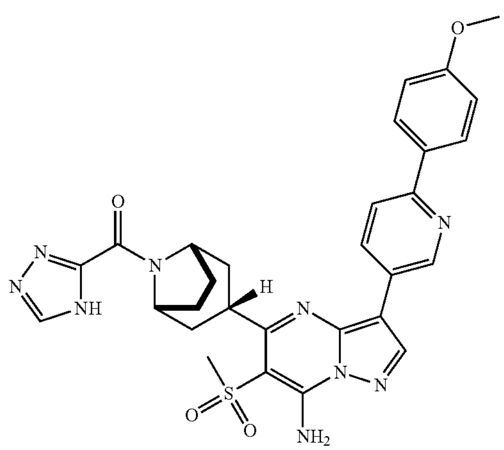 | ((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 600.2/600.0 | A | A |
| 3.34 | 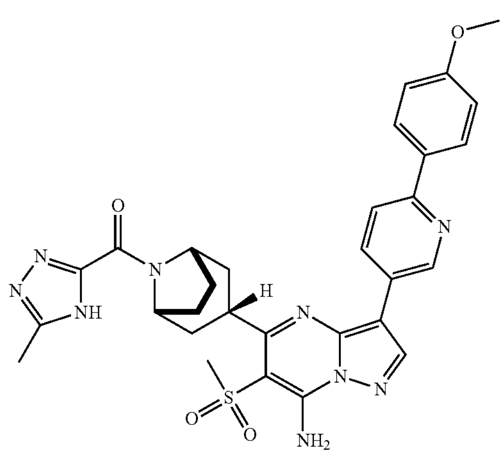 | ((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 614.2/614.0 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.35 | 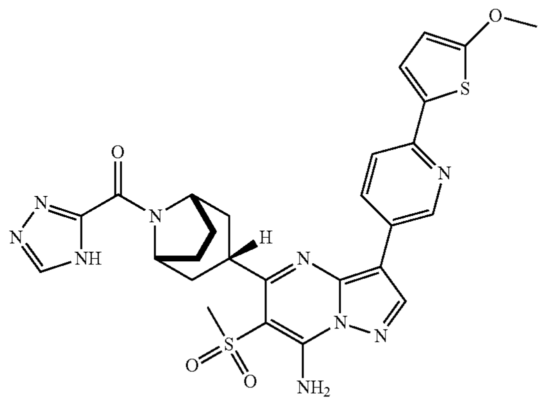 | ((1R,3s,5S)-3-(7-amino-3-(6-(5-methoxythiophen-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 606.2/605.9 | A | A |
| 3.36 | 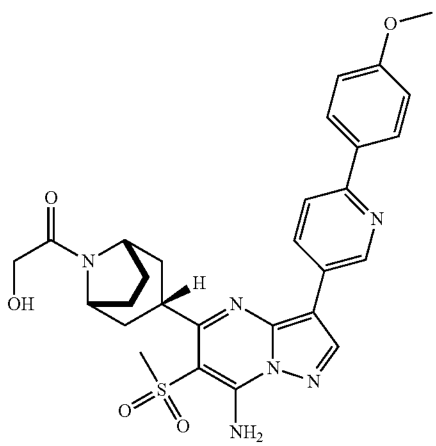 | 1-((1R,3s,5S)-3-(7-amino-3-(6-(4-methoxphenyl)pyridin-3-yl)-6-(methylsulfonyl)pyrazolo[1,5-a]pyrimidin-5-yl)-8-azabicyclo[3.2.1]octan-8-yl)-2-hydroxyethanone | 563.2/563.0 | A | A |
| 3.37 | 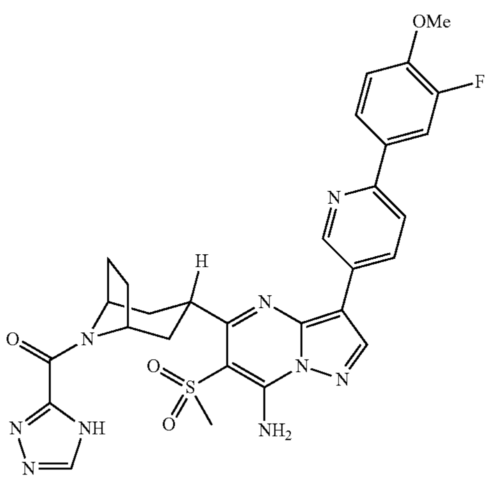 [SMILES: COc1ccc(-c2ccc(-c3cnn4c(N)c(S(C)(=O)=O)c(C5CC6CCC(C5)N6C(=O)c5nnc[nH]5)nc34)cn2)cc1F] | ((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 618.2/618.0 | A | A |

| Compound ID | Structures | Compound Name | M + H (calculated)/ M + H (observed) | pAKT S473 IC50 | p4E-BP1 Thr37/46 IC50 |
|---|---|---|---|---|---|
| 3.38 | 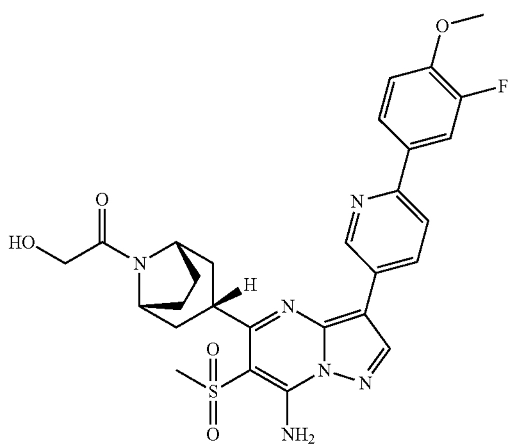 [SMILES: COc1ccc(-c2ccc(-c3cnn4c(N)c(S(C)(=O)=O)c([C@@H]5C[C@H]6CC[C@@H](C5)N6C(=O)CO)nc34)cn2)cc1F] | 1-((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)-2-hydroxyethanone | 581.2/580.7 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.39 | 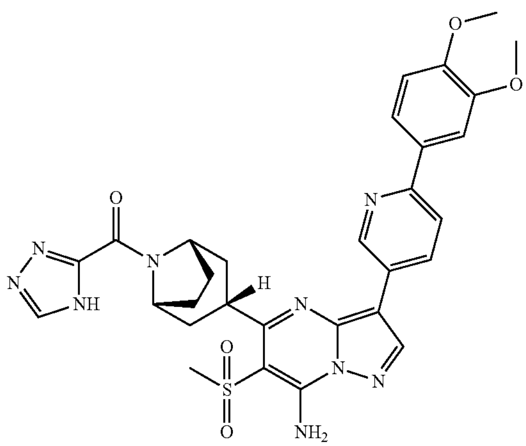 [SMILES: COc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cc1OC] | ((1R,3s,5S)-3-(7-amino-3-(6-(3,4-dimethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 630.2/630.0 | B | B |
| 3.40 | 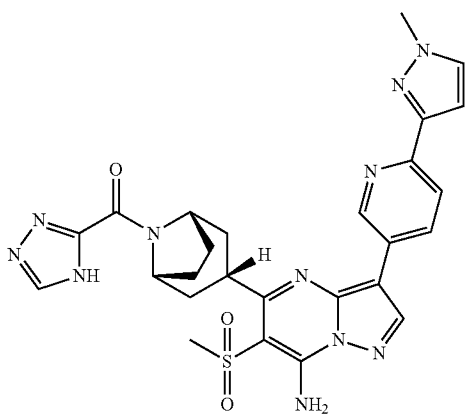 [SMILES: Cn1ccc(-c2ccc(-c3cnn4c(N)c(S(C)(=O)=O)c([C@@H]5C[C@H]6CC[C@@H](C5)N6C(=O)c5nnc[nH]5)nc34)cn2)n1] | ((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 574.2/574.2 | A | A |
| 3.41 | 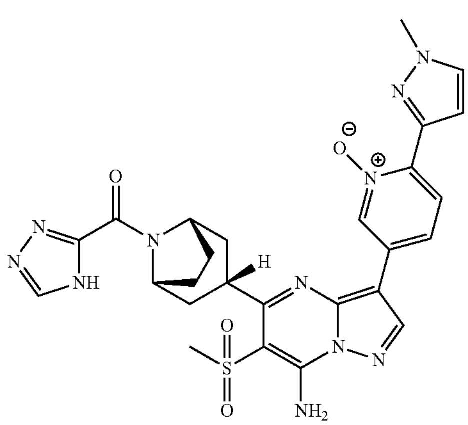 [SMILES: Cn1ccc(-c2ccc(-c3cnn4c(N)c(S(C)(=O)=O)c([C@@H]5C[C@H]6CC[C@@H](C5)N6C(=O)c5nnc[nH]5)nc34)c[n+]2[O-])n1] | 5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-(1-methyl-1H-pyrazol-3-yl)pyridine 1-oxide | 590.2/590.1 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.42 | 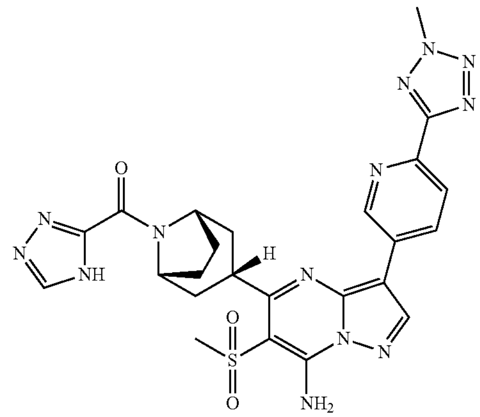 [SMILES: Cn1nnc(-c2ccc(-c3cnn4c(N)c(S(C)(=O)=O)c([C@@H]5C[C@H]6CC[C@@H](C5)N6C(=O)c5nnc[nH]5)nc34)cn2)n1] | ((1R,3a,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 576.2/576.4 | B | C |
| 3.43 | 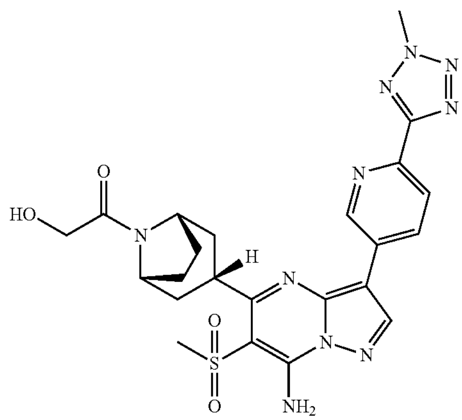 [SMILES: Cn1nnc(-c2ccc(-c3cnn4c(N)c(S(C)(=O)=O)c([C@@H]5C[C@H]6CC[C@@H](C5)N6C(=O)CO)nc34)cn2)n1] | 1-((1R,3a,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)-2-hydroxyethanone | 539.2/539.4 | C | D |
| 3.44 | 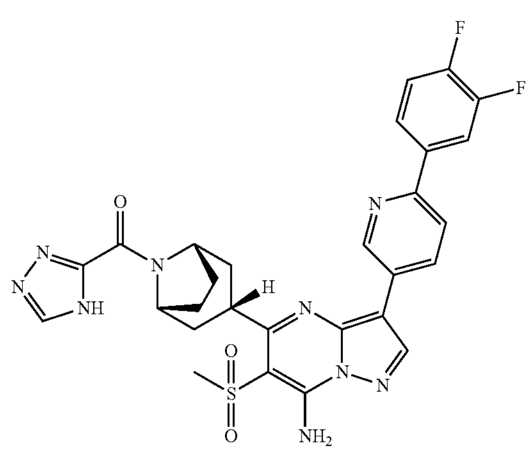 [SMILES: CS(=O)(=O)c1c([C@@H]2C[C@H]3CC[C@@H](C2)N3C(=O)c2nnc[nH]2)nc2c(-c3ccc(-c4ccc(F)c(F)c4)nc3)cnn2c1N] | ((1R,3s,5S)-3-(7-amino-3-(6-(3,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 606.2/606.1 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.45 | 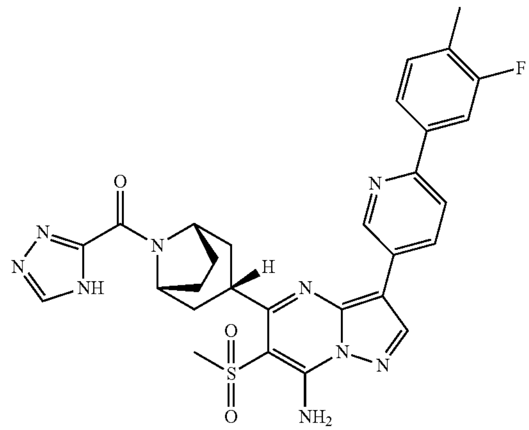 [SMILES: Cc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cc1F] | ((1R,3s,5S)-3-(7-amino-3-(6-(3-fluoro-4-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 602.2/601.9 | A | A |
| 3.46 | 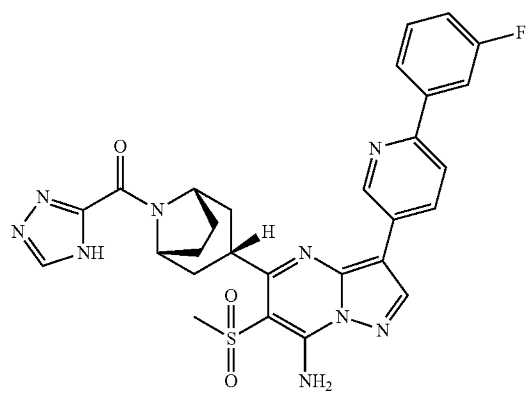 [SMILES: CS(=O)(=O)c1c([C@@H]2C[C@H]3CC[C@@H](C2)N3C(=O)c2nnc[nH]2)nc2c(-c3ccc(-c4cccc(F)c4)nc3)cnn2c1N] | ((1R,3s,5S)-3-(7-amino-3-(6-(3-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 588.2/587.9 | A | A |
| 3.47 | 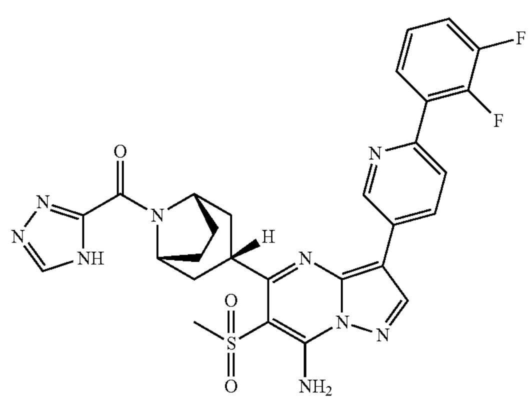 [SMILES: CS(=O)(=O)c1c([C@@H]2C[C@H]3CC[C@@H](C2)N3C(=O)c2nnc[nH]2)nc2c(-c3ccc(-c4cccc(F)c4F)nc3)cnn2c1N] | ((1R,3s,5S)-3-(7-amino-3-(6-(2,3-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 606.2/605.9 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.48 | 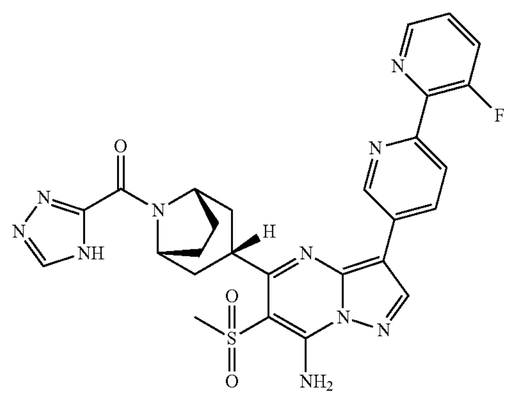 [SMILES: CS(=O)(=O)c1c([C@@H]2C[C@H]3CC[C@@H](C2)N3C(=O)c2nnc[nH]2)nc2c(-c3ccc(-c4ncccc4F)nc3)cnn2c1N] | ((1R,3s,5S)-3-(7-amino-3-(3'-fluoro-2,2'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 589.2/588.9 | A | A |
| 3.49 | 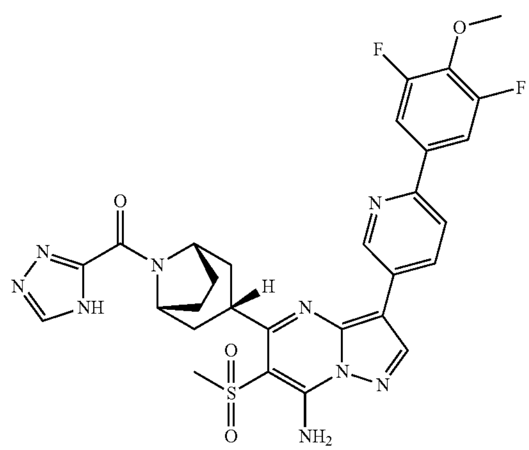 [SMILES: COc1c(F)cc(-c2ccc(-c3cnn4c(N)c(S(C)(=O)=O)c([C@@H]5C[C@H]6CC[C@@H](C5)N6C(=O)c5nnc[nH]5)nc34)cn2)cc1F] | ((1R,3s,5S)-3-(7-amino-3-(6-(3,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 636.2/635.9 | B | B |
| 3.50 | 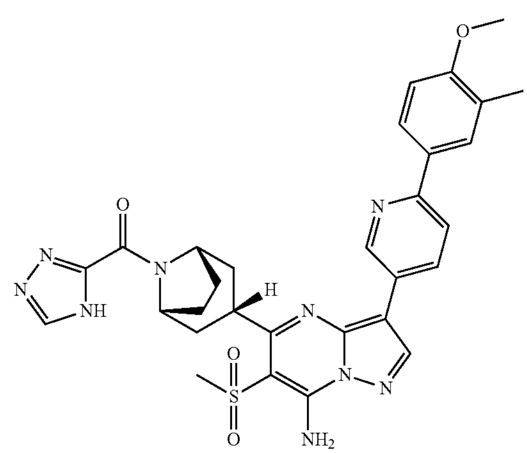 [SMILES: COc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cc1C] | ((1R,3s,5S)-3-(7-amino-3-(6-(4-methoxy-3-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 614.2/613.9 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.51 | 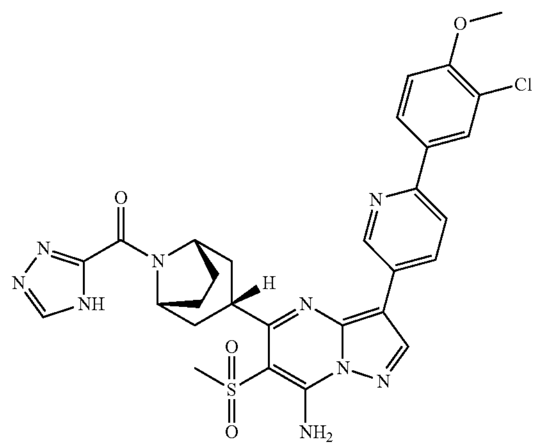 [SMILES: COc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cc1Cl] | ((1R,3s,5S)-3-(7-amino-3-(6-(3-chloro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 634.2/633.9 | A | A |
| 3.52 | 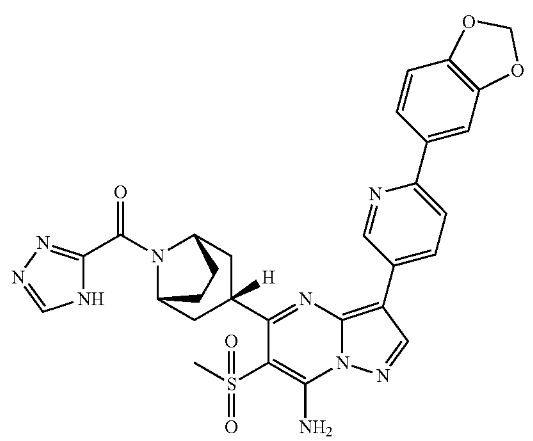 [SMILES: CS(=O)(=O)c1c([C@@H]2C[C@H]3CC[C@@H](C2)N3C(=O)c2nnc[nH]2)nc2c(-c3ccc(-c4ccc5c(c4)OCO5)nc3)cnn2c1N] | ((1R,3s,5S)-3-(7-amino-3-(6-(benzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 614.2/613.9 | A | A |
| 3.53 | 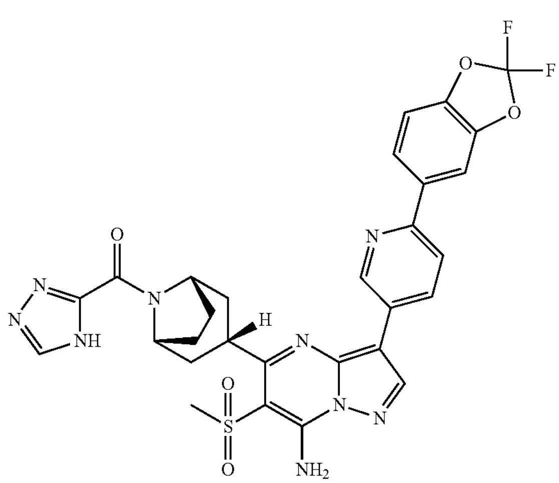 [SMILES: CS(=O)(=O)c1c([C@@H]2C[C@H]3CC[C@@H](C2)N3C(=O)c2nnc[nH]2)nc2c(-c3ccc(-c4ccc5c(c4)OC(F)(F)O5)nc3)cnn2c1N] | ((1R,3s,5S)-3-(7-amino-3-(6-(2,2-difluorobenzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 650.2/650.1 | B | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.54 | 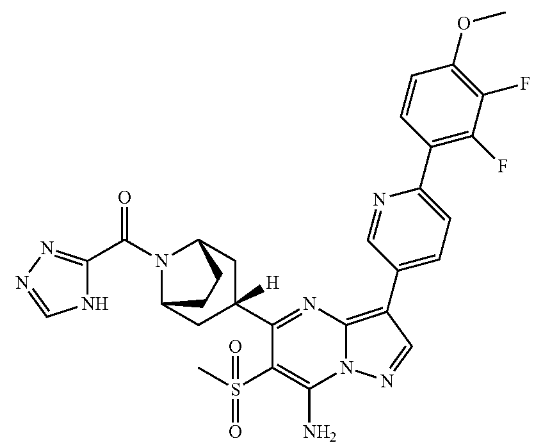 [SMILES: COc1ccc(-c2ccc(-c3cnn4c(N)c(S(C)(=O)=O)c([C@@H]5C[C@H]6CC[C@@H](C5)N6C(=O)c5nnc[nH]5)nc34)cn2)c(F)c1F] | ((1R,3s,5S)-3-(7-amino-3-(6-(2,3-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 636.2/635.9 | A | A |
| 3.55 | 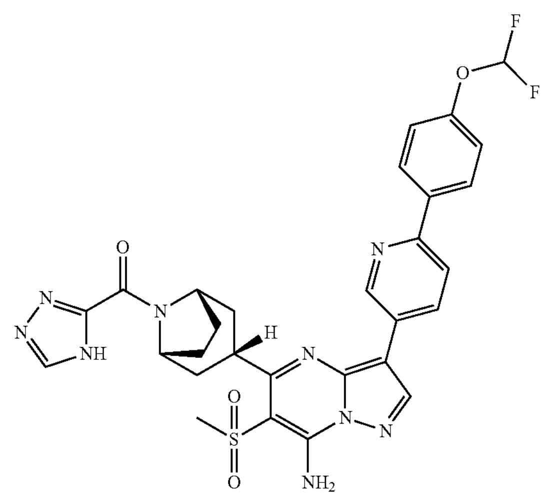 [SMILES: CS(=O)(=O)c1c([C@@H]2C[C@H]3CC[C@@H](C2)N3C(=O)c2nnc[nH]2)nc2c(-c3ccc(-c4ccc(OC(F)F)cc4)nc3)cnn2c1N] | ((1R,3s,5S)-3-(7-amino-3-(6-(4-(difluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 636.2/636.0 | A | A |
| 3.56 | 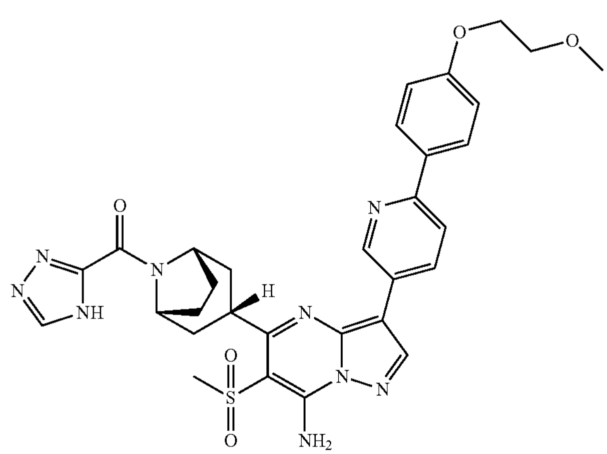 [SMILES: COCCOc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cc1] | ((1R,3s,5S)-3-(7-amino-3-(6-(4-(2-methoxyethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 644.2/644.5 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.57 | 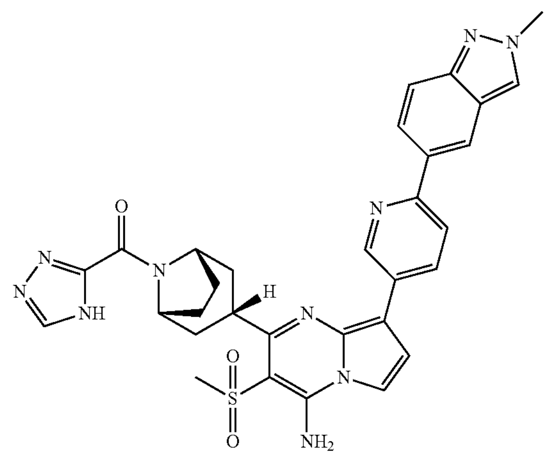 | ((1R,3s,5S)-3-(7-amino-3-(6-(2-methyl-2H-indazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 624.2/624.5 | A | A |
| 3.58 | 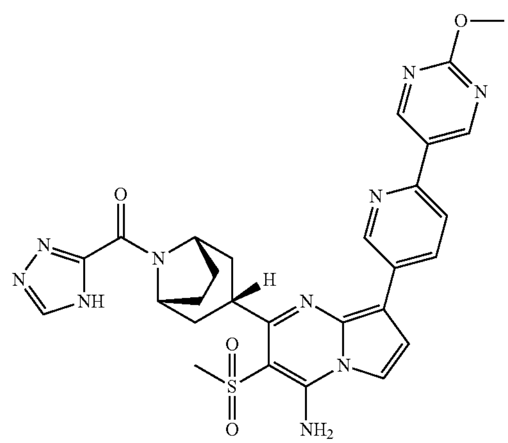 [SMILES: COc1ncc(-c2ccc(-c3ccn4c(N)c(S(C)(=O)=O)c([C@@H]5C[C@H]6CC[C@@H](C5)N6C(=O)c5nnc[nH]5)nc34)cn2)cn1] | ((1R,3s,5S)-3-(7-amino-3-(6-(2-methoxypyrimidin-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 602.2/602.3 | C | C |
| 3.59 | 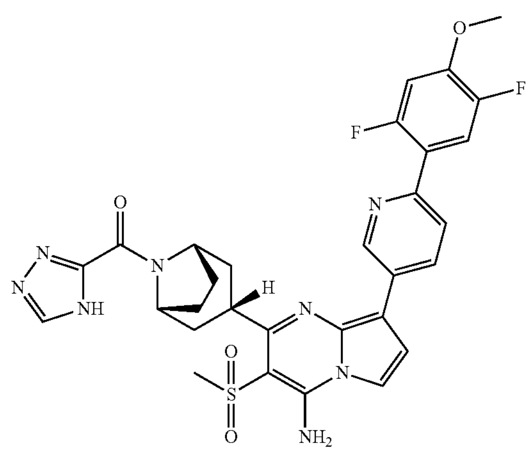 [SMILES: COc1cc(F)c(-c2ccc(-c3ccn4c(N)c(S(C)(=O)=O)c([C@@H]5C[C@H]6CC[C@@H](C5)N6C(=O)c5nnc[nH]5)nc34)cn2)cc1F] | ((1R,3s,5S)-3-(7-amino-3-(6-(2,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 636.18/635.95 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.60 | 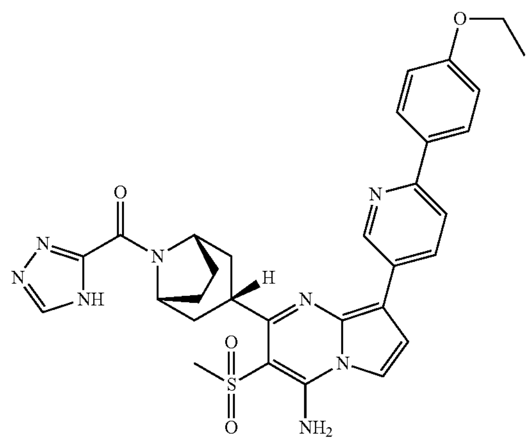 [SMILES: CCOc1ccc(-c2ccc(-c3ccn4c(N)c(S(C)(=O)=O)c([C@@H]5C[C@H]6CC[C@@H](C5)N6C(=O)c5nnc[nH]5)nc34)cn2)cc1] | ((1R,3s,5S)-3-(7-amino-3-(6-(4-ethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 614.2/614.0 | A | A |
| 3.61 | 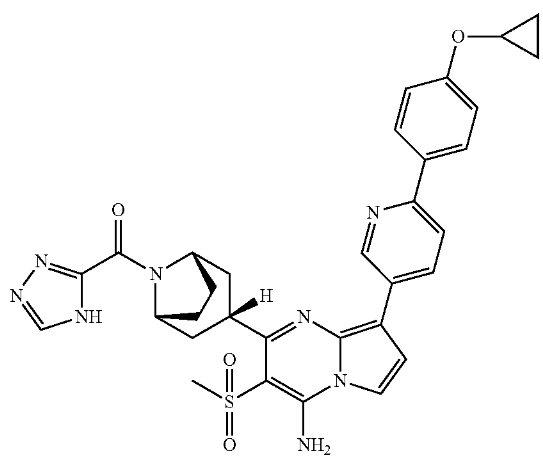 [SMILES: CS(=O)(=O)c1c([C@@H]2C[C@H]3CC[C@@H](C2)N3C(=O)c2nnc[nH]2)nc2c(-c3ccc(-c4ccc(OC5CC5)cc4)nc3)ccn2c1N] | ((1R,3s,5S)-3-(7-amino-3-(6-(4-cyclopropoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 626.2/626.0 | B | B |
| 3.62 | 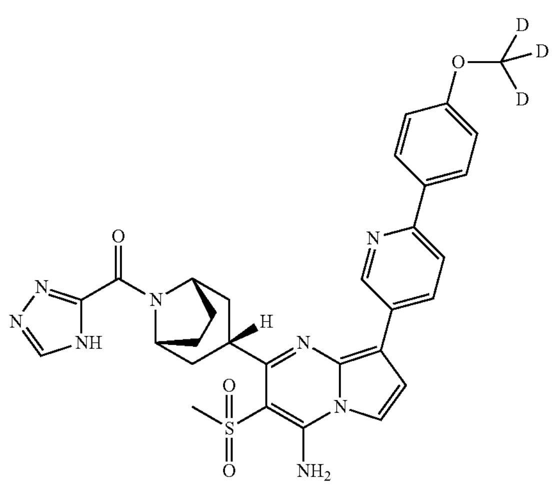 [SMILES: [2H]C([2H])([2H])Oc1ccc(-c2ccc(-c3ccn4c(N)c(S(C)(=O)=O)c([C@@H]5C[C@H]6CC[C@@H](C5)N6C(=O)c5nnc[nH]5)nc34)cn2)cc1] | ((1R,3s,5S)-3-(7-amino-3-(6-(4-methoxy-(D$_3$)-phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 603.2/603.0 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.63 | 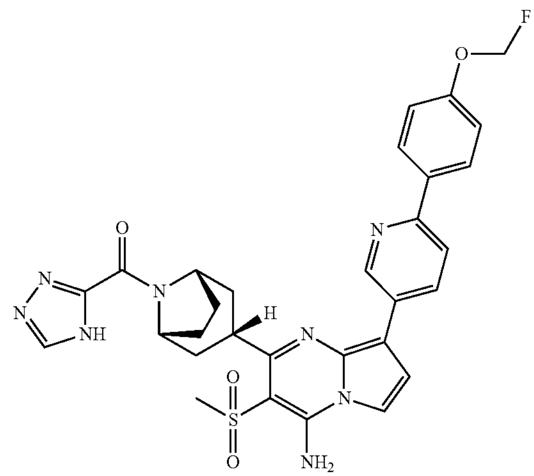 [SMILES: CS(=O)(=O)c1c([C@@H]2C[C@H]3CC[C@@H](C2)N3C(=O)c2nnc[nH]2)nc2c(-c3ccc(-c4ccc(OCF)cc4)nc3)ccn2c1N] | ((1R,3s,5S)-3-(7-amino-3-(6-(4-(fluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 618.2/618.0 | A | A |
| 3.64 | 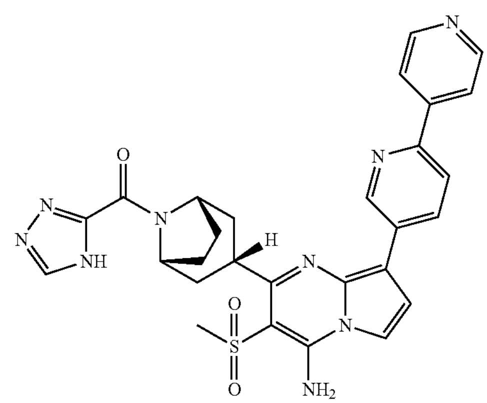 [SMILES: CS(=O)(=O)c1c([C@@H]2C[C@H]3CC[C@@H](C2)N3C(=O)c2nnc[nH]2)nc2c(-c3ccc(-c4ccncc4)nc3)ccn2c1N] | ((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone | 571.2/571.0 | C | C |
| 3.65 | 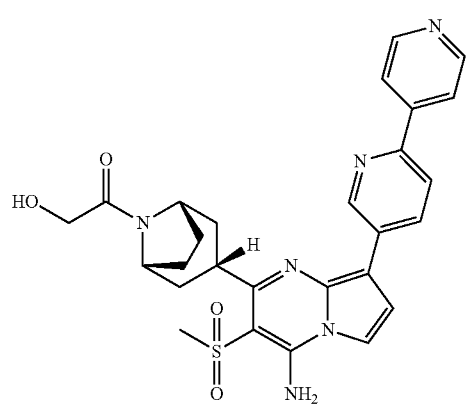 [SMILES: CS(=O)(=O)c1c([C@@H]2C[C@H]3CC[C@@H](C2)N3C(=O)CO)nc2c(-c3ccc(-c4ccncc4)nc3)ccn2c1N] | 1-((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)-2-hydroxyethanone | 534.2/533.9 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.66 | 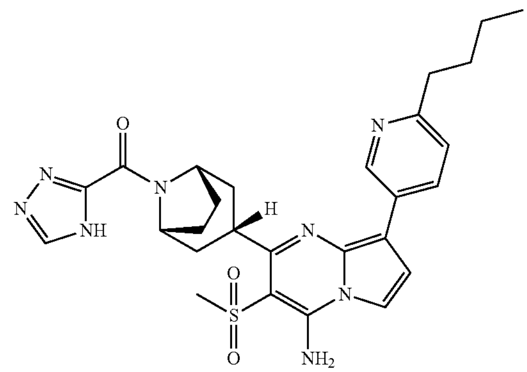 [SMILES: CCCCc1ccc(-c2ccn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-butylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 550.2/550.0 | ND | ND |
| 3.67 | 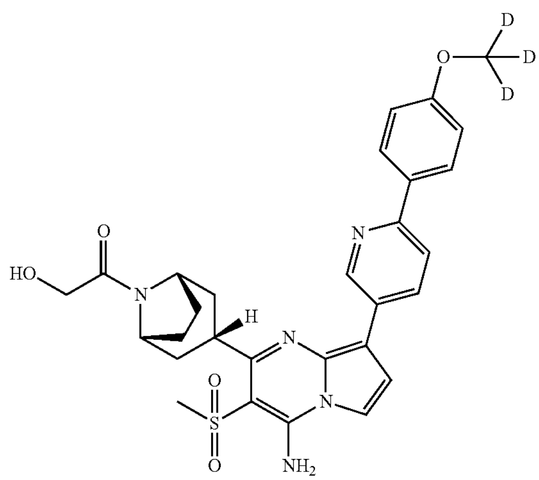 [SMILES: [2H]C([2H])([2H])Oc1ccc(-c2ccc(-c3ccn4c(N)c(S(C)(=O)=O)c([C@@H]5C[C@H]6CC[C@@H](C5)N6C(=O)CO)nc34)cn2)cc1] | 1-((1R,3s,5S)-3-(7-amino-3-(6-(4-methoxy-(D$_3$)-phenyl)pyridin-3-yl)-6-(methylsulfonyl)pyrazolo[1,5-a]pyrimidin-5-yl)-8-azabicyclo[3.2.1]octan-8-yl)-2-hydroxyethanone | 566.2/566.2 | A | B |
| 3.68 | 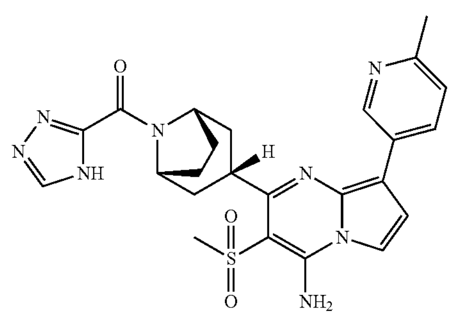 [SMILES: Cc1ccc(-c2ccn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 508.2/507.9 | B | B |
| 3.69 | 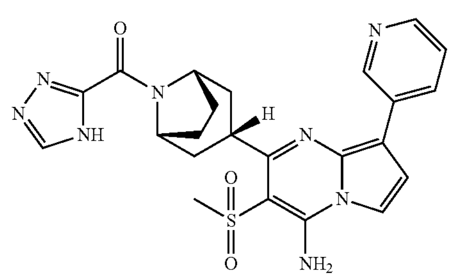 [SMILES: CS(=O)(=O)c1c([C@@H]2C[C@H]3CC[C@@H](C2)N3C(=O)c2nnc[nH]2)nc2c(-c3cccnc3)ccn2c1N] | ((1R,3s,5S)-3-(7-amino-6-(methylsulfonyl)-3-(pyridin-3-yl)pyrazolo[1,5-a]pyrimidin-5-yl)-8-azabicyclo[3.2.1]octan-8-yl)(4H-1,2,4-triazol-3-yl)methanone | 494.2/493.9 | B | B |

| Compound ID | Structures | Compound Name | M + H (calculated)/ M + H (observed) | pAKT S473 IC50 | p4E-BP1 Thr37/46 IC50 |
|---|---|---|---|---|---|
| 3.70 | 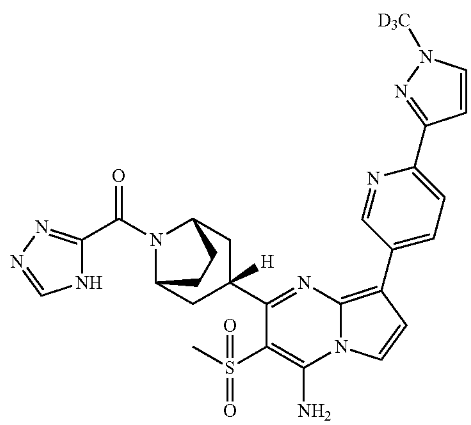 [SMILES: [2H]C([2H])([2H])n1ccc(-c2ccc(-c3ccn4c(N)c(S(C)(=O)=O)c([C@@H]5C[C@H]6CC[C@@H](C5)N6C(=O)c5nnc[nH]5)nc34)cn2)n1] | ((1R,3s,5S)-3-(7-amino-3-(6-(1-methyl-(D$_3$)-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 577.2/577.0 | B | B |
| 3.71 | 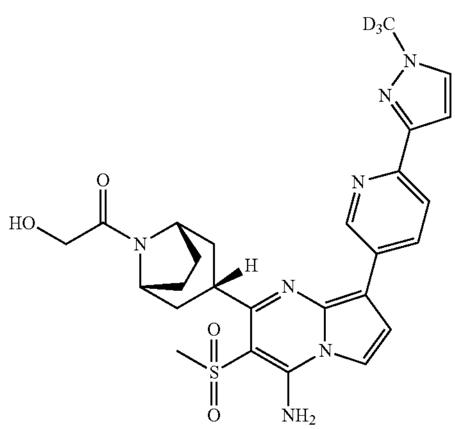 [SMILES: [2H]C([2H])([2H])n1ccc(-c2ccc(-c3ccn4c(N)c(S(C)(=O)=O)c([C@@H]5C[C@H]6CC[C@@H](C5)N6C(=O)CO)nc34)cn2)n1] | 1-((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)-2-hydroxyethanone | 540.2/540.0 | ND | ND |
| 3.72 | 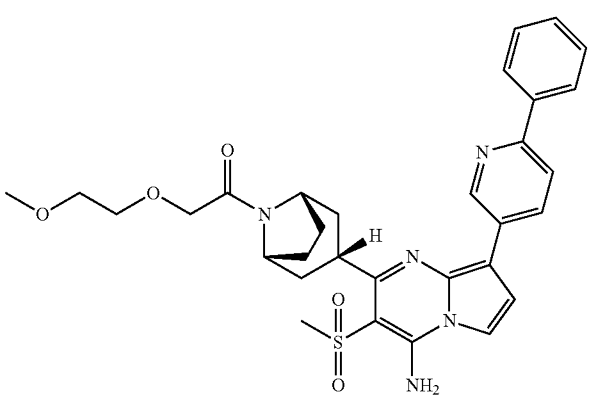 [SMILES: COCCOCC(=O)N1[C@@H]2CC[C@H]1C[C@H](c1nc3c(-c4ccc(-c5ccccc5)nc4)ccn3c(N)c1S(C)(=O)=O)C2] | 1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(2-methoxyethoxy)ethanone | 591.2/591.0 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.73 | 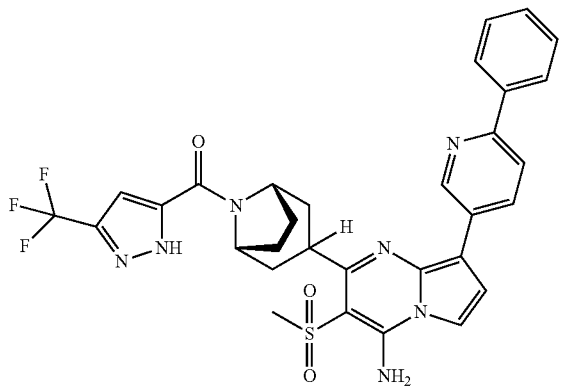 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-pyrazol-5-yl)methanone | 637.2/636.8 | C | D |
| 3.74 | 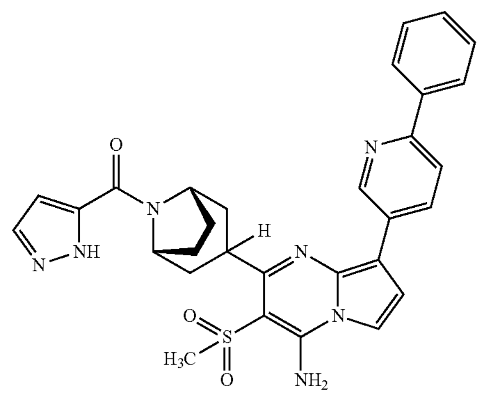 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-5-yl)methanone | 569.2/568.9 | A | A |
| 3.75 | 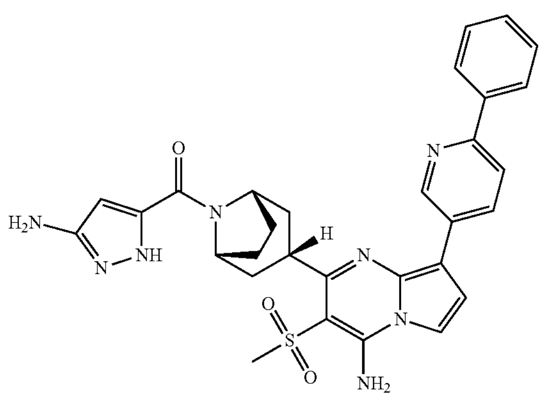 [SMILES: CS(=O)(=O)c1c([C@@H]2C[C@H]3CC[C@@H](C2)N3C(=O)c2cc(N)n[nH]2)nc2c(-c3ccc(-c4ccccc4)nc3)ccn2c1N] | (3-amino-1H-pyrazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone | 584.2/583.9 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.76 | 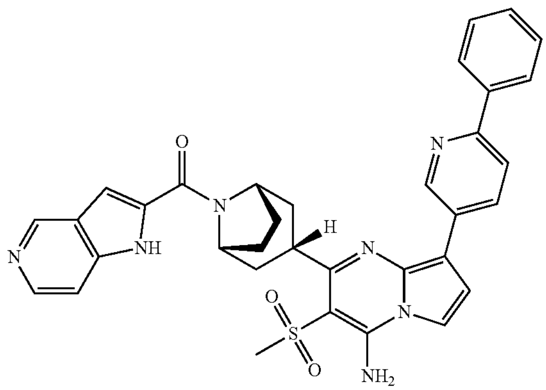 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[3,2-c]pyridin-2-yl)methanone | 619.2/619.0 | A | A |
| 3.77 | 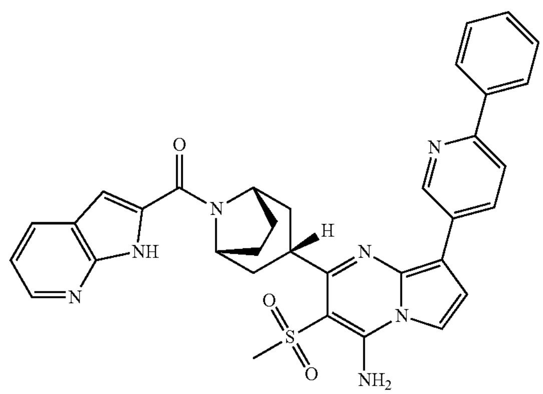 [SMILES: CS(=O)(=O)c1c([C@@H]2C[C@H]3CC[C@@H](C2)N3C(=O)c2cc3cccnc3[nH]2)nc2c(-c3ccc(-c4ccccc4)nc3)ccn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[2,3-b]pyridin-2-yl)methanone | 619.2/619.0 | C | D |
| 3.78 | 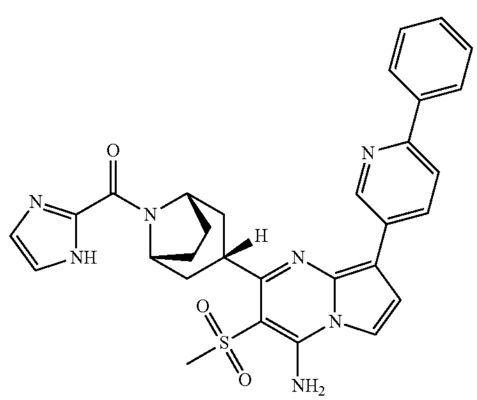 [SMILES: CS(=O)(=O)c1c([C@@H]2C[C@H]3CC[C@@H](C2)N3C(=O)c2ncc[nH]2)nc2c(-c3ccc(-c4ccccc4)nc3)ccn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-imidazol-2-yl)methanone | 569.2/568.9 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.79 | 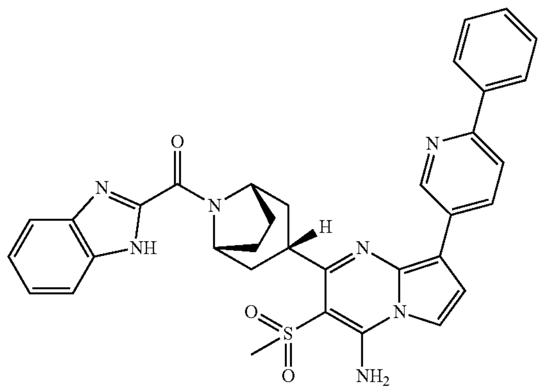 [SMILES: CS(=O)(=O)c1c([C@@H]2C[C@H]3CC[C@@H](C2)N3C(=O)c2nc3ccccc3[nH]2)nc2c(-c3ccc(-c4ccccc4)nc3)ccn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-benzo[d]imidazol-2-yl)methanone | 619.2/619.0 | ND | ND |
| 3.80 | 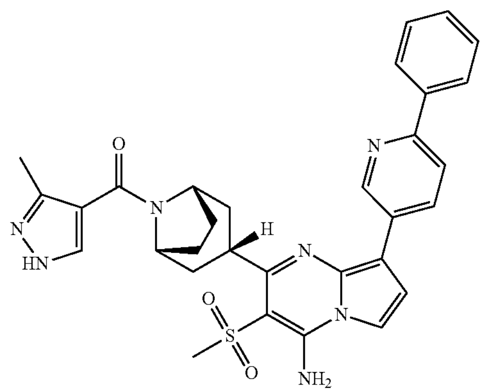 [SMILES: Cc1n[nH]cc1C(=O)N1[C@@H]2CC[C@H]1C[C@H](c1nc3c(-c4ccc(-c5ccccc5)nc4)ccn3c(N)c1S(C)(=O)=O)C2] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-4-yl)methanone | 583.2/582.8 | A | A |
| 3.81 | 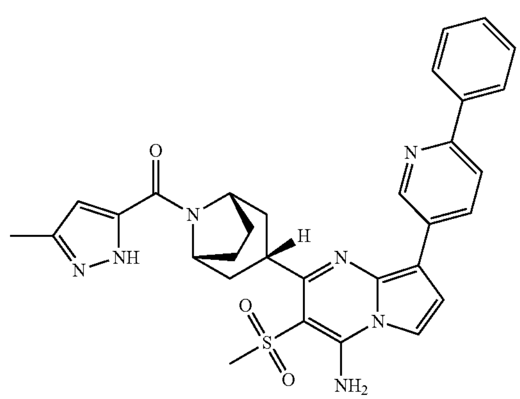 [SMILES: Cc1cc(C(=O)N2[C@@H]3CC[C@H]2C[C@H](c2nc4c(-c5ccc(-c6ccccc6)nc5)ccn4c(N)c2S(C)(=O)=O)C3)[nH]n1] | ((1R,3s,5S)-3-(7-amino-6-(methyslulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-5-yl)methanone | 583.2/582.8 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.82 | 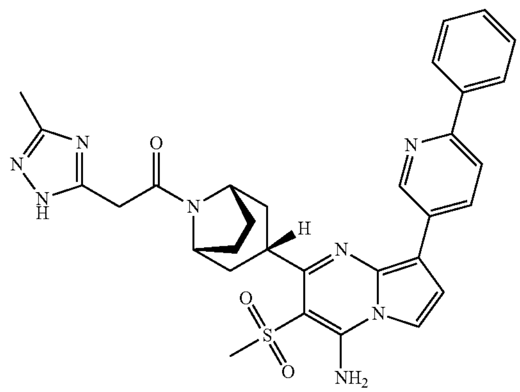 | 1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(3-methyl-1H-1,2,4-triazol-5-yl)ethanone | 598.2/597.9 | B | B |
| 3.83 | 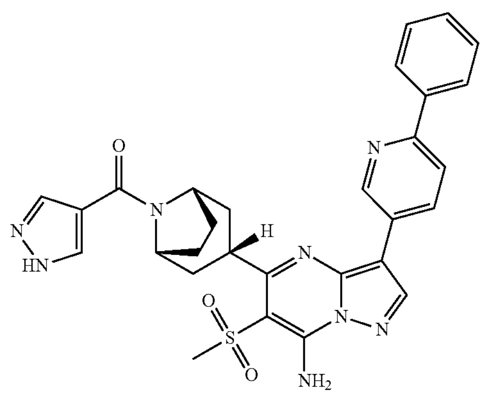 [SMILES: CS(=O)(=O)c1c([C@@H]2C[C@H]3CC[C@@H](C2)N3C(=O)c2cn[nH]c2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-4-yl)methanone | 569.2/568.9 | A | A |
| 3.84 | 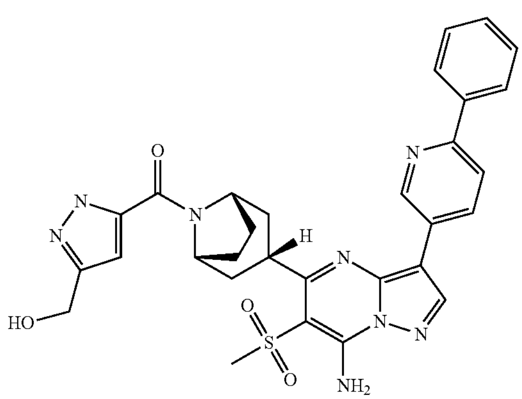 [SMILES: CS(=O)(=O)c1c([C@@H]2C[C@H]3CC[C@@H](C2)N3C(=O)c2cc(CO)n[nH]2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(hydroxymethyl)-1H-pyrazol-5-yl)methanone | 599.2/599.2 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.85 | 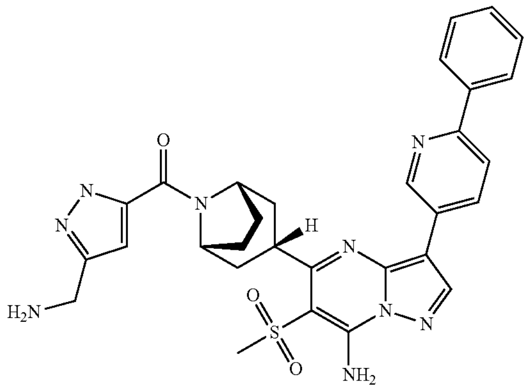 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(aminomethyl)-1H-pyrazol-5-yl)methanone | 598.2/598.3 | A | A |
| 3.86 | 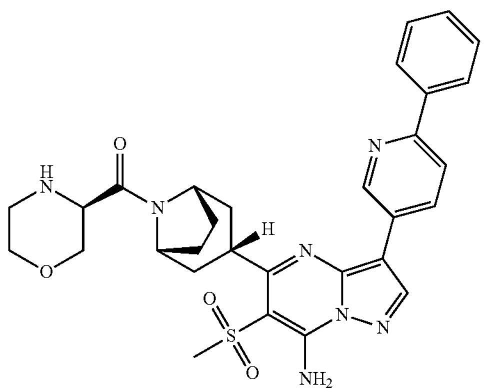 [SMILES: CS(=O)(=O)c1c([C@@H]2C[C@H]3CC[C@@H](C2)N3C(=O)[C@H]2COCCN2)nc2c(-c3ccc(-c4ccccc4)nc3)cnn2c1N] | ((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-morpholin-3-yl)methanone | 588.2/588.0 | ND | ND |
| 3.87 | 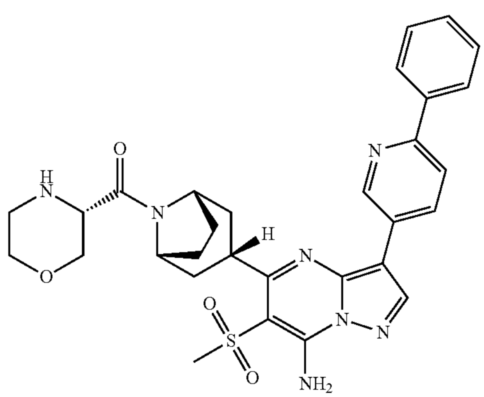 [SMILES: CS(=O)(=O)c1c([C@@H]2C[C@H]3CC[C@@H](C2)N3C(=O)[C@@H]2COCCN2)nc2c(-c3ccc(-c4ccccc4)nc3)cnn2c1N] | ((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-morpholin-3-yl)methanone | 588.2/588.0 | ND | ND |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.88 | 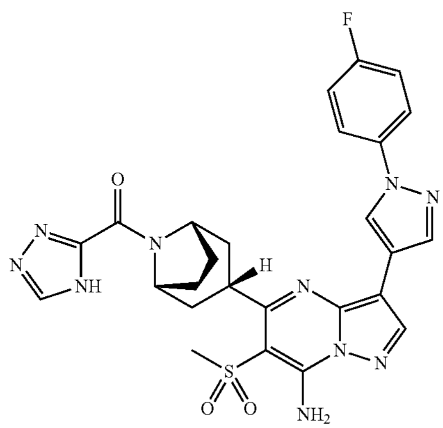 | ((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 577.2/577.2 | B | C |
| 3.89 | 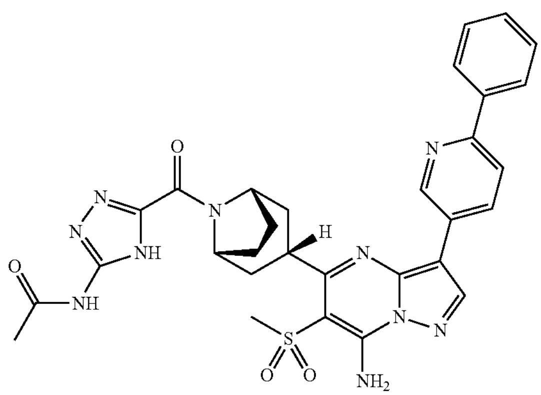 | N-(4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide | 627.2/627.1 | B | B |
| 3.90 | 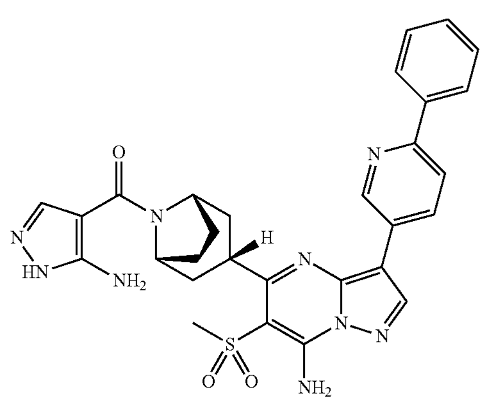 | (5-amino-1H-pyrazol-4-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone | 584.2/584.2 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.91 | 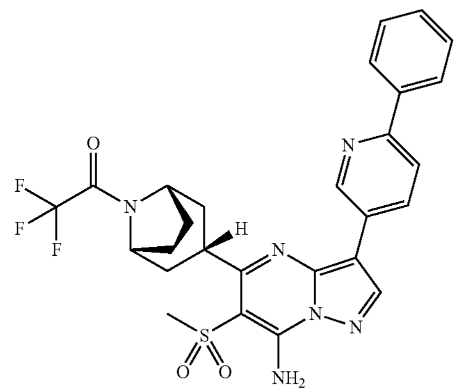 | 1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,2,2-trifluoroethanone | 571.2/571.0 | C | C |
| 3.92 | 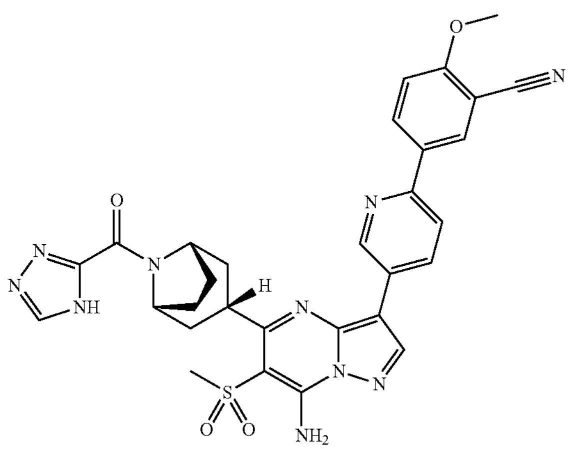 | 5-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)-2-methoxybenzonitrile | 625.2/625.2 | B | B |
| 3.93 | 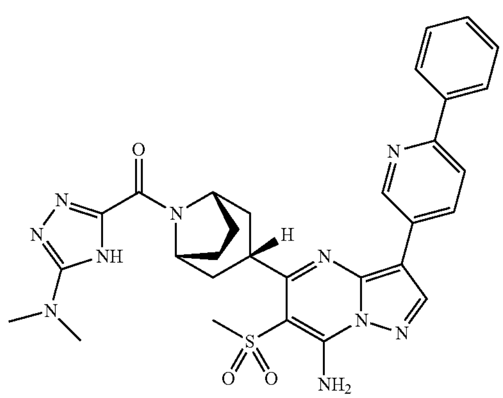 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-(dimethylamino)-4H-1,2,4-triazol-3-yl)methanone | 613.2/613.2 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.94 | 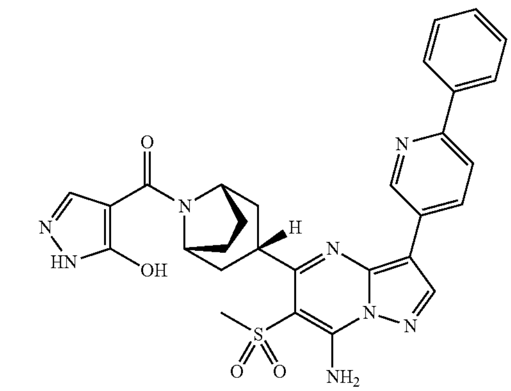 | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-1H-pyrazol-4-yl)methanone | 585.2/585.3 | B | B |
| 3.95 | 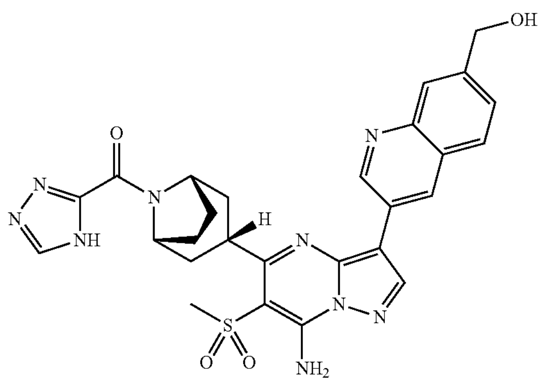 | ((1R,3s,5S)-3-(7-amino-3-(7-(hydroxymethyl)quinolin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 574.2/574.2 | ND | ND |
| 3.96 | 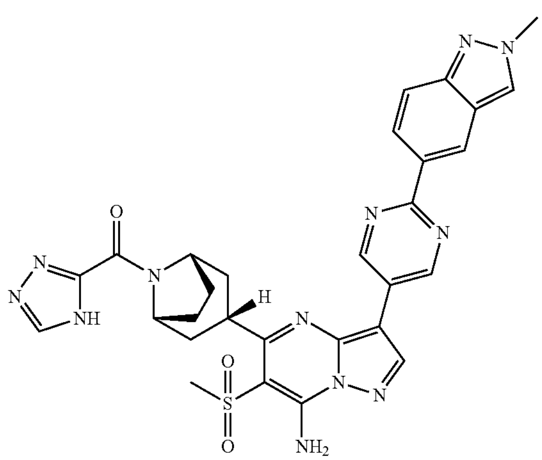 [SMILES: Cn1cc2cc(-c3ncc(-c4cnn5c(N)c(S(C)(=O)=O)c([C@@H]6C[C@H]7CC[C@@H](C6)N7C(=O)c6nnc[nH]6)nc45)cn3)ccc2n1] | ((1R,3s,5S)-3-(7-amino-3-(2-(2-methyl-2H-indazol-5-yl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 625.2/625.0 | ND | ND |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.97 | 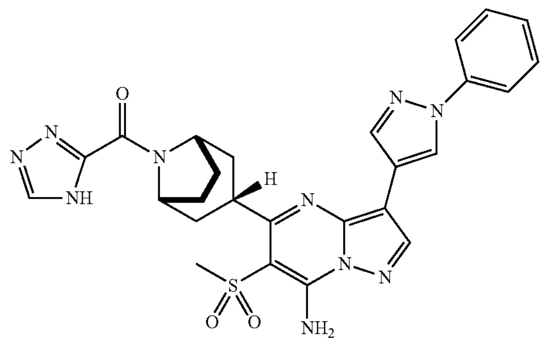 | ((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone | 559.2/559.2 | A | A |
| 3.98 | 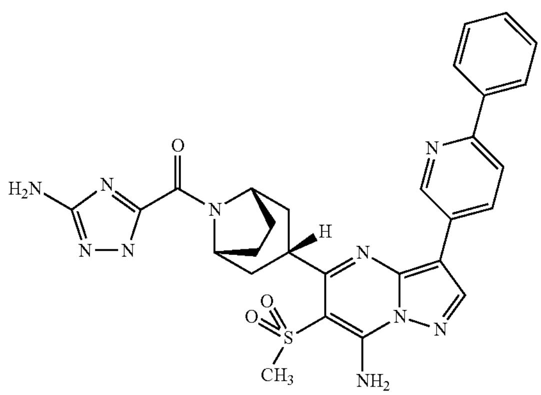 [SMILES: CS(=O)(=O)c1c([C@@H]2C[C@H]3CC[C@@H](C2)N3C(=O)c2nc(N)n[nH]2)nc2c(-c3ccc(-c4ccccc4)nc3)cnn2c1N] | (3-amino-1H-1,2,4-triazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone | 585.2/585.1 | A | A |
| 3.99 | 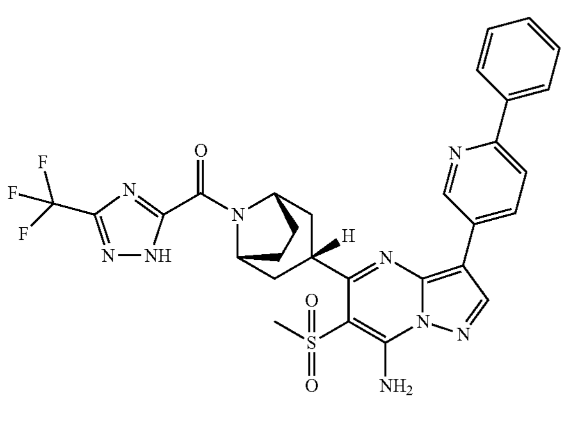 [SMILES: CS(=O)(=O)c1c([C@@H]2C[C@H]3CC[C@@H](C2)N3C(=O)c2nc(C(F)(F)F)n[nH]2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-1,2,4-triazol-5-yl)methanone | 638.2/638.0 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.100 | 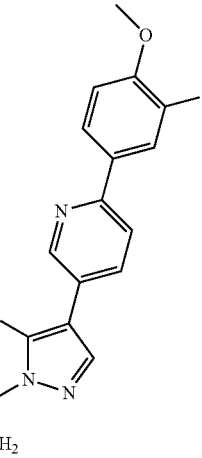 | ((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(5-amino-4H-1,2,4-triazol-3-yl)methanone | 633.2/633.1 | A | A |
| 3.101 | 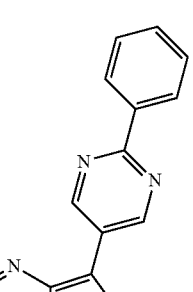 | ((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone | 571.2/571.0 | N/A | N/A |
| 3.102 | 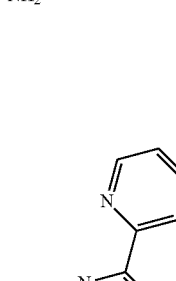 | ((1R,3s,5S)-3-(3-(2,2'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone | 571.2/571.2 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.103 | 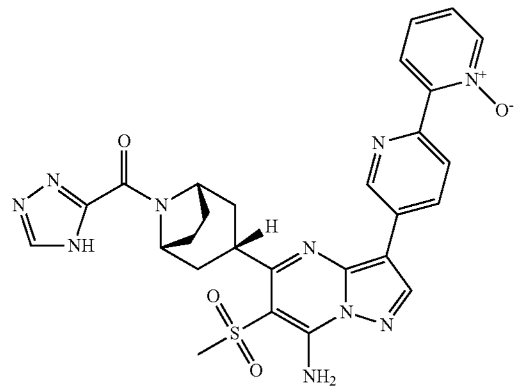 [SMILES: CS(=O)(=O)c1c([C@@H]2C[C@H]3CC[C@@H](C2)N3C(=O)c2nnc[nH]2)nc2c(-c3ccc(-c4cccc[n+]4[O-])nc3)cnn2c1N] | 2-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)pyridine 1-oxide | 587.2/587.1 | ND | ND |
| 3.104 | 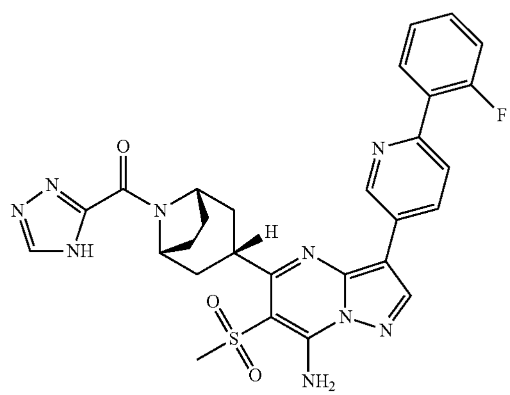 [SMILES: CS(=O)(=O)c1c([C@@H]2C[C@H]3CC[C@@H](C2)N3C(=O)c2nnc[nH]2)nc2c(-c3ccc(-c4ccccc4F)nc3)cnn2c1N] | ((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 588.2/588.1 | A | A |
| 3.105 | 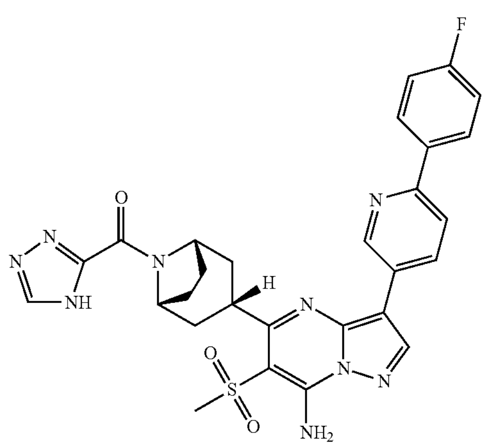 [SMILES: CS(=O)(=O)c1c([C@@H]2C[C@H]3CC[C@@H](C2)N3C(=O)c2nnc[nH]2)nc2c(-c3ccc(-c4ccc(F)cc4)nc3)cnn2c1N] | ((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 588.2/588.1 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.106 | 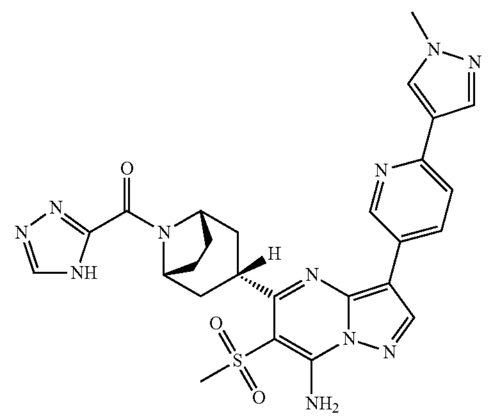 [SMILES: Cn1cc(-c2ccc(-c3cnn4c(N)c(S(C)(=O)=O)c([C@@H]5C[C@H]6CC[C@@H](C5)N6C(=O)c5nnc[nH]5)nc34)cn2)cn1] | ((1R,3s,5S)-3-(7-amino-3-(6-(1-methyl-1H-pyrazol-4-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 574.2/574.2 | A | A |
| 3.107 | 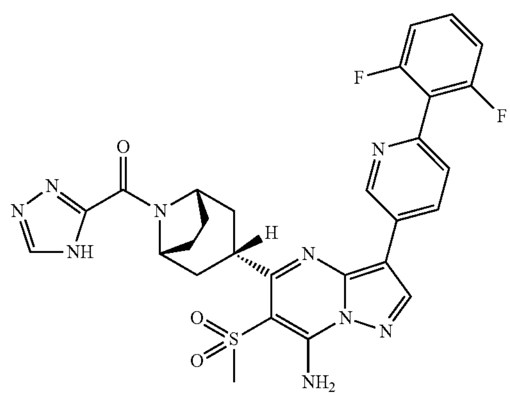 [SMILES: CS(=O)(=O)c1c([C@@H]2C[C@H]3CC[C@@H](C2)N3C(=O)c2nnc[nH]2)nc2c(-c3ccc(-c4c(F)cccc4F)nc3)cnn2c1N] | ((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 606.2/606.1 | A | A |
| 3.108 | 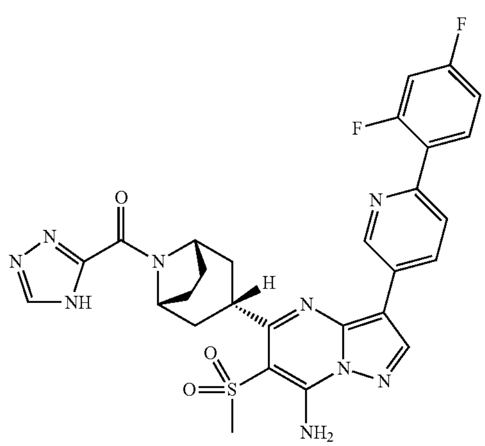 [SMILES: CS(=O)(=O)c1c([C@@H]2C[C@H]3CC[C@@H](C2)N3C(=O)c2nnc[nH]2)nc2c(-c3ccc(-c4ccc(F)cc4F)nc3)cnn2c1N] | ((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 606.2/606.1 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.109 | 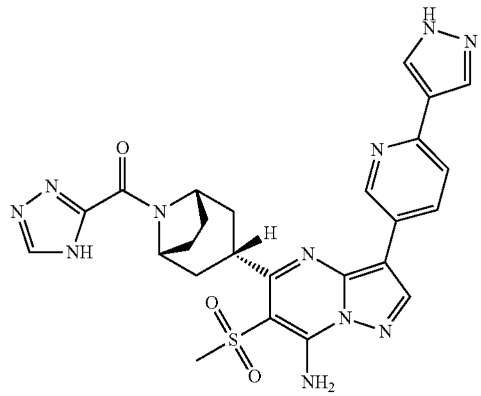 [SMILES: CS(=O)(=O)c1c([C@@H]2C[C@H]3CC[C@@H](C2)N3C(=O)c2nnc[nH]2)nc2c(-c3ccc(-c4cn[nH]c4)nc3)cnn2c1N] | ((1R,3s,5S)-3-(3-(6-(1H-pyrazol-4-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone | 560.2/560.2 | C | C |
| 3.110 | 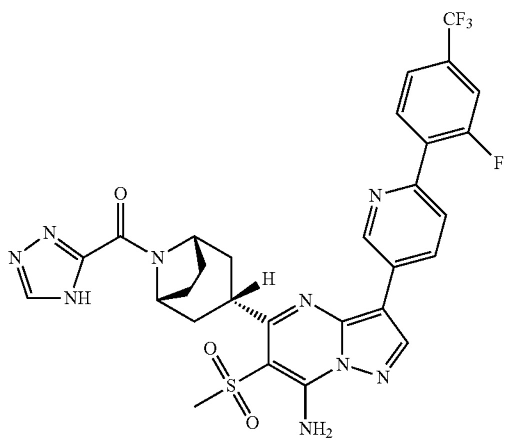 [SMILES: CS(=O)(=O)c1c([C@@H]2C[C@H]3CC[C@@H](C2)N3C(=O)c2nnc[nH]2)nc2c(-c3ccc(-c4ccc(C(F)(F)F)cc4F)nc3)cnn2c1N] | ((1R,3s,5S)-3-(7-amino-3-(6-(2-fluoro-4-(trifluoromethyl)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 656.2/656.2 | B | C |
| 3.111 | 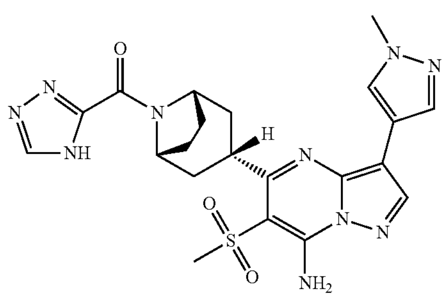 [SMILES: Cn1cc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 497.2/497.1 | C | C |
| 3.112 | 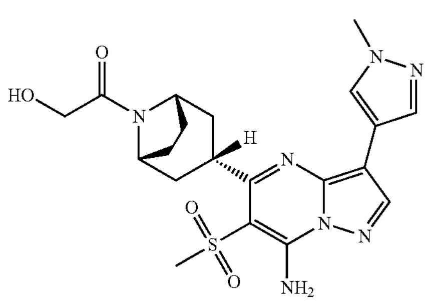 [SMILES: Cn1cc(-c2cnn3c(N)c(S(C)(=O)=O)c([C@@H]4C[C@H]5CC[C@@H](C4)N5C(=O)CO)nc23)cn1] | 1-((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)-2-hydroxyethanone | 460.2/460.1 | D | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.113 | 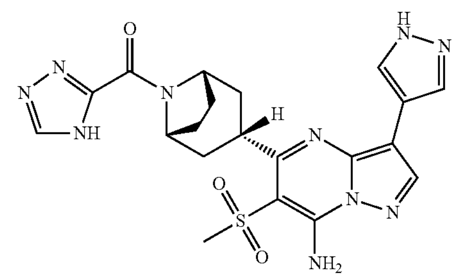 [SMILES: CS(=O)(=O)c1c([C@@H]2C[C@H]3CC[C@@H](C2)N3C(=O)c2nnc[nH]2)nc2c(-c3cn[nH]c3)cnn2c1N] | ((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(4H-1,2,4-triazol-3-yl)methanone | 483.2/483.1 | D | C |
| 3.114 | 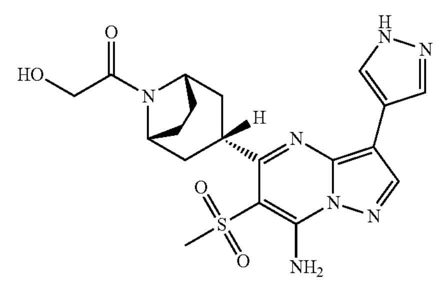 [SMILES: CS(=O)(=O)c1c([C@@H]2C[C@H]3CC[C@@H](C2)N3C(=O)CO)nc2c(-c3cn[nH]c3)cnn2c1N] | 1-((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)-1-hydroxyethanone | 446.2/446.1 | D | D |
| 3.115 | 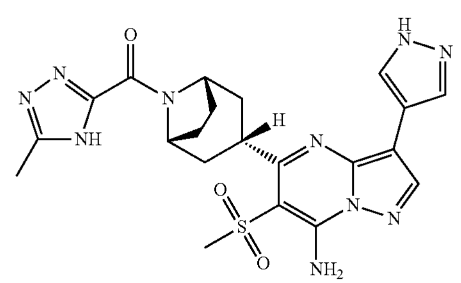 [SMILES: Cc1nnc(C(=O)N2[C@@H]3CC[C@H]2C[C@H](c2nc4c(-c5cn[nH]c5)cnn4c(N)c2S(C)(=O)=O)C3)[nH]1] | ((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(5-methyl-4H-1,2,4-triazol-3-yl)methanone | 497.2/497.0 | D | D |
| 3.116 | 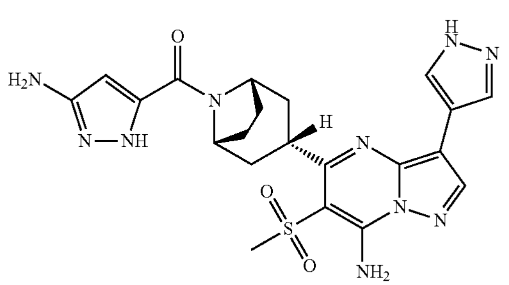 [SMILES: CS(=O)(=O)c1c([C@@H]2C[C@H]3CC[C@@H](C2)N3C(=O)c2cc(N)n[nH]2)nc2c(-c3cn[nH]c3)cnn2c1N] | (3-amino-1H-pyrazol-5-yl)((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)methanone | 497.2/497.1 | ND | ND |
| 3.117 | 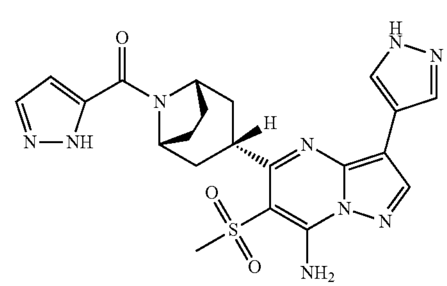 [SMILES: CS(=O)(=O)c1c([C@@H]2C[C@H]3CC[C@@H](C2)N3C(=O)c2ccn[nH]2)nc2c(-c3cn[nH]c3)cnn2c1N] | ((1R,3a,4S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(1H-pyrazol-5-yl)methanone | 482.2/482.0 | D | D |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.118 | 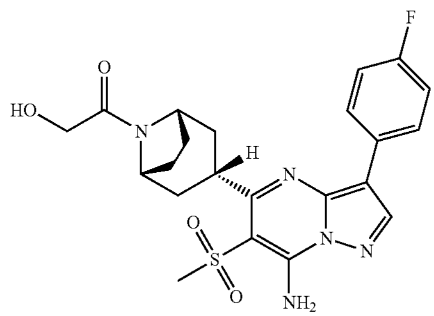 [SMILES: CS(=O)(=O)c1c([C@@H]2C[C@H]3CC[C@@H](C2)N3C(=O)CO)nc2c(-c3ccc(F)cc3)cnn2c1N] | 1-((1R,3a,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone | 551.2/551.1 | B | ND |
| 3.119 | 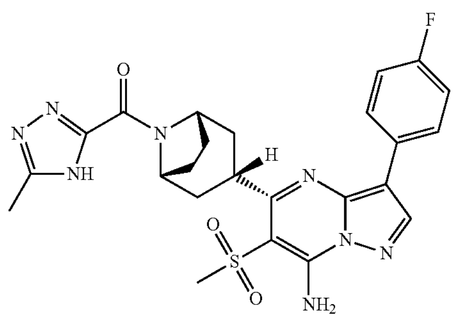 | ((1R,3s,5S)-3-(7-amino-3-(6-(4-fuorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 602.2/601.9 | A | A |
| 3.120 | 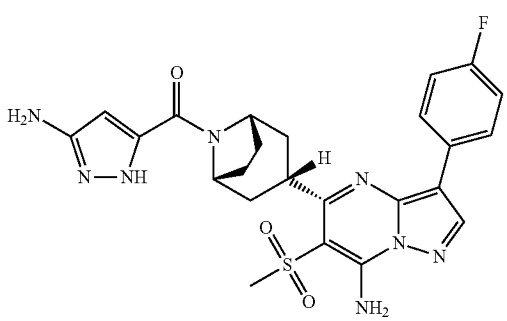 | (3-amino-1H-pyrazol-5-yl)((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)methanone | 602.2/602.1 | A | A |
| 3.121 | 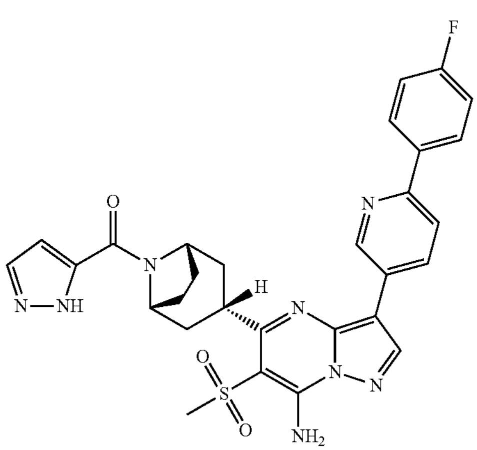 [SMILES: CS(=O)(=O)c1c([C@@H]2C[C@H]3CC[C@@H](C2)N3C(=O)c2ccn[nH]2)nc2c(-c3ccc(-c4ccc(F)cc4)nc3)cnn2c1N] | ((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone | 587.2/587.2 | A | ND |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.122 | 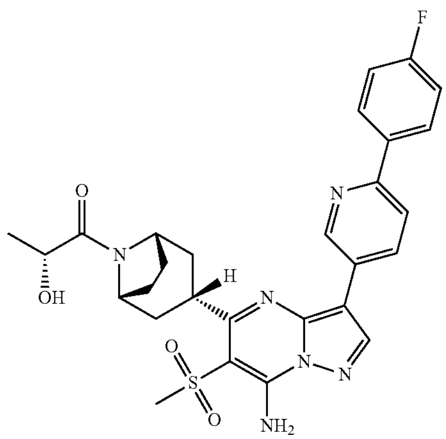 [SMILES: C[C@@H](O)C(=O)N1[C@@H]2CC[C@H]1C[C@H](c1nc3c(-c4ccc(-c5ccc(F)cc5)nc4)cnn3c(N)c1S(C)(=O)=O)C2] | (R)-1-((1R,3S,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxypropan-1-one | 565.2/565.2 | B | ND |
| 3.123 | 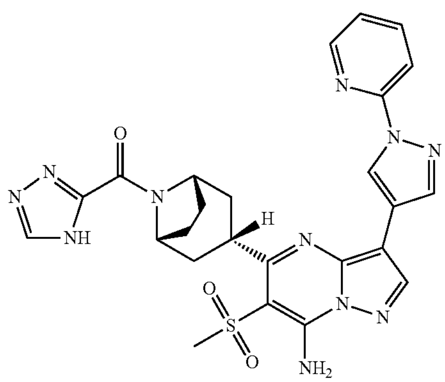 [SMILES: CS(=O)(=O)c1c([C@@H]2C[C@H]3CC[C@@H](C2)N3C(=O)c2nnc[nH]2)nc2c(-c3cnn(-c4ccccn4)c3)cnn2c1N] | (((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)(4H-1,2,4-triazol-3-yl)methanone | 560.2/560.0 | B | B |
| 3.124 | 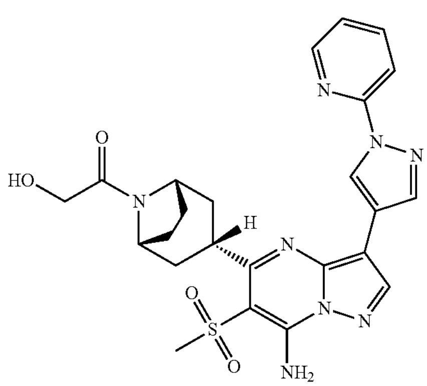 [SMILES: CS(=O)(=O)c1c([C@@H]2C[C@H]3CC[C@@H](C2)N3C(=O)CO)nc2c(-c3cnn(-c4ccccn4)c3)cnn2c1N] | 1-((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone | 523.2/523.2 | B | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.125 | 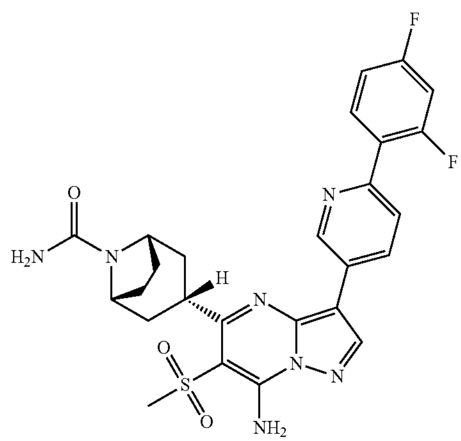 [SMILES: CS(=O)(=O)c1c([C@@H]2C[C@H]3CC[C@@H](C2)N3C(N)=O)nc2c(-c3ccc(-c4ccc(F)cc4F)nc3)cnn2c1N] | (1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octane-8-carboxamide | 554.2/554.1 | A | B |
| 3.126 | 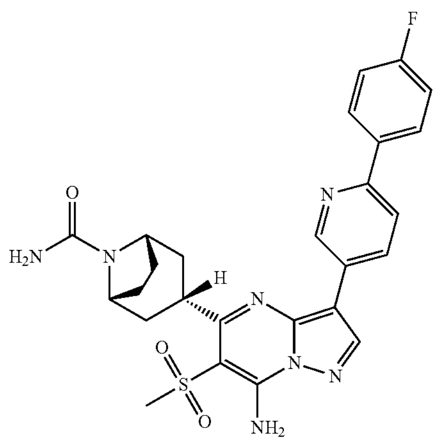 [SMILES: CS(=O)(=O)c1c([C@@H]2C[C@H]3CC[C@@H](C2)N3C(N)=O)nc2c(-c3ccc(-c4ccc(F)cc4)nc3)cnn2c1N] | (1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octane-8-carboxamide | 536.2/536.2 | A | A |
| 3.127 | 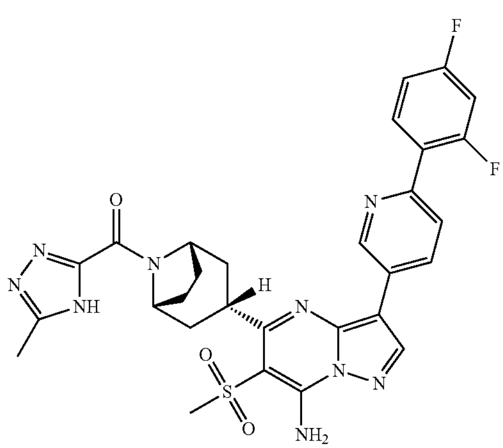 [SMILES: Cc1nnc(C(=O)N2[C@@H]3CC[C@H]2C[C@H](c2nc4c(-c5ccc(-c6ccc(F)cc6F)nc5)cnn4c(N)c2S(C)(=O)=O)C3)[nH]1] | ((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 620.2/620.2 | B | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.128 | 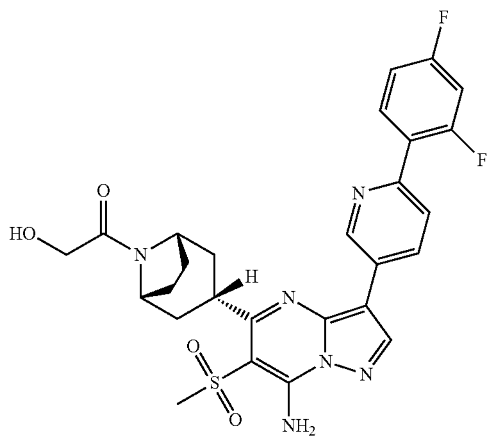 [SMILES: CS(=O)(=O)c1c([C@@H]2C[C@H]3CC[C@@H](C2)N3C(=O)CO)nc2c(-c3ccc(-c4ccc(F)cc4F)nc3)cnn2c1N] | 1-((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone | 569.2/569.2 | B | B |
| 3.129 | 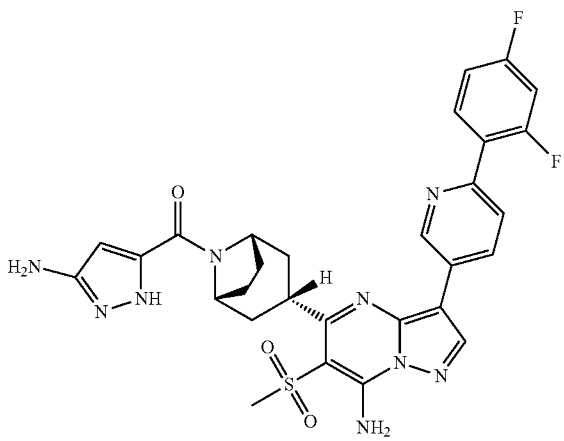 [SMILES: CS(=O)(=O)c1c([C@@H]2C[C@H]3CC[C@@H](C2)N3C(=O)c2cc(N)n[nH]2)nc2c(-c3ccc(-c4ccc(F)cc4F)nc3)cnn2c1N] | (3-amino-1H-pyrazol-5-yl)((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)methanone | 620.2/620.2 | A | A |
| 3.130 | 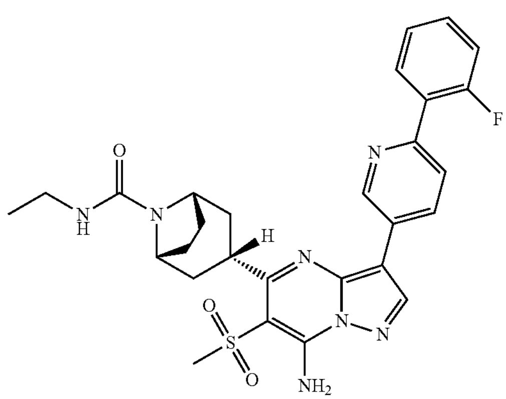 [SMILES: CCNC(=O)N1[C@@H]2CC[C@H]1C[C@H](c1nc3c(-c4ccc(-c5ccccc5F)nc4)cnn3c(N)c1S(C)(=O)=O)C2] | (1R,3s,5S)-3-(7-amino-3-(6-(2-fluorophenyl)pyridin-3-yl)-6-(methylsulfonyl)pyrazolo[1,5-a]pyrimidin-5-yl)-N-ethyl-8-azabicyclo[3.2.1]octane-8-carboxamide | 564.2/564.1 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.131 | 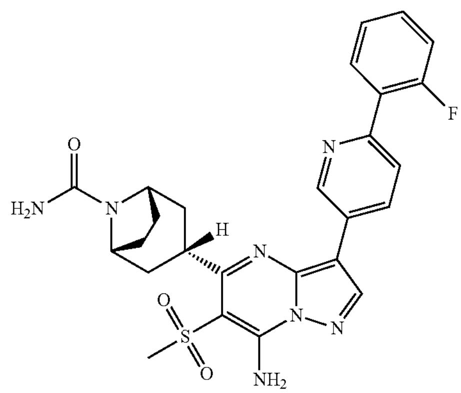 [SMILES: CS(=O)(=O)c1c([C@@H]2C[C@H]3CC[C@@H](C2)N3C(N)=O)nc2c(-c3ccc(-c4ccccc4F)nc3)cnn2c1N] | (1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carboxamide | 536.2/536.2 | A | A |
| 3.132 | 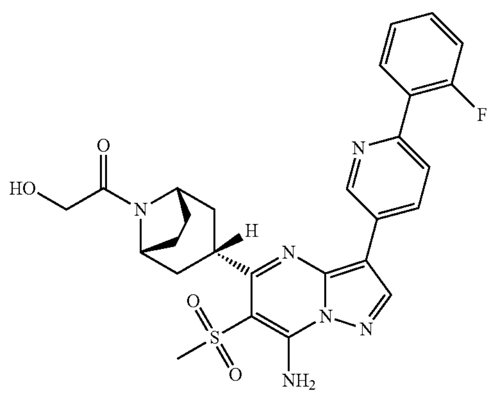 [SMILES: CS(=O)(=O)c1c([C@@H]2C[C@H]3CC[C@@H](C2)N3C(=O)CO)nc2c(-c3ccc(-c4ccccc4F)nc3)cnn2c1N] | 1-((1R,3a,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone | 551.2/551.2 | A | B |
| 3.133 | 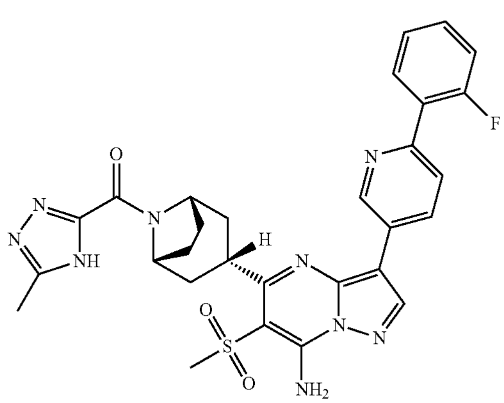 [SMILES: Cc1nnc(C(=O)N2[C@@H]3CC[C@H]2C[C@H](c2nc4c(-c5ccc(-c6ccccc6F)nc5)cnn4c(N)c2S(C)(=O)=O)C3)[nH]1] | ((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 602.2/602.2 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.134 | 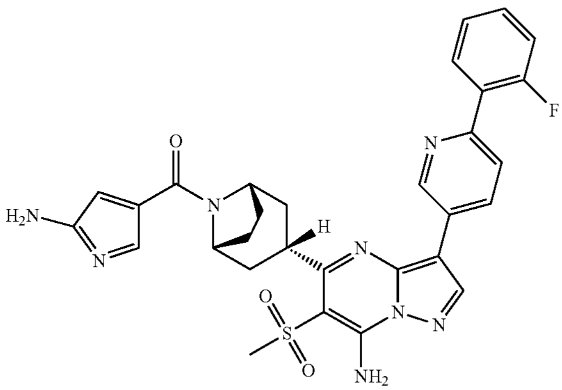 | (3-amino-1H-pyrazol-5-yl)(1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)methanone | 602.2/602.2 | A | A |
| 3.135 | 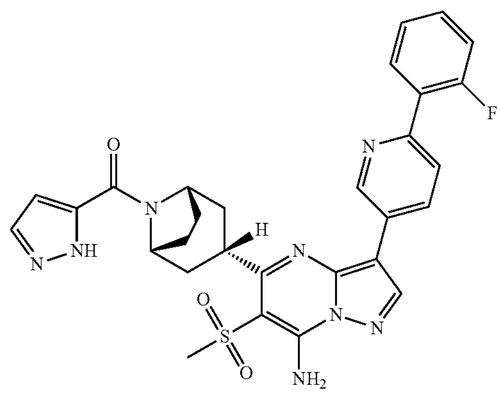 [SMILES: CS(=O)(=O)c1c([C@@H]2C[C@H]3CC[C@@H](C2)N3C(=O)c2ccn[nH]2)nc2c(-c3ccc(-c4ccccc4F)nc3)cnn2c1N] | ((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone | 587.2/587.2 | A | A |
| 3.136 | 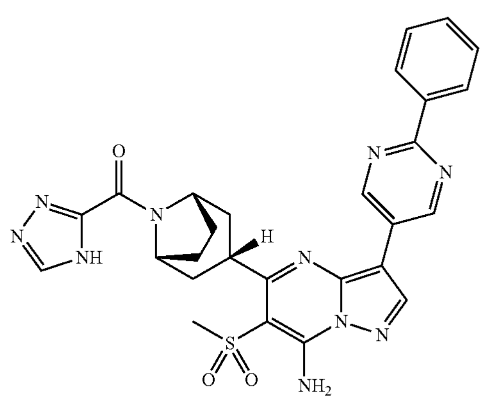 [SMILES: CS(=O)(=O)c1c([C@@H]2C[C@H]3CC[C@@H](C2)N3C(=O)c2nnc[nH]2)nc2c(-c3cnc(-c4ccccc4)nc3)cnn2c1N] | ((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(4H-1,2,4-triazol-3-yl)methanone | 571.2/571.3 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.137 | 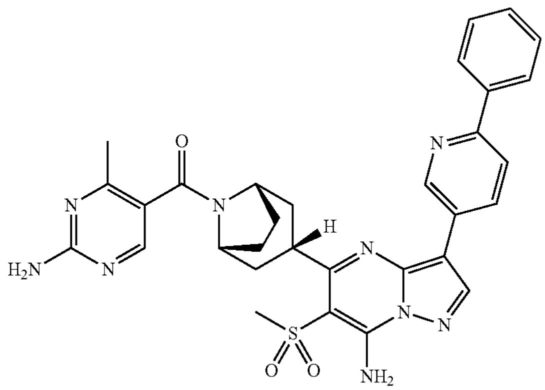 [SMILES: Cc1nc(N)ncc1C(=O)N1[C@@H]2CC[C@H]1C[C@H](c1nc3c(-c4ccc(-c5ccccc5)nc4)cnn3c(N)c1S(C)(=O)=O)C2] | (2-amino-4-methylpyrimidin-5-yl)((1R,3a,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone | 610.2/610.1 | C | C |
| 3.138 | 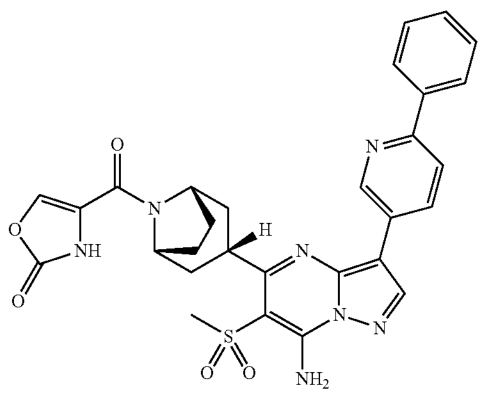 [SMILES: CS(=O)(=O)c1c([C@@H]2C[C@H]3CC[C@@H](C2)N3C(=O)c2coc(=O)[nH]2)nc2c(-c3ccc(-c4ccccc4)nc3)cnn2c1N] | 4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazol-2(3H)-one | 586.2/586.3 | B | B |
| 3.139 | 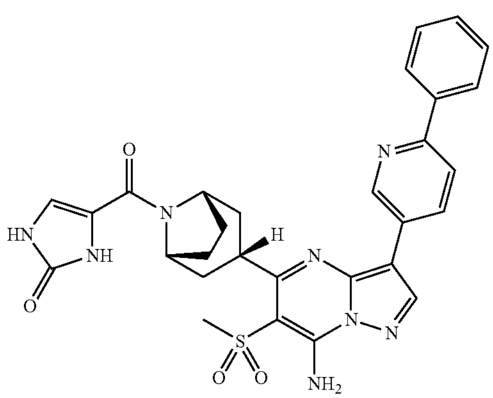 [SMILES: CS(=O)(=O)c1c([C@@H]2C[C@H]3CC[C@@H](C2)N3C(=O)c2c[nH]c(=O)[nH]2)nc2c(-c3ccc(-c4ccccc4)nc3)cnn2c1N] | 4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-1H-imidazol-2(3H)-one | 585.2/585.1 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.140 | 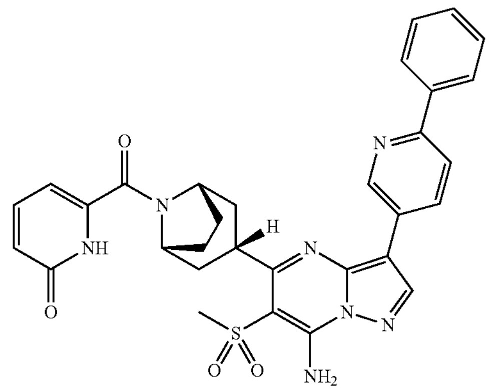 [SMILES: CS(=O)(=O)c1c([C@@H]2C[C@H]3CC[C@@H](C2)N3C(=O)c2cccc(=O)[nH]2)nc2c(-c3ccc(-c4ccccc4)nc3)cnn2c1N] | 6-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)pyridin-2(1H)-one | 596.2/596.3 | A | B |
| 3.141 | 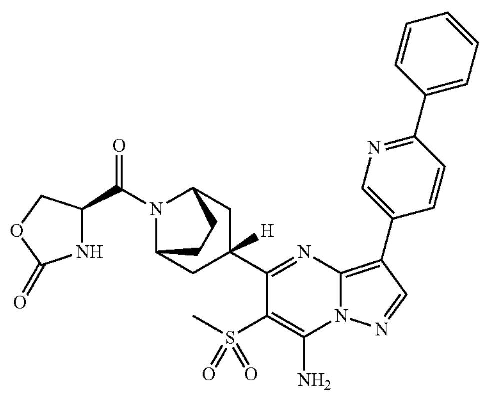 [SMILES: CS(=O)(=O)c1c([C@@H]2C[C@H]3CC[C@@H](C2)N3C(=O)[C@@H]2COC(=O)N2)nc2c(-c3ccc(-c4ccccc4)nc3)cnn2c1N] | (S)-4-((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one | 588.2/588.3 | C | C |
| 3.142 | 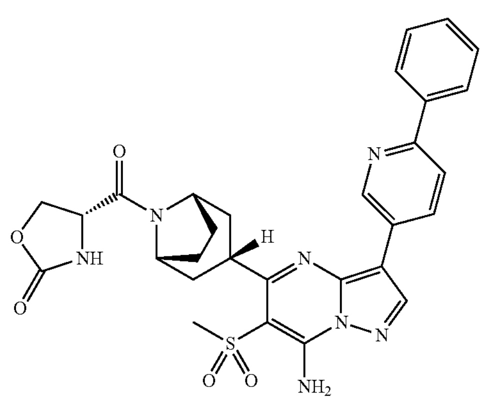 [SMILES: CS(=O)(=O)c1c([C@@H]2C[C@H]3CC[C@@H](C2)N3C(=O)[C@H]2COC(=O)N2)nc2c(-c3ccc(-c4ccccc4)nc3)cnn2c1N] | (R)-4-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one | 588.2/588.1 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.143 | 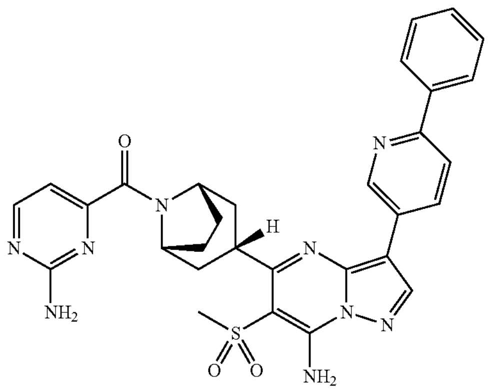 [SMILES: CS(=O)(=O)c1c([C@@H]2C[C@H]3CC[C@@H](C2)N3C(=O)c2ccnc(N)n2)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyrimidin-4-yl)methanone | 596.2/596.4 | B | B |
| 3.144 | 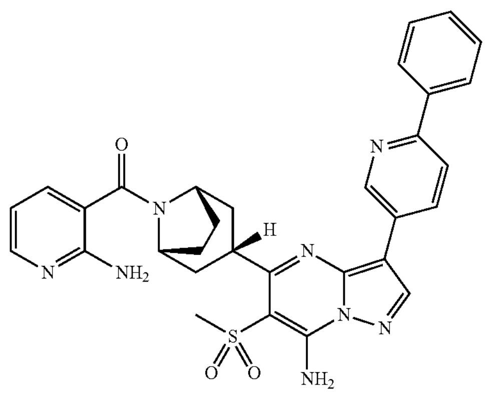 [SMILES: CS(=O)(=O)c1c([C@@H]2C[C@H]3CC[C@@H](C2)N3C(=O)c2cccnc2N)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyridin-3-yl)methanone | 595.2/595.0 | NA | NA |
| 3.145 | 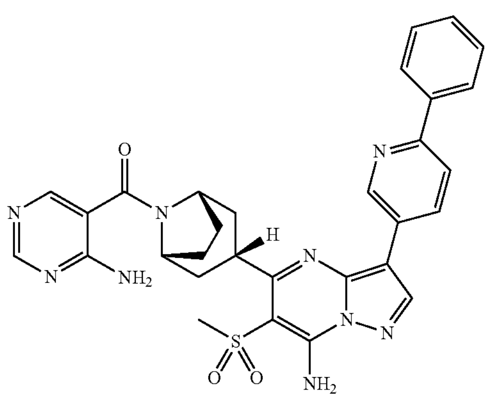 [SMILES: CS(=O)(=O)c1c([C@@H]2C[C@H]3CC[C@@H](C2)N3C(=O)c2cncnc2N)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-aminopyrimidin-5-yl)methanone | 596.2/596.3 | NA | NA |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.146 | 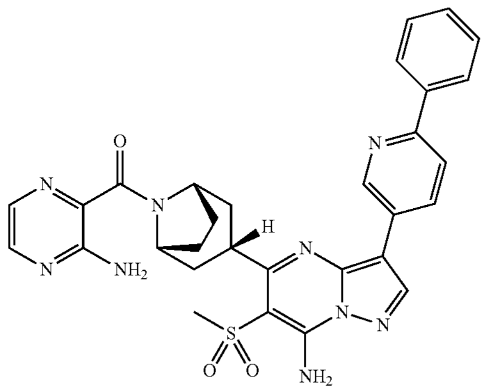 [SMILES: CS(=O)(=O)c1c([C@@H]2C[C@H]3CC[C@@H](C2)N3C(=O)c2nccnc2N)nc2c(-c3ccc(-c4ccccc4)nc3)cnn2c1N] | ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-aminopyrazin-2-yl)methanone | 596.2/596.0 | NA | NA |
| 3.147 | 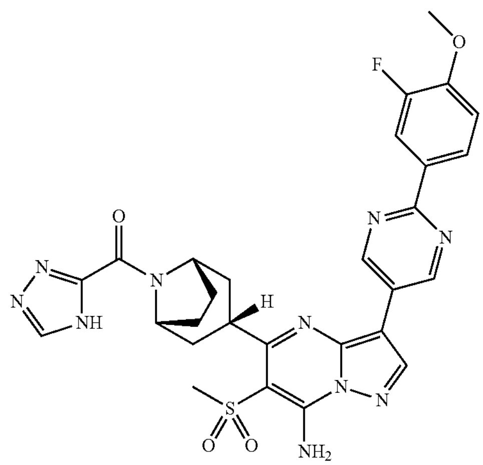 [SMILES: COc1ccc(-c2ncc(-c3cnn4c(N)c(S(C)(=O)=O)c([C@@H]5C[C@H]6CC[C@@H](C5)N6C(=O)c5nnc[nH]5)nc34)cn2)cc1F] | ((1R,3s,5S)-3-(7-amino-3-(2-(3-fluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 619.2/619.3 | C | C |
| 3.148 | 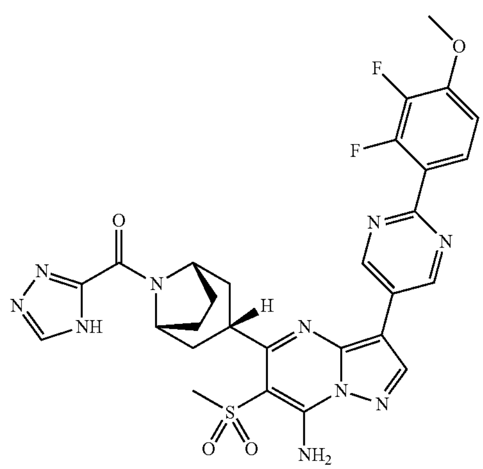 [SMILES: COc1ccc(-c2ncc(-c3cnn4c(N)c(S(C)(=O)=O)c([C@@H]5C[C@H]6CC[C@@H](C5)N6C(=O)c5nnc[nH]5)nc34)cn2)c(F)c1F] | ((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 637.2/637.4 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.149 | 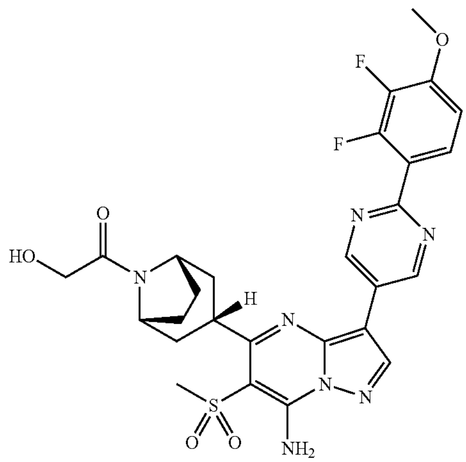 [SMILES: COc1ccc(-c2ncc(-c3cnn4c(N)c(S(C)(=O)=O)c([C@@H]5C[C@H]6CC[C@@H](C5)N6C(=O)CO)nc34)cn2)c(F)c1F] | 1-((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)-2-hydroxyethanone | 600.2/600.2 | C | B |
| 3.150 | 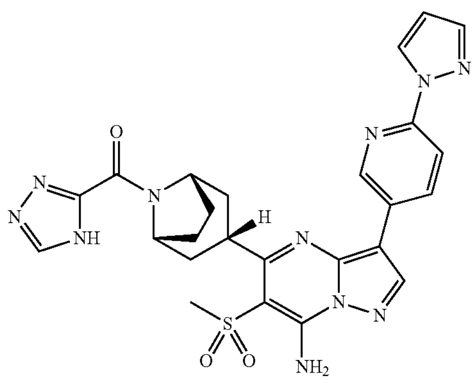 [SMILES: CS(=O)(=O)c1c([C@@H]2C[C@H]3CC[C@@H](C2)N3C(=O)c2nnc[nH]2)nc2c(-c3ccc(-n4cccn4)nc3)cnn2c1N] | ((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone | 560.2/560.0 | A | A |
| 3.151 | 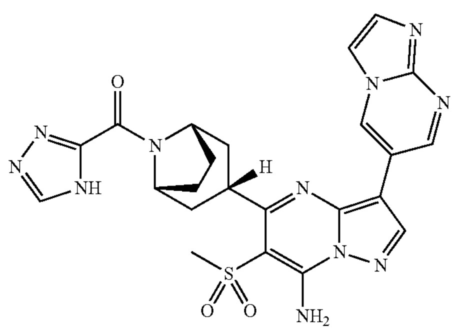 [SMILES: CS(=O)(=O)c1c([C@@H]2C[C@H]3CC[C@@H](C2)N3C(=O)c2nnc[nH]2)nc2c(-c3cnc4nccn4c3)cnn2c1N] | ((1R,3s,5S)-3-(7-amino-3-(imidazo[1,2-a]pyrimidin-6-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 534.2/534.1 | NA | NA |
| 3.152 | 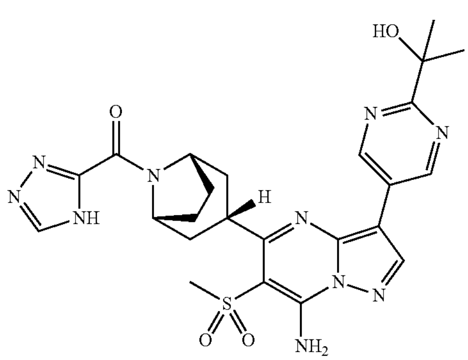 [SMILES: CC(C)(O)c1ncc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(2-(2-hydroxypropan-2-yl)pyimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 553./553.1 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.153 | 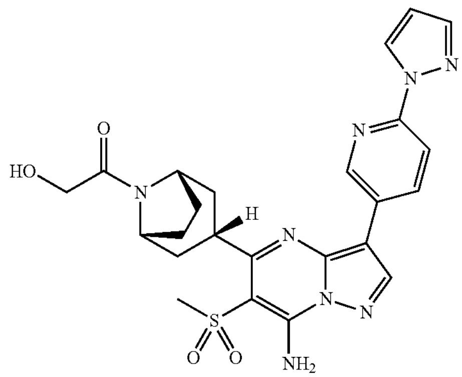 [SMILES: CS(=O)(=O)c1c([C@@H]2C[C@H]3CC[C@@H](C2)N3C(=O)CO)nc2c(-c3ccc(-n4cccn4)nc3)cnn2c1N] | 1-((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone | 523.2/523.3 | B | C |
| 3.154 | 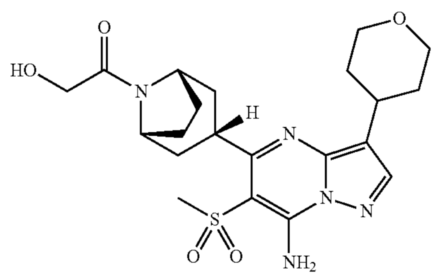 [SMILES: CS(=O)(=O)c1c([C@@H]2C[C@H]3CC[C@@H](C2)N3C(=O)CO)nc2c(C3CCOCC3)cnn2c1N] | 1-((1R,3s,5S)-3-(7-amino-6-(methylsulfonyl)-3-(tetrahydro-2H-pyran-4-yl)pyrazolo[1,5-a]pyrimidin-5-yl)-8-azabicyclo[3.2.1]octan-8-yl)-2-hydroxyethanone | 464.2/464.1 | NA | NA |
| 3.155 | 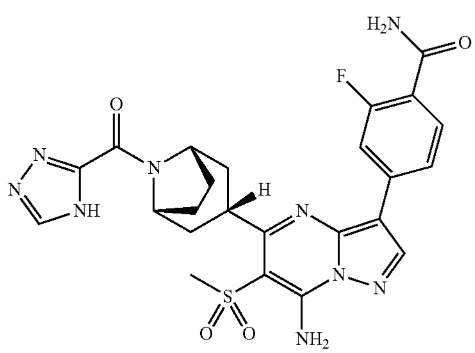 [SMILES: CS(=O)(=O)c1c([C@@H]2C[C@H]3CC[C@@H](C2)N3C(=O)c2nnc[nH]2)nc2c(-c3ccc(C(N)=O)c(F)c3)cnn2c1N] | 4-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-fluorobenzamide | 554.2/554.3 | D | C |
| 3.156 | 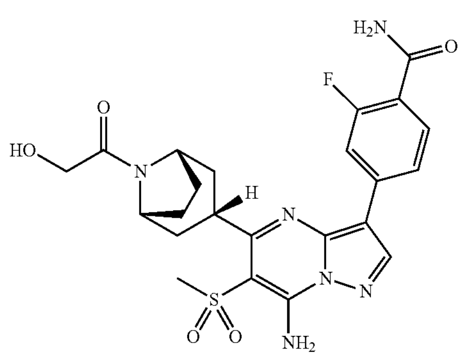 [SMILES: CS(=O)(=O)c1c([C@@H]2C[C@H]3CC[C@@H](C2)N3C(=O)CO)nc2c(-c3ccc(C(N)=O)c(F)c3)cnn2c1N] | 4-(7-amino-5-((1R,3a,5S)-8-(2-hydroxyacetyl)-8-azabicyclo[3.2.1]octan-3-yl)-6-(methylsulfonyl)pyrazolo[1,5-a]pyrimidin-3-yl)-2-fluorobenzamide | 517.2/517.1 | D | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.157 | 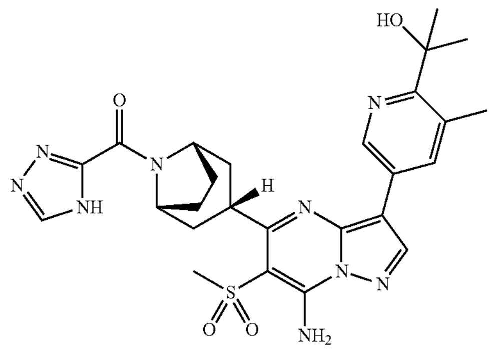 [SMILES: Cc1cc(-c2cnn3c(N)c(S(C)(=O)=O)c([C@@H]4C[C@H]5CC[C@@H](C4)N5C(=O)c4nnc[nH]4)nc23)cnc1C(C)(C)O] | ((1R,3s,5S)-3-(7-amino-3-(6-(2-hydroxypropan-2-yl)-5-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 566.2/566.4 | A | A |
| 3.158 | 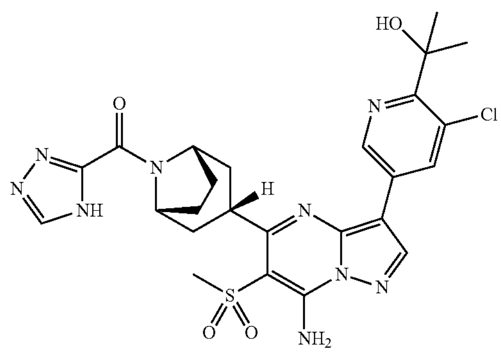 [SMILES: CC(C)(O)c1ncc(-c2cnn3c(N)c(S(C)(=O)=O)c([C@@H]4C[C@H]5CC[C@@H](C4)N5C(=O)c4nnc[nH]4)nc23)cc1Cl] | ((1R,3s,5S)-3-(7-amino-3-(5-chloro-6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 586.2/586.4 | A | A |
| 3.159 | 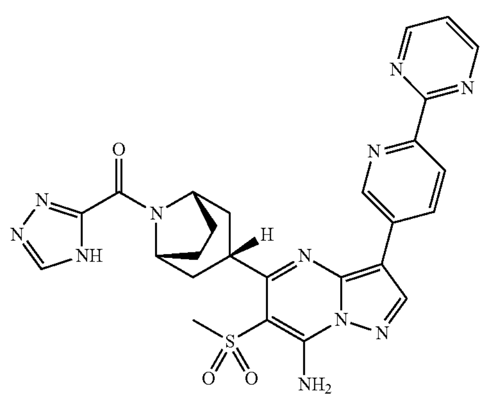 [SMILES: CS(=O)(=O)c1c([C@@H]2C[C@H]3CC[C@@H](C2)N3C(=O)c2nnc[nH]2)nc2c(-c3ccc(-c4ncccn4)nc3)cnn2c1N] | ((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(4H-1,2,4-triazol-3-yl)methanone | 572.2/572.0 | NA | NA |
| 3.160 | 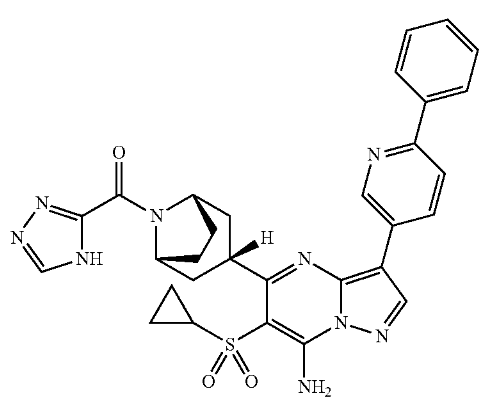 [SMILES: Nc1c(S(=O)(=O)C2CC2)c([C@@H]2C[C@H]3CC[C@@H](C2)N3C(=O)c2nnc[nH]2)nc2c(-c3ccc(-c4ccccc4)nc3)cnn12] | ((1R,3s,5S)-3-(7-amino-6-(cyclopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 596.2/596.0 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.161 | 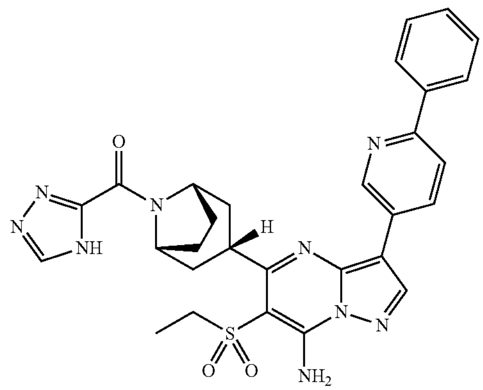 [SMILES: CCS(=O)(=O)c1c([C@@H]2C[C@H]3CC[C@@H](C2)N3C(=O)c2nnc[nH]2)nc2c(-c3ccc(-c4ccccc4)nc3)cnn2c1N] | ((1R,3s,5S)-3-(7-amino-6-(ethylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 584.2/584.3 | A | A |
| 3.162 | 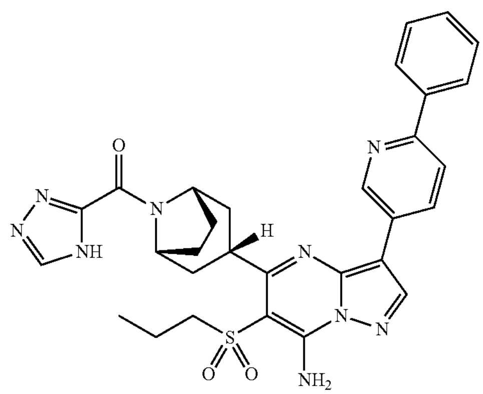 [SMILES: CCCS(=O)(=O)c1c([C@@H]2C[C@H]3CC[C@@H](C2)N3C(=O)c2nnc[nH]2)nc2c(-c3ccc(-c4ccccc4)nc3)cnn2c1N] | ((1R,3s,5S)-3-(7-amino-3-(6-phenylpyridin-3-yl)-6-(propylsulfonyl)pyrazolo[1,5-a]pyrimidin-5-yl)-8-azabicyclo[3.2.1]octan-8-yl)(4H-1,2,4-triazol-3-yl)methanone | 598.2/598.3 | B | B |
| 3.163 | 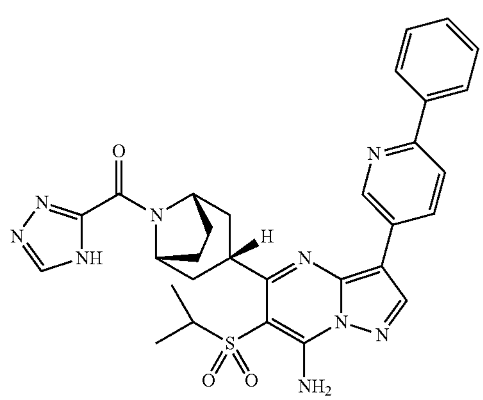 [SMILES: CC(C)S(=O)(=O)c1c([C@@H]2C[C@H]3CC[C@@H](C2)N3C(=O)c2nnc[nH]2)nc2c(-c3ccc(-c4ccccc4)nc3)cnn2c1N] | ((1R,3s,5S)-3-(7-amino-6-(isopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 598.2/598.4 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.164 | 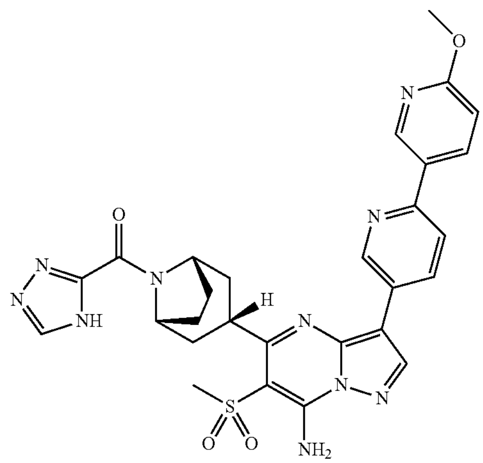 [SMILES: COc1ccc(-c2ccc(-c3cnn4c(N)c(S(C)(=O)=O)c([C@@H]5C[C@H]6CC[C@@H](C5)N6C(=O)c5nnc[nH]5)nc34)cn2)cn1] | (((1R,3s,5S)-3-(7-amino-3-(6'-methoxy-2,3'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 601.2/601.3 | B | B |
| 3.165 | 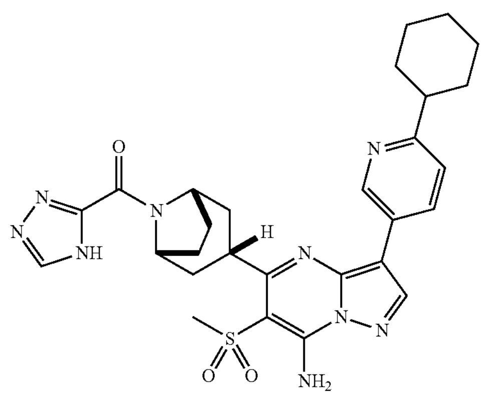 | (((1R,3s,5S)-3-(7-amino-3-(6-cyclohexylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 576.3/576.5 | B | B |
| 3.166 | 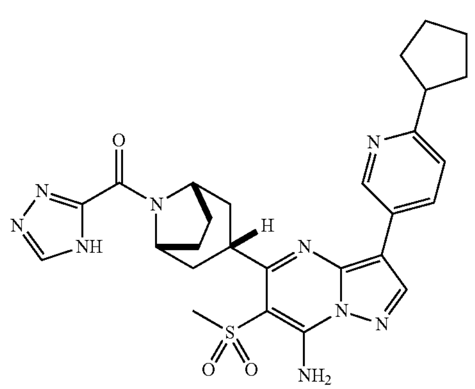 | (((1R,3s,5S)-3-(7-amino-3-(6-cyclopentylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 562.2/562.4 | B | B |

TABLE 3-1-continued

| Compound ID | Structures | Compound Name | M + H (calculated)/ M + H (observed) | pAKT S473 IC50 | p4E-BP1 Thr37/46 IC50 |
| --- | --- | --- | --- | --- | --- |
| 3.167 | 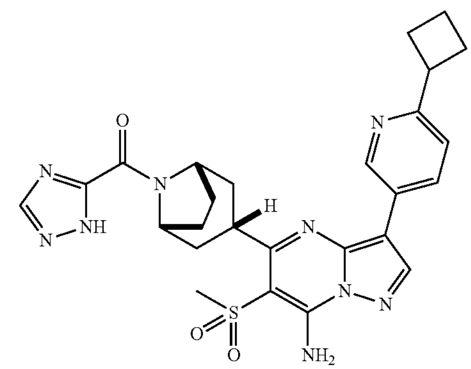 | ((1R,3s,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone | 548.2/548.1 | B | B |
| 3.168 | 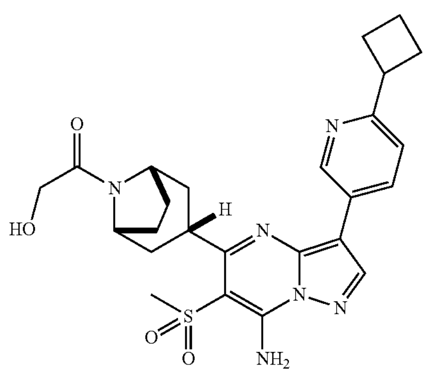 | 1-((1R,3a,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)-2-hydroxyethanone | 511.2/511.3 | ND | ND |
| 3.169 | 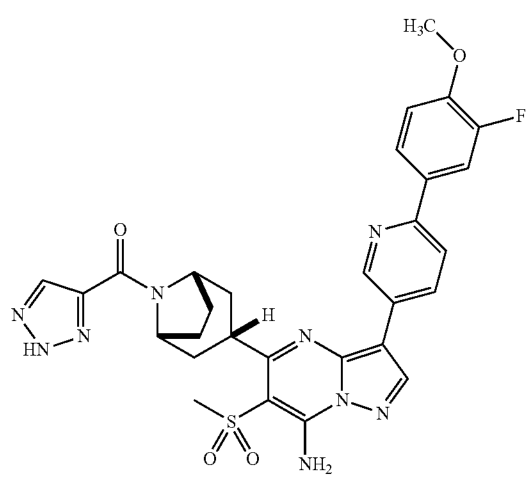 | ((1R,3a,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone | 618.2/618.7 | A | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.170 | 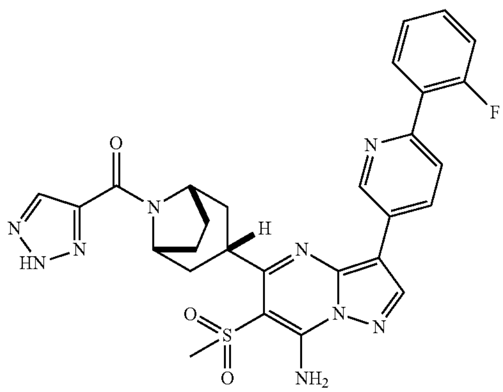 | ((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone | 588.20/588.2 | B | B |
| 3.171 | 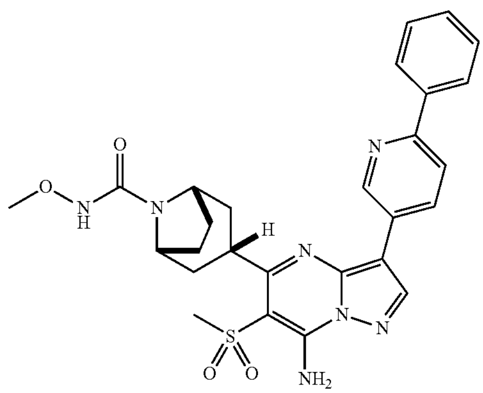 | (1R,3s,5S)-3-(7-amino-6-(methylsulfonyl)-3-(6-phenylpyridin-3-yl)pyrazolo[1,5-a]pyrimidin-5-yl)-N-methoxy-8-azabicyclo[3.2.1]octane-8-carboxamide | 548.2/548.5 | B | B |
| 3.172 | 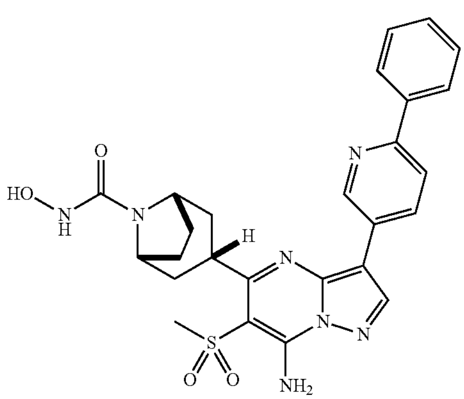 | (1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboxamide | 534.2/534.2 | B | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.173 | 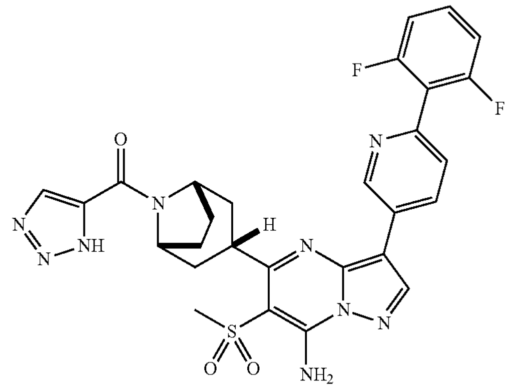 | ((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone | 606.2/606.2 | B | B |
| 3.174 | 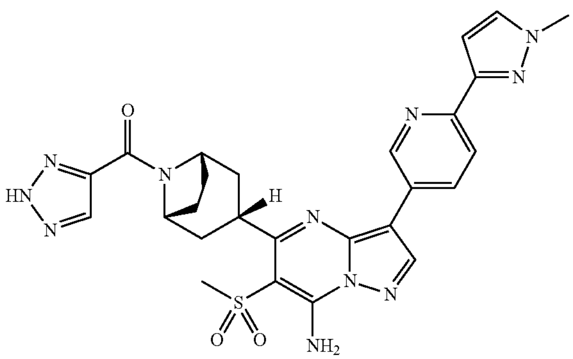 [SMILES: Cn1ccc(-c2ccc(-c3cnn4c(N)c(S(C)(=O)=O)c([C@@H]5C[C@H]6CC[C@@H](C5)N6C(=O)c5cn[nH]n5)nc34)cn2)n1] | ((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone | 574.2/574.2 | B | B |
| 3.175 | 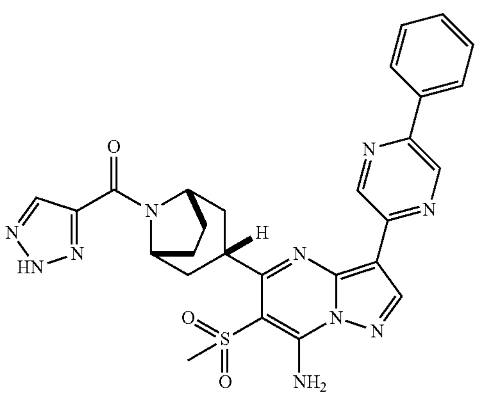 | ((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone | 571.20/571.2 | C | C |
| 3.176 | 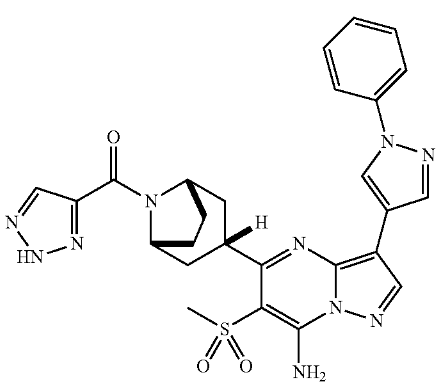 | ((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(2H-1,2,3-triazol-4-yl)methanone | 559.2/559.1 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.177 | 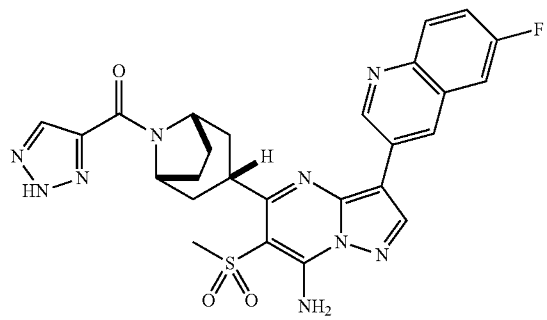 | ((1R,3s,5S)-3-(7-amino-3-(6-fluoroquinolin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone | 562.2/562.1 | B | B |
| 3.178 | 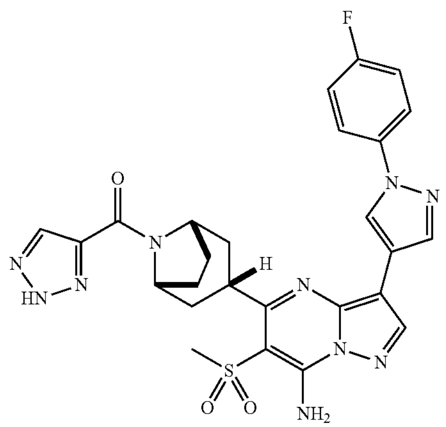 | ((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(2H-1,2,3-triazol-4-yl)methanone | 577.2/577.1 | C | C |
| 3.179 | 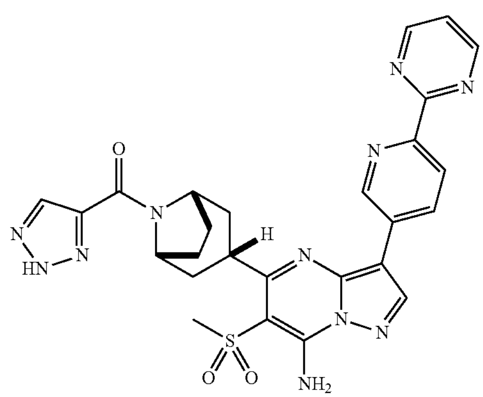 | ((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(2H-1,2,3-triazol-4-yl)methanone | 572.2/572.2 | ND | ND |
| 3.180 | 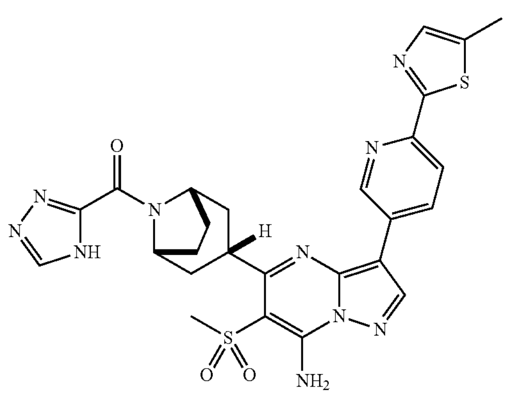 | ((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone | 591.2/591.1 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.181 | 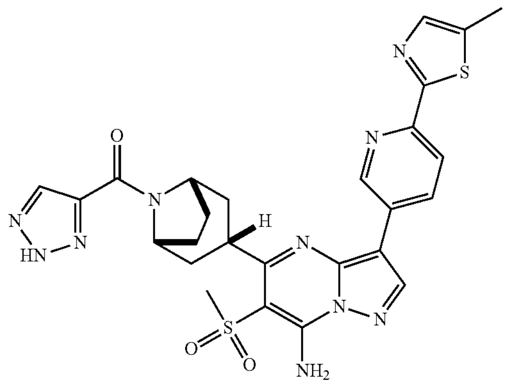 | ((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone | 591.2/591.2 | B | A |
| 3.182 | 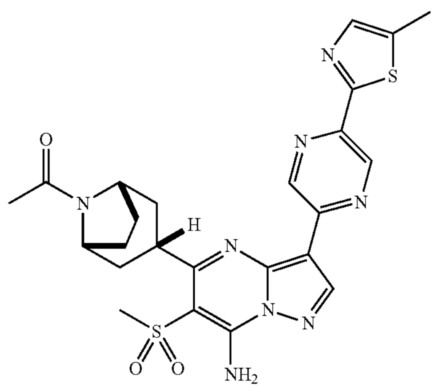 | 1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)ethanone | 538.2/538.4 | B | B |
| 3.183 | 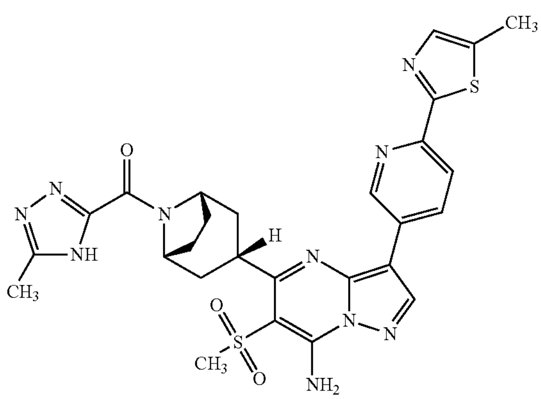 | ((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone | 526.2/526.3 | B | B |
| 3.184 | 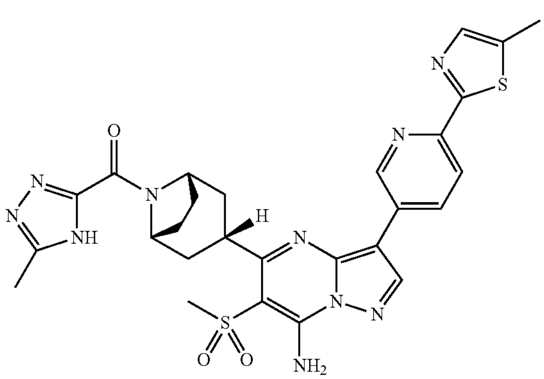 [SMILES: Cc1nnc(C(=O)N2[C@@H]3CC[C@H]2C[C@H](c2nc4c(-c5ccc(-c6ncc(C)s6)nc5)cnn4c(N)c2S(C)(=O)=O)C3)[nH]1] | ((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone | 605.2/605.2 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.185 | 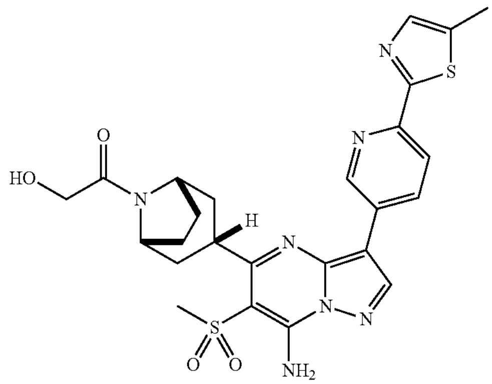 [SMILES: Cc1cnc(-c2ccc(-c3cnn4c(N)c(S(C)(=O)=O)c([C@@H]5C[C@H]6CC[C@@H](C5)N6C(=O)CO)nc34)cn2)s1] | 1-((1R,3a,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-2-hydroxyethanone | 554.2/554.2 | B | B |
| 3.186 | 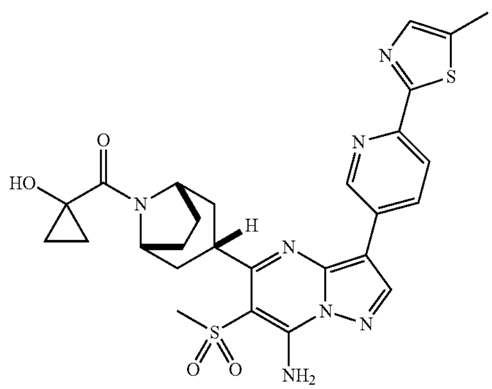 [SMILES: Cc1cnc(-c2ccc(-c3cnn4c(N)c(S(C)(=O)=O)c([C@@H]5C[C@H]6CC[C@@H](C5)N6C(=O)C5(O)CC5)nc34)cn2)s1] | ((1R,3s,5S)-3-(7-amino-6-(methylsulfonyl)-3-(6-(5-methylthiazol-2-yl)pyridin-3-yl)pyrazolo[1,5-a]pyrimidin5-yl)-8-azabicyclo[3.2.1]octan-8-yl)(1-hydroxycyclopropyl)methanone | 580.2/580.2 | C | C |
| 3.187 | 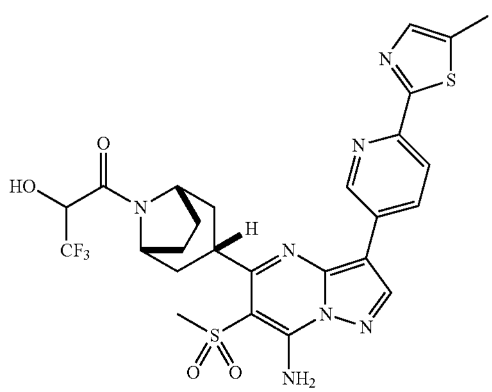 [SMILES: Cc1cnc(-c2ccc(-c3cnn4c(N)c(S(C)(=O)=O)c([C@@H]5C[C@H]6CC[C@@H](C5)N6C(=O)C(O)C(F)(F)F)nc34)cn2)s1] | 1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoro-2-hydroxypropan-1-one | 622.2/621.9 | C | C |
| 3.188 | 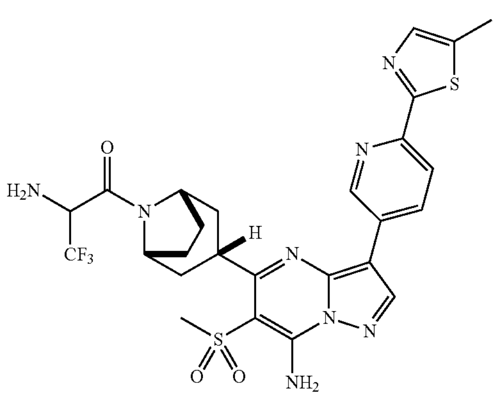 [SMILES: Cc1cnc(-c2ccc(-c3cnn4c(N)c(S(C)(=O)=O)c([C@@H]5C[C@H]6CC[C@@H](C5)N6C(=O)C(N)C(F)(F)F)nc34)cn2)s1] | 2-amino-1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoropropan-1-one | 621.2/621.3 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.189 | 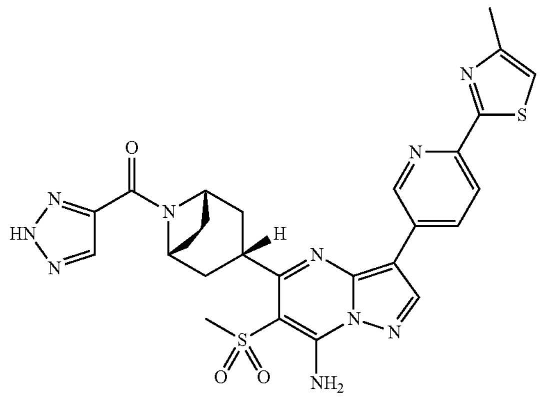 [SMILES: Cc1csc(-c2ccc(-c3cnn4c(N)c(S(C)(=O)=O)c([C@@H]5C[C@H]6CC[C@@H](C5)N6C(=O)c5cn[nH]n5)nc34)cn2)n1] | ((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone | 591.2/591.0 | C | C |
| 3.190 | 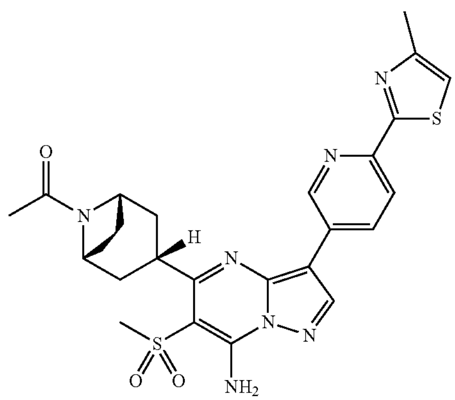 [SMILES: CC(=O)N1[C@@H]2CC[C@H]1C[C@H](c1nc3c(-c4ccc(-c5nc(C)cs5)nc4)cnn3c(N)c1S(C)(=O)=O)C2] | 1-((1R,3a,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)ethanone | 538.2/538.2 | C | C |
| 3.191 | 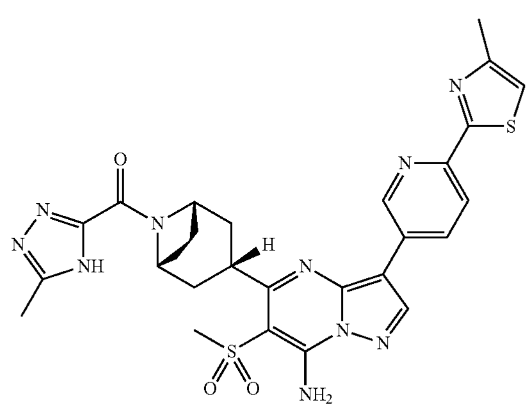 [SMILES: Cc1csc(-c2ccc(-c3cnn4c(N)c(S(C)(=O)=O)c([C@@H]5C[C@H]6CC[C@@H](C5)N6C(=O)c5nnc(C)[nH]5)nc34)cn2)n1] | ((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone | 605.2/605.2 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.192 | 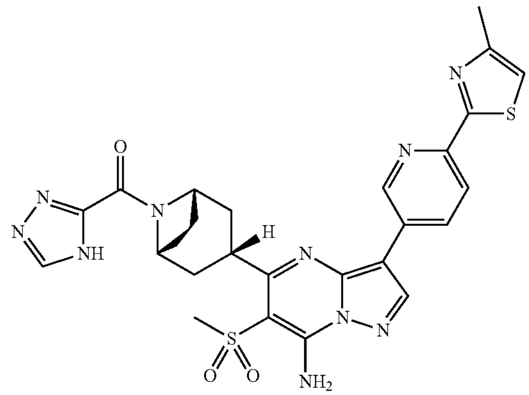 [SMILES: Cc1csc(-c2ccc(-c3cnn4c(N)c(S(C)(=O)=O)c([C@@H]5C[C@H]6CC[C@@H](C5)N6C(=O)c5nnc[nH]5)nc34)cn2)n1] | ((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone | 591.2/591.0 | B | B |
| 3.193 | 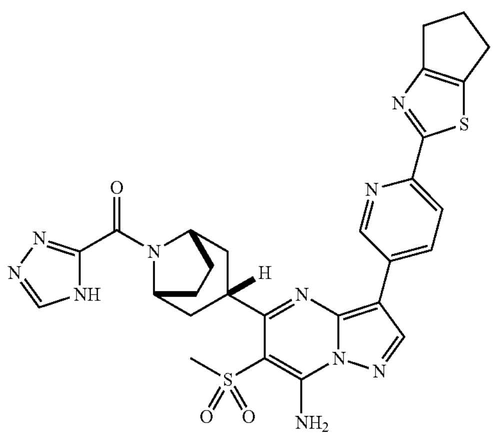 [SMILES: CS(=O)(=O)c1c([C@@H]2C[C@H]3CC[C@@H](C2)N3C(=O)c2nnc[nH]2)nc2c(-c3ccc(-c4nc5c(s4)CCC5)nc3)cnn2c1N] | ((1R,3s,5)S-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 617.2/617.1 | B | B |
| 3.194 | 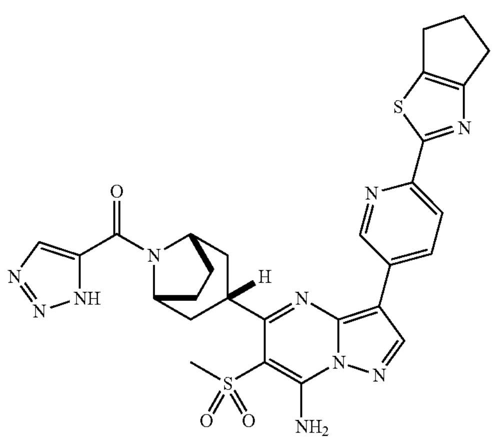 [SMILES: CS(=O)(=O)c1c([C@@H]2C[C@H]3CC[C@@H](C2)N3C(=O)c2cnn[nH]2)nc2c(-c3ccc(-c4nc5c(s4)CCC5)nc3)cnn2c1N] | ((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimdiin-5-yl)-8-azabicyclo[3.2.1]octan-8-yl)(1H-1,2,3-triazol-5-yl)methanone | 617.2/617.5 | ND | ND |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.195 | 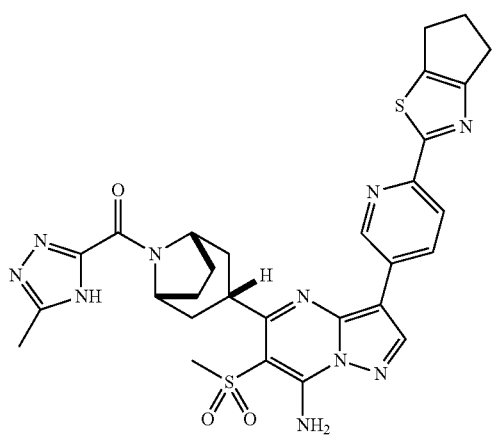 [SMILES: Cc1nnc(C(=O)N2[C@@H]3CC[C@H]2C[C@H](c2nc4c(-c5ccc(-c6nc7c(s6)CCC7)nc5)cnn4c(N)c2S(C)(=O)=O)C3)[nH]1] | ((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 631.2/631.2 | C | C |
| 3.196 | 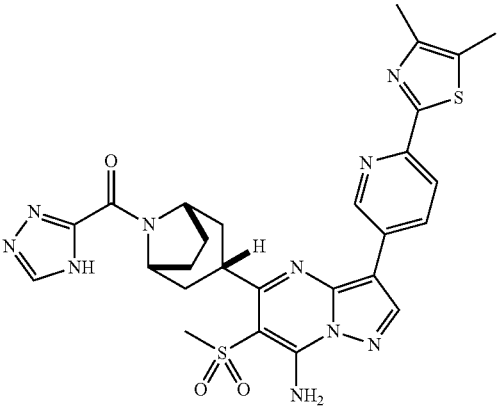 | ((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 605.2/605.0 | B | B |
| 3.197 | 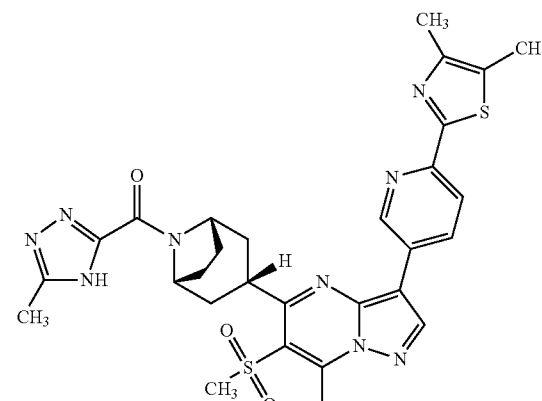 | ((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone | 619.2/619.4 | B | B |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.198 | 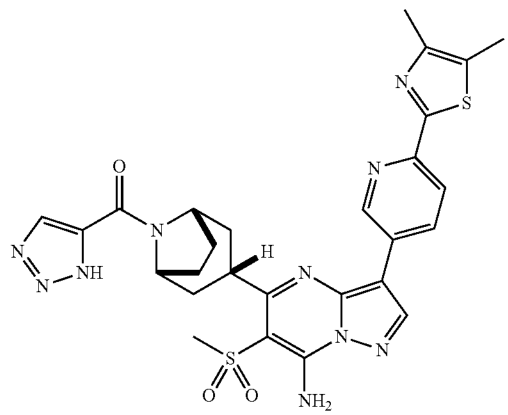 [SMILES: Cc1nc(-c2ccc(-c3cnn4c(N)c(S(C)(=O)=O)c([C@@H]5C[C@H]6CC[C@@H](C5)N6C(=O)c5cnn[nH]5)nc34)cn2)sc1C] | ((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone | 605.2/605.3 | ND | ND |
| 3.199 | 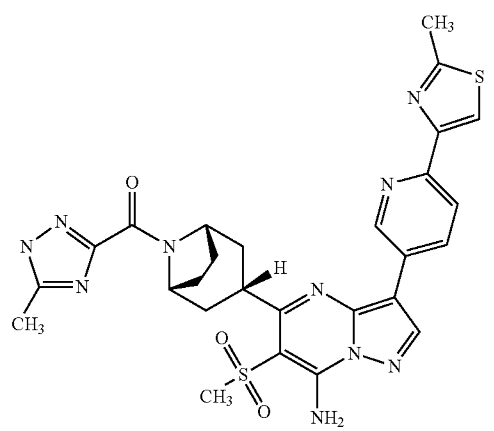 [SMILES: Cc1nc(C(=O)N2[C@@H]3CC[C@H]2C[C@H](c2nc4c(-c5ccc(-c6csc(C)n6)nc5)cnn4c(N)c2S(C)(=O)=O)C3)n[nH]1] | ((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(5-methyl-1H-1,2,4-triazol-3-yl)methanone | 605.2/605.2 | A | B |
| 3.200 | 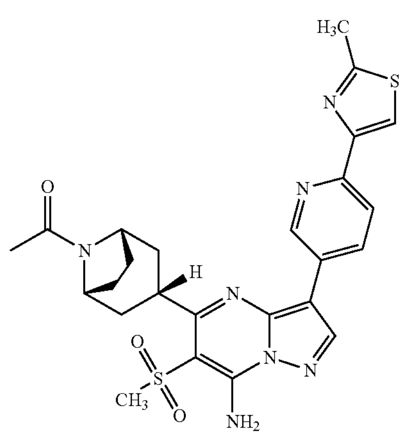 [SMILES: CC(=O)N1[C@@H]2CC[C@H]1C[C@H](c1nc3c(-c4ccc(-c5csc(C)n5)nc4)cnn3c(N)c1S(C)(=O)=O)C2] | 1-((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)ethanone | 538.2/538.2 | C | C |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.201 | 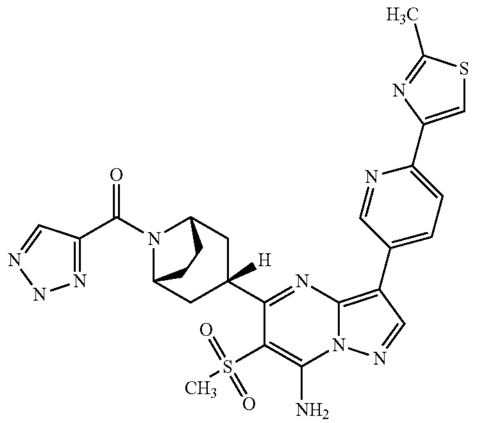 [SMILES: Cc1nc(-c2ccc(-c3cnn4c(N)c(S(C)(=O)=O)c([C@@H]5C[C@H]6CC[C@@H](C5)N6C(=O)c5cn[nH]n5)nc34)cn2)cs1] | ((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(2H-1,2,3-triazol-4-yl)methanone | 591.2/591.1 | B | C |
| 3.202 | 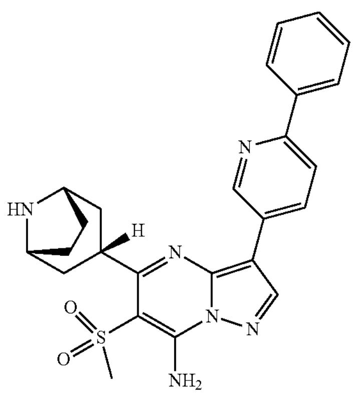 [SMILES: CS(=O)(=O)c1c([C@@H]2C[C@H]3CC[C@@H](C2)N3)nc2c(-c3ccc(-c4ccccc4)nc3)cnn2c1N] | 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine | 474.18/475.0 | C | C |
| 3.203 | 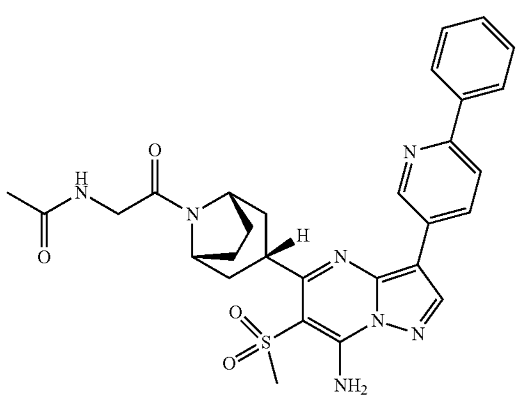 [SMILES: CC(=O)NCC(=O)N1[C@@H]2CC[C@H]1C[C@H](c1nc3c(-c4ccc(-c5ccccc5)nc4)cnn3c(N)c1S(C)(=O)=O)C2] | N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-oxoethyl)acetamide | 573.22/574.0 | A | A |

TABLE 3-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 3.204 | 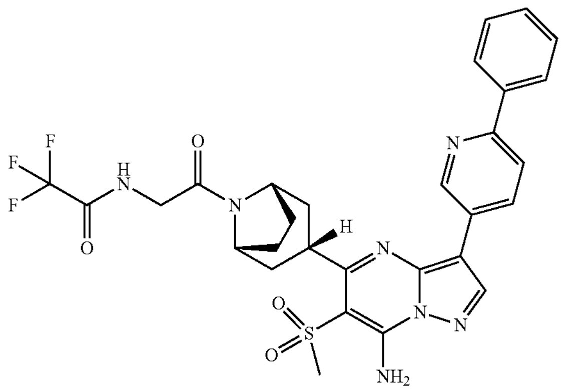 [SMILES: CS(=O)(=O)c1c([C@@H]2C[C@H]3CC[C@@H](C2)N3C(=O)CNC(=O)C(F)(F)F)nc2c(-c3ccc(-c4ccccc4)nc3)cnn2c1N] | N-(2-((1R,3s,5S)-3-(7-amino-6-(methylsulfonyl)-3-(6-phenylpyridin-3-yl)pyrazolo[1,5-a]pyrimidin-5-yl-8-azabicyclo[3.2.1]octan-8-yl)-2-oxoethyl)-2,2,2-trifluoroacetamide | 627.19/628.0 | ND | ND |
| 3.205 | 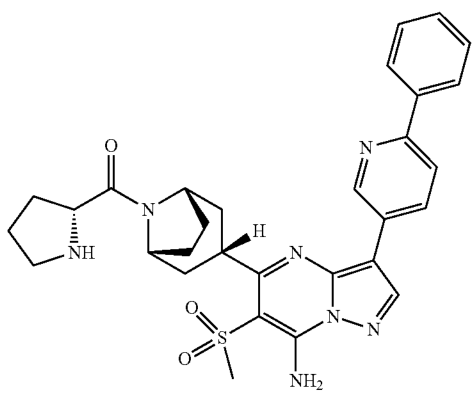 [SMILES: CS(=O)(=O)c1c([C@@H]2C[C@H]3CC[C@@H](C2)N3C(=O)[C@H]2CCCN2)nc2c(-c3ccc(-c4ccccc4)nc3)cnn2c1N] | ((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-pyrrolidin-2-yl)methanone | 571.24/572.2 | B | B |
| 3.206 | 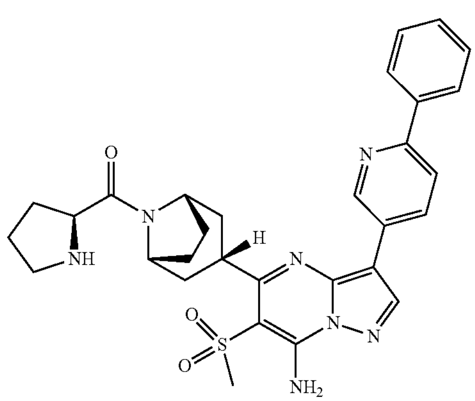 [SMILES: CS(=O)(=O)c1c([C@@H]2C[C@H]3CC[C@@H](C2)N3C(=O)[C@@H]2CCCN2)nc2c(-c3ccc(-c4ccccc4)nc3)cnn2c1N] | ((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-pyrrolidin-2-yl)methanone | 571.24/572.2 | C | C |

467

Example 4-1

SCHEME 4-1

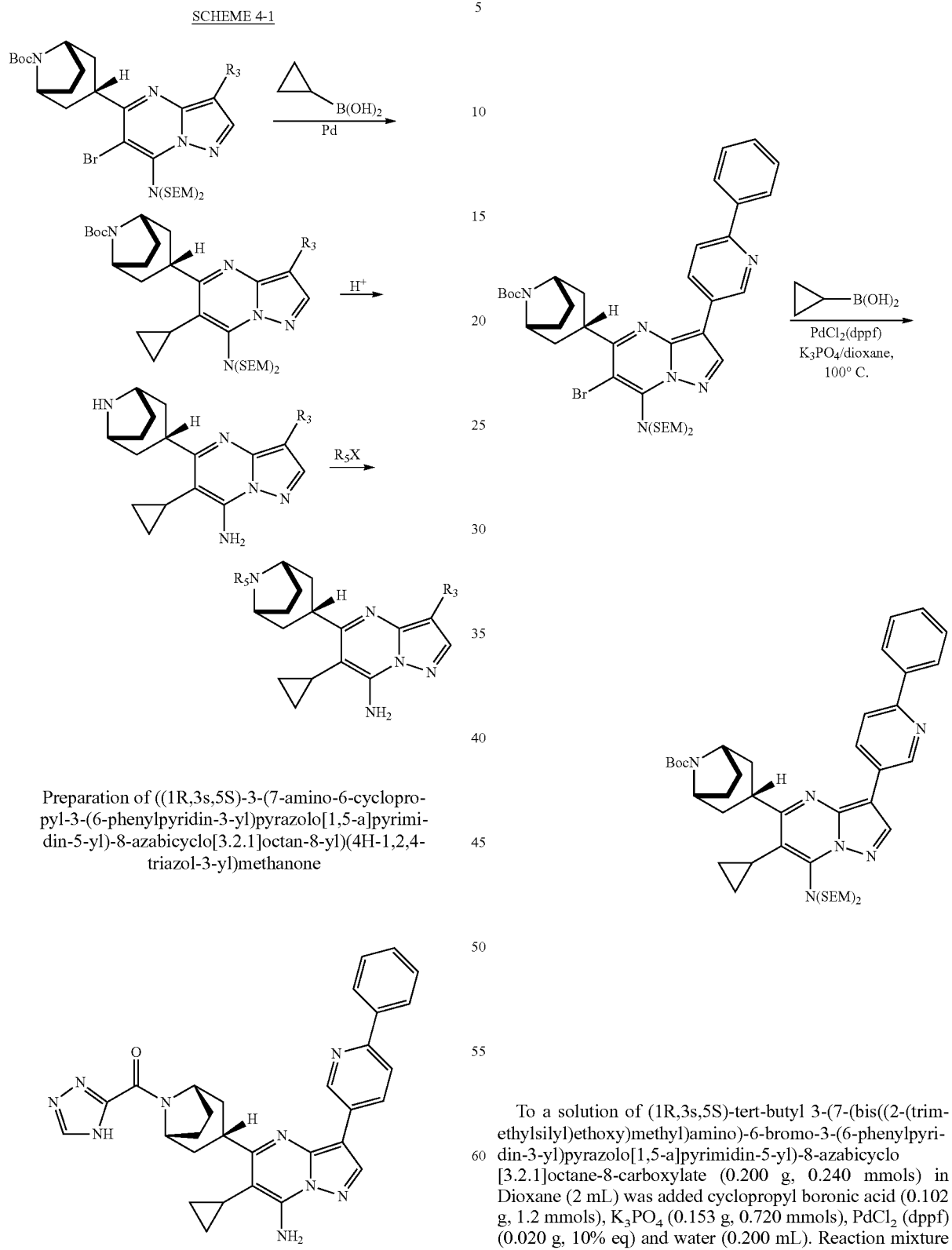

Preparation of ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

468

Step A—Synthesis of (1R,3s,5S)-tert-butyl 3-(7-(bis((2-(trimethylsilyl)ethoxy)methyl)amino)-6-cyclopropyl-3-(6-phenylpyridin-3-yl)pyrazolo[1,5-a]pyrimidin-5-yl)-8-azabicyclo[3.2.1]octane-8-carboxylate To a solution of (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (0.200 g, 0.240 mmols) in Dioxane (2 mL) was added cyclopropyl boronic acid (0.102 g, 1.2 mmols), $K_3PO_4$ (0.153 g, 0.720 mmols), $PdCl_2$ (dppf) (0.020 g, 10% eq) and water (0.200 mL). Reaction mixture was degassed and heated at 100° C. for 15 h. The reaction was passed through celite, diluted with EtOAc and washed with sat. $NaHCO_3$ and water. The organic layer dried with $MgSO_4$ and concentrated. ISCO purification (20% EtOAc in Hexane) gave the title compound as yellow oil (0.102 g).

Step B—Synthesis of (((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

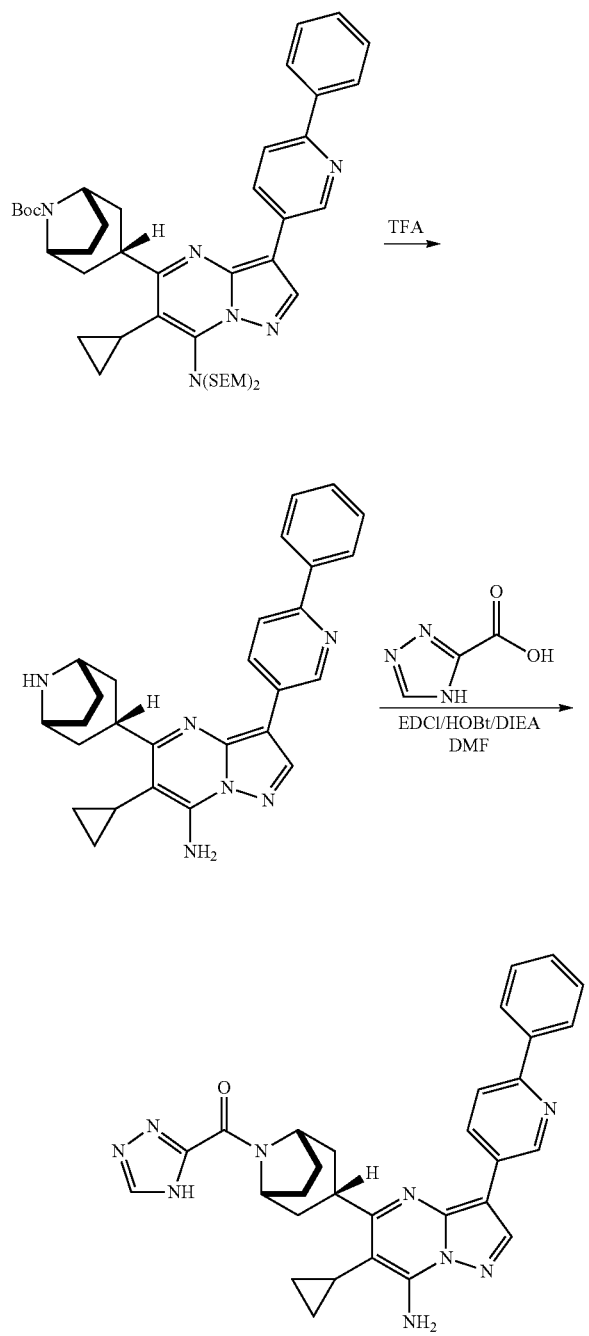

Intermediate (1R,3s,5S)-tert-butyl 3-(7-(bis((2-(trimethylsilyl)ethoxy)methyl)amino)-6-cyclopropyl-3-(6-phenylpyridin-3-yl)pyrazolo[1,5-a]pyrimidin-5-yl)-8-azabicyclo[3.2.1]octane-8-carboxylate was treated with TFA/water (9:1, 1 mL) for 5 minutes, concentrated and lyophilized to provide the corresponding amine which was converted to the title product following standard amide coupling reaction described before.

Example 4-2

Preparation of ((1R,3s,5S)-3-(7-amino-6-cyclopropyl-3-(6-methoxyquinolin-3-yl)pyrazolo[1,5-a]pyrimidin-5-yl)-8-azabicyclo[3.2.1]octan-8-yl)(4H-1,2,4-triazol-3-yl)methanone Step 1: Preparation of (1R,3s,5S)-tert-butyl 3-((R)-7-(bis((2-(trimethylsilyl)ethoxy)methyl)amino)-6-bromo-3-(7-methoxynaphthalen-2-yl)-4,5-dihydropyrazolo[1,5-a]pyrimidin-5-yl)-8-azabicyclo[3.2.1]octane-8-carboxylate To a solution of (1R,3s,5S)-tert-butyl 3-(7-(bis((2-(trimethylsilyl)ethoxy)methyl)amino)-3-(7-methoxynaphthalen-2-yl)pyrazolo[1,5-a]pyrimidin-5-yl-8-azabicyclo[3.2.1]octane-8-carboxylate (773 mg, 1.02 mmol) in CH₃CN (20 mL) was added NBS (1.1 eq) at rt and stirred for 15 min. All the volatiles were removed under reduced pressure and the residue was purified by a SiO₂ column (0-40%, EtOAc/Hexanes, $R_f$=0.7 in 50% EtOAc) to afford the titled compound as a yellow forming solid (354 mg).

Step 2: Preparation of (1R,3s,5S)-tert-butyl 3-((R)-7-(bis((2-(trimethylsilyl)ethoxy)methyl)amino)-6-cyclopropyl-3-(7-methoxynaphthalen-2-yl)-4,5-dihydropyrazolo[1,5-a]pyrimidin-5-yl)-8-azabicyclo[3.2.1]octane-8-carboxylate

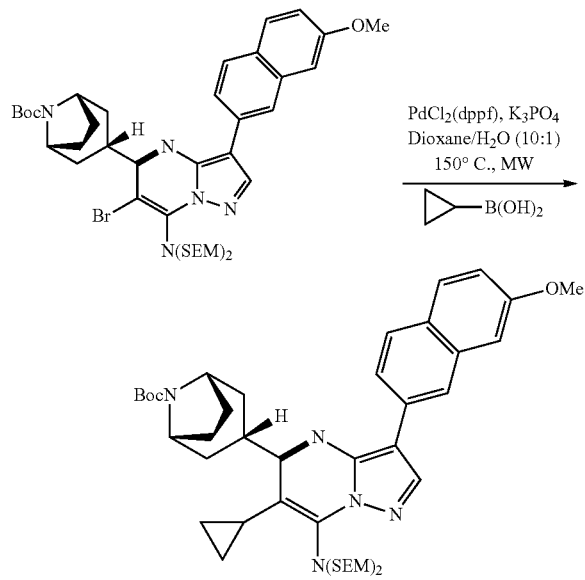

A mixture of (1R,3s,5S)-tert-butyl 3-((R)-7-(bis((2-(trimethylsilyl)ethoxy)methyl)amino)-6-bromo-3-(7-methoxynaphthalen-2-yl)-4,5-dihydropyrazolo[1,5-a]pyrimidin-5-yl)-8-azabicyclo[3.2.1]octane-8-carboxylate (177 mg, 0.211 mmol), cyclopropylboronic acid (181 mg, 2.11 mmol), PdCl$_2$(dppf)DCM (34.5 mg, 0.042 mmol), and K$_3$PO$_4$ (134 mg, 0.633 mmol) in dioxane/H$_2$O (2/0.2 mL) was degassed and then heated at 150° C. under microwave radiation for 3 h. The reaction mixture was diluted with EtOAc, filtered through a short pad of celite, washed with H$_2$O and brine, dried over Na$_2$SO$_4$, and concentrated. The crude product was purified by a SiO$_2$ column (0-30% EtOAc/Hexanes, $R_f$=0.75 in 50% EtOAc) to afford the titled compound as a pale yellow forming solid (71.2 mg).

Step 3: Preparation of ((1R,3s,5S)-3-(7-amino-6-cyclopropyl-3-(6-methoxyquinolin-3-yl)-pyrazolo[1,5-a]pyrimidin-5-yl-8-azabicyclo[3.2.1]octan-8-yl)(4H-1,2,4-triazol-3-yl)methanone

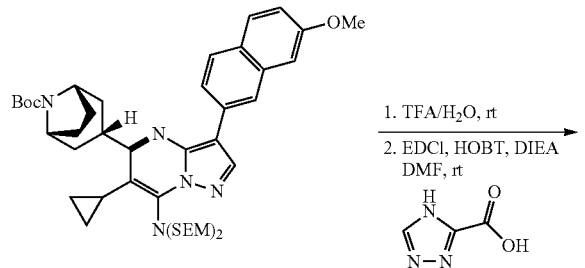

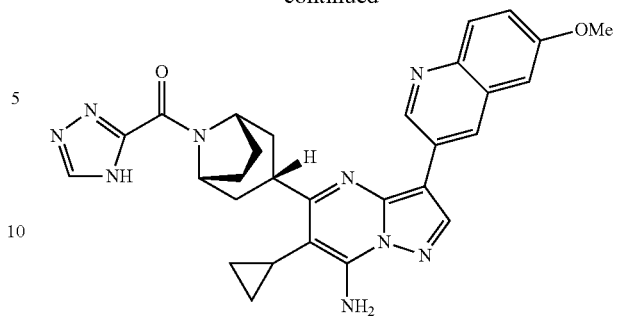

This compound was prepared from (1R,3s,5S)-tert-butyl 3-((R)-7-(bis((2-(trimethylsilyl)ethoxy)methyl)amino)-6-cyclopropyl-3-(7-methoxynaphthalen-2-yl)-4,5-dihydropyrazolo[1,5-a]pyrimidin-5-yl)-8-azabicyclo[3.2.1]octane-8-carboxylate and 4H-1,2,4-triazole-3-carboxylic acid, following essentially the similar procedures given in Preparative Example 4-1.

Example 4-3

Preparation of 4-nitrophenyl {[tert-butyl(dimethyl)silyl]oxy}carbamate

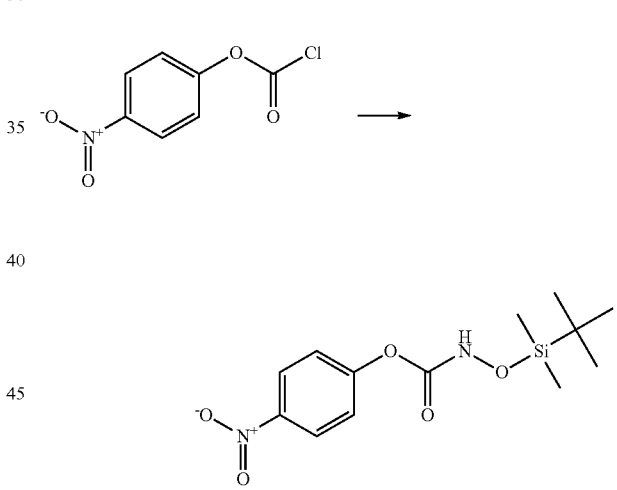

(Aminooxy) (tert-butyl)dimethylsilane (1.00 g, 6.79 mmol) was dissolved in a mixture of dry pyridine (0.549 mL, 6.79 mmol) and dichloroethane (15 mL; dichloromethane could also be used), and a solution of 4-nitrophenyl chlorocarbonate (1.37 g, 6.79 mmol) in dichloroethane (7 mL) was added over 5 min. The resulting mixture was stirred at room temperature overnight and was then diluted with dichloromethane, washed twice with water, twice with saturated aqueous sodium bicarbonate, and brine, dried over magnesium sulfate, and concentrated under reduced pressure. The crude product was purified by chromatography (90 g silica gel, 20% EtOAc/hexanes eluent) to give the title compound (1.73 g, 81%) as a white solid.

Following Scheme 4-1 and using procedures similar to the preparation of example 4-1, the following compounds listed in Table 4-1 were prepared:

TABLE 4-1

| | | | | | |
|---|---|---|---|---|---|
| 4.1 | 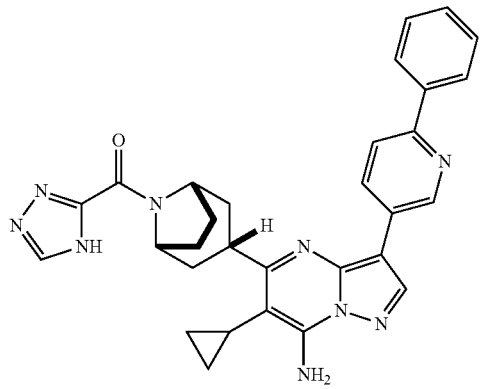 | ((1R,3a,5S)-3-(7-amino-6-cyclopropyl-3-(6-phenyl-pyridin-3-yl)pyra-zolo[1,5-a]pyrimidin-5-yl)-8-azabicyclo[3.2.1]octan-8-yl)(4H-1,2,4-triazol-3-yl)methanone | 532.3/532.0 | A | A |
| 4.2 | 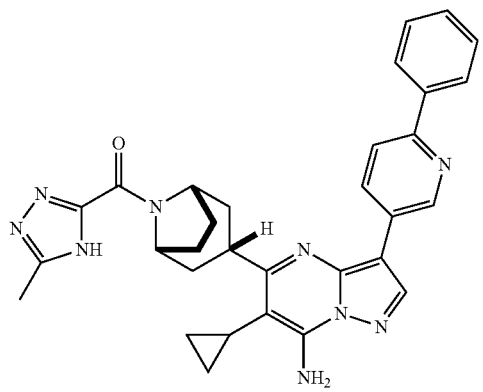 | ((1R,3a,5S)-3-(7-amino-6-cyclopropyl-3-(6-phenyl-pyridin-3-yl)pyrazolo[1,5-a]pyrimidin-5-yl)-8-azabicyclo[3.2.1]octan-8-yl)(5-methyl-4H-1,2,4-triazol-3-yl)methanone | 546.3/546.0 | A | A |
| 4.3 | 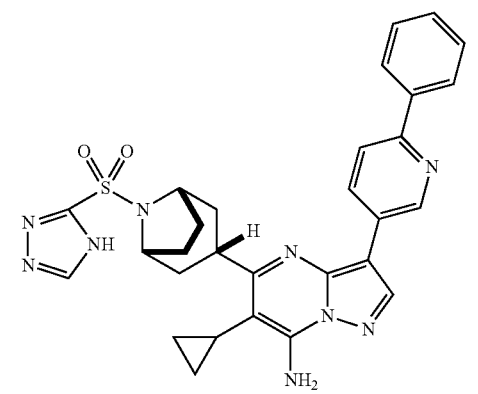 | 5-((1R,3a,5S)-8-(4H-1,2,4-triazol-3-ylsulfonyl)-8-azabicyclo[3.2.1]octan-3-yl)-6-cyclopropyl-3-(6-phenylpyridin-3-yl)pyrazolo[1,5-a]pyrimidin-7-amine | 568.2/568.2 | C | C |
| 4.4 | 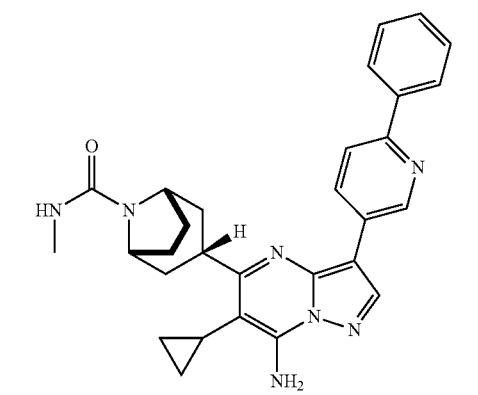 | (1R,3a,5S)-3-(7-amino-6-cyclopropyl-3-(6-phenyl-pyridin-3-yl)pyrazolo[1,5-a]pyrimidin-5-yl)-N-methyl-8-azabicyclo[3.2.1]octane-8-carboxamide | 494.3/494.0 | A | B |

TABLE 4-1-continued

| 4.5 | 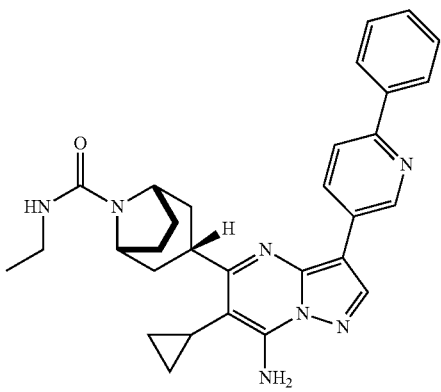 | (1R,3s,5S)-3-(7-amino-6-cyclopropyl-3-(6-phenyl-pyridin-3-yl)pyrazolo[1,5-a]pyrimidin-5-yl)-N-ethyl-8-azabicyclo[3.2.1]octane-8-carboxamide | 508.3/508.0 | B | B |
|---|---|---|---|---|---|
| 4.6 | 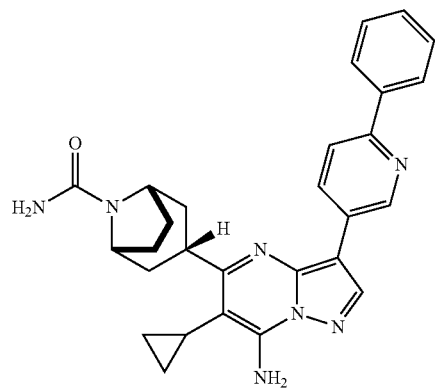 | (1R,3s,5S)-3-(7-amino-6-cyclopropyl-3-(6-phenyl-pyridin-3-yl)pyrazolo[1,5a]pyrimidin-5-yl)-8-azabicyclo[3.2.1]octane-8-carboxamide | 480.2/480.0 | A | A |
| 4.7 | 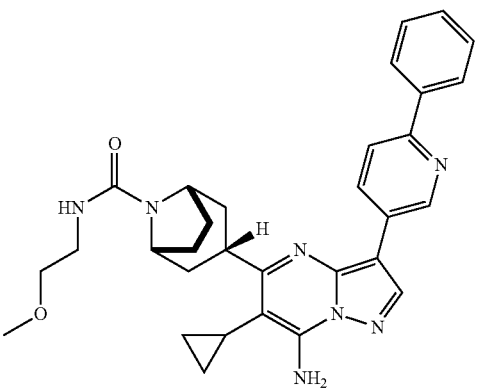 | (1R,3s,5S)-3-(7-amino-6-cyclopropyl-3-(6-phenyl-pyridin-3-yl)pyrazolo[1,5-a]pyrimidin-5-yl)-N-(2-methoxyethyl)-8-azabicyclo[3.2.1]octane-8-carboxamide | 538.3/538.1 | B | B |
| 4.8 | 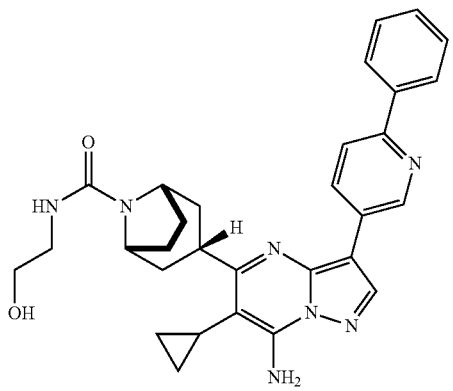 | (1R,3s,5S)-3-(7-amino-6-cyclopropyl-3-(6-phenyl-pyridin-3-yl)pyrazolo[1,5-a]pyrimidin-5-yl)-N-(2-hydroxyethyl)-8-azabicyclo[3.2.1]octane-8-carboxamide | 524.3/524.0 | A | B |

| | | | | | |
|---|---|---|---|---|---|
| 4.9 | 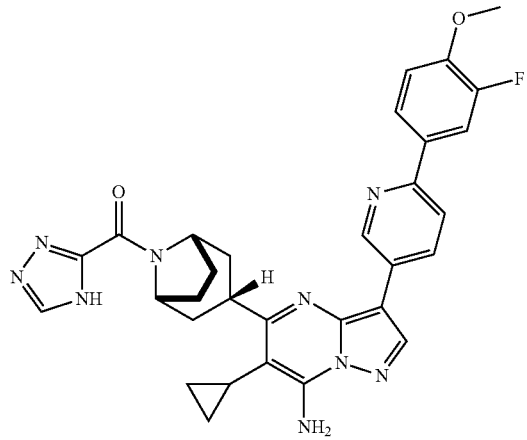 | ((1R,3s,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 580.25/580.0 | A | B |
| 4.10 | 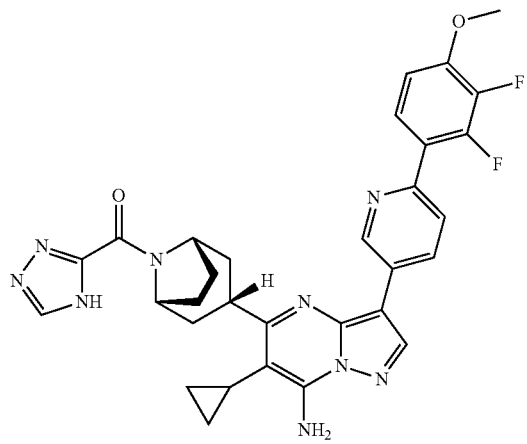 | ((1R,3a,5S)-3-(7-amino-6-cyclopropyl-3-(6-(2,3-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 598.24/598.0 | A | A |
| 4.11 | 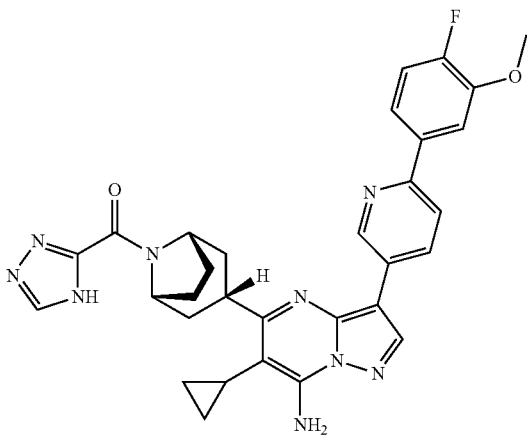 | ((1R,3a,5S)-3-(7-amino-6-cyclopropyl-3-(6-(4-fluoro-3-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 580.25/580.0 | ND | D |

| | | | | | |
|---|---|---|---|---|---|
| 4.12 | 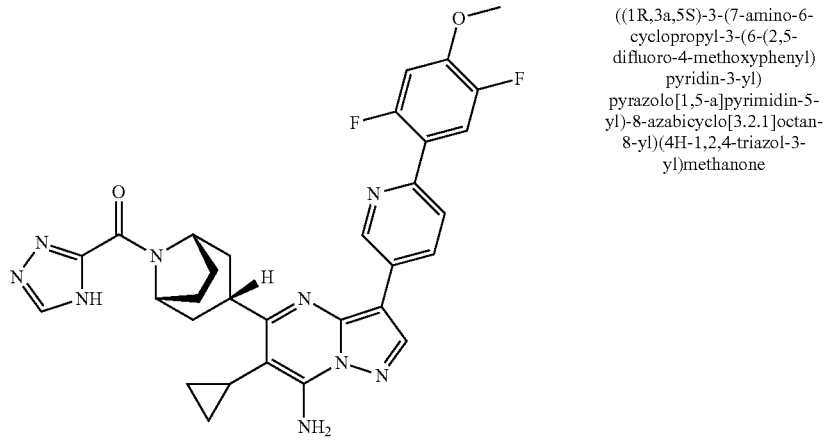 | ((1R,3a,5S)-3-(7-amino-6-cyclopropyl-3-(6-(2,5-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 598.24/598.0 | A | A |
| 4.13 | 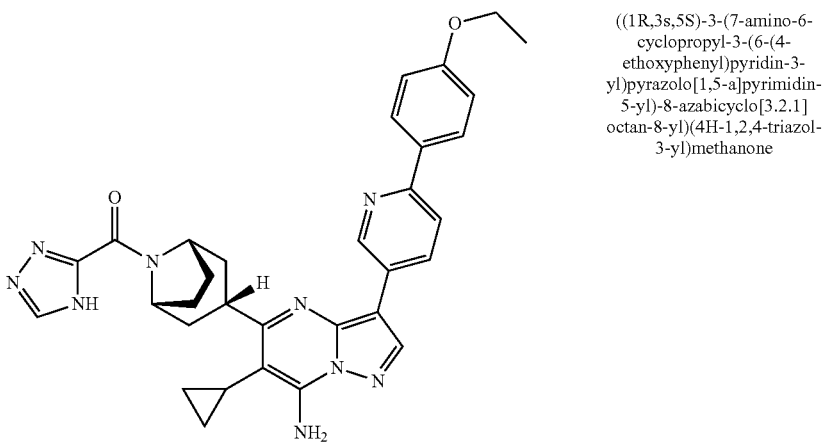 | ((1R,3s,5S)-3-(7-amino-6-cyclopropyl-3-(6-(4-ethoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 576.27/576.1 | B | B |
| 4.14 | 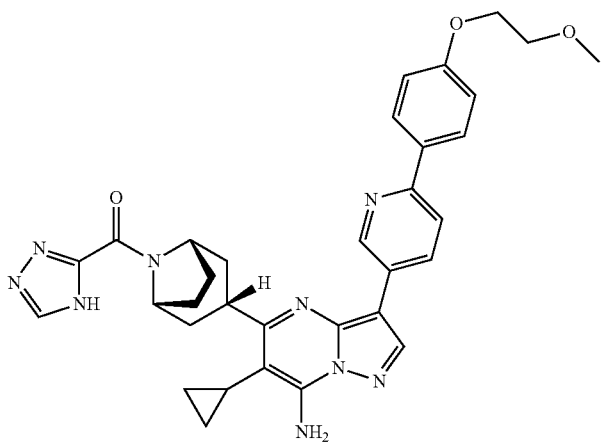 | ((1R,3s,5S)-3-(7-amino-6-cyclopropyl-3-(6-(4-(2-methoxyethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone | 606.28/606.1 | B | B |

TABLE 4-1-continued

| | | | | | |
|---|---|---|---|---|---|
| 4.15 | | ((1R,3s,5S)-3-(7-amino-6-cyclopropyl-3-(6-(4-(difluoromethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone | 598.24/598.0 | B | B |
| 4.16 | | ((1R,3s,5S)-3-(7-amino-6-cyclopropyl-3-(6-methyl-pyridin-3-yl)pyrazolo[1,5-a]pyrimidin-5-yl)-8-aza-bicyclo[3.2.1]octan-8-yl)(4H-1,2,4-triazol-3-yl)methanone | 470.23/470.0 | B | ND |
| 4.17 | | ((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone | 536.25/536.0 | A | A |
| 4.18 | | 1-((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 497.25/499.0 | A | A |

TABLE 4-1-continued

| 4.19 | 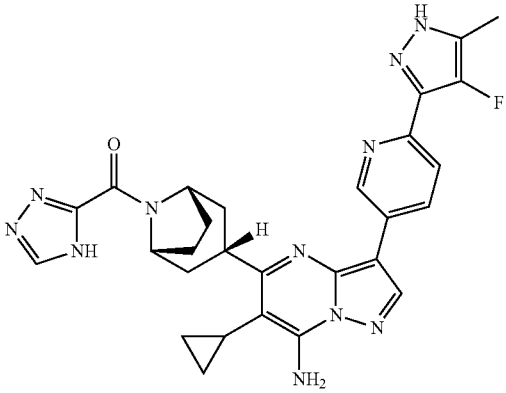 [SMILES: Cc1[nH]nc(-c2ccc(-c3cnn4c(N)c(C5CC5)c([C@@H]5C[C@H]6CC[C@@H](C5)N6C(=O)c5nnc[nH]5)nc34)cn2)c1F] | ((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone | 554.24/554.0 | B | B |
| 4.20 | 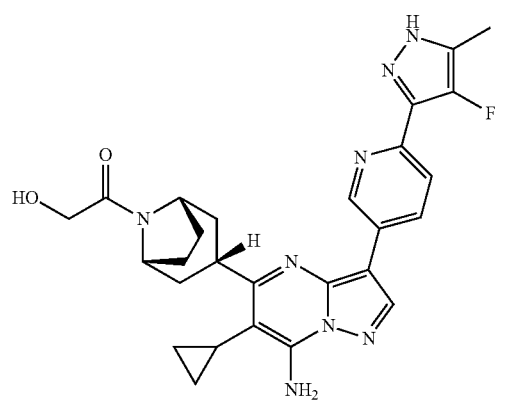 [SMILES: Cc1[nH]nc(-c2ccc(-c3cnn4c(N)c(C5CC5)c([C@@H]5C[C@H]6CC[C@@H](C5)N6C(=O)CO)nc34)cn2)c1F] | 1-((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone | 517.24/517.0 | B | B |
| 4.21 | 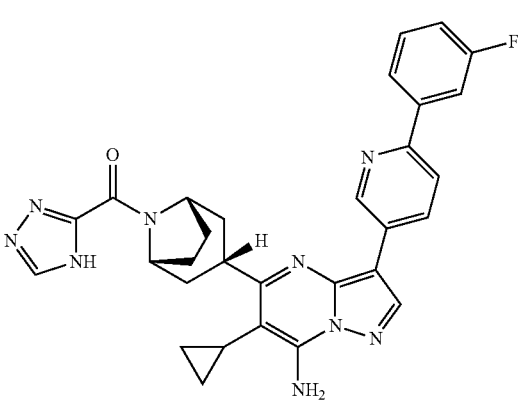 [SMILES: Nc1c(C2CC2)c([C@@H]2C[C@H]3CC[C@@H](C2)N3C(=O)c2nnc[nH]2)nc2c(-c3ccc(-c4cccc(F)c4)nc3)cnn12] | ((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone | 550.24/550.0 | A | A |
| 4.22 | 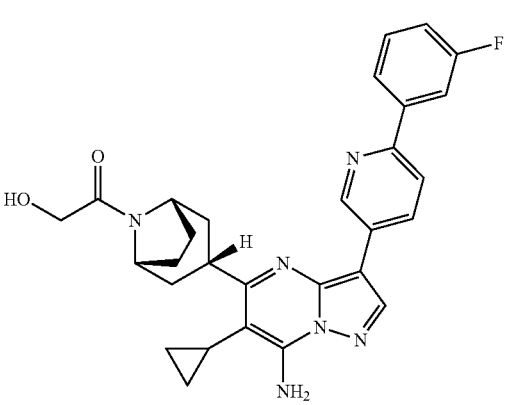 [SMILES: Nc1c(C2CC2)c([C@@H]2C[C@H]3CC[C@@H](C2)N3C(=O)CO)nc2c(-c3ccc(-c4cccc(F)c4)nc3)cnn12] | 1-((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)-2-hydroxyethanone | 513.23/513.0 | B | B |

TABLE 4-1-continued

| 4.23 | 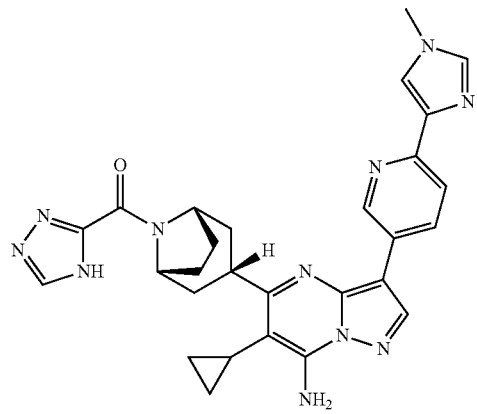 [SMILES: Cn1cnc(-c2ccc(-c3cnn4c(N)c(C5CC5)c([C@@H]5C[C@H]6CC[C@@H](C5)N6C(=O)c5nnc[nH]5)nc34)cn2)c1] | ((1R,3a,5S)-3-(7-amino-6-cyclopropyl-3-(6-(1-methyl-1H-imidazol-4-yl)pyridin-3-yl)pyrazolo[1,5-a]pyrimidin-5-yl)-8-azabicyclo[3.2.1]octan-8-yl)(4H-1,2,4-triazol-3-yl)methanone | 536.25/536.0 | C | ND |
| --- | --- | --- | --- | --- | --- |
| 4.24 | 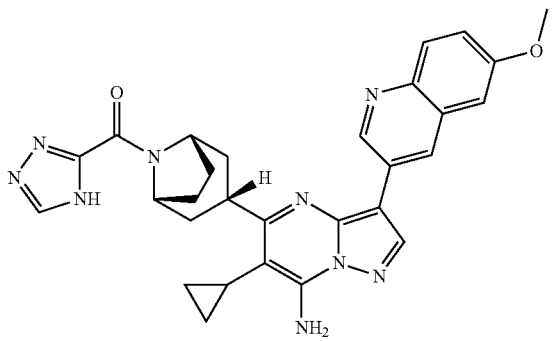 [SMILES: COc1ccc2ncc(-c3cnn4c(N)c(C5CC5)c([C@@H]5C[C@H]6CC[C@@H](C5)N6C(=O)c5nnc[nH]5)nc34)cc2c1] | ((1R,3s,5S)-3-(7-amino-6-cyclopropyl-3-(6-methoxyquinolin-3-yl)pyrazolo[1,5-a]pyrimidin-5-yl)-8-azabicyclo[3.2.1]octan-8-yl)(4H-1,2,4-triazol-3-yl)methanone | 536.2/536.2 | B | B |
| 4.25 | 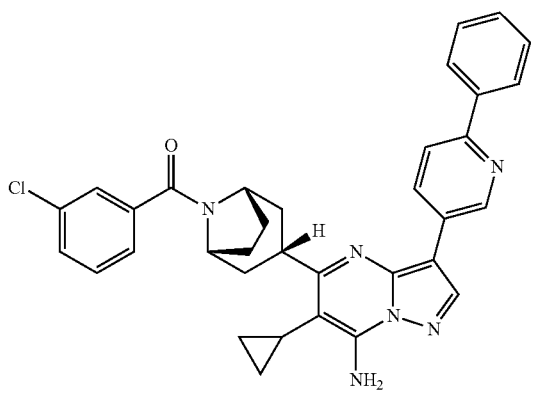 [SMILES: Nc1c(C2CC2)c([C@@H]2C[C@H]3CC[C@@H](C2)N3C(=O)c2cccc(Cl)c2)nc2c(-c3ccc(-c4ccccc4)nc3)cnn12] | ((1R,3s,5S)-3-(7-amino-6-cyclopropyl-3-(6-phenyl-pyridin-3-yl)pyrazolo[1,5-a]pyrimidin-5-yl)-8-azabicyclo[3.2.1]octan-8-yl)(3-chlorophenyl)methanone | 575.22/575.0 | ND | ND |
| 4.26 | 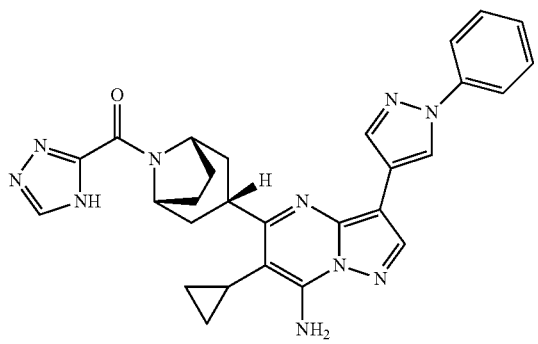 [SMILES: Nc1c(C2CC2)c([C@@H]2C[C@H]3CC[C@@H](C2)N3C(=O)c2nnc[nH]2)nc2c(-c3cnn(-c4ccccc4)c3)cnn12] | ((1R,3s,5S)-3-(7-amino-6-cyclopropyl-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone | 521.2/521.0 | A | B |

TABLE 4-1-continued

| | | | | | |
|---|---|---|---|---|---|
| 4.27 | | (5-amino-4H-1,2,4-triazol-3-yl)((1R,3a,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)methanone | 595.3/595.2 | A | A |
| 4.28 | | N-(5-((1R,3s,5S)-3-(7-amino-6-cyclopropyl-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide | 589.3/589.2 | B | B |
| 4.29 | | ((1R,3s,5S)-3-(7-amino-6-cyclopropyl-3-(6-phenyl-pyridin-3-yl)pyrazolo[1,5-a]pyrimidin-5-yl)-8-azabicyclo[3.2.1]octan-8-yl)(5-(2-methoxyethyl-amino)-4H-1,2,4-triazol-3-yl)methanone | 575.3/575.0 | N/A | N/A |
| 4.30 | | (3-amino-1H-pyrazol-4-yl)((1R,3s,5S)-3-(7-amino-6-cyclopropyl-3-(6-phenyl-pyridin-3-yl)pyrazolo[1,5-a]pyrimidin-5-yl)-8-azabicyclo[3.2.1]octan-8-yl)methanone | 546.3/546.0 | A | B |

TABLE 4-1-continued

| 4.31 | | ((1R,3s,5S)-3-(7-amino-6-cyclopropyl-3-(6-phenyl-pyridin-3-yl)pyrazolo[1,5-a]pyrimidin-5-yl)-8-azabicyclo[3.2.1]octan-8-yl)(5-(2-methoxyethylamino)-4H-1,2,4-triazol-3-yl)methanone | 605.3/605.3 | C | C |
|---|---|---|---|---|---|
| 4.32 | | (1R,3s,5S)-3-(7-amino-6-cyclopropyl-3-(6-phenyl-pyridin-3-yl)pyrazolo[1,5-a]pyrimidin-5-yl)-N-hydroxy-8-azabicyclo[3.2.1]octane-8-carboxamide | 496.2/496.5 | A | A |
| 4.33 | | (1R,3s,5S)-3-(7-amino-6-cyclopropyl-3-(6-phenyl pyridin-3-yl)pyrazolo[1,5-a]pyrimidin-5-yl)-N-hydroxy-8-azabicyclo[3.2.1]octane-8-carboxamide | 496.2/496.5 | A | A |

Example 5-1

Scheme 5-1

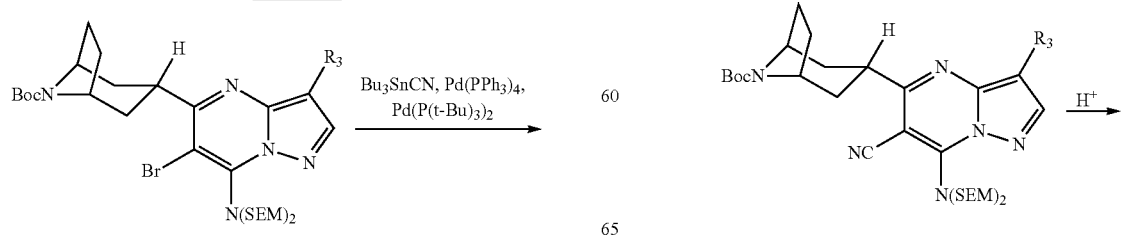

-continued

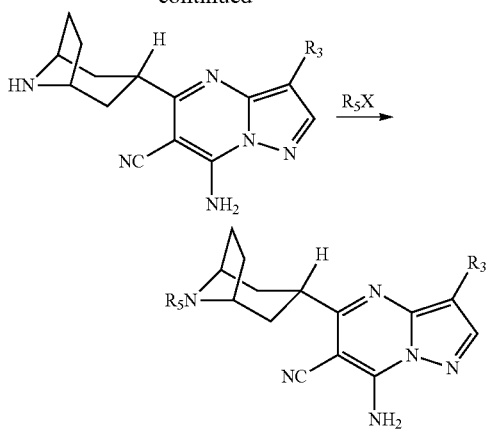

Preparation of 5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carbonitrile

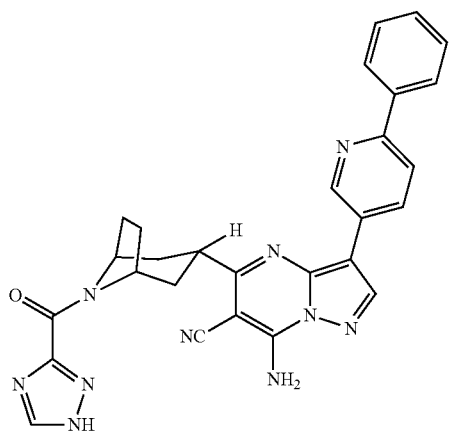 [SMILES: N#Cc1c(C2CC3CCC(C2)N3C(=O)c2nc[nH]n2)nc2c(-c3ccc(-c4ccccc4)nc3)cnn2c1N]

Step 1

Synthesis of (1R,3s,5S)-tert-butyl 3-(7-(bis((2-(trimethylsilyl)ethoxy)methyl)amino)-6-cyano-3-(6-phenylpyridin-3-yl)pyrazolo[1,5-a]pyrimidin-5-yl)-8-azabicyclo[3.2.1]octane-8-carboxylate

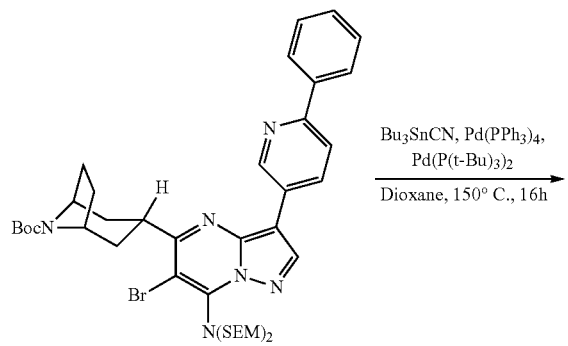

-continued

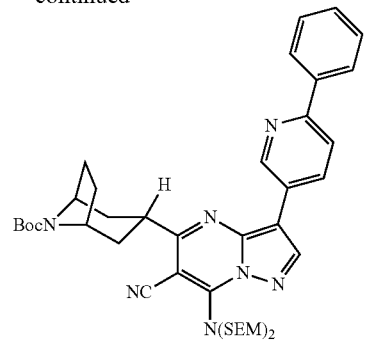

To a Schlenk tube were charged (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl-8-azabicyclo[3.2.1]octane-8-carboxylate (83 mg, 0.1 mmol), $Bu_3SnCN$ (47 mg, 0.15 mmol), $Pd(PPh_3)_4$ (23 mg, 0.02 mmol), Bis(tri-t-butylphosphine)palladium (10 mg, 0.02 mmol). The tube was evacuated and charged with Ar for three cycles. Dioxane (3 ml) was added; the tube was capped and heated at 150° C. with stirring for 16 h. After cooling, the mixture was diluted with EtOAc and washed with brine once. Organic layer separated, dried over $MgSO_4$ and concentrated. The residue was purified on silica gel. Elution with EtOAc/hexane (0-25%) gave the desired product (59 mg).

Step 2

Preparation of 7-amino-5-((1R,3s,5S)-8-azabicyclo[3.2.1]octan-3-yl)-3-(6-phenylpyridin-3-yl)pyrazolo[1,5-a]pyrimidine-6-carbonitrile

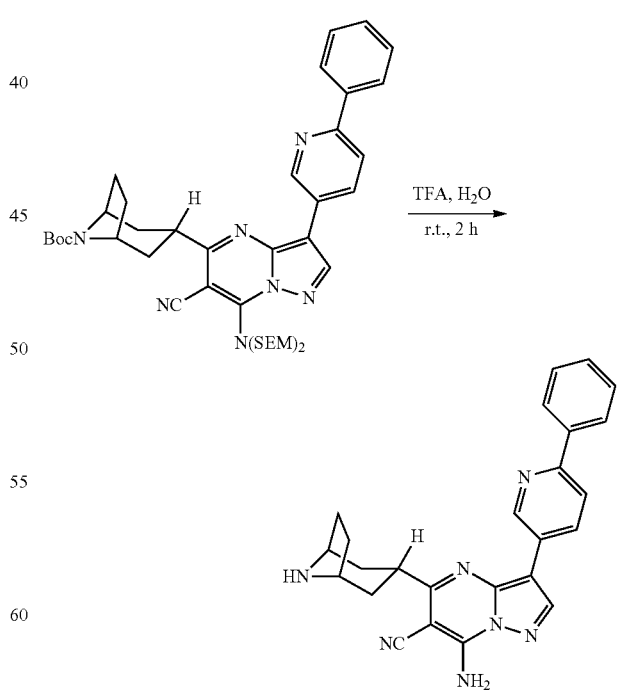

To a solution of (1R,3s,5S)-tert-butyl 3-(7-(bis((2-(trimethylsilyl)ethoxy)methyl)amino)-6-cyano-3-(6-phenylpyridin-3-yl)pyrazolo[1,5-a]pyrimidin-5-yl)- 8-azabicyclo

[3.2.1]octane-8-carboxylate (59 mg, 0.08 mmol) in TFA (2 ml) was added few drops of water and stirring continued for 2 h at room temperature. LC/MS showed no starting material remaining. TFA along with water was rotoevaporated, and the crude was dried under the high vacuum for 4 h, which was used without further purification for the next step.

Step 3

Synthesis of 5-((1R,3s,5S)-8-(1H-1,2,4-triazole-3-carbonyl)-8-azabicyclo[3.2.1]octan-3-yl-7-amino-3-(6-phenylpyridin-3-yl)pyrazolo[1,5-a]pyrimidine-6-carbonitrile

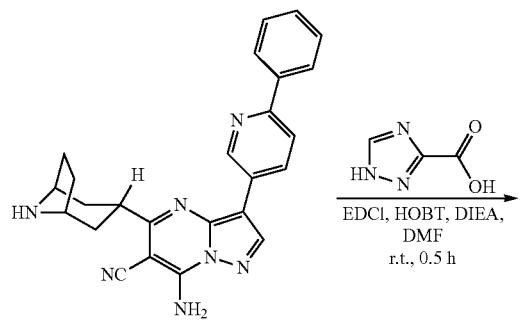

EDCl, HOBT, DIEA, DMF
r.t., 0.5 h

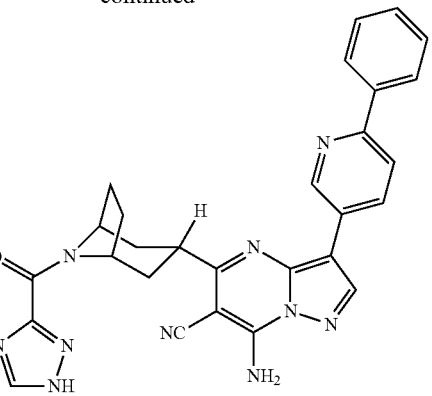

A mixture of 1H-1,2,4-triazole-3-carboxylic acid (29.4 mg, 0.26 mmol), EDCI (76.7 mg, 0.4 mmol), and 1-hydroxybenzotriazole (27 mg, 0.2 mmol) in DMF (2 mL) was stirred at room temperature for 10 min. Substrate 7-amino-5-((1R,3s,5S)-8-azabicyclo[3.2.1]octan-3-yl)-3-(6-phenylpyridin-3-yl)pyrazolo[1,5-a]pyrimidine-6-carbonitrile (0.2 mmol) was added followed by N,N-diisopropylethylamine (0.17 ml, 1 mmol). It was stirred further for 20 min at room temperature at which time LC/MS analysis confirmed full consumption of starting material. This crude compound was submitted to the analytical group for purification to afford the desired product.

Following the Scheme 5-1 and the procedures similar to preparation of (5-(8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carbonitrile, the following compounds (Table 5-1) can be prepared:

TABLE 5-1

| Compound ID | Structures | Compound Name | M + H (calculate)/ M + H (observed) | pAKT S473 IC50 | p4E-BP1 Thr37/46 IC50 |
|---|---|---|---|---|---|
| 5.1 | 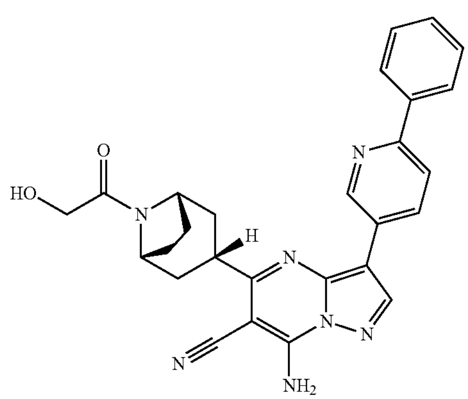 [SMILES: N#Cc1c([C@@H]2C[C@H]3CC[C@@H](C2)N3C(=O)CO)nc2c(-c3ccc(-c4ccccc4)nc3)cnn2c1N] | 7-amino-5-((1R,3s,5S)-8-(2-hydroxyacetyl)-8-azabicyclo[3.2.1]octan-3-yl)-3-(6-phenylpyridin-3-yl)pyrazolo[1,5-a]pyrimidine-6-carbonitrile | 480.2/479.9 | A | B |

TABLE 5-1-continued
| Compound ID | Structures | Compound Name | M + H (calculate)/ M + H (observed) | pAKT S473 IC50 | p4E-BP1 Thr37/46 IC50 |
|---|---|---|---|---|---|
| 5.2 | 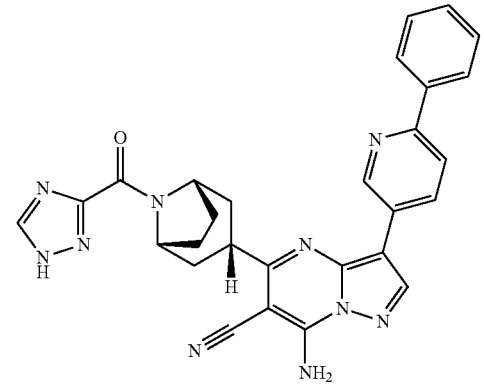 | 5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carbonitrile | 517.2/516.9 | A | A |
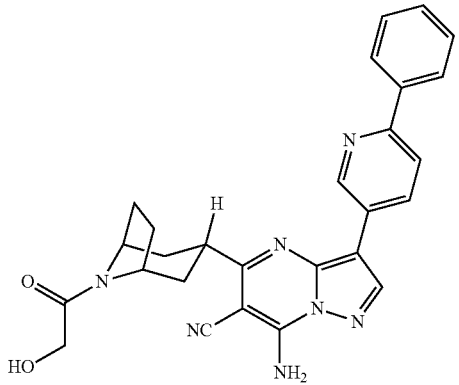 [SMILES: N#Cc1c(C2CC3CCC(C2)N3C(=O)CO)nc2c(-c3ccc(-c4ccccc4)nc3)cnn2c1N]
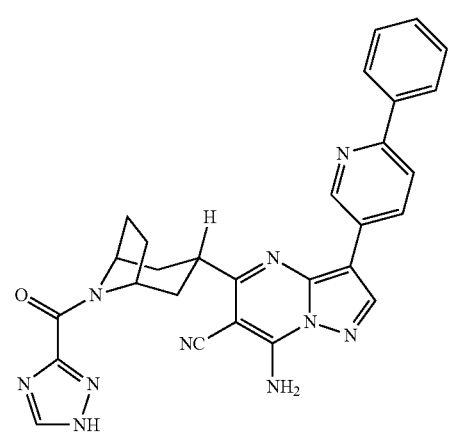 [SMILES: N#Cc1c(C2CC3CCC(C2)N3C(=O)c2nc[nH]n2)nc2c(-c3ccc(-c4ccccc4)nc3)cnn2c1N]

TABLE 5-1-continued
| Compound ID | Structures | Compound Name | M + H (calculate)/ M + H (observed) | pAKT S473 IC50 | p4E-BP1 Thr37/46 IC50 |
|---|---|---|---|---|---|
| 5.3 | 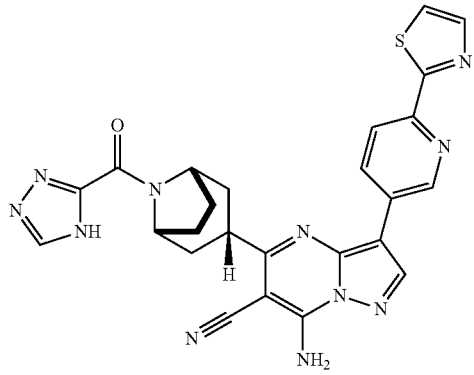 | 5-((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidine-6-carbonitrile | 524.2/523.8 | A | A |
Example 5-2
Preparation of (((1R,3s,5S)-3-(7-amino-6-methyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone
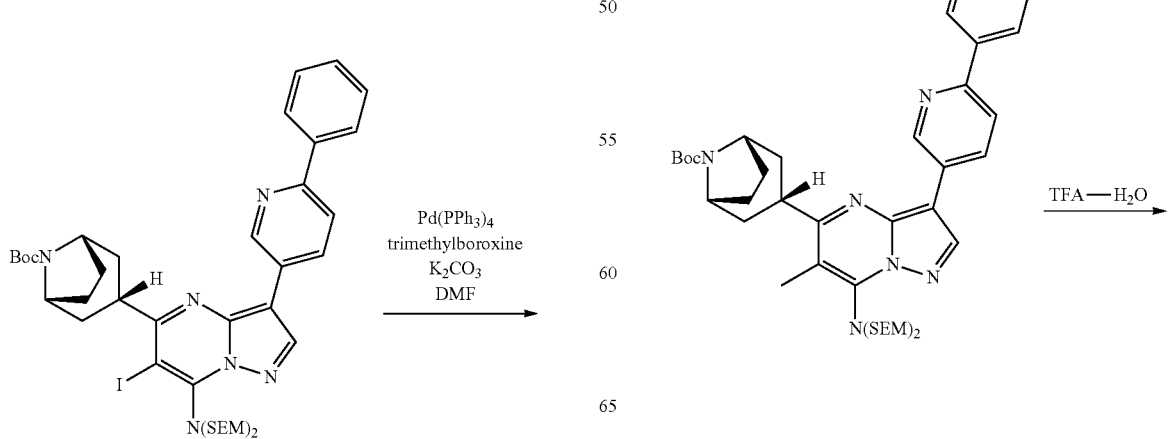
-continued

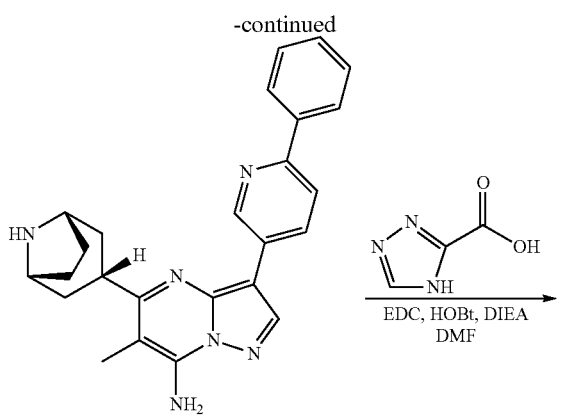

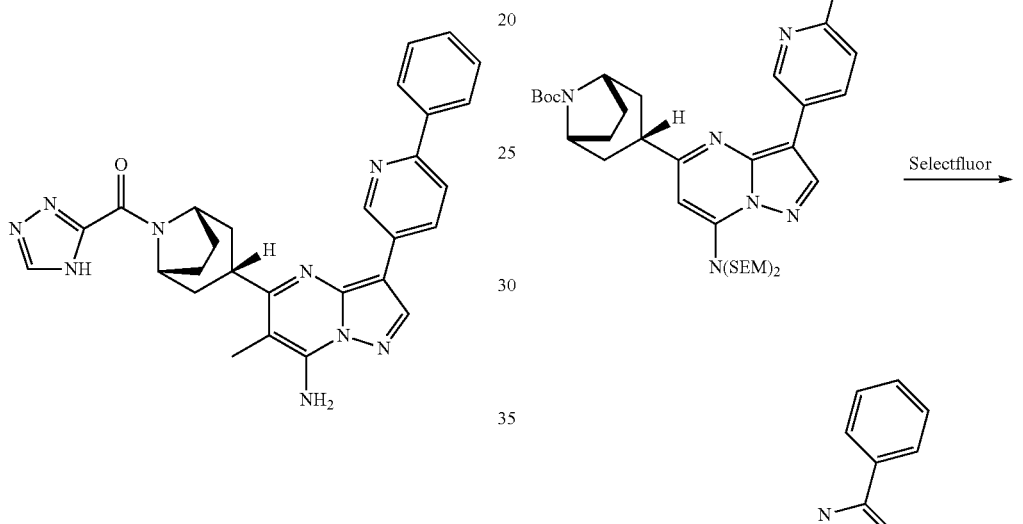

A degassed mixture of (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate (65 mg, 0.74 mmol), Pd(PPh$_3$)$_4$ (8.5 mg, 0.0074 mmol), trimethylboroxine (20.5 ul, 0.15 mmol), and K$_2$CO$_3$ (30.5 mg, 0.22 mmol) in DMF (3 ml) was heated at 120° C. for 30 min under microwave condition. The mixture was diluted with H$_2$O and then extracted with ethyl acetate (×2). The combined organic layers were washed with brine and dried with Na$_2$SO$_4$ and concentrated to provide crude (1R,3s,5S)-tert-butyl 3-(7-(bis((2-(trimethylsilyl)ethoxy)methyl)amino)-6-methyl-3-(6-phenylpyridin-3-yl)pyrazolo[1,5-a]pyrimidin-5-yl)-8-azabicyclo[3.2.1]octane-8-carboxylate. LCMS t$_R$=1.75 Min (5 min run, UV$_{254nm}$). Mass calculated for, M+ 770.4, observed LC/MS m/z 771.4 (M+H).

By applying the chemistry described in Example 5-1, the crude (1R,3s,5S)-tert-butyl 3-(7-(bis((2-(trimethylsilyl)ethoxy)methyl)amino)-6-methyl-3-(6-phenylpyridin-3-yl)pyrazolo[1,5-a]pyrimidin-5-yl)-8-azabicyclo[3.2.1]octane-8-carboxylate was first treated with 50% TFA in H$_2$O to remove the BOC and SEM protecting group and then followed by EDCI-mediated amide coupling reaction to afford ((1R,3s,5S)-3-(7-amino-6-methyl-3-(6-phenylpyridin-3-yl)pyrazolo[1,5-a]pyrimidin-5-yl-8- azabicyclo[3.2.1]octan-8-yl)(4H-1,2,4-triazol-3-yl)methanone: LCMS t$_R$=2.26 Min (10 min run, UV$_{254nm}$). Mass calculated for, M+ 505.2, observed LC/MS m/z 505.97 (M+H).

Example 5-3

Preparation of (((1R,3s,5S)-3-(7-amino-6-fluoro-3-(6-phenylpyridin-3-yl)pyrazolo[1,5-a]pyrimidin-5-yl)-8-azabicyclo[3.2.1]octan-8-yl)(4H-1,2,4-triazol-3-yl) methanone

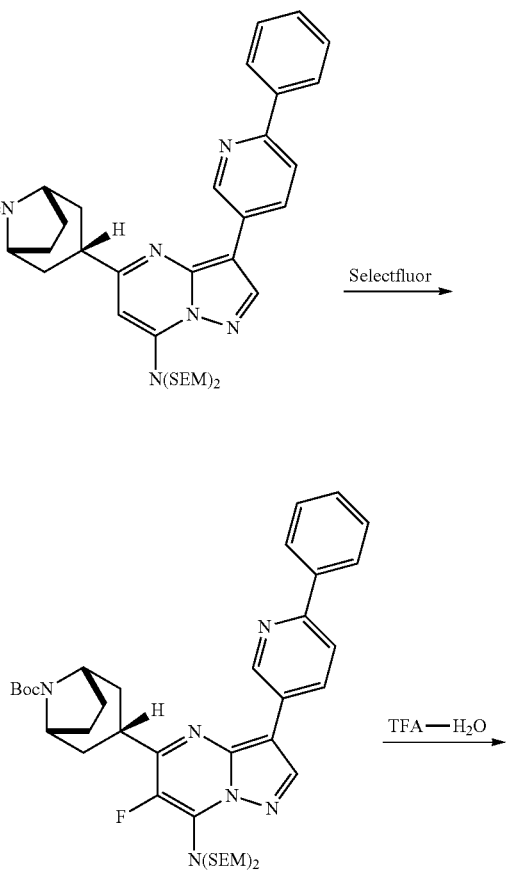

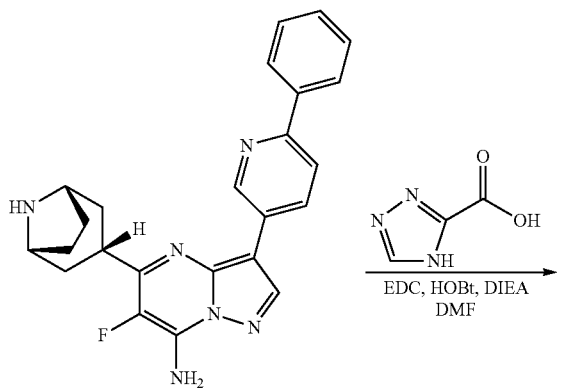

501
-continued

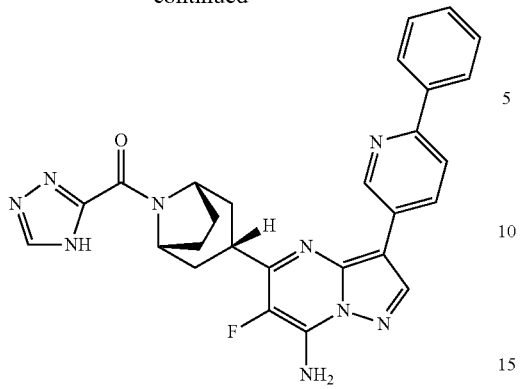

At 0° C., Selectfluoro® (25.3 mg, 0.071 mmol) was added to (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate (18.0 mg, 0.023 mmol) in CH₃CN (3 ml). The mixture was slowly warmed up to room temperature. Once LCMS indicated complete conversion, the mixture was diluted with sat. NaHCO₃ and then extracted with ethyl acetate (×2). The combined organic layers were washed with brine and dried with Na₂SO₄ and concentrated to provide crude (1R,3s,5S)-tert-butyl 3-(7-(bis((2-(trimethylsilyl)ethoxy)methyl)amino)-6-fluoro-3-(6-phenylpyridin-3-yl)pyrazolo[1,5-a]pyrimidin-5-yl)-8-azabicyclo[3.2.1]octane-8-carboxylate LCMS $t_R$=2.01 Min (5 min run, UV$_{254nm}$). Mass calculated for, M+ 774.4, observed LC/MS m/z 775.3 (M+H).

By applying the chemistry described in Example 5-1, the crude (1R,3s,5S)-tert-butyl 3-(7-(bis((2-(trimethylsilyl)ethoxy)methyl)amino)-6-fluoro-3-(6-phenylpyridin-3-yl)pyrazolo[1,5-a]pyrimidin-5-yl)-8-azabicyclo[3.2.1]octane-8-carboxylate was first treated with 50% TFA in H₂O to remove the BOC and SEM protecting group and then followed by EDCI-mediated amide coupling reaction to afford ((1R,3s,5S)-3-(7-amino-6-fluoro-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone: LCMS $t_R$=2.23 Min (10 min run, UV$_{254nm}$). Mass calculated for, M+ 509.2, observed LC/MS m/z 509.97 (M+H).

Example 5-4

Preparation of 5-((1R,3s,5S)-8-azabicyclo[3.2.1]octan-3-yl)-6-isopropyl-3-(6-phenylpyridin-3-yl)pyrazolo[1,5-a]pyrimidin-7-amine

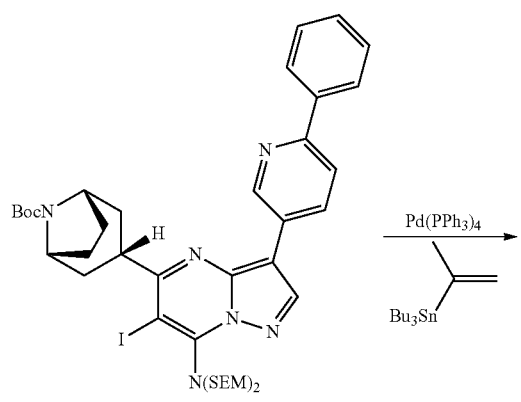

502
-continued

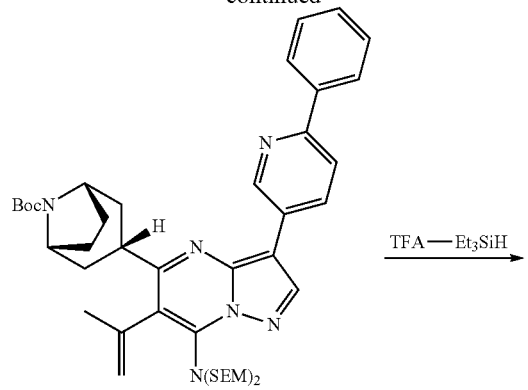

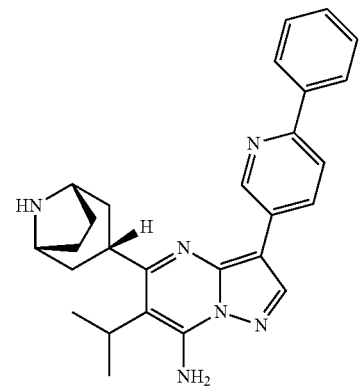

A degassed mixture of (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate (315 mg, 0.35 mmol), Pd(PPh₃)₄ (41.3 mg, 0.035 mmol), tributyl(prop-1-en-2-yl)stannane (354.7 mg, 1.07 mmol) in Dioxane (6 mL) was heated at 80° C. overnight. The reaction mixture was cooled to room temperature, filtered through 9:1 SiO₂:KF plug and concentrated in vacuo to afford crude (1R,3s,5S)-tert-butyl 3-(7-(bis((2-(trimethylsilyl)ethoxy)methyl)amino)-3-(6-phenylpyridin-3-yl)-6-(prop-1-en-2-yl)pyrazolo[1,5-a]pyrimidin-5-yl)-8-azabicyclo[3.2.1]octane-8-carboxylate, LCMS $t_R$=1.89 Min (5 min run, UV$_{254nm}$). Mass calculated for, M+ 796.4, observed LC/MS m/z 797.4 (M+H).

At 0° C., TFA (3 ml) and then Et₃SiH (1 ml) were added to the crude (1R,3s,5S)-tert-butyl 3-(7-(bis((2-(trimethylsilyl)ethoxy)methyl)amino)-3-(6-phenylpyridin-3-yl)-6-(prop-1-en-2-yl)pyrazolo[1,5-a]pyrimidin-5-yl)-8-azabicyclo[3.2.1]octane-8-carboxylate. The mixture was stirred at room temperature for 2 h and then concentrated. Purification by prep-LC provided 5-((1R,3s,5S)-8-azabicyclo[3.2.1]octan-3-yl)-6-isopropyl-3-(6-phenylpyridin-3-yl)pyrazolo[1,5-a]pyrimidin-7-amine: LCMS $t_R$=1.94 Min (10 min run, UV$_{254nm}$). Mass calculated for, M+ 438.2, observed LC/MS m/z 439.0 (M+H).

Example 5-5

Preparation of (((1R,3s,5S)-3-(7-amino-6-isopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

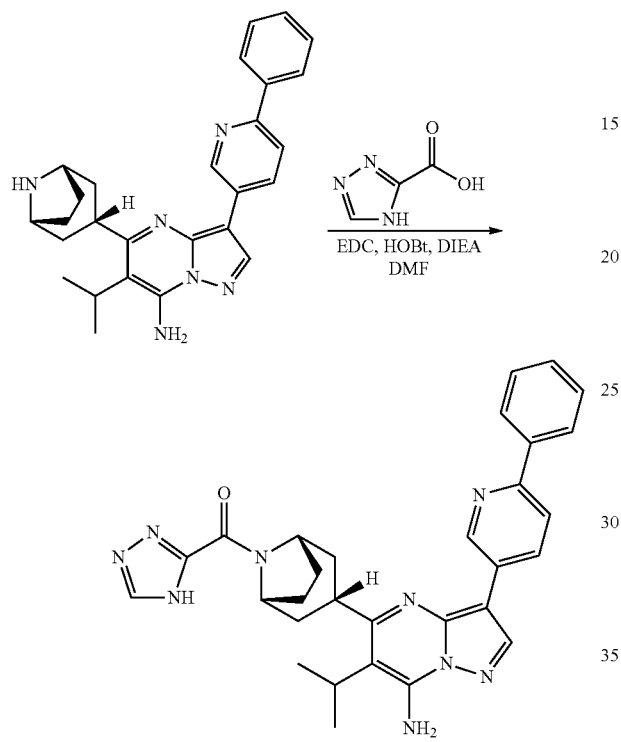

A mixture of 5-((1R,3s,5S)-8-azabicyclo[3.2.1]octan-3-yl)-6-isopropyl-3-(6-phenylpyridin-3-yl)pyrazolo[1,5-a]pyrimidin-7-amine (30 mg, 0.068 mmol), 4H-1,2,4-triazole-3-carboxylic acid (10.1 mg, 0.085 mmoL), EDC (26.0 mg, 0.14 mmoL), HOBt (18.4 mg, 0.14 mmoL) and DIEA (70.9 ul, 0.41 mmoL) in DMF (2 mL) was stirred at room temperature. Purification with prep-LC provided ((1R,3s,5S)-3-(7-amino-6-isopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone, LCMS $t_R$=2.25 Min (10 min run, $UV_{254nm}$). Mass calculated for, M+ 533.2, observed LC/MS m/z 533.99 (M+H).

Scheme 5-2

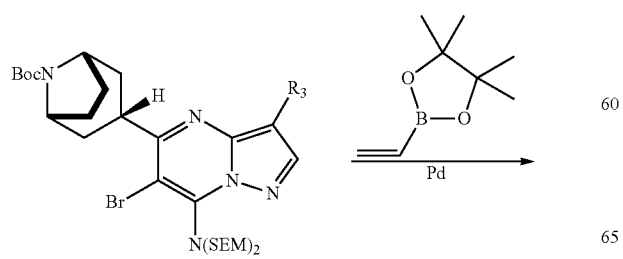

-continued

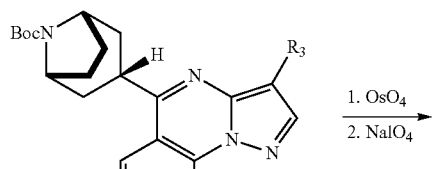

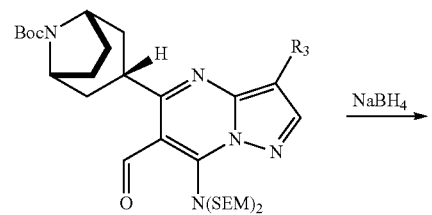

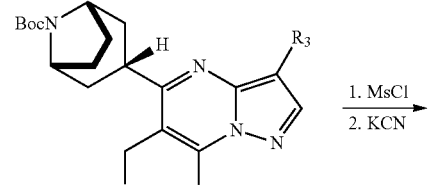

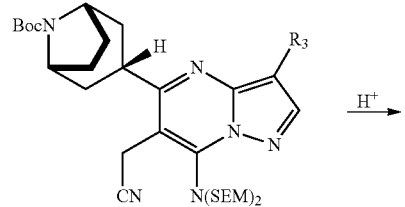

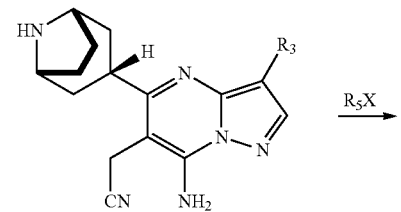

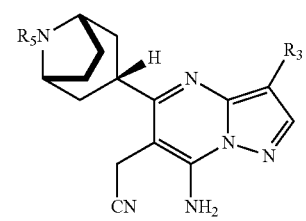

Preparation of 2-(5-((1R,3s,5S)-8-(4H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)acetonitrile

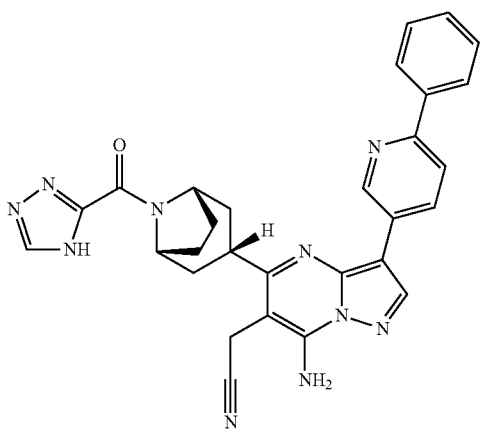 [SMILES: N#CCc1c([C@@H]2C[C@H]3CC[C@@H](C2)N3C(=O)c2nnc[nH]2)nc2c(-c3ccc(-c4ccccc4)nc3)cnn2c1N]

Step A—Synthesis of (1R,3s,5S)-tert-butyl 3-(7-(bis((2-(trimethylsilyl)ethoxy)methyl)amino)-3-(6-phenylpyridin-3-yl)-6-vinylpyrazolo[1,5-a]pyrimidin-5-yl)-8-azabicyclo[3.2.1]octane-8-carboxylate

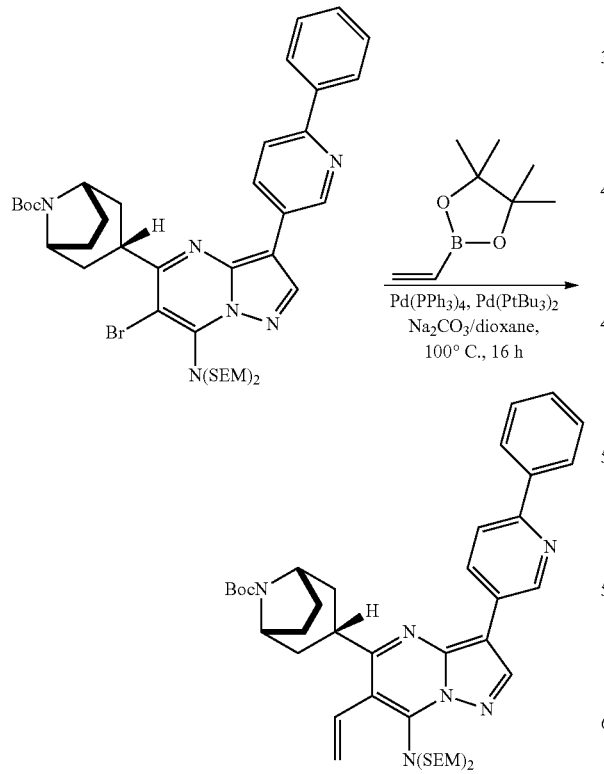

To a pressure tube were charged (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (834 mg, 1 mmol), vinylboronic acid pinacol ester (170 mmol, mmol), Pd(PPh$_3$)$_4$ (230 mg, 0.2 mmol), Pd(PtBu$_3$)$_2$ (100 mg, 0.2 mmol), 2 M Na$_2$CO$_3$ (5 mL) and dioxane (15 mL). The mixture was degassed with Ar and stirred at 100° C. for 16 hours. On cooling, EtOAc (50 mL) was added, and resulting mixture was washed with water (1×20 mL), brine, and dried over MgSO$_4$. After filtration and concentration the residue was purified on silica gel. Gradient elution with EtOAc/hexanes (0 to 30%) gave the desired product (630 mg).

Step B—Synthesis of (1R,3s,5S)-tert-butyl 3-(7-(bis((2-(trimethylsilyl)ethoxy)methyl)amino)-6-formyl-3-(6-phenylpyridin-3-yl)pyrazolo[1,5-a]pyrimidin-5-yl)-8-azabicyclo[3.2.1]octane-8-carboxylate

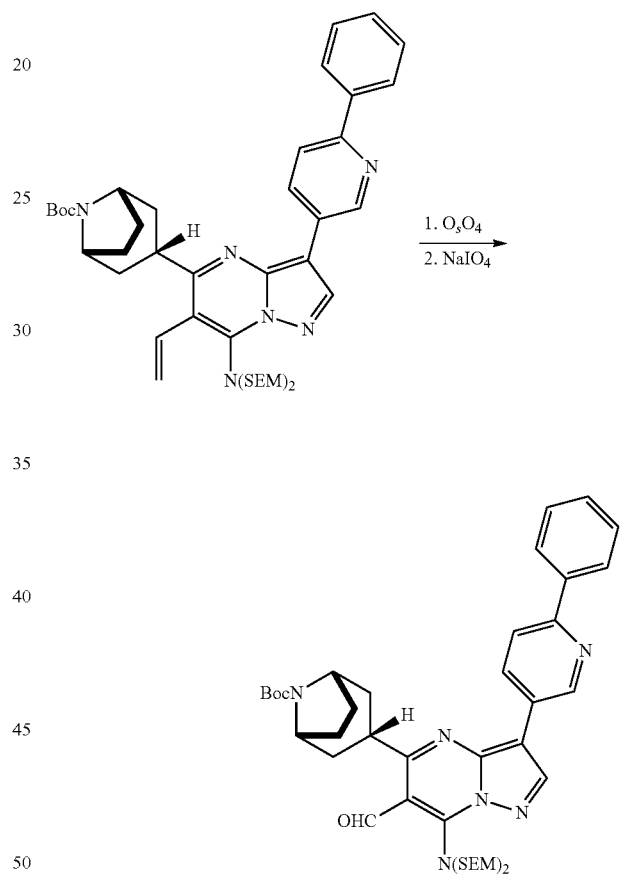

To a solution of (1R,3s,5S)-tert-butyl 3-(7-(bis((2-(trimethylsilyl)ethoxy)methyl)amino)-3-(6-phenylpyridin-3-yl)-6-vinylpyrazolo[1,5-a]pyrimidin-5-yl)-8-azabicyclo[3.2.1]octane-8-carboxylate (128 mg, 0.16 mmol) in dioxane (3 mL) and water (250 mL) was added OsO$_4$ (2.5% in t-BuOH, 154 uL, 0.012 mmol). After stirring for 20 minutes, NaIO$_4$ (103 mg, 0.48 mmol) was added followed by addition of more water (0.25 mL) and dioxane (1 mL). After stirring for 16 hours, the reaction was quenched with saturated Na$_2$S$_2$O$_3$ (5 mL), and stirred for 20 minutes. The reaction mixture was extracted with dichloromethane (3×20 mL), washed with brine and dried over MgSO$_4$. After filtration and concentration the residue was purified on silica gel. Gradient elution with EtOAc/hexanes (0 to 30%) gave the desired product (107 mg).

Step C—Synthesis of (1R,3s,5S)-tert-butyl 3-(7-(bis((2-(trimethylsilyl)ethoxy)methyl)amino)-6-(hydroxymethyl)-3-(6-phenylpyridin-3-yl)pyrazolo[1,5-a]pyrimidin-5-yl)-8-azabicyclo[3.2.1]octane-8-carboxylate

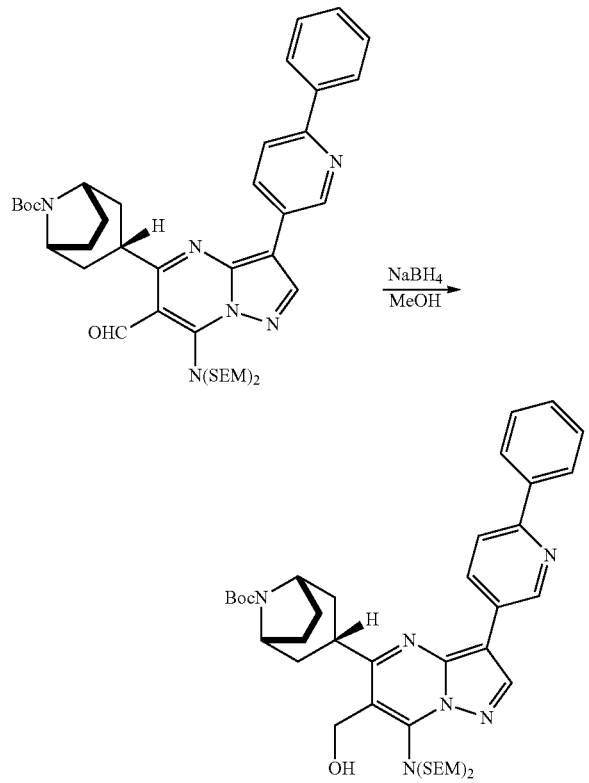

To a solution of (1R,3s,5S)-tert-butyl 3-(7-(bis((2-(trimethylsilyl)ethoxy)methyl)amino)-6-formyl-3-(6-phenylpyridin-3-yl)pyrazolo[1,5-a]pyrimidin-5-yl)-8-azabicyclo[3.2.1]octane-8-carboxylate (477 mg, 0.61 mmol) in MeOH (4 mL) was added NaBH₄ (23 mg, 0.61 mmol) and the resulting mixture was stirred for 10 minutes. After concentration the residue was purified on silica gel. Gradient elution with EtOAc/hexanes (0 to 40%) gave the title product (420 mg).

Step D—Synthesis of (1R,3s,5S)-tert-butyl 3-(7-(bis((2-(trimethylsilyl)ethoxy)methyl)amino)-6-(cyanomethyl)-3-(6-phenylpyridin-3-yl)pyrazolo[1,5-a]pyrimidin-5-yl)-8-azabicyclo[3.2.1]octane-8-carboxylate

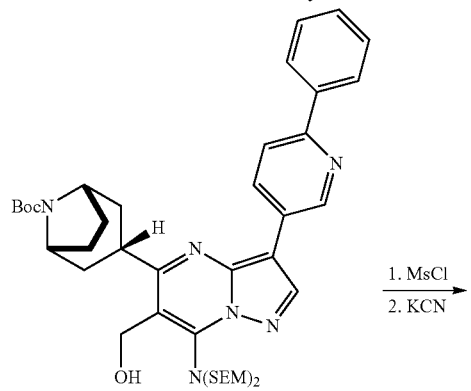

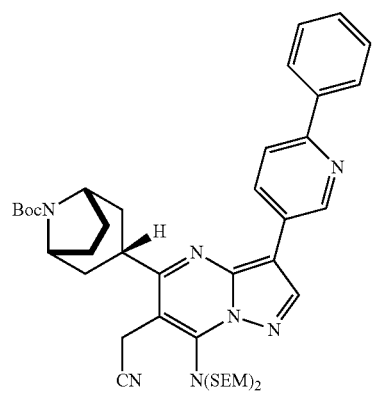

To a solution of (1R,3s,5S)-tert-butyl 3-(7-(bis((2-(trimethylsilyl)ethoxy)methyl)amino)-6-(cyanomethyl)-3-(6-phenylpyridin-3-yl)pyrazolo[1,5-a]pyrimidin-5-yl)-8-azabicyclo[3.2.1]octane-8-carboxylate (140 mg, 0.18 mmol) in triethylamine (74 uL, 0.56 mmol) and dichloromethane (1 mL) was added mesyl chloride (14 uL, 0.18 mmol) and the resulting mixture was stirred for 10 minutes, diluted with dichloromethane (10 mL), washed with water (2×5 mL), brine and dried (MgSO₄). After concentration, the residue was taken into a solution of DMSO (1 mL) and acetonitrile (1 mL), and 18-crown-6 (6 mg) was added followed by addition of KCN (11 mg, 0.17 mml). The reaction mixture was allowed to stir for 2 days, diluted with dichloromethane (10 mL), washed with water (3×5 mL), brine and dried (MgSO₄). After concentration the residue was purified on silica gel. Gradient elution with EtOAc/hexanes (0 to 40%) gave the title product (50 mg).

Step E—Synthesis of 2-(5-((1R,3s,5S)-8-(4H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)acetonitrile

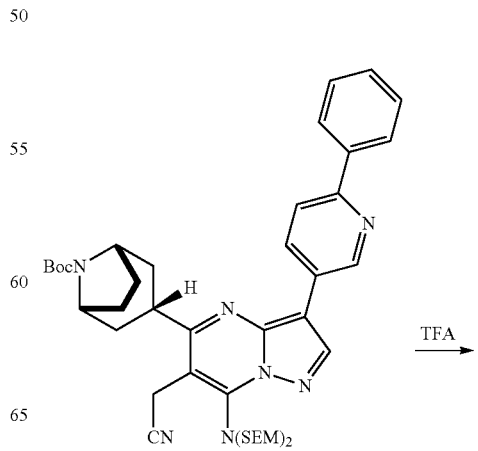

509
-continued

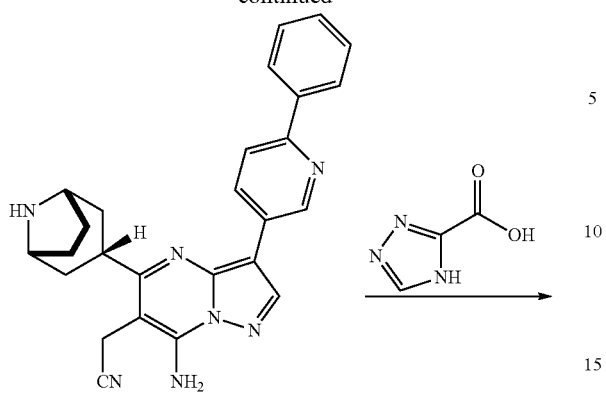

510
-continued

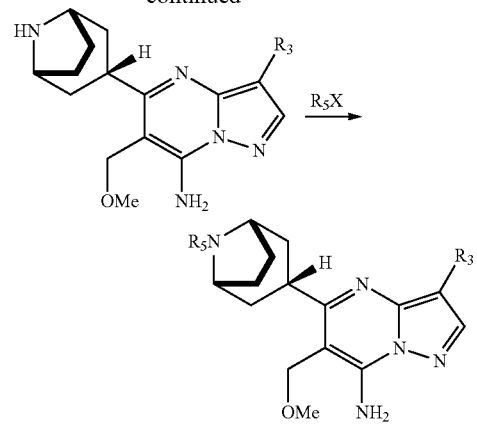

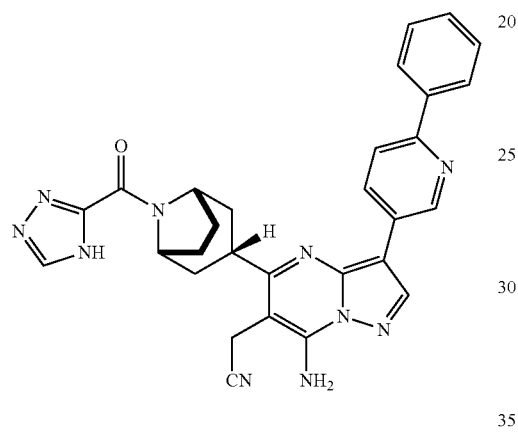

Compound (1R,3s,5S)-tert-butyl 3-(7-(bis((2-(trimethylsilyl)ethoxy)methyl)amino)-6-(cyanomethyl)-3-(6-phenylpyridin-3-yl)pyrazolo[1,5-a]pyrimidin-5-yl)-8-azabicyclo[3.2.1]octane-8-carboxylate (50 mg) was treated with TFA/water (9:1, 1 mL) for 5 minutes, concentrated and lyophilized to provide the corresponding amine which was converted to the title product following standard amide coupling reaction.

Preparation of ((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

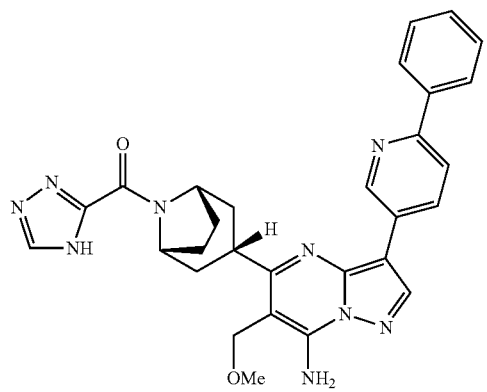 [SMILES: COCc1c([C@@H]2C[C@H]3CC[C@@H](C2)N3C(=O)c2nnc[nH]2)nc2c(-c3ccc(-c4ccccc4)nc3)cnn2c1N]

Step A—Synthesis of (1R,3s,5S)-tert-butyl 3-(7-(bis((2-(trimethylsilyl)ethoxy)methyl)amino)-6-(methoxymethyl)-3-(6-phenylpyridin-3-yl)pyrazolo[1,5-a]pyrimidin-5-yl)-8-azabicyclo[3.2.1]octane-8-carboxylate Scheme 5-3

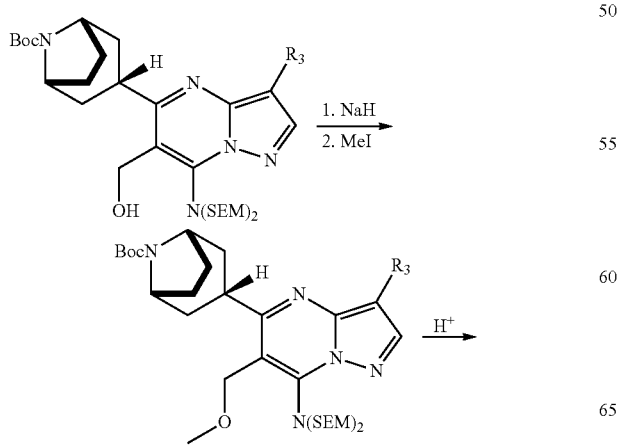

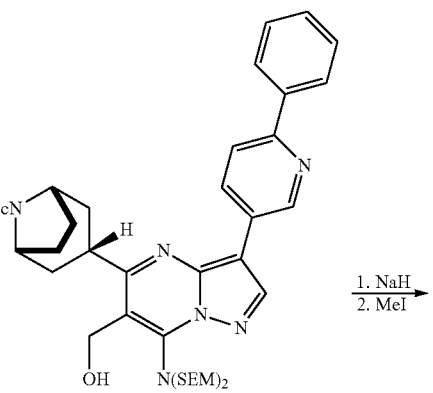

511
-continued

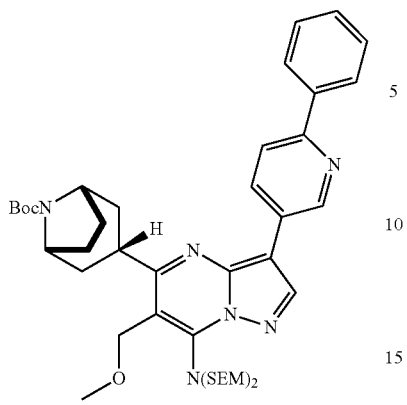

To a 0° C. solution of (1R,3s,5S)-tert-butyl 3-(7-(bis((2-(trimethylsilyl)ethoxy)methyl)amino)-6-(hydroxymethyl)-3-(6-phenylpyridin-3-yl)pyrazolo[1,5-a]pyrimidin-5-yl)-8-azabicyclo[3.2.1]octane-8-carboxylate (0.83 g, 1.1 mmol) in DMF (8.5 mL) was added NaH (0.05 g, 1.3 mmol, 60% in mineral oil). It was then warmed up to room temperature. After 30 minutes at room temperature, iodomethane (0.09 mL, 1.4 mmol) was added and stirring was continued for 25 minutes, at which time LC/MS analysis confirmed full consumption of starting material. Reaction mixture was diluted with EtOAc (125 mL), washed with water (3×25 mL), brine (1×25 mL), and dried over MgSO₄. Gradient column chromatography on silica gel eluting with 0 to 50% EtOAc/hexanes gave the desired (1R,3s,5S)-tert-butyl 3-(7-(bis((2-(trimethylsilyl)ethoxy)methyl)amino)-6-(methoxymethyl)-3-(6-phenylpyridin-3-yl)pyrazolo[1,5-a]pyrimidin-5-yl)-8-azabicyclo[3.2.1]octane-8-carboxylate (0.7 g).

Step B—Synthesis of 5-((1R,3s,5S)-8-azabicyclo[3.2.1]octan-3-yl)-6-(methoxymethyl)-3-(6-phenylpyridin-3-yl)pyrazolo[1,5-a]pyrimidin-7-amine

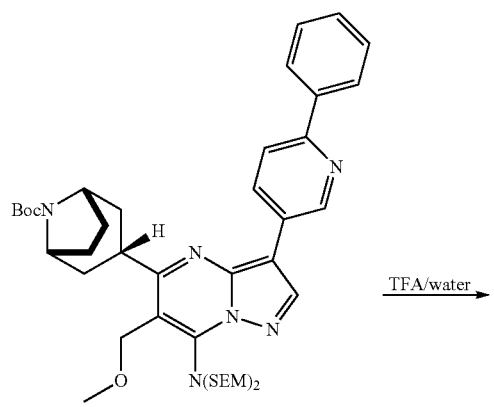

512
-continued

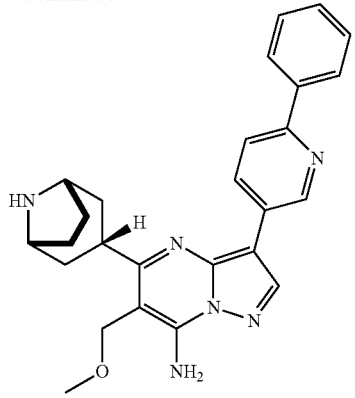

Intermediate (1R,3s,5S)-tert-butyl 3-(7-(bis((2-(trimethylsilyl)ethoxy)methyl)amino)-6-(methoxymethyl)-3-(6-phenylpyridin-3-yl)pyrazolo[1,5-a]pyrimidin-5-yl)-8-azabicyclo[3.2.1]octane-8-carboxylate (74 mg) was treated with TFA/water (9:1, 20 uL) and mixture was stirred for 2 minutes, and diluted with water (1 mL) and acetonitriled (0.2 mL). The crude reaction mixture was directly purified by HPLC to afford the title product.

Step C—Synthesis of (((1R,3s,5S)-3-(7-amino-6-(methoxymethyl)-3-(6-phenylpyridin-3-yl)pyrazolo[1,5-a]pyrimidin-5-yl-8-azabicyclo[3.2.1]octan-8-yl)(4H-1,2,4-triazol-3-yl)methanone

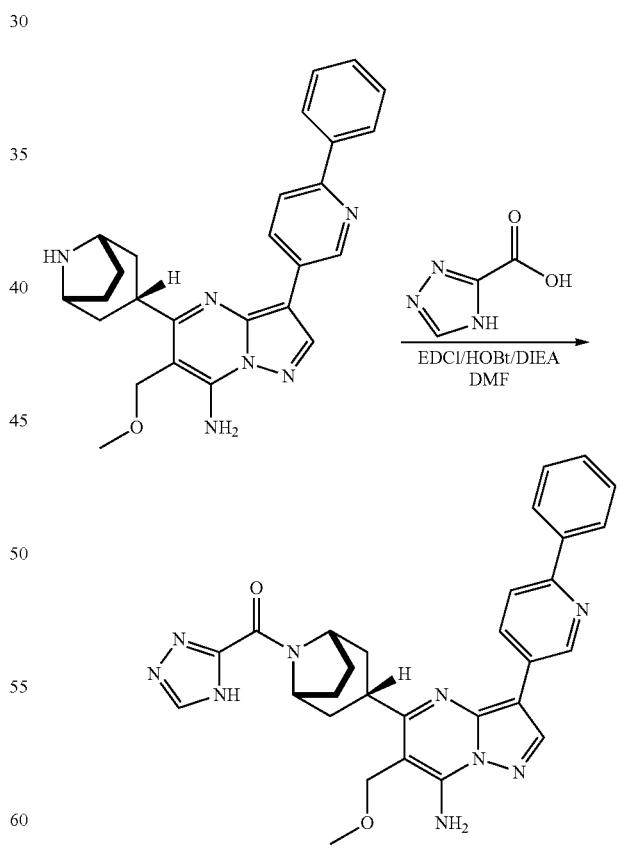

The title compound was prepared by following standard amide coupling procedure described before.

Following—and using procedures similar to the preparation of example 5-3, the following compounds listed in Table 5-2 were prepared:

TABLE 5-2

| | | | | | |
|---|---|---|---|---|---|
| 5.4 | 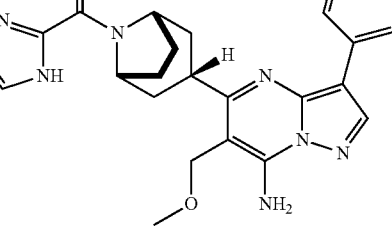 | ((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 536.2/536.0 | A | A |
| 5.5 | 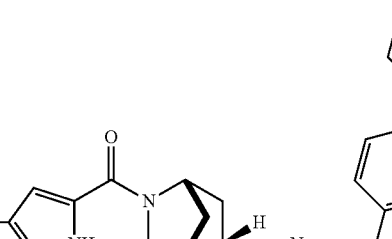 | (3-amino-1H-pyrazol-5-yl)((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)methanone | 550.3/550.0 | B | C |
| 5.6 | 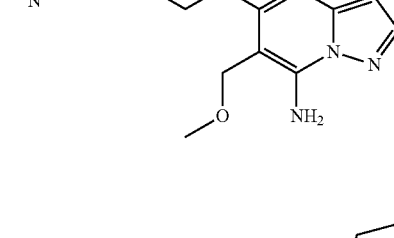 | ((1R,3s,5S)-3-(7-amino-6-(methoxymethyl)-3-(6-(4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone | 566.3/566.0 | A | A |
| 5.7 | 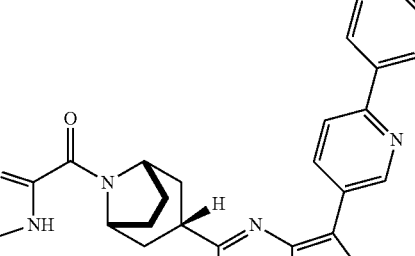 | ((1R,3s,5S)-3-(7-amino-6-(hydroxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 522.2/522.0 | A | A |

Example 5-4

Scheme 5-4

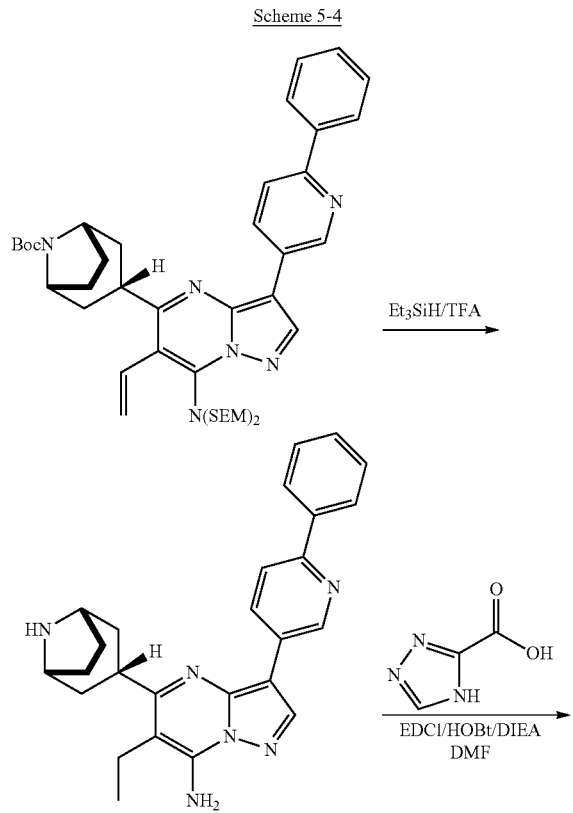

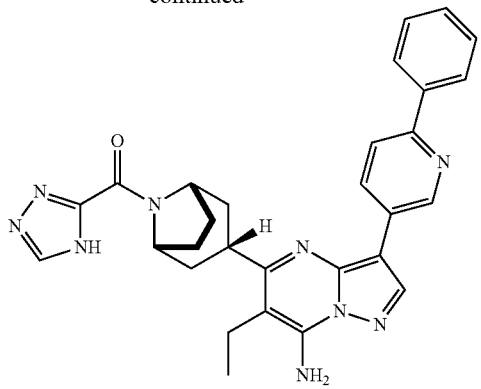

Preparation of (((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone Intermediate (1R,3s,5S)-tert-butyl 3-(7-(bis((2-(trimethylsilyl)ethoxy)methyl)amino)-3-(6-phenylpyridin-3-yl)-6-vinylpyrazolo[1,5-a]pyrimidin-5-yl)-8-azabicyclo[3.2.1]octane-8-carboxylate (313 mg, 0.4 mmol) was treated with TFA (1 mL) and Et$_3$SiH (256 µL, 0.6 mmol) and the reaction was stirred for 1 hr. After concentration, the residue was purified by HPLC to provide intermediate 5-((1R,3s,5S)-8-azabicyclo[3.2.1]octan-3-yl)-6-ethyl-3-(6-phenylpyridin-3-yl)pyrazolo[1,5-a]pyrimidin-7-amine (10 mg) which was further converted to the title product by standard amide coupling reaction.

Following Scheme 5-4 the following compounds (Table 5-3) were made:

TABLE 5-3

| Compound ID | Structures | Compound Name | M + H (calculate)/ M + H (observed) | pAKT S473 IC50 | p4E-BP1 Thr37/ 46 IC50 |
|---|---|---|---|---|---|
| 5.8 | 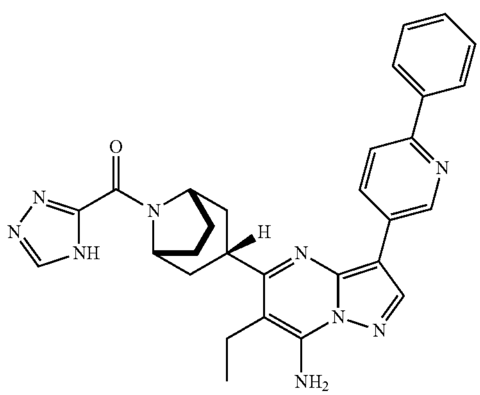 | ((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 520.3/520.0 | A | A |

TABLE 5-3-continued

| Compound ID | Structures | Compound Name | M + H (calculate)/ M + H (observed) | pAKT S473 IC50 | p4E-BP1 Thr37/ 46 IC50 |
|---|---|---|---|---|---|
| 5.9 | 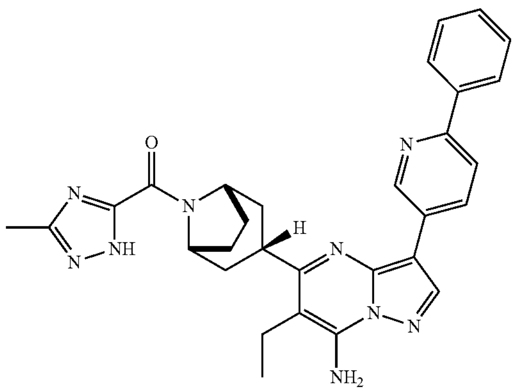 [SMILES: CCc1c([C@@H]2C[C@H]3CC[C@@H](C2)N3C(=O)c2nc(C)n[nH]2)nc2c(-c3ccc(-c4ccccc4)nc3)cnn2c1N] | ((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone | 534.2/534 | A | A |

Example 6-1

Preparation of 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone

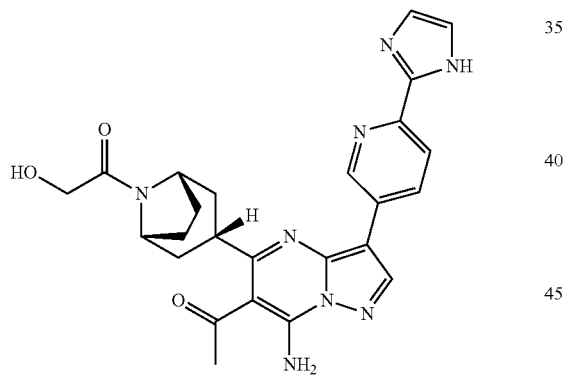

Step A—Synthesis of (1R,3s,5S)-tert-butyl 3-(7-(bis((2-(trimethylsilyl)ethoxy)methyl)amino)-3-(6-formylpyridin-3-yl)pyrazolo[1,5-a]pyrimidin-5-yl)-8-azabicyclo[3.2.1]octane-8-carboxylate

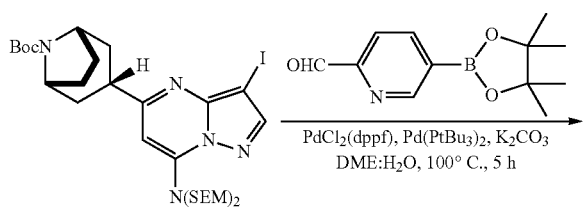

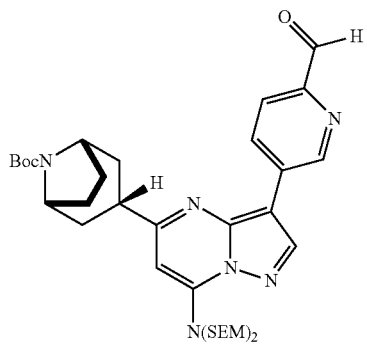

To a pressure tube were charged (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (9.4 g, 12.9 mmol), 2-formylpyridinyl-5-boronic acid pinacolo ester (6 g, 25.75 mmol), $PdCl_2$(dppf) (2.1 g, 2.57 mmol), Pd(PtBu$_3$)$_2$ (80 mg, 0.16 mmol) and $K_2CO_3$ (5.3 g, 38.4 mmol), DME (80 mL) and water (40 mL). The mixture was degassed with Ar and stirred at 100° C. for 5 hours. On cooling, EtOAc (100 mL) was added, and resulting mixture was washed with water (1×60 mL), brine (1×125 mL), and dried over $MgSO_4$. After filtration and concentration the residue was purified on silica gel. Gradient elution with EtOAc/hexanes (0 to 40%) gave the desired product (2.84 g).

Step B—Synthesis of (1R,3s,5S)-tert-butyl 3-(7-(bis ((2-(trimethylsilyl)ethoxy)methyl)amino)-6-bromo-3-(6-formylpyridin-3-yl)pyrazolo[1,5-a]pyrimidin-5-yl)-8-azabicyclo[3.2.1]octane-8-carboxylate

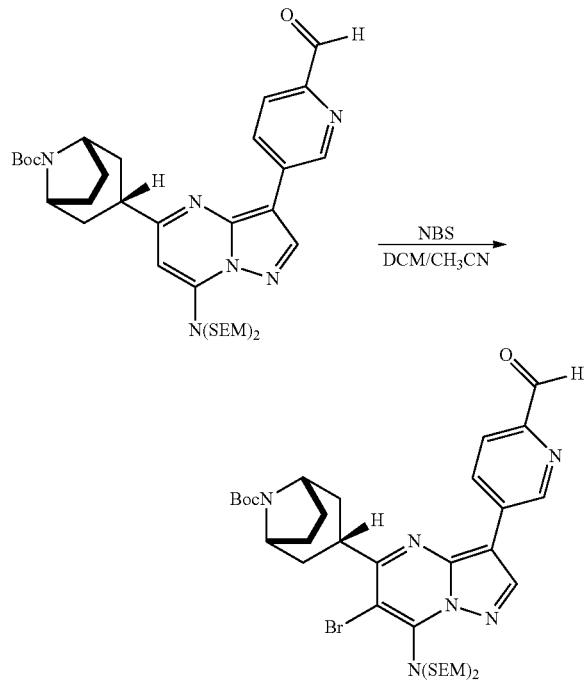

To a suspension of (1R,3s,5S)-tert-butyl 3-(7-(bis((2-(trimethylsilyl)ethoxy)methyl)amino)-3-(6-formylpyridin-3-yl)pyrazolo[1,5-a]pyrimidin-5-yl)-8-azabicyclo[3.2.1]octane-8-carboxylate (708 mg, 1 mmol) in DCM and acetonitrile (1:1, 4 mL) was added NBS (178 mg, 1 mmol) and the mixture was stirred for 5 minutes. After concentration, the residue was purified on silica gel. Gradient elution with EtOAc/hexanes (0 to 40%) gave the desired product (670 mg).

Step C—Synthesis of (1R,3s,5S)-tert-butyl 3-(7-(bis ((2-(trimethylsilyl)ethoxy)methyl)amino)-6-(1-ethoxyvinyl)-3-(6-formylpyridin-3-yl)pyrazolo[1,5-a]pyrimidin-5-yl)-8-azabicyclo[3.2.1]octane-8-carboxylate

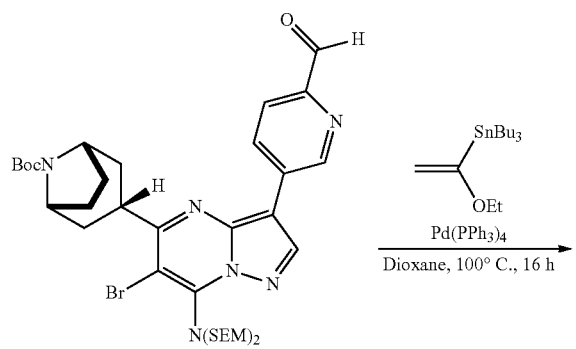

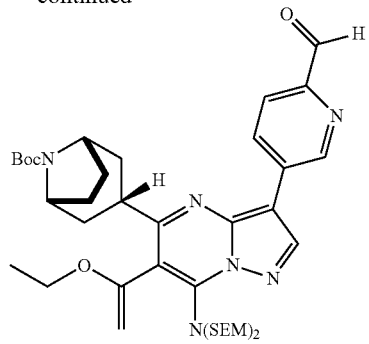

A mixture of compound (1R,3s,5S)-tert-butyl 3-(7-(bis((2-(trimethylsilyl)ethoxy)methyl)amino)-6-bromo-3-(6-formylpyridin-3-yl)pyrazolo[1,5-a]pyrimidin-5-yl)-8-azabicyclo[3.2.1]octane-8-carboxylate (394 mg, 0.5 mmol), tributyl(1-ethoxyvinyl)tin (338 uL, 1 mmol), tetrakis(triphenylphosphine)palladium (29 mg, 0.025 mmol) in dioxane (6 mL) was degassed with argon for 1 minute. It was then heated at 100° C. in a sealed tube for 16 h. On cooling, the reaction mixture was diluted with EtOAc (30 mL), washed with 0.5 M KF solution (1×10 mL), brine (1×25 mL), and dried over $MgSO_4$. The solvent was removed in vacuo and the residue was purified by column chromatography on silica gel. Elution with EtOAc/Hexanes (0-25%) gave the title product 454 mg as yellow oil.

Step D—Synthesis of (1R,3s,5S)-tert-butyl 3-(3-(6-(1H-imidazol-2-yl)pyridin-3-yl)-7-(bis((2-(trimethylsilyl)ethoxy)methyl)amino)-6-(1-ethoxyvinyl)pyrazolo[1,5-a]pyrimidin-5-yl)-8-azabicyclo[3.2.1]octane-8-carboxylate

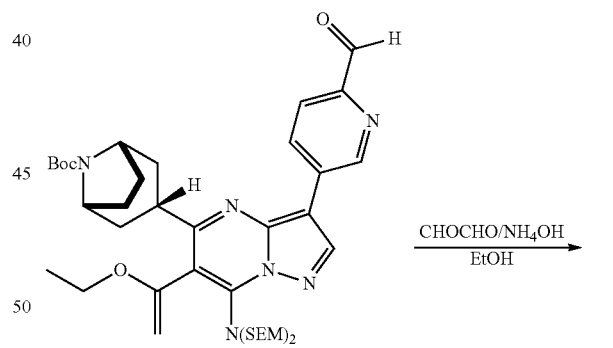

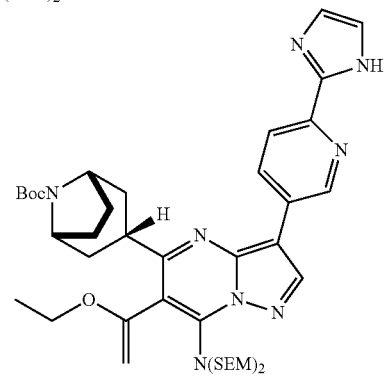

To a pressure tube were charged (1R,3s,5S)-tert-butyl 3-(7-(bis((2-(trimethylsilyl)ethoxy)methyl)amino)-6-(1-ethoxyvinyl)-3-(6-formylpyridin-3-yl)pyrazolo[1,5-a]pyrimidin-5-yl)-8-azabicyclo[3.2.1]octane-8-carboxylate (450 mg) and EtOH (2 mL) and the solution was cooled to 0-5° C. by an ice bath. To the solution was added NH₄OH (28%, 0.55 mL), followed by glyoxal (40%, 85 uL). The tube was sealed and the reaction mixture was heated at 90° C. with stirring for 1 hour. After concentration under reduced pressure, the residue was re-taken into EtOAc (20 mL), washed with water (5 mL), brine (10 mL) and dried over MgSO₄. The solvent was removed in vacuo and the residue was purified by column chromatography on silica gel. Elution with EtOAc gave the title product (340 mg).

Step E—Synthesis of 1-(3-(6-(1H-imidazol-2-yl)pyridin-3-yl)-7-amino-5-((1R,3s,5S)-8-azabicyclo[3.2.1]octan-3-yl)pyrazolo[1,5-a]pyrimidin-6-yl)ethanone

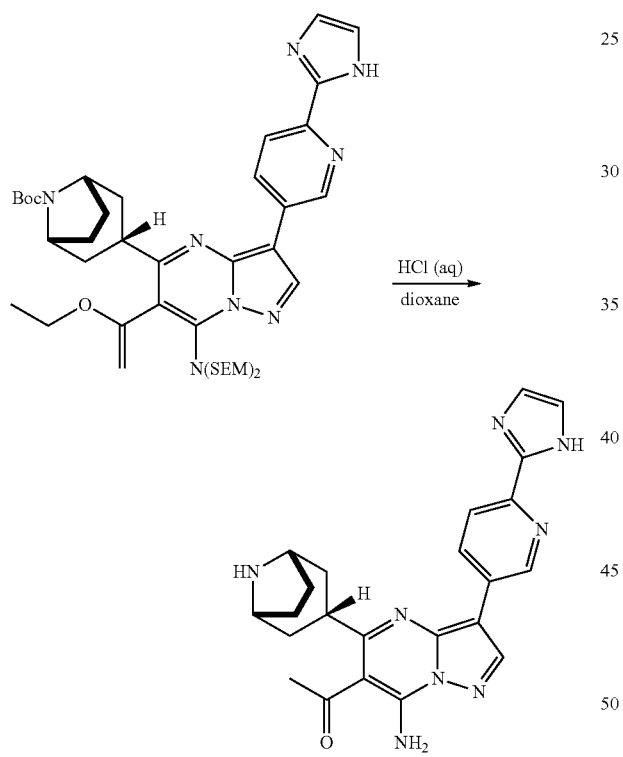

To a solution of (1R,3s,5S)-tert-butyl 3-(3-(6-(1H-imidazol-2-yl)pyridin-3-yl)-7-(bis((2-(trimethylsilyl)ethoxy)methyl)amino)-6-(1-ethoxyvinyl)pyrazolo[1,5-a]pyrimidin-5-yl)-8-azabicyclo[3.2.1]octane-8-carboxylate in dioxane (2 mL) was added 4 M HCl in water (2 mL) at 0° C. After stirring for 5 minutes at 0° C., 4 M HCl in dioxane (3 mL) was added. The reaction mixture was warmed to it for 20 min and heated at 50° C. for 40 minutes. The LC-MS indicated that reaction was almost complete. Additional 4 M HCl in dioxane (2 mL) was added and the mixture was heated to boiling for 2 minutes to complete the reaction. After cooling, the dioxane supernatant was taken out by a glass pipette and aqueous layer was lyophilized to furnish the title product as HCl salt.

Step F—Synthesis of 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone

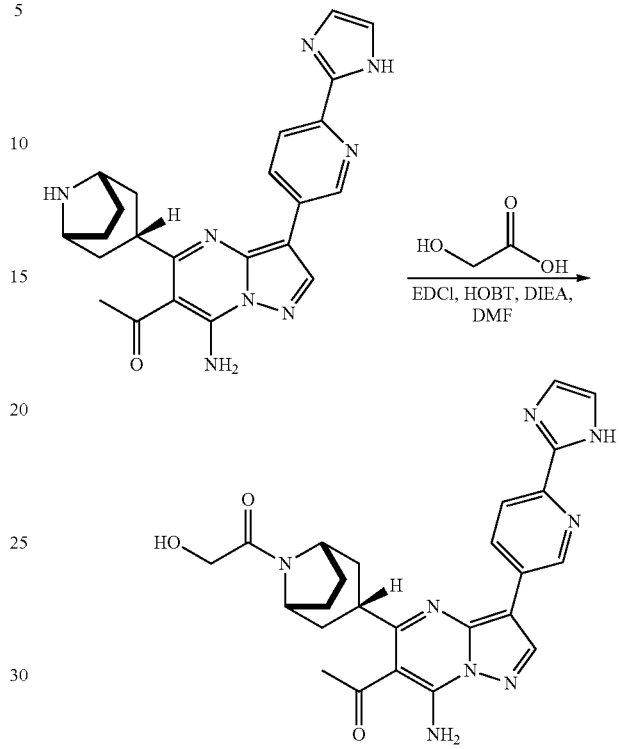

A mixture of glycolic acid (25 mg, 0.3 mmol), EDCI (72 mg, 0.38 mmol), and 1-hydroxybenzotriazole (34 mg, 0.25 mmol) in DMF (1 ml) was warmed up to a homogeneous solution. This mixture was added into a solution of 1-(3-(6-(1H-imidazol-2-yl)pyridin-3-yl)-7-amino-5-((1R,3s,5S)-8-azabicyclo[3.2.1]octan-3-yl)pyrazolo[1,5-a]pyrimidin-6-yl)ethanone (0.25 mmol) and N,N diisopropylethylamine (130 µL, 0.75 mmol) in DMF (2 mL). It was stirred further for 10 min and the crude compound was directly purified by HPLC to afford the desired product.

Example 6-2

Preparation of 1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxyethanone

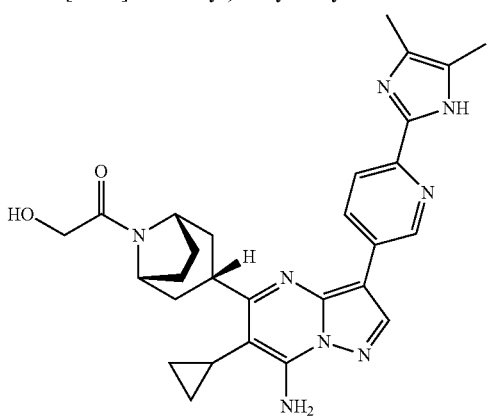

523

Step A. Synthesis of (1R,3s,5S)-tert-butyl 3-(7-(bis ((2-(trimethylsilyl)ethoxy)methyl)amino)-6-cyclopropyl-3-(6-formylpyridin-3-yl)pyrazolo[1,5-a]pyrimidin-5-yl-8-aza bicyclo[3.2.1]octane-8-carboxylate

524

Step B. (1R,3s,5S)-tert-butyl 3-(7-(bis((2-(trimethylsilyl)ethoxy)methyl)amino)-6-cyclo propyl-3-(6-(4,5-dimethyl-1H-imidazol-2-yl)pyridin-3-yl)pyrazolo[1,5-a]pyrimidin-5-yl)-8-azabicyclo[3.2.1]octane-8-carboxylate

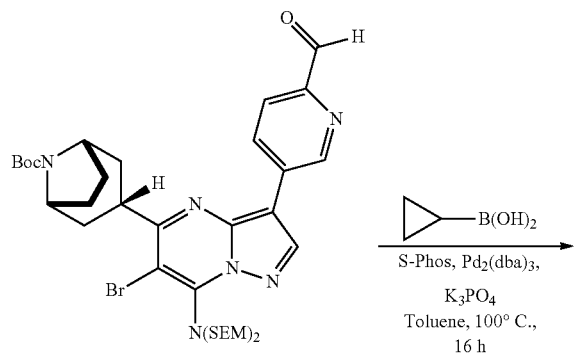

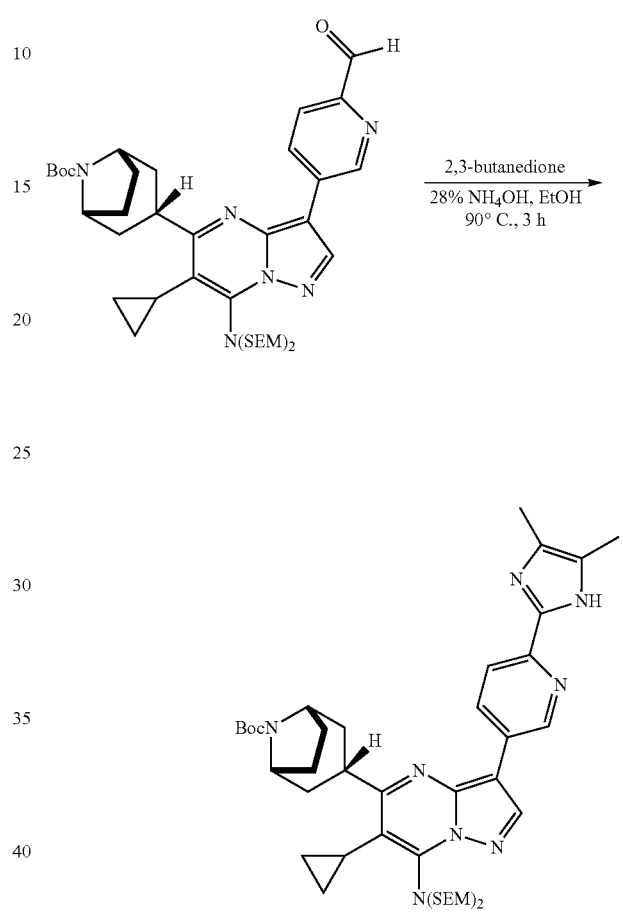

A mixture of ((1R,3s,5S)-tert-butyl 3-(7-(bis((2-(trimethylsilyl)ethoxy)methyl)amino)-6-bromo-3-(6-formylpyridin-3-yl)pyrazolo[1,5-a]pyrimidin-5-yl)-8-azabicyclo[3.2.1]octane-8-carboxylate (0.47 g, 0.6 mmol), cyclopropylboronic acid (0.31 g, 3.6 mmol), 2-dicyclohexylphosphino-2',6'-dimethoxybiphenyl (0.1 g, 0.24 mmol), Pd$_2$(dba)$_3$ (0.11 g, 0.12 mmol) and K$_3$PO$_4$ (0.38 g, 1.8 mmol) in toluene (5 mL) was degassed with argon and heated at 100° C. for 16 hours, at which time LC/MS analysis confirmed full consumption of starting material. On cooling, EtOAc (100 mL) was added and washed with water (2×20 mL), brine (1×20 mL), and dried over MgSO4. Solvent was removed in vacuo and the residue was purified by column chromatography on silica gel. Elution with EtOAc/hexanes (0-45%) gave desired product, (1R,3s,5S)-tert-butyl 3-(7-(bis((2-(trimethylsilyl)ethoxy)methyl)amino)-6-cyclopropyl-3-(6-formylpyridin-3-yl)pyrazolo[1,5-a]pyrimidin-5-yl)-8-azabicyclo[3.2.1]octane-8-carboxylate (0.14 g).

A mixture of (1R,3s,5S)-tert-butyl 3-(7-(bis((2-(trimethylsilyl)ethoxy)methyl)amino)-6-cyclopropyl-3-(6-formylpyridin-3-yl)pyrazolo[1,5-a]pyrimidin-5-yl)-8-azabicyclo[3.2.1]octane-8-carboxylate (0.14 g, 0.19 mmol), 2,3-butanedione (25 µL, 0.28 mmol) and NH$_4$OH (28% by weight, 0.2 mL, 1.7 mmol) in ethenol (2 mL) was heated at 90° C. for 3 hours, at which time LC/MS analysis confirmed full consumption of starting material. On cooling, DCM (50 mL) was added and washed with water (1×10 mL), brine (1×10 mL), and dried over MgSO$_4$. Solvent was removed in vacuo and the residue was purified by column chromatography on silica gel. Elution with EtOAc/Hexanes (25%-100%) gave desired product, (1R,3s,5S)-tert-butyl 3-(7-(bis((2-(trimethylsilyl)ethoxy)methyl)amino)-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octane-8-carboxylate (0.11 g).

525

Step C. Synthesis of 5-((1R,3s,5S)-8-azabicyclo [3.2.1]octan-3-yl)-6-cyclopropyl-3-(6-(4,5-dimethyl-1H-imidazol-2-yl)pyridin-3-yl)pyrazolo[1,5-a]pyrimidin-7-amine

526

Step D. Synthesis of 1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxy ethanone

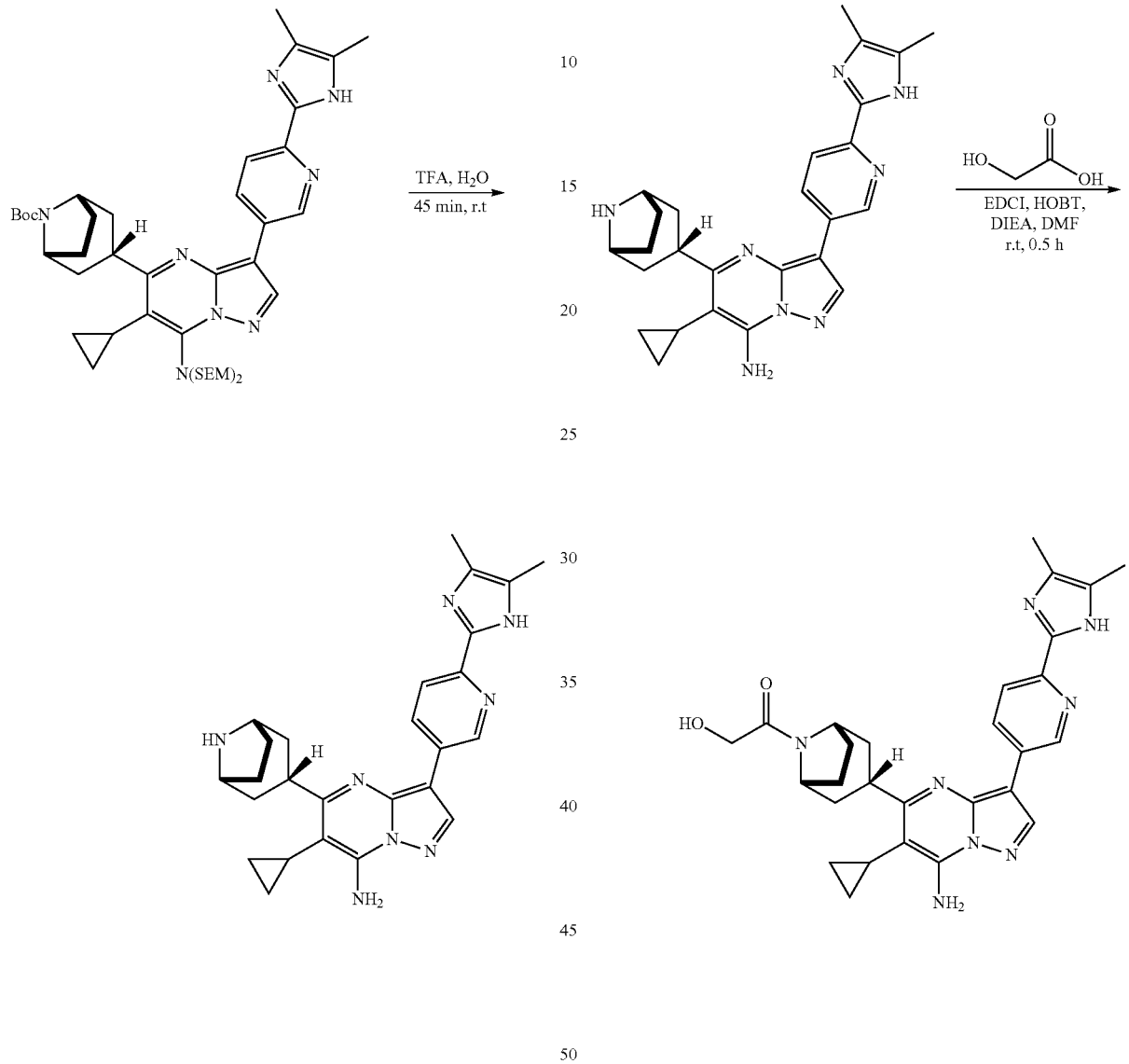

(1R,3s,5S)-tert-butyl 3-(7-(bis((2-(trimethylsilyl)ethoxy)methyl)amino)-6-cyclo propyl-3-(6-(4,5-dimethyl-1H-imidazol-2-yl)pyridin-3-yl)pyrazolo[1,5-a]pyrimidin-5-yl)-8-aza bicyclo[3.2.1]octane-8-carboxylate (0.11 g, 0.14 mmol) was dissolved in a mixture of TFA (2 mL) and water (0.2 mL) at room temperature. Stirring continued for 45 min at room temperature. LC/MS analysis confirmed full consumption of starting material to product. TFA along with water was rotoevaporated, and the crude product 5-((1R,3s,5S)-8-azabicyclo[3.2.1]octan-3-yl)-6-cyclopropyl-3-(6-(4,5-dimethyl-1H-imidazol-2-yl)pyridin-3-yl)pyrazolo[1,5-a]pyrimidin-7-amine was dried under the high vacuum for 24 hour, which was used without further purification for the next step.

A mixture of glycolic acid (3.8 mg, 0.05 mmol), EDCI (19.2 mg, 0.1 mmol), and 1-hydroxybenzotriazole (6.8 mg, 0.05 mmol) in DMF (1 mL) was stirred at room temperature for 10 minutes. Compound 5-((1R,3s,5S)-8-azabicyclo[3.2.1]octan-3-yl)-6-cyclopropyl-3-(6-(4,5-dimethyl-1H-imidazol-2-yl)pyridin-3-yl)pyrazolo[1,5-a]pyrimidin-7-amine (0.05 mmol) was added followed by N,N-diisopropylethylamine (0.04 mL, 0.25 mmol). It was stirred further for 20 minutes at room temperature at which time LC/MS analysis confirmed full consumption of starting material. Pure compound 1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxyethanone was isolated by preparative HPLC.

Example 6-3

Preparation of 1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone Step 1: Preparation of (1R,3s,5S)-tert-butyl 3-(7-(bis((2-(trimethylsilyl)ethoxy)methyl)amino)-6-cyclopropyl-3-(6-(4-fluoro-1-((2-(trimethylsilyl)ethoxy)methyl)-1H-imidazol-2-yl)pyridin-3-yl)pyrazolo[1,5-a]pyrimidin-5-yl)-8-azabicyclo[3.2.1]octane-8-carboxylate

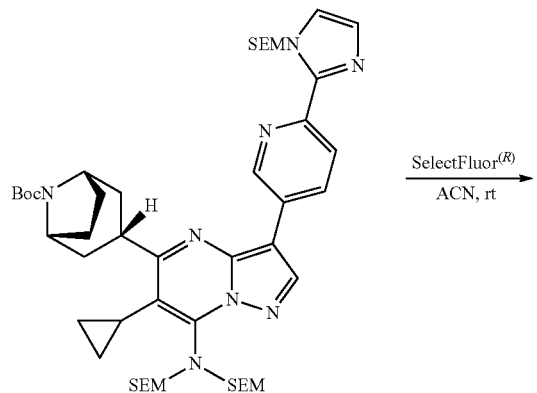

Step 2: Preparation of 5-((1R,3s,5S)-8-azabicyclo[3.2.1]octan-3-yl)-6-cyclopropyl-3-(6-(4-fluoro-1H-imidazol-2-yl)pyridin-3-yl)pyrazolo[1,5-a]pyrimidin-7-amine

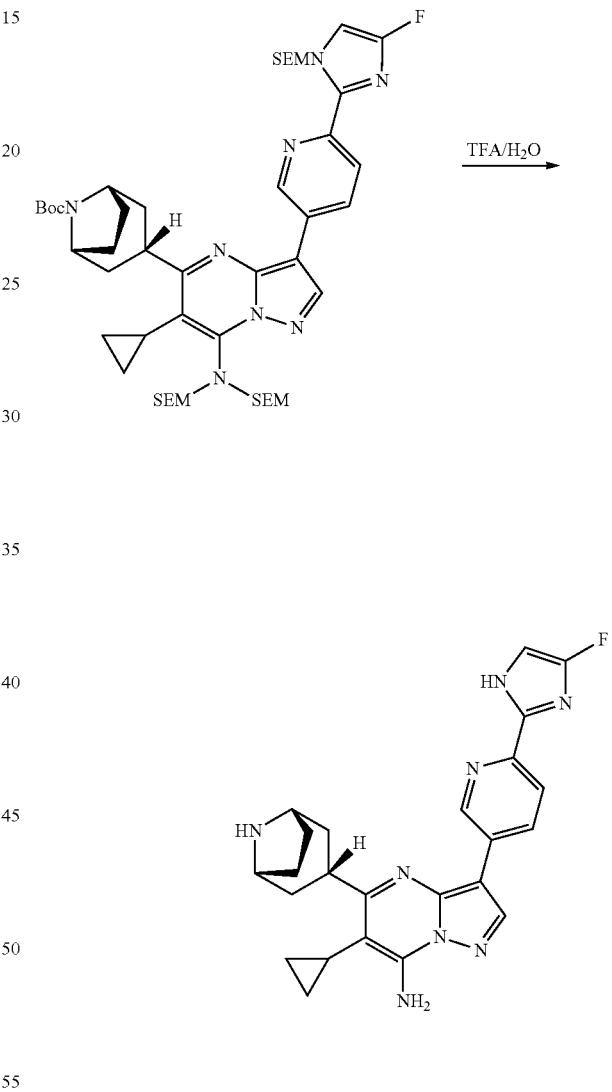

The compound (1R,3s,5S)-tert-butyl 3-(7-(bis((2-(trimethylsilyl)ethoxy)methyl)amino)-6-cyclopropyl-3-(6-(1-((2-(trimethylsilyl)ethoxy)methyl)-1H-imidazol-2-yl)pyridin-3-yl)pyrazolo[1,5-a]pyrimidin-5-yl)-8-azabicyclo[3.2.1]octane-8-carboxylate (Previously made, 210 mg, 0.229 mmol) was mixed with SelectFluor® in dry ACN (3 mL) and stirred overnight. The mixture was diluted with EtOAc and washed with NaHCO₃ (aq.) and water, brine. After concentration, the crude was used in the next step directly without further purification.

The compound 5-((1R,3s,5S)-8-azabicyclo[3.2.1]octan-3-yl)-6-cyclopropyl-3-(6-(4-fluoro-1H-imidazol-2-yl)pyridin-3-yl)pyrazolo[1,5-a]pyrimidin-7-amine was prepared with the same condition described previously.

Step 3: Preparation of 1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone

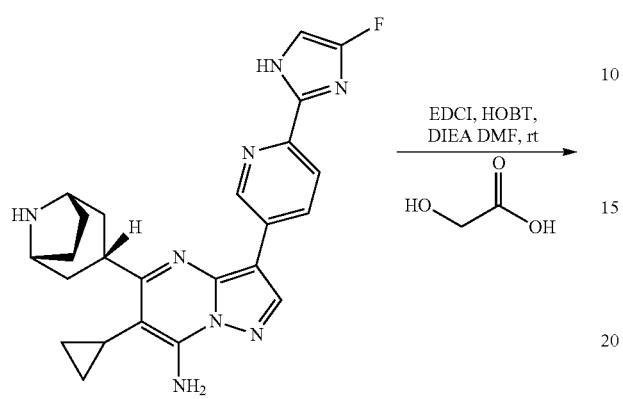

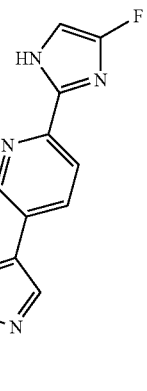

The compound 1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone was made with the same condition described previously.

Following the examples, the following compounds (Table 6-1) were prepared

TABLE 6-1

| Compound ID | Structures | Compound Name | M + H (calculated)/ M + H (observed) | pAKT S473 IC50 | p4E-BP1 Thr37/ 46 IC50 |
|---|---|---|---|---|---|
| 6.1 | 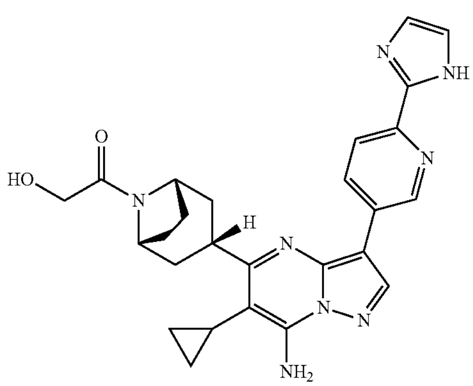 [SMILES: Nc1c(C2CC2)c([C@@H]2C[C@H]3CC[C@@H](C2)N3C(=O)CO)nc2c(-c3ccc(-c4ncc[nH]4)nc3)cnn12] | 1-((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)-2-hydroxyethanone | 485.2/485.1 | A | A |
| 6.2 | 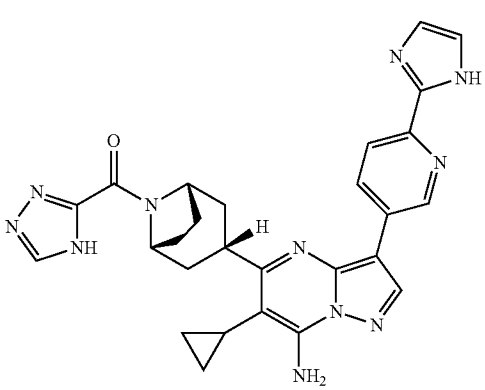 [SMILES: Nc1c(C2CC2)c([C@@H]2C[C@H]3CC[C@@H](C2)N3C(=O)c2nnc[nH]2)nc2c(-c3ccc(-c4ncc[nH]4)nc3)cnn12] | ((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(4H-1,2,4-triazol-3-yl)methanone | 522.2/522.1 | A | A |

TABLE 6-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 6.3 | 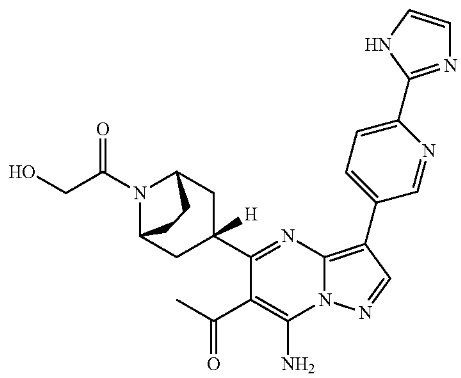 [SMILES: CC(=O)c1c([C@@H]2C[C@H]3CC[C@@H](C2)N3C(=O)CO)nc2c(-c3ccc(-c4ncc[nH]4)nc3)cnn2c1N] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone | 487.2/487.0 | A | A |
| 6.4 | 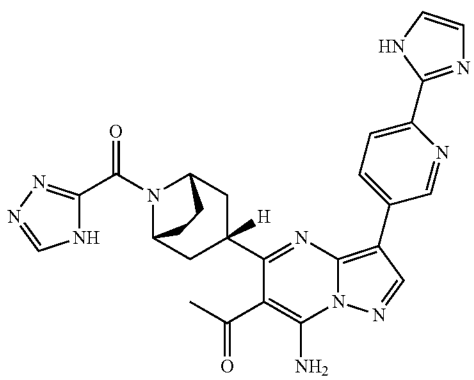 [SMILES: CC(=O)c1c([C@@H]2C[C@H]3CC[C@@H](C2)N3C(=O)c2nnc[nH]2)nc2c(-c3ccc(-c4ncc[nH]4)nc3)cnn2c1N] | 1-(3-(6-(1H-imidazol-2-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 524.2/524.2 | A | A |
| 6.5 | 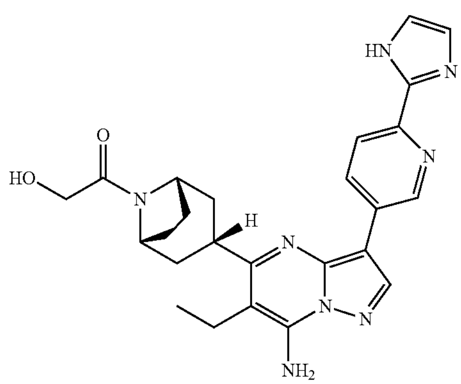 [SMILES: CCc1c([C@@H]2C[C@H]3CC[C@@H](C2)N3C(=O)CO)nc2c(-c3ccc(-c4ncc[nH]4)nc3)cnn2c1N] | 1-((1R,3s,5S)-3-(3-(6-(1H-imidazol-2-yl)pyridin-3-yl)-7-amino-6-ethylpyrazolo[1,5-a]pyrimidin-5-yl)-8-azabicyclo[3.2.1]octan-8-yl)-2-hydroxyethanone | 473.2/473.2 | A | A |
| 6.6 | 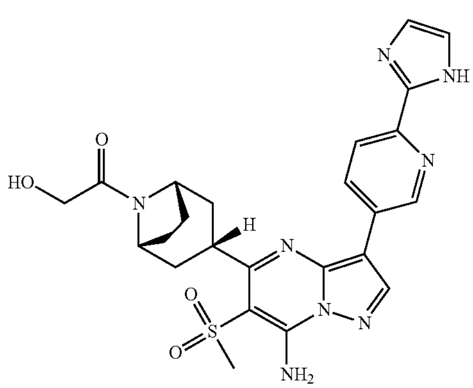 [SMILES: CS(=O)(=O)c1c([C@@H]2C[C@H]3CC[C@@H](C2)N3C(=O)CO)nc2c(-c3ccc(-c4ncc[nH]4)nc3)cnn2c1N] | 1-((1R,3s,5S)-3-(3-(6-(1H-imidazol-2-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone | 523.2/522.9 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.7 | 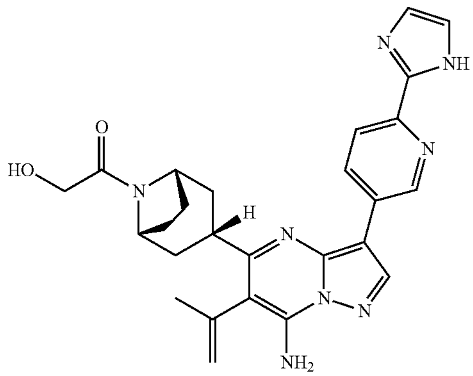 [SMILES: C=C(C)c1c([C@@H]2C[C@H]3CC[C@@H](C2)N3C(=O)CO)nc2c(-c3ccc(-c4ncc[nH]4)nc3)cnn2c1N] | 1-((1R,3s,5S)-3-(3-(6-(1H-imidazol-2-yl)pyridin-3-yl)-7-amino-6-(prop-1-en-2-yl)pyrazolo[1,5-a]pyrimidin-5-yl)-8-azabicyclo[3.2.1]octan-8-yl)-2-hydroxyethanone | 485.2/485.0 | A | A |
| 6.8 | 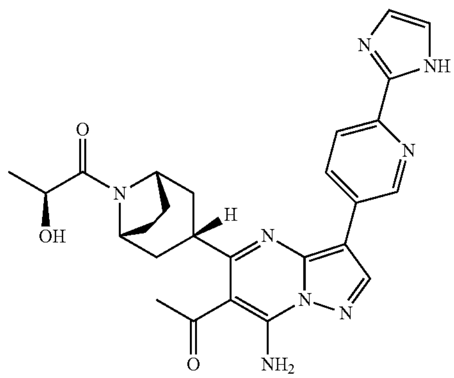 [SMILES: CC(=O)c1c([C@@H]2C[C@H]3CC[C@@H](C2)N3C(=O)[C@H](C)O)nc2c(-c3ccc(-c4ncc[nH]4)nc3)cnn2c1N] | (S)-1-((1R,3R,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one | 501.2/501.0 | A | ND |
| 6.9 | 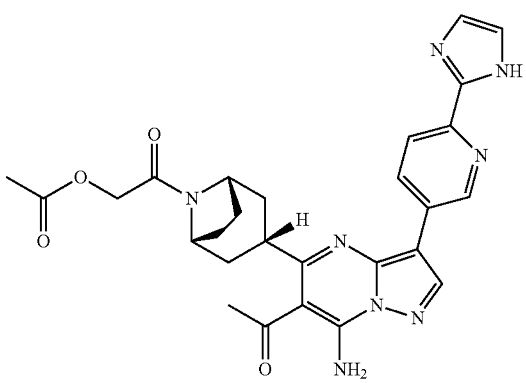 [SMILES: CC(=O)OCC(=O)N1[C@@H]2CC[C@H]1C[C@H](c1nc3c(-c4ccc(-c5ncc[nH]5)nc4)cnn3c(N)c1C(C)=O)C2] | 2-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-oxoethyl acetate | 529.2/529.0 | B | ND |
| 6.10 | 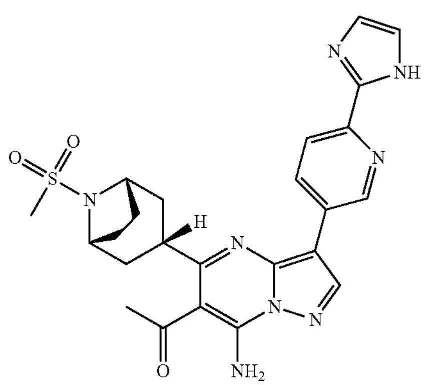 [SMILES: CC(=O)c1c([C@@H]2C[C@H]3CC[C@@H](C2)N3S(C)(=O)=O)nc2c(-c3ccc(-c4ncc[nH]4)nc3)cnn2c1N] | 1-(3-(6-(1H-imidazol-2-yl)pyridin-3-yl)-7-amino-5-((1R,3s,5S)-8-(methylsulfonyl)-8-azabicyclo[3.2.1]octan-3-yl)pyrazolo[1,5-a]pyrimidin-6-yl)ethanone | 507.2/507.0 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.11 | 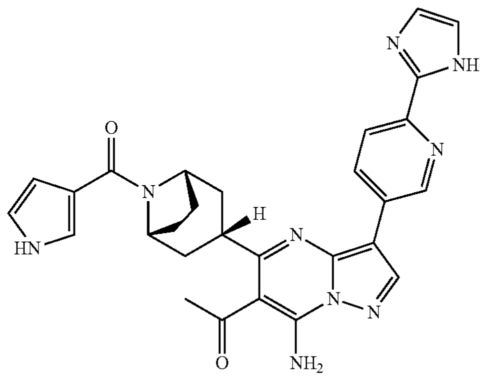 [SMILES: CC(=O)c1c([C@@H]2C[C@H]3CC[C@@H](C2)N3C(=O)c2cc[nH]c2)nc2c(-c3ccc(-c4ncc[nH]4)nc3)cnn2c1N] | 1-(3-(6-(1H-imidazol-2-yl)pyridin-3-yl)-5-((1R,3s,5S)-8-(1H-pyrrole-3-carbonyl)-8-azabicyclo[3.2.1]octan-3-yl)-7-aminopyrazolo[1,5-a]pyrimidin-6-yl)ethanone | 522.2/521.9 | A | A |
| 6.12 | 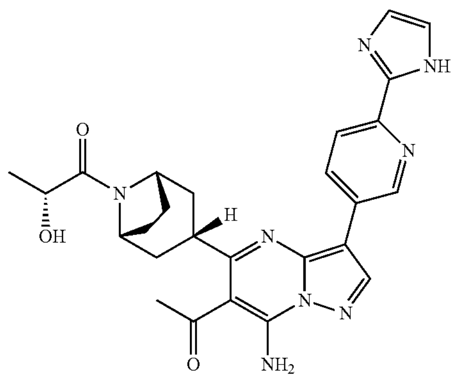 [SMILES: CC(=O)c1c([C@@H]2C[C@H]3CC[C@@H](C2)N3C(=O)[C@@H](C)O)nc2c(-c3ccc(-c4ncc[nH]4)nc3)cnn2c1N] | (R)-1-((1R,3S,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one | 501.2/501.0 | A | A |
| 6.13 | 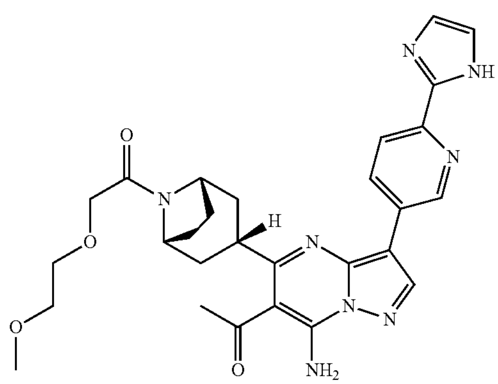 [SMILES: COCCOCC(=O)N1[C@@H]2CC[C@H]1C[C@H](c1nc3c(-c4ccc(-c5ncc[nH]5)nc4)cnn3c(N)c1C(C)=O)C2] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-(2-methoxyethoxy)ethanone | 545.3/545.0 | A | ND |
| 6.14 | 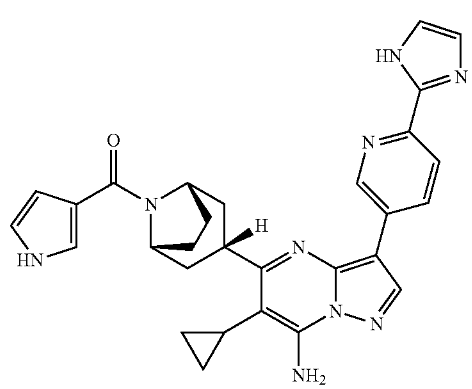 [SMILES: Nc1c(C2CC2)c([C@@H]2C[C@H]3CC[C@@H](C2)N3C(=O)c2cc[nH]c2)nc2c(-c3ccc(-c4ncc[nH]4)nc3)cnn12] | ((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(1H-pyrrol-3-yl)methanone | 520.2/520.0 | A | B |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.15 | 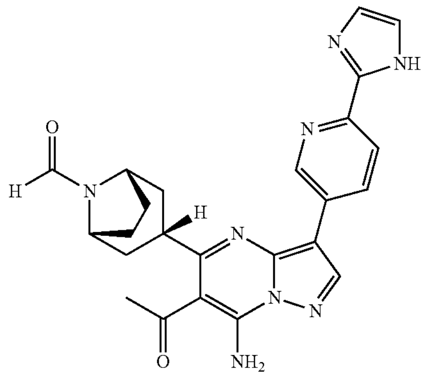 [SMILES: CC(=O)c1c([C@@H]2C[C@H]3CC[C@@H](C2)N3C=O)nc2c(-c3ccc(-c4ncc[nH]4)nc3)cnn2c1N] | (1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carbaldehyde | 457.2/456.9 | A | A |
| 6.16 | 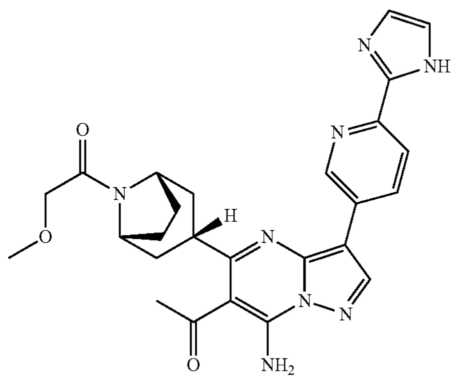 [SMILES: COCC(=O)N1[C@@H]2CC[C@H]1C[C@H](c1nc3c(-c4ccc(-c5ncc[nH]5)nc4)cnn3c(N)c1C(C)=O)C2] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-methoxyethanone | 501.2/501.0 | A | A |
| 6.17 | 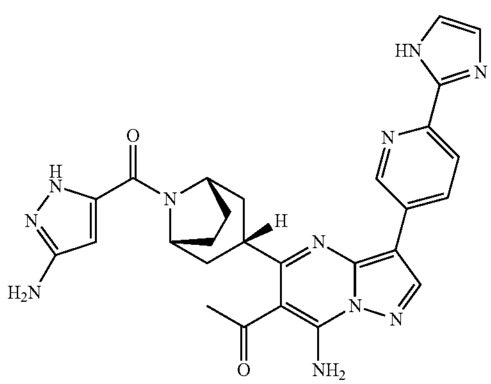 [SMILES: CC(=O)c1c([C@@H]2C[C@H]3CC[C@@H](C2)N3C(=O)c2cc(N)n[nH]2)nc2c(-c3ccc(-c4ncc[nH]4)nc3)cnn2c1N] | 1-(3-(6-(1H-imidazol-2-yl)pyridin-3-yl)-7-amino-5-((1R,3s,5S)-8-(3-amino-1H-pyrazole-5-carbonyl)-8-azabicyclo[3.2.1]octan-3-yl)pyrazolo[1,5-a]pyrimidin-6-yl)ethanone | 538.2/538.0 | A | ND |
| 6.18 | 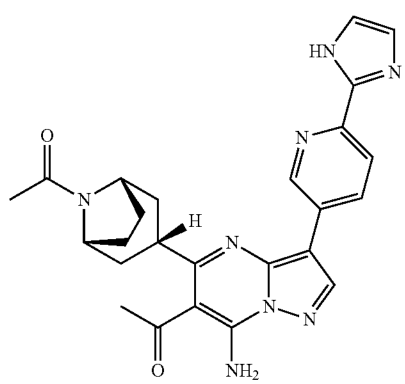 [SMILES: CC(=O)c1c([C@@H]2C[C@H]3CC[C@@H](C2)N3C(C)=O)nc2c(-c3ccc(-c4ncc[nH]4)nc3)cnn2c1N] | 1-(3-(6-(1H-imidazol-2-yl)pyridin-3-yl)-5-((1R,3s,5S)-8-acetyl-8-azabicyclo[3.2.1]octan-3-yl)-7-aminopyrazolo[1,5-a]pyrimidin-6-yl)ethanone | 471.2/471.0 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.19 | 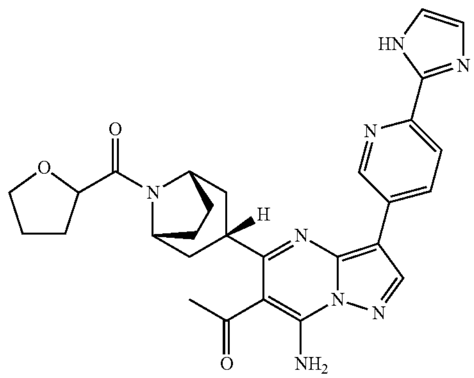 [SMILES: CC(=O)c1c([C@@H]2C[C@H]3CC[C@@H](C2)N3C(=O)C2CCCO2)nc2c(-c3ccc(-c4ncc[nH]4)nc3)cnn2c1N] | 1-(3-(6-(1H-imidazol-2-yl)pyridin-3-yl)-7-amino-5-((1R,3s,5S)-8-(tetrahydrofuran-2-carbonyl)-8-azabicyclo[3.2.1]octan-3-yl)pyrazolo[1,5-a]pyrimidin-6-yl)ethanone | 527.2/527.0 | A | B |
| 6.20 | 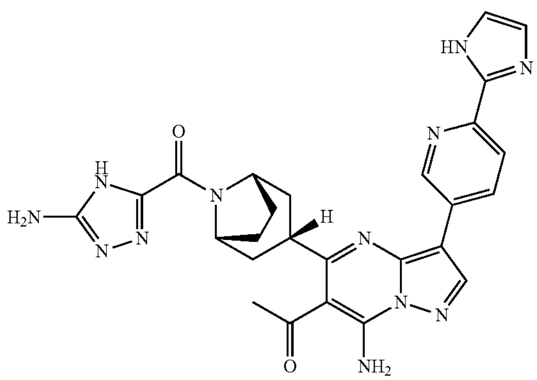 [SMILES: CC(=O)c1c([C@@H]2C[C@H]3CC[C@@H](C2)N3C(=O)c2nnc(N)[nH]2)nc2c(-c3ccc(-c4ncc[nH]4)nc3)cnn2c1N] | 1-(3-(6-(1H-imidazol-2-yl)pyridin-3-yl)-7-amino-5-((1R,3s,5S)-8-(5-amino-4H-1,2,4-triazole-3-carbonyl)-8-azabicyclo[3.2.1]octan-3-yl)pyrazolo[1,5-a]pyrimidin-6-yl)ethanone | 539.2/539.0 | A | A |
| 6.21 | 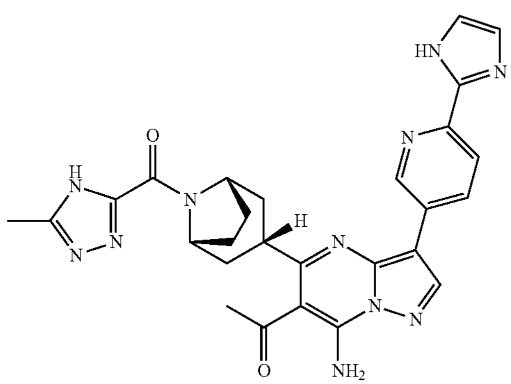 [SMILES: CC(=O)c1c([C@@H]2C[C@H]3CC[C@@H](C2)N3C(=O)c2nnc(C)[nH]2)nc2c(-c3ccc(-c4ncc[nH]4)nc3)cnn2c1N] | 1-(3-(6-(1H-imidazol-2-yl)pyridin-3-yl)-7-amino-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 538.2/538.0 | A | A |
| 6.22 | 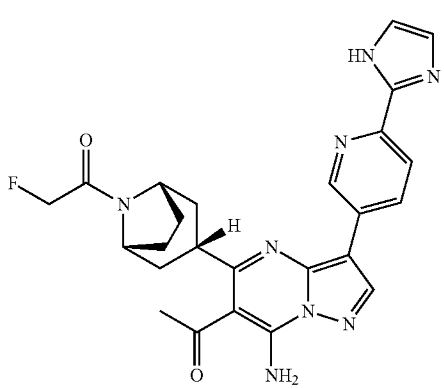 [SMILES: CC(=O)c1c([C@@H]2C[C@H]3CC[C@@H](C2)N3C(=O)CF)nc2c(-c3ccc(-c4ncc[nH]4)nc3)cnn2c1N] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoroethanone | 489.2/489.0 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.23 | 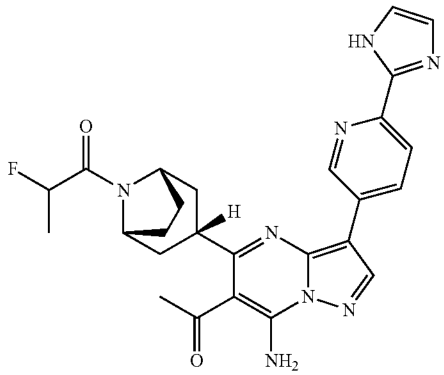 [SMILES: CC(=O)c1c([C@@H]2C[C@H]3CC[C@@H](C2)N3C(=O)C(C)F)nc2c(-c3ccc(-c4ncc[nH]4)nc3)cnn2c1N] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoropropan-1-one | 503.2/502.9 | A | B |
| 6.24 | 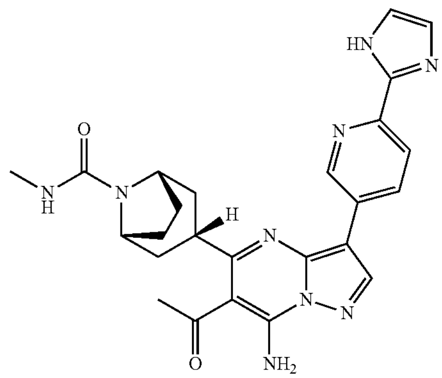 [SMILES: CNC(=O)N1[C@@H]2CC[C@H]1C[C@H](c1nc3c(-c4ccc(-c5ncc[nH]5)nc4)cnn3c(N)c1C(C)=O)C2] | (1R,3s,5S)-3-(3-(6-(1H-imidazol-2-yl)pyridin-3-yl)-6-acetyl-7-aminopyrazolo[1,5-a]pyrimidin-5-yl)-N-methyl-8-azabicyclo[3.2.1]octane-8-carboxamide | 486.2/486.0 | A | A |
| 6.25 | 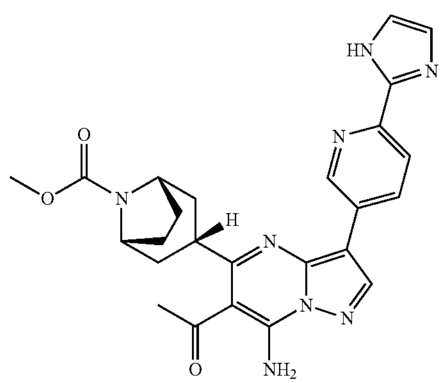 [SMILES: COC(=O)N1[C@@H]2CC[C@H]1C[C@H](c1nc3c(-c4ccc(-c5ncc[nH]5)nc4)cnn3c(N)c1C(C)=O)C2] | (1R,3s,5S)-methyl 3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxylate | 487.2/487.0 | A | A |
| 6.26 | 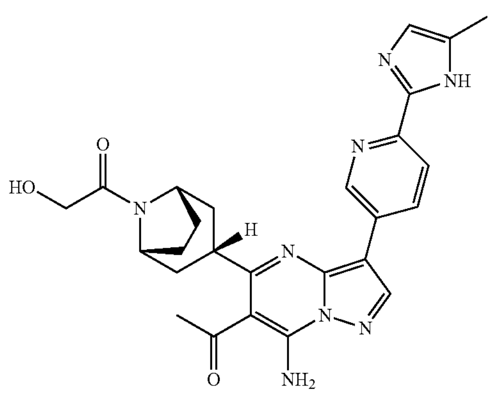 [SMILES: CC(=O)c1c([C@@H]2C[C@H]3CC[C@@H](C2)N3C(=O)CO)nc2c(-c3ccc(-c4ncc(C)[nH]4)nc3)cnn2c1N] | 1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone | 501.2/501.0 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.27 | 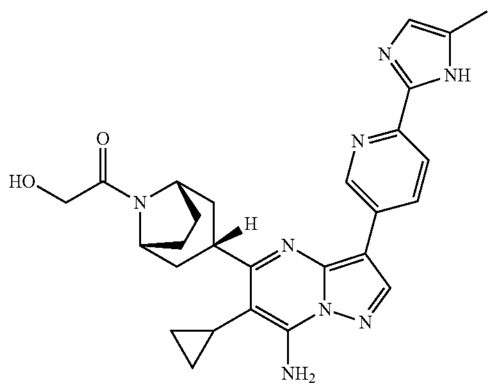 [SMILES: Cc1cnc(-c2ccc(-c3cnn4c(N)c(C5CC5)c([C@@H]5C[C@H]6CC[C@@H](C5)N6C(=O)CO)nc34)cn2)[nH]1] | 1-((1R,3s,5S)-3-(7-amino-6-cyclopropyl-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone | 499.2/499.1 | A | A |
| 6.28 | 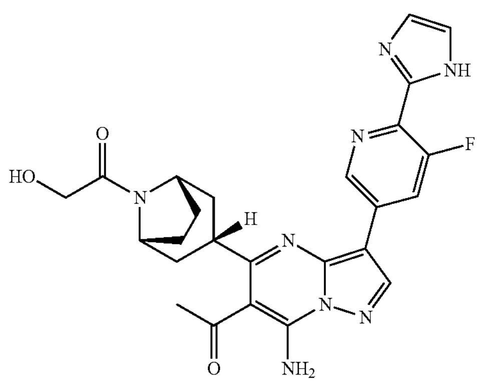 [SMILES: CC(=O)c1c([C@@H]2C[C@H]3CC[C@@H](C2)N3C(=O)CO)nc2c(-c3cnc(-c4ncc[nH]4)c(F)c3)cnn2c1N] | 1-((1R,3s,5S)-3-(6-acetyl-7-amino-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone | 505.2/505.1 | A | N/A |
| 6.29 | 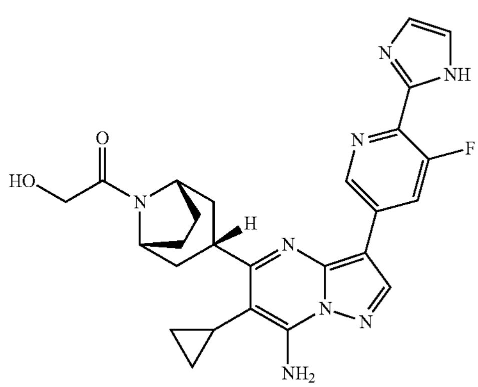 [SMILES: Nc1c(C2CC2)c([C@@H]2C[C@H]3CC[C@@H](C2)N3C(=O)CO)nc2c(-c3cnc(-c4ncc[nH]4)c(F)c3)cnn12] | 1-((1R,3s,5S)-3-(7-amino-6-cyclopropyl-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone | 503.2/503.0 | B | N/A |

TABLE 6-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 6.30 | 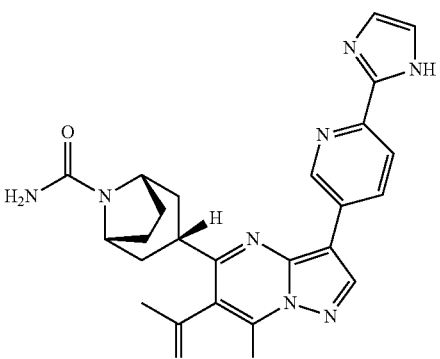 | (1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxamide | 472.2/472.0 | A | A |
| 6.31 | 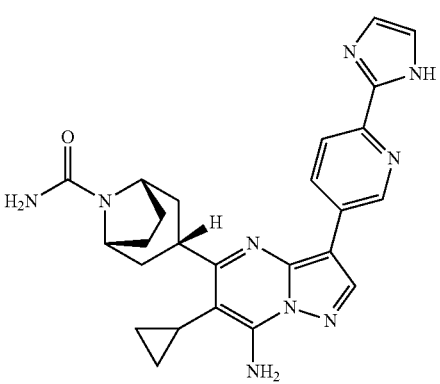 [SMILES: NC(=O)N1[C@@H]2CC[C@H]1C[C@H](c1nc3c(-c4ccc(-c5ncc[nH]5)nc4)cnn3c(N)c1C1CC1)C2] | (1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octane-8-carboxamide | 470.2/470.0 | A | A |
| 6.32 | 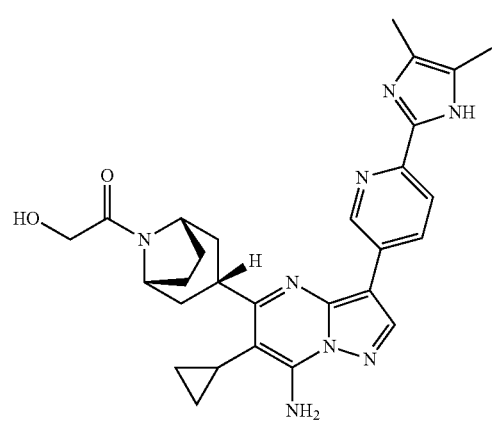 [SMILES: Cc1nc(-c2ccc(-c3cnn4c(N)c(C5CC5)c([C@@H]5C[C@H]6CC[C@@H](C5)N6C(=O)CO)nc34)cn2)[nH]c1C] | 1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxyethanone | 513.2/513.3 | A | B |

TABLE 6-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 6.33 | 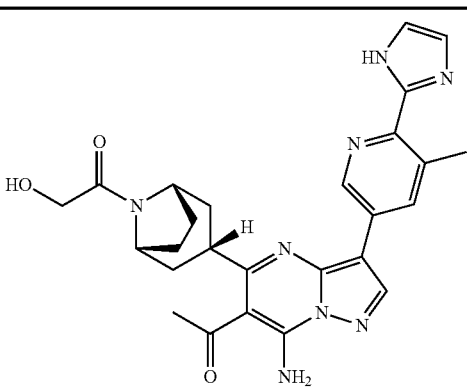 | 1-((1R,3s,5S)-3-(3-(6-(1H-imidazol-2-yl)-5-methylpyridin-3-yl)-6-acetyl-7-aminopyrazolo[1,5-a]pyrimidin-5-yl)-8-azabicyclo[3.2.1]octan-8-yl)-2-hydroxyethanone | 501.23/501.1 | C | ND |
| 6.34 | 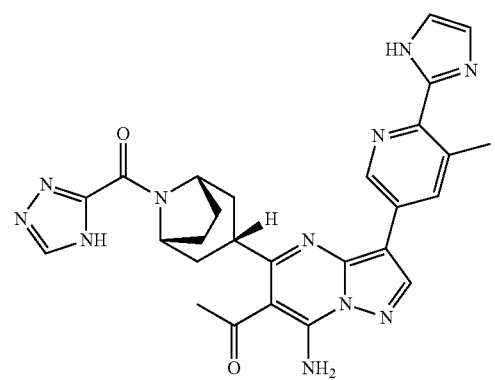 [SMILES: CC(=O)c1c([C@@H]2C[C@H]3CC[C@@H](C2)N3C(=O)c2nnc[nH]2)nc2c(-c3cnc(-c4ncc[nH]4)c(C)c3)cnn2c1N] | 1-(3-(6-(1H-imidazol-2-yl)-5-methylpyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 538.23/538.3 | ND | ND |
| 6.35 | 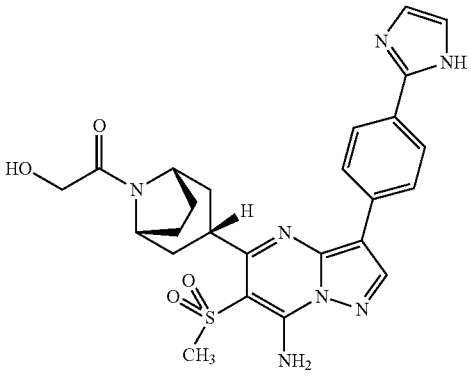 [SMILES: CS(=O)(=O)c1c([C@@H]2C[C@H]3CC[C@@H](C2)N3C(=O)CO)nc2c(-c3ccc(-c4ncc[nH]4)cc3)cnn2c1N] | 1-((1R,3s,5S)-3-(3-(4-(1H-imidazol-2-yl)phenyl)-7-amino-6-(methylsulfonyl)pyrazolo[1,5-a]pyrimidin-5-yl)-8-azabicyclo[3.2.1]octan-8-yl)-2-hydroxyethanone | 522.18/ 522.0 | A | B |
| 6.36 | 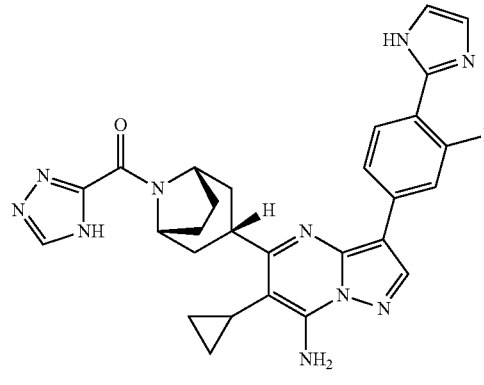 | ((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)(4H-1,2,4-triazol-3-yl)methanone | 539.24/ 539.1 | A | A |

TABLE 6-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 6.37 | 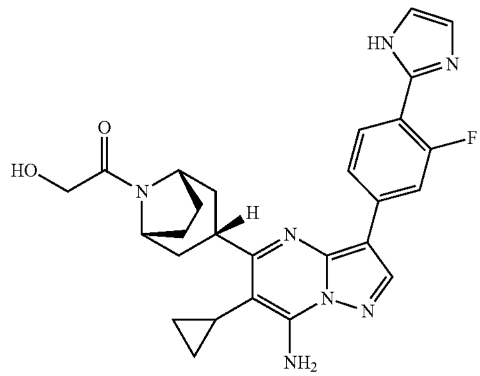 [SMILES: Nc1c(C2CC2)c([C@@H]2C[C@H]3CC[C@@H](C2)N3C(=O)CO)nc2c(-c3ccc(-c4ncc[nH]4)c(F)c3)cnn12] | 1-((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone | 502.23/ 502.1 | A | A |
| 6.38 | 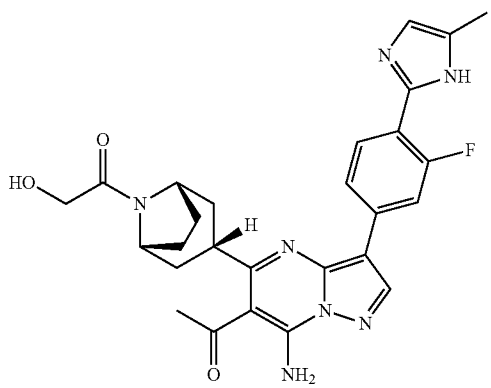 [SMILES: CC(=O)c1c([C@@H]2C[C@H]3CC[C@@H](C2)N3C(=O)CO)nc2c(-c3ccc(-c4ncc(C)[nH]4)c(F)c3)cnn2c1N] | 1-((1R,3s,5S)-3-(6-acetyl-7-amino-3-(3-fluoro-4-(5-methyl-1H-imidazol-2-yl)phenyl)pyrazolo[1,5-a]pyrimidin-5-yl)-8-azabicyclo[3.2.1]octan-8-yl)-2-hydroxyethanone | 518.22/ 518.1 | A | B |
| 6.39 | 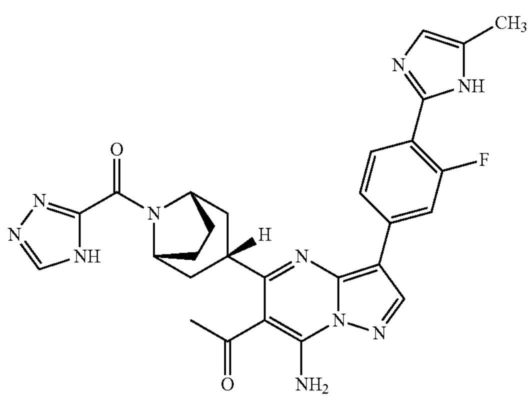 [SMILES: CC(=O)c1c([C@@H]2C[C@H]3CC[C@@H](C2)N3C(=O)c2nnc[nH]2)nc2c(-c3ccc(-c4ncc(C)[nH]4)c(F)c3)cnn2c1N] | 1-(5-((1R,3s,5S)-8-(4H-1,2,4-triazole-3-carbonyl)-8-azabicyclo[3.2.1]octan-3-yl)-7-amino-3-(3-fluoro-4-(5-methyl-1H-imidazol-2-yl)phenyl)pyrazolo[1,5-a]pyrimidin-6-yl)ethanone | 555.23/ 555.0 | A | B |
| 6.40 | 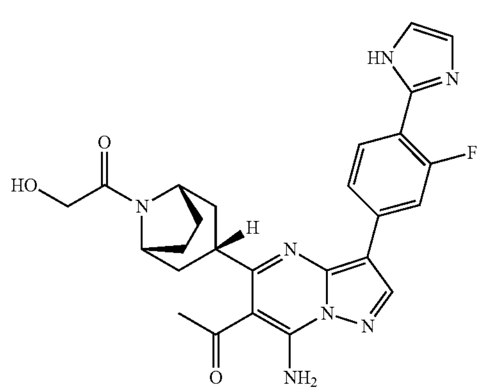 [SMILES: CC(=O)c1c([C@@H]2C[C@H]3CC[C@@H](C2)N3C(=O)CO)nc2c(-c3ccc(-c4ncc[nH]4)c(F)c3)cnn2c1N] | 1-((1R,3s,5S)-3-(6-acetyl-7-amino-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone | 504.21/ 504.0 | A | A |

TABLE 6-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 6.41 | 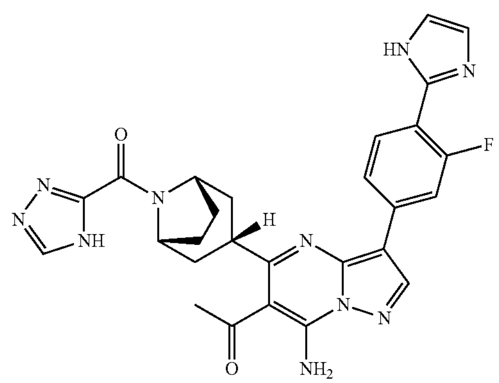 [SMILES: CC(=O)c1c([C@@H]2C[C@H]3CC[C@@H](C2)N3C(=O)c2nnc[nH]2)nc2c(-c3ccc(-c4ncc[nH]4)c(F)c3)cnn2c1N] | 1-(5-((1R,3s,5S)-8-(4H-1,2,4-triazole-3-carbonyl)-8-azabicyclo[3.2.1]octan-3-yl)-7-amino-3-(3-fluoro-4-(1H-imidazol-2-yl)phenyl)pyrazolo[1,5-a]pyrimidin-6-yl)ethanone | 541.21/ 541.0 | A | A |
| 6.42 | 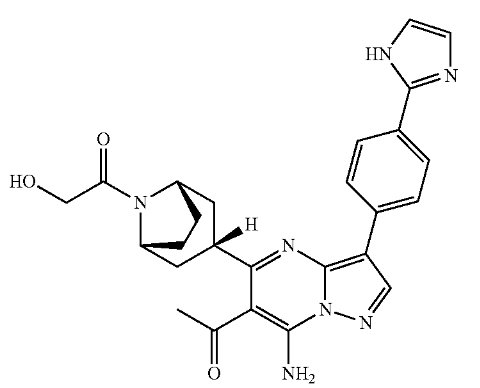 [SMILES: CC(=O)c1c([C@@H]2C[C@H]3CC[C@@H](C2)N3C(=O)CO)nc2c(-c3ccc(-c4ncc[nH]4)cc3)cnn2c1N] | 1-((1R,3s,5S)-3-(3-(4-(1H-imidazol-2-yl)phenyl)-6-acetyl-7-aminopyrazolo[1,5-a]pyrimidin-5-yl)-8-azabicyclo[3.2.1]octan-8-yl)-2-hydroxyethanone | 486.22/ 486.1 | A | A |
| 6.43 | 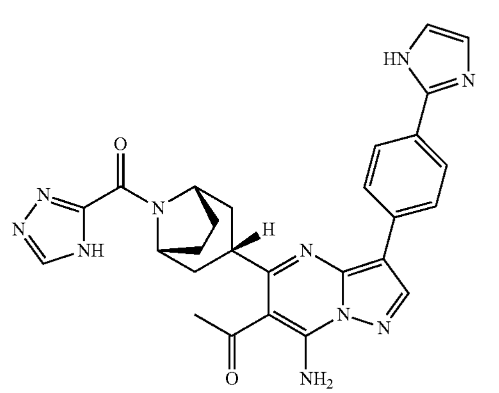 [SMILES: CC(=O)c1c([C@@H]2C[C@H]3CC[C@@H](C2)N3C(=O)c2nnc[nH]2)nc2c(-c3ccc(-c4ncc[nH]4)cc3)cnn2c1N] | 1-(3-(4-(1H-imidazol-2-yl)phenyl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone | 523.22/ 523.1 | A | A |

TABLE 6-1-continued

| Compound ID | Structures | Compound Name | M + H (calculated)/ M + H (observed) | pAKT S473 IC50 | p4E-BP1 Thr37/ 46 IC50 |
| --- | --- | --- | --- | --- | --- |
| 6.44 | 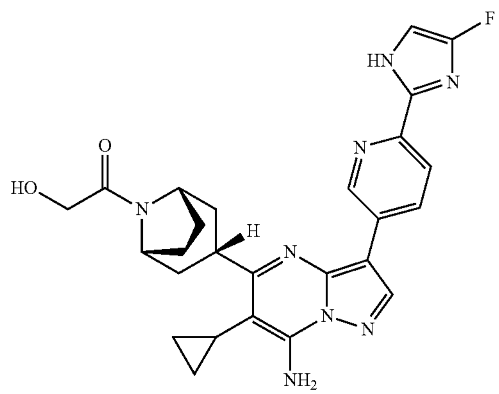 | 1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone | 503.2/503.3 | ND | ND |
| 6.45 | 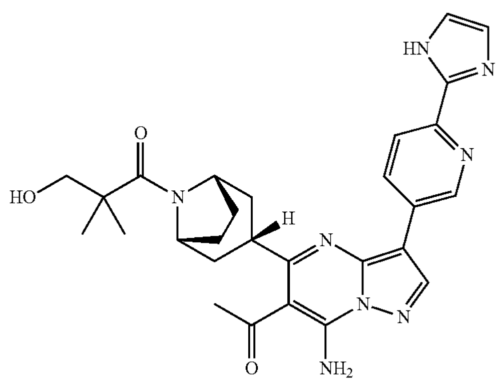 [SMILES: CC(=O)c1c([C@@H]2C[C@H]3CC[C@@H](C2)N3C(=O)C(C)(C)CO)nc2c(-c3ccc(-c4ncc[nH]4)nc3)cnn2c1N] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2,2-dimethylpropan-1-one | 528.26/529.2 | B | ND |
| 6.46 | 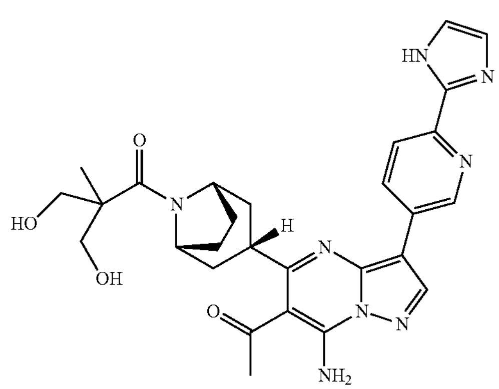 [SMILES: CC(=O)c1c([C@@H]2C[C@H]3CC[C@@H](C2)N3C(=O)C(C)(CO)CO)nc2c(-c3ccc(-c4ncc[nH]4)nc3)cnn2c1N] | 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2-(hydroxymethyl)-2-methylpropan-1-one | 544.25/545.0 | B | B |

Example 7-1

Preparation of 1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone

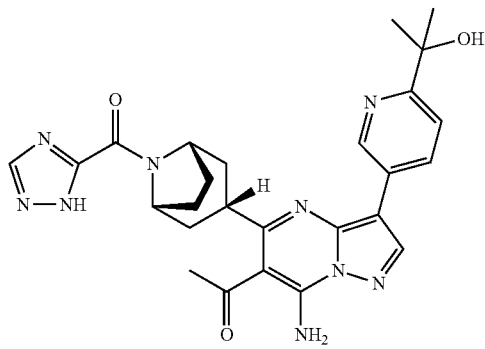

Step 1: Preparation of 2-(5-bromopyridin-2-yl)propan-2-ol

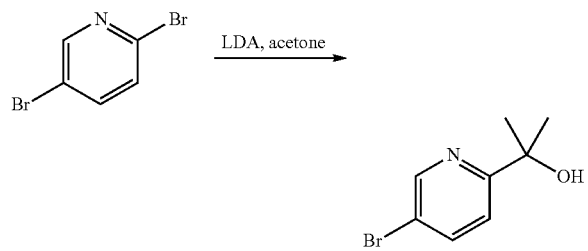

The title compound was prepared analogously to the procedure reported in (substituting acetone for dimethylformamide): Simone, F.; Kodanko J.; Morys, A.; Hayashi, T.; Moenne-Loccoz, P.; Lippard, S. *J. Am. Chem. Soc.* 2009, 131, 14508-14520. All achiral compounds and racemic precursors reported in Table 7-1 were made by substituting the appropriate ketone or aldehyde during the alkylation.

Step 2: Preparation of tert-butyl 3-{7-(bis{[2-(trimethylsilyl)ethoxy]methyl}amino)-3-[6-(1-hydroxy-1-methylethyl)pyridin-3-yl]pyrazolo[1,5-a]pyrimidin-5-yl}-8-azabicyclo[3.2.1]octane-8-carboxylate

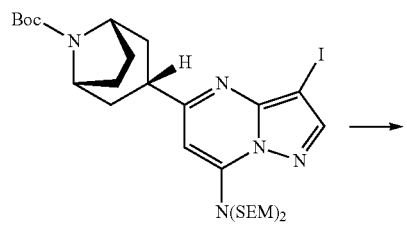

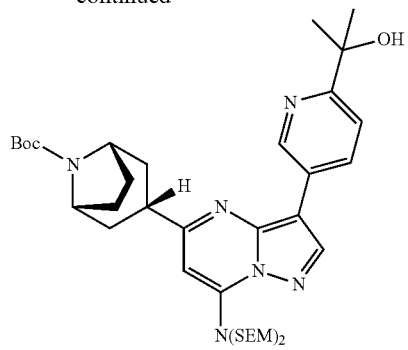

Potassium acetate (1.383 g, 14.09 mmol), [1,1'-bis(diphenylphosphino)ferrocene]dichloropalladium(II) (168 mg, 0.230 mmol), bis(pinacolato)diboron (1.40 g, 5.49 mmol), and 2-(5-bromopyridin-2-yl)propan-2-ol (1.099 g, 5.086 mmol) were combined in a microwave tube equipped with a stir bar. The headspace was exchanged for dry nitrogen (×3), and 1,4-dioxane (10 mL) was added. The vessel was lowered into a 90° C. oil bath, and stirred rapidly for 2.5 h. The mixture was cooled to room temperature and tert-butyl 3-[7-(bis{[2-(trimethylsilyl)ethoxy]methyl}amino)-3-iodopyrazolo[1,5-a]pyrimidin-5-yl]-8-azabicyclo[3.2.1]octane-8-carboxylate (1.774 g, 2.431 mmol) in 1,4-dioxane (6 mL, 80 mmol), and aqueous sodium carbonate (2.0 M, 3.3 mL, 6.6 mmol) were added. The organic layer became homogeneous, and the aq. becomes milky. The reaction was again lowered into the 90° C. bath, and stirred vigorously for 16 h, at which point HPLC shows the reaction to be complete. The mixture was cooled and partitioned between ethyl acetate (200 mL) and water (50 mL). The organics were washed with water (50 mL), brine (50 mL), dried with MgSO$_4$, filtered through celite, and concentrated. The crude material was purified by flash chromatography (20-100% ethyl acetate in hexanes). The title compound (1.01 g) was isolated as a brown oil.

Step 3: Preparation of tert-butyl 3-{7-(bis{[2-(trimethylsilyl)ethoxy]methyl}amino)-6-bromo-3-[6-(1-hydroxy-1-methylethyl)pyridin-3-yl]pyrazolo[1,5-a]pyrimidin-5-yl}-8-azabicyclo[3.2.1]octane-8-carboxylate

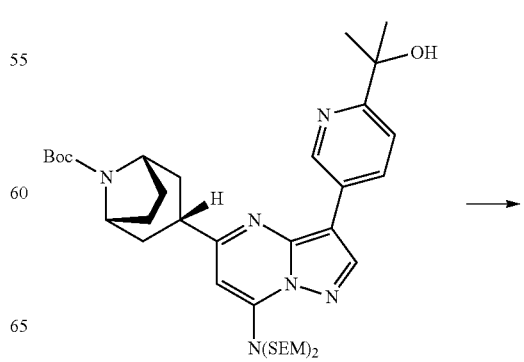

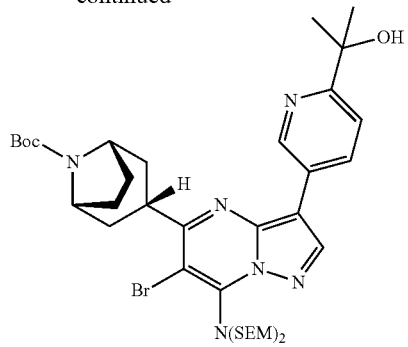

Step 4: Preparation of tert-butyl 3-{7-(bis{[2-(trimethylsilyl)ethoxy]methyl}amino)-6-(1-ethoxyvinyl)-3-[6-(1-hydroxy-1-methylethyl) pyridin-3-yl]pyrazolo[1,5-a]pyrimidin-5-yl}-8-azabicyclo[3.2.1]octane-8-carboxylate tert-butyl 3-{7-(bis{[2-(trimethylsilyl)ethoxy]methyl}amino)-3-[6-(1-hydroxy-1-methylethyl)pyridin-3-yl]pyrazolo[1,5-a]pyrimidin-5-yl}-8-azabicyclo[3.2.1]octane-8-carboxylate (0.500 g, 0.676 mmol) was dissolved in acetic acid (3.5 mL, 62 mmol) and N-bromosuccinimide (144.2 mg, 0.8105 mmol) was added in a single portion, and the reaction was monitored by HPLC. The reaction was complete in less than 10 min and the mixture was diluted with ethyl acetate and poured into a 1:1 mixture of saturated aq. sodium bicarbonate and aq. sodium thiosulfate (20%). The layers were separated and the organics washed several times with sodium bicarbonate solution then brine. The organics were dried with magnesium sulfate, filtered and concentrated to provide 550 mg of the desired material.

tert-butyl 3-{7-(bis{[2-(trimethylsilyl)ethoxy]methyl}amino)-6-bromo-3-[6-(1-hydroxy-1-methylethyl)pyridin-3-yl]pyrazolo[1,5-a]pyrimidin-5-yl}-8-azabicyclo[3.2.1]octane-8-carboxylate (0.550 g, 0.672 mmol), tributyl [1-(ethyloxy)ethenyl]stannane (681 μL, 2.02 mmol) and tetrakis(triphenylphosphine)palladium(0) (78 mg, 0.067 mmol) were placed in a 3-neck 25-mL round bottom flask equipped with a reflux condenser and rubber septa. Then, the flask was evacuated and back-filled with nitrogen three times before adding 1,4-dioxane (20 mL). The resulting solution was sparged with nitrogen for 15 minutes and then lowered into an oil bath that was heated at 100° C. and the resulting solution stirred overnight at the same temperature. Another portion of tetrakis(triphenylphosphine)palladium(0) (78 mg, 0.067 mmol) was added after 14 h, and the reaction allowed to progress for another 24 h, at which point, analysis showed consumption of the starting material and formation of the desired product. The reaction was cooled to ambient temperature and concentrated in vacuo. The crude dark oil was purified by flash chromatography (40 g silica gel, 0 to 8% methanol in chloroform) to afford the title compound (476 mg).

Step 5: Preparation of 1-{7-amino-5-[(3-exo)-8-azabicyclo[3.2.1]oct-3-yl]-3-[6-(1-hydroxy-1-methylethyl)pyridin-3-yl]pyrazolo[1,5-a]pyrimidin-6-yl}ethanone tris(trifluoroacetate)

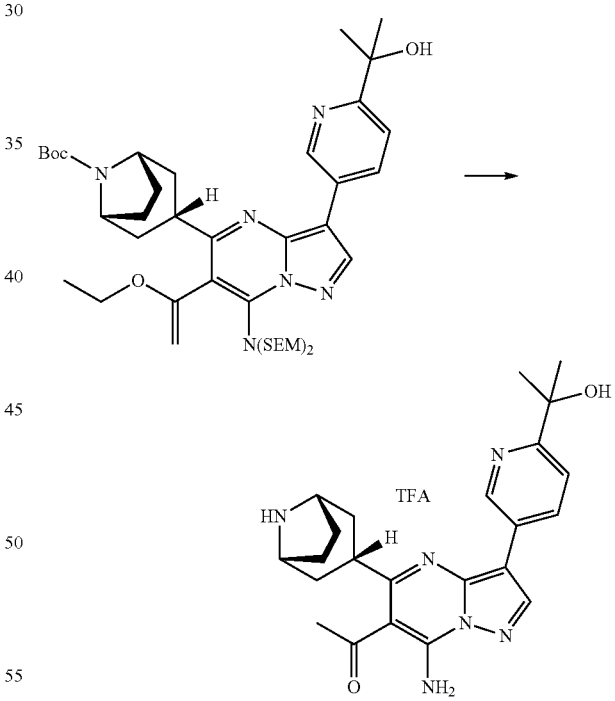

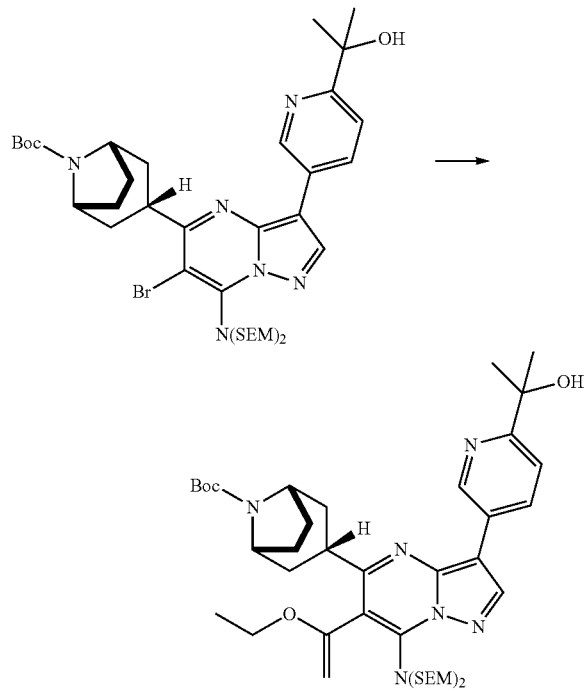

To a vial containing tert-butyl (3-exo)-3-{7-(bis{[2-(trimethylsilyl)ethoxy]methyl}amino)-6-(1-ethoxyvinyl)-3-[6-(1-hydroxy-1-methylethyl)pyridin-3-yl]pyrazolo[1,5-a]pyrimidin-5-yl}-8-azabicyclo[3.2.1]octane-8-carboxylate (0.476 g, 0.588 mmol) was added a preformed solution of trifluoroacetic acid (8 mL) and water (4 mL). The mixture was stirred to dissolve the solids. After 30 min, HPLC samples show the complete consumption of starting material. The reation was concentrated, dissolved in methanol and concentrated, and twice dissolved with toluene and concentrated to provide a yellow oil. The oil was treated with diethyl ether and sonicated to provide the title compound (271 mg) as a yellow solid which was collected by filtration.

Step 6: Preparation of 1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone

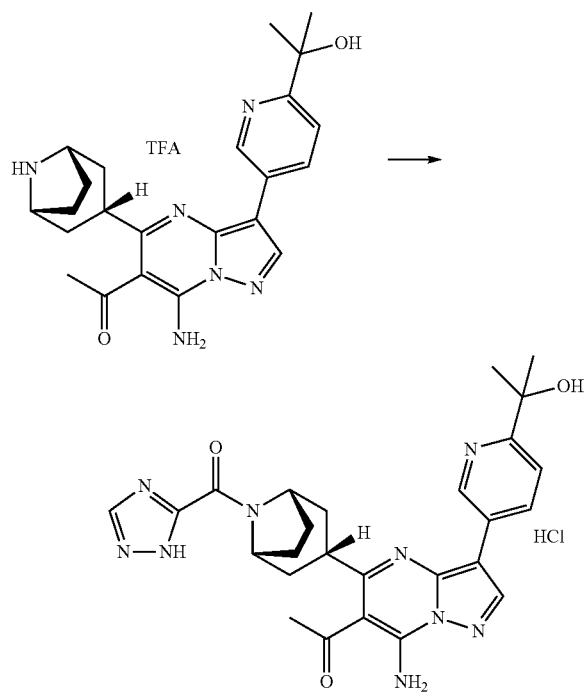

To a round bottom flask under nitrogen was added 1-{7-amino-5-(8-azabicyclo[3.2.1]oct-3-yl)-3-[6-(1-hydroxy-1-methylethyl)pyridin-3-yl]pyrazolo[1,5-a]pyrimidin-6-yl}ethanone tris(trifluoroacetate) (0.270 g, 0.354 mmol), N,N-dimethylformamide (6 mL) and N,N-diisopropylethylamine (0.370 mL, 2.12 mmol). In a separate oven dried flask under nitrogen was added N-(3-dimethylaminopropyl)-N'-ethylcarbodiimide hydrochloride (0.102 g, 0.531 mmol), 1-hydroxybenzotriazole hydrate (0.0868 g, 0.566 mmol), N,N-dimethylformamide (6 mL) and 1H-1,2,4-triazole-5-carboxylic acid (0.0600 g, 0.531 mmol). This flask went from cloudy to homogeneous over the course of 5-10 min and was stirred an additional 20 min before adding to the other flask via syringe. The mixture was stirred for 15 min before checking by HPLC and shown to be complete at this time. LCMS had a mass consistent with the desired product. The mixture was partitioned between sat'd $NaHCO_3$ and 10% IPA in dichloromethane. The layers were separated and the aqueous extracted with dichloromethane. The combined organics were washed twice with water, and brine, dried with $MgSO_4$, filtered and evaporated. The residue was purified by flash chromatography (0-15% (10% $NH_4OH$ in MeOH) in $CHCl_3$) to provide a yellow solid. Methanol and 2 mL of 1M HCl were added to the solids. The solution was concentrated, and this process repeated 4 times to give a yellow solid which was not of the desired purity. The solids were dissolved in 0.1N HCl (2 ml) and aq. $NaHCO_3$ was added (6 ml). The resulting white solid was filtered and washed with water, and the residue was again submitted to aq. methanolic HCl as described above to provide the title compound (103 mg) as a colorless solid The following compounds listed in Table 7-1 were prepared following procedures similar to the preparation of 1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone.

TABLE 7-1

| Compound ID | Structure | Compound Name | M + H (calculated)/ M + H (observed) | pAKT S473 IC50 | p4E-BP1 Thr37/46 IC50 |
|---|---|---|---|---|---|
| 7.1 | 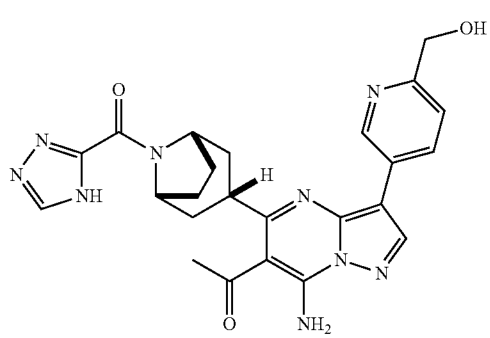 [SMILES: CC(=O)c1c([C@@H]2C[C@H]3CC[C@@H](C2)N3C(=O)c2nnc[nH]2)nc2c(-c3ccc(CO)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(hydroxymethyl)pyridin-3-yl)pyrazolo[1,5-a]pyrimidin-6-yl)ethanone | 488.2/488.3 | A | A |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.2 | 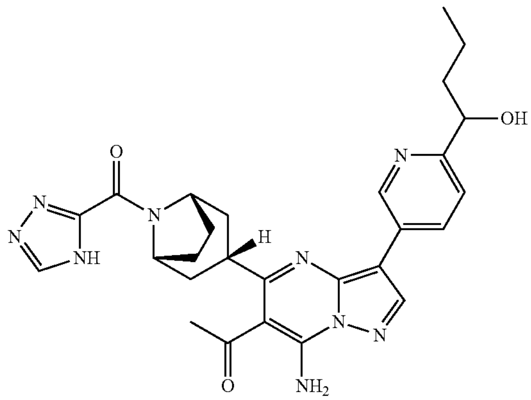 [SMILES: CCCC(O)c1ccc(-c2cnn3c(N)c(C(C)=O)c([C@@H]4C[C@H]5CC[C@@H](C4)N5C(=O)c4nnc[nH]4)nc23)cn1] | 1-(5-((1R,3s,5S)-8-(4H-1,2,4-triazole-3-carbonyl)-8-azabicyclo[3.2.1]octan-3-yl)-7-amino-3-(6-(1-hydroxybutyl)pyridin-3-yl)pyrazolo[1,5-a]pyrimidin-6-yl)ethanone | 530.3/530.4 | ND | ND |
| 7.3 | 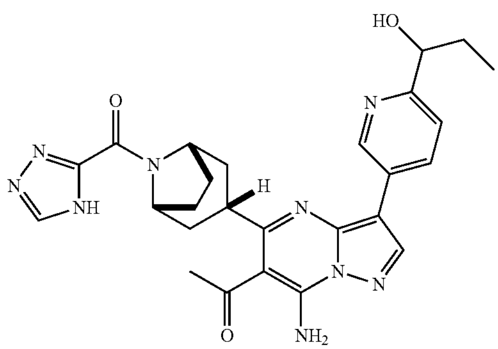 [SMILES: CCC(O)c1ccc(-c2cnn3c(N)c(C(C)=O)c([C@@H]4C[C@H]5CC[C@@H](C4)N5C(=O)c4nnc[nH]4)nc23)cn1] | 1-(5-((1R,3s,5S)-8-(4H-1,2,4-triazole-3-carbonyl)-8-azabicyclo[3.2.1]octan-3-yl)-7-(1amino-3-(6-(1-hydroxypropyl)pyridin-3-yl)pyrazolo[1,5-a]pyrimidin-6-yl)ethanone | 516.2/516.5 | A | B |
| 7.4 | 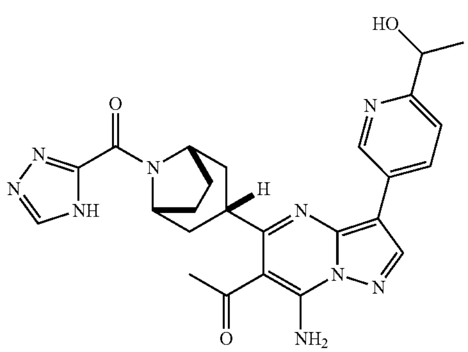 [SMILES: CC(=O)c1c([C@@H]2C[C@H]3CC[C@@H](C2)N3C(=O)c2nnc[nH]2)nc2c(-c3ccc(C(C)O)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-hydroxyethyl)pyridin-3-yl)pyrazolo[1,5-a]pyrimidin-6-yl)ethanone | 502.2/502.4 | A | A |
| 7.5 | 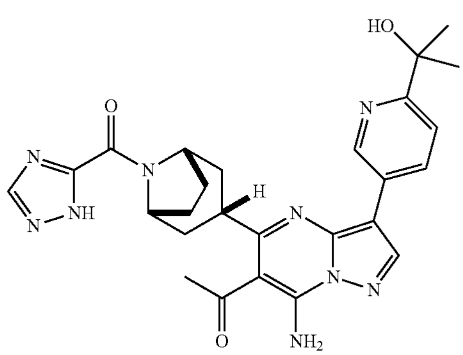 [SMILES: CC(=O)c1c([C@@H]2C[C@H]3CC[C@@H](C2)N3C(=O)c2ncn[nH]2)nc2c(-c3ccc(C(C)(C)O)nc3)cnn2c1N] | 1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone | 516.25/516.2 | A | A |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.6 | 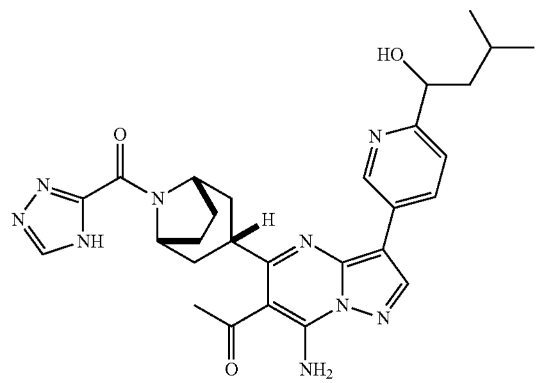 [SMILES: CC(=O)c1c([C@@H]2C[C@H]3CC[C@@H](C2)N3C(=O)c2nnc[nH]2)nc2c(-c3ccc(C(O)CC(C)C)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(1-hydroxy-3-methylbutyl)pyridin-3-yl)pyrazolo[1,5-a]pyrimidin-6-yl)ethanone | 544.3/544.4 | C | B |
| 7.7 | 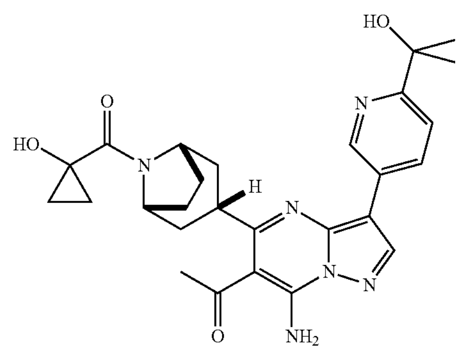 [SMILES: CC(=O)c1c([C@@H]2C[C@H]3CC[C@@H](C2)N3C(=O)C2(O)CC2)nc2c(-c3ccc(C(C)(C)O)nc3)cnn2c1N] | 1-(7-amino-5-((1R,3s,5S)-8-(1-hydroxycyclopropanecarbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone | 505.3/505.4 | ND | ND |
| 7.8 | 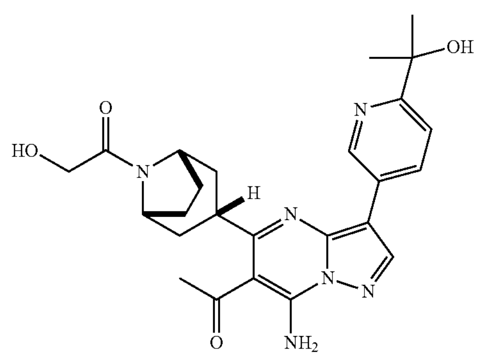 [SMILES: CC(=O)c1c([C@@H]2C[C@H]3CC[C@@H](C2)N3C(=O)CO)nc2c(-c3ccc(C(C)(C)O)nc3)cnn2c1N] | 1-((1R,3s,5S)-3-(6-acetyl-7-amino-3-(6-(2-hydroxypropan-2-yl)pyridin-3-yl)pyrazolo[1,5-a]pyrimidin-5-yl)-8-azabicyclo[3.2.1]octan-8-yl)-2-hydroxyethanone | 479.2/479.5 | B | B |
| 7.9 | 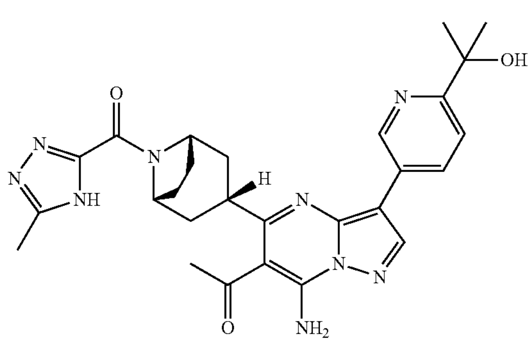 [SMILES: CC(=O)c1c([C@@H]2C[C@H]3CC[C@@H](C2)N3C(=O)c2nnc(C)[nH]2)nc2c(-c3ccc(C(C)(C)O)nc3)cnn2c1N] | 1-(7-amino-3-(6-(2-hydroxypropan-2-yl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 530.3/530.4 | B | B |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.10 | 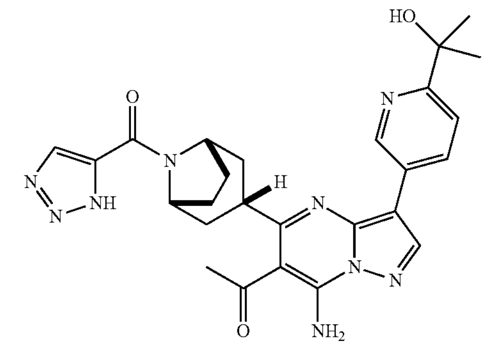 [SMILES: CC(=O)c1c([C@@H]2C[C@H]3CC[C@@H](C2)N3C(=O)c2cnn[nH]2)nc2c(-c3ccc(C(C)(C)O)nc3)cnn2c1N] | 1-(5-((1R,3s,5S)-8-(1H-1,2,3-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone | 516.25/516.5 | B | B |
| 7.11 | 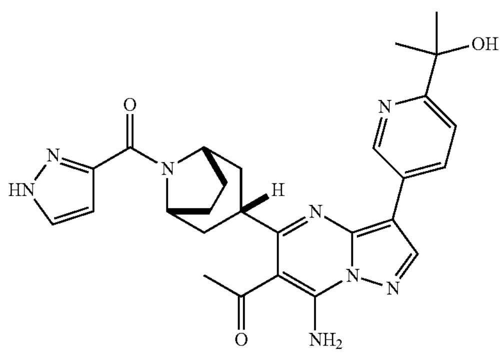 [SMILES: CC(=O)c1c([C@@H]2C[C@H]3CC[C@@H](C2)N3C(=O)c2cc[nH]n2)nc2c(-c3ccc(C(C)(C)O)nc3)cnn2c1N] | 1-(5-((1R,3s,5S)-8-(1H-pyrazole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone | 515.2/515.3 | A | B |
| 7.12 | 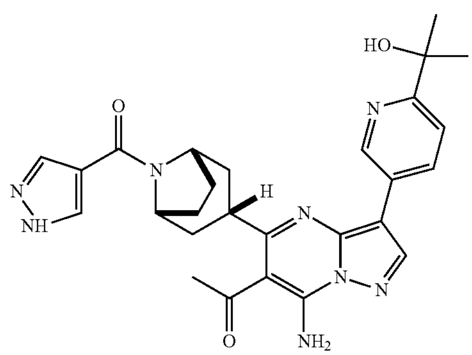 [SMILES: CC(=O)c1c([C@@H]2C[C@H]3CC[C@@H](C2)N3C(=O)c2cn[nH]c2)nc2c(-c3ccc(C(C)(C)O)nc3)cnn2c1N] | 1-(5-((1R,3s,5S)-8-(1H-pyrazole-4-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone | 515.3/515.4 | B | B |
| 7.13 | 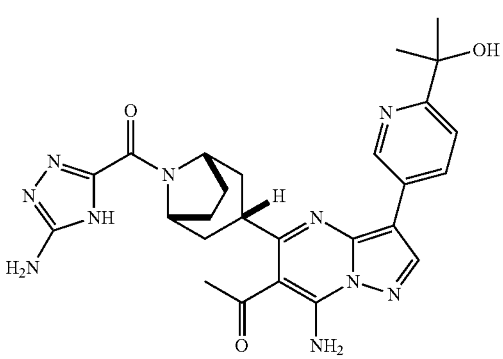 [SMILES: CC(=O)c1c([C@@H]2C[C@H]3CC[C@@H](C2)N3C(=O)c2nnc(N)[nH]2)nc2c(-c3ccc(C(C)(C)O)nc3)cnn2c1N] | 1-(7-amino-5-((1R,3s,5S)-8-(5-amino-4H-1,2,4-triazole-3-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone | 531.3/531.3 | B | B |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.14 | 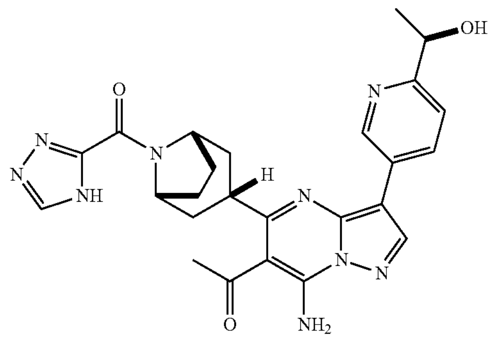 [SMILES: CC(=O)c1c([C@@H]2C[C@H]3CC[C@@H](C2)N3C(=O)c2nnc[nH]2)nc2c(-c3ccc([C@@H](C)O)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone | 502.2/502.4 | B | B |
| 7.15 | 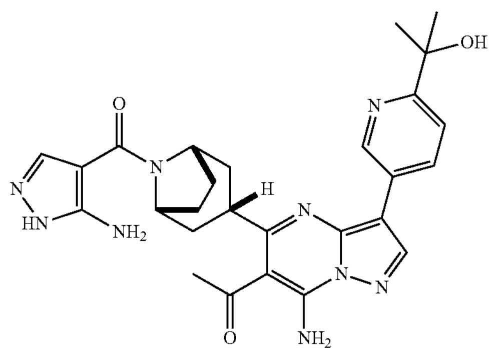 [SMILES: CC(=O)c1c([C@@H]2C[C@H]3CC[C@@H](C2)N3C(=O)c2cn[nH]c2N)nc2c(-c3ccc(C(C)(C)O)nc3)cnn2c1N] | 1-(7-amino-5-((1R,3s,5S)-8-(5-amino-1H-pyrazole-4-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone | 530.3/530.5 | B | B |
| 7.16 | 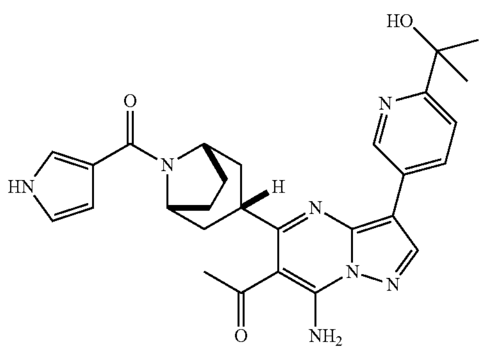 [SMILES: CC(=O)c1c([C@@H]2C[C@H]3CC[C@@H](C2)N3C(=O)c2cc[nH]c2)nc2c(-c3ccc(C(C)(C)O)nc3)cnn2c1N] | 1-(5-((1R,3s,5S)-8-(1H-pyrrole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone | 514.26/514.5 | A | B |
| 7.17 | 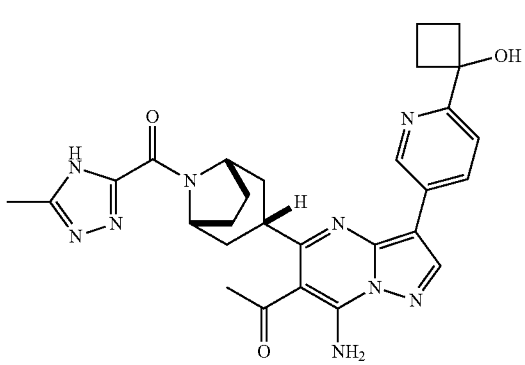 [SMILES: CC(=O)c1c([C@@H]2C[C@H]3CC[C@@H](C2)N3C(=O)c2nnc(C)[nH]2)nc2c(-c3ccc(C4(O)CCC4)nc3)cnn2c1N] | 1-(7-amino-3-(6-(1-hydroxycyclobutyl)pyridin-3-yl)-5-((1R,3s,5S)-8-(3-methyl-1H-1,2,4-triazole-5-carbonyl)-8-azabicyclo[3.2.1]octan-3-yl)pyrazolo[1,5-a]pyrimidin-6-yl)ethanone | 542.3/542.4 | B | B |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.18 | 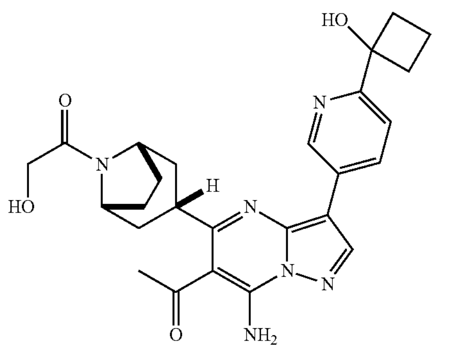 [SMILES: CC(=O)c1c([C@@H]2C[C@H]3CC[C@@H](C2)N3C(=O)CO)nc2c(-c3ccc(C4(O)CCC4)nc3)cnn2c1N] | 1-((1R,3s,5S)-3-(6-acetyl-7-amino-3-(6-(1-hydroxycyclobutyl)pyridin-3-yl)pyrazolo[1,5-a]pyrimidin-5-yl)-8-azabicyclo[3.2.1]octan-8-yl)-2-hydroxyethanone | 491.24/491.5 | B | B |
| 7.19 | 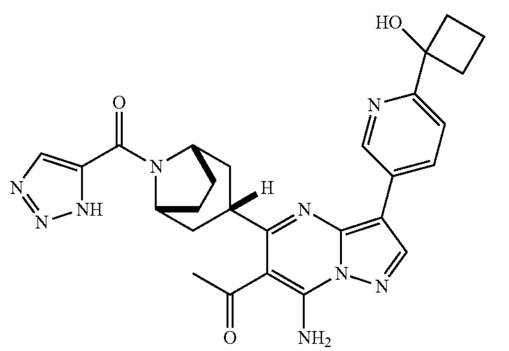 [SMILES: CC(=O)c1c([C@@H]2C[C@H]3CC[C@@H](C2)N3C(=O)c2cnn[nH]2)nc2c(-c3ccc(C4(O)CCC4)nc3)cnn2c1N] | 1-(5-((1R,3s,5S)-8-(1H-1,2,3-triazole-5-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone | 528.2/528.5 | B | ND |
| 7.20 | 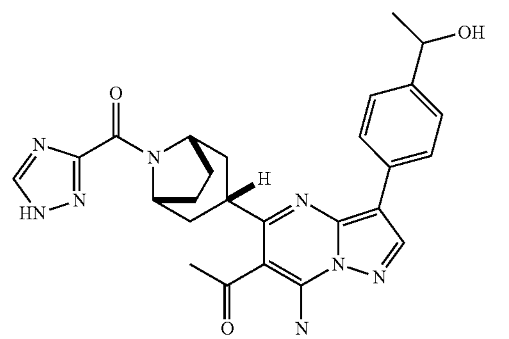 [SMILES: CC(=O)c1c([C@@H]2C[C@H]3CC[C@@H](C2)N3C(=O)c2nc[nH]n2)nc2c(-c3ccc(C(C)O)cc3)cnn2c1N] | 1-(5-((1R,3s,5S)-8-(1H-1,2,4-triazole-3-carbonyl)-8-azabicyclo[3.2.1]octan-3-yl)-7-amino-3-(4-(1-hydroxyethyl)phenyl)pyrazolo[1,5-a]pyrimidin-6-yl)ethanone | 501.2/501.1 | A | A |
| 7.21 | 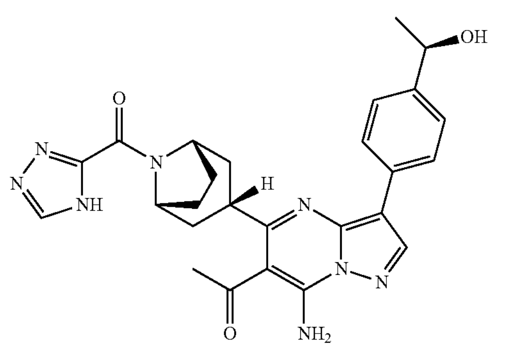 [SMILES: CC(=O)c1c([C@@H]2C[C@H]3CC[C@@H](C2)N3C(=O)c2nnc[nH]2)nc2c(-c3ccc([C@@H](C)O)cc3)cnn2c1N] | 1-(5-((1R,3s,5S)-8-(4H-1,2,4-triazole-3-carbonyl)-8-azabicyclo[3.2.1]octan-3-yl)-7-amino-3-(4-((R)-1-hydroxyethyl)phenyl)pyrazolo[1,5-a]pyrimidin-6-yl)ethanone | 501.2/501.1 | A | A |

TABLE 7-1-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.22 | 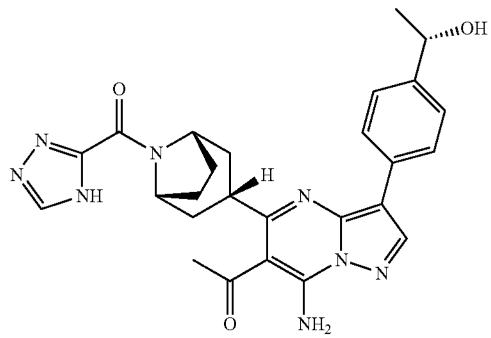 [SMILES: CC(=O)c1c([C@@H]2C[C@H]3CC[C@@H](C2)N3C(=O)c2nnc[nH]2)nc2c(-c3ccc([C@H](C)O)cc3)cnn2c1N] | 1-(5-((1R,3s,5S)-8-(4H-1,2,4-triazole-3-carbonyl)-8-azabicyclo[3.2.1]octan-3-yl)-7-amino-3-(4-((S)-1-hydroxyethyl)phenyl)pyrazolo[1,5-a]pyrimidin-6-yl)ethanone | 501.2/501.2 | A | A |
| 7.23 | 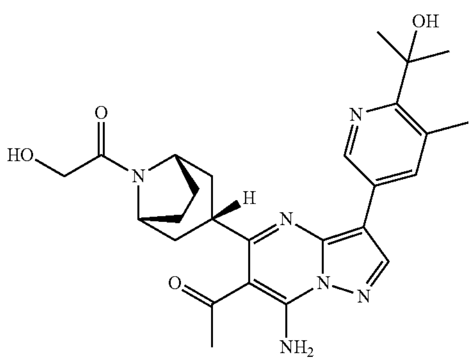 [SMILES: CC(=O)c1c([C@@H]2C[C@H]3CC[C@@H](C2)N3C(=O)CO)nc2c(-c3cnc(C(C)(C)O)c(C)c3)cnn2c1N] | 1-((1R,3s,5S)-3-(6-acetyl-7-amino-3-(6-(2-hydroxypropan-2-yl)-5-methylpyridin-3-yl)pyrazolo[1,5-a]pyrimidin-5-yl)-8-azabicyclo[3.2.1]octan-8-yl)-2-hydroxyethanone | 493.25/493.06 | B | B |
| 7.24 | 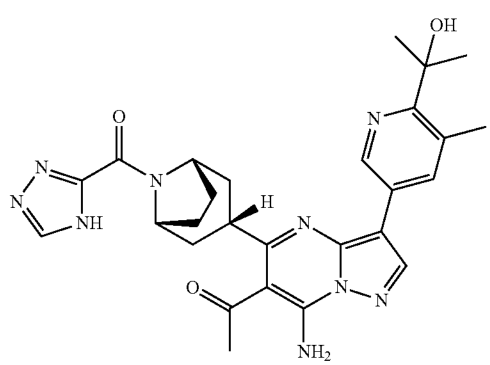 [SMILES: CC(=O)c1c([C@@H]2C[C@H]3CC[C@@H](C2)N3C(=O)c2nnc[nH]2)nc2c(-c3cnc(C(C)(C)O)c(C)c3)cnn2c1N] | 1-(5-((1R,3s,5S)-8-(4H-1,2,4-triazole-3-carbonyl)-8-azabicyclo[3.2.1]octan-3-yl)-7-amino-3-(6-(2-hydroxypropan-2-yl)-5-methylpyridin-3-yl)pyrazolo[1,5-a]pyrimidin-6-yl)ethanone | 530.25/530.10 | A | A |

Example 7-2

Preparation of ((1R,3s,5S)-3-(7-amino-3-(6-(2-hydroxypropan-2-yl)pyridin-3-yl-6-(methylsulfonyl)pyrazolo[1,5-a]pyrimidin-5-yl)-8-azabicyclo[3.2.1]octan-8-yl)(1H-1,2,4-triazol-5-yl)methanone

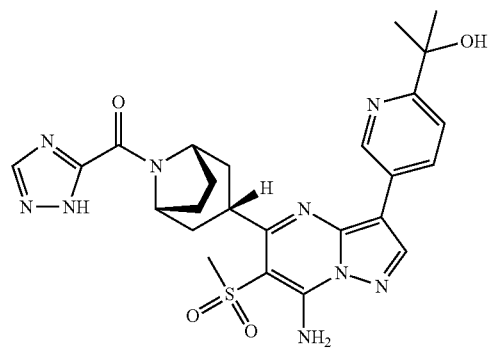

Step 1: Preparation of 2-(5-(7-amino-5-((1R,3s,5S)-8-azabicyclo[3.2.1]octan-3-yl-6-iodopyrazolo[1,5-a]pyrimidin-3-yl)pyridin-2-yl)propan-2-ol

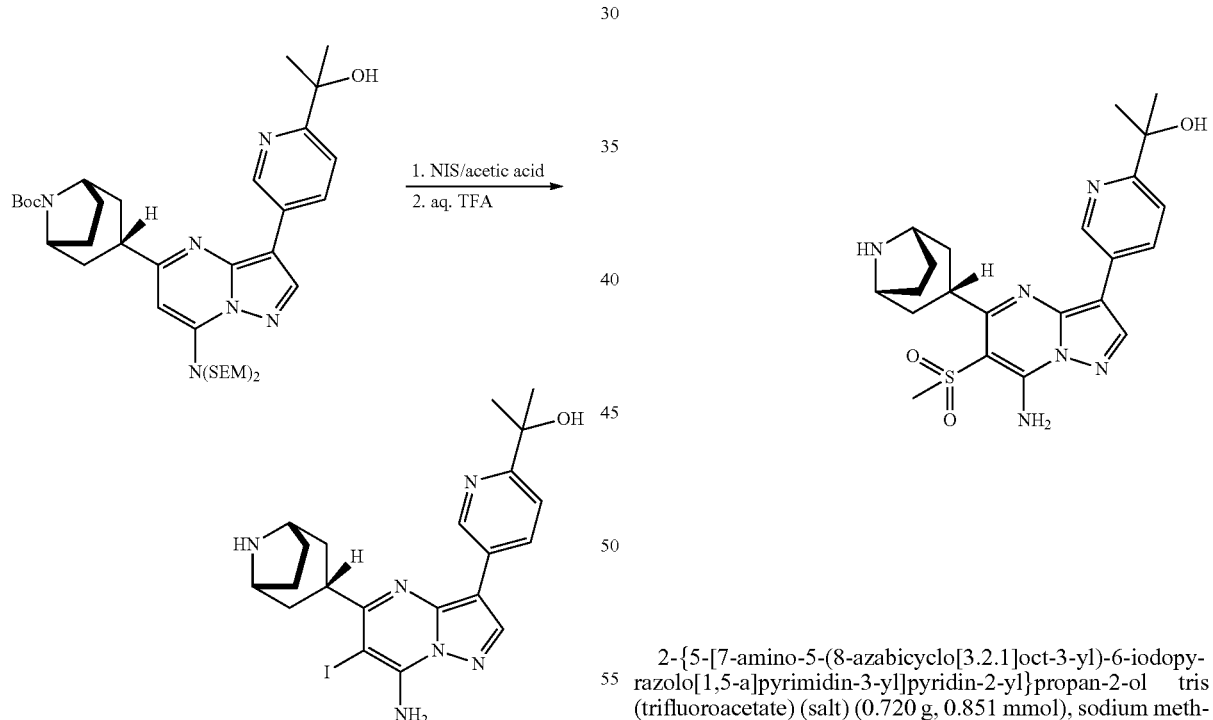

tert-butyl 3-{7-(bis{[2-(trimethylsilyl)ethoxy]methyl}amino)-3-[6-(1-hydroxy-1-methylethyl)pyridin-3-yl]pyrazolo[1,5-a]pyrimidin-5-yl}-8-azabicyclo[3.2.1]octane-8-carboxylate (1.01 g, 1.37 mmol) was dissolved in acetic acid (7.1 mL, 120 mmol) and N-Iodosuccinimide (368.3 mg, 1.637 mmol) was added in a single portion, and the reaction was monitored by HPLC. The reaction was complete in less than 10 minutes and the mixture was diluted with ethyl acetate and poured into a 1:1 mixture of sodium bicarbonate (sat'd) and sodium thiosulfate (20%). The layers were separated and the organics washed several times with sodium bicarbonate solution, then brine. The organics were dried with magnesium sulfate, filtered and concentrated to provide the desired material (860 mg) which was subsequently treated with aqueous TFA to afford the desired product as TFA salt following procedure described previously.

Step 2: preparation of 2-{5-[7-amino-5-(8-azabicyclo[3.2.1]oct-3-yl)-6-(methylsulfonyl)pyrazolo[1,5-a]pyrimidin-3-yl]pyridin-2-yl}propan-2-ol

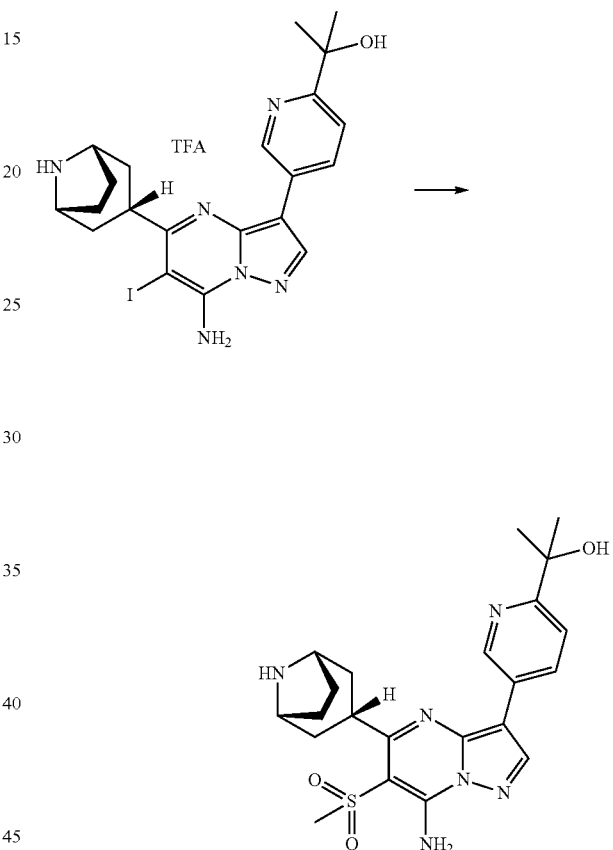

2-{5-[7-amino-5-(8-azabicyclo[3.2.1]oct-3-yl)-6-iodopyrazolo[1,5-a]pyrimidin-3-yl]pyridin-2-yl}propan-2-ol tris(trifluoroacetate) (salt) (0.720 g, 0.851 mmol), sodium methanesulfinate (306 mg, 2.55 mmol), and Copper(I) iodide (486 mg, 2.55 mmol) were dissolved/suspended in dry dimethyl sulfoxide (18 mL, 250 mmol) under a nitrogen atmosphere. The reaction was placed in an oil bath at 90° C. After mixing 15 min, HPLC showed the starting material to have been consumed and a mixture of the desired material:des-iodo material was observed. The reaction mixture was poured into a 7:3 mixture of sat'd NH$_4$Cl:20% NH$_4$OH (200 ml) and extracted 3×75 ml with 10% IPA in DCM. The combined organics were washed with brine, dried, filtered and evaporated to provide a yellow oil, which was purified by silica gel chromatography, eluted with 0-15% (10% NH₄OH in MeOH) in chloroform to provide the desired material as a yellow solid (319 mg).

Step 3: Synthesis of (((1R,3s,5S)-3-(7-amino-3-(6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone

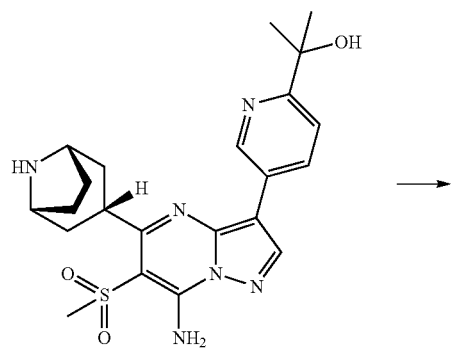

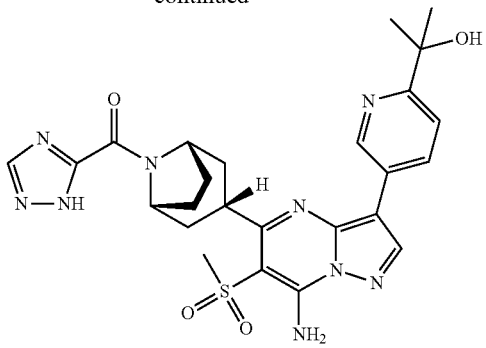

The title compound was prepared following standard amide coupling procedure described before.

The following compounds listed in Table 7-2 were prepared following procedures similar to the preparation of 1-(5-(((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone.

TABLE 7-2

| Compound ID | Structure | Compound Name | M + H (calculated)/ M + H (observed) | pAKT S473 IC50 | p4E-BP1 Thr37/46 IC50 |
|---|---|---|---|---|---|
| 7.25 | 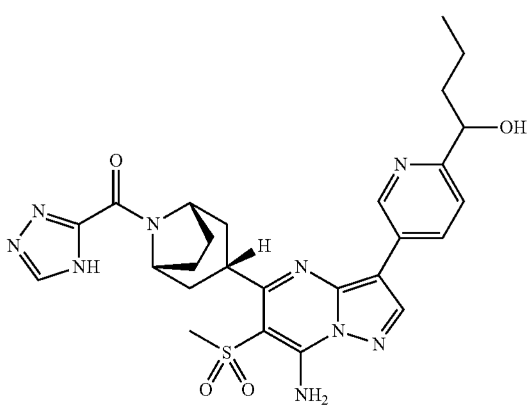 [SMILES: CCCC(O)c1ccc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-(1-hydroxybutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 566.2/ 566.5 | C | C |
| 7.26 | 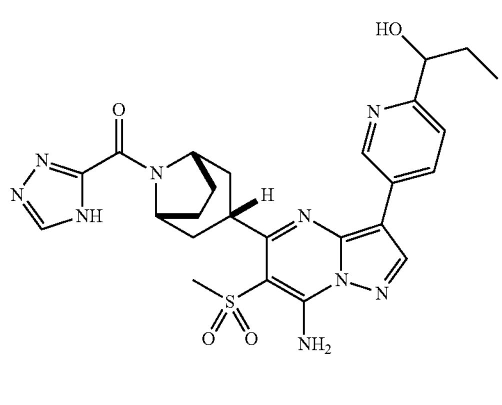 [SMILES: CCC(O)c1ccc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-(1-hydroxypropyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 552.2/ 552.2 | B | B |

TABLE 7-2-continued

| Compound ID | Structure | Compound Name | M + H (calculated)/ M + H (observed) | pAKT S473 IC50 | p4E-BP1 Thr37/46 IC50 |
|---|---|---|---|---|---|
| 7.27 | 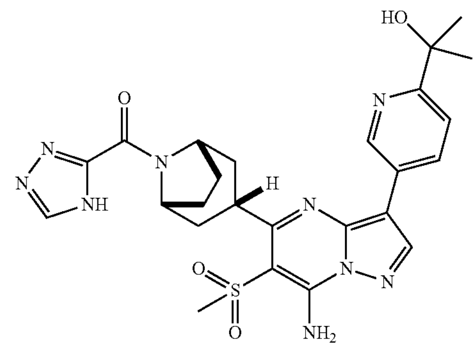 [SMILES: CC(C)(O)c1ccc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone | 552.23/ 552.2 | A | A |
| 7.28 | 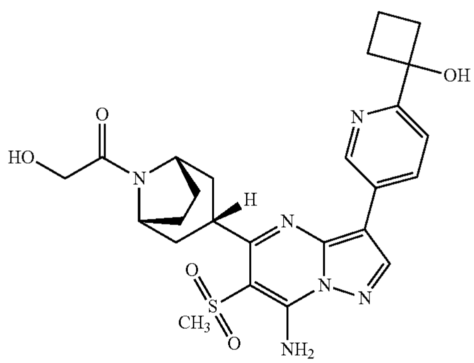 | 1-((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)-2-hydroxyethanone | 527.2/ 527.5 | B | ND |
| 7.29 | 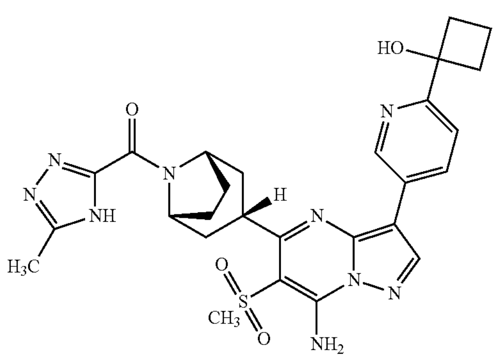 | ((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(3-methyl-1H-1,2,4-triazol-5-yl)methanone | 578.3/ 578.4 | B | B |
| 7.30 | 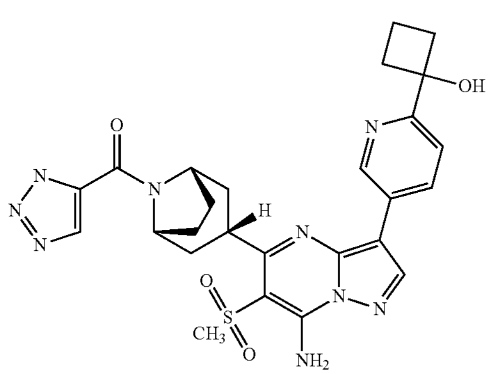 | ((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone | 563.2/ 564.4 | B | B |

Example 7-3

Preparation of
5-bromo-2-[(2-methoxyethoxy)methyl]pyridine

The title compound was prepared following the method for the preparation of 3-bromo-6-((R)-2-ethoxy-propoxymethyl)-2-propyl-pyridine reported by Herold, P.; Mah, R.; Tschinke, V.; Jelakovic, S.; Stutz, S.; and Marti, C. International Patent Application WO 2009/056617 A2, May 7, 2009. The following two compounds (Table 7-3) were prepared following similar procedures described before.

TABLE 7-3

| Compound ID | Structure | Compound Name | M + H (calculated)/ M + H (observed) | pAKT S473 IC50 | p4E-BP1 Thr37/46 IC50 |
|---|---|---|---|---|---|
| 7.31 | 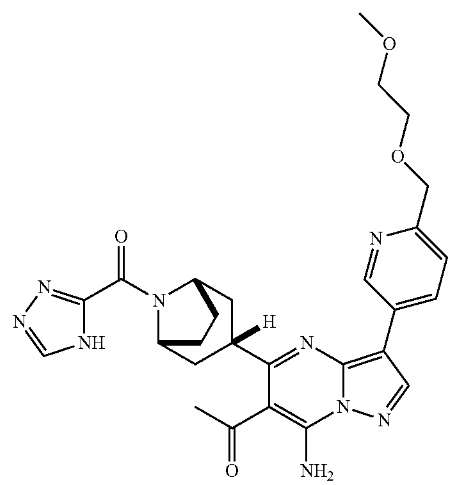 [SMILES: COCCOCc1ccc(-c2cnn3c(N)c(C(C)=O)c([C@@H]4C[C@H]5CC[C@@H](C4)N5C(=O)c4nnc[nH]4)nc23)cn1] | 1-(5-((1R,3s,5S)-8-(4H-1,2,4-triazole-3-carbonyl)-8-azabicyclo[3.2.1]octan-3-yl)-7-amino-3-(6-((2-methoxyethoxy)methyl)pyridin-3-yl)pyrazolo[1,5-a]pyrimidin-6-yl)ethanone | 546.3/546.3 | C | C |
| 7.32 | 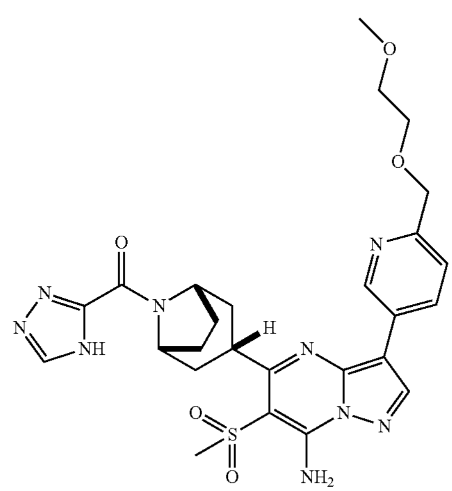 [SMILES: COCCOCc1ccc(-c2cnn3c(N)c(S(C)(=O)=O)c([C@@H]4C[C@H]5CC[C@@H](C4)N5C(=O)c4nnc[nH]4)nc23)cn1] | ((1R,3s,5S)-3-(7-amino-3-(6-((2-methoxyethoxy)methyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 582.23/582.4 | D | C |

Example 7-4

Preparation of (1S)-1-(5-bromopyridin-2-yl)ethanol

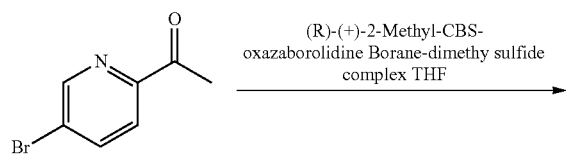

(R)-(+)-2-Methyl-CBS-oxazaborolidine Borane-dimethy sulfide complex THF

The (R)-(+)-2-Methyl-CBS-oxazaborolidine (2.08 g, 7.5 mmol) was dissolved in THF (10 mL), cooled to 0° C. and borane-dimethyl sulfide complex (2 M solution in THF, 7.50 mL, 15.0 mmol, 2.0 equiv.) was added dropwise. The resulting solution was stirred for 1 hour, then cooled to −40° C. and a solution of 1-(5-bromopyridin-2-yl)ethanone in THF (8.0 mL) was added dropwise over 5 min. A white precipitate formed toward the end of the addition. The slurry was stirred for 1 hour, warmed to −10° C., and stirred for another 60 min at this temperature. Analysis of the solution (HPLC) showed >95% conversion to the desired product. The reaction was poured into ethyl acetate (100 mL), washed with saturated ammonium chloride, water, and brine (50 ml each), dried over magnesium sulfate, filtered, and concentrated by rotary evaporation. The residual oil was purified by flash chromatography over silica gel (90 g), eluting with 40% ethyl acetate in hexanes to give the title compound (1.34 g) as a colorless oil.

The following two compounds (Table 7-4) were prepared following similar procedures described before.

TABLE 7-4

| Compound ID | Structure | Compound Name | M + H (calculated)/ M + H (observed) | pAKT S473 IC50 | p4E-BP1 Thr37/46 IC50 |
|---|---|---|---|---|---|
| 7.33 | 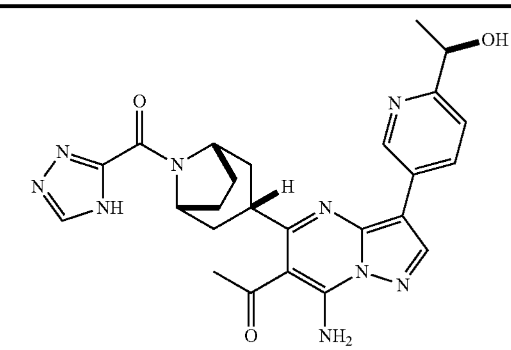 | 1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone | 502.2/ 502.4 | B | B |
| 7.34 | 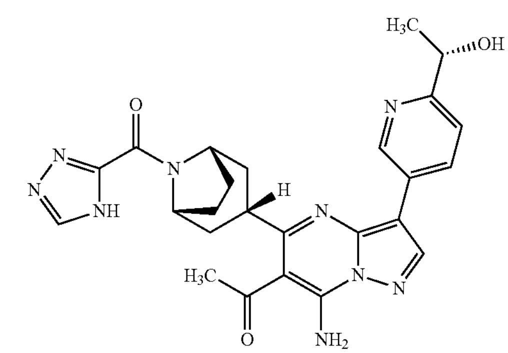 [SMILES: CC(=O)c1c([C@@H]2C[C@H]3CC[C@@H](C2)N3C(=O)c2nnc[nH]2)nc2c(-c3ccc([C@H](C)O)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-((S)-1-hydroxyethyl)pyridin-3-yl)pyrazolo[1,5-a]pyrimidin-6-yl)ethanone | 502.3/ 502.4 | A | A |

-continued

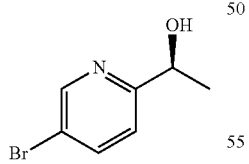

Example 7-5

Preparation of (5-bromopyridin-2-yl)methanol

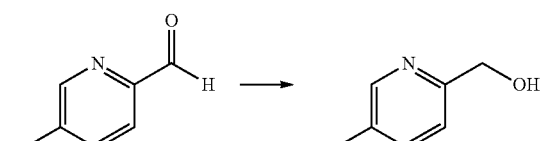

The commercially available 5-bromopyridine-2-carbaldehyde (2.0 g, 10.8 mmol) was dissolved in methanol (60 mL) and solid sodium borohydride (407 mg, 10.8 mmol) was added at 20° C. The reaction was stirred 30 minutes then the solvent was removed and 25 mL of saturated ammonium chloride solution was added and the reaction was extracted with 200 mL EtOAc which was washed with water and brine, 30 mL each. The organic phase was dried over magnesium sulfate and filtered through a 2 cm silica gel pad. The clear filtrate was concentrated by rotary evaporation to give a white solid, 1.99 g which was used as is.

The following compound (Table 7-5) was prepared following similar procedures described before.

A mixture of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (2.95 g, 4.04 mmol, preparation described previously), 5-(tributylstannyl)thiazole (3.02 g, 8.08 mmol), Pd(PPh$_3$)$_4$ (934 mg, 0.81 mmol) in dioxane (40 mL) was stirred at 100° C. under Argon for 2 h. The reaction mixture was concentrated and

TABLE 7-5

| Compound ID | Structures | Compound Name | M + H (calculated)/ M + H (observed) | pAKT S473 IC50 | p4E-BP1 Thr37/46 IC50 |
|---|---|---|---|---|---|
| 7.35 | 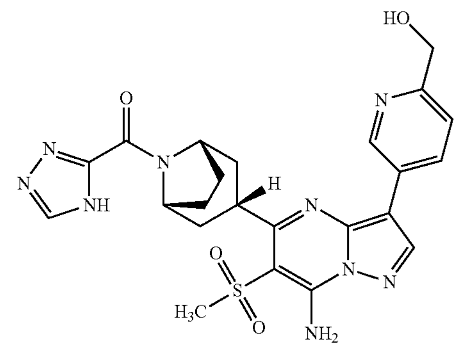 [SMILES: CS(=O)(=O)c1c([C@@H]2C[C@H]3CC[C@@H](C2)N3C(=O)c2nnc[nH]2)nc2c(-c3ccc(CO)nc3)cnn2c1N] | ((1R,3s,5S)-3-(7-amino-3-(6-(hydroxymethyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 524.2/ 524.3 | B | B |

Example 7-6

Preparation of 1-(5-(((1R,3s,5S)-8-(4H-1,2,4-triazole-3-carbonyl)-8-azabicyclo[3.2.1]octan-3-yl)-7-amino-3-(2-(1-hydroxyethyl)thiazol-5-yl)pyrazolo[1,5-a]pyrimidin-6-yl)ethanone Step 1: Preparation of (1R,3s,5S)-tert-butyl 3-(7-(bis((2-(trimethylsilyl)ethoxy)methyl)amino)-3-(thiazol-5-yl)pyrazolo[1,5-a]pyrimidin-5-yl)-8-azabicyclo[3.2.1]octane-8-carboxylate

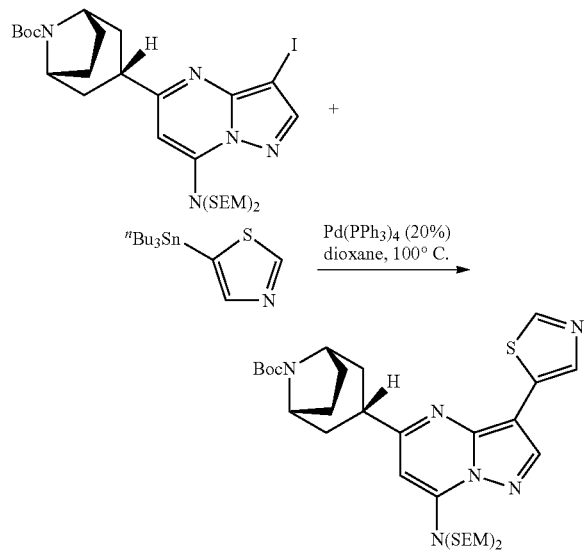

purified by a SiO$_2$ column (0-40% EtOAc/Hexanes, R$_f$=0.5 in 50% EtOAc) to afford the titled compound as a brownish oil (514 mg).

Step 2: Preparation of (1R,3s,5S)-tert-butyl 3-(7-(bis((2-(trimethylsilyl)ethoxy)methyl)amino)-3-(2-(1-hydroxyethyl)thiazol-5-yl)pyrazolo[1,5-a]pyrimidin-5-yl)-8-azabicyclo[3.2.1]octane-8-carboxylate

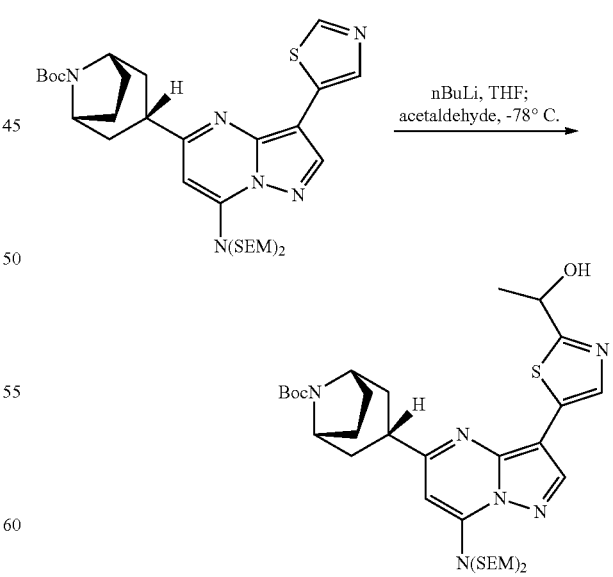

To a solution of (1R,3s,5S)-tert-butyl 3-(7-(bis((2-(trimethylsilyl)ethoxy)methyl)amino)-3-(thiazol-5-yl)pyrazolo[1,5-a]pyrimidin-5-yl)-8-azabicyclo[3.2.1]octane-8-carboxylate (290 mg, 0.422 mmol) in THF (3 mL) was added n-BuLi (1.1 eq) dropwise at −78° C. The mixture was warmed to −50° C. and kept for 30 min before recooling to −78° C. A solution of acetaldehyde (71 uL, 1.27 mmol) in THF (2 mL) was added dropwise. The reaction mixture was slowly warmed to rt and stirred for 30 min. The reaction was quenched with H₂O and extracted with EtOAc, washed with brine, dried over Na₂SO₄ and concentrated. The crude product was purified by a SiO₂ column (0-50% EtOAc/Hexanes, $R_f$=0.3 in 50% EtOAc) to afford the titled compound as a yellow solid (210 mg).

Step 3: Preparation of 1-(5-(((1R,3s,5S)-8-(4H-1,2,4-triazole-3-carbonyl)-8-azabicyclo[3.2.1]octan-3-yl)-7-amino-3-(2-(1-hydroxyethyl)thiazol-5-yl)pyrazolo[1,5-a]pyrimidin-6-yl)ethanone

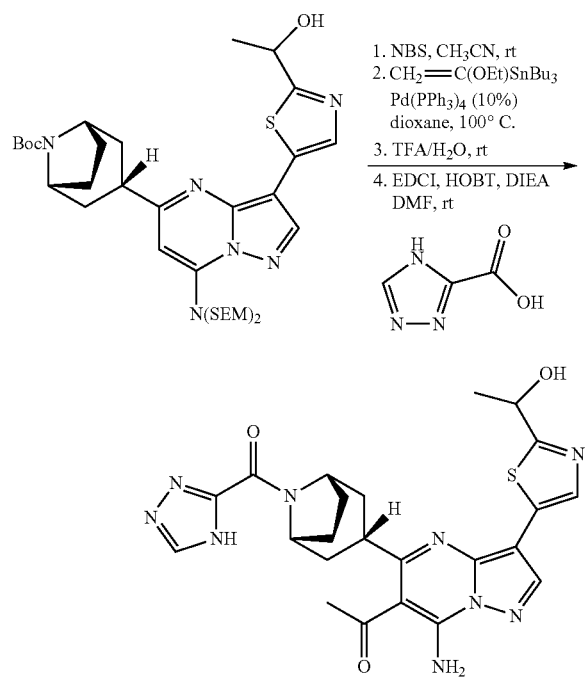

This compound was prepared from (1R,3s,5S)-tert-butyl 3-(7-(bis((2-(trimethylsilyl)ethoxy)methyl)amino)-3-(2-(1-hydroxyethyl)thiazol-5-yl)pyrazolo[1,5-a]pyrimidin-5-yl-8-azabicyclo[3.2.1]octane-8-carboxylate, following essentially the same procedures given in previous examples.

Example 7-7

Preparation of ((1R,3s,5S)-3-(7-amino-3-(2-(1-hydroxyethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone Step 1: Preparation of (1R,3s,5S)-tert-butyl 3-(7-(bis((2-(trimethylsilyl)ethoxy)methyl)amino)-3-(2-(1-hydroxyethyl)thiazol-5-yl)-6-iodopyrazolo[1,5-a]pyrimidin-5-yl)-8-azabicyclo[3.2.1]octane-8-carboxylate

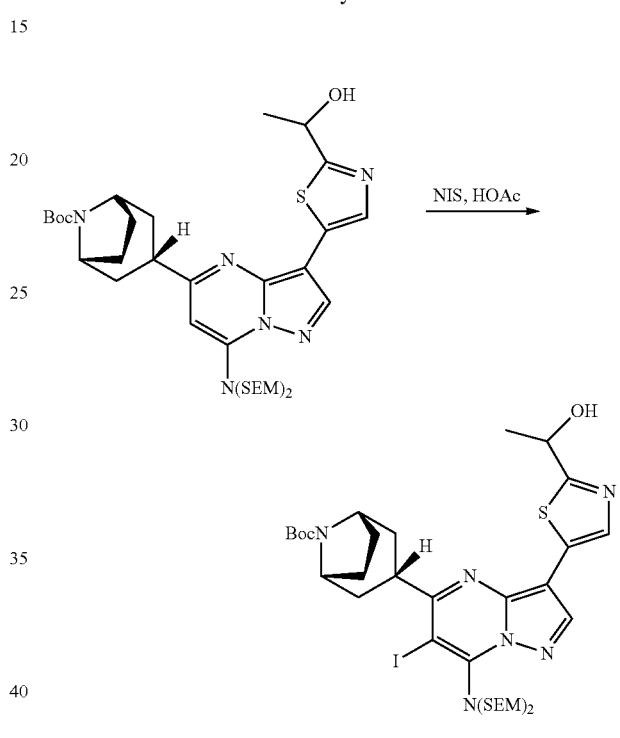

To a solution of (1R,3s,5S)-tert-butyl 3-(7-(bis((2-(trimethylsilyl)ethoxy)methyl)amino)-3-(2-(1-hydroxyethyl)thiazol-5-yl)pyrazolo[1,5-a]pyrimidin-5-yl)-8-azabicyclo[3.2.1]octane-8-carboxylate (131 mg, 0.179 mmol) in HOAc (3 mL) was added NIS (48.4 mg, 0.215 mmol) and stirred at it for 30 min. HOAc was removed under reduced pressure and the residue was purified by a SiO₂ column (0-40% EtOAc/

TABLE 7-6

| 7.36 | | | | |
|---|---|---|---|---|
| | | 1-(5-(((1R,3s,5S)-8-(4H-1,2,4-triazole-3-carbonyl)-8-azabicyclo[3.2.1]octan-3-yl)-7-amino-3-(2-(1-hydroxyethyl)thiazol-5-yl)pyrazolo[1,5-a]pyrimidin-6-yl)ethanone | 508.2/508.1 | C C |

Hexanes, $R_f$=0.7 in 50% EtOAc) to afford the titled compound as a pale yellow oil (116 mg).

Step 2: Preparation of (1R,3s,5S)-tert-butyl 3-(7-(bis((2-(trimethylsilyl)ethoxy)methyl)amino)-3-(2-(1-hydroxyethyl)thiazol-5-yl)-6-(methylsulfonyl)pyrazolo[1,5-a]pyrimidin-5-yl)-8-azabicyclo[3.2.1]octane-8-carboxylate

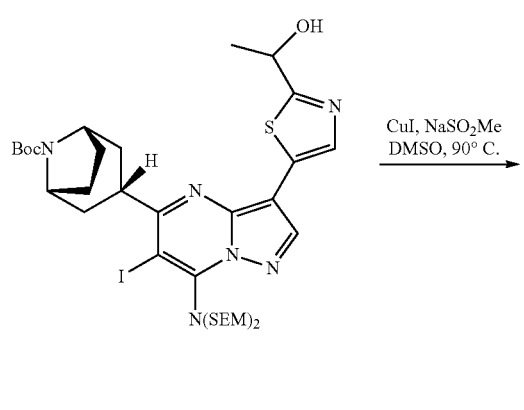

A mixture of (1R,3s,5S)-tert-butyl 3-(7-(bis((2-(trimethylsilyl)ethoxy)methyl)amino)-3-(2-(1-hydroxyethyl)thiazol-5-yl)-6-iodopyrazolo[1,5-a]pyrimidin-5-yl)-8-azabicyclo[3.2.1]octane-8-carboxylate (116 mg, 0.135 mmol), MeSO₂Na (41.5 mg, 0.406 mmol), and CuI (154 mg, 0.810 mmol) in DMSO (1.3 mL) was heated at 90° C. for 2 h. The reaction mixture was diluted with 15 mL of EtOAc and filtered through a short pad of celite and washed with extra EtOAc. The combined filtrate was washed with NH₄Cl and then brine, dried over Na₂SO₄, and concentrated. The crude product was purified by a SiO₂ column (0-40% EtOAc/Hexanes, $R_f$=0.4 in 50% EtOAc) to afford the titled product as a colorless oil (90.0 mg).

Step 3: Preparation of ((1R,3s,5S)-3-(7-amino-3-(2-(1-hydroxyethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone

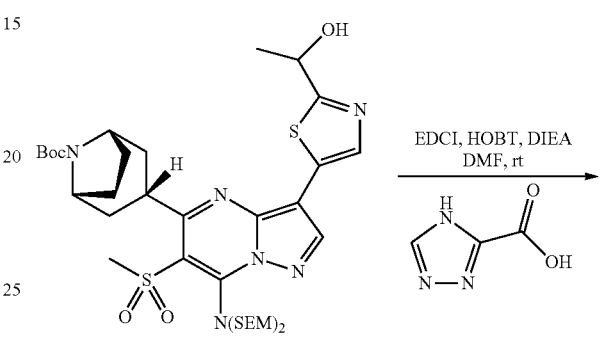

This compound was prepared from (3-(7-amino-5-((1R,3s,5S)-8-azabicyclo[3.2.1]octan-3-yl)-6-(methylsulfonyl)pyrazolo[1,5-a]pyrimidin-3-yl)quinolin-7-yl)methanol TFA salt following essentially the same procedure given previously.

TABLE 7-7

| | | | | |
|---|---|---|---|---|
| 7.37 | 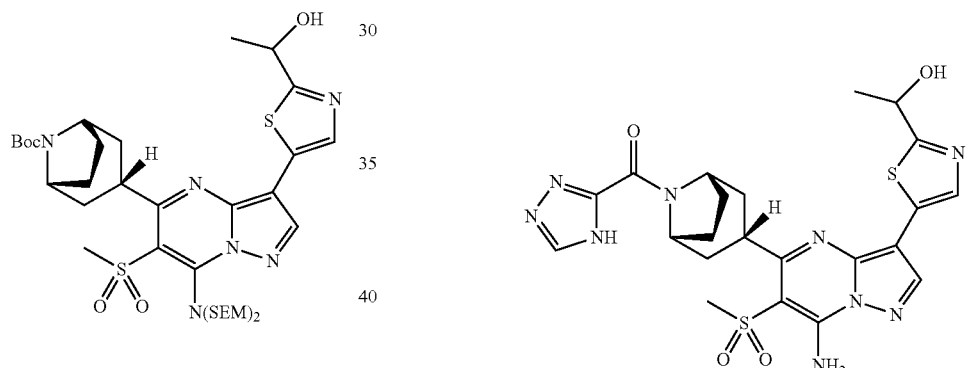 | ((1R,3s,5S)-3-(7-amino-3-(2-(1-hydroxyethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 544.2/ 544.2 | ND ND |

Example 7-8

Preparation of 1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone

Step 1: Preparation of 1-(5-bromopyridin-2-yl)cyclobutanol

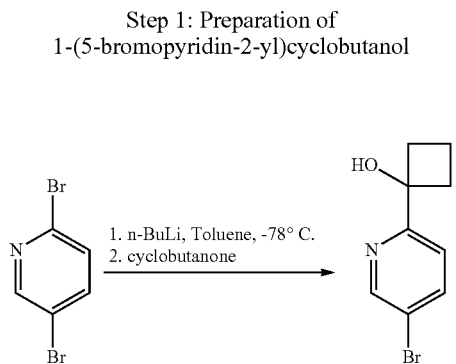

To a solution of 2,5-dibromopyridine (4.74 g, 20.0 mmol) in toluene (200 mL) was added n-BuLi (1.2 eq) dropwise at −50° C. The mixture was stirred at that temperature for 40 min, then cooled to −78° C. before cyclobutanone (1.82 g, 26.0 mmol) was added dropwise. The reaction mixture was stirred at −78° C. for 1 h, then warmed to 0° C. and quenched with 40 mL of NH$_4$Cl (sat.). The organic layer was separated and concentrated. The crude product was purified by a SiO$_2$ column (0-40% EtOAc/Hexanes, R$_f$=0.7 in 50% EtOAc) to afford the titled compound as a red oil (3.11 g).

Step 2: Preparation of 1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone

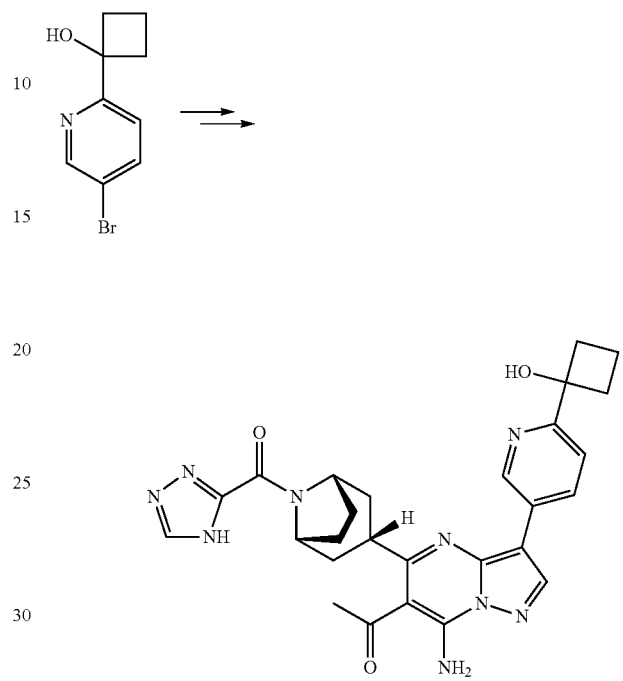

This compound was prepared from 1-(5-bromopyridin-2-yl)cyclobutanol, following essentially the same procedures given previously. Compounds in Table 7-8 were made in a similar way.

TABLE 7-8

| Compound ID | Structures | Compound Name | M + H (calculated)/ M + H (observed) | pAKT S473 IC50 | p4E-BP1 Thr37/46 IC50 |
|---|---|---|---|---|---|
| 7.38 | 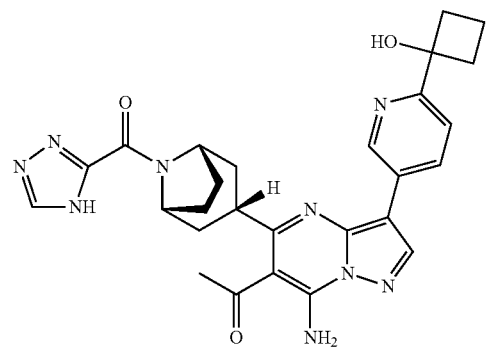 | 1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone | 528.2/ 528.3 | A | A |

TABLE 7-8-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.39 | 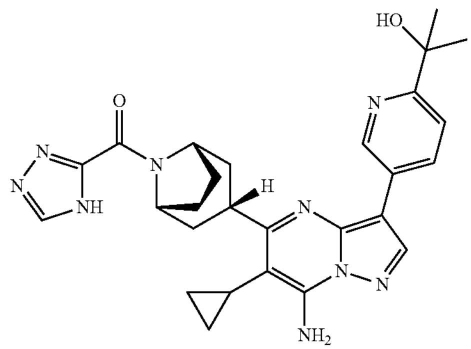 | ((1R,3s,5S)-3-(7-amino-6-cyclopropyl-3-(6-(2-hydroxypropan-2-yl)pyridin-3-yl)pyrazolo[1,5-a]pyrimidin-5-yl)-8-azabicyclo[3.2.1]octan-8-yl)(4H-1,2,4-triazol-3-yl)methanone | 514.3/ 514.2 | A | A |
| 7.40 | 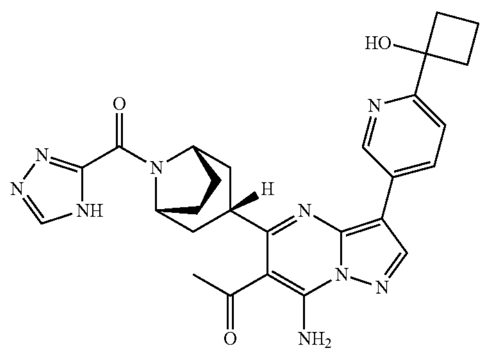 | 1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone | 528.2/ 528.3 | A | A |
| 7.41 | 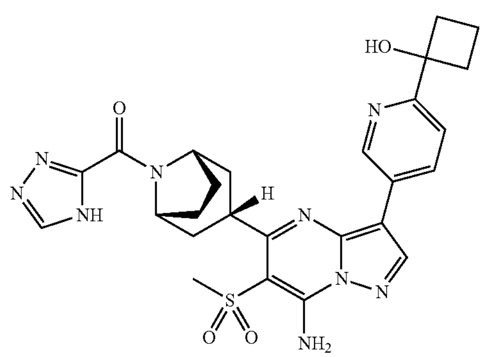 | ((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 564.2/ 564.1 | A | A |
| 7.42 | 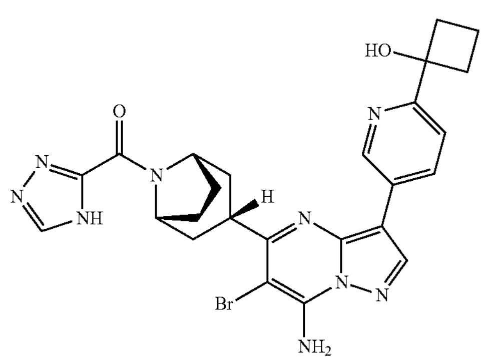 | ((1R,3s,5S)-3-(7-amino-6-bromo-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone | 564.1/ 564.1 | C | B |

TABLE 7-8-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.43 | 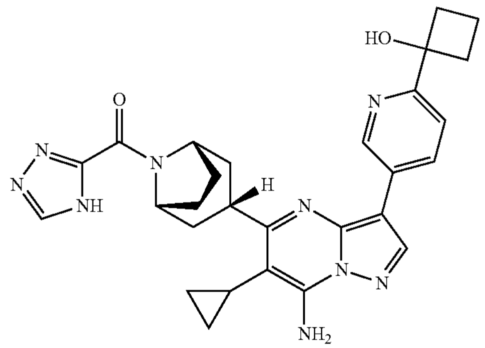 | ((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone | 526.3/ 526.2 | B | B |
| 7.44 | 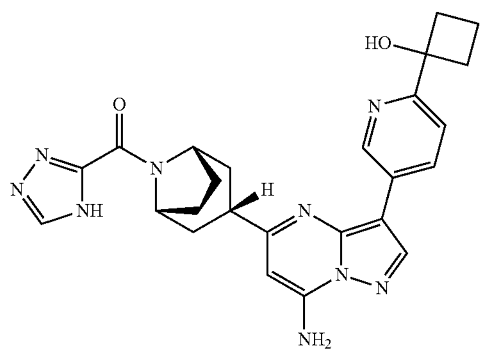 | ((1R,3s,5S)-3-(7-amino-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone | 486.2/ 486.2 | ND | C |
| 7.45 | 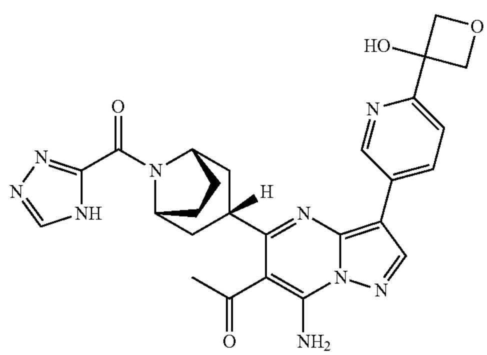 | 1-(5-((1R,3s,5S)-8-(4H-1,2,4-triazole-3-carbonyl)-8-azabicyclo[3.2.1]octan-3-yl)-7-amino-3-(6-(3-hydroxyoxetan-3-yl)pyridin-3-yl)pyrazolo[1,5-a]pyrimidin-6-yl)ethanone | 530.2/ 530.2 | B | B |
| 7.46 | 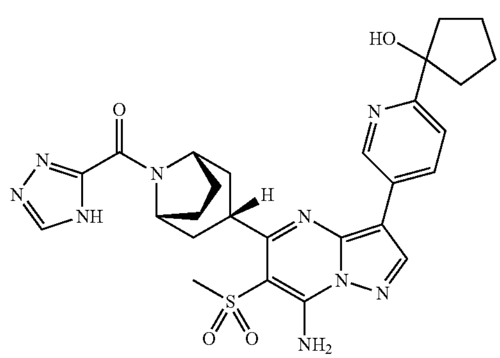 | ((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 578.2/ 578.2 | A | A |

TABLE 7-8-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.47 | 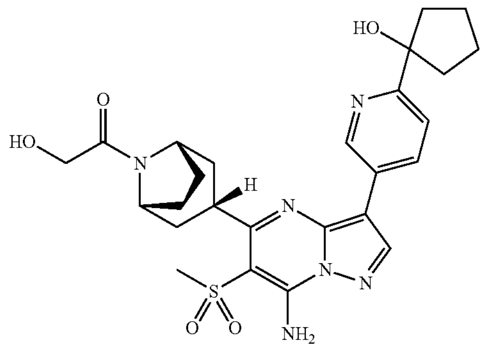 | 1-((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)-2-hydroxyethanone | 541.2/ 541.2 | B | B |
| 7.48 | 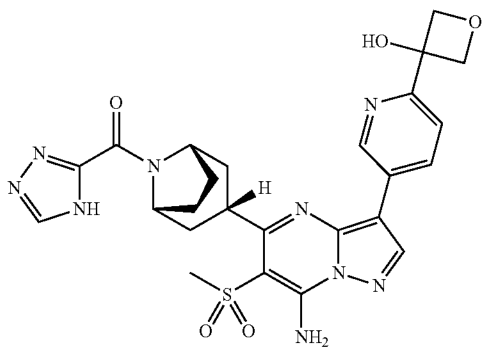 | ((1R,3s,5S)-3-(7-amino-3-(6-(3-hydroxyoxetan-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 566.2/ 566.0 | C | C |
| 7.49 | 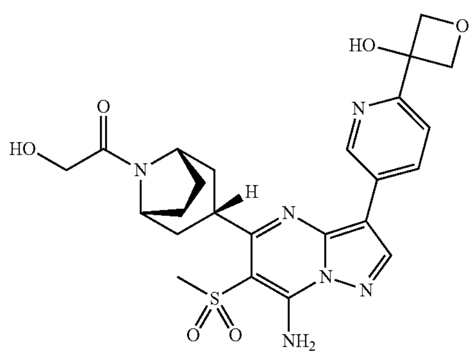 | 1-((1R,3s,5S)-3-(7-amino-3-(6-(3-hydroxyoxetan-3-yl)pyridin-3-yl)-6-(methylsulfonyl)pyrazolo[1,5-a]pyrimidin-5-yl)-8-azabicyclo[3.2.1]octan-8-yl)-2-hydroxyethanone | 529.2/ 529.2 | C | C |
| 7.50 | 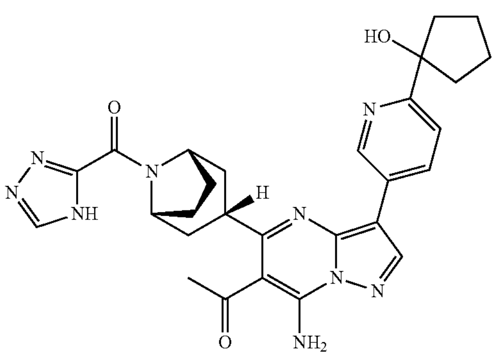 | 1-(5-((1R,3s,5S)-8-(4H-1,2,4-triazole-3-carbonyl)-8-azabicyclo[3.2.1]octan-3-yl)-7-amino-3-(6-(1-hydroxycyclopentyl)pyridin-3-yl)pyrazolo[1,5-a]pyrimidin-6-yl)ethanone | 542.3/ 542.2 | A | A |

TABLE 7-8-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.51 | 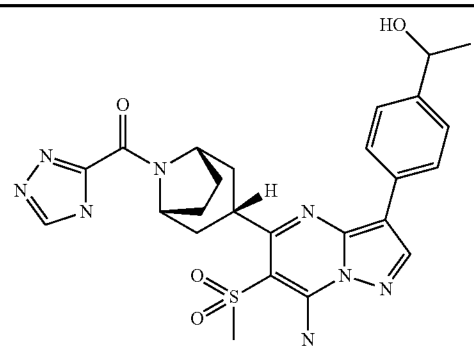 | ((1R,3s,5S)-3-(7-amino-3-(4-(1-hydroxyethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone | 537.2/ 537.0 | A | A |

Example 7-9

Preparation of 1-(5-((1R,3s,5S)-8-(4H-1,2,4-triazole-3-carbonyl)-8-azabicyclo[3.2.1]octan-3-yl)-7-amino-3-(6-(1,2-dihydroxyethyl)pyridin-3-yl)pyrazolo[1,5-a]pyrimidin-6-yl)ethanone Step 1: Preparation of (1R,3s,5S)-tert-butyl 3-(7-(bis((2-(trimethylsilyl)ethoxy)methyl)amino)-3-(6-vinylpyridin-3-yl)pyrazolo[1,5-a]pyrimidin-5-yl)-8-azabicyclo[3.2.1]octane-8-carboxylate A mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.63 g, 2.28 mmol, preparation described previously), tributyl(vinyl)stannane (1.33 mL, 4.56 mmol), Pd(PPh3)4 (263 mg, 0.228 mmol) in dioxane (20 mL) was stirred at 100° C. under Argon for 16 h. The reaction mixture was concentrated and purified by a SiO2 column (0-40% EtOAc/Hexanes, Rf=0.75 in 50% EtOAc) to afford the titled compound as pale yellow solid (1.48 g).

Step 2: Preparation of (1R,3s,5S)-tert-butyl 3-(7-(bis((2-(trimethylsilyl)ethoxy)methyl)amino)-3-(6-(1,2-dihydroxyethyl)pyridin-3-yl)pyrazolo[1,5-a]pyrimidin-5-yl)-8-azabicyclo[3.2.1]octane-8-carboxylate

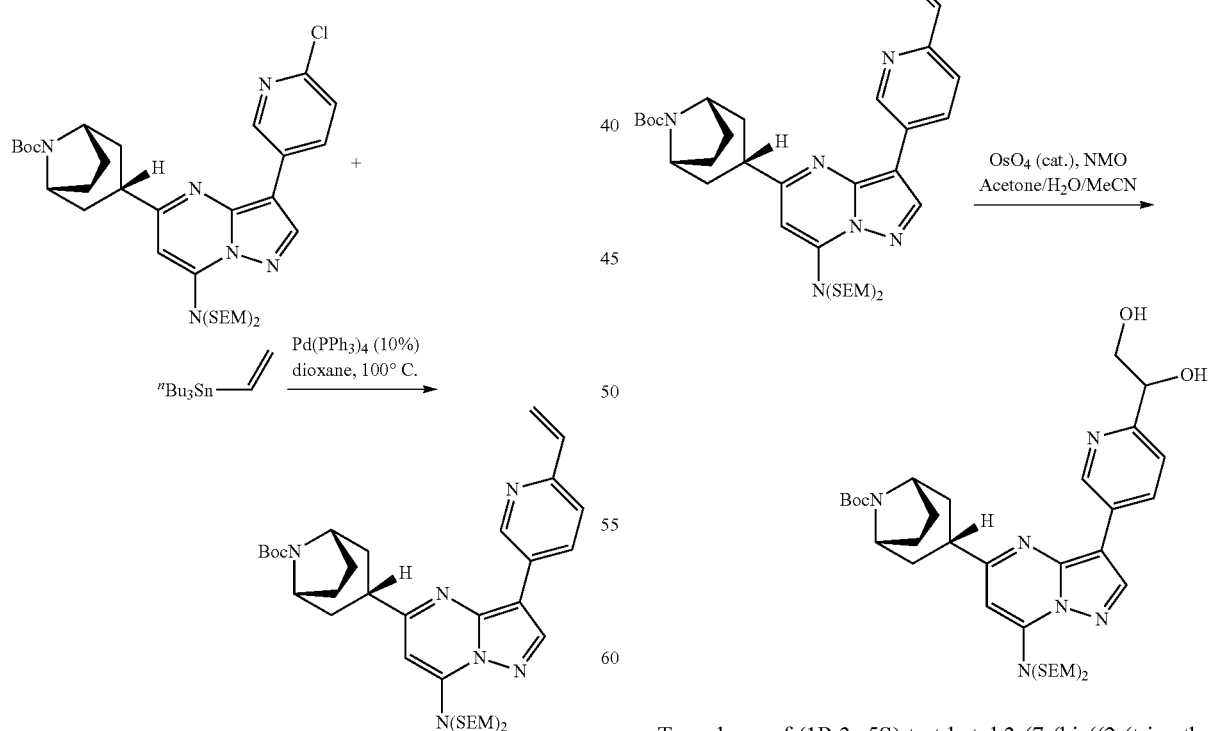

To a slurry of (1R,3s,5S)-tert-butyl 3-(7-(bis((2-(trimethylsilyl)ethoxy)methyl)amino)-3-(6-vinylpyridin-3-yl)pyrazolo[1,5-a]pyrimidin-5-yl)-8-azabicyclo[3.2.1]octane-8-carboxylate (1.48 g, 2.09 mmol) in Acetone/H2O/MeCN (12/4/4 mL) was added NMO (50 wt. % in H2O, 0.867 mL, 4.18 mmol), followed by OsO₄ (2.5 wt. % in ᵗBuOH, 1.31 mL, 0.105 mmol) at rt. The resulting reaction mixture was stirred at it overnight. The organic solvents were evaporated and the aqueous residue was extracted with EtOAc (×3). The combined organic layers were dried over Na₂SO₄, concentrated, and purified by a SiO₂ column (0-100% EtOAc/Hexanes, R$_f$=0.1 in 50% EtOAc) to afford the titled compound as a brownish oil (176 mg).

Step 3: Preparation of 1-(5-((1R,3s,5S)-8-(4H-1,2,4-triazole-3-carbonyl)-8-azabicyclo[3.2.1]octan-3-yl)-7-amino-3-(6-(1,2-dihydroxyethyl)pyridin-3-yl)pyrazolo[1,5-a]pyrimidin-6-yl)ethanone

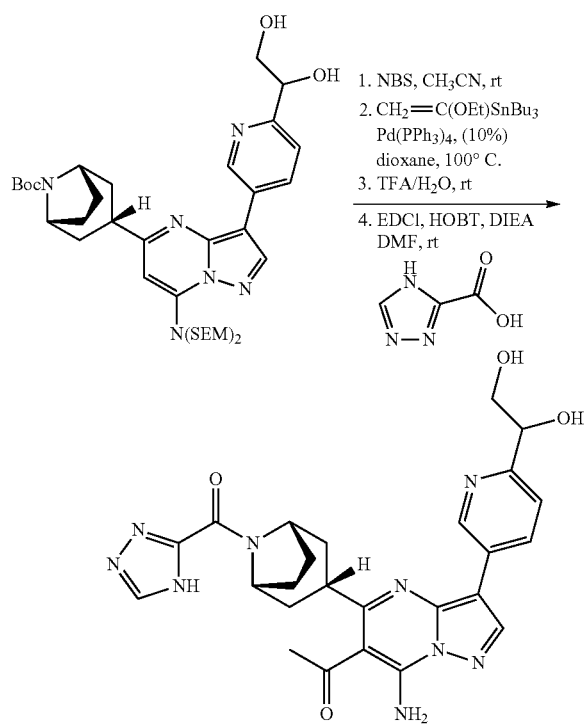

This compound was prepared from (1R,3s,5S)-tert-butyl 3-(7-(bis((2-(trimethylsilyl)ethoxy)methyl)amino)-3-(6-(1,2-dihydroxyethyl)pyridin-3-yl)pyrazolo[1,5-a]pyrimidin-5-yl)-8-azabicyclo[3.2.1]octane-8-carboxylate, following essentially the same procedures given in previous examples.

Example 7-10

Preparation of 8-(tert-butyldimethylsilyloxy)-3-(4,4,5,5-tetramethyl-1,3,2-dioxaborolan-2-yl)-5,6,7,8-tetrahydroquinoline Step 1: Synthesis of 8-(tert-butyldimethylsilyloxy)-5,6,7,8-tetrahydroquinoline

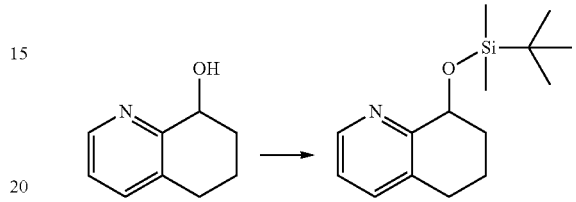

To a cooled (0° C.) solution of tetrahydro-quinolin-8-ol (1.0 g, 6.7 mmol) and imidazole (1.0 g, 14.74 mmol) in anhydrous DMF was added TBS-Cl (1.1 g, 7.4 mmol). The reaction mixture was stirred at room temperature for 12 h. Added ethylacetate (20 mL). The organic layer was washed with H₂O (3×10 mL). Dried over sodium sulfate and filtered. The organic layer was concentrated in vacuo and purification of the crude material via Isco (10-20% ethyl acetate/hexanes) gave rise to the desired tetrahydro-quinolin-8-OTBS (1.76 g) in quantitative yield.

Step 2: Synthesis of 8-(tert-butyldimethylsilyloxy)-3-(4,4,5,5-tetramethyl-1,3,2-dioxaborolan-2-yl-5,6,7,8-tetrahydroquinoline

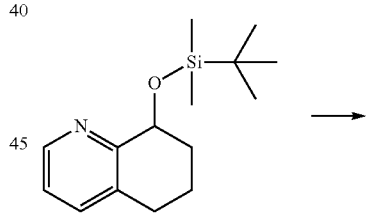

TABLE 7-9

| 7.52 | ![structure] | 1-(5-((1R,3s,5S)-8-(4H-1,2,4-triazole-3-carbonyl)-8-azabicyclo[3.2.1]octan-3-yl)-7-amino-3-(6-(1,2-dihydroxyethyl)pyridin-3-yl)pyrazolo[1,5-a]pyrimidin-6-yl)ethanone | 518.2/ 518.2 | C | C |

-continued

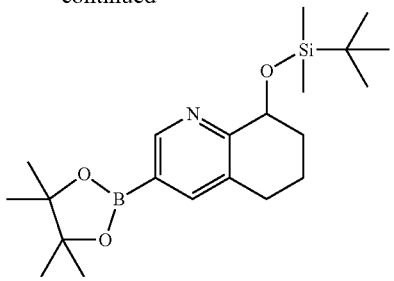

To a solution of 8-(tert-butyldimethylsilyloxy)-5,6,7,8-tetrahydroquinoline (1.0 g, 3.8 mmol), bispinacolatodiboron (1.4 g, 5.32 mmol), 4,4'-di-tert-butyl-2-2' dipyridyl (126 mg, 0.19 mmol) in MTBE (10 mL) was added 1,5 cyclooctadiene (methoxy) Iridium(I)dimer (51 mg, 0.19 mmol). The reaction mixture was degassed before heating at 90° C. in a sealed tube for 8 h. The mixture was cooled to room temperature and was concentrated in vacuo. Purification of the crude material via Isco (20-30-50% ethyl acetate/hexanes) gave rise to the desired boronic ester (1.08 g).

Example 7-11

Synthesis of tetrahydro-quinolin-8-D-8-ol

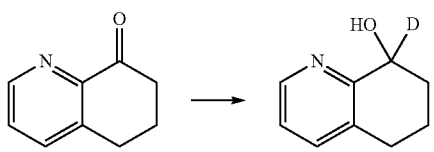 [SMILES: O=C1CCCc2cccnc21 ; [2H]C1(O)CCCc2cccnc21]

To a cooled (0° C.) solution of 6,7-dihydroquinolin-8(5H)-one (1.0 g, 6.8 mmol) in anhydrous THF:MeOH (10 mL, 1:4) was added NaBD$_4$ (342 mg, 8.16 mmol). The reaction mixture was stirred at 0° C. for 20 minutes and stirring was continued at room temperature for 2 h. The reaction mixture was quenched with saturated ammonium chloride (2 mL). The mixture was extracted with ethylacetate (3×10 mL). Dried over sodium sulfate and filtered. The organic layer was concentrated in vacuo and purification of the crude material via Isco (50% ethyl acetate/hexanes) gave rise to the desired alcohol (1.02 g).

Example 7-12

Synthesis of 8-(tert-butyldimethylsilyloxy)-8-methyl-5,6,7,8-tetrahydroquinoline Step 1: Synthesis of 8-methyl-5,6,7,8-tetrahydroquinolin-8-ol

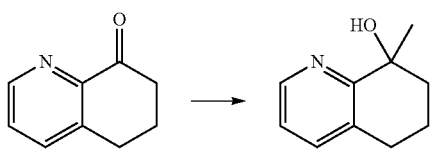

To a cooled (0° C.) solution of the ketone (1.4 g, 9.52 mmol) in anhydrous THF (50 mL) was added 1.4M of MeMgBr (10.2 mL, 14.3 mmol). The reaction mixture was stirred at 0° C. for 10 minutes and stirring was continued at room temperature for 2 h. The reaction mixture was cooled to 0° C. and CH$_2$Cl$_2$ (5 mL) was added. The reaction was quenched with H$_2$O (2-5 mL) and extracted with ethylacetate (3×10 mL). Dried over sodium sulfate and filtered. The organic layer was concentrated in vacuo and purification of the crude material via Isco (30% ethyl acetate/hexanes) gave rise to the desired alcohol (477 mg).

Step 2: Synthesis of 8-(tert-butyldimethylsilyloxy)-8-methyl-5,6,7,8-tetrahydroquinoline

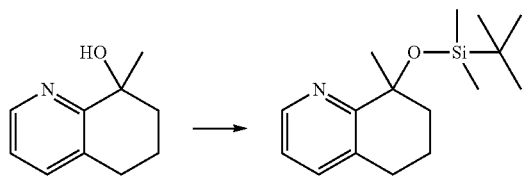 [SMILES: CC1(O)CCCc2cccnc21 ; CC1(O[Si](C)(C)C(C)(C)C)CCCc2cccnc21]

To a cooled (0° C.) solution of the alcohol (477 g, 2.92 mmol) and 2,6-lutidine (0.75 mL, 6.4 mmol) in anhydrous CH$_2$Cl$_2$ was added TBSOTf (0.81 mL, 3.51 mmol). The reaction mixture was stirred at room temperature for 12 h. Ethyl acetate (10 mL) was added. The organic layer was washed with H$_2$O (3×10 mL). Dried over sodium sulfate and filtered. The organic layer was concentrated in vacuo and purification of the crude material via Isco (10-20% ethyl acetate/hexanes) gave rise to the desired product (736.5 mg).

Example 7-13

Preparation of 3-(4,4,5,5-tetramethyl-1,3,2-dioxaborolan-2-yl)-6,7-dihydro-5H-cyclopenta[b]pyridin-7-yl acetate Step 1: Synthesis of 6,7-dihydro-5H-cyclopenta[b]pyridine 1-oxide

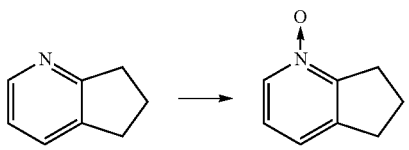 [SMILES: c1cnc2c(c1)CCC2 ; [O-][n+]1cccc2c1CCC2]

3-Chloroperoxybenzoic acid (11.6 g, 67.1 mmol) was dissolved in EtOAc (70 mL, 6 ml/g). The reaction mixture was stirred for 10 minutes at room temperature, and then cooled to 0° C. 2,3-cyclopentenopyridine was dissolved in EtoAc (25 ml, 5 mL/g) which was added dropwise to reaction mixture over 15 minutes keeping the temperature constant below 10° C. The reaction mixture was stirred overnight at ambient temperature. The reaction mixture was quenched with Sat. NaHCO₃ (50 mL). The organic layer was dried over sodium sulfate and filtered. Acqu layer was extracted with DCM (40 mL) twice. The organic layer was dried over sodium sulfate and filtered. Combined organic layer was concentrated in vacuo and purification of the crude material via Isco (0-5% Methanol/DCM) gave rise to the desired 6,7-dihydro-5H-cyclopenta[b]pyridine 1-oxide (1.4 g).

Step 2: Synthesis of
6,7-dihydro-5H-cyclopenta[b]pyridine-7-yl acetate

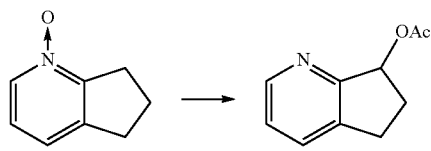 [SMILES: [O-][n+]1cccc2c1CCC2 ; CC(=O)OC1CCc2cccnc21]

A mixture of 6,7-dihydro-5H-cyclopenta[b]pyridine 1-oxide and acetic anhydride was stirred for 30 minutes at 100° C. Concentrated and added DCM (30 mL). The organic layer was washed with Sat. NaHCO₃. The organic layer was dried over sodium sulfate and filtered. The organic layer was concentrated in vacuo and purification of the crude material via Isco (3-5% Methanol/DCM) gave rise to the desired 6,7-dihydro-5H-cyclopenta[b]pyridine-7-yl acetate (900 mg).

Step 2: Synthesis of 3-(4,4,5,5-tetramethyl-1,3,2-dioxaborolan-2-yl)-6,7-dihydro-5H-cyclopenta[b]pyridin-7-yl acetate

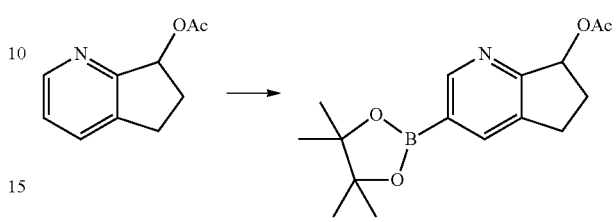

A solution of bispinacolatodiboron (246.0 mg, 2.54 mmol), 4,4'-di-tert-butyl-2-2' dipyridyl (23 mg, 0.085 mmol) and 1,5 cyclooctadiene(methoxy) Iridium(I)dimer (56 mg, 0.085 mmol) in MTBE (10 mL) was degassed with Ar three time and then stirred at room temperature 10 minutes until the solution became read and then added compound 6,7-dihydro-5H-cyclopenta[b]pyridine-7-yl acetate (300.0 mg, 1.7 mmol). The reaction mixture heated at 90° C. in a sealed tube for 2 h. The mixture was cooled to room temperature and was concentrated in vacuo. Purification of the crude material via Isco (30-50% ethyl acetate/hexanes) gave rise to the desired boronic ester (169 mg).

Following previous examples, the following compounds in Table 7-10 were prepared:

TABLE 7-10

| Compound ID | Structures | Compound Name | M + H (calculated)/ M + H (observed) | pAKT S473 IC50 | p4E-BP1 Thr37/ 46 IC50 |
|---|---|---|---|---|---|
| 7.53 | 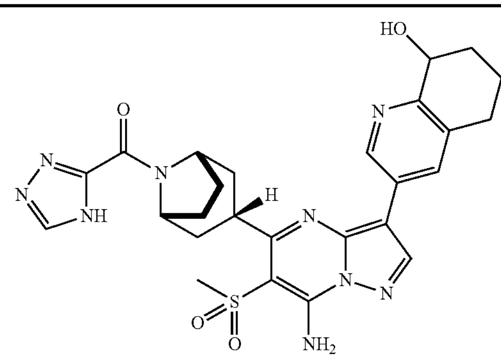 | ((1R,3s,5S)-3-(7-amino-3-(8-hydroxy-5,6,7,8-tetrahydroquinolin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 564.21/ 564.0 | B | B |
| 7.54 | 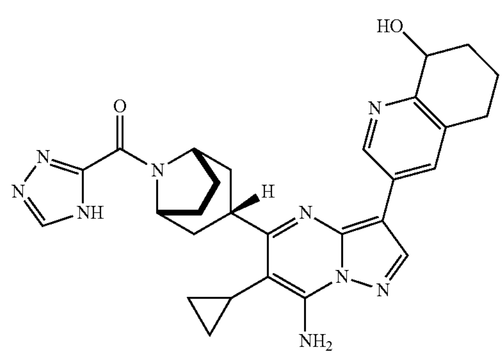 | ((1R,3s,5S)-3-(7-amino-6-cyclopropyl-3-(8-hydroxy-5,6,7,8-tetrahydroquinolin-3-yl)pyrazolo[1,5-a]pyrimidin-5-yl)-8-azabicyclo[3.2.1]octan-8-yl)(4H-1,2,4-triazol-3-yl)methanone | 526.26/ 526.1 | A | A |

TABLE 7-10-continued

| Compound ID | Structures | Compound Name | M + H (calculated)/ M + H (observed) | pAKT S473 IC50 | p4E-BP1 Thr37/46 IC50 |
|---|---|---|---|---|---|
| 7.55 | 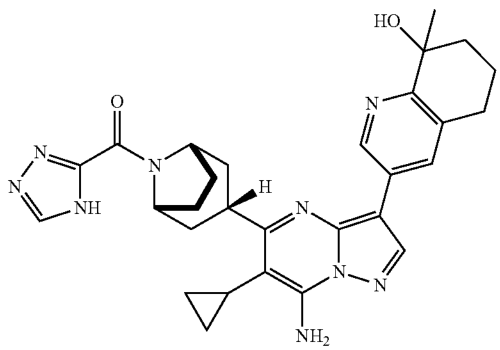 | ((1R,3s,5S)-3-(7-amino-6-cyclopropyl-3-(8-hydroxy-8-methyl-5,6,7,8-tetrahydroquinolin-3-yl)pyrazolo[1,5-a]pyrimidin-5-yl)-8-azabicyclo[3.2.1]octan-8-yl)(4H-1,2,4-triazol-3-yl)methanone | 540.28/ 540.1 | B | B |
| 7.56 | 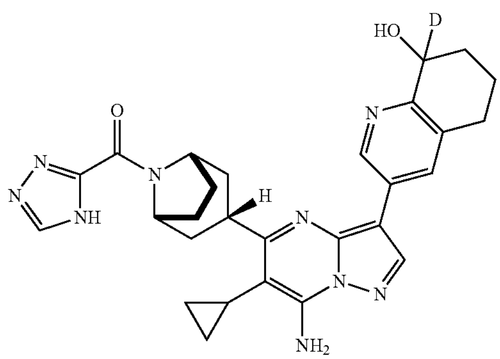 | DEUTERATED-(3-EXO)-3-[7-AMINO-6-CYCLOPROPYL-3-(5,6,7,8-TETRAHYDRO-8-HYDROXY-3-QUINOLINYL-(D))PYRAZOLO[1,5-a]PYRIMIDIN-5-YL]-8-(4H-1,2,4-TRIAZOL-3-YLCARBONYL)-8-AZABICYCLO[3.2.1]OCTANE | 527.27/ 527.0 | A | A |
| 7.57 | 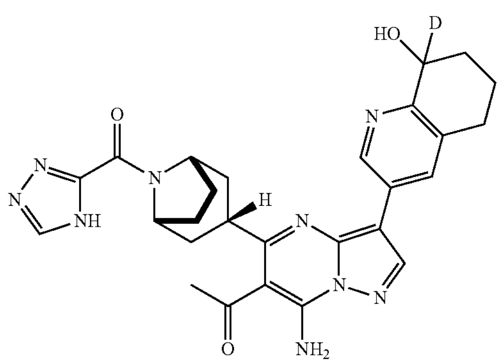 | DEUTERATED-(3-EXO)-3-[6-ACETYL-7-AMINO-3-(5,6,7,8-TETRAHYDRO-8-HYDROXY-3-QUINOLINYL-(D))PYRAZOLO[1,5-a]PYRIMIDIN-5-YL]-8-(4H-1,2,4-TRIAZOL-3-YLCARBONYL)-8-AZABICYCLO[3.2.1]OCTANE | 529.25/ 529.1 | B | A |
| 7.58 | 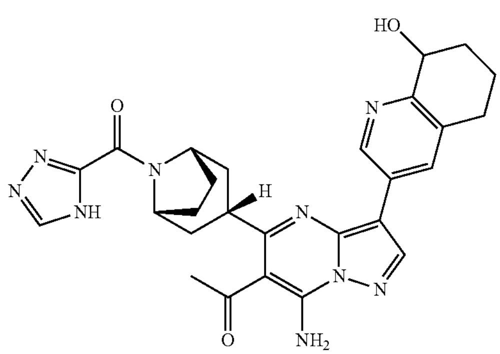 [SMILES: CC(=O)c1c([C@@H]2C[C@H]3CC[C@@H](C2)N3C(=O)c2nnc[nH]2)nc2c(-c3cnc4c(c3)CCCC4O)cnn2c1N] | 1-(5-((1R,3s,5S)-8-(4H-1,2,4-triazole-3-carbonyl)-8-azabicyclo[3.2.1]octan-3-yl)-7-amino-3-(8-hydroxy-5,6,7,8-tetrahydroquinolin-3-yl)pyrazolo[1,5-a]pyrimidin-6-yl)ethanone | 528.24 528.1 | A | A |

TABLE 7-10-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.59 | 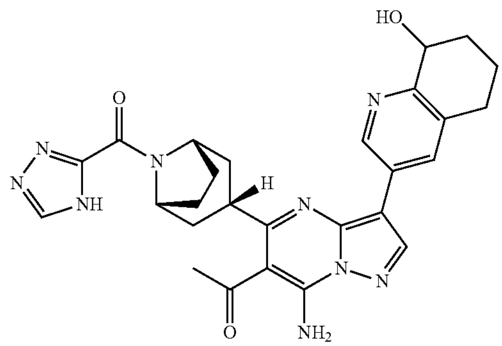 [SMILES: CC(=O)c1c([C@@H]2C[C@H]3CC[C@@H](C2)N3C(=O)c2nnc[nH]2)nc2c(-c3cnc4c(c3)CCCC4O)cnn2c1N] | 1-(5-((1R,3s,5S)-8-(4H-1,2,4-triazole-3-carbonyl)-8-azabicyclo[3.2.1]octan-3-yl)-7-amino-3-(8-hydroxy-5,6,7,8-tetrahydroquinolin-3-yl)pyrazolo[1,5-a]pyrimidin-6-yl)ethanone | 528.24/ 528.1 | B | A |
| 7.60 | 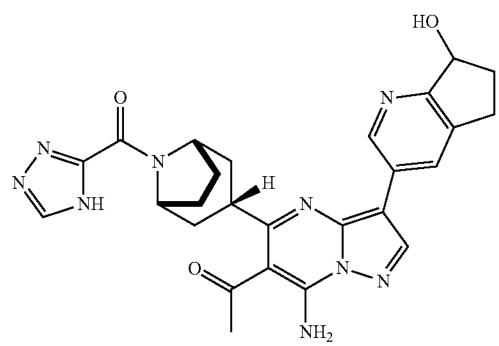 | 1-(5-((1R,3s,5S)-8-(4H-1,2,4-triazole-3-carbonyl)-8-azabicyclo[3.2.1]octan-3-yl)-7-amino-3-(7-hydroxy-6,7-dihydro-5H-cyclopenta[b]pyridin-3-yl)pyrazolo[1,5-a]pyrimidin-6-yl)ethanone | 514.2/ 514.2 | B | ND |
| 7.61 | 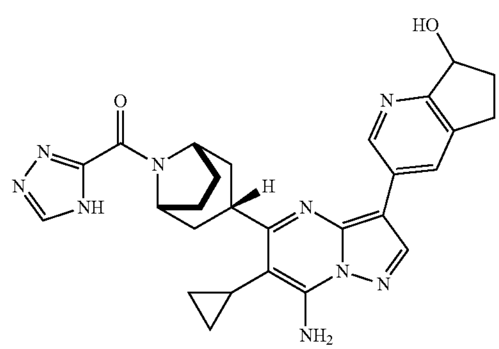 | ((1R,3s,5S)-3-(7-amino-6-cyclopropyl-3-(7-hydroxy-6,7-dihydro-5H-cyclopenta[b]pyridin-3-yl)pyrazolo[1,5-a]pyrimidin-5-yl)-8-azabicyclo[3.2.1]octan-8-yl)(4H-1,2,4-triazol-3-yl)methanone | 512.2/ 512.2 | A | A |
| 7.62 | 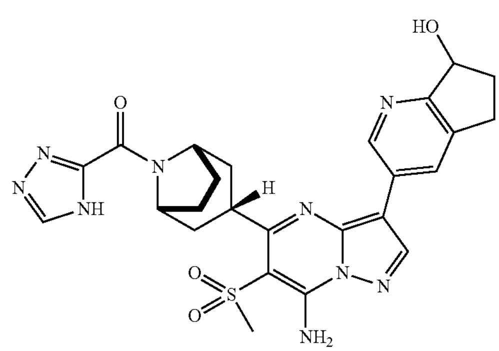 | ((1R,3s,5S)-3-(7-amino-3-(7-hydroxy-6,7-dihydro-5H-cyclopenta[b]pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 550.2/ 550.1 | C | C |

TABLE 7-10-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.63 | 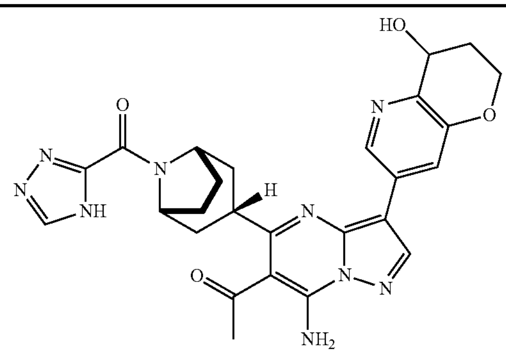 | 1-(5-((1R,3s,5S)-8-(4H-1,2,4-triazole-3-carbonyl)-8-azabicyclo[3.2.1]octan-3-yl)-7-amino-3-(4-hydroxy-3,4-dihydro-2H-pyrano[3,2-b]pyridin-7-yl)pyrazolo[1,5-a]pyrimidin-6-yl)ethanone | 530.2/ 530.0 | B | A |
| 7.64 | 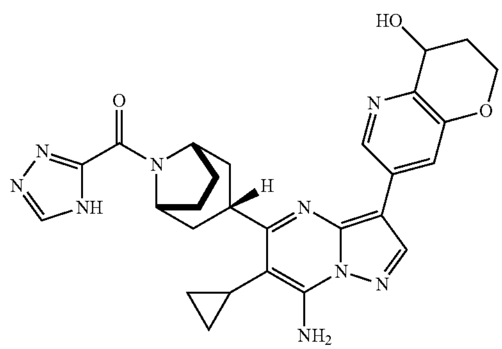 | ((1R,3s,5S)-3-(7-amino-6-cyclopropyl-3-(4-hydroxy-3,4-dihydro-2H-pyrano[3,2-b]pyridin-7-yl)pyrazolo[1,5-a]pyrimidin-5-yl)-8-azabicyclo[3.2.1]octan-8-yl)(4H-1,2,4-triazol-3-yl)methanone | 528.2/ 528.0 | B | B |

Example 7-14

Preparation of 1-(5-((1R,3s,5S)-8-(4H-1,2,4-triazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone Step 1: Preparation of 1-(5-bromopyridin-2-yl)-2,2,2-trifluoroethanone

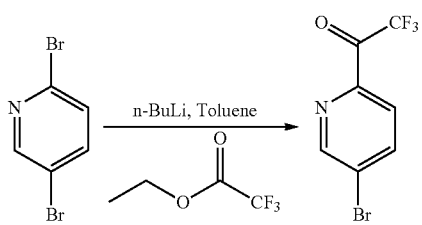

2,5-Dibromopyridine (7.11 g, 30 mmol) was dissolved in dry toluene (200 mL) and cooled to −78° C. n-BuLi (14.4 mL, 2.5 M in THF, 36 mmol) was added dropwise. The mixture was stirred at −78° C. for 2 hours and ethyl trifluoroacetate (6.39 g, 45 mmol) was added. The resulting mixture was allowed to warm to room temperature slowly and stirred at room temperature for 30 min. The reaction was quenched with NH₄Cl (aq.) and extracted with EtOAc. The organics were dried and concentrated and the resulting residue was purified by column chromatography (silica gel, 0-30% EtOAc/Hexane) to give the product 1-(5-bromopyridin-2-yl)-2,2,2-trifluoroethanone (5.87 g).

Step 2: Preparation of 1-(5-bromopyridin-2-yl)-2,2,2-trifluoroethanol

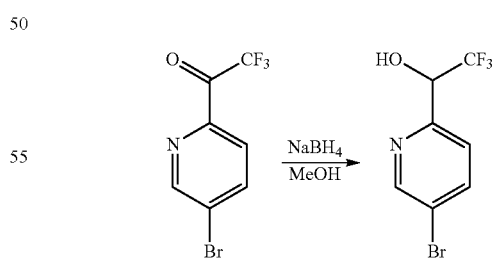

To a suspension of 1-(5-bromopyridin-2-yl)-2,2,2-trifluoroethanol (3.81 g, 15.0 mmol) MeOH (20 mL) was added sodium borohydride (1.70 g, 45.0 mmol). The solution was stirred at it for 1 h. The reaction solution was quenched by water, extracted by ethyl acetate and dried over sodium sulfate. After concentration the crude product was purified by column (silica gel, EtOAc/Hexane 0-40%) gave the product 1-(5-bromopyridin-2-yl)-2,2,2-trifluoroethanol (3.57 g).

Step 3: Preparation of 2,2,2-trifluoro-1-(5-(4,4,5,5-tetramethyl-1,3,2-dioxaborolan-2-yl)pyridin-2-yl)ethanol

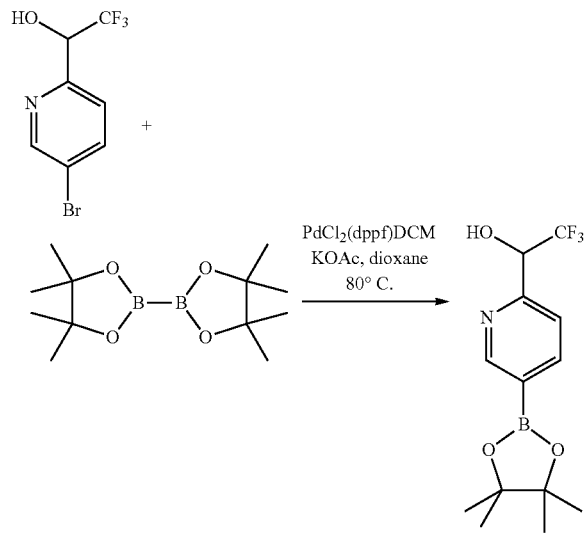

A mixture of 1-(5-bromopyridin-2-yl)-2,2,2-trifluoroethanol (1.28 g, 5.00 mmol), bis(pinacolato)diboron (1.52 g, 6.00 mmol), $PdCl_2$(dppf) (408 mg, 0.500 mmol), and KOAc (1.47 g, 15.0 mmol) in dioxane (20 mL) was degassed and then heated at 80° C. and stirred overnight. The reaction mixture was filtered and concentrated to afford the crude titled compound, which was used without further purification.

Step 4: Preparation of (1R,3s,5S)-tert-butyl 3-(7-(bis((2-(trimethylsilyl)ethoxy)methyl)amino)-3-(6-(2,2,2-trifluoro-1-hydroxyethyl)pyridin-3-yl)pyrazolo[1,5-a]pyrimidin-5-yl)-8-azabicyclo[3.2.1]octane-8-carboxylate

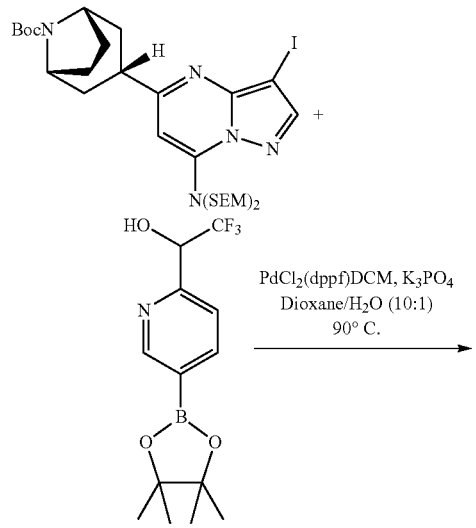

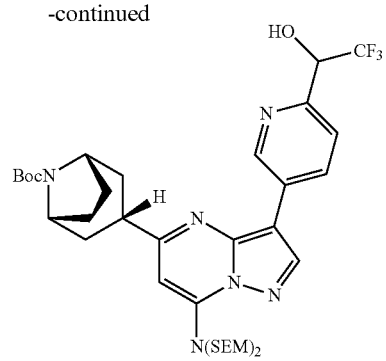

A mixture of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (2.43 g, 3.3 mmol, preparation described previously), 2,2,2-trifluoro-1-(5-(4,4,5,5-tetramethyl-1,3,2-dioxaborolan-2-yl)pyridin-2-yl)ethanol (crude product from step 3, 5.0 mmol), $PdCl_2$(dppf) (243 mg, 0.3 mmol), and $K_3PO_4$ (2.12 g, 10 mmol) in dioxane/$H_2O$ (20/2 mL) was degassed and then heated at 90° C. for overnight. The reaction mixture was diluted with EtOAc, filtered through a short pad of celite, washed with $H_2O$ and brine, dried over $Na_2SO_4$, and concentrated. The crude product was purified by column (silica gel, 0-50% EtOAc/Hexanes) to afford the titled compound as brownish oil (2.62 g).

Step 5: Preparation of (1R,3s,5S)-tert-butyl 3-(7-(bis((2-(trimethylsilyl)ethoxy)methyl)amino)-6-bromo-3-(6-(2,2,2-trifluoro-1-hydroxyethyl)pyridin-3-yl)pyrazolo[1,5-a]pyrimidin-5-yl)-8-azabicyclo[3.2.1]octane-8-carboxylate

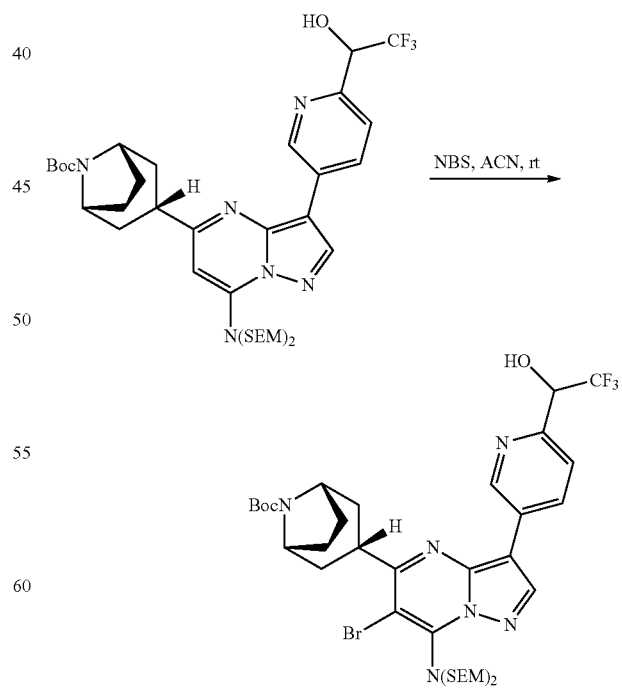

The compound of (1R,3s,5S)-tert-butyl 3-(7-(bis((2-(trimethylsilyl)ethoxy)methyl)amino)-6-bromo- 3-(6-(2,2,2-trifluoro-1-hydroxyethyl)pyridin-3-yl)pyrazolo[1,5-a]pyrimidin-5-yl)-8-azabicyclo[3.2.1]octane-8-carboxylate was made following procedure described previously.

Step 6: Preparation of (1R,3s,5S)-tert-butyl 3-(7-(bis((2-(trimethylsilyl)ethoxy)methyl)amino)-6-(1-ethoxyvinyl)-3-(6-(2,2,2-trifluoro-1-hydroxyethyl)pyridin-3-yl)pyrazolo[1,5-a]pyrimidin-5-yl)-8-azabicyclo[3.2.1]octane-8-carboxylate

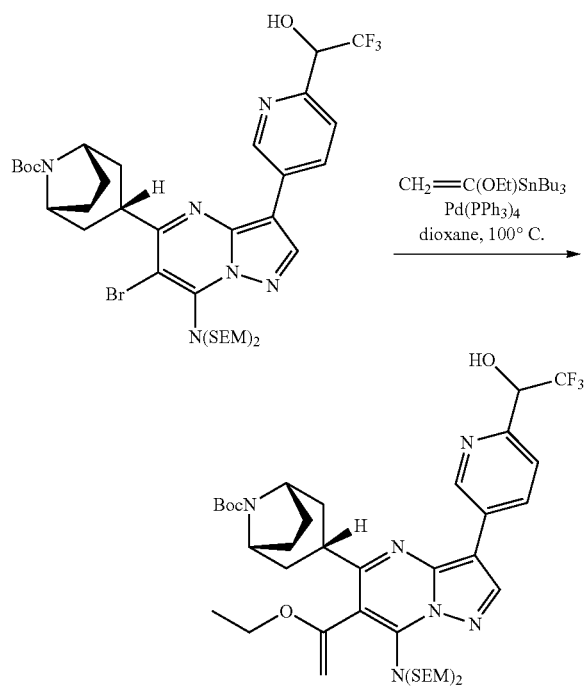

The compound of (1R,3s,5S)-tert-butyl 3-(7-(bis((2-(trimethylsilyl)ethoxy)methyl)amino)-6-(1-ethoxyvinyl)-3-(6-(2,2,2-trifluoro-1-hydroxyethyl)pyridin-3-yl)pyrazolo[1,5-a]pyrimidin-5-yl)-8-azabicyclo[3.2.1]octane-8-carboxylate was made following procedure described previously.

Step 7: Preparation of 1-(7-amino-5-((1R,3s,5S)-8-azabicyclo[3.2.1]octan-3-yl)-3-(6-(2,2,2-trifluoro-1-hydroxyethyl)pyridin-3-yl)pyrazolo[1,5-a]pyrimidin-6-yl)ethanone

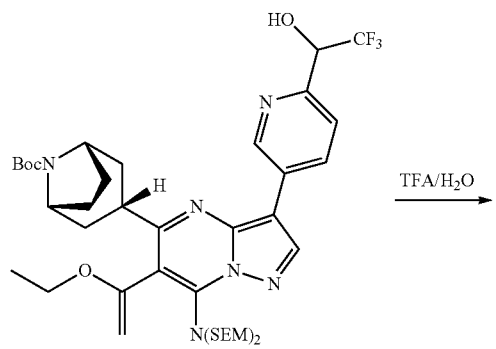

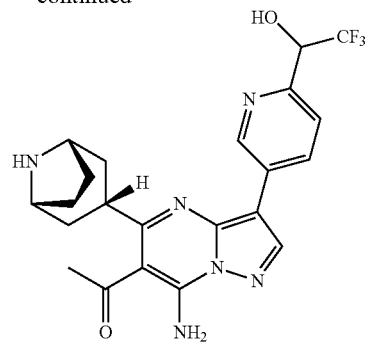

The compound of 1-(7-amino-5-((1R,3s,5S)-8-azabicyclo[3.2.1]octan-3-yl)-3-(6-(2,2,2-trifluoro-1-hydroxyethyl)pyridin-3-yl)pyrazolo[1,5-a]pyrimidin-6-yl)ethanone was prepared following procedure described previously.

Step 8: Preparation of 1-(5-((1R,3s,5S)-8-(4H-1,2,4-triazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone

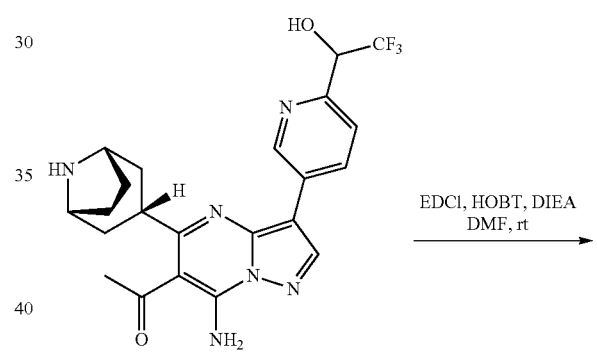

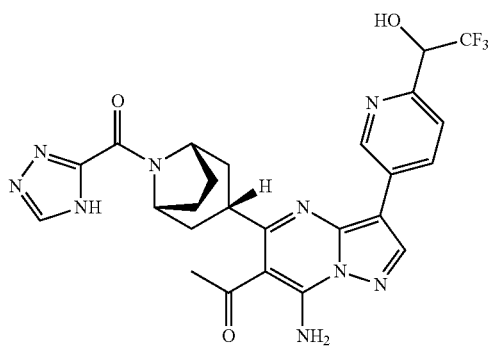

The compound of 1-(5-((1R,3s,5S)-8-(4H-1,2,4-triazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone was made following procedure described previously.

Example 7-15

Preparation of benzyl 1-(5-(4,4,5,5-tetramethyl-1,3,2-dioxaborolan-2-yl)pyridin-2-yl)cyclopropylcarbamate Step 1: 1-(5-bromopyridin-2-yl)cyclopropanamine

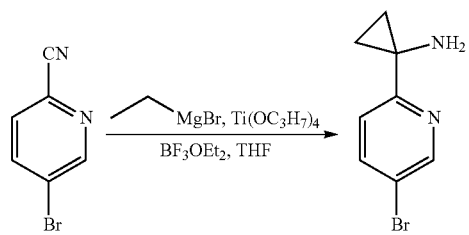

To a mixture of 5-bromopicolinonitrile (1.82 g, 10.0 mmol), tetrapropoxytitanium (3.26 ml, 11.0 mmol) and boron trifluoride diethyl etherate (2.51 ml 20.0 mmol) at 0° C. was added ethylmagnesium bromide (1.0M in ether, 22 ml, 22.0 mmol) The resulting solution was allowed to stir at it for 3 h. Ammonium chloride solution was added and the solution was extracted with ethyl acetate for three times. The organic layers were collected and washed with brine and dried over sodium sulfate. After concentration the crude product was purified by SiO$_2$ column.

Step 2: benzyl 1-(5-bromopyridin-2-yl)cyclopropylcarbamate

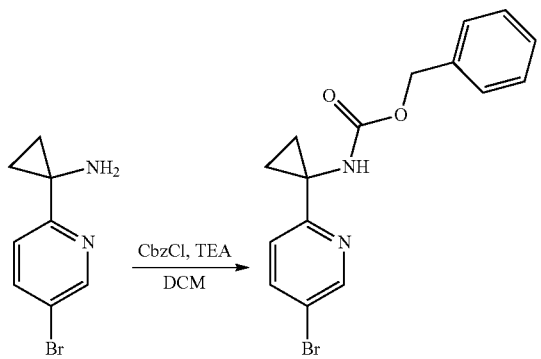 [SMILES: NC1(c2ccc(Br)cn2)CC1 ; O=C(NC1(c2ccc(Br)cn2)CC1)OCc1ccccc1]

At 0° C., to the mixture of 1-(5-bromopyridin-2-yl)cyclopropanamine (1.07 g, 5.0 mmol), triethylamine (766 ul, 5.5 mmol) was added benzyl chloroformate (785 ul, 5.5 mmol). The resulting mixture was allowed to stir at it for 1 h. After work up, the crude product was purified by column chromatography on SiO$_2$.

Step 3: benzyl 1-(5-(4,4,5,5-tetramethyl-1,3,2-dioxaborolan-2-yl)pyridin-2-yl)cyclopropylcarbamate

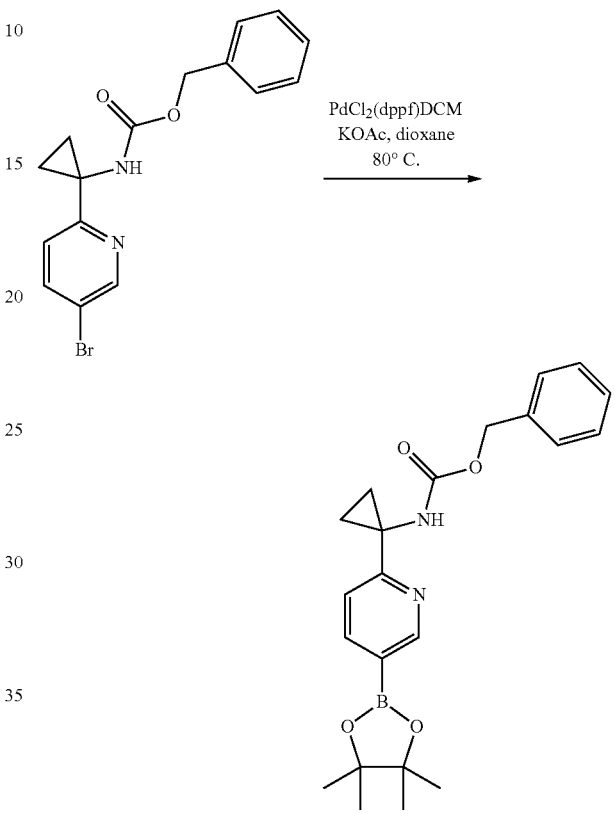

This compound was prepared from benzyl 1-(5-bromopyridin-2-yl)cyclopropylcarbamate, following essentially the same procedures given previously.

Following these examples, compounds in Table 7-11 were made similarly:

TABLE 7-11

| Compound ID | Structures | Compound Name | M + H (calculated)/ M + H (observed) | pAKT S473 IC50 | p4E-BP1 Thr37/ 46 IC50 |
| --- | --- | --- | --- | --- | --- |
| 7.65 | 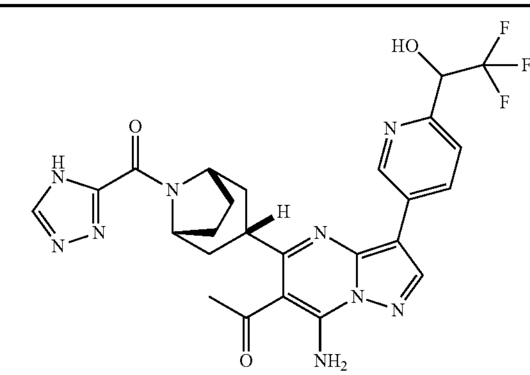 | 1-(5-((1R,3s,5S)-8-(4H-1,2,4-triazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone | 556.2/ 556.2 | B | B |

TABLE 7-11-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.66 | 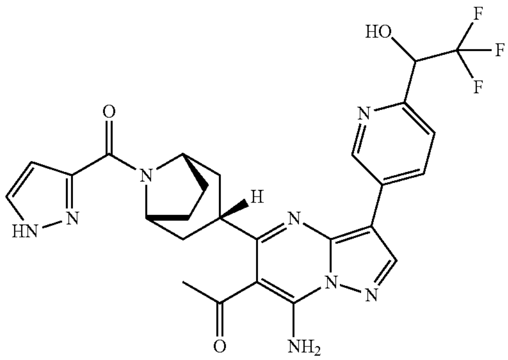 [SMILES: CC(=O)c1c([C@@H]2C[C@H]3CC[C@@H](C2)N3C(=O)c2cc[nH]n2)nc2c(-c3ccc(C(O)C(F)(F)F)nc3)cnn2c1N] | 1-(5-((1R,3s,5S)-8-(1H-pyrazole-3-carbonyl)-8-azabicyclo[3.2.1]octan-3-yl)-7-amino-3-(6-(2,2,2-trifluoro-1-hydroxyethyl)pyridin-3-yl)pyrazolo[1,5-a]pyrimidin-6-yl)ethanone | 555.2/ 555.1 | C | B |
| 7.67 | 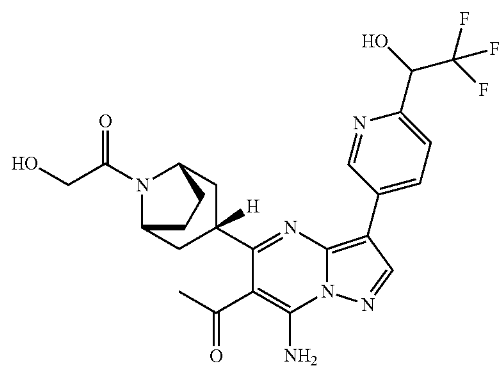 [SMILES: CC(=O)c1c([C@@H]2C[C@H]3CC[C@@H](C2)N3C(=O)CO)nc2c(-c3ccc(C(O)C(F)(F)F)nc3)cnn2c1N] | 1-((1R,3s,5S)-3-(6-acetyl-7-amino-3-(6-(2,2,2-trifluoro-1-hydroxyethyl)pyridin-3-yl)pyrazolo[1,5-a]pyrimidin-5-yl)-8-azabicyclo[3.2.1]octan-8-yl)-2-hydroxyethanone | 519.2/ 519.1 | C | B |
| 7.68 | 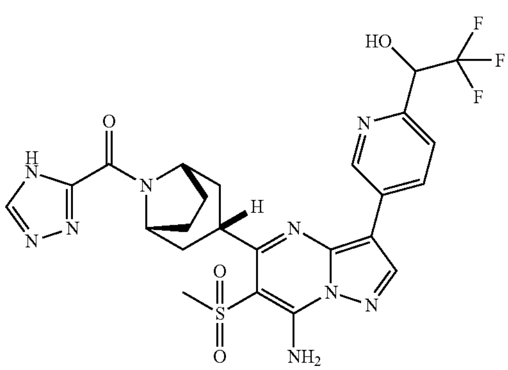 | ((1R,3s,5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)(4H-1,2,4-triazol-3-yl)methanone | 592.2/ 591.8 | ND | ND |
| 7.69 | 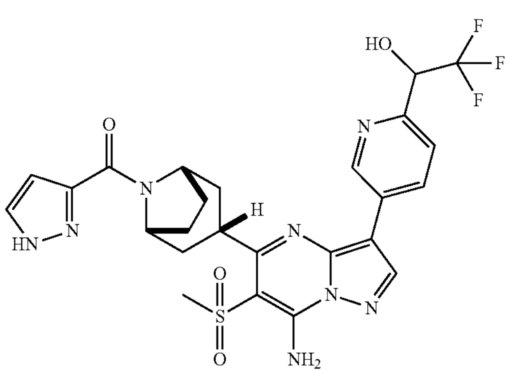 | ((1R,3s,5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)(1H-pyrazol-3-yl)methanone | 591.2/ 590.8 | C | C |

TABLE 7-11-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.70 | 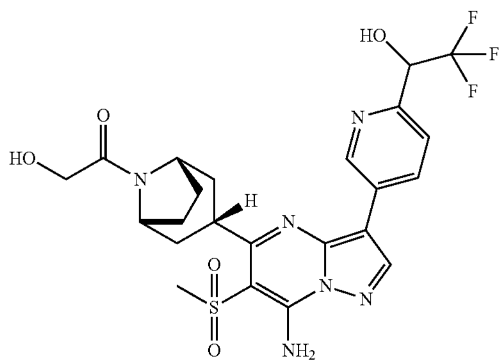 [SMILES: CS(=O)(=O)c1c([C@@H]2C[C@H]3CC[C@@H](C2)N3C(=O)CO)nc2c(-c3ccc(C(O)C(F)(F)F)nc3)cnn2c1N] | 1-((1R,3s,5S)-3-(7-amino-6-(methylsulfonyl)-3-(6-(2,2,2-trifluoro-1-hydroxyethyl)pyridin-3-yl)pyrazolo[1,5-a]pyrimidin-5-yl)-8-azabicyclo[3.2.1]octan-8-yl)-2-hydroxyethanone | 555.2/ 555.0 | C | C |
| 7.71 | 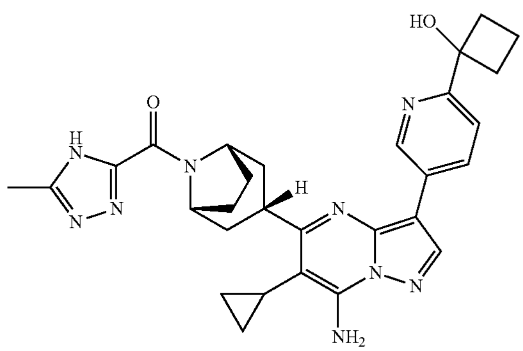 [SMILES: Cc1nnc(C(=O)N2[C@@H]3CC[C@H]2C[C@H](c2nc4c(-c5ccc(C6(O)CCC6)nc5)cnn4c(N)c2C2CC2)C3)[nH]1] | ((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)(5-methyl-4H-1,2,4-triazol-3-yl)methanone | 540.3/ 540.3 | B | B |
| 7.72 | 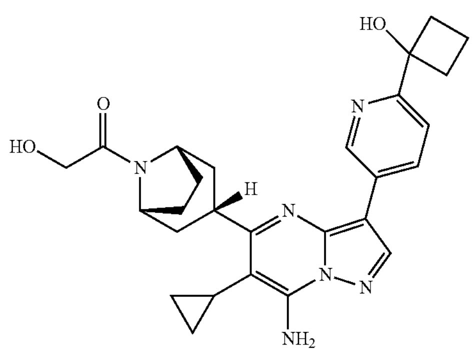 [SMILES: Nc1c(C2CC2)c([C@@H]2C[C@H]3CC[C@@H](C2)N3C(=O)CO)nc2c(-c3ccc(C4(O)CCC4)nc3)cnn12] | 1-((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)-2-hydroxyethanone | 489.3/ 489.2 | B | B |
| 7.73 | 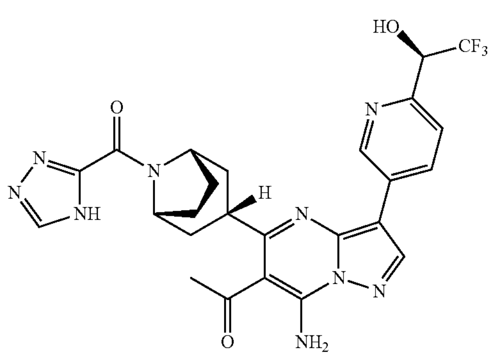 | 1-(5-((1R,3s,5S)-8-(4H-1,2,4-triazole-3-carbonyl)-8-azabicyclo[3.2.1]octan-3-yl)-7-amino-3-(6-((R)-2,2,2-trifluoro-1-hydroxyethyl)pyridin-3-yl)pyrazolo[1,5-a]pyrimidin-6-yl)ethanone | 556.2/ 556.2 | B | B |

TABLE 7-11-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.74 | 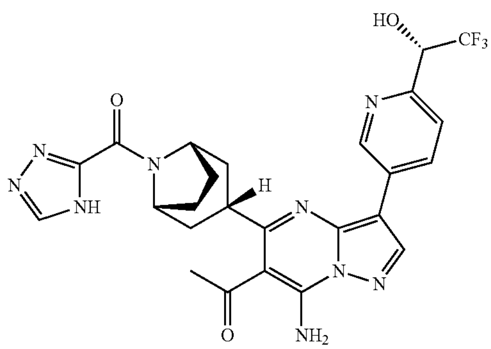 | 1-(5-((1R,3s,5S)-8-(4H-1,2,4-triazole-3-carbonyl)-8-azabicyclo[3.2.1]octan-3-yl)-7-amino-3-(6-((S)-2,2,2-trifluoro-1-hydroxyethyl)pyridin-3-yl)pyrazolo[1,5-a]pyrimidin-6-yl)ethanone | 556.2/ 556.2 | B | B |
| 7.75 | 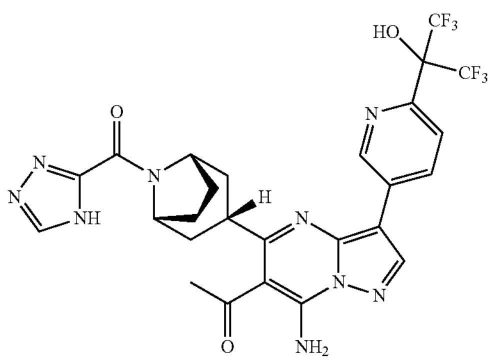 | 1-(5-((1R,3s,5S)-8-(4H-1,2,4-triazole-3-carbonyl)-8-azabicyclo[3.2.1]octan-3-yl)-7-amino-3-(6-(1,1,1,3,3,3-hexafluoro-2-hydroxypropan-2-yl)pyridin-3-yl)pyrazolo[1,5-a]pyrimidin-6-yl)ethanone | 624.2/ 624.0 | ND | ND |
| 7.76 | 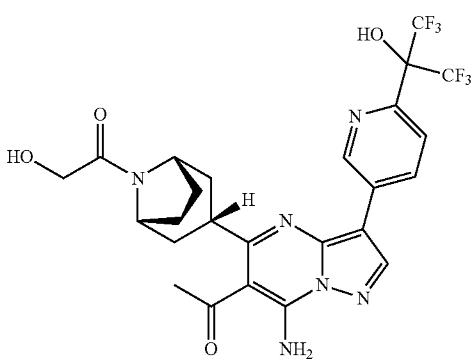 | 1-((1R,3s,5S)-3-(6-acetyl-7-amino-3-(6-(1,1,1,3,3,3-hexafluoro-2-hydroxypropan-2-yl)pyridin-3-yl)pyrazolo[1,5-a]pyrimidin-5-yl)-8-azabicyclo[3.2.1]octan-8-yl)-2-hydroxyethanone | 587.2/ 587.0 | ND | ND |
| 7.77 | 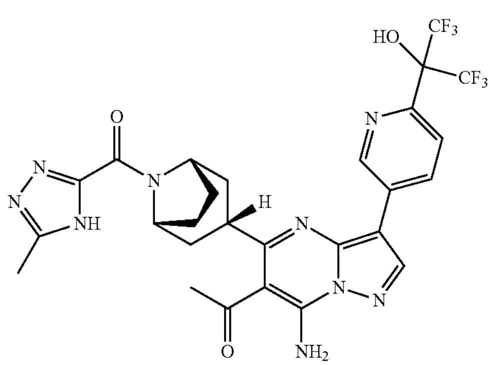 | 1-(7-amino-3-(6-(1,1,1,3,3,3-hexafluoro-2-hydroxypropan-2-yl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 638.2/ 638.1 | ND | ND |

TABLE 7-11-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.78 | 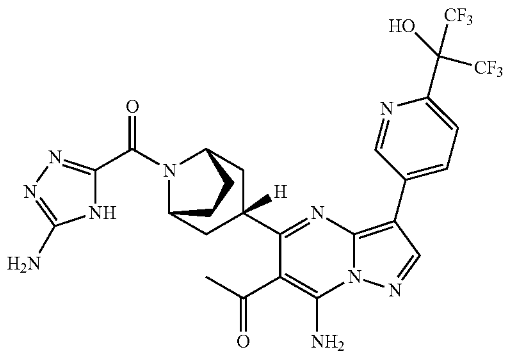 | 1-(7-amino-5-((1R,3s,5S)-8-(5-amino-4H-1,2,4-triazole-3-carbonyl)-8-azabicyclo[3.2.1]octan-3-yl)-3-(6-(1,1,1,3,3,3-hexafluoro-2-hydroxypropan-2-yl)pyridin-3-yl)pyrazolo[1,5-a]pyrimidin-6-yl)ethanone | 639.2/ 639.0 | B | B |
| 7.79 | 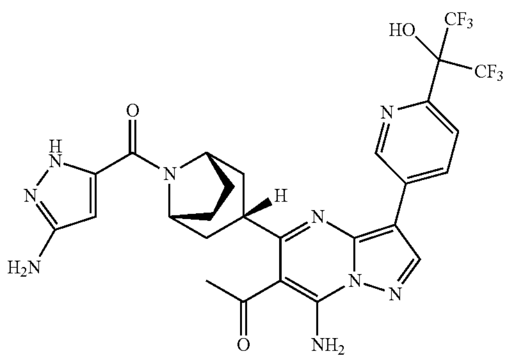 | 1-(7-amino-5-((1R,3s,5S)-8-(3-amino-1H-pyrazole-5-carbonyl)-8-azabicyclo[3.2.1]octan-3-yl)-3-(6-(1,1,1,3,3,3-hexafluoro-2-hydroxypropan-2-yl)pyridin-3-yl)pyrazolo[1,5-a]pyrimidin-6-yl)ethanone | 638.2/ 638.2 | B | B |
| 7.80 | 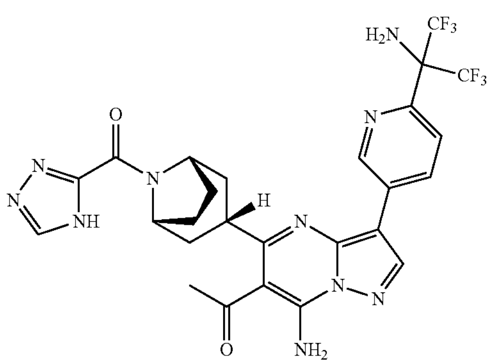 | 1-(5-((1R,3s,5S)-8-(4H-1,2,4-triazole-3-carbonyl)-8-azabicyclo[3.2.1]octan-3-yl)-7-amino-3-(6-(2-amino-1,1,1,3,3,3-hexafluoropropan-2-yl)pyridin-3-yl)pyrazolo[1,5-a]pyrimidin-6-yl)ethanone | 623.2/ 623.2 | C | B |
| 7.81 | 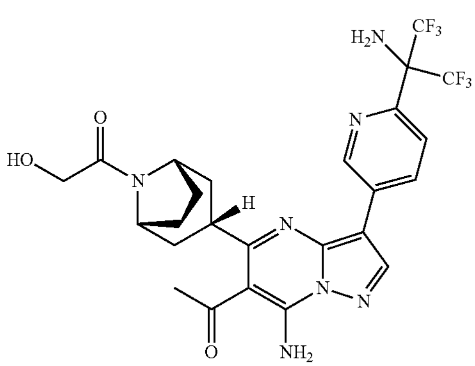 | 1-((1R,3s,5S)-3-(6-acetyl-7-amino-3-(6-(2-amino-1,1,1,3,3,3-hexafluoropropan-2-yl)pyridin-3-yl)pyrazolo[1,5-a]pyrimidin-5-yl)-8-azabicyclo[3.2.1]octan-8-yl)-2-hydroxyethanone | 586.2/ 586.2 | D | C |

TABLE 7-11-continued

| Compound ID | Structures | Compound Name | M + H (calculated)/ M + H (observed) | pAKT S473 IC50 | p4E-BP1 Thr37/46 IC50 |
|---|---|---|---|---|---|
| 7.82 | 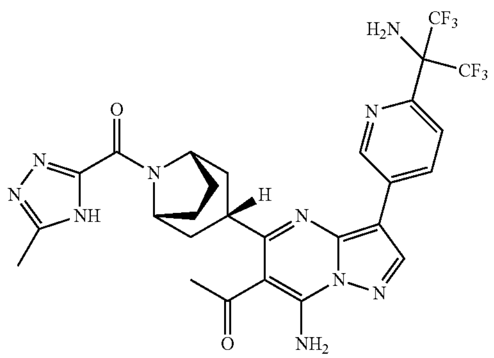 | 1-(7-amino-3-(6-(2-amino-1,1,1,3,3,3-hexafluoropropan-2-yl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone | 637.2/ 637.2 | C | C |
| 7.83 | 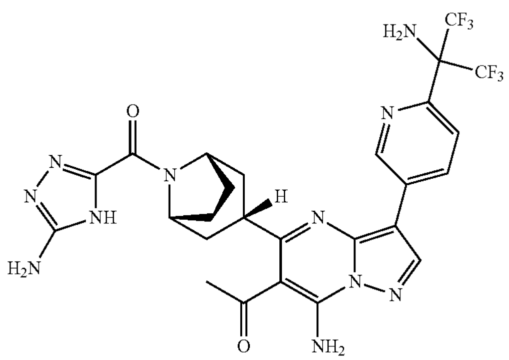 | 1-((1R,3s,5S)-3-(6-acetyl-7-amino-3-(6-(1,1,1,3,3,3-hexafluoro-2-hydroxypropan-2-yl)pyridin-3-yl)pyrazolo[1,5-a]pyrimidin-5-yl)-8-azabicyclo[3.2.1]octan-8-yl)-2-hydroxyethanone | 638.2/ 638.2 | C | B |
| 7.84 | 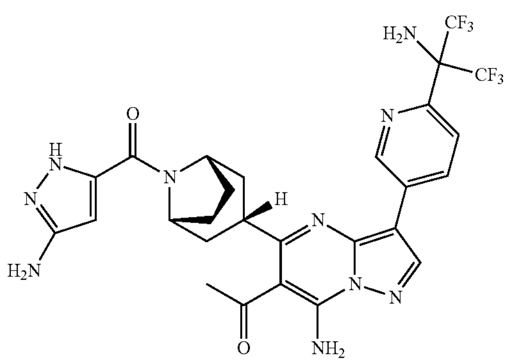 | 1-(7-amino-3-(6-(2-amino-1,1,1,3,3,3-hexafluoropropan-2-yl)pyridin-3-yl)-5-((1R,3s,5S)-8-(3-amino-1H-pyrazole-5-carbonyl)-8-azabicyclo[3.2.1]octan-3-yl)pyrazolo[1,5-a]pyrimidin-6-yl)ethanone | 637.2/ 637.2 | C | C |
| 7.85 | 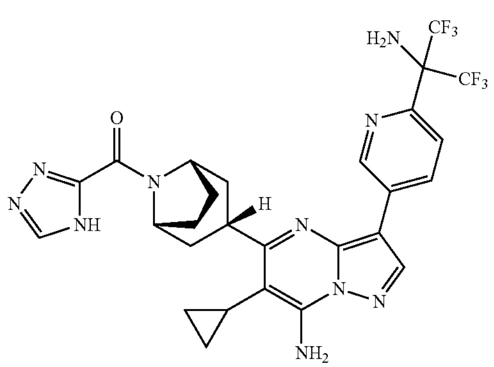 | ((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(4H-1,2,4-triazol-3-yl)methanone | 621.2/ 621.2 | C | C |

TABLE 7-11-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.86 | 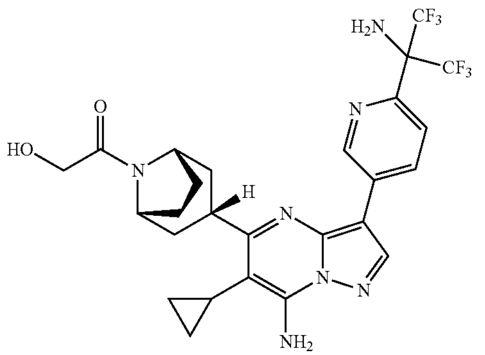 | 1-((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)-2-hydroxyethanone | 584.2/ 584.1 | ND | ND |
| 7.87 | 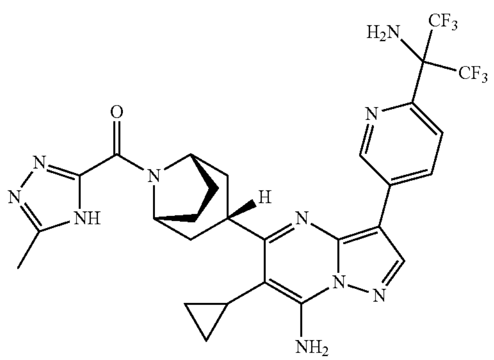 | ((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-methyl-4H-1,2,4-triazol-3-yl)methanone | 635.2/ 635.3 | ND | ND |
| 7.88 | 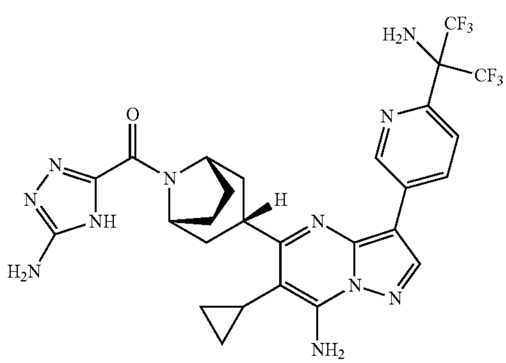 | ((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-amino-4H-1,2,4-triazol-3-yl)methanone | 636.2/ 636.2 | C | C |
| 7.89 | 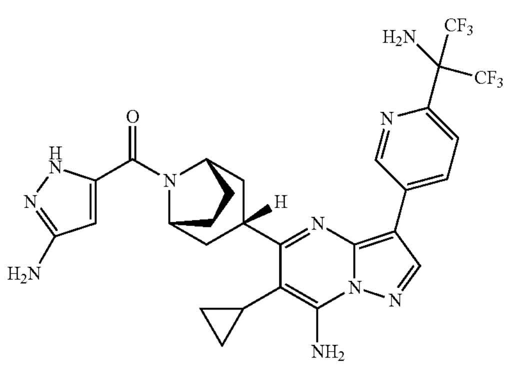 | (3-amino-1H-pyrazol-5-yl)((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)methanone | 635.2/ 635.3 | ND | ND |

Example 7-15

Preparation of 1-(5-(((1R,3s,5S)-8-(4H-1,2,4-triazole-3-carbonyl)-8-azabicyclo[3.2.1]octan-3-yl)-7-amino-3-(2-(hydroxymethyl)thiazol-5-yl)pyrazolo[1,5-a]pyrimidin-6-yl)ethanone

Step 1: Preparation of 2-((tert-butyldimethylsilyloxy)methyl)-5-(tributylstannyl)thiazole

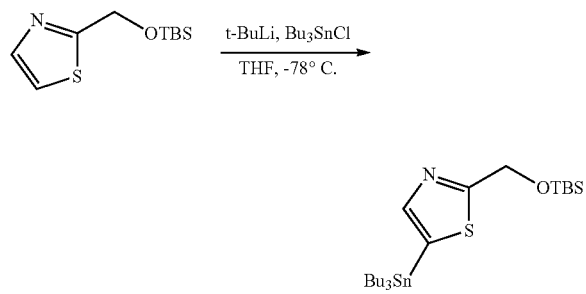

2-((tert-butyldimethylsilyloxy)methyl)thiazole (8.0 g, 35 mmol) was dissolved in dry THF (350 mL) and the solution was cooled to −78° C. To this solution, t-BuLi (1.7 M, 25 mL, 42 mmol) was added dropwise. The reaction was warmed to −40° C. and stirred for 2 hours. Then, Bu₃SnCl (14.6 g, 45 mmol) was added and the resulting mixture was allowed to warm to room temperature slowly and stirred for another 30 min. NH₄Cl (aq.) was added to quench the reaction and extracted with EtOAc. The organics was dried and concentrated. The residue was purified with column (silica gel, 0~30 EtOAc/hexane) to give the product 2-((tert-butyldimethylsilyloxy)methyl)-5-(tributylstannyl)thiazole (14.1 g)

Step 2: Preparation of (1R,3s,5S)-tert-butyl 3-(7-(bis((2-(trimethylsilyl)ethoxy)methyl)amino)-3-(2-((tert-butyldimethylsilyloxy)methyl)thiazol-5-yl)pyrazolo[1,5-a]pyrimidin-5-yl)-8-azabicyclo[3.2.1]octane-8-carboxylate

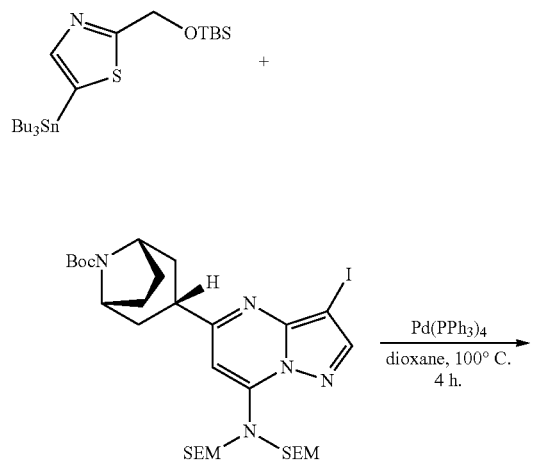

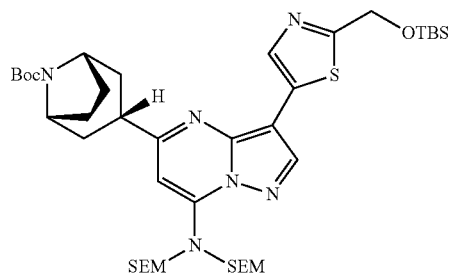

A mixture of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (1.46 g, 2.0 mmol), 2-((tert-butyldimethylsilyloxy)methyl)-5-(tributylstannyl)thiazole (2.08 g, 4.0 mmol), Pd(PPh₃)₄ (230 mg, 0.2 mmol) in dioxane (10 mL) was stirred at 100° C. under Argon for 4 h. The reaction mixture was passed through a short plug filled with SiO₂/KF (9:1) to remove majority of the Sn species (eluting with EtOAc). The filtrate was concentrated and purified by a SiO₂ column to afford the titled compound as a brownish oil (580 mg).

Step 3: Preparation of (1R,3s,5S)-tert-butyl 3-(7-(bis((2-(trimethylsilyl)ethoxy)methyl)amino)-6-bromo-3-(2-((tert-butyldimethylsilyloxy)methyl)thiazol-5-yl)pyrazolo[1,5-a]pyrimidin-5-yl-8-azabicyclo[3.2.1]octane-8-carboxylate

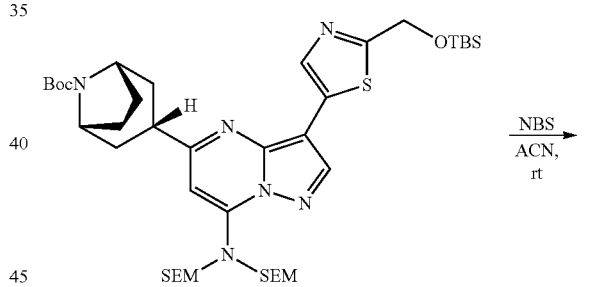

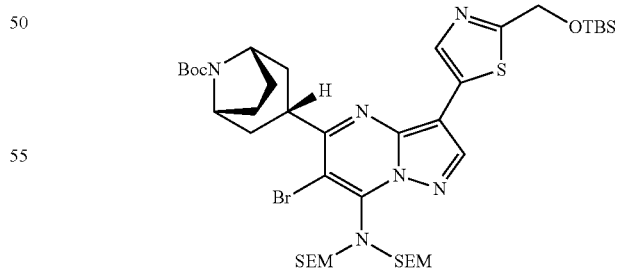

To a solution of (1R,3s,5S)-tert-butyl 3-(7-(bis((2-(trimethylsilyl)ethoxy)methyl)amino)-3-(2-((tert-butyldimethylsilyloxy)methyl)thiazol-5-yl)pyrazolo[1,5-a]pyrimidin-5-yl)-8-azabicyclo[3.2.1]octane-8-carboxylate (250 mg, 0.3 mmol) in CH₃CN (10 mL) was added NBS (54 mg, 0.3 mmol) at rt and the reaction was stirred for 1 hour. All the volatiles Step 4: Preparation of (1R,3s,5S)-tert-butyl 3-(7-(bis ((2-(trimethylsilyl)ethoxy)methyl)amino)-3-(2-((tert-butyldimethylsilyloxy)methyl)thiazol-5-yl)-6-(1-ethoxyvinyl)pyrazolo[1,5-a]pyrimidin-5-yl)-8-azabicyclo[3.2.1]octane-8-carboxylate

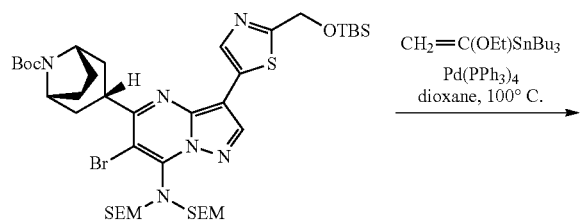

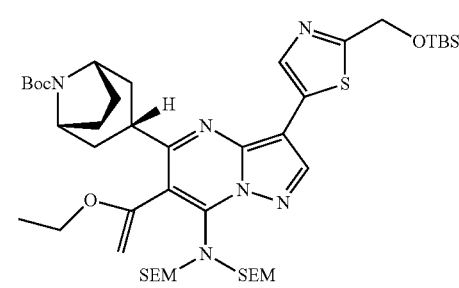

A mixture of (1R,3s,5S)-tert-butyl 3-(7-(bis((2-(trimethylsilyl)ethoxy)methyl)amino)-6-bromo-3-(2-((tert-butyldimethylsilyloxy)methyl)thiazol-5-yl)pyrazolo[1,5-a]pyrimidin-5-yl)-8-azabicyclo[3.2.1]octane-8-carboxylate (240 mg, 0.26 mmol), tributyl(1-ethoxyvinyl)tin (250 uL, 0.75 mmol), Pd(PPh$_3$)$_4$ (29.0 mg, 0.025 mmol) in dioxane (2 mL) was stirred at 100° C. under Argon for 16 h. The reaction mixture was passed through a short plug filled with SiO$_2$/KF (9:1) to remove majority of the Sn species (eluting with EtOAc). The filtrate was concentrated and purified by a SiO$_2$ column to afford the titled compound as brownish oil (177 mg).

Step 5: Preparation of 1-(7-amino-5-((1R,3s,5S)-8-azabicyclo[3.2.1]octan-3-yl)-3-(2-(hydroxymethyl)thiazol-5-yl)pyrazolo[1,5-a]pyrimidin-6-yl)ethanone

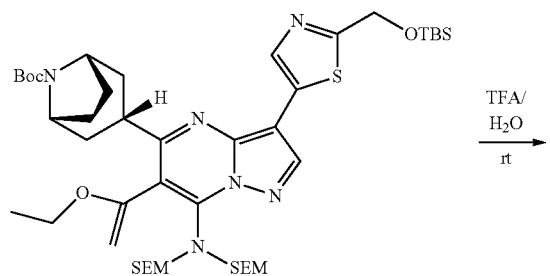

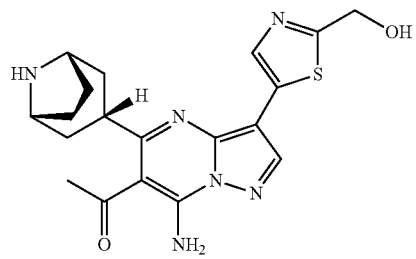

(1R,3s,5S)-tert-butyl 3-(7-(bis((2-(trimethylsilyl)ethoxy) methyl)amino)-3-(2-((tert-butyldimethylsilyloxy)methyl) thiazol-5-yl)-6-(1-ethoxyvinyl)pyrazolo[1,5-a]pyrimidin-5-yl)-8-azabicyclo[3.2.1]octane-8-carboxylate (177 mg) was treated with a mixture of TFA/H$_2$O (50%, 5 mL) at rt for 3 h and 50° C. for another hour. All the volatiles were removed to afford the titled compound as pale yellow oil, which was used in the next step without further purification.

Step 6: Preparation of 1-(5-(((1R,3s,5S)-8-(4H-1,2,4-triazole-3-carbonyl)-8-azabicyclo[3.2.1]octan-3-yl)-7-amino-3-(2-(hydroxymethyl)thiazol-5-yl)pyrazolo[1,5-a]pyrimidin-6-yl)ethanone

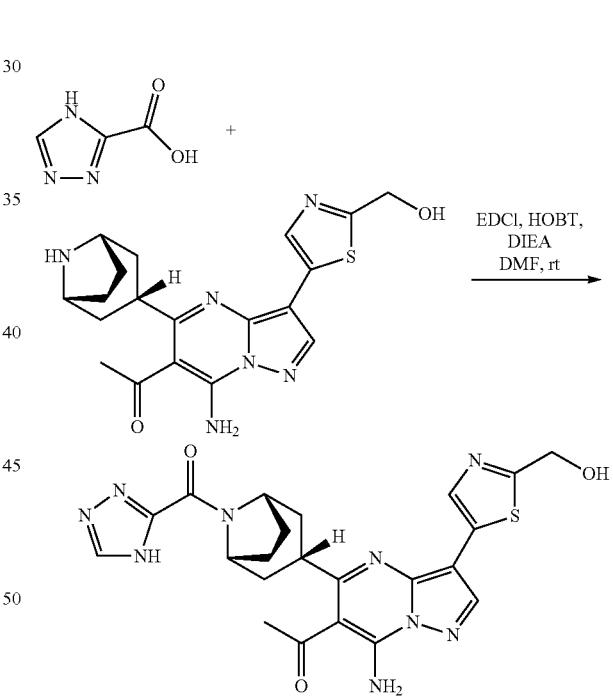

A mixture of 4H-1,2,4-triazole-3-carboxylic acid (34 mg, 0.3 mmol), HOBT (41 mg, 0.3 mmol), EDCI.HCl (57 mg, 0.3 mmol), DIEA (157 uL, 1.0 mmol) and 1-(7-amino-5-((1R,3s,5S)-8-azabicyclo[3.2.1]octan-3-yl)-3-(2-(hydroxymethyl)thiazol-5-yl)pyrazolo[1,5-a]pyrimidin-6-yl)ethanone (around 0.3 mmol) in DMF (2 mL) was stirred at rt for 6 h. The reaction mixture was concentrated to half volume, diluted with DMSO and purified by a reverse phase HPLC to afford the titled compound (Table 7-12).

TABLE 7-12

| | | | |
|---|---|---|---|
| 7.90 | (structure) | 1-(5-((1R,3s,5S)-8-(4H-1,2,4-triazole-3-carbonyl)-8-azabicyclo[3.2.1]octan-3-yl)-7-amino-3-(2-(hydroxymethyl)thiazol-5-yl)pyrazolo[1,5-a]pyrimidin-6-yl)ethanone | 494.2/ 494.3 ND ND |

Example 7-16

Preparation of ((1R,3s,5S)-3-(7-amino-3-(2-(hydroxymethyl)thiazol-5-yl-6-(methylsulfonyl)pyrazolo[1,5-a]pyrimidin-5-yl)-8-azabicyclo[3.2.1]octan-8-yl)(4H-1,2,4-triazol-3-yl)methanone and (5-(5-((1R,3s, 5S)-8-(4H-1,2,4-triazole-3-carbonyl)-8-azabicyclo[3.2.1]octan-3-yl-7-amino-6-(methylsulfonyl)pyrazolo[1,5-a]pyrimidin-3-yl)thiazol-2-yl)methyl 4H-1,2,4-triazole-3-carboxylate Step 1: Preparation of (1R,3s,5S)-tert-butyl 3-(7-(bis((2-(trimethylsilyl)ethoxy)methyl)amino)-6-iodo-3-(2-((tert-butyldimethylsilyloxy)methyl)thiazol-5-yl)pyrazolo[1,5-a]pyrimidin-5-yl-8-azabicyclo[3.2.1]octane-8-carboxylate

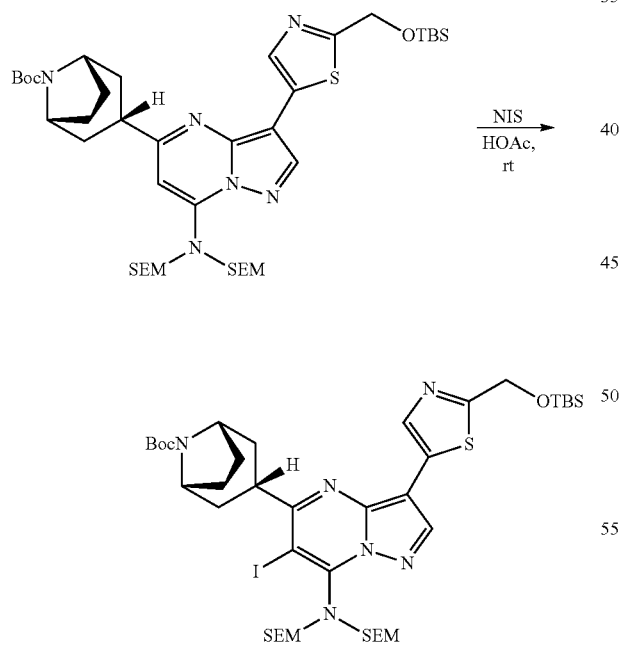

To a solution of (1R,3s,5S)-tert-butyl 3-(7-(bis((2-(trimethylsilyl)ethoxy)methyl)amino)-3-(2-((tert-butyldimethylsilyloxy)methyl)thiazol-5-yl)pyrazolo[1,5-a]pyrimidin-5-yl)-8-azabicyclo[3.2.1]octane-8-carboxylate (330 mg, 0.398 mmol) in HOAc (3 mL) was added NIS (90 mg, 0.4 mmol) at it and the reaction was stirred for 30 min. All the volatiles were removed under reduced pressure and the residue was purified by a SiO₂ column to afford the titled compound as brownish oil (253 mg).

Step 2: Preparation of (1R,3s,5S)-tert-butyl 3-(7-(bis((2-(trimethylsilyl)ethoxy)methyl)amino)-3-(2-((tert-butyldimethylsilyloxy)methyl)thiazol-5-yl)-6-(methylsulfonyl)pyrazolo[1,5-a]pyrimidin-5-yl)-8-azabicyclo[3.2.1]octane-8-carboxylate

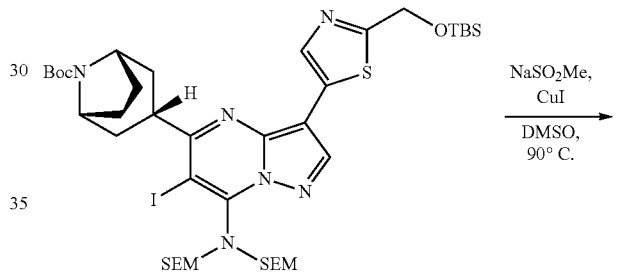

A mixture of (1R,3s,5S)-tert-butyl 3-(7-(bis((2-(trimethylsilyl)ethoxy)methyl)amino)-3-(2-((tert-butyldimethylsilyloxy)methyl)thiazol-5-yl)-6-iodopyrazolo[1,5-a]pyrimidin-5-yl)-8-azabicyclo[3.2.1]octane-8-carboxylate (253 mg, 0.26 mmol), MeSO₂Na (83 mg, 0.78 mmol), and CuI (301 mg, 1.59 mmol) in DMSO (2 mL) was heated at 90° C. for 2.5 h. The reaction mixture was cooled to room temperature and diluted with EtOAc. The mixture was washed with ammonia (1N), water and brine and dried over Na₂SO₄. After concentration, the crude was used in the next step directly without further purification.

Step 3: Preparation of (5-(7-amino-54(1R,3s,5S)-8-azabicyclo[3.2.1]octan-3-yl)-6-(methylsulfonyl)pyrazolo[1,5-a]pyrimidin-3-yl)thiazol-2-yl)methanol

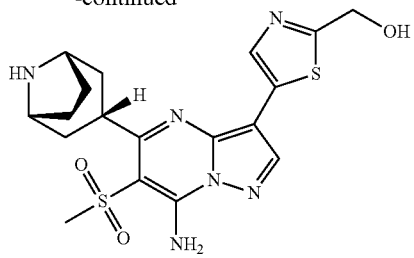

The title compound was prepared with the same conditions described previously.

Step 4: Preparation of ((1R,3s,5S)-3-(7-amino-3-(2-(hydroxymethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone and (5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl 4H-1,2,4-triazole-3-carboxylate

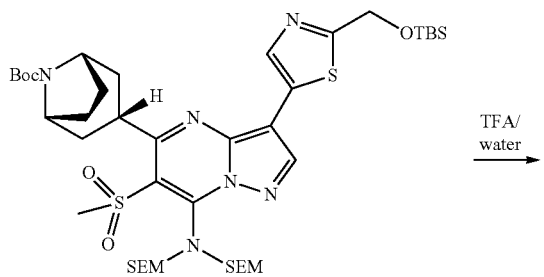

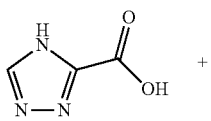

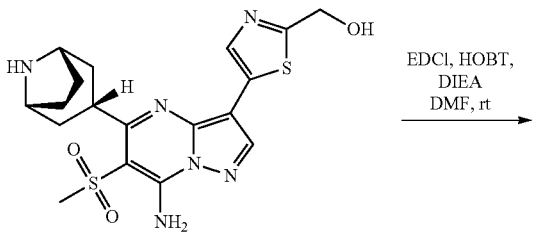

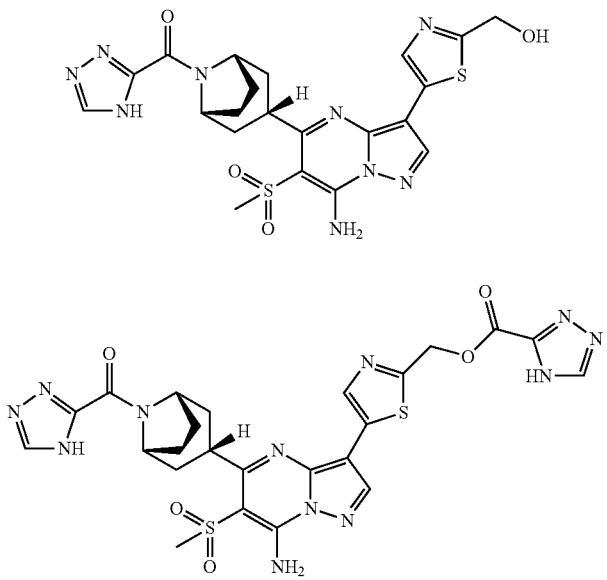

The compounds ((1R,3s,5S)-3-(7-amino-3-(2-(hydroxymethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone and (5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl 4H-1,2,4-triazole-3-carboxylate were prepared with the same conditions described previously.

Similarly compounds in Table 7-13 were made.

TABLE 7-13

| Compound ID | Structures | Compound Name | M + H (calculated)/ M + H (observed) | pAKT S473 IC50 | p4E-BP1 Thr37/ 46 IC50 |
|---|---|---|---|---|---|
| 7.91 | 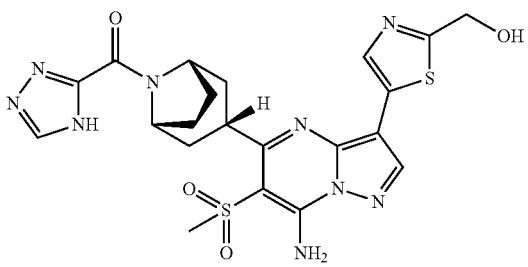 | ((1R,3s,5S)-3-(7-amino-3-(2-(hydroxymethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 530.1/ 530.2 | ND | ND |
| 7.92 | 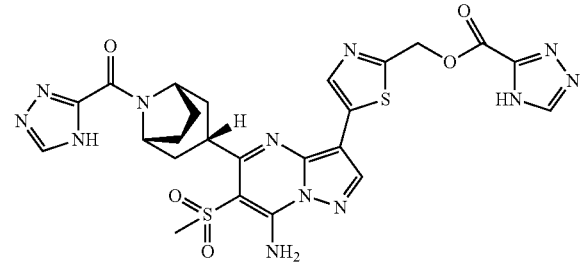 | (5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl 4H-1,2,4-triazole-3-carboxylate | 625.1/ 625.3 | ND | ND |
| 7.93 | 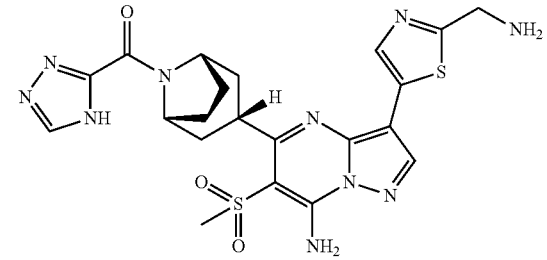 | ((1R,3s,5S)-3-(7-amino-3-(2-(aminomethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 529.1/ 529.2 | ND | ND |
| 7.94 | 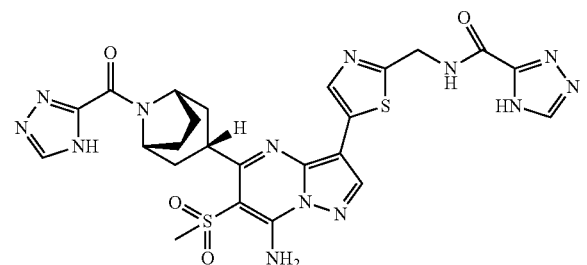 | N-((5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl)-4H-1,2,4-triazole-3-carboxamide | 624.2/ 624.3 | ND | ND |
| 7.95 | 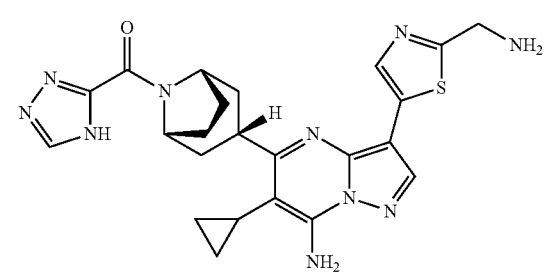 | ((1R,3s,5S)-3-(7-amino-3-(2-(aminomethyl)thiazol-5-yl)-6-cyclopropylpyrazolo[1,5-a]pyrimidin-5-yl)-8-azabicyclo[3.2.1]octan-8-yl)(4H-1,2,4-triazol-3-yl)methanone | 491.2/ 491.2 | ND | ND |

TABLE 7-13-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 7.96 | 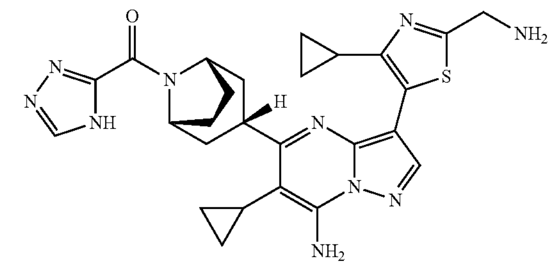 | ((1R,3s,5S)-3-(7-amino-3-(2-(aminomethyl)-4-cyclopropylthiazol-5-yl)-6-cyclopropylpyrazolo[1,5-a]pyrimidin-5-yl)-8-azabicyclo[3.2.1]octan-8-yl)(4H-1,2,4-triazol-3-yl)methanone | 531.2/ 531.4 | ND | ND |

Example 7-17

Preparation of ((1R,3s,5S)-3-(7-amino-3-(6-(hydroxymethyl)pyridin-3-yl)pyrazolo[1,5-a]pyrimidin-5-yl)-8-azabicyclo[3.2.1]octan-8-yl)(1H-1,2,4-triazol-5-yl)methanone

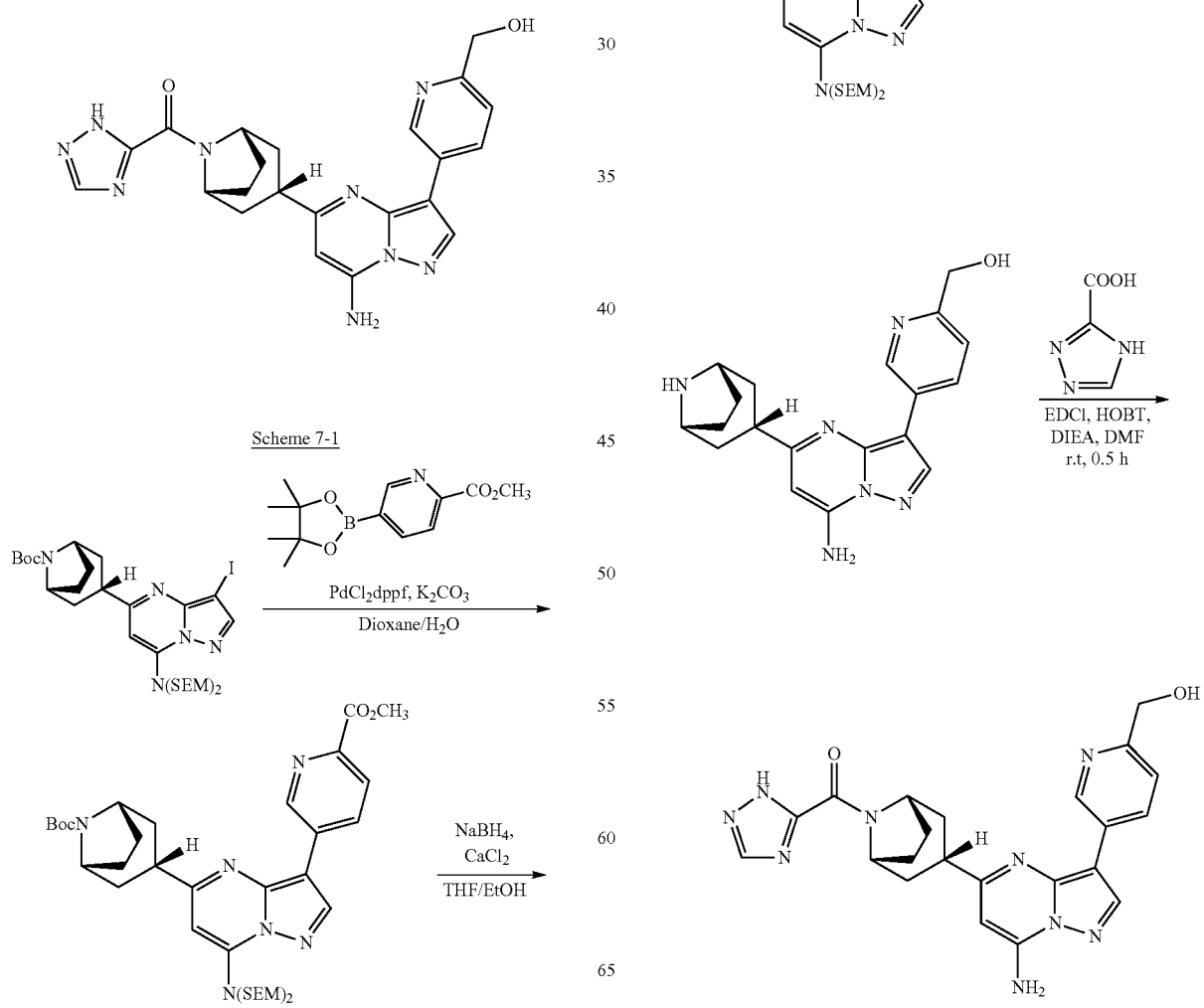

Step A—Synthesis of (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate

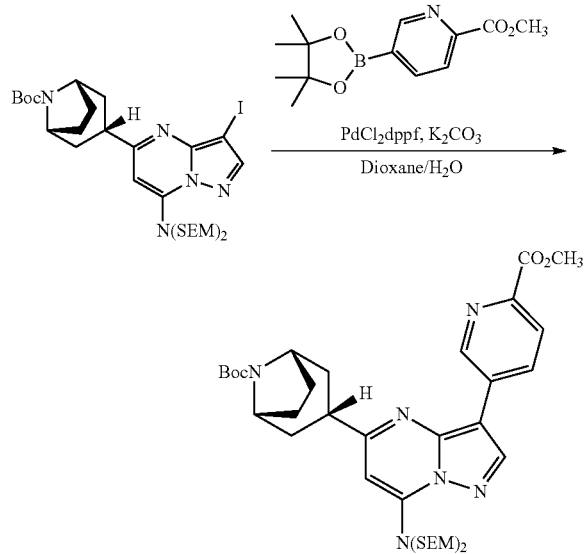

To tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (1.0 g, 1.37 mmol) in dioxane (10 mL) and H₂O (1.5 mL) was added methyl 5-(4,4,5,5-tetramethyl-1,3,2-dioxaborolan-2-yl)picolinate (0.61 g, 2.33 mmol), PdCl₂(dppf).CH₂Cl₂ (0.48 g, 0.58 mmol) and K₂CO₃ (0.97 g, 6.99 mmol). The reaction was heated at 100° C. for 15 hours, at which time LC/MS analysis confirmed full consumption of starting material. On cooling, H₂O (5 mL) and EtOAc (25 mL) were added and separated the layers. The aqueous layer was extracted with EtOAc (2×10 mL). The combined organic layer was dried (Na₂SO₄) and concentrated in vacuo to afford crude product. Gradient column chromatography on silica eluting with 30 to 90% EtOAc/hexanes gave the desired product (607 mg).

Step B—Synthesis of (1R,3s,5S)-tert-butyl 3-(7-(bis((2-(trimethylsilyl)ethoxy)methyl)amino)-3-(6-(hydroxymethyl)pyridin-3-yl)pyrazolo[1,5-a]pyrimidin-5-yl)-8-azabicyclo[3.2.1]octane-8-carboxylate

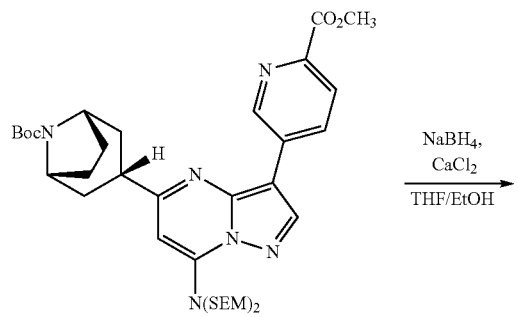

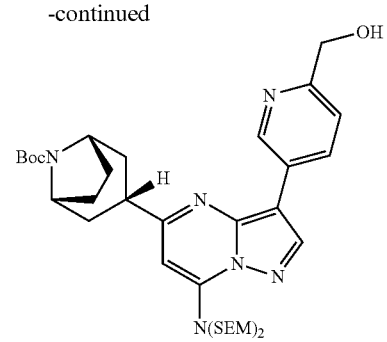

To a solution of (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate (Int-4-a) (570 mg, 0.77 mmol) in anh tetrahydrofuran (6 mL) was added ethanol (9 mL). To the resulting solution was added calcium chloride powder (257 mg, 2.31 mmol) followed by sodium borohydride (117 mg, 3.09 mmol). Stirred reaction mixture at room temperature for 1.5 hours at which point LC-MS analysis confirmed full consumption of starting material. The reaction was diluted with dichloromethane and then quenched by slowly adding 2N HCl (aq) slowly until reaction mixture stopped bubbling. The mixture was further diluted with water (100 mL). Separated the layers, the aqueous layer was extracted with dichloromethane. The combined organic layer was washed with saturated sodium bicarbonate, brine, dried over anhydrous sodium sulfate and concentrated in vacuo to give a thick brown oil (560 mg) which was used without further purification in the next step.

Step C—Synthesis of (5-(7-amino-5-((1R,3s,5S)-8-azabicyclo[3.2.1]octan-3-yl)pyrazolo[1,5-a]pyrimidin-3-yl)pyridin-2-yl)methanol

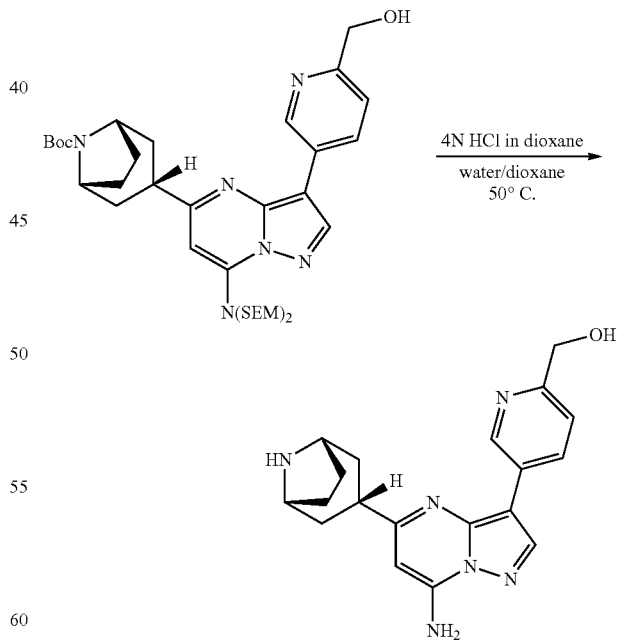

To (1R,3s,5S)-tert-butyl 3-(7-(bis((2-(trimethylsilyl)ethoxy)methyl)amino)-3-(6-(hydroxymethyl)pyridin-3-yl)pyrazolo[1,5-a]pyrimidin-5-yl)-8-azabicyclo[3.2.1]octane-8-carboxylate (Int-4-b) (549 mg, 0.77 mmol) was added 1,4-dioxane (10 mL) followed by 4N HCl in dioxane (10 mL) and water (5 mL). The resulting solution was stirred at 50° C. for 30 minutes at which point LC-MS analysis indicated that the reaction was complete. The solvent was removed in vacuo to get the desired product as an HCl salt. This HCl product was lyophilized to afford the desired product (5-(7-amino-5-((1R,3s,5S)-8-azabicyclo[3.2.1]octan-3-yl)pyrazolo[1,5-a]pyrimidin-3-yl)pyridin-2-yl)methano as a brown solid.

Step C—Synthesis of (((1R,3s,5S)-3-(7-amino-3-(6-(hydroxymethyl)pyridin-3-yl)pyrazolo[1,5-a]pyrimidin-5-yl)-8-azabicyclo[3.2.1]octan-8-yl)(1H-1,2,4-triazol-5-yl)methanone

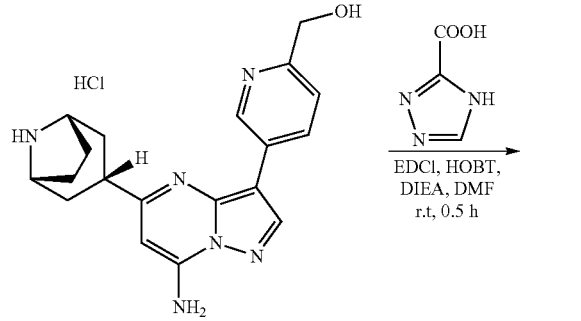

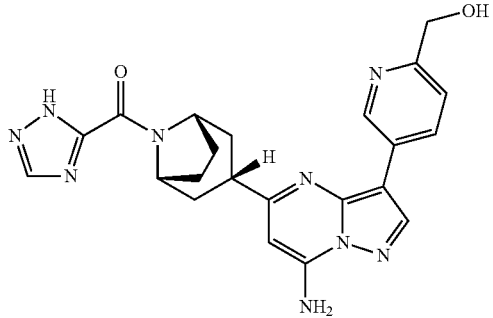 [SMILES: Nc1cc([C@@H]2C[C@H]3CC[C@@H](C2)N3C(=O)c2ncn[nH]2)nc2c(-c3ccc(CO)nc3)cnn12]

A mixture of 1H-1,2,4-triazole-3-carboxylic acid (56 mg, 0.50 mmol), EDCI (147 mg, 0.77 mmol), and 1-hydroxybenzotriazole (52 mg, 0.38 mmol) in DMF (5 ml) was stirred at room temperature for 10 min. (5-(7-amino-5-((1R,3s,5S)-8-azabicyclo[3.2.1]octan-3-yl)pyrazolo[1,5-a]pyrimidin-3-yl)pyridin-2-yl)methanol hydrochloride (0.38 mmol) was added followed by N,N-diisopropylethylamine (0.33 ml, 1.92 mmol). It was stirred further for 20 min at room temperature at which time LC/MS analysis confirmed full consumption of starting material. This crude compound was purified by HPLC to afford the desired product (Table 7-14). LC/MS RT=1.59 min.

TABLE 7-14

| Compound ID | Structures | Compound Name | M + H (calculated)/ M + H (observed) | pAKT S473 IC50 | p4E-BP1 Thr37/ 46 IC50 |
|---|---|---|---|---|---|
| 7.97 | 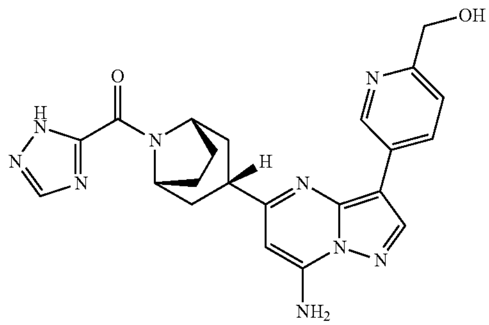 [SMILES: Nc1cc([C@@H]2C[C@H]3CC[C@@H](C2)N3C(=O)c2ncn[nH]2)nc2c(-c3ccc(CO)nc3)cnn12] | ((1R,3s,5S)-3-(7-amino-3-(6-(hydroxymethyl)pyridin-3-yl)pyrazolo[1,5-a]pyrimidin-5-yl)-8-azabicyclo[3.2.1]octan-8-yl)(1H-1,2,4-triazol-5-yl)methanone | 446.2/ 445.9 | D | C |

Example 7-18

Preparation of 1-(5-((1R,3s,5S)-8-(1H-1,2,4-triazole-5-carbonyl)-8-azabicyclo[3.2.1]octan-3-yl)-7-amino-3-(5-fluoro-6-(2-hydroxypropan-2-yl) pyridin-3-yl) pyrazolo[1,5-a]pyrimidin-6-yl)ethanone Scheme 7-2

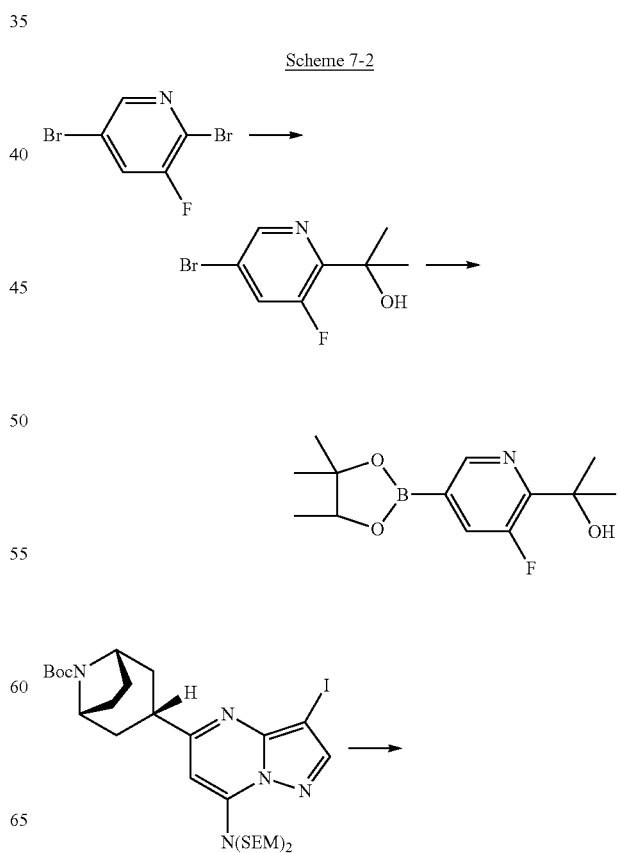

-continued

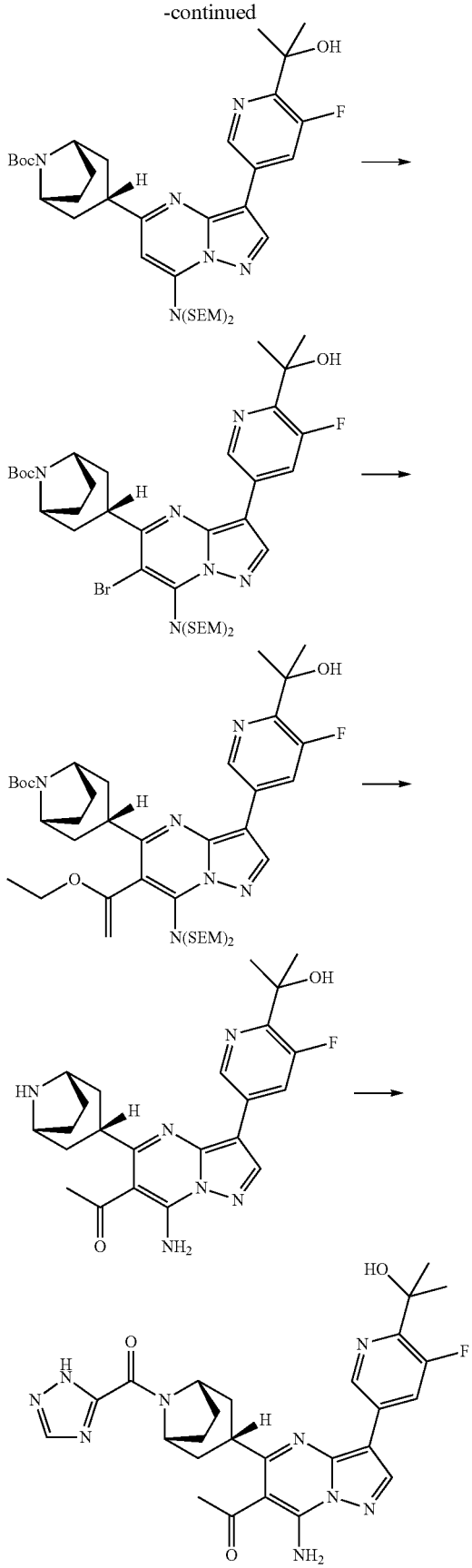

Step A—Synthesis of 2-(5-bromo-3-fluoropyridin-2-yl)propan-2-ol

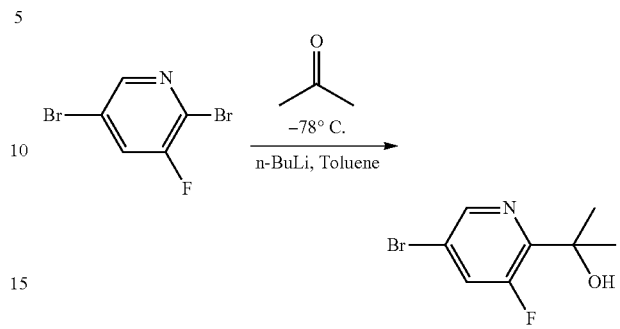

To 2,5-dibromo-3-fluoropyridine in toluene at −78° C. was added n-butyllithium drop wise. The resulting solution was stirred at −78° C. for 1.5 hours. Then at −78° C., added acetone drop wise to the reaction mixture and continue to stir reaction at −78° C. for 2 hours at which point LC-MS and TLC indicated the reaction was complete. The reaction was warmed to 0° C. and quenched with saturated ammonium chloride solution (aq.) and then diluted with water (50 mL) and extracted with ethyl acetate (2×100 mL). The organic layer was dried ($Na_2SO_4$) and concentrated in vacuo to afford crude product. Gradient column chromatography on silica eluting with 0 to 30% EtOAc/hexanes gave the desired product (1.04 g).

Step B—Synthesis of 2-(3-fluoro-5-(4,4,5,5-tetramethyl-1,3,2-dioxaborolan-2-yl)pyridin-2-yl)propan-2-ol

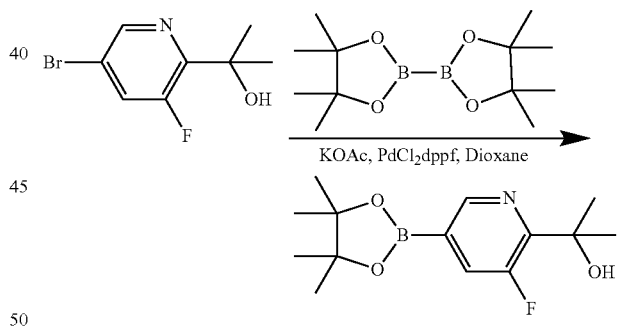

A 50 mL round-bottomed flask was charged with 2-(5-bromo-3-fluoropyridin-2-yl)propan-2-ol (Int-5a) (0.5 g, 2.15 mmol), 4,4,4',4',5,5,5',5'-octamethyl-2,2'-bi(1,3,2-dioxaborolane) (1.1 g, 4.29 mmol), potassium acetate (0.63 g, 6.44 mmol), $PdCl_2$(dppf).$CH_2Cl_2$ (0.17 g, 0.22 mmol). The reaction vessel was sealed with a rubber septum, flushed with Argon and 1,4-dioxane (10 mL) added to the reaction. The reaction mixture was stirred at 80° C. for 2 hours at which point TLC and LC-MS indicated full consumption of the starting material. The solvent was removed in vacuo and the residue was partitioned between dichloromethane and water. The organic layer was dried ($Na_2SO_4$) and concentrated in vacuo to afford crude product 2-(3-fluoro-5-(4,4,5,5-tetramethyl-1,3,2-dioxaborolan-2-yl)pyridin-2-yl)propan-2-ol which was used in the next reaction without further purification.

Step C—Synthesis of (1R,3s,5S)-tert-butyl 3-(7-(bis ((2-(trimethylsilyl)ethoxy)methyl)amino)-3-(5-fluoro-6-(2-hydroxypropan-2-yl)pyridin-3-yl) pyrazolo[1,5-a]pyrimidin-5-yl)-8-azabicyclo[3.2.1] octane-8-carboxylate

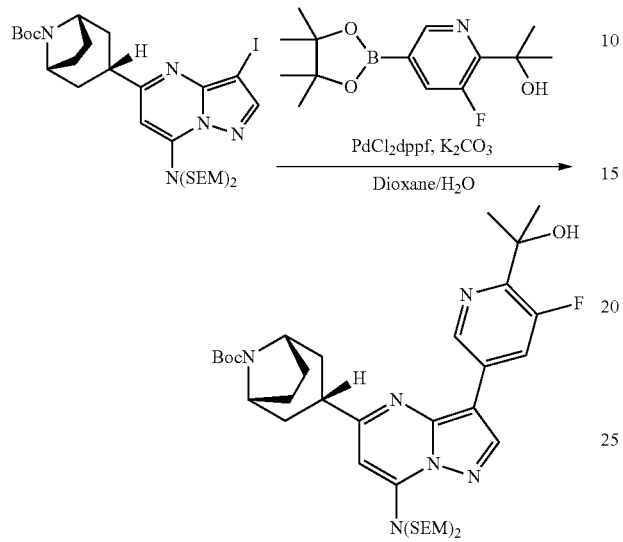

To tert-butyl 3-(7-(bis((2-(trimethylsilyl)ethoxy)methyl) amino)-3-iodopyrazolo[1,5-a]pyrimidin-5-yl)-8-azabicyclo [3.2.1]octane-8-carboxylate (0.46 g, 0.63 mmol) in dioxane (10 mL) and H₂O (1.5 mL) was added 2-(3-fluoro-5-(4,4,5, 5-tetramethyl-1,3,2-dioxaborolan-2-yl)pyridin-2-yl)propan-2-ol (0.30 g, 1.07 mmol), PdCl₂(dppf).CH₂Cl₂ (0.13 g, 0.16 mmol) and K₂CO₃ (0.26 g, 1.88 mmol). The reaction was heated at 85° C. for 15 hours, at which time LC/MS analysis confirmed full consumption of starting material. On cooling, H₂O (5 ml) and EtOAc (25 mL) were added and separated the layers. The aqueous layer was extracted with EtOAc (2×10 ml). The combined organic layer was dried (Na₂SO₄) and concentrated in vacuo to afford crude product. Gradient column chromatography on silica eluting with 30 to 90% EtOAc/hexanes gave the desired product (0.25 g).

Step D—Synthesis of (1R,3s,5S)-tert-butyl 3-(7-(bis ((2-(trimethylsilyl)ethoxy)methyl)amino)-6-bromo-3-(5-fluoro-6-(2-hydroxypropan-2-yl)pyridin-3-yl (pyrazolo[1,5-a]pyrimidin-5-yl-8-azabicyclo[3.2.1] octane-8-carboxylate

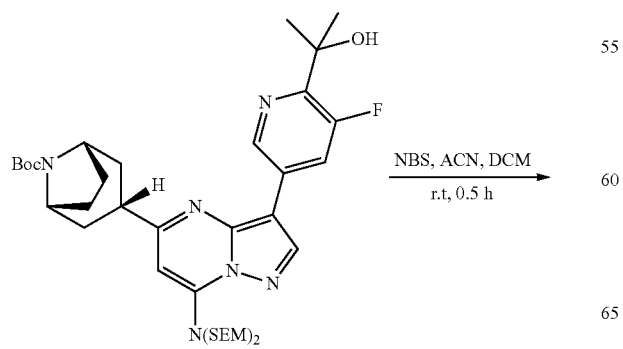

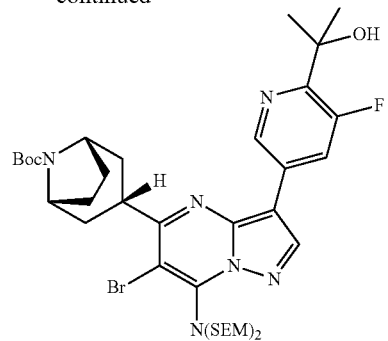

To a mixture of (1R,3s,5S)-tert-butyl 3-(7-(bis((2-(trimethylsilyl)ethoxy)methyl)amino)-3-(5-fluoro-6-(2-hydroxypropan-2-yl)pyridin-3-yl)pyrazolo[1,5-a]pyrimidin-5-yl)-8-azabicyclo[3.2.1]octane-8-carboxylate (1.1 g, 1.45 mmol) in CH₃CN (15 mL) and dichloromethane (15 mL) was added N-bromosuccinimide (0.28 g, 1.59 mmol) in one portion and the resulting mixture was stirred at room temperature for 0.5 h, at which time LC/MS confirmed reaction was not complete. Added more N-bromosuccinimide (0.28 g, 1.59 mmol) in one portion and the resulting mixture was stirred at room temperature for 1.5 h at which time LC/MS confirmed full conversion of starting material to product. The solvent was removed in vacuo and the residue was purified by column chromatography on silica gel. Elution with EtOAc/Hexanes (0-30%) gave the title product (0.87 g).

Step E—Synthesis of (1R,3s,5S)-tert-butyl 3-(7-(bis ((2-(trimethylsilyl)ethoxy)methyl)amino)-6-(1-ethoxyvinyl)-3-(5-fluoro-6-(2-hydroxypropan-2-yl) pyridin-3-yl)pyrazolo[1,5-a]pyrimidin-5-yl)-8-azabicyclo[3.2.1]octane-8-carboxylate

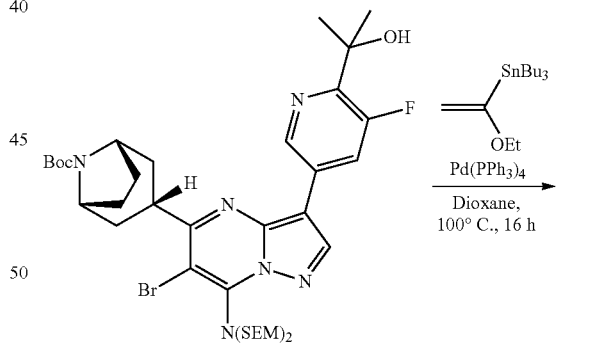

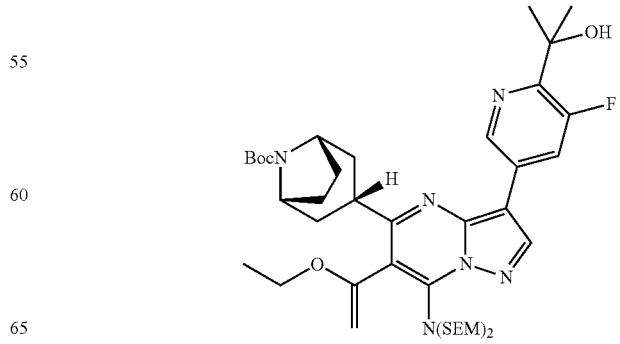

A mixture of compound (1R,3s,5S)-tert-butyl 3-(7-(bis((2-(trimethylsilyl)ethoxy)methyl)amino)-6-bromo-3-(5-fluoro-6-(2-hydroxypropan-2-yl)pyridin-3-yl)pyrazolo[1,5-a]pyrimidin-5-yl)-8-azabicyclo[3.2.1]octane-8-carboxylate (0.86 g, 1.03 mmol), tributyl(1-ethoxyvinyl)tin (0.75 g, 2.06 mmol), tetrakis(triphenylphosphine)palladium (0.12 g, 0.103 mmol) in dioxane (20 mL) was degassed with argon for five minutes. It was then heated at 100° C. in a sealed tube for 16 h, at which time LC/MS analysis confirmed full consumption of starting material. On cooling, the solvent was concentrated in vacuo, and the crude residue was dissolved in EtOAc (125 mL), washed with 0.5 M KF solution (1×20 mL), water (1×25 mL), brine (1×25 mL), and dried over MgSO$_4$. The solvent was removed in vacuo and the residue was purified by column chromatography on silica gel. Elution with EtOAc/Hexanes (20-50%) gave the title product (0.78 g).

Step F—Synthesis of 1-(7-amino-5-((1R,3s,5S)-8-azabicyclo[3.2.1]octan-3-yl)-3-(5-fluoro-6-(2-hydroxypropan-2-yl)pyridin-3-yl)pyrazolo[1,5-a]pyrimidin-6-yl)ethanone

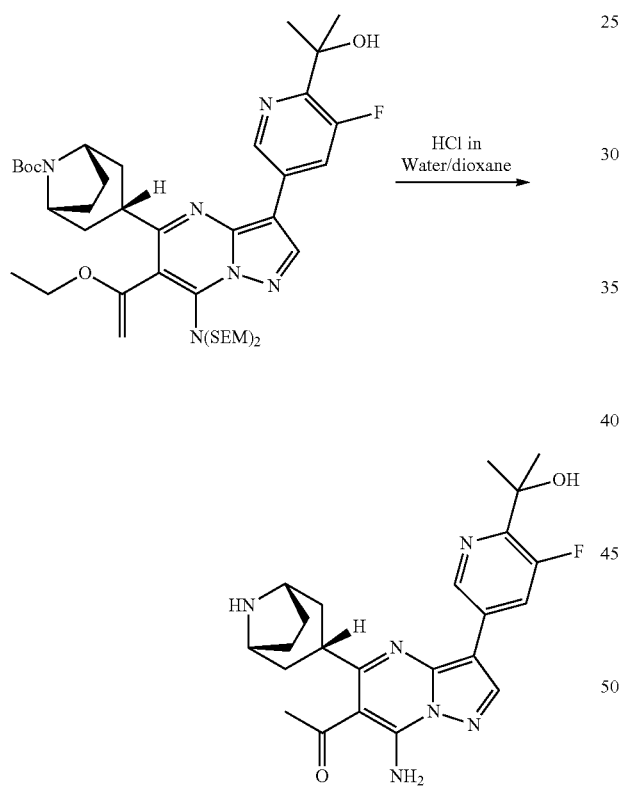

To a mixture of (1R,3s,5S)-tert-butyl 3-(7-(bis((2-(trimethylsilyl)ethoxy)methyl)amino)-6-(1-ethoxyvinyl)-3-(5-fluoro-6-(2-hydroxypropan-2-yl)pyridin-3-yl)pyrazolo[1,5-a]pyrimidin-5-yl)-8-azabicyclo[3.2.1]octane-8-carboxylate (0.85 g, 0.103 mmol) in dioxane (2 mL) was added 4 M HCl in water (1 ml) at 0° C. After stirring for 10 min at 0° C., 4 M HCl in dioxane (1 mL) was added. The reaction mixture was stirred at 0° C. for 30 min and the cooling bath was removed to warm it up to room temperature for 30 minutes, and then heated at 50° C. for 1 hour at which time LC/MS analysis confirmed full consumption of starting material. The solvent was removed in vacuo to get the desired product as an HCl salt. This HCl product was lyophilized to afford the desired product as a yellow solid (51 mg).

Step G—Synthesis of 1-(5-((1R,3s,5S)-8-(1H-1,2,4-triazole-5-carbonyl)-8-azabicyclo[3.2.1]octan-3-yl)-7-amino-3-(5-fluoro-6-(2-hydroxypropan-2-yl)pyridin-3-yl)pyrazolo[1,5-a]pyrimidin-6-yl)ethanone

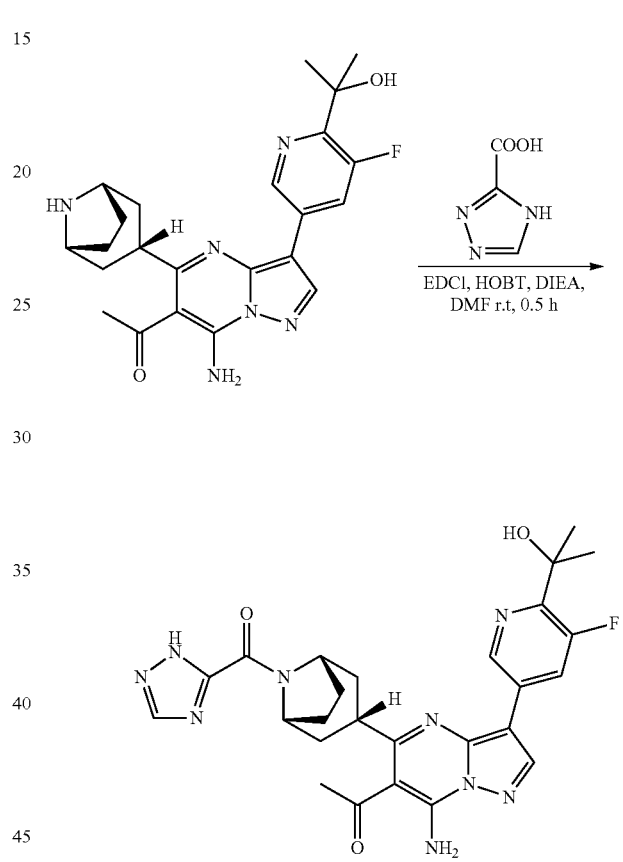

A mixture of 1H-1,2,4-triazole-3-carboxylic acid (15.4 mg, 0.14 mmol), EDCI (41.3 mg, 0.22 mmol), and 1-hydroxybenzotriazole (14.2 mg, 0.11 mmol) in DMF (2 ml) was stirred at room temperature for 10 minutes. 1-(7-amino-5-((1R,3s,5S)-8-azabicyclo[3.2.1]octan-3-yl)-3-(5-fluoro-6-(2-hydroxypropan-2-yl)pyridin-3-yl)pyrazolo[1,5-a]pyrimidin-6-yl)ethanone hydrochloride (50 mg, 0.11 mmol) was added followed by N,N-diisopropylethylamine (0.57 ml, 0.33 mmol). It was stirred further for 20 min at room temperature at which time LC/MS analysis confirmed full consumption of starting material. This crude compound was purified by HPLC to afford the desired product (Table 7-15).

TABLE 7-15
| Compound ID | Structures | Compound Name | M + H (calculated)/ M + H (observed) | pAKT S473 IC50 | p4E-BP1 Thr37/46 IC50 |
|---|---|---|---|---|---|
| 7.98 | 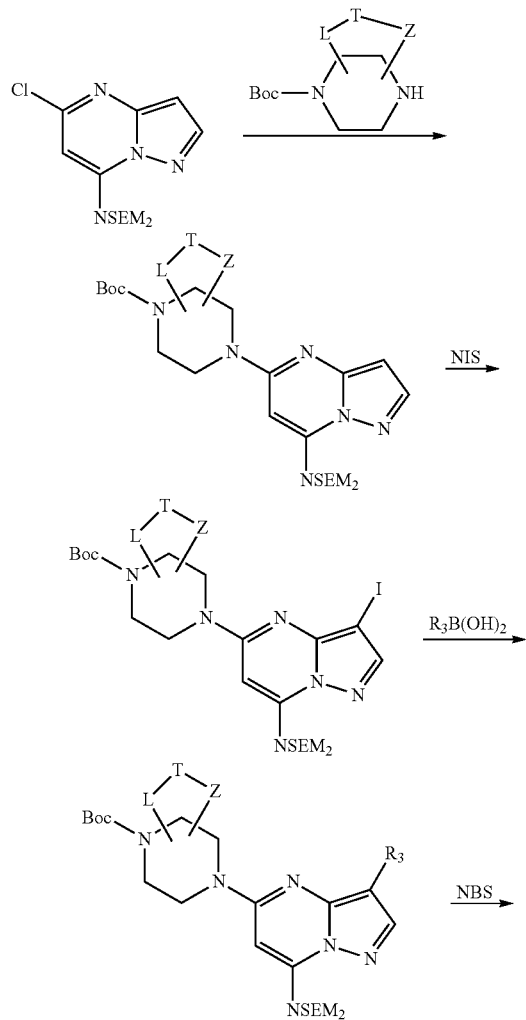 | 1-(5-(((1R,3s,5S)-8-(1H-1,2,4-triazole-5-carbonyl)-8-azabicyclo[3.2.1]octan-3-yl)-7-amino-3-(5-fluoro-6-(2-hydroxypropan-2-yl)pyridin-3-yl)pyrazolo[1,5-a]pyrimidin-6-yl)ethanone | 534.2/ 534.0 | A | A |
Example 8-1
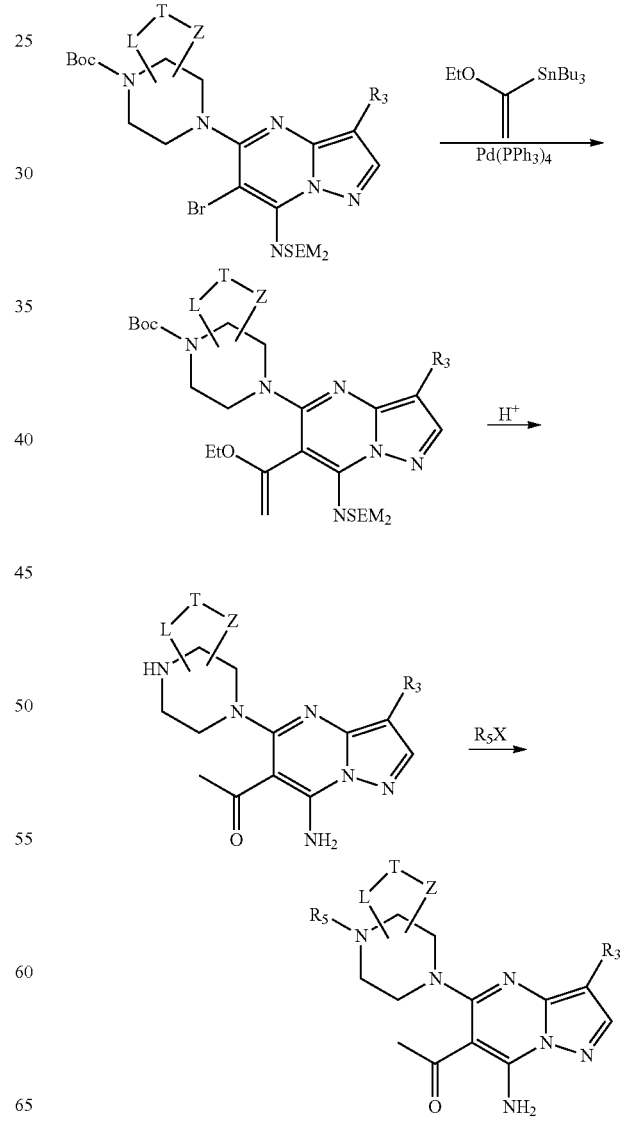

Preparation of 1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone

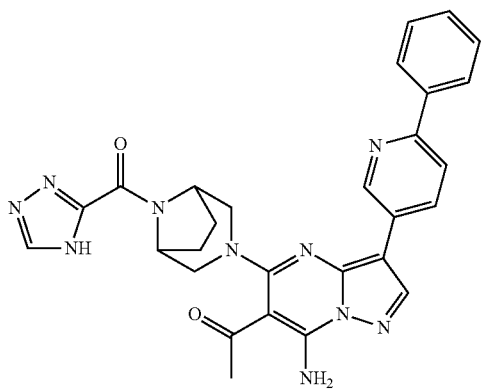 [SMILES: CC(=O)c1c(N2CC3CCC(C2)N3C(=O)c2nnc[nH]2)nc2c(-c3ccc(-c4ccccc4)nc3)cnn2c1N]

Step 1

Preparation of 5-chloro-3-(6-phenylpyridin-3-yl)-N,N-bis((2-(trimethylsilyl)ethoxy)methyl)pyrazolo[1,5-a]pyrimidin-7-amine

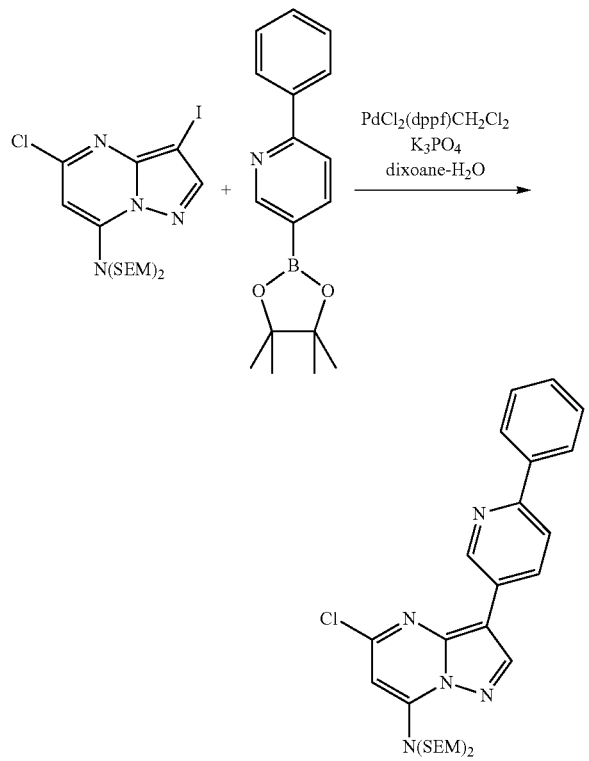

Substrate 2-phenyl-5-(4,4,5,5-tetramethyl-1,3,2-dioxaborolan-2-yl)pyridine (2.38 mmol, 675 mg), K$_3$PO$_4$ (5.96 mmol, 1264 mg), and PdCl$_2$(dppf).CH$_2$Cl$_2$ (0.20 mmol, 162 mg) were added to a solution of 5-chloro-3-iodo-N,N-bis((2-(trimethylsilyl)ethoxy)methyl)pyrazolo[1,5-a]pyrimidin-7-amine (1.98 mmol, 1101 mg) in dioxane (18 mL) and H$_2$O (3 mL). The resulting solution was stirred at 70° C. under argon overnight. The mixture was diluted with H$_2$O and then extracted with ethyl acetate (×2). The combined organic layers were washed with brine and dried with Na$_2$SO$_4$. Evaporation and purification by column chromatography afforded 5-chloro-3-(6-phenylpyridin-3-yl)-N,N-bis((2-(trimethylsilyl)ethoxy)methyl)pyrazolo[1,5-a]pyrimidin-7-amine: LCMS t$_R$=3.36 Min (5 min run, UV$_{254nm}$). Mass calculated for M+H 582.2, observed LC/MS m/z 582.2 (M+H).

Step 2

Preparation of tert-butyl 3-(7-(bis((2-(trimethylsilyl)ethoxy)methyl)amino)-3-(6-phenylpyridin-3-yl)pyrazolo[1,5-a]pyrimidin-5-yl)-3,8-diazabicyclo[3.2.1]octane-8-carboxylate

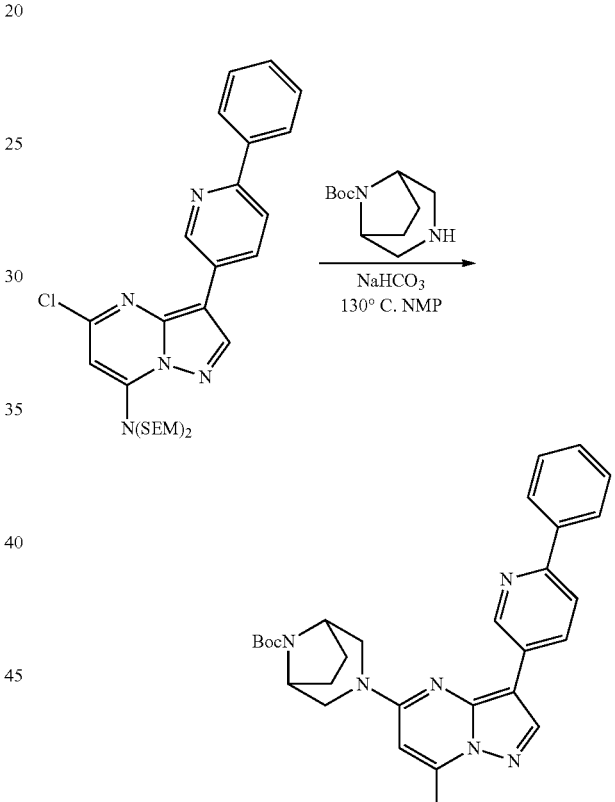

A mixture of 5-chloro-3-(6-phenylpyridin-3-yl)-N,N-bis((2-(trimethylsilyl)ethoxy)methyl)pyrazolo[1,5-a]pyrimidin-7-amine (226 mg, 0.39 mmol), tert-butyl 3,8-diazabicyclo[3.2.1]octane-8-carboxylate (330 mg, 1.56 mmol), NaHCO$_3$ (196 mg, 2.33 mmol) in NMP (4 mL) was heated at 130° C. overnight. The mixture was cooled to room temperature and diluted with H$_2$O and then extracted with ethyl acetate (×2). The combined organic layers were washed with brine and dried with Na$_2$SO$_4$. Evaporation of solvent afforded the crude displacement compound. Purification by column chromatography afforded tert-butyl 3-(7-(bis((2-(trimethylsilyl)ethoxy)methyl)amino)-3-(6-phenylpyridin-3-yl)pyrazolo[1,5-a]pyrimidin-5-yl)-3,8-diazabicyclo[3.2.1]octane-8-carboxylate: LCMS t$_R$=3.38 Min (5 min run, UV$_{254nm}$). Mass calculated for, M+H 758.4, observed m/z 758.3 (M+H).

655

Step 3

Preparation of tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl-3,8-diazabicyclo[3.2.1]octane-8-carboxylate

656

Step 4

Preparation of tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-3,8-diazabicyclo[3.2.1]octane-8-carboxylate

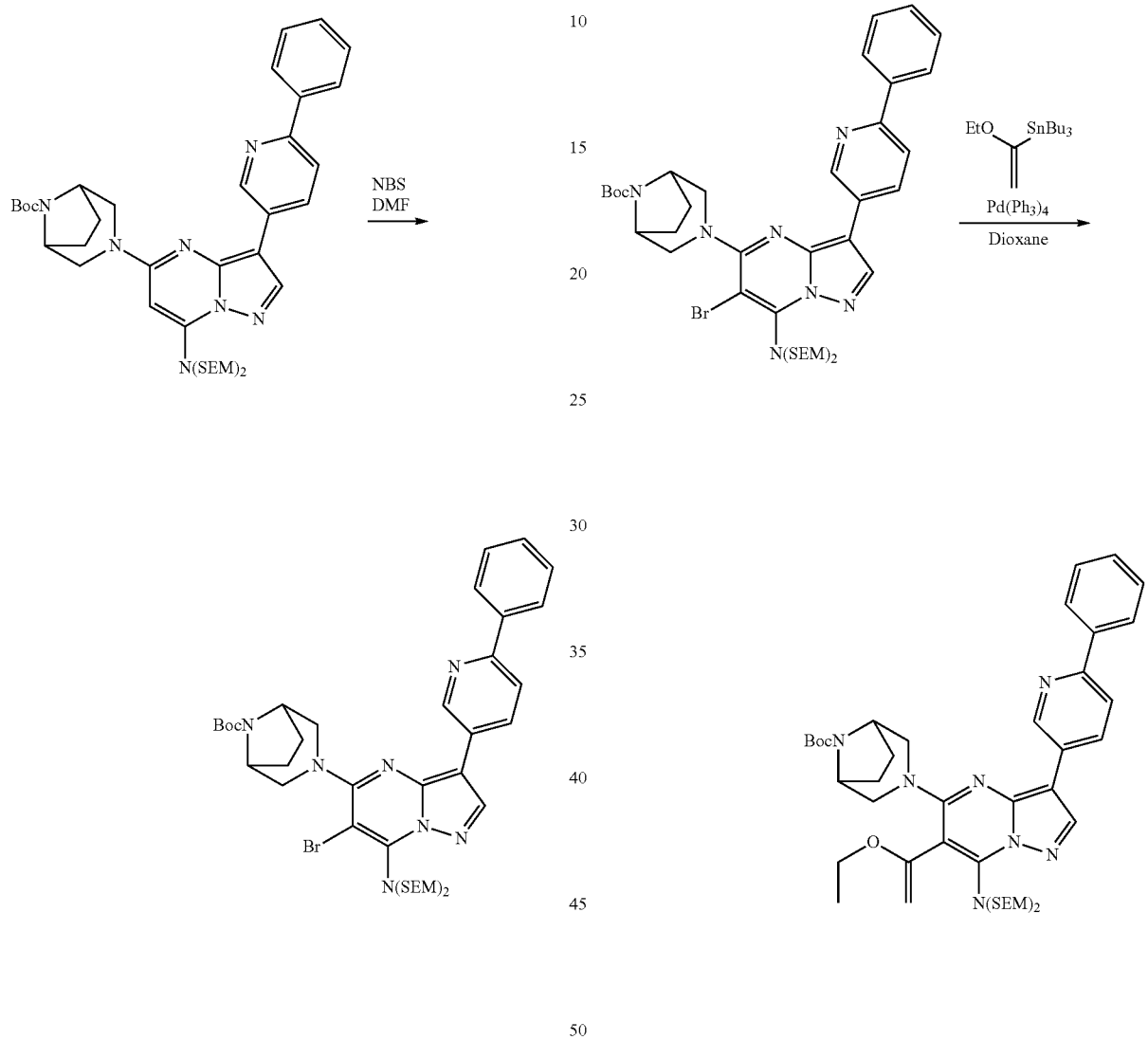

NBS (64 mg, 0.36 mmol) was added to a solution of tert-butyl 3-(7-(bis((2-(trimethylsilyl)ethoxy)methyl)amino)-3-(6-phenylpyridin-3-yl)pyrazolo[1,5-a]pyrimidin-5-yl)-3,8-diazabicyclo[3.2.1]octane-8-carboxylate (249 mg, 0.33 mmol) in DMF (6 mL). After stirring at room temperature for 1 h, the mixture was diluted with $H_2O$ and then extracted with ethyl acetate (×2). The combined organic layers were washed with brine and dried with $Na_2SO_4$. Evaporation and purification by column chromatography afforded tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-3,8-diazabicyclo[3.2.1]octane-8-carboxylate: LCMS $t_R$=3.66 Min (5 min run, $UV_{254nm}$). Mass calculated for M+H 836.3, observed m/z 836.06 (M+H).

A degassed mixture of tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-3,8-diazabicyclo[3.2.1]octane-8-carboxylate (256 mg, 0.31 mmol), $Pd(PPh_3)_4$ (35 mg, 0.031 mmol), tributyl(1-ethoxyvinyl)stannane (221 mg, 0.61 mmol) in dioxane (6 mL) was heated at 100° C. overnight. The reaction mixture was cooled to room temperature, filtered through a 9:1 $SiO_2$:KF plug and concentrated in vacuo. Purification by column chromatography afforded tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-3,8-diazabicyclo[3.2.1]octane-8-carboxylate, LCMS $t_R$=3.58 Min (10 min run, $UV_{254nm}$). Mass calculated for M+H 828.45, observed LC/MS m/z 828.07 (M+H).

Step 5

Preparation of 1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone

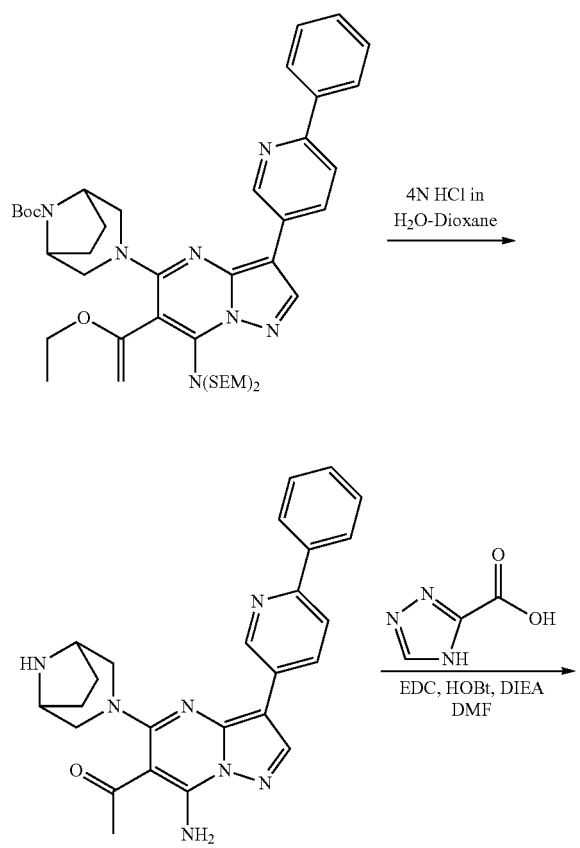

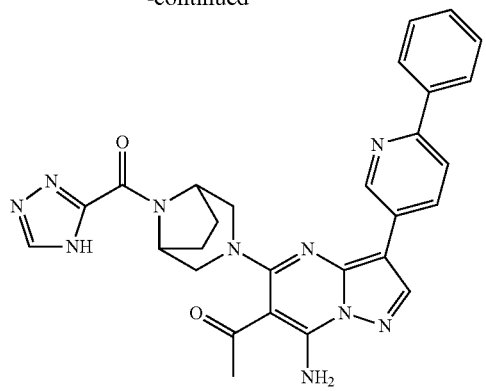

The tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-3,8-diazabicyclo[3.2.1]octane-8-carboxylate (31 mg) was treated with 4N HCl in H$_2$O (2 mL) and Dixoane (2 mL) until the disappearance of starting material in LCMS. Concentration afforded crude 1-(7-amino-5-(3,8-diazabicyclo[3.2.1]octan-3-yl)-3-(6-phenylpyridin-3-yl)pyrazolo[1,5-a]pyrimidin-6-yl)ethanone, which was used for next step without further purification, LCMS t$_R$=1.08 Min (10 min run, UV$_{254nm}$). Mass calculated for, M+H 440.2, observed LC/MS m/z 440.2 (M+H).

A mixture of 1-(7-amino-5-(3,8-diazabicyclo[3.2.1]octan-3-yl)-3-(6-phenylpyridin-3-yl)pyrazolo[1,5-a]pyrimidin-6-yl)ethanone (11 mg, 0.025 mmol), 4H-1,2,4-triazole-3-carboxylic acid (3.1 mg, 0.027 mmol), EDCI (9.5 mg, 0.05 mmol), HOBt (6.75 mg, 0.05 mmol) and DIEA (26 ul, 0.15 mmol) in DMF (1 ml) was stirred at room temperature overnight. Purification with prep-LC provided 1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone, LCMS t$_R$=3.31 Min (10 min run, UV 254 nm). Mass calculated for M+H 535.2, observed LC/MS m/z 534.95 (M+H).

Following the Scheme 8-1 and the procedures similar to preparation of 1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone, the following compounds (Table 8-1) can be prepared:

TABLE 8-1

| Compound ID | Structures | Compound Name | M + H (calculated)/ M + H (observed) | pAKT S473 IC50 | p4E-BP1 Thr37/ 46 IC50 |
| --- | --- | --- | --- | --- | --- |
| 8.1 | 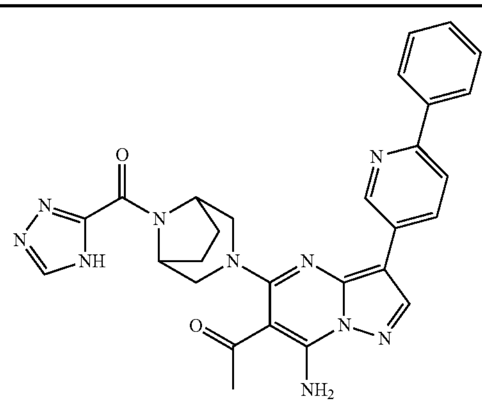 | 1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone | 535.2/ 535.0 | B | ND |

TABLE 8-1-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.2 | 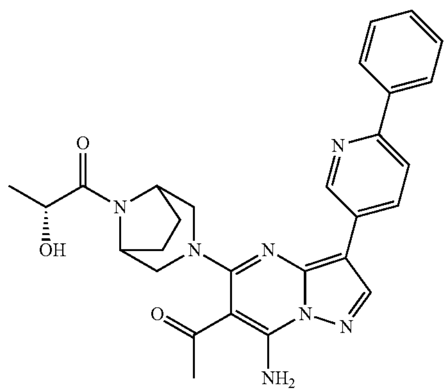 [SMILES: CC(=O)c1c(N2CC3CCC(C2)N3C(=O)[C@@H](C)O)nc2c(-c3ccc(-c4ccccc4)nc3)cnn2c1N] | (2R)-1-(3-(6-acetyl-7-amino-3-(6-phenylpyridin-3-yl)pyrazolo[1,5-a]pyrimidin-5-yl)-3,8-diazabicyclo[3.2.1]octan-8-yl)-2-hydroxypropan-1-one | 512.2/ 512.0 | B | ND |
| 8.3 | 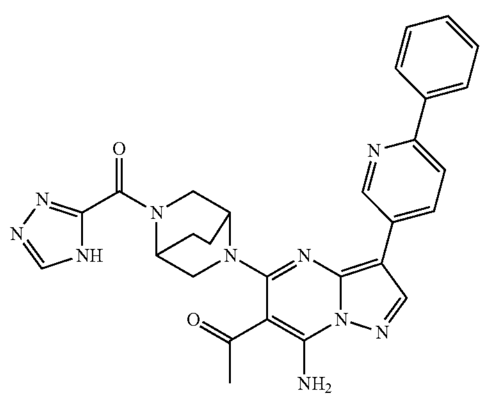 [SMILES: CC(=O)c1c(N2CC3CCC2CN3C(=O)c2nnc[nH]2)nc2c(-c3ccc(-c4ccccc4)nc3)cnn2c1N] | 1-(5-(5-(4H-1,2,4-triazole-3-carbonyl)-2,5-diazabicyclo[2.2.2]octan-2-yl)-7-amino-3-(6-phenylpyridin-3-yl)pyrazolo[1,5-a]pyrimidin-6-yl)ethanone | 535.2/ 535.2 | B | ND |
| 8.4 | 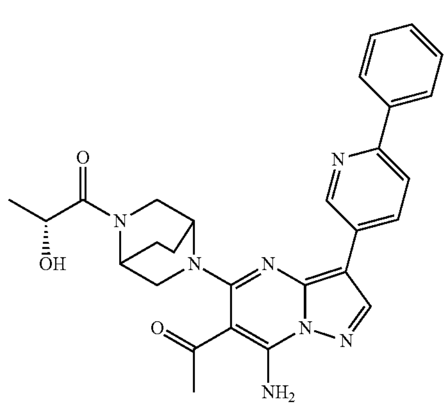 [SMILES: CC(=O)c1c(N2CC3CCC2CN3C(=O)[C@@H](C)O)nc2c(-c3ccc(-c4ccccc4)nc3)cnn2c1N] | (2R)-1-(5-(6-acetyl-7-amino-3-(6-phenylpyridin-3-yl)pyrazolo[1,5-a]pyrimidin-5-yl)-2,5-diazabicyclo[2.2.2]octan-2-yl)-2-hydroxypropan-1-one | 512.2/ 512.0 | C | ND |

TABLE 8-1-continued

| Compound ID | Structures | Compound Name | M + H (calculated)/ M + H (observed) | pAKT S473 IC50 | p4E-BP1 Thr37/ 46 IC50 |
|---|---|---|---|---|---|
| 8.5 | 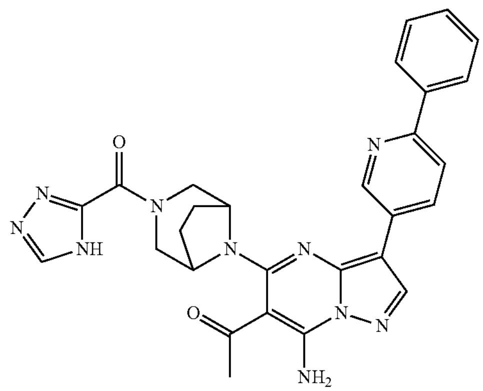 [SMILES: CC(=O)c1c(N2C3CCC2CN(C(=O)c2nnc[nH]2)C3)nc2c(-c3ccc(-c4ccccc4)nc3)cnn2c1N] | 1-(5-(3-(4H-1,2,4-triazole-3-carbonyl)-3,8-diazabicyclo[3.2.1]octan-8-yl)-7-amino-3-(6-phenylpyridin-3-yl)pyrazolo[1,5-a]pyrimidin-6-yl)ethanone | 535.2/ 535.0 | B | C |
| 8.6 | 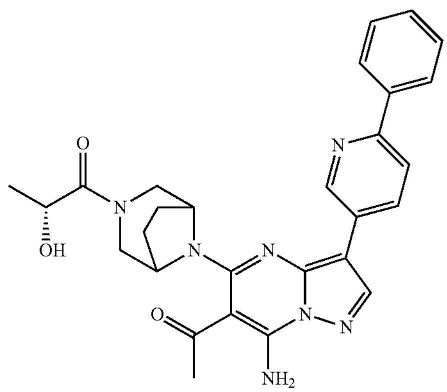 [SMILES: CC(=O)c1c(N2C3CCC2CN(C(=O)[C@@H](C)O)C3)nc2c(-c3ccc(-c4ccccc4)nc3)cnn2c1N] | (2R)-1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxypropan-1-one | 512.2/ 512.2 | B | C |
| 8.7 | 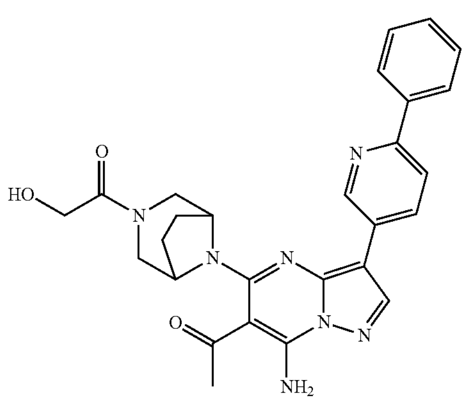 [SMILES: CC(=O)c1c(N2C3CCC2CN(C(=O)CO)C3)nc2c(-c3ccc(-c4ccccc4)nc3)cnn2c1N] | 1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxyethanone | 498.2/ 497.9 | B | C |

Example 8-2

Preparation of N-(5-((1R,3s,5S)-8-(4H-1,2,4-triazole-3-carbonyl)-8-azabicyclo[3.2.1]octan-3-yl-6-cyclopropyl-3-(6-phenylpyridin-3-yl)pyrazolo[1,5-a]pyrimidin-7-yl)acetamide

Step 1: Preparation of (1R,3s,5S)-tert-butyl 3-(7-acetamido-6-cyclopropyl-3-(6-phenylpyridin-3-yl)pyrazolo[1,5-a]pyrimidin-5-yl)-8-azabicyclo[3.2.1]octane-8-carboxylate

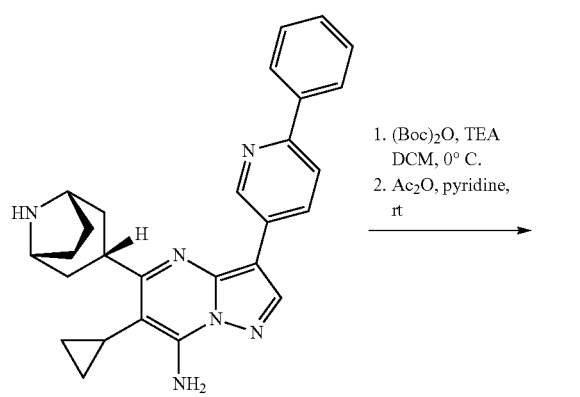

To a slurry of 5-((1R,3s,5S)-8-azabicyclo[3.2.1]octan-3-yl)-6-cyclopropyl-3-(6-phenylpyridin-3-yl)pyrazolo[1,5-a]pyrimidin-7-amine TFA salt (204 mg, 0.262 mmol, preparation described previously) in DCM (3 mL) was added TEA (5 eq), followed by (Boc)$_2$O (1.0 eq) in DCM (3 mL) at 0° C. The resulting reaction mixture was warmed to it and stirred for 1 h. All the volatiles were removed. The residue was dissolved in a mixture of pyridine/Ac$_2$O (1:2) and DMAP (1.1 eq) was added. The resulting mixture was heated at 60° C. for 4 h. After an aqueous workup, the crude mixture was purified by a SiO$_2$ column (0-100% EtOAc/Hexanes, R$_f$=0.1 in 50% EtOAc) to afford the titled compound as a pale yellow oil (22 mg).

Step 2: Preparation of N-(5-((1R,3s,5S)-8-azabicyclo[3.2.1]octan-3-yl-6-cyclopropyl-3-(6-phenylpyridin-3-yl)pyrazolo[1,5-a]pyrimidin-7-yl)acetamide TFA salt

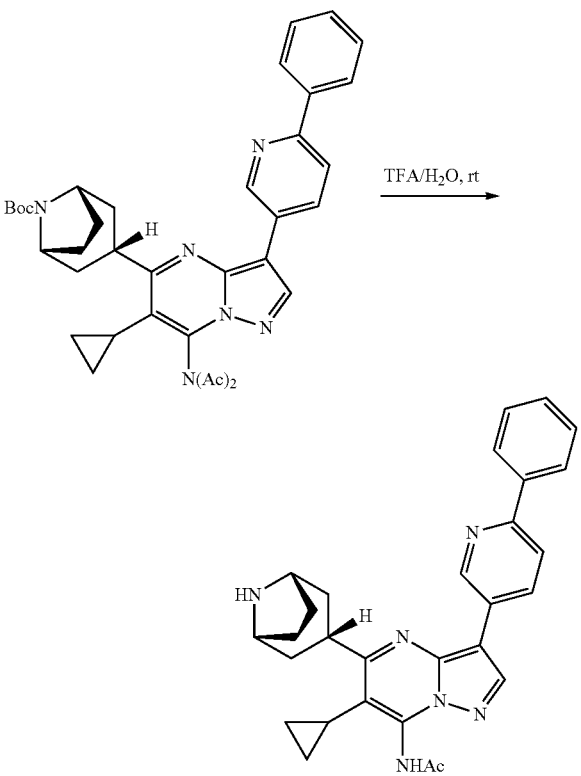

(1R,3s,5S)-tert-Butyl 3-(7-acetamido-6-cyclopropyl-3-(6-phenylpyridin-3-yl)pyrazolo[1,5-a]pyrimidin-5-yl)-8-azabicyclo[3.2.1]octane-8-carboxylate (22.0 mg, 0.0354 mmol) was treated with a mixture of TFA/H$_2$O (1.2 mL, 5/1) at it for 2 h. All the volatiles were removed to afford the titled compound as a pale yellow oil, which was used without further purification.

Step 3: Preparation of N-(5-((1R,3s,5S)-8-(4H-1,2,4-triazole-3-carbonyl)-8-azabicyclo[3.2.1]octan-3-yl-6-cyclopropyl-3-(6-phenylpyridin-3-yl)pyrazolo[1,5-a]pyrimidin-7-yl)acetamide

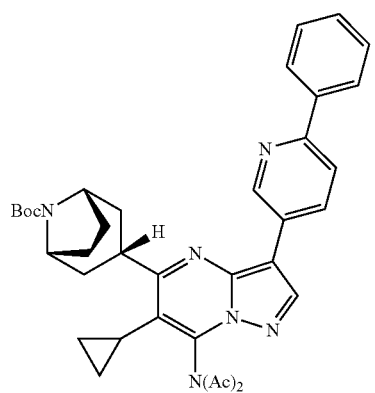

665
-continued

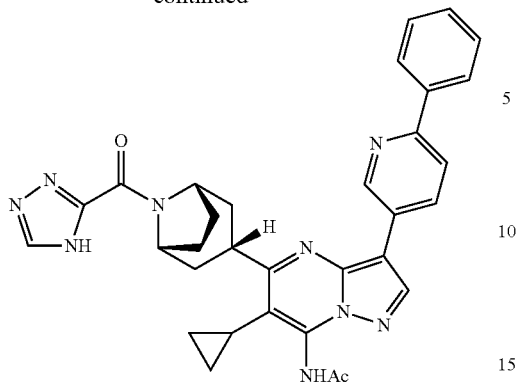

This compound was prepared from N-(5-((1R,3s,5S)-8-azabicyclo[3.2.1]octan-3-yl)-6-cyclopropyl-3-(6-phenylpyridin-3-yl)pyrazolo[1,5-a]pyrimidin-7-yl)acetamide TFA salt and 4H-1,2,4-triazole-3-carboxylic acid, following essentially the same amide coupling procedure described above (Scheme 8-1, step 5).

666
-continued

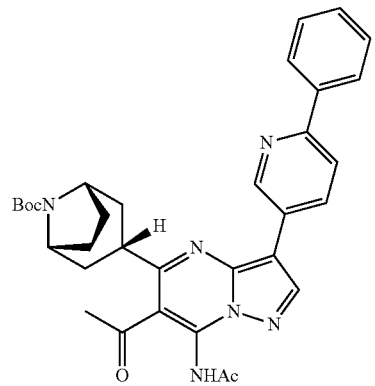

TABLE 8-2

| 8.8 | N-(5-((1R,3s,5S)-8-(4H-1,2,4-triazole-3-carbonyl)-8-azabicyclo[3.2.1]octan-3-yl)-6-cyclopropyl-3-(6-phenylpyridin-3-yl)pyrazolo[1,5-a]pyrimidin-7-yl)acetamide | 574.3/ 574.2 | ND | ND |
|---|---|---|---|---|

Example 8-3
Preparation of N-(5-((1R,3s,5S)-8-(4H-1,2,4-triazole-3-carbonyl)-8-azabicyclo[3.2.1]octan-3-yl)-6-acetyl-3-(6-phenylpyridin-3-yl)pyrazolo[1,5-a]pyrimidin-7-yl)acetamide
Step 1: Preparation of (1R,3s,5S)-tert-butyl 3-(7-acetamido-6-acetyl-3-(6-phenylpyridin-3-yl)pyrazolo[1,5-a]pyrimidin-5-yl)-8-azabicyclo[3.2.1]octane-8-carboxylate

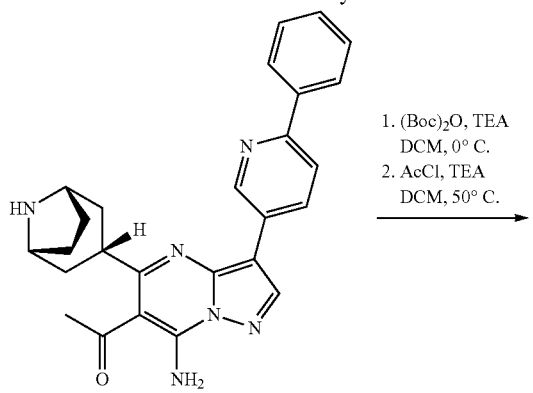

1. (Boc)₂O, TEA
DCM, 0° C.
2. AcCl, TEA
DCM, 50° C.

To a slurry of 1-(7-amino-5-((1R,3s,5S)-8-azabicyclo[3.2.1]octan-3-yl)-3-(6-phenylpyridin-3-yl)pyrazolo[1,5-a]pyrimidin-6-yl)ethanone HCl salt (565 mg, 1.03 mmol, preparation described previously) in DCM (5 mL) was added TEA (5 eq), followed by (Boc)₂O (1.0 eq) in DCM (5 mL) at 0° C. The resulting reaction mixture was warmed to rt and stirred for 1 h. To this solution was added 3.0 eq of AcCl, followed by 3.0 eq of TEA and 1.5 eq of DMAP at rt. The resulting reaction mixture was stirred at 50° C. overnight. After an aqueous workup, the crude mixture was purified by a SiO2 column (0-100% EtOAc/Hexanes, R$_f$=0.4 in 100% EtOAc) to afford the titled compound as an orange solid (320 mg).

667

Step 2: Preparation of N-(5-((1R,3s,5S)-8-(4H-1,2,4-triazole-3-carbonyl)-8-azabicyclo[3.2.1]octan-3-yl)-6-acetyl-3-(6-phenylpyridin-3-yl)pyrazolo[1,5-a]pyrimidin-7-yl)acetamide

668

Example 8-4

Preparation of N-(5-((1R,3s,5S)-8-(4H-1,2,4-triazole-3-carbonyl)-8-azabicyclo[3.2.1]octan-3-yl)-3-(6-phenylpyridin-3-yl)pyrazolo[1,5-a]pyrimidin-7-yl)acetamide Step 1: Preparation of (1R,3s,5S)-tert-butyl 3-(7-acetamido-3-(6-phenylpyridin-3-yl)pyrazolo[1,5-a]pyrimidin-5-yl)-8-azabicyclo[3.2.1]octane-8-carboxylate

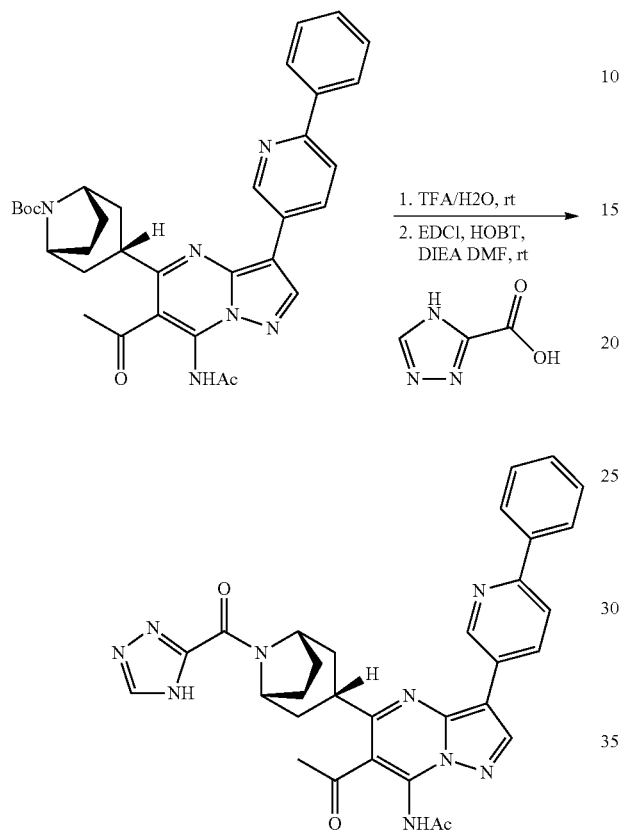

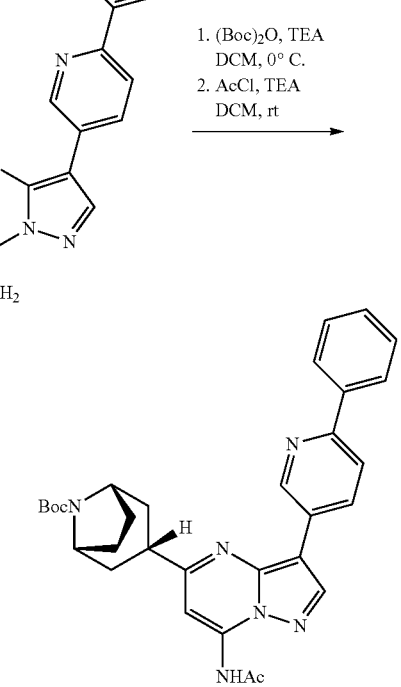

This compound was prepared from (1R,3s,5S)-tert-butyl 3-(7-acetamido-6-acetyl-3-(6-phenylpyridin-3-yl)pyrazolo[1,5-a]pyrimidin-5-yl-8-azabicyclo[3.2.1]octane-8-carboxylate and 4H-1,2,4-triazole-3-carboxylic acid, following standard amide coupling procedure described previously (Scheme 8-1, step 5).

TABLE 8-3

| 8.9 | | N-(5-((1R,3s,5S)-8-(4H-1,2,4-triazole-3-carbonyl)-8-azabicyclo[3.2.1]octan-3-yl)-6-acetyl-3-(6-phenylpyridin-3-yl)pyrazolo[1,5-a]pyrimidin-7-yl)acetamide | 576.2/ 576.2 | ND | ND |
|---|---|---|---|---|---|

To a slurry of 5-((1R,3s,5S)-8-azabicyclo[3.2.1]octan-3-yl)-3-(6-phenylpyridin-3-yl)pyrazolo[1,5-a]pyrimidin-7-amine TFA salt (198 mg, 0.268 mmol, preparation described previously) in DCM (3 mL) was added TEA (5 eq), followed by (Boc)$_2$O (1.0 eq) in DCM (3 mL) at 0° C. The resulting reaction mixture was warmed to it and stirred for 1 h. To this solution was added 3.0 eq of AcCl, followed by 3.0 eq of TEA and 1.5 eq of DMAP at rt. The resulting reaction mixture was stirred at it for overnight. After an aqueous workup, the crude mixture was purified by a SiO$_2$ column (0-60% EtOAc/Hexanes, R$_f$=0.3 in 50% EtOAc) to afford the titled compound as pale yellow forming solid (190 mg).

Step 2: Preparation of N-(5-((1R,3s,5S)-8-(4H-1,2,4-triazole-3-carbonyl)-8-azabicyclo[3.2.1]octan-3-yl-3-(6-phenylpyridin-3-yl)pyrazolo[1,5-a]pyrimidin-7-yl)acetamide

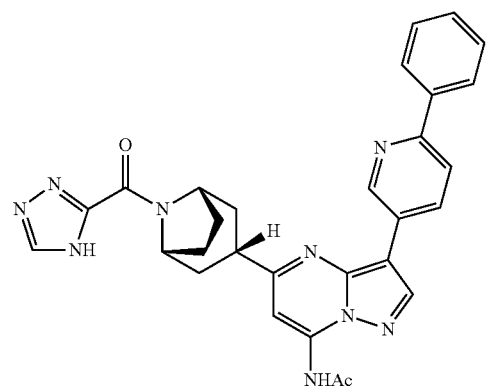

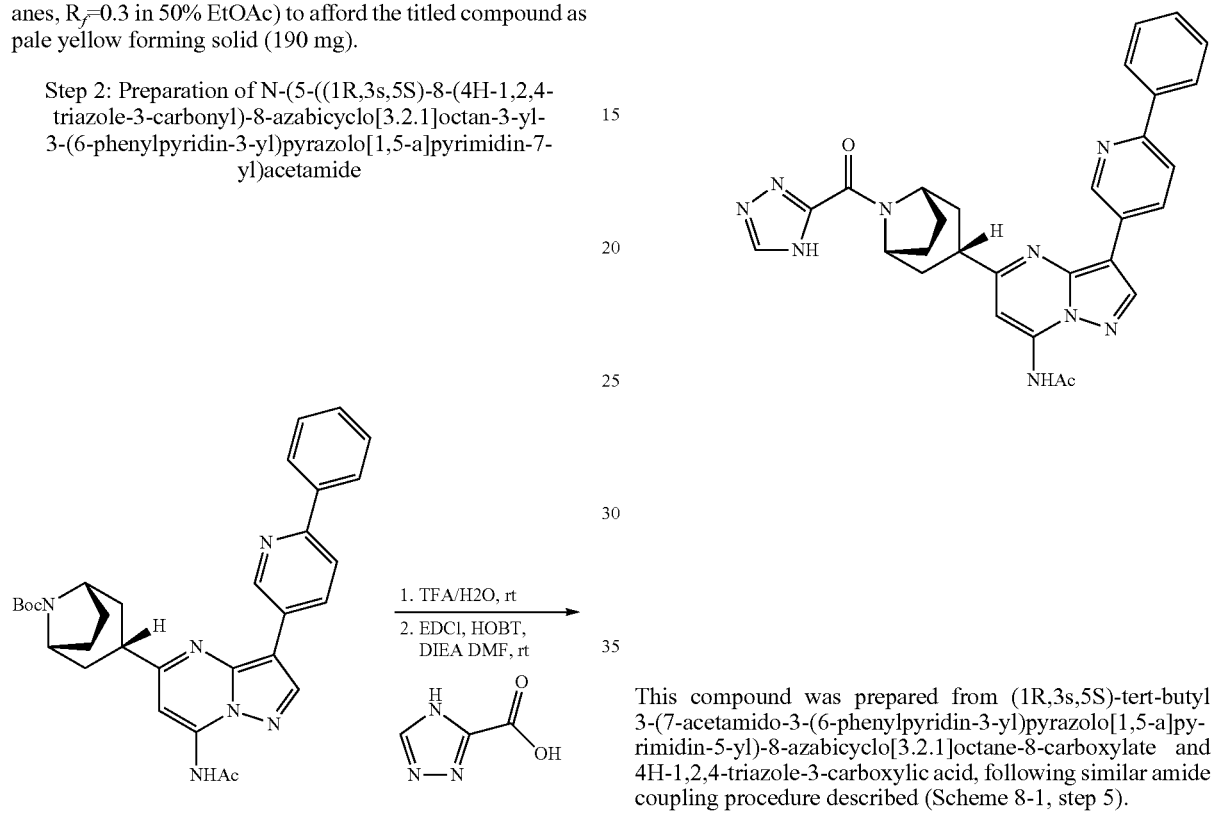

This compound was prepared from (1R,3s,5S)-tert-butyl 3-(7-acetamido-3-(6-phenylpyridin-3-yl)pyrazolo[1,5-a]pyrimidin-5-yl)-8-azabicyclo[3.2.1]octane-8-carboxylate and 4H-1,2,4-triazole-3-carboxylic acid, following similar amide coupling procedure described (Scheme 8-1, step 5).

TABLE 8-4

| 8.10 | | N-(5-((1R,3s,5S)-8-(4H-1,2,4-triazole-3-carbonyl)-8-azabicyclo[3.2.1]octan-3-yl)-3-(6-phenylpyridin-3-yl)pyrazolo[1,5-a]pyrimidin-7-yl)acetamide | 534.2/ 534.2 | ND | ND |

Example 8-5

Preparation of 1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone Step 1: Preparation of benzyl 2-(5-bromopyridin-2-yl)pyrrolidine-1-carboxylate

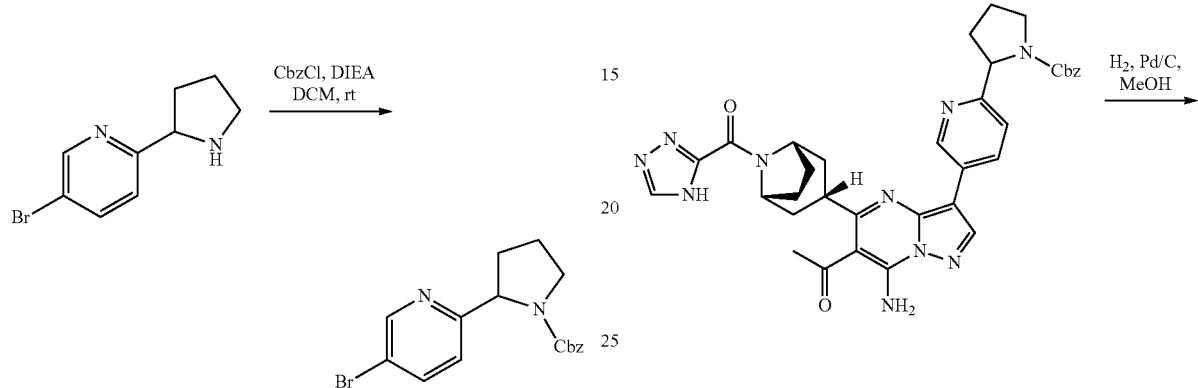

To a suspension of 5-bromo-2-(pyrrolidin-2-yl)pyridine (2.67 g, 11.8 mmol) in DCM (20 mL) at 0° C. was added DIEA (1.5 eq), followed by CbzCl (1.1 eq). The resulting clear solution was warmed to rt and stirred for 2 h. The reaction mixture was washed with brine, dried over $Na_2SO_4$, and concentrated. The crude product was purified by a $SiO_2$ column (0-50% EtOAc/Hexanes, $R_f$=0.35 in 50% EtOAc) to afford the titled compound as a brownish oil (3.63 g).

Step 2: Preparation of benzyl 2-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrrolidine-1-carboxylate This compound was prepared from benzyl 2-(5-bromopyridin-2-yl)pyrrolidine-1-carboxylate, following essentially the similar procedures given in Preparative Example 1-1.

Step 3: Preparation of 1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone

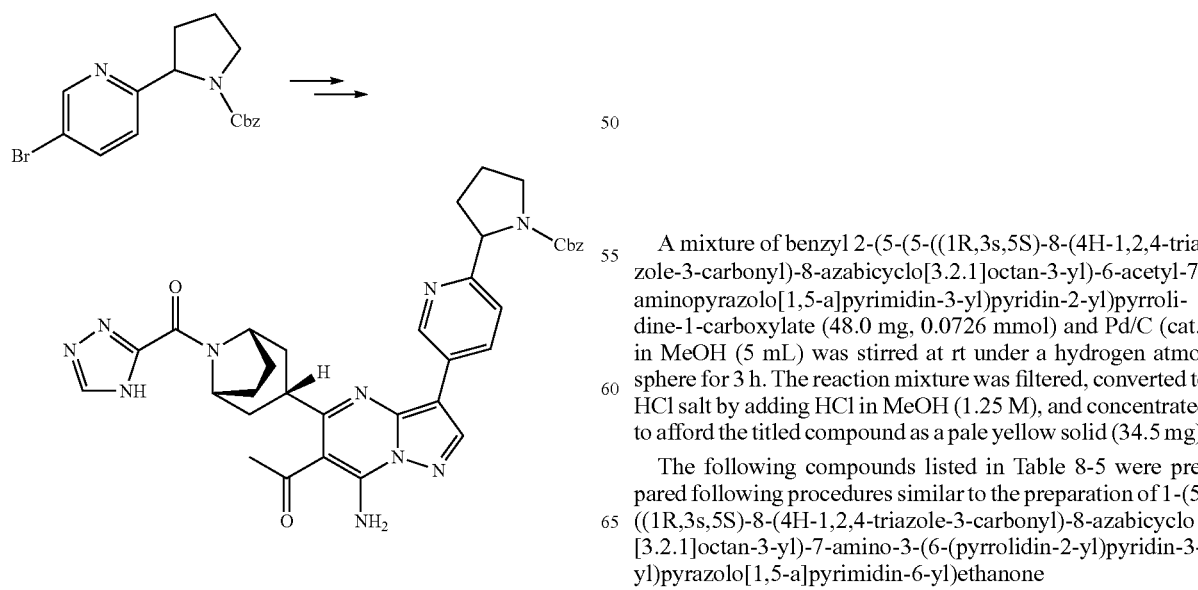

A mixture of benzyl 2-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrrolidine-1-carboxylate (48.0 mg, 0.0726 mmol) and Pd/C (cat.) in MeOH (5 mL) was stirred at rt under a hydrogen atmosphere for 3 h. The reaction mixture was filtered, converted to HCl salt by adding HCl in MeOH (1.25 M), and concentrated to afford the titled compound as a pale yellow solid (34.5 mg).

The following compounds listed in Table 8-5 were prepared following procedures similar to the preparation of 1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone

TABLE 8-5

| Compound ID | Structures | Compound Name | M + H (calculated)/ M + H (observed) | pAKT S473 IC50 | p4E-BP1 Thr37/46 IC50 |
|---|---|---|---|---|---|
| 8.11 | 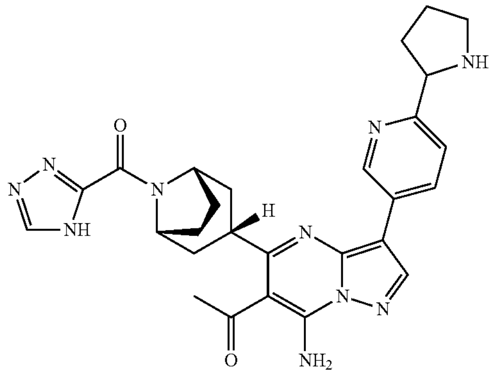 | 1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone | 527.3/527.2 | ND | ND |
| 8.12 | 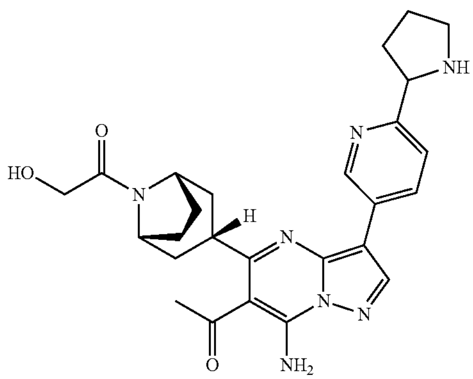 | 1-((1R,3s,5S)-3-(6-acetyl-7-amino-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone | 490.3/490.1 | ND | ND |
| 8.13 | 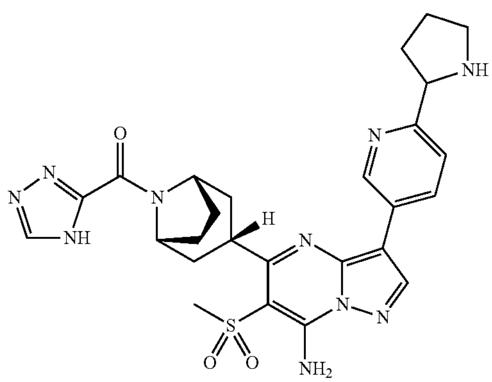 | ((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone | 563.2/563.2 | ND | ND |
| 8.14 | 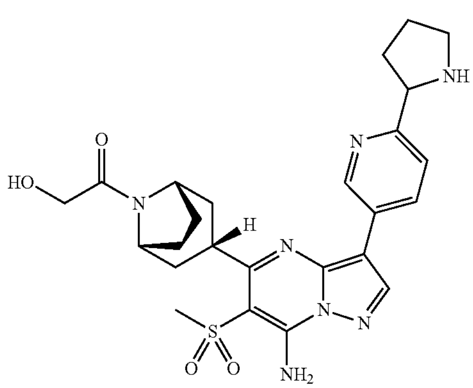 | 1-((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone | 526.2/526.0 | ND | ND |

| Compound ID | Structures | Compound Name | M + H (calculated)/ M + H (observed) | pAKT S473 IC50 | p4E-BP1 Thr37/46 IC50 |
|---|---|---|---|---|---|
| 8.15 | 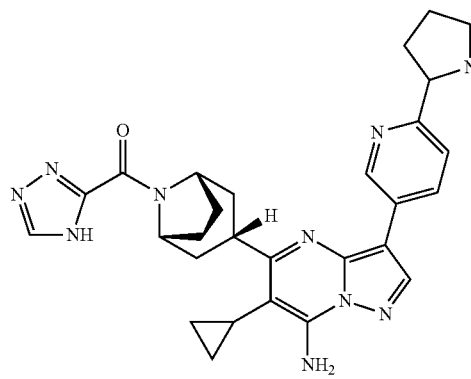 | ((1R,3s,5S)-3-(7-amino-6-cyclopropyl-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone | 525.3/525.3 | ND | ND |

Example 8-6

Preparation of (R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one Step 1: Preparation of (R)-4-(5-bromopyridin-2-yl)oxazolidin-2-one

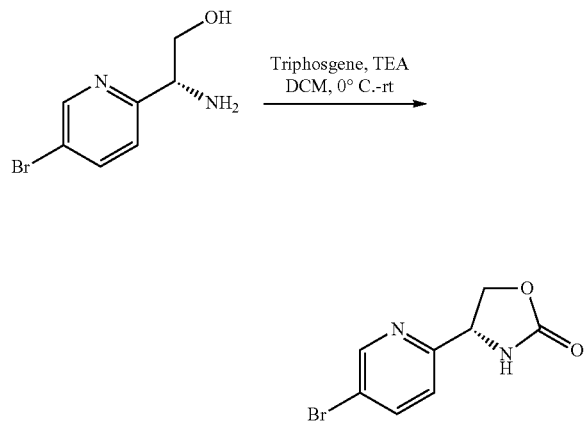 [SMILES: N[C@@H](CO)c1ccc(Br)cn1 ; O=C1N[C@H](c2ccc(Br)cn2)CO1]

To a suspension of (R)-2-amino-2-(5-bromopyridin-2-yl) ethanol hydrogen chloride (4.97 g, 19.6 mmol) and TEA (9.02 mL, 64.7 mmol) in DCM (60 mL) at 0° C. was added a solution of triphosgene (2.91 g, 9.80 mmol) in DCM (20 mL) during 45 min. The resulting mixture was stirred at 0° C. for 15 min, then warmed to it and stirred for 1 h. The reaction was quenched with NH₄Cl (15 mL) and stirred for 15 min. The aqueous layer was separated, basicified with Na₂CO₃, and extracted with DCM (x3). The combined organic layers were washed with brine, dried over Na₂SO₄, and concentrated. The crude product was purified by a SiO₂ column (0-80% EtOAc/Hexanes, R$_f$=0.15 in 50% EtOAc) to afford the titled compound as an off-white solid (3.60 g).

Step 2: Preparation of (R)-4-(5-bromopyridin-2-yl)-3-((2-(trimethylsilyl)ethoxy)methyl)oxazolidin-2-one To a solution of (R)-4-(5-bromopyridin-2-yl)oxazolidin-2-one (1.66 g, 6.83 mmol) in THF (28 mL) at 0° C. was added NaH (1.3 eq) and stirred for 10 min, and then, SEMCI (1.81 mL, 10.2 mmol) was added dropwise. The resulting reaction mixture was warmed to it and stirred for 2 h. THF was removed under reduced pressure. The residue was diluted with EtOAc, washed with H₂O and brine, dried over Na₂SO₄, and concentrated. The crude product was purified by a SiO₂ column (0-40% EtOAc/Hexanes, R$_f$=0.6 in 50% EtOAc) to afford the titled compound as a pale yellow oil (1.91 g).

Step 3: Preparation of (R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one

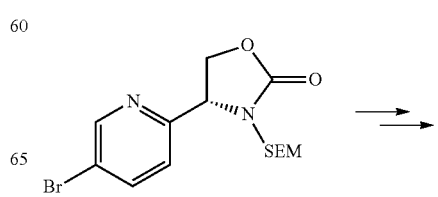

-continued

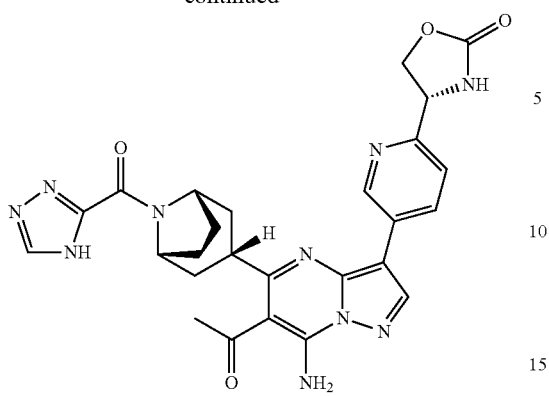

This compound was prepared from (R)-4-(5-bromopyridin-2-yl)-3-((2-(trimethylsilyl)ethoxy)methyl)oxazolidin-2-one, following essentially the similar procedures given in Preparative Example 1-1

| 8.06 | [structure] | (R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one | 543.2/543.1 | ND | ND |

The following compounds listed in Table 8-6 were prepared following procedures similar to the preparation of (R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one

TABLE 8-6

| Compound ID | Structures | Compound Name | M + H (calculated)/ M + H (observed) | pAKT S473 IC50 | p4E-BP1 Thr37/46 IC50 |
|---|---|---|---|---|---|
| 8.17 | [structure] | (S)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one | 543.2/543.1 | ND | ND |

TABLE 8-6-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.18 | 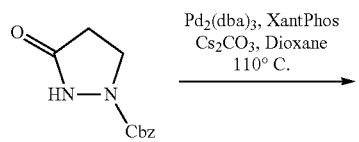 | (S)-4-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)oxazolidin-2-one | 506.2/506.2 | ND | ND |

Example 8-7

Preparation of 2-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrazolidin-3-one

Step 1: Preparation of benzyl 3-oxopyrazolidine-1-carboxylate

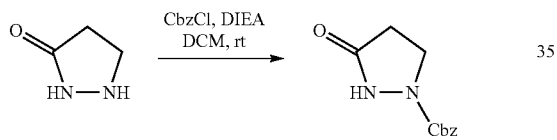

To a suspension of pyrazolidin-3-one hydrogen chloride (5.00 g, 40.8 mmol) in DCM (120 mL) at 0° C. was added DIEA (2.5 eq), followed by CbzCl (1.15 eq). The resulting clear solution was warmed to it and stirred 3 h. The reaction mixture was washed with brine. The aqueous layer was separated and back-extracted with DCM (×2). The combined organic layers were dried over Na$_2$SO$_4$, and concentrated. The crude product was purified by a SiO$_2$ column (0-100% EtOAc/Hexanes, R$_f$=0.35 in 100% EtOAc) to afford the desired product as a white solid (5.31 g).

Step 2: Preparation of (1R,3s,5S)-tert-butyl 3-(3-(6-(2-(benzyloxycarbonyl)-5-oxopyrazolidin-1-yl)pyridin-3-yl)-7-(bis((2-(trimethylsilyl)ethoxy)methyl) amino)pyrazolo[1,5-a]pyrimidin-5-yl)-8-azabicyclo [3.2.1]octane-8-carboxylate

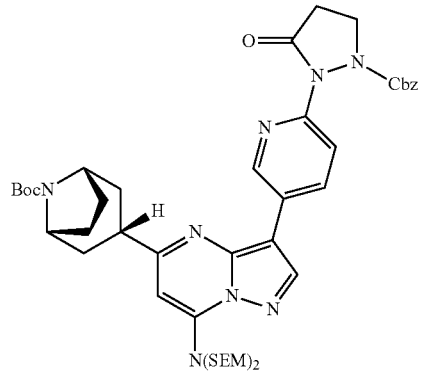

A mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (1.50 g, 2.10 mmol, preparation described previously), benzyl 3-oxopyrazolidine-1-carboxylate (925 mg, 4.20 mmol), Pd$_2$(dba)$_3$ (96.1 mg, 0.105 mmol), XantPhos (182 mg, 0.315 mmol) and Cs$_2$CO$_3$ (1.03 g, 3.15 mmol) in dioxane (20 mL) was stirred at 110° C. under Argon for 16 h. After cooling to it, the reaction mixture was filtered and purified by a SiO$_2$ column (0-50% EtOAc/Hexanes, R$_f$=0.5 in 50% EtOAc) to afford the titled compound as a light brown forming solid (1.23 g).

Step 3: Preparation of 2-(5-(5-(((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrazolidin-3-one

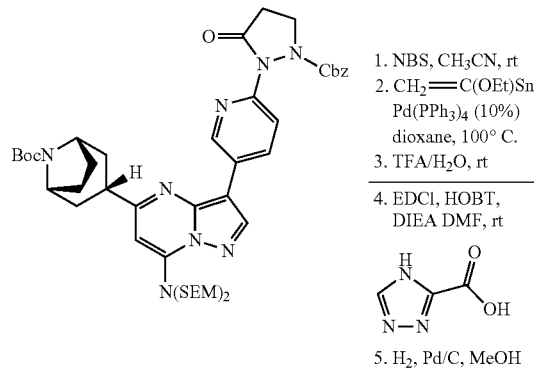

1. NBS, CH₃CN, rt
2. CH₂=C(OEt)SnBu₃
   Pd(PPh₃)₄ (10%)
   dioxane, 100° C.
3. TFA/H₂O, rt
4. EDCl, HOBT, DIEA DMF, rt
5. H₂, Pd/C, MeOH This compound was prepared from (1R,3s,5S)-tert-butyl 3-(3-(6-(2-(benzyloxycarbonyl)-5-oxopyrazolidin-1-yl)pyridin-3-yl)-7-(bis((2-(trimethylsilyl)ethoxy)methyl)amino)pyrazolo[1,5-a]pyrimidin-5-yl)-8-azabicyclo[3.2.1]octane-8-carboxylate, following essentially the similar procedures given in Preparative Example 1-1.

TABLE 8-7

| | | | | | |
|---|---|---|---|---|---|
| 8.19 | | 2-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrazolidin-3-one | 542.2/542.2 | B | B |
| 8.20 | | 2-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)pyrazolidin-3-one | 505.2/505.1 | ND | ND |

Example 8-8

Preparation of 1-(7-amino-5-((1R,3r,5S)-3-hydroxy-8-(4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone Step 1: Preparation of (1R,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]oct-3-ene-8-carboxylate

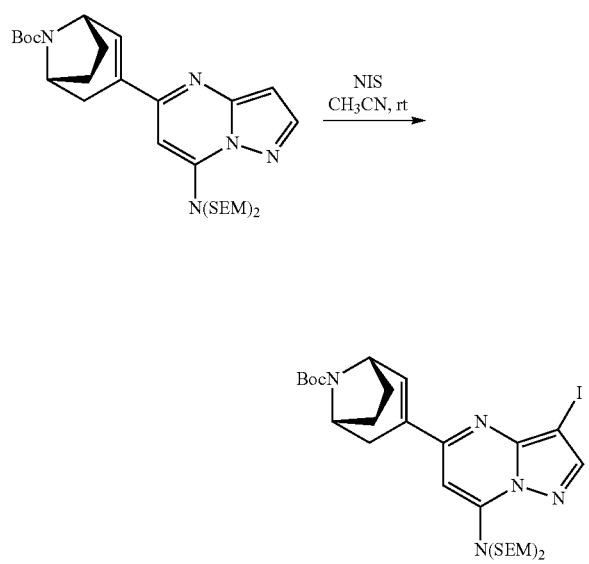

To a solution of (1R,5S)-tert-butyl 3-(7-(bis((2-(trimethylsilyl)ethoxy)methyl)amino)pyrazolo[1,5-a]pyrimidin-5-yl)-8-azabicyclo[3.2.1]oct-3-ene-8-carboxylate (6.32 g, 10.5 mmol, preparation described previously) in CH₃CN (50 mL) was added NIS (2.60 g, 11.5 mmol). The resulting solution was stirred at it for 1 h. The reaction quenched with Na₂SO₃ and CH₃CN was evaporated. The aqueous residue was extracted with EtOAc, washed with brine, dried over Na₂SO₄ and concentrated. The crude product was purified by a SiO₂ column (0-15% EtOAc/Hexanes, $R_f$=0.4 in 20% EtOAc) to afford the titled compound as a pale yellow oil (6.94 g).

Step 2: Preparation of (1R,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]oct-3-ene-8-carboxylate

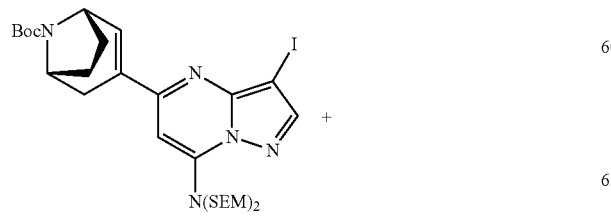

+

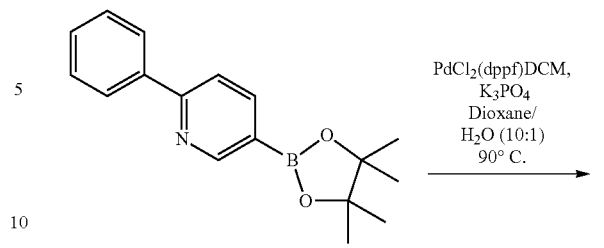

This compound was prepared from (1R,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]oct-3-ene-8-carboxylate and 2-phenyl-5-(4,4,5,5-tetramethyl-1,3,2-dioxaborolan-2-yl)pyridine, following essentially the similar procedures given in Preparative Example 1-1.

Step 3: Preparation of (1R,3r,5S)-tert-butyl 3-(7-(bis((2-(trimethylsilyl)ethoxy)methyl)amino)-3-(6-phenylpyridin-3-yl)pyrazolo[1,5-a]pyrimidin-5-yl-3-hydroxy-8-azabicyclo[3.2.1]octane-8-carboxylate and (1R,3s,5S)-tert-butyl 3-(7-(bis((2-(trimethylsilyl)ethoxy)methyl)amino)-3-(6-phenylpyridin-3-yl)pyrazolo[1,5-a]pyrimidin-5-yl-3-hydroxy-8-azabicyclo[3.2.1]octane-8-carboxylate

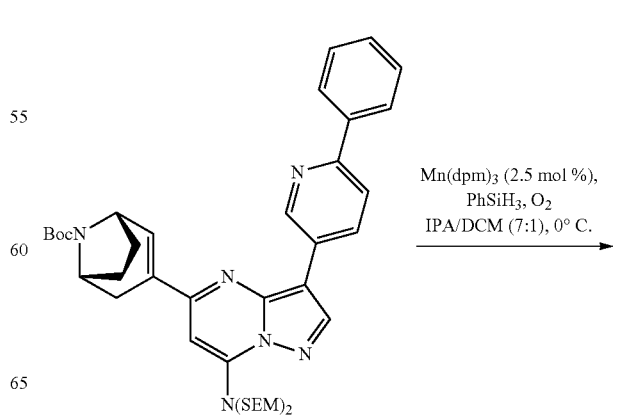

-continued

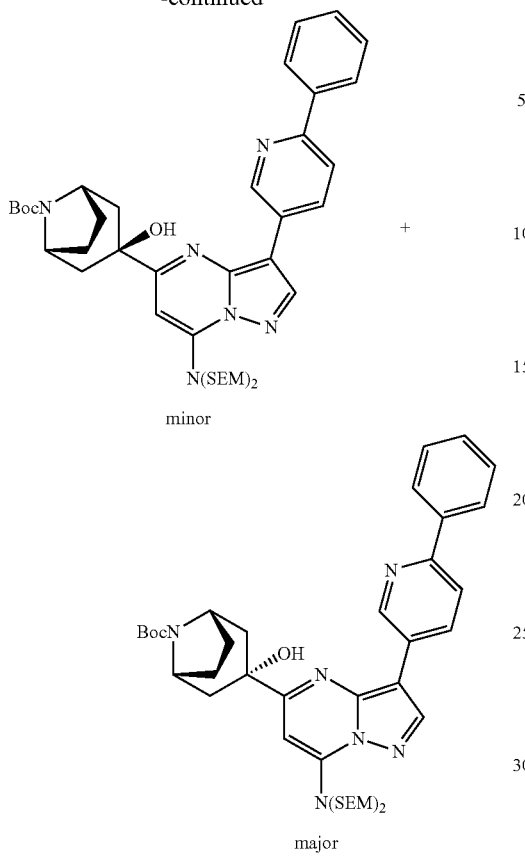

minor major

To solution of (1R,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]oct-3-ene-8-carboxylate (251 mg, 0.332 mmol) and Mn(dpm)₃ (5.0 mg, 0.0083 mmol) in a mixed solvent of IPA/DCM (1.4/0.2 mL) under an oxygen atmosphere was added PhSiH₃ (82.5 uL, 0.664 mmol). The resulting mixture was stirred at 0° C. for 3 h. The reaction was quenched with sat. Na₂S₂O₃ and stirred at it for 1 h. Brine was added and the mixture was extracted with EtOAc. The combined organic layers were dried over Na₂SO₄ and concentrated. The crude product was purified by a SiO₂ column (0-30% EtOAc/Hexanes) to afford the major product (R$_f$=0.65 in 50% EtOAc/Hexanes) as a pale yellow oil (164 mg), and the minor isomer (R$_f$=0.75 in 50% EtOAc/Hexanes) as a pale yellow solid (46 mg).

Step 4: Preparation of 1-(7-amino-5-((1R,3r,5S)-3-hydroxy-8-(4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone

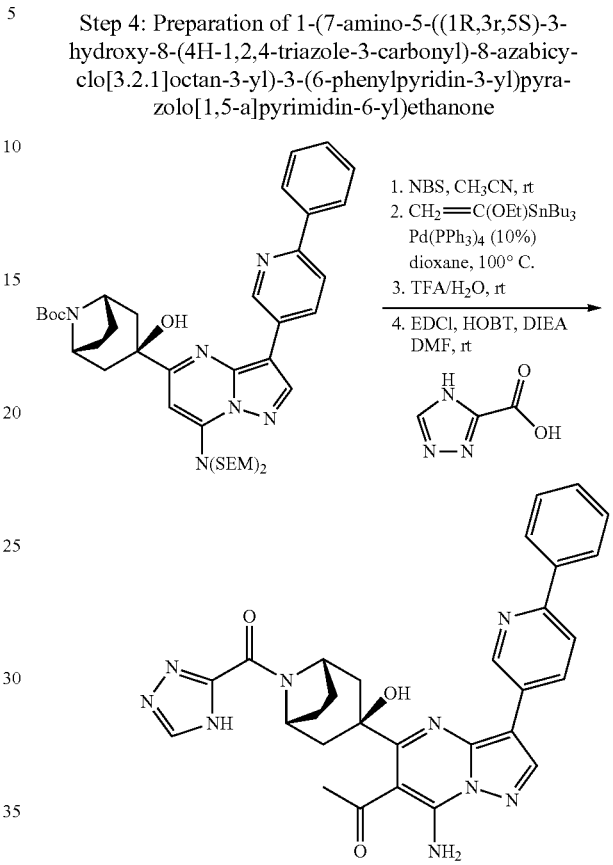

1. NBS, CH₃CN, rt
2. CH₂=C(OEt)SnBu₃
   Pd(PPh₃)₄ (10%)
   dioxane, 100° C.
3. TFA/H₂O, rt
4. EDCl, HOBT, DIEA
   DMF, rt This compound was prepared from (1R,3r,5S)-tert-butyl 3-(7-(bis((2-(trimethylsilyl)ethoxy)methyl)amino)-3-(6-phenylpyridin-3-yl)pyrazolo[1,5-a]pyrimidin-5-yl)-3-hydroxy-8-azabicyclo[3.2.1]octane-8-carboxylate, following essentially the similar procedures given in Preparative Example 1-1. Following similar procedures the following compounds were prepared (Table 8-8):

TABLE 8-8

| Compound ID | Structures | Compound Name | M + H (calculated)/ M + H (observed) | pAKT S473 IC50 | p4E-BP1 Thr37/46 IC50 |
|---|---|---|---|---|---|
| 8.21 | 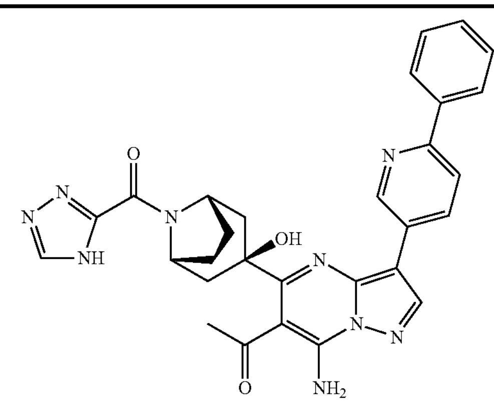 | 1-(7-amino-5-((1R,3r,5S)-3-hydroxy-8-(4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone | 550.2/550.2 | C | C |

TABLE 8-8-continued

| Compound ID | Structures | Compound Name | M + H (calculated)/ M + H (observed) | pAKT S473 IC50 | p4E-BP1 Thr37/46 IC50 |
| --- | --- | --- | --- | --- | --- |
| 8.22 | 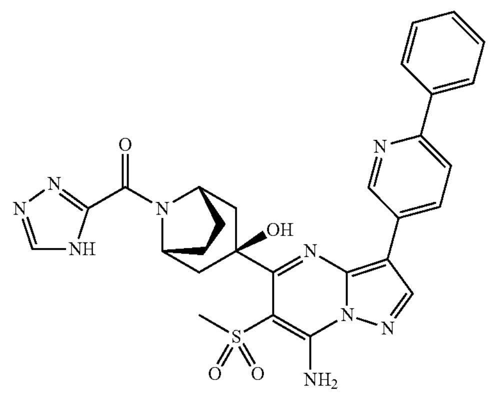 | ((1R,3r,5S)-3-(7-amino-6-(methylsulfonyl)-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone | 586.2/586.2 | B | C |
| 8.23 | 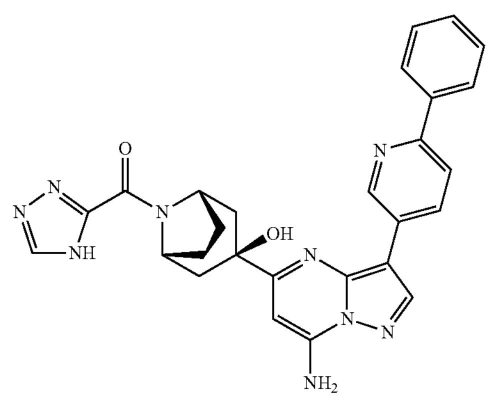 | ((1R,3r,5S)-3-(7-amino-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone | 508.2/508.1 | C | C |
| 8.24 | 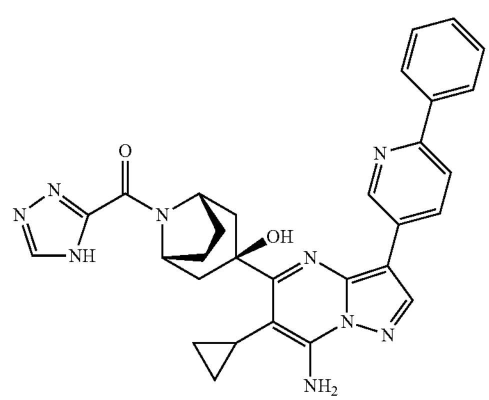 | ((1R,3r,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone | 548.2/548.2 | B | C |

TABLE 8-8-continued
| Compound ID | Structures | Compound Name | M + H (calculated)/ M + H (observed) | pAKT S473 IC50 | p4E-BP1 Thr37/46 IC50 |
|---|---|---|---|---|---|
| 8.25 | 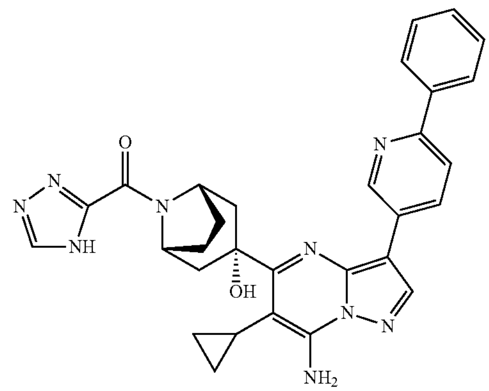 | ((1R,3s,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone | 548.2/548.2 | B | C |
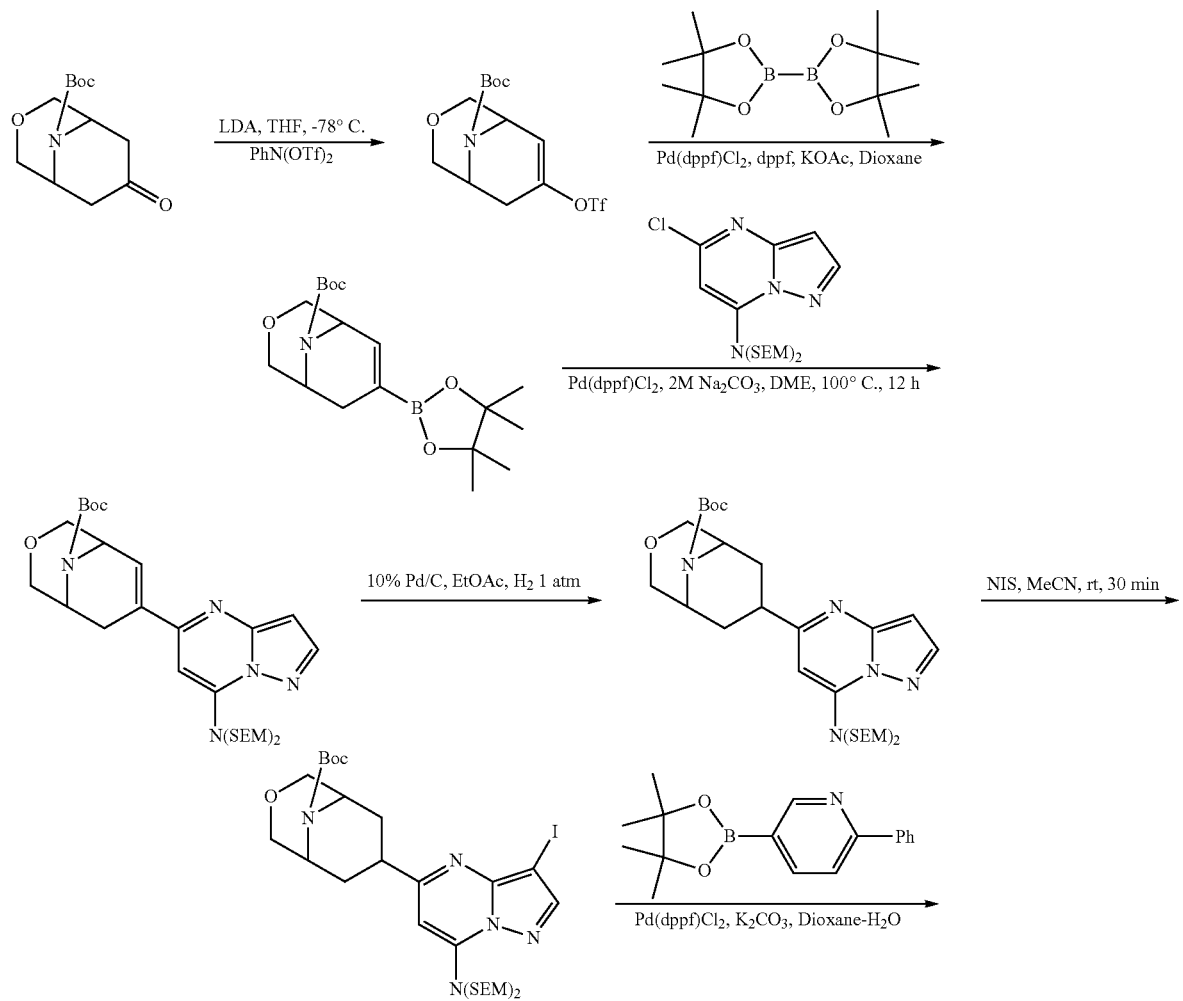
Scheme 8-2

691 692
-continued
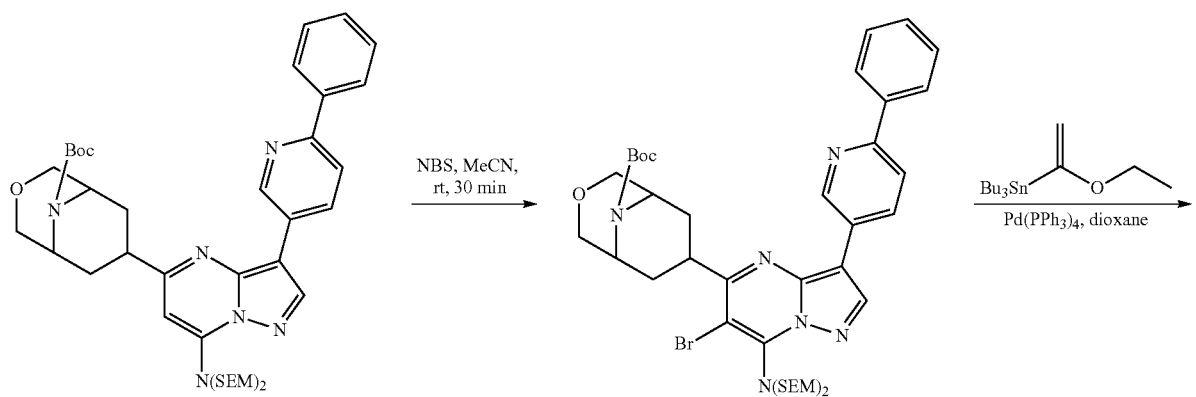
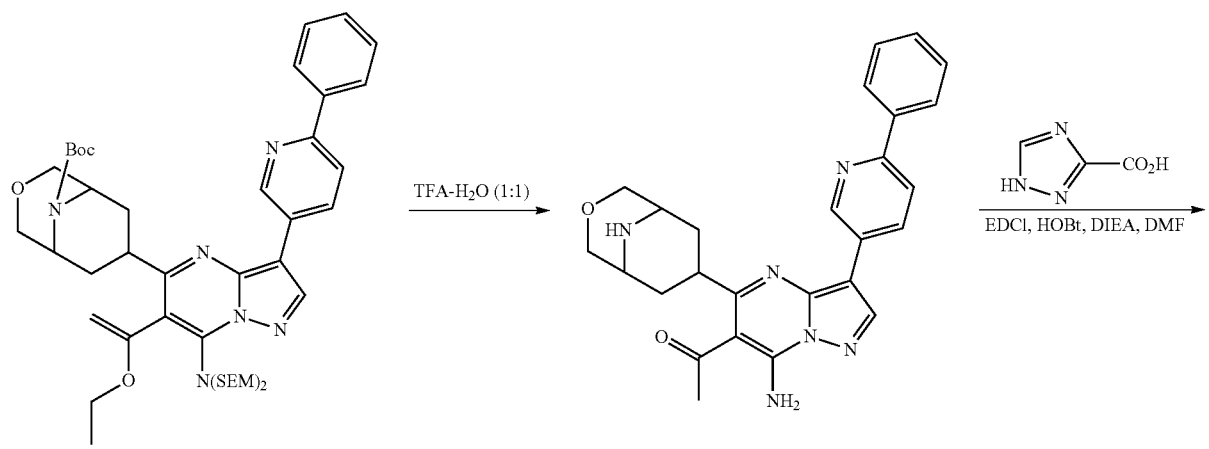
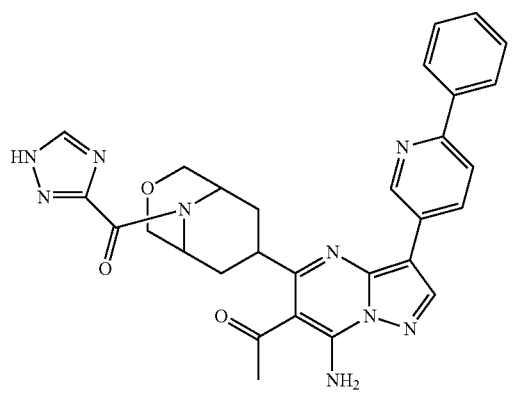

Example 8-9

Preparation of 1-(5-(9-(1H-1,2,4-triazole-3-carbonyl)-3-oxa-9-azabicyclo[3.3.1]nonan-7-yl)-7-amino-3-(6-phenylpyridin-3-yl)pyrazolo[1,5-a]pyrimidin-6-yl)ethanone

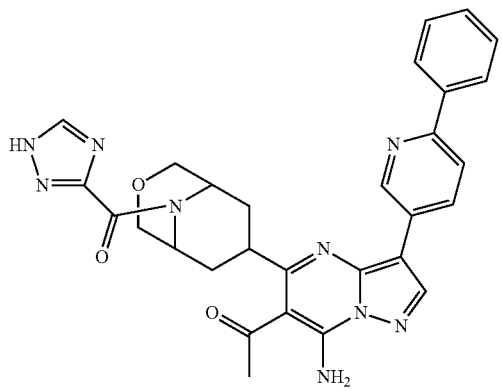 [SMILES: CC(=O)c1c(C2CC3COCC(C2)N3C(=O)c2nc[nH]n2)nc2c(-c3ccc(-c4ccccc4)nc3)cnn2c1N]

Step 1

Preparation of tert-butyl 7-(4,4,5,5-tetramethyl-1,3,2-dioxaborolan-2-yl)-3-oxa-9-azabicyclo[3.3.1]non-6-ene-9-carboxylate (C)

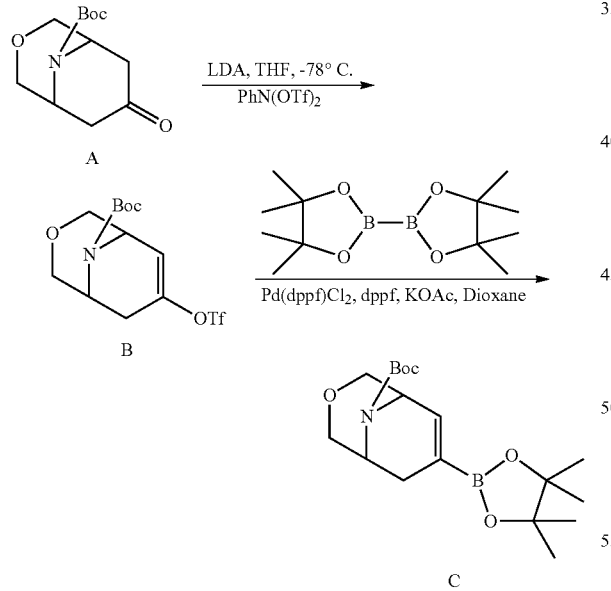

Compound A was prepared following literature procedures (US2008080462). Preparation of B: Substrate A (500 mg, 2.07 mmol) was dissolved in THF (6 mL) and cooled to −78° C. and treated with LDA (1.55 mL, 3.11 mmol, 2M solution). After 5 min., N-phenylbis(trifluoromethanesulfonimide) (817.1 mg, 2.28 mmol) in THF (6 mL) was added dropwise. The mixture was stirred at −78° C. for 30 min. and then gradually warmed to it and continued to stir until starting material completely disappeared (~1.5 h). The reaction was quenched with saturated aqueous ammonium chloride (20 mL) followed by addition of ethyl acetate (50 mL). Two layers were separated and organic layer was collected. The aqueous layer was extracted with ethyl acetate (2×50 mL). The combined organic layer was washed with water (1×100 mL), brine (1×100 mL) and dried (Na$_2$SO$_4$), filtered and evaporated under reduced pressure to provide crude material which was purified by column chromatography (0-40% hexane-ethyl acetate) to give desired product B (701 mg).

Preparation of C: A mixture of substrate B (701 mg, 1.879 mmol), bis(pinacolato)diboron (573.1 mg, 2.256 mmol), Pd(dppf)Cl$_2$.CH$_2$Cl$_2$ (87.11 mg, 0.112 mmol), dppf (65.4 mg, 0.118 mmol) and KOAc (554 mg, 5.64 mmol) in dioxane (11 ml) was heated under argon at 80° C. for 16 h. Upon cooling, the solvent was evaporated off under reduced pressure and the residue was dissolved in ethyl acetate (50 mL). The organic layer was washed with water (1×50 ml), brine (1×50 mL), dried (Na$_2$SO$_4$) and evaporated under reduced pressure to give crude material which was purified by column chromatography (0-40% hexane-ethyl acetate) to provide the desired product C (390 mg) as a white solid.

Step 2

Preparation of tert-butyl 7-(7-(bis((2-(trimethylsilyl)ethoxy)methyl)amino)pyrazolo[1,5-a]pyrimidin-5-yl)-3-oxa-9-azabicyclo[3.3.1]non-6-ene-9-carboxylate (E)

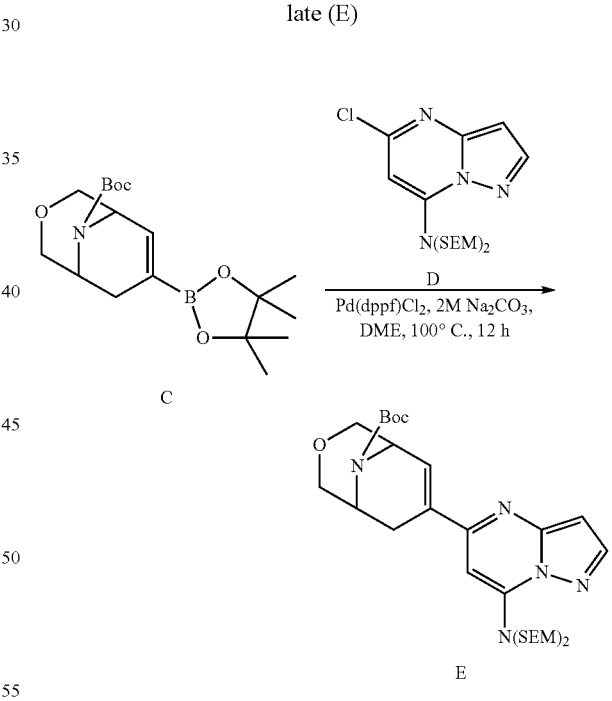

A solution of D (1.01 g, 2.35 mmol) in DME (18 mL) was treated with boronate C (910 mg, 2.59 mmol), Pd(dppf)Cl$_2$.CH$_2$Cl$_2$ (191 mg, 0.24 mmol), 2M aqueous Na$_2$CO$_3$ (9.1 mL) under argon and heated at 100° C. for 16 h. Upon cooling, water (50 mL) and ethyl acetate (70 mL) was added. Two layers were separated and organic layer was collected. Aqueous layer was then extracted with ethyl acetate (2×70 mL). Combined organic layer was washed with brine (1×150 mL), dried (Na$_2$SO$_4$) and evaporated under reduced pressure to give crude material which was purified by column chromatography (0-40% hexane-ethyl acetate) to provide the desired product E (1.27 g). HPLC-MS $t_R$=3.09 min (UV$_{254\,nm}$). Mass calculated for formula $C_{30}H_{51}N_5O_5Si_2$ 617.3; observed M+H$^+$ (LCMS) 618.2 (m/z).

Step 3

Preparation of tert-butyl 7-(7-(bis((2-(trimethylsilyl)ethoxy)methyl)amino)pyrazolo[1,5-a]pyrimidin-5-yl)-3-oxa-9-azabicyclo[3.3.1]nonane-9-carboxylate (F)

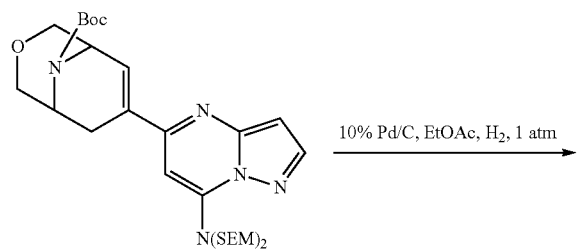

Substrate E (1.27 g, 2.06 mmol) in EtOAc (50 mL) was hydrogenated at 50° C. using 10% Pd/C catalyst (200 mg) and 1 atmospheric hydrogen pressure for 16 h. After filtering off the catalyst, the solvent was evaporated off under reduced pressure and crude material was purified by column chromatography (0-40% hexane-ethyl acetate) to give desired product F (1.1 g). HPLC-MS $t_R$=3.15 min (UV$_{254\,nm}$). Mass calculated for formula $C_{30}H_{53}N_5O_5Si_2$ 619.3; observed M+H$^+$ (LCMS) 620.2 (m/z).

Step 4

Preparation of tert-butyl 7-(7-(bis((2-(trimethylsilyl)ethoxy)methyl)amino)-3-iodopyrazolo[1,5-a]pyrimidin-5-yl)-3-oxa-9-azabicyclo[3.3.1]nonane-9-carboxylate (G)

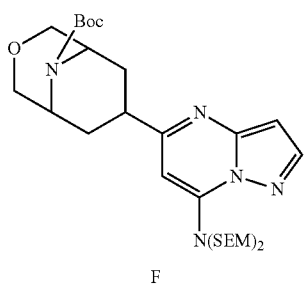

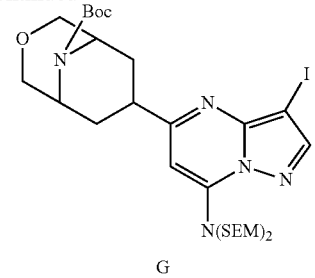

Substrate F (1.1 g, 1.77 mmol) was suspended in acetonitrile (20 mL) and treated with NIS (396.4 mg, 1.77 mmol) at room temperature. The mixture was stirred for 30 min. Then solvent was evaporated off under reduced pressure, and the crude material was purified by column chromatography (SiO$_2$, 0-40% hexane-EtOAc) to provide desired compound G (1.37 g). HPLC-MS $t_R$=3.37 min (UV$_{254\,nm}$). Mass calculated for formula $C_{30}H_{52}IN_5O_5Si_2$ 745.2; observed M+H$^+$ (LCMS) 746.0 (m/z).

Step 5

Preparation of tert-butyl 7-(7-(bis((2-(trimethylsilyl)ethoxy)methyl)amino)-3-(6-phenylpyridin-3-yl)pyrazolo[1,5-a]pyrimidin-5-yl)-3-oxa-9-azabicyclo[3.3.1]nonane-9-carboxylate (H)

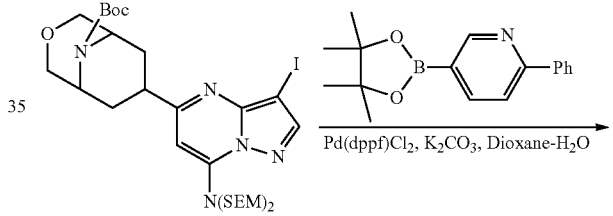

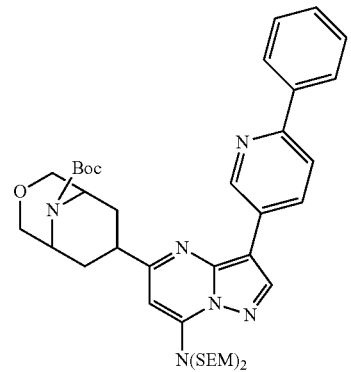

The iodide G (1.37 g, 1.84 mmol) in dioxane (10 mL) and water (2.5 mL) was treated with boronate (1.22 g, 3.2 mmol), Pd(dppf)Cl$_2$·CH$_2$Cl$_2$ (182.6 mg, 0.22 mmol) and K$_2$CO$_3$ (763 mg, 5.52 mmol) under argon and heated at 100° C. for 16 h. Upon cooling, the mixture was filtered through Celite and the filtrate was evaporated off under reduced pressure to give crude residue which was purified by column chromatography (SiO$_2$, 0-40% hexane-EtOAc) to provide desired product H (1.14 g). HPLC-MS $t_R$=3.49 min (UV$_{254\,nm}$). Mass calculated for formula $C_{41}H_{60}N_6O_5Si_2$ 772.4; observed M+H$^+$ (LCMS) 773.2 (m/z).

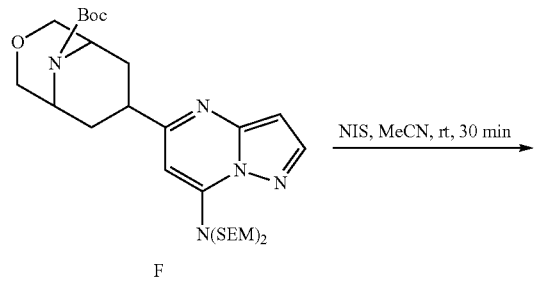

Step 6

Preparation of tert-butyl 7-(7-(bis((2-(trimethylsilyl)ethoxy)methyl)amino)-6-bromo-3-(6-phenylpyridin-3-yl)pyrazolo[1,5-a]pyrimidin-5-A-3-oxa-9-azabicyclo[3.3.1]nonane-9-carboxylate (I)

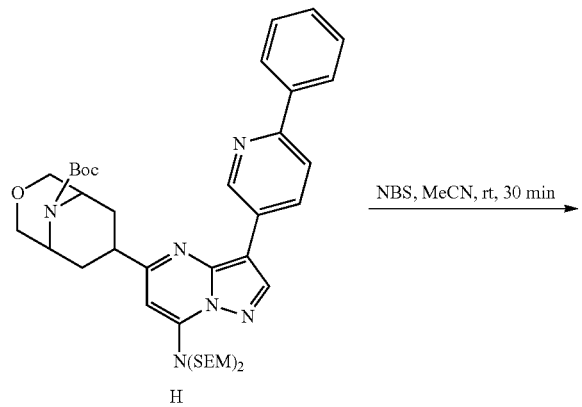

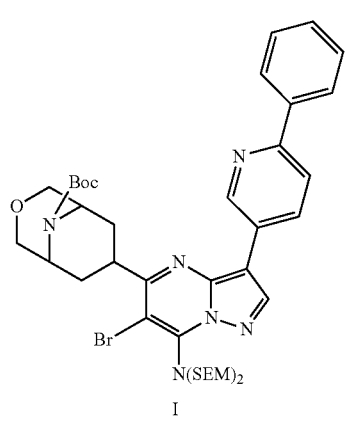

Substrate H (1.14 g, 1.47 mmol) was suspended in acetonitrile (15 mL) and treated with NBS (263.1 mg, 1.47 mmol) at room temperature. The mixture was stirred for 30 min. Then solvent was evaporated off under reduced pressure, and the crude material was purified by column chromatography (SiO$_2$, 0-40% hexane-EtOAc) to provide desired compound 1 (1.13 g). HPLC-MS t$_R$=3.58 min (UV$_{254\,nm}$). Mass calculated for formula C$_{41}$H$_{59}$BrN$_6$O$_5$Si$_2$ 850.3; observed MH$^+$ (LCMS) 851.2 (m/z).

Step 7

Preparation of tert-butyl 7-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-3-oxa-9-azabicyclo[3.3.1]nonane-9-carboxylate (J)

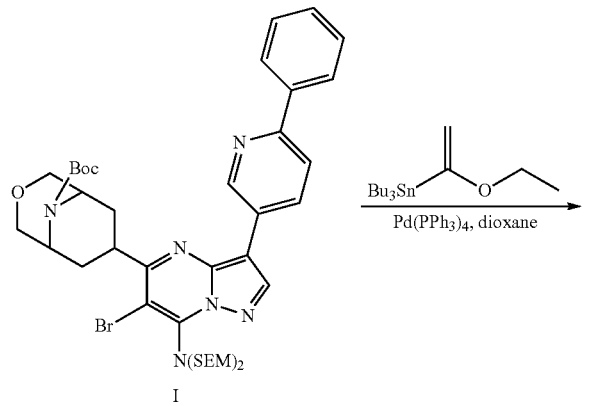

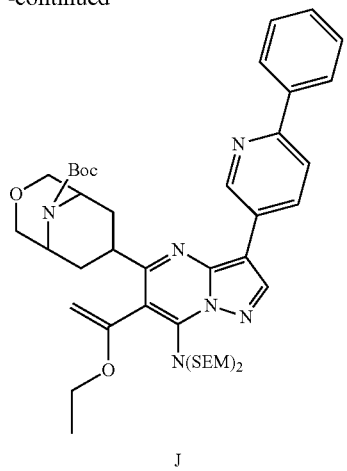

Substrate I (1.13 g, 1.33 mmol) in dioxane (20 mL) was treated with Pd(PPh$_3$)$_4$ (307.2 mg, 0.26 mmol) and tributyl (1-ethoxyvinyl)tin (1.35 mL, 3.99 mmol) under argon and the mixture was heated at 100° C. for 16 h. Upon cooling, the mixture was filtered through a pad of 10% KF—SiO$_2$ and the filtrate was evaporated off under reduced pressure to give a residue which was purified by column chromatography (SiO$_2$, 0-40% hexane-EtOAc) to provide desired compound J (1.08 g). HPLC-MS t$_R$=3.65 min (UV$_{254\,nm}$). Mass calculated for formula C$_{45}$H$_{66}$N$_6$O$_6$Si$_2$ 842.4; observed M+H$^+$ (LCMS) 843.2 (m/z).

Step 8

Preparation of 1-(7-amino-5-(3-oxa-9-azabicyclo[3.3.1]nonan-7-yl-3-(6-phenylpyridin-3-yl)pyrazolo[1,5-a]pyrimidin-6-yl)ethanone (K)

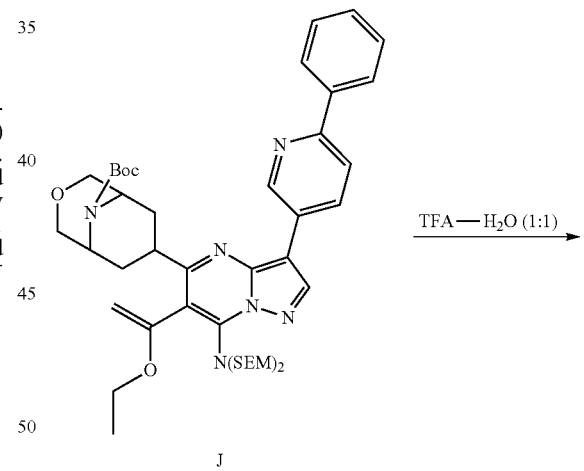

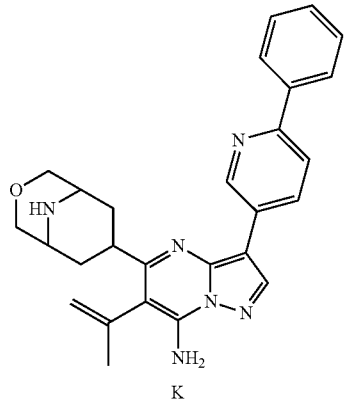

Substrate J (1.08 g, 1.28 mmol) was treated with TFA-H$_2$O (1:1, 24 mL) at rt and the mixture was stirred for 16 h. Then the solvent was evaporated off under reduced pressure and the material was lyophilized from acetonitrile:water (3:1) to give yellow solid K (612 mg) which was used without further purification. HPLC-MS $t_R$=1.16 min (UV$_{254\ nm}$). Mass calculated for formula C$_{26}$H$_{26}$N$_6$O$_2$ 454.2; observed MH$^+$ (LCMS) 455.2 (m/z).

Step 9

Preparation of 1-(5-(9-(1H-1,2,4-triazole-3-carbonyl)-3-oxa-9-azabicyclo[3.3.1]nonan-7-yl-7-amino-3-(6-phenylpyridin-3-yl)pyrazolo[1,5-a]pyrimidin-6-yl)ethanone (L)

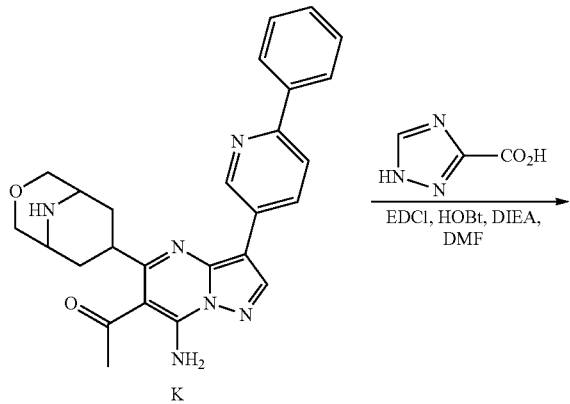

Carboxylic acid (0.44 mmol) in DMF (2 mL) was treated with EDCI (0.68 mmol) and HOBt (0.34 mmol). Then substrate K (0.33 mmol) followed by DIEA (1.69 mmol) was added. After 30 min, the reaction mixture was treated with water (0.4 mL) and DMSO-MeCN (3:1, 3 mL). Pure compound L was isolated by preparative HPLC. HPLC-MS $t_R$=3.18 min (UV$_{254\ nm}$). Mass calculated for formula C$_{29}$H$_{27}$N$_9$O$_3$ 549.2; observed M+H$^+$ (LCMS) 549.9 (m/z).

Following the Scheme 8-2 and the procedures similar to preparation of 1-(5-(9-(1H-1,2,4-triazole-3-carbonyl)-3-oxa-9-azabicyclo[3.3.1]nonan-7-yl-7-amino-3-(6-phenylpyridin-3-yl)pyrazolo[1,5-a]pyrimidin-6-yl)ethanone, the following compounds (Table 8-9) can be prepared:

TABLE 8-9

| | | | | |
|---|---|---|---|---|
| 8.26 | (structure) | 1-(5-(9-(1H-1,2,4-triazole-3-carbonyl)-3-oxa-9-azabicyclo[3.3.1]nonan-7-yl)-7-amino-3-(1-phenyl-1H-pyrazol-4-yl)pyrazolo[1,5-a]pyrimidin-6-yl)ethanone | 539.2 | A  B |
| 8.27 | (structure) | 1-(5-(9-(1H-1,2,4-triazole-3-carbonyl)-3-oxa-9-azabicyclo[3.3.1]nonan-7-yl)-7-amino-3-(6-phenylpyridin-3-yl)pyrazolo[1,5-a]pyrimidin-6-yl)ethanone | 550.2 | A  B |

TABLE 8-9-continued

| | | | | | |
|---|---|---|---|---|---|
| 8.28 | 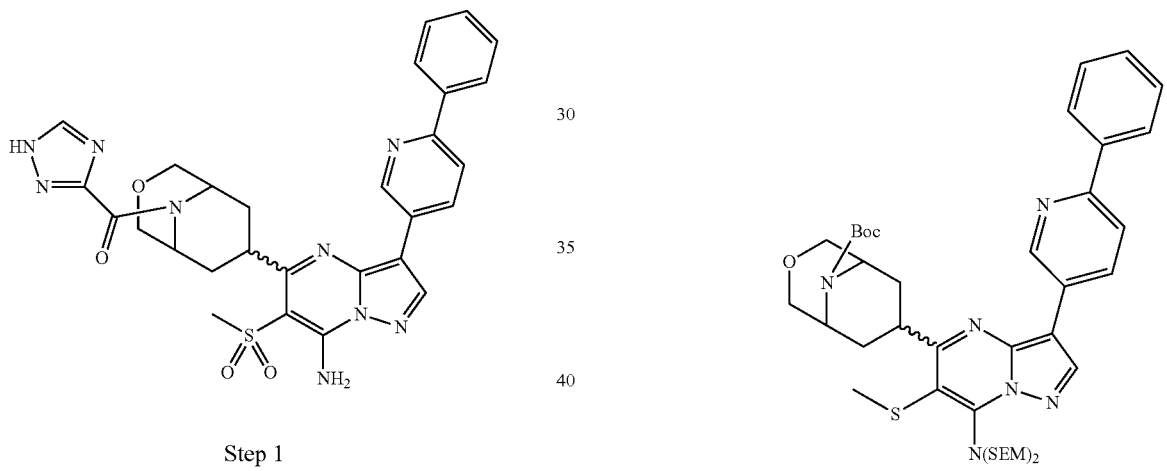 | 1-(7-(6-acetyl-7-amino-3-(6-phenylpyridin-3-yl)pyrazolo[1,5-a]pyrimidin-5-yl)-3-oxa-9-azabicyclo[3.3.1]nonan-9-yl)-2-hydroxyethanone | 513.2 | B | B |

Example 8-10

Preparation of (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone

Step 1

Synthesis of tert-butyl 7-(7-(bis((2-(trimethylsilyl)ethoxy)methyl)amino)-6-(methylthio)-3-(6-phenylpyridin-3-yl)pyrazolo[1,5-a]pyrimidin-5-yl-3-oxa-9-azabicyclo[3.3.1]nonane-9-carboxylate

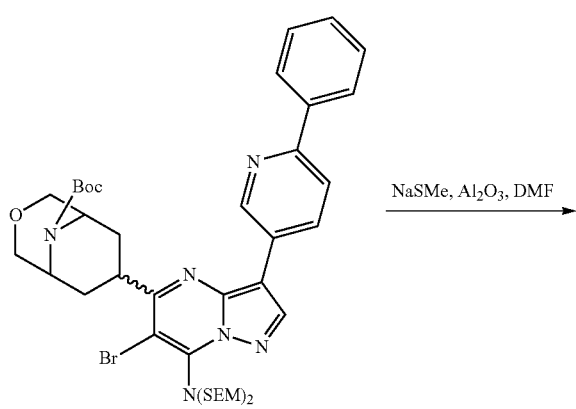

Substrate (303 mg, 0.35 mmol) in DMF (6 mL) was treated with $Al_2O_3$ (537.7 mg, 5.3 mmol) and NaSMe (73.54 mg, 1.05 mmol) under argon and the mixture was heated at 80° C. for 16 h. Upon cooling, the mixture was filtered through a pad of Celite and the filtrate was evaporated off under reduced pressure to give a residue which was purified by column chromatography ($SiO_2$, 0-80% hexane-EtOAc) to provide desired compound tert-butyl 7-(7-(bis((2-(trimethylsilyl)ethoxy)methyl)amino)-6-(methylthio)-3-(6-phenylpyridin-3-yl)pyrazolo[1,5-a]pyrimidin-5-yl)-3-oxa-9-azabicyclo[3.3.1]nonane-9-carboxylate.

Step 2

Preparation of tert-butyl 7-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-3-oxa-9-azabicyclo[3.3.1]nonane-9-carboxylate

Method B

Step A: Preparation of tert-butyl 7-(7-(bis((2-(trimethylsilyl)ethoxy)methyl)amino)-6-iodo-3-(6-phenylpyridin-3-yl)pyrazolo[1,5-a]pyrimidin-5-yl)-3-oxa-9-azabicyclo[3.3.1]nonane-9-carboxylate

Method A

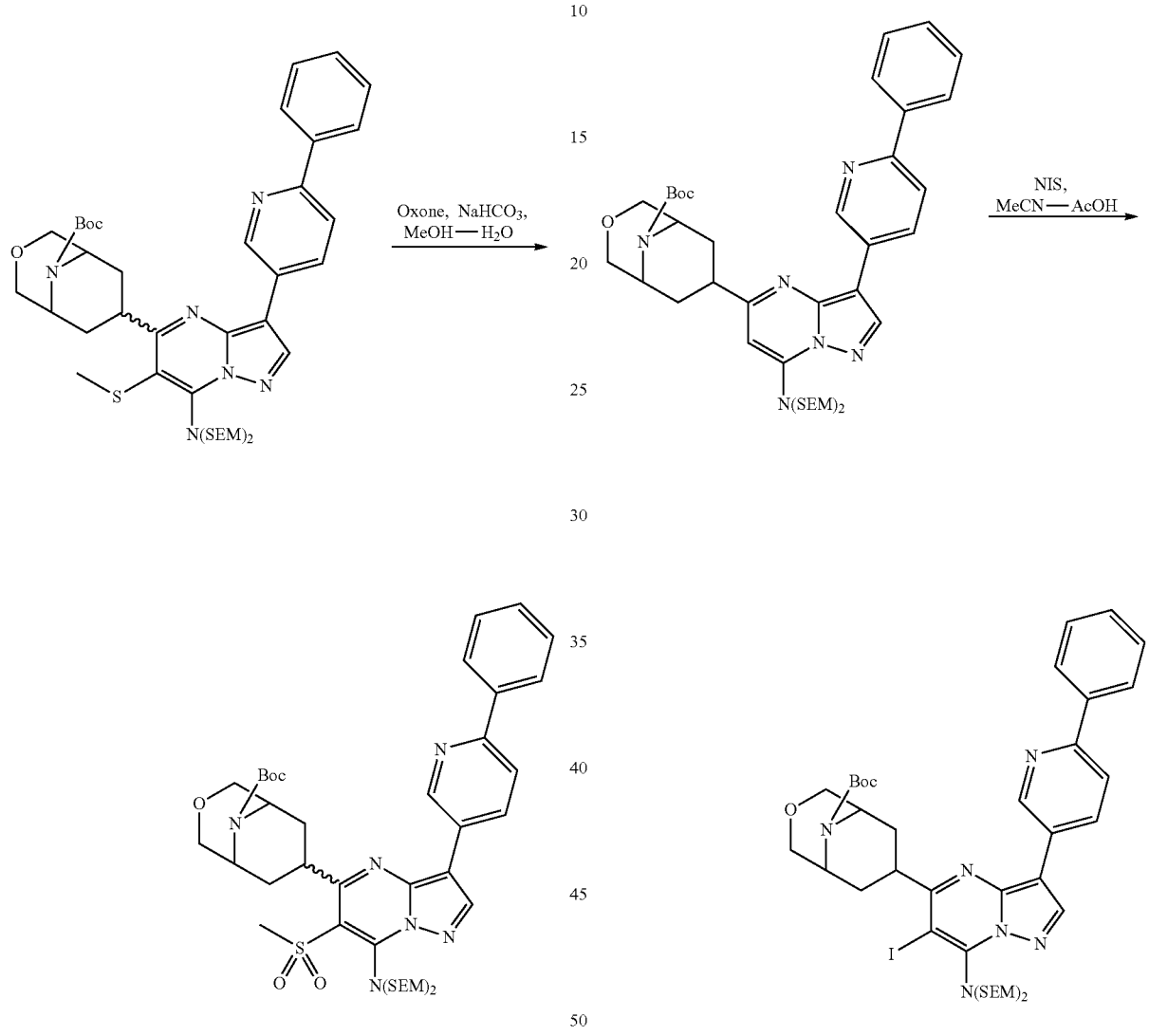

Substrate (234 mg, 0.28 mmol) was dissolved in MeOH (12 mL) and water (3 mL) and treated with NaHCO$_3$ (237.3 mg, 2.86 mmol) followed by oxone (878 mg, 1.43 mmol). The mixture was stirred for 12 h and treated with CH$_2$Cl$_2$ and filtered. The filtrate was washed with water and the organic layer was dried (Na$_2$SO$_4$), filtered and evaporated under reduced pressure to give crude product tert-butyl 7-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-3-oxa-9-azabicyclo[3.3.1]nonane-9-carboxylate.

Substrate (300 mg, 0.38 mmol) (isomer I was separated from isomer II by chiral HPLC) was dissolved in MeCN (10 mL) and treated with AcOH (0.44 mL, 7.76 mmol) and NIS (174.86 mg, 0.77 mmol). The mixture was stirred over night and the solvent was evaporated off. The residue was then purified by the column chromatography. Isomer II was also processed similarly to obtaining corresponding iodide.

705

Step B: Preparation of tert-butyl 7-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-3-oxa-9-azabicyclo[3.3.1]nonane-9-carboxylate

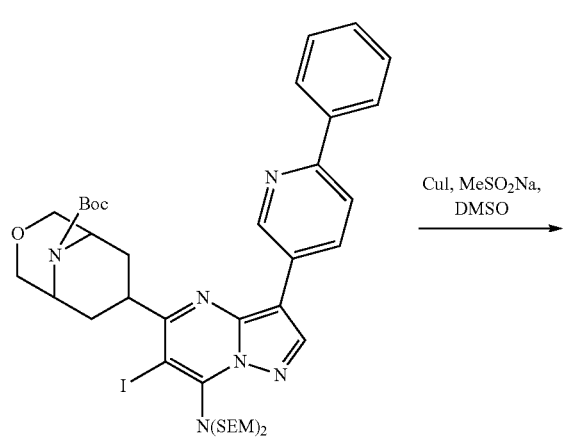

Substrate (220 mg, isomer I, 0.24 mmol) was dissolved in DMSO (2.5 mL) under argon and treated with CuI (278.8 mg, 1.46 mmol) and MeSO$_2$Na (74.66 mg, 0.732 mmol). The mixture was heated at 90° C. for 4 h and the cooled to room temperature and diluted with EtOAc (10 mL). It was filtered and the filtrate was washed with water (15 ml) and saturated NH$_4$Cl (15 mL). The organic layer was dried (Na$_2$SO$_4$), filtered and evaporated under reduced pressure to provide crude material which was purified by column chromatography (0-80% hexane-ethyl acetate) to give desired product tert-butyl 7-(7-(bis((2-(trimethylsilyl)ethoxy)methyl)amino)-6-(methylsulfonyl)-3-(6-phenylpyridin-3-yl)pyrazolo[1,5-a]pyrimidin-5-yl)-3-oxa-9-azabicyclo[3.3.1]nonane-9-carboxylate. Similarly isomer 2 was also processed.

706

Step 3

Preparation of 5-(3-oxa-9-azabicyclo[3.3.1]nonan-7-yl)-6-(methylsulfonyl)-3-(6-phenylpyridin-3-yl)pyrazolo[1,5-a]pyrimidin-7-amine

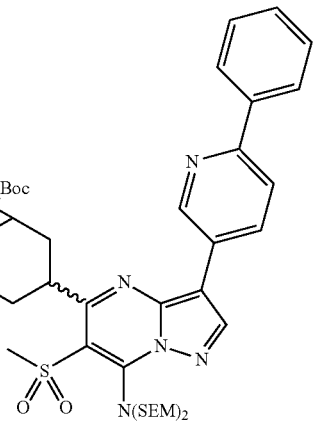

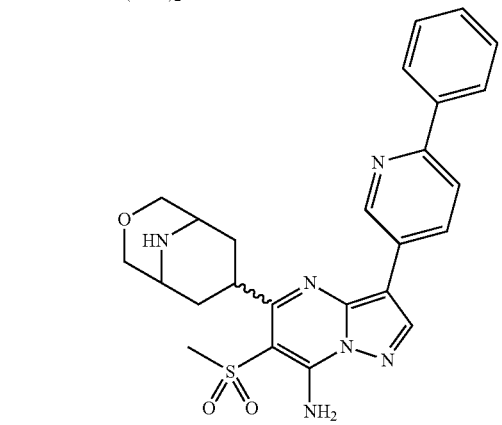

Crude substrate was treated with TFA-H$_2$O (1:1, 6 mL) at room temperature and the mixture was stirred for 16 h. Then the solvent was evaporated off under reduced pressure and the material was lyophilized from acetonitrile:water (3:1) to give a yellow solid which was used without further purification.

Step 4

Preparation of (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone

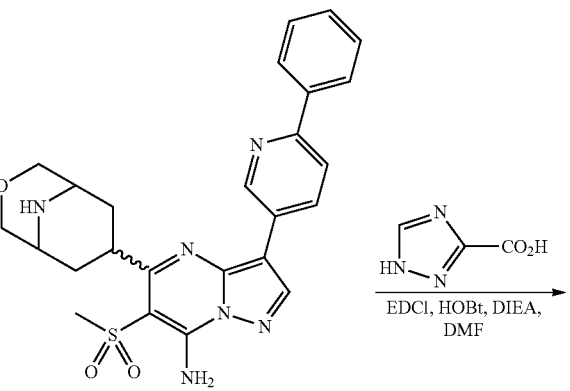

-continued

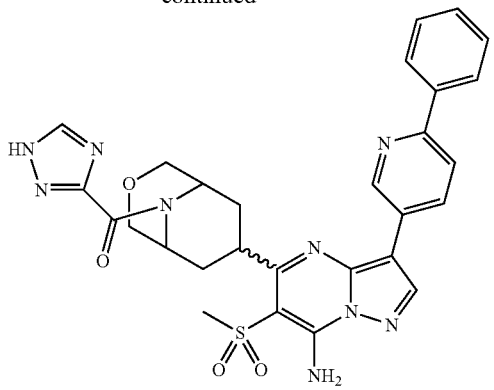

Carboxylic acid (120 mg) in DMF (2 mL) was treated with EDCI (122 mg) and HOBt (61.2 mg). Then substrate (122 mg) was added followed by DIEA (0.3 mL). After the reaction was complete, the reaction mixture was treated with water (0.4 mL) and DMSO-MeCN (3:1, 3 mL). Pure compound was isolated by preparative HPLC.

Final stereochemically pure isomer was prepared following similar procedures.

Example 8-11

Preparation of endo/exo-7-[6-acetyl-7-amino-3-(6-phenyl-3-pyridinyl)pyrazolo[1,5-a]pyrimidin-5-yl]-9-(4h-1,2,4-triazol-3-ylcarbonyl)-3-thia-9-azabicyclo[3.3.1]nonane, 3,3-dioxide

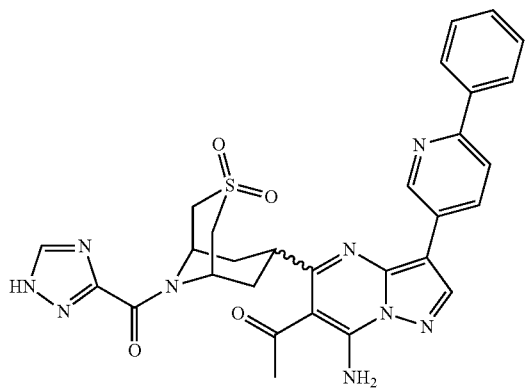 [SMILES: CC(=O)c1c(C2CC3CS(=O)(=O)CC(C2)N3C(=O)c2nc[nH]n2)nc2c(-c3ccc(-c4ccccc4)nc3)cnn2c1N]

Step 1

Synthesis of tert-butyl 7-oxo-3-thia-9-azabicyclo[3.3.1]nonane-9-carboxylate

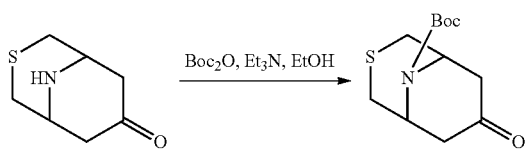 [SMILES: O=C1CC2CSCC(C1)N2 ; CC(C)(C)OC(=O)N1C2CSCC1CC(=O)C2]

The substrate 3-thia-9-azabicyclo[3.3.1]nonan-7-one (Bowers, Simeon; Probst, Gary D.; Truong, Anh P.; Hom, Roy K.; Konradi, Andrei W.; Sham, Hing L.; Garofalo, Albert W.; Wong, Karina; Goldbach, Erich; Quinn, Kevin P.; Sauer, John-Michael; Wallace, William; Nguyen, Lan; Hemphill, Susanna S.; Bova, Michael P.; Basi, Guriqbal S. *Bioorganic & Medicinal Chemistry Letters* 2009, 19, 6952-6956) (1.068 g, 5.63 mmol) was dissolved in EtOH (50 ml) and treated with Et₃N (1.17 mL, 8.44 mmol) and Boc₂O (1.35 g, 6.14 mmol). The mixture was stirred at room temperature and then the solvent was evaporated off to provide a residue which was purified by column chromatography.

Step 2

Preparation of tert-butyl 7-(trifluoromethylsulfonyloxy)-3-thia-9-azabicyclo[3.3.1]non-6-ene-9-carboxylate

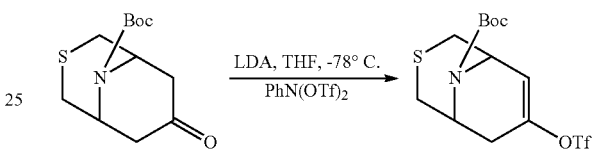

Substrate (400 mg, 1.55 mmol) was dissolved in THF (15 mL) and cooled to −78° C. and treated with LDA (1.29 mL, 2.33 mmol, 2M solution). After 5 min., N-phenylbis(trifluoromethanesulfonimide) (606.9 mg, 1.7 mmol) in THF (15 mL) was added dropwise. The mixture was stirred at −78° C. for 30 min. and then gradually warmed to it and continued to stir until starting material completely disappeared (~1.5 h). The reaction was quenched with saturated aqueous ammonium chloride (20 mL) followed by addition of ethyl acetate (50 mL). Two layers were separated and organic layer was collected. The aqueous layer was extracted with ethyl acetate (2×50 mL). The combined organic layer was washed with water (1×100 mL), brine (1×100 mL) and dried (Na₂SO₄), filtered and evaporated under reduced pressure to provide crude material which was purified by column chromatography (0-40% hexane-ethyl acetate) to give desired product tert-butyl 7-(trifluoromethylsulfonyloxy)-3-thia-9-azabicyclo[3.3.1]non-6-ene-9-carboxylate (704 mg).

Step 3

Preparation of tert-butyl 7-(4,4,5,5-tetramethyl-1,3,2-dioxaborolan-2-yl-3-thia-9-azabicyclo[3.3.1]non-6-ene-9-carboxylate

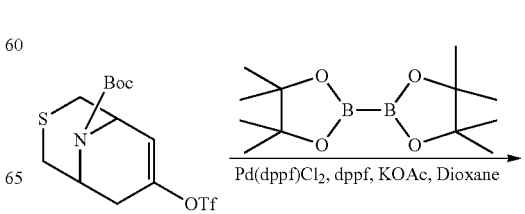

-continued

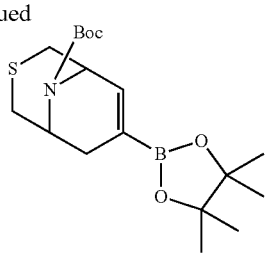

A mixture of substrate (704 mg, 1.81 mmol), bis(pinacolato)diboron (551.8 mg, 2.17 mmol), Pd(dppf)Cl$_2$.CH$_2$Cl$_2$ (88.2 mg, 0.113 mmol), dppf (63.4 mg, 0.114 mmol) and KOAc (548 mg, 5.57 mmol) in dioxane (10 ml) was heated under argon at 80° C. for 16 h. Upon cooling, the solvent was evaporated off under reduced pressure and the residue was dissolved in ethyl acetate (50 mL). The organic layer was washed with water (1×50 ml), brine (1×50 mL), dried (Na$_2$SO$_4$) and evaporated under reduced pressure to give crude material which was purified by column chromatography (0-40% hexane-ethyl acetate) to provide the desired product tert-butyl 7-(4,4,5,5-tetramethyl-1,3,2-dioxaborolan-2-yl)-3-thia-9-azabicyclo[3.3.1]non-6-ene-9-carboxylate.

Step 4

Preparation of tert-butyl 7-(7-(bis((2-(trimethylsilyl)ethoxy)methyl)amino)pyrazolo[1,5-a]pyrimidin-5-yl)-3-thia-9-azabicyclo[3.3.1]non-6-ene-9-carboxylate

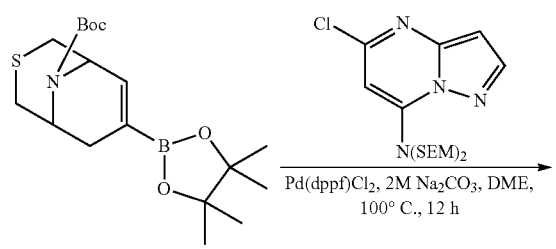

A solution of 5-chloro-N,N-bis((2-(trimethylsilyl)ethoxy)methyl)pyrazolo[1,5-a]pyrimidin-7-amine (239.6 mg, 0.56 mmol) in DME (7.4 mL) was treated with boronate (206 mg, 0.56 mmol), Pd(dppf)Cl$_2$.CH$_2$Cl$_2$ (78.3 mg, 0.098 mmol), 2M aqueous Na$_2$CO$_3$ (3.68 mL) under argon and heated at 100° C. for 16 h. Upon cooling, water (50 mL) and ethyl acetate (70 mL) was added. Two layers were separated and the organic layer was collected. Aqueous layer was then extracted with ethyl acetate (2×70 mL). Combined organic layer was washed with brine (1×150 mL), dried (Na$_2$SO$_4$) and evaporated under reduced pressure to give crude material which was purified by column chromatography (0-40% hex-ane-ethyl acetate) to provide the desired product tert-butyl 7-(7-(bis((2-(trimethylsilyl)ethoxy)methyl)amino)pyrazolo[1,5-a]pyrimidin-5-yl)-3-thia-9-azabicyclo[3.3.1]non-6-ene-9-carboxylate (262 mg).

Step 5

Preparation of tert-butyl 7-(7-(bis((2-(trimethylsilyl)ethoxy)methyl)amino)pyrazolo[1,5-a]pyrimidin-5-yl)-3-thia-9-azabicyclo[3.3.1]nonane-9-carboxylate

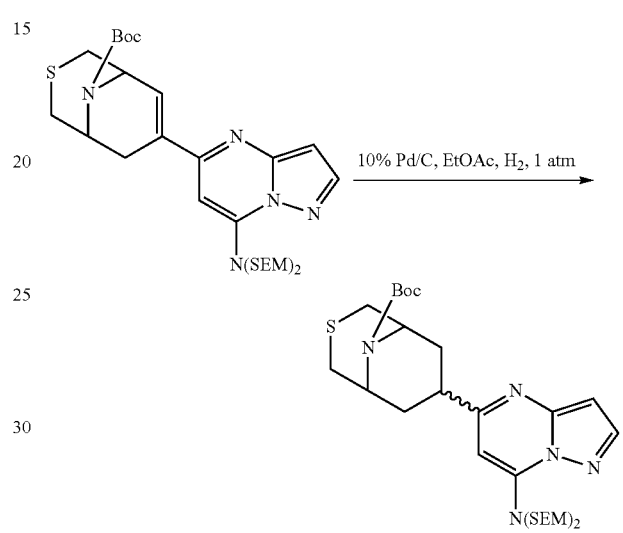

Substrate (744 mg, 1.17 mmol) in EtOAc (25 mL) was hydrogenated at 50° C. using 10% Pd/C catalyst (520 mg) and 1 atmospheric hydrogen pressure for 16 h. After filtering off the catalyst, the solvent was evaporated off under reduced pressure and the crude material was purified by column chromatography (0-40% hexane-ethyl acetate) to give the desired product tert-butyl 7-(7-(bis((2-(trimethylsilyl)ethoxy)methyl)amino)pyrazolo[1,5-a]pyrimidin-5-yl)-3-thia-9-azabicyclo[3.3.1]nonane-9-carboxylate as a mixture of stereoisomers.

Step 6

Preparation of tert-butyl 7-(7-(bis((2-(trimethylsilyl)ethoxy)methyl)amino)-3-iodopyrazolo[1,5-a]pyrimidin-5-yl)-3-thia-9-azabicyclo[3.3.1]nonane-9-carboxylate

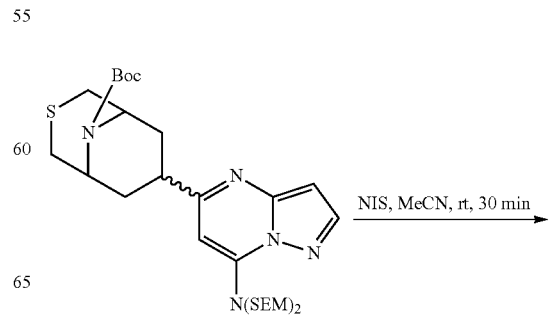

711

-continued

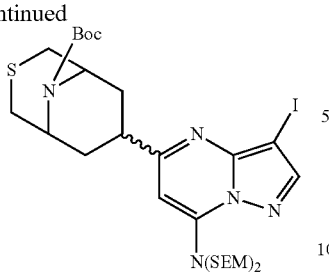

Substrate (61 mg, 0.096 mmol) was suspended in acetonitrile (2 mL) and treated with NIS (23.77 mg, 0.105 mmol) at room temperature. The mixture was stirred for 30 min. Then solvent was evaporated off under reduced pressure, and the crude material was purified by column chromatography (SiO$_2$, 0-40% hexane-EtOAc) to provide the desired product tert-butyl 7-(7-(bis((2-(trimethylsilyl)ethoxy)methyl)amino)-3-iodopyrazolo[1,5-a]pyrimidin-5-yl)-3-thia-9-azabicyclo[3.3.1]nonane-9-carboxylate.

Step 7

Preparation of tert-butyl 7-(7-(bis((2-(trimethylsilyl)ethoxy)methyl)amino)-3-(6-phenylpyridin-3-yl)pyrazolo[1,5-a]pyrimidin-5-yl)-3-thia-9-azabicyclo[3.3.1]nonane-9-carboxylate

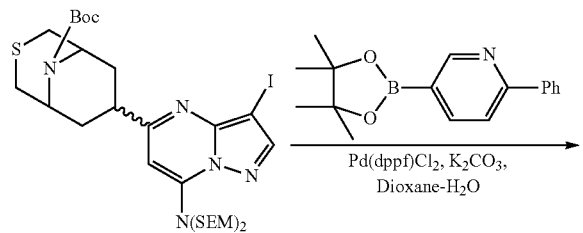

The substrate (279 mg, 0.366 mmol) in dioxane (14 mL) and water (3.5 mL) was treated with boronate (162.6 mg, 0.55 mmol), Pd(dppf)Cl$_2$.CH$_2$Cl$_2$ (40.66 mg, 0.048 mmol) and K$_2$CO$_3$ (162.6 mg, 1.11 mmol) under argon and heated at 100° C. for 16 h. Upon cooling, the mixture was filtered through Celite and the filtrate was evaporated off under reduced pressure to give crude residue which was purified by column chromatography (SiO$_2$, 0-40% hexane-EtOAc) to provide desired product tert-butyl 7-(7-(bis((2-(trimethylsilyl)ethoxy)methyl)amino)-3-(6-phenylpyridin-3-yl)pyrazolo[1,5-a]pyrimidin-5-yl)-3-thia-9-azabicyclo[3.3.1]nonane-9-carboxylate.

712

Step 8

Preparation of Intermediate Sulfone

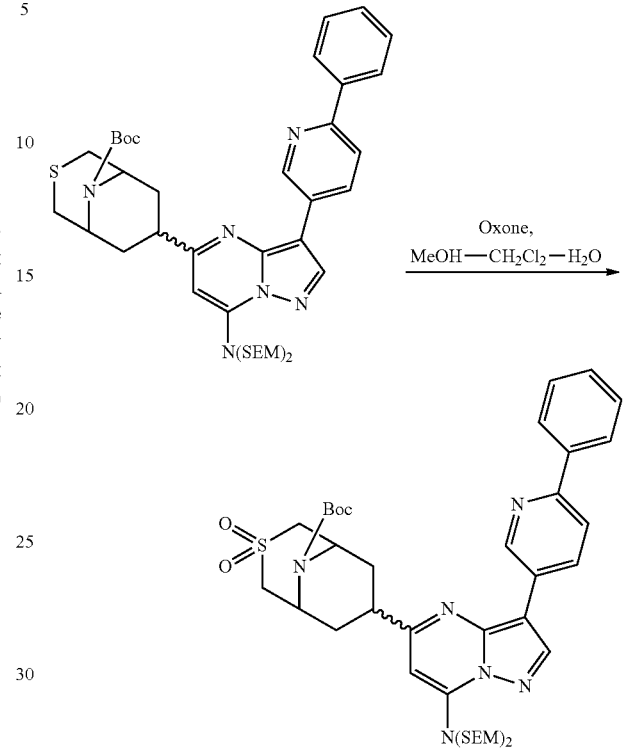

The substrate (157 mg, 0.199 mmol) was dissolved in MeOH (5 mL) and CH$_2$Cl$_2$ (10 mL) at room temperature and treated with oxone (269 mg, 0.478 mmol) in water (4 ml). After reaction was complete, solvent was evaporated and the residue was taken up in EtOAc (20 mL). Washing with saturated aqueous NaHCO$_3$ (20 mL), brine (20 ml), drying (Na$_2$SO$_4$), filtration and evaporation under reduced pressure gave the crude product which as purified by column chromatography.

Step 9

Preparation of Intermediate Bromide

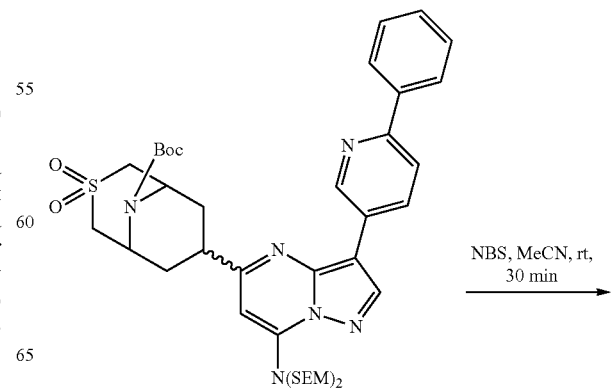

-continued

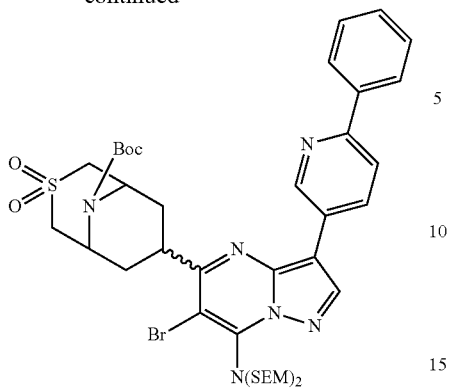

Substrate (66 mg, 0.08 mmol) was suspended in acetonitrile (2 mL) and treated with NBS (15.73 mg, 0.088 mmol) at room temperature. The mixture was stirred for 30 min. Then solvent was evaporated off under reduced pressure, and the crude material was purified by column chromatography (SiO$_2$, 0-40% hexane-EtOAc) to provide desired compound.

Step 10

Preparation of Intermediate Vinyl Ether

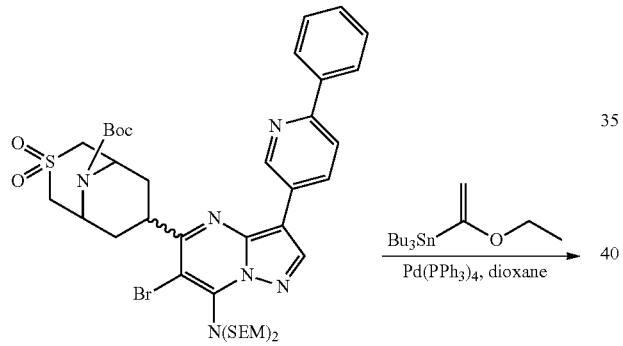

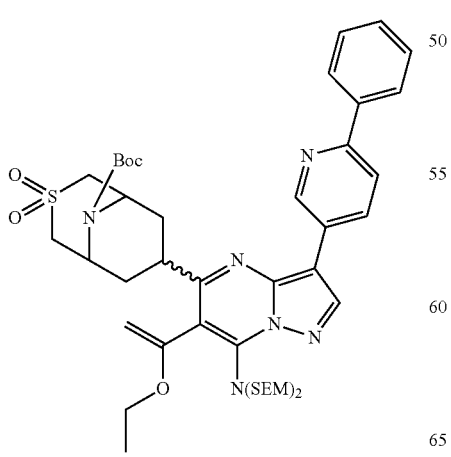

Substrate (64 mg, 0.071 mmol) in dioxane (4 mL) was treated with Pd(PPh$_3$)$_4$ (7.92 mg, 0.006 mmol) and tributyl (1-ethoxyvinyl)tin (46.6 μL, 0.13 mmol) under argon and the mixture was heated at 100° C. for 16 h. Upon cooling, the mixture was filtered through a pad of 10% KF—SiO$_2$ and the filtrate was evaporated off under reduced pressure to give a residue which was purified by column chromatography (SiO$_2$, 0-40% hexane-EtOAc) to provide desired product.

Step 11

Preparation of Intermediate Ketone

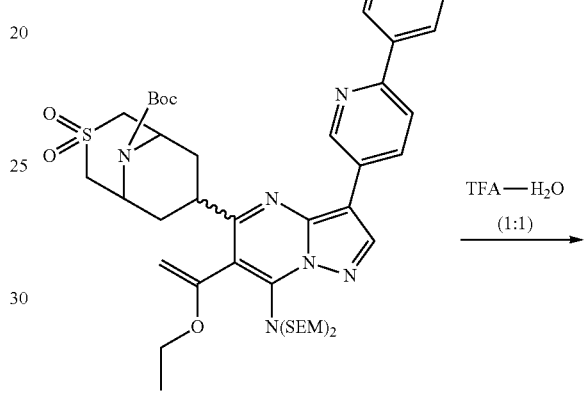

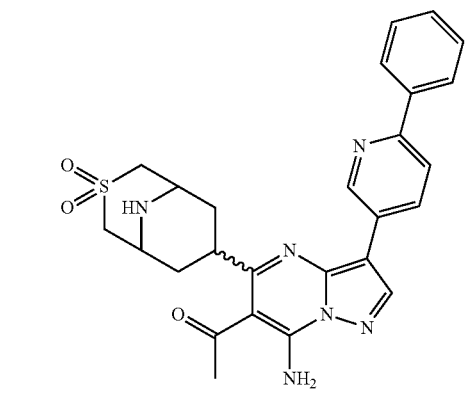

Substrate (45 mg, 0.05 mmol) was treated with TFA-H$_2$O (10 mL, 1:1) at room temperature and the mixture was stirred for 16 h. Then the solvent was evaporated off under reduced pressure and the material was lyophilized from acetonitrile: water (3:1) to give the desired product which was used without further purification.

715
Step 12

Preparation of endo/exo-7-[6-acetyl-7-amino-3-(6-phenyl-3-pyridinyl)pyrazolo[1,5-a]pyrimidin-5-yl]-9-(4h-1,2,4-triazol-3-ylcarbonyl)-3-thia-9-azabicyclo[3.3.1]nonane, 3,3-dioxide

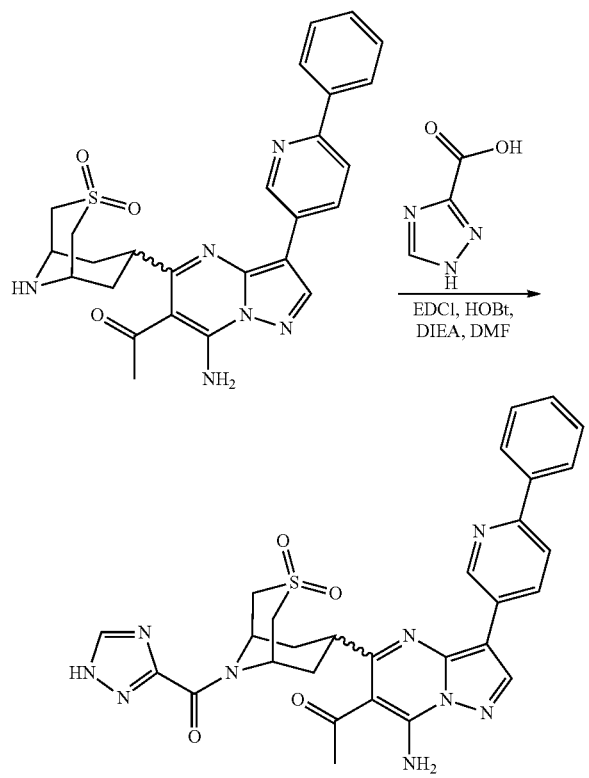

Carboxylic acid (60 mg) in DMF (1 mL) was treated with EDCI (270 mg) and HOBt (122 mg). Then substrate (26 mg) followed by DIEA (0.48) was added. Then the reaction mixture was treated with water (0.1 mL) and DMSO-MeCN (3:1, 3 mL). Pure product was isolated by preparative HPLC.

Example 8-12

Preparation of 1-(5-((1R,5S)-9-(1H-1,2,4-triazole-3-carbonyl)-9-azabicyclo[3.3.1]nonan-3-yl)-7-amino-3-(6-phenylpyridin-3-yl)pyrazolo[1,5-a]pyrimidin-6-yl)ethanone

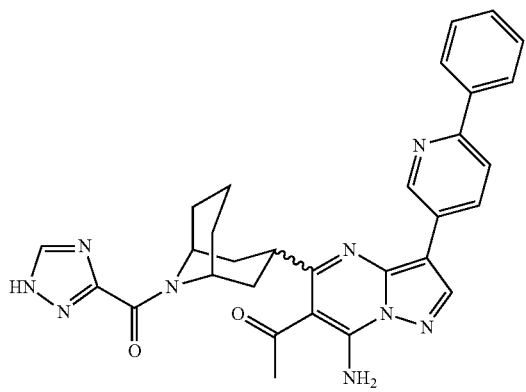 [SMILES: CC(=O)c1c(C2CC3CCCC(C2)N3C(=O)c2nc[nH]n2)nc2c(-c3ccc(-c4ccccc4)nc3)cnn2c1N]

716
Step 1

Preparation of tert-butyl 3-(trifluoromethylsulfonyloxy)-9-azabicyclo[3.3.1]non-3-ene-9-carboxylate

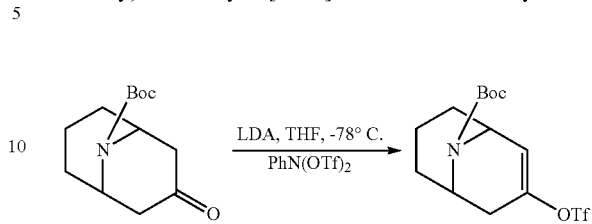

Substrate (1.0 g, 4.18 mmol) was dissolved in THF (50 mL) and cooled to −78° C. and treated with LDA (3.15 mL, 6.27 mmol, 2M solution). After 5 min., N-phenylbis(trifluoromethanesulfonimide) (1.64 g, 4.59 mmol) in THF (15 mL) was added dropwise. The mixture was stirred at −78° C. for 30 min. and then gradually warmed to it and continued to stir until starting material completely disappeared (~1.5 h). The reaction was quenched with saturated aqueous ammonium chloride (80 mL) followed by addition of ethyl acetate (100 mL). Two layers were separated and the organic layer was collected. The aqueous layer was extracted with ethyl acetate (2×100 mL). The combined organic layers were washed with water (1×100 mL), brine (1×100 mL) and dried (Na$_2$SO$_4$), filtered and evaporated under reduced pressure to provide crude material which was purified by column chromatography (0-40% hexane-ethyl acetate) to give the desired product tert-butyl 3-(trifluoromethylsulfonyloxy)-9-azabicyclo[3.3.1]non-3-ene-9-carboxylate.

Step 2

Preparation of tert-butyl 3-(4,4,5,5-tetramethyl-1,3,2-dioxaborolan-2-yl)-9-azabicyclo[3.3.1]non-3-ene-9-carboxylate

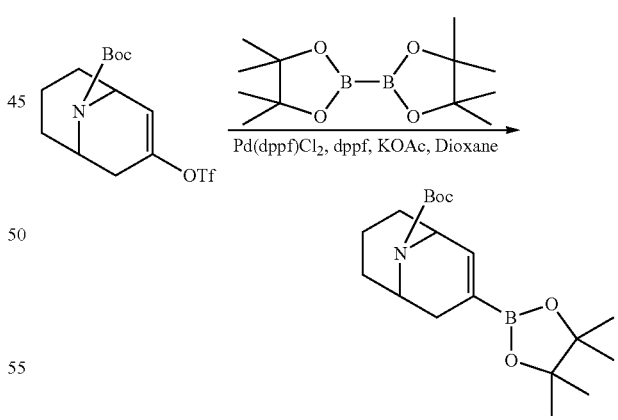

A mixture of substrate (1.46 g, 3.95 mmol), bis(pinacolato)diboron (1.2 g, 4.75 mmol), Pd(dppf)Cl$_2$.CH$_2$Cl$_2$ (184 mg, 0.236 mmol), dppf (138 mg, 0.249 mmol) and KOAc (1.16 g, 11.85 mmol) in dioxane (80 ml) was heated under argon at 80° C. for 16 h. Upon cooling, the solvent was evaporated off under reduced pressure and the residue was dissolved in ethyl acetate (100 mL). The organic layer was washed with water (1×100 ml), brine (1×50 mL), dried (Na$_2$SO$_4$) and evaporated under reduced pressure to give crude material which was purified by column chromatography (0-40% hexane-ethyl acetate) to provide the desired product tert-butyl 3-(4,4,5,5-tetramethyl-1,3,2-dioxaborolan-2-yl)-9-azabicyclo[3.3.1]non-3-ene-9-carboxylate.

Step 3

Preparation of tert-butyl 3-(7-(bis((2-(trimethylsilyl)ethoxy)methyl)amino)pyrazolo[1,5-a]pyrimidin-5-yl-9-azabicyclo[3.3.1]non-3-ene-9-carboxylate

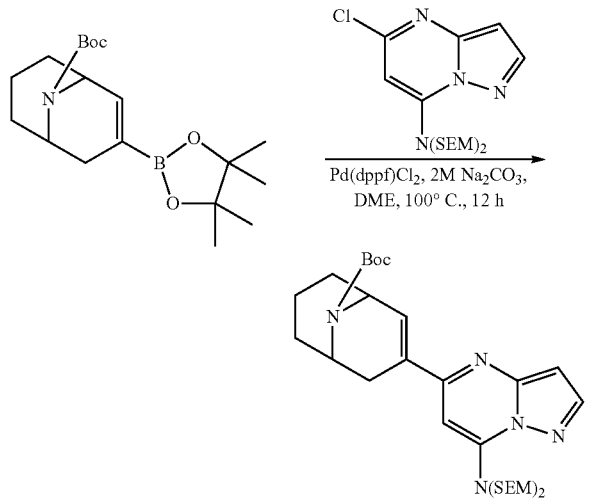

A solution of 5-chloro-N,N-bis((2-(trimethylsilyl)methyl)pyrazolo[1,5-a]pyrimidin-7-amine (1.42 g, 3.31 mmol) in DME (20 mL) was treated with boronate (1.28 g, 3.68 mmol), Pd(dppf)Cl₂.CH₂Cl₂ (268 mg, 0.335 mmol), 2M aqueous Na₂CO₃ (12.79 mL) under argon and heated at 100° C. for 16 h. Upon cooling, water (50 mL) and ethyl acetate (70 mL) was added. Two layers were separated and organic layer was collected. The aqueous layer was then extracted with ethyl acetate (2×70 mL). Combined organic layers were washed with brine (1×150 mL), dried (Na₂SO₄) and evaporated under reduced pressure to give crude material which was purified by column chromatography (0-40% hexane-ethyl acetate) to provide the desired product tert-butyl 3-(7-(bis((2-(trimethylsilyl)ethoxy)methyl)amino)pyrazolo[1,5-a]pyrimidin-5-yl)-9-azabicyclo[3.3.1]non-3-ene-9-carboxylate.

Step 4

Preparation of tert-butyl 3-(7-(bis((2-(trimethylsilyl)ethoxy)methyl)amino)pyrazolo[1,5-a]pyrimidin-5-yl)-9-azabicyclo[3.3.1]nonane-9-carboxylate

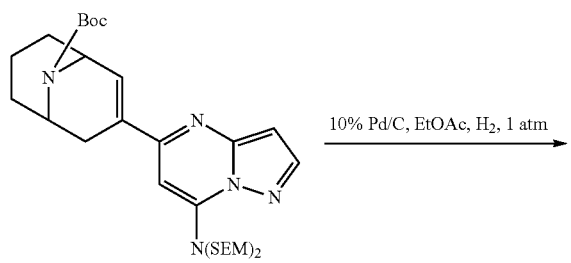

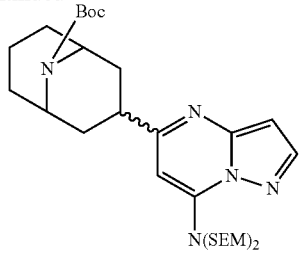

Substrate (1.25 g, 2.03 mmol) in EtOAc (100 mL) was hydrogenated at 50° C. using 10% Pd/C catalyst (159 mg) and 1 atmospheric hydrogen pressure for 16 h. After filtering off the catalyst, the solvent was evaporated off under reduced pressure and crude material was purified by column chromatography (0-40% hexane-ethyl acetate) to give the desired product tert-butyl 3-(7-(bis((2-(trimethylsilyl)ethoxy)methyl)amino)pyrazolo[1,5-a]pyrimidin-5-yl)-9-azabicyclo[3.3.1]nonane-9-carboxylate as a mixture of stereoisomers.

Step 5

Preparation of tert-butyl 3-(7-(bis((2-(trimethylsilyl)ethoxy)methyl)amino)-3-iodopyrazolo[1,5-a]pyrimidin-5-yl)-9-azabicyclo[3.3.1]nonane-9-carboxylate

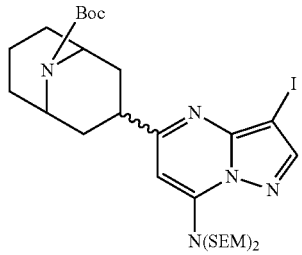

Substrate (611 g, 0.99 mmol) was suspended in acetonitrile (10 mL) and treated with NIS (221.8 mg, 0.99 mmol) at room temperature. The mixture was stirred for 30 min. Then solvent was evaporated off under reduced pressure, and the crude material was purified by column chromatography (SiO₂, 0-40% hexane-EtOAc) to provide desired compound tert-butyl 3-(7-(bis((2-(trimethylsilyl)ethoxy)methyl)amino)-3-iodopyrazolo[1,5-a]pyrimidin-5-yl)-9-azabicyclo[3.3.1]nonane-9-carboxylate.

Step 6

Preparation of tert-butyl 3-(7-(bis((2-(trimethylsilyl)ethoxy)methyl)amino)-3-(6-phenylpyridin-3-yl)pyrazolo[1,5-a]pyrimidin-5-yl)-9-azabicyclo[3.3.1]nonane-9-carboxylate

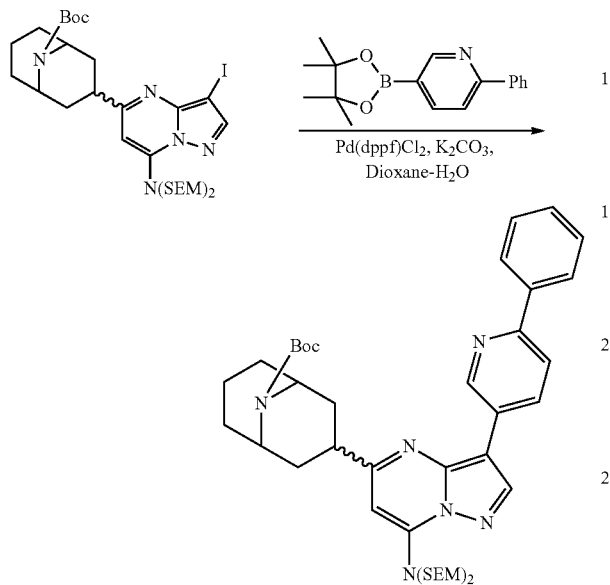

The substrate (695 mg, 0.93 mmol) in dioxane (10 mL) and water (2.5 mL) was treated with boronate (615 mg, 1.62 mmol), Pd(dppf)Cl$_2$·CH$_2$Cl$_2$ (90.3 mg, 0.106 mmol) and K$_2$CO$_3$ (385 mg, 2.63 mmol) under argon and heated at 100° C. for 16 h. Upon cooling, the mixture was filtered through Celite and the filtrate was evaporated off under reduced pressure to give crude residue which was purified by column chromatography (SiO$_2$, 0-40% hexane-EtOAc) to provide the desired product tert-butyl 3-(7-(bis((2-(trimethylsilyl)ethoxy)methyl)amino)-3-(6-phenylpyridin-3-yl)pyrazolo[1,5-a]pyrimidin-5-yl)-9-azabicyclo[3.3.1]nonane-9-carboxylate.

Step 7

Preparation of tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-9-azabicyclo[3.3.1]nonane-9-carboxylate

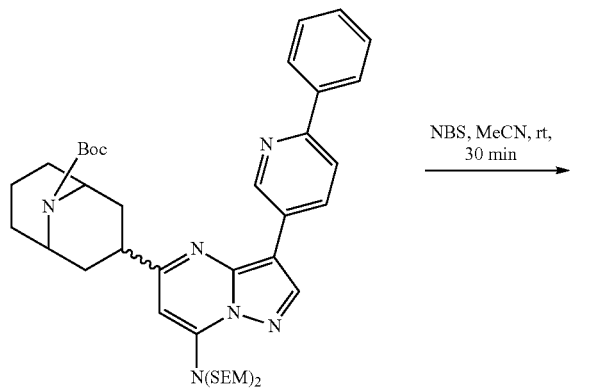

Substrate (500 mg, 0.649 mmol) was suspended in acetonitrile (10 mL) and treated with NBS (127.13 mg, 0.71 mmol) at room temperature. The mixture was stirred for 30 min. Then solvent was evaporated off under reduced pressure, and the crude material was purified by column chromatography (SiO$_2$, 0-40% hexane-EtOAc) to provide the desired compound tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-9-azabicyclo[3.3.1]nonane-9-carboxylate.

Step 8

Preparation of tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-9-azabicyclo[3.3.1]nonane-9-carboxylate

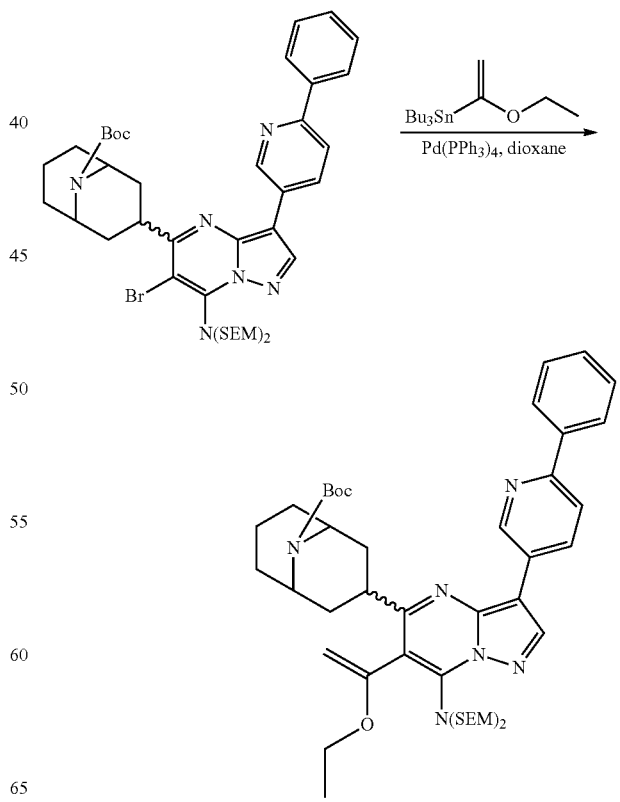

721

Substrate (499 mg, 0.588 mmol) in dioxane (6 mL) was treated with Pd(PPh$_3$)$_4$ (67.93 mg, 0.0588 mmol) and tributyl (1-ethoxyvinyl)tin (0.59 mL, 0.176 mmol) under argon and the mixture was heated at 100° C. for 16 h. Upon cooling, the mixture was filtered through a pad of 10% KF—SiO$_2$ and the filtrate was evaporated off under reduced pressure to give a residue which was purified by column chromatography (SiO$_2$, 0-40% hexane-EtOAc) to provide the desired product tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-9-azabicyclo[3.3.1]nonane-9-carboxylate.

Step 9

Preparation of 1-(7-amino-5-(9-azabicyclo[3.3.1]nonan-3-yl)-3-(6-phenylpyridin-3-yl)pyrazolo[1,5-a]pyrimidin-6-yl)ethanone

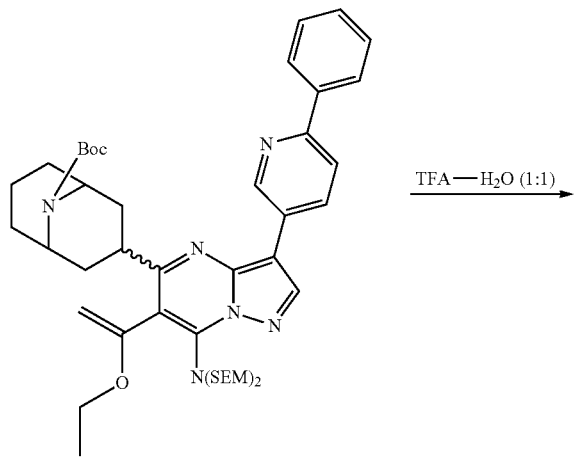

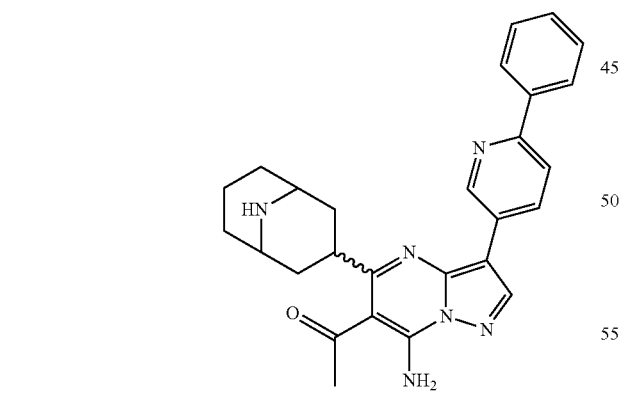

Substrate (45 mg, 0.05 mmol) was treated with TFA-H$_2$O (10 mL, 1:1) at room temperature and the mixture was stirred for 16 h. Then the solvent was evaporated off under reduced pressure and the material was lyophilized from acetonitrile:water (3:1) to give compound which was used without further purification.

722

Step 10

Preparation of 1-(5-((1R,5S)-9-(1H-1,2,4-triazole-3-carbonyl)-9-azabicyclo[3.3.1]nonan-3-yl)-7-amino-3-(6-phenylpyridin-3-yl)pyrazolo[1,5-a]pyrimidin-6-yl)ethanone

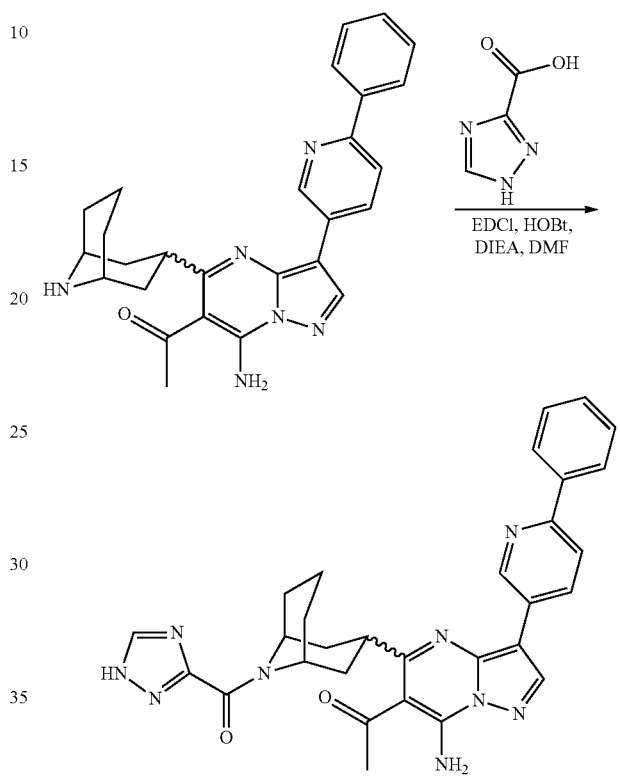

Carboxylic acid (63.1 mg) in DMF (2 mL) was treated with EDCI (170 mg) and HOBt (56.3 mg). Then substrate (136 mg) followed by DIEA (0.36) was added. Once the reaction was complete, the reaction mixture was treated with water (0.1 mL) and DMSO-MeCN (3:1, 3 mL). Pure compound was isolated by preparative HPLC.

Example 8-13

Preparation of ((1R,5S)-7-(7-amino-3-(6-phenylpyridin-3-yl)pyrazolo[1,5-a]pyrimidin-5-yl-3,9-diazabicyclo[3.3.1]nonan-9-yl)(1H-1,2,4-triazol-3-yl)methanone

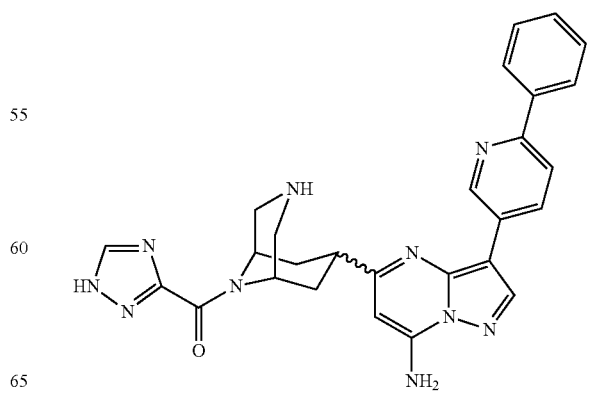

Step 1

Preparation of 3-benzyl 9-tert-butyl 7-(trifluoromethylsulfonyloxy)-3,9-diazabicyclo[3.3.1]non-6-ene-3,9-dicarboxylate

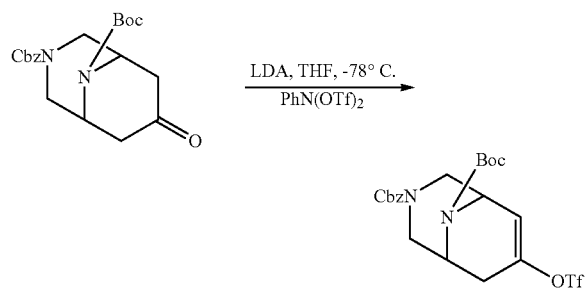

Substrate (110 mg, 0.29 mmol) was dissolved in THF (5 mL) and cooled to −78° C. and treated with LDA (0.24 mL, 0.44 mmol, 2M solution). After 5 min., N-phenylbis(trifluoromethanesulfonimide) (114.2 g, 0.32 mmol) in THF (5 mL) was added dropwise. The mixture was stirred at −78° C. for 30 min. and then gradually warmed to it and continued to stir until starting material completely disappeared (~1.5 h). The reaction was quenched with saturated aqueous ammonium chloride (20 mL) followed by addition of ethyl acetate (50 mL). Two layers were separated and the organic layer was collected. The aqueous layer was extracted with ethyl acetate (2×50 mL). The combined organic layers were washed with water (1×100 mL), brine (1×50 mL) and dried (Na$_2$SO$_4$), filtered and evaporated under reduced pressure to provide crude material which was purified by column chromatography (0-40% hexane-ethyl acetate) to give the desired product 3-benzyl 9-tert-butyl 7-(trifluoromethylsulfonyloxy)-3,9-diazabicyclo[3.3.1]non-6-ene-3,9-dicarboxylate.

Step 2

Preparation of 3-benzyl 9-tert-butyl 7-(4,4,5,5-tetramethyl-1,3,2-dioxaborolan-2-yl)-3,9-diazabicyclo[3.3.1]non-6-ene-3,9-dicarboxylate

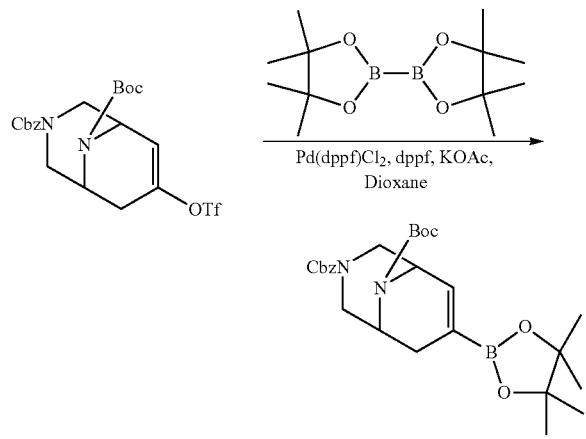

A mixture of substrate (52 mg, 0.10 mmol), bis(pinacolato)diboron (31.1 mg, 0.122 mmol), Pd(dppf)Cl$_2$.CH$_2$Cl$_2$ (5 mg, 0.006 mmol), dppf (3.59 mg, 0.0.006 mmol) and KOAc (30.1 mg, 0.30 mmol) in dioxane (80 ml) was heated under argon at 80° C. for 16 h. Upon cooling, the solvent was evaporated off under reduced pressure and the residue was dissolved in ethyl acetate (10 mL). The organic layer was washed with water (1×10 ml), brine (1×10 mL), dried (Na$_2$SO$_4$) and evaporated under reduced pressure to give crude material which was purified by column chromatography (0-40% hexane-ethyl acetate) to provide the desired product 3-benzyl 9-tert-butyl 7-(4,4,5,5-tetramethyl-1,3,2-dioxaborolan-2-yl)-3,9-diazabicyclo[3.3.1]non-6-ene-3,9-dicarboxylate.

Step 3

Preparation of 3-benzyl 9-tert-butyl 7-(7-(bis((2-(trimethylsilyl)ethoxy)methyl)amino)-3-(6-phenylpyridin-3-yl)pyrazolo[1,5-a]pyrimidin-5-yl-3,9-diazabicyclo[3.3.1]non-6-ene-3,9-dicarboxylate

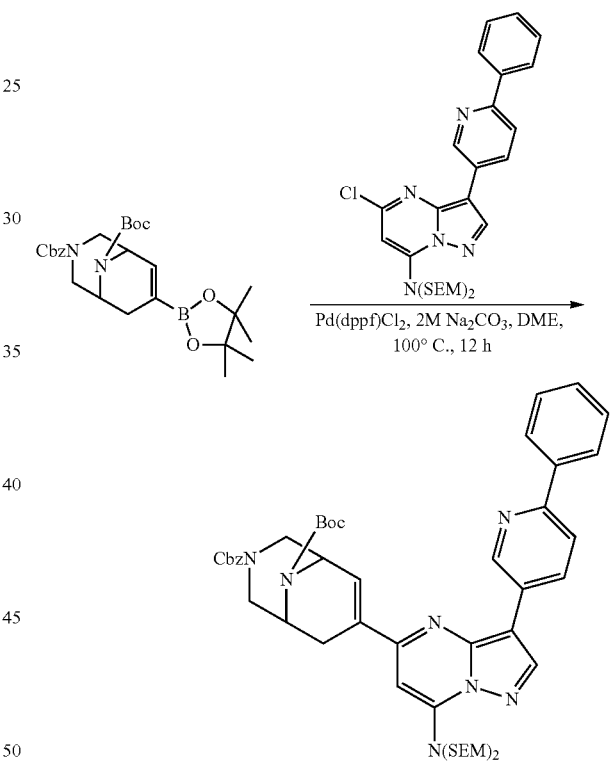

A solution of chloride (24.01 mg, 0.041 mmol) in DME (2 mL) was treated with boronate (30 mg, 0.062 mmol), Pd(dppf)Cl$_2$.CH$_2$Cl$_2$ (5.73 mg, 0.007 mmol), 2M aqueous Na$_2$CO$_3$ (0.27 mL) under argon and heated at 100° C. for 16 h. Upon cooling, water (5 mL) and ethyl acetate (10 mL) was added. Two layers were separated and the organic layer was collected. The aqueous layer was then extracted with ethyl acetate (2×20 mL). Combined organic layers were washed with brine (1×15 mL), dried (Na$_2$SO$_4$) and evaporated under reduced pressure to give crude material which was purified by column chromatography (0-40% hexane ethyl acetate) to provide the desired product 3-benzyl 9-tert-butyl 7-(7-(bis ((2-(trimethylsilyl)ethoxy)methyl)amino)-3-(6-phenylpyridin-3-yl)pyrazolo[1,5-a]pyrimidin-5-yl)-3,9-diazabicyclo[3.3.1]non-6-ene-3,9-dicarboxylate.

Step 4

Preparation of tert-butyl 7-(7-(bis((2-(trimethylsilyl)ethoxy)methyl)amino)-3-(6-phenylpyridin-3-yl)pyrazolo[1,5-a]pyrimidin-5-yl)-3,9-diazabicyclo[3.3.1]nonane-9-carboxylate

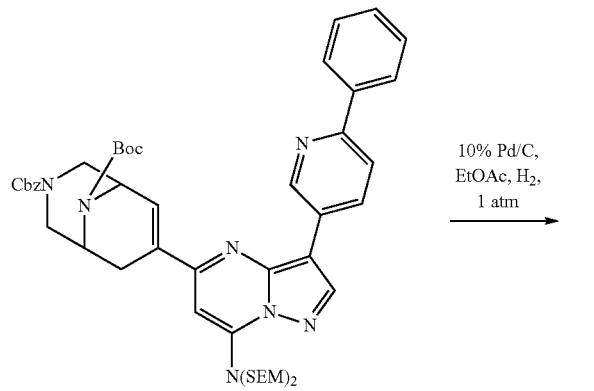

Substrate (3.6 g, 0.39 mmol) in EtOAc (5 mL) was hydrogenated at 50° C. using 10% Pd/C catalyst (25 mg) and at 1 atmospheric hydrogen pressure for 16 h. After filtering off the catalyst, the solvent was evaporated off under reduced pressure and crude material was purified by column chromatography (0-40% hexane-ethyl acetate) to give the desired product as a mixture of stereoisomers.

Step 5

Preparation of (1R,5S)-tert-butyl 7-(7-(bis((2-(trimethylsilyl)ethoxy)methyl)amino)-3-(6-phenylpyridin-3-yl)pyrazolo[1,5-a]pyrimidin-5-yl)-9-(1H-1,2,4-triazole-3-carbonyl)-3,9-diazabicyclo[3.3.1]nonane-3-carboxylate

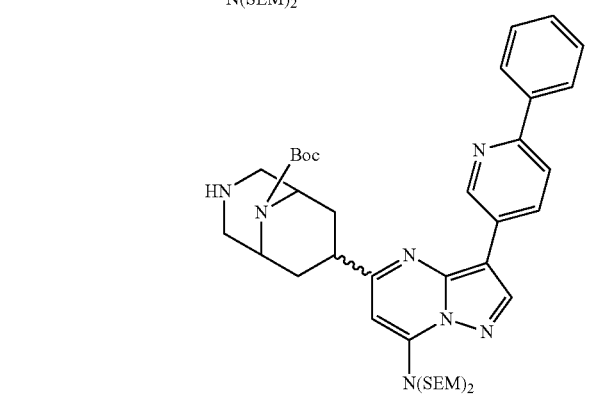

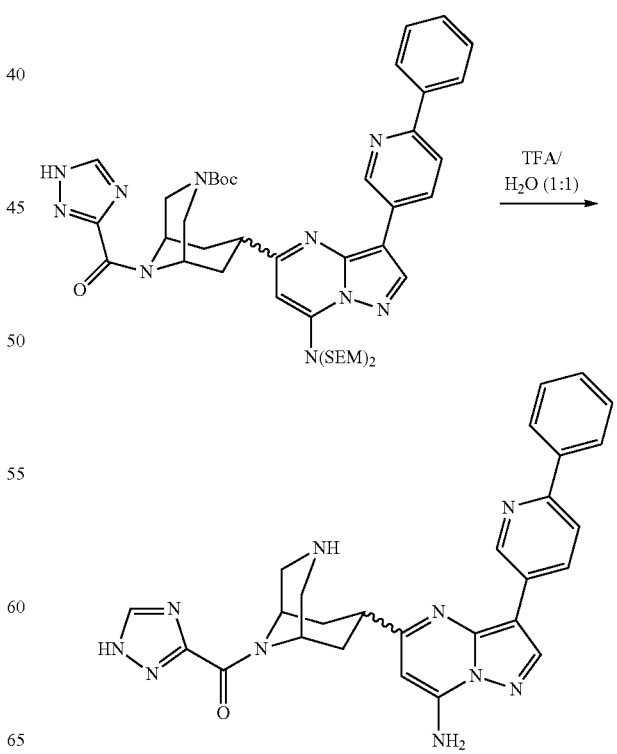

Carboxylic acid (25 mg) in DMF (2 mL) was treated with EDCI (108.8 mg) and HOBt (49.1 mg). Then substrate (32 mg) followed by DIEA (0.19) was added. Once the reaction was complete the reaction mixture was treated with water (0.1 mL) and DMSO-MeCN (3:1, 3 mL). Pure compound (1R, 5S)-tert-butyl 7-(7-(bis((2-(trimethylsilyl)ethoxy)methyl)amino)-3-(6-phenylpyridin-3-yl)pyrazolo[1,5-a]pyrimidin-5-yl)-9-(1H-1,2,4-triazole-3-carbonyl)-3,9-diazabicyclo[3.3.1]nonane-3-carboxylate was isolated by preparative HPLC.

Step 6

Preparation of ((1R,5S)-7-(7-amino-3-(6-phenylpyridin-3-yl)pyrazolo[1,5-a]pyrimidin-5-yl)-3,9-diazabicyclo[3.3.1]nonan-9-yl)(1H-1,2,4-triazol-3-yl)methanone

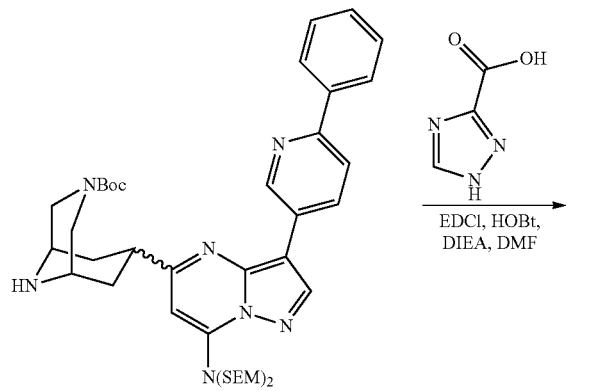

Substrate (45 mg, 0.05 mmol) was treated with TFA-H₂O (10 mL, 1:1) at room temperature and the mixture was stirred for 16 h. Then the solvent was evaporated off under reduced pressure and the material was purified by preparative HPLC to give the desired product.

Example 8-14

Preparation of 1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone

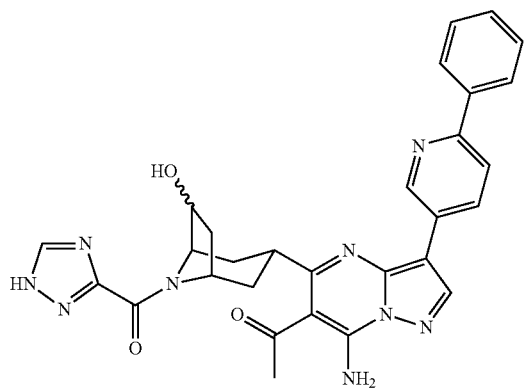 [SMILES: CC(=O)c1c(C2CC3CC(O)C(C2)N3C(=O)c2nc[nH]n2)nc2c(-c3ccc(-c4ccccc4)nc3)cnn2c1N]

Step 1

Preparation of (1R,5R)-tert-butyl 6-(tert-butyldimethylsilyloxy)-3-oxo-8-azabicyclo[3.2.1]octane-8-carboxylate

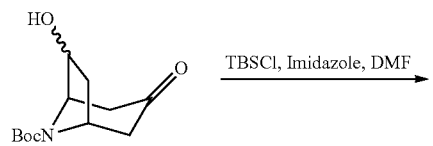

Substrate (918 mg, 3.79 mmol) was dissolved in DMF (50 mL) and treated with imidazole (515.4 mg, 7.58 mmol) and TBSCl (625.5 mg, 4.17 mmol). The mixture was stirred at room temperature for 12 h. The reaction was diluted with EtOAc (200 mL) and washed with water (200 mL), saturated aqueous NaHCO₃ (200 mL) and brine (200 mL). The organic layer was then dried (Na₂SO₄), filtered and evaporated under reduced pressure to provide crude material which was purified by column chromatography (SiO₂, 0-10% EtOAc-hexane).

Step 2

Preparation of (1R,5R)-tert-butyl 6-(tert-butyldimethylsilyloxy)-3-(trifluoromethylsulfonyloxy)-8-azabicyclo[3.2.1]oct-2-ene-8-carboxylate

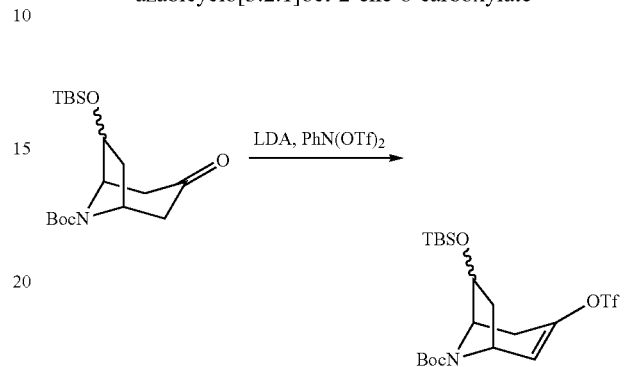

Substrate (334 mg, 0.94 mmol) was dissolved in THF (10 mL) and cooled to −78° C. and treated with LDA (0.83 mL, 1.41 mmol, 2M solution). After 5 min., N-phenylbis(trifluoromethanesulfonimide) (370 mg, 1.03 mmol) in THF (10 mL) was added dropwise. The mixture was stirred at −78° C. for 30 min. and then gradually warmed to it and continued to stir until starting material completely disappeared (~1.5 h). The reaction was quenched with saturated aqueous ammonium chloride (20 mL) followed by addition of ethyl acetate (50 mL). Two layers were separated and the organic layer was collected. The aqueous layer was extracted with ethyl acetate (2×50 mL). The combined organic layers were washed with water (1×100 mL), brine (1×100 mL) and dried (Na₂SO₄), filtered and evaporated under reduced pressure to provide crude material which was purified by column chromatography (0-40% hexane-ethyl acetate) to give the desired product (1R,5R)-tert-butyl 6-(tert-butyldimethylsilyloxy)-3-(trifluoromethylsulfonyloxy)-8-azabicyclo[3.2.1]oct-2-ene-8-carboxylate.

Step 3

Preparation of (1R,5R)-tert-butyl 6-(tert-butyldimethylsilyloxy)-3-(4,4,5,5-tetramethyl-1,3,2-dioxaborolan-2-yl)-8-azabicyclo[3.2.1]oct-2-ene-8-carboxylate

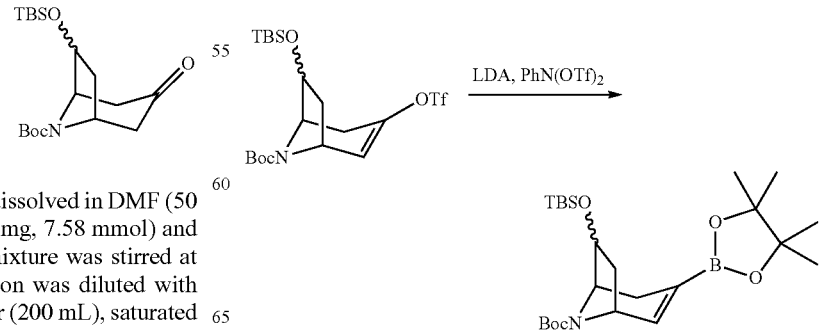

A mixture of substrate (386 mg, 0.79 mmol), bis(pinacolato)diboron (240.8 mg, 0.94 mmol), Pd(dppf)Cl$_2$.CH$_2$Cl$_2$ (38.5 mg, 0.049 mmol), dppf (27.65 mg, 0.0.048 mmol) and KOAc (239.5 mg, 2.43 mmol) in dioxane (5 ml) was heated under argon at 80° C. for 16 h. Upon cooling, the solvent was evaporated off under reduced pressure and the residue was dissolved in ethyl acetate (50 mL). The organic layer was washed with water (1×50 ml), brine (1×50 mL), dried (Na$_2$SO$_4$) and evaporated under reduced pressure to give crude material which was purified by column chromatography (0-40% hexane-ethyl acetate) to provide the desired product (1R,5R)-tert-butyl 6-(tert-butyldimethylsilyloxy)-3-(4,4,5,5-tetramethyl-1,3,2-dioxaborolan-2-yl)-8-azabicyclo[3.2.1]oct-2-ene-8-carboxylate.

Step 4

Preparation of (1R,5R)-tert-butyl 3-(7-(bis((2-(trimethylsilyl)ethoxy)methyl)amino)-3-(6-phenylpyridin-3-yl)pyrazolo[1,5-a]pyrimidin-5-yl-6-(tert-butyldimethylsilyloxy)-8-azabicyclo[3.2.1]oct-2-ene-8-carboxylate

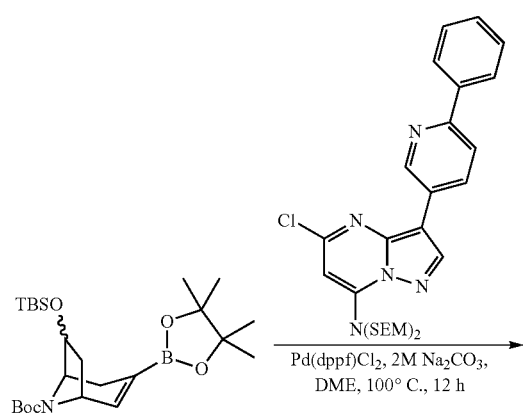

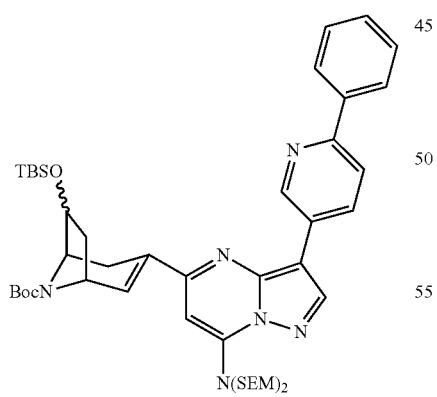

A solution of chloride (600 mg, 1.03 mmol) in DME (7.4 mL) was treated with boronate (303 mg, 0.65 mmol), Pd(dppf)Cl$_2$.CH$_2$Cl$_2$ (78.3 mg, 0.098 mmol), 2M aqueous Na$_2$CO$_3$ (3.5 mL) under argon and heated at 100° C. for 16 h. Upon cooling, water (50 mL) and ethyl acetate (70 mL) was added. Two layers were separated and the organic layer was collected. The aqueous layer was then extracted with ethyl acetate (2×70 mL). The combined organic layers were washed with brine (1×150 mL), dried (Na$_2$SO$_4$) and evaporated under reduced pressure to give crude material which was purified by column chromatography (0-40% hexane-ethyl acetate) to provide the desired product (1R,5R)-tert-butyl 3-(7-(bis((2-(trimethylsilyl)ethoxy)methyl)amino)-3-(6-phenylpyridin-3-yl)pyrazolo[1,5-a]pyrimidin-5-yl)-6-(tert-butyldimethylsilyloxy)-8-azabicyclo[3.2.1]oct-2-ene-8-carboxylate.

Step 5

Preparation of (1S)-tert-butyl 3-(7-(bis((2-(trimethylsilyl)ethoxy)methyl)amino)-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate

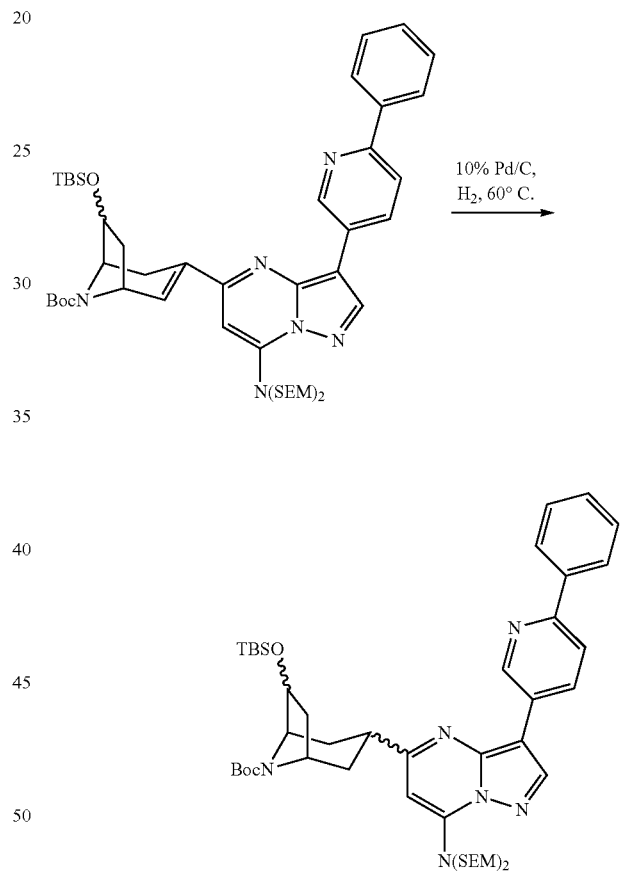

Substrate (490 mg, 0.67 mmol) in EtOAc (25 mL) was hydrogenated at 60° C. using 10% Pd/C catalyst (150 mg) under 1 atmospheric hydrogen pressure for 16 h. After filtering off the catalyst, the solvent was evaporated off under reduced pressure and crude material was purified by column chromatography (0-40% hexane-ethyl acetate) to give the desired product (1S)-tert-butyl 3-(7-(bis((2-(trimethylsilyl)ethoxy)methyl)amino)-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate as a mixture of stereoisomers.

731

Step 6

Preparation of (1S,3R,5R)-tert-butyl 3-(7-(bis((2-(trimethylsilyl)ethoxy)methyl)amino)-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate

732

Step 7

Preparation of (1S,3R,5R)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate

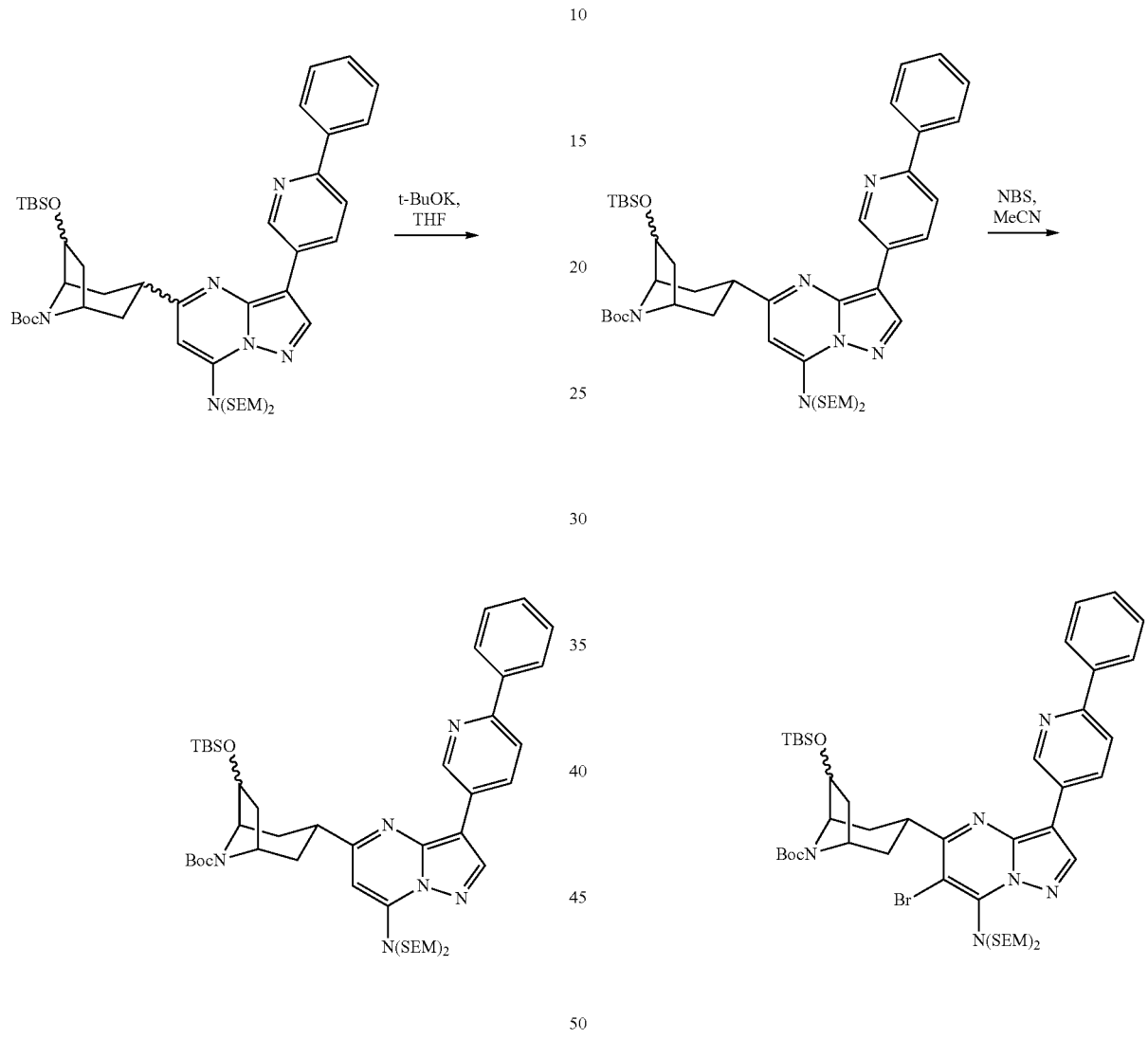

Substrate (387 mg, 0.43 mmol) was dissolved in THF (5 mL) and cooled to 0° C. and treated with t-BuOK (1.3 mmol, 1.3 mL, 1 M solution). The reaction mixture was warmed to room temperature and stirred for 30 min. Then the reaction was quenched with saturated NH₄Cl (10 mL) and EtOAc (30 mL) was added. The two layers were separated and the organic layer was collected. The organic layer was washed with brine (50 mL), dried (Na₂SO₄), and evaporated under reduced pressure to give a residue which was purified by column chromatography (SiO2, 0-30% EtOAc-hexane).

Substrate (54 mg, 0.061 mmol) was suspended in acetonitrile (2 mL) and treated with NBS (12 mg, 0.067 mmol) at room temperature. The mixture was stirred for 30 min. Then solvent was evaporated off under reduced pressure, and the crude material was purified by column chromatography (SiO₂, 0-40% hexane-EtOAc) to provide the desired compound (1S,3R,5R)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate.

733

Step 8

Preparation of (1S,3R,5R)-tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate

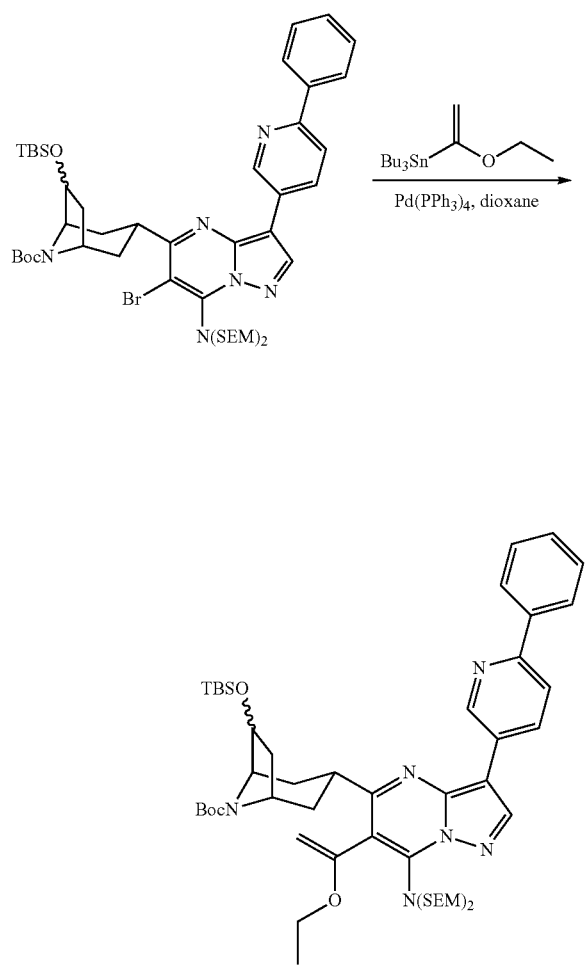

Substrate (61 mg, 0.063 mmol) in dioxane (4 mL) was treated with Pd(PPh$_3$)$_4$ (7.92 mg, 0.006 mmol) and tributyl (1-ethoxyvinyl)tin (47.6 µL, 0.13 mmol) under argon and the mixture was heated at 100° C. for 16 h. Upon cooling, the mixture was filtered through a pad of 10% KF—SiO$_2$ and the filtrate was evaporated off under reduced pressure to give a residue which was purified by column chromatography (SiO$_2$, 0-40% hexane-EtOAc) to provide the desired product (1S,3R,5R)-tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-6-(tert-butyldimethylsilyloxy)-8-azabicyclo[3.2.1]octane-8-carboxylate.

734

Step 9

Preparation of 1-(7-amino-5-((1S,3R,5R)-6-hydroxy-8-azabicyclo[3.2.1]octan-3-yl)-3-(6-phenylpyridin-3-yl)pyrazolo[1,5-a]pyrimidin-6-yl)ethanone

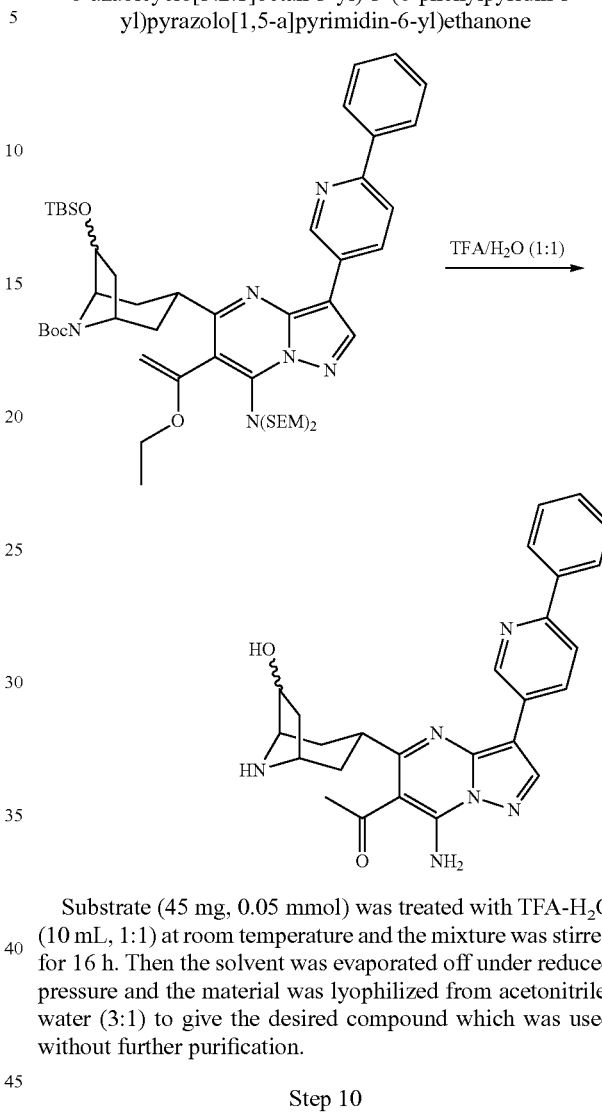

Substrate (45 mg, 0.05 mmol) was treated with TFA-H$_2$O (10 mL, 1:1) at room temperature and the mixture was stirred for 16 h. Then the solvent was evaporated off under reduced pressure and the material was lyophilized from acetonitrile:water (3:1) to give the desired compound which was used without further purification.

Step 10

Preparation of 1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone

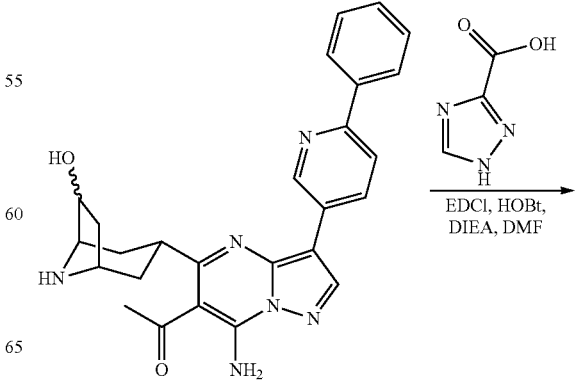

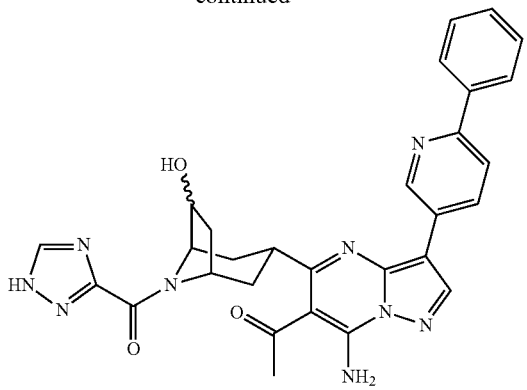

Carboxylic acid (49.2 mg, 0.145 mmol) in DMF (2 mL) was treated with EDCI (138.3 mg, 0.725 mmol) and HOBt (62.44 mg, 0.47 mmol). Then substrate (66.3 mg, 0.145 mmol)) followed by DIEA (0.48) was added. Once the reaction was complete the reaction mixture was treated with water (0.1 mL) and DMSO-MeCN (3:1, 3 mL). Pure compound 1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone was isolated by preparative HPLC.

Example 8-15

Preparation of 1-(5-(7-(1H-1,2,4-triazole-3-carbonyl)-7-azabicyclo[2.2.1]heptan-2-yl)-7-amino-3-(6-phenylpyridin-3-yl)pyrazolo[1,5-a]pyrimidin-6-yl)ethanone

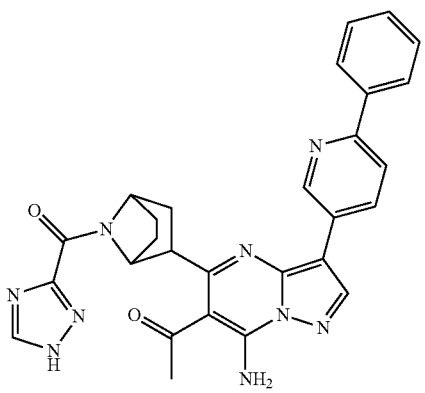 [SMILES: CC(=O)c1c(C2CC3CCC2N3C(=O)c2nc[nH]n2)nc2c(-c3ccc(-c4ccccc4)nc3)cnn2c1N]

Step 1

Preparation of tert-butyl 2-(2-cyanoacetyl)-7-azabicyclo[2.2.1]heptane-7-carboxylate

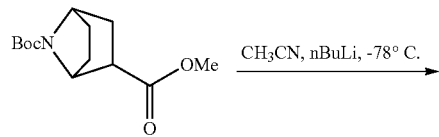

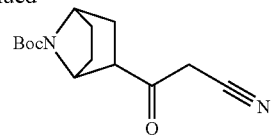

CH$_3$CN (0.40 mL, 7.67 mmol) was added dropwise to a solution of nBuLi (3.06 ml, 7.67 mmol) in THF (30 mL) at −78° C. After stirring for 1 h at −78° C., a solution of ester (892 mg, 3.49 mmol) in THF (10 mL) was added dropwise and the resulting reaction mixture was stirred at −78° C. for 1 h, then slowly warmed to 0° C. before being quenched with saturated NH$_4$Cl (30 mL). THF was removed and the residue was diluted with EtOAc. The organic layer was separated and washed with brine, dried over Na$_2$SO$_4$, and concentrated. The crude product was purified by column chromatography (SiO$_2$, 0-30% EtOAc/Hexanes) to afford the desired product tert-butyl 2-(2-cyanoacetyl)-7-azabicyclo[2.2.1]heptane-7-carboxylate.

Step 2

Preparation of tert-butyl 2-(7-(bis((2-(trimethylsilyl)ethoxy)methyl)amino)pyrazolo[1,5-a]pyrimidin-5-yl)-7-azabicyclo[2.2.9]heptane-7-carboxylate

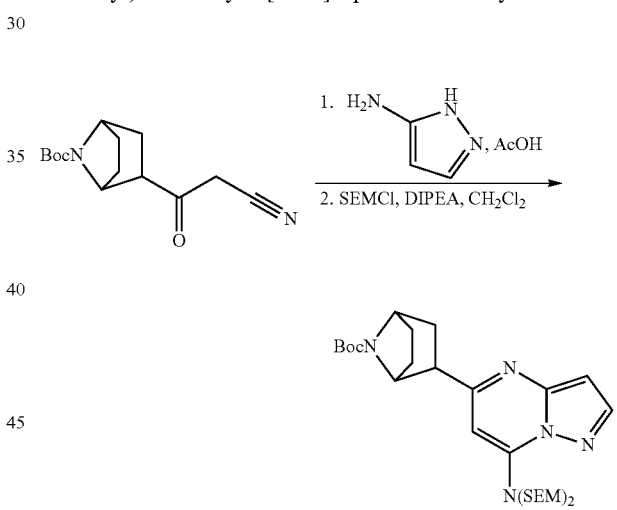

A mixture of 3-aminopyrazole (261 mg, 3.14 mmol) and ketonitrile (756 mg, 2.86 mmol) in HOAc (10 mL) was heated at 100° C. in a sealed tube overnight. After cooling to room temperature, all the volatiles were removed under reduced pressure to afford crude material, which was used without further purification.

To a slurry of above crude material in CH$_2$Cl$_2$ (10 mL) was added SEMCl (2.01 mL, 11.45 mmol), followed by DIPEA (3.98 mL, 22.85 mmol). The resulting reaction mixture was stirred at 45° C. for 1 h. After cooling to rt, all the volatiles were removed under reduced pressure. The residue was diluted with EtOAc, washed with H$_2$O and brine, and concentrated. The crude product was purified by column chromatography (SiO$_2$, 0-15% EtOAc/Hexane) to afford the desired product tert-butyl 2-(7-(bis((2-(trimethylsilyl)ethoxy)methyl)amino)pyrazolo[1,5-a]pyrimidin-5-yl)-7-azabicyclo[2.2.1]heptane-7-carboxylate.

Step 3

Preparation of tert-butyl 2-(7-(bis((2-(trimethylsilyl)ethoxy)methyl)amino)-3-iodopyrazolo[1,5-a]pyrimidin-5-yl)-7-azabicyclo[2.2.1]heptane-7-carboxylate

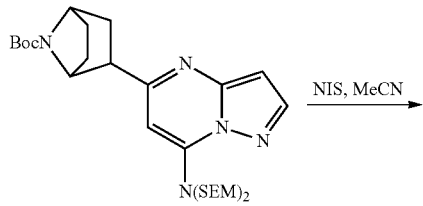

To a solution of substrate (257 mg, 0.43 mmol) in CH₃CN (10 mL) was added NIS (97.66 mg, 0.436 mmol). The resulting solution was stirred at room temperature for 1 h. TLC showed complete consumption of SM. The reaction mixture was evaporated and purified by column chromatography (SiO₂, 0-40% EtOAc/Hexanes) to afford desired product tert-butyl 2-(7-(bis((2-(trimethylsilyl)ethoxy)methyl)amino)-3-iodopyrazolo[1,5-a]pyrimidin-5-yl-7-azabicyclo[2.2.1]heptane-7-carboxylate.

Step 4

Preparation of tert-butyl 2-(7-(bis((2-(trimethylsilyl)ethoxy)methyl)amino)-3-(6-phenylpyridin-3-yl)pyrazolo[1,5-a]pyrimidin-5-yl)-7-azabicyclo[2.2.1]heptane-7-carboxylate

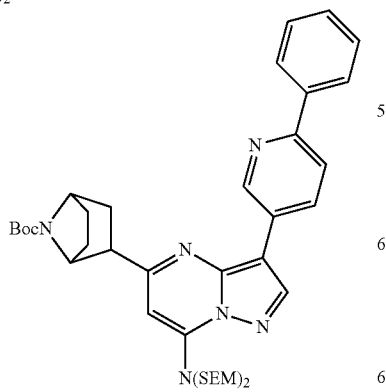

The substrate (241 mg, 0.34 mmol) in dioxane (10 mL) and water (2.5 mL) was treated with boronate (231.8 mg, 0.61 mmol), Pd(dppf)Cl₂.CH₂Cl₂ (34 mg, 0.039 mmol) and K₂CO₃ (145 mg, 0.99 mmol) under argon and heated at 100° C. for 16 h. Upon cooling, the mixture was filtered through Celite and the filtrate was evaporated off under reduced pressure to give crude residue which was purified by column chromatography (SiO₂, 0-40% hexane-EtOAc) to provide the desired product tert-butyl 2-(7-(bis((2-(trimethylsilyl)ethoxy)methyl)amino)-3-(6-phenylpyridin-3-yl)pyrazolo[1,5-a]pyrimidin-5-yl)-7-azabicyclo[2.2.1]heptane-7-carboxylate.

Step 5

Preparation of tert-butyl 2-(7-(bis((2-(trimethylsilyl)ethoxy)methyl)amino)-6-bromo-3-(6-phenylpyridin-3-yl)pyrazolo[1,5-a]pyrimidin-5-yl)-7-azabicyclo[2.2.1]heptane-7-carboxylate

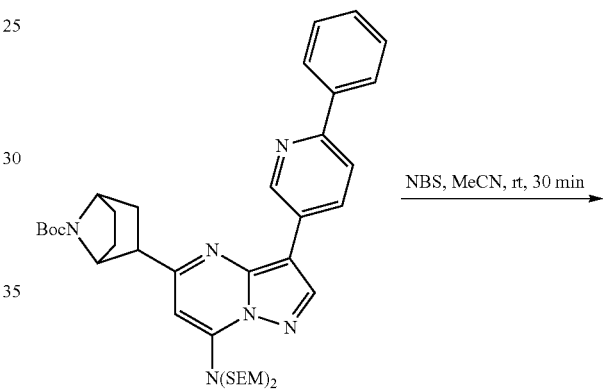

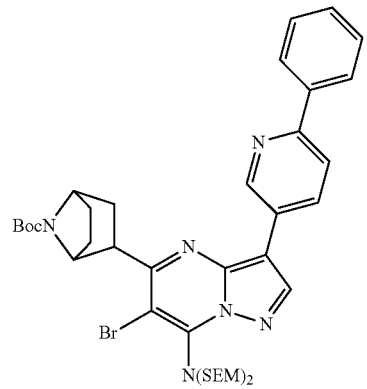

Substrate (286 mg, 0.0.35 mmol) was suspended in acetonitrile (5 mL) and treated with NBS (68.8 mg, 0.38 mmol) at room temperature. The mixture was stirred for 30 min. Then solvent was evaporated off under reduced pressure, and the crude material was purified by column chromatography (SiO₂, 0-40% hexane-EtOAc) to provide the desired compound tert-butyl 2-(7-(bis((2-(trimethylsilyl)ethoxy)methyl)amino)-6-bromo-3-(6-phenylpyridin-3-yl)pyrazolo[1,5-a]pyrimidin-5-yl)-7-azabicyclo[2.2.1]heptane-7-carboxylate.

Step 6

Preparation of tert-butyl 2-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-7-azabicyclo[2.2.1]heptane-7-carboxylate

Step 7

Preparation of 1-(7-amino-5-(7-azabicyclo[2.2.1]heptan-2-yl)-3-(6-phenylpyridin-3-yl)pyrazolo[1,5-a]pyrimidin-6-yl)ethanone

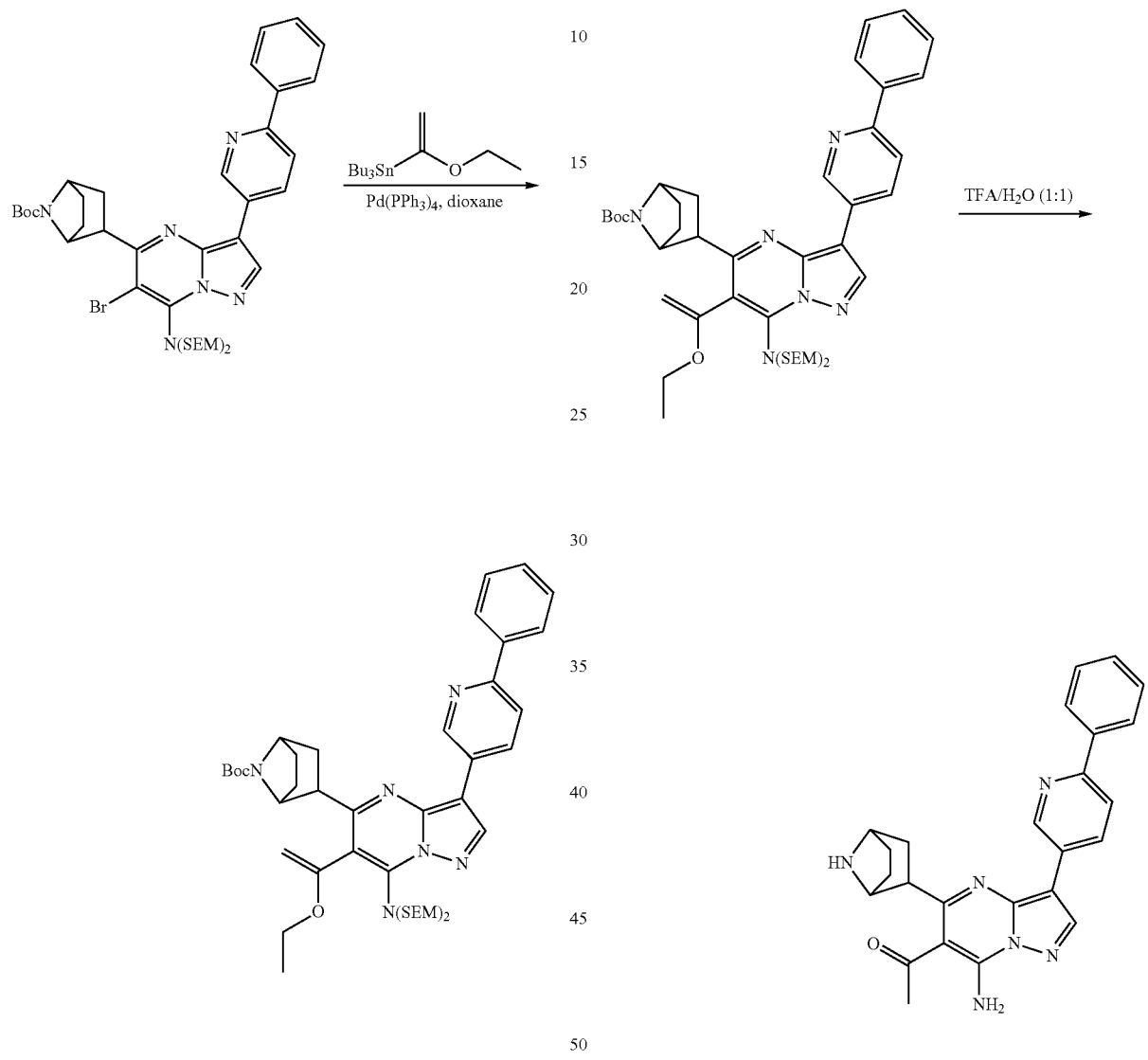

Substrate (212 mg, 0.258 mmol) in dioxane (3 mL) was treated with Pd(PPh₃)₄ (29.8 mg, 0.025 mmol) and tributyl(1-ethoxyvinyl)tin (0.77 mL, 0.26 mmol) under argon and the mixture was heated at 100° C. for 16 h. Upon cooling, the mixture was filtered through a pad of 10% KF—SiO₂ and the filtrate was evaporated off under reduced pressure to give a residue which was purified by column chromatography (SiO₂, 0-40% hexane-EtOAc) to provide the desired compound tert-butyl 2-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-7-azabicyclo[2.2.1]heptane-7-carboxylate.

Substrate (188 mg, 0.23 mmol) was treated with TFA-H₂O (10 mL, 1:1) at room temperature and the mixture was stirred for 16 h. Then the solvent was evaporated off under reduced pressure and the material was lyophilized from acetonitrile:water (3:1) to give the desired compound which was used without further purification.

Step 8

Preparation of 1-(5-(7-(1H-1,2,4-triazole-3-carbonyl)-7-azabicyclo[2.2.1]heptan-2-yl-7-amino-3-(6-phenylpyridin-3-yl)pyrazolo[1,5-a]pyrimidin-6-yl)ethanone

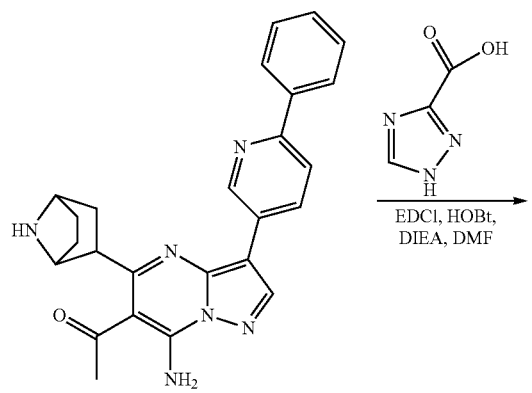

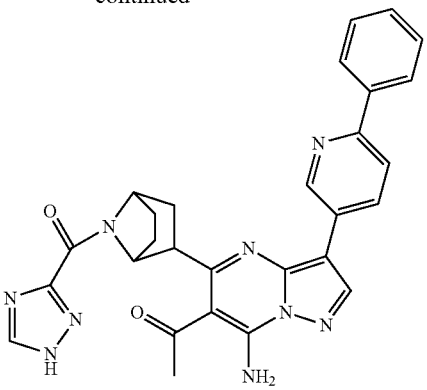

Carboxylic acid (49.78 mg) in DMF (2 mL) was treated with EDCI (129 mg) and HOBt (45.6 mg). Then substrate (97.8 mg) followed by DIEA (0.29) was added. Once the reaction was complete the reaction mixture was treated with water (0.1 mL) and DMSO-MeCN (3:1, 3 mL). Pure compound 1-(5-(7-(1H-1,2,4-triazole-3-carbonyl)-7-azabicyclo[2.2.1]heptan-2-yl)-7-amino-3-(6-phenylpyridin-3-yl)pyrazolo[1,5-a]pyrimidin-6-yl)ethanone was isolated by preparative HPLC. Following these examples, the following compounds were prepared (Table 8-10)

TABLE 8-10

| Compound ID | Structures | Compound Name | M + H (calculate)/ M + H (observed) | pAKT S473 IC50 | p4E-BP1 Thr37/46 IC50 |
|---|---|---|---|---|---|
| 8.29 | 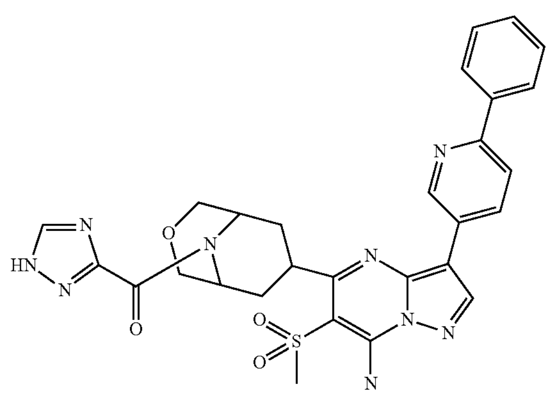 [SMILES: CS(=O)(=O)c1c(C2CC3COCC(C2)N3C(=O)c2nc[nH]n2)nc2c(-c3ccc(-c4ccccc4)nc3)cnn2c1N] | (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone (mixture of stereoisomer) | 586.1/585.2 | A | A |
| 8.30 | 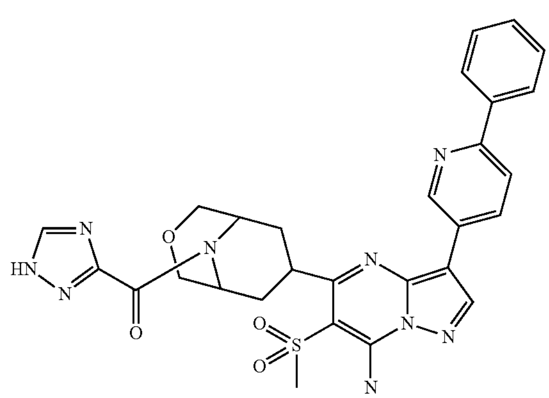 [SMILES: CS(=O)(=O)c1c(C2CC3COCC(C2)N3C(=O)c2nc[nH]n2)nc2c(-c3ccc(-c4ccccc4)nc3)cnn2c1N] | (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone (isomer 1) | 586.1/586.2 | A | A |

TABLE 8-10-continued

| Compound ID | Structures | Compound Name | M + H (calculate)/ M + H (observed) | pAKT S473 IC50 | p4E-BP1 Thr37/46 IC50 |
|---|---|---|---|---|---|
| 8.31 | 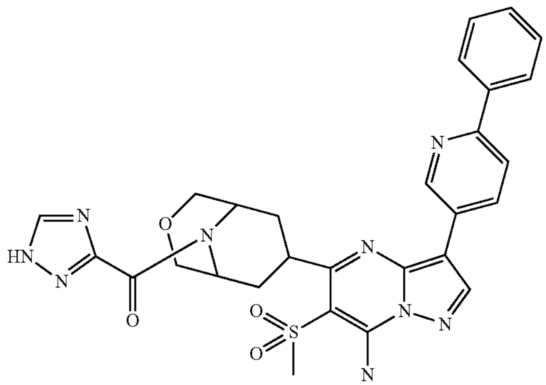 [SMILES: CS(=O)(=O)c1c(C2CC3COCC(C2)N3C(=O)c2nc[nH]n2)nc2c(-c3ccc(-c4ccccc4)nc3)cnn2c1N] | (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone (isomer II) | 586.1/586.2 | B | B |
| 8.32 | 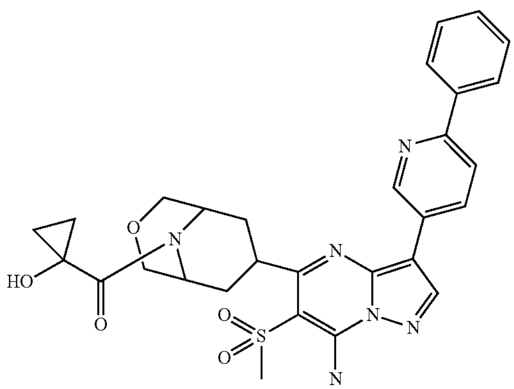 [SMILES: CS(=O)(=O)c1c(C2CC3COCC(C2)N3C(=O)C2(O)CC2)nc2c(-c3ccc(-c4ccccc4)nc3)cnn2c1N] | (7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1-hydroxycyclopropyl)methanone (isomer II) | 575.2/575.2 | A | B |
| 8.33 | 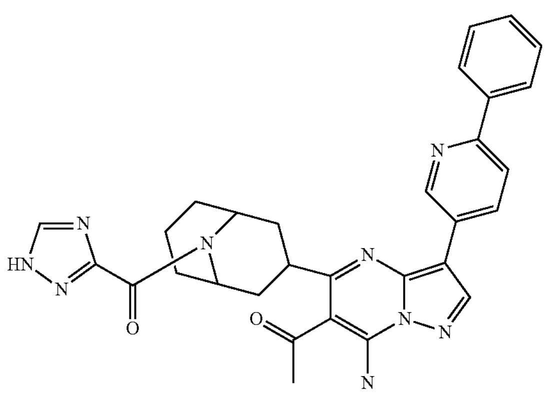 [SMILES: CC(=O)c1c(C2CC3CCCC(C2)N3C(=O)c2nc[nH]n2)nc2c(-c3ccc(-c4ccccc4)nc3)cnn2c1N] | 1-(5-(9-(1H-1,2,4-triazole-3-carbonyl)-9-azabicyclo[3.3.1]nonan-3-yl)-7-amino-3-(6-phenylpyridin-3-yl)pyrazolo[1,5-a]pyrimidin-6-yl)ethanone | 548.2/548.2 | B | B |
| 8.34 | 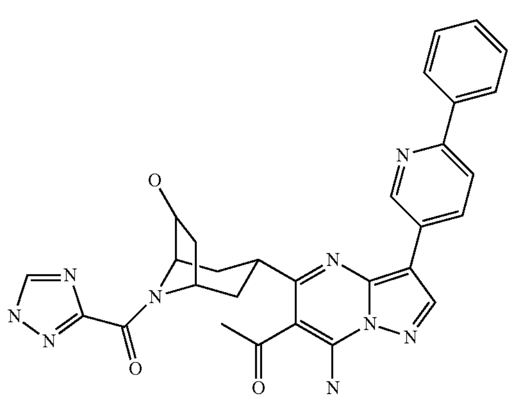 [SMILES: CC(=O)c1c(C2CC3CC(O)C(C2)N3C(=O)c2nc[nH]n2)nc2c(-c3ccc(-c4ccccc4)nc3)cnn2c1N] | 1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone | 550.2/550.2 | A | A |

TABLE 8-10-continued

| Compound ID | Structures | Compound Name | M + H (calculate)/ M + H (observed) | pAKT S473 IC50 | p4E-BP1 Thr37/46 IC50 |
|---|---|---|---|---|---|
| 8.35 | 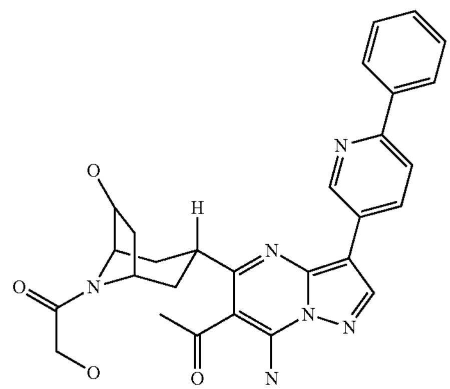 [SMILES: CC(=O)c1c(C2CC3CC(O)C(C2)N3C(=O)CO)nc2c(-c3ccc(-c4ccccc4)nc3)cnn2c1N] | 1-((1S,3R,5R)-3-(6-acetyl-7-amino-3-(6-phenylpyridin-3-yl)pyrazolo[1,5-a]pyrimidin-5-yl)-6-hydroxy-8-azabicyclo[3.2.1]octan-8-yl)-2-hydroxyethanone | 513.2/513.1 | A | A |
| 8.36 | 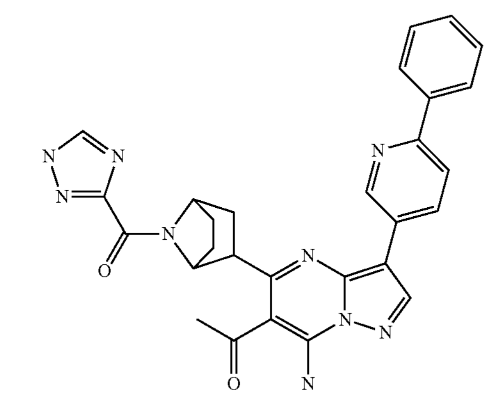 [SMILES: CC(=O)c1c(C2CC3CCC2N3C(=O)c2nc[nH]n2)nc2c(-c3ccc(-c4ccccc4)nc3)cnn2c1N] | 1-(5-(7-(1H-1,2,4-triazole-3-carbonyl)-7-azabicyclo[2.2.1]heptan-2-yl)-7-amino-3-(6-phenylpyridin-3-yl)pyrazolo[1,5-a]pyrimidin-6-yl)ethanone | 520.2/520.2 | ND | ND |
| 8.37 | 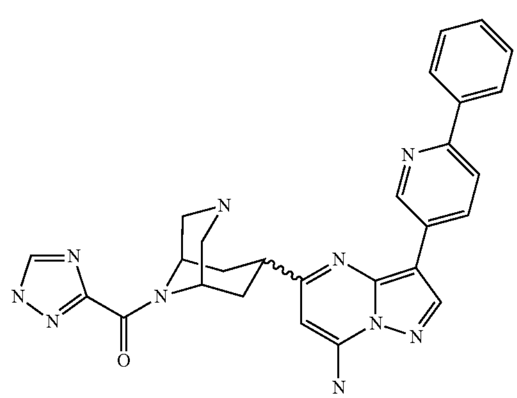 [SMILES: Nc1cc(C2CC3CNCC(C2)N3C(=O)c2nc[nH]n2)nc2c(-c3ccc(-c4ccccc4)nc3)cnn12] | ((1R,3s,5S)-7-(7-amino-3-(6-phenylpyridin-3-yl)pyrazolo[1,5-a]pyrimidin-5-yl)-3,9-diazabicyclo[3.3.1]nonan-9-yl)(1H-1,2,4-triazol-3-yl)methanone | 507.2/507.0 | ND | ND |

TABLE 8-10-continued

| Compound ID | Structures | Compound Name | M + H (calculate)/ M + H (observed) | pAKT S473 IC50 | p4E-BP1 Thr37/46 IC50 |
|---|---|---|---|---|---|
| 8.38 | 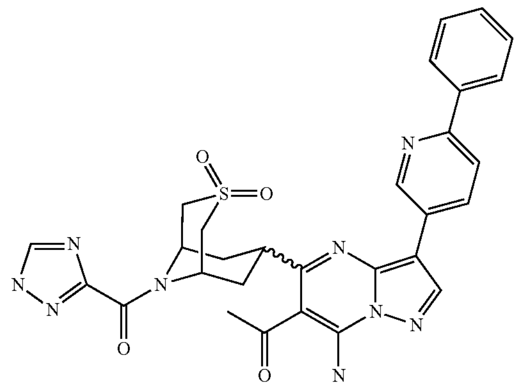 [SMILES: CC(=O)c1c(C2CC3CS(=O)(=O)CC(C2)N3C(=O)c2nc[nH]n2)nc2c(-c3ccc(-c4ccccc4)nc3)cnn2c1N] | endo/exo-7-[6-acetyl-7-amino-3-(6-phenyl-3-pyridinyl)pyrazolo[1,5-a]pyrimidin-5-yl]-9-(4h-1,2,4-triazol-3-ylcarbonyl)-3-thia-9-azabicyclo[3.3.1]nonane, 3,3-dioxide | 598.1/598.2 | B | B |

Example 8-16

Preparation of (1R,3s,5S)-tert-butyl 3-(7-(bis((2-(trimethylsilyl)ethoxy)methyl)amino)-6-(1-hydroxy-cyclopropyl)-3-(6-phenylpyridin-3-yl)pyrazolo[1,5-a]pyrimidin-5-yl-8-azabicyclo[3.2.1]octane-8-carboxylate

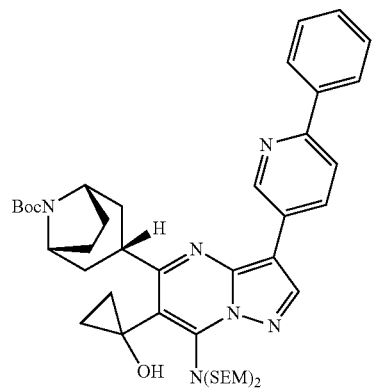

Step A. Synthesis of methyl 7-(bis((2-(trimethylsilyl)ethoxy)methyl)amino)-5-((1R,3s,5S)-8-(tert-butoxycarbonyl)-8-azabicyclo[3.2.1]octan-3-yl)-3-(6-phenylpyridin-3-yl)pyrazolo[1,5-a]pyrimidine-6-carboxylate

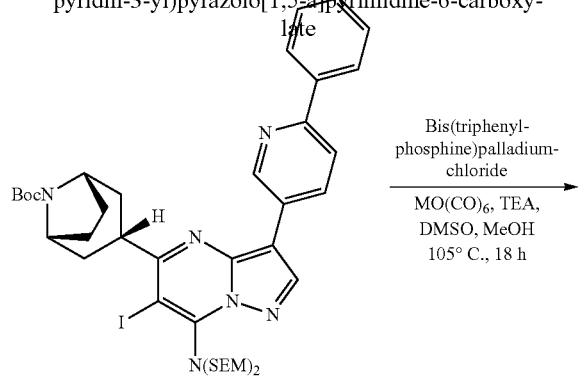

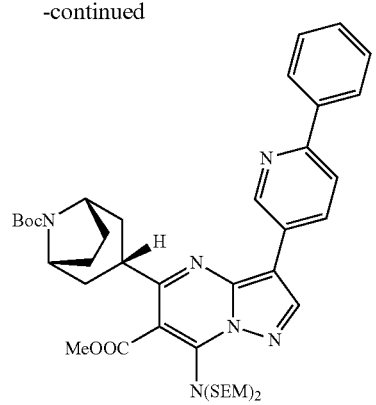

A mixture of (1R,3s,5S)-tert-butyl 3-(7-(bis((2-(trimethylsilyl)ethoxy)methyl)amino)-6-iodo-3-(6-phenylpyridin-3-yl)pyrazolo[1,5-a]pyrimidin-5-yl)-8-azabicyclo[3.2.1]octane-8-carboxylate (0.23 g, 0.3 mmol), bis(triphenylphosphine)palladium chloride (0.04 g, 0.05 mmol), DMSO (0.06 mL), triethylamine (0.08 mL, 0.6 mmol) and molybdenumhexacarbonyl (0.27 g, 1 mmol) in methanol (7 mL) were heated at 105° C. for 18 hour, at which time LC/MS analysis confirmed full consumption of starting material. On cooling, solids were filtered on a celite pad and washed with EtOAc (25 mL). Filtrate was washed with sat. NaHCO₃ (1×5 mL), water (3×5 mL), brine (1×5 mL), and dried over MgSO₄. Gradient column chromatography on silica gel eluting with 0 to 50% EtOAc/hexanes gave the desired methyl 7-(bis((2-(trimethylsilyl)ethoxy)methyl)amino)-5-((1R,3s,5S)-8-(tert-butoxycarbonyl)-8-azabicyclo[3.2.1]octan-3-yl)-3-(6-phenylpyridin-3-yl)pyrazolo[1,5-a]pyrimidine-6-carboxylate (0.1 g).

Step B. Synthesis of (1R,3s,5S)-tert-butyl 3-(7-(bis((2-(trimethylsilyl)ethoxy)methyl)amino)-6-(1-hydroxycyclopropyl)-3-(6-phenylpyridin-3-yl)pyrazolo[1,5-a]pyrimidin-5-yl-8-aza bicyclo[3.2.1]octane-8-carboxylate

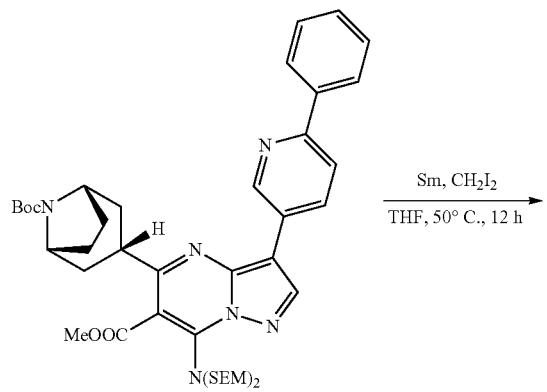

Samarium powder was placed in a 10 mL two necked flask and covered with 2 mL of dry THF. It was then warmed up to 50° C. followed by addition of methyl 7-(bis((2-(trimethylsilyl)ethoxy)methyl)amino)-5-((1R,3s,5S)-8-(tert-butoxycarbonyl)-8-aza bicyclo[3.2.1]octan-3-yl)-3-(6-phenylpyridin-3-yl)pyrazolo[1,5-a]pyrimidine-6-carboxylate (48 mg, 0.06 mmol), diiodomethane (15 L) in THF (1 mL) over a 30 min period. After stirring for 12 hour at 50° C., it was cooled to 0° C. and quenched with sat. NH$_4$Cl (0.5 mL). Stirring continued for 5 minutes before the reaction mixture was transferred to a separatory funnel using DCM (15 mL). Organics were then extracted with DCM (2×15 mL), and washed with brine (1×20 mL), and dried over MgSO$_4$. Solvent was removed in vacuo and the crude product (1R,3s,5S)-tert-butyl 3-(7-(bis((2-(trimethyl silyl)ethoxy)methyl)amino)-6-(1-hydroxycyclopropyl)-3-(6-phenylpyridin-3-yl)pyrazolo[1,5-a]pyrimidin-5-yl)-8-azabicyclo[3.2.1]octane-8-carboxylate was used for the next step without any further purification.

Procedures similar to those described for the preparation of ((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone, the following compound listed in Table 8-11 was prepared:

TABLE 8-11

| 8.39 | | ((1R,3s,5S)-3-(7-amino-6-(1-hydroxycyclopropyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone | 548.2/547.9 | C | C |
|---|---|---|---|---|---|

Example 8-17

Preparation of 7-amino-5-((1R,3s,5S)-8-azabicyclo[3.2.1]octan-3-yl)-3-(6-phenyl pyridin-3-yl)pyrazolo[1,5-a]pyrimidine-6-carboxamide

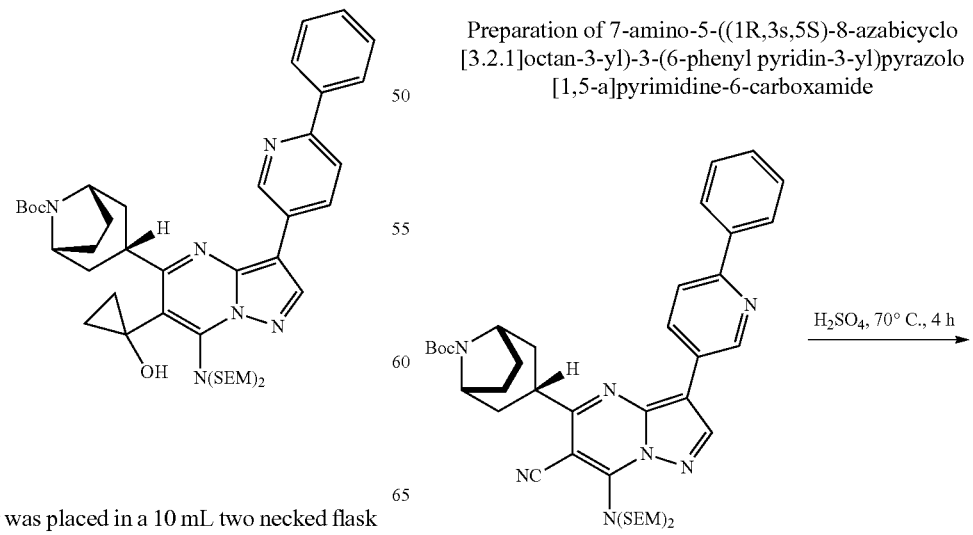

751
-continued

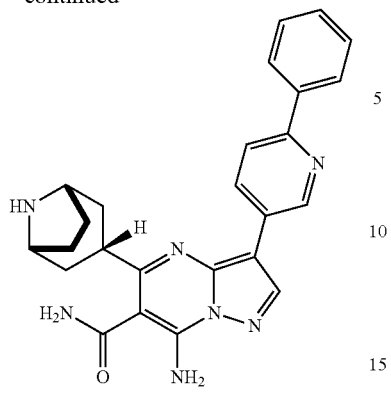

(1R,5S)-tert-butyl 3-(7-(bis((2-(trimethylsilyl)ethoxy)methyl)amino)-6-cyano-3-(6-phenylpyridin-3-yl)pyrazolo[1,5-a]pyrimidin-5-yl)-8-azabicyclo[3.2.1]octane-8-carboxylate (0.27 g, 0.35 mmol) in $H_2SO_4$ (3 mL) was heated at 70° C. for four hours, at which time LC/MS analysis confirmed full consumption of starting material. On cooling to 0° C. in a icebath, 7N $NH_3$ in MeOH (15 mL) was added slowly to neutralize the reaction mixture. Solids were filtered off and washed with additional DCM (200 mL). Solvent was removed from the filtrate in vacuo and the pure compound 7-amino-5-((1R,3s,5S)-8-azabicyclo[3.2.1]octan-3-yl)-3-(6-phenyl pyridin-3-yl)pyrazolo[1,5-a]pyrimidine-6-carboxamide was isolated by preparative HPLC.

Procedure similar to that described for the preparation of ((1R,3s,5S)-3-(7-amino-6-bromo-3-(6-(2-hydroxypropan-2-yl)pyridin-3-yl)pyrazolo[1,5-a]pyrimidin-5-yl)-8-azabicyclo[3.2.1]octan-8-yl)(1H-1,2,4-triazol-3-yl)methanone, the following compound listed in Table 8-12 was prepared:

752
Example 8-18

Preparation of ((1R,3s,5S)-3-(7-(methylamino)-6-(methylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

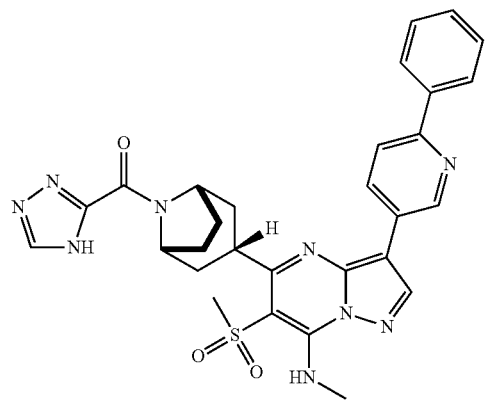

Step 1

Synthesis of (1R,3s,5S)-tert-butyl 3-(7-amino-6-(methylsulfonyl)-3-(6-phenylpyridin-3-yl)pyrazolo[1,5-a]pyrimidin-5-yl)-8-azabicyclo[3.2.1]octane-8-carboxylate

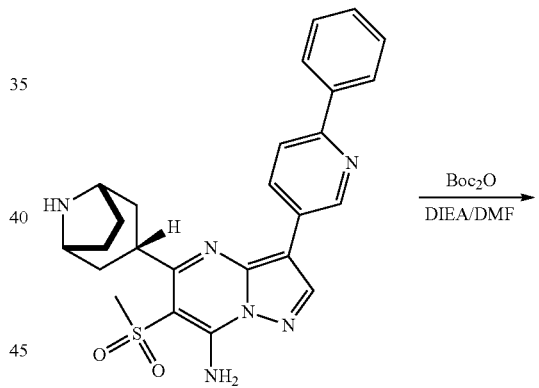

TABLE 8-12

| 8.40 | | 5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carboxamide | 535.2/534.9 | A | A |

753

-continued

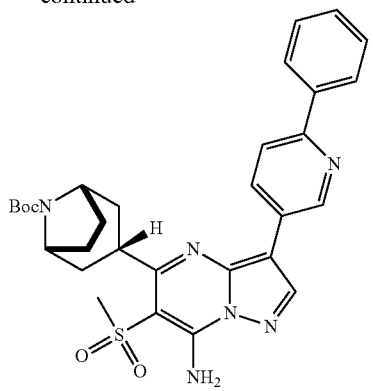

To a solution of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine TFA salt (434 mg, 0.62 mmol) in DMF (2 mL) was added DIEA (261 uL, 1.47 mmol) was added Boc$_2$O (140 mg, 0.64 mmol), and the resulting solution was stirred for 10 minutes. EtOAc (20 mL) was added, and resulting solution was washed with water (3×), brine and dried (MgSO$_4$). After evaporation, a crude product (340 mg) was obtained and used in the next step without further purification.

Step 2

Synthesis of (1R,3s,5S)-tert-butyl 3-(7-(methylamino)-6-(methylsulfonyl)-3-(6-phenylpyridin-3-yl)pyrazolo[1,5-a]pyrimidin-5-yl)-8-azabicyclo[3.2.1]octane-8-carboxylate

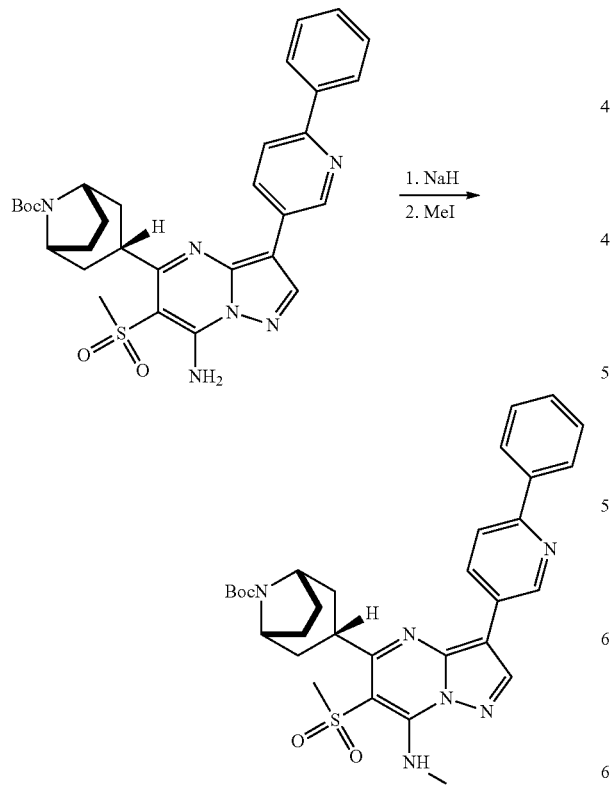

754

To a solution of (1R,3s,5S)-tert-butyl 3-(7-amino-6-(methylsulfonyl)-3-(6-phenylpyridin-3-yl)pyrazolo[1,5-a]pyrimidin-5-yl)-8-azabicyclo[3.2.1]octane-8-carboxylate (215 mg, 0.37 mmol) in DMF (2 mL) was added NaH (60%, 19 mg, 0.48 mmol). After stirring 20 minutes, MeI (30 μL, 0.48 mmol) was added. The resulting solution was stirred for 2 hours, diluted with EtOAc (20 mL), washed with water (3×), brine and dried (MgSO$_4$). After concentration, the residue was purified by gradient column chromatography on silica gel. Eluting with 0 to 50% EtOAc/hexanes gave a relatively pure product (100 mg).

Step 3

Synthesis ((1R,3s,5S)-3-(7-(methylamino)-6-(methylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone

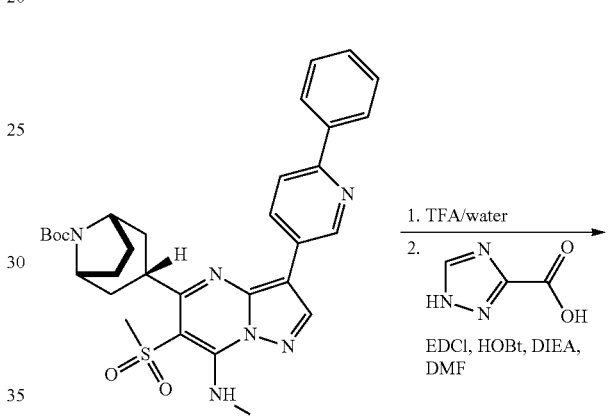

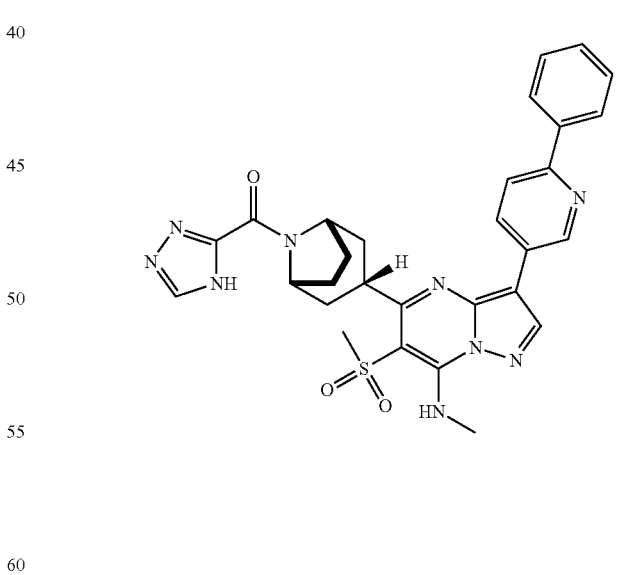

The synthesis of the title compound from (1R,3s,5S)-tert-butyl 3-(7-(methylamino)-6-(methylsulfonyl)-3-(6-phenylpyridin-3-yl)pyrazolo[1,5-a]pyrimidin-5-yl)-8-azabicyclo[3.2.1]octane-8-carboxylate using TFA to remove Boc group and amide coupling was achieved by similar procedures described in previous examples.

TABLE 8-13
| 8.41 | 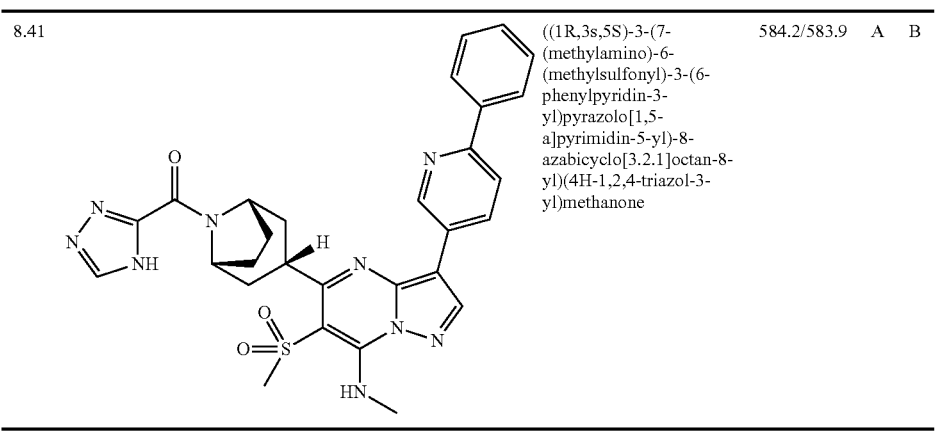 | ((1R,3s,5S)-3-(7-(methylamino)-6-(methylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone | 584.2/583.9 | A | B |
Example 8-19
Preparation of ((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone
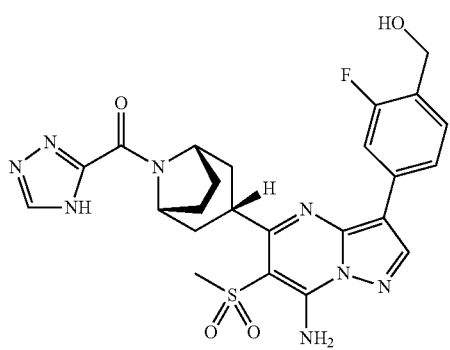
Scheme 8-3
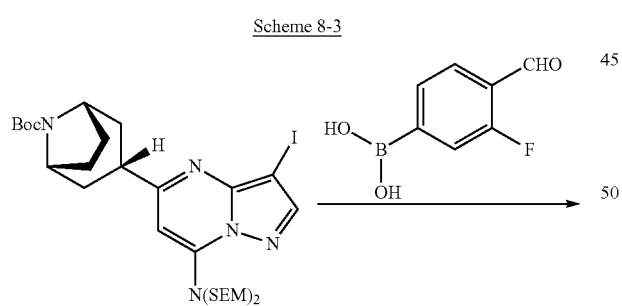
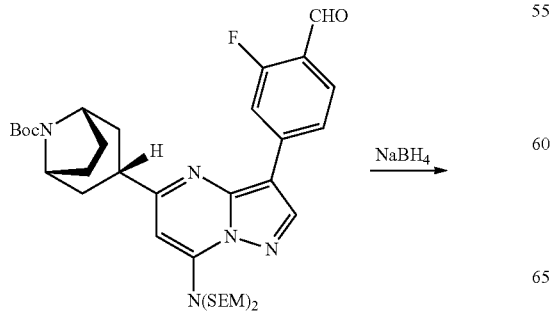
-continued
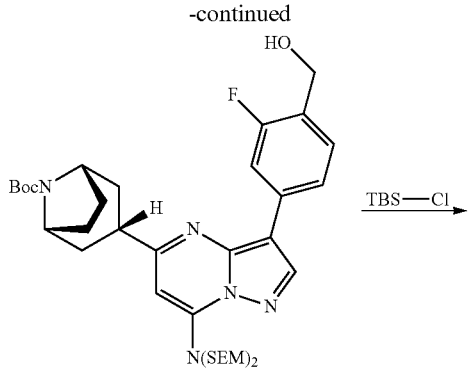
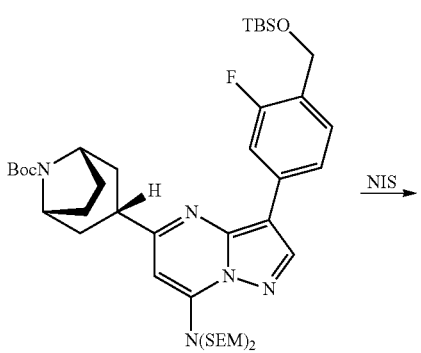
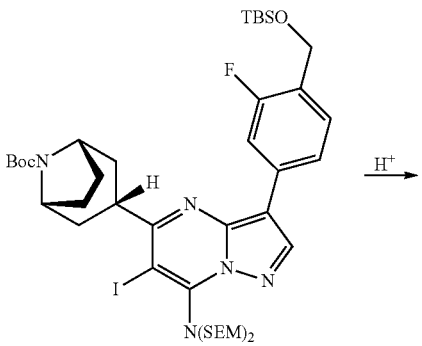

757
-continued

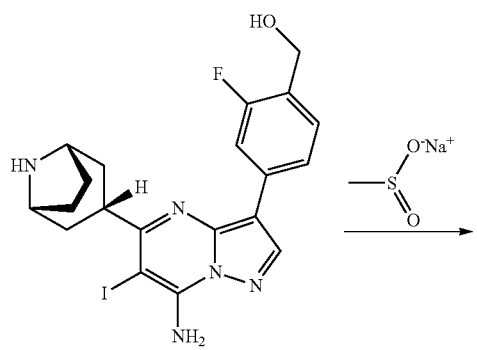

758
-continued

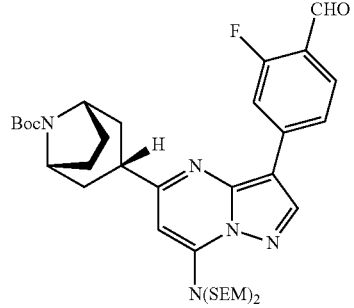

(1R,3s,5S)-tert-butyl 3-(7-(bis((2-(trimethylsilyl)ethoxy)methyl)amino)-3-(3-fluoro-4-formylphenyl)pyrazolo[1,5-a]pyrimidin-5-yl)-8-azabicyclo[3.2.1]octane-8-carboxylate was prepared using the protocol described previously. HPLC-MS tR=2.11 min (UV254 nm); mass calculated for formula C37H56FN5O5Si2 725.38, observed LCMS m/z 726.3 (M+H).

Step B—Synthesis of (1R,3s,5S)-tert-butyl 3-(7-(bis ((2-(trimethylsilyl)ethoxy)methyl)amino)-3-(3-fluoro-4-(hydroxymethyl)phenyl)pyrazolo[1,5-a]pyrimidin-5-yl)-8-azabicyclo[3.2.1]octane-8-carboxylate

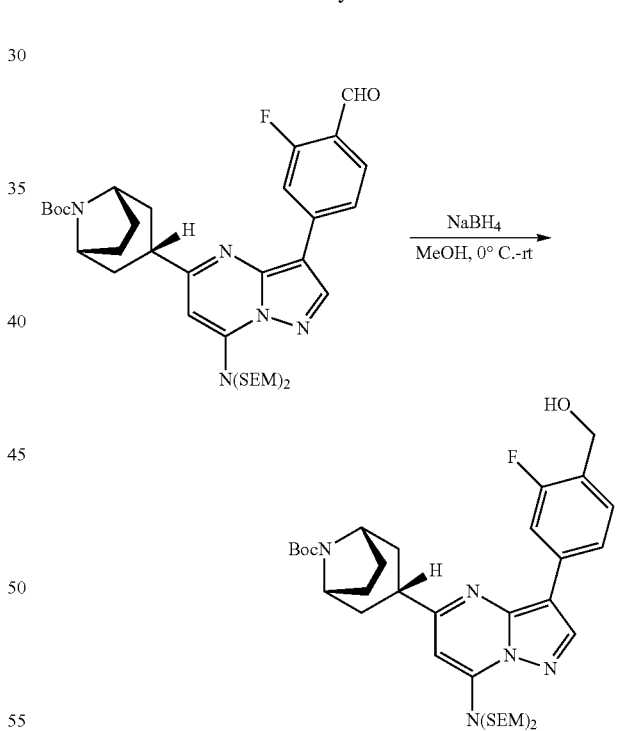

Step A—Synthesis of (1R,3s,5S)-tert-butyl 3-(7-(bis ((2-(trimethylsilyl)ethoxy)methyl)amino)-3-(3-fluoro-4-formylphenyl)pyrazolo[1,5-a]pyrimidin-5-yl)-8-azabicyclo[3.2.1]octane-8-carboxylate

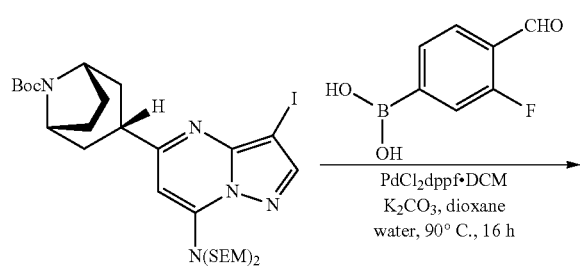

To an ice-cooled solution of (1R,3s,5S)-tert-butyl 3-(7-(bis ((2-(trimethylsilyl)ethoxy)methyl)amino)-3-(3-fluoro-4-formylphenyl)pyrazolo[1,5-a]pyrimidin-5-yl)-8-azabicyclo [3.2.1]octane-8-carboxylate (400 mg, 0.55 mmol) in MeOH (5.5 mL) and THF (5.5 mL) was added sodium borohydride (84 mg, 2.2 mmol). The reaction mixture was warmed to it over 1 h until LC/MS analysis confirmed the reaction was complete. DCM (10 mL) was added and the reaction mixture quenched with the addition of 1N HCl. Extraction into DCM, drying over MgSO4 and concentration afforded crude product. HPLC-MS tR=1.76 min (UV254 nm); mass calculated for formula C37H58FN5O5Si2 727.40, observed LCMS m/z 728.0 (M+H).

Step C—Synthesis of (1R,3s,5S)-tert-butyl 3-(7-(bis((2-(trimethylsilyl)ethoxy)methyl)amino)-3-(4-((tert-butyldimethylsilyloxy)methyl)-3-fluorophenyl)pyrazolo[1,5-a]pyrimidin-5-yl)-8-azabicyclo[3.2.1]octane-8-carboxylate

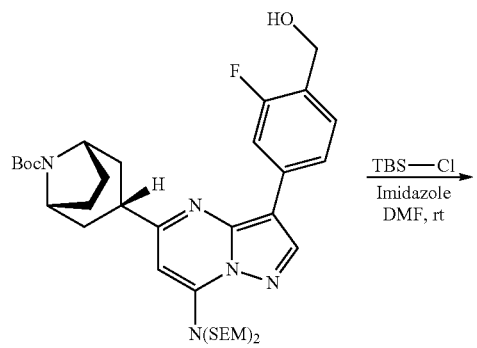

To a mixture of (1R,3s,5S)-tert-butyl 3-(7-(bis((2-(trimethylsilyl)ethoxy)methyl)amino)-3-(3-fluoro-4-(hydroxymethyl)phenyl)pyrazolo[1,5-a]pyrimidin-5-yl)-8-azabicyclo[3.2.1]octane-8-carboxylate (0.55 mmol) and imidazole (75 mg, 1.1 mmol) in DMF (5.5 mL) was added tert-butyldimethylchlorosilane (100 mg, 0.66 mmol). The reaction mixture was stirred at it for 16 h until LC/MS analysis confirmed the reaction was complete. The volatiles were removed in vacuo, the resulting residue redissolved in EtOAc (10 mL) and washed with saturated NaHCO$_3$ (2×20 mL). Drying over MgSO$_4$ and purification by column chromatography on silica gel, gradient EtOAc/Hexanes (0-50%), yielded the title product as a white solid (320 mg, 69%). HPLC-MS tR=2.2 min (UV254 nm); mass calculated for formula C43H72FN5O5Si3 841.48, observed LCMS m/z 742.0 (M+H).

Step C—Synthesis of (1R,3s,5S)-tert-butyl 3-(7-(bis((2-(trimethylsilyl)ethoxy)methyl)amino)-3-(4-((tert-butyldimethylsilyloxy)methyl)-3-fluorophenyl)-6-iodopyrazolo[1,5-a]pyrimidin-5-yl)-8-azabicyclo[3.2.1]octane-8-carboxylate

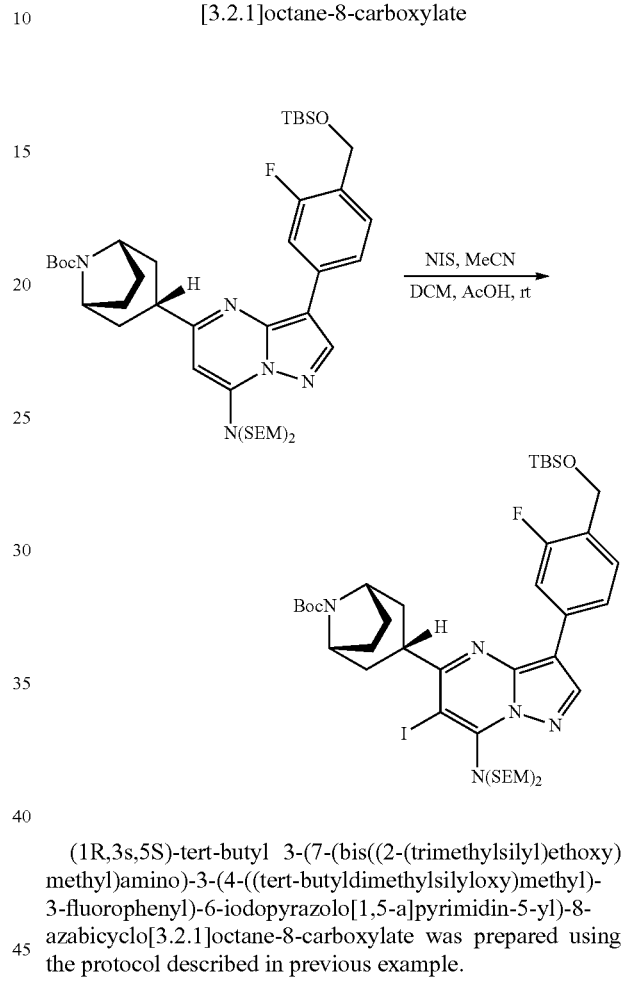

(1R,3s,5S)-tert-butyl 3-(7-(bis((2-(trimethylsilyl)ethoxy)methyl)amino)-3-(4-((tert-butyldimethylsilyloxy)methyl)-3-fluorophenyl)-6-iodopyrazolo[1,5-a]pyrimidin-5-yl)-8-azabicyclo[3.2.1]octane-8-carboxylate was prepared using the protocol described in previous example.

Step D—Synthesis of (4-(7-amino-5-((1R,3s,5S)-8-azabicyclo[3.2.1]octan-3-yl-6-iodopyrazolo[1,5-a]pyrimidin-3-yl)-2-fluorophenyl)methanol

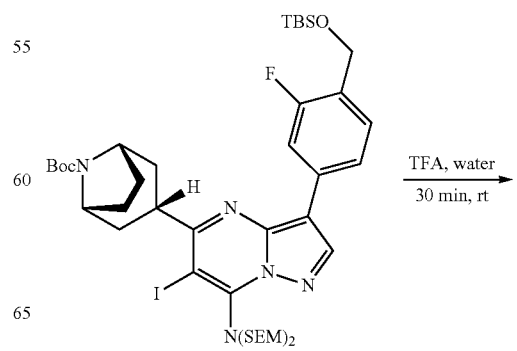

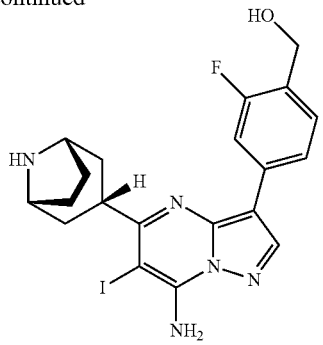

(4-(7-amino-5-((1R,3s,5S)-8-azabicyclo[3.2.1]octan-3-yl)-6-iodopyrazolo[1,5-a]pyrimidin-3-yl)-2-fluorophenyl)methanol was prepared using the protocol described in Scheme 5, Step B. HPLC-MS tR=0.86 min (UV254 nm); mass calculated for formula C20H21FIN5O 493.08, observed LCMS m/z 494.0 (M+H).

Step E—Synthesis of (4-(7-amino-5-((1R,3s,5S)-8-azabicyclo[3.2.1]octan-3-yl-6-(methylsulfonyl)pyrazolo[1,5-a]pyrimidin-3-yl)-2-fluorophenyl)methanol

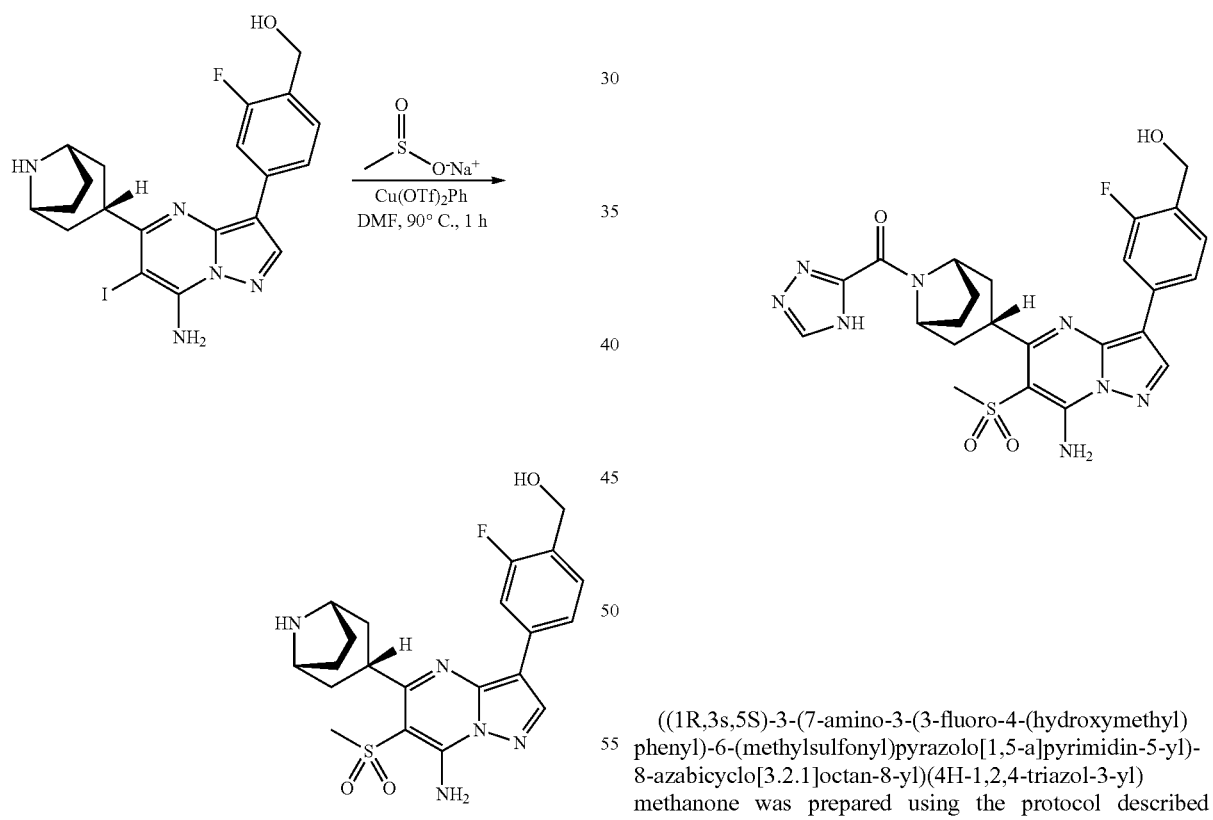

(4-(7-amino-5-((1R,3s,5S)-8-azabicyclo[3.2.1]octan-3-yl)-6-(methylsulfonyl)pyrazolo[1,5-a]pyrimidin-3-yl)-2-fluorophenyl)methanol was prepared using the protocol described previously. HPLC-MS tR=0.62 min (UV254 nm); mass calculated for formula C21H23FN6O3S 458.158, observed LCMS m/z 459.0 (M+H).

Step F—Synthesis of ((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone

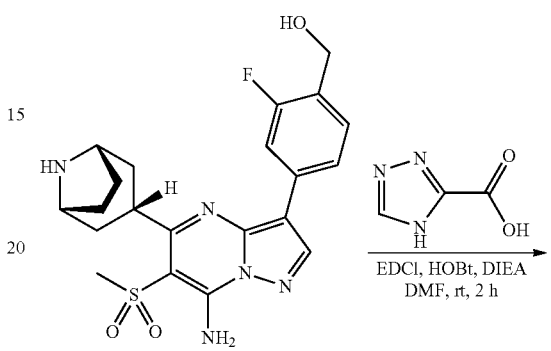

((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone was prepared using the protocol described previously. HPLC-MS tR=0.96 min (UV254 nm); mass calculated for formula C23H26FN5O5S 503.16, observed LCMS m/z 504.1 (M+H).

Following Scheme 8 and procedures similar to those described above for the preparation of ((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone the following compounds listed in Table 8-14 were prepared:

TABLE 8-14

| 8.42 | 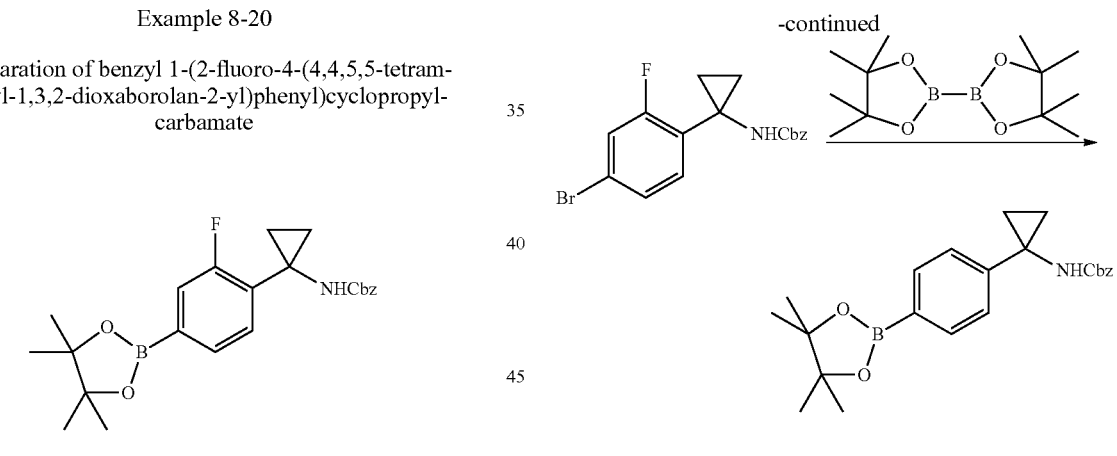 | ((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone | 541.17/541.3 | A | A |
|---|---|---|---|---|---|
| 8.43 | | 1-((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)-2-hydroxyethanone | 504.16/504.3 | B | B |

Example 8-20

Preparation of benzyl 1-(2-fluoro-4-(4,4,5,5-tetramethyl-1,3,2-dioxaborolan-2-yl)phenyl)cyclopropylcarbamate

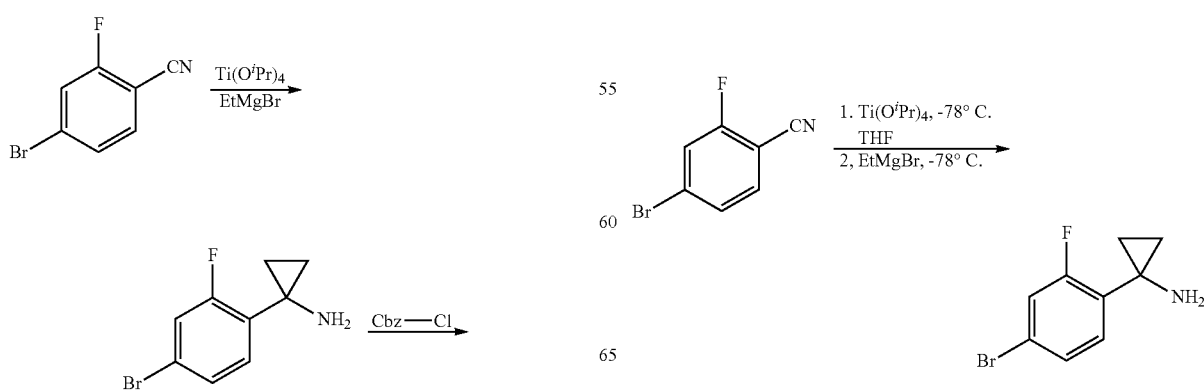

Step A—Synthesis of 1-(4-bromo-2-fluorophenyl)cyclopropanamine

To a cooled solution of 4-bromo-2-fluorobenzonitrile (432 mg, 2.16 mmol) in THF (10 mL) at −78° C., was added titanium (IV) isopropoxide (0.7 mL, 2.4 mmol). After stirring for 10 minutes, ethylmagnesium bromide (1M, 4.75 mL, 4.75 mmol) was added and the reaction mixture warmed to 0° C. and then to rt. $BF_3 \cdot OEt$ (0.53 mL, 4.32 mmol) was then added and the reaction mixture stirred for an additional 1 h at rt. The reaction was quenched with saturated $NH_4Cl$ and NaOH (1N). Extraction with EtOAc, and drying over $MgSO_4$ yielded crude product which was taken forward as crude in the next step. HPLC-MS tR=0.34 min (UV254 nm); mass calculated for formula C9H9BrFN 228.99, observed LCMS m/z 230.0 (M+H).

Step B—Synthesis of benzyl 1-(4-bromo-2-fluorophenyl)cyclopropylcarbamate

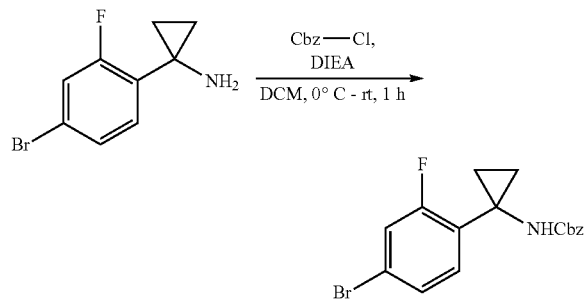

To a cooled solution of 1-(4-bromo-2-fluorophenyl)cyclopropanamine (2.16 mmol) in DCM (10 mL) at 0° C., was added DIEA (0.75 mL, 4.32 mmol) and benzyl chloroformate (0.37 mL, 2.59 mmol). The reaction mixture was warmed to it and stirred for 1 h until LC/MS analysis indicated the reaction was complete. The reaction was quenched with HCl (1N) and extracted with DCM. Drying over $MgSO_4$, yielded crude product which was purified by flash chromatography (gradient EtOAc/Hexanes (0-50%). HPLC-MS tR=1.31 min (UV254 nm); mass calculated for formula C17H15BrFNO2 363.02, observed LCMS m/z 363.9 (M+H)

Step C—Synthesis of benzyl benzyl 1-(2-fluoro-4-(4,4,5,5-tetramethyl-1,3,2-dioxaborolan-2-yl)phenyl)cyclopropylcarbamate

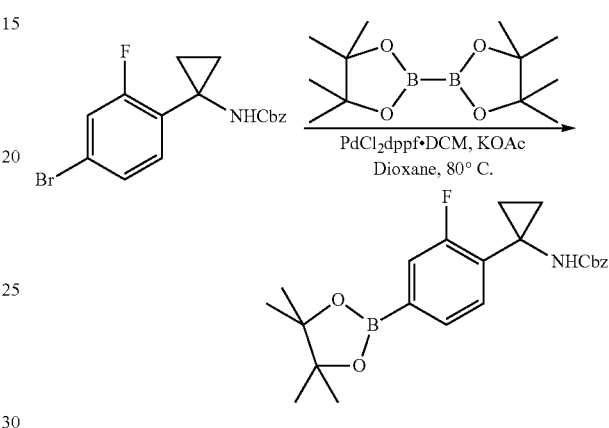

benzyl benzyl 1-(2-fluoro-4-(4,4,5,5-tetramethyl-1,3,2-dioxaborolan-2-yl)phenyl)cyclopropylcarbamate was prepared using the protocol described previously.

Following procedures similar to those described above, the following compounds listed in Table 8-15 were prepared:

TABLE 8-15

| 8.44 | ((1R,3s,5S)-3-(7-amino-3-(4-(1-aminocyclopropyl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone | 566.20/566.3 | C | C |
| 8.45 | ((1R,3s,5S)-3-(7-amino-3-(4-(2-aminopropan-2-yl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone | 568.22/568.3 | NA | NA |

Example 8-21

Preparation of (E)-4-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carbonyl)-N'-(3-(dimethylamino)propyl)-N-ethyl-2H-1,2,3-triazole-2-carboximidamide

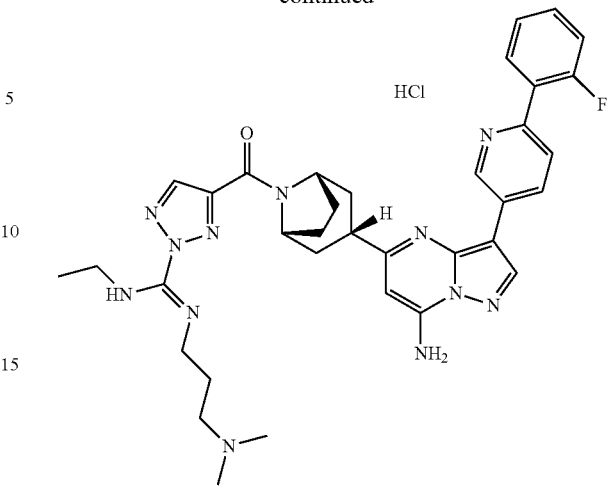

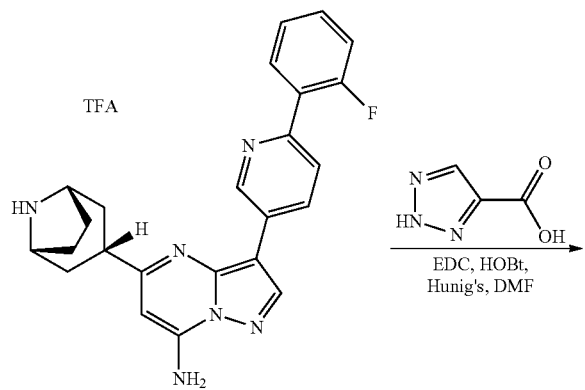

5-[(3-exo)-8-azabicyclo[3.2.1]oct-3-yl]-3-[6-(2-fluorophenyl)pyridin-3-yl]-6-(methylsulfonyl)pyrazolo[1,5-a]pyrimidin-7-amine (50.0 mg, 0.102 mmol) was slurried in dry N,N-Dimethylformamide (3.9 mL, 50 mmol). 1,2,3-triazole-4-carboxylic acid (14.9 mg, 0.132 mmol), [C]N-(3-Dimethylaminopropyl)-N'-ethylcarbodiimide hydrochloride (48.6 mg, 0.254 mmol), 1-Hydroxybenzotriazole hydrate (35.0 mg, 0.228 mmol), and N,N-Diisopropylethylamine (88.4 uL, 0.508 mmol) were then added sequentially. The brown mixture was stirred under an atmosphere of Nitrogen. After 16 hours, the mixture was partitioned between ethyl acetate and saturated aqueous sodium bicarbonate. The aqueous layer was re-extracted with EtOAc and the organic layers were washed with aqueous sodium bicarbonate and brine, dried with sodium sulfate, filtered, and rotoevaporated. The residue was purified via Prep HPLC to provide 10 mg of TFA salt. The TFA salt was then dissolved in methanol and 5 ml of 0.1M HCl was added and the solvent removed on the rotovap. this procedure was repeated 3× to provide the HCl salt (10 mg) as a yellow solid (Table 8-16).

TABLE 8-16

| Compound ID | Structures | Compound Name | M + H (calculated)/ M + H (observed) | pAKT S473 IC50 | p4E-BP1 Thr37/46 IC50 |
|---|---|---|---|---|---|
| 8.46 | 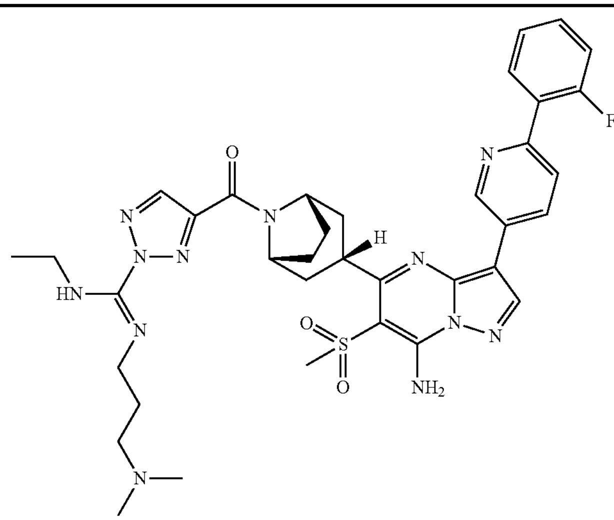 | (E)-4-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carbonyl)-N'-(3-(dimethylamino)propyl)-N-ethyl-2H-1,2,3-triazole-2-carboximidamide | 743.34/742.93 | A | B |

Example 8-22

Preparation of 1-(5-((1R,3s,5S)-8-(4H-1,2,4-triazole-3-carbonyl)-8-azabicyclo[3.2.1]octan-3-yl)-7-amino-3-(6-(cyclopropylamino)pyridin-3-yl)pyrazolo[1,5-a]pyrimidin-6-yl)ethanone

Step 1: Preparation of 5-Bromo-pyridin-2-yl-cyclopropylamine

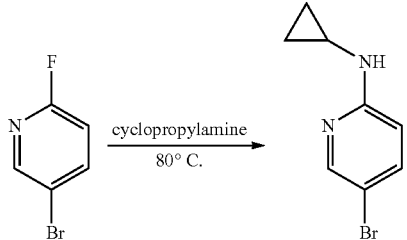 [SMILES: Fc1ccc(Br)cn1 ; Brc1ccc(NC2CC2)nc1]

To a sealed tube was added 5-bromo-2-fluoropyridine (1.25 g, 7.10 mmol) and cyclopropylamine (5.0 mL, 72 mmol). Upon heating at 80° C. for 48 hours the reaction was complete. The contents of the tube were transferred to a round bottom flask and concentrated in vacuo. The remaining residue was dissolved in dichloromethane and washed twice with saturated sodium bicarbonate and twice with brine. The organics were dried over sodium sulfate, filtered and concentrated in vacuo to afford the title compound (1.13 g, 75%) as a tan solid.

Step 2: Preparation of tert-butyl (5-bromopyridin-2-yl)cyclopropylcarbamate

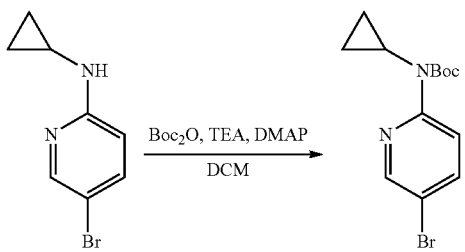 [SMILES: Brc1ccc(NC2CC2)nc1 ; CC(C)(C)OC(=O)N(c1ccc(Br)cn1)C1CC1]

5-Bromo-pyridin-2-yl-cyclopropylamine (3.91 g, 16.5 mmol) was suspended in triethylamine (15.0 mL, 110 mmol). Di-tert-butyldicarbonate (10.8 g, 49.6 mmol) was then added followed by 4-dimethylaminopyridine (252 mg, 2.1 mmol). Upon heating at 70° C. for 2.5 hours the reaction was complete. The contents of the flask were concentrated in vacuo and the remaining residue partitioned between dichloromethane and saturated sodium bicarbonate. The dichloromethane layer was washed twice more with saturated sodium bicarbonate and twice with brine before drying the organics over magnesium sulfate, filtering and concentrating in vacuo. This residue was purified by flash chromatography (120 g of silica gel) using 0-20% ethyl acetate in hexanes to afford the title compound (4.97 g,) as a colorless oil.

Step 3: Preparation of ((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone

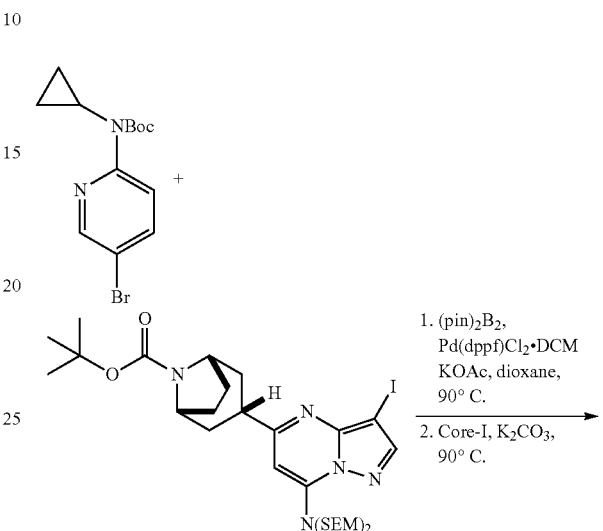

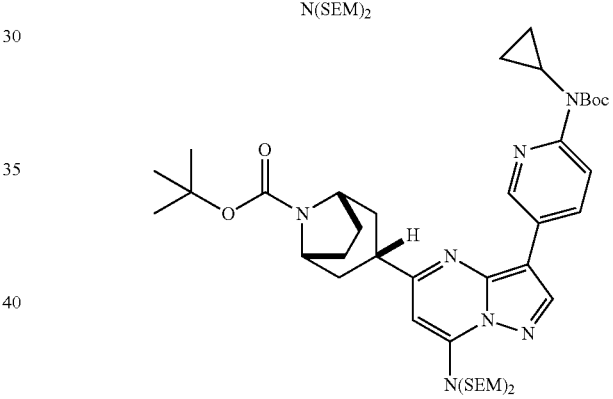

To a mixture of potassium acetate (868 mg, 8.85 mmol), Bis(pinacolato)diboron (876 mg, 3.45 mmol) and [1,1'-Bis(diphenylphosphino)ferrocene]dichloropalladium(II) (105 mg, 0.14 mmol) under an atmosphere of nitrogen was added (5-Bromo-pyridin-2-yl)-cyclopropyl-carbamic acid tert-butyl ester (1.00 g, 3.19 mmol) as a solution in dioxane (20 mL). The flask was evacuated and charged with nitrogen three times and then lowered into a bath at 90° C. Upon stirring for 3 hours the starting material was consumed (by LC-MS) so the flask was removed from the oil bath and allowed to cool to room temperature. Upon cooling to room temperature (1R,3s,5S)-tert-butyl 3-(7-(bis((2-(trimethylsilyl)ethoxy)-methyl)amino)-3-iodopyrazolo[1,5-a]pyrimidin-5-yl)-8-azabicyclo[3.2.1]octane-8-carboxylate (1.11 g, 1.52 mmol) was added as a solution in dioxane (10 mL) to the reaction mixture along with 2.1 mL (4.14 mmol) of a 2.0M solution of sodium carbonate and [1,1'-Bis(diphenylphosphino)ferrocene]-dichloropalladium(II) (70 mg, 0.09 mmol). The flask was evacuated and charged with nitrogen three times and then lowered back into the bath at 90° C. Upon stirring overnight the starting iodide had been consumed. The reaction mixture was cooled to room temperature and the crude mixture was Step 4: Preparation of (1R,3s,5S)-tert-butyl 3-(7-(bis((2-(trimethylsilyl)ethoxy)-methyl)amino)-6-bromo-3-(6-((tert-butoxycarbonyl)(cyclopropyl)amino)-pyridin-3-yl)pyrazolo[1,5-a]pyrimidin-5-yl)-8-azabicyclo[3.2.1]octane-8-carboxylate

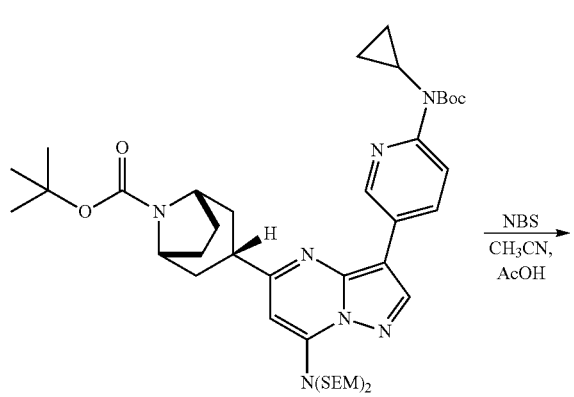

Step 5: Preparation of (1R,3s,5S)-tert-butyl 3-(7-(bis((2-(trimethylsilyl)ethoxy)-methyl)amino)-3-(6-((tert-butoxycarbonyl)(cyclopropyl)amino)pyridin-3-yl)-6-(1-ethoxyvinyl)pyrazolo[1,5-a]pyrimidin-5-yl)-8-azabicyclo[3.2.1]octane-8-carboxylate

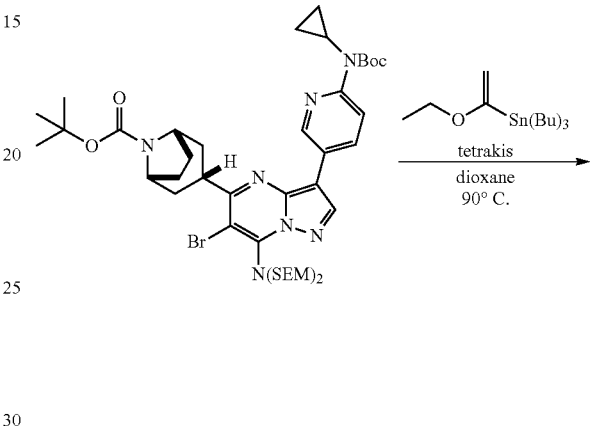

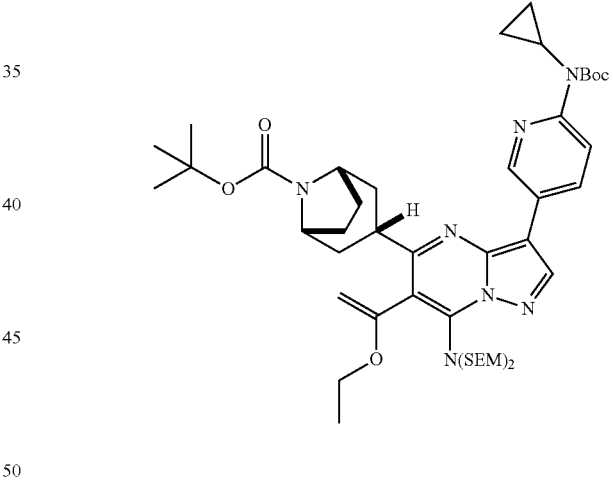

To a round bottom flask containing ((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo-[3.2.1]octan-8-yl)(2H-1,2,3-triazol-4-yl)methanone (400 mg, 0.48 mmol), acetonitrile (15 mL) and acetic acid (680 μL, 12.0 mmol) was added N-bromosuccinimide (85 mg, 0.48 mmol). After stirring for 20 minutes at room temperature starting material was consumed. The contents of the flask were transferred to a separatory funnel using 40 mL of ethyl acetate and 20 mL of water before neutralizing with saturated sodium bicarbonate. Washed the organics three additional times with saturated sodium bicarbonate and then twice with brine. Dried the organics over sodium sulfate, filtered and concentrated in vacuo to afford the title compound (425 mg) as a yellow-brown foam.

To a flask containing (1R,3s,5S)-tert-butyl 3-(7-(bis((2-(trimethylsilyl)ethoxy)-methyl)amino)-6-bromo-3-(6-((tert-butoxycarbonyl)(cyclopropyl)amino)-pyridin-3-yl)pyrazolo[1,5-a]pyrimidin-5-yl)-8-azabicyclo[3.2.1]octane-8-carboxylate (425 mg, 0.46 mmol) and dioxane (10 mL) was added tributyl[1-(ethyloxy)ethenyl]stannane. The system was evacuated and charged with nitrogen three times before adding tetrakis (54 mg, 0.05 mmol). The process of evacuating and charging with nitrogen was repeated three times and then the flask lowered into a bath at 90° C. Upon stirring overnight starting material was consumed (by LC-MS). Removed the solvent in vacuo and purified the remaining residue by flash chromatography (50 g silica gel) using 0.5% methanol in chloroform to afford the title compound (400 mg)

partitioned between EtOAc and water. The organics were washed twice more with water and twice with brine before drying over sodium sulfate, filtering and concentrating in vacuo. This residue was purified by flash chromatography (125 g of silica gel) using 0-30% ethyl acetate in hexane to afford the title compound (425 mg) as a tan solid.

Step 6: Preparation of 1-(7-amino-5-((1R,3s,5S)-8-azabicyclo[3.2.1]octan-3-yl)-3-(6-(cyclopropylamino)pyridin-3-yl)pyrazolo[1,5-a]pyrimidin-6-yl)ethanone Step 7: Preparation of 1-(5-((1R,3s,5S)-8-(4H-1,2,4-triazole-3-carbonyl)-8-azabicyclo[3.2.1]octan-3-yl)-7-amino-3-(6-(cyclopropylamino)pyridin-3-yl)pyrazolo[1,5-a]pyrimidin-6-yl)ethanone

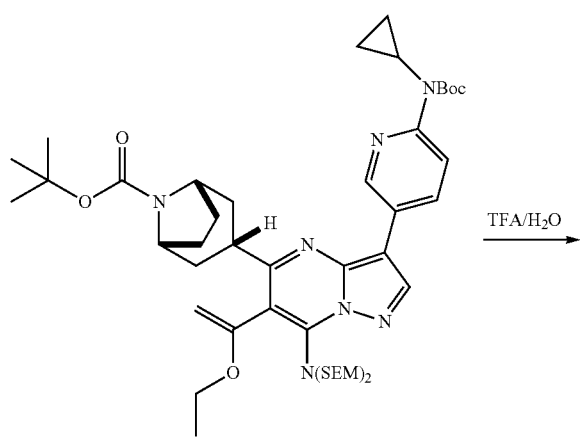

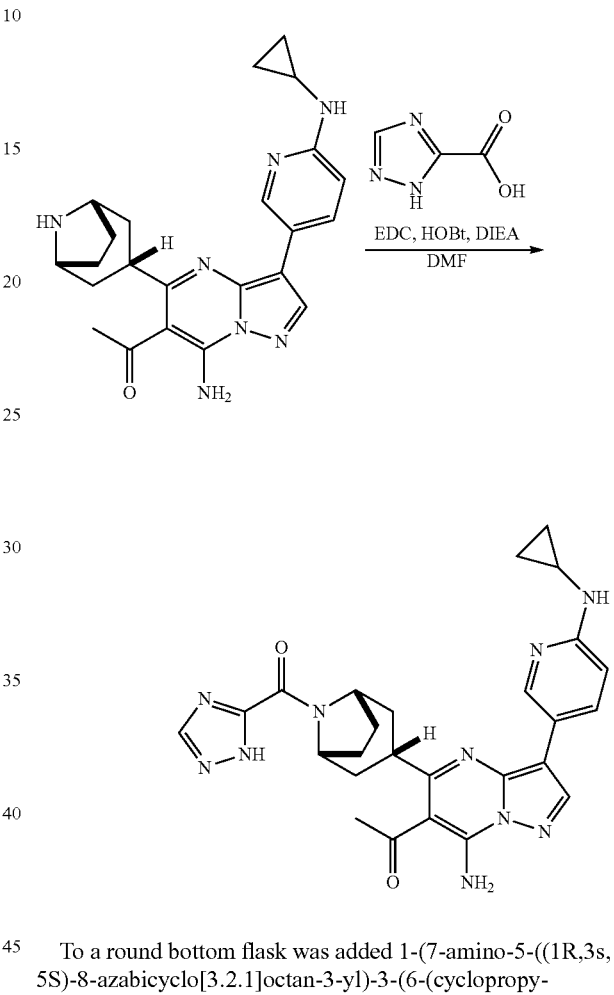

To a round bottom flask containing (1R,3s,5S)-tert-butyl 3-(7-(bis((2-(trimethylsilyl)-ethoxy)-methyl)amino)-3-(6-((tert-butoxycarbonyl)(cyclopropyl)amino)pyridin-3-yl-6-(1-ethoxyvinyl)pyrazolo[1,5-a]pyrimidin-5-yl-8-azabicyclo[3.2.1]octane-8-carboxylate (360 mg, 0.40 mmol) was added a premixed solution of TFA (10 mL) and water (4 mL). Upon stirring for 6 hours the reaction was complete. The TFA and water were removed in vacuo. To the residue that remained was added 100 mL of ether. This led to the formation of a yellow precipitate that was then sonicated for approximately 5 minutes to break up all the solids. The solids were filtered onto a glass frit (with two 50 mL ether washes) and then dried under high vacuum to afford the title compound (186 mg, 73%) as a yellow solid (bis TFA salt).

To a round bottom flask was added 1-(7-amino-5-((1R,3s,5S)-8-azabicyclo[3.2.1]octan-3-yl)-3-(6-(cyclopropylamino)pyridin-3-yl)pyrazolo[1,5-a]pyrimidin-6-yl)ethanone (180 mg, 0.28 mmol), DMF (5 mL) and N,N-diisopropylethylamine (0.24 mL, 1.39 mmol). In a separate flask was added EDC (107 mg, 0.56 mmol), HOBT monohydrate (94 mg, 0.61 mmol), 1H-1,2,4-triazole-5-carboxylic acid (63 mg, 0.56 mmol) and DMF (5 mL). Stirred the contents of the second flask for 15 minutes and then added the solution to the flask containing 1-(7-amino-5-((1R,3s,5S)-8-azabicyclo[3.2.1]octan-3-yl)-3-(6-(cyclopropylamino)pyridin-3-yl)pyrazolo[1,5-a]pyrimidin-6-yl)ethanone. After 50 minutes at room temperature the starting material was consumed. The contents of the flask were therefore transferred to a separatory funnel and partitioned between ethyl acetate and water. Washed the organics twice with saturated sodium bicarbonate, water and brine before drying over sodium sulfate, filtering and concentrating in vacuo. Purified the remaining solids by flash chromatography using 0-10% methanol (containing 1% NH$_4$OH) in chloroform to afford the title compound as a yellow solid. The following compounds (Table 8-17) were made similarly.

TABLE 8-17

| Compound ID | Structure | Compound Name | M + H (calculated)/ M + H (observed) | pAKT S473 IC50 | p4E-BP1 Thr37/46 IC50 |
|---|---|---|---|---|---|
| 8.47 | 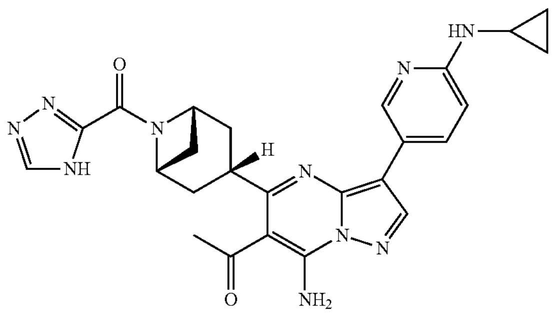 [SMILES: CC(=O)c1c([C@H]2C[C@@H]3C[C@H](C2)N3C(=O)c2nnc[nH]2)nc2c(-c3ccc(NC4CC4)nc3)cnn2c1N] | 1-(5-((1R,3s,5S)-8-(4H-1,2,4-triazole-3-carbonyl)-8-azabicyclo[3.2.1]octan-3-yl)-7-amino-3-(6-(cyclopropylamino)pyridin-3-yl)pyrazolo[1,5-a]pyrimidin-6-yl)ethanone | 513.2/513.4 | A | A |
| 8.48 | 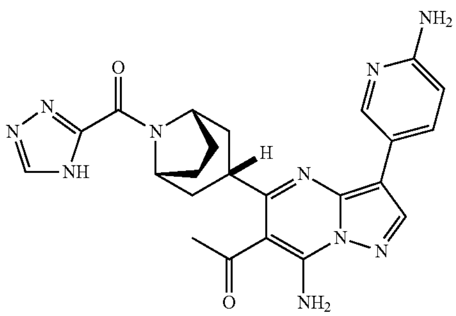 | 1-(5-((1R,3s,5S)-8-(4H-1,2,4-triazole-3-carbonyl)-8-azabicyclo[3.2.1]octan-3-yl)-7-amino-3-(6-aminopyridin-3-yl)pyrazolo[1,5-a]pyrimidin-6-yl)ethanone | 473.2/473.4 | A | A |
| 8.49 | 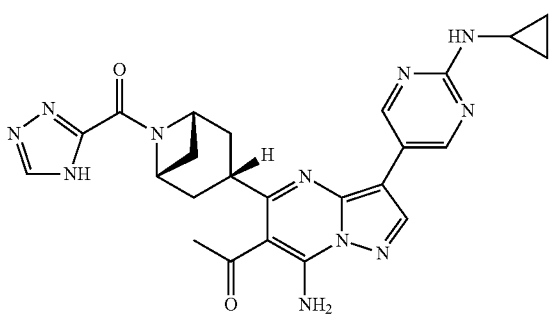 [SMILES: CC(=O)c1c([C@H]2C[C@@H]3C[C@H](C2)N3C(=O)c2nnc[nH]2)nc2c(-c3cnc(NC4CC4)nc3)cnn2c1N] | 1-(5-((1R,3s,5S)-8-(4H-1,2,4-triazole-3-carbonyl)-8-azabicyclo[3.2.1]octan-3-yl)-7-amino-3-(2-(cyclopropylamino)pyrimidin-5-yl)pyrazolo[1,5-a]pyrimidin-6-yl)ethanone | 514.3/514.0 | A | A |
| 8.50 | 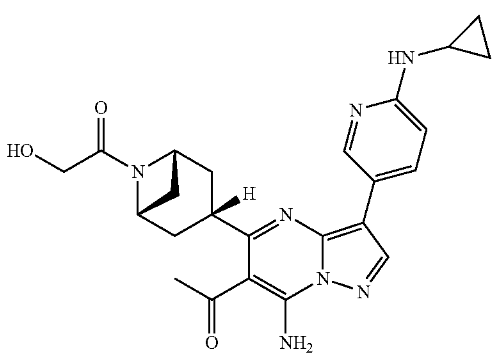 [SMILES: CC(=O)c1c([C@H]2C[C@@H]3C[C@H](C2)N3C(=O)CO)nc2c(-c3ccc(NC4CC4)nc3)cnn2c1N] | 1-((1R,3s,5S)-3-(6-acetyl-7-amino-3-(6-(cyclopropylamino)pyridin-3-yl)pyrazolo[1,5-a]pyrimidin-5-yl)-8-azabicyclo[3.2.1]octan-8-yl)-2-hydroxyethanone | 477.3/477.0 | B | B |

Example 8-23

Preparation of di-tert-butyl 1-acetyl-2-(5-(4,4,5,5-tetramethyl-1,3,2-dioxaborolan-2-yl)pyridin-2-yl)hydrazine-1,2-dicarboxylate

Step 1: Preparation of N'-(5-bromopyridin-2-yl)acetohydrazide

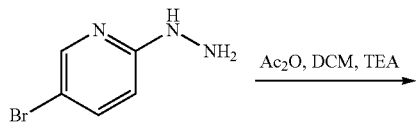

Acetic anhydride (1.13 mL, 12.0 mmol) was added to a solution of 5-bromo-2-hydrazinylpyridine (1.90 g, 10.0 mmol) and TEA (2.09 mL, 15.0 mmol) in DCM (200 mL). After 16 hours, the reaction mixture was concentrated by rotoevaporation and the residue was partitioned between EtOAc and saturated aqueous $NaHCO_3$. The organic layer was washed with water and brine, dried with $Na_2SO_4$, and the solvent was removed under vacuum. The resulting residue was triturated with DCM to afford the title compound as a white solid (1.86 g).

Step 2: Preparation of di-tert-butyl 1-acetyl-2-(5-bromopyridin-2-yl)hydrazine-1,2-dicarboxylate

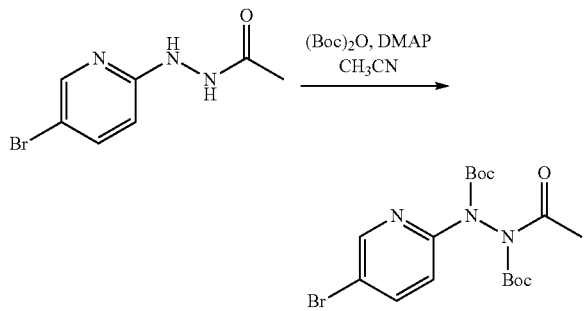

$(Boc)_2O$ (8.29 mL, 36.8 mmol) was added to a slurry of N'-(5-bromopyridin-2-yl)acetohydrazide (2.65 g, 11.5 mmol) and DMAP (35.5 mg, 0.288 mmol) in $CH_3CN$ (18 mL). After an hour, the solution was diluted with $Et_2O$ and sequentially washed with 1M $KHSO_4$, saturated aqueous $NaHCO_3$, and brine. The organic layer was dried with $Na_2SO_4$, and the solvent was removed under vacuum. The resulting residue was purified by a $SiO_2$ column (5-10% $Et_2O$/hexane) to afford the titled compound as clear syrup (4.80 g). (Modified synthesis of O. Loog, et al., *Synthesis*, 2000, 11, 1591-1597).

Step 3: Preparation of di-tert-butyl 1-acetyl-2-(5-(4,4,5,5-tetramethyl-1,3,2-dioxaborolan-2-yl)pyridin-2-yl)hydrazine-1,2-dicarboxylate

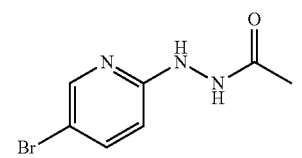

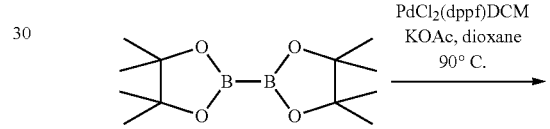

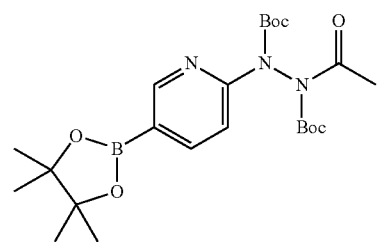

A mixture of di-tert-butyl 1-acetyl-2-(5-bromopyridin-2-yl)hydrazine-1,2-dicarboxylate (4.80 g, 11.2 mmol), bis(pinacolato)diboron (5.66 g, 22.3 mmol), $PdCl_2$(dppf).DCM (683 mg, 0.837 mmol), and KOAc (6.57 g, 66.9 mmol) in dioxane (43.5 mL) was degassed and then heated at 90° C. for 15 hours. It was then partitioned between 20% i-PrOH/DCM and (3:7) saturated aqueous $NH_4Cl$/concentrated aqueous $NH_4OH$. The organic layer was washed with brine, dried with $Na_2SO_4$, and the solvent was removed under vacuum. The resulting residue was purified by a SiO$_2$ column (15-25% EtOAc/hexane) to afford the titled compound as yellow glass (3.54 g).

Example 8-24

Preparation of di-tert-butyl 1-(5-(7-(bis((2-(trimethylsilyl)ethoxy)methyl)amino)-6-bromo-5-((1R,3s,5S)-8-(tert-butoxycarbonyl)-8-azabicyclo[3.2.1]octan-3-yl)pyrazolo[1,5-a]pyrimidin-3-yl)pyridin-2-yl)-2-propionylhydrazine-1,2-dicarboxylate Step 1: Preparation of di-tert-butyl 1-(5-(7-(bis((2-(trimethylsilyl)ethoxy)methyl)amino)-6-bromo-5-((1R,3s,5S)-8-(tert-butoxycarbonyl)-8-azabicyclo[3.2.1]octan-3-yl)pyrazolo[1,5-a]pyrimidin-3-yl)pyridin-2-yl)hydrazine-1,2-dicarboxylate

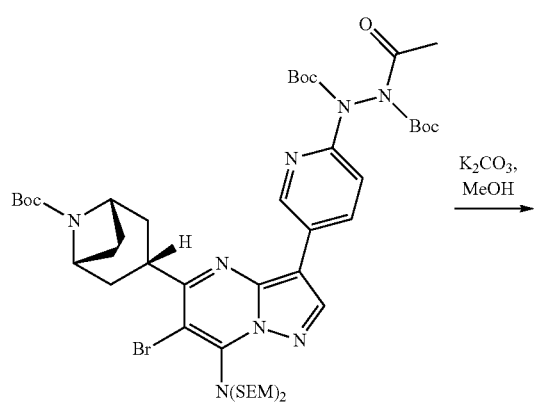

Di-tert-butyl 1-acetyl-2-(5-(7-(bis((2-(trimethylsilyl)ethoxy)methyl)amino)-6-bromo-5-((1R,3s,5S)-8-(tert-butoxycarbonyl)-8-azabicyclo[3.2.1]octan-3-yl)pyrazolo[1,5-a]pyrimidin-3-yl)pyridin-2-yl)hydrazine-1,2-dicarboxylate (0.33 g, 1.48 mmol) and K$_2$CO$_3$ (0.03 g, 0.22 mmol) were dissolved in MeOH (3.2 mL). After 16 hours, the solution was partitioned between Et$_2$O/DCM and water. The organic layer was washed with brine, dried with Na$_2$SO$_4$, and the solvent was removed under vacuum to afford the title compound as yellow solid (0.30 g) that was used as is in the next reaction.

Step 2: Preparation of di-tert-butyl 1-(5-(7-(bis((2-(trimethylsilyl)ethoxy)methyl)amino)-6-bromo-5-((1R,3s,5S)-8-(tert-butoxycarbonyl)-8-azabicyclo[3.2.1]octan-3-yl)pyrazolo[1,5-a]pyrimidin-3-yl)pyridin-2-yl-2-propionylhydrazine-1,2-dicarboxylate

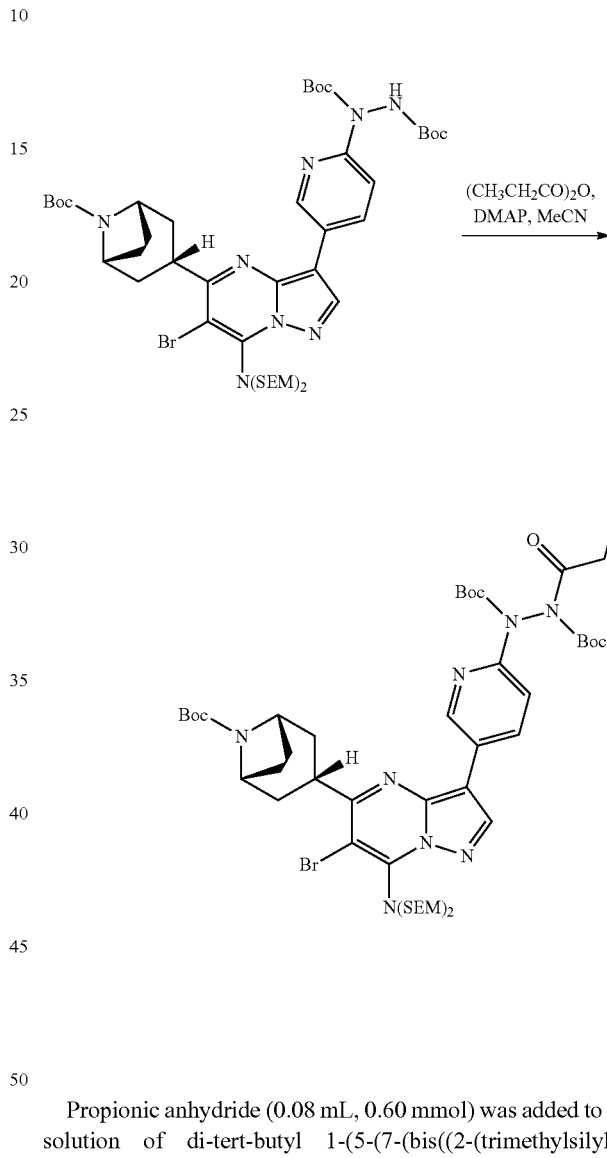

Propionic anhydride (0.08 mL, 0.60 mmol) was added to a solution of di-tert-butyl 1-(5-(7-(bis((2-(trimethylsilyl)ethoxy)methyl)amino)-6-bromo-5-((1R,3s,5S)-8-(tert-butoxycarbonyl)-8-azabicyclo[3.2.1]octan-3-yl)pyrazolo[1,5-a]pyrimidin-3-yl)pyridin-2-yl)hydrazine-1,2-dicarboxylate (0.30 g, 0.30 mmol) and DMAP (0.02 g, 0.12 mmol) in MeCN (3 mL) and the reaction was heated at 50° C. More propionic anhydride was added in portions (0.77 mL total) until no more conversion was seen, monitored by HPLC. The reaction partitioned between Et$_2$O and 1N aqueous HCl. The organic layer was washed with water, saturated aqueous NaHCO$_3$, and brine. It was dried with Na$_2$SO$_4$ and solvent was removed under vacuum. The resulting residue was purified by a SiO$_2$ column (20-25% Et$_2$O/hexane) to afford the titled compound as yellow glass (0.25 g).

Following previously procedures and examples, the following two compounds were prepared (Table 8-18):

TABLE 8-18

| Compound ID | Structures | Compound Name | M + H (calculated)/ M + H (observed) | pAKT S473 IC50 | p4E-BP1 Thr37/46 IC50 |
|---|---|---|---|---|---|
| 8.51 | 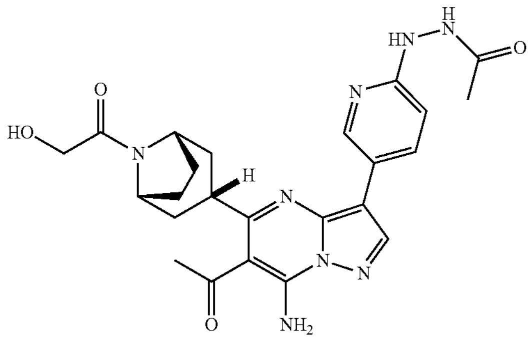 [SMILES: CC(=O)NNc1ccc(-c2cnn3c(N)c(C(C)=O)c([C@@H]4C[C@H]5CC[C@@H](C4)N5C(=O)CO)nc23)cn1] | N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)acetohydrazide | 493.2/493.4 | ND | ND |
| 8.52 | 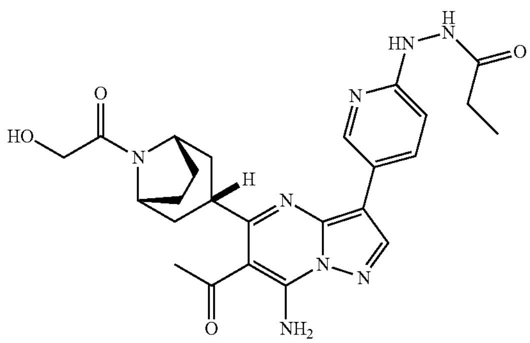 [SMILES: CCC(=O)NNc1ccc(-c2cnn3c(N)c(C(C)=O)c([C@@H]4C[C@H]5CC[C@@H](C4)N5C(=O)CO)nc23)cn1] | N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)propionohydrazide | 507.2/507.4 | C | D |

Example 8-25

Preparation of (1R,3s,5S)-tert-butyl 3-(7-(bis((2-(trimethylsilyl)ethoxy)methyl)amino)-3-(6-(cyclopropylmethoxy)pyridin-3-yl-6-(methylsulfonyl)pyrazolo[1,5-a]pyrimidin-5-yl)-8-azabicyclo[3.2.1]octane-8-carboxylate Step 1: Preparation of tert-butyl (3-exo)-3-{7-(bis{[2-(trimethylsilyl)ethoxy]methyl}amino)-3-[6-(cyclopropylmethoxy)pyridin-3-yl]-6-iodopyrazolo[1,5-a]pyrimidin-5-yl}-8-azabicyclo[3.2.1]octane-8-carboxylate

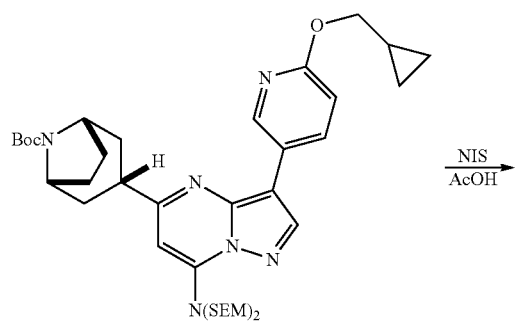

tert-butyl (3-exo)-3-{7-(bis{[2-(trimethylsilyl)ethoxy]methyl}amino)-3-[6-(cyclopropylmethoxy)pyridin-3-yl]pyrazolo[1,5-a]pyrimidin-5-yl}-8-azabicyclo[3.2.1]octane-8-carboxylate (868 mg, 1.16 mmol) was dissolved in acetonitrile (10 mL), and N-iodosuccinimide (274 mg, 1.16 mmol) was added. No reaction had occurred after 1 h. The solvent was removed, and the residue was dissolved in acetic acid (10 mL). The reaction was complete after stirring 1 h at room temperature. The reaction was added to a mixture of dichloromethane and saturated aqueous sodium bicarbonate. The pH of the reaction was adjusted to 7 with sodium bicarbonate, and the layers were separated. The aqueous layer was extracted three more times with dichloromethane, and the combine organics were dried over sodium sulfate and concentrated to give a dark oil (1.18 g). The crude product was purified by flash chromatography (45 g silica gel, 10% EtOAc in hexane). Like fractions of the major product were combined and concentrated to give desired product (0.7086 g) as an orange foam.

Step 2: Preparation of tert-butyl (3-exo)-3-[7-(bis{[2-(trimethylsilyl)ethoxy]methyl}amino)-3-[6-(cyclopropylmethoxy)pyridin-3-yl]-6-(methylsulfonyl)pyrazolo[1,5-a]pyrimidin-5-yl]-8-azabicyclo[3.2.1]octane-8-carboxylate

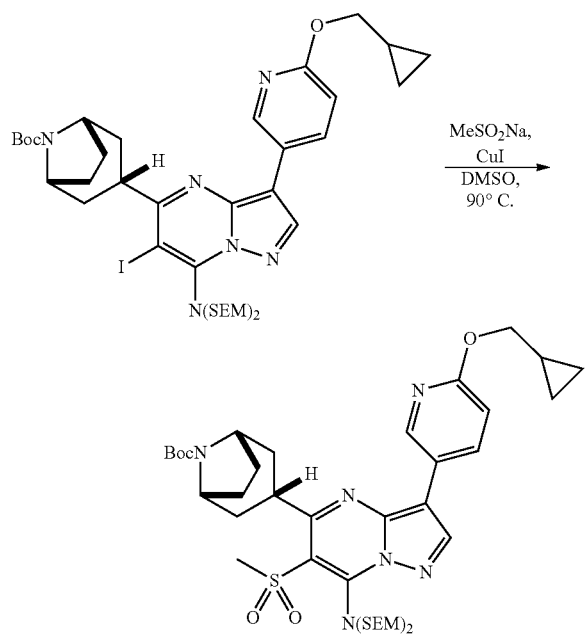

Sodium methanesulfinate (289 mg, 2.41 mmol), and copper iodide (837 mg, 4.40 mmol) were weighed into a 100 mL RBF. The flask was flushed with nitrogen for 5 min, and dry DMSO (5 ml) was added to the solids. The suspension with purged with nitrogen for 5 min, and the reaction was placed in an oil bath at 90° C. After stirring for approx. 5 min, a solution of tert-butyl (3-exo)-3-{7-(bis{[2-(trimethylsilyl)ethoxy]methyl}amino)-3-[6-(cyclopropylmethoxy)pyridin-3-yl]-6-iodopyrazolo[1,5-a]pyrimidin-5-yl}-8-azabicyclo[3.2.1]octane-8-carboxylate (705 mg, 0.803 mmol) and dry DMSO (8 mL) were added to the reaction. After heating to 90° C. for 70 min, the reaction was cooled to room temperature and partitioned between EtOAc and saturated aqueous ammonium chloride. The organic layer was washed two more times with saturated aqueous ammonium chloride and then twice with saturated aqueous LiCl. The organic layers were dried with sodium sulfate and concentrated in vacuo to give crude product (776 mg) as an orange oil. The crude oil was dissolved in 20% EtOAc in hexane and loaded onto a 90 g silica gel column that had been pre-equilibrated with 10% EtOAC in hexane. The column was eluted sequentially with 10% EtOAc in hexane (500 mL), 12% EtOAc in hexane (500 mL), 15% EtOAc in hexane (500 mL) and 20% EtOAc in hexane (approx. 700 mL). Like fractions of pure product were combined and concentrated in vacuo. Like fractions of impure product were combined, concentrated in vacuo and purified by radial chromatography using 20% EtOAC in hexane. Pure product fractions were combined with those above and concentrated in vacuo to give desired product (375 mg).

Following previously procedures and examples, the following two compounds were prepared (Table 8-19):

TABLE 8-19

| Compound ID | Structure | Compound Name | M + H (calculated)/ M + H (observed) | pAKT S473 IC50 | p4E-BP1 Thr37/46 IC50 |
|---|---|---|---|---|---|
| 8.53 | 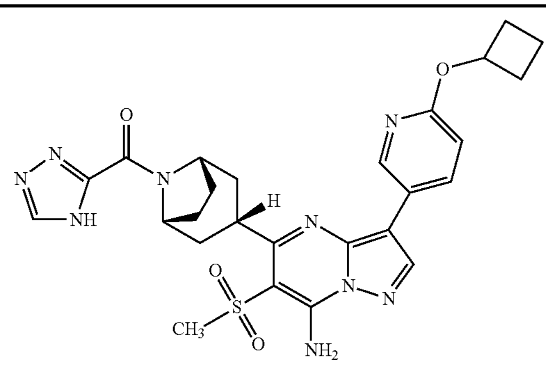 | ((1R,3s,5S)-3-(7-amino-3-(6-cyclobutoxypyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 564.2/564.3 | C | C |
| 8.54 | 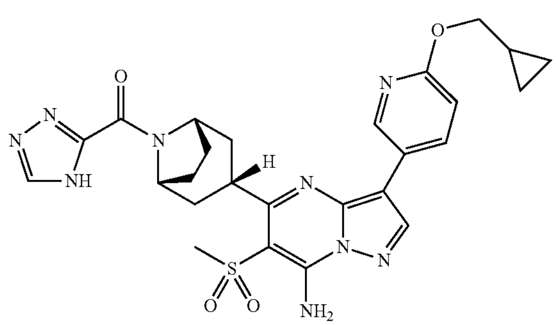 [SMILES: CS(=O)(=O)c1c([C@@H]2C[C@H]3CC[C@@H](C2)N3C(=O)c2nnc[nH]2)nc2c(-c3ccc(OCC4CC4)nc3)cnn2c1N] | ((1R,3s,5S)-3-(7-amino-3-(6-(cyclopropylmethoxy)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone | 564.2/564.2 | D | D |

Example 8-26

Synthesis of tert-butyl 7-(4,4,5,5-tetramethyl-1,3,2-dioxaborolan-2-yl)-[4,3-h]pyrano[3,2-b]pyridin-7-yl)-2-carboxylate (1D)

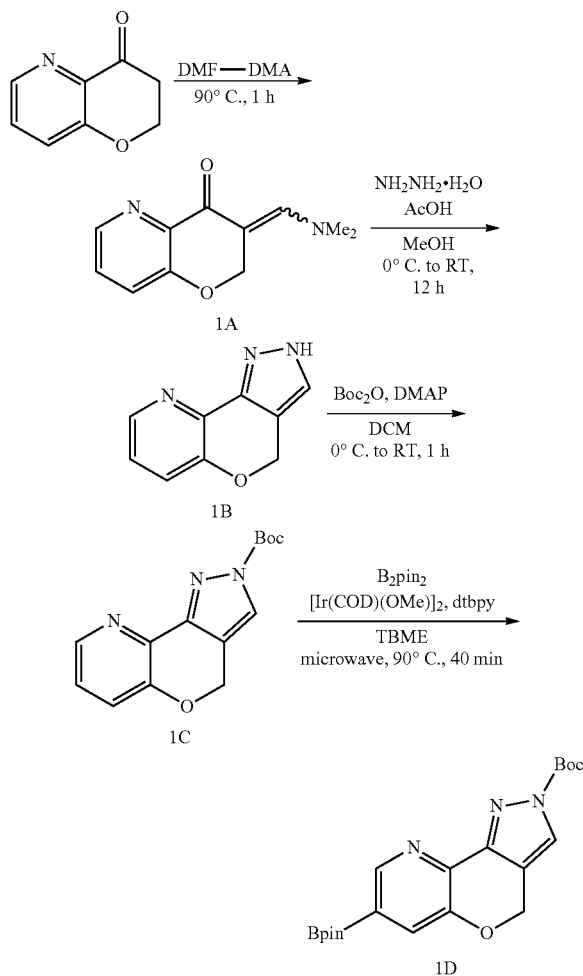

2,3-Dihydro-4H-pyrano[3,2-b]pyridin-4-one (1.2 g, 8.04 mmol) was dissolved in DMF (10 mL) and dimethylformaldehyde dimethylacetal (20 mL). The solution was allowed to stir at 80° C. for 1 h and concentrated to dryness through rotary evaporation in vacuo. The residue was dissolved in dichloromethane (50 mL); the resulting solution was washed with water (30 mL×2), dried over $Na_2SO_4$, and concentrated to get intermediate 1A. HPLC-MS $t_R$=0.321 min ($UV_{254\ nm}$). Mass calculated for formula $C_{11}H_{12}N_2O_2$ 204.1; observed $MH^+$ (LCMS) 205.1 (m/z).

The above solid was dissolved in MeOH, and the solution was allowed to cool to 0° C. in a ice/water bath. Hydrazine monohydrate (1.2 mL) was added dropwise, followed by acetic acid (0.92 mL). The reaction mixture was then allowed to stir at room temperature overnight and concentrated to dryness. The residue was taken up with ethyl acetate (80 mL), washed with saturated $NaHCO_3$, brine, dried over $Na_2SO_4$, and concentrated to dryness to afford a brown solid (~700 mg) as intermediate 1B. HPLC-MS $t_R$=0.431 min ($UV_{254\ nm}$). Mass calculated for formula $C_9H_7N_3O$ 173.1; observed $MH^+$ (LCMS) 174.1 (m/z).

The brown solid was suspended in dichloromethane (20 mL), a piece of DMAP (~20 mg) was added. Then, di-tert-butyl dicarbonate (1.32 g, 6.06 mmol) in dichloromethane (5 mL) was added dropwise via syringe. After stirring for 1 h, the reaction mixture was washed with water (30 mL×2), dried over $Na_2SO_4$, and concentrated. Flask column chromatography over silica (EtOAc/hexanes 40% to 55%) gave rise to a white solid (1.0 g) as intermediate 1C. HPLC-MS $t_R$=0.431 min ($UV_{254\ nm}$). Mass calculated for formula $C_{14}H_{15}N_3O_3$ 273.1; observed $MH^+$ (LCMS) 274.2 (m/z).

Intermediate 1C. (500 mg, 1.83 mmol), bis(pinacolate) bidboron (511 mg), Ir catalyst [Ir(COD)(OMe)]2 (61 mg, 0.082 mmol) and ligand 4,4'-di-tert-butyl-2,2'-bipyridine (49 mg, 0.18 mmol) were charged in a microwave reaction tube, after flushing with Argone, tert-butyl methyl ether (10 mL) was added. The tuble was capped and heated at 90° C. for 40 min under microwave irradiation. After cooling to room temperature and standing overnight, some crystals were formed, which was filtered, washed with cold TBME and dried in vacuo, giving rise to a pale brown solid (150 mg) as intermediate 1D. HPLC-MS $t_R$=0.772 min ($UV_{254\ nm}$). observed $MH^+$ (LCMS) 318.0 (m/z), Mass calculated for the corresponding boronic acid formula $C_{14}H_{16}BN_3O_5$ 317.1.

Following similar procedures described previously, the following compound (Table 8-20) was made.

TABLE 8-20

| Compound ID | Structures | Compound Name | M(calculated)/ M + H (observed) | pAKT S473 IC50 | p4E-BP1 Thr37/46 IC50 |
|---|---|---|---|---|---|
| 8.55 | 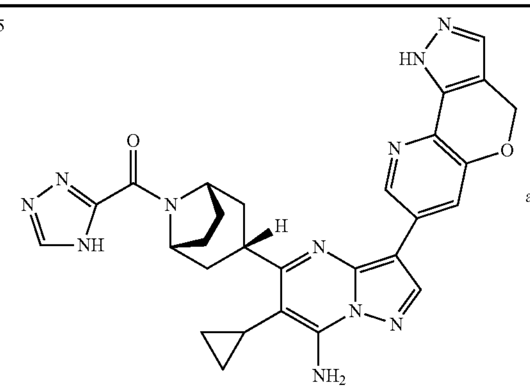 | ((1R,3r,5S)-3-(7-amino-6-cyclopropyl-3-(2H-pyrazolo[4,3-h]pyrano[3,2-b]pyridin-7-yl)pyrazolo[1,5-a]pyrimidin-5-yl)-8-azabicyclo[3.2.1]octan-8-yl)(4H-1,2,4-triazol-3-yl)methanone | 550.0/549.2 | C | C |

Example 8-27

Preparation of 1-(5-((1R,3s,5S)-8-(4H-1,2,4-triazole-3-carbonyl)-8-azabicyclo[3.2.1]octan-3-yl)-7-amino-3-(6-(3-hydroxyprop-1-ynyl)pyridin-3-yl)pyrazolo[1,5-a]pyrimidin-6-yl)

Step 1: Preparation of (1R,3s,5S)-tert-butyl 3-(7-(bis((2-(trimethylsilyl)ethoxy)methyl)amino)-3-(6-(3-hydroxyprop-1-ynyl)pyridin-3-yl)pyrazolo[1,5-a]pyrimidin-5-yl-8-azabicyclo[3.2.1]octane-8-carboxylate

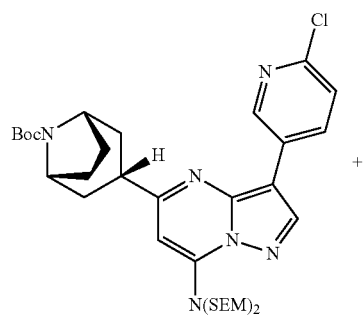

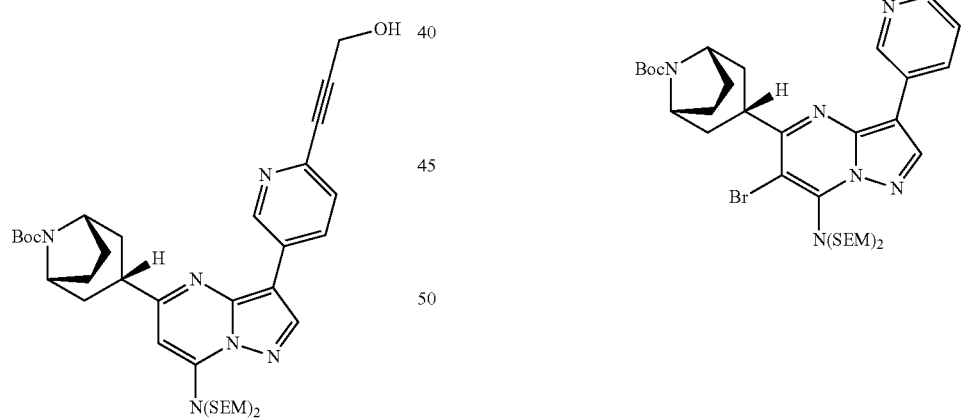

A mixture of (1R,3s,5S)-tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (358 mg, 0.500 mmol, preparation described previously), propargyl alcohol (59.0 uL, 1.00 mmol), allylpalladium(II) chloride dimer (4.6 mg, 0.013 mmol), triphenylphosphine (26.2 mg, 0.100 mmol), CuI (4.8 mg, 0.025 mmol), and K₂CO₃ (138 mg, 1.00 mmol) in DMF (2 mL) was heated at 100° C. under Argon for 20 h. The reaction mixture was diluted with EtOAc, washed with H₂O and brine, dried over Na₂SO₄, and concentrated. The crude product was purified by a SiO₂ column (0-60% EtOAc/Hexanes, R$_f$=0.25 in 50% EtOAc) to afford the titled compound as a brownish solid (295 mg).

Step 2: Preparation of (1R,3s,5S)-tert-butyl 3-(7-(bis((2-(trimethylsilyl)ethoxy)methyl)amino)-6-bromo-3-(6-(3-hydroxyprop-1-ynyl)pyridin-3-pyrazolo[1,5-a]pyrimidin-5-yl-8-azabicyclo[3.2.1]octane-8-carboxylate

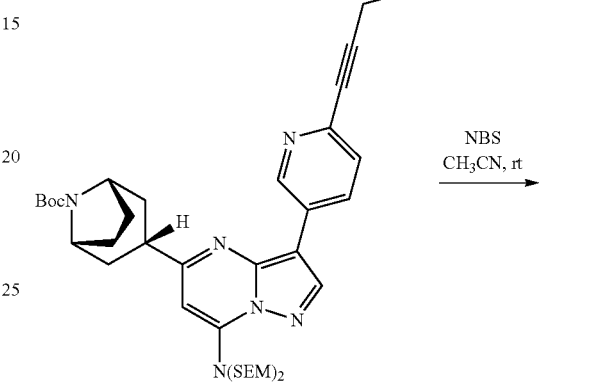

To a solution of (1R,3s,5S)-tert-butyl 3-(7-(bis((2-(trimethylsilyl)ethoxy)methyl)amino)-3-(6-(3-hydroxyprop-1-ynyl)pyridin-3-yl)pyrazolo[1,5-a]pyrimidin-5-yl)-8-azabicyclo[3.2.1]octane-8-carboxylate (499 mg, 0.679 mmol) in CH₃CN (15 mL) was added NBS (1.1 eq) at 0° C. and stirred at 0° C. for 30 min, then at rt for 15 min. All the volatiles were removed under reduced pressure and the residue was purified by a SiO₂ column (0-50%, EtOAc/Hexanes, R$_f$=0.35 in 50% EtOAc) to afford the titled compound as a brownish oil (312 mg).

Step 3: Preparation of (1R,3s,5S)-tert-butyl 3-(7-(bis ((2-(trimethylsilyl)ethoxy)methyl)amino)-6-(1-ethoxyvinyl)-3-(6-(3-hydroxyprop-1-ynyl)pyridin-3-yl)pyrazolo[1,5-a]pyrimidin-5-yl)-8-azabicyclo [3.2.1]octane-8-carboxylate

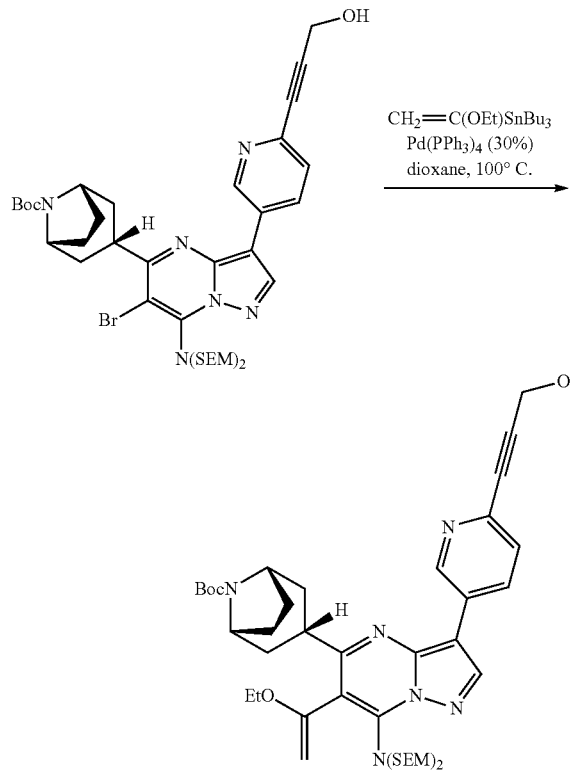

A mixture of (1R,3s,5S)-tert-butyl 3-(7-(bis((2-(trimethylsilyl)ethoxy)methyl)amino)-6-bromo-3-(6-(3-hydroxyprop-1-ynyl)pyridin-3-yl)pyrazolo[1,5-a]pyrimidin-5-yl)-8-azabicyclo[3.2.1]octane-8-carboxylate (67.9 mg, 0.0835 mmol), tributyl(1-ethoxyvinyl)tin (84.6 uL, 0.251 mmol), Pd(PPh$_3$)$_4$ (29.0 mg, 0.025 mmol) in dioxane (2 mL) was stirred at 100° C. under Argon for 2 h. The reaction mixture was passed through a short plug filled with SiO$_2$/KF (9:1) to remove majority of the Sn species (eluting with EtOAc). The filtrate was concentrated and purified by a SiO$_2$ column (0-50% EtOAc/Hexanes, R$_f$=0.4 in 50% EtOAc) to afford the titled compound as a brownish oil (28.3 mg).

Step 4: Preparation of 1-(5-((1R,3s,5S)-8-(4H-1,2,4-triazole-3-carbonyl)-8-azabicyclo[3.2.1]octan-3-yl)-7-amino-3-(6-(3-hydroxyprop-1-ynyl)pyridin-3-yl) pyrazolo[1,5-a]pyrimidin-6-yl)ethanone

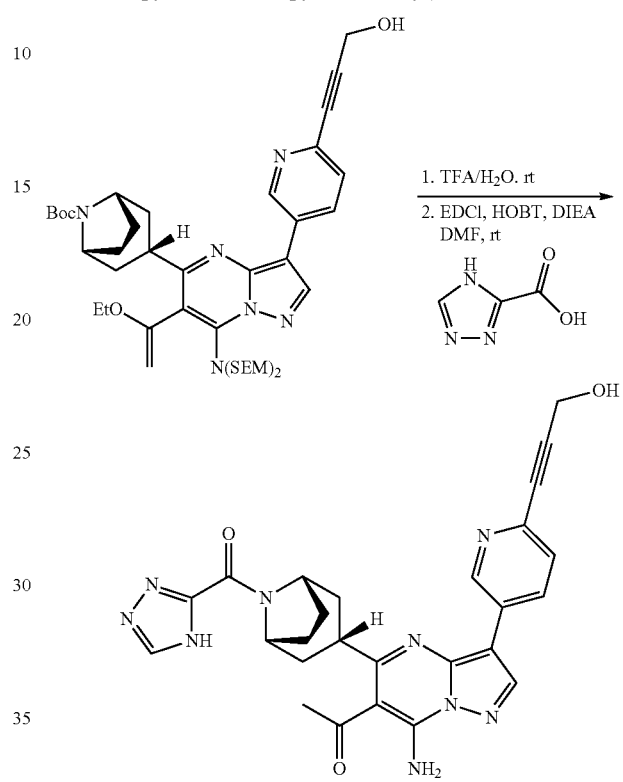

This title compound was prepared from (1R,3s,5S)-tert-butyl 3-(7-(bis((2-(trimethylsilyl)ethoxy)methyl)amino)-6-(1-ethoxyvinyl)-3-(6-(3-hydroxyprop-1-ynyl)pyridin-3-yl) pyrazolo[1,5-a]pyrimidin-5-yl)-8-azabicyclo[3.2.1]octane-8-carboxylate and 4H-1,2,4-triazole-3-carboxylic acid, following essentially the same procedures given previously. Similarly compounds in Table 8-21 were made:

TABLE 8-21

| Compound ID | Structures | Compound Name | M + H (calculated)/ M + H (observed) | pAKT S473 IC50 | p4E-BP1 Thr37/46 IC50 |
|---|---|---|---|---|---|
| 8.56 | 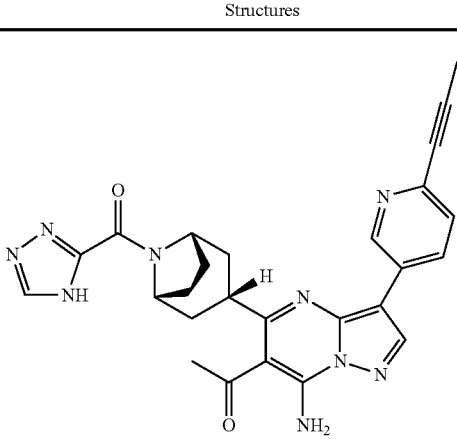 | 1-(5-((1R,3s,5S)-8-(4H-1,2,4-triazole-3-carbonyl)-8-azabicyclo[3.2.1]octan-3-yl)-7-amino-3-(6-(3-hydroxyprop-1-ynyl)pyridin-3-yl)pyrazolo[1,5-a]pyrimidin-6-yl)ethanone | 512.2/512.2 | B | B |

TABLE 8-21-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.57 | 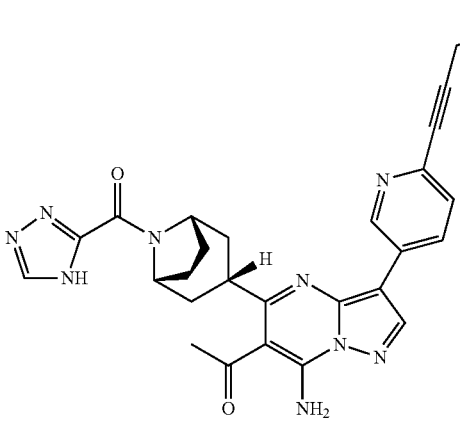 | 1-(5-((1R,3s,5S)-8-(4H-1,2,4-triazole-3-carbonyl)-8-azabicyclo[3.2.1]octan-3-yl)-7-amino-3-(6-(3-methoxyprop-1-ynyl)pyridin-3-yl)pyrazolo[1,5-a]pyrimidin-6-yl)ethanone | 526.2/526.3 | ND | ND |
| 8.58 | 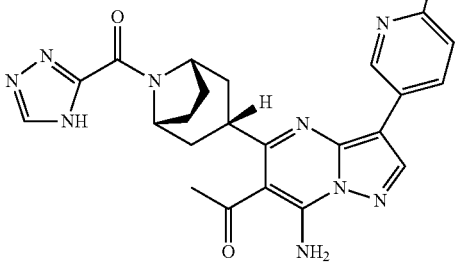 | 1-(5-((1R,3s,5S)-8-(4H-1,2,4-triazole-3-carbonyl)-8-azabicyclo[3.2.1]octan-3-yl)-7-amino-3-(6-(3-(2-hydroxyethoxy)prop-1-ynyl)pyridin-3-yl)pyrazolo[1,5-a]pyrimidin-6-yl)ethanone | 556.2/556.2 | ND | ND |
| 8.59 | 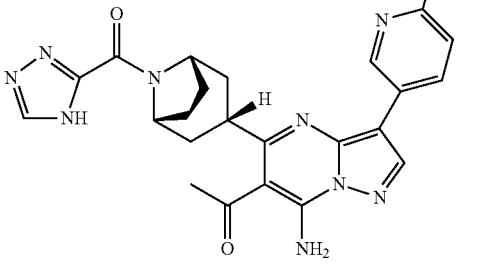 | 1-(5-((1R,3s,5S)-8-(4H-1,2,4-triazole-3-carbonyl)-8-azabicyclo[3.2.1]octan-3-yl)-7-amino-3-(6-(3-(2-methoxyethoxy)prop-1-ynyl)pyridin-3-yl)pyrazolo[1,5-a]pyrimidin-6-yl)ethanone | 570.3/570.2 | ND | ND |

TABLE 8-21-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.60 | 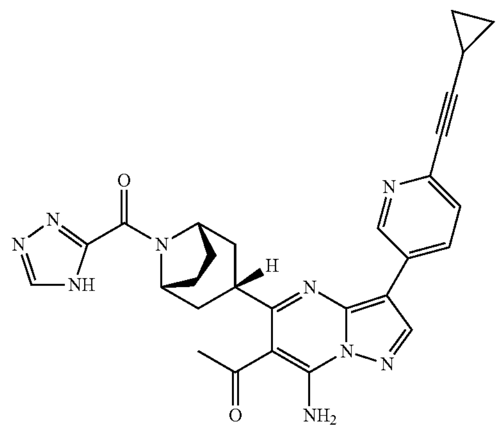 | 1-(5-((1R,3s,5S)-8-(4H-1,2,4-triazole-3-carbonyl)-8-azabicyclo[3.2.1]octan-3-yl)-7-amino-3-(6-(cyclopropylethynyl)pyridin-3-yl)pyrazolo[1,5-a]pyrimidin-6-yl)ethanone | 522.2/522.0 | B | B |
| 8.61 | 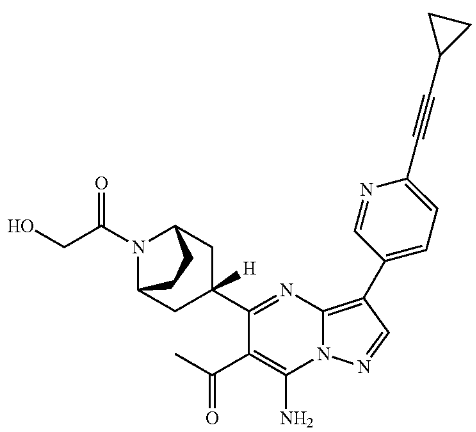 | 1-((1R,3s,5S)-3-(6-acetyl-7-amino-3-(6-(cyclopropylethynyl)pyridin-3-yl)pyrazolo[1,5-a]pyrimidin-5-yl)-8-azabicyclo[3.2.1]octan-8-yl)-2-hydroxyethanone | 485.2/485.2 | B | B |
| 8.62 | 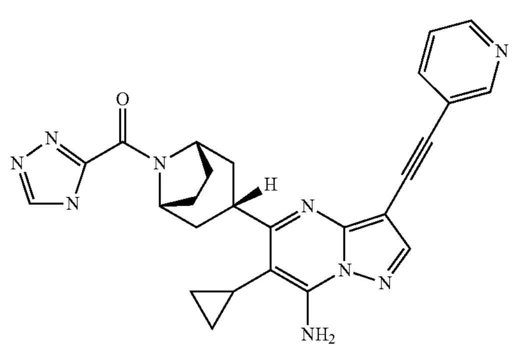 [SMILES: Nc1c(C2CC2)c([C@@H]2C[C@H]3CC[C@@H](C2)N3C(=O)c2nnc[nH]2)nc2c(C#Cc3cccnc3)cnn12] | ((1R,3s,5S)-3-(7-amino-6-cyclopropyl-3-(pyridin-3-ylethynyl)pyrazolo[1,5-a]pyrimidin-5-yl)-8-azabicyclo[3.2.1]octan-8-yl)(4H-1,2,4-triazol-3-yl)methanone | 480.0/480.2 | C | C |

Example 8-28

Preparation of 5-((1R,3s,5S)-8-(4-aminopyrimidin-2-yl)-8-azabicyclo[3.2.1]octan-3-yl)-6-(methylsulfonyl)-3-(6-phenylpyridin-3-yl)pyrazolo[1,5-a]pyrimidin-7-amine

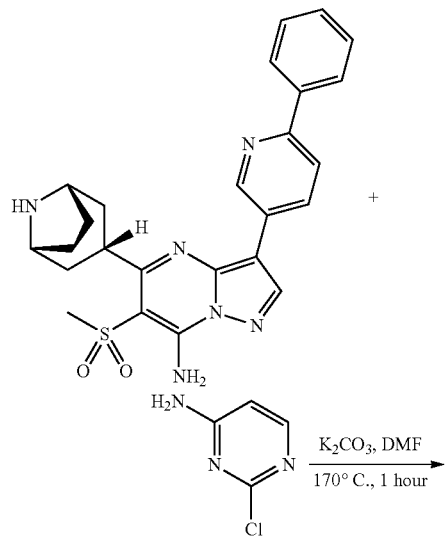

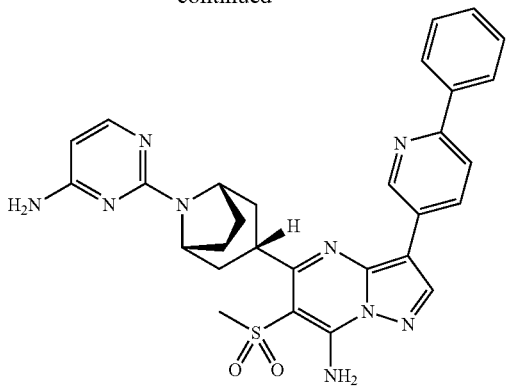

A suspension of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine (66 mg, 0.1 mmol), 4-amino-2-chloropyrimidine (26 mg, 0.2 mmol) and $K_2CO_3$ (28 mg, 0.2 mmol) in DMF (2 mL) was heated up to 170° C. with MW reactor and stirred for 1 hour. The solution was evaporated to dryness and $H_2O$ (4 mL) was added. The resulting suspension was collected and purified with HPLC to give the desired product 5-((1R,3s,5S)-8-(4-aminopyrimidin-2-yl)-8-azabicyclo[3.2.1]octan-3-yl)-6-(methylsulfonyl)-3-(6-phenylpyridin-3-yl)pyrazolo[1,5-a]pyrimidin-7-amine.

Similarly compounds in Table 8-22 were made:

TABLE 8-22

| Compound ID | Structures | Compound Name | M + H (calculated)/ M + H (observed) | pAKT S473 IC50 | p4E-BP1 Thr3746 IC50 |
|---|---|---|---|---|---|
| 8.63 | 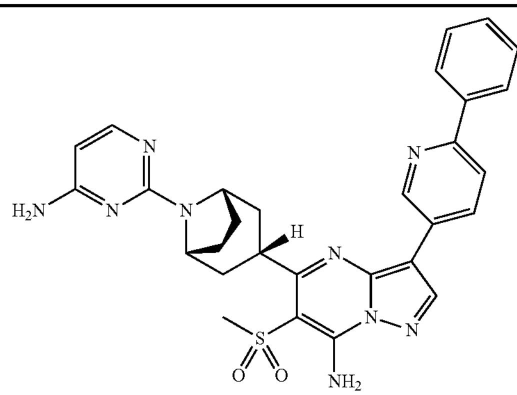 | 5-((1R,3s,5S)-8-(4-aminopyrimidin-2-yl)-8-azabicyclo[3.2.1]octan-3-yl)-6-(methylsulfonyl)-3-(6-phenylpyridin-3-yl)pyrazolo[1,5-a]pyrimidin-7-amine | 568.2/568.2 | C | C |
| 8.64 | 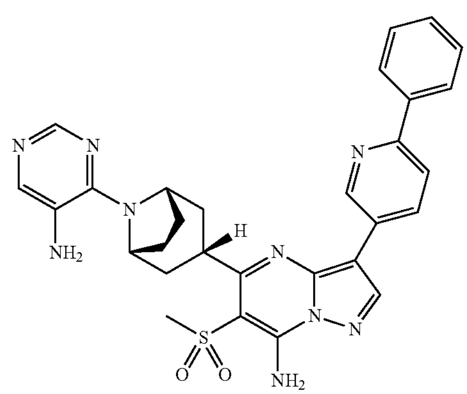 | 5-((1R,3s,5S)-8-(5-aminopyrimidin-4-yl)-8-azabicyclo[3.2.1]octan-3-yl)-6-(methylsulfonyl)-3-(6-phenylpyridin-3-yl)pyrazolo[1,5-a]pyrimidin-7-amine | 568.2/568.3 | B | C |

TABLE 8-22-continued

| Compound ID | Structures | Compound Name | M + H (calculated)/ M + H (observed) | pAKT S473 IC50 | p4E-BP1 Thr3746 IC50 |
|---|---|---|---|---|---|
| 8.65 | 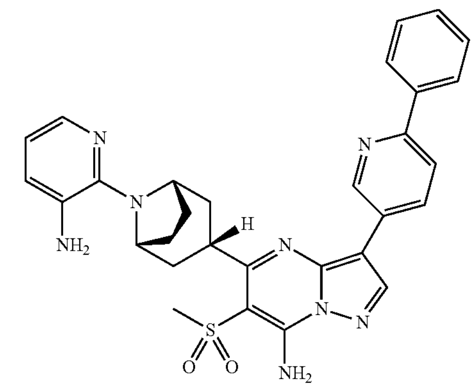 | 5-((1R,3s,5S)-8-(3-aminopyridin-2-yl)-8-azabicyclo[3.2.1]octan-3-yl)-6-(methylsulfonyl)-3-(6-phenylpyridin-3-yl)pyrazolo[1,5-a]pyrimidin-7-amine | 567.2/567.3 | ND | ND |
| 8.66 | 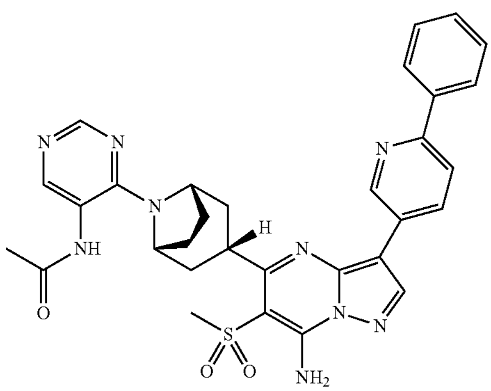 | N-(4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyrimidin-5-yl)acetamide | 610.2/610.2 | ND | ND |
| 8.67 | 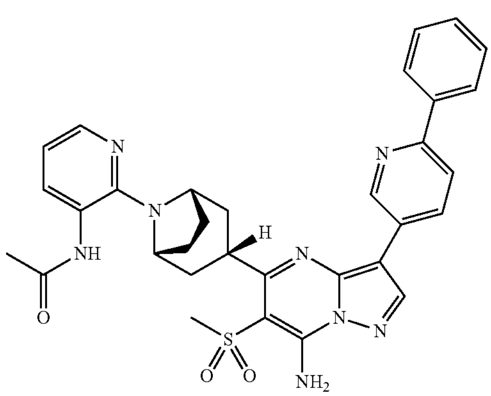 | N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyridin-3-yl)acetamide | 609.2/609.3 | ND | ND |

Example 8-29

Preparation of 5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-5-methylimidazolidine-2,4-dione Step 1: Preparation of (1R,3s,5S)-tert-butyl 3-(7-(bis((2-(trimethylsilyl)ethoxy)methyl)amino)-6-bromo-3-(6-(4-methyl-2,5-dioxoimidazolidin-4-yl)pyridin-3-yl)pyrazolo[1,5-a]pyrimidin-5-yl)-8-azabicyclo[3.2.1]octane-8-carboxylate

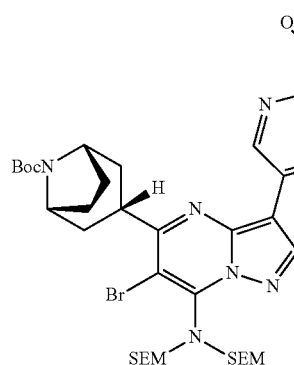

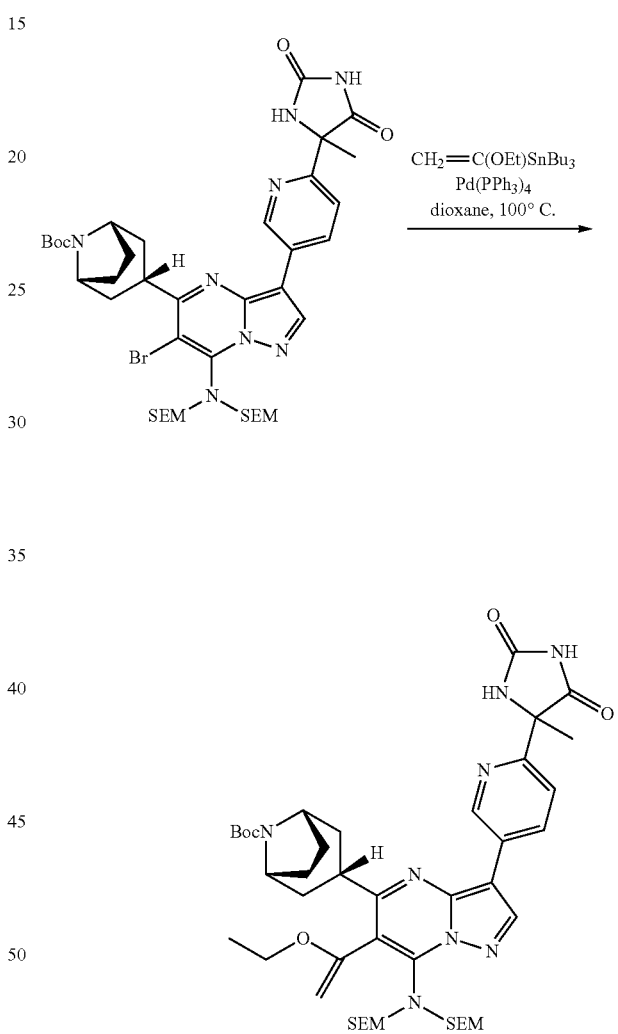

The compound (1R,3s,5S)-tert-butyl 3-(3-(6-acetylpyridin-3-yl)-7-(bis((2-(trimethylsilyl)ethoxy)methyl)amino)-6-bromopyrazolo[1,5-a]pyrimidin-5-yl)-8-azabicyclo[3.2.1]octane-8-carboxylate (previously made. 401 mg, 0.5 mmol) was mixed with KCN (36 mg, 0.55 mmol) and (NH$_4$)$_2$CO$_3$ (216 mg, 4.5 mmol) in EtOH/H$_2$O (5 mL/5 mL) and the resulting mixture was heated up to 80° C. and stirred overnight. After cooling to room temperature, the reaction was diluted with EtOAc and washed with water and brine. After concentration, the crude was purified with column chromatography (silica gel, 0-60% EtOAc/hexane) gave the product (428 mg).

Step 2: Preparation of (1R,3s,5S)-tert-butyl 3-(7-(bis((2-(trimethylsilyl)ethoxy)methyl)amino)-6-(1-ethoxyvinyl)-3-(6-(4-methyl-2,5-dioxoimidazolidin-4-yl)pyridin-3-yl)pyrazolo[1,5-a]pyrimidin-5-yl)-8-azabicyclo[3.2.1]octane-8-carboxylate The compound of (1R,3s,5S)-tert-butyl 3-(7-(bis((2-(trimethylsilyl)ethoxy)methyl)amino)-6-(1-ethoxyvinyl)-3-(6-(4-methyl-2,5-dioxoimidazolidin-4-yl)pyridin-3-yl)pyrazolo[1,5-a]pyrimidin-5-yl)-8-azabicyclo[3.2.1]octane-8-carboxylate was made following similar examples described previously.

801

Step 3: Preparation of 5-(5-(6-acetyl-7-amino-5-((1R,3s,5S)-8-azabicyclo[3.2.1]octan-3-yl)pyrazolo[1,5-a]pyrimidin-3-yl)pyridin-2-yl-5-methylimidazolidine-2,4-dione

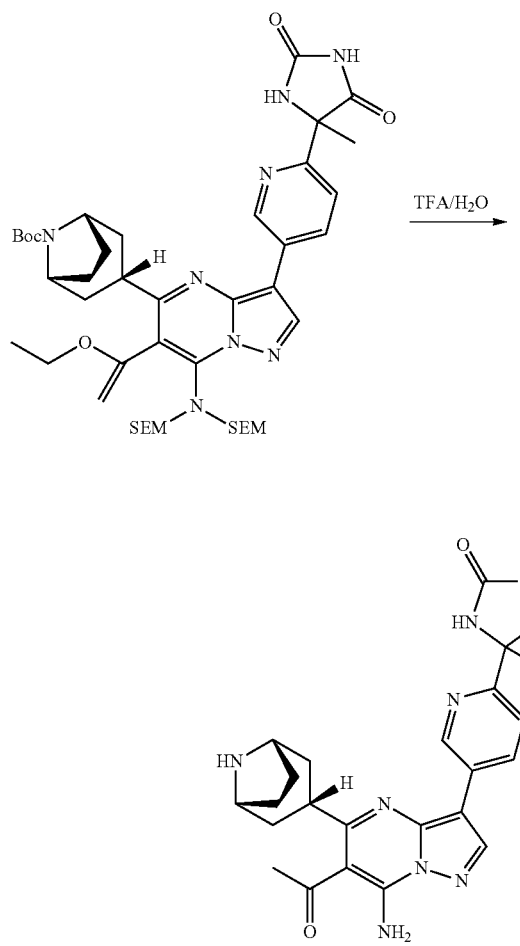

The compound of 5-(5-(6-acetyl-7-amino-5-((1R,3s,5S)-8-azabicyclo[3.2.1]octan-3- yl)pyrazolo[1,5-a]pyrimidin-3-

802 yl)pyridin-2-yl)-5-methylimidazolidine-2,4-dione was made with the same condition described previously.

Step 4: Preparation of 5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-5-methylimidazolidine-2,4-dione

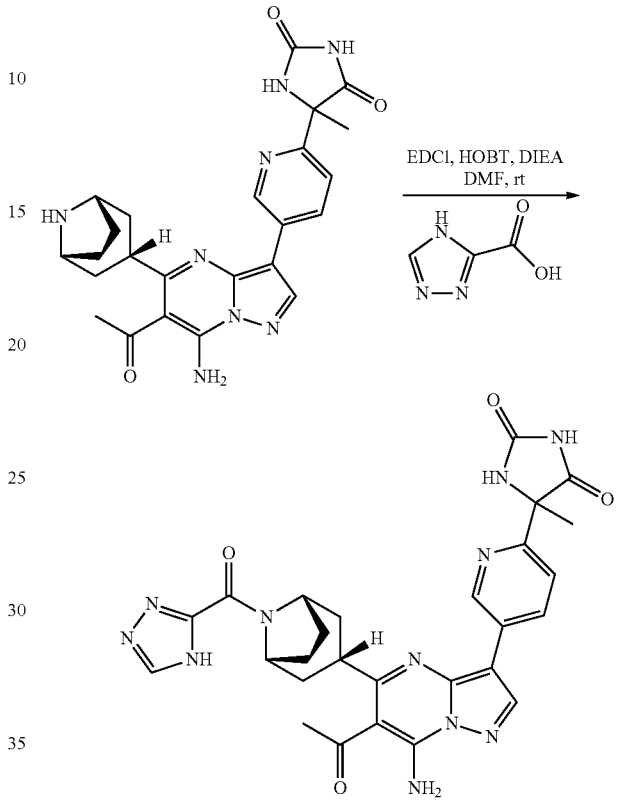

The compound of 5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-5-methylimidazolidine-2,4-dione was made with the same condition described previously.

Similarly compounds in Table 8-23 were made:

TABLE 8-23

| Compound ID | Structures | Compound Name | M + H (calculated)/ M + H (observed) | pAKT S473 IC50 | p4E-BP1 Thr37/46 IC50 |
|---|---|---|---|---|---|
| 8.68 | 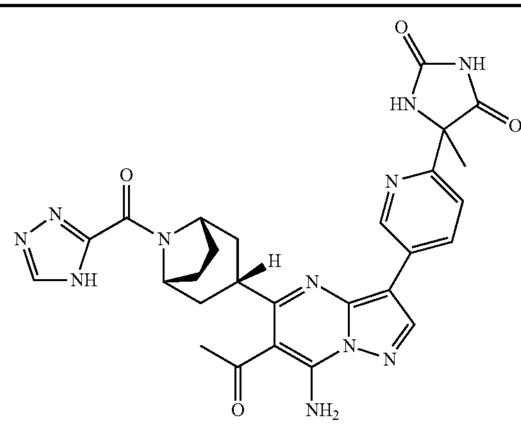 | 5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-5-methylimidazolidine-2,4-dione | 570.2/570.3 | ND | ND |

TABLE 8-23-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.69 | 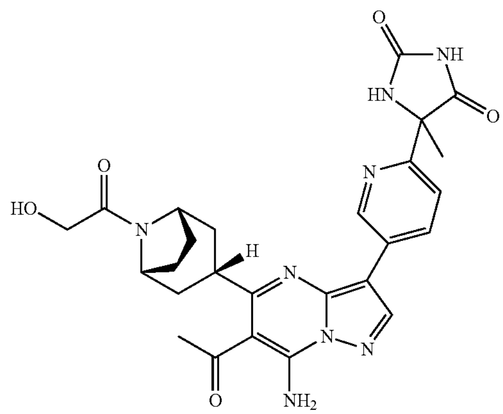 | 5-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)-5-methylimidazolidine-2,4-dione | 533.2/533.3 | ND | ND |

Example 8-30

Preparation of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile Step 1: Preparation of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile

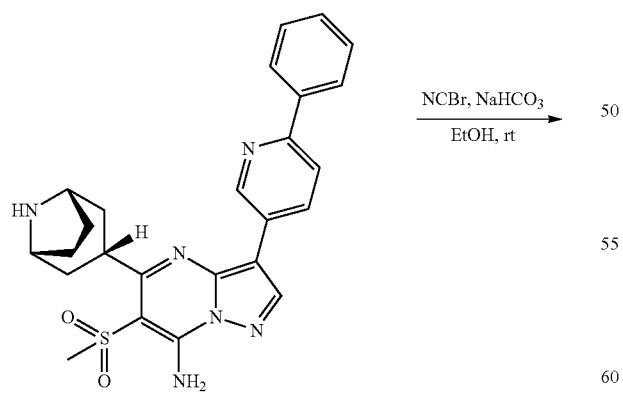

NCBr, NaHCO₃
⎯⎯⎯⎯⎯⎯→
EtOH, rt

-continued

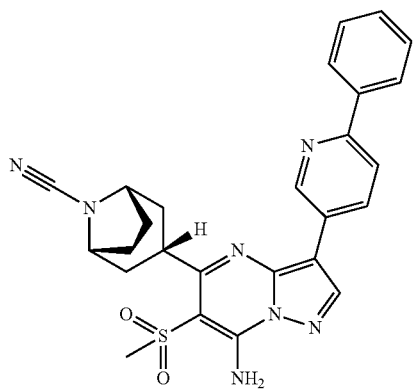

The compound 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine TFA salt (329 mg, 0.49 mmol) was mixed with NaHCO₃ (126 mg, 1.5 mmol) and NCBr (52 mg, 0.49 mmol) in EtOH (8 mL) and DMF (2 mL). The mixture was stirred at room temperature overnight and the solvent was removed under reduced pressure. The residue was taken up with water and the solid was collected through filtration and washed with water. The product was dried under air to give yellowish solid (213 mg).

Similarly compounds in Table 8-24 were made:

TABLE 8-24

| Compound ID | Structures | Compound Name | M + H (calculated)/ M + H (observed) | pAKT S473 IC50 | p4E-BP1 Thr37/46 IC50 |
|---|---|---|---|---|---|
| 8.70 | 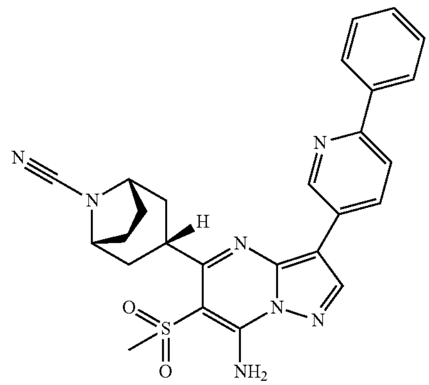 | (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile | 500.2/500.3 | B | C |
| 8.71 | 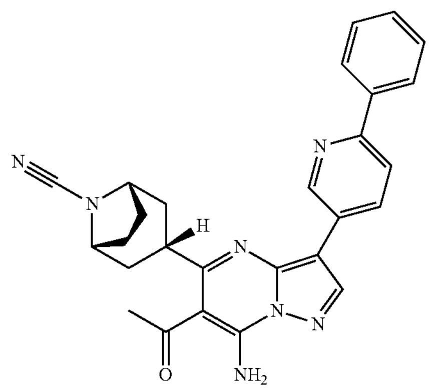 | (1R,3s,5S)-3-(6-acetyl-7-amino-3-(6-phenylpyridin-3-yl)pyrazolo[1,5-a]pyrimidin-5-yl)-8-azabicyclo[3.2.1]octane-8-carbonitrile | 464.2/464.2 | B | B |

Example 8-31

Preparation of (1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboximidamide

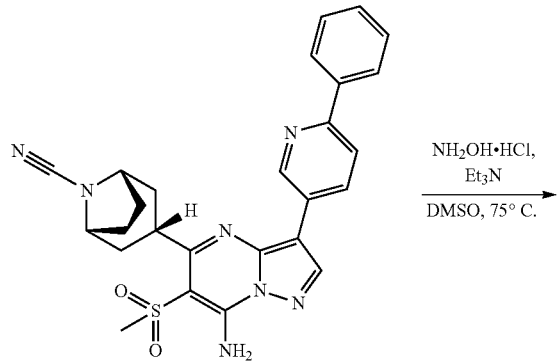

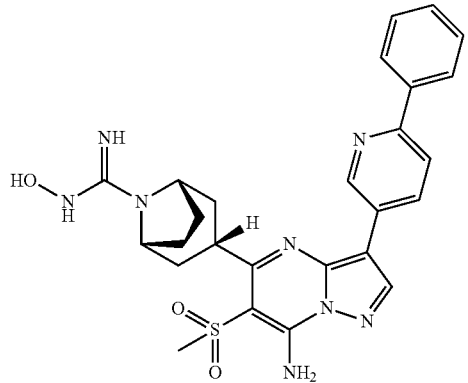

The compound (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile (213 mg, 0.426 mmol) was mixed with NH$_2$OH HCl salt (148 mg, 2.13 mmol) and Et$_3$N (326 uL mg, 2.34 mmol) in DMSO (2 mL). The mixture was heated up to 75° C. and stirred overnight. The solution was filtered and purified with HPLC to give the desired product (Table 8-25).

TABLE 8-25

| 8.72 | 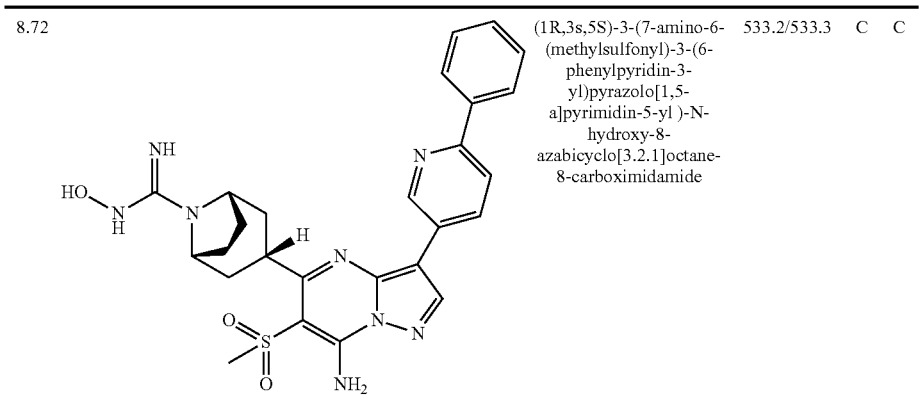 | (1R,3s,5S)-3-(7-amino-6-(methylsulfonyl)-3-(6-phenylpyridin-3-yl)pyrazolo[1,5-a]pyrimidin-5-yl )-N-hydroxy-8-azabicyclo[3.2.1]octane-8-carboximidamide | 533.2/533.3 | C | C |
|------|---|---|---|---|---|

Example 8-32

Preparation of (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboximidamide and 3-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one Step 1: Preparation of (1R,3s,5S)-3-(7-amino-6-(methylsulfonyl)-3-(6-phenylpyridin-3-yl)pyrazolo[1,5-a]pyrimidin-5-yl-8-azabicyclo[3.2.1]octane-8-carboximidamide and 3-((1R,3s, 5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one

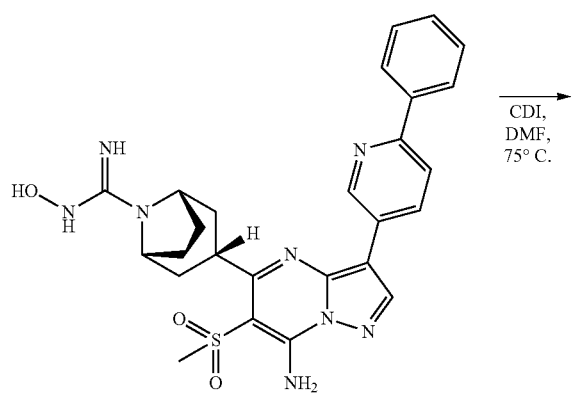

CDI, DMF, 75° C.

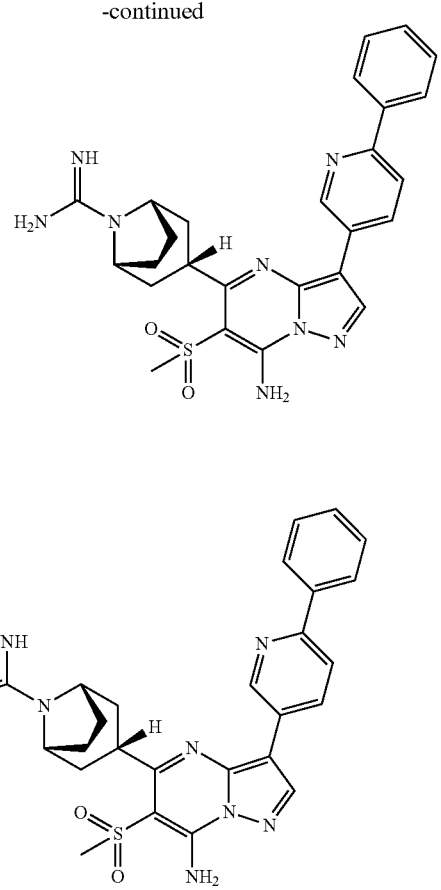

The compound (1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboximidamide (100 mg, 0.188 mmol) was mixed with CDI (31 mg, 0.19 mmol) in dry DMF (2 mL). The mixture was heated up to 75° C. and stirred for 1 hour. The mixture was diluted with more DMSO and purified with HPLC to give the product (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboximidamide and 3-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one (Table 8-26).

TABLE 8-26
| 8.73 | 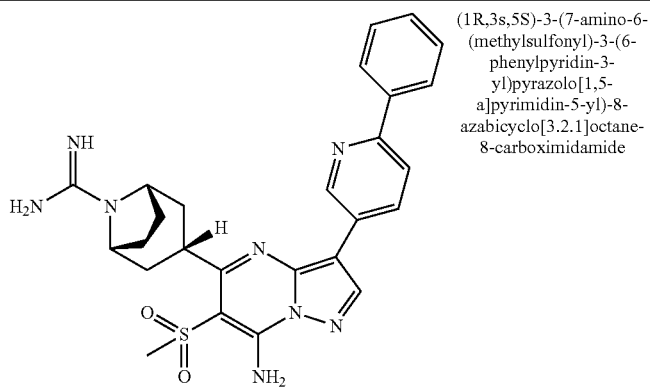 | (1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboximidamide | 517.2/517.2 | C | C |
| --- | --- | --- | --- | --- | --- |
| 8.74 | 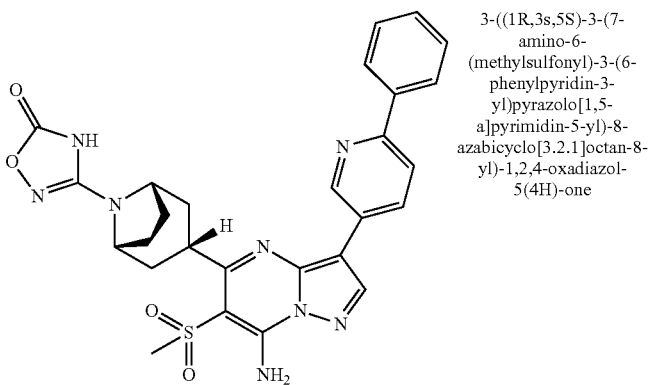 | 3-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one | 559.2/559.3 | C | D |
Example 8-33
Preparation of 1-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)-3-methylurea
Scheme 8-5
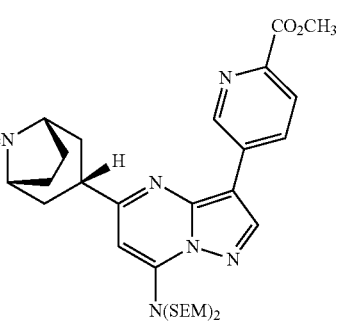
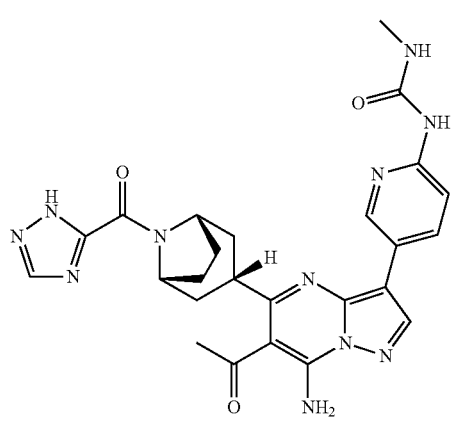 [SMILES: CNC(=O)Nc1ccc(-c2cnn3c(N)c(C(C)=O)c([C@@H]4C[C@H]5CC[C@@H](C4)N5C(=O)c4ncn[nH]4)nc23)cn1]
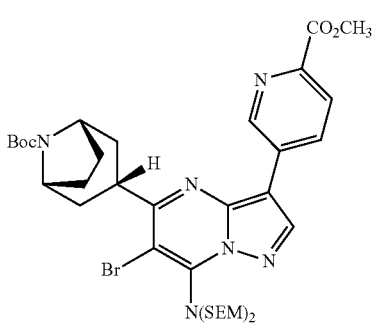

811
-continued
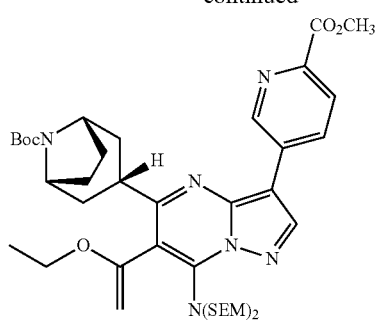
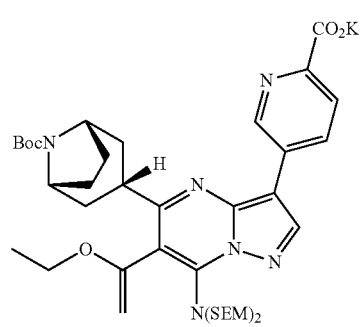
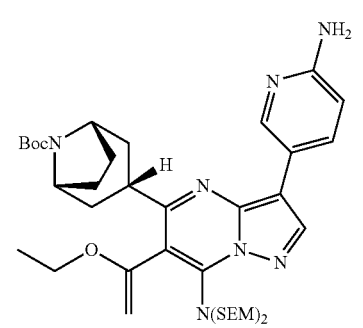
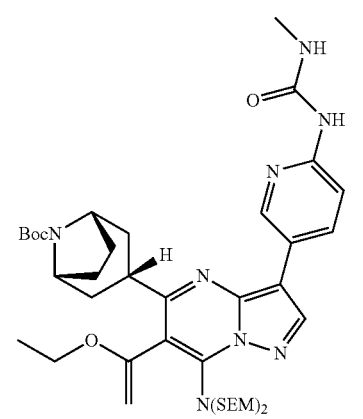
812
-continued
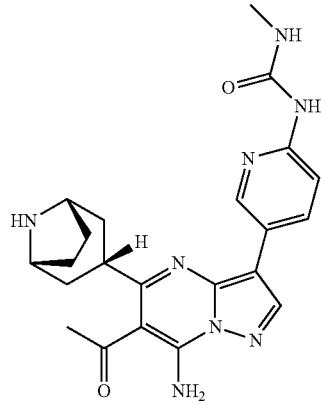
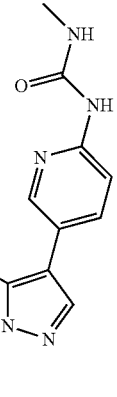
Step A—Synthesis of (1R,3s,5S)-tert-butyl 3-(7-(bis((2-(trimethylsilyl)ethoxy)methyl)amino)-6-bromo-3-(6-(methoxycarbonyl)pyridin-3-yl)pyrazolo[1,5-a]pyrimidin-5-yl)-8-azabicyclo[3.2.1]octane-8-carboxylate
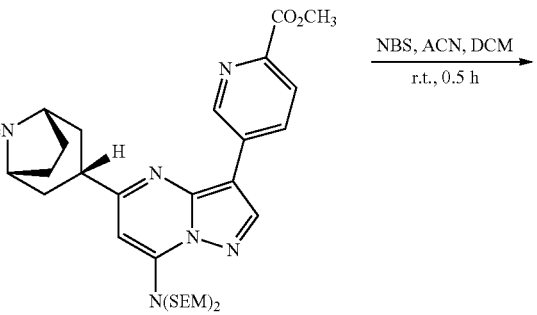

-continued

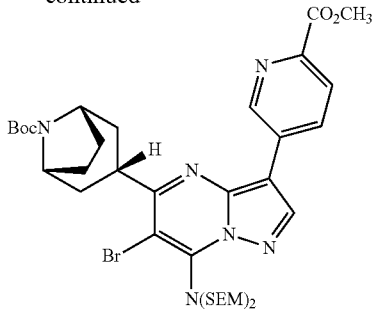

To a mixture of (1R,3s,5S)-tert-butyl 3-(7-(bis((2-(trimethylsilyl)ethoxy)methyl)amino)-3-(6-(methoxycarbonyl)pyridin-3-yl)pyrazolo[1,5-a]pyrimidin-5-yl)-8-azabicyclo[3.2.1]octane-8-carboxylate (3.7 g, 5.01 mmol) in CH$_3$CN (25 mL) and dichloromethane (25 mL) was added N-bromosuccinimide (0.98 g, 5.5 mmol) in one portion and the resulting mixture was stirred at room temperature for 0.5 h, at which time LC/MS confirmed reaction was not complete. Added more N-bromosuccinimide (0.98 g, 5.5 mmol) in one portion and the resulting mixture was stirred at room temperature for 1.5 h at which time LC/MS confirmed full conversion of starting material to product. The solvent was removed in vacuo and the residue was purified by column chromatography on silica gel. Elution with EtOAc/Hexanes (20-50%) gave the title product (3.2 g).

Step B—Synthesis of (1R,3s,5S)-tert-butyl 3-(7-(bis((2-(trimethylsilyl)ethoxy)methyl)amino)-6-(1-ethoxyvinyl)-3-(6-(methoxycarbonyl)pyridin-3-yl)pyrazolo[1,5-a]pyrimidin-5-yl-8-azabicyclo[3.2.1]octane-8-carboxylate

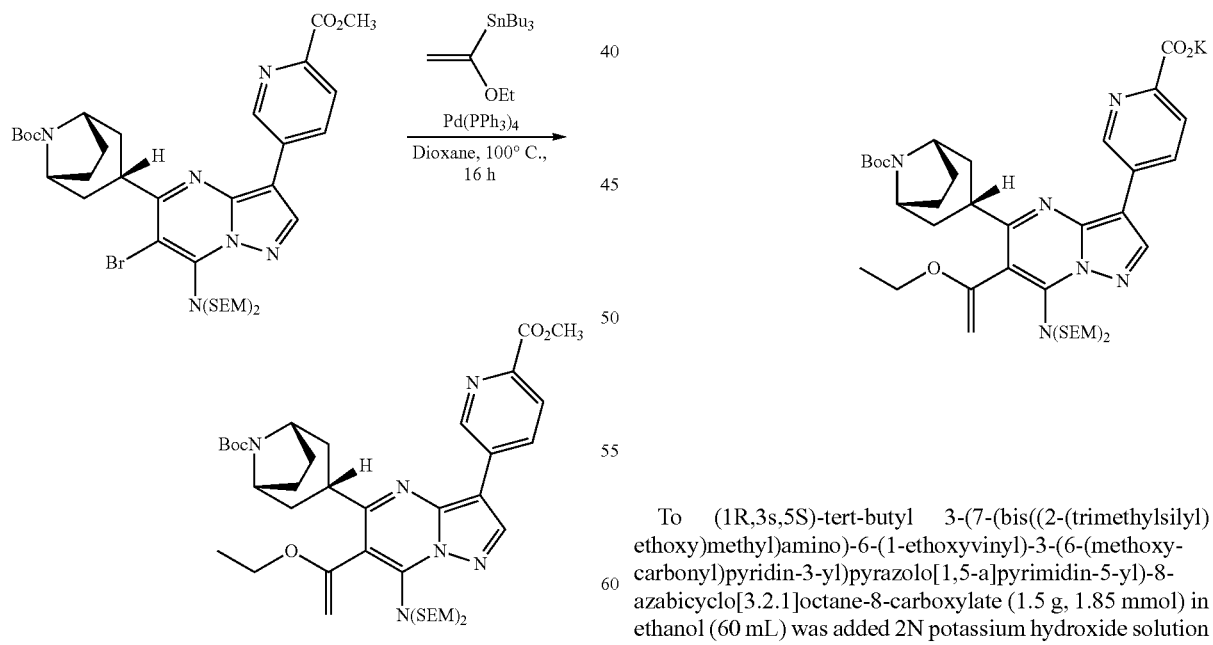

A mixture of compound (1R,3s,5S)-tert-butyl 3-(7-(bis((2-(trimethylsilyl)ethoxy)methyl)amino)-6-bromo-3-(6-(methoxycarbonyl)pyridin-3-yl)pyrazolo[1,5-a]pyrimidin-5-yl)-8-azabicyclo[3.2.1]octane-8-carboxylate (2.6 g, 3.18 mmol), tributyl(1-ethoxyvinyl)tin (2.30 g, 6.37 mmol), tetrakis(triphenylphosphine)palladium (0.73 g, 0.64 mmol) in dioxane (30 mL) was degassed with argon for five minutes. It was then heated at 100° C. in a sealed tube for 16 h, at which time LC/MS analysis confirmed full consumption of starting material. On cooling, the solvent was concentrated in vacuo, and the crude residue was dissolved in EtOAc (150 mL), washed with 0.5 M KF solution (1×50 mL), water (1×50 mL), brine (1×50 mL), and dried over MgSO$_4$. The solvent was removed in vacuo and the residue was purified by column chromatography on silica gel. Elution with EtOAc/Hexanes (20-70%) gave the title product (1.9 g).

Step C—Synthesis of potassium 5-(7-(bis((2-(trimethylsilyl)ethoxy)methyl)amino)-5-((1R,3s,5S)-8-(tert-butoxycarbonyl)-8-azabicyclo[3.2.1]octan-3-yl)-6-(1-ethoxyvinyl)pyrazolo[1,5-a]pyrimidin-3-yl)picolinate

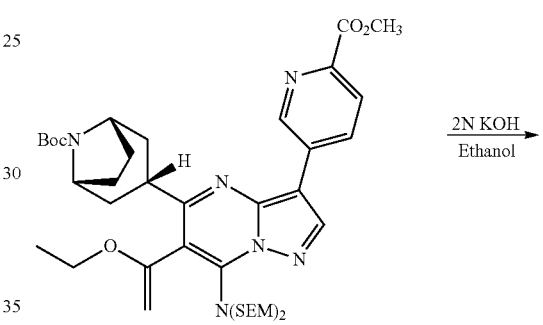

To (1R,3s,5S)-tert-butyl 3-(7-(bis((2-(trimethylsilyl)ethoxy)methyl)amino)-6-(1-ethoxyvinyl)-3-(6-(methoxycarbonyl)pyridin-3-yl)pyrazolo[1,5-a]pyrimidin-5-yl)-8-azabicyclo[3.2.1]octane-8-carboxylate (1.5 g, 1.85 mmol) in ethanol (60 mL) was added 2N potassium hydroxide solution (1.1 mL, 2.2 mmol). The resulting solution was stirred at room temperature for 16 h at which time LC-MS analysis indicated full conversion of starting material to product. The solvent was removed in vacuo to afford desired product 1.51 g.

Step D—Synthesis of (1R,3s,5S)-tert-butyl 3-(3-(6-aminopyridin-3-yl)-7-(bis((2-(trimethylsilyl)ethoxy)methyl)amino)-6-(1-ethoxyvinyl)pyrazolo[1,5-a]pyrimidin-5-yl)-8-azabicyclo[3.2.1]octane-8-carboxylate

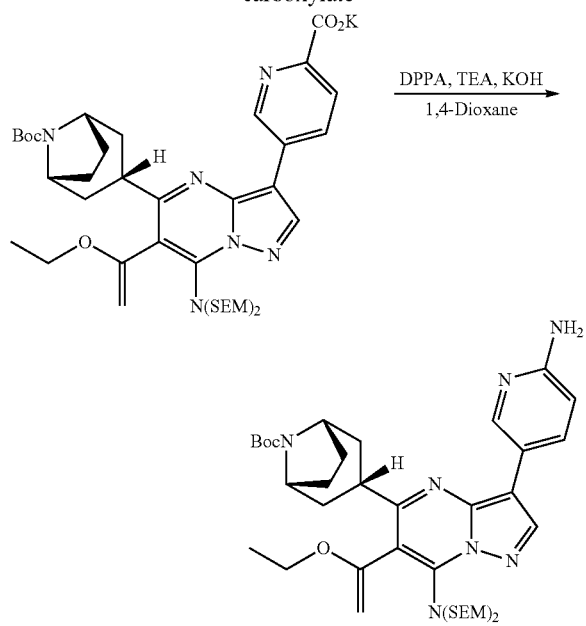

To potassium 5-(7-(bis((2-(trimethylsilyl)ethoxy)methyl)amino)-5-((1R,3s,5S)-8-(tert-butoxycarbonyl)-8-azabicyclo[3.2.1]octan-3-yl)-6-(1-ethoxyvinyl)pyrazolo[1,5-a]pyrimidin-3-yl)picolinate (0.5 g, 0.63 mmol) in 1,4-dioxane (20 mL) was added followed by potassium hydroxide (0.7 mg, 0.13 mmol), diphenylphosphoryl azide (0.2 mL, 0.94 mmol) and triethylamine (0.18 mL, 1.26 mmol). The resulting solution was stirred at 80° C. for 2 hours at which time LC-MS analysis indicated reaction was complete. The reaction mixture was cooled to room temperature, poured into water (30 mL) and then extracted with ethyl acetate (3×50 mL). The combined organic extract was washed with brine (50 mL), and dried over MgSO₄. The solvent was removed in vacuo and the residue was purified by column chromatography on silica gel. Elution with EtOAc/Hexanes (20-70%) gave the title product (202 mg).

Step E—Synthesis of (1R,3s,5S)-tert-butyl 3-(7-(bis((2-(trimethylsilyl)ethoxy)methyl)amino)-6-(1-ethoxyvinyl)-3-(6-(3-methylureido)pyridin-3-yl)pyrazolo[1,5-a]pyrimidin-5-yl)-8-azabicyclo[3.2.1]octane-8-carboxylate

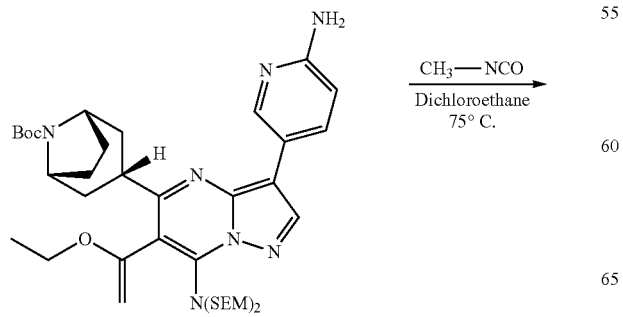

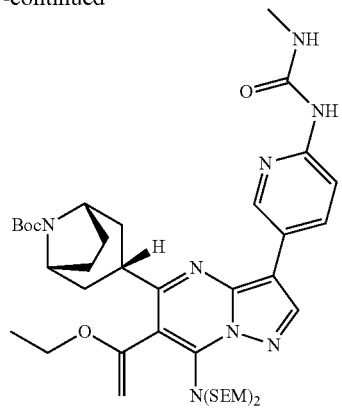

To (1R,3s,5S)-tert-butyl 3-(3-(6-aminopyridin-3-yl)-7-(bis((2-(trimethylsilyl)ethoxy)methyl)amino)-6-(1-ethoxyvinyl)pyrazolo[1,5-a]pyrimidin-5-yl)-8-azabicyclo[3.2.1]octane-8-carboxylate (150 mg, 0.195 mmol) in 1,2-dichloroethane (3 mL) was added methyl isocyanate (12.7 uL, 0.205 mmol) and the resulting solution stirred at 75° C. for 16 hours, at which time LC-MS analysis indicated the reaction was complete. The solvent was removed in vacuo to afford desired product which was used without further purification in the next reaction step in the synthetic sequence.

Step F—Synthesis of 1-(5-(6-acetyl-7-amino-5-((1R,3s,5S)-8-azabicyclo[3.2.1]octan-3-yl)pyrazolo[1,5-a]pyrimidin-3-yl)pyridin-2-yl)-3-methylurea

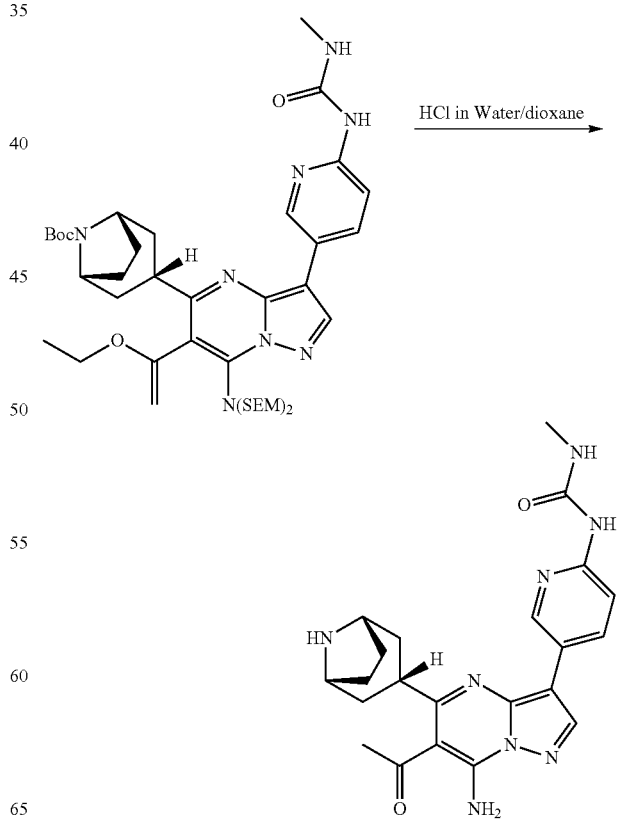

To a mixture of (1R,3s,5S)-tert-butyl 3-(7-(bis((2-(trimethylsilyl)ethoxy)methyl)amino)-6-(1-ethoxyvinyl)-3-(6-(3-methylureido)pyridin-3-yl)pyrazolo[1,5-a]pyrimidin-5-yl)-8-azabicyclo[3.2.1]octane-8-carboxylate (0.13 g, 0.156 mmol) in dioxane (2 mL) was added 4 M HCl in water (1 ml) at 0° C. After stirring for 10 min at 0° C., 4 M HCl in dioxane (1 mL) was added. The reaction mixture was stirred at 0° C. for 30 min and the cooling bath was removed to warm it up to room temperature for 30 minutes, and then heated at 50° C. for 1 hour at which time LC/MS analysis confirmed full consumption of starting material. The solvent was removed in vacuo to get the desired product as an HCl salt. This HCl product was lyophilized to afford the desired product as a yellow solid (70 mg).

Step G—Synthesis of 1-(5-(6-acetyl-7-amino-5-((1R,3s,5S)-8-(1-((2-(trimethylsilyl)ethoxy)methyl)-1H-1,2,4-triazole-5-carbonyl)-8-azabicyclo[3.2.1]octan-3-yl)pyrazolo[1,5-a]pyrimidin-3-yl)pyridin-2-yl)-3-methylurea

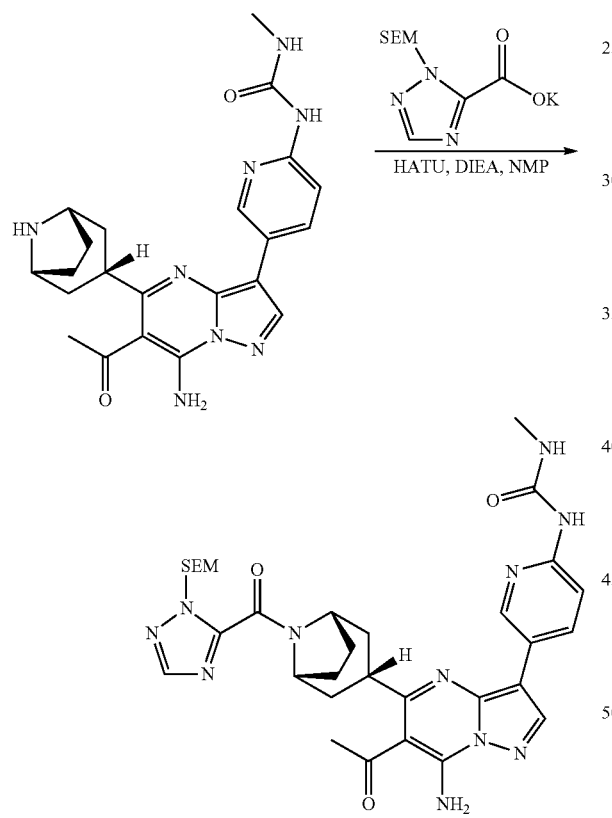

A mixture of potassium 1((2-(trimethylsilyl)ethoxy)methyl)-1H-1,2,4-triazole-5-carboxylate (41.0 mg, 0.145 mmol), 1-(5-(6-acetyl-7-amino-5-((1R,3s,5S)-8-azabicyclo[3.2.1]octan-3-yl)pyrazolo[1,5-a]pyrimidin-3-yl)pyridin-2-yl)-3-methylurea (68 mg 0.145 mmol), N,N-diisopropylethylamine (0.051 mL, 0.289 mmol in NMP (2 ml) was stirred at room temperature for 10 min. 2-(7-Aza-1H-benzotriazole-1-yl)-1,1,3,3-tetramethyluronium hexafluorophosphate (HATU) (55 mg, 0.145 mmol) was added to the reaction mixture at room temperature in one portion. The reaction was stirred for 30 min at room temperature at which time LC/MS analysis confirmed full consumption of starting material. The reaction was diluted with ethyl acetate (10 mL) and extracted with water (2×5 mL) and brine (1×5 mL). The organic layer was dried using anhydrous sodium sulfate, filtered, and concentrated in vacuo and the residue was purified by column chromatography on silica gel. Elution with EtOAc/Hexanes (75-100%) gave the title product (67 mg).

Step H—Synthesis of 1-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)-3-methylurea

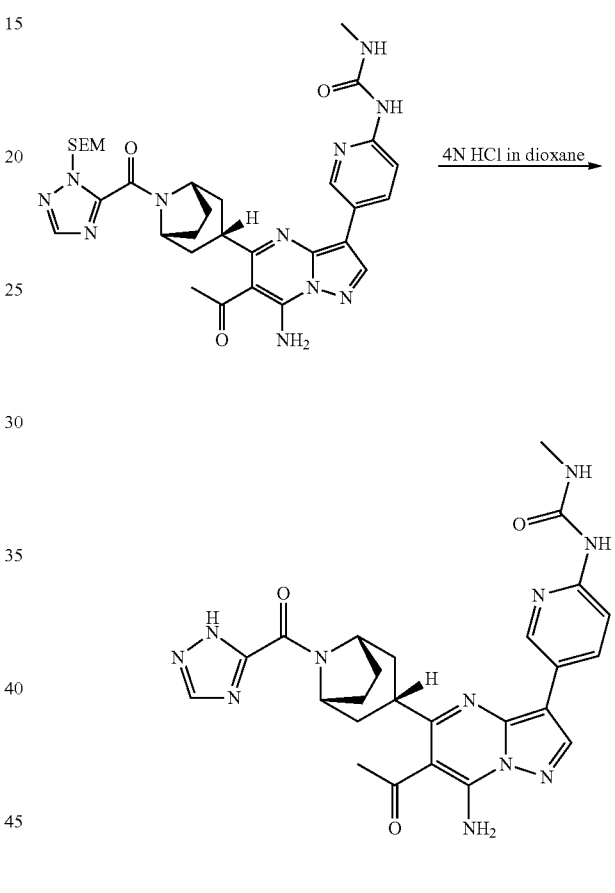

To a mixture of 1-(5-(6-acetyl-7-amino-5-((1R,3s,5S)-8-(1-((2-(trimethylsilyl)ethoxy)methyl)-1H-1,2,4-triazole-5-carbonyl)-8-azabicyclo[3.2.1]octan-3-yl)pyrazolo[1,5-a]pyrimidin-3-yl)pyridin-2-yl-3-methylure (67 mg, 0.102 mmol) in dioxane (2 mL) and water (1 mL) was added 4 M HCl in dioxane (2 ml) at room temperature. The reaction mixture was heated at 50° C. for 1 hour at which time LC/MS analysis confirmed full consumption of starting material. The solvent was removed in vacuo. This crude compound was purified by HPLC to afford the desired product. LC/MS RT=2.01 min. Mass calculated for M+H 530.2, observed 530.0.

Following Scheme 8-5 and procedures similar to the preparation of 1-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)-3-methylurea, the following compounds listed in Table 8-26 below were prepared:

TABLE 8-26

| Compound ID | Structures | Compound Name | M + H (calculated)/ M + H (observed) | pAKT S473 IC50 | p4E-BP1 Thr37/46 IC50 |
|---|---|---|---|---|---|
| 8.75 | 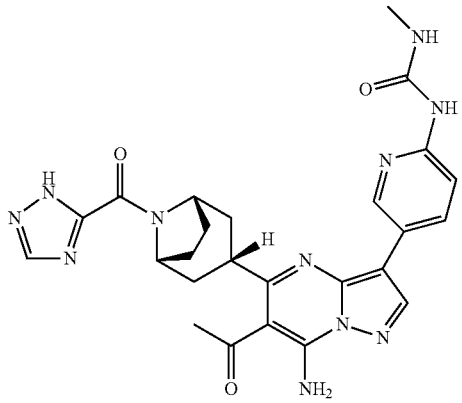 [SMILES: CNC(=O)Nc1ccc(-c2cnn3c(N)c(C(C)=O)c([C@@H]4C[C@H]5CC[C@@H](C4)N5C(=O)c4ncn[nH]4)nc23)cn1] | 1-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)-3-methylurea | 530.2/530.0 | A | B |
| 8.76 | 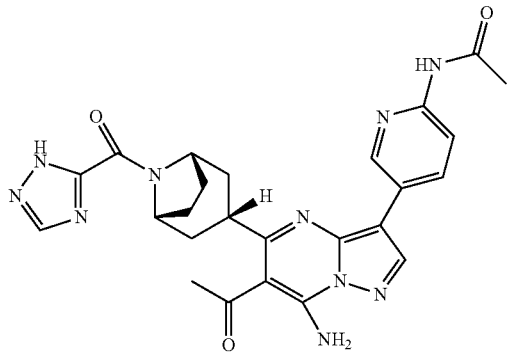 [SMILES: CC(=O)Nc1ccc(-c2cnn3c(N)c(C(C)=O)c([C@@H]4C[C@H]5CC[C@@H](C4)N5C(=O)c4ncn[nH]4)nc23)cn1] | N-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)acetamide | 515.2/514.9 | A | A |
| 8.77 | 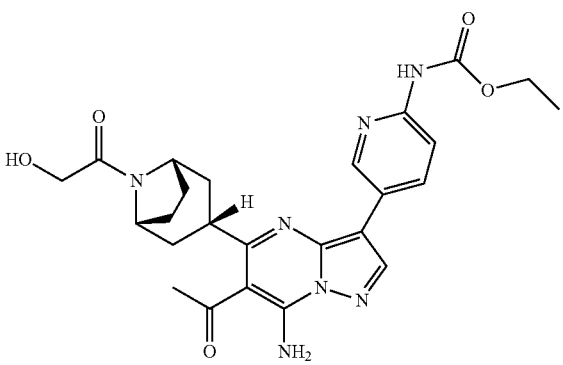 [SMILES: CCOC(=O)Nc1ccc(-c2cnn3c(N)c(C(C)=O)c([C@@H]4C[C@H]5CC[C@@H](C4)N5C(=O)CO)nc23)cn1] | ethyl 5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-ylcarbamate | 508.2/508.0 | B | ND |
| 8.78 | 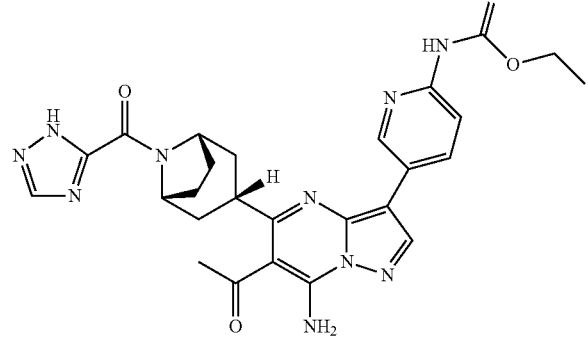 | ethyl 5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-ylcarbamate | 545.2/544.9 | A | A |

TABLE 8-26-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.79 | 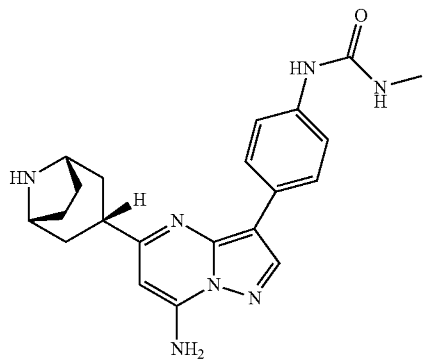 [SMILES: CNC(=O)Nc1ccc(-c2cnn3c(N)cc([C@@H]4C[C@H]5CC[C@@H](C4)N5)nc23)cc1] | 1-(4-(7-amino-5-((1R,3s,5S)-8-azabicyclo[3.2.1]octan-3-yl)pyrazolo[1,5-a]pyrimidin-3-yl)phenyl)-3-methylurea | 391.2/392.0 | ND | ND |
| 8.80 | 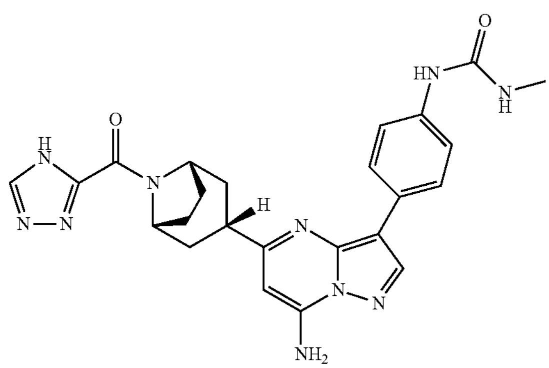 [SMILES: CNC(=O)Nc1ccc(-c2cnn3c(N)cc([C@@H]4C[C@H]5CC[C@@H](C4)N5C(=O)c4nnc[nH]4)nc23)cc1] | 1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)phenyl)-3-methylurea | 486.22/487.0 | D | D |
| 8.81 | 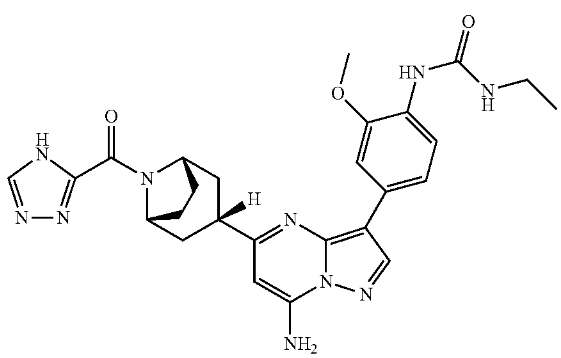 [SMILES: CCNC(=O)Nc1ccc(-c2cnn3c(N)cc([C@@H]4C[C@H]5CC[C@@H](C4)N5C(=O)c4nnc[nH]4)nc23)cc1OC] | 1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)-2-methoxyphenyl)-3-ethylurea | 530.25/531.0 | ND | ND |
| 8.82 | 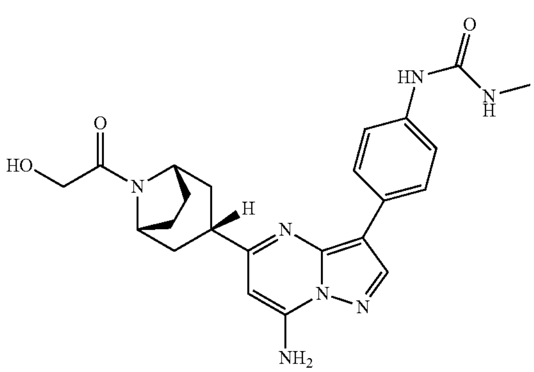 [SMILES: CNC(=O)Nc1ccc(-c2cnn3c(N)cc([C@@H]4C[C@H]5CC[C@@H](C4)N5C(=O)CO)nc23)cc1] | 1-(4-(7-amino-5-((1R,3s,5S)-8-(2-hydroxyacetyl)-8-azabicyclo[3.2.1]octan-3-yl)pyrazolo[1,5-a]pyrimidin-3-yl)phenyl)-3-methylurea | 449.22/450.0 | D | D |

TABLE 8-26-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.83 | 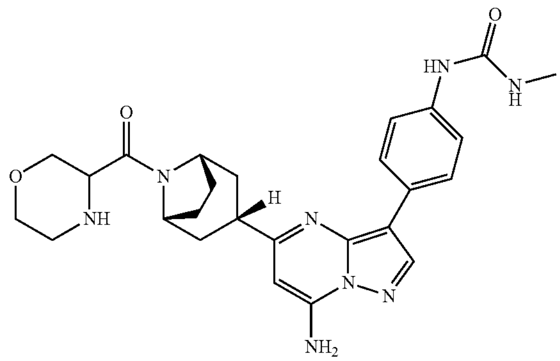 [SMILES: CNC(=O)Nc1ccc(-c2cnn3c(N)cc([C@@H]4C[C@H]5CC[C@@H](C4)N5C(=O)C4COCCN4)nc23)cc1] | 1-(4-(7-amino-5-((1R,3s,5S)-8-(morpholine-3-carbonyl)-8-azabicyclo[3.2.1]octan-3-yl)pyrazolo[1,5-a]pyrimidin-3-yl)phenyl)-3-methylurea | 504.26/505.0 | ND | ND |
| 8.84 | 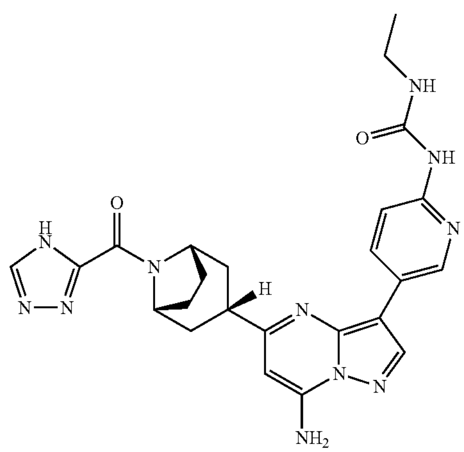 [SMILES: CCNC(=O)Nc1ccc(-c2cnn3c(N)cc([C@@H]4C[C@H]5CC[C@@H](C4)N5C(=O)c4nnc[nH]4)nc23)cn1] | 1-(5-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyridin-2-yl)-3-ethylurea | 501.23/502.0 | ND | ND |
| 8.85 | 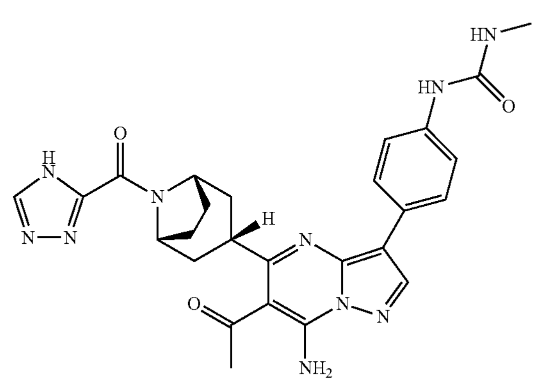 [SMILES: CNC(=O)Nc1ccc(-c2cnn3c(N)c(C(C)=O)c([C@@H]4C[C@H]5CC[C@@H](C4)N5C(=O)c4nnc[nH]4)nc23)cc1] | 1-(4-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)phenyl)-3-methylurea | 528.23/529.0 | A | B |

Example 8-34

Preparation of (1R,3s,5S,E)-3-(7-amino-3-(6-phenylpyridin-3-yl)pyrazolo[1,5-a]pyrimidin-5-yl)-N'-cyano-8-azabicyclo[3.2.1]octane-8-carboximidamide

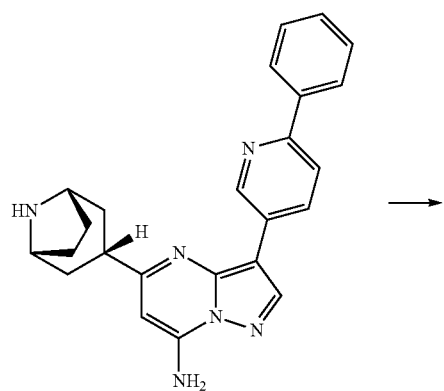

→

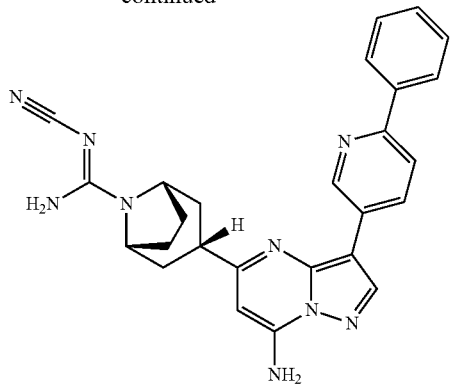

To 5-((1R,3s,5S)-8-azabicyclo[3.2.1]octan-3-yl)-3-(6-phenylpyridin-3-yl)pyrazolo[1,5-a]pyrimidin-7-amine (142 mg, 0.299 mmol, 1.00 equiv) and DIEA (0.16 mL, 0.90 mmol, 3.0 equiv) in DCM (3 mL) was added diphenyl cyanocarbonimidate (71 mg, 0.30 mmol, 1.0 equiv). The resulting solution was allowed to stir at it for 18 hr and then was concentrated. The residue was dissolved in DMF (3 mL) and conc. $NH_4OH$ (10 mL) and then was heated in a sealed vessel at 100° C. for 24 hr. Concentration and purification of the residue by preparative chromatography afforded the title compound (1R,3s,5S,E)-3-(7-amino-3-(6-phenylpyridin-3-yl)pyrazolo[1,5-a]pyrimidin-5-yl)-N'-cyano-8-azabicyclo[3.2.1]octane-8-carboximidamide (11.1 mg).

Following this example and previous procedures, compounds (Table 8-27) were made:

TABLE 8-27

| Compound ID | Structures | Compound Name | M + H (calculated)/ M + H (observed) | pAKT S473 IC50 | p4E-BP1 Thr37/46 IC50 |
|---|---|---|---|---|---|
| 8.86 | (structure) | (1R,3s,5S,E)-3-(7-amino-3-(6-phenylpyridin-3-yl)pyrazolo[1,5-a]pyrimidin-5-yl)-N'-cyano-8-azabicyclo[3.2.1]octane-8-carboxamide | 463.22/464.0 | C | C |
| 8.87 | (structure) | (1R,3s,5S,E)-3-(7-amino-6-(methylsulfonyl)-3-(6-phenylpyridin-3-yl)pyrazolo[1,5-a]pyrimidin-5-yl)-N'-cyano-8-azabicyclo[3.2.1]octane-8-carboximidamide | 541.20/541.9 | A | B |

Example 8-35

Preparation of ((1R,3s,5S)-3-(7-amino-3-(2-aminopyrimidin-5-yl)pyrazolo[1,5-a]pyrimidin-5-yl)-8-azabicyclo[3.2.1]octan-8-yl)(4H-1,2,4-triazol-3-yl)methanone

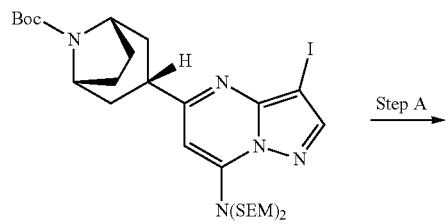

Step A →

Preparation of ((1R,3s,5S)-3-(7-amino-3-(2-aminopyrimidin-5-yl)pyrazolo[1,5-a]pyrimidin-5-yl)-8-azabicyclo[3.2.1]octan-8-yl)(4H-1,2,4-triazol-3-yl)methanone Step A: A suspension of (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (500 mg, 0.686 mmol, 1.00 equiv), 2-aminopyrimidin-5-ylboronic acid (143 mg, 1.03 mmol, 1.50 equiv), $PdCl_2(dppf)$ (56 mg, 0.069 mmol, 0.1 mmol) in dioxane/water (7/0.7 mL) was allowed to stir at 85° C. for 18 hr. After cooling to rt, the crude reaction mixture was filtered, concentrated affording the title compound that was used directly in Step B.

Step B: The crude residue was treated with 4N HCl dioxane/water (5/1) for 30 min. Lyophilization afforded the crude residue which was converted to the final product (1R,3s,5S)-tert-butyl 3-(3-(2-aminopyrimidin-5-yl)-7-(bis((2-(trimethylsilyl)ethoxy)methyl)amino)pyrazolo[1,5-a]pyrimidin-5-yl)-8-azabicyclo[3.2.1]octane-8-carboxylate with an EDCI-mediated coupling.

TABLE 8-28

| Compound ID | Structures | Compound Name | M + H (calculated)/ M + H (observed) | pAKT S473 IC50 | p4E-BP1 Thr37/46 IC50 |
|---|---|---|---|---|---|
| 8.88 | 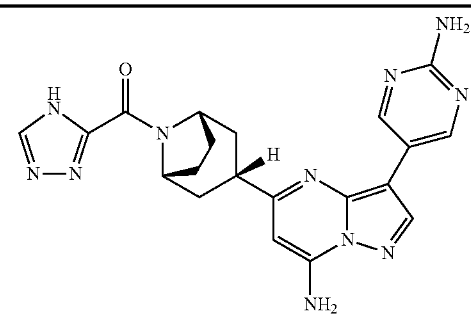 | ((1R,3s,5S)-3-(7-amino-3-(2-aminopyrimidin-5-yl)pyrazolo[1,5-a]pyrimidin-5-yl)-8-azabicyclo[3.2.1]octan-8-yl)(4H-1,2,4-triazol-3-yl)methanone | 431.19/432.0 | D | ND |

Example 8-36

Preparation of 6-(methylsulfonyl)-3-(6-phenylpyridin-3-yl)-5-((1R,3s,5S)-8-(2,2,2-trifluoroethyl)-8-azabicyclo[3.2.1]octan-3-yl)pyrazolo[1,5-a]pyrimidin-7-amine

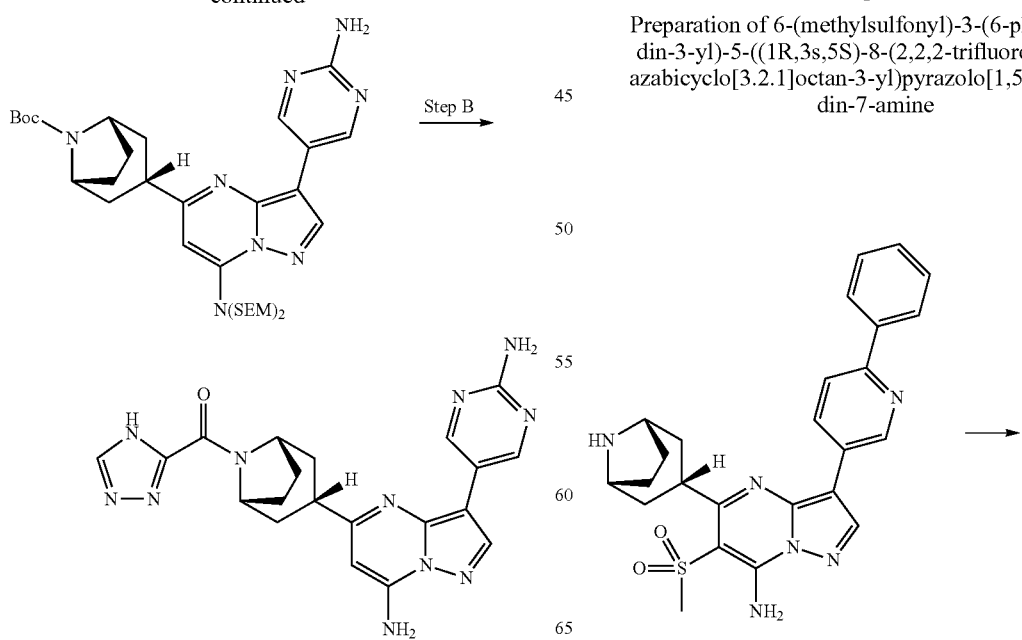

829
-continued

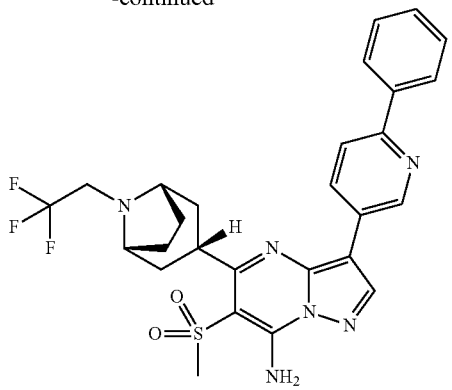

830

To a solution of 5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine (0.22 g, 0.051 mmol, 1.00 equiv) and DIEA (0.44 mL, 2.6 mmol, 5.0 equiv) in DMF (2 mL) at it was added 2,2,2-trifluoroethyl trifluoromethanesulfonate (0.12 mL, 0.51 mmol, 1.0 equiv). The resulting solution was stirred at it for 24 hr, concentrated and preparative chromatography afforded the title compound 6-(methylsulfonyl)-3-(6-phenylpyridin-3-yl)-5-((1R,3s,5S)-8-(2,2,2-trifluoroethyl)-8-azabicyclo[3.2.1]octan-3-yl)pyrazolo[1,5-a]pyrimidin-7-amine.

Similarly, compounds (Table 8-29) were prepared:

TABLE 8-29

| Compound ID | Structures | Compound Name | M + H (calculated)/ M + H (observed) | pAKT S473 IC50 | p4E-BP1 Thr37/46 IC50 |
|---|---|---|---|---|---|
| 8.89 | 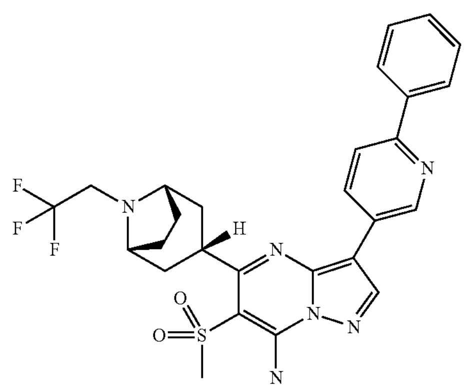 [SMILES: CS(=O)(=O)c1c([C@@H]2C[C@H]3CC[C@@H](C2)N3CC(F)(F)F)nc2c(-c3ccc(-c4ccccc4)nc3)cnn2c1N] | 6-(methylsulfonyl)-3-(6-phenylpyridin-3-yl)-5-((1R,3s,5S)-8-(2,2,2-trifluoroethyl)-8-azabicyclo[3.2.1]octan-3-yl)pyrazolo[1,5-a]pyrimidin-7-amine | 556.19/556.2 | ND | ND |
| 8.90 | 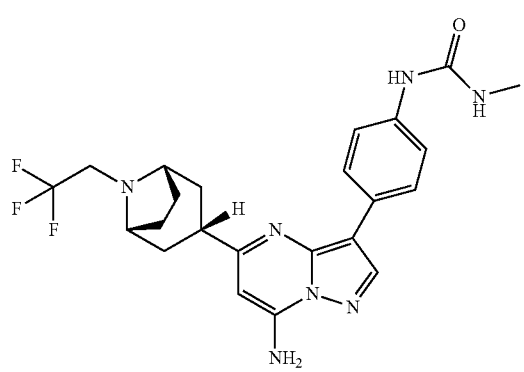 [SMILES: CNC(=O)Nc1ccc(-c2cnn3c(N)cc([C@@H]4C[C@H]5CC[C@@H](C4)N5CC(F)(F)F)nc23)cc1] | 1-(4-(7-amino-5-((1R,3s,5S)-8-(2,2,2-trifluoroethyl)-8-azabicyclo[3.2.1]octan-3-yl)pyrazolo[1,5-a]pyrimidin-3-yl)phenyl)-3-methylurea | 473.22/474.0 | ND | ND |

TABLE 8-29-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.91 | 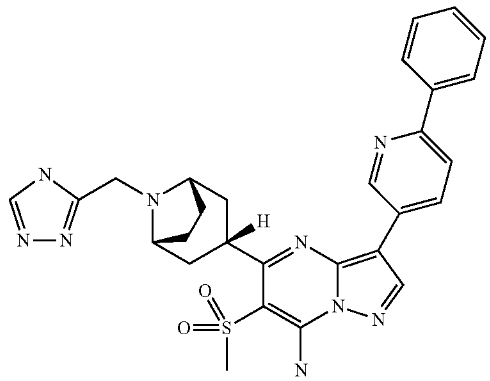 [SMILES: CS(=O)(=O)c1c([C@@H]2C[C@H]3CC[C@@H](C2)N3Cc2nnc[nH]2)nc2c(-c3ccc(-c4ccccc4)nc3)cnn2c1N] | 5-((1R,3s,5S)-8-((4H-1,2,4-triazol-3-yl)methyl)-8-azabicyclo[3.2.1]octan-3-yl)-6-(methylsulfonyl)-3-(6-phenylpyridin-3-yl)pyrazolo[1,5-a]pyrimidin-7-amine | 555.22/556.2 | ND | ND |
| 8.92 | 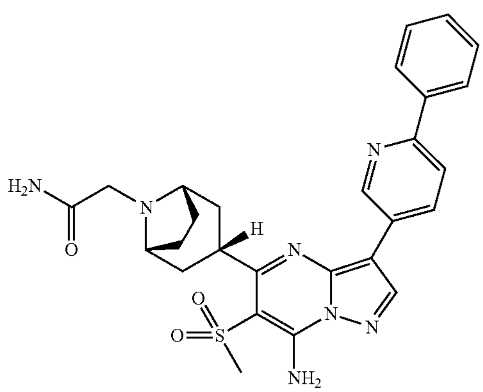 [SMILES: CS(=O)(=O)c1c([C@@H]2C[C@H]3CC[C@@H](C2)N3CC(N)=O)nc2c(-c3ccc(-c4ccccc4)nc3)cnn2c1N] | 2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)acetamide | 531.21/532.0 | C | ND |

Example 8-37

Preparation of 1-(5-((1R,3s,5S)-8-(4H-1,2,4-triazole-3-carbonyl)-8-azabicyclo[3.2.1]octan-3-A-7-amino-3-(6-(1-amino-2,2,2-trifluoroethyl)pyridin-3-yl)pyrazolo[1,5-a]pyrimidin-6-yl)ethanone

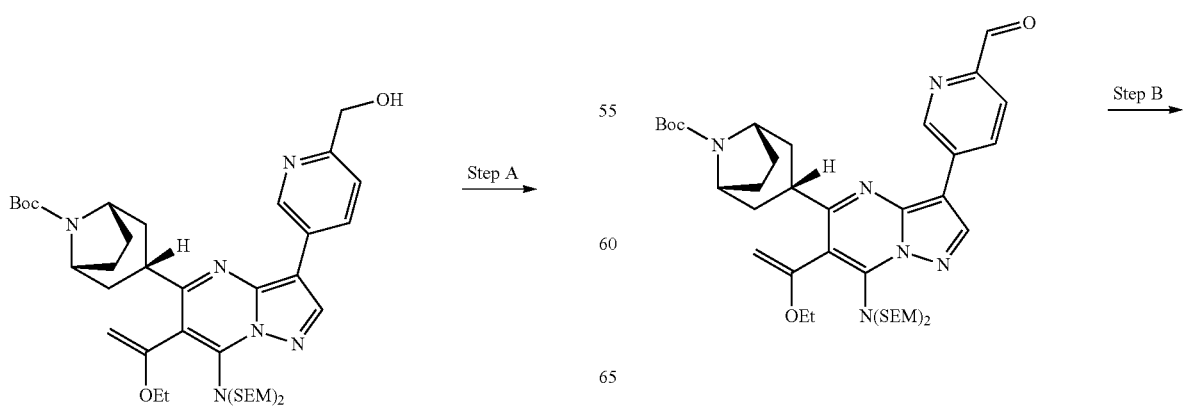

833
-continued

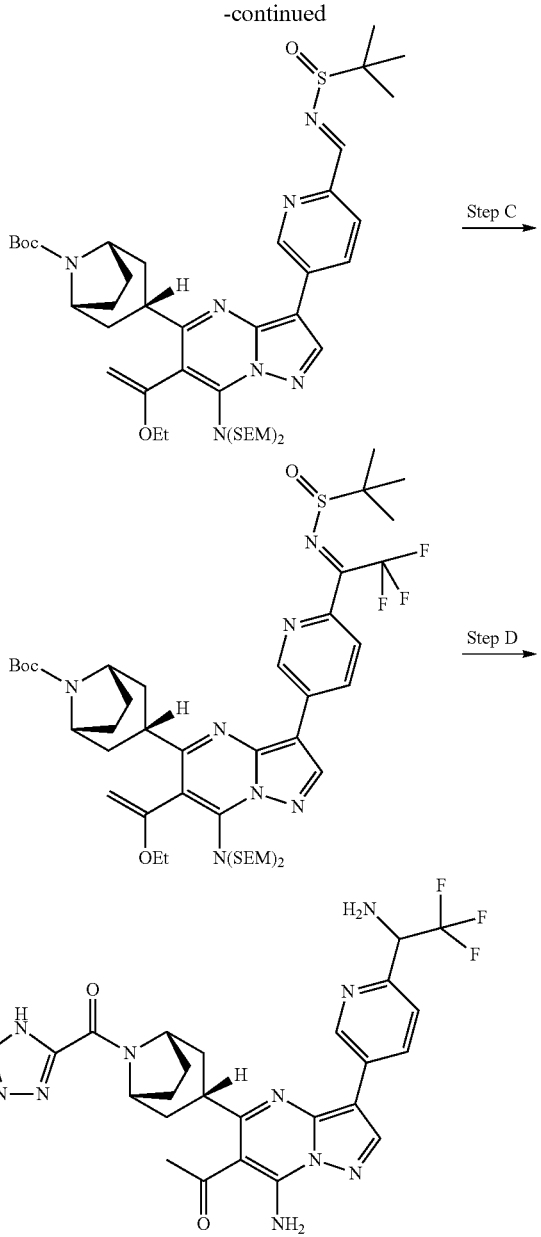

Step A: To a solution of (1R,3s,5S)-tert-butyl 3-(7-(bis((2-(trimethylsilyl)ethoxy)methyl)amino)-6-(1-ethoxyvinyl)-3-(6-(hydroxymethyl)pyridin-3-yl)pyrazolo[1,5-a]pyrimidin-5-yl)-8-azabicyclo[3.2.1]octane-8-carboxylate (0.25 g, 0.32 mmol, 1.00 equiv) in 1,2-DCE (3 mL) was added Dess-Martin periodinane (0.271 mg, 0.640 mmol, 2.00 equiv) in one portion. The resulting heterogeneous reaction mixture was allowed to stir at it for 2 hr. The reaction was quenched with the addition of ethyl acetate (10 mL) and saturated 1/1 NaHCO$_3$/Na$_2$S$_2$O$_3$ (10 mL). After stirring for 30 min at rt, the mixture was partitioned between ethyl acetate and water (2×). The organic phase was washed with brine and dried (magnesium sulfate). Filtration and concentration afforded (1R,3s,5S)-tert-butyl 3-(7-(bis((2-(trimethylsilyl)ethoxy)methyl)amino)-6-(1-ethoxyvinyl)-3-(6-formylpyridin-3-yl)pyrazolo[1,5-a]pyrimidin-5-yl)-8-azabicyclo[3.2.1]octane-8-carboxylate as a yellow compound (246 mg) that was used without additional purification.

Step B: A suspension of (1R,3s,5S)-tert-butyl 3-(7-(bis((2-(trimethylsilyl)ethoxy)methyl)amino)-6-(1-ethoxyvinyl)-3-(6-formylpyridin-3-yl)pyrazolo[1,5-a]pyrimidin-5-yl)-8-azabicyclo[3.2.1]octane-8-carboxylate (0.246 g, 0.316 mmol, 1.00 equiv) from Step A, 2-methylpropane-2-sulfinamide (46 mg, 0.38 mmol, 1.2 equiv) and CuSO$_4$ (0.10 g. 0.63 mmol, 2.0 equiv) in DCM (3 mL) was heated at 45° C. for 2 hr. After cooling to it and filtering through Celite and concentration, the residue was purified by Biotage (15% ethyl acetate in hexanes to 100% ethyl acetate gradient) affording the title compound as a yellow oil (218 mg).

Step C: To a solution of (1R,3s,5S)-tert-butyl 3-(7-(bis((2-(trimethylsilyl)ethoxy)methyl)amino)-3-(6-((E)-(tert-butyl-sulfinylimino)methyl)pyridin-3-yl)-6-(1-ethoxyvinyl)pyrazolo[1,5-a]pyrimidin-5-yl)-8-azabicyclo[3.2.1]octane-8-carboxylate (120 mg, 0.136 mmol, 1.0 equiv) and KOAc (13 mg) in DMF (4 mL) at −40° C. was added trimethyl(trifluoromethyl)silane (2.0 M in THF, 0.28 mL, 0.28 mmol) dropwise. After warming to rt, the reaction mixture was stirred for 6 hr, partitioned between ethyl acetate and water, dried.

Step D: The residue from Step C was dissolved in THF and treated with HCl. After 5 hr, the mixture was concentrated and lyophilized. EDCI mediated coupling afforded the title compound.

Preparation of 4-((2-(trimethylsilyl)ethoxy)methyl)-4H-1,2,4-triazole-3-carboxylic acid

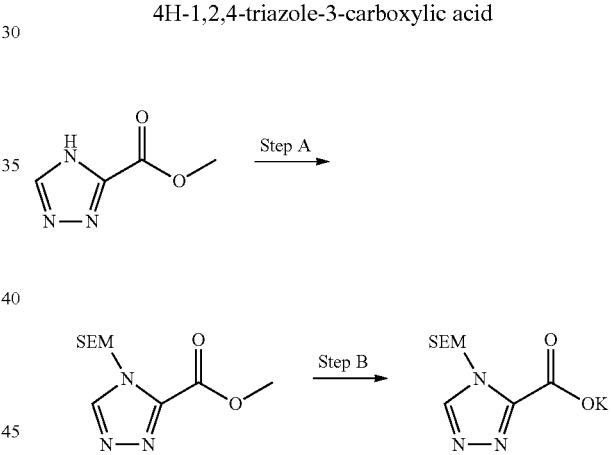

Step A: To a solution of methyl 4H-1,2,4-triazole-3-carboxylate (5.00 g, 39.4 mmol, 1.00 equiv) in DMF (200 mL) at 0° C. was added dropwise LiHMDS (1.0 M solution in toluene, 43 mL, 43 mmol, 1.1 equiv). The resulting solution was aged 15 minutes, then SEMCl (7.3 mL, 41 mmol, 1.0 equiv) was added dropwise over 5 minutes. After stirring for 5 min at 0° C., the ice bath was removed and the yellow solution was allowed to warm to rt, and then stirred for 1 hr. The mixture was quenched by the addition of water, partitioned between ethyl acetate and water, washed with brine and dried over magnesium sulfate. Concentration and final purification by Biotage (15% to 70% ethyl acetate in hexanes) afforded the title compound as pale oil (5.13 g)

Step B: To a solution of methyl 4-((2-(trimethylsilyl)ethoxy)methyl)-4H-1,2,4-triazole-3-carboxylate (225 mg, 0.874 mmol, 1.00 equiv) in EtOH (1.5 mL) was added aq. KOH (2N, 0.9 mL, 0.87 mmol, 1.0 equiv). After stirring at rt for 1 hr, the reaction mixture was concentrated affording the title compound as a colorless solid (271 mg) (Table 8-30).

TABLE 8-30

| Compound ID | Structures | Compound Name | M + H (calculated)/ M + H (observed) | pAKT S473 IC50 | p4E-BP1 Thr37/46 IC50 |
|---|---|---|---|---|---|
| 8.93 | 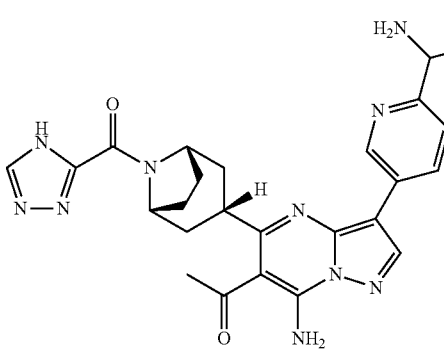 | 1-(5-((1R,3s,5S)-8-(4H-1,2,4-triazole-3-carbonyl)-8-azabicyclo[3.2.1]octan-3-yl)-7-amino-3-(6-(1-amino-2,2,2-trifluoroethyl)pyridin-3-yl)pyrazolo[1,5-a]pyrimidin-6-yl)ethanone | 554.21/555.1 | ND | ND |

Example 8-38

Preparation of ((1R,3s,5S)-3-(7-amino-3-(2-(aminomethyl)pyrimidin-5-yl)-6-bromopyrazolo[1,5-a]pyrimidin-5-yl-8-azabicyclo[3.2.1]octan-8-yl)(4H-1,2,4-triazol-3-yl)methanone

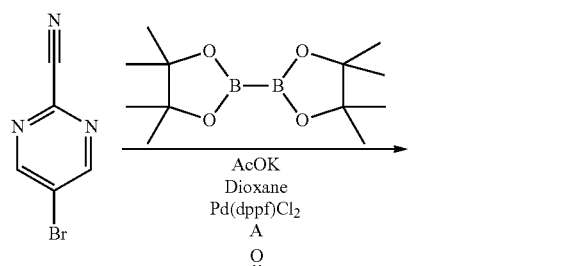

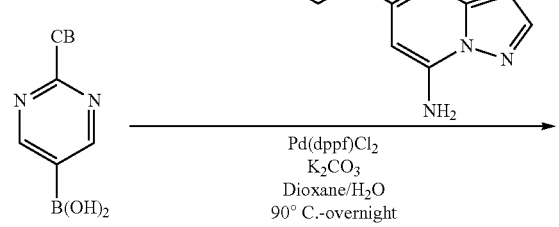

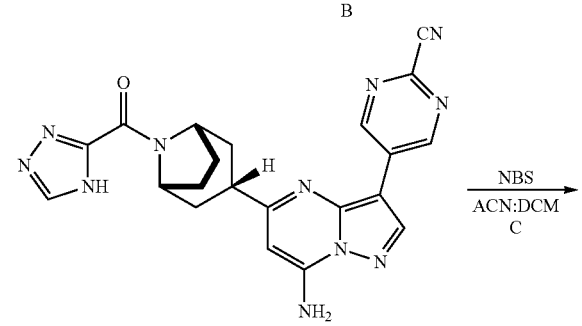

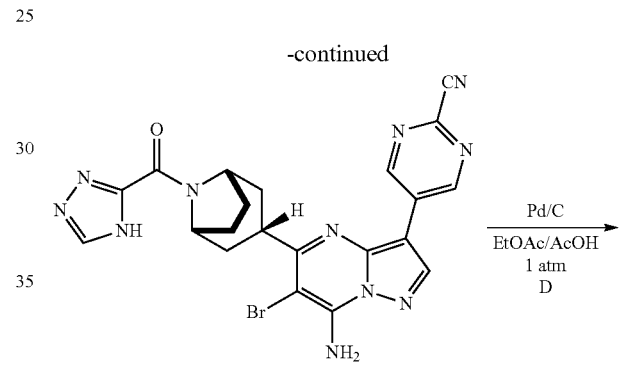

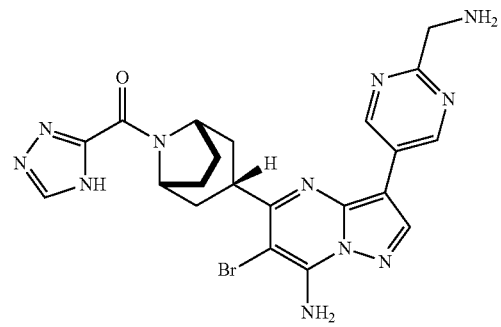

Step A, B and C: preparation of the boronic acid, the Suzuki reaction and bromination were realized following similar examples described previously.

Step D: To a solution of 5-(5-((1R,3s,5S)-8-(4H-1,2,4-triazole-3-carbonyl)-8-azabicyclo[3.2.1]octan-3-yl)-7-amino-6-bromopyrazolo[1,5-a]pyrimidin-3-yl)pyrimidine-2-carbonitrile (0.020 g, 0.385 mmol) in EtOAc (1 mL) was added Pd/C (catalytic) and AcOH (1 mL). The reaction was stirred under H$_2$ for 15 h. The reaction was passed through celite, washed with EtOAc and concentrated. HPLC purification gave ((1R,3s,5S)-3-(7-amino-3-(2-(aminomethyl)pyrimidin-5-yl)-6-bromopyrazolo[1,5-a]pyrimidin-5-yl)-8-azabicyclo[3.2.1]octan-8-yl)(4H-1,2,4-triazol-3-yl)methanone (0.003 g) as a light yellow solid.

Following previous examples, compounds in Table 8-31 were made:

TABLE 8-31

| Compound ID | Structures | Compound Name | M + H (calculated)/ M + H (observed) | pAKT S473 IC50 | p4E-BP1 Thr37/46 IC50 |
|---|---|---|---|---|---|
| 8.94 | 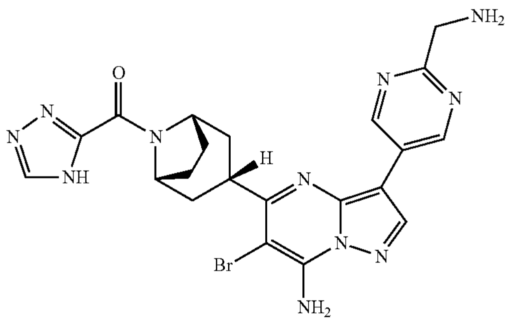 [SMILES: NCc1ncc(-c2cnn3c(N)c(Br)c([C@@H]4C[C@H]5CC[C@@H](C4)N5C(=O)c4nnc[nH]4)nc23)cn1] | ((1R,3s,5S)-3-(7-amino-3-(2-(aminomethyl)pyrimidin-5-yl)-6-bromopyrazolo[1,5-a]pyrimidin-5-yl)-8-azabicyclo[3.2.1]octan-8-yl)(4H-1,2,4-triazol-3-yl)methanone | 524.12/523.84 | ND | ND |
| 8.95 | 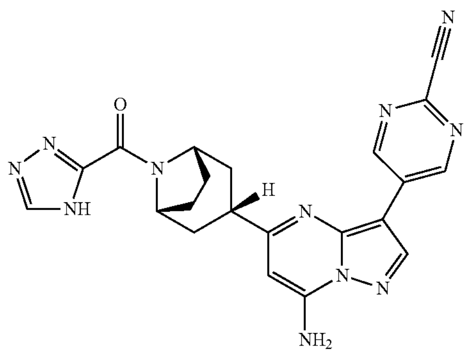 [SMILES: N#Cc1ncc(-c2cnn3c(N)cc([C@@H]4C[C@H]5CC[C@@H](C4)N5C(=O)c4nnc[nH]4)nc23)cn1] | 5-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyrimidine-2-carbonitrile | 442.18/441.95 | D | D |
| 8.96 | 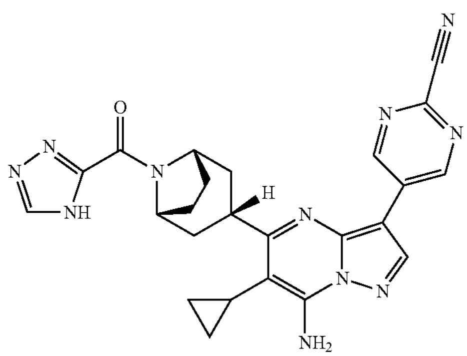 [SMILES: N#Cc1ncc(-c2cnn3c(N)c(C4CC4)c([C@@H]4C[C@H]5CC[C@@H](C4)N5C(=O)c4nnc[nH]4)nc23)cn1] | 5-(5-((1R,3s,5S)-8-(4H-1,2,4-triazole-3-carbonyl)-8-azabicyclo[3.2.1]octan-3-yl)-7-amino-6-cyclopropylpyrazolo[1,5-a]pyrimidin-3-yl)pyrimidine-2-carbonitrile | 482.21/482.00 | C | C |
| 8.97 | 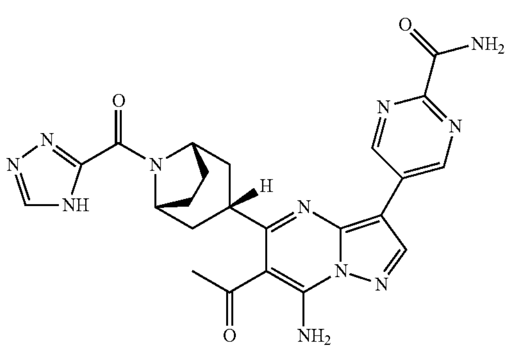 [SMILES: CC(=O)c1c([C@@H]2C[C@H]3CC[C@@H](C2)N3C(=O)c2nnc[nH]2)nc2c(-c3cnc(C(N)=O)nc3)cnn2c1N] | 5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyrimidine-2-carboxamide | 502.20/501.97 | C | ND |

Example 8-39

Preparation of ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-morpholino-4H-1,2,4-triazol-3-yl)methanone

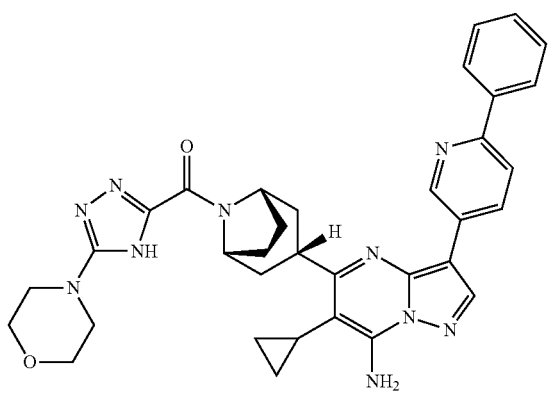

Step-A: Synthesis of methyl hydrazinecarbimidothioate hydroiodide

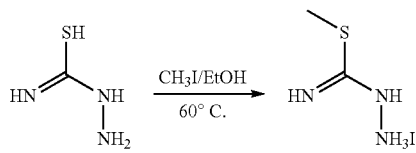

To a solution of hydrazinecarbimidothioic acid (1.0 g, 10.97 mmols) in EtOH (10 mL) was added Methyl Iodide (0.700 mL, 11.34 mmol) and heated to 60° C. for 30 minutes. The reaction mixture was cooled to it and the solid was filtered out. The solid was washed with ether, to get methyl hydrazinecarbimidothioate hydroiodide as a white solid (2.25 g).

Step-B: Synthesis of morpholine-4-carboximidhydrazide

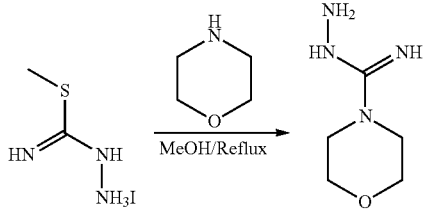

To a solution of methyl hydrazinecarbimidothioate hydroiodide (0.100 g, 0.429 mmol) in MeOH (2 mL) was added morpholine (0.075 mL, 0.858 mmol) and refluxed overnight. Reaction was cool to RT and concentrated to get morpholine-4-carboximidhydrazide as a white solid in quantitative yield.

Step-C: Synthesis of methyl 5-morpholino-4H-1,2,4-triazole-3-carboxylate

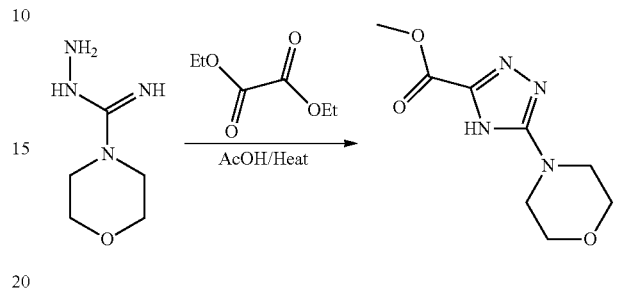

To a solution of 4, morpholine-4-carboximidhydrazide (0.100 g, 0.429 mmol) in ACOH (1 mL) was added 5, diethyl oxalate (0.582 mL, 4.29 mmol) and refluxed for 2 h. Reaction was concentrated, diluted with EtOAc and washed with water. The organic layer dried and concentrated. ISCO purification (0-1% MeOH in DCM) to obtain 6, methyl 5-morpholino-4H-1,2,4-triazole-3-carboxylate (0.213 g).

Step-D: Synthesis of 5-morpholino-4H-1,2,4-triazole-3-carboxylic acid

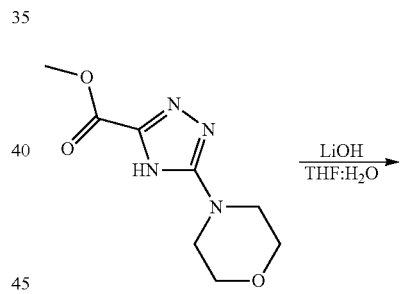

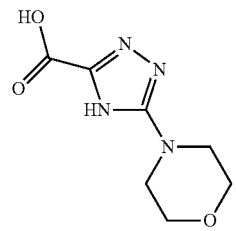

To a solution of methyl 5-morpholino-4H-1,2,4-triazole-3-carboxylate (0.090 g, 0.398 mmols†) in THF (1 mL) was added 1 N LiOH (0.800 mL, 0.80 mmol) and H₂O (1 mL). The reaction was stirred at rt for 12 h. The reaction mixture was concentrated and lypholized to get 5-morpholino-4H-1,2,4-triazole-3-carboxylic acid quantative yield and used as it is in next step.

Step-E: Synthesis of ((1R,3s, 5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-morpholino-4H-1,2,4-triazol-3-yl)methanone

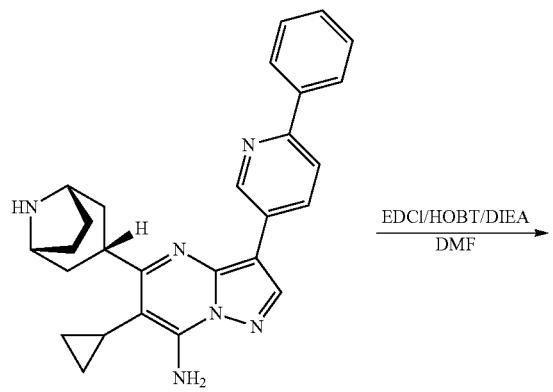

The title compound was made following the standard coupling conditions described before.

Example 8-40

Preparation of building block tert-butyl 4-(5-(methoxycarbonyl)-4H-1,2,4-triazol-3-yl)piperazine-1-carboxylate

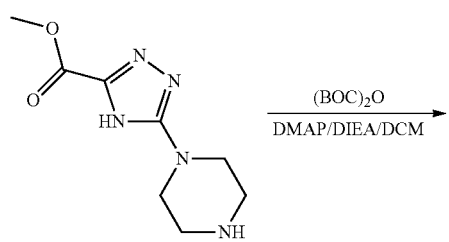

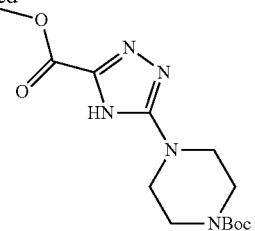

To a solution of methyl 5-(piperazin-1-yl)-4H-1,2,4-triazole-3-carboxylate (1.0 g, 4.44 mmols) in DCM (10 mL) was added (BOC)₂O (0.970 g, 4.44 mmol), DMAP (0.050 g, 0.41 mmol), DIEA (3.9 mL, 22.4 mmol). The reaction was stirred at RT overnight. Reaction concentrated and ISCO purification (0-5% MeOH in DCM) to obtain tert-butyl 4-(5-(methoxycarbonyl)-4H-1,2,4-triazol-3-yl)piperazine-1-carboxylate (0.580 g).

Example 8-41

Preparation of building block 5-(2-methoxyethoxy)-4H-1,2,4-triazole-3-carboxylic acid

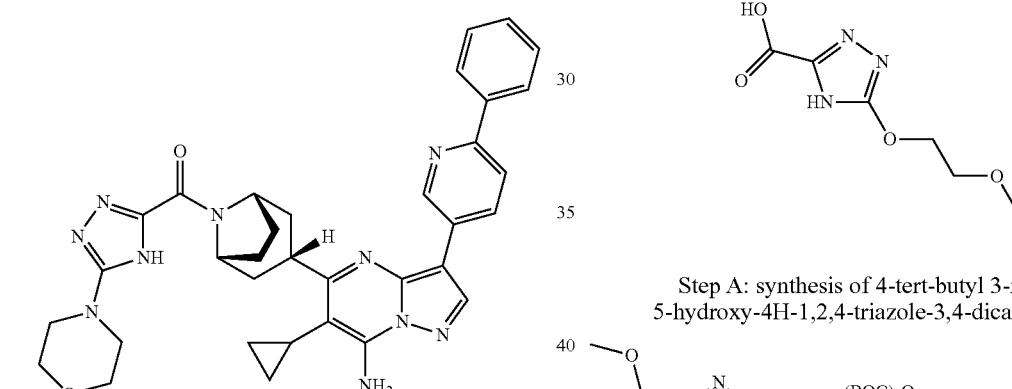

Use the same reaction conditions described above.

Step B: Synthesis of methyl 5-(2-methoxyethoxy)-4H-1,2,4-triazole-3-carboxylate

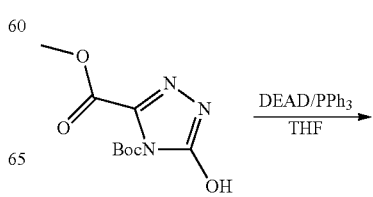

843

-continued

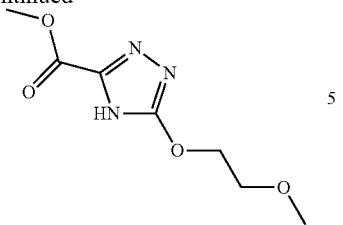

To a solution of 4-tert-butyl 3-methyl 5-hydroxy-4H-1,2,4-triazole-3,4-dicarboxylate (0.170 g, 0.453 mmol) in THF (4 mL) was added 2-methoxyethanol (0.053 mL, 0.672 mmol), DEAD (0.107 mL, 0.682 mmol), PPh$_3$ (0.142 g, 0.542 mmol) and stirred at it for 15 h. Reaction concentrated and ISCO purification (0-5% MeOH in DCM) to get methyl 5-(2-methoxyethoxy)-4H-1,2,4-triazole-3-carboxylate (0.050 g) as a colorless oil.

Step-C: Synthesis of 5-(2-methoxyethoxy)-4H-1,2,4-triazole-3-carboxylic acid

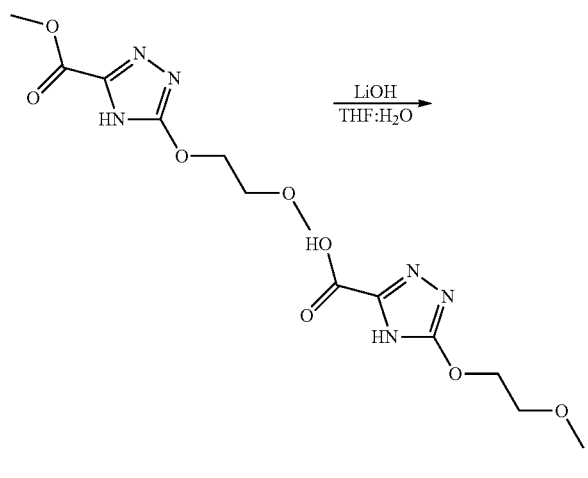

Standard hydrolysis condition described previously gave the title compound.

Example 8-42

Preparation of building block 5-methoxy-4H-1,2,4-triazole-3-carboxylic acid and 5-methoxy-4-methyl-4H-1,2,4-triazole-3-carboxylic acid

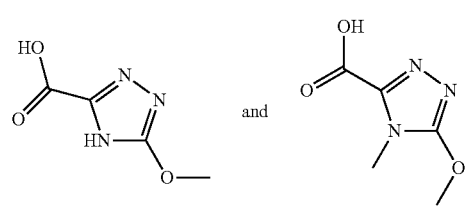

844

Step-A: Synthesis of methyl 5-methoxy-4H-1,2,4-triazole-3-carboxylate and methyl 5-methoxy-4-methyl-4H-1,2,4-triazole-3-carboxylate

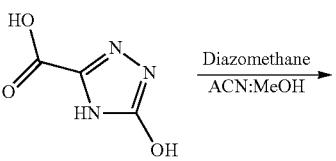

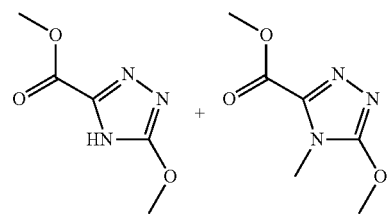

To a solution of 5-hydroxy-4H-1,2,4-triazole-3-carboxylic acid (0.033 g, 0.250 mmol) was added ACN:MeOH (1 mL: 1 mL) and diazomethane (0.500 mL, 1 mmols). The reaction was stirred for 20 min. and was concentrated to give a mixture of methyl 5-methoxy-4H-1,2,4-triazole-3-carboxylate and methyl 5-methoxy-4-methyl-4H-1,2,4-triazole-3-carboxylate. The crude was used in next step.

Step-B: Synthesis of 5-methoxy-4H-1,2,4-triazole-3-carboxylic acid and 5-methoxy-4-methyl-4H-1,2,4-triazole-3-carboxylic acid

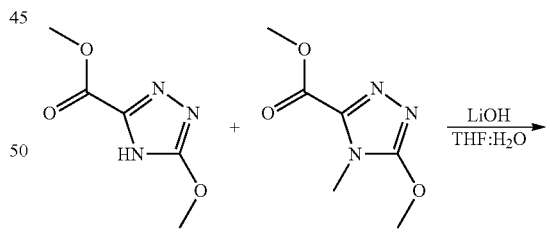

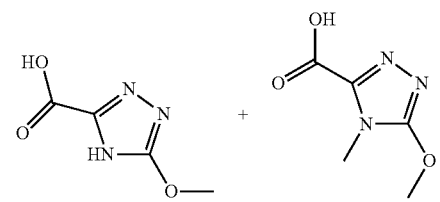

Use the same reaction conditions as above section to provide mixture of two compounds.

Following similar procedures describe above, the following compounds (Table 8-32) were made:

TABLE 8-32

| Compound ID | Structures | Compound Name | M + H (calculated)/ M + H (observed) | pAKT S473 IC50 | p4E-BP1 Thr37/46 IC50 |
|---|---|---|---|---|---|
| 8.98 | 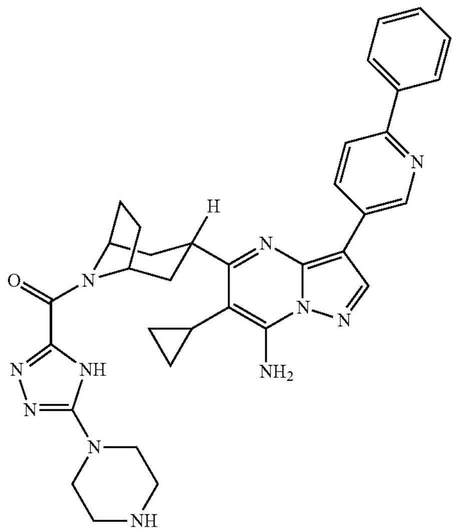 [SMILES: Nc1c(C2CC2)c(C2CC3CCC(C2)N3C(=O)c2nnc(N3CCNCC3)[nH]2)nc2c(-c3ccc(-c4ccccc4)nc3)cnn12] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(piperazin-1-yl)-4H-1,2,4-triazol-3-yl)methanone | 616.32/616.1 | C | C |
| 8.99 | 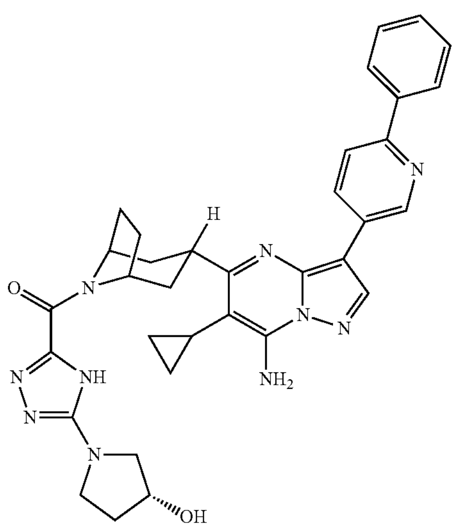 [SMILES: Nc1c(C2CC2)c(C2CC3CCC(C2)N3C(=O)c2nnc(N3CC[C@@H](O)C3)[nH]2)nc2c(-c3ccc(-c4ccccc4)nc3)cnn12] | ((1R,3S,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-((R)-3-hydroxypyrrolidin-1-yl)-4H-1,2,4-triazol-3-yl)methanone | 617.30/617.1 | ND | ND |

TABLE 8-32-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.100 | 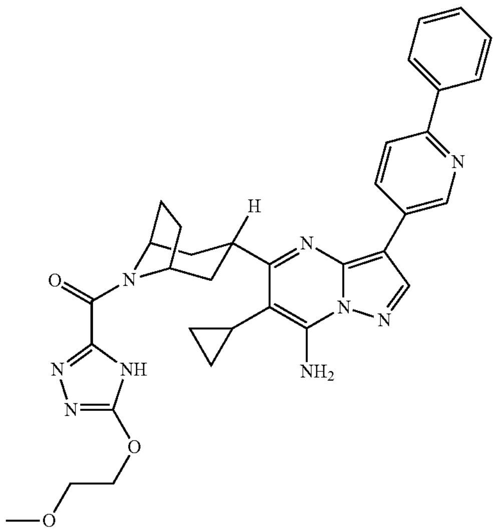 [SMILES: COCCOc1nnc(C(=O)N2C3CCC2CC(c2nc4c(-c5ccc(-c6ccccc6)nc5)cnn4c(N)c2C2CC2)C3)[nH]1] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(2-methoxyethoxy)-4H-1,2,4-triazol-3-yl)methanone | 606.29/606.1 | B | B |
| 8.101 | 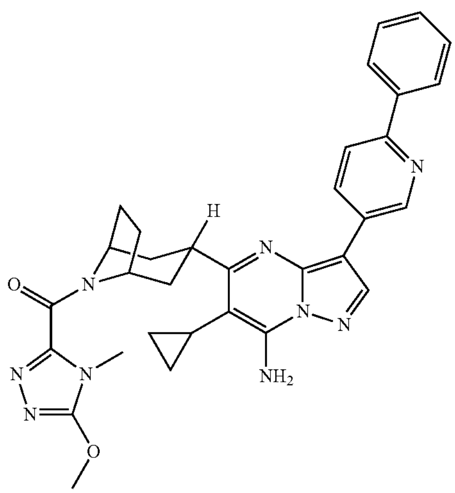 [SMILES: COc1nnc(C(=O)N2C3CCC2CC(c2nc4c(-c5ccc(-c6ccccc6)nc5)cnn4c(N)c2C2CC2)C3)n1C] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4-methyl-4H-1,2,4-triazol-3-yl)methanone | 576.28/576.0 | ND | ND |
| 8.102 | 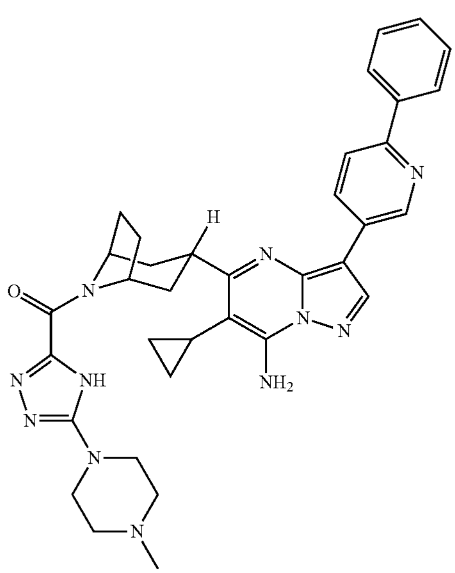 [SMILES: CN1CCN(c2nnc(C(=O)N3C4CCC3CC(c3nc5c(-c6ccc(-c7ccccc7)nc6)cnn5c(N)c3C3CC3)C4)[nH]2)CC1] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(4-methylpiperazin-1-yl)-4H-1,2,4-triazol-3-yl)methanone | 630.33/630.1 | C | C |

TABLE 8-32-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.103 | 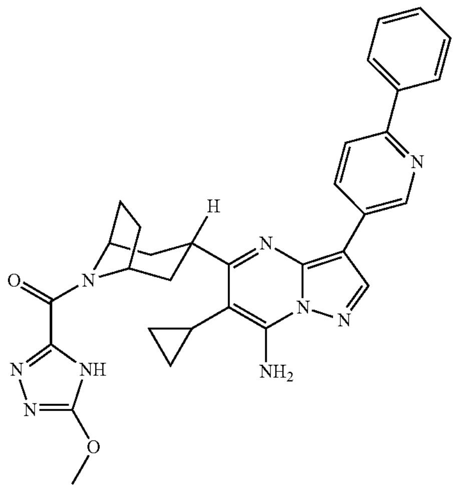 [SMILES: COc1nnc(C(=O)N2C3CCC2CC(c2nc4c(-c5ccc(-c6ccccc6)nc5)cnn4c(N)c2C2CC2)C3)[nH]1] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4H-1,2,4-triazol-3-yl)methanone | 562.26/562.0 | B | B |
| 8.104 | 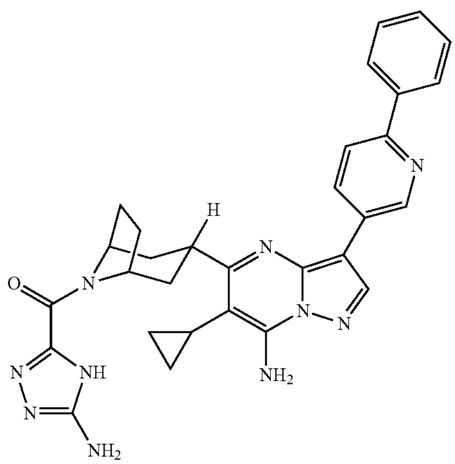 [SMILES: Nc1nnc(C(=O)N2C3CCC2CC(c2nc4c(-c5ccc(-c6ccccc6)nc5)cnn4c(N)c2C2CC2)C3)[nH]1] | (5-amino-4H-1,2,4-triazol-3-yl)((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)methanone | 547.26/547.1 | A | A |
| 8.105 | 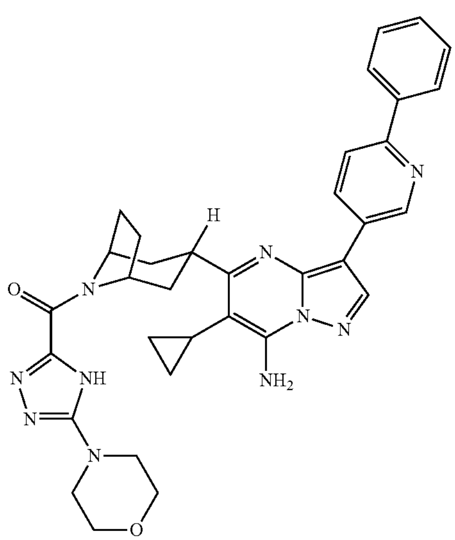 [SMILES: Nc1c(C2CC2)c(C2CC3CCC(C2)N3C(=O)c2nnc(N3CCOCC3)[nH]2)nc2c(-c3ccc(-c4ccccc4)nc3)cnn12] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-morpholino-4H-1,2,4-triazol-3-yl)methanone | 617.30/617.3 | C | C |

TABLE 8-32-continued

| Compound ID | Structures | Compound Name | M + H (calculated)/ M + H (observed) | pAKT S473 IC50 | p4E-BP1 Thr37/46 IC50 |
|---|---|---|---|---|---|
| 8.106 | 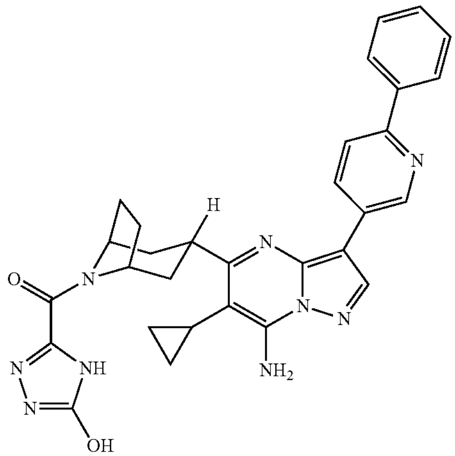 [SMILES: Nc1c(C2CC2)c(C2CC3CCC(C2)N3C(=O)c2nnc(O)[nH]2)nc2c(-c3ccc(-c4ccccc4)nc3)cnn12] | ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone | 548.24/548.0 | A | A |

Example 8A

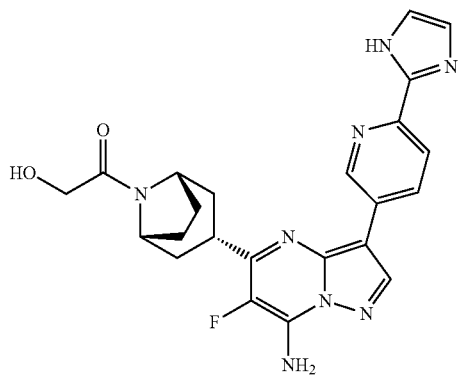 [SMILES: Nc1c(F)c([C@@H]2C[C@H]3CC[C@@H](C2)N3C(=O)CO)nc2c(-c3ccc(-c4ncc[nH]4)nc3)cnn12]

1-[(3-Exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone Step 1. tert-Butyl (3-exo)-3-[7-(bis{[2-(trimethylsilyl)ethoxy]methyl}amino)pyrazolo[1,5-a]pyrimidin-5-yl]-8-azabicyclo[3.2.1]octane-8-carboxylate An oven-dried, nitrogen cooled round bottom flask was charged with tert-butyl (3-exo)-3-[7-(bis{[2-(trimethylsilyl)ethoxy]methyl}amino)-3-iodopyrazolo[1,5-a]pyrimidin-5-yl]-8-azabicyclo[3.2.1]octane-8-carboxylate (2.20 g, 3.01 mmol), sodium formate (2.20 g, 32.3 mmol) and PdCl$_2$(dppf)-dichloromethane adduct (0.13 g, 0.16 mmol), dioxane (10 mL) and water (5 mL), sparged with a stream of nitrogen gas and heated to reflux for 3 hours. The reaction mixture was cooled to room temperature, filtered through celite, eluted with EtOAc, concentrated in vacuo and purified by flash chromatography (Biotage, 0-50% EtOAc/hexanes) to obtain tert-butyl (3-exo)-3-[7-(bis{[2-(trimethylsilyl)ethoxy]methyl}amino)pyrazolo[1,5-a]pyrimidin-5-yl]-8-azabicyclo[3.2.1]octane-8-carboxylate.

LRMS (ESI) calc'd for C30H54N5O4Si2 [M+H]$^+$: 604. Found: 604.

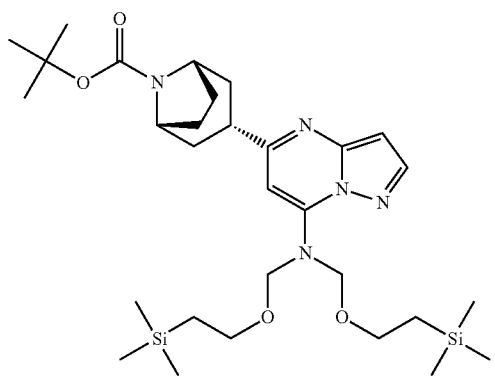 [SMILES: CC(C)(C)OC(=O)N1[C@@H]2CC[C@H]1C[C@H](c1cc(N(COCC[Si](C)(C)C)COCC[Si](C)(C)C)n3nccc3n1)C2]

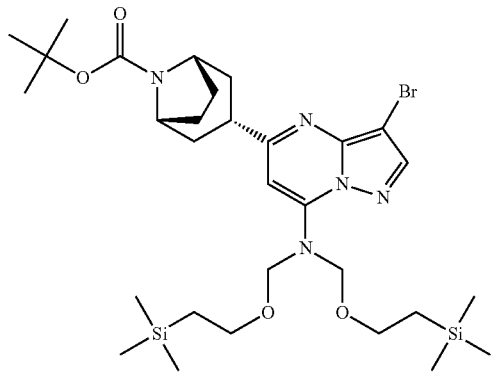 [SMILES: CC(C)(C)OC(=O)N1[C@@H]2CC[C@H]1C[C@H](c1cc(N(COCC[Si](C)(C)C)COCC[Si](C)(C)C)n3ncc(Br)c3n1)C2]

Step 2. tert-Butyl (3-exo)-3-[7-(bis{[2-(trimethylsilyl)ethoxy]methyl}amino)-3-bromopyrazolo[1,5-a]pyrimidin-5-yl]-8-azabicyclo[3.2.1]octane-8-carboxylate A stirring solution of tert-butyl (3-exo)-3-[7-(bis{[2-(trimethylsilyl)ethoxy]methyl}amino)pyrazolo[1,5-a]pyrimidin-5-yl]-8-azabicyclo[3.2.1]octane-8-carboxylate (1.58 g, 2.62 mmol) in MeCN (20 mL) was charged with NBS (0.49 g, 2.75 mmol) and stirred at room temperature for 1 hour. The reaction mixture was concentrated under vacuum and purified by flash chromatography (Biotage, 0-50% EtOAc/hexanes) to obtain tert-butyl (3-exo)-3-[7-(bis{[2-(trimethylsilyl)ethoxy]methyl}amino)-3-bromopyrazolo[1,5-a]pyrimidin-5-yl]-8-azabicyclo[3.2.1]octane-8-carboxylate.

LRMS (ESI) calc'd for C30H53BrN5O4Si2 [M+H]+: 682. Found: 682.

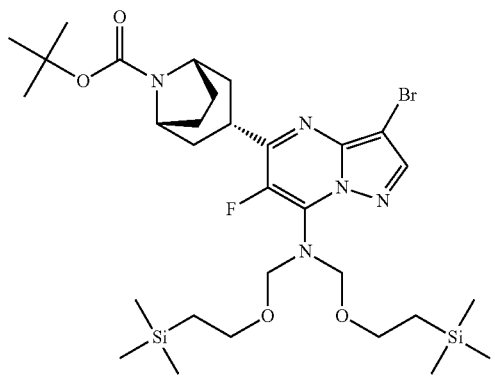 [SMILES: CC(C)(C)OC(=O)N1[C@@H]2CC[C@H]1C[C@H](c1nc3c(Br)cnn3c(N(COCC[Si](C)(C)C)COCC[Si](C)(C)C)c1F)C2]

Step 3. tert-Butyl (3-exo)-3-[7-(bis{[2-(trimethylsilyl)ethoxy]methyl}amino)-3-bromo-6-fluoropyrazolo[1,5-a]pyrimidin-5-yl]-8-azabicyclo[3.2.1]octane-8-carboxylate A 5 mL microwave vial was charged with tert-butyl (3-exo)-3-[7-(bis{[2-(trimethylsilyl)ethoxy]methyl}amino)-3-bromopyrazolo[1,5-a]pyrimidin-5-yl]-8-azabicyclo[3.2.1]octane-8-carboxylate (1.11 g, 1.63 mmol) and MeCN (10 mL), cooled to 0° C. and charged dropwise with a solution of Selectfluor® (0.61 g, 1.7 mmol) in MeCN (15 mL). The reaction mixture was stirred at 0° C. for a total of 2.5 hours, including addition time then poured into 10:1 hexanes:DCM, filtered through celite, eluted with Et2O, concentrated in vacuo and purified by flash chromatography (Biotage, 0-20% EtOAc/Hex) to obtain tert-butyl (3-exo)-3-[7-(bis{[2-(trimethylsilyl)ethoxy]methyl}amino)-3-bromo-6-fluoropyrazolo[1,5-a]pyrimidin-5-yl]-8-azabicyclo[3.2.1]octane-8-carboxylate.

LRMS (ESI) calc'd for C30H52BrFN5O4Si2 [M+H]+: 700. Found: 700.

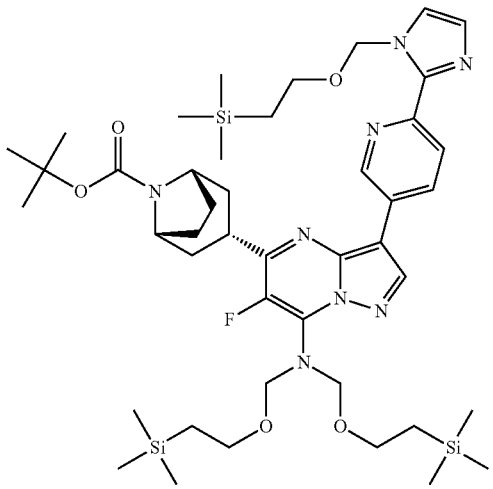 [SMILES: CC(C)(C)OC(=O)N1[C@@H]2CC[C@H]1C[C@H](c1nc3c(-c4ccc(-c5nccn5COCC[Si](C)(C)C)nc4)cnn3c(N(COCC[Si](C)(C)C)COCC[Si](C)(C)C)c1F)C2]

Step 4. tert-Butyl (3-exo)-3-{7-(bis{[2-(trimethylsilyl)ethoxy]methyl}amino)-6-fluoro-3-[6-(1-{[2-(trimethylsilyl)ethoxy]methyl}-1H-imidazol-2-yl)pyridin-3-yl]pyrazolo[1,5-a]pyrimidin-5-yl}-8-azabicyclo[3.2.1]octane-8-carboxylate An oven-dried, nitrogen cooled 5 mL microwave vial was charged with PdCl2(dppf)-dichloromethane adduct (28 mg, 0.034 mmol) and cesium carbonate (0.34 g, 1.044 mmol), sealed under a nitrogen atmosphere, charged with a degassed solution of tert-butyl (3-exo)-3-[7-(bis{[2-(trimethylsilyl)ethoxy]methyl}amino)-3-bromo-6-fluoropyrazolo[1,5-a]pyrimidin-5-yl]-8-azabicyclo[3.2.1]octane-8-carboxylate (243 mg, 0.347 mmol) and 5-(4,4,5,5-tetramethyl-1,3,2-dioxaborolan-2-yl)-2-(1-{[2-(trimethylsilyl)ethoxy]methyl}-1H-imidazol-2-yl)pyridine (0.28 g, 0.70 mmol) in dioxane (2.0 mL) and water (0.5 mL) and heated to 100° C. for 18 hours. The reaction mixture was cooled to room temperature, filtered through celite, eluted with EtOAc, concentrated under vacuum and purified by flash chromatography (Biotage, 0-50% EtOAc/hexanes) to obtain tert-butyl (3-exo)-3-{7-(bis{[2-(trimethylsilyl)ethoxy]methyl}amino)-6-fluoro-3-[6-(1-{[2-(trimethylsilyl)ethoxy]methyl}-1H-imidazol-2-yl)pyridin-3-yl]pyrazolo[1,5-a]pyrimidin-5-yl}-8-azabicyclo[3.2.1]octane-8-carboxylate.

LRMS (ESI) calc'd for C44H72FN8O5Si3 [M+H]+: 895. Found: 895.

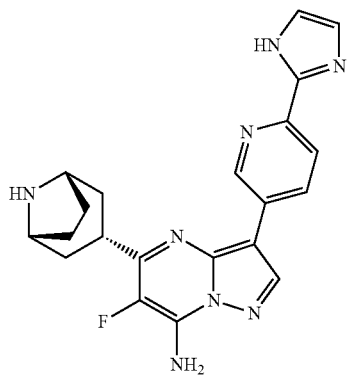 [SMILES: Nc1c(F)c([C@@H]2C[C@H]3CC[C@@H](C2)N3)nc2c(-c3ccc(-c4ncc[nH]4)nc3)cnn12]

Step 5. 5-[(3-Exo)-8-azabicyclo[3.2.1]oct-3-yl]-6-fluoro-3-[6-(1H-imidazol-2-yl)Pyridin-3-yl]pyrazolo[1,5-a]pyrimidin-7-amine A solution of tert-butyl (3-exo)-3-{7-(bis{[2-(trimethylsilyl)ethoxy]methyl}amino)-6-fluoro-3-[6-(1-{[2-(trimethylsilyl)ethoxy]methyl}-1H-imidazol-2-yl)pyridin-3-yl]pyrazolo[1,5-a]pyrimidin-5-yl}-8-azabicyclo[3.2.1]octane-8-carboxylate (188.5 mg, 0.211 mmol) in TFA (2.0 mL) and water (2.0 mL) was stirred at room temperature for 72.5 hours and then heated to 50° C. for 24 hours. The reaction mixture was cooled to room temperature, concentrated in vacuo, dissolved in DMSO and purified by mass-triggered reverse-phase HPLC to provide 5-[(3-Exo)-8-azabicyclo[3.2.1]oct-3-yl]-6-fluoro-3-[6-(1H-imidazol-2-yl)pyridin-3-yl]pyrazolo[1,5-a]pyrimidin-7-amine as the tris TFA salt.

LRMS (ESI) calc'd for C21H22FN8 [M+H]$^+$: 405. Found: 405.

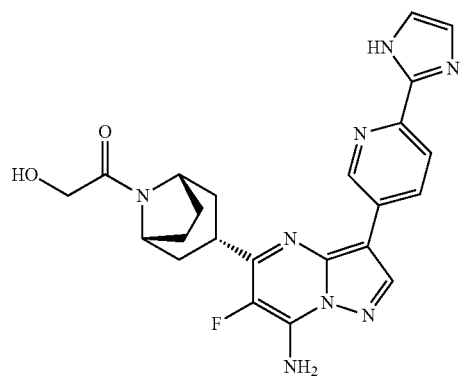 [SMILES: Nc1c(F)c([C@@H]2C[C@H]3CC[C@@H](C2)N3C(=O)CO)nc2c(-c3ccc(-c4ncc[nH]4)nc3)cnn12]

1-[(3-Exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone

Step 6. 1-[(3-Exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone A stirring solution of 5-[(3-exo)-8-azabicyclo[3.2.1]oct-3-yl]-6-fluoro-3-[6-(1H-imidazol-2-yl)pyridin-3-yl]pyrazolo[1,5-a]pyrimidin-7-amine (27 mg, 0.036 mmol), glycolic acid (10 mg, 0.131 mmol), EDC-HCl (20 mg, 0.104 mmol), HOBT (15 mg, 0.098 mmol) and DIPEA (0.07 mL, 0.401 mmol) in DMF (0.5 mL) was heated to 60° C. for 14 hours. The reaction mixture was cooled to room temperature, diluted with DMSO and purified by mass-triggered reverse-phase HPLC to provide 1-[(3-exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone as the bis TFA salt.

LRMS (ESI) calc'd for C23H24FN8O2 [M+H]$^+$: 463. Found: 463.

The final compound had an Mtor IC$_{50}$ of 2 nM, pAKT473 IC$_{50}$ of 101 nM, pAKT473 IC$_{50}$ of 374 nM.

Example 8B

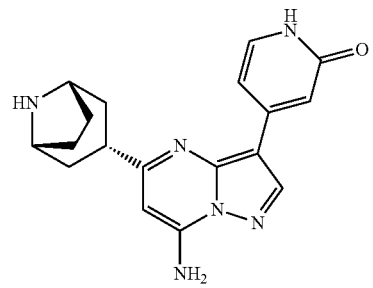 [SMILES: Nc1cc([C@@H]2C[C@H]3CC[C@@H](C2)N3)nc2c(-c3cc[nH]c(=O)c3)cnn12]

4-{7-Amino-5-[(3-exo)-8-azabicyclo[3.2.1]oct-3-yl]pyrazolo[1,5-a]pyrimidin-3-yl}pyridin-2(1H)-one

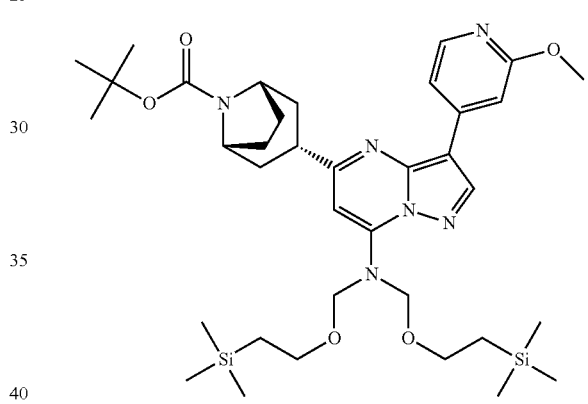

Step 1. tert-Butyl (3-exo)-3-[7-(bis{[2-(trimethylsilyl)ethoxy]methyl}amino)-3-(2-methoxypyridin-4-yl)pyrazolo[1,5-a]pyrimidin-5-yl]-8-azabicyclo[3.2.1]octane-8-carboxylate An oven-dried, nitrogen cooled 5 mL microwave vial was charged with tert-butyl (3-exo)-3-[7-(bis{[2-(trimethylsilyl)ethoxy]methyl}amino)-3-iodopyrazolo[1,5-a]pyrimidin-5-yl]-8-azabicyclo[3.2.1]octane-8-carboxylate (0.20 g, 0.27 mmol), PdCl2(dppf)-dichloromethane adduct (22 mg, 0.027 mmol) and cesium carbonate (0.27 g, 0.83 mmol), sealed under a nitrogen atmosphere, charged with a degassed mixture of 2-methoxy-4-(4,4,5,5-tetramethyl-1,3,2-dioxaborolan-2-yl)pyridine (214 mg, 0.565 mmol), dioxane (1.0 mL) and water (0.2 mL) and heated to 100° C. for 17.5 hours. The reaction mixture was cooled to room temperature, filtered through celite, eluted with EtOAc, concentrated under vacuum and purified by flash chromatography (Biotage, 0-50% EtOAc/hexanes) to obtain tert-butyl (3-exo)-3-[7-(bis{[2-(trimethylsilyl)ethoxy]methyl}amino)-3-(2-methoxypyridin-4-yl)pyrazolo[1,5-a]pyrimidin-5-yl]-8-azabicyclo[3.2.1]octane-8-carboxylate.

LRMS (ESI) calc'd for C36H59N6O5Si2 [M+H]$^+$: 711. Found: 711.

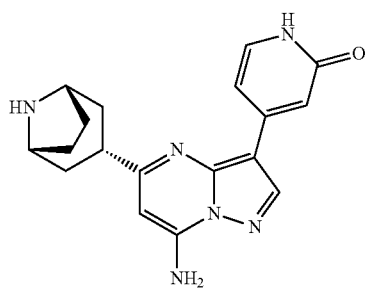 [SMILES: Nc1cc([C@@H]2C[C@H]3CC[C@@H](C2)N3)nc2c(-c3cc[nH]c(=O)c3)cnn12]

Step 2. 4-{7-Amino-5-[(3-exo)-8-azabicyclo[3.2.1]oct-3-yl]pyrazolo[1,5-a]pyrimidin-3-yl}pyridin-2(1H)-one A solution of tert-butyl (3-exo)-3-[7-(bis{[2-(trimethylsilyl)ethoxy]methyl}amino)-3-(2-methoxypyridin-4-yl)pyrazolo[1,5-a]pyrimidin-5-yl]-8-azabicyclo[3.2.1]octane-8-carboxylate (21.0 mg, 0.0300 mmol) and HBr (0.03 mL, 0.3 mmol) in acetic acid (0.5 mL) was stirred for 1.5 hours at 100° C., diluted with DMSO and purified by mass-triggered reverse-phase HPLC to provide 4-(7-amino-5-[(3-exo)-8-azabicyclo[3.2.1]oct-3-yl]pyrazolo[1,5-a]pyrimidin-3-yl)pyridin-2(1H)one.

LRMS (ESI) calc'd for C18H21N6O [M+H]⁺: 337. Found: 337.

Mtor IC$_{50}$ of the final compound was 489 nM.

Example 9

Compounds of Formula (I), wherein m is 0; L and Z are CH$_2$; and T is absent in ring A can be prepared according to Scheme 7 below.

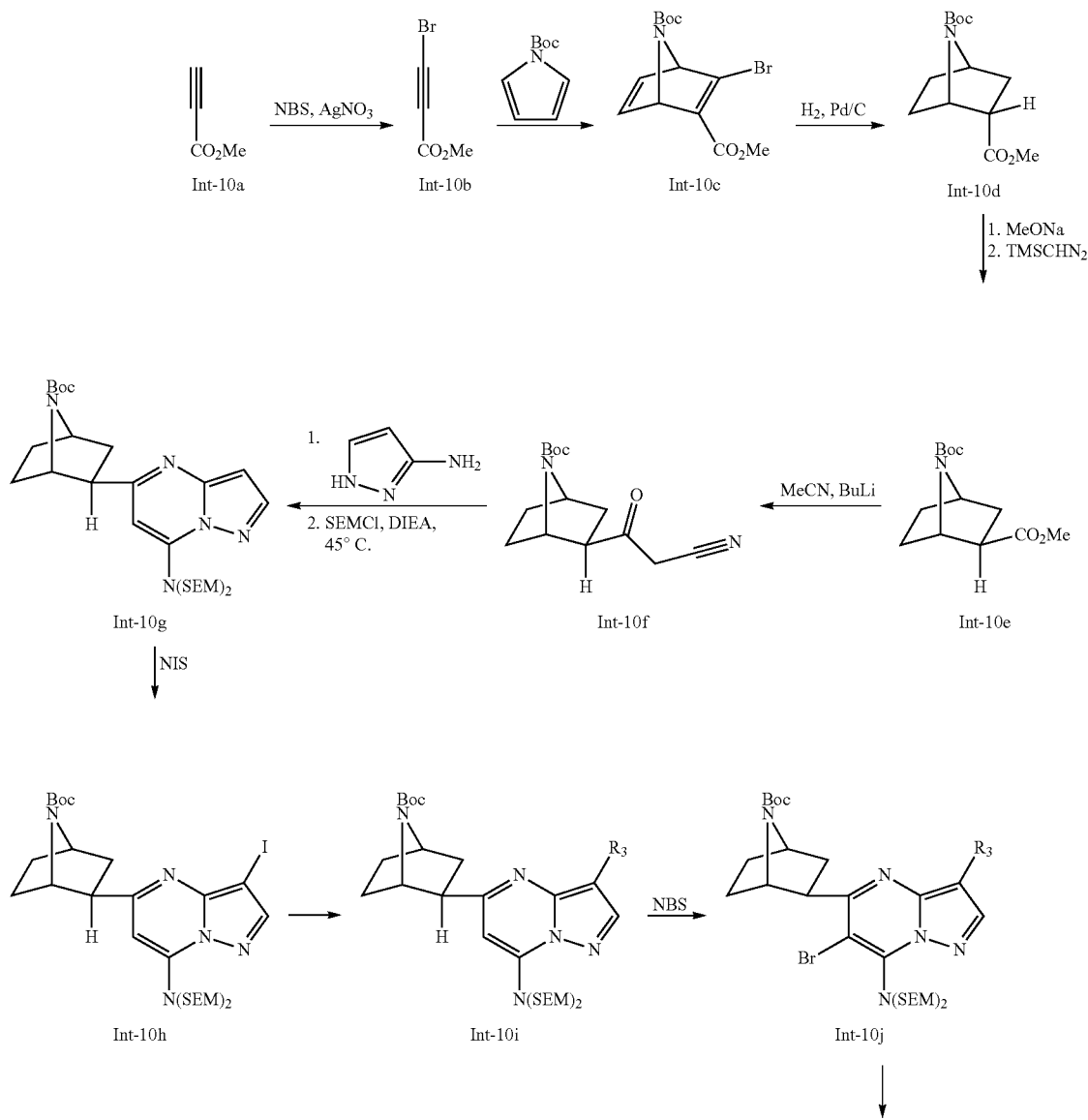

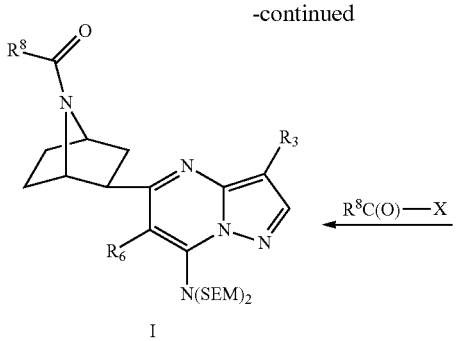

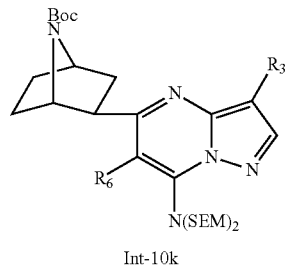

Compound I can be prepared from the propargylic acid intermediate Int-10a through the steps depicted in Scheme 8-2 above. Briefly, bromination of Int-10a using N-bromosuccinimide and silver nitrate provides the bromo intermediate Int-10b. Diels-Alder cycloaddition with N-Boc-protected pyrrole provides the diene intermediate Int-10c. Catalytic reduction of Int-10c affords the reduced intermediate Int-10d. Treatment of Int-10d with sodium methoxide and TMSCHN$_2$ provides Int-10e. Treatment of Int-10e with the lithium salt of acetonitrile affords the cyano-keto intermediate Int-10f. Cycloaddition of Int-10f with 3-aminopyrazole followed by protection of the amino moiety with SEM-Cl provides the pyrazolo[1,5-a]pyrimidine Int-10 g. Iodination of Int-10 g using a procedure similar to the one describing in step 9 of Example 1 affords the iodo intermediate Int-10h. Coupling of the iodo intermediate Int-10h, such as by using Suzuki coupling conditions described in Step 10 of Example 1, affords the 3-substituted intermediate Int-10i. Treatment of Int-10i with N-bromosuccinimide such as by using the procedure described in Step 11 of Example 1 provide the 6-bromo intermediate Int-10j. Depending on the desired 6-substituent, the 6-bromo intermediate Int-10j can be converted to the 6-substituted Int-10k using a variety of procedures. For instance, alkanoyl substitution of the 6-position can be accomplished by using procedures similar to those described in Step 12 of Example 1. Sulfonyl substitution of the 6-position can be performed either using procedures similar to those described in scheme-3-1 (Steps A and B) or scheme-3-2 (step 3) of Example 3-1. Nitrile substitution of the 6-position can be accomplished using a procedure similar to that described in Step 1 of Example 5. Acylation of the amino moiety of ring A of Int-10k can be performed using a procedure similar to that described in Step 14 of Example 1.

Example 10

Compounds of Formula (I), wherein m is 1; and L, Z, and T are CH$_2$ in ring A can be prepared according to Scheme 8 below.

Scheme 8

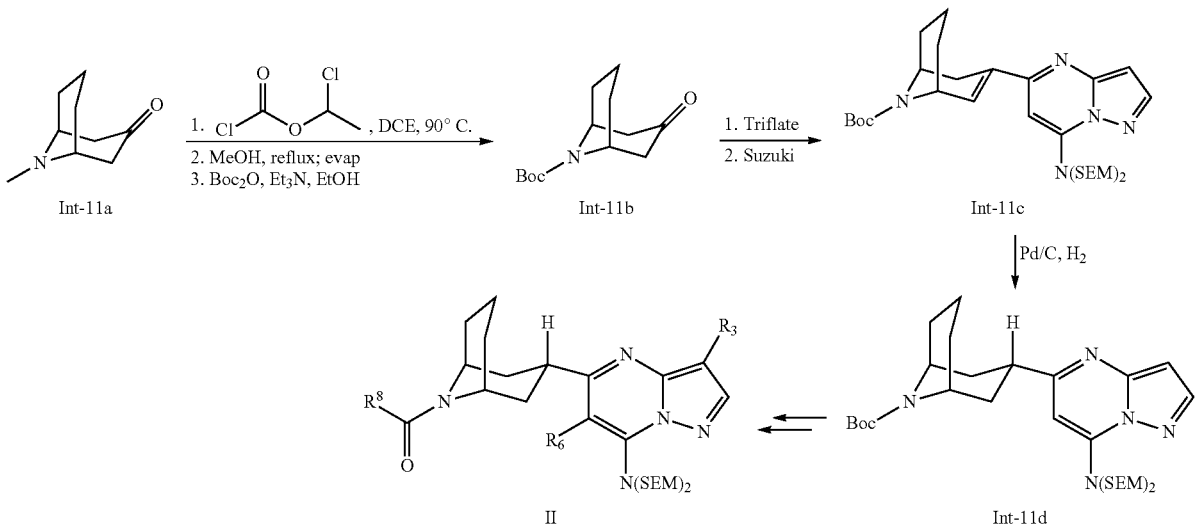

Compound II can be prepared from keto intermediate Int-11a using the sequence summarized in Scheme 8 above. Int-11a is converted to the N Boc-protected intermediate Int-11b by a three step sequence. Int-11a is treated with 1-chloroethyl chloroformate, followed by treatment with refluxing methanol. The nitrogen atom is Boc protected using Boc$_2$O to provide the N Boc-protected intermediate Int-11b. The triflate is formed by treating Int-11b under conditions similar to those described in Step 5 of Example 1.1. The triflate is then converted to the boronate ester such as by using the procedure described in Step 6 of Example 1-1. The boronate ester is then combined with Int-1d (prepared as described in Steps 1-4 of Example 1-1, scheme-1-1) under Suzuki coupling conditions, such as those described in Step 7 of Example 1-1 to afford Int-11c. Int-11c is then reduced using palladium on charcoal such as by using a procedure similar to that described in Step 8 of Example 1-1. The $R^3$, $R^6$ and the $R^8$ substituents can be installed using procedures similar to those described in steps 9 through 14 as in Examples 1-1 above. Sulfonyl substitution of the 6-position can be performed either using procedures similar to those described in scheme-3-1 (Steps A and B) or scheme-3-2 (step 3) of Example 3-1. Nitrile substitution of the 6-position can be accomplished using a procedure similar to that described in Step 1 of Example 5.

Example 11

Compounds of the of Formula (I) that incorporate deuterium atoms can be prepared from commercially available or known deuterium-containing reagents using modifications of the procedures described above in Examples 1-10. For instance, a deuterated compound of Formula (I) wherein $R^3$ is pyridyl substituted by Y, wherein Y is phenyl substituted by five $^2H$, i.e., compound 54, can be prepared as shown in Scheme 8 below. Compound 54 is a deuterated analog of compound 7.

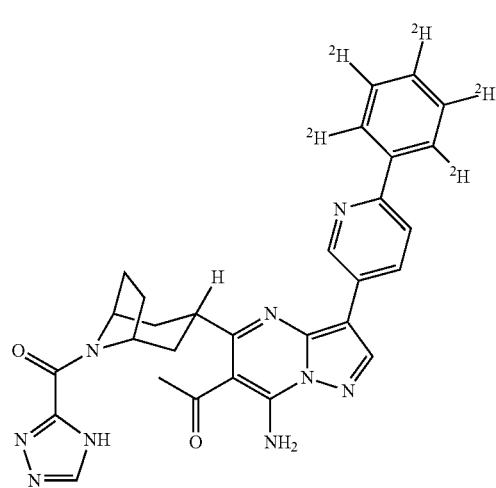

Scheme 9

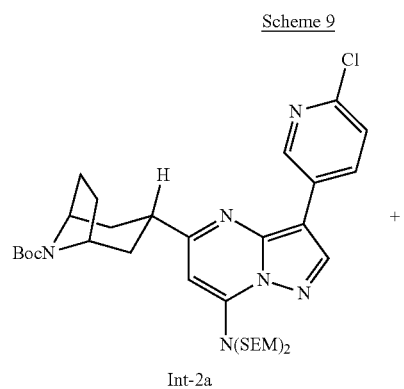

Step A—Synthesis of tert-butyl 3-(7-(bis((2-(trimethylsilyl)ethoxy)methyl)amino)-3-(6-phenyl-d5-pyridin-3-yl)pyrazolo[1,5-a]pyrimidin-5-yl)-8-azabicyclo[3.2.1]octane-8-carboxylate (Int-12a)

Phenyl-d5-boronic acid (2.79 mmol, 354.3 mg), $K_3PO_4$ (4.20 mmol, 890.4 mg), and $PdCl_2(dppf).CH_2Cl_2$ (0.14 mmol, 114.3 mg) are added to a solution of tert-butyl 3-(7-(bis((2-(trimethylsilyl)ethoxy)methyl)amino)-3-(6-chloropyridin-3-yl)pyrazolo[1,5-a]pyrimidin-5-yl)-8-azabicyclo[3.2.1]octane-8-carboxylate (which can be prepared as described in Step 2 of Example 1-2) (1.40 mmol, 1000 mg) in dioxane (12 mL) and $H_2O$ (1.5 mL). The resulting solution is stirred at 150° C. under microwave condition for 1 h. The mixture is diluted with $H_2O$ and then extracted with ethyl acetate (x2). The combined organic layers are washed with brine and dried with $Na_2SO_4$. Evaporation and purification by column chromatography affords the desired compound Int-12a.

Step B—Synthesis of Compound 54

Compound 1-(5-(8-(4H-1,2,4-triazole-3-carbonyl)-8-azabicyclo[3.2.1]octan-3-yl)-7-amino-3-(6-phenyl-d5-pyridin-3-yl)pyrazolo[1,5-a]pyrimidin-6-yl)ethanone (54) can be prepared using methods similar to those described in Steps 13 & 14 of Example 1-1 from Int-12a.

Example 12 mTOR Kinase Assay

Methods:
An HTRF mTOR enzyme assay was developed to assess the compounds' inhibitory activity. The mTOR assay buffer contained 10 mM Hepes (pH 7.4), 50 mM NaCl, 100 μg/ml BSA, 50 mM B-glycerophosphate, 10 mM $MnCl_2$ and 0.5 mM DTT. An active truncated mTOR enzyme was prepared similarly to that reported by Toral-Barza et al., *Biochemical and Biophysical Research Communications* 332, pp 304-310 (2005). 20 ng of human mTOR enzyme (<5% pure was pre-incubated with the compound for 10 minutes followed by the addition of 5 µM ATP and 0.2 µM GST-S6K (Zhang et al., *Protein Expression and Purification* 46, pp 414-420 (2006)). The reaction was incubated for one hour at 30° C. Anti phospho p70-S6K(Thr389) (~1.7 ng/well, anti-phospho-p70S6K-cryptate (Pho-p70S6-Kin-K cat#64CUSKAY, from Cisbio)) and anti GST-XL665 (1:1 Ratio with the substrate GST-S6K, anti GST-XL665, cat#61 GSTXLB) Cisbio) were added after the reaction was stopped. The plates were read (PHERAstar, BMG) at least 2 hours after adding the anti phospho p70-S6K and the anti GST-XL665.

$IC_{50}$ Determinations:

Dose-response curves were plotted from the inhibition data generated, each in duplicate, from 8 point serial dilutions of inhibitory compounds. Concentration of compound was plotted against the HTRF em665/em590 ratio signal. To generate $IC_{50}$ values, the dose-response curves were fitted to a standard sigmoidal curve and $IC_{50}$ values were derived by nonlinear regression analysis.

Results:

All Compounds were tested in the mTOR assay to determine their $IC_{50}$ values. All compounds had an mTor $IC_{50}$ value between 0.5-2000 nM. For example, compound 1.1.93 had an mTor $IC_{50}$ value of 2.3 nM. Compounds 1-46, 48, 49, and 51-54 had an $IC_{50}$ value in the range of 1-10 nM. Compounds 47 and 50 had an $IC_{50}$ value in the range of 10 nM to 25 nM.

Example 13 mTOR Target Engagement Assay

The target engagement of mTOR kinase inhibitors was evaluated using an immunofluorescent cell-based assay. In this assay, inhibition of mTORC1 activity was measured by the reduction in the level of phosphorylated 4E-BP1$^{Thr37/46}$ (p4E-BP1 Thr37/46), and inhibition of mTORC2 activity was measured by the reduction of phosphorylated AKT$^{Ser473}$ (pAKT S473).

PC3 cells (prostate tumor cell-line that contains a mutation in the tumor suppressor PTEN, that promotes the phosphorylation and activation of AKT and 4E-BP1) were used in the immunofluorescence assay. PC3 cells were seeded on 384 well plates (black clear bottom, Matrix #4332) overnight. PC3 cells were then treated with 40 µl of the serially diluted test compounds (in 5% fetal bovine serum, F12 medium containing 0.25% DMSO) for ninety minutes at 37° C. The test compound solution was removed, and the plates were washed gently two times with 25 µl phosphate buffered saline (PBS). The cells were fixed by adding 25 µl of Prefer reagent (from Anatech LTD, Cat#414, a glyoxal fixative for fixing proteins within a cell) for sixty minutes followed by three washes with PBS. 5% Goat serum in PBS/0.3% Triton was used to block non-specific binding (60 minutes).

The primary antibodies targeting pAKT S473 and p4E-BP1 Thr37/46 were diluted into PBS/0.3% Triton and incubated with the cells overnight at 4° C. The antibodies targeting pAKTS473 (Cat#4085, Cell signaling) and p4E-BP1 Thr37/46 (Cat#2855, Cell signaling) were used at a 1:100 dilution. Plates were washed three times with PBS/0.1% Tween 20 before adding the secondary antibody at a 1:200 dilution. (goat anti-rabbit containing a fluorescent label, Alexa Fluor 488, Cat#A11008, Invitrogen) in PBS/0.3% Triton for 60 minutes.

Finally, the plates were washed three times with PBS/0.1% Tween 20 and the fluorescent intensity was read using an Analyst HT from Molecular Devices. The fluorescent intensity values from the serially diluted compound treatment group were analyzed using the Xlfit 4 program (Microsoft) (Formula 205: Y=Bottom+(Top-Bottom)/(1+($IC_{50}$/X)^Hillslope) to generate the $IC_{50}$ value. Where Top is the maximum signal without Compound (+DMSO only) and Bottom represents maximum inhibition. Y is the fluorescence at some compound concentration. The control used to determine the fluorescent intensities for 100% pAKT S473 or 100% phosphorylated p4E-BP1 Thr37/46 were measured from untreated wells that contained only DMSO, instead of test compound.

The above tables lists representative compounds of the invention with activity data whereby the $IC_{50}$ values are rated "A", "B," "C," or "D." The $IC_{50}$ values are rated "A" for $IC_{50}$ values in the range of 1 nM to 100 nM, "B" for $IC_{50}$ values in the range from 100 nM to 1000 nM, "C" for $IC_{50}$ values in the range from 1000 nM to 10 µM, and "D" for $IC_{50}$ values greater than 10 µM. The designation "ND" or "NA" means that the $IC_{50}$ was not determined.

Uses of the Pyrazolopyrimidine Compounds

The Pyrazolopyrimidine Compounds are useful in human and veterinary medicine in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974.

While not being bound by any specific theory it believed that the Pyrazolopyrimidine Compounds are useful in the treatment of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease because of their mTOR inhibitory activity.

The general value of the compounds of the invention in inhibiting mTOR can be determined, for example, using the assay described above in Example 12. In addition, the general value in inhibiting mTORC1 or mTORC2 function can be evaluated using the assays described above in Example 13.

More specifically, the Pyrazolopyrimidine Compounds can be useful in the treatment of a variety of cancers, including (but not limited to) the following: tumor of the bladder, breast (including BRCA-mutated breast cancer), colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma;

head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas; melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

While not being bound by any specific theory, due to the key role of kinases in the regulation of cellular proliferation in general, inhibitors of kinases could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The Pyrazolopyrimidine Compounds may induce or inhibit apoptosis. The apoptotic response is aberrant in a variety of human diseases. The Pyrazolopyrimidine Compounds, as modulators of apoptosis, can be useful in the treatment of cancer (including but not limited to those types mentioned hereinabove), viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

While not being bound by any specific theory, the Pyrazolopyrimidine Compounds, as inhibitors of kinases, can modulate the level of cellular RNA and DNA synthesis. These compounds can therefore be useful in the treatment of viral infections (including but not limited to HIV, human papilloma virus, herpesvirus, poxvirus, Epstein-Barr virus, Sindbis virus and adenovirus).

In particular embodiments of the invention, Pyrazolopyrimidine Compounds, as inhibitors of mTOR kinase could act in diseases or disorders other than cancer that are associated with dysregulated mTOR activity such as viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The Pyrazolopyrimidine Compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Pyrazolopyrimidine Compounds may also be useful in inhibiting tumor angiogenesis and metastasis.

Another aspect of this invention is a method of treating a patient (e.g., human) having a disease or condition associated with mTOR kinases by administering a therapeutically effective amount of a Pyrazolopyrimidine Compound, or a pharmaceutically acceptable salt of said compound to the patient. Another aspect of the invention is the use of the Pyrazolopyrimidine Compound for the preparation of a medicament for the treatment of cancer. In another embodiment, the Pyrazolopyrimidine Compound is for use in method of treating cancer. In the therapies described above, a preferred dosage for administration to a patient is about 0.001 to 1000 mg/kg of body weight/day of the Pyrazolopyrimidine Compound. An especially preferred dosage is about 0.01 to 25 mg/kg of body weight/day of the Pyrazolopyrimidine Compound, or a pharmaceutically acceptable salt of said compound.

Combination Therapy

The compounds of the present invention can be administered alone or in combination with other therapies suitable for the disease or disorder being treated. Where separate dosage formulations are used, the compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Therefore, the present invention encompasses pharmaceutical compositions comprising a therapeutically effective amount of the compound of the invention and a pharmaceutically acceptable carrier and optionally other threrapeutic ingredients, such as an anti-cancer agent. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, Ifulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, 38 ntimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO 03/39460 and WO2003/079973, WO2003/099211, WO2004/039774, WO2003/105855, WO2003/106417. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N242(E),4(E)-tetradecadienoyl]glycylaminoR-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-ylacetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin. Orthop. Vol. 313, p. 76 (1995); J. Mot. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonylyfumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor

[TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K kinase family (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

Examples of mTOR inhibitors include ridaforolimus, temsirolimus, everolimus, a rapamycin-analog. Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse even profile, and possess anti-tumor activity in a broad range of cancers. A description and preparation of ridaforolimus is described in U.S. Pat. No. 7,091,213 to Ariad Gene Therapeutics, Inc. Temsirolimus, also known as Torisel®, is currently marketed for the treatment of renal cell carcinoma. A description and preparation of temsirolimus is described in U.S. Pat. No. 5,362,718 to American Home Products Corporation. Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of 1050 for COX-2 over 1050 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, imatinib (ST1571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WTI, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res. Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nudel, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The compounds of the instant invention are useful in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); and zoledronate (Zometa®).

Non-limiting examples of other suitable anti-cancer agents for combination with the instant compounds are selected from the group consisting of a Cytostatic agent, Cisplatin, Deforolimus (described in PCT publication No. 2003/064383), Doxorubicin, liposomal doxorubicin (e.g., Caelyx®, Myocet®, Doxil®), Taxotere, Taxol, Etoposide, Irinotecan, Camptostar, Topotecan, Paclitaxel, Docetaxel, Epothilones, Tamoxifen, 5-Fluorouracil, Methoxtrexate, Temozolomide, cyclophosphamide, SCH 66336, R115777®, L778, 123®, BMS 214662®, Iressa®, Tarceva®, Antibodies to EGFR, antibodies to IGFR (including, for example, those published in US 2005/0136063 published Jun. 23, 2005), ESK inhibitors, KSP inhibitors (such as, for example, those published in WO 2006/098962 and WO 2006/098961; ispinesib, SB-743921 from Cytokinetics), Centrosome associated protein E ("CENP-E") inhibitors (e.g., GSK-923295), Gleevec®, Intron, Ara-C, Adriamycin, Cytoxan, Gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6 Mercaptopurine, 6 Thioguanine, Fludarabine phosphate, Oxaliplatin, Leucovirin, ELOXATIN™, Vinblastine, Vincristine, Vindesine, Bleomycin, Dactinomycin, Daunorubicin, Doxorubicin, Epirubicin, Idarubicin, Mithramycin, Deoxycoformycin, Mitomycin C, L Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, bortezomib ("Velcade"), Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225®, Satriplatin, mylotarg, Avastin, Rituxan, Panitubimab, Sutent, Sorafinib, Sprycel (dastinib), Nilotinib, Tykerb (Lapatinib) and Campath.

In one embodiment, the invention provides a method of treating cancer, the method comprising administering an amount of a Pyrazolopyrimidine Compound or a pharmaceutically acceptable salt thereof, and an amount of one additional anticancer agent selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus, Deoxycoformycin, Didox, Diethylstilbestrol, Docetaxel, Doxorubicin, Dromostanolone, Droloxafine, Epirubicin, Epothilones, ERK inhibitors, Erlotinib, Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamcicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Irinotecan, ispinesib, KSP inhibitors, L778, 123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6 Mercaptopurine, Methoxtrexate, Methylprednisolone, Methyltestosterone, Mithramycin, Mitomycin C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, SmI1, Sorafinib, Streptozocin, Sunitinib, Tamoxifen, Taxotere, Taxol, Temozolomide, Teniposide, Testolactone, Testosterone, Tezacitabine, 6 Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine.

In one embodiment, the invention provides a method of treating cancer, the method comprising administering an amount of a Pyrazolopyrimidine Compound or a pharmaceutically acceptable salt thereof, and an amount of one or more of a MAP Kinase pathway inhibitor such as bRaf, MEK, or ERK inhibitors to a patient in need thereof.

In another embodiment, the invention provides a method of treating cancer, the method comprising administering an amount of a Pyrazolopyrimidine Compound or a pharmaceutically acceptable salt thereof, and an amount of one or more of ERK inhibitors (for example, compounds described in WO2008/156739, WO2007/070398, WO 2008/156739 and US publication 2007/0232610) to a patient in need thereof.

In one embodiment, the invention provides a method of treating cancer, the method comprising administering an amount of a Pyrazolopyrimidine Compound or a pharmaceutically acceptable salt thereof, and an amount of one or more of an anti-IGF-1R antibody. Specific anti-IGF-1R antibodies include, but are not limited to, dalotuzumab, figitumumab, cixutumumab, SHC 717454, Roche R1507, EM164 or Amgen AMG479.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the instant compounds described herein are within the scope of the present invention.

Compositions and Administration

This invention is also directed to pharmaceutical compositions which comprise at least one Pyrazolopyrimidine Compound, or a pharmaceutically acceptable salt of said compound and at least one pharmaceutically acceptable carrier.

When administered to a patient, the Pyrazolopyrimidine Compounds can be administered as a component of a composition that comprises a pharmaceutically acceptable carrier or vehicle. The present invention provides pharmaceutical compositions comprising an effective amount of at least one Pyrazolopyrimidine Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Pyrazolopyrimidine Compounds of the present invention may also be delivered transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anti-cancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Pyrazolopyrimidine Compound is administered orally.

In another embodiment, the Pyrazolopyrimidine Compound is administered intravenously.

In another embodiment, the Pyrazolopyrimidine Compound is administered topically.

In still another embodiment, the Pyrazolopyrimidine Compounds is administered sublingually.

In one embodiment, a pharmaceutical preparation comprising at least one Pyrazolopyrimidine Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Pyrazolopyrimidine Compound(s) by weight or volume. In various embodiments, the present compositions can contain, in one embodiment, from about 1% to about 70% or from about 5% to about 60% of the Pyrazolopyrimidine Compound(s) by weight or volume.

The quantity of Pyrazolopyrimidine Compound in a unit dose of preparation may be varied or adjusted from about 0.1 mg to about 5000 mg. In various embodiments, the quantity is from about 10 mg to about 5000 mg, about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion.

In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Pyrazolopyrimidine Compounds will be regulated according to the judgment of the attending clinician considering such factors as age, condition and size of the patient as well as severity of the symptoms being treated. Generally, a total daily dosage of the Pyrazolopyrimidine Compounds range from about 0.1 to about 5000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 5000 mg/day, administered in a single dose or in 2-4 divided doses. In another embodiment, the dosage is from about 100 to about 5000 mg/day, administered in a single dose or in 2-4 divided doses. In still another embodiment, the dosage is from about 500 to about 5000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Pyrazolopyrimidine Compound or a pharmaceutically acceptable salt thereof; (ii) one or more additional therapeutic agents that are not a Pyrazolopyrimidine Compound; and (iii) a pharmaceutically acceptable carrier, wherein the amounts in the composition are together effective to treat disease or disorder associated with dysregulated mTOR activity, such as a cancer.

Kits

Another aspect of this invention is a kit comprising a therapeutically effective amount of at least one Pyrazolopyrimidine Compound, or a pharmaceutically acceptable salt of said compound, and a pharmaceutically acceptable carrier, vehicle or diluent.

Yet another aspect of this invention is a kit comprising an amount of at least one Pyrazolopyrimidine Compound, or a pharmaceutically acceptable salt of said compound and an amount of at least one additional anti-cancer agent listed above, wherein the amounts of the two or more active ingredients result in a desired therapeutic effect. In one embodiment, the at least one Pyrazolopyrimidine Compound and the at least one additional anti-cancer agent are provided in the same container. In one embodiment, the at least one Pyrazolopyrimidine Compound and the at least one additional anti-cancer agent are provided in separate containers.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:
1. A compound having the Formula (I):

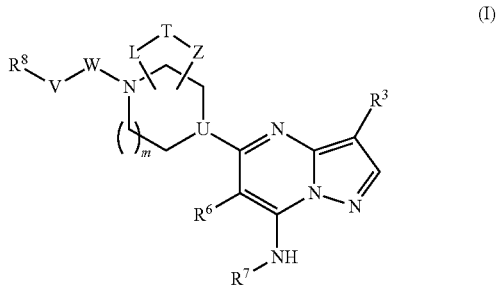

or a pharmaceutically acceptable salt thereof, wherein
U is N, CH, or $C(R^{13})$;
$R^{13}$ is selected from the group consisting of
$C_1$-$C_6$ alkyl, hydroxy, —$OR^{16}$, —$N(R^{14})(R^{15})$, —$N(R^{14})$—$C(O)$—$R^{16}$, —$N(R^{14})$—$S(O)$—$R^{16}$, —$N(R^{14})$—$S(O)_2R^{16}$, —$N(R^{14})$—$C(O)$—$N(R^{14})(R^{15})$, $C_3$-$C_8$ cycloalkyl, $C_6$-$C_{10}$ mono or bicyclic aryl, —$C(O)R^{16}$, —$C(O)OR^{16}$, —$C(O)N(R^{14})(R^{15})$, —$S(O)R^{16}$, —$S(O)_2R^{16}$, —$S(O)$—$N(R^{14})(R^{15})$, —$S(O)_2$—$N(R^{14})(R^{15})$, —O—$C(O)OR^{17}$, —O—$C(O)N(R^{17})(R^{18})$,
3- to 8-membered monocyclic heterocyclyl and having one to three heteroatoms selected from the group consisting of N, O, and S; and
$C_5$-$C_{10}$ mono or bicyclic heteroaryl and having one to three heteroatoms selected from the group consisting of N, O, and S;
$R^{14}$ and $R^{15}$ are independently selected from the group consisting of H, $C_1$-$C_6$ alkyl, $C_3$-$C_8$ cycloalkyl, and phenyl;
$R^{16}$ is independently selected from the group consisting of $C_1$-$C_6$ alkyl, $C_3$-$C_8$ cycloalkyl, and phenyl;
$R^{17}$ and $R^{18}$ are independently selected from the group consisting of $C_1$-$C_6$ alkyl, $C_3$-$C_8$ cycloalkyl, $C_6$-$C_{10}$ mono or bicyclic aryl, 3- to 8-membered monocyclic heterocyclyl, and $C_5$-$C_{10}$ mono or bicyclic heteroaryl;
wherein L and Z are bonded to any two carbon atoms of the ring comprising U and are independently selected from the group consisting of $CH_2$, $C(H)(R^1)$, $C(R^1)(R^2)$, $N(R^1)$, C(O), O, S, S(O), and $S(O)_2$; and T is absent such that L is bonded directly to Z, or T is selected from the group consisting of C(O), O, S, $N(R^1)$, S(O), $S(O)_2$, and $C_1$-$C_4$ alkylene, wherein said alkylene of T is unsubstituted or substituted with 1 to 2 moieties, which moieties are independently selected from the group consisting of $C_1$-$C_3$ alkyl, halo, hydroxy, $C_1$-$C_3$ alkoxy, amino, $C_1$-$C_3$ alkylamino and $C_1$-$C_3$ dialkylamino; or L-T-Z is —$CH_2CH_2OCH_2$—;
m is 0 or 1;
$R^1$ and $R^2$ are independently selected from the group consisting of H, $C_1$-$C_3$ alkyl, halo, hydroxy, $C_1$-$C_3$ alkoxy, amino, $C_1$-$C_3$ alkylamino and $C_1$-$C_3$ dialkylamino;
W is absent, or W is selected from the group consisting of C(O), C(NH), S(O), $S(O)_2$, $C_1$-$C_4$ alkylene, $C_3$-$C_8$ cycloalkyl, phenyl, 5- to 6-membered heteroaryl, and 3- to 8-membered heterocyclyl;
V is absent, or V is selected from the group consisting of C(O), O, S, N(H), $N(C_1$-$C_3$ alkyl), $N(C_3$-$C_8$ cycloalkyl), S(O), $S(O)_2$, and $C_1$-$C_4$ alkylene;

or W and V together form a $C_3$-$C_8$ cycloalkyl, phenyl, 5- to 6-membered heteroaryl, or 3 to 8-membered heterocyclyl ring;

$R^8$ is selected from the group consisting of
  (i) $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, halo, trifluoromethyl, carboxy, 5- to 6-membered heteroaryl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;
  (ii) 3- to 8-membered heterocyclyl wherein said heterocyclyl of $R^8$ is unsubstituted or substituted with one to three moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino;
  (iii) $C_6$-$C_{10}$ aryl or 5- to 10-membered heteroaryl, wherein said aryl or heteroaryl of $R^8$ is unsubstituted or is substituted with one to three moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and
  (iv) —N(H)OH or —N(H)—$C_1$-$C_3$ alkoxy;

$R^3$ is H, $C_1$-$C_6$ alkyl, $C_1$-$C_6$ alkenyl, $C_1$-$C_6$ alkynyl, —C(O)$R^9$, $C_6$-$C_{12}$ aryl, $C_3$-$C_8$ cycloalkyl, $C_3$-$C_8$ cycloalkenyl, 5- to 10-membered heteroaryl, 3- to 8-membered heterocyclyl, 3- to 8-membered heterocyclenyl, ($C_6$-$C_{12}$)aryl($C_1$-$C_6$)alkyl, ($C_3$-$C_8$)cycloalkyl($C_1$-$C_6$)alkyl, ($C_3$-$C_8$)cycloalkenyl($C_1$-$C_6$)alkyl, (5- to 10-membered)heteroaryl($C_1$-$C_6$)alkyl, (3- to 8-membered)heterocyclyl($C_1$-$C_6$)alkyl, (3- to 8-membered)heterocyclenyl($C_1$-$C_6$)alkyl, wherein said aryl, cycloalkyl, cycloalkenyl, heteroaryl, heterocyclyl, heterocyclenyl, arylalkyl, cycloalkylalkyl, cycloalkenylalkyl, heteroarylalkyl, heterocyclylalkyl, and heterocyclenylalkyl of $R^3$ is unsubstituted or substituted with one to three moieties independently selected from the group consisting of Y, halogen, $C_1$-$C_6$ alkyl, $C_3$-$C_{10}$ cycloalkyl, trifluoromethyl, cyano, —C(O)OH, —($CH_2$)$_x$—C(O)OH, trifluoromethoxy, —$OR^{11}$, —C(O)$R^{10}$, —$NR^9R^{10}$, —C(O)$_2$-alkyl, —C(O)$NR^9R^{10}$, —$SR^9$, and —S(O)$_2R^{12}$;
  Y is $C_6$-$C_{10}$ aryl or 5- to 10-membered heteroaryl, wherein said aryl or heteroaryl of Y is unsubstituted or substituted with one to five moieties independently selected from the group consisting of $^2$H, halo, cyano, hydroxy, amino, $C_1$-$C_6$ alkylamino, $C_1$-$C_6$ dialkylamino, trifluoromethyl, trifluoromethoxy, $C_1$-$C_6$ alkyl, $C_1$-$C_6$ hydroxyalkyl, and $C_1$-$C_6$ alkoxy; and
  each occurrence of $R^9$ is independently H, $C_1$-$C_6$ alkyl, $C_3$-$C_{10}$ cycloalkyl, phenyl, 5- to 6-membered heteroaryl or 3- to 8-membered heterocyclyl;
  each occurrence of $R^{10}$ is independently H, $C_1$-$C_6$ alkyl, $C_3$-$C_{10}$ cycloalkyl, phenyl, 5- to 6-membered heteroaryl, or 3- to 8-membered heterocyclyl, or $R^9$ and $R^{10}$ together with the nitrogen atom to which they are attached form a 3- to 6-membered heterocyclyl ring;
  each occurrence of $R^{11}$ is independently H, $C_1$-$C_6$ alkyl, $C_3$-$C_{10}$ cycloalkyl, phenyl, 5- to 6-membered heteroaryl, or 3- to 8-membered heterocyclyl;
  each occurrence of $R^{12}$ is independently $C_1$-$C_6$ alkyl, $C_3$-$C_{10}$ cycloalkyl, phenyl, 5- to 6-membered heteroaryl, or 3- to 8-membered heterocyclyl; and
  x is an integer from 1 to 4;

$R^6$ is selected from the group consisting of H, halo, hydroxyl, cyano, $C_1$-$C_6$ alkyl, $C_1$-$C_6$ alkanoyl, $C_1$-$C_6$ alkylsulfonyl, $C_1$-$C_6$ alkylsulfinyl, $C_1$-$C_6$ alkoxy, $C_1$-$C_6$ haloalkyl, amino, $C_1$-$C_6$ alkylamino, $C_1$-$C_6$ dialkylamino, $C_3$-$C_8$ cycloalkyl, $C_6$-$C_{10}$ aryl, 5- to 10-membered heteroaryl, and 5- to 10-membered heterocyclyl, wherein each of said aryl, heteroaryl, and heterocyclyl of $R^6$ is unsubstituted or substituted with one to two moieties selected from the group consisting of halo, $C_1$-$C_3$ alkyl, $C_1$-$C_3$ alkoxy, amino, $C_1$-$C_3$ alkylamino, and $C_1$-$C_3$ dialkylamino; and $R^7$ is selected from the group consisting of H, $C_1$-$C_6$ alkyl, and $C_3$-$C_8$ cycloalkyl, wherein said alkyl or cycloalkyl of $R^7$ is unsubstituted or substituted with one to two moieties selected from the group consisting of halo, $C_1$-$C_3$ alkyl, $C_1$-$C_3$ alkoxy, amino, $C_1$-$C_3$ alkylamino, and $C_1$-$C_3$ dialkylamino.

2. The compound of claim 1 or a pharmaceutically acceptable salt thereof, wherein m is 1.

3. The compound of claim 1 or a pharmaceutically acceptable salt thereof, wherein the group -L-T-Z— is selected from the group consisting of —$CH_2OCH_2$—, —$CH_2CH_2OCH_2$—, and $C_2$-$C_4$ alkylene, wherein said alkylene is unsubstituted or substituted with one to two moieties selected from the group consisting of $C_1$-$C_3$ alkyl, fluoro, and hydroxy.

4. The compound of claim 1 or a pharmaceutically acceptable salt thereof, wherein W is C(O).

5. The compound of claim 1 or a pharmaceutically acceptable salt thereof, wherein V is absent.

6. The compound of claim 1 or a pharmaceutically acceptable salt thereof, wherein $R^8$ is selected from the group consisting of
  (i) $C_1$-$C_6$ alkyl or $C_3$-$C_{10}$ cycloalkyl, wherein said alkyl or cycloalkyl of $R^8$ is unsubstituted or substituted with one to three moieties independently selected from the group consisting of hydroxy, $C_1$-$C_6$ alkoxy, fluoro, trifluoromethyl, carboxy, tetrazolyl, —$SO_2H$, $C_1$-$C_6$ alkyl-C(O)—NH—, $C_1$-$C_6$ alkyl-$SO_2$—NH—, and $C_1$-$C_6$ alkyl-SO—NH—;
  (ii) 5- to 6-membered heterocyclyl containing 1 to 3 heteroatoms selected from the group consisting of N, O, S, and S(O)$_2$ wherein said heterocyclyl of $R^8$ is unsubstituted or substituted with one to two moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino; and
  (iii) phenyl or 5- to 6-membered heteroaryl containing 1 to 3 heteroatoms selected from the group consisting of N, O, and S, wherein said phenyl or heteroaryl of $R^8$ is unsubstituted or is substituted with one to two moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino.

7. The compound of claim 1 or a pharmaceutically acceptable salt thereof, wherein $R^6$ is selected from the group consisting of H, $C_1$-$C_6$ alkyl, $C_1$-$C_6$ alkanoyl, cyano, $C_1$-$C_6$ alkylsulfonyl, halo, hydroxy, amino, $C_1$-$C_6$ alkylamino, and $C_1$-$C_6$ dialkylamino.

8. The compound of claim 1 or a pharmaceutically acceptable salt thereof, wherein $R^7$ is H.

9. The compound of claim 1, or a pharmaceutically acceptable salt thereof, wherein the compound is:
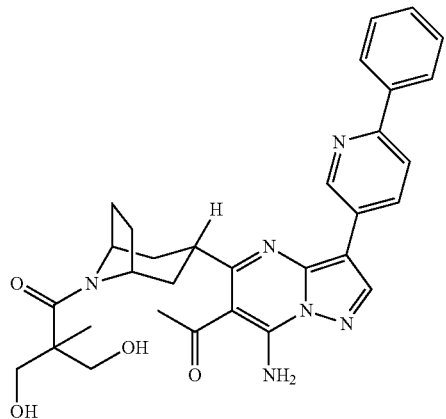
1
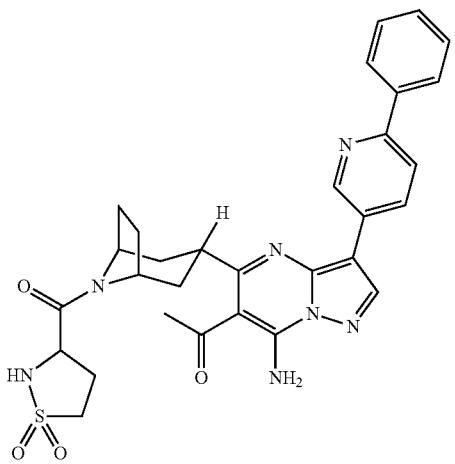
4
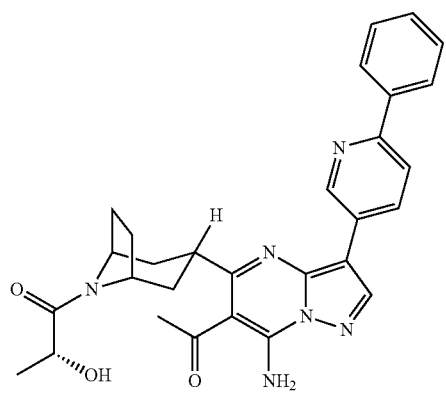
2
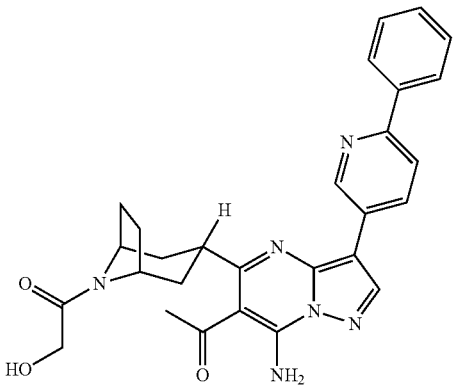
5
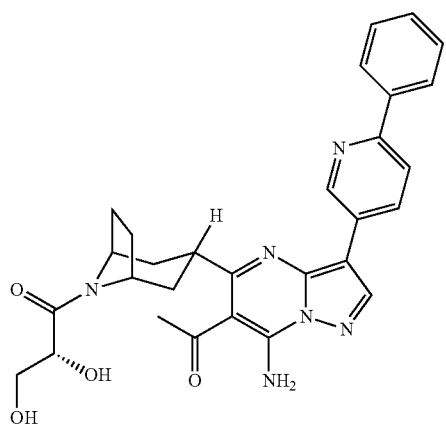
3
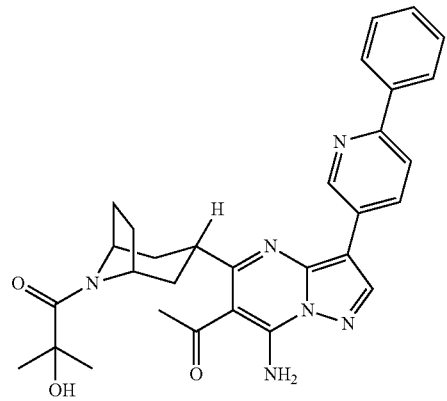
6

| 7 | 11 |
|---|---|
| 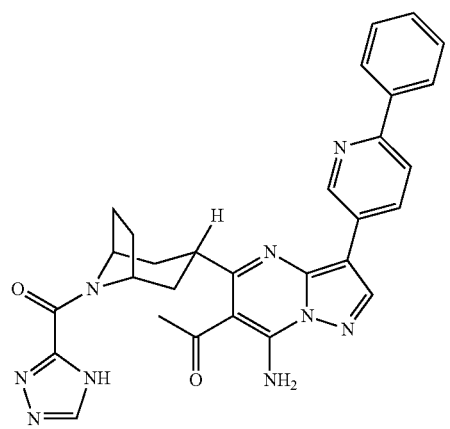 | 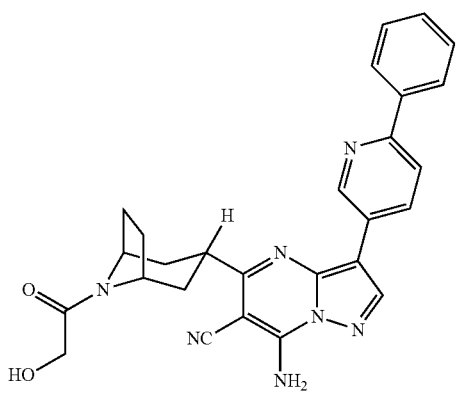 |
| 8 | 12 |
| 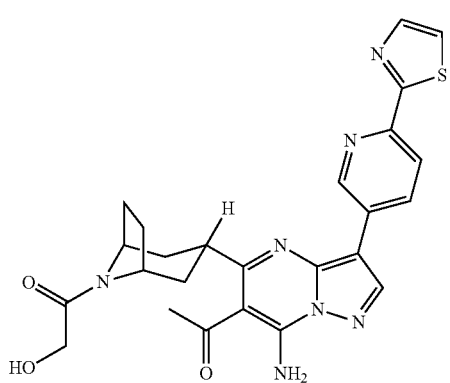 | 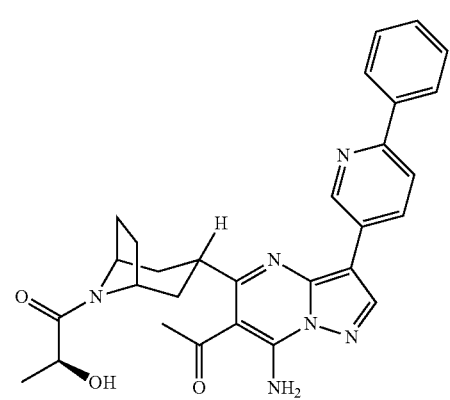 |
| 9 | 13 |
| 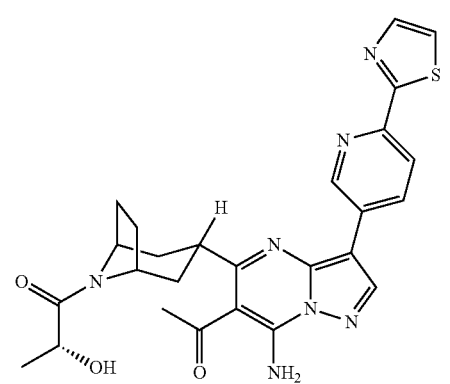 | 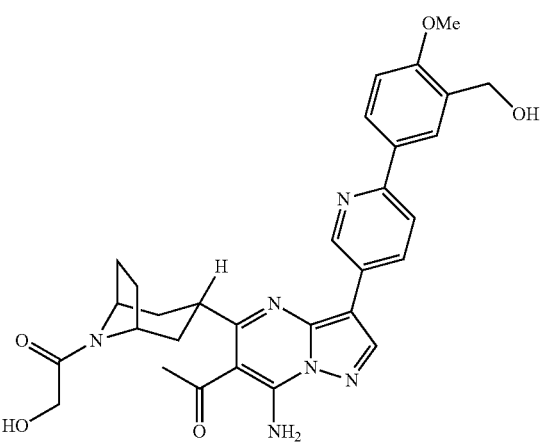 |
| 10 | 14 |
| 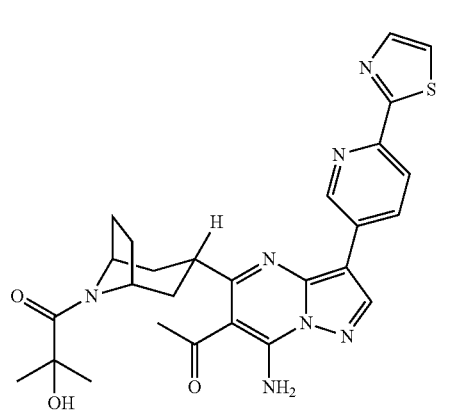 | 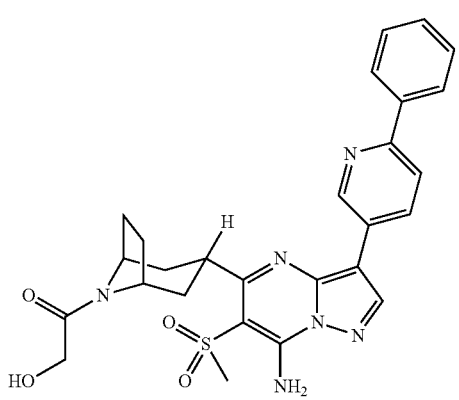 |

-continued
15
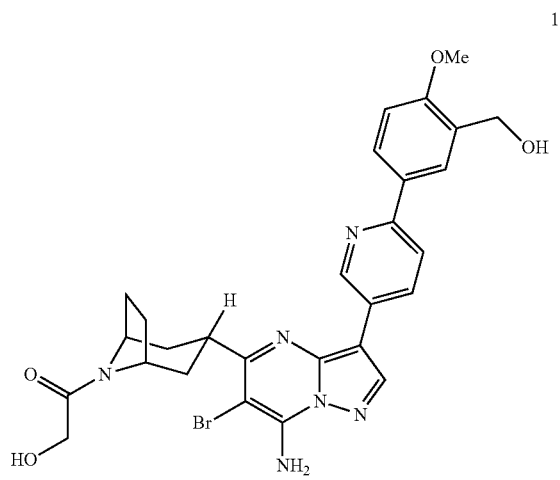
16
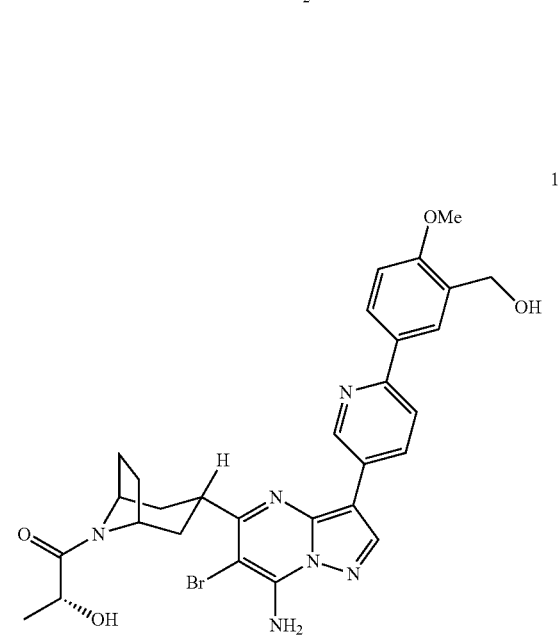
17
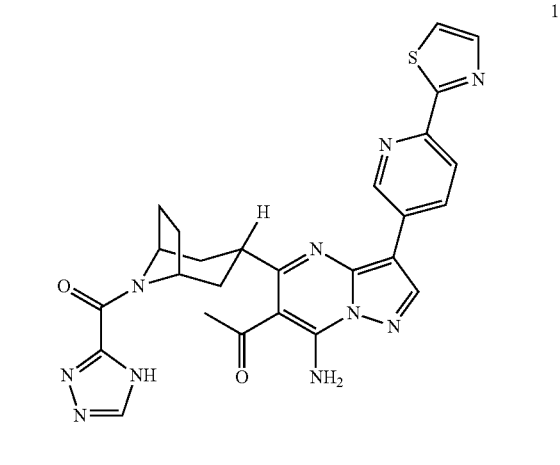
-continued
18
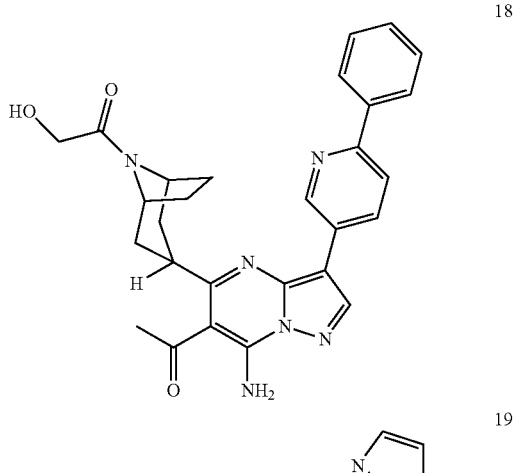
19
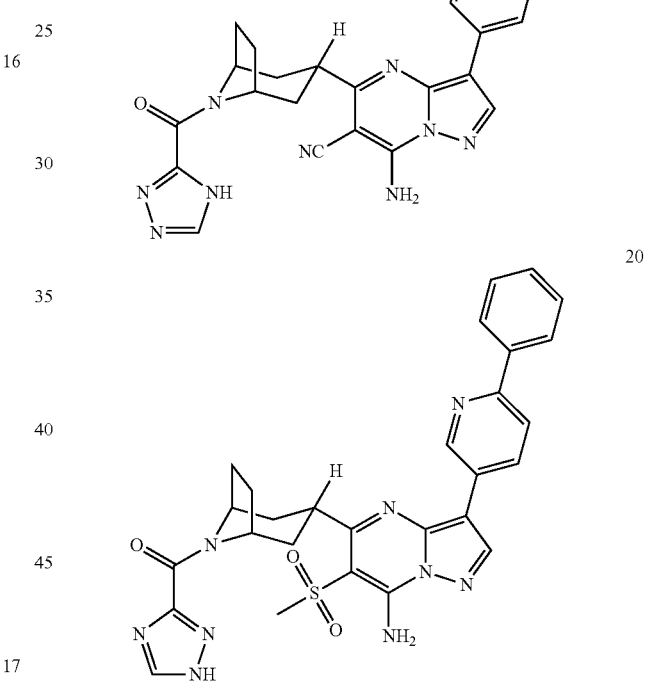
20
21
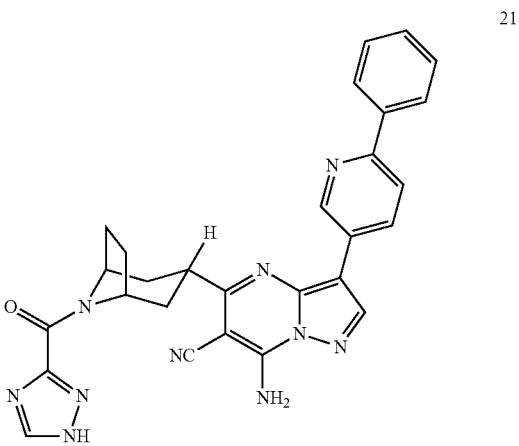

891
-continued
22
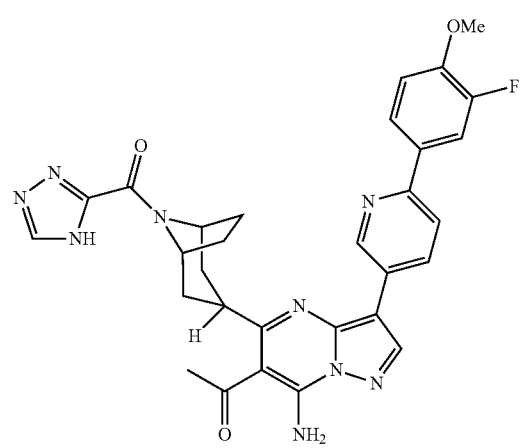
23
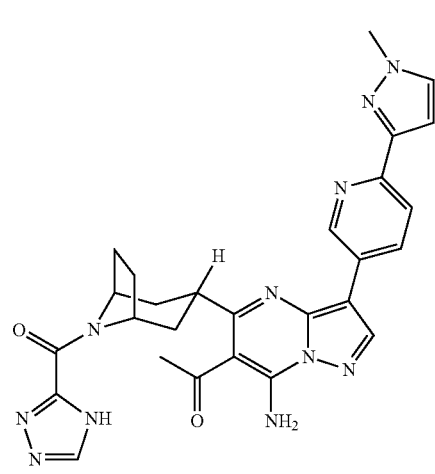
24
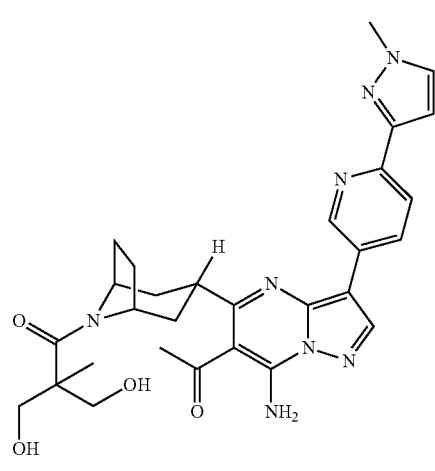
892
-continued
25
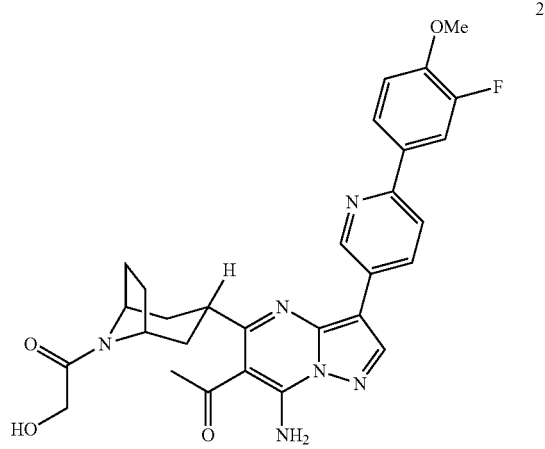
26
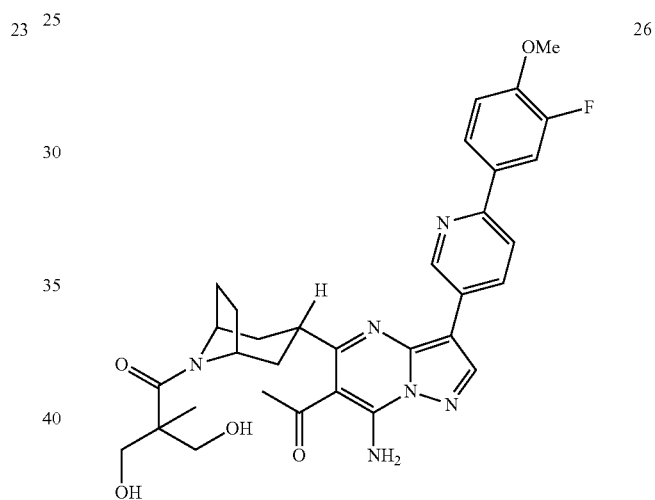
27
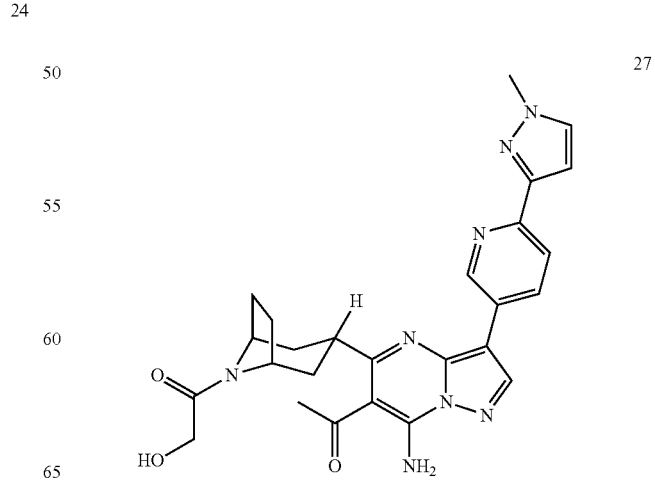

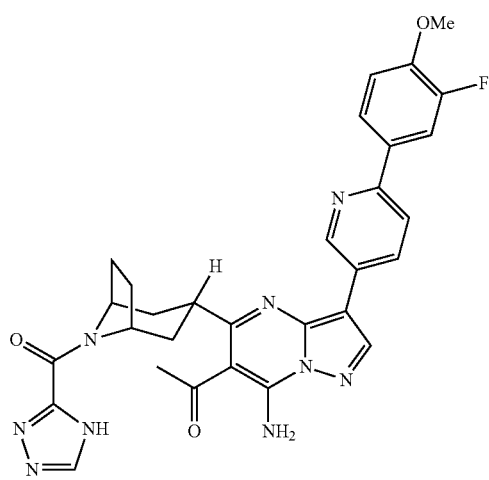
28
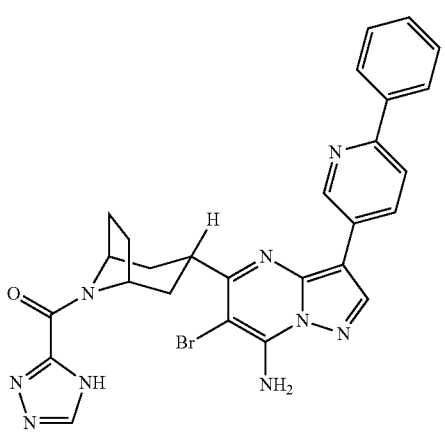
31
29
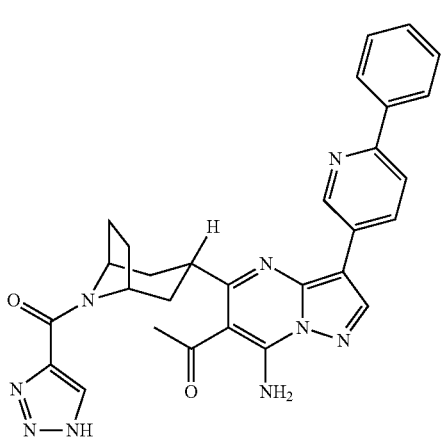
32
30
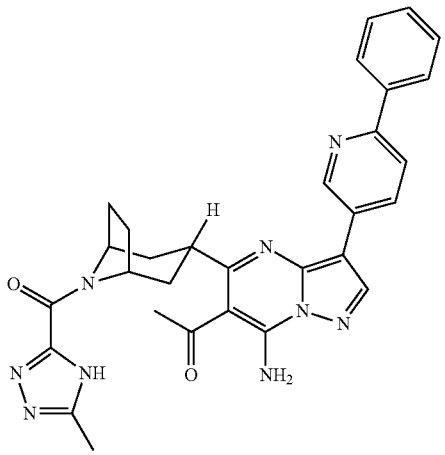
33

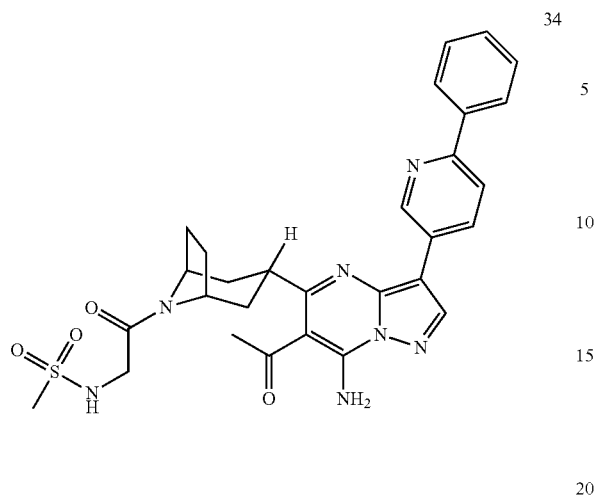
34
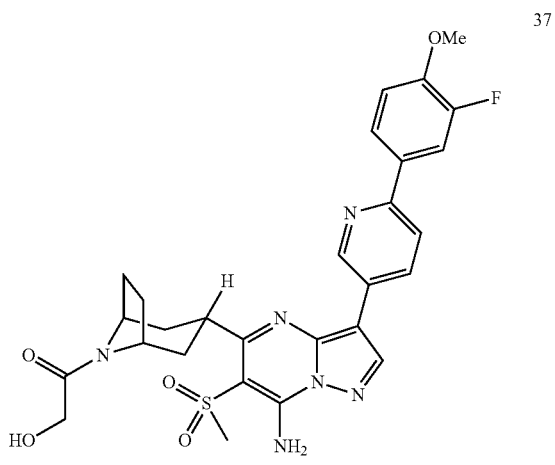
37
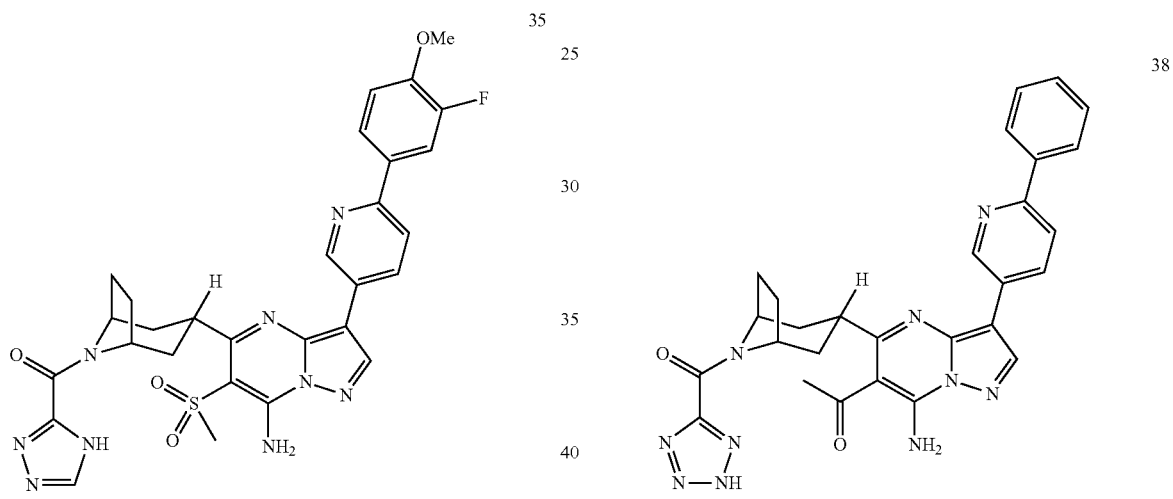
35
36
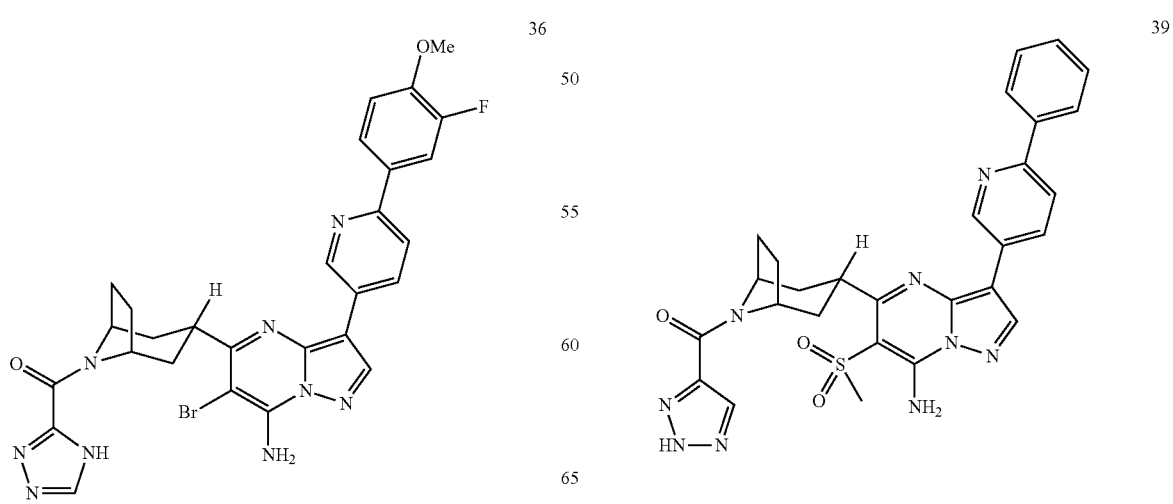
38
39

40
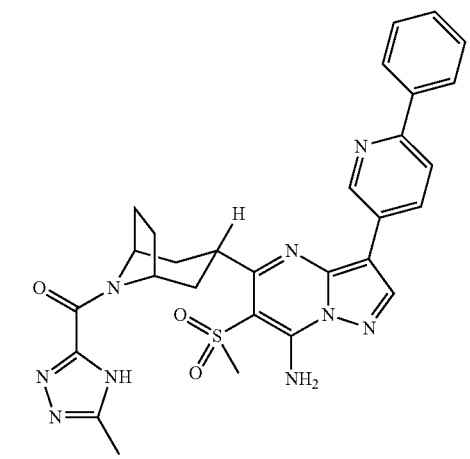
41
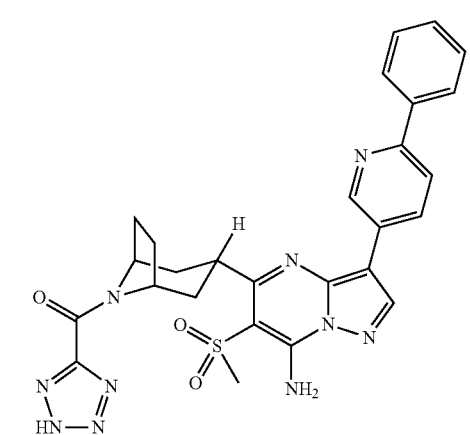
42
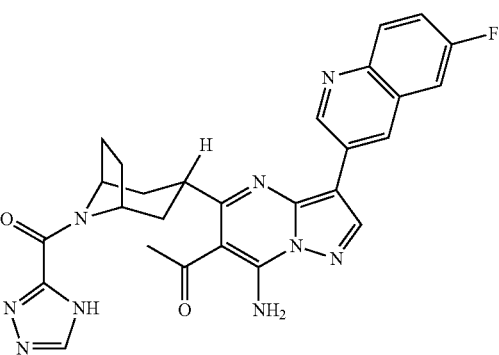
43
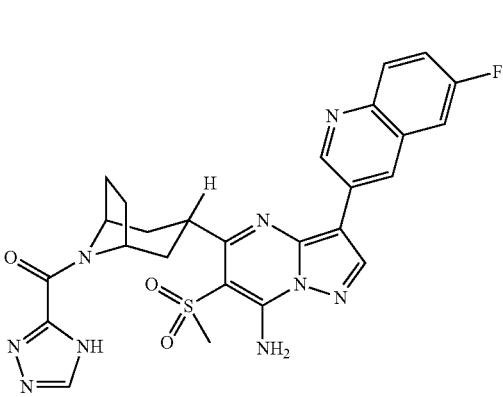
44
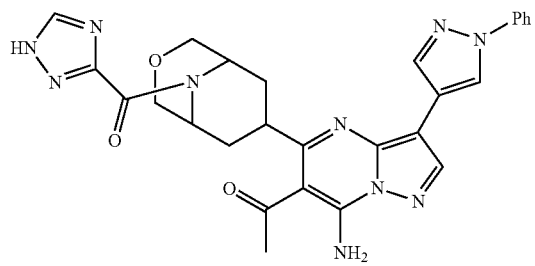
45
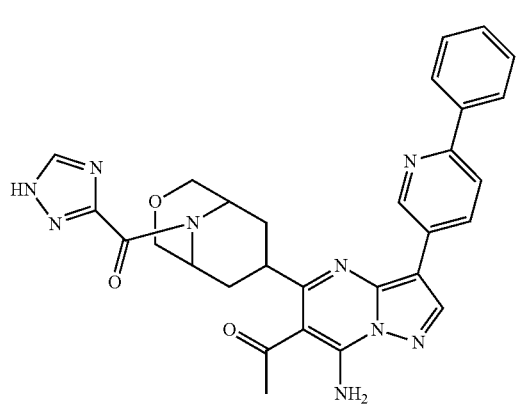
47
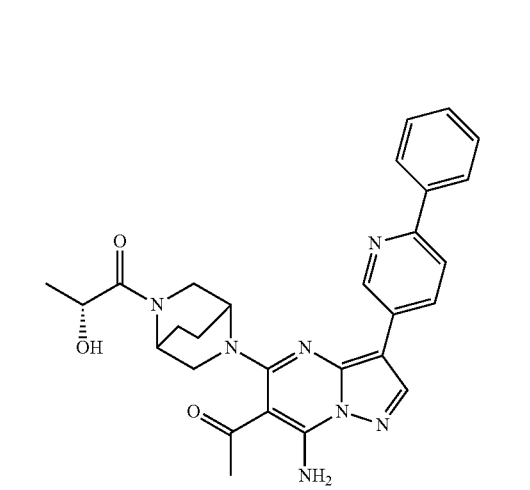
48
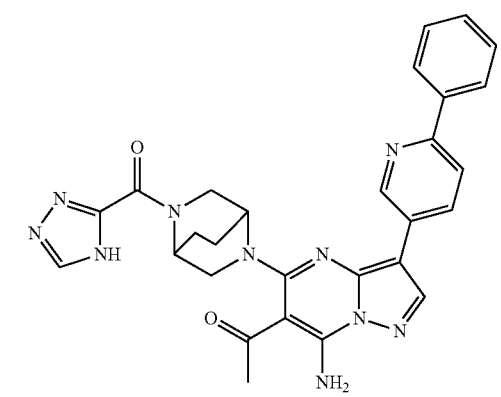

899

-continued

49
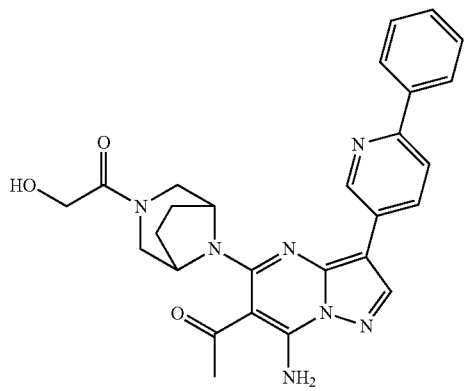

50
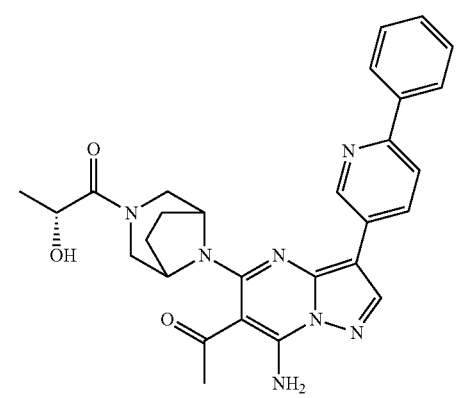

51
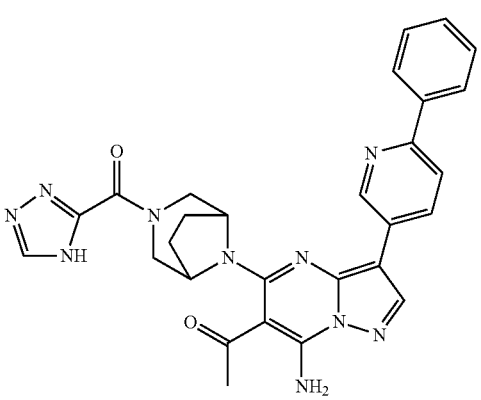

52
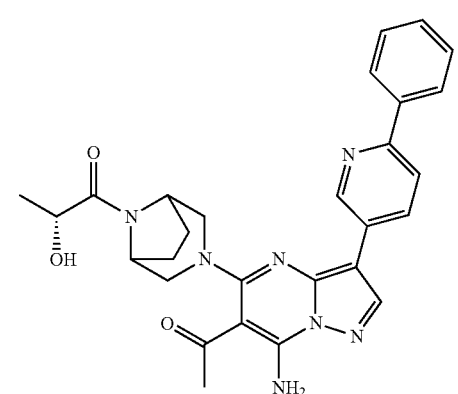

900

-continued

53
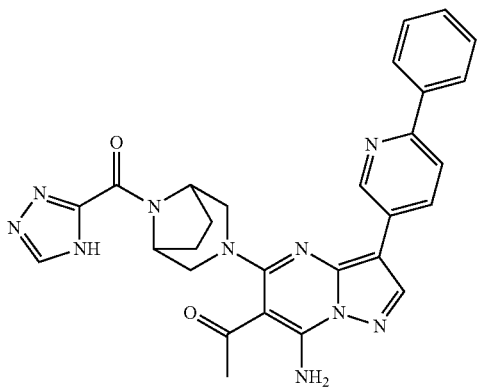

or

54
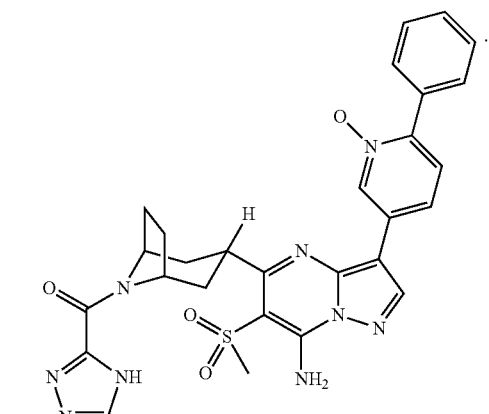

10. A compound selected from the group consisting of:
1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-3-hydroxy-2-(hydroxymethyl)-2-methyl-propan-1-one;

((R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one;

(R)-1-((1R,3S,5S)-3-(6-acetyl-7-amino-3-(6-phenylpyridin-3-yl)pyrazolo[1,5-a]pyrimidin-5-yl)-8-azabicyclo[3.2.1]octan-8-yl)-2,3-dihydroxypropan-1-one;

(exo)-3-[6-acetyl-7-amino-3-(6-phenyl-3-pyridinyl)pyrazolo[1,5-a][pyrimidin-5-yl]-8-[(1,1-dioxido-3-isothiazolidinyl)carbonyl]-8-azabicyclo[3.2.1]octane;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxy-2-methylpropan-1-one;

1-(5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidin-6-yl)ethanone;

(S)-1-((1R,3R,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxypropan-1-one;

1-((1R,3r,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-(1H-tetrazol-5-yl)ethanone;

1-(5-(((1R,3s,5S)-8-(1H-1,2,3-triazole-5-carbonyl)-8-azabicyclo[3.2.1]octan-3-yl)-7-amino-3-(6-phenylpyridin-3-yl)pyrazolo[1,5-a]pyrimidin-6-yl)ethanone;

1-(7-amino-5-((1R,3s,5S)-8-(3-methyl-1H-1,2,4-triazole-5-carbonyl)-8-azabicyclo[3.2.1]octan-3-yl)-3-(6-phenylpyridin-3-yl)pyrazolo[1,5-a]pyrimidin-6-yl)ethanone;

N-(2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoethyl)methanesulfonamide;

1-(5-(((1R,3s,5S)-8-(1H-tetrazole-5-carbonyl)-8-azabicyclo[3.2.1]octan-3-yl)-7-amino-3-(6-phenylpyridin-3-yl)pyrazolo[1,5-a]pyrimidin-6-yl)ethanone;

5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carboxamide;

1-(5-(((1R,3s,5S)-8-(1H-1,2,4-triazole-3-carbonyl)-8-azabicyclo[3.2.1]octan-3-yl)-7-amino-3-(6-(5-(difluoromethyl)thiazol-2-yl)pyridin-3-yl)pyrazolo[1,5-a]pyrimidin-6-yl)ethanone;

1-(5-(((1R,3s,5S)-8-(1H-1,2,4-triazole-3-carbonyl)-8-azabicyclo[3.2.1]octan-3-yl)-7-amino-3-(4-(pyrimidin-2-yl)phenyl)pyrazolo[1,5-a]pyrimidin-6-yl)ethanone;

5-(5-(((1R,3s,5S)-8-(1H-1,2,4-triazole-3-carbonyl)-8-azabicyclo[3.2.1]octan-3-yl)-6-acetyl-7-aminopyrazolo[1,5-a]pyrimidin-3-yl)-N-methylpicolinamide;

5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)-N-methylpicolinamide;

1-(7-amino-5-((1R,3s,5S)-8-azabicyclo[3.2.1]octan-3-yl)-3-(6-(1-methyl-1H-pyrazol-3-yl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(5-hydroxy-6-phenylpyridin-3-yl)pyrazolo[1,5-a]pyrimidin-6-yl)ethanone;

1-((1R,3s,5S)-3-(6-acetyl-7-amino-3-(5-hydroxy-6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxyethanone;

(R)-1-((1R,3S,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxypropan-1-one;

1-((1R,3s,5S)-3-(6-acetyl-7-amino-3-(6-(thiazol-2-yl)pyridin-3-yl)pyrazolo[1,5-a]pyrimidin-5-yl)-8-azabicyclo[3.2.1]octan-8-yl)-2-hydroxy-2-methylpropan-1-one;

1-((1R,3s,5S)-3-(6-acetyl-7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(7-fluoronaphthalen-2-yl)pyrazolo[1,5-a]pyrimidin-6-yl)ethanone;

(1R,3s,5S)-3-(6-acetyl-7-amino-3-(6-phenylpyridin-3-yl)pyrazolo[1,5-a]pyrimidin-5-yl)-N-methyl-8-azabicyclo[3.2.1]octane-8-carboxamide;

1-(7-amino-5-((1R,3s,5S)-8-(5-hydroxy-4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-(5-(((1R,3s,5S)-8-(1H-pyrrole-3-carbonyl)-8-azabicyclo[3.2.1]octan-3-yl)-7-amino-3-(6-phenylpyridin-3-yl)pyrazolo[1,5-a]pyrimidin-6-yl)ethanone;

1-(5-(((1R,3s,5S)-8-(4H-1,2,4-triazol-3-ylsulfonyl)-8-azabicyclo[3.2.1]octan-3-yl)-7-amino-3-(6-phenylpyridin-3-yl)pyrazolo[1,5-a]pyrimidin-6-yl)ethanone;

1-(5-(((1R,3s,5S)-8-(1H-pyrrole-2-carbonyl)-8-azabicyclo[3.2.1]octan-3-yl)-7-amino-3-(6-phenylpyridin-3-yl)pyrazolo[1,5-a]pyrimidin-6-yl)ethanone;

1-((1R,3s,5S)-3-(6-acetyl-7-amino-3-(6-(4-methoxy-3-(methoxymethyl)phenyl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(6-(4-methoxy-3-(methoxymethyl)phenyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(4-methoxyphenyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(2-fluoro-4-methoxyphenyl)pyridin-3-yl)pyrazolo[1,5-a]pyrimidin-6-yl)ethanone;

1-(7-amino-5-((1R,3s,5S)-8-(1-hydroxycyclopropanecarbonyl)-8-azabicyclo[3.2.1]octan-3-yl)-3-(6-phenylpyridin-3-yl)pyrazolo[1,5-a]pyrimidin-6-yl)ethanone;

(1R,3s,5S)-3-(6-acetyl-7-amino-3-(6-phenylpyridin-3-yl)pyrazolo[1,5-a]pyrimidin-5-yl)-8-azabicyclo[3.2.1]octane-8-sulfonic acid;

1-(7-amino-5-((1R,3s,5S)-8-(5-hydroxynicotinoyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s,5S)-8-(4-hydroxynicotinoyl)-8-azabicyclo[3.2.1]octan-3-yl)-3-(6-phenylpyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(5-(methoxymethyl)thiazol-2-yl)pyridin-3-yl)pyrazolo[1,5-a]pyrimidin-6-yl)ethanone;

1-(5-(((1R,3s,5S)-8-(1H-imidazole-4-carbonyl)-8-azabicyclo[3.2.1]octan-3-yl)-7-amino-3-(6-phenylpyridin-3-yl)pyrazolo[1,5-a]pyrimidin-6-yl)ethanone;

1-(5-(((1R,3r,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one;

1-(5-(((1R,3s,5S)-8-(4H-1,2,4-triazole-3-carbonyl)-8-azabicyclo[3.2.1]octan-3-yl)-7-amino-3-(6-(3-fluoro-4-methoxyphenyl)pyridin-3-yl)pyrazolo[1,5-a]pyrimidin-6-yl)ethanone;

1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(3-fluoro-4-methoxyphenyl)pyridin-3-yl)pyrazolo[1,5-a]pyrimidin-5-yl)-8-azabicyclo[3.2.1]octan-8-yl)-3-hydroxy-2-(hydroxymethyl)-2-methylpropan-1-one;

1-((1R,3s,5S)-3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(2,3-difluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2'-fluoro-2,3'-bipyridin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-methyl-2H-tetrazol-5-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3,5-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,3-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-methoxy-3-methylphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-chloro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(benzo[d][1,3]dioxol-5-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-(difluoromethoxy)phenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-fluoro-3-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-(2-methoxyethoxyl)phenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2-methyl-2H-indazol-5-yl)pyridin-3-yl)pyrazolo[1,5-a]pyrimidin-6-yl)ethanone;

1-(3-(6-(1H-benzo[d]imidazol-6-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(2,5-difluoro-4-methoxyphenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-ethoxyphenyl)pyridin-3-yl)pyrazolo[1,5-a]pyrimidin-6-yl)ethanone;

1-(3-(6-(1H-pyrazol-3-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-pyrazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(3-(2,4'-bipyridin-5-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(4-methoxy-(D$_3$)-phenyl)pyridin-3-yl)pyrazolo[1,5-a]pyrimidin-6-yl)ethanone;

1-((1R,3s,5S)-3-(6-acetyl-7-amino-3-(6-(4-methoxy-(D$_3$)-phenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-methylpyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(pyridin-3-yl)pyrazolo[1,5-a]pyrimidin-6-yl)ethanone;

5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)picolinic acid;

1-(5-((1R,3s,5S)-8-(4H-1,2,4-triazole-3-carbonyl)-8-azabicyclo[3.2.1]octan-3-yl)-7-amino-3-(6-(1-methyl-(D$_3$)-1H-pyrazol-3-yl)pyridin-3-yl)pyrazolo[1,5-a]pyrimidin-6-yl)ethanone;

1-(5-(5-((1R,3s,5S)-8-(4H-1,2,4-thiazole-3-carbonyl)-8-azabicyclo[3.2.1]octan-3-yl)-6-acetyl-7-aminopyrazolo[1,5-a]pyrimidin-3-yl)pyridin-2-yl)propan-1-one;

1-((1R,3s,5S)-3-(6-acetyl-7-amino-3-(6-(1-methyl-(D$_3$)-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(3-hydroxypentan-3-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-(fluoromethyl)-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(1-(fluoromethyl)-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-1,2,4-triazol-3-yl)pyridin-3-yl)pyrazolo[1,5-a]pyrimidin-6-yl)ethanone;

1-((1R,3s,5S)-3-(6-acetyl-7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-methylpyridin-3-yl)pyrazolo[1,5-a]pyrimidin-5-yl)-8-azabicyclo[3.2.1]octan-8-yl)-2-hydroxyethanone;

1-(3-(6-(1H-1,2,4-triazol-3-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(6-acetyl-7-amino-3-(6-(fluoromethyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(4-fluoro-1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(5-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(3-(6-(1H-imidazol-4-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-imidazol-4-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-ethylpyridin-3-yl)pyrazolo[1,5-a]pyrimidin-6-yl)ethanone;

1-(5-((1R,3r,5S)-8-(4H-1,2,4-triazole-3-carbonyl)-8-azabicyclo[3.2.1]octan-3-yl)-7-amino-3-(6-(3,5-difluorophenyl)pyridin-3-yl)pyrazolo[1,5-a]pyrimidin-6-yl)ethanone;

1-((1R,3r,5S)-3-(6-acetyl-7-amino-3-(6-(3,5-difluorophenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-1,2,4-triazol-3-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3r,5S)-8-(4H-1,2,4-triazole-3-carbonyl)-8-azabicyclo[3.2.1]octan-3-yl)-7-amino-3-(6-(3-fluorophenyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(trifluoromethyl)pyridin-3-yl)pyrazolo[1,5-a]pyrimidin-6-yl)ethanone;

1-((1R,3r,5S)-3-(6-acetyl-7-amino-3-(6-(3-fluorophenyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluoro-1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(1-methyl-1H-imidazol-4-yl)pyridin-3-yl)pyrazolo[1,5-a]pyrimidin-6-yl)ethanone;

(1R,3s,5S)-2-methoxyethyl 3-(6-acetyl-7-amino-3-(6-(1-methyl-1H-pyrazol-3-yl)pyridin-3-yl)pyrazolo[1,5-a]pyrimidin-5-yl)-8-azabicyclo[3.2.1]octane-8-carboxylate;

1-(5-((1R,3s,5S)-8-(4H-1,2,4-triazole-3-carbonyl)-8-azabicyclo[3.2.1]octan-3-yl)-7-amino-3-(5-fluoro-6-(1H-pyrazol-3-yl)pyridin-3-yl)pyrazolo[1,5-a]pyrimidin-6-yl)ethanone;

1-((1R,3s,5S)-3-(6-acetyl-7-amino-3-(5-fluoro-6-(1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(5-fluoro-6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(5-fluoro-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(5-methyl-6-(1-methyl-1H-pyrazol-3-yl)pyridin-3-yl)pyrazolo[1,5-a]pyrimidin-6-yl)ethanone;

1-((1R,3s,5S)-3-(6-acetyl-7-amino-3-(5-methyl-6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyridin-2(1H)-one;

1-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)propane-1,2-dione;

2-((1R,3s,5S)-3-(6-acetyl-7-amino-3-(6-phenylpyridin-3-yl)pyrazolo[1,5-a]pyrimidin-5-yl)-8-azabicyclo[3.2.1]octan-8-yl)-2-oxoacetamide;

1-(5-((1R,3s,5S)-8-(4H-1,2,4-triazole-3-carbonyl)-8-azabicyclo[3.2.1]octan-3-yl)-7-amino-3-(5-fluoropyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-methyl-2H-indazol-6-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(1-methyl-1H-pyrazol-3-yl)pyridin-3-yl)pyrazolo[1,5-a]pyrimidin-6-yl)ethanone;

1-(7-amino-5-((1R,3s,5S)-8-(morpholine-4-carbonyl)-8-azabicyclo[3.2.1]octan-3-yl)-3-(6-phenylpyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(1-(4-fluorophenyl)-1H-pyrazol-4-yl)pyrazolo[1,5-a]pyrimidin-6-yl)ethanone;

5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-2-methoxybenzonitrile;

1-(5-((1R,3s,5S)-8-(4H-1,2,4-triazole-3-carbonyl)-8-azabicyclo[3.2.1]octan-3-yl)-7-amino-3-(6-methoxyquinolin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(hydroxymethyl)quinolin-3-yl)pyrazolo[1,5-a]pyrimidin-6-yl)ethanone;

1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(6-(4-methyl-1H-imidazol-1-yl)pyridin-3-yl)pyrazolo[1,5-a]pyrimidin-6-yl)ethanone;

1-(3-(6-(1H-imidazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-(7-amino-5-((1R,3s,5S)-8-(5-amino-4H-1,2,4-triazole-3-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone;

1-(5-(((1R,3s,5S)-8-(1H-pyrazole-5-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(4-methyl-1H-pyrazol-1-yl)pyridin-3-yl)pyrazolo[1,5-a]pyrimidin-6-yl)ethanone;

1-((1R,3s,5S)-3-(6-acetyl-7-amino-3-(6-(3-methyl-1H-pyrazol-1-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(4-methyl-1H-pyrazol-1-yl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-thiazole-3-carbonyl)-8-azabicyclo[3.2.1]octan-3-yl)-7-amino-3-(6-(4-methyl-1H-pyrazol-1-yl)pyridin-3-yl)pyrazolo[1,5-a]pyrimidin-6-yl)ethanone;

1-(5-(((1R,3s,5S)-8-(4H-1,2,4-thiazole-3-carbonyl)-8-azabicyclo[3.2.1]octan-3-yl)-7-amino-3-(6-(3-methyl-1H-pyrazol-1-yl)pyridin-3-yl)pyrazolo[1,5-a]pyrimidin-6-yl)ethanone;

1-((1R,3s,5S)-3-(6-acetyl-7-amino-3-(6-(1-ethyl-1H-pyrazol-3-yl)pyridin-3-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-thiazole-3-carbonyl)-8-azabicyclo[3.2.1]octan-3-yl)-7-amino-3-(6-(1-ethyl-1H-pyrazol-3-yl)pyridin-3-yl)pyrazolo[1,5-a]pyrimidin-6-yl)ethanone;

1-(7-amino-5-((1R,3s,5S)-8-(5-(dimethylamino)-1H-1,2,4-thiazole-3-carbonyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s,5S)-8-(5-amino-1H-1,2,4-thiazole-3-carbonyl)-8-azabicyclo[3.2.1]octan-3-yl)-3-(6-phenylpyridin-3-yl)pyrazolo[1,5-a]pyrimidin-6-yl)ethanone;

1-(7-amino-5-((1R,3s,5S)-8-(5-amino-1H-pyrazole-4-carbonyl)-8-azabicyclo[3.2.1]octan-3-yl)-3-(6-phenylpyridin-3-yl)pyrazolo[1,5-a]pyrimidin-6-yl)ethanone;

N-(3-((1R,3s,5S)-3-(6-acetyl-7-amino-3-(6-phenylpyridin-3-yl)pyrazolo[1,5-a]pyrimidin-5-yl)-8-azabicyclo[3.2.1]octane-8-carbonyl)-1H-1,2,4-triazol-5-yl)acetamide;

1-(5-(((1R,3s,5S)-8-(4H-1,2,4-thiazole-3-carbonyl)-8-azabicyclo[3.2.1]octan-3-yl)-7-amino-3-(1-phenyl-1H-pyrazol-4-yl)pyrazolo[1,5-a]pyrimidin-6-yl)ethanone;

1-(7-amino-5-((1R,3s,5S)-8-(5-amino-4H-1,2,4-thiazole-3-carbonyl)-8-azabicyclo[3.2.1]octan-3-yl)-3-(6-(3-fluoro-4-methoxyphenyl)pyridin-3-yl)pyrazolo[1,5-a]pyrimidin-6-yl)ethanone;

1-(5-(((1R,3s,5S)-8-(4H-1,2,4-thiazole-3-carbonyl)-8-azabicyclo[3.2.1]octan-3-yl)-7-amino-3-(6-(2-fluorophenyl)pyridin-3-yl)pyrazolo[1,5-a]pyrimidin-6-yl)ethanone;

1-(3-(2,2'-bipyridin-5-yl)-5-((1R,3s,5S)-8-(4H-1,2,4-thiazole-3-carbonyl)-8-azabicyclo[3.2.1]octan-3-yl)-7-aminopyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(2,6-difluorophenyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone;

1-(5-(((1R,3s,5S)-8-(4H-1,2,4-triazole-3-carbonyl)-8-azabicyclo[3.2.1]octan-3-yl)-7-amino-3-(6-(1-methyl-1H-pyrazol-4-yl)pyridin-3-yl)pyrazolo[1,5-a]pyrimidin-6-yl)ethanone;

1-((1R,3s,5S)-3-(6-acetyl-7-amino-3-(1-methyl-1H-pyrazol-4-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(1-methyl-1H-pyrazol-4-yl)pyrazolo[1,5-a]pyrimidin-6-yl)ethanone;

1-((1R,3s,5S)-3-(6-acetyl-7-amino-3-(1-(2-hydroxy-2-methylpropyl)-1H-pyrazol-4-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(1-(2-hydroxy-2-methylpropyl)-1H-pyrazol-4-yl)pyrazolo[1,5-a]pyrimidin-6-yl)ethanone;

1-((1R,3s,5S)-3-(6-acetyl-7-amino-3-(1-(2-hydroxyethyl)-1H-pyrazol-4-yl)pyrazolo[1,5-a]pyrimidin-5-yl)-8-azabicyclo[3.2.1]octan-8-yl)-2-hydroxyethanone;

1-(5-(((1R,3s,5S)-8-(4H-1,2,4-triazole-3-carbonyl)-8-azabicyclo[3.2.1]octan-3-yl)-7-amino-3-(1-(2-hydroxyethyl)-1H-pyrazol-4-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(4-fluorophenyl)pyridin-3-yl)pyrazolo[1,5-a]pyrimidin-6-yl)ethanone;

1-(5-(((1R,3s,5S)-8-(1H-pyrazole-5-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone;

(R)-1-((1R,3S,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxypropan-1-one;

1-((1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(4-fluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(1-(pyridin-2-yl)-1H-pyrazol-4-yl)pyrazolo[1,5-a]pyrimidin-6-yl)ethanone;

1-((1R,3s,5S)-3-(6-acetyl-7-amino-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(4-fluorophenyl)pyridin-3-yl)pyrazolo[1,5-a]pyrimidin-6-yl)ethanone;

1-((1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(2,4-difluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(7-amino-5-((1R,3s,5S)-8-(3-amino-1H-pyrazole-5-carbonyl)-8-azabicyclo[3.2.1]octan-3-yl)-3-(6-(2,4-difluorophenyl)pyridin-3-yl)pyrazolo[1,5-a]pyrimidin-6-yl)ethanone;

1-(5-((1R,3s,5S)-8-(1H-pyrazole-5-carbonyl)-8-azabicyclo[3.2.1]octan-3-yl)-7-amino-3-(6-(2,4-difluorophenyl)pyridin-3-yl)pyrazolo[1,5-a]pyrimidin-6-yl)ethanone;

(R)-1-((1R,3S,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octan-8-yl)-2-hydroxypropan-1-one;

(1R,3s,5S)-3-(6-acetyl-7-amino-3-(6-(2,4-difluorophenyl)pyridin-3-yl)pyrazolo[1,5-a]pyrimidin-5-yl)-8-azabicyclo[3.2.1]octane-8-carboxamide;

(1R,3s,5S)-3-(6-acetyl-7-amino-3-(6-(4-fluorophenyl)pyridin-3-yl)pyrazolo[1,5-a]pyrimidin-5-yl)-8-azabicyclo[3.2.1]octane-8-carboxamide;

1-((1R,3s,5S)-3-(6-acetyl-7-amino-3-(6-(2,6-difluorophenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-fluorophenyl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

(1R,3s,5S)-3-(6-acetyl-7-amino-3-(6-(2-fluorophenyl)pyridin-3-yl)pyrazolo[1,5-a]pyrimidin-5-yl)-8-azabicyclo[3.2.1]octane-8-carboxamide;

(1R,3s,5S)-3-(6-acetyl-7-amino-3-(6-(1-methyl-1H-pyrazol-4-yl)pyridin-3-yl)pyrazolo[1,5-a]pyrimidin-5-yl)-8-azabicyclo[3.2.1]octane-8-carboxamide;

1-(7-amino-5-((1R,3s,5S)-8-(3-amino-1H-pyrazole-5-carbonyl)-8-azabicyclo[3.2.1]octan-3-yl)-3-(6-(1-methyl-1H-pyrazol-4-yl)pyridin-3-yl)pyrazolo[1,5-a]pyrimidin-6-yl)ethanone;

1-(3-(6-(1H-pyrazol-1-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-pyrazol-1-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(2-phenylpyrimidin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-(2-hydroxypropan-2-yl)pyrimidin-5-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(5-chloro-6-(2-hydroxypropan-2-yl)pyridin-3-yl)pyrazolo[1,5-a]pyrimidin-6-yl)ethanone;

1-(5-((1R,3r,5S)-8-(4H-1,2,4-triazole-3-carbonyl)-8-azabicyclo[3.2.1]octan-3-yl)-7-amino-3-(6-fluoro-8-methoxyquinolin-3-yl)pyrazolo[1,5-a]pyrimidin-6-yl)ethanone;

1-((1R,3r,5S)-3-(6-acetyl-7-amino-3-(6-fluoro-8-methoxyquinolin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(5-(hydroxymethyl)pyridin-3-yl)pyrazolo[1,5-a]pyrimidin-6-yl)ethanone;

1-((1R,3s,5S)-3-(6-acetyl-7-amino-3-(1H-benzo[d]imidazol-5-yl)pyrazolo[1,5-a]pyrimidin-5-yl)-8-azabicyclo[3.2.1]octan-8-yl)-2-hydroxyethanone;

((1R,3s,5S)-3-(7-amino-6-bromo-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone;

1-((1R,3s,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;

(R)-1-((1R,3S,5S)-3-(7-amino-6-bromo-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxypropan-1-one;

((1R,3s,5S)-3-(7-amino-6-bromo-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(3-(hydroxymethyl)-4-methoxyphenyl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(7-amino-3-(6-phenylpyridin-3-yl)pyrazolo[1,5-a]pyrimidin-5-yl)-8-azabicyclo[3.2.1]octan-8-yl)-2-hydroxyethanone;

1-((1R,3s,5S)-3-(7-1-((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-3-(6-(1-methyl-1H-1,2,4-triazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(1H-indazol-5-yl)pyrazolo[1,5-a]pyrimidin-5-yl)-8-azabicyclo[3.2.1]octan-8-yl)(1H-1,2,4-triazol-5-yl)methanone;

((1R,3s,5S)-3-(7-amino-3-(1H-pyrrolo[2,3-b]pyridin-5-yl)pyrazolo[1,5-a]pyrimidin-5-yl)-8-azabicyclo[3.2.1]octan-8-yl)(1H-1,2,4-triazol-5-yl)methanone;

((1R,3s,5S)-3-(7-amino-3-(1H-indazol-6-yl)pyrazolo[1,5-a]pyrimidin-5-yl)-8-azabicyclo[3.2.1]octan-8-yl)(1H-1,2,4-triazol-5-yl)methanone;

((1R,3s,5S)-3-(7-amino-3-(1H-indazol-4-yl)pyrazolo[1,5-a]pyrimidin-5-yl)-8-azabicyclo[3.2.1]octan-8-yl)(1H-1,2,4-triazol-5-yl)methanone;

((1R,3s,5S)-3-(7-amino-3-(6-(2-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-fluoro-4-(trifluoromethyl)phenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(1-methyl-1H-pyrazol-4-yl)pyrazolo[1,5-a]pyrimidin-5-yl)-8-azabicyclo[3.2.1]octan-8-yl)(4H-1,2,4-triazol-3-yl)methanone;

((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-pyrrolidin-2-yl)methanone;

((1R,3R,5S)-3-(7-amino-3-(6-phenylpyridin-3-yl)pyrazolo[1,5-a]pyrimidin-5-yl)-8-azabicyclo[3.2.1]octan-8-yl)((S)-pyrrolidin-2-yl)methanone;

((1R,3s,5S)-3-(7-amino-3-(6-phenylpyridin-3-yl)pyrazolo[1,5-a]pyrimidin-5-yl)-8-azabicyclo[3.2.1]octan-8-yl)(morpholin-3-yl)methanone;

((1R,3S,5S)-3-(7-amino-3-(6-phenylpyridin-3-yl)pyrazolo[1,5-a]pyrimidin-5-yl)-8-azabicyclo[3.2.1]octan-8-yl)((R)-piperidin-2-yl)methanone;

5-((1R,3s,5S)-8-azabicyclo[3.2.1]octan-3-yl)-3-(6-phenylpyridin-3-yl)pyrazolo[1,5-a]pyrimidin-7-amine;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-1,2,3-triazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-tetrazol-5-yl)methanone;

5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-phenylpyridine 1-oxide;

(R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,3-dihydroxypropan-1-one;

(1R,3s,5S)-3-(7-amino-6-(methylsulfonyl)-3-(6-phenylpyridin-3-yl)pyrazolo[1,5-a]pyrimidin-5-yl)-N-ethyl-8-azabicyclo[3.2.1]octane-8-carboxamide;

(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboxamide;

(1R,3s,5S)-3-(7-amino-6-(methylsulfonyl)-3-(6-phenylpyridin-3-yl)pyrazolo[1,5-a]pyrimidin-5-yl)-N-cyclopropyl-8-azabicyclo[3.2.1]octane-8-carboxamide;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1-hydroxycyclopropyl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-hydroxypyridin-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-hydroxypyridin-2-yl)methanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-3,3,3-trifluoro-2-hydroxypropan-1-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxypyridin-2-yl)methanone;

5-(5-((1R,3s,5S)-8-(1H-1,2,4-triazole-3-carbonyl)-8-azabicyclo[3.2.1]octan-3-yl)-7-amino-6-(methylsulfonyl)pyrazolo[1,5-a]pyrimidin-3-yl)-N-methylpicolinamide;

5-((1R,3s,5S)-8-(1H-tetrazol-5-yl)-8-azabicyclo[3.2.1]octan-3-yl)-6-(methylsulfonyl)-3-(6-phenylpyridin-3-yl)pyrazolo[1,5-a]pyrimidin-7-amine;

(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbaldehyde;

5-((1R,3s,5S)-8-(5-methyl-4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine;

5-((1R,3s,5S)-8-(4H-1,2,4-triazol-3-yl)-8-azabicyclo[3.2.1]octan-3-yl)-6-(methylsulfonyl)-3-(6-phenylpyridin-3-yl)pyrazolo[1,5-a]pyrimidin-7-amine;

((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(5-hydroxy-6-phenylpyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(thiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(7-fluoronaphthalen-2-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

5-((1R,3s,5S)-8-(4H-1,2,4-triazol-3-ylsulfonyl)-8-azabicyclo[3.2.1]octan-3-yl)-6-(methylsulfonyl)-3-(6-phenylpyridin-3-yl)pyrazolo[1,5-a]pyrimidin-7-amine;

(S)-1-((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one;

(R)-1-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-hydroxypropan-1-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone;

(1R,3s,5S)-3-(7-amino-6-(methylsulfonyl)-3-(6-phenylpyridin-3-yl)pyrazolo[1,5-a]pyrimidin-5-yl)-N-methyl-8-azabicyclo[3.2.1]octane-8-carboxamide;

((1R,3s,5S)-3-(7-amino-6-(methylsulfonyl)-3-(4-(pyridin-2-yl)phenyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(5-methoxythiophen-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(4-methoxyphenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3,4-dimethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

5-(5-(((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-(1-methyl-1H-pyrazol-3-yl)pyridine 1-oxide;

((1R,3s,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(2-methyl-2H-tetrazol-5-yl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluoro-4-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,3-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(3'-fluoro-2,2'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxy-3-methylphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(3-chloro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(benzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,2-difluorobenzo[d][1,3]dioxol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,3-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(difluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(2-methoxyethoxyl)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-methyl-2H-indazol-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-methoxypyrimidin-5-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,5-difluoro-4-methoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-ethoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-cyclopropoxyphenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-methoxy-(D₃)-phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-(fluoromethoxy)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(2,4'-bipyridin-5-yl)-7-amino-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-butylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(4-methoxy-(D₃)-phenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-(D₃)-1H-pyrazol-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(1-methyl-(D₃)-1H-pyrazol-3-yl)pyridin-3-yl)-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(2-methoxyethoxy)ethanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-pyrazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-5-yl)methanone;

(3-amino-1H-pyrazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[3,2-c]pyridin-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrrolo[2,3-b]pyridin-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-imidazol-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-benzo[d]imidazol-2-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-methyl-1H-pyrazol-5-yl)methanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-(3-methyl-1H-1,2,4-triazol-5-yl)ethanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(1H-pyrazol-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(hydroxymethyl)-1H-pyrazol-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(aminomethyl)-1H-pyrazol-5-yl)methanone;

((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-morpholin-3-yl)methanone;

((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-morpholin-3-yl)methanone;

((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

N-(5-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide;

(5-amino-1H-pyrazol-4-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

1-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2,2,2-trifluoroethanone;

5-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)-2-methoxybenzonitrile;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-(dimethylamino)-4H-1,2,4-triazol-3-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(5-hydroxy-1H-pyrazol-4-yl)methanone;

((1R,3s,5S)-3-(7-amino-3-(7-(hydroxymethyl)quinolin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2-methyl-2H-indazol-5-yl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone;

(3-amino-1H-1,2,4-triazol-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-(trifluoromethyl)-1H-1,2,4-triazol-5-yl)methanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(5-amino-4H-1,2,4-triazol-3-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(3-(2,2'-bipyridin-5-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

2-(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)pyridin-2-yl)pyridine 1-oxide;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-methyl-1H-pyrazol-4-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(3-(6-(1H-pyrazol-4-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-fluoro-4-(trifluoromethyl)phenyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(1-methyl-1H-pyrazol-4-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(1H-pyrazol-4-yl)pyrazolo[1,5-a]pyrimidin-5-yl)-8-azabicyclo[3.2.1]octan-8-yl)(1H-pyrazol-5-yl)methanone;

1-((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)methanone;

((1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone;

(R)-1-((1R,3S,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octan-8-yl)-2-hydroxypropan-1-one;

((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(1-(pyridin-2-yl)-1H-pyrazol-4-yl)pyrazolo[1,5-a]pyrimidin-5-yl)-8-azabicyclo[3.2.1]octan-8-yl)-2-hydroxyethanone;

(1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octane-8-carboxamide;

(1R,3s,5S)-3-(7-amino-3-(6-(4-fluorophenyl)pyridin-3-yl)-6-(methylsulfonyl)pyrazolo[1,5-a]pyrimidin-5-yl)-8-azabicyclo[3.2.1]octane-8-carboxamide;

((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

1-((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

(3-amino-1H-pyrazol-5-yl)((1R,3s,5S)-3-(7-amino-3-(6-(2,4-difluorophenyl)pyridin-3-yl)-6-(methylsulfonyl)pyrazolo[1,5-a]pyrimidin-5-yl)-8-azabicyclo[3.2.1]octan-8-yl)methanone;

(1R,3s,5S)-3-(7-amino-3-(6-(2-fluorophenyl)pyridin-3-yl)-6-(methylsulfonyl)pyrazolo[1,5-a]pyrimidin-5-yl)-N-ethyl-8-azabicyclo[3.2.1]octane-8-carboxamide;

(1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carboxamide;

1-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

(3-amino-1H-pyrazol-5-yl)((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)methanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(1H-pyrazol-5-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(4H-1,2,4-triazol-3-yl)methanone;

(2-amino-4-methylpyrimidin-5-yl)((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)methanone;

4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazol-2(3H)-one;

4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)-1H-imidazol-2(3H)-one;

6-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)pyridin-2(1H)-one;

(S)-4-((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one;

(R)-4-((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonyl)oxazolidin-2-one;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyrimidin-4-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(2-aminopyridin-3-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(4-aminopyrimidin-5-yl)methanone;

((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)(3-aminopyrazin-2-yl)methanone;

((1R,3s,5S)-3-(7-amino-3-(2-(3-fluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(2-(2,3-difluoro-4-methoxyphenyl)pyrimidin-5-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(imidazo[1,2-a]pyrimidin-6-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(2-hydroxypropan-2-yl)pyrimidin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(6-(1H-pyrazol-1-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(7-amino-6-(methylsulfonyl)-3-(tetrahydro-2H-pyran-4-yl)pyrazolo[1,5-a]pyrimidin-5-yl)-8-azabicyclo[3.2.1]octan-8-yl)-2-hydroxyethanone;

4-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)-2-fluorobenzamide;

4-(7-amino-5-((1R,3s,5S)-8-(2-hydroxyacetyl)-8-azabicyclo[3.2.1]octan-3-yl)-6-(methylsulfonyl)pyrazolo[1,5-a]pyrimidin-3-yl)-2-fluorobenzamide;

((1R,3s,5S)-3-(7-amino-3-(6-(2-hydroxypropan-2-yl)-5-methylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(5-chloro-6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(cyclopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(ethylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-phenylpyridin-3-yl)-6-(propylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(isopropylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6'-methoxy-2,3'-bipyridin-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclohexylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclopentylpyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone;

1-((1R,3s,5S)-3-(7-amino-3-(6-cyclobutylpyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-fluoro-4-methoxyphenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

(1R,3s,5S)-3-(7-amino-6-(methylsulfonyl)-3-(6-phenylpyridin-3-yl)pyrazolo[1,5-a]pyrimidin-5-yl)-N-methoxy-8-azabicyclo[3.2.1]octane-8-carboxamide;

(1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboxamide;

((1R,3s,5S)-3-(7-amino-3-(6-(2,6-difluorophenyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

((1R,3s,5S)-3-(7-amino-3-(6-(1-methyl-1H-pyrazol-3-yl)pyridin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(2-phenylpyrimidin-5-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(1-phenyl-1H-pyrazol-4-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(6-fluoroquinolin-3-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-3-(1-(4-fluorophenyl)-1H-pyrazol-4-yl)-6-(methylsulfonyl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(6-(pyrimidin-2-yl)pyridin-3-yl)pyrazolo[1,5-a]pyrimidin-5-yl)-8-azabicyclo[3.2.1]octan-8-yl)(2H-1,2,3-triazol-4-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)ethanone;

(3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-1H-1,2,4-triazol-3-yl)methanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)(1-hydroxycyclopropyl)methanone;

1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoro-2-hydroxypropan-1-one;

2-amino-1-((1R,3s,5S)-3-(7-amino-6-(methylsulfonyl)-3-(6-(5-methylthiazol-2-yl)pyridin-3-yl)pyrazolo[1,5-a]pyrimidin-5-yl)-8-azabicyclo[3.2.1]octan-8-yl)-3,3,3-trifluoropropan-1-one;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(2H-1,2,3-triazol-4-yl)methanone;

1-((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)ethanone;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-6-(methylsulfonyl)-3-(6-(4-methylthiazol-2-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

((1R,3s,5S)-3-(7-amino-3-(6-(5,6-dihydro-4H-cyclopenta[d]thiazol-2-yl)pyridin-3-yl)-6-(methylsulfonyl)pyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

(3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(5-methyl-1H-1,2,4-triazol-3-yl)methanone;

((1R,3s,5S)-3-(7-amino-3-(6-(4,5-dimethylthiazol-2-yl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

(3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(5-methyl-1H-1,2,4-triazol-3-yl)methanone;

1-((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)methanone;

((1R,3s,5S)-3-(7-amino-6-(methylsulfonyl)-3-(6-(2-methylthiazol-4-yl)pyridin-3-yl)pyrazolo[1,5-a]pyrimidin-5-yl)-8-azabicyclo[3.2.1]octan-8-yl)(2H-1,2,3-triazol-4-yl)methanone;

5-((1R,3s,5S)-8-azabicyclo[3.2.1]octan-3-yl)-6-(methylsulfonyl)-3-(6-phenylpyridin-3-yl)pyrazolo[1,5-a]pyrimidin-7-amine;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-oxoethyl)acetamide;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-2-oxoethyl)-2,2,2-trifluoroacetamide;

((1R,3S,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((R)-pyrrolidin-2-yl)methanone;

((1R,3R,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)((S)-pyrrolidin-2-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methyl-4H-1,2,4-triazol-3-yl)methanone;

5-((1R,3s,5S)-8-(4H-1,2,4-triazol-3-ylsulfonyl)-8-azabicyclo[3.2.1]octan-3-yl)-6-cyclopropyl-3-(6-phenylpyridin-3-yl)pyrazolo[1,5-a]pyrimidin-7-amine;

(1R,3s,5S)-3-(7-amino-6-cyclopropyl-3-(6-phenylpyridin-3-yl)pyrazolo[1,5-a]pyrimidin-5-yl)-N-methyl-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-ethyl-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-(2-methoxyethyl)-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-(2-hydroxyethyl)-8-azabicyclo[3.2.1]octane-8-carboxamide;

((1R,3s,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(2,3-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-fluoro-3-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(2,5-difluoro-4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-ethoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-(2-methoxyethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(4-(difluoromethoxy)phenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-methylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(1-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(4-fluoro-5-methyl-1H-pyrazol-3-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(6-(3-fluorophenyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(1-methyl-1H-imidazol-4-yl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-methoxyquinolin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(3-chlorophenyl)methanone;

((1R,3s,5S)-3-(7-amino-6-cyclopropyl-3-(1-phenyl-1H-pyrazol-4-yl)pyrazolo[1,5-a]pyrimidin-5-yl)-8-azabicyclo[3.2.1]octan-8-yl)(4H-1,2,4-triazol-3-yl)methanone;

(5-amino-4H-1,2,4-triazol-3-yl)((1R,3s,5S)-3-(7-amino-6-cyclopropyl-3-(6-(3-fluoro-4-methoxyphenyl)pyridin-3-yl)pyrazolo[1,5-a]pyrimidin-5-yl)-8-azabicyclo[3.2.1]octan-8-yl)methanone;

N-(5-((1R,3s,5S)-3-(7-amino-6-cyclopropyl-3-(6-phenylpyridin-3-yl)pyrazolo[1,5-a]pyrimidin-5-yl)-8-azabicyclo[3.2.1]octane-8-carbonyl)-4H-1,2,4-triazol-3-yl)acetamide;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(dimethylamino)-4H-1,2,4-triazol-3-yl)methanone;

(3-amino-1H-pyrazol-4-yl)((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(2-methoxyethylamino)-4H-1,2,4-triazol-3-yl)methanone;

(1R,3s,5S)-3-(7-amino-6-cyclopropyl-3-(6-phenylpyridin-3-yl)pyrazolo[1,5-a]pyrimidin-5-yl)-N-hydroxy-8-azabicyclo[3.2.1]octane-8-carboxamide;

(1R,3s,5S)-3-(7-amino-6-cyclopropyl-3-(6-phenylpyridin-3-yl)pyrazolo[1,5-a]pyrimidin-5-yl)-N-hydroxy-8-azabicyclo[3.2.1]octane-8-carboxamide;

7-amino-5-((1R,3s,5S)-8-(2-hydroxyacetyl)-8-azabicyclo[3.2.1]octan-3-yl)-3-(6-phenylpyridin-3-yl)pyrazolo[1,5-a]pyrimidine-6-carbonitrile;

5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carbonitrile;

5-((1R,3s,5S)-8-(4H-1,2,4-triazole-3-carbonyl)-8-azabicyclo[3.2.1]octan-3-yl)-7-amino-3-(6-(thiazol-2-yl)pyridin-3-yl)pyrazolo[1,5-a]pyrimidine-6-carbonitrile;

((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

(3-amino-1H-pyrazol-5-yl)((1R,3s,5S)-3-(7-amino-6-(methoxymethyl)-3-(6-phenylpyridin-3-yl)pyrazolo[1,5-a]pyrimidin-5-yl)-8-azabicyclo[3.2.1]octan-8-yl)methanone;

((1R,3s,5S)-3-(7-amino-6-(methoxymethyl)-3-(6-(4-methoxyphenyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-(hydroxymethyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-ethyl-3-(6-phenylpyridin-3-yl)pyrazolo[1,5-a]pyrimidin-5-yl)-8-azabicyclo[3.2.1]octan-8-yl)(3-methyl-1H-1,2,4-triazol-5-yl)methanone;

1-((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)-2-hydroxyethanone;

((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(4H-1,2,4-triazol-3-yl)methanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone;

1-(3-(6-(1H-imidazol-2-yl)pyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(6-(1H-imidazol-2-yl)pyridin-3-yl)-7-amino-6-ethylpyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-7-amino-6-(methylsulfonyl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-7-amino-6-(prop-1-en-2-yl)pyrazolo[1,5-a]pyrimidin-5-yl)-8-azabicyclo[3.2.1]octan-8-yl)-2-hydroxyethanone;

(S)-1-((1R,3R,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one;

2-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-oxoethyl acetate;

1-(3-(6-(1H-imidazol-2-yl)pyridin-3-yl)-7-amino-5-((1R,3s,5S)-8-(methylsulfonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-5-((1R,3s,5S)-8-(1H-pyrrole-3-carbonyl)-8-azabicyclo[3.2.1]octan-3-yl)-7-aminopyrazolo[1,5-a]pyrimidin-6-yl)ethanone;

(R)-1-((1R,3S,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxypropan-1-one;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-(2-methoxyethoxy)ethanone;

((1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octan-8-yl)(1H-pyrrol-3-yl)methanone;

(1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carbaldehyde;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-methoxyethanone;

1-(3-(6-(1H-imidazol-2-yl)pyridin-3-yl)-7-amino-5-((1R,3s,5S)-8-(3-amino-1H-pyrazole-5-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-5-((1R,3s,5S)-8-acetyl-8-azabicyclo[3.2.1]octan-3-yl)-7-aminopyrazolo[1,5-a]pyrimidin-6-yl)ethanone;

1-(3-(6-(1H-imidazol-2-yl)pyridin-3-yl)-7-amino-5-((1R,3s,5S)-8-(tetrahydrofuran-2-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-7-amino-5-((1R,3s,5S)-8-(5-amino-4H-1,2,4-triazole-3-carbonyl)-8-azabicyclo[3.2.1]octan-3-yl)pyrazolo[1,5-a]pyrimidin-6-yl)ethanone;

1-(3-(6-(1H-imidazol-2-yl)pyridin-3-yl)-7-amino-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoroethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-fluoropropan-1-one;

(1R,3s,5S)-3-(3-(6-(1H-imidazol-2-yl)pyridin-3-yl)-6-acetyl-7-aminopyrazolo[1,5-a]pyrimidin-5-yl)-N-methyl-8-azabicyclo[3.2.1]octane-8-carboxamide;

(1R,3s,5S)-methyl 3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxylate;

1-((1R,3s,5S)-3-(6-acetyl-7-amino-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(7-amino-6-cyclopropyl-3-(6-(5-methyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(7-amino-6-cyclopropyl-3-(5-fluoro-6-(1H-imidazol-2-yl)pyridin-3-yl)pyrazolo[1,5-a]pyrimidin-5-yl)-8-azabicyclo[3.2.1]octan-8-yl)-2-hydroxyethanone;

(1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octane-8-carboxamide;

(1R,3s,5S)-3-(3-(6-(1H-imidazol-2-yl)pyridin-3-yl)-7-amino-6-cyclopropylpyrazolo[1,5-a]pyrimidin-5-yl)-8-azabicyclo[3.2.1]octane-8-carboxamide;

1-((1R,3s,5S)-3-(7-amino-6-cyclopropyl-3-(6-(4,5-dimethyl-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)-5-methylpyridin-3-yl)-6-acetyl-7-aminopyrazolo[1,5-a]pyrimidin-5-yl)-8-azabicyclo[3.2.1]octan-8-yl)-2-hydroxyethanone;

1-(3-(6-(1H-imidazol-2-yl)-5-methylpyridin-3-yl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(3-(4-(1H-imidazol-2-yl)phenyl)-7-amino-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-cyclopropyl-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone;

1-((1R,3s,5S)-3-(6-acetyl-7-amino-3-(3-fluoro-4-(5-methyl-1H-imidazol-2-yl)phenyl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(3-fluoro-4-(5-methyl-1H-imidazol-2-yl)phenyl)pyrazolo[1,5-a]pyrimidin-6-yl)ethanone;

1-((1R,3s,5S)-3-(6-acetyl-7-amino-3-(3-fluoro-4-(1H-imidazol-2-yl)phenyl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(3-fluoro-4-(1H-imidazol-2-yl)phenyl)pyrazolo[1,5-a]pyrimidin-6-yl)ethanone;

1-((1R,3s,5S)-3-(3-(4-(1H-imidazol-2-yl)phenyl)-6-acetyl-7-aminopyrazolo[1,5-a]pyrimidin-5-yl)-8-azabicyclo[3.2.1]octan-8-yl)-2-hydroxyethanone;

1-(3-(4-(1H-imidazol-2-yl)phenyl)-5-((1R,3s,5S)-8-(4H-1,2,4-triazole-3-carbonyl)-8-azabicyclo[3.2.1]octan-3-yl)-7-aminopyrazolo[1,5-a]pyrimidin-6-yl)ethanone;

1-((1R,3s,5S)-3-(7-amino-6-cyclopropyl-3-(6-(4-fluoro-1H-imidazol-2-yl)pyridin-3-yl)pyrazolo[1,5-a]pyrimidin-5-yl)-8-azabicyclo[3.2.1]octan-8-yl)-2-hydroxyethanone;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2,2-dimethylpropan-1-one;

1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-3-hydroxy-2-(hydroxymethyl)-2-methylpropan-1-one;

1-(5-((1R,3s,5S)-8-(4H-1,2,4-triazole-3-carbonyl)-8-azabicyclo[3.2.1]octan-3-yl)-7-amino-3-(6-(hydroxymethyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxybutyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxypropyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxyethyl)pyridin-3-yl)pyrazolo[1,5-a]pyrimidin-6-yl)ethanone;

1-(5-((1R,3s,5S)-8-(1H-1,2,4-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(1-hydroxy-3-methylbutyl)pyridin-3-yl)pyrazolo[1,5-a]pyrimidin-6-yl)ethanone;

1-(7-amino-5-((1R,3s,5S)-8-(1-hydroxycyclopropanecarbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-((1R,3s,5S)-3-(6-acetyl-7-amino-3-(6-(2-hydroxypropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-hydroxypropan-2-yl)pyridin-3-yl)-5-((1R,3s,5S)-8-(5-methyl-4H-1,2,4-triazole-3-carbonyl)-8-azabicyclo[3.2.1]octan-3-yl)pyrazolo[1,5-a]pyrimidin-6-yl)ethanone;

1-(5-((1R,3s,5S)-8-(1H-1,2,3-triazole-5-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(1H-pyrazole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(5-((1R,3s,5S)-8-(1H-pyrazole-4-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(7-amino-5-((1R,3s,5S)-8-(5-amino-4H-1,2,4-triazole-3-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone;

1-(7-amino-5-((1R,3s,5S)-8-(5-amino-1H-pyrazole-4-carbonyl)-8-azabicyclo[3.2.1]octan-3-yl)-3-(6-(2-hydroxypropan-2-yl)pyridin-3-yl)pyrazolo[1,5-a]pyrimidin-6-yl)ethanone;

1-(5-((1R,3s,5S)-8-(1H-pyrrole-3-carbonyl)-8-azabicyclo[3.2.1]octan-3-yl)-7-amino-3-(6-(2-hydroxypropan-2-yl)pyridin-3-yl)pyrazolo[1,5-a]pyrimidin-6-yl)ethanone;

1-(7-amino-3-(6-(1-hydroxycyclobutyl)pyridin-3-yl)-5-((1R,3s,5S)-8-(3-methyl-1H-1,2,4-triazole-5-carbonyl)-8-azabicyclo[3.2.1]octan-3-yl)pyrazolo[1,5-a]pyrimidin-6-yl)ethanone;

1-((1R,3s,5S)-3-(6-acetyl-7-amino-3-(6-(1-hydroxycyclobutyl)pyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(1H-1,2,3-triazole-5-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

1-(5-((1R,3s,5S)-8-(1H-1,2,4-triazole-3-carbonyl)-8-azabicyclo[3.2.1]octan-3-yl)-7-amino-3-(4-(1-hydroxyethyl)phenyl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(4-((R)-1-hydroxyethyl)phenyl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(4-((S)-1-hydroxyethyl)phenyl)pyrazolo[1,5-a]pyrimidin-6-yl)ethanone;

1-((1R,3s,5S)-3-(6-acetyl-7-amino-3-(6-(2-hydroxypropan-2-yl)-5-methylpyridin-3-yl)pyrazolo[1,5-a]pyrimidin-5-yl)-8-azabicyclo[3.2.1]octan-8-yl)-2-hydroxyethanone;

1-(5-((1R,3s,5S)-8-(4H-1,2,4-triazole-3-carbonyl)-8-azabicyclo[3.2.1]octan-3-yl)-7-amino-3-(6-(2-hydroxypropan-2-yl)-5-methylpyridin-3-yl)pyrazolo[1,5-a]pyrimidin-6-yl)ethanone;

((1R,3s,5S)-3-(7-amino-3-(6-(1-hydroxybutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-hydroxypropyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(2-hydroxypropan-2-yl)pyridin-3-yl)-6-(methylsulfonyl)pyrazolo[1,5-a]pyrimidin-5-yl)-8-azabicyclo[3.2.1]octan-8-yl)(1H-1,2,4-triazol-5-yl)methanone;

1-((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(3-methyl-1H-1,2,4-triazol-5-yl)methanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(1H-1,2,3-triazol-5-yl)methanone;

1-(5-((1R,3s,5S)-8-(4H-1,2,4-triazole-3-carbonyl)-8-azabicyclo[3.2.1]octan-3-yl)-7-amino-3-(6-((2-methoxyethoxy)methyl)pyridin-3-yl)pyrazolo[1,5-a]pyrimidin-6-yl)ethanone;

((1R,3s,5S)-3-(7-amino-3-(6-((2-methoxyethoxy)methyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-((R)-1-hydroxyethyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-((S)-1-hydroxyethyl)pyridin-3-yl)pyrazolo[1,5-a]pyrimidin-6-yl)ethanone;

((1R,3s,5S)-3-(7-amino-3-(6-(hydroxymethyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(2-(1-hydroxyethyl)thiazol-5-yl)pyrazolo[1,5-a]pyrimidin-6-yl)ethanone;

((1R,3s,5S)-3-(7-amino-3-(2-(1-hydroxyethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

((1R,3s,5S)-3-(7-amino-6-cyclopropyl-3-(6-(2-hydroxypropan-2-yl)pyridin-3-yl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(1-hydroxycyclobutyl)pyridin-3-yl)pyrazolo[1,5-a]pyrimidin-6-yl)ethanone;

((1R,3s,5S)-3-(7-amino-3-(6-(1-hydroxycyclobutyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-bromo-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-6-cyclopropyl-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(1-hydroxycyclobutyl)pyridin-3-yl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(3-hydroxyoxetan-3-yl)pyridin-3-yl)pyrazolo[1,5-a]pyrimidin-6-yl)ethanone;

((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(1-hydroxycyclopentyl)pyridin-3-yl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(6-(3-hydroxyoxetan-3-yl)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(3-hydroxyoxetan-3-yl)
pyridin-3-yl)-6-(methylsulfonyl)pyrazolo[1,5-a]pyri-
midin-5-yl)-8-azabicyclo[3.2.1]octan-8-yl)-2-hydroxy-
ethanone;

1-(5-((1R,3s,5S)-8-(4H-1,2,4-triazole-3-carbonyl)-8-
azabicyclo[3.2.1]octan-3-yl)-7-amino-3-(6-(1-hy-
droxycyclopentyl)pyridin-3-yl)pyrazolo[1,5-a]pyrimi-
din-6-yl)ethanone;

((1R,3s,5S)-3-(7-amino-3-(4-(1-hydroxyethyl)phenyl)-6-
(methylsulfonyl)pyrazolo[1,5-a]pyrimidin-5-yl)-8-
azabicyclo[3.2.1]octan-8-yl)(4H-1,2,4-triazol-3-yl)
methanone;

1-(5-((1R,3s,5S)-8-(4H-1,2,4-triazole-3-carbonyl)-8-
azabicyclo[3.2.1]octan-3-yl)-7-amino-3-(6-(1,2-dihy-
droxyethyl)pyridin-3-yl)pyrazolo[1,5-a]pyrimidin-6-
yl)ethanone;

((1R,3s,5S)-3-(7-amino-3-(8-hydroxy-5,6,7,8-tetrahydro-
quinolin-3-yl)-6-(methylsulfonyl)pyrazolo[1,5-a]pyri-
midin-5-yl)-8-azabicyclo[3.2.1]octan-8-yl)(4H-1,2,4-
triazol-3-yl)methanone;

((1R,3s,5S)-3-(7-amino-6-cyclopropyl-3-(8-hydroxy-5,6,
7,8-tetrahydroquinolin-3-yl)pyrazolo[1,5-a]pyrimidin-
5-yl)-8-azabicyclo[3.2.1]octan-8-yl)(4H-1,2,4-triazol-
3-yl)methanone;

((1R,3s,5S)-3-(7-amino-6-cyclopropyl-3-(8-hydroxy-8-
methyl-5,6,7,8-tetrahydroquinolin-3-yl)pyrazolo[1,5-
a]pyrimidin-5-yl)-8-azabicyclo[3.2.1]octan-8-yl)(4H-
1,2,4-triazol-3-yl)methanone;

Deuterated-(3-exo)-3-[7-amino-6-cyclopropy-3-(5,6,7,8-
tetrahydro-8-hydroxy-3-quinolinyl-(D))pyrazolo[1,5-
a]pyrimidin-5-yl]-8-(4H-1,2,4-triazol-3-ylcarbonyl)-8-
azabicyclo[3.2.1]octane;

Deuterated-(3-exo)-3-[6-acetyl-7-amino-3-(5,6,7,8-tet-
rhydro-8-hydroxy-3-quinolinyl-(D))pyrazolo[1,5-a]py-
rimidin-5-yl]-8-(4H-1,2,4-triazol-3-ylcarbonyl)-8-
azabicyclo[3.2.1]octane;

1-(5-((1R,3s,5S)-8-(4H-1,2,4-triazole-3-carbonyl)-8-
azabicyclo[3.2.1]octan-3-yl)-7-amino-3-(8-hydroxy-5,
6,7,8-tetrahydroquinolin-3-yl)pyrazolo[1,5-a]pyrimi-
din-6-yl)ethanone;

1-(5-((1R,3s,5S)-8-(4H-1,2,4-triazole-3-carbonyl)-8-
azabicyclo[3.2.1]octan-3-yl)-7-amino-3-(8-hydroxy-5,
6,7,8-tetrahydroquinolin-3-yl)pyrazolo[1,5-a]pyrimi-
din-6-yl)ethanone;

1-(5-((1R,3s,5S)-8-(4H-1,2,4-triazole-3-carbonyl)-8-
azabicyclo[3.2.1]octan-3-yl)-7-amino-3-(7-hydroxy-6,
7-dihydro-5H-cyclopenta[b]pyridin-3-yl)pyrazolo[1,5-
a]pyrimidin-6-yl)ethanone;

((1R,3s,5S)-3-(7-amino-6-cyclopropyl-3-(7-hydroxy-6,7-
dihydro-5H-cyclopenta[b]pyridin-3-yl)pyrazolo[1,5-a]
pyrimidin-5-yl)-8-azabicyclo[3.2.1]octan-8-yl)(4H-1,
2,4-triazol-3-yl)methanone;

((1R,3s,5S)-3-(7-amino-3-(7-hydroxy-6,7-dihydro-5H-
cyclopenta[b]pyridin-3-yl)-6-(methylsulfonyl)pyrazolo
[1,5-a]pyrimidin-5-yl)-8-azabicyclo[3.2.1]octan-8-yl)
(4H-1,2,4-triazol-3-yl)methanone;

1-(5-((1R,3s,5S)-8-(4H-1,2,4-triazole-3-carbonyl)-8-
azabicyclo[3.2.1]octan-3-yl)-7-amino-3-(4-hydroxy-3,
4-dihydro-2H-pyrano[3,2-b]pyridin-7-yl)pyrazolo[1,5-
a]pyrimidin-6-yl)ethanone;

((1R,3s,5S)-3-(7-amino-6-cyclopropyl-3-(4-hydroxy-3,4-
dihydro-2H-pyrano[3,2-b]pyridin-7-yl)pyrazolo[1,5-a]
pyrimidin-5-yl)-8-azabicyclo[3.2.1]octan-8-yl)(4H-1,
2,4-triazol-3-yl)methanone;

1-(5-((1R,3s,5S)-8-(4H-1,2,4-triazole-3-carbonyl)-8-
azabicyclo[3.2.1]octan-3-yl)-7-amino-3-(6-(2,2,2-trif-
luoro-1-hydroxyethyl)pyridin-3-yl)pyrazolo[1,5-a]py-
rimidin-6-yl)ethanone;

1-(5-((1R,3s,5S)-8-(1H-pyrazole-3-carbonyl)-8-azabicy-
clo[3.2.1]octan-3-yl)-7-amino-3-(6-(2,2,2-trifluoro-1-
hydroxyethyl)pyridin-3-yl)pyrazolo[1,5-a]pyrimidin-
6-yl)ethanone;

1-((1R,3s,5S)-3-(6-acetyl-7-amino-3-(6-(2,2,2-trifluoro-
1-hydroxyethyl)pyridin-3-yl)pyrazolo[1,5-a]pyrimi-
din-5-yl)-8-azabicyclo[3.2.1]octan-8-yl)-2-hydroxy-
ethanone;

((1R,3s,5S)-3-(7-amino-6-(methylsulfonyl)-3-(6-(2,2,2-
trifluoro-1-hydroxyethyl)pyridin-3-yl)pyrazolo[1,5-a]
pyrimidin-5-yl)-8-azabicyclo[3.2.1]octan-8-yl)(4H-1,
2,4-triazol-3-yl)methanone;

((1R,3s,5S)-3-(7-amino-6-(methylsulfonyl)-3-(6-(2,2,2-
trifluoro-1-hydroxyethyl)pyridin-3-yl)pyrazolo[1,5-a]
pyrimidin-5-yl)-8-azabicyclo[3.2.1]octan-8-yl)(1H-
pyrazol-3-yl)methanone;

1-((1R,3s,5S)-3-(7-amino-6-(methylsulfonyl)-3-(6-(2,2,
2-trifluoro-1-hydroxyethyl)pyridin-3-yl)pyrazolo[1,5-
a]pyrimidin-5-yl)-8-azabicyclo[3.2.1]octan-8-yl)-2-
hydroxyethanone;

((1R,3s,5S)-3-(7-amino-cyclopropyl-3-(6-(1-hydroxy-
cyclobutyl)pyridin-3-yl)pyrazolo[1,5-a]pyrimidin-5-
yl)-8-azabicyclo[3.2.1]octan-8-yl)(5-methyl-4H-1,2,4-
triazol-3-yl)methanone;

1-((1R,3s,5S)-3-(7-amino-6-cyclopropyl-3-(6-(1-hy-
droxycyclobutyl)pyridin-3-yl)pyrazolo[1,5-a]pyrimi-
din-5-yl)-8-azabicyclo[3.2.1]octan-8-yl)-2-hydroxy-
ethanone;

1-(5-((1R,3s,5S)-8-(4H-1,2,4-triazole-3-carbonyl)-8-
azabicyclo[3.2.1]octan-3-yl)-7-amino-3-(6-((R)-2,2,2-
trifluoro-1-hydroxyethyl)pyridin-3-yl)pyrazolo[1,5-a]
pyrimidin-6-yl)ethanone;

1-(5-((1R,3s,5S)-8-(4H-1,2,4-triazole-3-carbonyl)-8-
azabicyclo[3.2.1]octan-3-yl)-7-amino-3-(6-((S)-2,2,2-
trifluoro-1-hydroxyethyl)pyridin-3-yl)pyrazolo[1,5-a]
pyrimidin-6-yl)ethanone;

1-(5-((1R,3s,5S)-8-(4H-1,2,4-triazole-3-carbonyl)-8-
azabicyclo[3.2.1]octan-3-yl)-7-amino-3-(6-(1,1,1,3,3,
3-hexafluoro-2-hydroxypropan-2-yl)pyridin-3-yl)pyra-
zolo[1,5-a]pyrimidin-6-yl)ethanone;

1-((1R,3s,5S)-3-(6-acetyl-7-amino-3-(6-(1,1,1,3,3,3-
hexafluoro-2-hydroxypropan-2-yl)pyridin-3-yl)pyra-
zolo[1,5-a]pyrimidin-5-yl)-8-azabicyclo[3.2.1]octan-
8-yl)-2-hydroxyethanone;

1-(7-amino-3-(6-(1,1,1,3,3,3-hexafluoro-2-hydroxypro-
pan-2-yl)pyridin-3-yl)-5-((1R,3s,5S)-8-(5-methyl-4H-
1,2,4-triazole-3-carbonyl)-8-azabicyclo[3.2.1]octan-3-
yl)pyrazolo[1,5-a]pyrimidin-6-yl)ethanone;

1-(7-amino-5-((1R,3s,5S)-8-(5-amino-4H-1,2,4-thiazole-
3-carbonyl)-8-azabicyclo[3.2.1]octan-3-yl)-3-(6-(1,1,
1,3,3,3-hexafluoro-2-hydroxypropan-2-yl)pyridin-3-
yl)pyrazolo[1,5-a]pyrimidin-6-yl)ethanone;

1-(7-amino-5-((1R,3s,5S)-8-(3-amino-1H-pyrazole-5-
carbonyl)-8-azabicyclo[3.2.1]octan-3-yl)-3-(6-(1,1,1,
3,3,3-hexafluoro-2-hydroxypropan-2-yl)pyridin-3-yl)
pyrazolo[1,5-a]pyrimidin-6-yl)ethanone;

1-(5-((1R,3s,5S)-8-(4H-1,2,4-thiazole-3-carbonyl)-8-
azabicyclo[3.2.1]octan-3-yl)-7-amino-3-(6-(2-amino-
1,1,1,3,3,3-hexafluoropropan-2-yl)pyridin-3-yl)pyra-
zolo[1,5-a]pyrimidin-6-yl)ethanone;

1-((1R,3s,5S)-3-(6-acetyl-7-amino-3-(6-(2-amino-1,1,1,3,3,3-hexafluoropropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-amino-1,1,1,3,3,3-hexafluoropropan-2-yl)pyridin-3-yl)-5-((1R,3s,5S)-8-(5-methyl-4H-1,2,4-thiazole-3-carbonyl)-8-azabicyclo[3.2.1]octan-3-yl)pyrazolo[1,5-a]pyrimidin-6-yl)ethanone;

1-((1R,3s,5S)-3-(6-acetyl-7-amino-3-(6-(1,1,1,3,3,3-hexafluoro-2-hydroxypropan-2-yl)pyridin-3-yl)pyrazolo[1,5-a]pyrimidin-5-yl)-8-azabicyclo[3.2.1]octan-8-yl)-2-hydroxyethanone;

1-(7-amino-3-(6-(2-amino-1,1,1,3,3,3-hexafluoropropan-2-yl)pyridin-3-yl)-5-((1R,3s,5S)-8-(3-amino-1H-pyrazole-5-carbonyl)-8-azabicyclo[3.2.1]octan-3-yl)pyrazolo[1,5-a]pyrimidin-6-yl)ethanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)-2-hydroxyethanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-methyl-4H-1,2,4-triazol-3-yl)methanone;

((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)(5-amino-4H-1,2,4-triazol-3-yl)methanone;

(3-amino-1H-pyrazol-5-yl)((1R,3s,5S)-3-(7-amino-3-(6-(2-amino-1,1,1,3,3,3-hexafluoropropan-2-yl)pyridin-3-yl)-6-cyclopropylpyrazolo[1,5-a]pyrimidin-5-yl)-8-azabicyclo[3.2.1]octan-8-yl)methanone;

1-(5-((1R,3s,5S)-8-(4H-1,2,4-triazole-3-carbonyl)-8-azabicyclo[3.2.1]octan-3-yl)-7-amino-3-(2-(hydroxymethyl)thiazol-5-yl)pyrazolo[1,5-a]pyrimidin-6-yl)ethanone;

((1R,3s,5S)-3-(7-amino-3-(2-(hydroxymethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

(5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl 4H-1,2,4-triazole-3-carboxylate;

((1R,3s,5S)-3-(7-amino-3-(2-(aminomethyl)thiazol-5-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

N-((5-(5-((1R,3s,5S)-8-(4H-1,2,4-triazole-3-carbonyl)-8-azabicyclo[3.2.1]octan-3-yl)-7-amino-6-(methylsulfonyl)pyrazolo[1,5-a]pyrimidin-3-yl)thiazol-2-yl)methyl)-4H-1,2,4-triazole-3-carboxamide;

((1R,3s,5S)-3-(7-amino-3-(2-(aminomethyl)thiazol-5-yl)-6-cyclopropylpyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(2-(aminomethyl)-4-cyclopropylthiazol-5-yl)-6-cyclopropylpyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(1H-1,2,4-triazole-5-carbonyl)-8-azabicyclo[3.2.1]octan-3-yl)-7-amino-3-(5-fluoro-6-(2-hydroxypropan-2-yl)pyridin-3-yl)pyrazolo[1,5-a]pyrimidin-6-yl)ethanone;

1-(5-(8-(4H-1,2,4-triazole-3-carbonyl)-3,8-diazabicyclo[3.2.1]octan-3-yl)-7-amino-3-(6-phenylpyridin-3-yl)pyrazolo[1,5-a]pyrimidin-6-yl)ethanone;

(2R)-1-(3-(6-acetyl-7-amino-3-(6-phenylpyridin-3-yl)pyrazolo[1,5-a]pyrimidin-5-yl)-3,8-diazabicyclo[3.2.1]octan-8-yl)-2-hydroxypropan-1-one;

1-(5-(5-(4H-1,2,4-triazole-3-carbonyl)-2,5-diazabicyclo[2.2.2]octan-2-yl)-7-amino-3-(6-phenylpyridin-3-yl)pyrazolo[1,5-a]pyrimidin-6-yl)ethanone;

(2R)-1-(5-(6-acetyl-7-amino-3-(6-phenylpyridin-3-yl)pyrazolo[1,5-a]pyrimidin-5-yl)-2,5-diazabicyclo[2.2.2]octan-2-yl)-2-hydroxypropan-1-one;

1-(5-(3-(4H-1,2,4-triazole-3-carbonyl)-3,8-diazabicyclo[3.2.1]octan-8-yl)-7-amino-3-(6-phenylpyridin-3-yl)pyrazolo[1,5-a]pyrimidin-6-yl)ethanone;

(2R)-1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxypropan-1-one;

1-(8-(6-acetyl-7-amino-3-(6-phenylpyridin-3-yl)pyrazolo[1,5-a]pyrimidin-5-yl)-3,8-diazabicyclo[3.2.1]octan-3-yl)-2-hydroxyethanone;

N-(5-((1R,3s,5S)-8-(4H-1,2,4-triazole-3-carbonyl)-8-azabicyclo[3.2.1]octan-3-yl)-6-cyclopropyl-3-(6-phenylpyridin-3-yl)pyrazolo[1,5-a]pyrimidin-7-yl)acetamide;

N-(5-((1R,3s,5S)-8-(4H-1,2,4-triazole-3-carbonyl)-8-azabicyclo[3.2.1]octan-3-yl)-6-acetyl-3-(6-phenylpyridin-3-yl)pyrazolo[1,5-a]pyrimidin-7-yl)acetamide;

N-(5-((1R,3s,5S)-8-(4H-1,2,4-triazole-3-carbonyl)-8-azabicyclo[3.2.1]octan-3-yl)-3-(6-phenylpyridin-3-yl)pyrazolo[1,5-a]pyrimidin-7-yl)acetamide;

1-(5-((1R,3s,5S)-8-(4H-1,2,4-triazole-3-carbonyl)-8-azabicyclo[3.2.1]octan-3-yl)-7-amino-3-(6-(pyrrolidin-2-yl)pyridin-3-yl)pyrazolo[1,5-a]pyrimidin-6-yl)ethanone;

1-((1R,3s,5S)-3-(6-acetyl-7-amino-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-6-(methylsulfonyl)-3-(6-(pyrrolidin-2-yl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(6-(pyrrolidin-2-yl)pyridin-3-yl)pyrazolo[1,5-a]pyrimidin-5-yl)-8-azabicyclo[3.2.1]octan-8-yl)(4H-1,2,4-triazol-3-yl)methanone;

(R)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one;

(S)-4-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)oxazolidin-2-one;

(S)-4-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)oxazolidin-2-one;

2-(5-(5-(((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)pyrazolidin-3-one;

2-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)pyrazolidin-3-one;

1-(7-amino-5-((1R,3r,5S)-3-hydroxy-8-(4H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

((1R,3r,5S)-3-(7-amino-6-(methylsulfonyl)-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3r,5S)-3-(7-amino-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3r,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-3-hydroxy-8-azabicyclo[3.2.1]octan-8-yl)(4H-1,2,4-triazol-3-yl)methanone;

1-(5-(9-(1H-1,2,4-triazole-3-carbonyl)-3-oxa-9-azabicyclo[3.3.1]nonan-7-yl)-7-amino-3-(1-phenyl-1H-pyrazol-4-yl)pyrazolo[1,5-a]pyrimidin-6-yl)ethanone;

1-(5-(9-(1H-1,2,4-triazole-3-carbonyl)-3-oxa-9-azabicyclo[3.3.1]nonan-7-yl)-7-amino-3-(6-phenylpyridin-3-yl)pyrazolo[1,5-a]pyrimidin-6-yl)ethanone;

1-(7-(6-acetyl-7-amino-3-(6-phenylpyridin-3-yl)pyrazolo[1,5-a]pyrimidin-5-yl)-3-oxa-9-azabicyclo[3.3.1]nonan-9-yl)-2-hydroxyethanone;

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (mixture of stereoisomer);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (isomer I);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1H-1,2,4-triazol-3-yl)methanone; (isomer II);

(7-(7-amino-6-(methylsulfonyl)-3-(6-phenylpyridin-3-yl)pyrazolo[1,5-a]pyrimidin-5-yl)-3-oxa-9-azabicyclo[3.3.1]nonan-9-yl)(1-hydroxycyclopropyl)methanone; (isomer II);

1-(5-(9-(1H-1,2,4-triazole-3-carbonyl)-9-azabicyclo[3.3.1]nonan-3-yl)-7-amino-3-(6-phenylpyridin-3-yl)pyrazolo[1,5-a]pyrimidin-6-yl)ethanone;

1-(7-amino-5-((1S,3R,5R)-6-hydroxy-8-(1H-1,2,4-triazole-3-carbonyl)-8-azabicyclo[3.2.1]octan-3-yl)-3-(6-phenylpyridin-3-yl)pyrazolo[1,5-a]pyrimidin-6-yl)ethanone;

1-((1S,3R,5R)-3-(6-acetyl-7-amino-3-(6-phenylpyridin-3-yl)pyrazolo[1,5-a]pyrimidin-5-yl)-6-hydroxy-8-azabicyclo[3.2.1]octan-8-yl)-2-hydroxyethanone;

1-(5-(7-(1H-1,2,4-triazole-3-carbonyl)-7-azabicyclo[2.2.1]heptan-2-yl)-7-amino-3-(6-phenylpyridin-3-yl)pyrazolo[1,5-a]pyrimidin-6-yl)ethanone;

((1R,3s,5S)-7-(7-amino-3-(6-phenylpyridin-3-yl)pyrazolo[1,5-a]pyrimidin-5-yl)-3,9-diazabicyclo[3.3.1]nonan-9-yl)(1H-1,2,4-triazol-3-yl)methanone;

endo/exo-7-[6-acetyl-7-amino-3-(6-phenyl-3-pyridinyl)pyrazolo[1,5-a]pyrimidin-5-yl]-9-(4h-1,2,4-triazol-3-ylcarbonyl)-3-thia-9-azabicyclo[3.3.1]nonane, 3,3-dioxide;

((1R,3s,5S)-3-(7-amino-6-(1-hydroxycyclopropyl)-3-(6-phenylpyridin-3-yl)pyrazolo[1,5-a]pyrimidin-5-yl)-8-azabicyclo[3.2.1]octan-8-yl)(1H-1,2,4-triazol-3-yl)methanone;

5-((1R,3s,5S)-8-(1H-1,2,4-triazole-3-carbonyl)-8-azabicyclo[3.2.1]octan-3-yl)-7-amino-3-(6-phenylpyridin-3-yl)pyrazolo[1,5-a]pyrimidine-6-carboxamide;

((1R,3s,5S)-3-(7-(methylamino)-6-(methylsulfonyl)-3-(6-phenylpyridin-3-yl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

1-((1R,3s,5S)-3-(7-amino-3-(3-fluoro-4-(hydroxymethyl)phenyl)-6-(methylsulfonyl)pyrazolo[1,5-a]pyrimidin-5-yl)-8-azabicyclo[3.2.1]octan-8-yl)-2-hydroxyethanone;

((1R,3s,5S)-3-(7-amino-3-(4-(1-aminocyclopropyl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(4-(2-aminopropan-2-yl)-3-fluorophenyl)-6-(methylsulfonyl)pyrazolo[1,5-a]pyrimidin-5-yl)-8-azabicyclo[3.2.1]octan-8-yl)(4H-1,2,4-triazol-3-yl)methanone;

(E)-4-((1R,3s,5S)-3-(7-amino-3-(6-(2-fluorophenyl)pyridin-3-yl)-6-(methylsulfonyl)pyrazolo[1,5-a]pyrimidin-5-yl)-8-azabicyclo[3.2.1]octane-8-carbonyl)-N'-(3-(dimethylamino)propyl)-N-ethyl-2H-1,2,3-triazole-2-carboximidamide;

1-(5-((1R,3s,5S)-8-(4H-1,2,4-triazole-3-carbonyl)-8-azabicyclo[3.2.1]octan-3-yl)-7-amino-3-(6-(cyclopropylamino)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-aminopyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(2-(cyclopropylamino)pyrimidin-5-yl)pyrazolo[1,5-a]pyrimidin-6-yl)ethanone;

1-((1R,3s,5S)-3-(6-acetyl-7-amino-3-(6-(cyclopropylamino)pyridin-3-yl)pyrazolo[1,5-a]pyrimidin-5-yl)-8-azabicyclo[3.2.1]octan-8-yl)-2-hydroxyethanone;

N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)acetohydrazide;

N'-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)propionohydrazide;

((1R,3s,5S)-3-(7-amino-3-(6-cyclobutoxypyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3s,5S)-3-(7-amino-3-(6-(cyclopropylmethoxy)pyridin-3-yl)-6-(methylsulfonyl)pyrazolo[1,5-a]pyrimidin-5-yl)-8-azabicyclo[3.2.1]octan-8-yl)(4H-1,2,4-triazol-3-yl)methanone;

((1R,3r,5S)-3-(7-amino-6-cyclopropyl-3-(2H-pyrazolo[4,3-h]pyrano[3,2-b]pyridin-7-yl)pyrazolo[1,5-a]pyrimidin-5-yl)-8-azabicyclo[3.2.1]octan-8-yl)(4H-1,2,4-triazol-3-yl)methanone;

1-(5-((1R,3s,5S)-8-(4H-1,2,4-triazole-3-carbonyl)-8-azabicyclo[3.2.1]octan-3-yl)-7-amino-3-(6-(3-hydroxyprop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-methoxyprop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-(2-hydroxyethoxy)prop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(3-(2-methoxyethoxy)prop-1-ynyl)pyridin-3-yl)pyrazolo[1,5-a]pyrimidin-6-yl)ethanone;

1-(5-((1R,3s,5S)-8-(4H-1,2,4-triazole-3-carbonyl)-8-azabicyclo[3.2.1]octan-3-yl)-7-amino-3-(6-(cyclopropylethynyl)pyridin-3-yl)pyrazolo[1,5-a]pyrimidin-6-yl)ethanone;

1-((1R,3s,5S)-3-(6-acetyl-7-amino-3-(6-(cyclopropylethynyl)pyridin-3-yl)pyrazolo[1,5-a]pyrimidin-5-yl)-8-azabicyclo[3.2.1]octan-8-yl)-2-hydroxyethanone;

((1R,3s,5S)-3-(7-amino-6-cyclopropyl-3-(pyridin-3-ylethynyl)pyrazolo[1,5-a]pyrimidin-5-yl)-8-azabicyclo[3.2.1]octan-8-yl)(4H-1,2,4-triazol-3-yl)methanone;

5-((1R,3s,5S)-8-(4-aminopyrimidin-2-yl)-8-azabicyclo[3.2.1]octan-3-yl)-6-(methylsulfonyl)-3-(6-phenylpyridin-3-yl)pyrazolo[1,5-a]pyrimidin-7-amine;

5-((1R,3s,5S)-8-(5-aminopyrimidin-4-yl)-8-azabicyclo[3.2.1]octan-3-yl)-6-(methylsulfonyl)-3-(6-phenylpyridin-3-yl)pyrazolo[1,5-a]pyrimidin-7-amine;

5-((1R,3s,5S)-8-(3-aminopyridin-2-yl)-8-azabicyclo[3.2.1]octan-3-yl)-6-(methylsulfonyl)-3-(6-phenylpyridin-3-yl)pyrazolo[1,5-a]pyrimidin-7-amine;

N-(4-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyrimidin-5-yl)acetamide;

N-(2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)pyridin-3-yl)acetamide;

5-(5-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyridin-2-yl)-5-methylimidazolidine-2,4-dione;

5-(5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-yl)-5-methylimidazolidine-2,4-dione;

(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carbonitrile;

(1R,3s,5S)-3-(6-acetyl-7-amino-3-(6-phenylpyridin-3-yl)pyrazolo[1,5-a]pyrimidin-5-yl)-8-azabicyclo[3.2.1]octane-8-carbonitrile;

(1R,3s,5S)-3-(7-amino-6-(methylsulfonyl)-3-(6-phenylpyridin-3-yl)pyrazolo[1,5-a]pyrimidin-5-yl)-N-hydroxy-8-azabicyclo[3.2.1]octane-8-carboximidamide;

(1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octane-8-carboximidamide;

3-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)-1,2,4-oxadiazol-5(4H)-one;

1-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)-3-methylurea;

N-(5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-yl)acetamide;

ethyl 5-(6-acetyl-7-amino-5-((1R,3s,5S)-8-(2-hydroxyacetyl)-8-azabicyclo[3.2.1]octan-3-yl)pyrazolo[1,5-a]pyrimidin-3-yl)pyridin-2-ylcarbamate;

ethyl 5-(5-((1R,3s,5S)-8-(1H-1,2,4-triazole-5-carbonyl)-8-azabicyclo[3.2.1]octan-3-yl)-6-acetyl-7-aminopyrazolo[1,5-a]pyrimidin-3-yl)pyridin-2-ylcarbamate;

1-(4-(7-amino-5-((1R,3s,5S)-8-azabicyclo[3.2.1]octan-3-yl)pyrazolo[1,5-a]pyrimidin-3-yl)phenyl)-3-methylurea;

1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)phenyl)-3-methylurea;

1-(4-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)-2-methoxyphenyl)-3-ethylurea;

1-(4-(7-amino-5-((1R,3s,5S)-8-(2-hydroxyacetyl)-8-azabicyclo[3.2.1]octan-3-yl)pyrazolo[1,5-a]pyrimidin-3-yl)phenyl)-3-methylurea;

1-(4-(7-amino-5-((1R,3s,5S)-8-(morpholine-3-carbonyl)-8-azabicyclo[3.2.1]octan-3-yl)pyrazolo[1,5-a]pyrimidin-3-yl)phenyl)-3-methylurea;

1-(5-(5-((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyridin-2-yl)-3-ethylurea;

1-(4-(5-((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)phenyl)-3-methylurea;

(1R,3s,5S,E)-3-(7-amino-3-(6-phenylpyridin-3-yl)pyrazolo[1,5-a]pyrimidin-5-yl)-N'-cyano-8-azabicyclo[3.2.1]octane-8-carboximidamide;

(1R,3s,5S,E)-3-(7-amino-6-(methylsulfonyl)-3-(6-phenylpyridin-3-yl)pyrazolo[1,5-a]pyrimidin-5-yl)-N'-cyano-8-azabicyclo[3.2.1]octane-8-carboximidamide;

((1R,3s,5S)-3-(7-amino-3-(2-aminopyrimidin-5-yl)pyrazolo[1,5-a]pyrimidin-5-yl)-8-azabicyclo[3.2.1]octan-8-yl)(4H-1,2,4-triazol-3-yl)methanone;

6-(methylsulfonyl)-3-(6-phenylpyridin-3-yl)-5-((1R,3s,5S)-8-(2,2,2-trifluoroethyl)-8-azabicyclo[3.2.1]octan-3-yl)pyrazolo[1,5-a]pyrimidin-7-amine;

1-(4-(7-amino-5-((1R,3s,5S)-8-(2,2,2-trifluoroethyl)-8-azabicyclo[3.2.1]octan-3-yl)pyrazolo[1,5-a]pyrimidin-3-yl)phenyl)-3-methylurea;

5-((1R,3s,5S)-8-((4H-1,2,4-triazol-3-yl)methyl)-8-azabicyclo[3.2.1]octan-3-yl)-6-(methylsulfonyl)-3-(6-phenylpyridin-3-yl)pyrazolo[1,5-a]pyrimidin-7-amine;

2-((1R,3s,5S)-3-(7-amino-6-(methylsulfonyl)-3-(6-phenylpyridin-3-yl)pyrazolo[1,5-a]pyrimidin-5-yl)-8-azabicyclo[3.2.1]octan-8-yl)acetamide;

1-(5-((1R,3s,5S)-8-(4H-1,2,4-triazole-3-carbonyl)-8-azabicyclo[3.2.1]octan-3-yl)-7-amino-3-(6-(1-amino-2,2,2-trifluoroethyl)pyridin-3-yl)pyrazolo[1,5-a]pyrimidin-6-yl)ethanone;

((1R,3s,5S)-3-(7-amino-3-(2-(aminomethyl)pyrimidin-5-yl)-6-bromopyrazolo[1,5-a]pyrimidin-5-yl)-8-azabicyclo[3.2.1]octan-8-yl)(4H-1,2,4-triazol-3-yl)methanone;

5-(5-(((1R,3s,5S)-8-(4H-1,2,4-triazole-3-carbonyl)-8-azabicyclo[3.2.1]octan-3-yl)-7-aminopyrazolo[1,5-a]pyrimidin-3-yl)pyrimidine-2-carbonitrile;

5-(5-(((1R,3s,5S)-8-(4H-1,2,4-triazole-3-carbonyl)-8-azabicyclo[3.2.1]octan-3-yl)-7-amino-6-cyclopropylpyrazolo[1,5-a]pyrimidin-3-yl)pyrimidine-2-carbonitrile;

5-(5-(((1R,3s,5S)-8-(4H-1,2,4-triazole-3-carbonyl)-8-azabicyclo[3.2.1]octan-3-yl)-6-acetyl-7-aminopyrazolo[1,5-a]pyrimidin-3-yl)pyrimidine-2-carboxamide;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(piperazin-1-yl)-4H-1,2,4-triazol-3-yl)methanone;

((1R,3S,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-((R)-3-hydroxypyrrolidin-1-yl)-4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(2-methoxyethoxy)-4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4-methyl-4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-(4-methylpiperazin-1-yl)-4H-1,2,4-triazol-3-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-methoxy-4H-1,2,4-triazol-3-yl)methanone;

(5-amino-4H-1,2,4-triazol-3-yl)((1R,3s,5S)-3-(7-amino-6-cyclopropyl-3-(6-phenylpyridin-3-yl)pyrazolo[1,5-a]pyrimidin-5-yl)-8-azabicyclo[3 0.2.1]octan-8-yl)methanone;

((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-morpholino-4H-1,2,4-triazol-3-yl)methanone; and ((1R,3s,5S)-3-(7-amino-6-cyclopropyl-3-(6-phenylpyridin-3-yl)pyrazolo[1,5-a]pyrimidin-5-yl)-8-azabicyclo[3.2.1]octan-8-yl)(5-hydroxy-4H-1,2,4-triazol-3-yl)methanone;

or a stereoisomer thereof;
or a pharmaceutically acceptable salt thereof;
or a pharmaceutically acceptable salt of the stereoisomer thereof.

11. A compound that is 1-[(3-Exo)-3-{7-amino-6-fluoro-3-[6-(1H-imidazol-2-yl)pyridin-3-yl]pyrazolo[1,5-a]pyrimidin-5-yl}-8-azabicyclo[3.2.1]oct-8-yl]-2-hydroxyethanone
or a stereoisomer thereof;
or a pharmaceutically acceptable salt thereof;
or pharmaceutically acceptable salt of the stereoisomer thereof.

12. A pharmaceutical composition comprising the compound of claim 1 or a pharmaceutically acceptable salt thereof, and a pharmaceutically acceptable carrier.

13. A method of treating prostate tumor, solid tumors, lymphoma, multiple myeloma, macroglobulinemia, glioma and breast cancer by the inhibition of mTor, comprising administering a therapeutically effective amount of the compound of claim 1 or a pharmaceutically acceptable salt thereof to a patient in need thereof.

* * * * *